US012599679B2

(12) United States Patent (10) Patent No.: US 12,599,679 B2
Becker et al. (45) Date of Patent: Apr. 14, 2026

(54) CIRCULAR RNA COMPOSITIONS

(71) Applicant: Orna Therapeutics, Inc., Watertown, MA (US)

(72) Inventors: Amy M. Becker, Lexington, MA (US); Robert Alexander Wesselhoeft, IV, Somerville, MA (US); Akinola O. Emmanuel, Cambridge, MA (US); Jui Dutta-Simmons, Sudbury, MA (US); Allen T. Horhota, Westford, MA (US); Kevin J. Kauffman, Newton, MA (US); Bun Chau, Needham, MA (US); Thomas Lee, Watertown, MA (US)

(73) Assignee: Orna Therapeutics, Inc., Watertown, MA (US)

( * ) Notice: Subject to any disclaimer, the term of this patent is extended or adjusted under 35 U.S.C. 154(b) by 0 days.

(21) Appl. No.: 19/200,761

(22) Filed: May 7, 2025

(65) Prior Publication Data

US 2025/0262324 A1 Aug. 21, 2025

Related U.S. Application Data

(63) Continuation of application No. PCT/US2023/078875, filed on Nov. 7, 2023.

(60) Provisional application No. 63/509,361, filed on Jun. 21, 2023, provisional application No. 63/501,820, filed on May 12, 2023, provisional application No. 63/423,760, filed on Nov. 8, 2022.

(51) Int. Cl.
| | |
|---|---|
| *A61K 48/00* | (2006.01) |
| *A61K 9/1272* | (2025.01) |
| *A61K 9/51* | (2006.01) |
| *A61K 40/11* | (2025.01) |
| *A61K 40/15* | (2025.01) |
| *A61K 40/17* | (2025.01) |
| *A61K 40/31* | (2025.01) |
| *A61K 40/42* | (2025.01) |
| *A61P 35/00* | (2006.01) |
| *C07K 16/28* | (2006.01) |
| *C07K 16/32* | (2006.01) |
| *C12N 15/85* | (2006.01) |
| *C12N 15/88* | (2006.01) |

(52) U.S. Cl.
CPC .......... *A61K 48/005* (2013.01); *A61K 9/1272* (2013.01); *A61K 9/5123* (2013.01); *A61K 40/11* (2025.01); *A61K 40/15* (2025.01); *A61K 40/17* (2025.01); *A61K 40/31* (2025.01); *A61K 40/4205* (2025.01); *A61K 40/4211* (2025.01); *A61P 35/00* (2018.01); *C07K 16/2803* (2013.01); *C07K 16/32* (2013.01); *C12N 15/85* (2013.01); *C12N 15/88* (2013.01); *A61K 2239/13* (2023.05); *A61K 2239/17* (2023.05); *A61K 2239/21* (2023.05); *C07K 2317/565*

(2013.01); *C07K 2317/622* (2013.01); *C12N 2800/22* (2013.01); *C12N 2830/50* (2013.01); *C12N 2840/203* (2013.01)

(58) Field of Classification Search
None
See application file for complete search history.

(56) References Cited

U.S. PATENT DOCUMENTS

| | | | |
|---|---|---|---|
| 4,897,355 | A | 1/1990 | Eppstein et al. |
| 5,171,678 | A | 12/1992 | Behr et al. |
| 5,334,761 | A | 8/1994 | Gebeyehu et al. |
| 5,378,825 | A | 1/1995 | Cook et al. |
| 5,585,481 | A | 12/1996 | Arnold, Jr. et al. |
| 5,744,335 | A | 4/1998 | Wolff et al. |
| 5,885,613 | A | 3/1999 | Holland et al. |
| 5,948,902 | A | 9/1999 | Honkanen et al. |
| 6,319,494 | B1 | 11/2001 | Capon et al. |
| 6,417,326 | B1 | 7/2002 | Cullis et al. |
| 7,741,465 | B1 | 6/2010 | Eshhar et al. |
| 8,158,601 | B2 | 4/2012 | Chen et al. |
| 8,492,359 | B2 | 7/2013 | Yaworski et al. |
| 8,734,853 | B2 | 5/2014 | Sood et al. |
| 9,708,628 | B2 | 7/2017 | Tange et al. |
| 9,765,022 | B2 | 9/2017 | Xu et al. |
| 12,175,354 | B1 | 12/2024 | Dehghanpoor et al. |
| 2003/0022649 | A1 | 1/2003 | Voyer |

(Continued)

FOREIGN PATENT DOCUMENTS

| | | |
|---|---|---|
| WO | 9313121 A1 | 7/1993 |
| WO | 9532305 A1 | 11/1995 |

(Continued)

OTHER PUBLICATIONS

Ahmad, et al. (2022) Chimeric antigen receptor T cell structure, its manufacturing, and related toxicities; A comprehensive review, Advances in Cancer Biology: Metastasis, 4: Article 100035, 6 pages. (Year: 2022).*

(Continued)

*Primary Examiner* — Robert M Kelly
(74) *Attorney, Agent, or Firm* — McNeill PLLC

(57) ABSTRACT

Provided herein are circular RNA constructs comprising an IRES, and at least one expression sequence encoding binding molecule, compositions thereof, and methods of treatment, including for cancer and autoimmune disease. In particular, circular RNA comprising an IRES and a CD19 binder, a HER2 binder, or a BCMA binder are provided, optionally formulated with a delivery vehicle. Precursor polynucleotides comprising an IRES, and at least one expression sequence encoding a CAR construct are also described herein.

48 Claims, 162 Drawing Sheets

Specification includes a Sequence Listing.

(56) References Cited

U.S. PATENT DOCUMENTS

| | | | |
|---|---|---|---|
| 2005/0222064 | A1 | 10/2005 | Vargeese et al. |
| 2006/0008910 | A1 | 1/2006 | MacLachlan et al. |
| 2006/0051405 | A1 | 3/2006 | MacLachlan et al. |
| 2006/0083780 | A1 | 4/2006 | Heyes et al. |
| 2009/0023673 | A1 | 1/2009 | Manoharan et al. |
| 2010/0062967 | A1 | 3/2010 | Keil et al. |
| 2010/0130588 | A1 | 5/2010 | Yaworski et al. |
| 2010/0324120 | A1 | 12/2010 | Chen et al. |
| 2011/0076335 | A1 | 3/2011 | Yaworski et al. |
| 2011/0117125 | A1 | 5/2011 | Hope et al. |
| 2011/0256175 | A1 | 10/2011 | Hope et al. |
| 2012/0027796 | A1 | 2/2012 | Manoharan et al. |
| 2012/0058144 | A1 | 3/2012 | Manoharan et al. |
| 2012/0101148 | A1 | 4/2012 | Aking et al. |
| 2012/0128760 | A1 | 5/2012 | Manoharan et al. |
| 2012/0149894 | A1 | 6/2012 | Cameron et al. |
| 2012/0178702 | A1 | 7/2012 | Huang et al. |
| 2012/0202871 | A1 | 8/2012 | Heyes et al. |
| 2013/0065939 | A1 | 3/2013 | Judge et al. |
| 2013/0090372 | A1 | 4/2013 | Budzik et al. |
| 2013/0116307 | A1 | 5/2013 | Heyes et al. |
| 2013/0123338 | A1 | 5/2013 | Heyes et al. |
| 2013/0156845 | A1 | 6/2013 | Manoharan et al. |
| 2013/0164400 | A1 | 6/2013 | Knopov et al. |
| 2013/0178541 | A1 | 7/2013 | Stanton et al. |
| 2013/0195920 | A1 | 8/2013 | Maier et al. |
| 2013/0202684 | A1 | 8/2013 | Geall et al. |
| 2013/0274504 | A1 | 10/2013 | Colletti et al. |
| 2013/0274523 | A1 | 10/2013 | Bawiec, III et al. |
| 2013/0303587 | A1 | 11/2013 | Yaworski et al. |
| 2013/0323269 | A1 | 12/2013 | Manoharan et al. |
| 2013/0338210 | A1 | 12/2013 | Manoharan et al. |
| 2014/0039032 | A1 | 2/2014 | Kuboyama et al. |
| 2014/0141070 | A1 | 5/2014 | Geall et al. |
| 2014/0200257 | A1 | 7/2014 | Rajeev et al. |
| 2014/0255472 | A1 | 9/2014 | Geall et al. |
| 2014/0308304 | A1 | 10/2014 | Manoharan et al. |
| 2015/0057373 | A1 | 2/2015 | Stanton et al. |
| 2015/0064242 | A1 | 3/2015 | Heyes et al. |
| 2015/0140070 | A1 | 5/2015 | Heartlein et al. |
| 2015/0141678 | A1 | 5/2015 | Payne et al. |
| 2015/0203446 | A1 | 7/2015 | Manoharan et al. |
| 2015/0239926 | A1 | 8/2015 | Payne et al. |
| 2015/0376115 | A1 | 12/2015 | Ansell et al. |
| 2016/0151284 | A1 | 6/2016 | Heyes et al. |
| 2016/0311759 | A1 | 10/2016 | Brito et al. |
| 2016/0317458 | A1 | 11/2016 | Brito et al. |
| 2016/0376224 | A1 | 12/2016 | Du et al. |
| 2017/0114010 | A1 | 4/2017 | Payne et al. |
| 2017/0119904 | A1 | 5/2017 | Ansell et al. |
| 2017/0190661 | A1 | 7/2017 | Payne et al. |
| 2017/0210697 | A1 | 7/2017 | Benenato et al. |
| 2018/0005363 | A1 | 1/2018 | Nagatomo et al. |
| 2018/0028664 | A1 | 2/2018 | Besin et al. |
| 2018/0153822 | A1 | 6/2018 | Karve et al. |
| 2019/0091164 | A1 | 3/2019 | Horhota et al. |
| 2019/0314284 | A1 | 10/2019 | Guild et al. |
| 2019/0314524 | A1 | 10/2019 | Ansell et al. |
| 2019/0321489 | A1 | 10/2019 | Guild et al. |

FOREIGN PATENT DOCUMENTS

| | | | |
|---|---|---|---|
| WO | 2005120152 | A2 | 12/2005 |
| WO | 2005121348 | A1 | 12/2005 |
| WO | 2006007712 | A1 | 1/2006 |
| WO | 2006069782 | A2 | 7/2006 |
| WO | 2008042973 | A2 | 4/2008 |
| WO | 2008103276 | A2 | 8/2008 |
| WO | 2009086558 | A1 | 7/2009 |
| WO | 2009127060 | A1 | 10/2009 |
| WO | 2009132131 | A1 | 10/2009 |
| WO | 2010042877 | A1 | 4/2010 |
| WO | 2010048536 | A2 | 4/2010 |
| WO | 2010053572 | A2 | 5/2010 |
| WO | 2010054384 | A1 | 5/2010 |
| WO | 2010054401 | A1 | 5/2010 |
| WO | 2010054405 | A1 | 5/2010 |
| WO | 2010054406 | A1 | 5/2010 |
| WO | 2010088537 | A2 | 8/2010 |
| WO | 2010129709 | A1 | 11/2010 |
| WO | 2010144740 | A1 | 12/2010 |
| WO | 2011000106 | A1 | 1/2011 |
| WO | 2011000107 | A1 | 1/2011 |
| WO | 2011022460 | A1 | 2/2011 |
| WO | 2011038160 | A2 | 3/2011 |
| WO | 2011066651 | A1 | 6/2011 |
| WO | 2011068810 | A1 | 6/2011 |
| WO | 2011071860 | A2 | 6/2011 |
| WO | 2011075656 | A1 | 6/2011 |
| WO | 2011090965 | A1 | 7/2011 |
| WO | 2011127255 | A1 | 10/2011 |
| WO | 2011141704 | A1 | 11/2011 |
| WO | 2011141705 | A1 | 11/2011 |
| WO | 2011153120 | A1 | 12/2011 |
| WO | 2012000104 | A1 | 1/2012 |
| WO | 2012016184 | A2 | 2/2012 |
| WO | 2012024526 | A2 | 2/2012 |
| WO | 2012031043 | A1 | 3/2012 |
| WO | 2012040184 | A2 | 3/2012 |
| WO | 2012044638 | A1 | 4/2012 |
| WO | 2012054365 | A2 | 4/2012 |
| WO | 2012099755 | A1 | 7/2012 |
| WO | 2012162210 | A1 | 11/2012 |
| WO | 2013006825 | A1 | 1/2013 |
| WO | 2013016058 | A1 | 1/2013 |
| WO | 2013033563 | A1 | 3/2013 |
| WO | 2013049328 | A1 | 4/2013 |
| WO | 2013086322 | A1 | 6/2013 |
| WO | 2013086354 | A1 | 6/2013 |
| WO | 2013086373 | A1 | 6/2013 |
| WO | 2013089151 | A1 | 6/2013 |
| WO | 2013093648 | A2 | 6/2013 |
| WO | 2013116126 | A1 | 8/2013 |
| WO | 2013126803 | A1 | 8/2013 |
| WO | 2013148541 | A1 | 10/2013 |
| WO | 2014136086 | A1 | 9/2014 |
| WO | 2015061467 | A1 | 4/2015 |
| WO | 2015074085 | A1 | 5/2015 |
| WO | 2015095340 | A1 | 6/2015 |
| WO | 2015095346 | A1 | 6/2015 |
| WO | 2015130584 | A2 | 9/2015 |
| WO | 2015199952 | A1 | 12/2015 |
| WO | 2016081029 | A1 | 5/2016 |
| WO | 2017004143 | A1 | 1/2017 |
| WO | 2017049245 | A2 | 3/2017 |
| WO | 2017075531 | A1 | 5/2017 |
| WO | 2017099823 | A1 | 6/2017 |
| WO | 2017117528 | | 7/2017 |
| WO | 2017173054 | A1 | 10/2017 |
| WO | 2017185054 | A1 | 10/2017 |
| WO | 2018011633 | A1 | 1/2018 |
| WO | 2019067999 | A1 | 4/2019 |
| WO | 2019089828 | A1 | 5/2019 |
| WO | 2019094486 | A1 | 5/2019 |
| WO | 2019131770 | A1 | 7/2019 |
| WO | 2019152557 | A1 | 8/2019 |
| WO | 2019152848 | A1 | 8/2019 |
| WO | 2019191780 | A1 | 10/2019 |
| WO | 2019236673 | A1 | 12/2019 |
| WO | 2020237227 | A1 | 11/2020 |
| WO | 2020257611 | A1 | 12/2020 |
| WO | 2021021634 | A1 | 2/2021 |
| WO | 2021041473 | A1 | 3/2021 |
| WO | 2021113777 | A2 | 6/2021 |
| WO | 2021189059 | A2 | 9/2021 |
| WO | 2021226597 | A2 | 11/2021 |
| WO | 2021236855 | A1 | 11/2021 |
| WO | 2022261490 | A2 | 12/2022 |
| WO | 2023056033 | A1 | 4/2023 |
| WO | 2023081526 | A1 | 5/2023 |
| WO | 2023141586 | A1 | 7/2023 |
| WO | 2023250375 | A1 | 12/2023 |
| WO | 2024102677 | A1 | 5/2024 |
| WO | 2024102730 | A1 | 5/2024 |

(56) References Cited

FOREIGN PATENT DOCUMENTS

| WO | 2024102762 | A1 | 5/2024 |
|---|---|---|---|
| WO | 2024129982 | A2 | 6/2024 |
| WO | 2024205657 | A2 | 10/2024 |
| WO | 2024233308 | A2 | 11/2024 |
| WO | 2024263729 | A1 | 12/2024 |
| WO | 2025007148 | A1 | 1/2025 |
| WO | 2025049690 | A1 | 3/2025 |
| WO | 2025101501 | A1 | 5/2025 |
| WO | 2025117969 | A1 | 6/2025 |
| WO | 2025128871 | A2 | 6/2025 |
| WO | 2025166238 | A1 | 8/2025 |

OTHER PUBLICATIONS

Ahmad (2012) "scFv Antibody: Principles and Clinical Application", Clinical and Developmental Immunology, Article 980250, 15 pages. (Year: 2012).*
Goel et al. (2004) "Plasticity within the Antigen Combining Site May Manifest as Molecular Mimicry in the Humoral Immune Response", The Journal of Immunology 173(12):7358-7367. (Year: 2004).*
Lloyd et al. (2009) "Modelling the human immune response: performance of a 1011 human antibody repertoire against a broad panel of therapeutically relevant antigens", Protein Engineering, Design & Selection 22(3):159-168 (Year: 2009).*
Edwards et al. (2003) "The remarkable flexibility of the human antibody repertoire; isolation of over one thousand different antibodies to a single protein, BlyS", Journal of Molecular Biology 334:103-118 (Year: 2003).*
Xue, Hui Yi et al., "Lipid-Based Nanocarriers for RNA Delivery", Current Pharmaceutical Design, 2015, 21, 3140-3147.
Behr et al. "Efficient gene transfer into mammalian primary endocrine cells with lipopolyamine-coated DNA," PNAS 1989, 86(18):6982-6986.
Berge et al. "Pharmaceutical salts," J. Pharmaceutical Sciences, 1977, 66(1):1-19.
Budker, V. et al., "Protein/Amphipathic Polyamine Complexes Enable Highly Efficient Transfection with Minimal Toxicity", BioTechniques, (1997), 23:1, 139-147.
Caplen et al. "In vitro liposome-mediated DNA transfection of epithelial cell lines using the cationic liposome DC-Chol/DOPE," Gene Ther, 1995, 2(9):603-13 (abstract).
Chen, Tao et al., "Polyanionic Polymers Which Enhance Fusogenicity", U.S. Appl. No. 60/083,294, filed Apr. 28, 1998.
DeRosa, Frank et al., "Ionizable Cationic Lipids", U.S. Appl. No. 61/617,468, filed Mar. 29, 2012.
Dobrikova et al. "Activity of a type 1 picornavirus internal ribosomal entry site is determined by sequences within the 3' nontranslated region," PNAS, 2003, 100(25):15125-15130.
Eshhar et al., "Tumor-specific T-bodies: toward clinical application," Cancer Immunol Immunotherapy (1997) 45: 131-136.
Felgner et al. "Lipofection: A highly efficient, lipid-mediated DNA-transfection procedure," PNAS, 1987, 84:7413-7417.
Finney et al. "Chimeric receptors providing both primary and costimulatory signaling in T cells from a single gene product," J Immunol, 1998, 161(6):2791-7.
Gao et al. "A novel cationic liposome reagent for efficient transfection of mammalian cells," Biochem Biophys Res Commun, 1991, 179(1):280-5.
Garlapati et al. "Identification of a novel internal ribosome entry site in giardiavirus that extends to both sides of the initiation codon," J Biol Chem, 2004, 279(5):3389-97.
Godet, Anne-Claire et al., "IRES Trans-Acting Factors, Key Actors of the Stress Response", Int. J. Mol. Sci. 2019, 20; 294: 29 pages.
Gross et al. "Therapeutic Potential of T Cell Chimeric Antigen Receptors (CARs) in Cancer Treatment: Counteracting Off-Tumor Toxicities for Safe CAR T Cell Therapy," Annu Rev Pharmacol Toxicol, 2016, 56:59-83.

Gurtu et al. "IRES bicistronic expression vectors for efficient creation of stable mammalian cell lines," Biochem Biophys Res Commun, 1996, 229(1):295-8.
Haney, Matthew J. et al., "Exosomes as Drug Delivery Vehicles for Parkinson's Disease Therapy", J Control Release, 2015; 207: 18-30.
Heyes et al. "Cationic lipid saturation influences intracellular delivery of encapsulated nucleic acids," Journal of Controlled Release, 2005, 107:276-287.
Holdt, Lesca M. et al., "Circular RNAs as Therapeutic Agents and Targets", Front. Physiol. 2018, 9:1262, 16 pages.
Jang et al. "Initiation of Protein Synthesis by Internal Entry of Ribosomes into the 5' Nontranslated Region of Encephalomyocarditis Virus RNA in Vivo," J. Virol., 1989, 63(4):1651-1660.
Jayaraman et al. "Maximizing the potency of siRNA lipid nanoparticles for hepatic gene silencing in vivo," Angew. Chem. Int. Ed., 2012, 51(34):8529-8533.
Kalos et al. "T Cells with Chimeric Antigen Receptors Have Potent Antitumor Effects and Can Establish Memory in Patients with Advanced Leukemia," Sci Transl Med, 2011, 3:95.
Katano, Ikumi et al., "Long-term maintenance of peripheral blood derived human NK cells in a novel human IL-15-transgenic NOG mouse", Scientific Reports, 2017, 7:17230, 14 pages.
Kaufman et al. "Improved vectors for stable expression of foreign genes in mammalian cells by use of the untranslated leader sequence from EMC virus," Nucleic Acids Res, 1991, 19(16):4485-90.
Klibanov et al. "Amphipathic polyethyleneglycols effectively prolong the circulation time of liposomes," FEBS Lett., 1990, 268(1):235-7.
Kobayashi et al. "Improved dicistronic mRNA expression vectors for efficient selection of transfectants highly expressing foreign genes," Biotechniques, 1996, 21(3):398-402.
Koltover, et al. "An inverted hexagonal phase of cationic liposome-DNA complexes related to DNA release and delivery," Science (1998) 281: 78-81.
Krause et al. "Antigen-dependent CD28 signaling selectively enhances survival and proliferation in genetically modified activated human primary T lymphocytes," J Exp Med., 1998, 188(4):619-26.
Lasic et al. "Gelation of liposome interior. A novel method for drug encapsulation," FEBS Lett, 1992, 312(2-3):255-8.
Li et al. "In vivo gene transfer via intravenous administration of cationic lipid-protamine-DNA (LPD) complexes," Gene Ther, 1997, 4(9):891-900.
Luan, Xin et al., "Engineering exosomes as refined biological nanoplatforms for drug delivery", Acta Pharmacologica Sinica, 2017, 38: 754-763.
Mackensen, Andreas et al., "Anti-CD19 CAR T cell therapy for refractory systemic lupus erythematosus", Nature Medicine, 2022, 28:2124-2132.
Maier et al. "Biodegradable Lipids Enabling Rapidly Eliminated Lipid Nanoparticles for Systemic Delivery of RNAi Therapeutics," Mol. Ther., 2013, 21(8):1570-78.
Mendes, Livia Palmerston et al., "Dendrimers as Nanocarriers for Nucleic Acid and Drug Delivery in Cancer Therapy", Molecules 2017, 22(1401), 21 pages.
Morrissey et al. "Potent and persistent in vivo anti-HBV activity of chemically modified siRNAs," Nat Biotechnol, 2005, 23(8):1002-7.
Mosser et al. "Use of a dicistronic expression cassette encoding the green fluorescent protein for the screening and selection of cells expressing inducible gene products," Biotechniques, 1997, 22(1):150-4, 156, 158-61.
Mukherjee, Anubhab et al., "Lipid-polymer hybrid nanoparticles as a next-generation drug delivery platform: state of the art, emerging technologies, and perspectives", International Journal of Nanomedicine 2019, 14, 1937-1952.
Nikonov, O.S et al., "Enteroviruses: Classification, Diseases They Cause, and Approaches to Development of Antiviral Drugs", Biochemistry (Moscow), 2017, 82(13): 1615-1631.
Nunez, Daniel et al., "Cytokine and reactivity profiles in SLE patients following anti-CD19 CART therapy", Molecular Therapy: Methods & Clinical Development, 2023, vol. 31, 6 pages.

(56)  References Cited

OTHER PUBLICATIONS

PCT International Search Report and Written Opinion from PCT/US2023/078875, mailed Feb. 28, 2024, 20 pages.
Porter et al. "Chimeric antigen receptor-modified T cells in chronic lymphoid leukemia," N Engl J Med, 2011, 365 (8):725-33.
Ramesh, N. et al., "High-titer bicistronic retroviral vectors employing foot-and-mouth disease virus internal ribosome entry site", Nucleic Acids Research, 1996, 24(14): 2697-2700.
Rees et al. "Bicistronic vector for the creation of stable mammalian cell lines that predisposes all antibiotic-resistant cells to express recombinant protein," Biotechniques, 1996, 20(1):102-4, 106, 108-10.
Semple et al. "Rational design of cationic lipids for siRNA delivery," Nat Biotechnol, 2010, 28(2):172-6.
Shah, Nina et al., "B-cell maturation antigen (BCMA) in multiple myeloma: rationale for targeting and current therapeutic approaches", Leukemia (2020) 34: 985-1005.

Shobaki et al. "Mixing lipids to manipulate the ionization status of lipid nanoparticles for specific tissue targeting," Int J Nanomedicine, 2018, 13:8395-8410.
Son, Siejin, "Sugar-Nanocapsules Imprinted with Microbial Molecular Patterns for mRNA Vaccination", Nano Lett. 2020; 20(3) 1499-1509.
Song et al. "CD27 costimulation augments the survival and antitumor activity of redirected human T cells in vivo," Blood, 2012, 119(3):696-706.
Wang et al., "A combinatorial library of unsaturated lipidoids for efficient intracellular gene delivery," ACS Synthetic Biology, 1, 403-07 (2012).
Wang, Laixin et al., "Oligoribonucleotide circularization by template-mediated ligation with T4 Rna ligate: synthesis of circular hammerhaed ribozymes", Nucleic Acids Research, 1998, 26(10): 2502-2504.
Wender, et al., "The design of guanidinium-rich transporters and their internalization mechanisms," Adv. Drug Del. Rev., 2008, 60(4-5): 452-472.

* cited by examiner

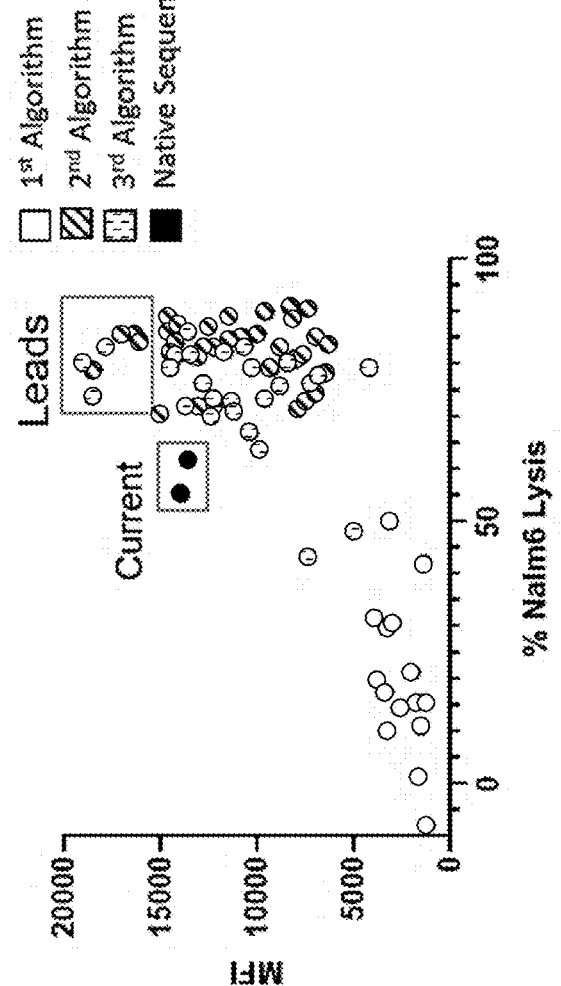
*Fig. 2A*
*Fig. 2B*

CAR IRES Activity Donor 4003
Day 1

CAR IRES Activity Donor 4003
Day 2

CAR % Positive Day 5

CAR % Positive Day 1

609C 24h

609C 48h

4003 24h

4003 48h

609C 24h

609C 48h

4003 24h

4003 48h

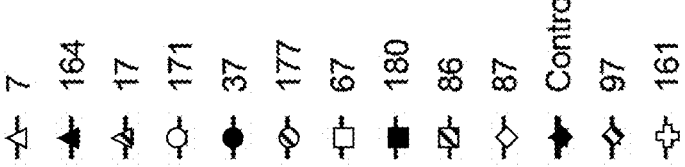
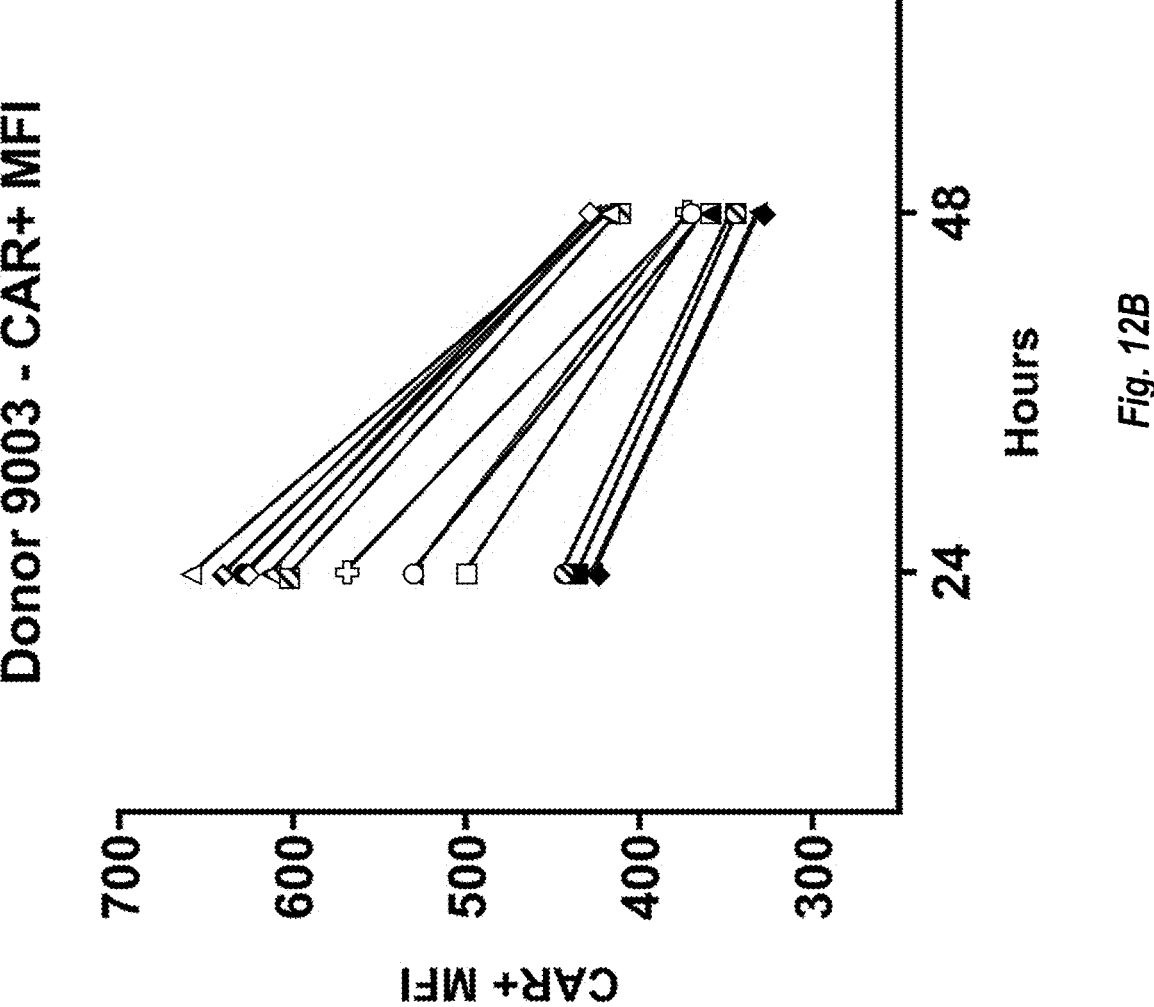
*Fig. 12B*

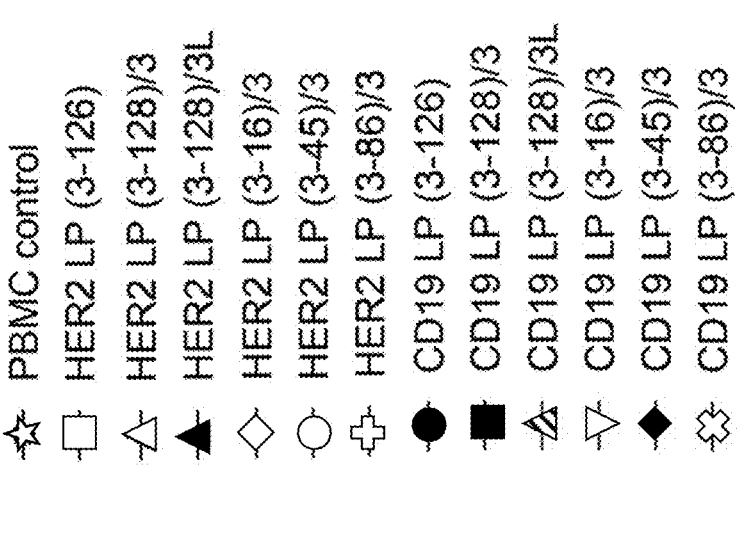
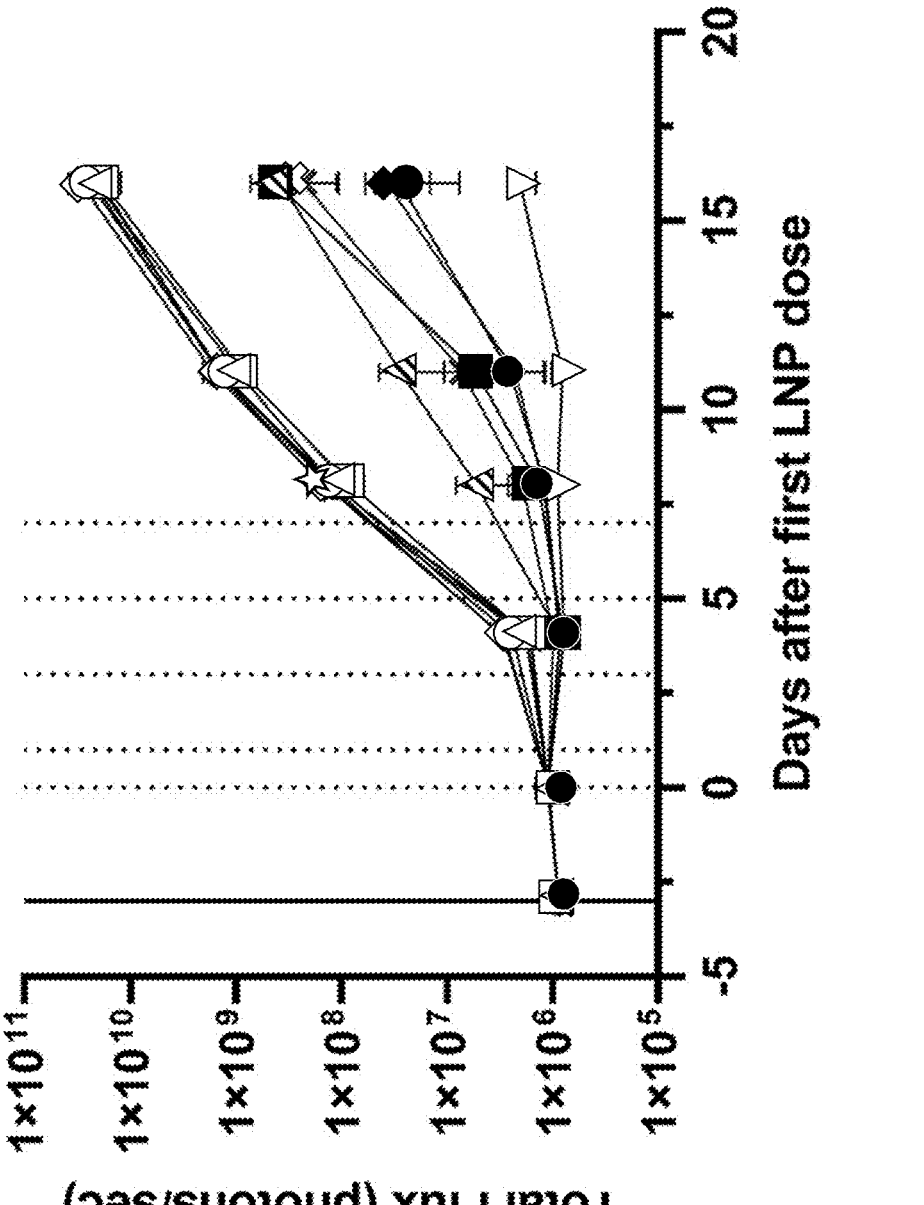
*Fig. 16*

24 Hr
BCMA CAR
Detected with soluble BCMA.PE
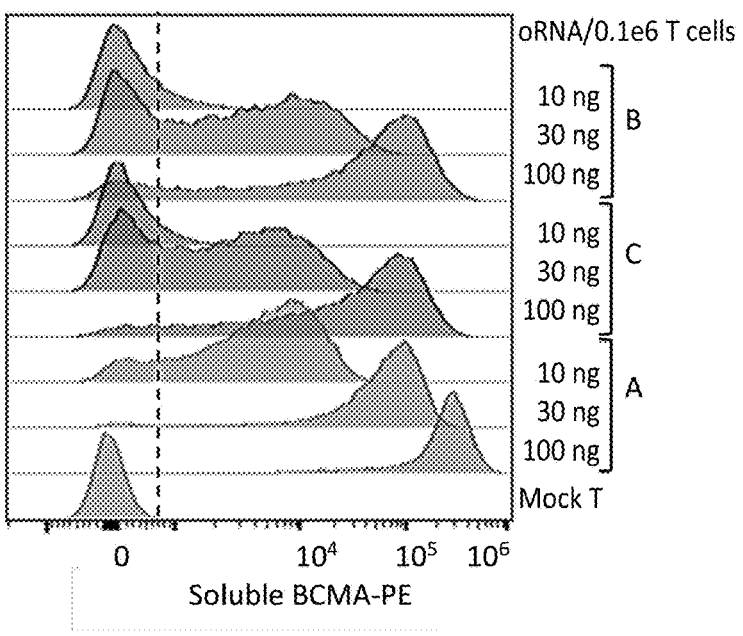
48 Hr
BCMA CAR
Detected with soluble BCMA.PE
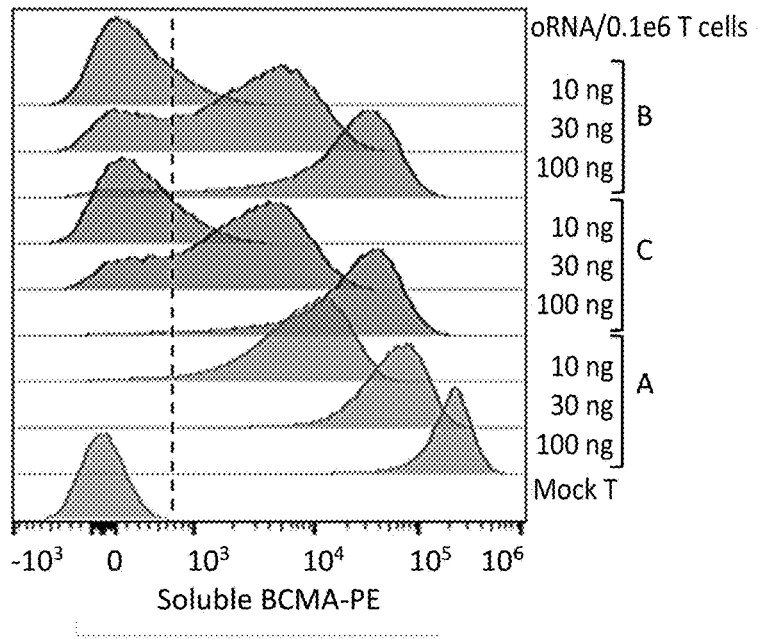
*Fig. 24A*

72 Hr

BCMA CAR

Detected with soluble BCMA.PE

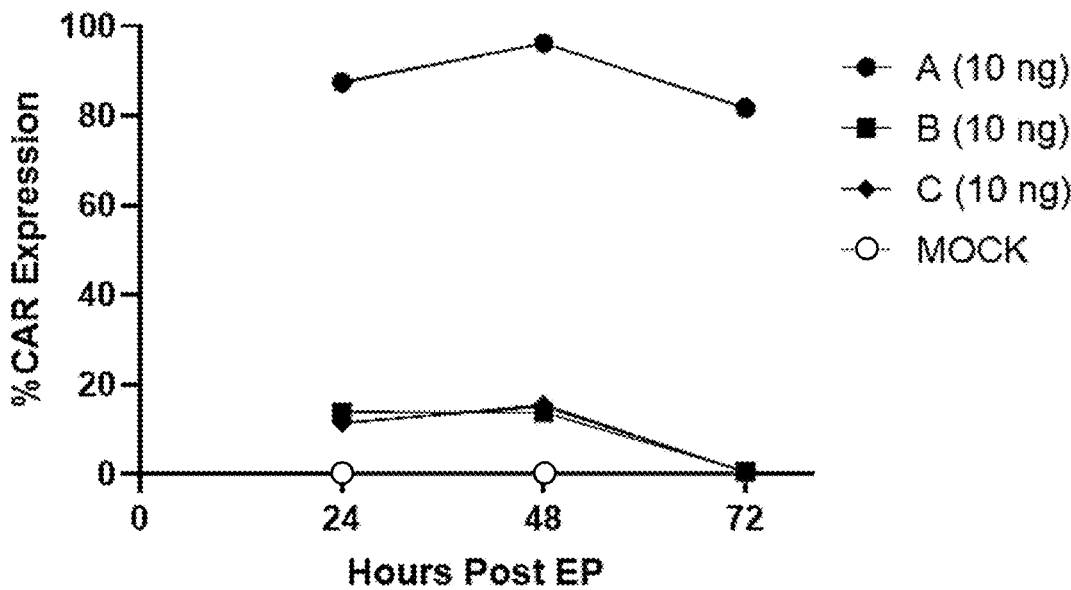
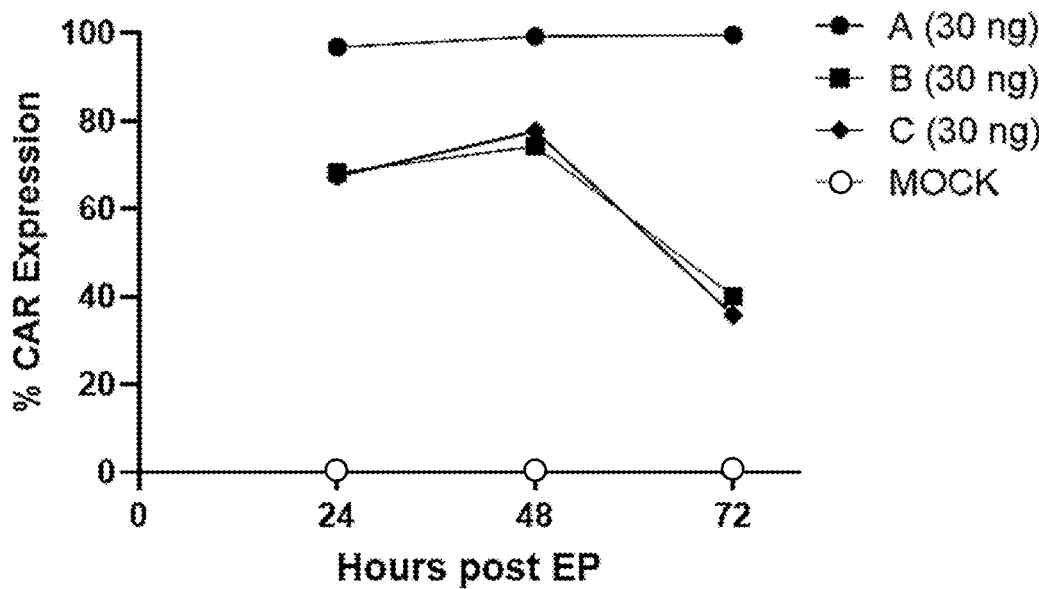
*Fig. 25A*

Expression Kinetics
100ng oRNA/0.1 e6 T cells

Expression Kinetics gMFI
10 ng oRNA/0.1 e6 T cells

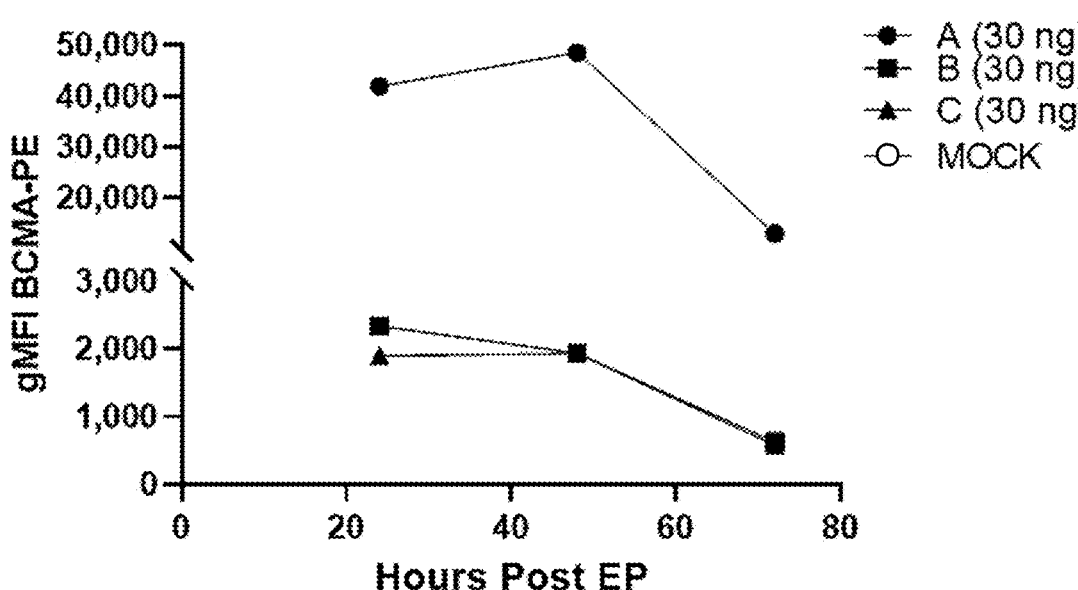
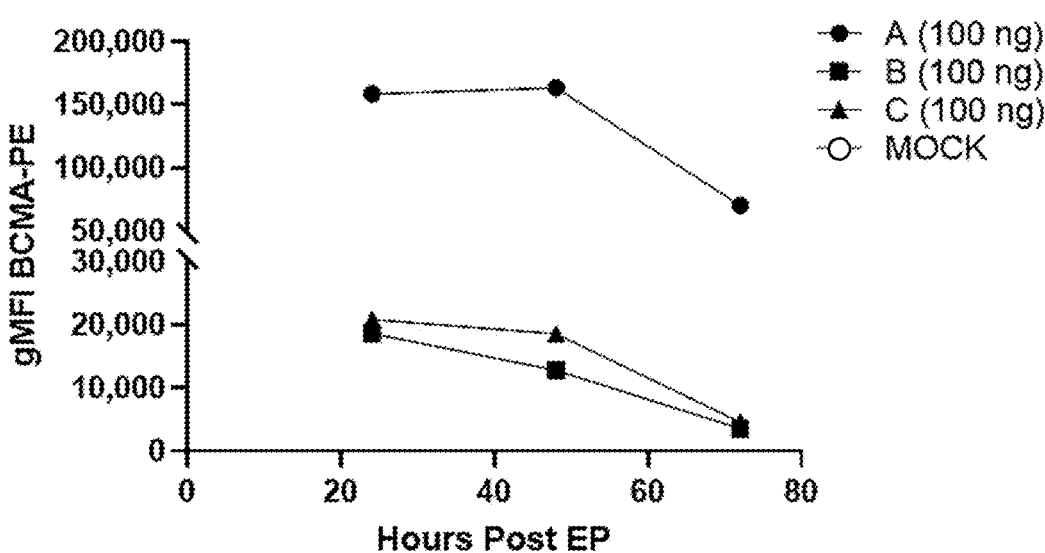
Fig. 25B (Cont.)

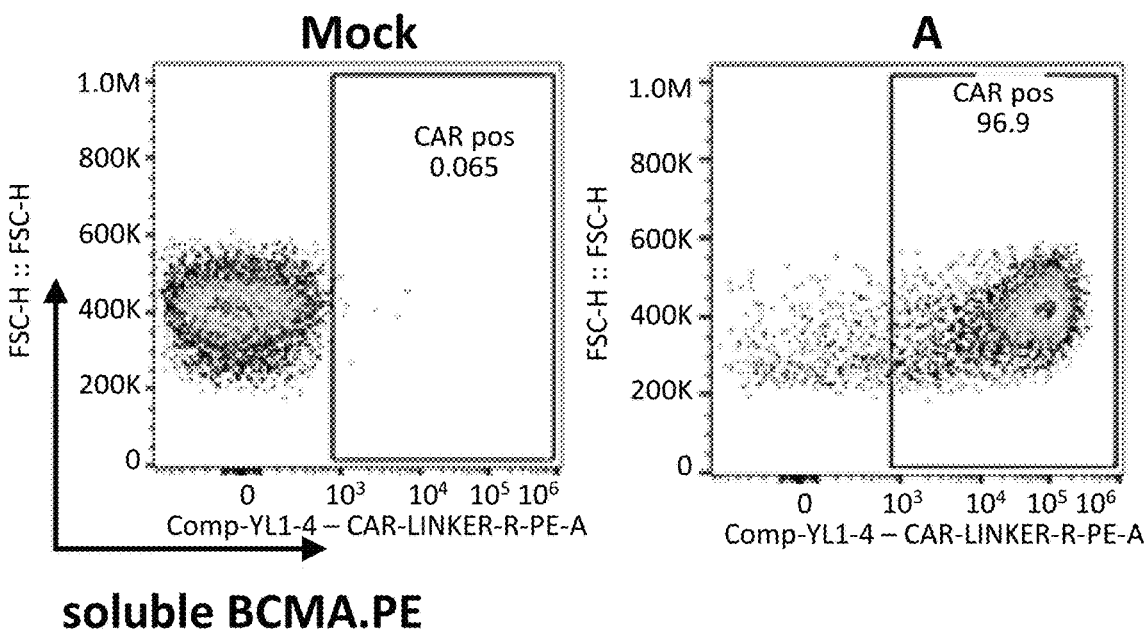
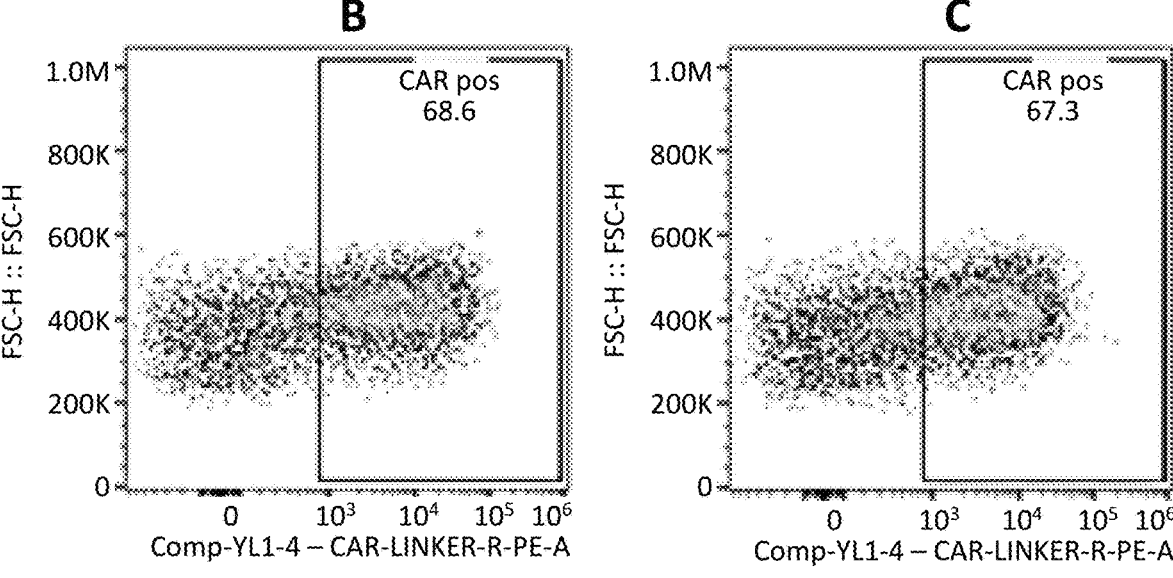
*Fig. 25C*

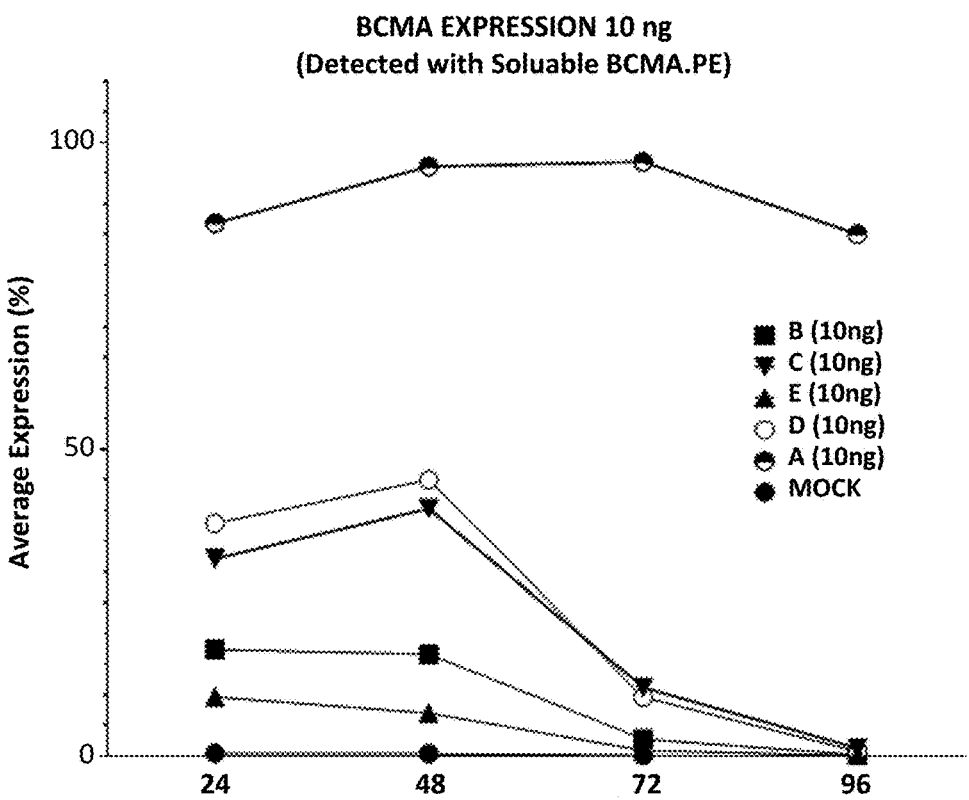
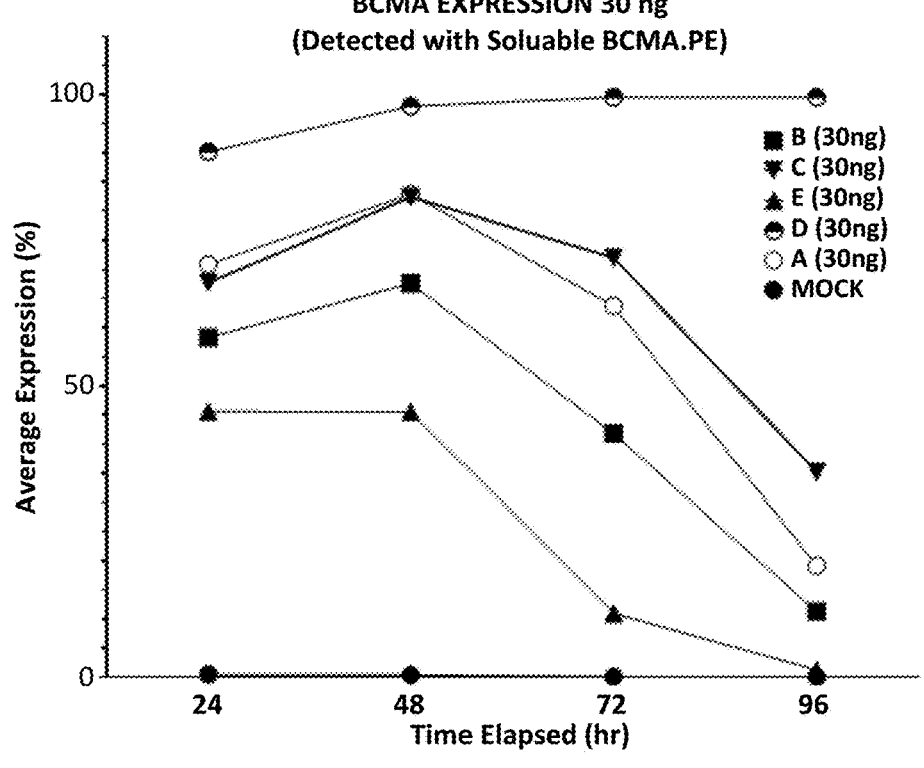
*Fig. 25D*

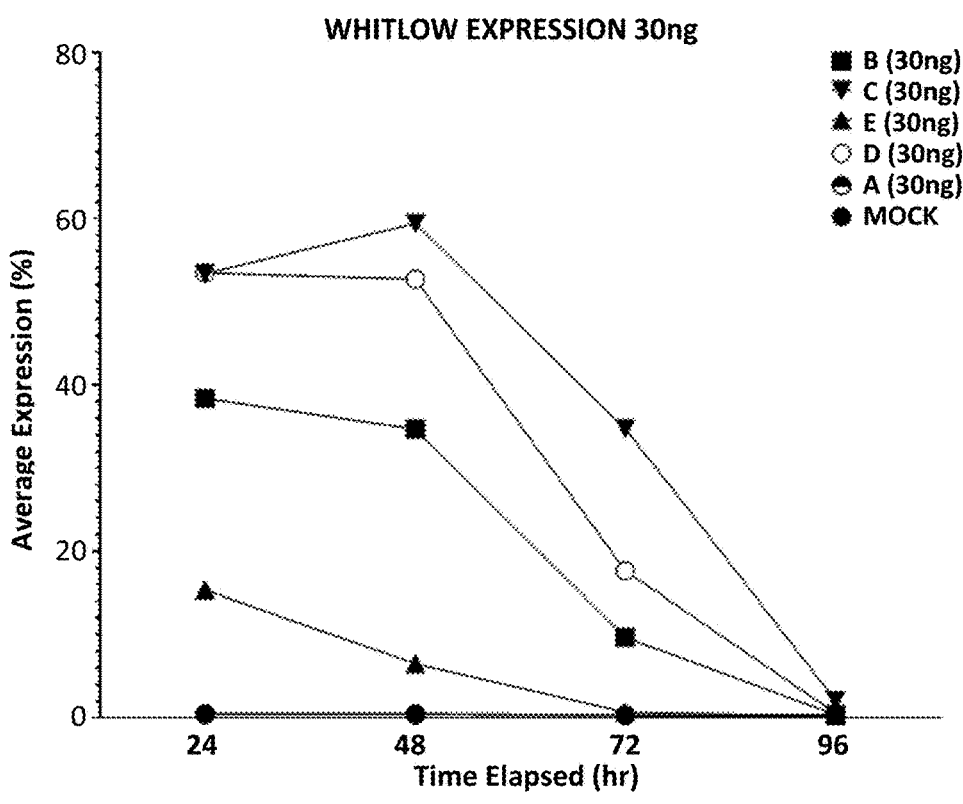
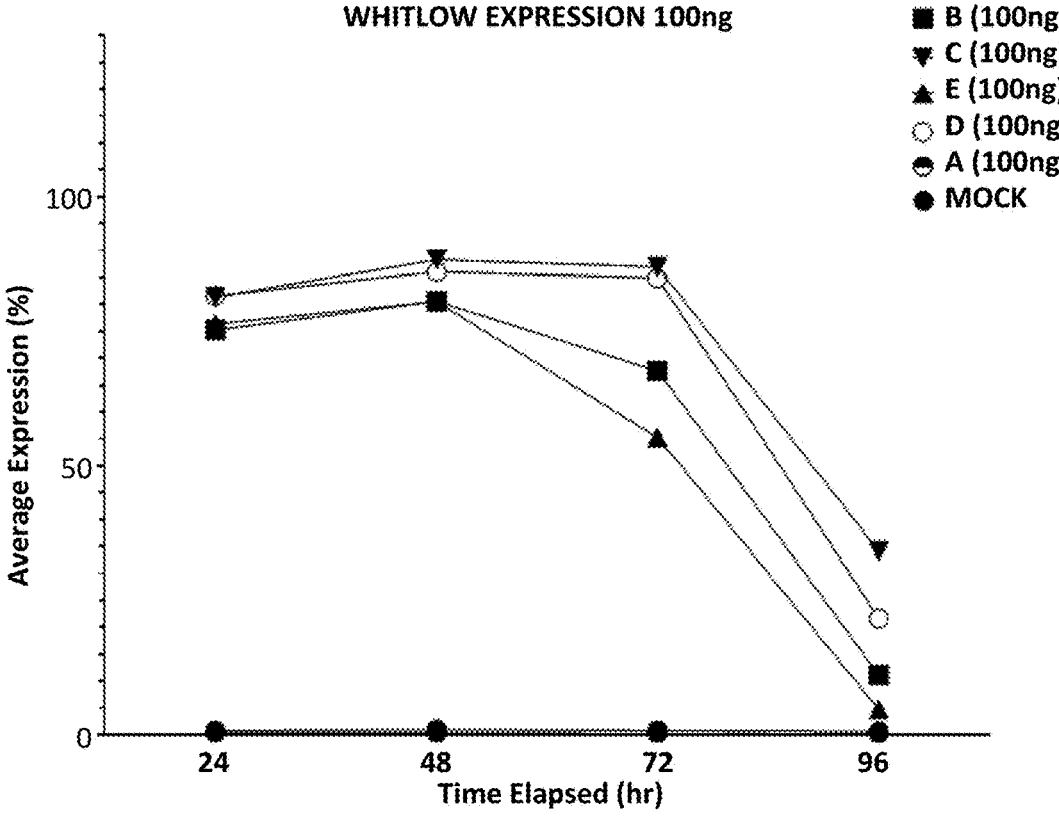
*Fig. 25E (cont.)*

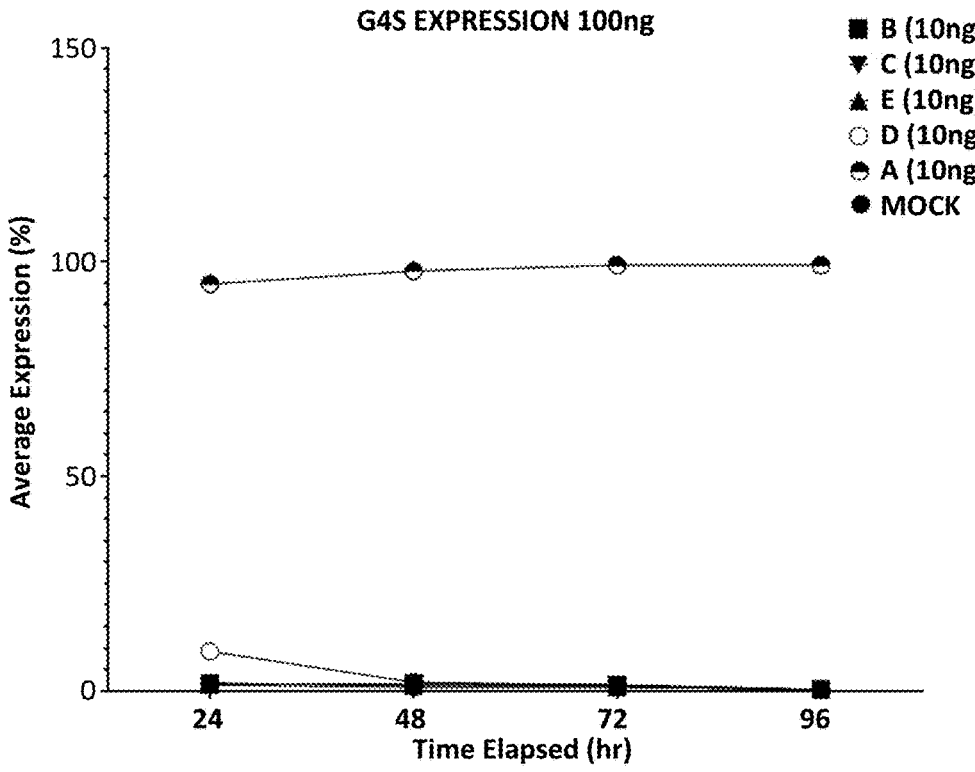
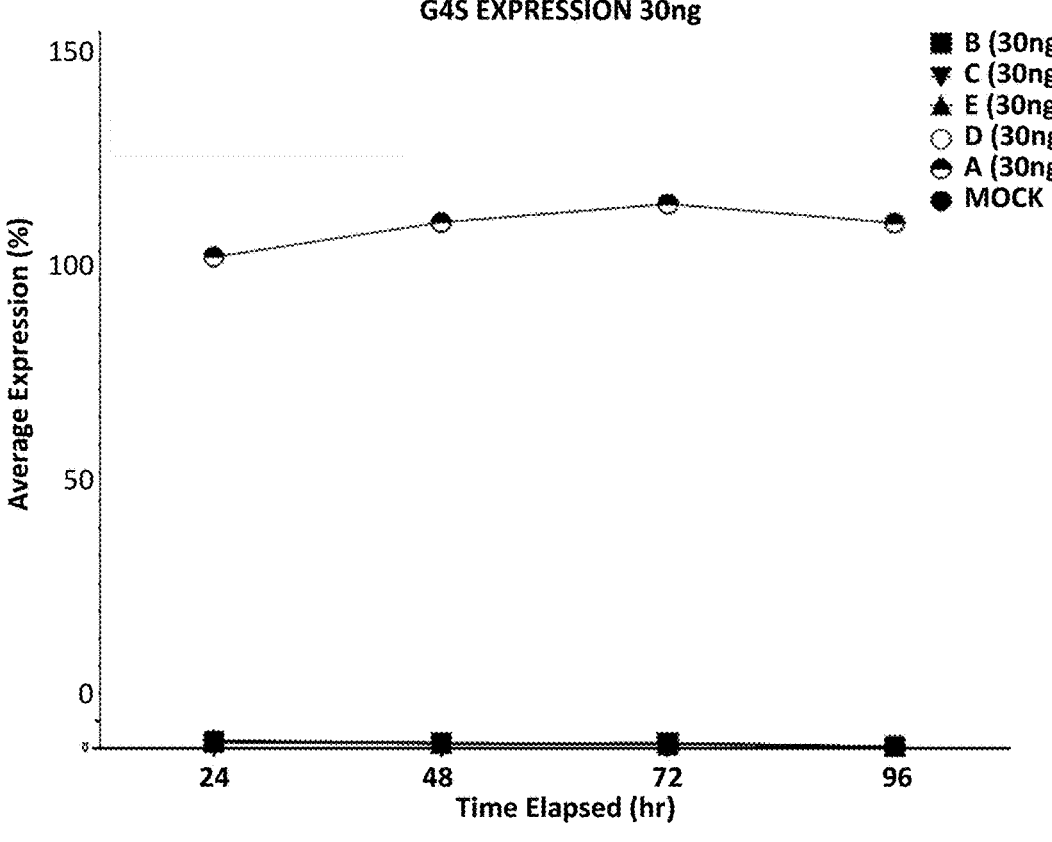
*Fig. 25F*

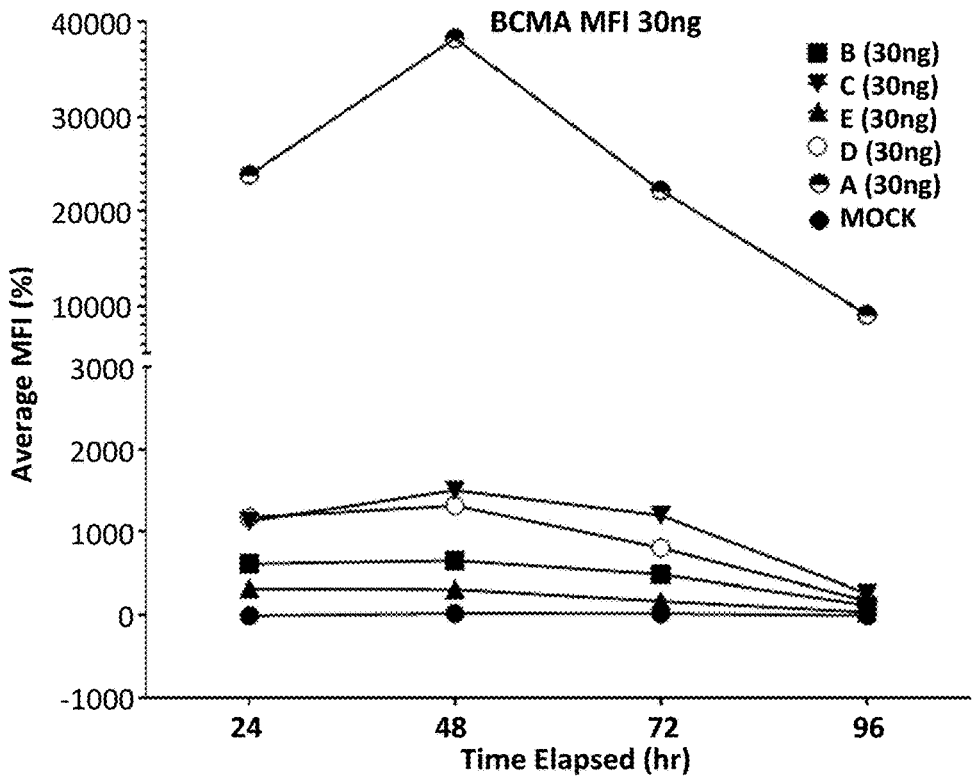
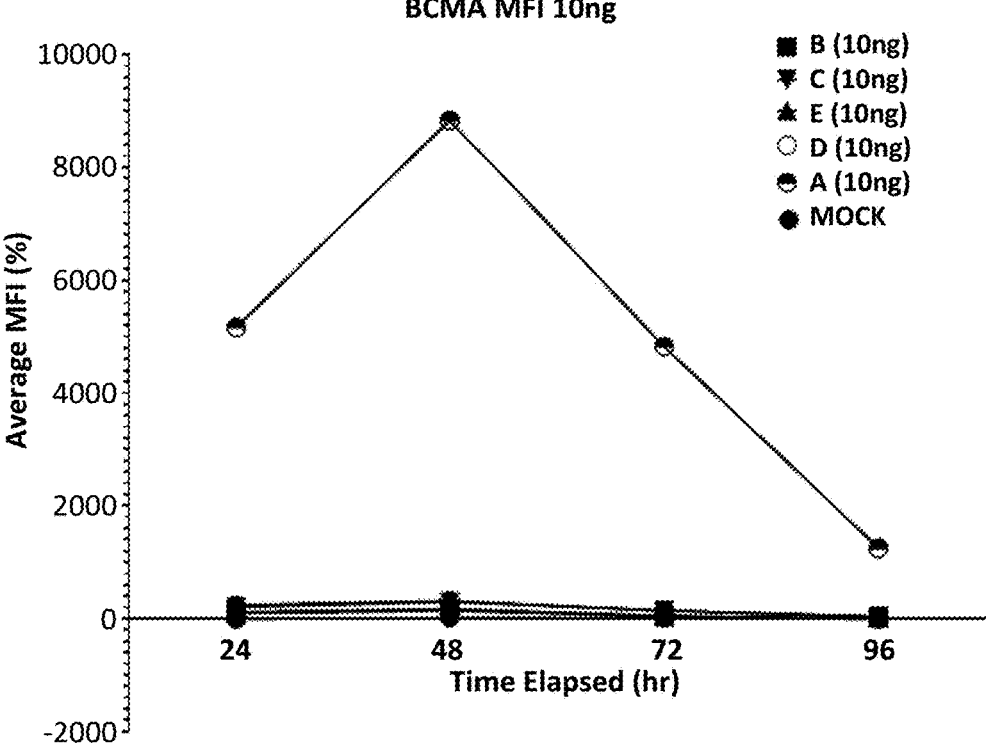
*Fig. 25G (cont.)*

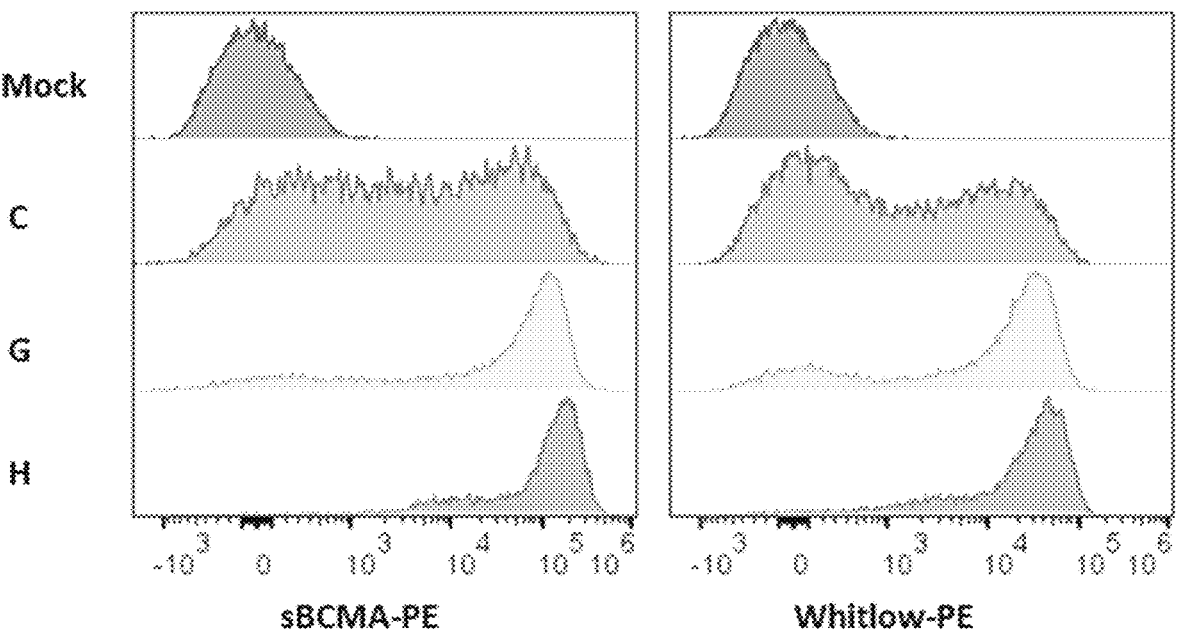
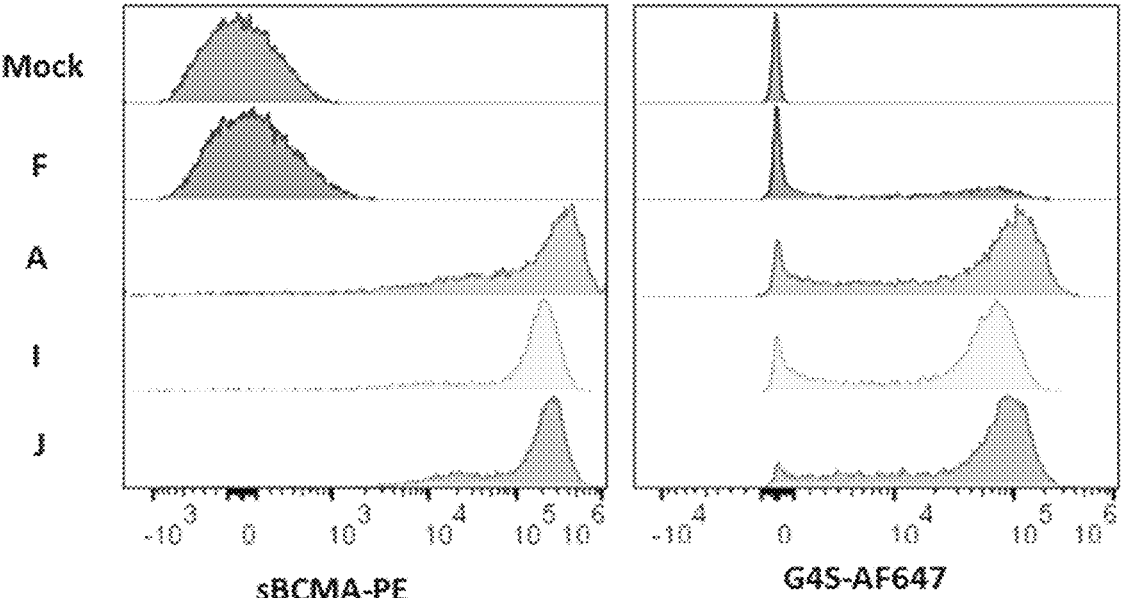
*Fig. 29A* gMFI Whitlow gMFI G4S

% Whitlow

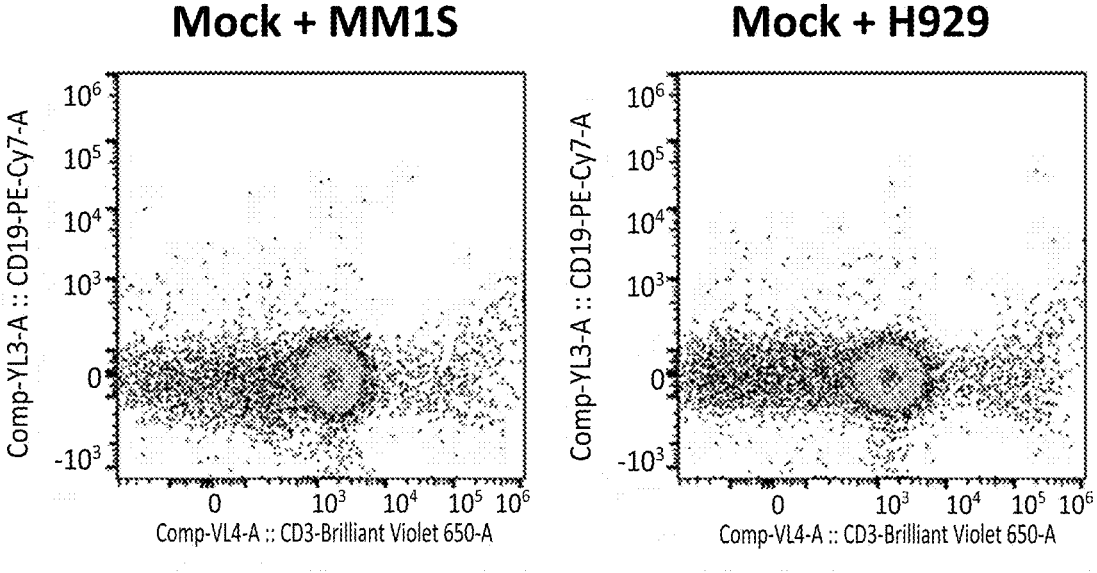
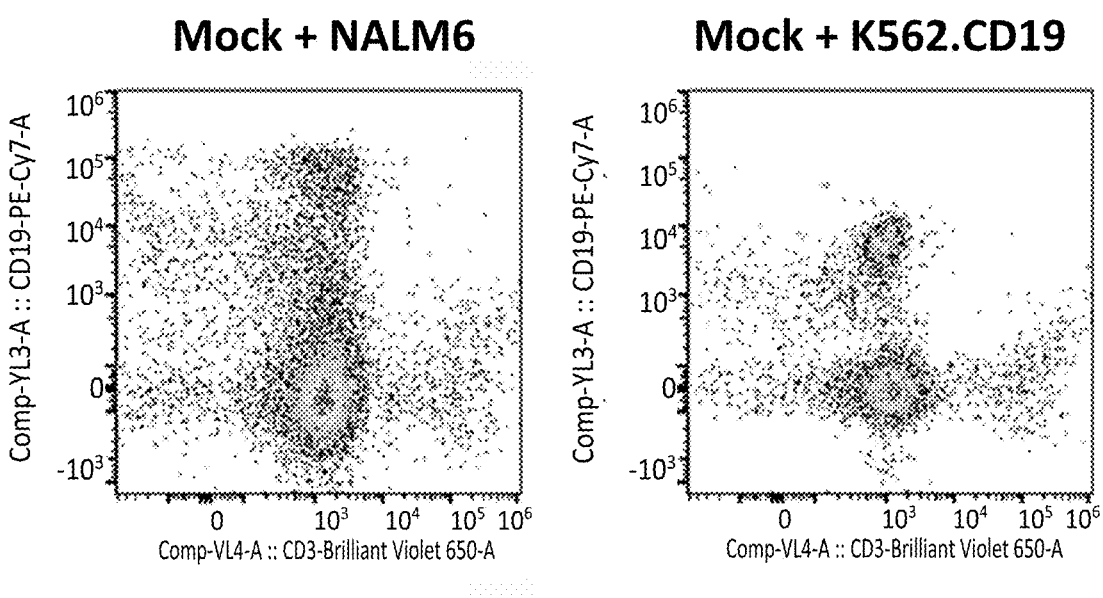
Fig. 35A

Protein L-Biotin/ Streptavidin PE

Mock

K_Fresh

K_Frozen

L_Fresh

L_Frozen

Surface CAR expression :
HER2.28z (K): 80% CAR+
HER2.BBz (L): 76% CAR+

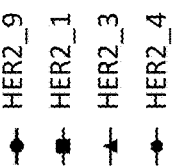
| Time | HER2_9 | | HER2_1 | | HER2_3 | | HER2_4 | |
|---|---|---|---|---|---|---|---|---|
| Hours | % pos | gMFI | % pos | gMFI | % pos | gMFI | % pos | gMFI |
| 24 | 96.7 | 8051 | 97.7 | 5350 | 97.9 | 5066 | 97.2 | 6105 |
| 48 | 98.1 | 7931 | 98.8 | 6927 | 99.0 | 5564 | 98.8 | 8373 |
| 72 | 99.3 | 2214 | 99.3 | 1621 | 99.3 | 1328 | 99.5 | 1989 |
*Fig. 43B*
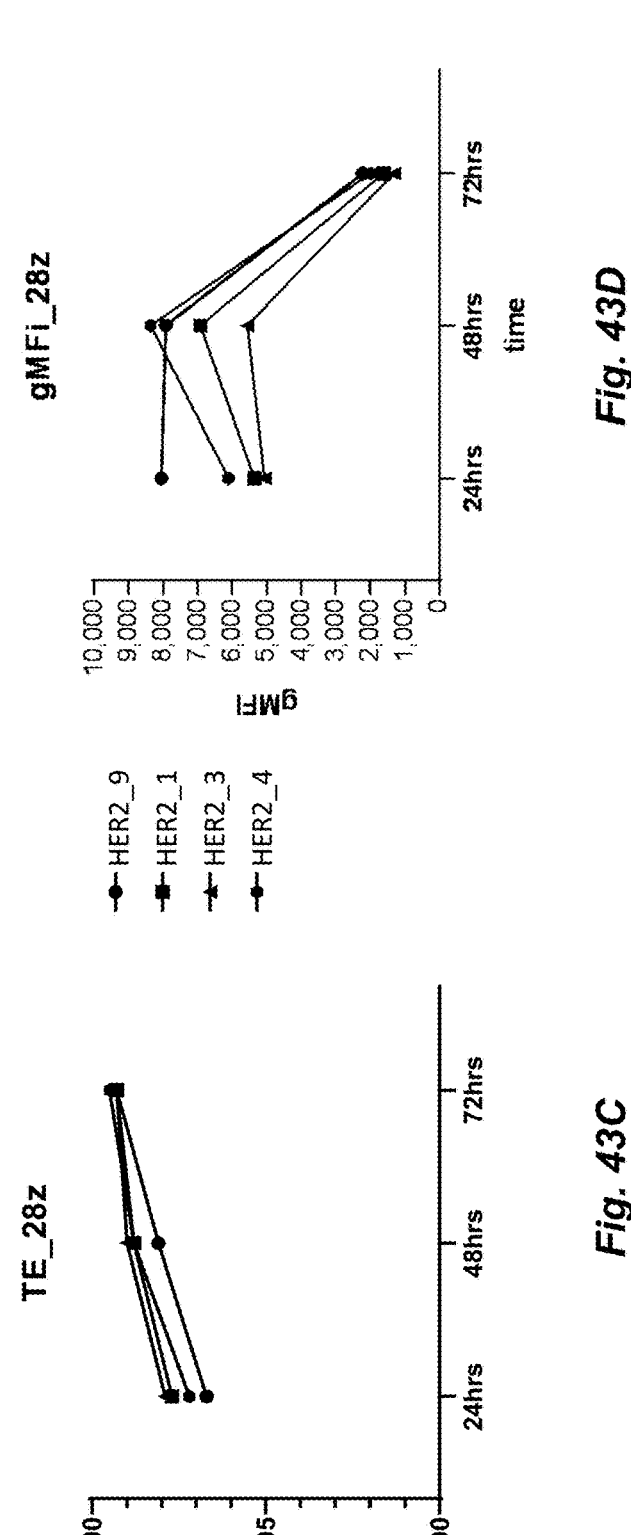
*Fig. 43C*
*Fig. 43D*

| Time | HER2_10 | | HER2_5 | | HER2_7 | | HER2_8 | |
|---|---|---|---|---|---|---|---|---|
| Hours | % pos | gMFI | % pos | gMFI | % pos | gMFI | % pos | gMFI |
| 24 | 96.1 | 6841 | 96.3 | 9147 | 96.2 | 6423 | 94.7 | 8505 |
| 48 | 99.2 | 6880 | 99.3 | 4895 | 99.3 | 8213 | 98.9 | 10309 |
| 72 | 99.3 | 3472 | 99.3 | 3692 | 99.6 | 2993 | 99.1 | 3750 |

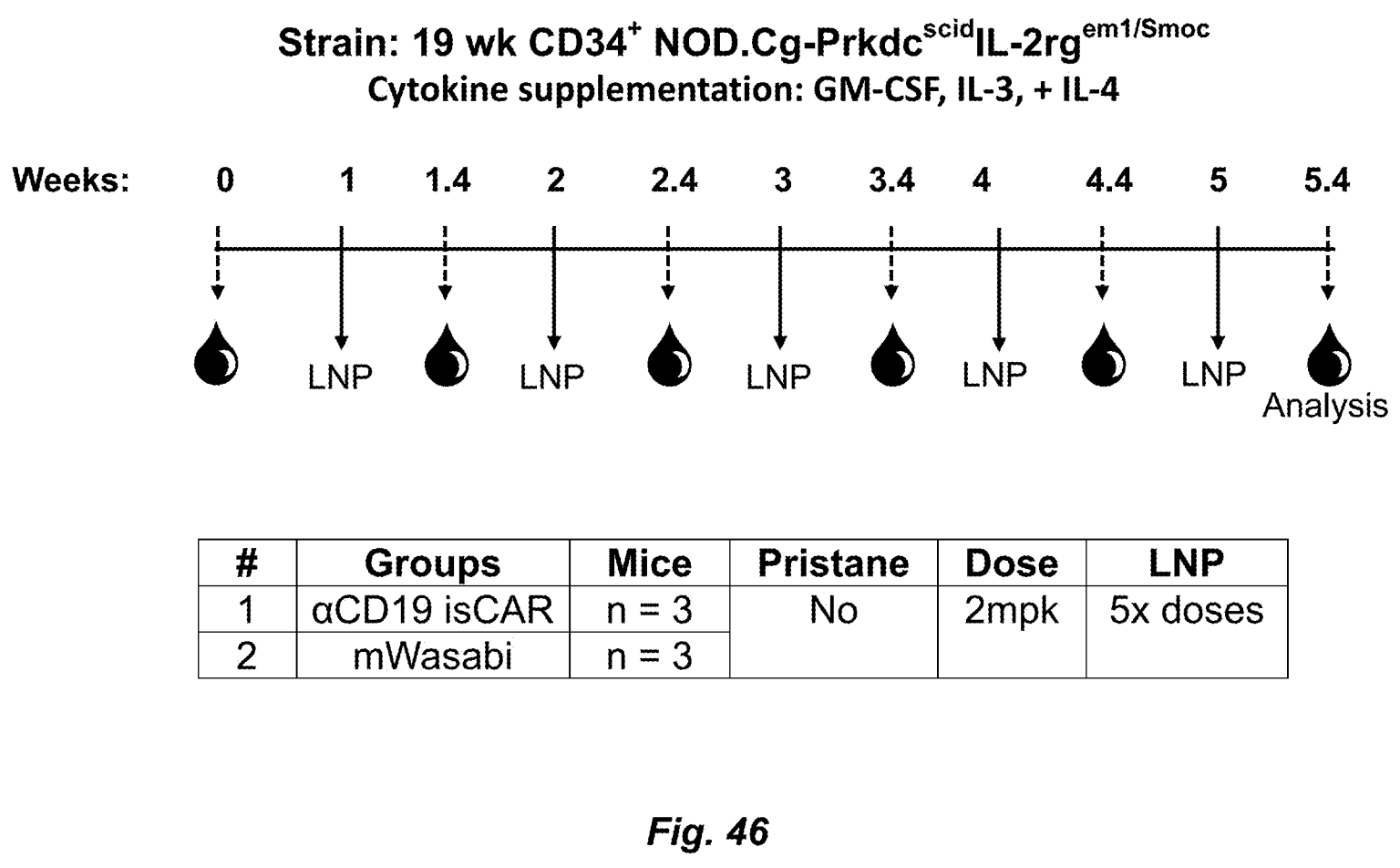

Strain: 19 wk CD34$^+$ NOD.Cg-Prkdc$^{scid}$IL-2rg$^{em1/Smoc}$
Cytokine supplementation: GM-CSF, IL-3, + IL-4

| # | Groups | Mice | Pristane | Dose | LNP |
|---|--------|------|----------|------|-----|
| 1 | αCD19 isCAR | n = 3 | No | 2mpk | 5x doses |
| 2 | mWasabi | n = 3 | | | |

*Fig. 46*

Peripheral Blood Panel

| No. | Fluorochrome | Markers | Company | Clone | Cat# | Lot# | Expiry Date |
|---|---|---|---|---|---|---|---|
| 1 | BUV395 | hCD45 | BD | HI30 | 563792 | 2182170 | 30-Apr-25 |
| 2 | DAPI | Live-Dead | Thermo | - | L34962 | 2339921 | - |
| 3 | BV421 | CD25 | BD | 2A3 | 564033 | 2206936 | 31-May-27 |
| 4 | AF488/FITC | mWasabi | Fluorescent protein signal | | | | |
| 5 | PE | G4S | CS&T | E702V | 38907 | 2 | 31-Jul-25 |
| 6 | BV605 | CD20 | Biolegend | 2H7 | 302334 | B372271 | 5-Jul-25 |
| 7 | BV650 | CD4 | BD | SK3 | 563875 | 2318919 | 31-Mar-24 |
| 8 | APC | CD14 | Biolegend | HCD14 | 325608 | B361508 | 22-Dec-26 |
| 9 | PerCp Cy5.5 | mCD45 | Biolegend | 30-F11 | 103132 | B370638 | 27-May-26 |
| 10 | BUV737 | CD3 | BD | UCHT1 | 612750 | 2329517 | 30-Sep-24 |
| 11 | PE Cy7 | HLADR | Biolegend | L243 | 307615 | B328868 | 31-Jul-24 |
| 12 | APC Cy7 | CD8 | Biolegend | RPA-T8 | 301015 | B391127 | 16-Aug-26 |

Splenocytes Panel

| No. | Fluorochrome | Markers | Company | Clone | Cat# | Lot# | Expiry Date |
|---|---|---|---|---|---|---|---|
| 1 | BUV395 | hCD45 | BD | HI30 | 563792 | 2182170 | 30-Apr-25 |
| 2 | DAPI | Live-Dead | Thermo | - | L34962 | 2339921 | - |
| 3 | BV421 | CD20 | Biolegend | 2H7 | 302330 | B361014 | 29-Sep-24 |
| 4 | BV510 | CD56 | Biolegend | HCD56 | 318340 | B367784 | 27-Apr-25 |
| 5 | AF488/FITC | mWasabi | Fluorescent protein signal | | | | |
| 6 | PE | G4S | CS&T | E702V | 38907 | 2 | 31-Jul-25 |
| 7 | BV605 | CD11c | BD | B-Ly6 | 563929 | 2273626 | 29-Feb-24 |
| 8 | BV650 | HLA-DR | Biolegend | L243 | 307649 | B375357 | 2-May-25 |
| 9 | APC | CD4 | Biolegend | OKT4 | 317415 | B323079 | 7-Jul-25 |
| 10 | PerCp Cy5.5 | mCD45 | Biolegend | 30-F11 | 103132 | B370638 | 27-May-26 |
| 11 | BV711 | CD14 | Biolegend | M5E2 | 301838 | B355789 | 10-Dec-24 |
| 12 | BUV737 | CD3 | BD | UCHT1 | 612750 | 2329517 | 30-Sep-24 |
| 13 | PE Cy7 | CD123 | BD | 7G3 | 560826 | 3031826 | 31-Dec-24 |
| 14 | APC Cy7 | CD8 | Biolegend | RPA-T8 | 301015 | B391127 | 16-Aug-26 |

*Fig. 47*

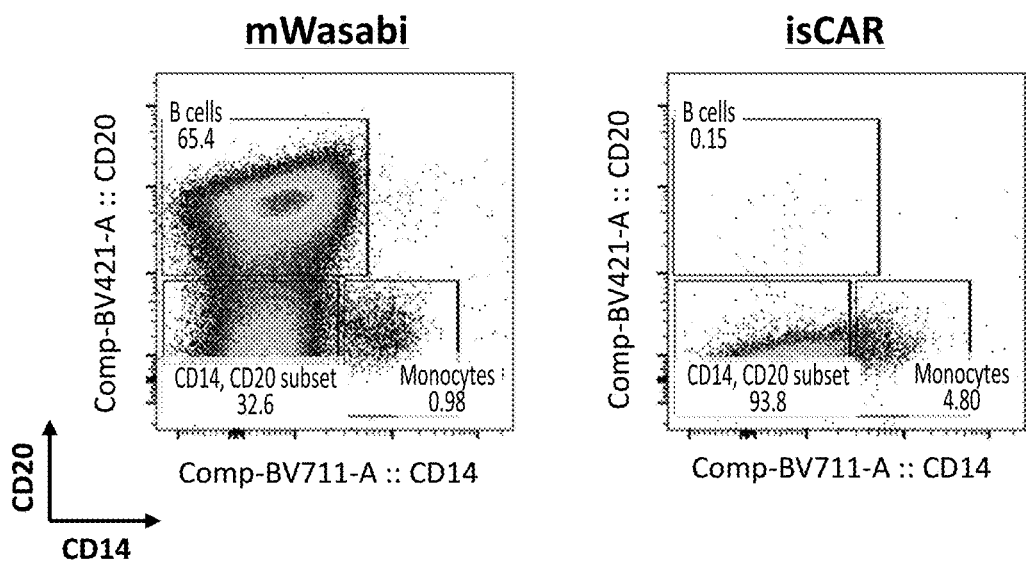
Fig. 49A
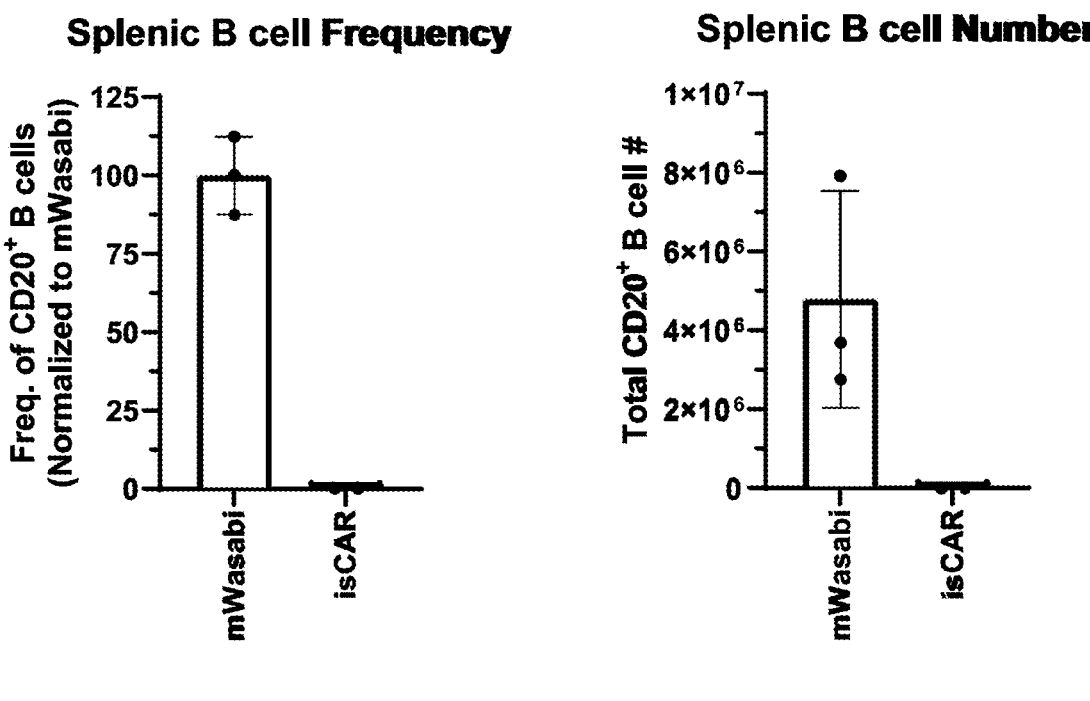
Fig. 49B                    Fig. 49C

| N | NK cell Donor | NK cells | Raji-Luc | TA | Dose | Frequency | Total Doses | TA Admin Route | Analytics |
|---|---|---|---|---|---|---|---|---|---|
| 5 | NA | NA | 0.3M | NA | - | | | | IVIS 2x week |
| 5 | A | 3M | 0.3M | PBS | - | 2x week | 10 | i.v. | IVIS 2x week |
| 5 | A | 3M | 0.3M | CTR - reporter | 1 mg/kg | 2x week | 10 | i.v. | IVIS 2x week |
| 5 | A | 3M | 0.3M | CD19 CAR | 1 mg/kg | 2x week | 10 | i.v. | IVIS 2x week |

| Group | N | Hu Cells | Tumor | TA | oRNA Dose (mg/kg) | Drug Route | Analysis Timepoint Post-Dose | Tissues to analyze |
|---|---|---|---|---|---|---|---|---|
| 1 | 5 | 34+CB | - | NA | NA | i.v. | 24hrs | Flow: Blood, Spleen, BM |
| 2 | 5 | 34+CB | - | LNP-mOX40L | 3 | i.v. | 24hrs | Flow: Blood, Spleen, BM |
| 3 | 5 | 34+CB | - | LNP-mOX40L | 3 | i.v. | 48hrs | Flow: Blood, Spleen, BM |
| 4 | 5 | 34+CB | - | LNP-mOX40L | 3 | i.v. | 72hrs | Flow: Blood, Spleen, BM |
| 5 | 5 | 34+CB | 0.3M Raji | - | - | - | IVIS 2x weekly | - |

24 hr    48 hr    72 hr

~10 wks post engraft CD34+ cells

Harvest group 1+2    Harvest group 3    Harvest group 4 bone marrow bone marrow bone marrow
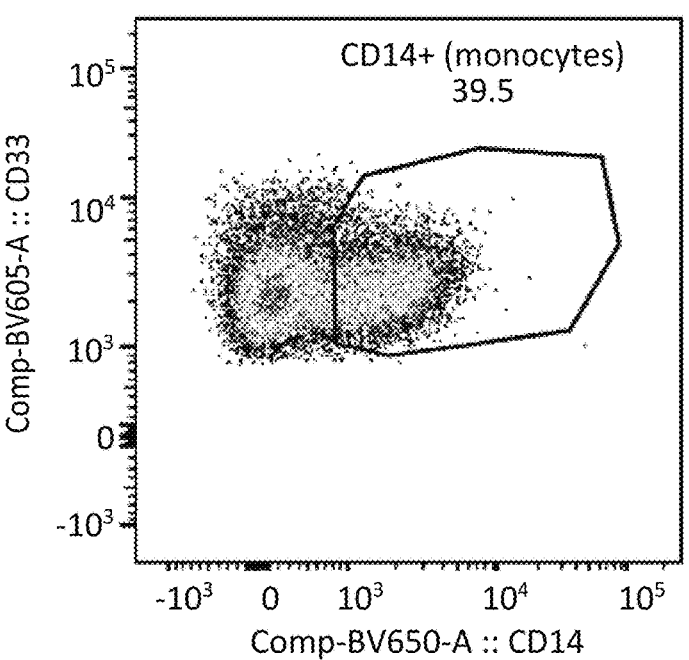
*Fig. 55A*
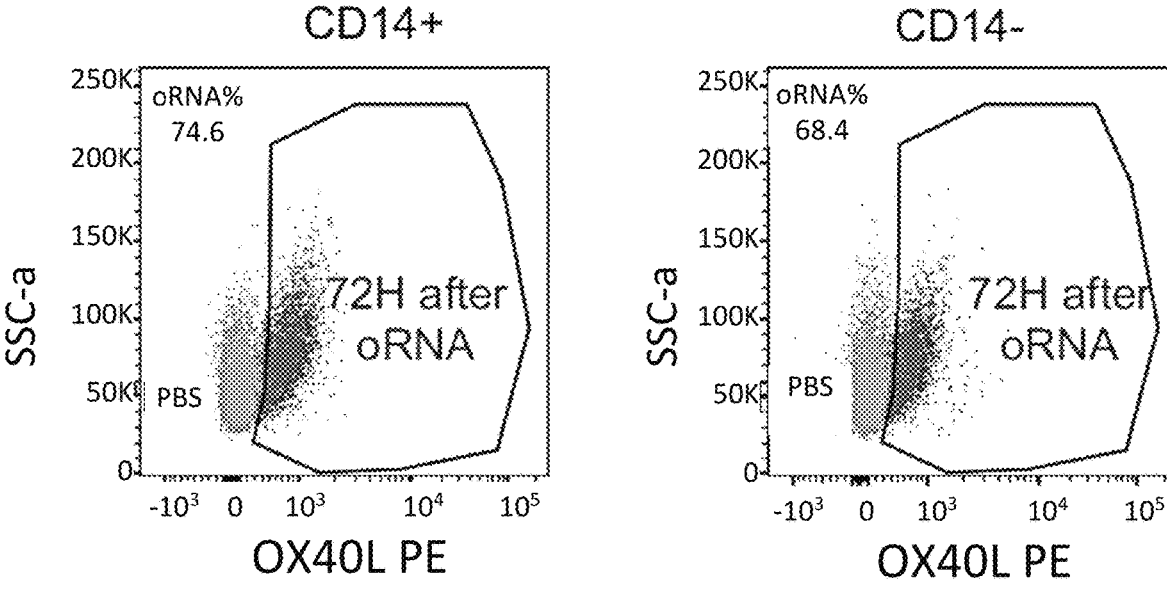
*Fig. 55B*                                                            *Fig. 55C* bone marrow

CD14+

CD14- bone marrow
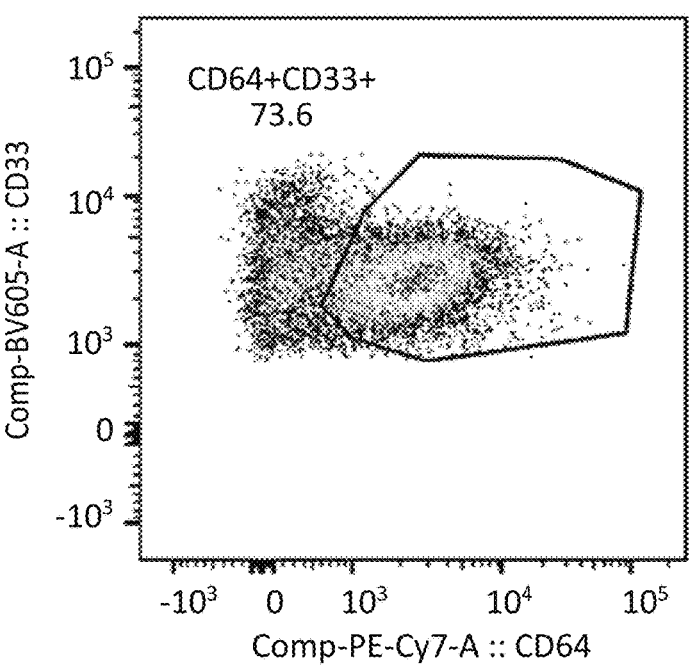
*Fig. 56A*
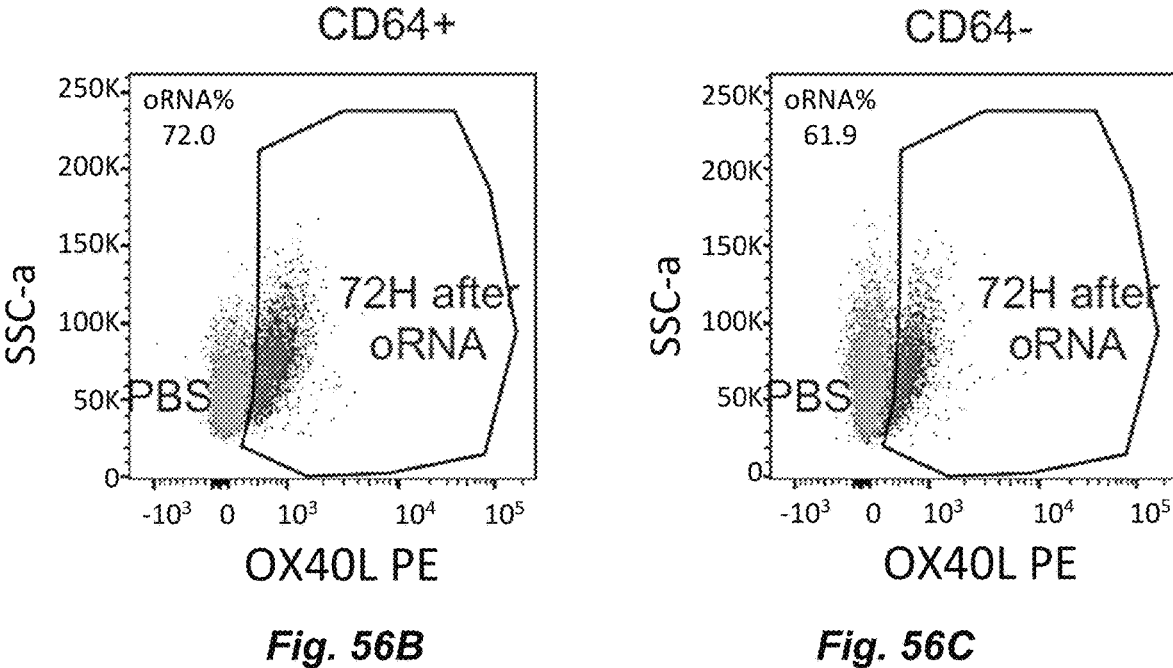
*Fig. 56B*                  *Fig. 56C* bone marrow
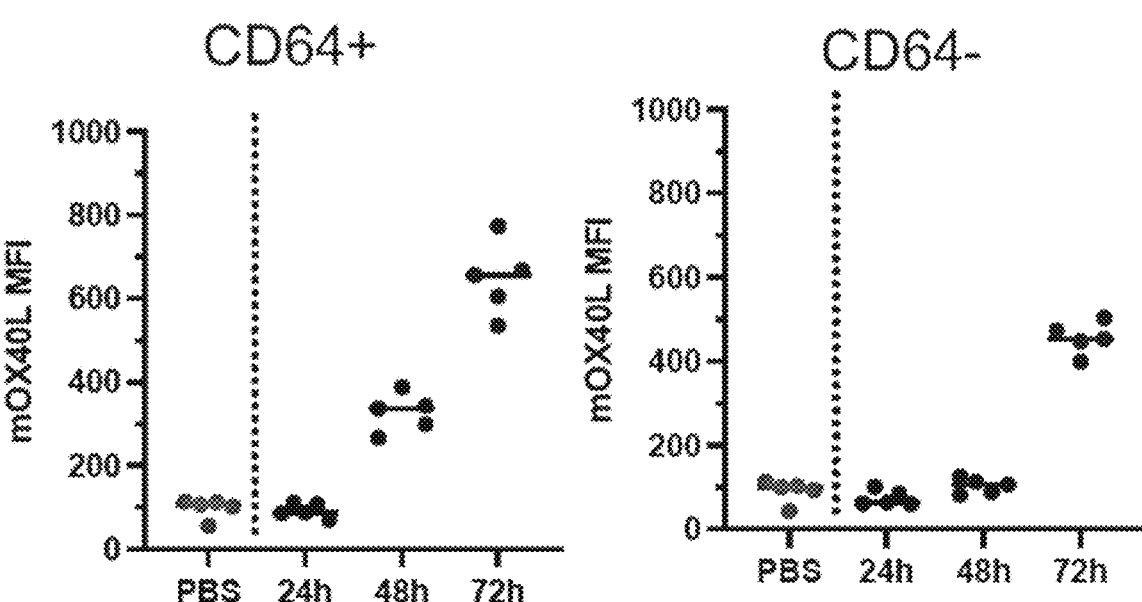
*Fig. 56D*                      *Fig. 56E*
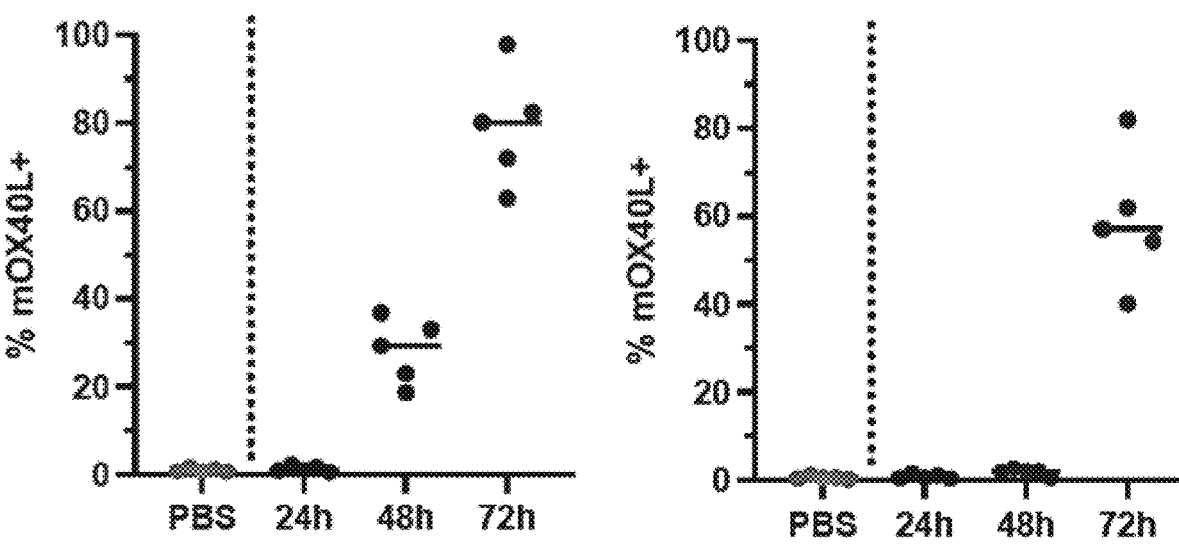
*Fig. 56F*                      *Fig. 56G* spleen spleen spleen spleen
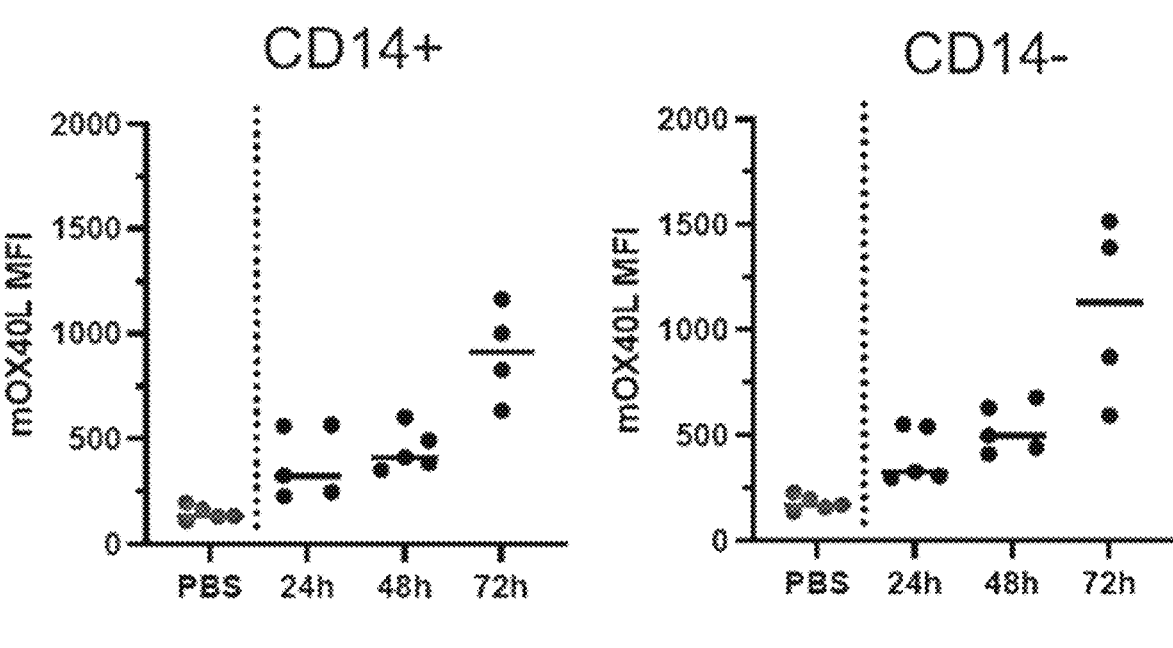
Fig. 58D                 Fig. 58E
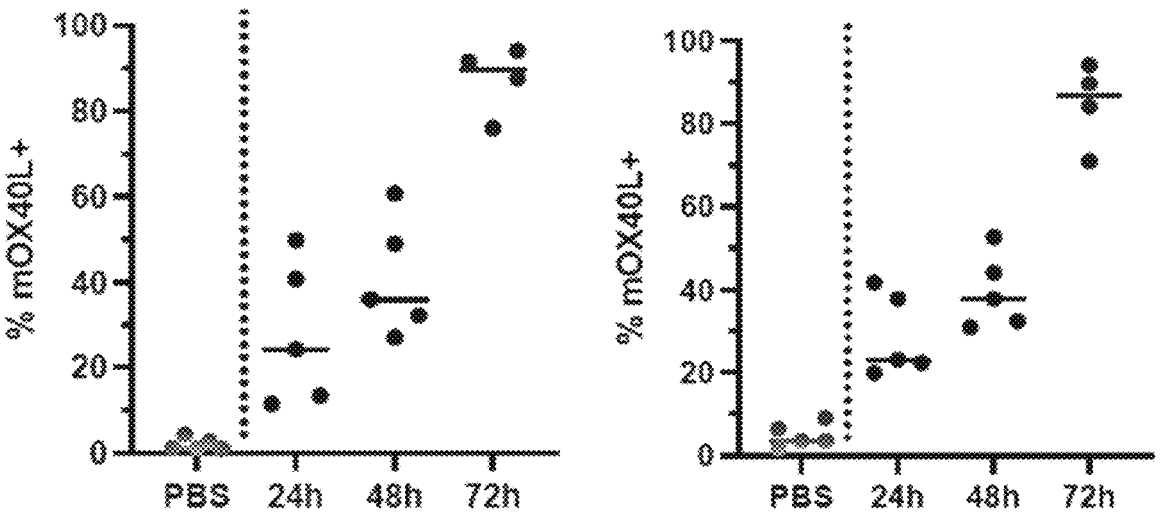
Fig. 58F                 Fig. 58G spleen

CD64+

CD64- spleen
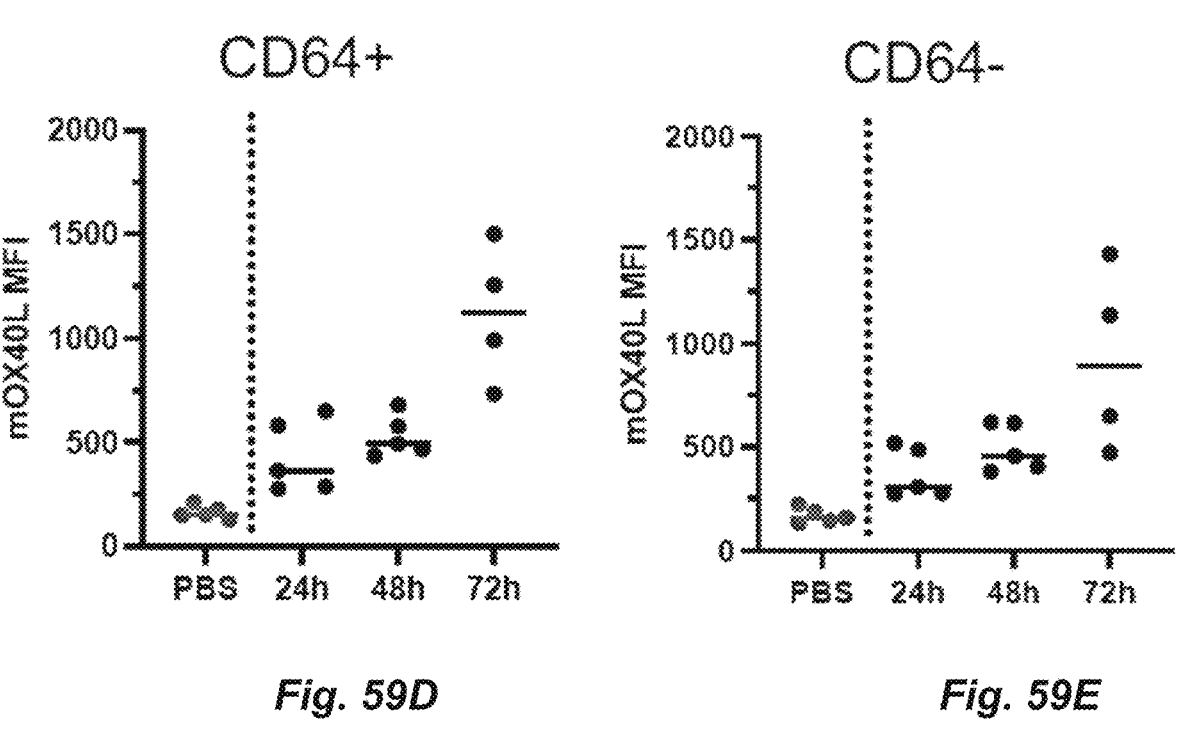
Fig. 59D
Fig. 59E
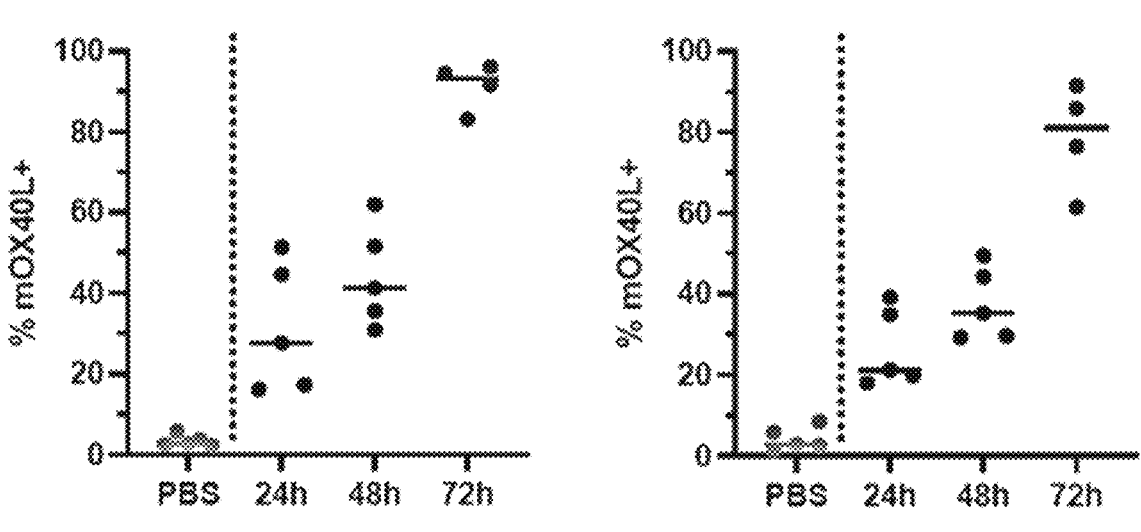
Fig. 59F
Fig. 59G

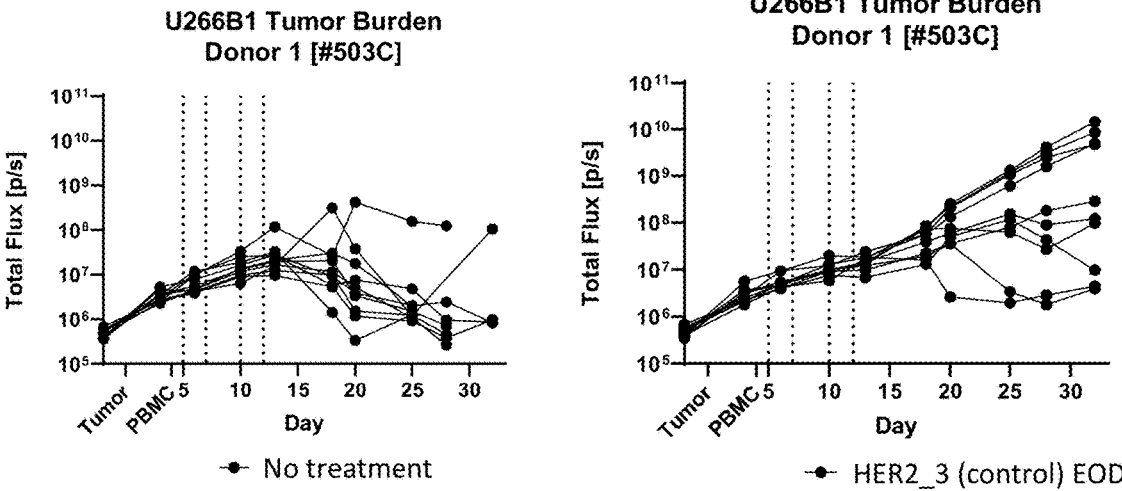
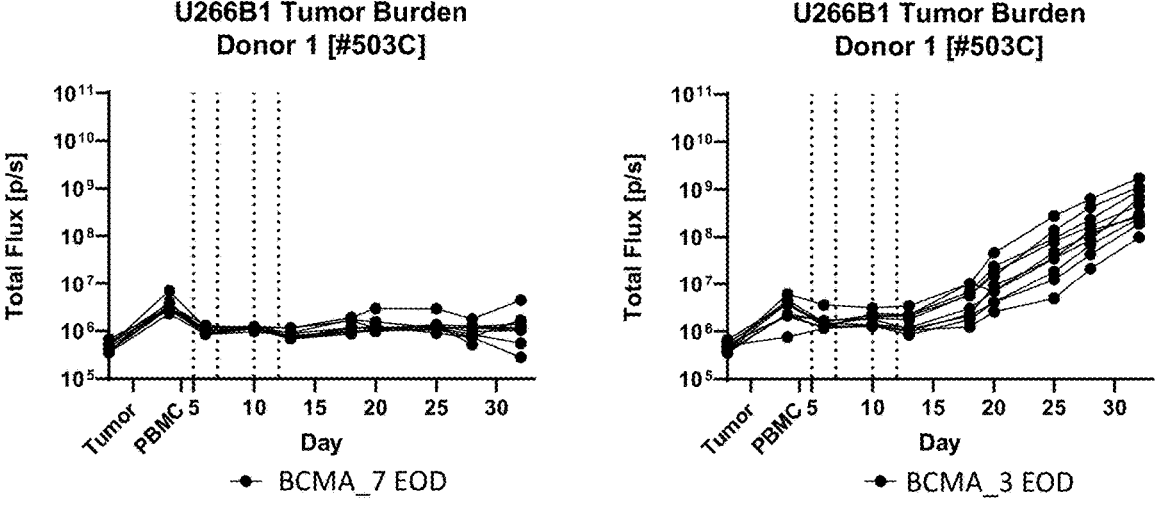
*Fig. 60A*

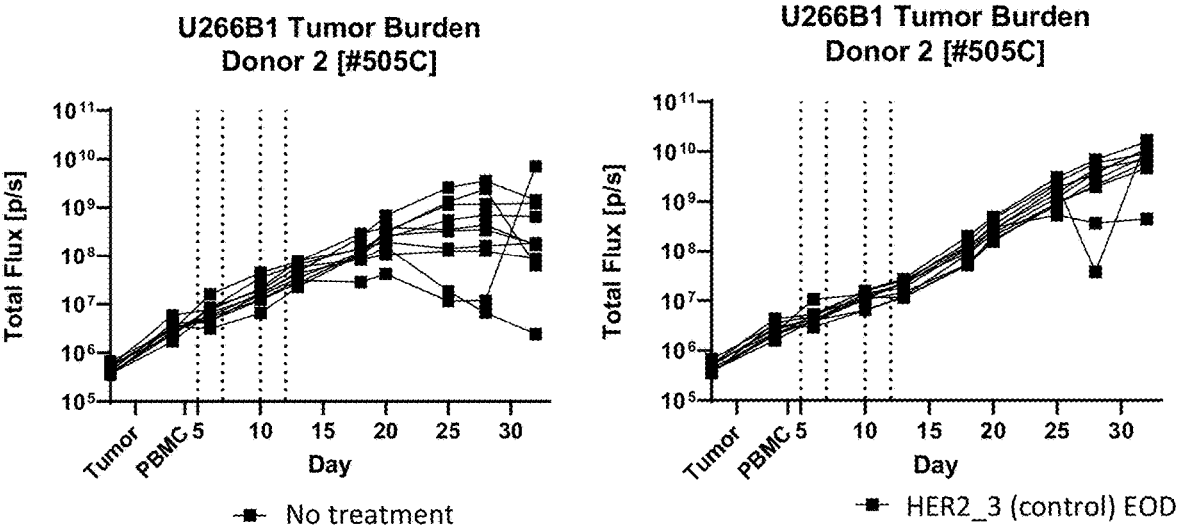
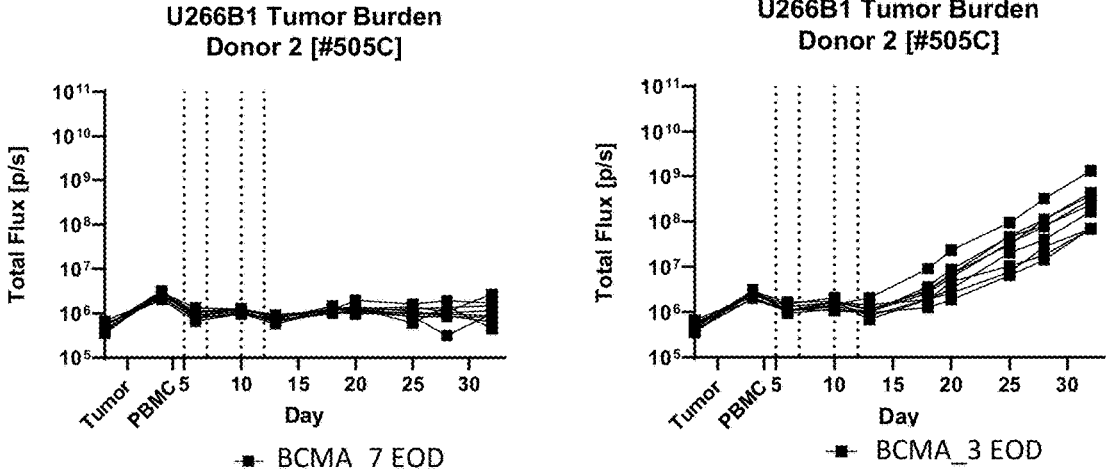
*Fig. 60B*

SEQUENCE LISTING

```
Sequence total quantity: 213
SEQ ID NO: 1              moltype = DNA  length = 747
FEATURE                   Location/Qualifiers
source                    1..747
                          mol_type = other DNA
                          organism = synthetic construct
SEQUENCE: 1
ttaaaacagc tctggggttg ttcccacccc agaggcccac gtggcggcca gtactccggt   60
attacggtac ccttgtacgc ctgtttttata ctcccttccc ctgtaactta gaagcataca  120
aaccaagttc aatagaaggg ggtacaaacc agtaccacca cgaacaagca ctcctgtttc  180
cccggtgaca ttgcatagac tgtacccacg gttgaaagcg atcgatccgt tacccgctcc  240
tgtacttcga gaagcctagt atcatcttgg aatcttcgat gcgttgcgct cagcactcaa  300
ccccagagtg tagcttaggc tgatgagtct ggacgtcccc caccggcgac ggtggtccag  360
gctgcgttgg cggcctacct gtggcccaaa gccacaggac gctagttgtg aacaaggtgt  420
gaagagccta ttgagctaca agagagtcct ccggcccctg aatgcggcta atcctaacca  480
cggagcaggc agttgcaaac cagcaaccgg cctgtcgtaa cgcgcaagtc tgtggcggaa  540
ccgactactt tgggtgtccg tgtttccttt tattttaca atggctgctt atggtgacaa  600
tcatagattg ttatcataaa gcgacttgga ttggccatcc ggtgaaagta aaacacattg  660
tttacttgtt tgttggattc actccaatta acacttttac ttacaaactc attacaacaa  720
ctctattaat tagagataag catcaca                                       747

SEQ ID NO: 2              moltype = DNA  length = 612
FEATURE                   Location/Qualifiers
source                    1..612
                          mol_type = other DNA
                          organism = synthetic construct
SEQUENCE: 2
tttcccctgt tcgtaactaa gtgtgtgccc aatctcctca ctcctgctgg cttcaccgac   60
cggcagtgtc caaaatgcta ggtgaatccc ctcccttttcc tctgggcttc tgcccagctt  120
cctcccccca gcctgacgtg acacaggctg tgcaaagacc ccgcgaaagc tgccaaaagt  180
ggcaattgtg ggtcccccct ttgtaaaggc gtcgagtctt tctccctcaa ggctagaccc  240
gtcagtgaat tctgtcgggc aactagtgac gccactgcac gcctctgacc tcggccgcgg  300
agtgctgccc cccaagtcgt gcccctgacc acaagttgtg ctgtctggca aacattgtct  360
gtgagaatgt tccgctgtgg ctgccaagcc tggcaacagg ctgccccagt gtgcgtagtt  420
ctcatccaga cttcggtctg gcaacttgct gttaagacac ggcgtaaggg gcgtgtgcca  480
acgccctgga acgagtgtcc actctaatac cccgaggaat gctacgcagg tacccctggt  540
tcgccaggga tctgagcgta ggctaattgt ctaagggtat tttcatttcc cattctttct  600
ttcttgttca ta                                                       612

SEQ ID NO: 3              moltype = DNA  length = 439
FEATURE                   Location/Qualifiers
source                    1..439
                          mol_type = other DNA
                          organism = synthetic construct
SEQUENCE: 3
tccccggcat gagaggaata gactctttca gggttgaagc cacgagtgtc gttacccgca   60
ctggtactac gcaaagccta gtaacatctt gaaactcttt ttggttggtc gttccactag  120
ttacccccta gtagacctgg cagatgaggc aggacgctcc ccactggcga cagtggtcct  180
gcctgcgtgg ctgcctgcac acccttcggg gtgtgaagcc aaaagaaaga caaggtgtga  240
agagccccgt gtgctaccag tgaatcctcc ggcccctgaa tgcggctaat cttaccccac  300
agctattgca cacaatccag tgtgtatgta gtcgtaatga gcaattgtgg gacggaaccg  360
actactttgg gtgtccgtgt ttccttttat tcccatgttt ctgcttatgg tgacaatact  420
gacgtatagt gttgttacc                                                439

SEQ ID NO: 4              moltype = DNA  length = 627
FEATURE                   Location/Qualifiers
source                    1..627
                          mol_type = other DNA
                          organism = synthetic construct
SEQUENCE: 4
ttaaaacagc ggatgggtat cccaccatcc ggcccactgg gtgtagtact ctggtacatt   60
gtacctttgt acgcctgttt tccccctctt gtacccgccc ttcaagctcc ttgcccaagt  120
aacgttagaa gtttgaacat tggtacaata ggaagcatca catccagtgg tgtactgtac  180
```

```
aaacacttct gttgccccgg agcgaggtat agatggtccc caccgtcaaa agcctttaac  240
cgttatccgc caatcaacta cgtaatggct agtagcacct tggatttaag ttggcgttcg  300
atcaggtggt aaccccact  agtttggtcg atgaggctag gaattccca  cgggtgaccg  360
tgtcctagcc tgcgtggcgg ccaacccagc atccgctggg acgccaattt aatgacatgt  420
tgtgaagacc tgcatgtgct tgattgtgag tcctccggcc cctgaatgcg gctaaccta  480
accccggagc cttgcagcac aatccagtgt tgttaaggtc gtaatgagca attctgggat  540
gggaccgact actttgggtg tccgtgtttc ttattttct  tgaatttttc ttatggtcac  600
agcatatata cattatatac tgtgatc                                     627
```

SEQ ID NO: 5          moltype = DNA   length = 737
FEATURE                Location/Qualifiers
source                 1..737
                        mol_type = other DNA
                        organism = synthetic construct
SEQUENCE: 5

```
ttaaaatagc ctcagggttg ttcccaccct gagggcccac gtggtgtagt actctggtat  60
tacggtacct ttgtacgcct attttatacc cccttcccca agtaatttag aagcaagcac  120
aaaccagttc agtagtaagc agtacaatcc agtactgtaa tgaacaagta cttctgttac  180
cccggaaggg tctatcggta agctgtaccc acggctgaag aatgacctac cgttaaccgg  240
ctacctactt cgagaagcct agtaatgccg ttgaagtttt attgacgtta cgctcagcac  300
actacccgt  gtgtagtttt ggctgatgag tcacggcact ccccacgggc gaccgtggcc  360
gtggctgcgt tggcggccaa ccaaggagtg caagctcctt gcctgtcata ttacagacat  420
ggtgtgaaga gcctattgag ctaggtggta gtcctccggc ccctgaatgc ggctaatcct  480
aactccggag catatcggtg cgaaccagca cttggtgtgt tgtaatacgt aagtctggag  540
cggaaccgac tactttgggt gtccgtgttt cctgtttaa  cttttatggc tgcttatggt  600
gacaatttaa cattgttacc atatagctgt tgggttggcc atccggattt tgttataaaa  660
ccatttcctc gtgccttgac ctttaacaca tttgtgaact tctttaaatc cctttttatta  720
gtccttaaat actaaga                                               737
```

SEQ ID NO: 6          moltype = DNA   length = 821
FEATURE                Location/Qualifiers
source                 1..821
                        mol_type = other DNA
                        organism = synthetic construct
SEQUENCE: 6

```
ttcaaacagc ctgggggttg tacccacccc tggggcccac gtggcgctag tactctggta  60
cgttagtacc tttgtacgcc tgtttttccc tcccttaaac aaattaagat taccactact  120
gaggggagta gtccgactcc gctccggtac tgccgcacca gtactccggt acacttagta  180
ccctagtacg gagtagatgg tatccccacc cgcaactta  gaagcatgca aacaaaccga  240
ccaataggcg cacgatatcc agtcgtgttt cggtcaagca cttctgtctc cccggtccga  300
aaggatcgtt acccgcccga cccactacga gaagcccagt aactggcaa  gtgattgcga  360
agttgcgctc agcacaacc  ccagtggtag ctctggaaga tggggctcgc gtctcccccg  420
tggtgacacg gtcgcttgcc cgcgtgtgct tccgggttcg gcctacgccg ttcacttcaa  480
tgtcacgtaa ccagccaaga gcctattgtg ctgggacggt tttcctccgg ggccgtgaat  540
gctgctaatc ccaacctccg agcgtgtgcg cacaacccag tgttgctacg tcgtaatgcg  600
taagttggag gcggaacaga ctactttcgg taccccgtgt ttcctttaaa ttttattcat  660
tattttatgg tgacaattgc tgagatctgc gaattagcga ctctgccgtt gaatattgct  720
ctgtactatt tggttgcatt ccacaaaacc tctgacatcc ccagtacata cattacttta  780
cttgtttacc tcaatctaaa gcacaagcta gataatacaa a                     821
```

SEQ ID NO: 7          moltype = DNA   length = 822
FEATURE                Location/Qualifiers
source                 1..822
                        mol_type = other DNA
                        organism = synthetic construct
SEQUENCE: 7

```
tttaaacagc ctgggggttg ttcccacccc tggggcccac gtggcgctag tactctggta  60
cgctagtacc tttgtacgcc tgtttttccc ctcccttaaa taaatcaagg ttgccactac  120
tgaggggagt agtccgactc cgctccagca atgctgacca agtgcactgg tacgctagta  180
cctttcacg  gagtagatgg tatccccttac cccggaacct agaagattgc acacaaaccg  240
accaataggc gcaccgcatc cagccgtgca gcggtcaagc acttctgtct ccccggtctg  300
taaagatcgt tatccgcccg acccactacg aaaagcctag taactggcca agtgaacgcg  360
aagttgcgct ccgccacaac cccagtggta gctctggaag atggggctcg caccaccccc  420
gtggtaacac ggttgcctgc ccgcgtgtgc ttccgggttc ggcctccgtg cgttcacttc  480
aacttcacgc aaccagccaa gagcctattg tgctggacg  gtttttcctcc ggggccgtga  540
atgctgctaa tcccaacctc cgagcgtgtg cgcacaatcc agtgttgcta cgtcgtaacg  600
cgtaagttgg aggcggaaca gactactttc ggtaccccgt gtttcctctc attttattta  660
atattttatg gtgacaattg ttgagatttg cgctcttgca acgttgccat tgaatattgg  720
cttatactat ttggttgcct tttacaaaac ctctgatata cccagttctt acattgatct  780
gcttgttttt ctcaatttga agtatagact acaaatagca aa                    822
```

SEQ ID NO: 8          moltype = DNA   length = 830
FEATURE                Location/Qualifiers
source                 1..830
                        mol_type = other DNA
                        organism = synthetic construct
SEQUENCE: 8

```
ccccctccc  ccccttccct tccctttgca acgcaacaat tgtaagtgcc ctcacctgtc  60
aattgggacc accactttca gtgaccccat gcgaagtgct gagagaaagg aagctttctt  120
```

```
accccttcatt tgtgaaccca ctggtctaag ccgcttggaa tacgatgagt ggaaaagttc   180
attcttaatg gagtgaaaca tgcttaaatt tccagctcgt gctggtcttt ccagtacggg   240
gcggccctgt ctggccgtaa ttcttcagag tgtcacgcca cacttgtgga tctcacgtgc   300
cacatgacag cgctacagct ggaactgggt gcttggtgcc catggagtaa cagcgaaaag   360
tgttagatca agccttgctt gggctatgag cctgcggaac aacaactggt aacagttgcc   420
tcaggggccg aaagccacgg tgttaacagc accctcatag tttgatccac ctcagggtgg   480
tgatgtttag cagttagtag ttgccaatct gtgttcactg aaatctcggc ataccgtgta   540
gtgtacaggg gtgaaggatg cccagaaggt acccgtaggt aaccttaaga gactatggat   600
ctgatctggg gccttgtccg gagtgcttta cacacggctc aaggttaaaa aacgtctagc   660
cccacagagc ccgagggatt cgggtttcc  ctttaaaaac ccgactagag cttatggtga   720
caattattgc tgttcagacg aacagtgtaa ttgttgtcta ttcacagcag ttctatcaga   780
gctttttccca caacggatct tcttggcaag caaatacagc aggagtcaat              830
```

SEQ ID NO: 9              moltype = DNA   length = 1000
FEATURE                   Location/Qualifiers
source                    1..1000
                          mol_type = other DNA
                          organism = synthetic construct
SEQUENCE: 9

```
cactacgtta cggttcccgc ccgggacaac tggtacccca ttaggctaca acatggctga   60
aaagggtatt gggtccccc  ggattgtgtc cgttcgtagt gtgtgtaacg tggtttacca   120
tctccactaa cattggacta agcatttcat cttttcctcc cgattgtgta ctcacttggc   180
taacgctggg tggtcgcggt tgggtccttg atttactttt tctcgtctaa gcattccgac   240
tgtcctcccc gattatgtgc tcattcagtt aactgctggg tggtcatgac taacatcgag   300
gaaccttctg tccacgctta ctttgagctc cggtcgcttg acgcttgtag ggcgataggg   360
ttatcttcct gacaacatct ttattctacc tccatagct  ctatctatgg agacggagtg   420
tggcacccgt cccttctttg ggagcttcgg tagtgacgcc ctttgtcact ctcgccagcc   480
gaggcatgcc tggtgccagg tagcaaagaa agcatatgtt taaggacttg actgatttag   540
cgcaagagtt tgtagcgatg tccatagtgt ctgcggattc cccacacggc gacgtgtgcc   600
gcggaggcca aaagccacgg tgttcacagc accctatgg  atgcccacag accccagtgg   660
gcactcttgt tgccggactt tcaggaaatt aggcatagg  tcttctcaaa ctcctggcat   720
tggactaggt aagaatgccc cggaggtacc ccagtactcc ttcgggagtc tgggatctga   780
ccggggggccc cacaaacatg ctttacgtgt ttcgtgcggt caaaaattgt ctaactagtc   840
ccaaccttga acaagggatt gttctttcct ttttattact gagactggcc tatggtgaca   900
acagagattg actgtgaata cagttatttt ctggtgttta tcatttggtt tttctccgtg   960
ctcttttacc tttgtggtat ttgttcttta gataggcaaa                          1000
```

SEQ ID NO: 10             moltype = DNA   length = 1000
FEATURE                   Location/Qualifiers
source                    1..1000
                          mol_type = other DNA
                          organism = synthetic construct
SEQUENCE: 10

```
cccggccacc ccctttcgac gcgggtactg cgatagtgcc accccagtct ttcctactcc   60
cgactcccga ctctaaccca ggttccttgg aacaggaaca ccaatatact catcccctgg   120
atgctgacta atcagaggaa cgtcagcatt ttccggccca ggctaagaga agtagataag   180
ttagattcca aattgattta tcatcccctt gacgaattcg cgttggaaat gcacctctca   240
cttgccgctc ttcacaccca ttaacttgat tcggcctctg tgttgagccc cttgttgaag   300
tgcttccctc catcgtgacg tggttggaga tctaagtcaa ccgactccga cgaaactacc   360
atcatgcctc cccgattatg tgatgctttc tgccctgctg ggtggagcat cctcgggttg   420
agaaaacctt cttccttttt ccttggaccc cggtccccg  gtctaagccg cttggaataa   480
gacaggggtta tcttcacctc ttccttcttc tacttcatag tgttctatac tatgaaaggg   540
tatgtgtcgc cccttccttc tttggagaac acgcgcggcg gtctttccgt ctctcgaaaa   600
gcgcgtgtgc gacatgcaga gaaccgtgaa gaaagcagtt tgcggactag ctttagtgcc   660
cacaagaaaa cagctgtagc gaccacacaa aggcagcgga cccccctcc  tggcaacagg   720
agcctctgcg gccaaaagcc acgtggataa gatccacctt tgtgtgcggc acaacccag   780
tgccctggtt tcttggtgac acttcagtga aaacgcaaat ggcgatctga agcgcctctg   840
taggaaagcc aagaatgtcc aggaggtacc ccttccctcg ggaagggatc tgacctggag   900
acacatcaca tgtgctttac acctgtgctt gtgtttaaaa attgtcacag ctttcccaaa   960
ccaagtggtc ttggttttca ctctttaaac tgatttcact                          1000
```

SEQ ID NO: 11             moltype = DNA   length = 1000
FEATURE                   Location/Qualifiers
source                    1..1000
                          mol_type = other DNA
                          organism = synthetic construct
SEQUENCE: 11

```
ccccggtta  cccctttcg  acgcgggtac tgcgatagtg ccacccagt  ctttcctact   60
cccgactccc gaccctaacc caggttcctc ggaacaggaa cacaaattta ctcatcccct   120
ggatgctgac taatcagagg aacgtcagca ttttccggcc caggcttaga gaagtagata   180
agttagaatc taaattgata tgacttcccc ttgacgaatt cacgttggaa atgcacccct   240
cacttgccgc tcttcacacc cactaattga ttcggcctac tgtgttgagc cccttgttga   300
agtgcttccc tccctcgtga cgtggttgga gaaatcttgt cacccgactc cgacgaaact   360
accatcatgc ctccccgatt atgtgtatgct ttctgccctg ctggtgggag tatcctcgga   420
ttgagaaatc cttcttcctt ttaccttgga ccttggtccc ccggtctaag ccgcttggaa   480
taagacaggg ttattttcac ctcttcttct tctacttcat ggtgctctat accatgaaag   540
ggtatgtgtc gcccttcct  tcttggagaa ctcacgcggc ggtcttccgt ctctcaaaaa   600
gcgcgagtgc gacatgcaga gtaacgcgaa gaaagcagtt cctggcctag ctctagtgcc   660
cacaagaaaa cggctgtagc gaccacacaa aggcagcgga actcccctcc tggtaacagg   720
```

-continued

```
agcctctgcg gccaaaagcc acgtggatta gatccacctt tgtgtgcggt gcaaccccag   780
caccccggtt tcttgttgac actctagtga atccttgaat ggcaatctca agcgcctctg   840
taggaaagcc aagaatgtcc aggaggtacc ccttcctcgc ggaagggatc tgacctggag   900
acacatcaca cgtgctttac acttgtgctt gtgtttaaaa attgtcacag ctttcccaaa   960
ccaagtggtc ttggttttcc tttttatcc tactgtcaat                          1000

SEQ ID NO: 12          moltype = DNA   length = 415
FEATURE                Location/Qualifiers
source                 1..415
                       mol_type = other DNA
                       organism = synthetic construct SEQUENCE: 12
tcctcaccca tgcttttcct accccacca cgcccgcatg tttactgctt tccttgatgc   60
tgcccgtgac tacttccatg acctcCccaa cccaaacctc aaacgcctta agctatcatg   120
ggctctctat caccaatccc cttccttccc acccagaacc cccccctccc tcccctacaa   180
cgtgtatgag caagacgagt ttgacaagct cgccgaagcc atgctcaccc actctccctt   240
ccccacatcc cattacctct tccaccccct cccgtccaac gcccgcacca tcgtcgagcg   300
tgaggctgac tgggatggct gtgatctaga aaagaaatgg ctcgacctcg tcatagagga   360
cgatgccaag ttccttctgg agaacggctc tctcccgttt ggctccaccc ttgcc         415

SEQ ID NO: 13          moltype = DNA   length = 659
FEATURE                Location/Qualifiers
source                 1..659
                       mol_type = other DNA
                       organism = synthetic construct SEQUENCE: 13
ttctcgcctg agtcaacaaa gcgagaaacc tgccctcca gcgccagacg agcggcataa   60
aacttgaact tctggcatgc tccaccaccc ttttccccat tccaaccccc attgcgctct   120
caaggtcgcg cttttcgag actagctcgg attcaaaagt tcctggcacc ctttgcccct   180
tcaggcccct aaggtaggaa ctgaccttgt gctgtgccct cggtgcggaa gtgctactgc   240
gtagcgattg taagatccct ttgtggttct gccctggcaa ggttatagag tactgtgatc   300
cgctgcggat gccatcctgg taacaggacc cccagtgtgc gcaacagtat gttcacggtc   360
ttccgtgtcc accacattcg gaacactgct ctcgtgaaac agtgtgtgtc caatccctgc   420
aatcagtatc aactacacca cctaggaatg ctaggaaggt accccggtcc gccgggatct   480
gatcctaggc taattgtcta cggtggtgct cctttttatt ttccacttca attcattggt   540
tacaactgct cgatccctgt gtttgctgcc cttctctgct ctcatcgcca ttctcaagtg   600
ttcacactgt ccaagttcct ttggttgttc gcttccactt gccactgtca actcttgtc    659

SEQ ID NO: 14          moltype = DNA   length = 711
FEATURE                Location/Qualifiers
source                 1..711
                       mol_type = other DNA
                       organism = synthetic construct SEQUENCE: 14
tcaccctctt ttccggtggt ccggacccag accaccgtta ctccattcag cttcttcgga   60
acctgtttgg aggaattaaa cgggcaccca cccaccttca cccccttttc gtaactaagt   120
gtgtgcccaa tctcatgact cctgctgact tcaccgacca gcagtgtcca aaacgctagg   180
tgaatttcct tcctcccct ctgggcttct gcccagctcc ctccctccag cctgacgtgc   240
cacaggctgt gcaaagaccc cgcgaaagct gccaaaagtg gcaattgtgg gtccccctt    300
tgtaaaggcg tcgagtcttt ctcccttaag gctagacccg tcagtgaatt ctgtcgggca   360
actagtgacg ccactgcatg cctccgacct cggccgcgga gtgctgcccc ccaagtcgtg   420
cccctgacta caagttgtgc tgtctcggcaa acattgtctg tgagaatgtt ccgctgtggc   480
tgccaagcct ggtaacaggc tgcccagtg tgcgtagttc tcatccagac ttcggtctgg    540
caacttgctg ttaagacacg gcgtaagggg cgtgtgccaa cgccctggaa cgagtgtcca   600
ctctaatacc ccgaggaatg ctacgcaggt acccctggct ccccagggat ctgagcgtag   660
gctaattgtc taagggtatt ttcatttccc actctttctt tcttgttcat a           711

SEQ ID NO: 15          moltype = DNA   length = 650
FEATURE                Location/Qualifiers
source                 1..650
                       mol_type = other DNA
                       organism = synthetic construct SEQUENCE: 15
tctgtcctca ccccatcttc ccttctttcc tgcaccgtta cgcttactcg catgtgcatt   60
gagtggtgca cgtgcttgaa caaacagcta cactcacatg ggggcgggtt ttcccgccct   120
gcggcctctc gcgaggccca cccctcccct tcctcccata actacagtgc tttggtaggt   180
aagcatcctg atccccgcg gaagctgctc acgtggcaac tgtggggacc cagacaggtt   240
atcaaaggca cccggtcttt ccgccttcag gagtatccct gctagtgaat tctagtaggg   300
ctctgcttgg tgccaacctc cccaaatgc gcgctgcggg agtgctcttc cccaactcac   360
cctagtatcc tctcatgtgt gtgcttggtc agcatatctg agacgatgtt ccgctgtccc   420
agaccagtcc agtaatggac gggccagtgt gcgtagtcgt cttccggctt gtccggcgca   480
tgtttggtga accggtgggg taaggttggt gtgcccaacg cccgtacttt ggtgatacct   540
caagaccacc caggaatgcc agggaggtac cccgcttcac agcgggatct gaccctgggc   600
taattgtcta cggtggttct tcttgcttcc acttcttttct actgttcatg              650

SEQ ID NO: 16          moltype = DNA   length = 625
FEATURE                Location/Qualifiers
source                 1..625
                       mol_type = other DNA
```

-continued

```
                                        organism = synthetic construct
SEQUENCE: 16
attctcgggc tacggccctg gagccactcc ggctcctaaa gatttagaag tttgagcaca    60
cccgcccact agggcccccc atccaggggg gcaacgggca agcacttctg tttccccggt   120
atgatctgat aggctgtaac cacggctgaa acagagatta tcgttatccg cttcactact   180
tcgagaagcc tagtaatgat gggtgaaatt gaatccgttg atccggtgtc tcccccacac   240
cagaaactca tgatgagggt tgccatcccg gctacggcga cgtagcgggc atccctgcgc   300
tggcatgagg cctcttagga ggacggatga tatggatctt gtcgtgaaga gcctattgag   360
ctagtgtcga ctcctccgcc cccgtgaatg cggctaatcc taaccccgga gcaggtgggt   420
ccaatccagg gcctggcctg tcgtaatgcg taagtctggg acggaaccga ctactttcgg   480
gaaggcgtgt ttccatttgt tcattatttg tgtgtttatg gtgacaactc tgggtaaacg   540
ttctattgcg tttattgaga gattcccaac aattgaacaa acgagaacta cctgttttat   600
taaatttaca cagagaagaa ttaca                                          625

SEQ ID NO: 17          moltype = DNA   length = 549
FEATURE                Location/Qualifiers
source                 1..549
                       mol_type = other DNA
                       organism = synthetic construct
SEQUENCE: 17
gtggccacgc ccgggccacc gatacttccc ttcactcctt cgggactgtt ggggaggaac    60
acaacagggc tccctgttt tcccattcct tcccccttt cccaacccca accgccgtat    120
ctggtggcgg caagacacac gggtcttttc ctctaaagca caattgtgtg tgtgtcccag   180
gtcctcctgc gtacggtgcg ggagtgctcc cacccaactg ttgtaagcct gtccaacgcg   240
tcgtcctggc aagactatga cgtcgcatgt tccgctgcgg atgccgaccg ggtaaccggt   300
tccccagtgt gtgtagtgcg atcttccagg tcctcctggt tgcgttgtc cagaaactgc   360
ttcaggtaag tggggtgtgc ccaatcccta caaaggttga ttctttcacc accttaggaa   420
tgctccggag gtaccccagc aacagctggg atctgaccgg aggctaattg tctacgggtg   480
gtgtttcctt tttctttttca cacaactcta ctgctgacaa ctcactgact atccacttgc   540
tctgtcacg                                                           549

SEQ ID NO: 18          moltype = DNA   length = 675
FEATURE                Location/Qualifiers
source                 1..675
                       mol_type = other DNA
                       organism = synthetic construct
SEQUENCE: 18
tttgctcagc gtaacttctc cgggttacgt ggagaccaaa aggctacgga gactcgggct    60
acggccctgg agcacctagg tgctcctaaa gacgttagaa gttgtacaaa ctcgcccaat   120
agggcccccc aaccaggggg gtagcgggca agcacttctg tttccccggt atgatctcat   180
aggctgtacc cacggctgaa agagagatta tcgttacccg cctcactact tcgagaagcc   240
cagtaatggt tcatgaagtt gatctcgttg acccggtgtt tccccacac cagaaacctg   300
tgatgggggt ggtcatcccg gtcatggcga catgacggac ctccccgcgc cggcacaggg   360
cctcttcgga ggacgagtga catggattca accgtgaaga gcctattgag ctagtgttga   420
ttcctccgcc cccgtgaatg cggctaatcc caactccgga gcaggcgggc ccaaaccagg   480
gtctggcctg tcgtaacgcg aaagtctgga gcggaaccga ctactttcgg gaaggcgtgt   540
ttccttttgt tccttttatc aagtttttatg gtgacaactc ctggtagacg tttttattgcg   600
tttattgaga gatttccaac aattgaacag actagaacca cttgttttat caaaccctca   660
cagaataaga taaca                                                    675

SEQ ID NO: 19          moltype = DNA   length = 1446
FEATURE                Location/Qualifiers
source                 1..1446
                       mol_type = other DNA
                       organism = synthetic construct
SEQUENCE: 19
atggcactgc ccgtcaccgc actcctgctc ccactggcac tgctgctcca tgcagctcgc    60
cccgatatcc agatgaccca gaccacctct agcctcagcg cctctctggg tgaccgcgtc   120
accatctctt gccgggccag ccaagacatc tctaagtacc tgaactggta ccagcagaaa   180
cctgacggaa ccgtgaagct gctgatctac cacaccagtc ggctgcattc cggggtgcct   240
tccaggttca gcgggttccgg ctctgggacc gattatagtc tcaccatctc caacctcgag   300
caggaggaca tcgcaaccta cttctgccag caggggaaca ccctgcccta caccttcggt   360
ggcgggacca agctggagat cactggaggt ggtggcagcg gaggtggagg atcaggtgga   420
ggcggtagcg aggtgaagct gcaggagtcc ggacctggcc tggtggcccc aagccagtcc   480
ctcagcgtca cctgcacagt gtccgggggtg tccctgcctg actacggtgt ctcctgatc   540
aggcaaccac cccggaaggg tctcgagtgg ctggcgtca tctgggggctc cgagaccacc   600
tactacaaca gcgctctgaa gtcccggctg accatcatca aagacaactc caagagccag   660
gtgttcttga agatgaactc cctgcaaacc gatgacaccg ccatctacta ctgcgccaag   720
cactactact atggcggtag ctacgccatg gattattggg gtcaggggac cagtgtcacc   780
gtctcctcca tcgaggtgat gtaccctcca ccctatctgg acaacgagaa gtccaacggc   840
accatcatcc acgtgaaggg caagcacctg tgccctagcc ctctgttccc aggaccctcc   900
aagcccttct gggtgctggt cgtggtggga ggagtcctgg cctgctattc cctcctcgtc   960
accgtggcat ttatcatctt ctgggtccgg agcaagcggt cacgcctgct ccactccgac  1020
tacatgaaca tgactcctcg cagacctgga cccacccgga agccttatgcc  1080
ccaccccgcg actttgccgc ttaccgctct cgggtcaagt tctctcggtc agcagacgcc  1140
cctgcatacc agcagggcca gaaccagctg tataacgagc tgaacctcgg cagacgggag  1200
gagtacgatg tgctggacaa gaggagaggc agagaccccg agatgggtgg taagccacgg  1260
cgcaagaacc cacaggaggg cttgtacaac gaactgcaga aggacaagat ggccgaggcc  1320
tacagcgaga tcggcatgaa gggagagagg cgcagggca aggtcacga cggcctgtac  1380
```

```
caagggctgt ccaccgcaac caaggacacc tacgatgccc tgcacatgca ggccctccca   1440
ccaagg                                                              1446

SEQ ID NO: 20            moltype = DNA  length = 1446
FEATURE                  Location/Qualifiers
source                   1..1446
                         mol_type = other DNA
                         organism = synthetic construct
SEQUENCE: 20
atggcactcc cagtcaccgc acttctgctg cctctcgccc tgctgctcca tgcagccaga   60
cccgacatcc agatgaccca aaccaccagc tccctgtccg cttccctggg tgaccgggtg   120
actatctctt gccgggcctc ccaagacatc tccaagtacc tgaactggta tcagcaaaag   180
cctgacggca ccgtcaagct cctcatctac catacctcca gactgcactc cggggtgcct   240
agcaggttca gcggaagtgg gagcggcacc gactacagcc tcaccatctc caacctggag   300
caggaggaca tcgccaccta cttctgccaa caggggaaca cactgcccta caccttcggc   360
ggtggcacca agctggagat cacaggtggc ggaggttccg gaggaggagg tagtggaggt   420
ggaggcagcg aggtgaagct ccaggaatcc ggaccaggtc tggtggctcc cagccagtcc   480
ctcagcgtga cctgcaccgt gagcggcgtg tctcttcccg attacggagt gtcctggatc   540
agacagccac cccggaaggg tctggagtgg ctgggagtga tctgggggttc cgagaccaca   600
tactacaact cagccctcaa gagccggctc accatcatca aggataactc caagtcccag   660
gtcttcctga agatgaactc tctccagacc gacgacaccg ccatctacta ctgcgccaag   720
cactactact acggcgggtc ctacgccatg gactactggg gtcagggaac ctccgtcacc   780
gtcagctcta tcgaggtgat gtaccctcct ccctacctcg acaacgagaa gagcaacggc   840
accatcatcc atgtgaaggg gaagcatctc tgcccctcac ccctgttccc cggaccatcc   900
aagccattct gggtgctggt ggttgttggt ggggtcctgg cttgctactc actcctggtc   960
accgtcgcct tcatcatctt ctgggtgcgg tcaaagaggt cccggctctt gcactccgat   1020
tacatgaaca tgactccaag gaggcctggt cccacacgga agcactacca accatatgcc   1080
ccaccacgcg acttcgctgc ttaccggagc cgggtcaagt tcagtcggag tgcagacgcc   1140
ccagcctacc agcagggcca gaaccaactc tacaacgagc ttaatctggg tcgccgggag   1200
gagtatgacg tgctcgataa gagaaggggc cgggatcctg gtggctcc cagccagtcc   1260
cggaagaacc ctcaggaggg gttgtataat gagctccaga aggacaagat ggccgaggca   1320
tactccgaga tcggcatgaa aggtgagcgg aggagaggca aggggcatga cggcctgtac   1380
caggggctca gcacagccac caaggatacc tatgacgcac tccacatgca ggcactgcct   1440
ccacgg                                                              1446

SEQ ID NO: 21            moltype = DNA  length = 1446
FEATURE                  Location/Qualifiers
source                   1..1446
                         mol_type = other DNA
                         organism = synthetic construct
SEQUENCE: 21
atggctctgc ctgtgacagc tctgctgctg cctctggctc tgcttctgca tgccgccaga   60
cctgacatcc agatgaccca gacaaccagc agcctgtccg cctctgtggg cgatagagtg   120
accatcagct gtagagccag ccaggacatc agcaagtacc tgaactggta tcagcagaaa   180
cccgacggca ccgtgaagct gctgatctac cacaccagca gactgcacag cggcgtgcca   240
agcagatttt ctggcagcgg ctctggcacc gactacagcc tgacaatcag caacctggaa   300
caagaggata tcgctaccta cttctgccaa caggccaaca ccctgcctta ccctttggc   360
ggaggcacca agctggaaat cacaggcggc ggaggaagcg gaggcggagg atctggtggt   420
ggtggatctg aagtgaaact gcaagagtct ggccctggcc tggtggcccc atctcaatct   480
ctgagcgtga cctgtaccgt cagcggagtg tccctgcctg attatggcgt gtcctggatc   540
cggcagcctc ctagaaaagg cctggaatgg ctgggcgtga tctggggcga cgagacaacc   600
tactacaaca gcgccctgaa gtcccggctg accatcatca aggacaactc caagagccag   660
gtgttcctga agatgaacag cctgcagacc gacgacaccg ccatctacta ttgcgccaag   720
cactactact acggcggcag ctacgccatg gattattggg gccagggcac cagcgtgacc   780
gtgtctagca tcgaagtgat gtaccctcca ccttacctgg acaacgagaa gtccaacggc   840
accatcatcc acgtgaaggg caagcacctg tgtccttctc cactgttccc cggacctagc   900
aagccttttct gggtgctcgt tgttgttggc ggcgtgctgg cctgttactc tctgctggtt   960
accgtggcct tcatcatctt tgggtccga agcaagcgga gccggctgct gcactccgac   1020
tacatgaaca tgacccctag acggcccgga ccaaccagaa agcactacca gccttacgct   1080
cctcctagag acttcgccgc ctaccggtcc agagtgaagt tcagcagatc cgccgatgct   1140
cccgcctatc agcagggcca aaaccagctg tacaacgagc tgaacctggg gagaagagaa   1200
gagtacgacg tgctggacaa gcggagaggc agagatcctg aaatgggcgg caagcccaga   1260
cggaagaatc ctcaagaggg cctgtataat gagctgcaga agacaagat ggccgaggcc   1320
tacagcgaga tcggaatgaa gggcgagcgc agaagaggca aggggcacga tggactgtac   1380
caggggctga gcaccgccac caaggatacc tatgatgccc tgcacatgca ggccctgcct   1440
ccaaga                                                              1446

SEQ ID NO: 22            moltype = DNA  length = 1446
FEATURE                  Location/Qualifiers
source                   1..1446
                         mol_type = other DNA
                         organism = synthetic construct
SEQUENCE: 22
atggcccttc ccgtcaccgc tctcctcctg ccactggcct tgctgctgca cgctgcacgg   60
ccagacatcc agatgaccca gacaaccagc tctctgtcag cctctctcgg cgatcgcgtc   120
acaatcagct gccgcgcttc ccaagacatc tccaagtacc tgaactggta ccagcaaaag   180
cccgacggca ccgtgaagct gctcatctac cacacctcca gactgcatag cggggtgccc   240
agcagattca gtggctcagg ctcaggcacc gactacagcc tgaccatctc caacctggag   300
caggaggaca ttgccacata cttctgccag cagggcaaca ccctgcccta caccttcgga   360
```

```
ggcggcacaa agctggagat caccggtgga ggagggagtg gaggaggagg cagtggtggc    420
ggaggttccg aggtgaagct ccaggaatca ggtccaggac tggtcgcccc ttcccagtcc    480
ctgtccgtca cctgcaccgt gagtggcgtc agcctcccag actacggtgt gtcttggatc    540
cgccaacctc ctcgcaaagg cctggaatgg ctcggcgtca tctgggggaag cgagacaacc   600
tactataact ccgcactgaa gtcccgcctc accatcatca aggataatag caagagccag    660
gtcttcctca agatgaactc cctgcagacc gacgataccg ccatctacta ctgtgccaag    720
cactactact acggaggttc ttacgccatg gattactggg gacagggaac ctctgtcacc    780
gtcagctcca tcgaggtcat gtatccacca ccctacctgg acaacgaaaa gagcaatggc    840
accatcatcc acgtgaaggg gaagcacctc tgccctcac ccctgttccc tggtccctcc     900
aagcctttct gggtcctggt cgtcgtggga ggcgtgttgg cctgttactc cctgctcgtc    960
accgtcgcct tcatcatctt ctgggttagg agtaagcggt cccggcttct gcactctgac   1020
tacatgaaca tgacacccag aagacctggg ccaacccgga agcactacca gccctacgct   1080
ccacccaggg actttgcagc ctacaggtcc cgcgtcaagt tctcccggtc tgctgacgca   1140
cctgcctacc agcagggcca aaaccagctc tacaacgagt tgaacctcgg cagacgggag   1200
gagtacgacg tcctcgacaa aaggcggggt cgggatcctg agatgggcgg taagccaagg   1260
cggaagaacc cacaggaagg cctctataat gagctccaga aggataagat ggctgaggcc   1320
tactccgaga tcgggatgaa gggcgaaagg agacggggta aggggcacga cggcctctat   1380
cagggtctga gcaccgccac caaggacacc tacgacgccc tgcacatgca ggcactgcca   1440
cctcgg                                                                1446
```

```
SEQ ID NO: 23              moltype = DNA  length = 1446
FEATURE                    Location/Qualifiers
source                     1..1446
                           mol_type = other DNA
                           organism = synthetic construct
SEQUENCE: 23
atggctctgc cagtgaccgc actgctgctg cccttagcct tactccttca cgcagccagg    60
cccgacatcc agatgaccca gaccaccagc tccctttccg caagcctcgg cgacagggtc    120
accatctcct gtcgggccag ccaggacatc agcaagtacc tgaactggta ccagcagaag    180
cccgacggca ccgtgaagct gctgatctac cacacctcac ggctgcactc aggcgtgccc    240
tcacggttta gcggatcagg cagcggcacc gactacagcc tgactatcag caacctggag    300
caggaggaca tcgccaccta cttctgccag cagggcaaca ccctgcccta caccttcgga    360
ggcggcacca agctggagat caccggtggc ggtggttcag gtggcggagg ctcaggagga    420
ggcggcagcg aggtgaagct gcaggagtca ggtccaggac tggtggcacc cagccagagc    480
ctgagcgtga cttgcaccgt gtcaggcgtg agcctgccag actacggcgt gagctggatc    540
cggcagcctc ctcggaaggg cttagagtgg ctgggcgtga tctgggggcag cgagaccacc   600
tactacaact cagccctgaa gagccggctg accatcatca aggacaacag caagagccag    660
gtgttcctga agatgaacag cctgcagacc gacgacaccg ccatctacta ctgcgccaag    720
cactactact acggcggcag ctacgccatg gactactggg gacagggtac cagcgtgacc    780
gtgagcagca tcgaggtgat gtaccctcct ccctacctgg acaacgagaa gagcaacggc    840
accatcatcc acgtgaaggg caagcacctg tgccctagcc ctttattccc cggccctca     900
aaaccttct gggtgctggt cgtcgtcggt ggcgtgctgg catgctacag cctgctggtg     960
accgtggcct tcatcatatt ctgggtccgg tcaaagcggt cgcggttact gcacagcgac   1020
tacatgaaca tgactccacg gcgtccaggt cccactcgga agcactacca accctacgct   1080
cctcccgtg actttgctgc ctaccgtagc cgggtgaagt tctccaggag cgccgatgcc    1140
ccagcctacc agcagggcca gaaccagctc tacaatgagc ttaaccttgg caggcgggag   1200
gagtacgacg tgctggacaa gaggaggggc cgtgatcccg agatgggagg caagcccgt    1260
aggaagaatc cccaggaggg cctttacaac gagctccaga aggacaagat ggccgaggcc   1320
tacagcgaga tcggcatgaa gggagagcgt aggcgtggaa agggcacga cggcctgtac    1380
cagggcctga gcactgctac caaggacacc tacgacgccc tgcacatgca ggctcttcca   1440
ccccgg                                                                1446
```

```
SEQ ID NO: 24              moltype = DNA  length = 1467
FEATURE                    Location/Qualifiers
source                     1..1467
                           mol_type = other DNA
                           organism = synthetic construct
SEQUENCE: 24
atgctcctcc tggtgaccag cttgctcctg tgcgaactgc cacacccgc cttcctcctc     60
atccccgata tccagatgac ccagaccacc tcctccctga gcgcaagcct cggccgatcg    120
gtgaccatct catgcagggc ctcccaggac atctccaagt atctgaactg gtatcagcag    180
aagcctgacg gcaccgtcaa gctgctcatc taccacacct cacggctgca ctcaggcgtc    240
ccctcaagat tcagcggtag cggatccggg accgactact cccttaccat cagcaacctg    300
gagcaggagg atatcgccac atacttctgc cagcagggca acacccctgcc ctataccttc    360
ggcggtggga ccaagctgga gatcaccggt tctacatccg gatccggcaa gcctggtagt    420
ggcgagggct ccaccaaagg gggaggtgaag ctgcaggagt ccggtccagg tctggtggct   480
ccaagtcagt ccctgtctgt gacttgcacc gtgtcaggcg tgagcctgcc tgactacggg   540
gtgagctgga tccggcagcc acctcggaag gggttggagt ggctgggagt catctgggga   600
tccgagacca cctactacaa ttccgccctc aaaagccgc tcaccatcat caaggacaac    660
tccaagtccc aggtcttcct gaagatgaat tccctgcaga ccgacgacac cgctatctat   720
tactgcgcca agcattacta ctacggcggg tcctacgcca tggactactg gggtcaaggc    780
acctccgtca ctgtttcctc cgcagcagcc atcgaggtca tgtatcctcc tcctacctc    840
gacaacgaga gtccaacgg gaccatcatc acgtgaagg gcaagcacct ctgcccaagc     900
ccactgttcc caggcccctc caaaccattc tgggtgctc tggtggtggg tggcgtgctc    960
gcttgctact ccctcctggt caccgtcgcc ttcatcatct tttgggtccg gagtaagcgc   1020
agccgcctgc tccatagcga ctacatgaac atgacccca ggagacctgg tcccacccgg    1080
aaacactacc agccctacgc accacccagg gacttcgctg cctatcggtc ccgggttaaa   1140
ttctctaggt ccgctgatgc cccagcctac cagcaggggc agaaccagct gtacaatgag   1200
ctgaacctgg gtagacggga ggagtatgac gtcctggata gcgcagagg gagagacccc   1260
```

```
gagatgggtg gaaagcccag gcggaagaat ccccaggagg gtctctataa cgagctccag   1320
aaggacaaga tggccgaggc ctacagcgag atcgggatga aaggggaaag aaggcgggga   1380
aagggccatg acggactgta ccagggtctg tccaccgcta ccaaggacac ctacgatgca   1440
ctgcacatgc aggcactgcc tcctcgg                                        1467

SEQ ID NO: 25              moltype = DNA  length = 1467
FEATURE                   Location/Qualifiers
source                    1..1467
                          mol_type = other DNA
                          organism = synthetic construct
SEQUENCE: 25
atgctgcttc tcgttacatc tctgttgctc tgcgagctgc ctcatccagc cttcctcctg   60
attcccgata tccagatgac ccagaccacc tctagcctca gcgcctctct gggtgaccgc   120
gtcaccatct cttgccgggc cagccaagac atctctaagt acctgaactg gtaccagcag   180
aaacctgacg gaaccgtgaa gctgctgatc taccacacca gtcggctgca ttccggggtg   240
ccttccaggt tcagcggttc cggctctggg accgattata gtctcaccat ctccaacctc   300
gagcaggagg acatcgcaac ctacttctgc cagcagggga acaccctgcc ctacaccttc   360
ggtggcggga ccaagctgga gatcactggc agcacctcag gctctgggaa gcctggcagc   420
ggtgaaggca gcaccaaggg tgaggtgaag ctgcaggagt ccggacctgg tctggtggca   480
ccaagccagt ccctcagcgt cacctgcaca gtgtccgggg tgtccctgcc tgactacggt   540
gtctcctgga tcaggcaacc accccggaag ggtctcgagt ggctgggcgt catctggggc   600
tccgagacca cctactacaa cagcgctctg aagtcccggc tgaccatcat caaagacaac   660
tccaagagcc aggtgttctt gaagatgaac tccctgcaaa ccgatgacac cgccatctac   720
tactgcgcca agcactacta ctatggcggt agctacgcca tggattattg gggtcagggc   780
accagtgtca ccgtctcctc cgctgccgct atcgaggtga tgtaccctcc accctatctg   840
gacaacgaga agtccaacgg caccatcatc cacgtgaaggca gcaagcacct gtgtccctagc   900
cctctgttcc caggaccctc caagcccttc tgggtgctgg tcgtggtggg aggagtcctg   960
gcctgctatt ccctcctcgt caccgtggca tttatcatct tctgggtccg gagcaagcgg   1020
tcacgcctgc tccactccga ctacatgaac atgactcctc gcagacctgg acccacccgg   1080
aagcactacc agccttatgc cccaccccgc gactttgccg cttaccgctc tcgggtcaag   1140
ttctctcggt cagcagacgc ccctgcatac cagcaggggc caagaaccagct gtataacag   1200
ctgaacctcg gcagacggga ggagtacgat gtgctggaca gaggagagg cagagacccc   1260
gagatgggtg gtaagccacg cgcaagaac ccacaggagg gcttgtacaa cgaactgcag   1320
aaggacaaga tggccgaggc ctacagcgag atcggcatga agggagagag gcgcagggggc   1380
aagggtcacg acggcctgta ccaagggctg tccaccgcaa ccaaggacac ctacgatgcc   1440
ctgcacatgc aggccctccc accaagg                                        1467

SEQ ID NO: 26              moltype = DNA  length = 1464
FEATURE                   Location/Qualifiers
source                    1..1464
                          mol_type = other DNA
                          organism = synthetic construct
SEQUENCE: 26
atggcacttc cagttacagc acttctgctt ccattggcac tgctgctcca tgcagctcgc   60
cccgatatcc agatgacca gaccacctct agcctcagcg cctctctggg tgaccgcgtc   120
accatctctt gccgggccag ccaagacatc tctaagtacc tgaactggta ccagcagaaa   180
cctgacggaa ccgtgaagct gctgatctac cacaccagtc ggctgcattc cggggtgcct   240
tccaggttca gcggttccgg ctctgggacc gattatagtc tcaccatctc caacctcgag   300
caggaggaca tcgcaaccta cttctgccag caggggaaca ccctgcccta caccttcggt   360
ggcgggacca agctggagat cactggcagc acctcaggct ctgggaagcc tggcagcggt   420
gaaggcagca ccaagggtga ggtgaagctg caggagtccg gacctggtct ggtggcccca   480
agccagtccc tcagcgtcac ctgcacagtg tccggggtgt ccctgcctga ctacggtgtc   540
tcctggatca ggcaaccacc ccggaagggt ctcgagtggc tgggcgtcat ctggggctcc   600
gagaccacct actacaacag cgctctgaag tcccggctga ccatcatcaa agacaactcc   660
aagagccagg tgttcttgaa gatgaactcc ctgcaaaccg atgacaccgc catctactac   720
tgcgccaagc actactacta tggcggtagc tacgccatgg attattgggg tcagggcacc   780
agtgtcaccg tctcctccgc tgccgctatc gaggtgatgt accctccacc ctatctggac   840
aacgagaagt ccaacggcac catcatccac gtgaagggca gcacctgtg ccctagccct   900
ctgttcccag gaccctccaa gcccttctgg gtgctggtcg tggtgggagg agtcctggcc   960
tgctattccc tcctcgtcac cgtggcattt atcatcttct gggtccggag caagcggtca   1020
cgcctgctcc actccgacta catgaacatg actcctcgca gacctggacc cacccggaag   1080
cactaccagc cttatgcccc accccgcgac tttgccgctt accgctctcg ggtcaagttc   1140
tctcggtcag cagacgcccc tgcataccag cagggccaga accagctgta taacgagctg   1200
aacctcggca gacgggagga gtacgatgtg ctggacagag gagaggcag agacccc      1260
atgggtggta gccacggcg caagaaccca caggagggct gtacaacga actgcagaag   1320
gacaagatgg ccgaggccta cagcgagatc ggcatgaag gagagaggcg caggggcaag   1380
ggtcacgacg gcctgtacca agggctgtcc accgcaacca aggacaccta cgatgccctg   1440
cacatgcagg ccctccccacc aagg                                          1464

SEQ ID NO: 27              moltype = DNA  length = 1464
FEATURE                   Location/Qualifiers
source                    1..1464
                          mol_type = other DNA
                          organism = synthetic construct
SEQUENCE: 27
atggcactgc ccgtcaccgc actcctgctc ccactggcac tgctgctcca tgcagctcgc   60
cccgatatcc agatgaccca gaccacctct agcctcagcg cctctctggg tgaccgcgtc   120
accatctctt gccgggccag ccaagacatc tctaagtacc tgaactggta ccagcagaaa   180
cctgacggaa ccgtgaagct gctgatctac cacaccagtc ggctgcattc cggggtgcct   240
```

-continued

```
tccaggttca gcggttccgg ctctgggacc gattatagtc tcaccatctc caacctcgag   300
caggaggaca tcgcaaccta cttctgccag caggggaaca ccctgcccta caccttcggt   360
ggcgggacca agctggagat cactggcagc acctcaggct ctgggaagcc tggcagcggt   420
gaaggcagca ccaagggtga ggtgaagctg caggagtccg gacctggtct ggtggcccca   480
agccagtccc tcagcgtcac ctgcacagtg tccggggtgt ccctgcctga ctacggtgtc   540
tcctggatca ggcaaccacc ccggaagggg ctcgagtggc tgggcgtcat ctggggctcc   600
gagaccacct actacaacag cgctctgaag tcccggctga ccatcatcaa agacaactcc   660
aagagccagg tgttcttgaa gatgaactcc ctgcaaaccg atgacaccgc catctactac   720
tgcgccaagc actactacta tggcggtagc tacgccatgg attattgggg tcagggcaca   780
agtgtcaccg tctcctccgc tgccgctatc gaggtgatgt accctccacc ctatctggac   840
aacgagaagt ccaacggcac catcatccac gtgaagggca agcacctgtg ccctagccct   900
ctgttcccag gacctccaa gcccttctgg gtgctggtcg tggtgggagg agtcctggcc   960
tgctattccc tcctcgtcac cgtggcattt atcatcttct gggtccggag caagcggtca  1020
cgcctgctcc actccgacta catgaacatg actcctccga gacctggacc caccggaag  1080
cactaccagc cttatgcccc accccgcgac tttgccgctt accgctctcg ggtcaagttc  1140
tctcggtcag cagacgcccc tgcataccag cagggccaga accagctgta taacgagctg  1200
aacctcggca gacgggagga gtacgatgtg ctggacaaga ggagaggcag agaccccgag  1260
atgggtggta gccacggcg caagaaccca caggaggct tgtacaacag actgcagaag  1320
gacaagatgg ccgaggccta cagcgagatc ggcatgaagg gagagaggcg caggggcaag  1380
ggtcacgacg gcctgtacca agggctgtcc accgcaacca aggacaccta cgatgccctg  1440
cacatgcagg ccctcccacc aagg                                          1464
```

```
SEQ ID NO: 28          moltype = DNA  length = 1446
FEATURE                Location/Qualifiers
source                 1..1446
                       mol_type = other DNA
                       organism = synthetic construct
SEQUENCE: 28
atggcacttc cagttacagc acttctgctt ccattggcac tgctgctcca tgcagctcgc   60
cccgatatcc agatgaccca gaccacctct agcctcagcg cctctctggg tgaccgcgtc  120
accatctctt gccgggccag ccaagacatc tctaagtacc tgaactggta ccagcagaaa  180
cctgacggaa ccgtgaagct gctgatctac cacaccagtc ggctgcattc cggggtgcct  240
tccaggttca gcggttccgg ctctgggacc gattatagtc tcaccatctc caacctcgag  300
caggaggaca tcgcaaccta cttctgccag caggggaaca ccctgcccta caccttcggt  360
ggcgggacca agctggagat cactggaggt ggtggcagcg gaggtggagg atcaggtgga  420
ggcggtagcg aggtgaagct gcaggagtcc ggacctggtc tggtggcccc aagccagtcc  480
ctcagcgtca cctgcacagt gtccggggtg tccctgcctg actacggtgt ctcctggatc  540
aggcaaccac cccggaaggg tctcgagtgg ctgggcgtca tctggggctc cgagaccacc  600
tactacaaca gcgctctgaa gtcccggctg accatcatca agacaactc caagagccag  660
gtgttcttga agatgaactc cctgcaaacc gatgacaccg ccatctacta ctgcgccaag  720
cactactact atggcggtag ctacgccatg gattattggg gtcagggcac cagtgtcacc  780
gtctcctcca tcgaggtgat gtaccctcca ccctatctgg acaacgagaa gtccaacggc  840
accatcatcc acgtgaaggg caagcacctg tgccctagcc ctctgttccc aggaccctc  900
aagcccttct gggtgctggt cgtggtggga ggagtcctgg cctgctattc cctcctcgtc  960
accgtggcat ttatcatctt ctgggtccgg agcaagcggt cacgcctgct ccactccgac 1020
tacatgaaca tgactcctcg cagacctgga cccaccggga agcactacca gccttatgcc 1080
ccacccgcg actttgccgc ttaccgctct cgggtctcgg tcagcagacg 1140
cctgcatacc agcagggcca gaaccagctg tataacgagc tgaacctcgg cagacgggga 1200
gagtacgatg tgctggacaa gaggagaggc agagaccccg agatgggtgg taagccacgg 1260
cgcaagaacc cacaggaggg cttgtacaac gaactgcaga aggacaagat ggccgaggcc 1320
tacagcgaga tcggcatgaa gggagagagg cgcaggggca agggtcacga cggcctgtac 1380
caagggctgt ccaccgcaac caaggacacc tacgatgccc tgcacatgca ggccctccca 1440
ccaagg                                                              1446
```

```
SEQ ID NO: 29          moltype = AA  length = 482
FEATURE                Location/Qualifiers
source                 1..482
                       mol_type = protein
                       organism = synthetic construct
SEQUENCE: 29
MALPVTALLL PLALLLHAAR PDIQMTQTTS SLSASLGDRV TISCRASQDI SKYLNWYQQK   60
PDGTVKLLIY HTSRLHSGVP SRFSGSGSGT DYSLTISNLE QEDIATYFCQ QGNTLPYTFG  120
GGTKLEITGG GGSGGGGSGG GGSEVKLQES GPGLVAPSQS LSVTCTVSGV SLPDYGVSWI  180
RQPPRKGLEW LGVIWGSETT YYNSALKSRL TIIKDNSKSQ VFLKMNSLQT DDTAIYYCAK  240
HYYYGGSYAM DYWGQGTSVT VSSIEVMYPP PYLDNEKSNG TIIHVKGKHL CPSPLFPGPS  300
KPFWVLVVVG GVLACYSLLV TVAFIIFWVR SKRSRLLHSD YMNMTPRRPG PTRKHYQPYA  360
PPRDFAAYRS RVKFSRSADA PAYQQGQNQL YNELNLGRRE EYDVLDKRRG RDPEMGGKPR  420
RKNPQEGLYN ELQKDKMAEA YSEIGMKGER RRGKGHDGLY QGLSTATKDT YDALHMQALP  480
PR                                                                  482
```

```
SEQ ID NO: 30          moltype = AA  length = 489
FEATURE                Location/Qualifiers
source                 1..489
                       mol_type = protein
                       organism = synthetic construct
SEQUENCE: 30
MLLLVTSLLL CELPHPAFLL IPDIQMTQTT SSLSASLGDR VTISCRASQD ISKYLNWYQQ   60
KPDGTVKLLI YHTSRLHSGV PSRFSGSGSG TDYSLTISNL EQEDIATYFC QQGNTLPYTF  120
GGGTKLEITG STSGSGKPGS GEGSTKGEVK LQESGPGLVA PSQSLSVTCT VSGVSLPDYG  180
```

```
VSWIRQPPRK GLEWLGVIWG SETTYYNSAL KSRLTIIKDN SKSQVFLKMN SLQTDDTAIY   240
YCAKHYYYGG SYAMDYWGQG TSVTVSSAAA IEVMYPPPYL DNEKSNGTII HVKGKHLCPS   300
PLFPGPSKPF WVLVVVGGVL ACYSLLVTVA FIIFWVRSKR SRLLHSDYMN MTPRRPGPTR   360
KHYQPYAPPR DFAAYRSRVK FSRSADAPAY QQGQNQLYNE LNLGRREEYD VLDKRRGRDP   420
EMGGKPRRKN PQEGLYNELQ KDKMAEAYSE IGMKGERRRG KGHDGLYQGL STATKDTYDA   480
LHMQALPPR                                                          489

SEQ ID NO: 31          moltype = AA  length = 489
FEATURE                Location/Qualifiers
source                 1..489
                       mol_type = protein
                       organism = synthetic construct
SEQUENCE: 31
MLLLVTSLLL CELPHPAFLL IPDIQMTQTT SSLSASLGDR VTISCRASQD ISKYLNWYQQ   60
KPDGTVKLLI YHTSRLHSGV PSRFSGSGSG TDYSLTISNL EQEDIATYFC QQGNTLPYTF   120
GGGTKLEITG STSGSGKPGS GEGSTKGEVK LQESGPGLVA PSQSLSVTCT VSGVSLPDYG   180
VSWIRQPPRK GLEWLGVIWG SETTYYNSAL KSRLTIIKDN SKSQVFLKMN SLQTDDTAIY   240
YCAKHYYYGG SYAMDYWGQG TSVTVSSAAA IEVMYPPPYL DNEKSNGTII HVKGKHLCPS   300
PLFPGPSKPF WVLVVVGGVL ACYSLLVTVA FIIFWVRSKR SRLLHSDYMN MTPRRPGPTR   360
KHYQPYAPPR DFAAYRSRVK FSRSADAPAY QQGQNQLYNE LNLGRREEYD VLDKRRGRDP   420
EMGGKPRRKN PQEGLYNELQ KDKMAEAYSE IGMKGERRRG KGHDGLYQGL STATKDTYDA   480
LHMQALPPR                                                          489

SEQ ID NO: 32          moltype = AA  length = 488
FEATURE                Location/Qualifiers
source                 1..488
                       mol_type = protein
                       organism = synthetic construct
SEQUENCE: 32
MALPVTALLL PLALLLHAAR PDIQMTQTTS SLSASLGDRV TISCRASQDI SKYLNWYQQK   60
PDGTVKLLIY HTSRLHSGVP SRFSGSGSGT DYSLTISNLE QEDIATYFCQ QGNTLPYTFG   120
GGTKLEITGS TSGSGKPGSG EGSTKGEVKL QESGPGLVAP SQSLSVTCTV SGVSLPDYGV   180
SWIRQPPRKG LEWLGVIWGS ETTYYNSALK SRLTIIKDNS KSQVFLKMNS LQTDDTAIYY   240
CAKHYYYGGS YAMDYWGQGT SVTVSSAAAI EVMYPPPYLD NEKSNGTIIH VKGKHLCPSP   300
LFPGPSKPFW VLVVVGGVLA CYSLLVTVAF IIFWVRSKRS RLLHSDYMNM TPRRPGPTRK   360
HYQPYAPPRD FAAYRSRVKF SRSADAPAYQ QGQNQLYNEL NLGRREEYDV LDKRRGRDPE   420
MGGKPRRKNP QEGLYNELQK DKMAEAYSEI GMKGERRRGK GHDGLYQGLS TATKDTYDAL   480
HMQALPPR                                                           488

SEQ ID NO: 33          moltype = AA  length = 488
FEATURE                Location/Qualifiers
source                 1..488
                       mol_type = protein
                       organism = synthetic construct
SEQUENCE: 33
MALPVTALLL PLALLLHAAR PDIQMTQTTS SLSASLGDRV TISCRASQDI SKYLNWYQQK   60
PDGTVKLLIY HTSRLHSGVP SRFSGSGSGT DYSLTISNLE QEDIATYFCQ QGNTLPYTFG   120
GGTKLEITGS TSGSGKPGSG EGSTKGEVKL QESGPGLVAP SQSLSVTCTV SGVSLPDYGV   180
SWIRQPPRKG LEWLGVIWGS ETTYYNSALK SRLTIIKDNS KSQVFLKMNS LQTDDTAIYY   240
CAKHYYYGGS YAMDYWGQGT SVTVSSAAAI EVMYPPPYLD NEKSNGTIIH VKGKHLCPSP   300
LFPGPSKPFW VLVVVGGVLA CYSLLVTVAF IIFWVRSKRS RLLHSDYMNM TPRRPGPTRK   360
HYQPYAPPRD FAAYRSRVKF SRSADAPAYQ QGQNQLYNEL NLGRREEYDV LDKRRGRDPE   420
MGGKPRRKNP QEGLYNELQK DKMAEAYSEI GMKGERRRGK GHDGLYQGLS TATKDTYDAL   480
HMQALPPR                                                           488

SEQ ID NO: 34          moltype = AA  length = 482
FEATURE                Location/Qualifiers
source                 1..482
                       mol_type = protein
                       organism = synthetic construct
SEQUENCE: 34
MALPVTALLL PLALLLHAAR PDIQMTQTTS SLSASLGDRV TISCRASQDI SKYLNWYQQK   60
PDGTVKLLIY HTSRLHSGVP SRFSGSGSGT DYSLTISNLE QEDIATYFCQ QGNTLPYTFG   120
GGTKLEITGG GGSGGGGSGG GGSEVKLQES GPGLVAPSQS LSVTCTVSGV SLPDYGVSWI   180
RQPPRKGLEW LGVIWGSETT YYNSALKSRL TIIKDNSKSQ VFLKMNSLQT DDTAIYYCAK   240
HYYYGGSYAM DYWGQGTSVT VSSIEVMYPP PYLDNEKSNG TIIHVKGKHL CPSPLFPGPS   300
KPFWVLVVVG GVLACYSLLV TVAFIIFWVR SKRSRLLHSD YMNMTPRRPG PTRKHYQPYA   360
PPRDFAAYRS RVKFSRSADA PAYQQGQNQL YNELNLGRRE EYDVLDKRRG RDPEMGGKPR   420
RKNPQEGLYN ELQKDKMAEA YSEIGMKGER RRGKGHDGLY QGLSTATKDT YDALHMQALP   480
PR                                                                 482

SEQ ID NO: 35          moltype =    length =
SEQUENCE: 35
000

SEQ ID NO: 36          moltype =    length =
SEQUENCE: 36
000
```

-continued

```
SEQ ID NO: 37          moltype =    length =
SEQUENCE: 37
000

SEQ ID NO: 38          moltype =    length =
SEQUENCE: 38
000

SEQ ID NO: 39          moltype =    length =
SEQUENCE: 39
000

SEQ ID NO: 40          moltype =    length =
SEQUENCE: 40
000

SEQ ID NO: 41          moltype =    length =
SEQUENCE: 41
000

SEQ ID NO: 42          moltype =    length =
SEQUENCE: 42
000

SEQ ID NO: 43          moltype =    length =
SEQUENCE: 43
000

SEQ ID NO: 44          moltype =    length =
SEQUENCE: 44
000

SEQ ID NO: 45          moltype =    length =
SEQUENCE: 45
000

SEQ ID NO: 46          moltype =    length =
SEQUENCE: 46
000

SEQ ID NO: 47          moltype =    length =
SEQUENCE: 47
000

SEQ ID NO: 48          moltype =    length =
SEQUENCE: 48
000

SEQ ID NO: 49          moltype =    length =
SEQUENCE: 49
000

SEQ ID NO: 50          moltype = DNA   length = 2193
FEATURE                Location/Qualifiers
source                 1..2193
                       mol_type = other DNA
                       organism = synthetic construct
SEQUENCE: 50
ttaaaacagc tctggggttg ttcccacccc agaggcccac gtggcggcca gtactccggt   60
attacggtac ccttgtacgc ctgtttttata ctcccttccc ctgtaactta gaagcataca  120
aaccaagttc aatagaaggg ggtacaaacc agtaccacca cgaacaagca ctcctgtttc  180
cccggtgaca ttgcatagac tgtacccacg gttgaaagcg atcgatccgt tacccgctcc  240
tgtacttcga gaagcctagt atcatcttgg aatcttcgat gcgttgcgct cagcactcaa  300
ccccagagtg tagcttaggc tgatgagtct ggacgtcccc caccggcgac ggtggtccag  360
gctgcgttgg cggcctacct gtggcccaaa gccacaggac gctagttgtg aacaaggtgt  420
gaagagccta ttgagctaca agagagtcct ccggcccctg aatgcggcta atcctaacca  480
cggagcaggc agttgcaaac cagcaaccgg cctgtcgtaa cgcgcaagtc tgtggcggaa  540
ccgactactt tgggtgtccg tgtttccttt tatttttaca atggctgctt atggtgacaa  600
tcatagattg ttatcataaa gcgacttgga ttggccatcc ggtgaaagta aaacacattg  660
tttacttgtt tgttggattc actccaatta acacttttac ttacaaactc attacaacaa  720
ctctattaat tagagataag catcacaatg gcactgcccg tcaccgcact cctgctccca  780
ctggcactgc tgctccatgc agctcgcccc gatatccaga tgacccagac cacctctagc  840
ctcagcgcct ctctgggtga ccgcgtcacc atctcttgcc gggccagcca agacatctct  900
aagtacctga actggtacca gcagaaacct gacggaaccg tgaagctgct gatctaccac  960
accagtcggc tgcattccgg ggtgccttcc aggttcagcg gttccggctc tgggaccgat 1020
tatagtctca ccatctccaa cctcgagcag gaggacatcg caacctactt ctgccagcag 1080
gggaacaccc tgcctacac cttcggtggc gggaccaagc tggagatcac tggaggtggt 1140
ggcagcggag gtgaggatc aggtggaggc ggtagcgagg tgaagctgca ggagtccgga 1200
cctggtctgg tggccccaag ccagtccctc agcgtcacct gcacagtgtc cggggtgtcc 1260
```

-continued

```
ctgcctgact acggtgtctc ctggatcagg caaccacccc ggaagggtct cgagtggctg   1320
ggcgtcatct ggggctccga gaccacctac tacaacagcg ctctgaagtc ccggctgacc   1380
atcatcaaag acaactccaa gagccaggtg ttcttgaaga tgaactccct gcaaaccgat   1440
gacaccgcca tctactactg cgccaagcac tactactatg gcggtagcta cgccatggat   1500
tattgggtc agggcaccag tgtcaccgtc tcctccacca aggtgatgta ccctccaccc   1560
tatctggaca cgagaagtc caacggcacc atcatccacg tgaagggcaa gcacctgtgc   1620
cctagccctc tgttcccagg accctccaag cccttctggg tgctggtcgt ggtgggagga   1680
gtcctggcct gctattccct cctcgtcacc gtggcattta tcatcttctg ggtccggagc   1740
aagcggtcac gcctgctcca ctccgactac atgaacatga ctcctcgcag acctggaccc   1800
acccggaagc actaccagcc ttatgcccca ccccgcgact ttgccgctta ccgctctcgg   1860
gtcaagttct ctcggtcagc agacgcccct gcataccagc agggccagaa ccagctgtat   1920
aacgagctga acctcggcag acgggaggag tacgatgtgc tggacaagag gagaggcaga   1980
gaccccgaga tgggtggtaa gccacggcgc aagaacccac aggagggctt gtacaacgaa   2040
ctgcagaagg acaagatggc cgaggcctac agcgagatcg gcatgaaggg agagaggcgc   2100
aggggcaagg gtcacgacgg cctgtaccaa gggctgtcca ccgcaaccaa ggacacctac   2160
gatgccctgc acatgcaggc cctcccacca agg                                2193
```

SEQ ID NO: 51           moltype = DNA   length = 2058
FEATURE                 Location/Qualifiers
source                  1..2058
                        mol_type = other DNA
                        organism = synthetic construct
SEQUENCE: 51

```
tttcccctgt tcgtaactaa gtgtgtgccc aatctcctca ctcctgctgg cttcaccgac   60
cggcagtgtc caaaatgcta ggtgaatccc ctccctttcc tctgggcttc tgcccagctt   120
cctcccccca gcctgacgtg acacaggctg tgcaaagacc ccgcgaaagc tgccaaaagt   180
ggcaattgtg ggtcccccct ttgtaaaggc gtcgagtctt tctccctcaa ggctagaccc   240
gtcagtgaat tctgtcgggc aactagtgac gccactgcac gcctctgacc tcggccgcgg   300
agtgctgccc cccaagtcgt gcccctgacc acaagttgtg ctgtctggca aacattgtct   360
gtgagaatgt tccgctgtgg ctgccaagcc tggcaacagg ctgccccagt gtgcgtagtt   420
ctcatccaga cttcggtctg gcaacttgct gttaagacac ggcgtaaggg gcgtgtgcca   480
acgccctgga acgagtgtcc actctaatac cccgaggaat gctacgcagg tacccctggt   540
tcgccaggga tctgagcgta ggctaattgt ctaagggtat tttcatttcc cattctttct   600
ttcttgttca taatggcact gcccgtcacc gcactcctgc tcccactggc actgctgctc   660
catgcagctc gccccgatat ccagatgacc cagaccacct ctagcctcag cgcctctctg   720
ggtgaccgcg tcaccatctc ttgccgggc agccaagaca tctctaagta cctgaactgg   780
taccagcaga aacctgacgg aaccgtgaag ctgctgatct accacaccag tcggctgcat   840
tccggggtgc cttccaggtt cagcggttcc ggctctggga ccgattatag tctcaccatc   900
tccaacctcg agcaggagga catcgcaacc tacttctgcc agcagggaa cacctgccc   960
tacaccttcg gtggcgggac caagctggag atcactggag gtggtggcag cggaggtgga   1020
ggatcaggtg gaggcggtag cgaggtgaag ctgcaggagt ccggacctgg tctggtggcc   1080
ccaagccagt ccctcagcgt cacctgcaca gtgtccgggg tgtccctgcc tgactacggt   1140
gtctcctgga tcaggcaacc accccggaag ggtctgggcg atctgggat catctgggat   1200
tccgagacca cctactacaa cagcgctctg agtcccggc tgaccatcat caaagacaac   1260
tccaagagcc aggtgttctt gaagatgaac tccctgcaaa ccgatgacac cgccatctac   1320
tactgcgcca agcactacta ctatggcggt agctacgcca tggattattg gggtcagggc   1380
accagtgtca ccgtctcctc catcgaggtg atgtaccctc caccctatct ggacaacgag   1440
aagtccaacg gcaccatcat ccacgtgaag ggcaagcacc tgtgccctag ccctctgttc   1500
ccaggaccct ccaagccctt ctgggtgctg gtcgtggtgg gaggagtcct ggcctgctat   1560
tccctcctcg tcaccgtggc atttatcatc ttctgggtcc ggagcaagcg gtcacgcctg   1620
ctccactccg actacatgaa catgactcct cgcagacctg gacccacccg gaagcactac   1680
cagccttatg ccccaccccg cgactttgcc gcttaccgct ctcgggtcaa gttctctcgg   1740
tcagcagacg cccctgcata ccagcagggc cagaaccagc tgtataacga gctgaacctc   1800
ggcagacggg aggagtacga tgtgctggac aagaggagag gcagagaccc cgagatgggt   1860
ggtaagccac ggcgcaagaa cccacaggag ggcttgtaca acgaactgca gaaggacaag   1920
atggccgagg cctacagcga gatcggcatg aagggagaga ggcgcagggg caagggtcac   1980
gacggcctgt accaagggct gtccaccgca accaaggaca cctacgatgc cctgcacatg   2040
caggccctcc accaagg                                                  2058
```

SEQ ID NO: 52           moltype = DNA   length = 2073
FEATURE                 Location/Qualifiers
source                  1..2073
                        mol_type = other DNA
                        organism = synthetic construct
SEQUENCE: 52

```
ttaaaacagc ggatgggtat cccaccatcc ggcccactgg gtgtagtact ctggtacatt   60
gtacctttgt acgcctgttt tcccctctt gtacccgccc ttcaagctcc ttgcccaagt   120
aacgttagaa gtttgaacat tggtacaata ggaagcatca catccagtgg tgtactgtac   180
aaacacttct gttgcccgg agcgaggtat agatggtcc caccgtcaaa agcctttaac   240
cgttatccgc caatcaacta cgtaatggct agtagcacct tggatttaag ttggcgttcg   300
atcaggtggt aaccccact agtttggtcg atgaggctag gaattcccca cgggtgaccg   360
tgtcctagcc tgcgtggcgg ccaacccagc atccgctggg acgccaattt aatgacatg   420
tgtgaagacc tgcatgtgct tgattgtgag tcctccggcc cctgaatgcg ctaaccta   480
accccggacc cttgcagcac aatccagtgt tgttaaggtc gtaatgagca attctgggat   540
gggaccgact actttgggtg tccgtgtttc ttatttttct tgaatttttc ttatggtcac   600
agcatatata cattatatac tgtgatcatg gcactgcccg tcaccgcact cctgctccca   660
ctggcactg tgtccatgc agctcgcccc gatatccaga tgacccagac cacctctagc   720
ctcagcgcct ctctgggtga ccgcgtcacc atctcttgcc gggccagcca agacatctct   780
aagtacctga actggtacca gcagaaacct gacggaaccg tgaagctgct gatctaccac   840
```

```
accagtcggc tgcattccgg ggtgccttcc aggttcagcg gttccggctc tgggaccgat  900
tatagtctca ccatctccaa cctcgagcag gaggacatcg caacctactt ctgccagcag  960
gggaacaccc tgccctacac cttcggtggc gggaccaagc tggagatcac tggaggtggt  1020
ggcagcggag gtggaggatc aggtggaggc ggtagcgagg tgaagctgca ggagtccgga  1080
cctggtctgg tggccccaag ccagtccctc agcgtcacct gcacagtgtc cgggggtgtcc  1140
ctgcctgact acggtgtctc ctggatcagg caaccacccc ggaagggtct cgagtggctg  1200
ggcgtcatct ggggctccga gaccacctac tacaacagcg ctctgaagtc ccggctgacc  1260
atcatcaaag acaactccaa gagccaggtg ttcttgaaga tgaactccct gcaaaccgat  1320
gacaccgcca tctactactg cgccaagcac tactactatg gcggtagcta cgccatggat  1380
tattggggtc agggcaccag tgtcaccgtc tcctccatcg aggtgatgta ccctccaccc  1440
tatctggaca acgagaagtc caacggcacc atcatccacg tgaagggcaa gcacctgtgc  1500
cctagccctc tgttcccagg accctccaag cccttctggg tgctggtcgt ggtgggagga  1560
gtcctggcct gctattccct cctcgtcacc gtggcattta tcatcttctg ggtccggagc  1620
aagcggtcac gcctgctcca ctccgactac atgaacatga tcctcgcag acctggaccc  1680
acccggaagc actaccagcc ttatgcccca ccccgcgact ttgccgctta ccgctctcgg  1740
gtcaagttct ctcggtcagc agacgcccct gcataccagc agggccagaa ccagctgtat  1800
aacgagctga acctcggcag acgggaggag tacgatgtgc tggacaagag gagaggcaga  1860
gaccccgaga tgggtggtaa gccacggcgc aagaacccaa aggagggctt gtacaacgaa  1920
ctgcagaagg acaagatggc cgaggcctac agcgagatcg gcatgaaggg agagaggcgc  1980
aggggcaagg gtcacgacgg cctgtaccaa gggctgtcca ccgcaaccaa ggacacctac  2040
gatgccctgc acatgcaggc cctcccacca agg                                2073
```

SEQ ID NO: 53          moltype = DNA  length = 2267
FEATURE                Location/Qualifiers
source                 1..2267
                       mol_type = other DNA
                       organism = synthetic construct
SEQUENCE: 53

```
ttcaaacagc ctgggggttg tacccacccc tggggcccac gtggcgctag tactctggta  60
cgttagtacc tttgtacgcc tgttttcccc tcccttaaac aaattaagat taccactact  120
gaggggagta gtccgactcc gctccggtac tgccgcacca gtactccggt acacttagta  180
ccctagtacg gagtagatgg tatccccacc ccgcaactta gaagcatgca aacaaaccga  240
ccaataggcg cacgatatcc agtcgtgttt cggtcaagca cttctgtctc cccggtccga  300
aaggatcgtt acccgcccga cccactacga gaagcccagt aactggccaa gtgattgcga  360
agttgcgctc agccacaacc ccagtggtag ctctggaaga tggggctcgc gtctcccccg  420
tggtgacacg gtcgcttgcc cgcgtgtgct tccgggttcg gcctacgccg ttcacttcaa  480
tgtcacgtaa ccagccaaga gcctattgtg ctgggacggt tttcctccgg ggccgtgaat  540
gctgctaatc ccaacctccg agcgtgtgcg cacaacccag tgttgctacg tcgtaatgcg  600
taagttggag gcggaacaga ctactttcgg tacccgtgt ttcctttaaa ttttattcat  660
tatttatgg tgacaattgc tgagatctgc gaattagcga ctctgccgtt gaatattgct  720
ctgtactatt tggttgcatt ccacaaaacc tctgacatcc ccagtacata cattacttta  780
cttgtttacc tcaatctaaa gcacaagcta gataatacaa aatggcactg cccgtcaccg  840
cactcctgct cccactggca ctgctgctcc atgcagctcg cccgatatc cagatgaccc  900
agaccacctc tagcctcagc gcctctctgg gtgaccgcgt caccatctct tgccgggcca  960
gccaagacat ctctaagtac ctgaactggt accagcagaa acctgacgga accgtggaagc  1020
tgctgatcta ccacaccagt cggctgcatt ccgggggtgcc ttccaggttc agcggttccg  1080
gctctgggac cgattatagt ctcaccatct ccaacctccg gcaggaggac atcgcaacct  1140
acttctgcca gcaggggaac accctgccct acaccttcgg tggcgggacc aagctggaga  1200
tcactggagg tggtggcagc ggaggtggag gatcaggtgg aggcggtagc gaggtgaagc  1260
tgcaggagtc cggacctggt ctggtggccc caagccagtc cctcagcgtc acctgcacag  1320
tgtccggggt gtccctgcct gactacggtg tctcctggat caggcaacca ccccggaacc  1380
gtctcgagtg gctgggcgtc atctggggct ccgagaccac ctactacaac agcgctctga  1440
agtcccggct gaccatcatc aaagacaact ccaagagcca ggtgttcttg aagatgaact  1500
ccctgcaaac cgatgacacc gccatctact actgcgccaa gcactactac tatggcggta  1560
gctacgccat ggattattgg ggtcagggca ccagtgtcac cgtctcctcc atcgaggtga  1620
tgtaccctcc accctatctg gacaacgaga gtccaacgg caccatcatc cacgtgaagg  1680
gcaagcacct gtgccctagc cctctgttcc caggaccctc caagcccttc tgggtgctgg  1740
tcgtggtggg aggagtcctg gcctgctatt ccctcctcgt caccgtggca tttatcatct  1800
tctgggtccg gagcaagcgg tcacgcctgc tccactccga ctacatgaac atgactcctc  1860
gcagacctgg acccacccgg aagcactacc agccttatgc cccaccccgc gactttgccg  1920
cttaccgctc tcgggtcaag ttctctcggt cagcagacgc ccctgcatac cagcagggcc  1980
agaaccagct gtataacgag ctgaacctcg gcagacggga ggagtacgat gtgctggaca  2040
agaggagagg cagagacccc gagatgggtg gtaagccacg gcgcaagaac ccacaggagg  2100
gcttgtacaa cgaactgcag aaggacaaga tggccgaggc ctacagcgag atcggcatga  2160
agggagagag gcgcaggggc aagggtcacg acggcctgta ccaagggctg tccaccgcaa  2220
ccaaggacac ctacgatgcc ctgcacatgc aggccctccc accaagg              2267
```

SEQ ID NO: 54          moltype = DNA  length = 2276
FEATURE                Location/Qualifiers
source                 1..2276
                       mol_type = other DNA
                       organism = synthetic construct
SEQUENCE: 54

```
ccccctccc cccttccct tccctttgca acgcaacaat tgtaagtgcc ctcacctgtc  60
aattgggacc accactttca gtgacccat gcgaagtgct gagagaaagg aagctttctt  120
acccttcatt tgtgaaccca ctggtctaag ccgcttggaa tacgatgagt ggaaaagttc  180
attcttaatg gagtgaaaca tgcttaaatt tccagctcgt gctggtcttt ccagtacggg  240
gcggccctgt ctggccgtaa ttcttcagag tgtcacgcca cacttgtgga tctcacgtgc  300
cacatgacag cgctacagct ggaactgggt gcttggtgcc catggagtaa cagcgaaaag  360
```

```
tgttagatca agccttgctt gggctatgag cctgcggaac aacaactggt aacagttgcc    420
tcaggggccg aaagccacgg tgttaacagc accctcatag tttgatccac ctcagggtgg    480
tgatgtttag cagttagtag ttgccaatct gtgttcactg aaatctcggc ataccgtgta    540
gtgtacaggg gtgaaggatg cccagaaggt acccgtaggt aaccttaaga gactatggat    600
ctgatctggg gccttgtccg gagtgcttta cacacggctc aaggttaaaa aacgtctagc    660
cccacagagc ccgagggatt cgggtttttcc ctttaaaaac ccgactagag cttatggtga    720
caattattgc tgttcagacg aacagtgtaa ttgttgtcta ttcacagcag ttctatcaga    780
gcttttccca caacggatct tcttggcaag caaatacagc aggagtcaat atggcactcc    840
cagtcaccgc acttctgctg cctctcgccc tgctgctcca tgcagccaga cccgacatcc    900
agatgaccca aaccaccagc tccctgtccg cttccctggg tgaccgggtg actatctctt    960
gccgggcctc ccaagacatc tccaagtacc tgaactggta tcagcaaaag cctgacggca   1020
ccgtcaagct cctcatctac catacctcca gactgcactc cggggtgcct agcaggttca   1080
gcggaagtgg gagcggcacc gactacagcc tcaccatctc caacctggag caggaggaca   1140
tcgccaccta cttctgccag caggggaaca cactgcccta cactttcggc ggtggcacca   1200
agctggagat cacaggtggc ggaggttccg gaggaggagg tagtggaggt ggaggcagcg   1260
aggtgaagct ccaggaatcc ggaccaggtc tggtggctcc cagccagtcc ctcagcgtga   1320
cctgcaccgt gagcggcgtg tctcttcccg attacggagt gtcctggatc agacagccac   1380
cccggaaggg tctggagtgg ctgggagtga tctgggggtc cgagaccaca tactacaact   1440
cagccctcaa gagccggctc accatcatca aggataactc caagtcccag gtcttcctga   1500
agatgaactc tctccagacc gacgacaccg ccatctacta ctgcgccaag cactactact   1560
acggcgggtc ctacgccatg gactactggg gtcagggaac ctccgtcacc gtcagctcta   1620
tcgaggtgat gtaccctcct cctcacctcg acaacgagaa gagcaacggc accatcatcc   1680
atgtgaaggg gaagcatctc tgcccctcac ccctgttccc cggaccatcc aagccattct   1740
gggtgctggt ggttgttggt ggggtcctgg cttgctactc actcctggtc accgtcgcct   1800
tcatcatctt ctgggtgcgg tcaaagaggt cccggctctt gcactccgat tacatgaaca   1860
tgactccaag gaggcctggt cccacacgga agcactacca ccatatgcc ccaccacgcg   1920
acttcgctgc ttaccggagc cgggtcaagt tcagtcggag tgcagacgcc ccagcctacc   1980
agcagggcca gaaccaactc tacaacgagc ttaatctggg tcgccgggag gagtatgacg   2040
tgctcgataa gagaaggggc cgggatcctg agatgggcgg taagcccaga cggaagaacc   2100
ctcaggaggg gttgtataat gagctccaga aggacaagat ggccgaggcc tactccgaga   2160
tcggcatgaa aggtgagcgg aggagaggca aggggcatga cggcctgtac caggggctca   2220
gcacagccac caaggatacc tatgacgcac tccacatgca ggcactgcct ccacgg       2276
```

SEQ ID NO: 55                moltype = DNA   length = 2276
FEATURE                      Location/Qualifiers
source                       1..2276
                             mol_type = other DNA
                             organism = synthetic construct
SEQUENCE: 55

```
cccccctccc cccttccct tccctttgca acgcaacaat tgtaagtgcc ctcacctgtc     60
aattgggacc accactttca gtgacccat gcgaagtgct gagagaaagg aagctttctt    120
acccttcatt tgtgaaccca ctggtctaag ccgcttggaa tacgatgagt ggaaaagttc    180
attcttaatg gagtgaaaca tgcttaaatt tccagctcgt gctggtcttt ccagtacggg    240
gcggccctgt ctggccgtaa ttcttcagag tgtcacgaca cacttgtgga tctcacgtgg    300
cacatgacag cgctacagct ggaactgggg gcttggtgcc catggagtaa cagcgaaaag    360
tgttagatca agccttgctt gggctatgag cctgcggaac aacaactggt aacagttgcc    420
tcagggccg aaagccacgg tgttaacagc accctcatag tttgatccac ctcagggtgg    480
tgatgtttag cagttagtag ttgccaatct gtgttcactg aaatctcggc ataccgtgta    540
gtgtacaggg gtgaaggatg cccagaaggt acccgtaggt aaccttaaga gactatggat    600
ctgatctggg gccttgtccg gagtgcttta cacacggctc aaggttaaaa aacgtctagc    660
cccacagagc ccgagggatt cgggtttttcc ctttaaaaac ccgactagag cttatggtga    720
caattattgc tgttcagacg aacagtgtaa ttgttgtcta ttcacagcag ttctatcaga    780
gcttttccca caacggatct tcttggcaag caaatacagc aggagtcaat atggcactgc    840
ccgtcaccgc actcctgctc ccactggcac tgctgctcca tgcagctcgc cccgatatcc    900
agatgaccca gaccacctct agcctcagcg cctctctggg tgaccgcgtc accatctctt    960
gccgggccag ccaagacatc tctaagtacc tgaactggta ccagcagaaa cctgacggaa   1020
ccgtgaagct gctgatctac cacaccagtg ggctgcattc cggggtgcct tccaggttca   1080
gcggttccgg ctctgggacc gattatagtc tcaccatctc caacctcgag caggaggaca   1140
tcgcaaccta cttctgccag caggggaaca ccctgcccta caccttcggt ggcgggacca   1200
agctggagat cactggaggt ggtggcagcg gaggtggagg atcaggtgga ggcggtagcg   1260
aggtgaagct gcaggagtcc ggacctggtc tggtggcccc aagccagtcc ctcagcgtca   1320
cctgcacagt gtccgggtg tccctgcctg actacggtgt ctcctggatc aggcaaccac   1380
cccggaaggg tctcgagtgg ctgggcgtca tctgggggtc cgagaccacc tactacaaca   1440
gcgctctgaa gtcccggctg accatcatca aagacaactc caagagccag gtgttcttga   1500
agatgaactc cctgcaaacc gatgacaccg ccatctacta ctgcgccaag cactactact   1560
atggcggtag ctacgccatg gattattggg gtcaggcac cagtgtcacc gtctcctcca   1620
tcgaggtgat gtaccctcca ccctatctgg acaacgagaa gtccaacggc accatcatcc   1680
acgtgaaggg caagcacctg tgccctagcc ctctgttccc aggaccctcc aagcccttct   1740
gggtgctgga cgtggtggga ggagtcctgg cctgctattc cctcctcgtc accgtggcat   1800
ttatcatctt ctgggtccgg agcaagcggg cacgcctgct ccactccgac tacatgaaca   1860
tgactcctcg cagacctgga cccacccgga agcactacca gccttatgcc ccaccccgcg   1920
actttgccgc ttaccgctct cgggtcaagt tctctcggtc agcagacgcc cctgcatacc   1980
agcagggcca gaaccagctg tataacgagc tgaatctcgg cagacgggag gagtacgatg   2040
tgctggacaa gaggagaggc agagaccccg agatgggtgg taagccacgg cgcaagaacc   2100
cacaggaggg cttgtacaac gaactgcaga aggacaagat ggccgaggcc tacagcgaga   2160
tcggcatgaa gggagagagg cgcagggca agggtcacga cggcctgtac caagggctgt   2220
ccaccgcaac caaggacacc tacgatgccc tgcacatgca ggccctccca ccaagg       2276
```

SEQ ID NO: 56                moltype = DNA   length = 2446

-continued

```
FEATURE            Location/Qualifiers
source             1..2446
                   mol_type = other DNA
                   organism = synthetic construct
SEQUENCE: 56
cactacgtta cggttcccgc ccgggacaac tggtacccca ttaggctaca acatggctga    60
aaagggtatt gggtcccccc ggattgtgtc cgttcgtagt gtgtgtaacg tggtttacca   120
tctccactaa cattggacta agcatttcat cttttcctccc cgattgtgta ctcacttggc   180
taacgctggg tggtcgcggt tgggtccttg atttactttt tctcgtctaa gcattccgac   240
tgtcctcccc gattatgtgc tcattcagtt aactgctggg tggtcatgac taacatcgag   300
gaaccttctg tccacgctta ctttgagctc cggtcgcttg acgcttgtag ggcgataggg   360
ttatcttcct gacaacatct ttattctacc tccataggct ctatctatgg agacggagtg   420
tggcaccgt ccccttcttg ggagcttcgg tagtgacgcc ctttgtcact ctcgccagcc     480
gaggcatgcc tggtgccagg tagcaaagaa agcatatgtt taaggacttg actgatttag   540
cgcaagagtt tgtagcgatg tccatagtgt ctgcggattc cccacacggc gacgtgtgcc   600
gcggaggcca aaagccacgg tgttcacagc acccctatgg atgcccacag accccagtgg   660
gcactcttgt tgccggactt tcaggaaatt aggcataggc tcttctcaaa ctcctggcat   720
tggactaggt aagaatgccc cggaggtacc ccagtactcc ttcgggagtc tgggatctga   780
ccgggggccc cacaaacatg ctttacgtgt ttcgtgcggt caaaaattgt ctaactagtc   840
ccaaccttga acaagggatt gttctttcct ttttattact gagactggcc tatggtgaca   900
acagagattg actgtgaata cagttatttt ctggtgttta tcatttggtt tttctccgtg   960
ctcttttacc tttgtggtat ttgttcttta gataggcaaa atggcactgc ccgtcaccgc  1020
actcctgctc ccactggcac tgctgctcca tgcagctcgc cccgatatcc agatgaccca  1080
gaccacctct agcctcagcg cctctctggg tgaccgcgtc accatctctt gccgggccag  1140
ccaagacatc tctaagtacc tgaactggta ccagcagaaa cctgacgaa ccgtgaagct   1200
gctgatctac cacaccagtc ggctgcattc cggggtgcct tccaggttca gcggttccgg  1260
ctctgggacc gattatagtc tcaccatctc caacctcgag caggaggaca tcgcaaccta  1320
cttctgccag caggggaaca ccctgcccta caccttcggt ggcgggacca agctggagat  1380
cactggaggt ggtggcagcg gaggtggagg atcaggtgga ggcggtagcg aggtgaagct  1440
gcaggagtcc ggacctggtc tggtggcccc aagccagtcc ctcagcgtca cctgcacagt  1500
gtccgggggtg tccctgcctg actacggtgt ctcctggatc aggcaaccac cccggaaggg  1560
tctcgagtgg ctgggcgtca tctgggggctc cgagaccacc tactacaaca gcgctctgaa  1620
gtcccggctg accatcatca aagacaactc caagagccag gtgttcttga agatgaactc  1680
cctgcaaacc gatgacaccg ccatctacta ctgcgcaaa cactactact atggcggtag   1740
ctacgccatg gattattggg gtcagggcac cagtgtcacc gtctcctcca tcgaggtgat  1800
gtaccctcca ccctatctgg acaacgagaa gtccaacggc accatcatcc acgtgaaggg  1860
caagcacctg tgccctagcc ctctgttccc aggaccctcc aagcccttct gggtgctggt  1920
cgtggtggga ggagtcctgg cctgctattc cctcctcgtc accgtggcat ttatcatctt  1980
ctgggtccgga agcaagcggt cacgcctgct ccactccgac tacatgaaca tgactcctcg  2040
cagacctgga cccacccgga agcactacca gccttatgcc ccaccccgcg actttgccgc  2100
ttaccgctct cgggtcaagt tctctcggtc agcagacgcc cctgcatacc agcagggcca  2160
gaaccagctg tataacgagc tgaacctcgg cagacgggag gagtacgatg tgctggacaa  2220
gaggagagcc agagacccc  agatgggtgg taagccacgg cgcaagaacc cacaggaggg  2280
cttgtacaac gaactgcaga aggacaagat ggccgaggcc tacagcgaga tcggcatgaa  2340
gggagagagg cgcagggca agggtcacga cggcctgtac caagggctgt ccaccgcaac  2400
caaggacacc tacgatgccc tgcacatgca ggccctccca ccaagg               2446

SEQ ID NO: 57        moltype = DNA  length = 2157
FEATURE            Location/Qualifiers
source             1..2157
                   mol_type = other DNA
                   organism = synthetic construct
SEQUENCE: 57
tcaccctctt ttccggtggt ccggaccag accaccgtta ctccattcag cttcttcgga     60
acctgtttgg aggaattaaa cgggcaccca cccaccttca ccccctttc gtaactaagt    120
gtgtgcccaa tctcatgact cctgctgact tcaccgacca gcagtgtcca aaacgctagg   180
tgaatttcct tcctcccccct ctgggcttct gcccagctcc ctccctccag cctgacgtgc  240
cacaggctgt gcaaagaccc cgcgaaagct gccaaaagtg gcaattgtgg gtccccctt    300
tgtaaaggcg tcgagtcttt ctcccttaag gctagacccg tcagtgaatt ctgtcgggca  360
actagtgacg ccactgcatg cctccgacct cggccgcgga gtgctgcccc ccaagtcgtg  420
cccctgacta caagttgtgc tgtctggcaa acattgtctg tgagaatgtt ccgctgtggc  480
tgccaagcct ggtaacaggc tgcccagtg  tgcgtagttc tcatccagac ttcggtctgg   540
caacttgctg ttaagacacg gcgtaagggg cgtgtgccaa cgccctggaa cgagtgtcca  600
ctctaatacc ccgaggaatg ctacgcaggt acccctgcct ctgagcgtag gctaattgtc  660
taagggtatt ttcatttccc actctttctt tcttgttcat aatggctctg               720
cctgtgacag ctctgctgct gcctctggct ctgcttctgc atgccgccag acctgacatc   780
cagatgaccc agacaaccag cagcctgtct gccagcctgg gcgatagagt gaccatcagc   840
tgtagagcca gcaggacat cagcaagtac ctgaactggt atcagcagaa acccgacggc    900
accgtgaagc tgctgatcta ccacaccagc agactgcaca gcggcgtgcc aagcagattt   960
tctggcagcg gctctggcac cgactacagc ctgacaatca gcaacctgga acaagaggat  1020
atcgctacct acttctgcca gcaaggcaac accctgcctt acacctttgg cggaggcacc  1080
aagctggaaa tcacaggcgg cggaggaagc ggaggcggag gatctggtgg tggtggatct  1140
gaagtgaaac tgcaagagtc tggccctggc ctggtggccc catctcaatc tctgagcgtg  1200
acctgtaccg tcagcggagt gtccctgcct gattatggcg tgtcctggat ccggcagcct  1260
cctagaaaag gcctggaatg gctgggcgtg atctggggca gcgagacaac ctactacaac  1320
agcgccctga gtcccggct gaccatcatc aaggacaact ccaagagcca ggtgttcctg   1380
aagatgaaca gcctgcagac cgacgacacc gccatctact attgcgccaa gcactactac  1440
tacggcggca gctacgccat ggattattgg ggccagggca ccagcgtgac cgtgtctagc  1500
atcgaagtga tgtaccctcc accttacctg gacaacgaga gtccaacgg caccatcatc   1560
```

-continued

```
cacgtgaagg gcaagcacct gtgtccttct ccactgttcc ccggacctag caagcctttc  1620
tgggtgctcg ttgttgttgg cggcgtgctg gcctgttact ctctgctggt taccgtggcc  1680
ttcatcatct tttgggtccg aagcaagcgg agccggctgc tgcactccga ctacatgaac  1740
atgacccta  gacggcccgg accaaccaga aagcactacc agccttacgc tcctcctaga  1800
gacttcgccg cctaccggtc cagagtgaag ttcagcagat ccgccgatgc tcccgcctat  1860
cagcagggcc aaaaccagct gtacaacgag ctgaacctgg ggagaagaga agagtacgac  1920
gtgctggaca agcggagagg cagagatcct gaaatgggcg gcaagcccag acggaagaat  1980
cctcaagagg gcctgtataa tgagctgcag aaagacaaga tggccgaggc ctacagcgag  2040
atcggaatga agggcgagcg cagaagaggc aagggacacg atggactgta ccagggcctg  2100
agcaccgcca ccaaggatac ctatgatgcc ctgcacatgc aggccctgcc tccaaga     2157
```

SEQ ID NO: 58          moltype = DNA   length = 2157
FEATURE                Location/Qualifiers
source                 1..2157
                       mol_type = other DNA
                       organism = synthetic construct
SEQUENCE: 58

```
tcaccctctt ttccggtggt ccggacccag accaccgtta ctccattcag cttcttcgga  60
acctgtttgg aggaattaaa cgggcaccca cccaccttca cccccttttc gtaactaagt  120
gtgtgcccaa tctcatgact cctgctgact tcaccgacca gcagtgtcca aaacgctagg  180
tgaatttcct tcctcccct  ctgggcttct gcccagctcc ctccctccag cctgacgtgc  240
cacaggctgt gcaaagaccc cgcgaaagct gccaaaagtg gcaattgtgg gtccccccct  300
tgtaaaggcg tcgagtcttt ctcccttaag gctagacccg tcagtgaatt ctgtcgggca  360
actagtgacg ccactgcatg cctccgacct cggccgcgga gtgctgcccc ccaagtcgtg  420
cccctgacta caagttgtgc tgtctggcaa acattgtctg tgagaatgtt ccgctgtggc  480
tgccaagcct ggtaacaggc tgccccagtg tgcgtagttc tcatccagac ttcggtctgg  540
caacttgctg ttaagacacg gcgtaagggg cgtgtgccaa cgccctggaa cgagtgtcca  600
ctctaatacc ccgaggaatg ctacgcaggt acccctggct ccccaggat  ctgagcgtag  660
gctaattgtc taagggtatt ttcatttccc actctttctt tcttgttcat aatggccctt  720
cccgtcaccg ctctcctcct gccactggcc ttgctgctgc acgctgcacg gccagacatc  780
cagatgaccc agacaaccag ctctctgtca gcctctctcg gcgatcgcgt cacaatcagc  840
tgccgcgctt cccaagacat ctccaagtac ctgaactggt accagcaaaa gcccgacggc  900
accgtgaagc tgctcatcta ccacacctcc agactgcata gcggggtgcc cagcagattc  960
agtggctcag gctcaggcac cgactacagc ctgaccatct ccaacctgga gcaggaggac  1020
attgccacat acttctgcca gcagggcaac accctgcct  acaccttcgg aggcggcaca  1080
aagctggaga tcaccggtgg aggagggagt ggaggaggag gcagtggtgg cggaggttcc  1140
gaggtgaagc tccaggaatc aggtccagga ctggtcgccc cttcccagtc cctgtccgtc  1200
acctgcaccg tgagtggcgt cagcctccca gactacggtg tgtcttggat ccgccaacct  1260
cctcgcaaag gcctggaatg gctcggcgtc atctgggga  gcgagacaac ctactataac  1320
tccgcactga gtcccgcct  caccatcatc aaggataata gcaagagcca ggtcttcctc  1380
aagatgaact ccctgcagac cgacgatacc gccatctact actgtgccaa gcactactac  1440
tacggaggtt cttacgccat ggattactgg ggacaggga  cctctgtcac cgtcagctcc  1500
atcgaggtca tgtatccacc accctacctg gacaacgaaa agagcaatgg caccatcatc  1560
cacgtgaagg ggaagcacct ctgccctca  ccctgttcc  ctggtccctc caagcctttc  1620
tgggtcctgg tcgtcgtggg aggcgtgttg gcctgttact ccctgctcgt caccgtcgcc  1680
ttcatcatct tctgggttag gagtaagcgg tcccggcttc tgcactctga ctacatgaac  1740
atgacaccca gaagacctgg gccaacccgg aagcactacc agccctacgg tccacccagg  1800
gactttgcag cctacaggtc ccgcgtcaag ttctcccggt ctgctgacgc acctgcctac  1860
cagcagggcc aaaaccagct ctacaacgag ttgaacctcg gcagacggga ggagtacgac  1920
gtcctcgaca aaaggcgggg tcgggatcct gagatgggcg gtaagccaag gcggaagaac  1980
ccacagaag  gcctctataa tgagctccag aaggataaga tggctgaggc ctactccagg  2040
atcgggatga agggcgaaag gagacggggt aagggcacg  acggcctcta tcagggtctg  2100
agcaccgcca ccaaggacac ctacgacgcc ctgcacatgc aggcactgcc acctcgg     2157
```

SEQ ID NO: 59          moltype = DNA   length = 2096
FEATURE                Location/Qualifiers
source                 1..2096
                       mol_type = other DNA
                       organism = synthetic construct
SEQUENCE: 59

```
tctgtcctca ccccatcttc ccttctttcc tgcaccgtta cgcttactcg catgtgcatt  60
gagtggtgca cgtgcttgaa caaacagcta cactcacatg ggggcggggtt ttcccgccct  120
gcggcctctc gcgaggccca ccctcccct  tcctcccata actacagtgc tttggtaggt  180
aagcatcctg atccccgcg  gaagctgctc acgtggcaac tgtggggacc cagacaggtt  240
atcaaaggca cccggtcttt ccgccttcag gagtatccct gctagtgaat tctagtaggg  300
ctctgcttgg tgccaacctc ccccaaatgc gcgctgcggg agtgctcttc cccaactcac  360
cctagtatcc tctcatgtgt gtgcttggtc agcatatctg agacgatgtt ccgctgtccc  420
agaccagtcc agtaatggac gggccagtgt gcgtagtcgt cttccggctt gtccggcgca  480
tgtttggtga accggtgggg taaggttggt gtgcccaacg cccgtacttt ggtgatacct  540
caagaccacc caggaatgcc agggaggtac cccgcttcac agcgggatct gaccctgggc  600
taattgtcta cggtggttct tcttgcttcc acttctttct actgttcatg atggctctgc  660
ctgtgacagc tctgctgctg cctctggctc tgcttctgca tgccgccaga cctgacatcc  720
agatgaccca gacaaccagc agcctgtctg ccagcctggg cgatagagtg accatcagct  780
gtagagccag ccaggacatc agcaagtacc tgaactggta tcagcagaaa cccgacggca  840
ccgtgaagct gctgatctac cacaccagca gactgcacag cggcgtgcca agcagatttt  900
ctggcagcgg ctctggcacc gactacagcc tgacaatcag caacctggaa caagaggata  960
tcgctaccta cttctgccag caaggcaaca ccctgcctta cacctttggc ggaggcacca  1020
agctggaaat cacaggcggc ggaggaagcg gaggcggagg atctggtggt ggtggatctg  1080
aagtgaaact gcaagagtct ggccctggcc tggtggcccc atctcaatct ctgagcgtga  1140
```

```
cctgtaccgt cagcggagtg tccctgcctg attatggcgt gtcctggatc cggcagcctc  1200
ctagaaaagg cctggaatgg ctgggcgtga tctggggcag cgagacaacc tactacaaca  1260
gcgccctgaa gtcccggctg accatcatca aggacaactc caagagccag gtgttcctga  1320
agatgaacag cctgcagacc gacgacaccg ccatctacta ttgcgccaag cactactact  1380
acggcggcag ctacgccatg gattattggg gccagggcac cagcgtgacc gtgtctagca  1440
tcgaagtgat gtaccctcca ccttacctgg acaacgagaa gtccaacggc accatcatcc  1500
acgtgaaggg caagcacctg tgtccttctc cactgttccc cggacctagc aagcctttct  1560
gggtgctcgt tgttgttggc ggcgtgctgg cctgttactc tctgctggtt accgtggcct  1620
tcatcatctt ttgggtccga agcaagcgga gccggctgct gcactccgac tacatgaaca  1680
tgacccctag acggcccgga ccaaccagaa agcactacca gccttacgct cctcctagag  1740
acttcgccgc ctaccggtcc agagtgaagt tcagcagatc cgccgatgct cccgcctatc  1800
agcagggcca aaaccagctg tacaacgagc tgaacctggg gagaagagaa gagtacgacg  1860
tgctggacaa gcggagaggc agagatcctg aaatgggcgg caagcccaga cggaagaatc  1920
ctcaagaggg cctgtataat gagctgcaga agacaagat ggccgaggcc tacagcgaga  1980
tcggaatgaa gggcgagcgc agaagaggca agggacacga tggactgtac cagggcctga  2040
gcaccgccac caaggatacc tatgatgccc tgcacatgca ggccctgcct ccaaga  2096
```

SEQ ID NO: 60            moltype = DNA  length = 2096
FEATURE               Location/Qualifiers
source                1..2096
                        mol_type = other DNA
                        organism = synthetic construct
SEQUENCE: 60

```
tctgtcctca ccccatcttc ccttcttttcc tgcaccgtta cgcttactcg catgtgcatt  60
gagtggtgca cgtgcttgaa caaacagcta cactcacatg ggggcgggtt ttcccgccct  120
gcggcctctc gcgaggccca cccctcccct tcctcccata actacagtgc tttggtaggt  180
aagcatcctg atccccgcg gaagctgctc acgtggcaac tgtgggacc cagacaggtt  240
atcaaaggca cccggtcttt ccgccttcag gagtatccct gctagtgaat tctagtaggg  300
ctctgcttgg tgccaacctc ccccaaatgc gcgctgcggg agtgctcttc cccaactcac  360
cctagtatcc tctcatgtgt gtgcttggtc agcatatctg agacgatgtt ccgctgtccc  420
agaccagtcc agtaatggac gggccagtgt gcgtagtcgt cttccggctt gtccggcgca  480
tgtttggtga accggtgggg taaggttggt gtgcccaacg cccgtacttt ggtgatacct  540
caagaccacc caggaatgcc agggaggtac cccgcttcac agcgggatct gaccctgggc  600
taattgtcta cggtggttct tcttgcttcc acttctttct actgttcatg atggcactgc  660
ccgtcaccgc actcctgctc ccactggcac tgctgctcca tgcagctcgc cccgatatcc  720
agatgaccca gaccacctct agcctcagcg cctctctggg tgaccgcgtc accatctctt  780
gccgggccag ccaagacatc tctaagtacc tgaactggta ccagcagaaa cctgacggaa  840
ccgtgaagct gctgatctac cacaccagtc ggctgcattc cggggtgcct tccaggttca  900
gcggttccgg ctctgggacc gattatagtc tcaccatctc caacctcgag caggaggaca  960
tcgcaaccta cttctgccag caggggaaca ccctgcccta caccttcggt ggcgggacca  1020
agctggagat cactggaggt ggtggcagcg gaggtggagg atcaggtgga ggcggtagcg  1080
aggtgaagct gcaggagtcc ggacctggtc tggtggcccc aagccagtcc ctcagcgtca  1140
cctgcacagt gtccggggtg tccctgcctg actacggttt ctcctggatc aggcaaccac  1200
cccggaaggg tctcgagtgg ctgggcgtca tctgggggctc cgagaccacc tactacaaca  1260
gcgctctgaa gtcccggctg accatcatca aagacaactc caagagccag gtgttcttga  1320
agatgaactc cctgcaaacc gatgacaccg ccatctacta ctgcgccaag cactactact  1380
atggcggtag ctacgccatg gattattggg gtcagggcac cagtgtcacc gtctcctcca  1440
tcgaggtgat gtaccctcca ccctatctgg acaacgagaa gtccaacggc accatcatcc  1500
acgtgaaggg caagcacctg tgccctagcc ctctgttccc aggacctcc aagcccttct  1560
gggtgctggt cgtggtggga ggagtcctgg cctgctattc cctcctcgtc accgtggcat  1620
ttatcatctt ctgggtccgg agcaagcggt cacgcctgct ccactccgac tacatgaaca  1680
tgactcctcg cagacctgga cccaccggga agcactacca gccttatgcc ccaccccgcg  1740
actttgccgc ttaccgctct cgggtcaagt tctctcggtc agcagacgcc cctgcatacc  1800
agcagggcca gaaccagctg tataacgagc tgaacctcgg cagacgggag gagtacgatg  1860
tgctggacaa gaggagaggc agagaccccg agatgggtgg taagccacgg cgcaagaacc  1920
cacaggaggg cttgtacaac gaactgcaga aggacaagat ggccgaggcc tacagcgaga  1980
tcggcatgaa gggagagagg cgcagggca agggtcacga cggcctgtac caagggctgt  2040
ccaccgcaac caaggacacc tacgatgccc tgcacatgca ggccctccca ccaagg  2096
```

SEQ ID NO: 61            moltype = DNA  length = 2096
FEATURE               Location/Qualifiers
source                1..2096
                        mol_type = other DNA
                        organism = synthetic construct
SEQUENCE: 61

```
tctgtcctca ccccatcttc ccttcttttcc tgcaccgtta cgcttactcg catgtgcatt  60
gagtggtgca cgtgcttgaa caaacagcta cactcacatg ggggcgggtt ttcccgccct  120
gcggcctctc gcgaggccca cccctcccct tcctcccata actacagtgc tttggtaggt  180
aagcatcctg atccccgcg gaagctgctc acgtggcaac tgtgggacc cagacaggtt  240
atcaaaggca cccggtcttt ccgccttcag gagtatccct gctagtgaat tctagtaggg  300
ctctgcttgg tgccaacctc ccccaaatgc gcgctgcggg agtgctcttc cccaactcac  360
cctagtatcc tctcatgtgt gtgcttggtc agcatatctg agacgatgtt ccgctgtccc  420
agaccagtcc agtaatggac gggccagtgt gcgtagtcgt cttccggctt gtccggcgca  480
tgtttggtga accggtgggg taaggttggt gtgcccaacg cccgtacttt ggtgatacct  540
caagaccacc caggaatgcc agggaggtac cccgcttcac agcgggatct gaccctgggc  600
taattgtcta cggtggttct tcttgcttcc acttctttct actgttcatg atggctctgc  660
cagtgaccgc actgctgctg cccttagcct tactccttca cgcagccagg cccgacatcc  720
agatgaccca gaccaccagc tccctttccg caagcctcgg cgacagggtc accatctcct  780
gtcgggccag ccaggacatc agcaagtacc tgaactggta ccagcagaag cccgacgca  840
```

```
ccgtgaagct gctgatctac cacacctcac ggctgcactc aggcgtgccc tcacggttta   900
gcggatcagg cagcggcacc gactacagcc tgactatcag caacctggag caggaggaca   960
tcgccaccta cttctgccag cagggcaaca ccctgcccta caccttcgga ggcggcacca  1020
agctggagat caccggtggc ggtggttcag gtggcggagg ctcaggagga ggcggcagcg  1080
aggtgaagct gcaggagtca ggtccaggac tggtggcacc cagccagagc ctgagcgtga  1140
cttgcaccgt gtcaggcgtg agcctgccag actacggcgt gagctggatc cggcagcctc  1200
ctcggaaggg cttagagtgg ctgggcgtga tctgggacag cgagaccacc tactacaact  1260
cagccctgaa gagccggctg accatcatca aggacaacag caagagccag gtgttcctga  1320
agatgaacag cctgcagacc gacgacaccg ccatctacta ctgcgccaag cactactact  1380
acggcggcag ctacgccatg gactactggg gacagggtac cagcgtgacc gtgagcagca  1440
tcgaggtgat gtaccctcct ccctacctgg acaacgagaa gagcaacggc accatcatcc  1500
acgtgaaggg caagcacctg tgccctagcc ctttattccc cggcccctca aaaccctcct  1560
gggtgctggt cgtcgtcggt ggcgtgctgg catgctacag cctgctggtg accgtggcct  1620
tcatcatatt ctgggtccgg tcaaagcgga gccggttact gcacagcgac tacatgaaca  1680
tgactccacg gcgtccaggt cccactcgga agcactacca accctacgct cctccccgtg  1740
actttgctgc ctaccgtagc cgggtgaagt tctccaggag cgccgatgcc ccagcctacc  1800
agcagggcca gaaccagctc tacaatgagc ttaaccttgg caggcgggag gagtacgacg  1860
tgctgacaa gaggaggggc cgtgatcccg agatgggagg caagccccgt aggaagaatc  1920
cccaggaggg cctttacaac gagctccaga aggacaagat ggccgaggcc tacagcgaga  1980
tcggcatgaa gggagagcgt aggcgtggaa agggccacga cggcctgtac cagggcctga  2040
gcactgctac caaggacacc tacgacgccc tgcacatgca ggctcttcca ccccgg      2096
```

SEQ ID NO: 62          moltype =    length =
SEQUENCE: 62
000

SEQ ID NO: 63          moltype =    length =
SEQUENCE: 63
000

SEQ ID NO: 64          moltype =    length =
SEQUENCE: 64
000

SEQ ID NO: 65          moltype =    length =
SEQUENCE: 65
000

SEQ ID NO: 66          moltype =    length =
SEQUENCE: 66
000

SEQ ID NO: 67          moltype =    length =
SEQUENCE: 67
000

SEQ ID NO: 68          moltype =    length =
SEQUENCE: 68
000

SEQ ID NO: 69          moltype =    length =
SEQUENCE: 69
000

SEQ ID NO: 70          moltype =    length =
SEQUENCE: 70
000

SEQ ID NO: 71          moltype =    length =
SEQUENCE: 71
000

SEQ ID NO: 72          moltype =    length =
SEQUENCE: 72
000

SEQ ID NO: 73          moltype =    length =
SEQUENCE: 73
000

SEQ ID NO: 74          moltype =    length =
SEQUENCE: 74
000

SEQ ID NO: 75          moltype =    length =
SEQUENCE: 75
000

SEQ ID NO: 76          moltype =    length =

SEQUENCE: 76
000

SEQ ID NO: 77          moltype =    length =
SEQUENCE: 77
000

SEQ ID NO: 78          moltype =    length =
SEQUENCE: 78
000

SEQ ID NO: 79          moltype =    length =
SEQUENCE: 79
000

SEQ ID NO: 80          moltype =    length =
SEQUENCE: 80
000

SEQ ID NO: 81          moltype =    length =
SEQUENCE: 81
000

SEQ ID NO: 82          moltype =    length =
SEQUENCE: 82
000

SEQ ID NO: 83          moltype =    length =
SEQUENCE: 83
000

SEQ ID NO: 84          moltype =    length =
SEQUENCE: 84
000

SEQ ID NO: 85          moltype =    length =
SEQUENCE: 85
000

SEQ ID NO: 86          moltype =    length =
SEQUENCE: 86
000

SEQ ID NO: 87          moltype =    length =
SEQUENCE: 87
000

SEQ ID NO: 88          moltype =    length =
SEQUENCE: 88
000

SEQ ID NO: 89          moltype =    length =
SEQUENCE: 89
000

SEQ ID NO: 90          moltype =    length =
SEQUENCE: 90
000

SEQ ID NO: 91          moltype =    length =
SEQUENCE: 91
000

SEQ ID NO: 92          moltype =    length =
SEQUENCE: 92
000

SEQ ID NO: 93          moltype =    length =
SEQUENCE: 93
000

SEQ ID NO: 94          moltype =    length =
SEQUENCE: 94
000

SEQ ID NO: 95          moltype =    length =
SEQUENCE: 95
000

-continued

```
SEQ ID NO: 96          moltype =    length =
SEQUENCE: 96
000

SEQ ID NO: 97          moltype =    length =
SEQUENCE: 97
000

SEQ ID NO: 98          moltype =    length =
SEQUENCE: 98
000

SEQ ID NO: 99          moltype =    length =
SEQUENCE: 99
000

SEQ ID NO: 100         moltype = DNA  length = 1425
FEATURE                Location/Qualifiers
source                 1..1425
                       mol_type = other DNA
                       organism = synthetic construct
SEQUENCE: 100
atgggcgtgc ctacccagct gctcggtctc ctgctgctct ggatcaccga cgctatctgc  60
gacatccaaa tgacccagag tcccgcttcc ctcagcacct ccctgggtga gaccgtcacc  120
atccagtgcc aggcatccga ggacatctac agtggtctcg cctggtacca gcagaagcct  180
ggtaagtccc ctcagctgct gatctacggt gcttccgatc tgcaggacgg agtccctagc  240
cgcttctcag gctctggctc cggtacccag tactccctga agatcacatc catgcagacc  300
gaagacgagg gagtgtactt ctgccagcag gggctgacct accctcggac attcggcggt  360
ggaaccaagc tcgagctgaa gggaggtgga ggcagtggtg gcggaggatc tggtggtggt  420
ggctccgagg tccaactgca gcagtccggc gctgagctgg tgaggcccgg aaccagcgtc  480
aaactcagct gcaaggtgag cggggacacc atcaccttct actacatgca cttcgtcaag  540
cagaggcctg ggcagggtct tgaatggatc ggccggatcg atccagagga cgagtctaca  600
aagtactccg agaagttcaa gaacaaagca accctgaccg ccgacacaag ctccaacacc  660
gcctacctga agctgtccag cctcacctct gaggacaccg ccacctactt ctgcatctac  720
ggcgggtact acttcgacta ttggggccaa ggggtgatgg tcaccgtgtc ctctatcgag  780
ttcatgtatc ctcctcccta cctggacaac gagcggagca acggcaccat catccacatc  840
aaagagaagc acctctgcca cacccaatcc tctcccaaac tcttctgggc cctcgttgtg  900
gtcgcaggcg tgctcttctg ctacgggctg ctggtgactg tggccttgtg cgtgatctgg  960
accaacagta gacggaatcg gggaggtcag agcgactaca tgaacatgac acctcgcaga  1020
ccaggcctga cacggaagcc ctaccaacca tacgctcctg cccgggattt tgcagcatat  1080
cggccacggg ccaagtttag caggtccgca gagaccgcag ccaacctgca agaccctaac  1140
cagctgtaca acgagctgaa ccttggtcgc cgggaggagt acgacgtcct ggagaagaag  1200
agagcaggga tcccgagat gggcggaaag caacaacgcc ggcggaatcc tcaggagggt  1260
gtctacaacg ccctccagaa ggacaagatg gctgaggcct actccgagat cggcactaag  1320
ggcgagcgca gacggggaaa gggtcacgac gggctgtacc agggtctcag caccgcaacc  1380
aaggatacct acgacgccct gcacatgcaa accctcgcac cccgg              1425

SEQ ID NO: 101         moltype = DNA  length = 1452
FEATURE                Location/Qualifiers
source                 1..1452
                       mol_type = other DNA
                       organism = synthetic construct
SEQUENCE: 101
atggctctgc ctgtgacagc tctgctgctg cctctggctc tgcttctgca tgccgccaga  60
cctgacatcc agatgactca gagccccagc agcctgtcc cctctgtggg agacagagtg  120
acaattacct gccgggccag ccaggatgtg aatactgctg tcgcctggta tcaacaaaag  180
cctggcaagg cccctaagct cctgatctac agcgccagct ttctgtacag cggcgtgccc  240
agcagattct ccggaagcag aagcggcaca gatttcacac tgaccataag cagcctgcag  300
ccagaggatt tcgccaccta ctattgccag cagcactaca ccacacctcc aacctttggc  360
cagggcacca aggtcgagat taagagaaca ggcagcacat ctggctctgg caaacctggc  420
tctggcgagg gctctgaagt ccagctggtg gaatctggcg gaggactggt tcaacctggc  480
ggctctctga gactgtcttg tgccgcctcc ggcttcaaca tcaaggacac ctacatccac  540
tgggtccgac aagcccccag gcaaaggactt gagtgggtcg ccaggatcta ccccaccaac  600
ggctacacca gatacgccga ctctgtgaag ggcagattca ccatctctgc cgacaccagc  660
aagaataccg cctacctgca gatgaactcc ctgagagccg aagataccgc tgtgtattac  720
tgttccagat ggggaggcga cggcttctac gccatggatg tttggggcca aggcaccctc  780
gtgaccgttt cttctatcga agtgatgtac cctccacctt acctggacaa cgagaagtcc  840
aacggcacca tcatccacgt gaagggcaag cacctgtgtc cttctccact gttccccgga  900
cctagcaagc ctttctgggt gctcgttgtt gttggcgcgc tgctggcctc ttactctctg  960
ctggttaccg tggccttcat catctttttg gtccgaagca gcggagccg gctgctgcac  1020
tccgactaca tgaacatgac ccctagacgg cccggaccaa ccagaaagca ctaccagcct  1080
tacgctcctc ctagagactt cgccgcctac cggtccagag tgaagttcag cagatccgcc  1140
gatgctcccg cctatcagca gggccaaaac cagctgtaca acgagctgaa cctggggaga  1200
agagaagagt acgacgtgct ggacaagcgg agaggcagag atcctgaaat gggcggcaag  1260
cccagacgga gaatcctca gagggcctg tataatgagc tgcagaaaga caagatggcc  1320
gaggcctaca gcgagatcgg aatgaagggc gagcagcagaa gaggcaaggg acacgatgga  1380
ctgtaccagg gcctgagcac cgccaccaag gataccatg atgccctgca catgcaggcc  1440
ctgcctccaa ga                                              1452
```

-continued

```
SEQ ID NO: 102          moltype = DNA   length = 1464
FEATURE                 Location/Qualifiers
source                  1..1464
                        mol_type = other DNA
                        organism = synthetic construct
SEQUENCE: 102
atggctctgc ctgtgacagc tctgctgctg cctctggctc tgcttctgca tgccgccaga    60
cctgacatcc agatgactca gagccccagc agcctgtctg cctctgtggg agacagagtg   120
acaattacct gccgggccag ccaggatgtg aatactgctg tcctggta tcaacaaaag     180
cctggcaagg cccctaagct cctgatctac agcgccagct ttctgtacag cggcgtgccc   240
agcagattct ccggaagcag aagcggcaca gatttcacac tgaccataag cagcctgcag   300
ccagaggatt tcgccaccta ctattgccag cagcactaca ccacacctcc aacctttggc   360
cagggcacca aggtcgagat taagagaaca ggcagcacat ctggctctgg caaacctgga   420
tctggcgagg gctctgaagt ccagctggtg gaatctggcg gaggactggt tcaacctggc   480
ggctctctga gactgtcttg tgccgcctcc ggcttcaaca tcaaggacac ctacatccac   540
tgggtccgac aagccccagg caaaggactt gagtgggtcg ccaggatcta ccccaccaac   600
ggctacacca gatacgccga ctctgtgaag ggcagattca ccatctctgc cgacaccagc   660
aagaataccg cctacctgca gatgaactcc ctgagagccg aagataccgc tgtgtattac   720
tgttccagat ggggaggcga cggcttctac gccatggatg tttggggcca aggcaccctc   780
gtgaccgttt cttctaccac cacaccagct cctcggcctc caactcctgc tcctacaatt   840
gccagccagc ctctgtctct gagggcccga agcttgtagac ctgctgctgg cggagccgtg   900
catacaagag gactggattt cgcctgcgac atctacatct gggttcctct ggccggaaca   960
tgtggcgttc tgctgctgag cctggtcatc accctgtact gtaagcgggg cagaaagaag  1020
ctgctgtaca tcttcaagca gcccttcatg cggcccgtgc agaccacaca agaggaagat  1080
ggctgctcct gcagattccc cgaggaagaa gaaggcggct gcgagctgag agtgaagttc  1140
agcagatccg ccgatgctcc cgcctatcag cagggccaaa accagctgta caacgagctg  1200
aacctgggga gaagagaaga gtacgacgtg ctggacaagc ggagaggcag agatcctgaa  1260
atgggcggca gcccagacg gaagaatcct caagagggcc tgtataatga gctgcagaaa  1320
gacaagatgc cgaggccta cagcgagatc ggaatgaagg gcgagcgcag aagaggcaag  1380
ggacacgatg gactgtacca gggcctgagc accgccacca aggatcccta tgatgccctg  1440
cacatgcagg ccctgcctcc aaga                                          1464

SEQ ID NO: 103          moltype = DNA   length = 1479
FEATURE                 Location/Qualifiers
source                  1..1479
                        mol_type = other DNA
                        organism = synthetic construct
SEQUENCE: 103
atggcactcc cggtaaccgc cttattgctt cccttgccc tcttgctcca cgcagcacgc     60
cccgatatag tcttgactca atccccaccc agtttggcaa tgtcattagg caaacgagca   120
acaatttcat gtagggcatc cgaaagtgta acgattttgg ggagtcattt aattcattgg   180
taccaacaaa agcctggaca accccgacg ctcttgatcc aattagcatc taacgtccaa    240
accggagtcc ccgcacgatt ctcaggatcc ggttcccgga ctgattttac attaactatt   300
gatccggtag aggaagatga cgtcgctgtc tattattgtc ttcaaagtag gacgattcca   360
cggacattcg gtgtgcggaac taaattggag attaaaggtt ccacctctgg tagtgggaaa   420
cccgggtccg tgaagggtc cactaaaggc caaattcaac tcgttcaatc cggaccagaa    480
ctgaagaagc caggagaaac tgtcaaaata agctgtaaag cttccggtta tacatttaca    540
gattattcca taaattgggt gaaaaggggc ccaggaaaag ggttaaaagt gatgggttgg   600
attaatacag agactcggga acctgcatat gcttatgatt ttaggggaag gtttgccttt    660
tctctggaga cttccgcttc aactgcttat ctccaaatta ataatcttaa atatgaggac   720
acagcaacat acttctgtgc tttggactat agttatgcta tggattactg ggacacaagga   780
accagtgtca ctgtaagttc cgctgctgcg acgaccactc ctgcaccgcg accacccact   840
cctgcccta ctattgctag tcaaccactt agcttgcgac ctgaggcatg tcggcccgcg    900
gcaggtggcg cagtccacac caggggttta gactttgctt gtgatattta tatttgggca   960
ccactcgccg ggacttgcgg tgttcttctc ttgtcccttg ttataactct ttattgtaag  1020
cgcggaagga agaaattgtt atatattttc aaacaacctt ttatgcgacc cgtacaaaca  1080
actcaggaag aggacgggtg ttcttgtcgg tttccagaag aggaagaggg tgggtgtgaa  1140
ctccgggtca aatttagtag gtcagcagat gcgccggcgt accaacaagg ccaaaaccaa  1200
ctgtataatg aactcaatct cggtaggcgt gaggaatatg atgtccttga taaaaggcgt  1260
gggagagatc cagaaatggg cggaaaacca cggcgaaaga atccgcagga agggttatat  1320
aacgaacttc aaaaggataa aatggctgaa gcttattccg aaattggcat gaaaggagag  1380
cgacgtaggc gcaaagggca tgatggcctt taccaagggc tctcaaccgc tacaaaagat  1440
acttacgacg ctttacatat gcaagcactt ccacccagg                          1479

SEQ ID NO: 104          moltype = DNA   length = 1476
FEATURE                 Location/Qualifiers
source                  1..1476
                        mol_type = other DNA
                        organism = synthetic construct
SEQUENCE: 104
atggccctcc ccgtcacagc tctcctgctc ccactggccc ttcttttgca cgctgctcgc     60
cccgatatcg tgctcaccca gtcacctcca agccttgcca tgagcctcgg aaacgggct    120
accatctcct gccgggcttc agagtccgtc accatcctcg gtcacacct catccactgg    180
taccaacaga aaccagggca gcctcctacc tccttgatcc agttggcctc caacgtgcaa   240
actggggttc ccgccaggtt cagtggctcc ggatcccgga cagatttcac acttaccatc   300
gatcctgtgg aggaggacga tgtggccgtc tattactgcc tgcagtctcg caccatccct   360
cggaccttcg gtgtgaggcac caagctcgag atcaagggta cacctccggg ctctggaaag   420
ccaggctctg tgagggttc taccaagggc caaatccagc tggtccagtc tgggcccgag   480
ctgaagaaac ccggggagac cgtgaagatc tcctgcaagg cctccggtta taccttcacc   540
```

-continued

```
gactactcca tcaactgggt caagcgcgct cctggaaagg gcctcaagtg gatgggctgg      600
atcaacaccg aaaccgcga  gcctgcctat gcttacgact tcaggggccg gttcgctttc      660
tcactggaga cctccgcttc cacagcctac ctccagatca acaacctcaa gtacgaagac      720
accgccacct atttctgcgc tctcgactat tcctacgcta tggactactg gggtcagggc      780
acctctgtga ccgtctctag cgcagccgcc accacaacac cagccccacg gccacctact      840
cccgcaccca ccatcgcatc ccaaccactc agtctgaggc ccgaggcctg tagacctgct      900
gctggaggcg cagtgcatac ccgcggtctc gacttcgcct gcgacatcta tatctgggcc      960
ccattggcag gtacctgtgg cgtgctgctg ctgtcactcg tcatcaccct gtactgccga     1020
agtaagcgct ctaggctgtt gcacagcgac tacatgaaca tgacccaag  aagaccaggg     1080
cctacccgga agcactacca gccatacgca cctccccggg actttgccgc ctatcggtct     1140
cgggtgaagt tctcacgctc cgctgatgcc ccagcatacc agcaggggca gaaccagctg     1200
tacaatgagc tcaacctcgg tcgccgcgaa gagtacgacg tgctcgacaa gagaagggc      1260
agggaccctg agatgggagg caagcccgc  agaaagaatc cccaggaagg tctgtacaac     1320
gagctgcaaa aggataagat ggctgaggcc tacagcgaga tcggcatgaa gggcgaaagg     1380
agacggggaa agggccacga cgggctctac cagggactct ccaccgccac caaggacacc     1440
tacgacgccc tccacatgca ggctctgcca cccagg                              1476

SEQ ID NO: 105        moltype = DNA   length = 1458
FEATURE               Location/Qualifiers
source                1..1458
                      mol_type = other DNA
                      organism = synthetic construct
SEQUENCE: 105
atggcacttc ccgtcaccgc tctcctgctg cccctcgcac tgctgctcca tgcagcccgc       60
ccagacatcg tcctgaccca gtcccctccc tccctcgcaa tgtccctcgg gaaacgggcc      120
accatcagct gccgggcctc tgagtcagtg acaatcctcg gaagccatct gatccattgg      180
taccagcaga aacccggtca gcctccaacc ctcctcatcg agctggcctc caacgtgcag      240
acaggagtcc ccgctcggtt ctcaggcagc ggttccagga ccgacttcac cctgaccatc      300
gaccccgtgg aagaggacga tgtggctgtg tactactgcc tccagtcccg gaccatccca      360
cggaccttcg gaggtgggac aaagctggag atcaaaggca gcaccagcgg ttctggcaag      420
ccagggtcag gtgaggggag cacaaagggt cagatccagc tggtgcagag cggtcccgag      480
ctgaagaagc ccgggggagac cgttaagatc tcctgcaagg ctagcgggta caccttcacc      540
gactatagta tcaactgggt caagcgcgct cctggcaagg ggctcaagtg gatggggtgg      600
atcaacaccg aaaccaggga gcccgcatac gcttatgact ttcggggccg gttcgccttc      660
tccctggaga ccagcgcctc taccgcctac ctccagatca acaacctgaa gtacgaggac      720
accgccacct acttctgcgc actcgactac tcctacgcta tggactactg gggtcagggt      780
acctccgtca ccgtctccag catcgaggtc atgtaccctc ctccctacct ggacaacgag      840
aagtccaacg gcaccatcat ccatgtgaag ggcaagcatc tctgccccag cccactgttc      900
cccggaccct ctaagccctt ctgggtcctg gtcgtcgtcg gcggtgttct ggcttgctac      960
agcttgctgg tcaccgtcgc cttcatcatc ttctgggtgc gctccaagag gagccggctg     1020
ctgcatagcg actacatgaa catgacccct agaaggcctg gtccaacccg caagcactac     1080
cagccttacg cccctccacg ggacttcgca gcctaccggt cacgggtgaa gttctctcgg     1140
agcgcagatg ccccagcata ccagcagggc cagaaccagc tgtacaacga acttaacctt     1200
ggtcggcggg aggaatacga tgtgctggac aagcgcaggg tcgggatcc  tgaaatgggc     1260
gggaaaccac gccggaagaa cccacaggag gggctctata cgagctcca  aaaggataag     1320
atggctgagc cttacagcga gattggaatg aagggagaaa gaagacgggg caagggtcac     1380
gacgggttgt accaggtctc tgagcaccgc caccaggaca cctacgacgc cctccacatg     1440
caagcccttc cacccgc                                                    1458

SEQ ID NO: 106        moltype = DNA   length = 1494
FEATURE               Location/Qualifiers
source                1..1494
                      mol_type = other DNA
                      organism = synthetic construct
SEQUENCE: 106
atggctctcc ccgtgaccgc tctgctgctc cctctggccc tccttctgca cgcagccaga       60
ccacaggtca agctggagga gtctggtggc ggtctggtgc aggcaggag  gagcctgagg      120
ctgagctgtg cagcttccga gcacacattc tcaagccacg tcatggggtg gttcagacag      180
gctcccggta aagagaggga gtccgtcgcc gtgatcggat ggcgggacat ctccacctcc      240
tacgccgact ctgtgaaggg ccggttcaca atctcacgcg ataatgccaa gaagacactg      300
tatctgcaga tgaattcctt gaagcccgaa gacaccgccg tctattactg tgctgctaga      360
cggatcgacg ctgccgactt cgacagctgg ggacagggta cccaagtgac cgtttcctcc      420
ggaggcggag gttctggagg aggtgggtca ggtggaggtc gctccgaggt gcagctggtc      480
gagtctgggc gtggcttggt ccagcctgga ggcagtctca gactctcctg cgctgcttca      540
gggcggacct tcaccatggg ctggttcagg caggccccag gtaaggagag ggagttcgtg      600
gccgccatct ccctctcccc taccctggca tactacgctg agtccgtgaa gggacggttt      660
accatctccc gggataacgc aaagaacact gtggtcctcc aaatgaactc cctcaaaccc      720
gaggacaccg ctctctacta ttgtgccgca gatcggaaga gcgtcatgtc catccggccc      780
gattactggg gccaaggcac acaggtgact gtgtccagca cctccaccac caccccagca      840
ccaaggcctc caaccctgc  accaaccatc gcctccagc  cactgtcttt gcggccagaa      900
gcatgccgcc cagcagcagg tggagccgtg catacaagag gcctggactt cgcctgcgat      960
atctacatct gggctcctct ggccggaaca tgcggagtcc tgctcttgtc cctggtgatc     1020
accctgtact gcaagcgggg tcggaagaag ctcctctaca tcttcaagca gcccttcatg     1080
agaccgtgc  agaccaccca ggaggaggac gggtgctcat gcaggttccc cgaagaggag     1140
gaggtggct  gtgagctgcg ggtgaagttc agcaggtcag cagacgcccc tgcctatcag     1200
cagggccaaa accagttgta caacgagctg aatctgggga cgggagga  gtacgatgtc      1260
cttgacaaga aaggggccgg gatccagag  atgggcggga gccaagacg  gaagaatcct      1320
caggagggtc tgtataacga gctgcagaag acaagatgg  ccgaggccta ctccgagatc      1380
ggcatgaaag gggagcgccg cagaggaaaa ggtcacgatg gtctgtacca ggggttgagc     1440
```

```
accgctacca aggatactta cgacgctctg cacatgcaag ctctgccacc ccgg            1494

SEQ ID NO: 107          moltype = DNA  length = 1491
FEATURE                 Location/Qualifiers
source                  1..1491
                        mol_type = other DNA
                        organism = synthetic construct
SEQUENCE: 107
atggcactcc ccgttaccgc ccttctgctg cctctcgcct tgctgctgca cgcagccaga     60
ccacaggtca agctggagga gtctggtggc gggctcgttc aagcaggtcg gagtctccgc     120
ctgtcttgcg cagcatcaga gcataccttc tcctcacacg tgatggggtg gttcaggcaa     180
gctcccggta aggagaggga gtccgtggcc gttatcggct ggcgcgatat cagcacctcc     240
tacgcagaca gcgttaaggg ccggttcact atctccaggg acaacgctaa gaagacactc     300
tacctccaga tgaacagtct gaagcccgag gacaccgcag tgtactattg cgctgctcgg     360
cggatcgatg ctgccgactt cgacagctgg ggtcaaggga cccaggtcac cgtttccagc     420
ggaggtggcg gaagtggtgg cggaggatca ggtggtggag gctccgaggt ccagctggtg     480
gaatcaggag gcggcttggt gcaggctggt gggtctttgc ggttgtcctg cgcagcttcc     540
ggcaggacct tcaccatggg atggttcaga caagccccag gtaaggagcg ggagtttgtc     600
gccgcaatct cactgtctcc caccctcgct tactacgccg agagtgtgaa ggggcgcttc     660
acaatcagtc gcgacaacgc aaagaacacc gtcgtcctgc aaatgaactc cctgaagcct     720
gaggataccg cactctatta ctgcgccgcc gatcggaaga gcgtcatgtc catccggccc     780
gactattggg gccaaggcac ccaagtgacc gtcagctcca ctccacaac cactcccgcc     840
ccaagaccac ctaccccagc cccaacaatc gcatcccagc ctctgtccct tcggcccgaa     900
gcttgtcgcc ctgcagcagg tggagcagtg cacaccgggg gactggactt cgcctgcgac     960
atctacatct gggcaccccct ggctggaacc tgcggcgtgt tgctgctgag cctggtgatc     1020
accctctact gccgctctaa gagaagccgg ctgctgcata cggctactac gaacatgacc     1080
cctaggagac caggacccac ccggaagcac taccagcctt acgctcctcc acgggatttc     1140
gctgcttacc gcagccgggt gaagtttttcc aggtcagctg acgcccctgc ctaccagcag     1200
ggccagaacc aattgtacaa cgaactgaat ctgggacggc gcgaggaata cgacgtcctg     1260
gacaagaggc ggggtagaga tcccgacatg gggcgggaaac ctcggcggaa gaaccctcag     1320
gaggggctct acaacgagct gcagaaggat aagatggccg aagcctactc cgagatcggg     1380
atgaagggtg aacggaggag gggcaaggga cacgacggcc tgtatcaggg cctcagcacc     1440
gctaccaagg acacctacga cgccctgcac atgcaggctc tcccaccacg g              1491

SEQ ID NO: 108          moltype = DNA  length = 1476
FEATURE                 Location/Qualifiers
source                  1..1476
                        mol_type = other DNA
                        organism = synthetic construct
SEQUENCE: 108
atggctcttc ccgtcaccgc tttgctgctg cccctggcac tcctcctcca tgctgctcgg     60
cctcaggtga agctggagga gagtggtggc ggtctggtgc aagctggcag atctctgcgc     120
ctgtcttgcg cagccagcga acacaccttc tcctcccacg tgatggggtg gtttcggcag     180
gcacccggga aagagcgcga gtccgtcgca gtcatcgggt ggcgggacat ctctaccagc     240
tacgcagatt ccgtcaaggg ccggttcacc atttcccggg ataacgctaa gaagaccctc     300
tacctgcaaa tgaactctct gaagcccgaa gacaccgccg tctactattg cgcagcaagg     360
cgcatcgacg ctgccgactt cgactcttgg ggccaaggaa cccaggtcac cgtgtcttcc     420
ggaggaggag gctccggtgg tggaggttct ggaggtggcg gctcagaggt gcagctcgtg     480
gagagcggtg gtggactcgt tcaggcaggc ggcagtttgc ggctgtcctg tgcagcctcc     540
ggtcgcactt tcactatggg atggttccgc caggctcctg gtaaagaaag ggagttcgtg     600
gccgccatca gtctgagccc caccctcgca tactacgccg agagcgtgaa gggtaggttc     660
actatcagcc gggacaacgc caagaacacc gtggtgctcc agatgaattc cctgaagcct     720
gaggataccg ccctctacta ctgcgctgcc gaccgcaaga gcgtgatgag catccggcct     780
gactattggg gtcagggggac acaggtgacc gtcagcagca tcgaggtgat gtatccacca     840
ccctacctcg acaacgagaa gtccaacggc accatcatcc acgtcaaggg gaagcacctc     900
tgcccttccc ctctgttccc tggcccctca aagcccttct gggtcctggt ggtggttggt     960
ggggtgctgg cttgctactc cctgctcgtg accgtggctt tcatcatctt ctgggttcgg     1020
agcaaacggt ccagactgct gcactccgac tacatgaaca tgaccccaag aagacctggg     1080
cccacacgga agcattacca accctatgca ccacctcggg atttcgccgc ctacagatcc     1140
cgggtcaagt tctccaggtc cgccgatgca ccagcctatc agcaggggca aaaccagctg     1200
tataatgagc tgaaccttgg acggcgcgag gagtacgacg tgctcgacaa aagacgcggt     1260
cgcgacccag agatgggcgg caagcctaga cgcaagaatc cccaggaggg gctctataac     1320
gagttgcaga aggataagat ggccgaggcc tacagcgaga tcgggatgaa aggcgaaaga     1380
cggcgcggaa agggtcacga cggactctac cagggcctga gcacagccac caaagacacc     1440
tacgacgctc tgcatatgca agcactgcct cccgg                                1476

SEQ ID NO: 109          moltype = DNA  length = 1095
FEATURE                 Location/Qualifiers
source                  1..1095
                        mol_type = other DNA
                        organism = synthetic construct
SEQUENCE: 109
atggctctcc ccgtgaccgc tctcctcctt cccttggcct tgttgctgca cgccgcaagg     60
cctcaggtga agctggagga atccggaggc ggactcgtcc aagcaggtcg gccctcagg      120
ctgtcttgcg ctgccagcga gcacaccttc tctagccacg tgatgggttg gttcagacag     180
gccccaggaa aggagcggga tccgtggca gtgatcggct ggcgggacat cagcacctcc     240
tacgccgact ccgtcaaggg ccggttcacc atcagccgcg acaacgccaa gaagaccctc     300
tacctgcaga tgaacagcct caagcctgag gacaccgccg tgtactactg cgccgccaga     360
aggatcgacg ccgcagactt cgactcctgg ggtcagggaa cccaggtgac cgtgtcctcc     420
```

```
acctctacca ccacaccagc acccagacct cctactcccg ctcccaccat cgcttcccag  480
cccctgtccc tcagacccga agcctgcaga ccagcagctg gcggtgcagt gcacaccagg  540
ggtcttgact tcgcctgtga catctacatc tgggctccac tggctgggac ttgcggcgtt  600
ctgctgctga gctggtgat cacccctgtac tgcaagcggg gccggaagaa gctgctctac  660
atcttcaagc agccttttcat gcggcccgtt cagaccaacc aggaggaaga cgggtgcagt  720
tgccgcttcc ctgaggagga ggagggagga tgcgagctgc gggtcaagtt ctctcggtcc  780
gctgatgccc cagcctacca gcaggccag aaccagctct ataacgagct gaacctcggt  840
aggcgggagg agtacgacgt cctggacaaa aggaggggac gggatcctga gatgggagga  900
aagccacggc ggaagaaccc tcaagagggg ctgtacaacg aactccagaa ggacaagatg  960
gctgaggctt attctgagat cggcatgaag ggagagcgca gacgcggcaa gggacacgat  1020
ggcctgtatc agggactgag caccgccacc aaggatacct acgacgccct ccatatgcag  1080
gctctcccac cacgg                                                    1095
```

```
SEQ ID NO: 110          moltype = DNA  length = 1092
FEATURE                 Location/Qualifiers
source                  1..1092
                        mol_type = other DNA
                        organism = synthetic construct
SEQUENCE: 110
atggcactgc ccgtcacagc tctgctgctg cccttggccc tcttgttgca cgcagcacgg  60
ccagaggtgc aacttgtcga gagcggtggt ggccttgtgc aggccggagg cagtttgcgc  120
ctcagttgtg cagcttctgg ccggaccttc accatggcct ggttcagaca ggcccctggt  180
aaggaacgcg agttcgtggc cgccatcagc ctgtccccaa ccctggccta ctacgcagag  240
agcgtgaagg gtcggttcac catctcccgc gacaacgcaa agaacaccgt ggtgctccag  300
atgaactccc tgaagccaga agacaccgcc ctgtactact gcgcagccga ccggaagagc  360
gtgatgtcca tccgccctga ctactggggc caaggcacac aggtcacagt gtccagcacc  420
tccactacca ctccagctcc acgccctcca acacccggac caaccatcgc cagccagcct  480
ctgagtctga cacccgaagc atgccggcca gctgctggag gtgccgtgca caccagaggg  540
ctggacttcg cctgcgacat ctacatctgg gctcctctgg ccggaacttg cggggtgctg  600
ctcctctcac tggtcatcac cctgtactgc aagaggggca ggaagaagct cctgtacatc  660
ttcaagcagc ccttcatgcg gccagtccag acaacccagg aggaagacg atgcagctgt  720
cgcttccccg aggaggagga aggcggctgc gaattgcggg tcaagttcag cagatccgct  780
gacgctcctg cctaccaaca gggacagaac cagctctaca acgagctgaa cctgggaagg  840
cgggaggagt acgacgtcct ggacaagaga agaggacgcg accccgagat gggaggtaag  900
cccagacgca agaaccctca agagggactg tataacgagc tgcagaagga caagatggcc  960
gaggcctaca gcgagatcgg catgaagggt gaaagaagac ggggaaaggg gcacgacggt  1020
ctgtatcagg ggctctccac cgcaaccaag gatacctatg acgctctgca catgcaggca  1080
ctccctccac gc                                                       1092
```

```
SEQ ID NO: 111          moltype = DNA  length = 1077
FEATURE                 Location/Qualifiers
source                  1..1077
                        mol_type = other DNA
                        organism = synthetic construct
SEQUENCE: 111
atggcactgc ccgtgaccgc tctgctgctg cctctcgccc tgctgctgca tgctgccagg  60
ccccaagtca agctcgagga gtctggtggt gggctcgtcc aagctggcag gtccctgaga  120
ctgagttgtg ccgcctccga gcacactttc agctctcacg tgatgggctg gttcaggcag  180
gcacccggta aggagcggga gtctgtggct gttatcgggt ggcgggatat ctctacctcc  240
tacgccgact ccgtcaaggg ccggttcacc atctccaggg acaacgcaaa gaagaccctc  300
tacctccaga tgaactcact caagcccgag gacaccgctg tgtactactg cgcagccgaa  360
cgcatcgatg ccgcagactt cgactcctgg ggccaaggta cccaagtgac agtgtccagc  420
atcgaggtga tgtacccacc tccctacctc gacaacgaga gagcaacgg caccatcatc  480
cacgtgaagg ggaagcacct gtgtccctct cccctttcc caggaccctc caagccattc  540
tgggtcctgg tcgttgtcgg aggcgtgctc gcttgctatt ccctgctcgt caccgtggcc  600
ttcatcatct tctgggtgcg gtccaagaga tcccggctgc tgcactctga ttacatgaac  660
atgacaccca ggaggccagg gcctaccagg aagcactacc agccctacgc tcctccacgc  720
gacttcgcag cataccggtc ccgcgtcaag ttctcccggt ccgcagatgc tccagcctat  780
cagcagggcc agaaccagct gtacaacgaa ctcaatttgg gaggcgcga ggagtatgat  840
gtgctcgata agagaagggg ccgggatcct gagatgggga gcaagcccag acggaagaac  900
cctcaggagg gcctgtacaa tgagctgcag aaggacaaga tggccgaggc ctactccgag  960
atcgggatga agggtgaaag aaggaggggt aaggggcacg acgggctcta ccaaggcctg  1020
agcaccgcta ccaaggacac ctacgatgca ctgcatatgc aagccctgcc accacgg  1077
```

```
SEQ ID NO: 112          moltype = DNA  length = 1074
FEATURE                 Location/Qualifiers
source                  1..1074
                        mol_type = other DNA
                        organism = synthetic construct
SEQUENCE: 112
atggccctcc ctgtcacagc cctcttgctg cccctcgcac tccttctgca cgcagctcgg  60
cctgaggtcc agctggtcga gagtggaggc ggactggtcc aggcaggtgg gagtcttcgg  120
ctttcctgcg cagcttccgg acggaccttc accatgggct ggttccggca ggcacctggg  180
aaggagaggg agttcgttgc cgctatcagc ctctcaccaa ccctggccta ctatgcagag  240
agcgtcaagg gccgcttcac catcagccgc gacaacgcca agaacaccgt cgtgctgcag  300
atgaactccc tcaagcccga ggataccgcc ctgtactact gcgctgccga tcggaagtcc  360
gtcatgtcca ttcggcccga ctactgggga cagggcacac aggtgaccgt cagcagcatc  420
gaggtcatgt accctccacc ctacctggac aacgagaaga gcaacgggac catcatccac  480
gtgaagggga agcacctctg tccaagtccc ctcttcccag gaccctccaa gccattctgg  540
```

```
gtcctcgtgg tggttggagg agtgctcgcc tgctactctc tgctggtgac cgtcgccttc  600
atcatcttct gggtgcggtc caagcggtct cgcctcctcc actccgacta catgaacatg  660
acaccacgca gacctgggcc cactaggaag cactatcagc cctatgcacc accccgggat  720
ttcgcagcct accggtcacg ggtgaagttc agcagatccg cagacgcacc agcctaccag  780
cagggcaga accagctgta taacgagctg aacctcgtc gcagggagga gtacgatgtc  840
ctggataaga aaggggcag ggatcccgag atgggtggca agcccagacg gaagaatcct  900
caggagggc tctacaacga gctgcagaag gacaagatgg ccgaggctta ctcagagatc  960
ggcatgaaag gggagaggag gcgcggaaaa ggccacgacg gcctctacca gggactgtcc  1020
accgcaacca aggataccta cgacgccctg cacatgcaag ccctcccacc tcgg  1074
```

SEQ ID NO: 113          moltype = DNA   length = 2232
FEATURE                 Location/Qualifiers
source                  1..2232
                        mol_type = other DNA
                        organism = synthetic construct
SEQUENCE: 113

```
atggctctcc ccgtgaccgc tctcctcctt cccttggcct tgttgctgca cgccgcaagg  60
cctcaggtga agctggagga atccgaggc ggactcgtcc aagcaggtcg gtccctcagg  120
ctgtcttgcg ctgccagcga gcacaccttc tctagccacg tgatgggttg gttcagacag  180
gccccaggaa aggagcggga atccgtggca gtgatcggct ggcgggacat cagcacctcc  240
tacgccgact ccgtcaaggg ccggttcacc atcagccgcg acaacgccaa gaagaccctg  300
tacctgcaga tgaacagcct caagcctgag gacaccgccg tgtactactg cgccgccaga  360
aggatcgacg ccgcagactt cgactcctgg ggtcagggaa cccaggtgac cgtgtcctcc  420
acctctacca ccacaccagc acccagacct cctactcccg ctcccaccat cgcttcccag  480
cccctgtccc tcagacccga agcctgcaga ccagcagctg gcggtgcagt gcacaccagg  540
ggtcttgact tcgcctgtga catctacatc tgggctccac tgggctgggac ttgcggcgtt  600
ctgctgctga gcctggtgat caccctgtac tgcaagcggg gccggaagaa gctgctctac  660
atcttcaagc agcctttcat gcggcccgtt cagaccaccc aggaggaaga cgggtgcagt  720
tgccgcttcc ctgaggagga ggaggagga tgcgagctgc gggtcaagtt ctctcggtcc  780
gctgatgcc cagcctacca gcagggccaa aaccagctct ataacgagct gaacctcggt  840
aggcgggagg agtacgacgt cctggacaaa aggaggggac gggatcctga gatgggagga  900
aagccacggc ggaagaaccc tcaagagggg ctgtacaacg aactccagaa ggacaagatg  960
gctgaggctt attctgagat cggcatgaag ggagagcgca gacgcggcaa gggacacgat  1020
ggcctgtatc agggactgag caccgccacc aaggatacct ccgacgccct ccatatgcag  1080
gctctcccac cacggggatc tggcgaaggc agaggatctc tgctgacatg cggcgacgtg  1140
gaagagaacc ctggacctat ggccctccct gtcacagccc tcttgctgcc cctcgcactc  1200
cttctgcacg cagctcggcc tgaggtccag ctggtcgaga gtggaggcgg actggtccag  1260
gcaggtggga gtcttcggct ttcctgcgca gcttccggac ggaccttcac catgggttgg  1320
ttccgggcagg cacctgggaa ggagagggag ttcgttgccg ctatcagcct ctcaccaacc  1380
ctggcctact atgcagagag cgtcaagggc cgcttcacca tcagccgcga caacgccaag  1440
aacaccgtcg tgctgcagat gaactccctc aagcccgagg ataccgccct gtactactgc  1500
gctgccgatc ggaagtccgt catgtccatt cggcccgact actggggaca gggcacacag  1560
gtgaccgtca gcagcatcga ggtcatgtac cctccaccct acctggacaa cgagaagagc  1620
aacgggacca tcatccacgt gaaggggaag cacctctgtc caagtcccct cttcccagga  1680
ccctccaagc cattctgggt cctcgtggtg gttggaggag tgctgcctg ctactctctg  1740
ctggtgaccg tcgccttcat catcttctgg gtgcggtcca agcggtctcg cctcctccac  1800
tccgactaca tgaacatgac accacgcaga cctgggccta ctaggaagca ctatcagccc  1860
tatgcaccac cccgggattt cgcagcctac cggtcacggg tgaagttcag cagatccgca  1920
gacgcaccag cctaccagca ggggcagaac cagctgtata acgagctgaa cctcggtcgc  1980
agggaggagt acgatgtcct ggataagaga aggggcaggg atcccgagat gggtggcaag  2040
cccagacgga gaatcctca ggagggctc tacaacgagc tgcagaagga caagatggcc  2100
gaggcttact cagagatcgg catgaaaggg gagaggaggc gcggaaaagg ccacgacggc  2160
ctctaccagg gactgtccac cgcaaccaag gatacctacg acgccctgca catgcaagcc  2220
ctcccacctc gg  2232
```

SEQ ID NO: 114          moltype = DNA   length = 2232
FEATURE                 Location/Qualifiers
source                  1..2232
                        mol_type = other DNA
                        organism = synthetic construct
SEQUENCE: 114

```
atggcactgc ccgtcacagc tctgctgctg cccttggccc tcttgttgca cgcagcacgg  60
ccagaggtga aacttgtcga gagcggtggt ggccttgtgc aggccggagg cagtttgcgc  120
ctcagttgtg cagcttctgg ccggaccttc accatggcac ggttcagaca ggcccctggc  180
aaggaacgcg agttcgtggc cgccatcagc ctgtccccaa ccctggccta ctacgcagag  240
agcgtgaagg tcggttcac catctcccgc gacaacgcaa agaacaccgt ggtgctccag  300
atgaactccc tgaagccaga agacaccgcc ctgtactact cgcagccga ccggaagagc  360
gtgatgtcca tccgccctga ctactggggc caaggcacac aggtcacagt gtccagcacc  420
tccactacca ctccagctcc acgccctcca acacccgcac caaccatcgc cagccagcct  480
ctgagtctga cccgaagc atgccggcca gctgctggag gtgccgtgca caccagaggg  540
ctggacttcg cctgcgacat ctacatctgg gctcctctgg ccggaacttg cggggtgctg  600
ctcctctcac tggtcatcac cctgtactgc aagaggggca ggaagaagct cctgtacatc  660
ttcaagcagc ccttcatgcg gccagtccag acaacccagg aggaagacgg atgcagctgt  720
cgcttcccca ggaggaggga ggggctgc gaattgcggg tcaagttcag cagatccgct  780
gacgctcctg cctaccaaca gggacagaac cagctctaca cgagctgaa cctgggaagg  840
cgggaggagt acgacgtcct ggacaagaga agaggacgcg accccgagat gggaggtaag  900
cccagacgca gaaccctca gagggactg tataacgagc tgcagaagga caagatggcc  960
gaggcctaca gcgagatcgg catgaagggt gaaagaagac ggggaaaggg cacgacggt  1020
ctgtatcagg ggctctccac cgcaaccaag gatacctatg acgctctgca catgcaggca  1080
```

-continued

```
ctccctccac gcggatctgg cgaaggcaga ggatctctgc tgacatgcgg cgacgtggaa      1140
gagaaccctg gacctatggc actgcccgtg accgctctgc tgctgcctct cgccctgctg      1200
ctgcatgctg ccaggcccca agtcaagctc gaggagtctg gtggtgggct cgtccaagct      1260
ggcaggtccc tgagactgag ttgtgccgcc tccgagcaca ctttcagctc tcacgtgatg      1320
ggctggttca ggcaggcacc cggtaaggag cgggagtctg tggctgttat cgggtggcag      1380
gatatctcta cctcctacgc cgactccgtc aagggccggt tcaccatctc cagggacaac      1440
gcaaagaaga ccctctacct ccagatgaac tcactcaagc ccgaggacac cgctgtgtac      1500
tactgcgcag ccagacgcat cgatgccgca gacttcgact cctgggggcca aggtacccaa      1560
gtgacagtgt ccagcatcga ggtgatgtac ccacctccct acctcgacaa cgagaagagc      1620
aacggcacca tcatccacgt gaaggggaag cacctgtgtc cctctcccct tttcccagga      1680
ccctccaagc cattctgggt cctggtcgtt gtcggaggcg tgctcgcttg ctattccctg      1740
ctcgtcaccg tggccttcat catcttctgg gtgcggtcca agagatcccg gctgctgcac      1800
tctgattaca tgaacatgac acccaggagg ccagggccta ccaggaagca ctaccagccc      1860
tacgctcctc cacgcgactt cgcagcatac cggtcccgcg tcaagttctc ccggtccgca      1920
gatgctccag cctatcagca gggccagaac cagctgtaca cgaactcaa tttggggagg       1980
cgcgaggagt atgatgtgct cgataagaga aggggccggg atcctgagat gggaggcaag      2040
cccagacgga agaaccctca ggagggcctg tacaatgagc tgcagaagga caagatggcc      2100
gaggcctact ccgagatcgg gatgaagggt gaaagaagga ggggtaaggg gcacgacggg      2160
ctctaccaag gcctgagcac cgctaccaag gacacctacg atgcactgca tatgcaagcc      2220
ctgccaccac gg                                                          2232
```

SEQ ID NO: 115          moltype = DNA   length = 1479
FEATURE              Location/Qualifiers
source               1..1479
                      mol_type = other DNA
                      organism = synthetic construct SEQUENCE: 115
```
atggcactcc cggtaaccgc cttattgctt ccccttgccc tcttgctcca cgcagcacgc       60
cccgatatag tcttgactca atccccaccc agtttggcaa tgtcattagg caaacgagca      120
acaatttcat gtagggcatc cgaaagtgta acgattttgg ggagtcattt aattcattgg      180
taccaacaaa agcctggaca accccccgacg ctcttgatcc aattagcatc taacgtccaa      240
accggagtcc ccgcacgatt ctcaggatcc ggttcccgga ctgattttac attaactatt      300
gatccggtag aggaagatga cgtcgctgtc tattattgtc ttcaaagtag gacgattcca      360
cggacattcg gtggcggaac taaattggag attaaaggtt ccacctctgg tagtgggaaa      420
cccgggtccg gtgaagggtc cactaaaggc caaattcaac tcgttcaatc cggaccagaa      480
ctgaagaagc caggagaaac tgtcaaaata agctgtaaag cttccggtta tacatttaca      540
gattattcca taaattgggt gaaaagggcg ccaggaaaag ggttaaagtg gatgggttgg      600
attaatacag agactcggga acctgcatat gcttatgatt ttaggggaag gtttgccttt      660
tctctggaga cttccgcttc aactgcttat ctccaaatta ataatcttaa atatgaggac      720
acagcaaacat acttcgtgtgc tttggactat agttatgcta tggattactg gggacaagga      780
accagtgtca ctgtaagttc cgctgctgcg acgaccactc ctgcaccgcg accaccccact      840
cctgcccta ctattgctag tcaaccactt agcttgcgac ctgaggcatg tcggcccgcg       900
gcaggtggcg cagtccacac caggggttta gactttgctt gtgatattta tatttgggcag      960
ccactcgccg ggacttgcgg tgttcttctc ttgtcccttg ttataactct ttattgtaag     1020
cgcggaagga agaaattgtt atatatttc aaacaacctt ttatgcgacc cgtacaaaca      1080
actcaggaag aggacgggtg ttcttgtcgg tttccagaag aggaagaggg tgggtgtgaa     1140
ctccgggtca aatttagtag gtcagcagat gcgccggcgt accaacaagg ccaaaaccaa     1200
ctgtataatg aactcaatct cggtaggcgt gaggaatatg atgtccttga taaaaggcgc     1260
gggagagatc cagaaatggg cggaaaacca cggcgaaaga atccgcagga agggttatat     1320
aacgaacttc aaaaggataa aatggctgaa gcttattccg aaattggcat gaaaggagag     1380
cgacgtaggg gcaaagggca tgatggcctt taccaagggc tctcaaccgc tacaaaagat     1440
acttacgacg ctttacatat gcaagcactt ccacccagg                            1479
```

SEQ ID NO: 116          moltype = AA   length = 475
FEATURE              Location/Qualifiers
source               1..475
                      mol_type = protein
                      organism = synthetic construct SEQUENCE: 116
```
MGVPTQLLGL LLLWITDAIC DIQMTQSPAS LSTSLGETVT IQCQASEDIY SGLAWYQQKP       60
GKSPQLLIYG ASDLQDGVPS RFSGSGSGTQ YSLKITSMQT EDEGVYFCQQ GLTYPRTFGG      120
GTKLELKGGG GSGGGGSGGG GSEVQLQQSG AELVRPGTSV KLSCKVSGDT ITFYYMHFVK      180
QRPGQGLEWI GRIDPEDEST KYSEKFKNKA TLTADTSSNT AYLKLSSLTS EDTATYFCIY      240
GGYYFDYWGQ GVMVTVSSIE FMYPPPYLDN ERSNGTIIHI KEKHLCHTQS SPKLFWALVV      300
VAGVLFCYGL LVTVALCVIW TNSRRNRGGQ SDYMNMTPRR PGLTRKPYQP YAPARDFAAY      360
RPRAKFSRSA ETAANLQDPN QLYNELNLGR REEYDVLEKK RARDPEMGGK QQRRRNPQEG      420
VYNALQKDKM AEAYSEIGTK GERRRGKGHD GLYQGLSTAT KDTYDALHMQ TLAPR           475
```

SEQ ID NO: 117          moltype = AA   length = 484
FEATURE              Location/Qualifiers
source               1..484
                      mol_type = protein
                      organism = synthetic construct SEQUENCE: 117
```
MALPVTALLL PLALLLHAAR PDIQMTQSPS SLSASVGDRV TITCRASQDV NTAVAWYQQK       60
PGKAPKLLIY SASFLYSGVP SRFSGSRSGT DFTLTISSLQ PEDFATYYCQ QHYTTPPTFG      120
QGTKVEIKRT GSTSGSGKPG SGEGSEVQLV ESGGGLVQPG GSLRLSCAAS GFNIKDTYIH      180
WVRQAPGKGL EWVARIYPTN GYTRYADSVK GRFTISADTS KNTAYLQMNS LRAEDTAVYY      240
CSRWGGDGFY AMDVWGQGTL VTVSSIEVMY PPPYLDNEKS NGTIIHVKGK HLCPSPLFPG      300
```

-continued

```
PSKPFWVLVV VGGVLACYSL LVTVAFIIFW VRSKRSRLLH SDYMNMTPRR PGPTRKHYQP  360
YAPPRDFAAY RSRVKFSRSA DAPAYQQGQN QLYNELNLGR REEYDVLDKR RGRDPEMGGK  420
PRRKNPQEGL YNELQKDKMA EAYSEIGMKG ERRRGKGHDG LYQGLSTATK DTYDALHMQA  480
LPPR                                                                484

SEQ ID NO: 118              moltype = AA   length = 488
FEATURE                     Location/Qualifiers
source                      1..488
                            mol_type = protein
                            organism = synthetic construct
SEQUENCE: 118
MALPVTALLL PLALLLHAAR PDIQMTQSPS SLSASVGDRV TITCRASQDV NTAVAWYQQK  60
PGKAPKLLIY SASFLYSGVP SRFSGSRSGT DFTLTISSLQ PEDFATYYCQ QHYTTPPTFG  120
QGTKVEIKRT GSTSGSGKPG SGEGSEVQLV ESGGGLVQPG GSLRLSCAAS GFNIKDTYIH  180
WVRQAPGKGL EWVARIYPTN GYTRYADSVK GRFTISADTS KNTAYLQMNS LRAEDTAVYY  240
CSRWGGDGFY AMDVWGQGTL VTVSSTTTPA PRPPTPAPTI ASQPLSLRPE ACRPAAGGAV  300
HTRGLDFACD IYIWAPLAGT CGVLLLSLVI TLYCKRGRKK LLYIFKQPFM RPVQTTQEED  360
GCSCRFPEEE EGGCELRVKF SRSADAPAYQ QGQNQLYNEL NLGRREEYDV LDKRRGRDPE  420
MGGKPRRKNP QEGLYNELQK DKMAEAYSEI GMKGERRRGK GHDGLYQGLS TATKDTYDAL  480
HMQALPPR                                                            488

SEQ ID NO: 119              moltype = AA   length = 493
FEATURE                     Location/Qualifiers
source                      1..493
                            mol_type = protein
                            organism = synthetic construct
SEQUENCE: 119
MALPVTALLL PLALLLHAAR PDIVLTQSPP SLAMSLGKRA TISCRASESV TILGSHLIHW  60
YQQKPGQPPT LLIQLASNVQ TGVPARFSGS GSRTDFTLTI DPVEEDDVAV YYCLQSRTIP  120
RTFGGGTKLE IKGSTSGSGK PGSGEGSTKG QIQLVQSGPE LKKPGETVKI SCKASGYTFT  180
DYSINWVKRA PGKGLKWMGW INTETREPAY AYDFRGRFAF SLETSASTAY LQINNLKYED  240
TATYFCALDY SYAMDYWGQG TSVTVSSAAA TTTPAPRPPT PAPTIASQPL SLRPEACRPA  300
AGGAVHTRGL DFACDIYIWA PLAGTCGVLL LSLVITLYCK RGRKKLLYIF KQPFMRPVQT  360
TQEEDGCSCR FPEEEEGGCE LRVKFSRSAD APAYQQGQNQ LYNELNLGRR EEYDVLDKRR  420
GRDPEMGGKP RRKNPQEGLY NELQKDKMAE AYSEIGMKGE RRRGKGHDGL YQGLSTATKD  480
TYDALHMQAL PPR                                                      493

SEQ ID NO: 120              moltype = AA   length = 492
FEATURE                     Location/Qualifiers
source                      1..492
                            mol_type = protein
                            organism = synthetic construct
SEQUENCE: 120
MALPVTALLL PLALLLHAAR PDIVLTQSPP SLAMSLGKRA TISCRASESV TILGSHLIHW  60
YQQKPGQPPT LLIQLASNVQ TGVPARFSGS GSRTDFTLTI DPVEEDDVAV YYCLQSRTIP  120
RTFGGGTKLE IKGSTSGSGK PGSGEGSTKG QIQLVQSGPE LKKPGETVKI SCKASGYTFT  180
DYSINWVKRA PGKGLKWMGW INTETREPAY AYDFRGRFAF SLETSASTAY LQINNLKYED  240
TATYFCALDY SYAMDYWGQG TSVTVSSAAA TTTPAPRPPT PAPTIASQPL SLRPEACRPA  300
AGGAVHTRGL DFACDIYIWA PLAGTCGVLL LSLVITLYCR SKRSRLLHSD YMNMTPRRPG  360
PTRKHYQPYA PPRDFAAYRS RVKFSRSADA PAYQQGQNQL YNELNLGRRE EYDVLDKRRG  420
RDPEMGGKPR RKNPQEGLYN ELQKDKMAEA YSEIGMKGER RRGKGHDGLY QGLSTATKDT  480
YDALHMQALP PR                                                       492

SEQ ID NO: 121              moltype = AA   length = 486
FEATURE                     Location/Qualifiers
source                      1..486
                            mol_type = protein
                            organism = synthetic construct
SEQUENCE: 121
MALPVTALLL PLALLLHAAR PDIVLTQSPP SLAMSLGKRA TISCRASESV TILGSHLIHW  60
YQQKPGQPPT LLIQLASNVQ TGVPARFSGS GSRTDFTLTI DPVEEDDVAV YYCLQSRTIP  120
RTFGGGTKLE IKGSTSGSGK PGSGEGSTKG QIQLVQSGPE LKKPGETVKI SCKASGYTFT  180
DYSINWVKRA PGKGLKWMGW INTETREPAY AYDFRGRFAF SLETSASTAY LQINNLKYED  240
TATYFCALDY SYAMDYWGQG TSVTVSSIEV MYPPPYLDNE KSNGTIIHVK GKHLCPSPLF  300
PGPSKPFWVL VVVGGVLACY SLLVTVAFII FWVRSKRSRL LHSDYMNMTP RRPGPTRKHY  360
QPYAPPRDFA AYRSRVKFSR SADAPAYQQG QNQLYNELNL GRREEYDVLD KRRGRDPEMG  420
GKPRRKNPQE GLYNELQKDK MAEAYSEIGM KGERRRGKGH DGLYQGLSTA TKDTYDALHM  480
QALPPR                                                              486

SEQ ID NO: 122              moltype = AA   length = 498
FEATURE                     Location/Qualifiers
source                      1..498
                            mol_type = protein
                            organism = synthetic construct
SEQUENCE: 122
MALPVTALLL PLALLLHAAR PQVKLEESGG GLVQAGRSLR LSCAASEHTF SSHVMGWFRQ  60
APGKERESVA VIGWRDISTS YADSVKGRFT ISRDNAKKTL YLQMNSLKPE DTAVYYCAAR  120
RIDAADFDSW GQGTQVTVSS GGGGSGGGGS GGGGSEVQLV ESGGGLVQAG GSLRLSCAAS  180
GRTFTMGWFR QAPGKEREFV AAISLSPTLA YYAESVKGRF TISRDNAKNT VVLQMNSLKP  240
```

-continued

```
EDTALYYCAA DRKSVMSIRP DYWGQGTQVT VSSTSTTTPA PRPPTPAPTI ASQPLSLRPE   300
ACRPAAGGAV HTRGLDFACD IYIWAPLAGT CGVLLLSLVI TLYCKRGRKK LLYIFKQPFM   360
RPVQTTQEED GCSCRFPEEE EGGCELRVKF SRSADAPAYQ QGQNQLYNEL NLGRREEYDV   420
LDKRRGRDPE MGGKPRRKNP QEGLYNELQK DKMAEAYSEI GMKGERRRGK GHDGLYQGLS   480
TATKDTYDAL HMQALPPR                                                 498

SEQ ID NO: 123           moltype = AA   length = 497
FEATURE                  Location/Qualifiers
source                   1..497
                         mol_type = protein
                         organism = synthetic construct
SEQUENCE: 123
MALPVTALLL PLALLLHAAR PQVKLEESGG GLVQAGRSLR LSCAASEHTF SSHVMGWFRQ   60
APGKERESVA VIGWRDISTS YADSVKGRFT ISRDNAKKTL YLQMNSLKPE DTAVYYCAAR   120
RIDAADFDSW GQGTQVTVSS GGGGSGGGGS GGGGSEVQLV ESGGGLVQAG GSLRLSCAAS   180
GRTFTMGWFR QAPGKEREFV AAISLSPTLA YYAESVKGRF TISRDNAKNT VVLQMNSLKP   240
EDTALYYCAA DRKSVMSIRP DYWGQGTQVT VSSTSTTTPA PRPPTPAPTI ASQPLSLRPE   300
ACRPAAGGAV HTRGLDFACD IYIWAPLAGT CGVLLLSLVI TLYCRSKRSR LLHSDYMNMT   360
PRRPGPTRKH YQPYAPPRDF AAYRSRVKFS RSADAPAYQQ GQNQLYNELN LGRREEYDVL   420
DKRRGRDPEM GGKPRRKNPQ EGLYNELQKD KMAEAYSEIG MKGERRRGKG HDGLYQGLST   480
ATKDTYDALH MQALPPR                                                  497

SEQ ID NO: 124           moltype = AA   length = 492
FEATURE                  Location/Qualifiers
source                   1..492
                         mol_type = protein
                         organism = synthetic construct
SEQUENCE: 124
MALPVTALLL PLALLLHAAR PQVKLEESGG GLVQAGRSLR LSCAASEHTF SSHVMGWFRQ   60
APGKERESVA VIGWRDISTS YADSVKGRFT ISRDNAKKTL YLQMNSLKPE DTAVYYCAAR   120
RIDAADFDSW GQGTQVTVSS GGGGSGGGGS GGGGSEVQLV ESGGGLVQAG GSLRLSCAAS   180
GRTFTMGWFR QAPGKEREFV AAISLSPTLA YYAESVKGRF TISRDNAKNT VVLQMNSLKP   240
EDTALYYCAA DRKSVMSIRP DYWGQGTQVT VSSIEVMYPP PYLDNEKSNG TIIHVKGKHL   300
CPSPLFPGPS KPFWVLVVVG GVLACYSLLV TVAFIIFWVR SKRSRLLHSD YMNMTPRRPG   360
PTRKHYQPYA PPRDFAAYRS RVKFSRSADA PAYQQGQNQL YNELNLGRRE EYDVLDKRRG   420
RDPEMGGKPR RKNPQEGLYN ELQKDKMAEA YSEIGMKGER RRGKGHDGLY QGLSTATKDT   480
YDALHMQALP PR                                                       492

SEQ ID NO: 125           moltype = AA   length = 365
FEATURE                  Location/Qualifiers
source                   1..365
                         mol_type = protein
                         organism = synthetic construct
SEQUENCE: 125
MALPVTALLL PLALLLHAAR PQVKLEESGG GLVQAGRSLR LSCAASEHTF SSHVMGWFRQ   60
APGKERESVA VIGWRDISTS YADSVKGRFT ISRDNAKKTL YLQMNSLKPE DTAVYYCAAR   120
RIDAADFDSW GQGTQVTVSS TSTTTPAPRP PTPAPTIASQ PLSLRPEACR PAAGGAVHTR   180
GLDFACDIYI WAPLAGTCGV LLLSLVITLY CKRGRKKLLY IFKQPFMRPV QTTQEEDGCS   240
CRFPEEEEGG CELRVKFSRS ADAPAYQQGQ NQLYNELNLG RREEYDVLDK RRGRDPEMGG   300
KPRRKNPQEG LYNELQKDKM AEAYSEIGMK GERRRGKGHD GLYQGLSTAT KDTYDALHMQ   360
ALPPR                                                               365

SEQ ID NO: 126           moltype = AA   length = 364
FEATURE                  Location/Qualifiers
source                   1..364
                         mol_type = protein
                         organism = synthetic construct
SEQUENCE: 126
MALPVTALLL PLALLLHAAR PEVQLVESGG GLVQAGGSLR LSCAASGRTF TMGWFRQAPG   60
KEREFVAAIS LSPTLAYYAE SVKGRFTISR DNAKNTVVLQ MNSLKPEDTA LYYCAADRKS   120
VMSIRPDYWG QGTQVTVSST STTTPAPRPP TPAPTIASQP LSLRPEACRP AAGGAVHTRG   180
LDFACDIYIW APLAGTCGVL LLSLVITLYC KRGRKKLLYI FKQPFMRPVQ TTQEEDGCSC   240
RFPEEEEGGC ELRVKFSRSA DAPAYQQGQN QLYNELNLGR REEYDVLDKR RGRDPEMGGK   300
PRRKNPQEGL YNELQKDKMA EAYSEIGMKG ERRRGKGHDG LYQGLSTATK DTYDALHMQA   360
LPPR                                                                364

SEQ ID NO: 127           moltype = AA   length = 359
FEATURE                  Location/Qualifiers
source                   1..359
                         mol_type = protein
                         organism = synthetic construct
SEQUENCE: 127
MALPVTALLL PLALLLHAAR PQVKLEESGG GLVQAGRSLR LSCAASEHTF SSHVMGWFRQ   60
APGKERESVA VIGWRDISTS YADSVKGRFT ISRDNAKKTL YLQMNSLKPE DTAVYYCAAR   120
RIDAADFDSW GQGTQVTVSS IEVMYPPPYL DNEKSNGTII HVKGKHLCPS PLFPGPSKPF   180
WVLVVVGGVL ACYSLLVTVA FIIFWVRSKR SRLLHSDYMN MTPRRPGPTR KHYQPYAPPR   240
DFAAYRSRVK FSRSADAPAY QQGQNQLYNE LNLGRREEYD VLDKRRGRDP EMGGKPRRKN   300
PQEGLYNELQ KDKMAEAYSE IGMKGERRRG KGHDGLYQGL STATKDTYDA LHMQALPPR    359
```

```
SEQ ID NO: 128            moltype = AA   length = 358
FEATURE                   Location/Qualifiers
source                    1..358
                          mol_type = protein
                          organism = synthetic construct
SEQUENCE: 128
MALPVTALLL PLALLLHAAR PEVQLVESGG GLVQAGGSLR LSCAASGRTF TMGWFRQAPG   60
KEREFVAAIS LSPTLAYYAE SVKGRFTISR DNAKNTVVLQ MNSLKPEDTA LYYCAADRKS  120
VMSIRPDYWG QGTQVTVSSI EVMYPPPYLD NEKSNGTIIH VKGKHLCPSP LFPGPSKPFW  180
VLVVVGGVLA CYSLLVTVAF IIFWVRSKRS RLLHSDYMNM TPRRPGPTRK HYQPYAPPRD  240
FAAYRSRVKF SRSADAPAYQ QGGNQLYNEL NLGRREEYDV LDKRRGRDPE MGGKPRRKNP  300
QEGLYNELQK DKMAEAYSEI GMKGERRRGK GHDGLYQGLS TATKDTYDAL HMQALPPR    358

SEQ ID NO: 129            moltype = AA   length = 744
FEATURE                   Location/Qualifiers
source                    1..744
                          mol_type = protein
                          organism = synthetic construct
SEQUENCE: 129
MALPVTALLL PLALLLHAAR PQVKLEESGG GLVQAGRSLR LSCAASEHTF SSHVMGWFRQ   60
APGKERESVA VIGWRDISTS YADSVKGRFT ISRDNAKKTL YLQMNSLKPE DTAVYYCAAR  120
RIDAADFDSW GQGTQVTVSS TSTTTPAPRP PTPAPTIASQ PLSLRPEACR PAAGGAVHTR  180
GLDFACDIYI WAPLAGTCGV LLLLSLVITLY CKRGRKKLLY IFKQPFMRPV QTTQEEDGCS  240
CRFPEEEEGG CELRVKFSRS ADAPAYQQGQ NQLYNELNLG RREEYDVLDK RRGRDPEMGG  300
KPRRKNPQEG LYNELQKDKM AEAYSEIGMK GERRRGKGHD GLYQGLSTAT KDTYDALHMQ  360
ALPPRGSGEG RGSLLTCGDV EENPGPMALP VTALLLPLAL LLHAARPEVQ LVESGGGLVQ  420
AGGSLRLSCA ASGRTFTMGW FRQAPGKERE FVAAISLSPT LAYYAESVKG RFTISRDNAK  480
NTVVLQMNSL KPEDTALYYC AADRKSVMSI RPDYWGQGTQ VTVSSIEVMY PPPYLDNEKS  540
NGTIIHVKGK HLCPSPLFPG PSKPFWVLVV VGGVLACYSL LVTVAFIIFW VRSKRSRLLH  600
SDYMNMTPRR PGPTRKHYQP YAPPRDFAAY RSRVKFSRSA DAPAYQQGQN QLYNELNLGR  660
REEYDVLDKR RGRDPEMGGK PRRKNPQEGL YNELQKDKMA EAYSEIGMKG ERRRGKGHDG  720
LYQGLSTATK DTYDALHMQA LPPR                                        744

SEQ ID NO: 130            moltype = AA   length = 744
FEATURE                   Location/Qualifiers
source                    1..744
                          mol_type = protein
                          organism = synthetic construct
SEQUENCE: 130
MALPVTALLL PLALLLHAAR PEVQLVESGG GLVQAGGSLR LSCAASGRTF TMGWFRQAPG   60
KEREFVAAIS LSPTLAYYAE SVKGRFTISR DNAKNTVVLQ MNSLKPEDTA LYYCAADRKS  120
VMSIRPDYWG QGTQVTVSST STTTPAPRPP TPAPTIASQP LSLRPEACRP AAGGAVHTRG  180
LDFACDIYIW APLAGTCGVL LLSLVITLYC KRGRKKLLYI FKQPFMRPVQ TTQEEDGCSC  240
RFPEEEEGGC ELRVKFSRSA DAPAYQQGQN QLYNELNLGR REEYDVLDKR RGRDPEMGGK  300
PRRKNPQEGL YNELQKDKMA EAYSEIGMKG ERRRGKGHDG LYQGLSTATK DTYDALHMQA  360
LPPRGSGEGR GSLLTCGDVE ENPGPMALPV TALLLPLALL LHAARPQVKL EESGGGLVQA  420
GRSLRLSCAA SEHTFSSHVM GWFRQAPGKE RESVAVIGWR DISTSYADSV KGRFTISRDN  480
AKKTLYLQMN SLKPEDTAVY YCAARRIDAA DFDSWGQGTQ VTVSSIEVMY PPPYLDNEKS  540
NGTIIHVKGK HLCPSPLFPG PSKPFWVLVV VGGVLACYSL LVTVAFIIFW VRSKRSRLLH  600
SDYMNMTPRR PGPTRKHYQP YAPPRDFAAY RSRVKFSRSA DAPAYQQGQN QLYNELNLGR  660
REEYDVLDKR RGRDPEMGGK PRRKNPQEGL YNELQKDKMA EAYSEIGMKG ERRRGKGHDG  720
LYQGLSTATK DTYDALHMQA LPPR                                        744

SEQ ID NO: 131            moltype = AA   length = 493
FEATURE                   Location/Qualifiers
source                    1..493
                          mol_type = protein
                          organism = synthetic construct
SEQUENCE: 131
MALPVTALLL PLALLLHAAR PDIVLTQSPP SLAMSLGKRA TISCRASESV TILGSHLIHW   60
YQQKPGQPPT LLIQLASNVQ TGVPARFSGS GSRTDFTLTI DPVEEDDVAV YYCLQSRTIP  120
RTFGGGTKLE IKGSTSGSGK PGSGEGSTKG QIQLVQSGPE LKKPGETVKI SCKASGYTFT  180
DYSINWVKRA PGKGLKWMGW INTETREPAY AYDFRGRFAF SLETSASTAY LQINNLKYED  240
TATYFCALDY SYAMDYWGQG TSVTVSSAAA TTTPAPRPPT PAPTIASQPL SLRPEACRPA  300
AGGAVHTRGL DFACDIYIWA PLAGTCGVLL LSLVITLYCK RGRKKLLYIF KQPFMRPVQT  360
TQEEDGCSCR FPEEEEGGCE LRVKFSRSAD APAYQQGQNQ LYNELNLGRR EEYDVLDKRR  420
GRDPEMGGKP RRKNPQEGLY NELQKDKMAE AYSEIGMKGE RRRGKGHDGL YQGLSTATKD  480
TYDALHMQAL PPR                                                    493

SEQ ID NO: 132            moltype = DNA   length = 1452
FEATURE                   Location/Qualifiers
source                    1..1452
                          mol_type = other DNA
                          organism = synthetic construct
SEQUENCE: 132
atggctctgc ctgtgacagc tctgctgctg cctctggctc tgcttctgca tgccgccaga   60
cctgacatcc agatgactca gagccccagc agcctgtctg cctctgtggg agacagagtg  120
acaattacct gccgggccag ccaggatgtg aatactgctg tcgcctggta tcaacaaaag  180
cctggcaagg cccctaagct cctgatctac agcgccagct ttctgtacag cggcgtgccc  240
```

```
agcagattct ccggaagcag aagcggcaca gatttcacac tgaccataag cagcctgcag    300
ccagaggatt tcgccaccta ctattgccag cagcactaca ccacacctcc aacctttggc    360
cagggcacca aggtcgagat taagagaaca ggcagcacat ctggctctgg caaacctgga    420
tctggcgagg gctctgaagt ccagctggtg gaatctggcg gaggactggt tcaacctggc    480
ggctctctga gactgtcttg tgccgcctcc ggcttcaaca tcaaggacac ctacatccac    540
tgggtccgac aagccccagg caaaggactt gagtgggtcg ccaggatcta ccccaccaac    600
ggctacacca gatacgccga ctctgtgaag ggcagattca ccatctctgc cgacaccagc    660
aagaataccg cctacctgca gatgaactcc ctgagagccg aagataccgc tgtgtattac    720
tgttccagat ggggaggcga cggcttctac gccatggatg tttggggcca aggcaccctc    780
gtgaccgttt cttctatcga agtgatgtac cctccacctt acctggacaa cgagaagtcc    840
aacggcacca tcatccacgt gaagggcaag cacctgtgtc cttctccact gttccccgga    900
cctagcaagc ctttctgggt gctcgttgtt gttggcggcg tgctggcctg ttactctctg    960
ctggttaccg tggccttcat catcttttgg gtccgaagca gcggagccg gctgctgcac   1020
tccgactaca tgaacatgac ccctagacgg cccggaccaa cagaaagca ctaccagcgc   1080
tacgctcctc ctagagactt cgccgcctac cggtccagag tgaagttcag cagatccgcc   1140
gatgctcccg cctatcagca gggccaaaac cagctgtaca acgagctgaa cctggggaga   1200
agagaagagt acgacgtgct ggacaagcgg agaggcagag atcctgaaat gggcggcaag   1260
cccagacgga agaatcctca gagggcctg tataatgac tgcagaaaga caagatggcc   1320
gaggcctaca gcgagatcgg aatgaagggc gagcgcagaa gaggcaaggg cacacgatgga   1380
ctgtaccagg gcctgagcac cgccaccaag gataccatg atgccctgca catgcaggcc   1440
ctgcctccaa ga                                                       1452
```

```
SEQ ID NO: 133          moltype = DNA   length = 1464
FEATURE                 Location/Qualifiers
source                  1..1464
                        mol_type = other DNA
                        organism = synthetic construct
SEQUENCE: 133
atggctctgc ctgtgacagc tctgctgctg cctctggctc tgcttctgca tgccgccaga     60
cctgacatcc agatgactca gagccccagc agcctgtctg cctctgtggg agacagagtg    120
acaattacct gccgggccag ccaggatgtg aatactgctg tcgcctggta tcaacaaaag    180
cctggcaagg cccctaagct cctgatctac agcgccagct ttctgtacag cggcgtgccc    240
agcagattct ccggaagcag aagcggcaca gatttcacac tgaccataag cagcctgcag    300
ccagaggatt tcgccaccta ctattgccag cagcactaca ccacacctcc aacctttggc    360
cagggcacca aggtcgagat taagagaaca ggcagcacat ctggctctgg caaacctgga    420
tctggcgagg gctctgaagt ccagctggtg gaatctggcg gaggactggt tcaacctggc    480
ggctctctga gactgtcttg tgccgcctcc ggcttcaaca tcaaggacac ctacatccac    540
tgggtccgac aagccccagg caaaggactt gagtgggtcg ccaggatcta ccccaccaac    600
ggctacacca gatacgccga ctctgtgaag ggcagattca ccatctctgc cgacaccagc    660
aagaataccg cctacctgca gatgaactcc ctgagagccg aagataccgc tgtgtattac    720
tgttccagat ggggaggcga cggcttctac gccatggatg tttggggcca aggcaccctc    780
gtgaccgttt cttctaccac cacaccagct cctcggcctc caactcctgc tcctacaatt    840
gccagccagc ctctgtctct gaggccggaa gcttgtagac ctgctgctgg cggagccgtg    900
catacaagag gactggattt cgcctgcgac atctacatct gggctcctct ggccggaaca    960
tgtggcgttc tgctgctgag cctggtcatc accctgtact gtaagcgggg cagaaagaag   1020
ctgctgtaca tcttcaagca gcccttcatg cggcccgtgc agaccacaca agaggaagat   1080
ggctgctcct gcagattccc cgaggaagaa gaaggcggct gcgagctgag agttgaagttc   1140
agcagatccg ccgatgctcc cgcctatcag cagggccaaa accagctgta caacgagctg   1200
aacctgggga agagaagaga gtacgacgtg ctggacaagc ggagaggcag agatcctgaa   1260
atgggcggca agcccagacg gaagaatcct caagagggc tgtataatga gctgcagaaa   1320
gacaagatgg ccgaggccta cagcgagatc ggaatgaagg gcgagcgcag aagaggcaag   1380
ggacacgatg gactgtacca gggcctgagc accgccacca aggatacct atgatgccctg   1440
cacatgcagg ccctgcctcc aaga                                          1464
```

```
SEQ ID NO: 134          moltype = AA   length = 484
FEATURE                 Location/Qualifiers
source                  1..484
                        mol_type = protein
                        organism = synthetic construct
SEQUENCE: 134
MALPVTALLL PLALLLHAAR PDIQMTQSPS SLSASVGDRV TITCRASQDV NTAVAWYQQK     60
PGKAPKLLIY SASFLYSGVP SRFSGSRSGT DFTLTISSLQ PEDFATYYCQ QHYTTPPTFG    120
QGTKVEIKRT GSTSGSGKPG SGEGSEVQLV ESGGGLVQPG GSLRLSCAAS GFNIKDTYIH    180
WVRQAPGKGL EWVARIYPTN GYTRYADSVK GRFTISADTS KNTAYLQMNS LRAEDTAVYY    240
CSRWGGDGFY AMDVWGQGTL VTVSSIEVMY PPPYLDNEKS NGTIIHVKGK HLCPSPLFPG    300
PSKPFWVLVV VGGVLACYSL LVTVAFIIFW VRSKRSRLLH SDYMNMTPRR PGPTRKHYQP    360
YAPPRDFAAY RSRVKFSRSA DAPAYQQGQN QLYNELNLGR REEYDVLDKR RGRDPEMGGK    420
PRRKNPQEGL YNELQKDKMA EAYSEIGMKG ERRRGKGHDG LYQGLSTATK DTYDALHMQA    480
LPPR                                                                 484
```

```
SEQ ID NO: 135          moltype = AA   length = 488
FEATURE                 Location/Qualifiers
source                  1..488
                        mol_type = protein
                        organism = synthetic construct
SEQUENCE: 135
MALPVTALLL PLALLLHAAR PDIQMTQSPS SLSASVGDRV TITCRASQDV NTAVAWYQQK     60
PGKAPKLLIY SASFLYSGVP SRFSGSRSGT DFTLTISSLQ PEDFATYYCQ QHYTTPPTFG    120
QGTKVEIKRT GSTSGSGKPG SGEGSEVQLV ESGGGLVQPG GSLRLSCAAS GFNIKDTYIH    180
```

-continued

```
WVRQAPGKGL EWVARIYPTN GYTRYADSVK GRFTISADTS KNTAYLQMNS LRAEDTAVYY  240
CSRWGGDGFY AMDVWGQGTL VTVSSTTTPA PRPPTPAPTI ASQPLSLRPE ACRPAAGGAV  300
HTRGLDFACD IYIWAPLAGT CGVLLLSLVI TLYCKRGRKK LLYIFKQPFM RPVQTTQEED  360
GCSCRFPEEE EGGCELRVKF SRSADAPAYQ QGQNQLYNEL NLGRREEYDV LDKRRGRDPE  420
MGGKPRRKNP QEGLYNELQK DKMAEAYSEI GMKGERRRGK GHDGLYQGLS TATKDTYDAL  480
HMQALPPR                                                          488

SEQ ID NO: 136          moltype = DNA  length = 2001
FEATURE                 Location/Qualifiers
source                  1..2001
                        mol_type = other DNA
                        organism = synthetic construct
SEQUENCE: 136
gtggccacgc ccgggccacc gatacttccc ttcactcctt cgggactgtt ggggaggaac  60
acaacagggc tccctgtttt tccattcct tcccccttt cccaacccca accgccgtat  120
ctggtggcgg caagacacac gggtctttcc ctctaaagca caattgtgtg tgtgtcccag  180
gtcctcctgc gtacggtgcg ggagtgctcc cacccaactg ttgtaagcct gtccaacgcg  240
tcgtcctggc aagactatga cgtcgcatgt tccgctgcgg atgccgaccg ggtaaccggt  300
tccccagtgt gtgtagtgcg atcttccagg tcctcctggt tggcgttgtc cagaaactgc  360
ttcaggtaag tggggtgtgc ccaatcccta caaaggttga ttctttcacc accttaggaa  420
tgctccggag gtaccccagc aacagctggg atctgaccgg aggctaattg tctacgggtg  480
gtgtttcctt tttcttttca cacaactcta ctgctgacaa ctcactgact atccacttgc  540
tctgtcacga tggctctgcc tgtgacagct ctgctgctgc ctctggctct gcttctgcat  600
gccgccagac ctgacatcca gatgactcag agcccagca gcctgtctgc ctctgtggga  660
gacagagtga caattacctg ccgggccagc caggatgtga atactgctgt cgcctggtat  720
caacaaaagc ctggcaaggc ccctaagctc ctgatctaca cgccagctt tctgtacagc  780
ggcgtgccca gcagattctc cggaagcaga agcggcacac atttcacact gaccataagc  840
agcctgcagc cagaggattt cgccacctac tattgccagc agcactacac cacacctcca  900
acctttggcc agggcaccaa ggtcgagatt aagagaacag gcagcacatc tggctctggc  960
aaacctggat ctggcgaggg ctctgaagtc cagctggttg aatctggcgg aggactggtt  1020
caacctggcg gctctctgag actgtcttgt gccgcctccg gcttcaacat caaggacacc  1080
tacatccact gggtccgaca agccccaggc aaaggacttg agtgggtcgc caggatctac  1140
cccaccaacg gctacaccag atacgccgac tctgtgaagg gcagattcac catctctgcc  1200
gacaccagca agaataccgc ctacctgcag atgaactccc tgagagccga agataccgct  1260
gtgtattact gttccagatg gggaggcgac ggcttctacg ccatggatgt ttggggccaa  1320
ggcaccctcg tgaccgtttc ttctatcgaa gtgatgtacc ctccacctta cctgacaac  1380
gagaagtcca acggcaccat catccacgtg aagggcaagc acctgtgtcc ttctccactg  1440
ttccccggac ctagcaagcc tttctgggtg ctcgttgttg ttggcggcgt gctggcctgt  1500
tactctctgc tggttaccgt ggccttcatc atcttttggg tccgaagcaa gcggagccgg  1560
ctgctgcact ccgactacat gaacatgacc cctagacggc ccggaccaac cagaaagcac  1620
taccagcctt acgctcctcc tagagacttc gccgcctacc ggtccagagt gaagttcagc  1680
agatccgccg atgctcccgc ctatcagcag ggccaaaacc agctgtacaa cgagctgaac  1740
ctggggagaa gagaagagta cgacgtgctg gacaagcgga tcctgaaatg  1800
ggcggcaagc ccagacgaaa gaatcctcaa gagggcctgt ataatgagct gcagaaagac  1860
aagatggccg aggcctacag cgagatcgga atgaagggcg agcgcagaag aggcaaggga  1920
cacgatggac tgtaccaggg cctgagcacc gccaccaagg atacctatga tgccctgcac  1980
atgcaggccc tgcctccaag a                                          2001

SEQ ID NO: 137          moltype = DNA  length = 2013
FEATURE                 Location/Qualifiers
source                  1..2013
                        mol_type = other DNA
                        organism = synthetic construct
SEQUENCE: 137
gtggccacgc ccgggccacc gatacttccc ttcactcctt cgggactgtt ggggaggaac  60
acaacagggc tccctgtttt tccattcct tcccccttt cccaacccca accgccgtat  120
ctggtggcgg caagacacac gggtctttcc ctctaaagca caattgtgtg tgtgtcccag  180
gtcctcctgc gtacggtgcg ggagtgctcc cacccaactg ttgtaagcct gtccaacgcg  240
tcgtcctggc aagactatga cgtcgcatgt tccgctgcgg atgccgaccg ggtaaccggt  300
tccccagtgt gtgtagtgcg atcttccagg tcctcctggt tggcgttgtc cagaaactgc  360
ttcaggtaag tggggtgtgc ccaatcccta caaaggttga ttctttcacc accttaggaa  420
tgctccggag gtaccccagc aacagctggg atctgaccgg aggctaattg tctacgggtg  480
gtgtttcctt tttcttttca cacaactcta ctgctgacaa ctcactgact atccacttgc  540
tctgtcacga tggctctgcc tgtgacagct ctgctgctgc ctctggctct gcttctgcat  600
gccgccagac ctgacatcca gatgactcag agcccagca gcctgtctgc ctctgtggga  660
gacagagtga caattacctg ccgggccagc caggatgtga atactgctgt cgcctggtat  720
caacaaaagc ctggcaaggc ccctaagctc ctgatctaca cgccagctt tctgtacagc  780
ggcgtgccca gcagattctc cggaagcaga agcggcacac atttcacact gaccataagc  840
agcctgcagc cagaggattt cgccacctac tattgccagc agcactacac cacacctcca  900
acctttggcc agggcaccaa ggtcgagatt aagagaacag gcagcacatc tggctctggc  960
aaacctggat ctggcgaggg ctctgaagtc cagctggtgg aatctggcgg aggactggtt  1020
caacctggcg gctctctgag actgtcttgt gccgcctccg gcttcaacat caaggacacc  1080
tacatccact gggtccgaca agccccaggc aaaggacttg agtgggtcgc caggatctac  1140
cccaccaacg gctacaccag atacgccgac tctgtgaagg gcagattcac catctctgcc  1200
gacaccagca agaataccgc ctacctgcag atgaactccc tgagagccga agataccgct  1260
gtgtattact gttccagatg gggaggcgac ggcttctacg ccatggatgt ttggggccaa  1320
ggcaccctcg tgaccgtttc ttctaccacc acaccagctc ctcggcctcc aactcctgct  1380
cctacaattg ccagcagcc tctgtctctg aggcccgaag cttgtagacc tgctgctggc  1440
ggagccgtgc atacaagagg actggatttc gcctgcgaca tctacatctg ggctcctctg  1500
```

```
gccggaacat gtggcgttct gctgctgagc ctggtcatca ccctgtactg taagcggggc   1560
agaaagaagc tgctgtacat cttcaagcag cccttcatgc ggcccgtgca gaccacacaa   1620
gaggaagatg gctgctcctg cagattcccc gaggaagaag aaggcggctg cgagctgaga   1680
gtgaagttca gcagatccgc cgatgctccc gcctatcagc agggccaaaa ccagctgtac   1740
aacgagctga acctggggag aagagaagag tacgacgtgc tggacaagcg gagaggcaga   1800
gatcctgaaa tgggcggcaa gcccagacgg aagaatcctc aagagggcct gtataatgag   1860
ctgcagaaag acaagatggc cgaggcctac agcgagatcg gaatgaaggg cgagcgcaga   1920
agaggcaagg gacacgatgg actgtaccag ggcctgagca ccgccaccaa ggatacctat   1980
gatgccctgc acatgcaggc cctgcctcca aga                                2013
```

```
SEQ ID NO: 138            moltype = DNA   length = 2028
FEATURE                   Location/Qualifiers
source                    1..2028
                          mol_type = other DNA
                          organism = synthetic construct
SEQUENCE: 138
gtggccacgc ccgggccacc gatacttccc ttcactcctt cgggactgtt ggggaggaac   60
acaacagggc tccctgttt tcccattcct tccccttttt cccaacccca accgccgtat    120
ctggtggcgg caagacacac gggtcttttc ctctaaagca caattgtgtg tgtgtcccag   180
gtcctcctgc gtacggtgcg ggagtgctcc cacccaactg ttgtaagcct gtccaacgcg   240
tcgtcctggc aagactatga cgtcgcatgt tccgctgcgg atgccgaccg ggtaaccggt   300
tccccagtgt gtgtagtgcg atcttccagg tcctcctggt tggcgttgtc cagaaactgt   360
ttcaggtaag tggggtgtgc ccaatcccta caaaggttga ttctttcacc accttaggaa   420
tgctccggag gtaccccagc aacagctggg atctgaccgg aggctaattg tctacgggtg   480
gtgtttcctt tttcttttca cacaactcta ctgctgacaa ctcactgact atccacttgc   540
tctgtcacga tggcactccc ggtaaccgcc ttattgcttc cccttgccct cttgctccac   600
gcagcacgcc ccgatatagt cttgactcaa tccccaccca gtttggcaat gtcattaggc   660
aaacgagcaa caatttcatg tagggcatcc gaaagtgtaa cgatttttggg gagtcattta   720
attcattggt accaacaaaa gcctggacaa cccccgacgc tcttgatcca attagcatct   780
aacgtccaaa ccggagtccc cgcacggattc tcaggatccg gttcccggac tgattttaca   840
ttaactattg atccggtaga ggaagatgac gtcgctgtct attattgtct tcaaagtagg   900
acgattccac ggacattcgg tggcggaact aaattggaga ttaaaggttc cacctctggt   960
agtgggaaac ccgggtccgg tgaagggtcc actaaaggcc aaattcaact cgttcaatcc   1020
ggaccagaac tgaagaagcc aggagaaact gtcaaaataa gctgtaaagc ttccggttat   1080
acatttacag attattccat aaattgggtg aaaaggggcgc caggaaaagg gttaaagtgg   1140
atgggttgga ttaatacaga gactcgggaa cctgcatatg cttatgattt taggggaagg   1200
tttgcctttt ctctggagac ttccgcttca actgcttatc tccaaattaa taatcttaaa   1260
tatgaggaca cagcaacata cttctgtgct ttggactata gttatgctat ggattactgg   1320
ggacaagga ccagtgtcac tgtaagttcc gctgctgcga cgaccactcc tgcaccgcga   1380
ccacccactc ctgcccctac tattgctagt caaccactta gcttgcgacc tgaggcatgt   1440
cggcccgcgg caggtggcgc agtccacacc aggggtttag actttgcttg tgatatttat   1500
atttgggcac cactcgccgg gacttgcggt gttcttctct tgtcccttgt tataactctt   1560
tattgtaagc gcggaaggaa gaaattgtta tatatttca aacaacctt tatgcgaccc     1620
gtacaaacaa ctcaggaaga ggacgggtgt tcttgtcggt ttccagaaga ggaagagggt   1680
gggtgtgaac tccgggtcaa atttagtagg tcagcagatg cgccggcgta ccaacaaggc   1740
caaaaccaac tgtataatga actcaatctc ggtaggcgtg aggaatatga tgtccttgat   1800
aaaaggcgcg ggagagatcc agaaatgggc ggaaaaccac ggcgaaagaa tccgcaggaa   1860
gggttatata acgaacttca aaaggataaa atggctgaag cttattccga aattggcatg   1920
aaaggagagc gacgtagggg caaagggcat gatggccttt accaagggct ctcaaccgct   1980
acaaaagata cttacgacgc tttacatatg caagcacttc cacccagg                2028
```

```
SEQ ID NO: 139            moltype =    length =
SEQUENCE: 139
000
```

```
SEQ ID NO: 140            moltype =    length =
SEQUENCE: 140
000
```

```
SEQ ID NO: 141            moltype =    length =
SEQUENCE: 141
000
```

```
SEQ ID NO: 142            moltype =    length =
SEQUENCE: 142
000
```

```
SEQ ID NO: 143            moltype =    length =
SEQUENCE: 143
000
```

```
SEQ ID NO: 144            moltype =    length =
SEQUENCE: 144
000
```

```
SEQ ID NO: 145            moltype =    length =
SEQUENCE: 145
000
```

-continued

```
SEQ ID NO: 146          moltype =    length =
SEQUENCE: 146
000

SEQ ID NO: 147          moltype =    length =
SEQUENCE: 147
000

SEQ ID NO: 148          moltype =    length =
SEQUENCE: 148
000

SEQ ID NO: 149          moltype =    length =
SEQUENCE: 149
000

SEQ ID NO: 150          moltype =    length =
SEQUENCE: 150
000

SEQ ID NO: 151          moltype =    length =
SEQUENCE: 151
000

SEQ ID NO: 152          moltype =    length =
SEQUENCE: 152
000

SEQ ID NO: 153          moltype =    length =
SEQUENCE: 153
000

SEQ ID NO: 154          moltype =    length =
SEQUENCE: 154
000

SEQ ID NO: 155          moltype =    length =
SEQUENCE: 155
000

SEQ ID NO: 156          moltype =    length =
SEQUENCE: 156
000

SEQ ID NO: 157          moltype =    length =
SEQUENCE: 157
000

SEQ ID NO: 158          moltype =    length =
SEQUENCE: 158
000

SEQ ID NO: 159          moltype =    length =
SEQUENCE: 159
000

SEQ ID NO: 160          moltype =    length =
SEQUENCE: 160
000

SEQ ID NO: 161          moltype =    length =
SEQUENCE: 161
000

SEQ ID NO: 162          moltype =    length =
SEQUENCE: 162
000

SEQ ID NO: 163          moltype =    length =
SEQUENCE: 163
000

SEQ ID NO: 164          moltype =    length =
SEQUENCE: 164
000

SEQ ID NO: 165          moltype =    length =
SEQUENCE: 165
000
```

-continued

```
SEQ ID NO: 166          moltype =   length =
SEQUENCE: 166
000

SEQ ID NO: 167          moltype =   length =
SEQUENCE: 167
000

SEQ ID NO: 168          moltype =   length =
SEQUENCE: 168
000

SEQ ID NO: 169          moltype =   length =
SEQUENCE: 169
000

SEQ ID NO: 170          moltype =   length =
SEQUENCE: 170
000

SEQ ID NO: 171          moltype =   length =
SEQUENCE: 171
000

SEQ ID NO: 172          moltype =   length =
SEQUENCE: 172
000

SEQ ID NO: 173          moltype =   length =
SEQUENCE: 173
000

SEQ ID NO: 174          moltype =   length =
SEQUENCE: 174
000

SEQ ID NO: 175          moltype =   length =
SEQUENCE: 175
000

SEQ ID NO: 176          moltype =   length =
SEQUENCE: 176
000

SEQ ID NO: 177          moltype =   length =
SEQUENCE: 177
000

SEQ ID NO: 178          moltype =   length =
SEQUENCE: 178
000

SEQ ID NO: 179          moltype =   length =
SEQUENCE: 179
000

SEQ ID NO: 180          moltype =   length =
SEQUENCE: 180
000

SEQ ID NO: 181          moltype =   length =
SEQUENCE: 181
000

SEQ ID NO: 182          moltype =   length =
SEQUENCE: 182
000

SEQ ID NO: 183          moltype =   length =
SEQUENCE: 183
000

SEQ ID NO: 184          moltype =   length =
SEQUENCE: 184
000

SEQ ID NO: 185          moltype =   length =
SEQUENCE: 185
```

-continued

```
000

SEQ ID NO: 186          moltype =    length =
SEQUENCE: 186
000

SEQ ID NO: 187          moltype =    length =
SEQUENCE: 187
000

SEQ ID NO: 188          moltype =    length =
SEQUENCE: 188
000

SEQ ID NO: 189          moltype =    length =
SEQUENCE: 189
000

SEQ ID NO: 190          moltype =    length =
SEQUENCE: 190
000

SEQ ID NO: 191          moltype =    length =
SEQUENCE: 191
000

SEQ ID NO: 192          moltype =    length =
SEQUENCE: 192
000

SEQ ID NO: 193          moltype =    length =
SEQUENCE: 193
000

SEQ ID NO: 194          moltype =    length =
SEQUENCE: 194
000

SEQ ID NO: 195          moltype =    length =
SEQUENCE: 195
000

SEQ ID NO: 196          moltype =    length =
SEQUENCE: 196
000

SEQ ID NO: 197          moltype =    length =
SEQUENCE: 197
000

SEQ ID NO: 198          moltype =    length =
SEQUENCE: 198
000

SEQ ID NO: 199          moltype =    length =
SEQUENCE: 199
000

SEQ ID NO: 200          moltype = DNA  length = 23
FEATURE                 Location/Qualifiers
source                  1..23
                        mol_type = other DNA
                        organism = synthetic construct
SEQUENCE: 200
caaacaccat tgtcacactc caa                                          23

SEQ ID NO: 201          moltype = AA  length = 493
FEATURE                 Location/Qualifiers
source                  1..493
                        mol_type = protein
                        organism = synthetic construct
SEQUENCE: 201
MALPVTALLL PLALLLHAAR PDIVLTQSPA SLAVSLGERA TINCRASESV SVIGAHLIHW  60
YQQKPGQPPK LLIYLASNLE TGVPARFSGS GSGTDFTLTI SSLQAEDAAI YYCLQSRIFP  120
RTFGQGTKLE IKGSTSGSGK PGSGEGSTKG QVQLVQSGSE LKKPGASVKV SCKASGYTFT  180
DYSINWVRQA PGQGLEWMGW INTETREPAY AYDFRGRFVF SLDTSVSTAY LQISSLKAED  240
TAVYYCARDY SYAMDYWGQG TLVTVSSAAA TTTPAPRPPT PAPTIASQPL SLRPEACRPA  300
AGGAVHTRGL DFACDIYIWA PLAGTCGVLL LSLVITLYCK RGRKKLLYIF KQPFMRPVQT  360
TQEEDGCSCR FPEEEGGCE LRVKFSRSAD APAYQQGQNQ LYNELNLGRR EEYDVLDKRR  420
```

```
GRDPEMGGKP RRKNPQEGLY NELQKDKMAE AYSEIGMKGE RRRGKGHDGL YQGLSTATKD    480
TYDALHMQAL PPR                                                       493

SEQ ID NO: 202          moltype = AA  length = 207
FEATURE                 Location/Qualifiers
source                  1..207
                        mol_type = protein
                        organism = synthetic construct
SEQUENCE: 202
KNQVEQSPQS LIILEGKNCT LQCNYTVSPF SNLRWYKQDT GRGPVSLTIM TFSENTKSNG     60
RYTATLDADT KQSSLHITAS QLSDSASYIC VVNHSGGSYI PTFGRGTSLI VHPYIQKPDP    120
AVYQLRDSKS SDKSVCLFTD FDSQTNVSQS KDSDVYITDK TVLDMRSMDF KSNSAVAWSN    180
KSDFACANAF NNSIIPEDTF FPSPESS                                        207

SEQ ID NO: 203          moltype = AA  length = 246
FEATURE                 Location/Qualifiers
source                  1..246
                        mol_type = protein
                        organism = synthetic construct
SEQUENCE: 203
DVKVTQSSRY LVKRTGEKVF LECVQDMDHE NMFWYRQDPG LGLRLIYFSY DVKMKEKGDI     60
PEGYSVSREK KERFSLILES ASTNQTSMYL CASSFLMTSG DPYEQYFGPG TRLTVTEDLK    120
NVFPPEVAVF EPSEAEISHT QKATLVCLAT GFYPDHVELS WWVNGKEVHS GVSTDPQPLK    180
EQPALNDSRY CLSSRLRVSA TFWQNPRNHF RCQVQFYGLS ENDEWTQDRA KPVTQIVSAE    240
AWGRAD                                                               246

SEQ ID NO: 204          moltype = AA  length = 115
FEATURE                 Location/Qualifiers
source                  1..115
                        mol_type = protein
                        organism = synthetic construct
SEQUENCE: 204
MQEVTQIPAA LSVPEGENLV LNCSFTDSAI YNLQWFRQDP GKGLTSLLLI QSSQREQTSG     60
RLNASLDKSS GRSTLYIAAS QPGDSATYLC AVRPTSGGSY IPTFGRGTSL IVHPY         115

SEQ ID NO: 205          moltype = AA  length = 112
FEATURE                 Location/Qualifiers
source                  1..112
                        mol_type = protein
                        organism = synthetic construct
SEQUENCE: 205
MGVTQTPKFQ VLKTGQSMTL QCAQDMNHEY MSWYRQDPGM GLRLIHYSVG AGITDQGEVP     60
NGYNVSRSTT EDFPLRLLSA APSQTSVYFC ASSYVGNTGE LFFGEGSRLT VL           112

SEQ ID NO: 206          moltype = AA  length = 166
FEATURE                 Location/Qualifiers
source                  1..166
                        mol_type = protein
                        organism = synthetic construct
SEQUENCE: 206
APPRLICDSR VLERYLLEAK EAENITTGCA EHCSLNENIT VPDTKVNFYA WKRMEVGQQA     60
VEVWQGLALL SEAVLRGQAL LVNSSQPWEP LQLHVDKAVS GLRSLTTLLR ALGAQKEAIS    120
PPDAASAAPL RTITADTFRK LFRVYSNFLR GKLKLYTGEA CRTGDR                   166

SEQ ID NO: 207          moltype = AA  length = 452
FEATURE                 Location/Qualifiers
source                  1..452
                        mol_type = protein
                        organism = synthetic construct
SEQUENCE: 207
MSTAVLENPG LGRKLSDFGQ ETSYIEDNCN QNGAISLIFS LKEEVGALAK VLRLFEENDV     60
NLTHIESRPS RLKKDEYEFF THLDKRSLPA LTNIIKILRH DIGATVHELS RDKKKDTVPW    120
FPRTIQELDR FANQILSYGA ELDADHPGFK DPVYRARRKQ FADIAYNYRH GQPIPRVEYM    180
EEEKKTWGTV FKTLKSLYKT HACYEYNHIF PLLEKYCGFH EDNIPQLEDV SQFLQTCTGF    240
RLRPVAGLLS SRDFLGGLAF RVFHCTQYIR HGSKPMYTPE PDICHELLGH VPLFSDRSFA    300
QFSQEIGLAS LGAPDEYIEK LATIYWFTVE FGLCKQGDSI KAYGAGLLSS FGELQYCLSE    360
KPKLLPLELE KTAIQNYTVT EFQPLYYVAE SFNDAKEKVR NFAATIPRPF SVRYDPYTQR    420
IEVLDNTQQL KILADSINSE IGILCSALQK IK                                  452

SEQ ID NO: 208          moltype = AA  length = 1462
FEATURE                 Location/Qualifiers
source                  1..1462
                        mol_type = protein
                        organism = synthetic construct
SEQUENCE: 208
LSVKAQTAHI VLEDGTKMKG YSFGHPSSVA GEVVFNTGLG GYPEAITDPA YKGQILTMAN     60
PIIGNGGAPD TTALDELGLS KYLESNGIKV SGLLVLDYSK DYNHWLATKS LGQWLQEEKV    120
PAIYGVDTRM LTKIIRDKGT MLGKIEFEGQ PVDFVDPNKQ NLIAEVSTKD VKVYGKGNPT    180
KVVAVDCGIK NNVIRLLVKR GAEVHLVPWN HDFTKMEYDG ILIAGGPGNP ALAEPLIQNV    240
```

```
RKILESDRKE PLFGISTGNL ITGLAAGAKT YKMSMANRGQ NQPVLNITNK QAFITAQNHG   300
YALDNTLPAG WKPLFVNVND QTNEGIMHES KPFFAVQFHP EVTPGPIDTE YLFDSFFSLI   360
KKGKATTITS VLPKPALVAS RVEVSKVLIL GSGGLSIGQA GEFDYSGSQA VKAMKEENVK   420
TVLMNPNIAS VQTNEVGLKQ ADTVYFLPIT PQFVTEVIKA EQPDGLILGM GGQTALNCGV   480
ELFKRGVLKE YGVKVLGTSV ESIMATEDRQ LFSDKLNEIN EKIAPSFAVE SIEDALKAAD   540
TIGYPVMIRS AYALGGLGSG ICPNRETLMD LSTKAFAMTN QILVEKSVTG WKEIEYEVVR   600
DADDNCVTVC NMENVDAMGV HTGDSVVVAP AQTLSNAEFQ MLRRTSINVV RHLGIVGECN   660
IQFALHPTSM EYCIIEVNAR LSRSSALASK ATGYPLAFIA AKIALGIPLP EIKNVVSGKT   720
SACFEPSLDY MVTKIPRWDL DRFHGTSSRI GSSMKSVGEV MAIGRTFEES FQKALRMCHP   780
SIEGFTPRLP MNKEWPSNLD LRKELSEPSS TRIYAIAKAI DDNMSLDEIE KLTYIDKWFL   840
YKMRDILNME KTLKGLNSES MTEETLKRAK EIGFSDKQIS KCLGLTEAQT RELRLKKNIH   900
PWVKQIDTLA AEYPSVTNYL YVTYNGQEHD VNFDDHGMMV LGCGPYHIGS SVEFDWCAVS   960
SIRTLRQLGK KTVVVNCNPE TVSTDFDECD KLYFEELSLE RILDIYHQEA CGGCIISVGG  1020
QIPNNLAVPL YKNGVKIMGT SPLQIDRAED RSIFSAVLDE LKVAQAPWKA VNTLNEALEF  1080
AKSVDYPCLL RPSYVLSGSA MNVVFSEDEM KKFLEEATRV SQEHPVVLTK FVEGAREVEM  1140
DAVGKDGRVI SHAISEHVED AGVHSGDATL MLPTQTISQG AIEKVKDATR KIAKAFAISG  1200
PFNVQFLVKG NDVLVIECNL RASRSFPFVS KTLGVDFIDV ATKVMIGENV DEKHLPTLDH  1260
PIIPADYVAI KAPMFSWPRL RDADPILRCE MASTGEVACF GEGIHTAFLK AMLSTGFKIP  1320
QKGILIGIQQ SFRPRFLGVA EQLHNEGFKL FATEATSDWL NANNVPATPV AWPSQEGQNP  1380
SLSSIRKLIR DGSIDLVINL PNNNTKFVHD NYVIRRTAVD SGIPLLTNFQ VTKLFAEAVQ  1440
KSRKVDSKSL FHYRQYSAGK AA                                          1462

SEQ ID NO: 209          moltype = AA  length = 1053
FEATURE                 Location/Qualifiers
source                  1..1053
                        mol_type = protein
                        organism = synthetic construct
SEQUENCE: 209
MKRNYILGLD IGITSVGYGI IDYETRDVID AGVRLFKEAN VENNEGRRSK RGARRLKRRR   60
RHRIQRVKKL LFDYNLLTDH SELSGINPYE ARVKGLSQKL SEEEFSAALL HLAKRRGVHN  120
VNEVEEDTGN ELSTKEQISR NSKALEEKYV AELQLERLKK DGEVRGSINR FKTSDYVKEA  180
KQLLKVQKAY HQLDQSFIDT YIDLLETRRT YYEGPGEGSP FGWKDIKEWY EMLMGHCTYF  240
PEELRSVKYA YNADLYNALN DLNNLVITRD ENEKLEYYEK FQIIENVFKQ KKKPTLKQIA  300
KEILVNEEDI KGYRVTSTGK PEFTNLKVYH DIKDITARKE IIENAELLDQ IAKILTIYQS  360
SEDIQEELTN LNSELTQEEI EQISNLKGYT GTHNLSLKAI NLILDELWHT NDNQIAIFNR  420
LKLVPKKVDL SQQKEIPTTL VDDFILSPVV KRSFIQSIKV INAIIKKYGL PNDIIIELAR  480
EKNSKDAQKM INEMQKRNRQ TNERIEEIIR TTGKENAKYL IEKIKLHDMQ EGKCLYSLEA  540
IPLEDLLNNP FNYEVDHIIP RSVSFDNSFN NKVLVKQEEN SKKGNRTPFQ YLSSSDSKIS  600
YETFKKHILN LAKGKGRISK TKKEYLLEER DINRFSVQKD FINRNLVDTR YATRGLMNLL  660
RSYFRVNNLD VKVKSINGGF TSFLRRKWKF KKERNKGYKH HAEDALIIAN ADFIFKEWKK  720
LDKAKKVMEN QMFEEKQAES MPEIETEQEY KEIFITPHQI KHIKDFKDYK YSHRVDKKPN  780
RELINDTLYS TRKDDKGNTL IVNNLNGLYD KDNDKLKKLI NKSPEKLLMY HHDPQTYQKL  840
KLIMEQYGDE KNPLYKYYEE TGNYLTKYSK KDNGPVIKKI KYYGNKLNAH LDITDDYPNS  900
RNKVVKLSLK PYRFDVYLDN GVYKFVTVKN LDVIKKENYY EVNSKCYEEA KKLKKISNQA  960
EFIASFYNND LIKINGELYR VIGVNNDLLN RIEVNMIDIT YREYLENMND KRPPRIIKTI 1020
ASKTQSIKKY STDILGNLYE VKSKKHPQII KKG                              1053

SEQ ID NO: 210          moltype = AA  length = 1353
FEATURE                 Location/Qualifiers
source                  1..1353
                        mol_type = protein
                        organism = synthetic construct
SEQUENCE: 210
AAGGILHLEL LVAVGPDVFQ AHQEDTERYV LTNLNIGAEL LRDPSLGAQF RVHLVKMVIL   60
TEPEGAPNIT ANLTSSLLSV CGWSQTINPE DDTDPGHADL VLYITRFDLE LPDGNRQVRG  120
VTQLGGACSP TWSCLITEDT GFDLGVTIAH EIGHSFGLEH DGAPGSGCGP SGHVMASDGA  180
APRAGLAWSP CSRRQLLSLL SAGRARCVWD PPRPQPGSAG HPPDAQPGLY YSANEQCRVA  240
FGPKAVACTF AREHLDMCQA LSCHTDPLDQ SSCSRLLVPL LDGTECGVEK WCSKGRCRSL  300
VELTPIAAVH GRWSSWGPRS PCSRSCGGGV VTRRRQCNNP RPAFGGRACV GADLQAEMCN  360
TQACEKTQLE FMSQQCARTD GQPLRSSPGG ASFYHWGAAV PHSQGDALCR HMCRAIGESF  420
IMKRGDSFLD GTRCMPSGPR EDGTLSLCVS GSCRTFGCDG RMDSQQVWDR CQVCGGDNST  480
CSPRKGSFTA GRAREYVTFL TVTPNLTSVY IANHRPLFTH LAVRIGGRYV VAGKMSISPN  540
TTYPSLLEDG RVEYRVALTE DRLPRLEEIR IWGPLQEDAD IQVYRRYGEE YGNLTRPDIT  600
FTYFQPKPRQ AWVWAAVRGP CSVSCGAGLR WVNYSCLDQA RKELVETVQC QGSQQPPAWP  660
EACVLEPCPP YWAVGDFGPC SASCGGGLRE RPVRCVEAQG SLLKTLPPAR CRAGAQQPAV  720
ALETCNPQPC PARWEVSEPS SCTSAGGAGL ALENETCVPG ADGLEAPVTE GPGSVDEKLP  780
APEPCVGMSC PPGWGHLDAT SAGEKAPSPW GSIRTGAQAA HVWTPAAGSC SVSCGRGLME  840
LRFLCMDSAL RVPVQEELCG LASKPGSRRE VCQAVPCPAR WQYKLAACSV SCGRGVVRRI  900
LYCARAHGED DGEEILLDTQ CQGLPRPEPQ EACSLEPCPP RWKVMSLGPC SASCGLGTAR  960
RSVACVQLDQ GQDVEVDEAA CAALVRPEAS VPCLIADCTY RWHVGTWMEC SVSCGDGIQR 1020
RRDTCLGPQA QAPVPADFCQ HLPKPVTVRG CWAGPCVGQG TPSLVPHEEA AAPGRTTATP 1080
AGASLEWSQA RGLLFSPAPQ PRRLLPGPQE NSVQSSACGR QHLEPTGTID MRGPGQADCA 1140
VAIGRPLGEV VTLRVLESSL NCSAGDMLLL WGRLTWRKMC KLLDMTFSS KTNTLVVRQR 1200
CGRPGGGVLL RYGSQLAPET FYRECDMQLF GPWGEIVSPS LSPATSNAGG CRLFINVAPH 1260
ARIAIHALAT NMGAGTEGAN ASYILIRDTH SLRTTAFHGQ QVLYWESESS QAEMEFSEGF 1320
LKAQASLRGQ YWTLQSWVPE MQDPQSWKGK EGT                              1353

SEQ ID NO: 211          moltype = AA  length = 431
FEATURE                 Location/Qualifiers
```

-continued

```
source                    1..431
                          mol_type = protein
                          organism = synthetic construct
SEQUENCE: 211
MPNPRPGKPS APSLALGPSP GASPSWRAAP KASDLLGARG PGGTFQGRDL RGGAHASSSS   60
LNPMPPSQLQ LPTLPLVMVA PSGARLGPLP HLQALLQDRP HFMHQLSTVD AHARTPVLQV  120
HPLESPAMIS LTPPTTATGV FSLKARPGLP PGINVASLEW VSREPALLCT FPNPSAPRKD  180
STLSAVPQSS YPLLANGVCK WPGCEKVFEE PEDFLKHCQA DHLLDEKGRA QCLLQREMVQ  240
SLEQQLVLEK EKLSAMQAHL AGKMALTKAS SVASSDKGSC CIVAAGSQGP VVPAWSGPRE  300
APDSLFAVRR HLWGSHGNST FPEFLHNMDY FKFHNMRPPF TYATLIRWAI LEAPEKQRTL  360
NEIYHWFTRM FAFFRNHPAT WKNAIRHNLS LHKCFVRVES EKGAVWTVDE LEFRKKRSQR  420
PSRCSNPTPG P                                                       431

SEQ ID NO: 212           moltype = AA   length = 160
FEATURE                  Location/Qualifiers
source                   1..160
                         mol_type = protein
                         organism = synthetic construct
SEQUENCE: 212
SPGQGTQSEN SCTHFPGNLP NMLRDLRDAF SRVKTFFQMK DQLDNLLLKE SLLEDFKGYL   60
GCQALSEMIQ FYLEEVMPQA ENQDPDIKAH VNSLGENLKT LRLRLRRCHR FLPCENKSKA  120
VEQVKNAFNK LQEKGIYKAM SEFDIFINYI EAYMTMKIRN                        160

SEQ ID NO: 213           moltype = AA   length = 133
FEATURE                  Location/Qualifiers
source                   1..133
                         mol_type = protein
                         organism = synthetic construct
SEQUENCE: 213
APTSSSTKKT QLQLEHLLLD LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR  120
WITFCQSIIS TLT                                                     133
```

CIRCULAR RNA COMPOSITIONS

CROSS-REFERENCE TO RELATED APPLICATIONS

This application is a continuation of International Application No. PCT/US2023/078875, filed Nov. 7, 2023, which claims the benefit of priority of U.S. Provisional Application No. 63/423,760, filed Nov. 8, 2022, U.S. Provisional Application No. 63/501,820, filed May 12, 2023, and U.S. Provisional Application No. 63/509,361, filed Jun. 21, 2023, each of which is incorporated by reference herein in its entirety for any purpose.

SEQUENCE LISTING

This application is filed with a Sequence Listing in electronic format. The Sequence Listing is provided as a file entitled "01318-0002-00PCT_SL.xml" created on Oct. 31, 2023, which is 213,220 bytes in size. The information in the electronic format of the sequence listing is incorporated herein by reference in its entirety.

INTRODUCTION AND BACKGROUND

Circular RNA (circRNA or oRNA™) is a known stable form of RNA that provides an advantage compared to linear RNA in structure and function, especially in the case of molecules that are prone to folding in an inactive conformation (Wang, Laixin et al., "Oligoribonucleotide circularization by "template-mediated ligation with T4 RNA ligase: synthesis of circular hammerhead ribozymes", Nucleic Acids Research, 1998, 26 (10); 2502-2504.). Circular RNA polynucleotides lack the free ends necessary for exonuclease-mediated degradation, causing them to be resistant to several mechanisms of RNA degradation and granting extended half-lives when compared to an equivalent linear RNA. Circularization may allow for the stabilization of RNA polynucleotides that generally suffer from short half-lives and may improve the overall efficacy of exogenous mRNA in a variety of applications. Circular RNA can also be particularly interesting and useful for in vivo applications, especially in the research area of RNA-based control of gene expression and therapeutics, including protein replacement therapy and vaccination.

Adoptive T-cell immunotherapy is a rapidly growing field, in particular in cancer treatments. In general, chimeric antigen receptor (CAR) T cell or "CAR-T" engagement of CD19-expressing cancer cells results in T-cell activation, proliferation and secretion of inflammatory cytokines and chemokines resulting in tumor cell lysis. However, while CAR-T therapies have become an important tool in cancer treatments, they have toxic side effects and involve complex procedures. Treatment with CAR-T can lead to a large and rapid release of cytokines into the blood and can cause cytokine release syndrome (CRS) or CAR-T cell-related encephalopathy syndrome (CRES), also referred to as neurotoxicity associated with CAR-T. CRS is the most common and well-described toxicity associated with CAR-T therapy, occurring in over 90% of patients at any grade and is characterized by high fever, hypotension, hypoxia and/or multiple organ toxicity and can lead to death. Neurotoxicity is characterized by damage to nervous tissue that can cause tremors, encephalopathy, dizziness or seizures. Additionally, prior to infusion, the patients generally undergo lymphodepletion. Lymphodepletion is known to increase CAR-T cell expansion and enhanced efficacy of infused CAR-T cells by, for example, altering the tumor phenotype and microenvironment. However, lymphodepletion agents often cause side effects to the patients. For example, lymphodepletion can cause neutropenia, anemia, thrombocytopenia, and immunosuppression, leading to a greater risk of infection, along with other toxicities. In addition to the toxicities associated with targeted CAR-T therapies, there are procedures, specialized equipment, and costs involved in producing the modified lymphocytes. CAR-T therapies require an assortment of protocols to isolate, genetically modify, and selectively expand the redirected cells before infusing them back into the patient.

In a compassionate-use anti-CD19 CAR T cell therapy for refractory systemic lupus erythematosus, autologous T cells from five SLE patients "were transduced with a lentiviral anti-CD19 CAR vector, expanded and reinfused . . . into the patients after lymphodepletion with fludarabine and cyclophosphamide. CAR T cells expanded in vivo led to deep depletion of B cells, improvement of clinical symptoms and normalization of laboratory parameters including seroconversion of anti-double-stranded DNA antibodies. Remission of SLE according to DORIS criteria was achieved in all five patients after 3 months and the median (range) Systemic Lupus Erythematosus Disease Activity Index score after 3 months was 0 (2)." See Mackensen et al., Anti-CD19 CAR T cell therapy for refractory systemic lupus erythematosus, Nature Medicine (2022); see also Nunez et al., Cytokine and reactivity profiles in SLE patients following anti-CD19 CART therapy, Molecular Therapy (2023).

Because circRNAs are more stable and can be expressed in tissue-specific manner, and because using circRNAs can avoid the lymphodepletion step of traditional therapies, circRNAs provide an attractive alternative to traditional CAR therapies and other therapies. Accordingly, provided herein are circular RNA constructs that comprise an internal ribosome entry site (IRES) and at least one expression sequence encoding a binding molecule. In certain embodiments, the binding molecule encodes a CAR that targets a cancer antigen, for use in treating cancer. The circular RNA can be formulated with a transfer vehicle to facilitate and/or enhance the delivery and release of circRNA to one or more target cells. Accordingly, lipid nanoparticles (LNPs) or other transfer vehicles containing ionizable lipids may be used to deliver the circular RNA described herein, for example, to a patient in need of treatment.

SUMMARY

The present disclosure provides circular RNAs that encode cancer-binding polypeptides paired with lipid transfer vehicles for use in treating cancer. In particular, the present disclosure provides circular RNA comprising an IRES and a nucleic acid encoding a binding molecule, wherein the IRES and the nucleic acid encoding the binding molecule are paired for optimal expression of the polypeptide binding molecule. It has surprisingly been found that certain IRESes and nucleic acid combinations work better than others for optimal expression. It has further been discovered that certain transfer vehicles may work better with certain IRES/binding molecule combinations. Thus, particularly preferred combinations of IRES/nucleic acid encoding binding molecule/transfer vehicles are provided herein. In some embodiments, the circular RNAs provided herein may be used in treating or preventing cancer. In some embodiments, the circular RNAs provided herein may be used in treating or preventing an autoimmune disease, e.g., a B cell mediated autoimmune disease, e.g., lupus.

In some embodiments engineered chimeric antigen receptors (CARs) are encoded by the circular RNA and may be inserted into and expressed by immune cells, including T cells, NK cells, macrophages, etc., via engineered circular RNAs (circRNAs or oRNAs) after delivery via a lipid transfer vehicle. In some embodiments, the CAR may recognize a specific antigen (e.g., CD19, HER2, or BCMA) and, when bound to that antigen, activate the immune cell to attack and destroy the cell. The circular RNAs, compositions, and methods herein are thus useful for reducing known side effects associated with CAR-T therapies by programming circulating immune cells, e.g., T cells, with tumor-recognizing capabilities and by using lipid transfer vehicles (e.g., LNPs) to deliver the circular RNA constructs that can efficiently introduce the CAR genes to the immune cells. Methods directed to the manufacture of such circularized RNA constructs, along with methods of treating a subject in need using the circular RNA are also provided. Linear precursor RNA polynucleotides are provided for producing circular RNA constructs, that comprises a core functional element comprising a translation initiation element (TIE). The TIE can comprise an untranslated region (UTR), aptamer complex or a combination thereof. The UTR can be in whole or in part from a viral or eukaryotic mRNA. The UTR can comprise a viral or eukaryotic internal ribosome entry site (IRES). Pharmaceutical compositions are also provided for the linear precursor and circular RNA constructs comprising an IRES, an expression sequence, and optionally a transfer vehicle. In certain embodiments, the circular RNA constructs comprise an expression sequence encoding a CAR construct targeting a cancer antigen. The pharmaceutical compositions of the present disclosure are particularly suitable for efficient protein expression in immune cells in vivo. The transfer vehicles can comprise, e.g., ionizable lipids, PEG-modified lipids, helper lipids, and/or structural lipids, that are capable of encapsulating the circular RNAs.

Accordingly, the following embodiments are provided:

Embodiment 1. A circular RNA construct comprising:

(A) an IRES comprising a sequence that is at least 80% identical to a sequence selected from any one of SEQ ID NOs: 1-18, and (B) at least one expression sequence encoding a binding molecule.

Embodiment 2. A circular RNA construct comprising:

(A) an IRES comprising a sequence that is at least 80% identical to a sequence selected from any one of SEQ ID NOs: 1-18, and (B) at least one expression sequence encoding a chimeric antigen receptor (CAR) targeting a cancer antigen.

Embodiment 3. A circular RNA construct comprising:

(A) an IRES comprising a sequence that is at least 80% identical to a sequence selected from any one of SEQ ID NOs: 1-18, and (B) at least one expression sequence encoding a CAR targeting a cancer antigen, wherein the CAR construct comprises a CD19 binder.

Embodiment 4. The circular RNA construct of embodiment 3, wherein the expression sequence comprises a sequence that is at least 80% identical to a sequence selected from any one of SEQ ID NOs: 19-34.

Embodiment 5. A circular RNA construct comprising:

(A) an IRES comprising a sequence that is at least 80% identical to a sequence selected from any one of SEQ ID NOs: 1-18, and (B) at least one expression sequence encoding a CAR targeting a cancer antigen, wherein the CAR construct comprises a BCMA binder.

Embodiment 6. The circular RNA construct of embodiment 5, wherein the expression sequence comprises a sequence that is at least 80% identical to a sequence selected from any one of SEQ ID NOs: 103-115.

Embodiment 7. A circular RNA construct comprising:

(A) an IRES selected from an Enterovirus, Kobuvirus, Parechovirus, Hunnivirus, Passerivirus, Mischivirus, and Cardiovirus, and (B) at least one expression sequence encoding a binding molecule.

Embodiment 8. A circular RNA construct comprising:

(A) an IRES selected from an Enterovirus, Kobuvirus, Parechovirus, Hunnivirus, Passerivirus, Mischivirus, and Cardiovirus, and (B) at least one expression sequence encoding a chimeric antigen receptor (CAR) targeting a cancer antigen.

Embodiment 9. A circular RNA construct comprising:

(A) an IRES selected from an Enterovirus, Kobuvirus, Parechovirus, Hunnivirus, Passerivirus, Mischivirus, and Cardiovirus, and (B) at least one expression sequence encoding a CAR targeting a cancer antigen, wherein the CAR construct comprises a CD19 binder.

Embodiment 10. The circular RNA construct of embodiment 9, wherein the expression sequence comprises a sequence that is at least 80% identical to a sequence selected from any one of SEQ ID NOs: 19-34.

Embodiment 11. A circular RNA construct comprising:

(A) an IRES selected from an Enterovirus, Kobuvirus, Parechovirus, Hunnivirus, Passerivirus, Mischivirus, and Cardiovirus, and (B) at least one expression sequence encoding a CAR targeting a cancer antigen, wherein the CAR construct comprises a BCMA binder.

Embodiment 12. The circular RNA construct of embodiment 11, wherein the expression sequence comprises a sequence that is at least 80% identical to a sequence selected from any one of SEQ ID NOs: 103-115.

Embodiment 13. A pharmaceutical composition comprising:

(A) a circular RNA construct comprising:

i. an IRES comprising a sequence that is at least 80% identical to a sequence selected from any one of SEQ ID NOs: 1-18, and ii. at least one expression sequence encoding a binding molecule, and (B) a transfer vehicle.

Embodiment 14. A pharmaceutical composition comprising:

(A) a circular RNA construct comprising:

i. an IRES comprising a sequence that is at least 80% identical to a sequence selected from any one of SEQ ID NOs: 1-18, and ii. at least one expression sequence encoding a CAR targeting a cancer antigen, and (B) a transfer vehicle.

Embodiment 15. A pharmaceutical composition comprising:

(A) a circular RNA construct comprising:

i. an IRES selected from an Enterovirus, Kobuvirus, Parechovirus, Hunnivirus, Passerivirus, Mischivirus, and Cardiovirus, and ii. at least one expression sequence encoding a binding molecule, and (B) a transfer vehicle.

Embodiment 16. A pharmaceutical composition comprising:
- (A) a circular RNA construct comprising:
  - i. an IRES selected from an Enterovirus, Kobuvirus, Parechovirus, Hunnivirus, Passerivirus, Mischivirus, and Cardiovirus, and
  - ii. at least one expression sequence encoding a CAR targeting a cancer antigen, and
- (B) a transfer vehicle.

Embodiment 17. A pharmaceutical composition comprising:
- (A) a circular RNA construct comprising:
  - i. an IRES comprising a sequence that is at least 80% identical to a sequence selected from any one of SEQ ID NOs: 1-18, and
  - ii, at least one expression sequence encoding a binding molecule, and
- (B) a transfer vehicle comprising an ionizable lipid.

Embodiment 18. A pharmaceutical composition comprising:
- (A) a circular RNA construct comprising:
  - i. an IRES comprising a sequence that is at least 80% identical to a sequence selected from any one of SEQ ID NOs: 1-18, and
  - ii. at least one expression sequence encoding a CAR targeting a cancer antigen, and
- (B) a transfer vehicle comprising an ionizable lipid.

Embodiment 19. A pharmaceutical composition comprising:
- (A) a circular RNA construct comprising:
  - i. an IRES comprising a sequence that is at least 80% identical to a sequence selected from any one of SEQ ID NOs: 1-18, and
  - ii. at least one expression sequence encoding a CAR targeting a cancer antigen, wherein the CAR construct comprises a CD19 binder, and
- (B) a transfer vehicle comprising an ionizable lipid.

Embodiment 20. The pharmaceutical composition of embodiment 19, wherein the expression sequence comprises a sequence that is at least 80% identical to a sequence selected from any one of SEQ ID NOs: 19-34.

Embodiment 21. A pharmaceutical composition comprising:
- (A) a circular RNA construct comprising:
  - i. an IRES comprising a sequence that is at least 80% identical to a sequence selected from any one of SEQ ID NOs: 1-18, and
  - ii. at least one expression sequence encoding a CAR targeting a cancer antigen, wherein the CAR construct comprises a BMCA binder, and
- (B) a transfer vehicle comprising an ionizable lipid.

Embodiment 22. The pharmaceutical composition of embodiment 21, wherein the expression sequence comprises a sequence that is at least 80% identical to a sequence selected from any one of SEQ ID NOs: 103-115.

Embodiment 23. A pharmaceutical composition comprising:
- (A) a circular RNA construct comprising:
  - i. an IRES selected from an Enterovirus, Kobuvirus, Parechovirus, Hunnivirus, Passerivirus, Mischivirus, and Cardiovirus, and
  - ii. at least one expression sequence encoding a binding molecule, and
- (B) a transfer vehicle comprising an ionizable lipid.

Embodiment 24. A pharmaceutical composition comprising:

- (A) a circular RNA construct comprising:
  - i. an IRES selected from an Enterovirus, Kobuvirus, Parechovirus, Hunnivirus, Passerivirus, Mischivirus, and Cardiovirus, and
  - ii. at least one expression sequence encoding a CAR targeting a cancer antigen, and
- (B) a transfer vehicle comprising an ionizable lipid.

Embodiment 25. A pharmaceutical composition comprising:
- (A) a circular RNA construct comprising:
  - i. an IRES selected from an Enterovirus, Kobuvirus, Parechovirus, Hunnivirus, Passerivirus, Mischivirus, and Cardiovirus, and
  - ii. at least one expression sequence encoding a CAR targeting a cancer antigen, wherein the CAR construct comprises a CD19 binder, and
- (B) a transfer vehicle comprising an ionizable lipid.

Embodiment 26. The pharmaceutical composition of embodiment 25, wherein the expression sequence comprises a sequence that is at least 80% identical to a sequence selected from any one of SEQ ID NOs: 19-34.

Embodiment 27. A pharmaceutical composition comprising:
- (A) a circular RNA construct comprising:
  - i. an IRES selected from an Enterovirus, Kobuvirus, Parechovirus, Hunnivirus, Passerivirus, Mischivirus, and Cardiovirus, and
  - ii. at least one expression sequence encoding a CAR targeting a cancer antigen, wherein the CAR construct comprises a BMCA binder, and
- (B) a transfer vehicle comprising an ionizable lipid.

Embodiment 28. The pharmaceutical composition of embodiment 27, wherein the expression sequence comprises a sequence that is at least 80% identical to a sequence selected from any one of SEQ ID NOs: 103-115.

Embodiment 29. A pharmaceutical composition comprising:
- (A) a circular RNA construct comprising:
  - i. an IRES comprising a sequence that is at least 80% identical to a sequence selected from any one of SEQ ID NOs: 1-18, and
  - ii. at least one expression sequence encoding a binding molecule, and
- (B) a transfer vehicle comprising:
  - (i) an ionizable lipid of Formula (I)

Formula (I)

wherein n is an integer between 1 and 4;

$R_a$ is hydrogen or hydroxyl; and $R_1$ and $R_2$ are each independently a linear or branched $C_6$-$C_{30}$ alkyl, $C_6$-$C_{30}$ alkenyl, or $C_6$-$C_{30}$ heteroalkyl, optionally substituted by one or more substituents selected from a group consisting of oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl) (alkyl)aminoalkyl, heterocyclyl, heteroaryl, alkylheteroaryl, alkynyl, alkoxy, amino, dialkylamino, aminoalkylcarbonylamino, aminocarbonyl-alkylamino, (aminocarbonylalkyl) (alkyl)amino, alkenylcarbonylamino, hydroxycarbonyl, dialkylami-noalkylaminocarbonyl, heterocyclylalkylaminocarbo-nyl, (alkylaminoalkyl) (alkyl)aminocarbonyl, alky-laminoalkylcarbonyl, dialkylaminoalkylcarbonyl, heterocyclylcarbonyl, alkenylcarbonyl, alkynylcarbo-nyl, alkylsulfoxide, alkylsulfoxidealkyl, alkylsulfonyl, and alkylsulfonealkyl; or (ii) an ionizable lipid of Formula (II)

$$R_1 - L_1 \underset{n}{\overset{}{\longleftrightarrow}} \underset{R_2}{\overset{}{N}} \underset{n}{\overset{}{\longleftrightarrow}} L_3 - R_3,$$

Formula (II)

wherein each n is independently an integer from 2-15;

$L_1$ and $L_3$ are each independently —OC(O)—* or —C(O)O—*, wherein "*" indicates the attachment point to $R_1$ or $R_3$;

$R_1$ and $R_3$ are each independently a linear or branched $C_9$-$C_{20}$ alkyl or $C_9$-$C_{20}$ alkenyl, optionally substi-tuted by one or more substituents selected from a group consisting of oxo, halo, hydroxy, cyano, alkyl, alkenyl, aldehyde, heterocyclylalkyl, hydroxyalkyl, dihydroxyalkyl, hydroxyalkylaminoalkyl, aminoal-kyl, alkylaminoalkyl, dialkylaminoalkyl, (heterocy-clyl) (alkyl)aminoalkyl, heterocyclyl, heteroaryl, alkylheteroaryl, alkynyl, alkoxy, amino, dialky-lamino, aminoalkylcarbonylamino, aminocarbonyl-alkylamino, (aminocarbonylalkyl) (alkyl)amino, alk-enylcarbonylamino, hydroxycarbonyl, alkyloxycarbonyl, aminocarbonyl, aminoalkylami-nocarbonyl, alkylaminoalkylaminocarbonyl, dialky-laminoalkylaminocarbonyl, heterocyclylalkylami-nocarbonyl, (alkylaminoalkyl) (alkyl) aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl, and alkylsulfone-alkyl; and $R_2$ is selected from a group consisting of:

-continued

Embodiment 30. A pharmaceutical composition compris-ing:

(A) a circular RNA construct comprising:

i. an IRES comprising a sequence that is at least 80% identical to a sequence selected from any one of SEQ ID NOs: 1-18, and ii. at least one expression sequence encoding a CAR targeting a cancer antigen, and (B) a transfer vehicle comprising:
   (i) an ionizable lipid of Formula (I)

Formula (I)

wherein n is an integer between 1 and 4;

$R_a$ is hydrogen or hydroxyl; and $R_1$ and $R_2$ are each independently a linear or branched $C_6$-$C_{30}$ alkyl, $C_6$-$C_{30}$ alkenyl, or $C_6$-$C_{30}$ heteroalkyl, optionally substituted by one or more substituents selected from a group consisting of oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl) (alkyl)aminoalkyl, heterocyclyl, heteroaryl, alkylheteroaryl, alkynyl, alkoxy, amino, dialkylamino, aminoalkylcarbonylamino, aminocarbonylalkylamino, (aminocarbonylalkyl) (alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl) (alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl, and alkylsulfonealkyl;

or (ii) an ionizable lipid of Formula (II)

Formula (II)

wherein each n is independently an integer from 2-15;

$L_1$ and $L_3$ are each independently —OC(O)—* or —C(O)O—*, wherein "*" indicates the attachment point to $R_1$ or $R_3$;

$R_1$ and $R_3$ are each independently a linear or branched $C_9$-$C_{20}$ alkyl or $C_0$-$C_{20}$ alkenyl, optionally substituted by one or more substituents selected from a group consisting of oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl) (alkyl)aminoalkyl, heterocyclyl, heteroaryl, alkylheteroaryl, alkynyl, alkoxy, amino, dialkylamino, aminoalkylcarbonylamino, aminocarbonylalkylamino, (aminocarbonylalkyl) (alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl) (alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl, and alkylsulfonealkyl; and $R_2$ is selected from a group consisting of:

-continued

, and

Embodiment 31. A pharmaceutical composition comprising:

(A) a circular RNA construct comprising:
  i. an IRES comprising a sequence that is at least 80% identical to a sequence selected from any one of SEQ ID NOs: 1-18, and
  ii. at least one expression sequence encoding a CAR construct targeting a cancer antigen, wherein the CAR construct comprises a CD19 binder, and (B) a transfer vehicle comprising:

(i) an ionizable lipid of Formula (I)

Formula (I)

wherein n is an integer between 1 and 4;

$R_a$ is hydrogen or hydroxyl; and $R_1$ and $R_2$ are each independently a linear or branched $C_6$-$C_{30}$ alkyl, $C_6$-$C_{30}$ alkenyl, or $C_6$-$C_{30}$ heteroalkyl, optionally substituted by one or more substituents selected from a group consisting of oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl) (alkyl)aminoalkyl, heterocyclyl, heteroaryl, alkylheteroaryl, alkynyl, alkoxy, amino, dialkylamino, aminoalkylcarbonylamino, aminocarbonylalkylamino, (aminocarbonylalkyl) (alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl) (alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl, and alkylsulfonealkyl;

or (ii) an ionizable lipid of Formula (II)

Formula (II)

wherein each n is independently an integer from 2-15;

$L_1$ and $L_3$ are each independently —OC(O)—* or —C(O)O—*, wherein "*" indicates the attachment point to $R_1$ or $R_3$;

$R_1$ and $R_3$ are each independently a linear or branched $C_9$-$C_{20}$ alkyl or $C_9$-$C_{20}$ alkenyl, optionally substituted by one or more substituents selected from a group consisting of oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl) (alkyl)aminoalkyl, heterocyclyl, heteroaryl, alkylheteroaryl, alkynyl, alkoxy, amino, dialkylamino, aminoalkylcarbonylamino, aminocarbonylalkylamino, (aminocarbonylalkyl) (alkyl)amino, alkenylcarbonylamino, hydroxycarbonyl, dialkylaminoalkylaminocarbonyl, heterocyclylalkylaminocarbonyl, (alkylaminoalkyl) (alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl, and alkylsulfonealkyl; and $R_2$ is selected from a group consisting of:

13

-continued

Embodiment 32. A pharmaceutical composition comprising:

(A) a circular RNA construct comprising:

i. an IRES comprising a sequence that is at least 80% identical to a sequence selected from any one of SEQ ID NOs: 1-18, and ii. at least one expression sequence encoding a CAR construct targeting a cancer antigen, wherein the CAR construct comprises a CD19 binder, and wherein the expression sequence comprises a sequence that is at least 80% identical to a sequence selected from any one of SEQ ID NOs: 19-34, and (B) a transfer vehicle comprising:

(i) an ionizable lipid of Formula (I)

wherein n is an integer between 1 and 4;

$R_a$ is hydrogen or hydroxyl; and $R_1$ and $R_2$ are each independently a linear or branched $C_6$-$C_{30}$ alkyl, $C_6$-$C_{30}$ alkenyl, or $C_6$-$C_{30}$ heteroalkyl, optionally substituted by one or more substituents selected from a group consisting of oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl) (alkyl)aminoalkyl, heterocyclyl, heteroaryl, alkylheteroaryl, alkynyl, alkoxy, amino, dialkylamino, aminoalkylcarbonylamino, aminocarbonylalkylamino, (aminocarbonylalkyl) (alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl) (alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl, and alkylsulfonealkyl;

or (ii) an ionizable lipid of Formula (II)

wherein each n is independently an integer from 2-15;

$L_1$ and $L_3$ are each independently —OC(O)—* or —C(O) O—*, wherein "*" indicates the attachment point to $R_1$ or $R_3$;

$R_1$ and $R_3$ are each independently a linear or branched $C_9$-$C_{20}$ alkyl or $C_9$-$C_{20}$ alkenyl, optionally substituted by one or more substituents selected from a group consisting of oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl) (alkyl)aminoalkyl, heterocyclyl, heteroaryl, alkylheteroaryl, alkynyl, alkoxy, amino, dialkylamino, aminoalkylcarbonylamino, aminocarbonylalkylamino, (aminocarbonylalkyl) (alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl) (alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl, and alkylsulfonealkyl; and $R_2$ is selected from a group consisting of:

-continued (B) a transfer vehicle comprising:
(i) an ionizable lipid of Formula (I)

Formula (I)

wherein n is an integer between 1 and 4;

$R_a$ is hydrogen or hydroxyl; and $R_1$ and $R_2$ are each independently a linear or branched $C_6$-$C_{30}$ alkyl, $C_6$-$C_{30}$ alkenyl, or $C_6$-$C_{30}$ heteroalkyl, optionally substituted by one or more substituents selected from a group consisting of oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl) (alkyl)aminoalkyl, heterocyclyl, heteroaryl, alkylheteroaryl, alkynyl, alkoxy, amino, dialkylamino, aminoalkylcarbonylamino, aminocarbonylalkylamino, (aminocarbonylalkyl) (alkyl)amino, alkenylcarbonylamino, hydroxycarbonyl, dialkylaminoalkylaminocarbonyl, heterocyclylalkylaminocarbonyl, (alkylaminoalkyl) (alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl, and alkylsulfonealkyl;

or (ii) an ionizable lipid of Formula (II)

Formula (II)

wherein each n is independently an integer from 2-15;

$L_1$ and $L_3$ are each independently —OC(O)—* or —C(O) O—*, wherein "*" indicates the attachment point to $R_1$ or $R_3$;

$R_1$ and $R_3$ are each independently a linear or branched $C_9$-$C_{20}$ alkyl or $C_9$-$C_{20}$ alkenyl, optionally substituted by one or more substituents selected from a group consisting of oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl) (alkyl)aminoalkyl, heterocyclyl, heteroaryl, alkylheteroaryl, alkynyl, alkoxy, amino, dialkylamino, aminoalkylcarbonylamino, aminocarbonylalkylamino, (aminocarbonylalkyl) (alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl) (alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl, and alkylsulfoncalkyl; and Embodiment 33. A pharmaceutical composition comprising:

(A) a circular RNA construct comprising:

i. an IRES comprising a sequence that is at least 80% identical to a sequence selected from any one of SEQ ID NOs: 1-18, and ii. at least one expression sequence encoding a CAR construct targeting a cancer antigen, wherein the CAR construct comprises a BCMA binder, and

17

R₂ is selected from a group consisting of:

18

-continued

Embodiment 34. A pharmaceutical composition comprising:

(A) a circular RNA construct comprising:

i. an IRES comprising a sequence that is at least 80% identical to a sequence selected from any one of SEQ ID NOs: 1-18, and ii. at least one expression sequence encoding a CAR construct targeting a cancer antigen, wherein the CAR construct comprises an anti-BCMA binder, wherein the expression sequence comprises a sequence that is at least 80% identical to a sequence selected from any one of SEQ ID NOs: 103-115, and (B) a transfer vehicle comprising:

(i) an ionizable lipid of Formula (I)

Formula (I)

wherein n is an integer between 1 and 4;

$R_a$ is hydrogen or hydroxyl; and $R_1$ and $R_2$ are each independently a linear or branched $C_6$-$C_{30}$ alkyl, $C_6$-$C_{30}$ alkenyl, or $C_6$-$C_{30}$ heteroalkyl, optionally substituted by one or more substituents selected from a group consisting of oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl) (alkyl)aminoalkyl, heterocyclyl, heteroaryl, alkylheteroaryl, alkynyl, alkoxy, amino, dialkylamino, aminoalkylcarbonylamino, aminocarbonylalkylamino, (aminocarbonylalkyl) (alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl) (alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl, and alkylsulfonealkyl;

or (ii) an ionizable lipid of Formula (II)

Formula (II)

wherein each n is independently an integer from 2-15;

$L_1$ and $L_3$ are each independently —OC(O)—* or —C(O)
O—*, wherein "*" indicates the attachment point to $R_1$
or $R_3$;

$R_1$ and $R_3$ are each independently a linear or branched
$C_9$-$C_{20}$ alkyl or $C_9$-$C_{20}$ alkenyl, optionally substituted
by one or more substituents selected from a group
consisting of oxo, halo, hydroxy, cyano, alkyl, alkenyl,
aldehyde, heterocyclylalkyl, hydroxyalkyl, dihydroxy-
alkyl, hydroxyalkylaminoalkyl, aminoalkyl, alkylami-
noalkyl, dialkylaminoalkyl, (heterocyclyl) (alkyl)ami-
noalkyl, heterocyclyl, heteroaryl, alkylheteroaryl,
alkynyl, alkoxy, amino, dialkylamino, aminoalkylcar-
bonylamino, aminocarbonylalkylamino, (aminocarbo-
nylalkyl) (alkyl)amino, alkenylcarbonylamino,
hydroxycarbonyl, alkyloxycarbonyl, aminocarbonyl,
aminoalkylaminocarbonyl, alkylaminoalkylaminocar-
bonyl, dialkylaminoalkylaminocarbonyl, heterocyclyl-
alkylaminocarbonyl, (alkylaminoalkyl) (alkyl)ami-
nocarbonyl, alkylaminoalkylcarbonyl,
dialkylaminoalkylcarbonyl, heterocyclylcarbonyl, alk-
enylcarbonyl, alkynylcarbonyl, alkylsulfoxide,
alkylsulfoxidealkyl, alkylsulfonyl, and alkylsulfoneal-
kyl; and $R_2$ is selected from a group consisting of:

-continued

Embodiment 35. A pharmaceutical composition compris-
ing:

(A) a circular RNA construct comprising:
  i. an IRES selected from an Enterovirus, Kobuvirus,
  Parechovirus, Hunnivirus, Passerivirus, Mischivirus,
  and Cardiovirus, and
  ii. at least one expression sequence encoding a binding
  molecule, and
(B) a transfer vehicle comprising:
(i) an ionizable lipid of Formula (I)

Formula (I)

wherein n is an integer between 1 and 4;
$R_a$ is hydrogen or hydroxyl; and
$R_1$ and $R_2$ are each independently a linear or branched
$C_6$-$C_{30}$ alkyl, $C_6$-$C_{30}$ alkenyl, or $C_6$-$C_{30}$ heteroalkyl,
optionally substituted by one or more substituents
selected from a group consisting of oxo, halo, hydroxy,
cyano, alkyl, alkenyl, aldehyde, heterocyclylalkyl,
hydroxyalkyl, dihydroxyalkyl, hydroxyalkylaminoal-
kyl, aminoalkyl, alkylaminoalkyl, dialkylaminoalkyl,
(heterocyclyl) (alkyl)aminoalkyl, heterocyclyl, het-
eroaryl, alkylheteroaryl, alkynyl, alkoxy, amino, dial-
kylamino, aminoalkylcarbonylamino, aminocarbonyl-
alkylamino, (aminocarbonylalkyl) (alkyl)amino,
alkenylcarbonylamino, hydroxycarbonyl, dialkylami-
noalkylaminocarbonyl, heterocyclylalkylaminocarbo-

21 nyl, (alkylaminoalkyl) (alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl, and alkylsulfonealkyl;

or (ii) an ionizable lipid of Formula (II)

$$R_1—L_1—[\quad]_n—N—[\quad]_n—L_3—R_3,$$

Formula (II)

wherein each n is independently an integer from 2-15;

L$_1$ and L$_3$ are each independently —OC(O)—* or —C(O)O—*, wherein "*" indicates the attachment point to R$_1$ or R$_3$;

R$_1$ and R$_3$ are each independently a linear or branched C$_9$-C$_{20}$ alkyl or C$_9$-C$_{20}$ alkenyl, optionally substituted by one or more substituents selected from a group consisting of oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl) (alkyl)aminoalkyl, heterocyclyl, heteroaryl, alkylheteroaryl, alkynyl, alkoxy, amino, dialkylamino, aminoalkylcarbonylamino, aminocarbonylalkylamino, (aminocarbonylalkyl) (alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl) (alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl, and alkylsulfoncalkyl; and R$_2$ is selected from a group consisting of:

22

Embodiment 36. A pharmaceutical composition comprising:

(A) a circular RNA construct comprising:
    i. an IRES selected from an Enterovirus, Kobuvirus, Parechovirus, Hunnivirus, Passerivirus, Mischivirus, and Cardiovirus, and
    ii. at least one expression sequence encoding a CAR construct targeting a cancer antigen, and

23

(B) a transfer vehicle comprising:
(i) an ionizable lipid of Formula (I)

Formula (I)

wherein n is an integer between 1 and 4;
$R_a$ is hydrogen or hydroxyl; and
$R_1$ and $R_2$ are each independently a linear or branched $C_6$-$C_{30}$ alkyl, $C_6$-$C_{30}$ alkenyl, or $C_6$-$C_{30}$ heteroalkyl, optionally substituted by one or more substituents selected from a group consisting of oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl) (alkyl)aminoalkyl, heterocyclyl, heteroaryl, alkylheteroaryl, alkynyl, alkoxy, amino, dialkylamino, aminoalkylcarbonylamino, aminocarbonylalkylamino, (aminocarbonylalkyl) (alkyl)amino, alkenylcarbonylamino, hydroxycarbonyl, dialkylaminoalkylaminocarbonyl, heterocyclylalkylaminocarbonyl, (alkylaminoalkyl) (alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl, and alkylsulfonealkyl;
or
(ii) an ionizable lipid of Formula (II)

Formula (II)

wherein each n is independently an integer from 2-15;
$L_1$ and $L_3$ are each independently —OC(O)—* or —C(O)O—*, wherein "*" indicates the attachment point to $R_1$ or $R_3$;
$R_1$ and $R_3$ are each independently a linear or branched $C_9$-$C_{20}$ alkyl or $C_9$-$C_{20}$ alkenyl, optionally substituted by one or more substituents selected from a group consisting of oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl) (alkyl)aminoalkyl, heterocyclyl, heteroaryl, alkylheteroaryl, alkynyl, alkoxy, amino, dialkylamino, aminoalkylcarbonylamino, aminocarbonylalkylamino, (aminocarbonylalkyl) (alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl) (alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl, and alkylsulfonealkyl; and

$R_2$ is selected from a group consisting of:

-continued

, and

Embodiment 37. A pharmaceutical composition comprising:

(A) a circular RNA construct comprising:
  i. an IRES selected from an Enterovirus, Kobuvirus, Parechovirus, Hunnivirus, Passerivirus, Mischivirus, and Cardiovirus, and
  ii. at least one expression sequence encoding a CAR construct targeting a cancer antigen, wherein the CAR construct comprises a CD19 binder, and (B) a transfer vehicle comprising:

(i) an ionizable lipid of Formula (I)

Formula (I)

wherein n is an integer between 1 and 4;

$R_a$ is hydrogen or hydroxyl; and $R_1$ and $R_2$ are each independently a linear or branched $C_6$-$C_{30}$ alkyl, $C_6$-$C_{30}$ alkenyl, or $C_6$-$C_{30}$ heteroalkyl, optionally substituted by one or more substituents selected from a group consisting of oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl) (alkyl)aminoalkyl, heterocyclyl, heteroaryl, alkylheteroaryl, alkynyl, alkoxy, amino, dialkylamino, aminoalkylcarbonylamino, aminocarbonylalkylamino, (aminocarbonylalkyl) (alkyl)amino, alkenylcarbonylamino, hydroxycarbonyl, dialkylaminoalkylaminocarbonyl, heterocyclylalkylaminocarbonyl, (alkylaminoalkyl) (alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl, and alkylsulfonealkyl;

or (ii) an ionizable lipid of Formula (II)

Formula (II)

wherein each n is independently an integer from 2-15;

$L_1$ and $L_3$ are each independently —OC(O)—* or —C(O) O—*, wherein "*" indicates the attachment point to $R_1$ or $R_3$;

$R_1$ and $R_3$ are each independently a linear or branched $C_9$-$C_{20}$ alkyl or $C_9$-$C_{20}$ alkenyl, optionally substituted by one or more substituents selected from a group consisting of oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl) (alkyl)aminoalkyl, heterocyclyl, heteroaryl, alkylheteroaryl, alkynyl, alkoxy, amino, dialkylamino, aminoalkylcarbonylamino, aminocarbonylalkylamino, (aminocarbonylalkyl) (alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl) (alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl, and alkylsulfonealkyl; and $R_2$ is selected from a group consisting of:

-continued kylamino, aminoalkylcarbonylamino, aminocarbonyl-alkylamino, (aminocarbonylalkyl) (alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl) (alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl, and alkylsulfonealkyl;

or (ii) an ionizable lipid of Formula (II)

$$R_1—L_1—[\ ]_n—N—[\ ]_n—L_3—R_3,$$

Formula (II)

$$R_2$$

wherein each n is independently an integer from 2-15;

$L_1$ and $L_3$ are each independently —OC(O)—* or —C(O)O—*, wherein "*" indicates the attachment point to $R_1$ or $R_3$;

$R_1$ and $R_3$ are each independently a linear or branched $C_9$-$C_{20}$ alkyl or $C_9$-$C_{20}$ alkenyl, optionally substituted by one or more substituents selected from a group consisting of oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl) (alkyl)aminoalkyl, heterocyclyl, heteroaryl, alkylheteroaryl, alkynyl, alkoxy, amino, dialkylamino, aminoalkylcarbonylamino, aminocarbonylalkylamino, (aminocarbonylalkyl) (alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl) (alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl, and alkylsulfonealkyl; and $R_2$ is selected from a group consisting of:

Embodiment 38. A pharmaceutical composition comprising:

(A) a circular RNA construct comprising:
  i. an IRES selected from an Enterovirus, Kobuvirus, Parechovirus, Hunnivirus, Passerivirus, Mischivirus, and Cardiovirus, and
  ii. at least one expression sequence encoding a CAR construct targeting a cancer antigen, wherein the CAR construct comprises an anti-CD19 binder, and wherein the expression sequence comprises a sequence that is at least 80% identical to a sequence selected from any one of SEQ ID NOs: 19-34, and
(B) a transfer vehicle comprising:
(i) an ionizable lipid of Formula (I)

Formula (I)

wherein n is an integer between 1 and 4;
$R_a$ is hydrogen or hydroxyl; and
$R_1$ and $R_2$ are each independently a linear or branched $C_6$-$C_{30}$ alkyl, $C_6$-$C_{30}$ alkenyl, or $C_6$-$C_{30}$ heteroalkyl, optionally substituted by one or more substituents selected from a group consisting of oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl) (alkyl)aminoalkyl, heterocyclyl, heteroaryl, alkylheteroaryl, alkynyl, alkoxy, amino, dial-

29

-continued

30

(B) a transfer vehicle comprising:

(i) an ionizable lipid of Formula (I)

Formula (I)

wherein n is an integer between 1 and 4;

$R_a$ is hydrogen or hydroxyl; and $R_1$ and $R_2$ are each independently a linear or branched $C_6$-$C_{30}$ alkyl, $C_6$-$C_{30}$ alkenyl, or $C_6$-$C_{30}$ heteroalkyl, optionally substituted by one or more substituents selected from a group consisting of oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl) (alkyl)aminoalkyl, heterocyclyl, heteroaryl, alkylheteroaryl, alkynyl, alkoxy, amino, dialkylamino, aminoalkylcarbonylamino, aminocarbonylalkylamino, (aminocarbonylalkyl) (alkyl)amino, alkenylcarbonylamino, hydroxycarbonyl, dialkylaminoalkylaminocarbonyl, heterocyclylalkylaminocarbonyl, (alkylaminoalkyl) (alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl, and alkylsulfonealkyl;

or (ii) an ionizable lipid of Formula (II)

Formula (II)

wherein each n is independently an integer from 2-15;

$L_1$ and $L_3$ are each independently —OC(O)—* or —C(O) O—*, wherein "*" indicates the attachment point to $R_1$ or $R_3$;

$R_1$ and $R_3$ are each independently a linear or branched $C_9$-$C_{20}$ alkyl or $C_9$-$C_{20}$ alkenyl, optionally substituted by one or more substituents selected from a group consisting of oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl) (alkyl)aminoalkyl, heterocyclyl, heteroaryl, alkylheteroaryl, alkynyl, alkoxy, amino, dialkylamino, aminoalkylcarbonylamino, aminocarbonylalkylamino, (aminocarbonylalkyl) (alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl) (alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl, and alkylsulfonealkyl; and Embodiment 39. A pharmaceutical composition comprising:

(A) a circular RNA construct comprising:

i. an IRES selected from an Enterovirus, Kobuvirus, Parechovirus, Hunnivirus, Passerivirus, Mischivirus, and Cardiovirus, and ii. at least one expression sequence encoding a CAR construct targeting a cancer antigen, wherein the CAR construct comprises a BCMA binder, and

31

R$_2$ is selected from a group consisting of:

32

-continued

, and

Embodiment 40. A pharmaceutical composition comprising:

(A) a circular RNA construct comprising:
    i. an IRES selected from an Enterovirus, Kobuvirus, Parechovirus, Hunnivirus, Passerivirus, Mischivirus, and Cardiovirus, and
    ii. at least one expression sequence encoding a CAR construct targeting a cancer antigen, wherein the CAR construct comprises an anti-BCMA binder, wherein the expression sequence comprises a sequence that is at least 80% identical to a sequence selected from any one of SEQ ID NOs: 103-115, and
(B) a transfer vehicle comprising:
(i) an ionizable lipid of Formula (I)

Formula (I)

wherein n is an integer between 1 and 4;

R$_a$ is hydrogen or hydroxyl; and

R$_1$ and R$_2$ are each independently a linear or branched C$_6$-C$_{30}$ alkyl, C$_6$-C$_{30}$ alkenyl, or C$_6$-C$_{30}$ heteroalkyl, optionally substituted by one or more substituents selected from a group consisting of oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl) (alkyl)aminoalkyl, heterocyclyl, heteroaryl, alkylheteroaryl, alkynyl, alkoxy, amino, dialkylamino, aminoalkylcarbonylamino, aminocarbonylalkylamino, (aminocarbonylalkyl) (alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl) (alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl, and alkylsulfonealkyl;

or (ii) an ionizable lipid of Formula (II)

Formula (II)

wherein each n is independently an integer from 2-15;

L$_1$ and L$_3$ are each independently —OC(O)—* or —C(O)
O—*, wherein "*" indicates the attachment point to R$_1$
or R$_3$;

R$_1$ and R$_3$ are each independently a linear or branched
C$_9$-C$_{20}$ alkyl or C$_9$-C$_{20}$ alkenyl, optionally substituted
by one or more substituents selected from a group
consisting of oxo, halo, hydroxy, cyano, alkyl, alkenyl,
aldehyde, heterocyclylalkyl, hydroxyalkyl, dihydroxy-
alkyl, hydroxyalkylaminoalkyl, aminoalkyl, alkylami-
noalkyl, dialkylaminoalkyl, (heterocyclyl) (alkyl)ami-
noalkyl, heterocyclyl, heteroaryl, alkylheteroaryl,
alkynyl, alkoxy, amino, dialkylamino, aminoalkylcar-
bonylamino, aminocarbonylalkylamino, (aminocarbo-
nylalkyl) (alkyl)amino, alkenylcarbonylamino,
hydroxycarbonyl, alkyloxycarbonyl, aminocarbonyl,
aminoalkylaminocarbonyl, alkylaminoalkylaminocar-
bonyl, dialkylaminoalkylaminocarbonyl, heterocyclyl-
alkylaminocarbonyl, (alkylaminoalkyl) (alkyl)ami-
nocarbonyl, alkylaminoalkylcarbonyl,
dialkylaminoalkylcarbonyl, heterocyclylcarbonyl, alk-
enylcarbonyl, alkynylcarbonyl, alkylsulfoxide,
alkylsulfoxidcalkyl, alkylsulfonyl, and alkylsulfoneal-
kyl; and R$_2$ is selected from a group consisting of:

34

-continued

Embodiment 41. The pharmaceutical composition of any
one of embodiments 1-4, 7-10, 13-20, 23-26, 29-32, and
35-38, wherein the CAR construct comprises a CD19 binder,
and wherein the circular RNA comprises a sequence that is
at least 80% identical to a sequence selected from any one
of SEQ ID NOs: 50-61.

Embodiment 42. The pharmaceutical composition of any
one of embodiments 1-4, 7-10, 13-20, 23-26, 29-32, and
35-38, wherein the CAR construct comprises a CD19 binder,
and wherein the circular RNA comprises a sequence selected
from any one of SEQ ID NOs: 50-61.

Embodiment 43. The pharmaceutical composition of
embodiment 42, wherein the circular RNA construct com-
prises a sequence selected from any one of SEQ ID NOs: 50,
51, 52, 54, 55, 56, 58, and 59.

Embodiment 44. A pharmaceutical composition compris-
ing a circular RNA construct and a transfer vehicle, wherein
the circular RNA construct comprises an IRES and at least
one expression sequence encoding a CAR construct target-
ing a cancer antigen, wherein the CAR construct comprises
a CD19 binder, wherein the circular RNA comprises a
sequence that is at least 80% identical to a sequence selected
from any one of SEQ ID NOs: 50-61.

Embodiment 45. A pharmaceutical composition compris-
ing a circular RNA construct and a transfer vehicle, wherein
the circular RNA construct comprises an IRES and at least
one expression sequence encoding a CAR construct target-
ing a cancer antigen, wherein the CAR construct comprises
a CD19 binder, wherein the circular RNA construct com-
prises a sequence selected from any one of SEQ ID NOs:
50-61.

Embodiment 46. The pharmaceutical composition of
embodiment 45, wherein the circular RNA construct com-
prises a sequence selected from any one of SEQ ID NOs: 50,
51, 52, 54, 55, 56, 58, and 59.

Embodiment 47. A pharmaceutical composition comprising a circular RNA construct and a transfer vehicle, wherein the circular RNA construct comprises an IRES and at least one expression sequence encoding a CAR construct targeting a cancer antigen, wherein the CAR construct comprises a CD19 binder, wherein the circular RNA comprises a sequence that is at least 80% identical to a sequence selected from any one of SEQ ID NOs: 50-61, and wherein the transfer vehicle comprises:

(i) an ionizable lipid of Formula (I)

Formula (I)

wherein n is an integer between 1 and 4;

$R_a$ is hydrogen or hydroxyl; and $R_1$ and $R_2$ are each independently a linear or branched $C_6$-$C_{30}$ alkyl, $C_6$-$C_{30}$ alkenyl, or $C_6$-$C_{30}$ heteroalkyl, optionally substituted by one or more substituents selected from a group consisting of oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl) (alkyl)aminoalkyl, heterocyclyl, heteroaryl, alkylheteroaryl, alkynyl, alkoxy, amino, dialkylamino, aminoalkylcarbonylamino, aminocarbonylalkylamino, (aminocarbonylalkyl) (alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl) (alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl, and alkylsulfonealkyl;

or (ii) an ionizable lipid of Formula (II)

Formula (II)

wherein each n is independently an integer from 2-15;

$L_1$ and $L_3$ are each independently —OC(O)—* or —C(O) O—*, wherein "*" indicates the attachment point to $R_1$ or $R_3$;

$R_1$ and $R_3$ are each independently a linear or branched $C_9$-$C_{20}$ alkyl or $C_9$-$C_{20}$ alkenyl, optionally substituted by one or more substituents selected from a group consisting of oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl) (alkyl)aminoalkyl, heterocyclyl, heteroaryl, alkylheteroaryl, alkynyl, alkoxy, amino, dialkylamino, aminoalkylcarbonylamino, aminocarbonylalkylamino, (aminocarbonylalkyl) (alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl) (alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl, and alkylsulfonealkyl; and $R_2$ is selected from a group consisting of:

-continued

, ,

, and

Embodiment 48. A pharmaceutical composition comprising a circular RNA construct and a transfer vehicle, wherein the circular RNA construct comprises an IRES and at least one expression sequence encoding a CAR construct targeting a cancer antigen, wherein the CAR construct comprises a CD19 binder, wherein the circular RNA comprises a sequence selected from any one of SEQ ID Nos: 50-61, and wherein the transfer vehicle comprises:

(i) an ionizable lipid of Formula (I)

Formula (I)

wherein n is an integer between 1 and 4;

$R_a$ is hydrogen or hydroxyl; and $R_1$ and $R_2$ are each independently a linear or branched $C_6$-$C_{30}$ alkyl, $C_6$-$C_{30}$ alkenyl, or $C_6$-$C_{30}$ heteroalkyl, optionally substituted by one or more substituents selected from a group consisting of oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl) (alkyl)aminoalkyl, heterocyclyl, heteroaryl, alkylheteroaryl, alkynyl, alkoxy, amino, dialkylamino, aminoalkylcarbonylamino, aminocarbonylalkylamino, (aminocarbonylalkyl) (alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl) (alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl, and alkylsulfonealkyl;

or (ii) an ionizable lipid of Formula (II)

Formula (II)

wherein each n is independently an integer from 2-15;

$L_1$ and $L_3$ are each independently —OC(O)—* or —C(O) O—*, wherein "*" indicates the attachment point to $R_1$ or $R_3$;

$R_1$ and $R_3$ are each independently a linear or branched $C_9$-$C_{20}$ alkyl or $C_9$-$C_{20}$ alkenyl, optionally substituted by one or more substituents selected from a group consisting of oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl) (alkyl)aminoalkyl, heterocyclyl, heteroaryl, alkylheteroaryl, alkynyl, alkoxy, amino, dialkylamino, aminoalkylcarbonylamino, aminocarbonylalkylamino, (aminocarbonylalkyl) (alkyl)amino, alkenylcarbonylamino, hydroxycarbonyl, dialkylaminoalkylaminocarbonyl, heterocyclylalkylaminocarbonyl, (alkylaminoalkyl) (alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl, and alkylsulfonealkyl; and $R_2$ is selected from a group consisting of:

-continued

-continued

Embodiment 49. The pharmaceutical composition of embodiment 48, wherein the circular RNA construct comprises a sequence selected from any one of SEQ ID NOs: 50, 51, 52, 54, 55, 56, 58, and 59.

Embodiment 50. The circular RNA construct or pharmaceutical composition of any one of embodiments 1-49, wherein the circular RNA construct comprises SEQ ID NO: 50.

Embodiment 51. The circular RNA construct or pharmaceutical composition of any one of embodiments 1 to 49, wherein the circular RNA construct comprises SEQ ID NO: 51.

Embodiment 52. The circular RNA construct or pharmaceutical composition of any one of embodiments 1 to 49, wherein the circular RNA construct comprises SEQ ID NO: 52.

Embodiment 53. The circular RNA construct or pharmaceutical composition of any one of embodiments 1 to 49, wherein the circular RNA construct comprises SEQ ID NO: 54.

Embodiment 54. The circular RNA construct or pharmaceutical composition of any one of embodiments 1 to 49, wherein the circular RNA construct comprises SEQ ID NO: 55.

Embodiment 55. The circular RNA construct or pharmaceutical composition of any one of embodiments 1 to 49, wherein the circular RNA construct comprises SEQ ID NO: 56.

Embodiment 56. The circular RNA construct or pharmaceutical composition of any one of embodiments 1 to 49, wherein the circular RNA construct comprises SEQ ID NO: 58.

Embodiment 57. The circular RNA construct or pharmaceutical composition of any one of embodiments 1 to 49, wherein the circular RNA construct comprises SEQ ID NO: 59.

Embodiment 58. The pharmaceutical composition of any one of embodiments 5-6, 21-22, 27,28, 33-34, or 39-40, wherein the IRES comprises the sequence of SEQ ID NO: 8, wherein the CAR construct comprises a BCMA binder, and wherein the BCMA binder comprises a sequence selected from any one of SEQ ID NOs: 104-115.

Embodiment 59. The pharmaceutical composition of any one of embodiments 13-58, wherein the transfer vehicle comprises an ionizable lipid of Formula (I).

Embodiment 60. The pharmaceutical composition of embodiment 59, wherein the transfer vehicle comprises a helper lipid, a structural lipid, and a PEG-lipid.

Embodiment 61. The pharmaceutical composition of any one of embodiments 59-60, wherein the transfer vehicle has a lipid molar ratio formulation as described in Table 4b.

Embodiment 62. The pharmaceutical composition of any one of embodiments 13-58, wherein the transfer vehicle comprises an ionizable lipid of Formula (II).

Embodiment 63. The pharmaceutical composition of embodiment 62, wherein the ionizable lipid is selected from an ionizable lipid selected from:

Embodiment 64. The pharmaceutical composition of embodiment 63, wherein the ionizable lipid is:

Embodiment 65. The pharmaceutical composition of any one of embodiments 13-64, wherein the transfer vehicle further comprises at least one lipid selected from a helper lipid, a structural lipid, and a PEG-modified lipid.

Embodiment 66. The pharmaceutical composition of embodiment 65, wherein the transfer vehicle comprises PEG-DSPC.

Embodiment 67. The pharmaceutical composition of any one of embodiments 13-66, wherein the transfer vehicle is a lipid nanoparticle.

Embodiment 68. The pharmaceutical composition of any one of embodiments 13-67, wherein the transfer vehicle further comprises a targeting moiety.

Embodiment 69. The pharmaceutical composition of embodiment 68, wherein the targeting moiety is a small molecule, scFv, nanobody, peptide, cyclic peptide, di or tri cyclic peptide, minibody, polynucleotide aptamer, engineered scaffold protein, heavy chain variable region, light chain variable region, or a fragment thereof.

Embodiment 70. The pharmaceutical composition of any of embodiments 13-69, further comprising a pharmaceutical salt, buffer, diluent, or combination thereof.

Embodiment 71. The circular RNA construct or pharmaceutical composition of any one of the preceding embodiments, wherein the circular RNA further comprises a polyA region.

Embodiment 72. The circular RNA construct or pharmaceutical composition of any one of the preceding embodiments, wherein the circular RNA further comprises at least one miRNA binding site.

Embodiment 73. The circular RNA construct or pharmaceutical composition of embodiment 72, wherein the circular RNA comprises at least one miR-122 binding site.

Embodiment 74. The circular RNA construct or pharmaceutical composition of any one of the preceding embodiments, wherein the at least one expression sequence encoding a CAR is codon optimized.

Embodiment 75. The circular RNA construct or pharmaceutical composition of any one of the preceding embodiments, wherein the RNA construct further comprises a 5' enhanced intron element, a 5' enhanced exon element, a 3' enhanced exon element, and a 3' enhanced intron fragment.

Embodiment 76. A method of preparing the circular RNA construct or pharmaceutical composition of any one of the preceding embodiments.

Embodiment 77. A method of treating cancer in a subject by administering an effective amount of a composition comprising the circular RNA construct or the pharmaceutical composition of any one of embodiments 1-75, thereby treating the cancer. Additionally, a method of treating an autoimmune disease in a subject by administering an effective amount of a composition comprising the circular RNA construct or the pharmaceutical composition of any one of embodiments 1-75, thereby treating the autoimmune disease.

Embodiment 78. Use of a composition comprising the circular RNA construct or the pharmaceutical composition of any one of embodiments 1-75 for the treatment of cancer. Additionally, use of a composition comprising the circular RNA construct or the pharmaceutical composition of any one of embodiments 1-75 for the treatment of an autoimmune disease.

Embodiment 79. A linear precursor RNA polynucleotide comprising:
  (A) an IRES comprising a sequence that is at least 80% identical to a sequence selected from any one of SEQ ID NOs: 1-18, and
  (B) at least one expression sequence encoding a binding molecule.

Embodiment 80. A linear precursor RNA polynucleotide comprising:
  (A) an IRES comprising a sequence that is at least 80% identical to a sequence selected from any one of SEQ ID NOs: 1-18, and
  (B) at least one expression sequence encoding a CAR construct targeting a cancer antigen.

Embodiment 81. A linear precursor RNA polynucleotide comprising:
  (A) an IRES comprising a sequence that is at least 80% identical to a sequence selected from any one of SEQ ID NOs: 1-18, and
  (B) at least one expression sequence encoding a CAR construct targeting a cancer antigen, wherein the CAR construct comprises a CD19 binder.

Embodiment 82. The linear precursor RNA polynucleotide of embodiment 81, wherein the expression sequence comprises a sequence that is at least 80% identical to a sequence selected from any one of SEQ ID NOs: 19-34.

Embodiment 83. A linear precursor RNA polynucleotide comprising:
  (A) an IRES comprising a sequence that is at least 80% identical to a sequence selected from any one of SEQ ID NOs: 1-18, and
  (B) at least one expression sequence encoding a CAR construct targeting a cancer antigen, wherein the CAR construct comprises a BCMA binder.

Embodiment 84. The linear precursor RNA polynucleotide of embodiment 83, wherein the expression sequence comprises a sequence that is at least 80% identical to a sequence selected from any one of SEQ ID NOs: 103-115.

Embodiment 85. A linear precursor RNA polynucleotide comprising:

(A) an IRES selected from an Enterovirus, Kobuvirus, Parechovirus, Hunnivirus, Passerivirus, Mischivirus, and Cardiovirus, and (B) at least one expression sequence encoding a binding molecule.

Embodiment 86. A linear precursor RNA polynucleotide comprising:

(A) an IRES selected from an Enterovirus, Kobuvirus, Parechovirus, Hunnivirus, Passerivirus, Mischivirus, and Cardiovirus, and (B) at least one expression sequence encoding a CAR construct targeting a cancer antigen.

Embodiment 87. A linear precursor RNA polynucleotide comprising:

(A) an IRES selected from an Enterovirus, Kobuvirus, Parechovirus, Hunnivirus, Passerivirus, Mischivirus, and Cardiovirus, and (B) at least one expression sequence encoding a CAR construct targeting a cancer antigen, wherein the CAR construct comprises a CD19 binder.

Embodiment 88. The linear precursor RNA polynucleotide of embodiment 87, wherein the expression sequence comprises a sequence that is at least 80% identical to a sequence selected from any one of SEQ ID NOs: 19-34.

Embodiment 89. A linear precursor RNA polynucleotide comprising:

(A) an IRES selected from an Enterovirus, Kobuvirus, Parechovirus, Hunnivirus, Passerivirus, Mischivirus, and Cardiovirus, and (B) at least one expression sequence encoding a CAR construct targeting a cancer antigen, wherein the CAR construct comprises a BCMA binder.

Embodiment 90. The linear precursor RNA polynucleotide of embodiment 89, wherein the expression sequence comprises a sequence that is at least 80% identical to a sequence selected from any one of SEQ ID NOs: 103-115.

Embodiment 91. The linear precursor RNA polynucleotide of any one of embodiments 79 to 90, wherein the expression sequence is codon optimized.

Embodiment 92. The linear precursor RNA polynucleotide of any one of embodiments 79 to 91, further comprising a 5' enhanced intron element, a 5' enhanced exon element, a 3' enhanced exon element, and a 3' enhanced intron fragment.

Embodiment 93. The linear precursor RNA polynucleotide of embodiment 92 comprising the following order:

(A) the 5' enhanced intron element, (B) the 5' enhanced exon element, (C) a core functional element comprising the IRES and at least one expression sequence encoding a CAR construct targeting a cancer antigen, and optionally a stop codon or stop cassette, (D) the 3' enhanced exon element, and (E) the 3' enhanced intron element.

Embodiment 94. The linear precursor RNA polynucleotide of any one of embodiments 79 to 93, further comprising at least one miRNA binding site.

Embodiment 95. The linear precursor RNA polynucleotide of embodiment 94, wherein the precursor RNA comprises at least one miR-122 binding site.

Embodiment 96. A DNA vector encoding the RNA polynucleotide of any one of embodiments 79-95.

Embodiment 97. A method of preparing a circular RNA construct, the method comprising incubating the linear RNA polynucleotide of any one of embodiments 79-95 under suitable conditions for circularization.

Embodiment 98. A pharmaceutical composition comprising a circular RNA construct and a transfer vehicle, wherein the circular RNA construct comprises (i) an IRES comprising a sequence selected from any one of SEQ ID NOs: 1, 2, 4, and 8, and (ii) at least one expression sequence encoding a CAR construct targeting a cancer antigen, wherein the CAR construct comprises a CD19 binder comprising a sequence selected from any one of SEQ ID NOs: 19 and 20, and wherein the transfer vehicle is a lipid nanoparticle.

Embodiment 99. A pharmaceutical composition comprising a circular RNA construct and a transfer vehicle, wherein the circular RNA construct comprises (i) an IRES comprising a sequence selected from any one of SEQ ID NOs: 8, 16, 17, and 18, and (ii) at least one expression sequence encoding a CAR construct targeting a cancer antigen, wherein the CAR construct comprises a BCMA binder comprising SEQ ID NO: 115, and wherein the transfer vehicle is a lipid nanoparticle.

Embodiment 100. A pharmaceutical composition comprising a circular RNA construct and a transfer vehicle, wherein the circular RNA construct comprises (i) an IRES comprising a sequence selected from any one of SEQ ID NOs: 8, 16, 17, and 18, and (ii) at least one expression sequence encoding a CAR construct targeting a cancer antigen, wherein the CAR construct comprises a HER2 binder comprising a nucleotide sequences selected from any one of SEQ ID NO: 132 or 133, and wherein the transfer vehicle is a lipid nanoparticle.

Embodiment 101. The pharmaceutical composition of any one of embodiments 98 to 100, wherein the lipid nanoparticle comprises: (i) an ionizable lipid of Formula (I)

Formula (I)

wherein n is an integer between 1 and 4;

$R_a$ is hydrogen or hydroxyl; and $R_1$ and $R_2$ are each independently a linear or branched $C_6$-$C_{30}$ alkyl, $C_6$-$C_{30}$ alkenyl, or $C_6$-$C_{30}$ heteroalkyl, optionally substituted by one or more substituents selected from a group consisting of oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl) (alkyl)aminoalkyl, heterocyclyl, heteroaryl, alkylheteroaryl, alkynyl, alkoxy, amino, dialkylamino, aminoalkylcarbonylamino, aminocarbonylalkylamino, (aminocarbonylalkyl) (alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl) (alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl, and alkylsulfonealkyl;

47 or (ii) an ionizable lipid of Formula (II)

$$R_1—L_1 \underset{L_n}{} N \underset{L_n}{} L_3—R_3, \quad \text{Formula (II)}$$

wherein each n is independently an integer from 2-15;

$L_1$ and $L_3$ are each independently —OC(O)—* or —C(O) O—*, wherein "*" indicates the attachment point to $R_1$ or $R_3$;

$R_1$ and $R_3$ are each independently a linear or branched $C_9$-$C_{20}$ alkyl or $C_9$-$C_{20}$ alkenyl, optionally substituted by one or more substituents selected from a group consisting of oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl) (alkyl)aminoalkyl, heterocyclyl, heteroaryl, alkylheteroaryl, alkynyl, alkoxy, amino, dialkylamino, aminoalkylcarbonylamino, aminocarbonylalkylamino, (aminocarbonylalkyl) (alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl) (alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl, and alkylsulfonealkyl; and $R_2$ is selected from a group consisting of:

48

-continued

Embodiment 102. The pharmaceutical composition of embodiment 101, wherein the lipid nanoparticle transfer vehicle comprises an ionizable lipid, wherein the ionizable lipid is Embodiment 103. The pharmaceutical composition of any one of embodiments 98-102, wherein lipid nanoparticle transfer vehicle further comprises at least one lipid selected from a helper lipid, a structural lipid, and a PEG-modified lipid.

Embodiment 104. A method of treating cancer comprising administering the pharmaceutical composition of any one of embodiments 98-103 to a human subject in need thereof.

Embodiment 105. A method of treating an autoimmune disease comprising administering the pharmaceutical composition of any one of embodiments 98-103 to a human subject in need thereof.

Embodiment 106. Use of a composition comprising the circular RNA construct for the treatment of cancer comprising administering the pharmaceutical composition of any one of embodiments 98-103 to a human subject in need thereof.

Embodiment 107. Use of a composition comprising the circular RNA construct for the treatment of an autoimmune disease comprising administering the pharmaceutical composition of any one of embodiments 98-103 to a human subject in need thereof.

Embodiment 108. The method of embodiment 77, or embodiment 104 or 105, or the use of embodiment 106 or 107, wherein the administering occurs every day, every other day, twice a week, every week, every ten days, every two weeks, every three weeks, every four weeks, once a month, every six weeks, every eight weeks, every three months, every four months, every six months, every eight months, every nine months, or annually.

DESCRIPTION OF FIGURES

FIG. 2A and FIG. 2B depict a schematic of the preliminary process by which the combinations of IRES and codons were selected for the circRNA constructs.

FIG. 12B shows CAR+MFI over 48 hours post electroporation for Donor 9003 for the 12 constructs.

FIG. 16 shows total flux (photons/second) after 4 doses of LNP/oCAR for different lipid compositions comprising circular RNA constructs of HER2 and CD19 as compared to a control. The HER2 and CD19 lipid compositions comprise ionizable lipids 126, 128, 16, 45, and 86 of Table 3. Ionizable lipids 126 and 128 of Table 3 are lipids of Formula II and ionizable lipids 16, 45, and 86 of Table 3 are lipids of Formula I. A "/3" designation indicates the lipid composition comprises a PEG-modified lipid. Lipids (3-128)/3, (3-16)/3, (3-45)/3, and (3-86)/3 contain a PEG-modified lipid. Lipid (3-128)/3 L contains ionizable lipid 128 of Table 3 and a PEG-modified lipid.

In FIG. 23A, the gray circles show response with control and the black squares show response with treatment with a CD19 oRNA CAR construct described herein. In FIG. 23B, the whole-body images show untreated and treated mice over time.

FIGS. 25A-25G depicts anti-BCMA chimeric antigen receptor (CAR) expression for exemplary circular RNAs encoding BCMA-41BBζ CAR post electroporation of the circular RNA into T cells. "A", "B", "C", "D", and "E" correspond to "DNA Template A", "DNA Template B", "DNA Template C", "DNA Template D", and "DNA Template E" in Table al respectively. "Mock" in the figure represents data for a control T cell that was not electroporated with circular RNA. FIG. 25A depicts percent CAR expression detected by soluble BCMA PE detection reagent over the span of 24-72 hours post electroporation of circR-NAs formed from DNA Template A, DNA Template B, and DNA Template C and dosed at either 10 ng, 30 ng, or 100 ng per $0.1\times10^6$ T cell into T cells. FIG. 25B depicts geometric mean fluorescence intensity (gMFI) of the T cells detected by soluble BCMA PE detection reagent over the span of 24-72 hours post electroporation of circRNAs formed from DNA Template A, DNA Template B, and DNA Template C and dosed at either 10 ng, 30 ng, or 100 ng per $0.1\times10^6$ T cell into T cells. FIG. 25C provides fluorescence activated cell sorting (FACS) imaging post introduction of circular RNA depicted in FIGS. 25A and 25B to T cells at a dosage of 30 ng after 24 hours. FIG. 25D depicts percent CAR expression detected by soluble BCMA PE detection reagent over the span of 24-96 hours post electroporation of circRNAs formed from DNA Template A, DNA Template B, DNA Template C, DNA Template D, and DNA Template E and dosed at either 10 ng, 30 ng, or 100 ng per $0.1\times10^6$ T cell into T cells. FIG. 25E depicts percent CAR expression detected by anti-Whitlow PE detection reagent over the span of 24-96 hours post electroporation of circRNAs formed from DNA Template A, DNA Template B, DNA Template C, DNA Template D, and DNA Template E and dosed at either 10 ng, 30 ng, or 100 ng per $0.1\times10^6$ T cell into T cells. FIG. 25F depicts percent CAR expression detected by anti-G4S detection reagent over the span of 24-96 hours post electroporation of circRNAs formed from DNA Template A, DNA Template B, DNA Template C, DNA Template D, and DNA Template E and dosed at either 10 ng, 30 ng, or 100 ng per $0.1\times10^6$ T cell into T cells. FIG. 25G depicts average MFI (%) of the T cells detected by soluble BCMA PE detection reagent over the span of 24-96 hours post electroporation of circRNAs formed from DNA Template A, DNA Template B, DNA Template C, DNA Template D, and DNA Template E and dosed at either 10 ng, 30 ng, or 100 ng per $0.1\times10^6$ T cell into T cells.

FIGS. 29A-29D provides gMFI collected from various circular RNA construct encoding a BCMA-41BBζ or BCMA-CD282 CAR or CD19-CD28° C. CAR electroporated onto T cells at a dosage of 50 ng per $0.1\times10^6$ T cells compared to "Mock" control T cells lacking any circular RNA (containing only electroporation buffer). Each of the circular RNAs solutions were given either soluble BCMA (sBCMA-PE), anti-Whitlow-PE, or anti-G4S linker PE (G4S-AF647) detection reagent. FIG. 29A shows the histograms of the gMFI collected from the cells. FIGS. 29B-29D provides the gMFI for each of cells wherein sBCMA-PE (FIG. 29B), anti-Whitlow-PE (FIG. 29C) and G4S-AF647 (FIG. 29D) detection reagents were used to collect the gMFI. "F", "C", "G", "H", "A", "T" and "J" correspond to "DNA Template F", "DNA Template C", "DNA Template G", "DNA Template H", "DNA Template A", "DNA Template I", and "DNA Template J" that were used to form the circular RNAs.

Figure 32B:
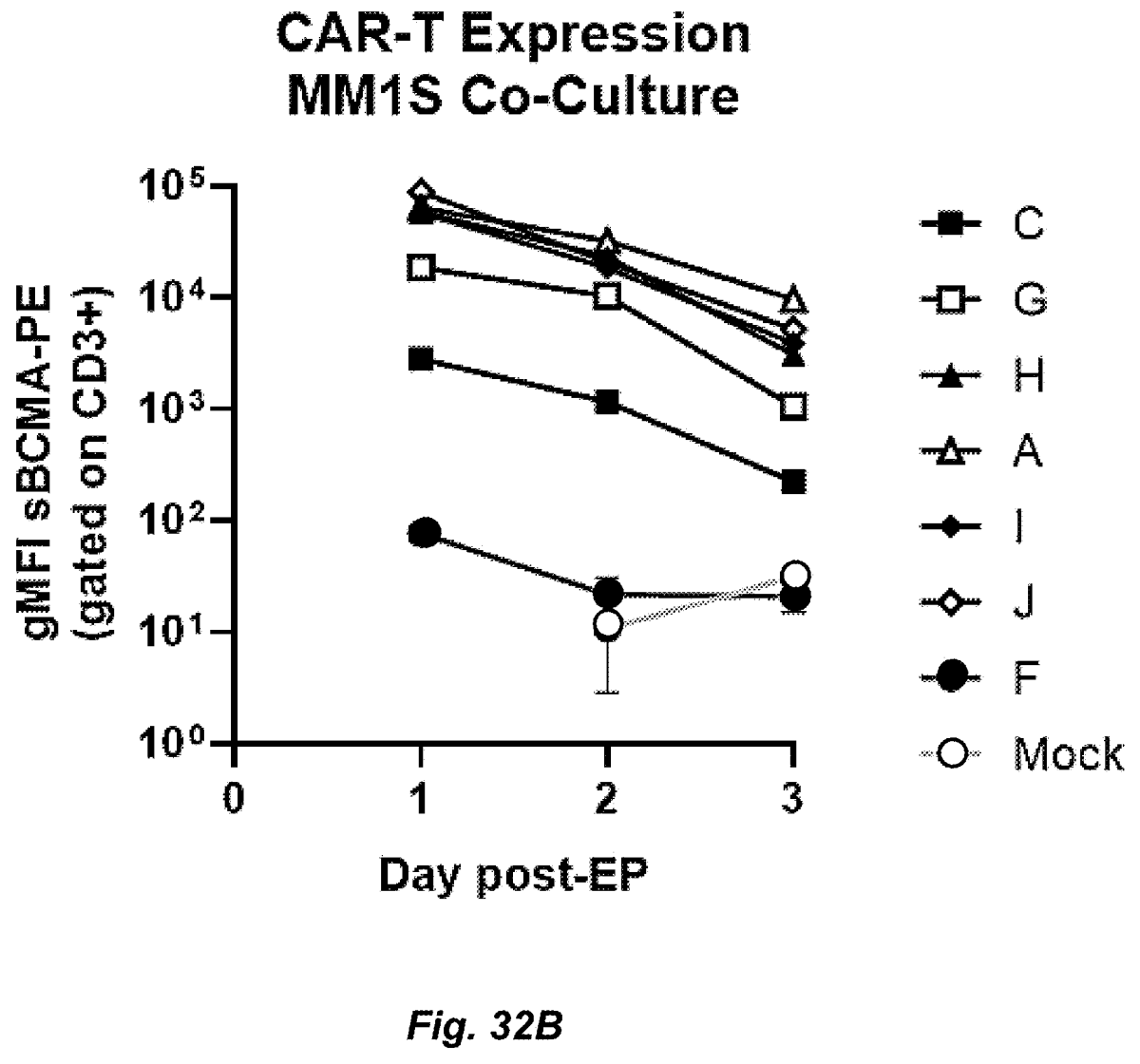
Figure 32C:
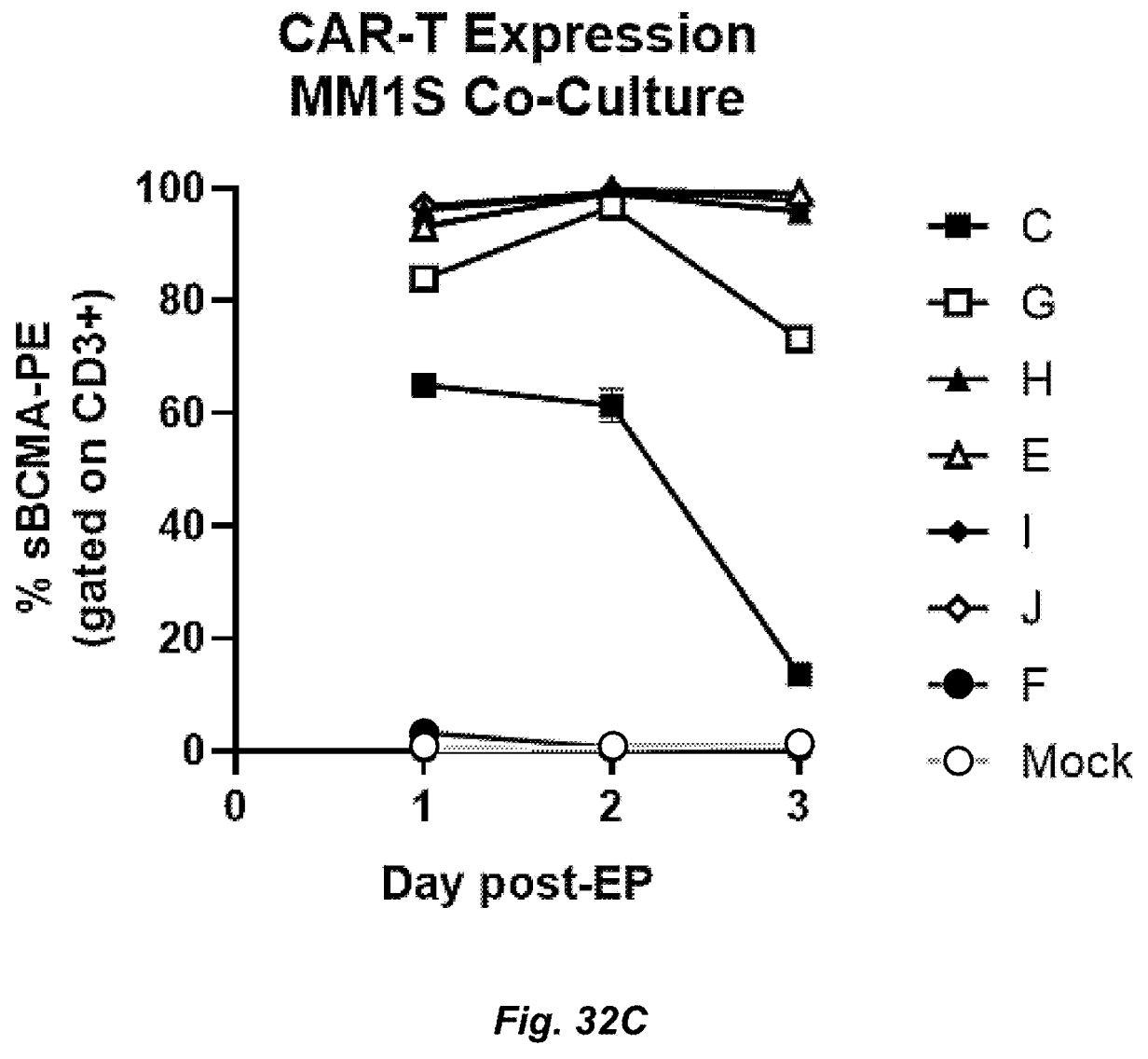

FIGS. 32A-32E shows BCMA expression via gMFI (FIGS. 32A, 32B and 32D) or percent soluble BCMA PE detection (indicated as "% sBCMA-PE") (FIG. 32C or 32E) post electroporation of circular RNAs encoding BCMA-41BBζ, BCMA-CD-CD285, or CD19-CD286 gated onto CD3+ cells. "Mock" indicates T cell solutions not electroporated with the circular RNA constructs. FIG. 32A provides a histogram with 24- and 48-hour collection of soluble BCMA-PE or anti-Whitlow.PE detection for the circular RNA constructs. FIGS. 32B and 32C provide gMFI and % sBCMA-PE expression over the span of 24-72 for each of the constructs after CD3+ cells comprising the circular RNAs have been co-cultured with multiple myeloma (MMIS) cells. FIGS. 32D and 32E provide gMFI and % sBCMA-PE expression at 72 post electroporation for each of the constructs after CD3+ cells comprising the circular RNAs have been co-cultured with multiple myeloma (MMIS) cells, NCI-H929 (indicated in the figures as "H929"), Nalm6 or K562.CD19 cells. "C", "G", "H", "A", "I" and "J" correspond to "DNA Template C", "DNA Template G", "DNA Template H", "DNA Template A", "DNA Template I", and "DNA Template J" that were used to form the circular RNAs. "Mock" in the figure represents data for a control T cell that was not electroporated with circular RNA.

FIG. 33A provides cytotoxicity of each of the circular RNAs encoding CAR constructs at a dosage of either 10 or 30 ng per $0.1\times10^6$ T cells on MMIS cells. Mock T cells (i.e., T cells not electroporated circular RNA referred to as "Mock" in the figure) and MMIS cells not co-cultured with T cells indicated as "MMIS" in FIG. 33A were used as controls. FIG. 33B provides cytotoxicity of each of the circular RNAs encoding CAR constructs at a dosage of either 10 or 30 ng per $0.1\times10^6$ T cells on Nalm6 cells. Mock T cells (i.e., T cells not electroporated circular RNA indicated as "Mock" in the figure) and Nalm6 cells not co-cultured with T cells as referred to as in FIG. 33B as "Nalm6" were used as controls. FIG. 33C provides cytotoxicity of each of the circular RNAs encoding CAR constructs at a dosage of 20 ng per $0.1\times10^6$ T cells on CD19 T stable cell line. Mock T cells (i.e., tumor T cells not electroporated circular RNA indicated as "Mock" in the figure) and CD19 T stable cells not co-cultured with T cells referred to as in FIG. 33C as "tumor" were used as controls. % Cytotoxicity was calculated by the (green area+ red area/green area) produced by the live-cell analysis portfolio system imaging. "A", "B", "C", "F", and "K" correspond to "DNA Template A", "DNA Template B", "DNA Template C", "DNA Template F", and "DNA Template K" that were used to form the circular RNAs.

FIG. 34A provides the FACS imaging of the cells (e.g., lymphocytes, CD3 negative cells, live cells, and BCMA positive cells) at 24 hours post co-culture of oCAR-T cells formed from introduction of circular RNA comprising a 3' Anabeana exon, a Caprine Kobuvirus internal ribosome entry site (IRES), a BCMA-41BBζ CAR, and a 5' *Anabaena* exon. FIG. 34B shows the percent cytotoxicity acquired from circular RNAs encoding BCMA-41BBζ, CD19-CD28° C. or HER2-CD28° C. CARs on MMIS (FIG. 24B) or Nalm6 (FIG. 24C). "MMIS+Mock" and "MMIS" as depicted in FIG. 34B refers to MMIS cell that was co-cultured with a T cell that was not transfected with a circular RNA. "Nalm6+Mock" and "Nalm6" as depicted in FIG. 34C refers to a Nalm6 cell that was co-cultured with a T cell that was not transfected with a circular RNA. "A", "B", "C", "F", and "K" correspond to "DNA Template A", "DNA Template B", "DNA Template C", "DNA Template F", and "DNA Template K" that were used to form the circular RNAs.

FIG. 35A depicts FACS imaging of "Mock+MMIS" (i.e., MMIS tumor cells cocultured with T cells not electroporated with circular RNAs, "Mock+Nalm6" (i.e., Nalm6 tumor cells cocultured with T cells not electroporated with circular RNAs), "Mock+H929" (i.e., NCI-H929 tumor cells cocultured with T cells not electroporated with circular RNAs), and "Mock+K562.CD19" (i.e., K562.CD19 tumor cells cocultured with T cells not electroporated with circular RNAs).

FIGS. 38A-38D provide INFγ cytokine levels, FIGS. 38E-38H provides TNFα cytokine levels, FIGS. 38I-38L provides IL-2 cytokine levels, and FIGS. 38M-38P GM-CSF levels. "A", "G", "C", "F", "H", "I", and "J" correspond to "DNA Template A", "DNA Template G", "DNA Template C", "DNA Template F", "DNA Template H", "DNA Template I", and "DNA Template J" that were used to form the circular RNAs.

FIGS. 42C-42F are some of the spider plots of the data collected in FIGS. 42A-42B. FIGS. 421-42L are spider plots of the data collected in FIGS. 42G and 42H. "K", "L", and "F" correspond to "DNA Template K", "DNA Template L", and "DNA Template F" that were used to form the circular RNAs. "Fresh" indicates that the LNP was not previously frozen. "Frozen" indicates that the LNP was previously frozen.

FIGS. 43A-D show CAR expression after electroporation in circular RNA constructs comprising an IRES sequence, an anti-HER2 CAR, and a 28z domain (HER2_9, HER2_1, HER2_3, HER2 4, described herein in Table 9).

FIG. 46 shows an exemplary method for assessing the ability of a circular RNA comprising anti-CD19 CAR (in situ CAR or isCAR™) to deplete human B cells in a CD34+engrafted humanize mouse model.

FIG. 47 shows an exemplary flow cytometry panel used in an autoimmunity study.

FIGS. 49A-C show splenic B cells were depleted in mice treated with a circular RNA encoding a reporter (m Wasabi) encapsulated in a lipid nanoparticle as described herein.

FIGS. 55A-G show mOX40L expression in CD33+ CD14+ and CD14-cells in bone marrow.

FIGS. 56A-G show mOX40L expression in CD33+ CD64+ and CD64-cells in bone marrow.

FIGS. 58A-G show mOX40L expression in CD33+ CD14+ and CD14-cells in spleen.

FIGS. 59A-G show mOX40L expression in CD33+ CD64+ and CD64-cells in spleen.

FIGS. 60A and B show tumor control in vivo by circular RNA encoding BCMA CAR (BCMA oCAR, BCMA_7 and BCMA_3) when dosed EOD in two donors as compared to HER2 and no-treatment controls.

DETAILED DESCRIPTION

Figure 1A:
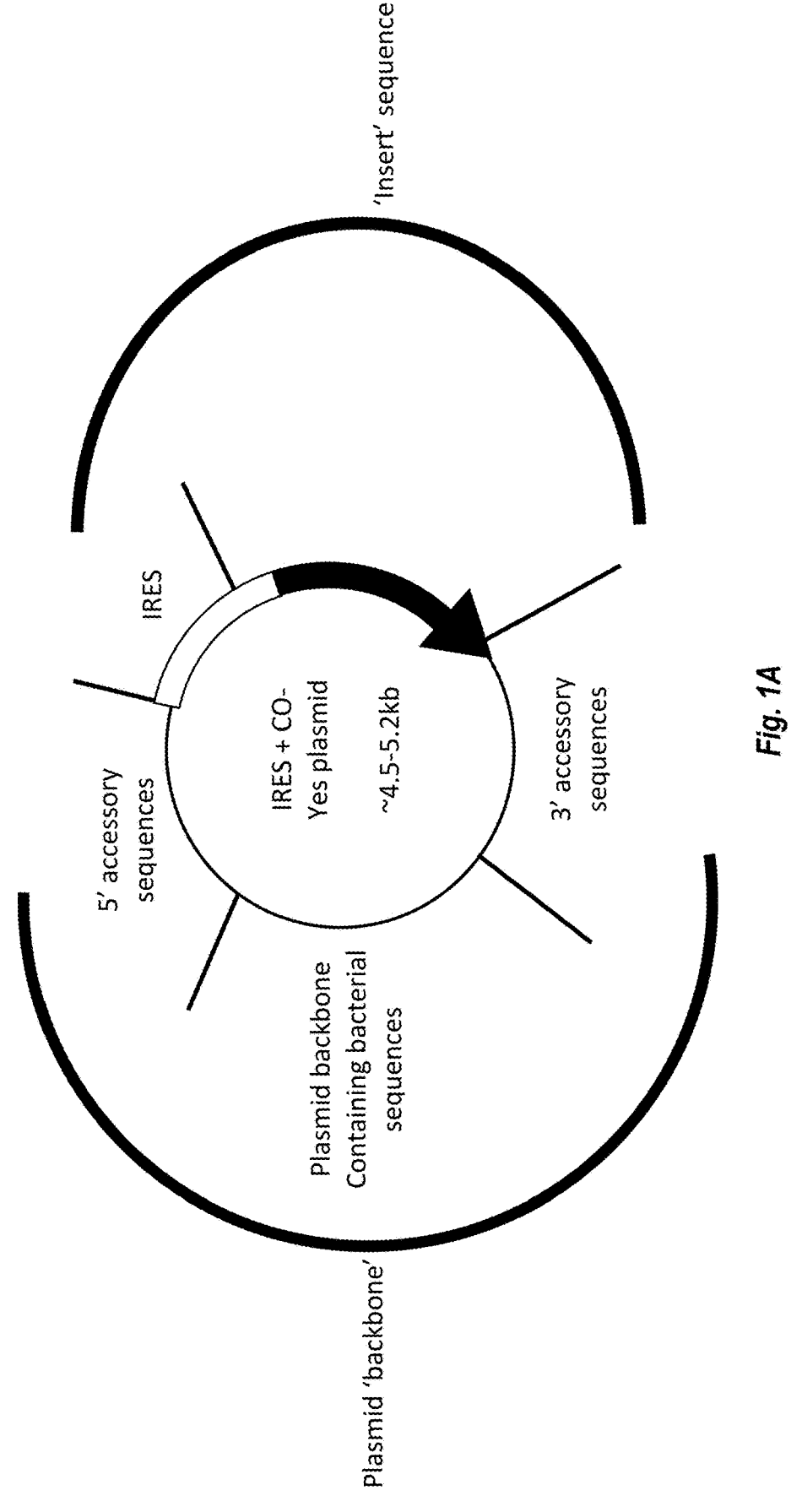
FIG. 1A shows a schematic of the sequence insertion site for exemplary IRES/codon plasmids. The IRES and the codon (expression sequence) were synthesized together and inserted into a circular RNA comprising a plasmid "backbone" containing bacterial sequences and 5' combined accessory elements and 3' combined accessory elements. The accessory elements can include, but are not limited to, the promoter, introns, exons, internal and external spacers, internal duplex regions, and polyA stretches.
Figures 1B, 1C:
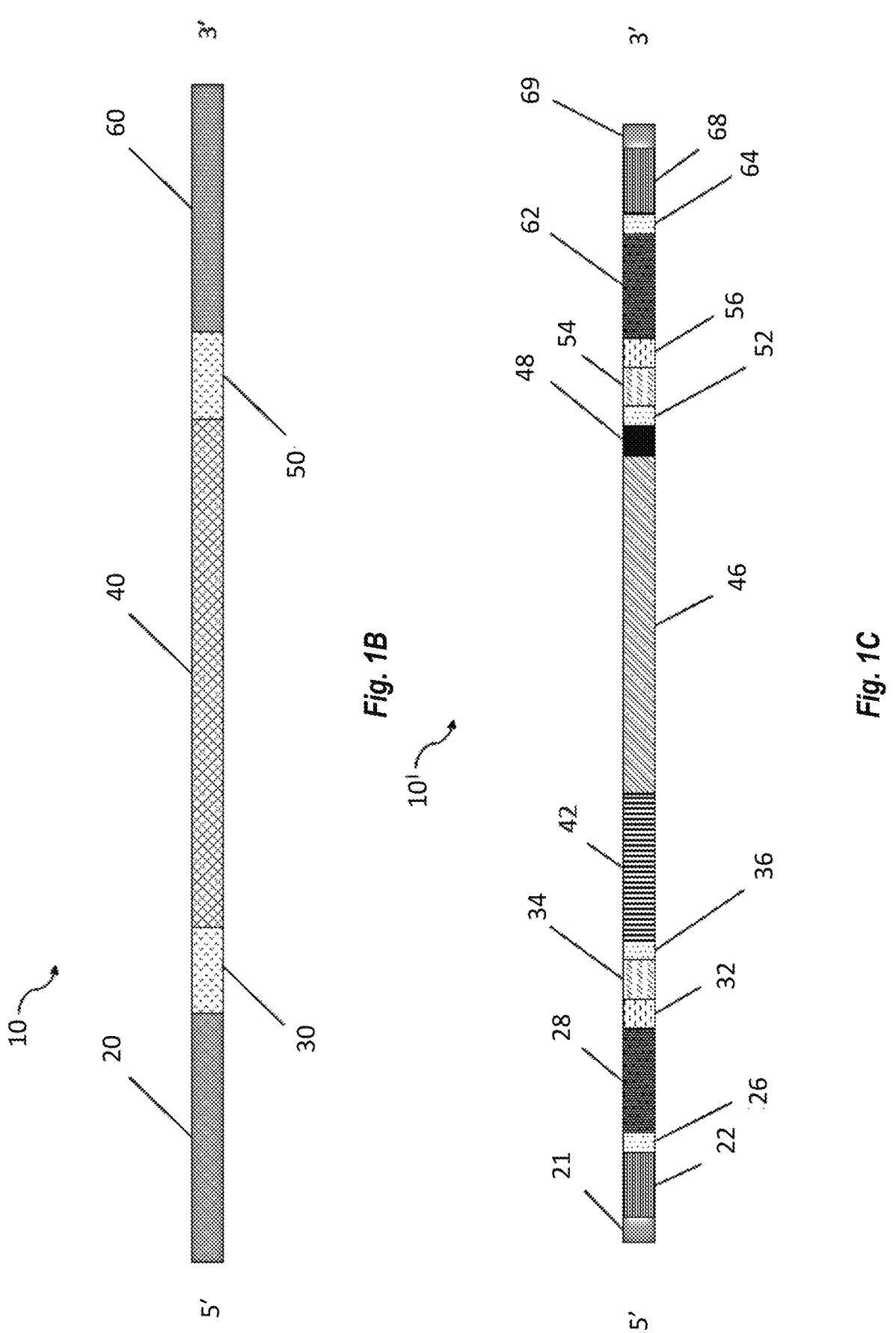
FIG. 1B depicts a general sequence construct of a linear RNA polynucleotide precursor (10). The sequence as provided is illustrated in a 5' to 3' order of a 5' enhanced intron element (20), a 5' enhanced exon element (30), a core functional element (40), a 3' enhanced exon element (50) and a 3' enhanced intron element (60).
FIG. 1C shows an exemplary linear RNA polynucleotide precursor (10) comprising in the following 5' to 3' order, a leading untranslated sequence (21), a 5' affinity tag (22), a 5' external spacer (26), a 3' intron fragment (28), a 3' exon fragment (32), a 5' internal duplex region (34), a 5' internal spacer (36), a TIE (42), a coding element (46), a stop region (48), a 3' internal spacer (52), a 3' internal duplex region (54), a 5' exon fragment (56), a 5' intron fragment (62), a 3' external spacer (64), a 3' affinity tag (68), and a terminal untranslated sequence (69).
Figure 1D:
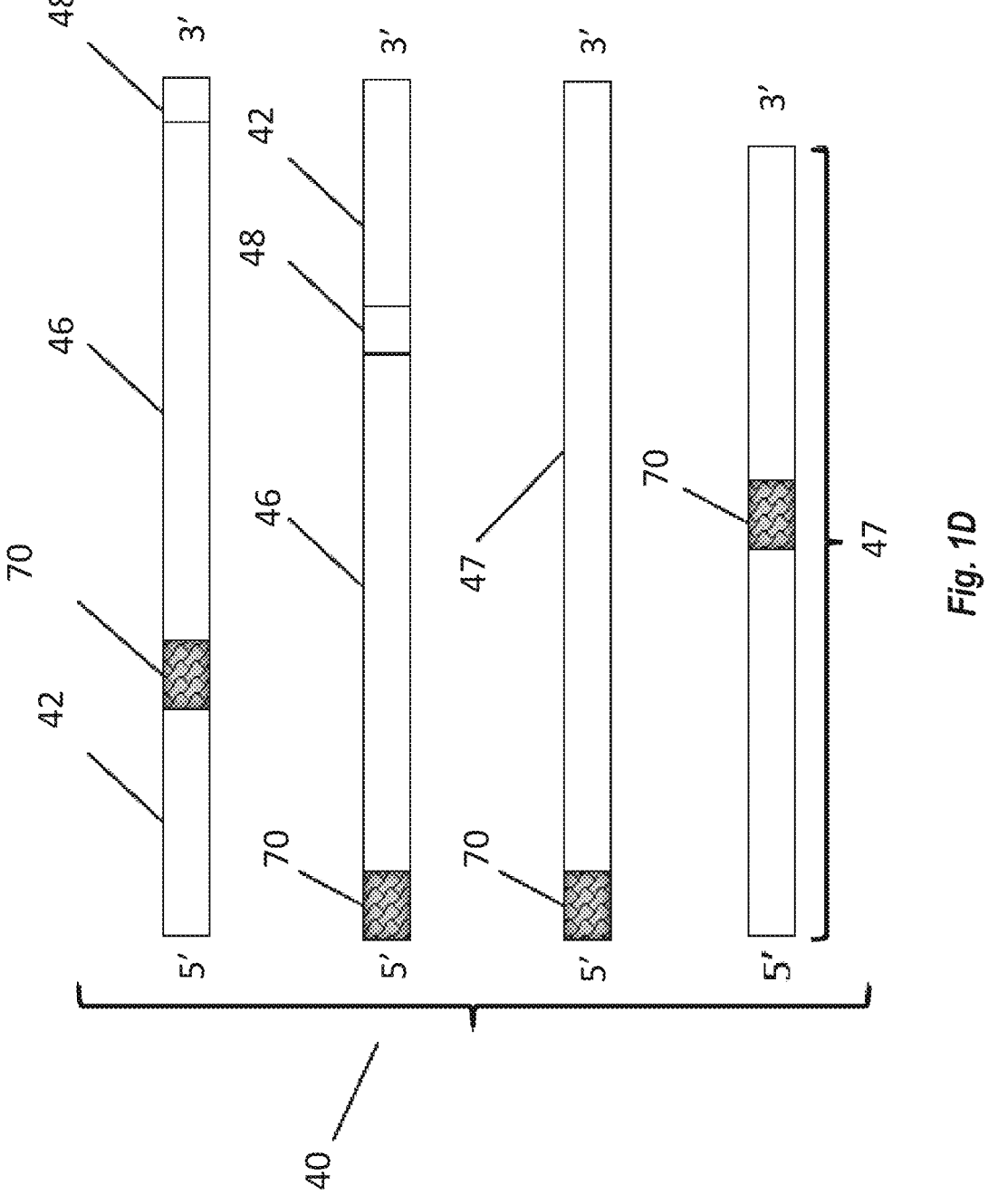
FIG. 1D illustrates exemplary locations for an accessory element (70) (e.g., a miRNA binding site) included in a linear RNA polynucleotide located within the core functional element (40), for example where 42 is the TIE (translation initiation element), 46 is the coding region, 47 is the noncoding region, and 48 is the stop region (stop codon or stop cassette).
Figure 3A:
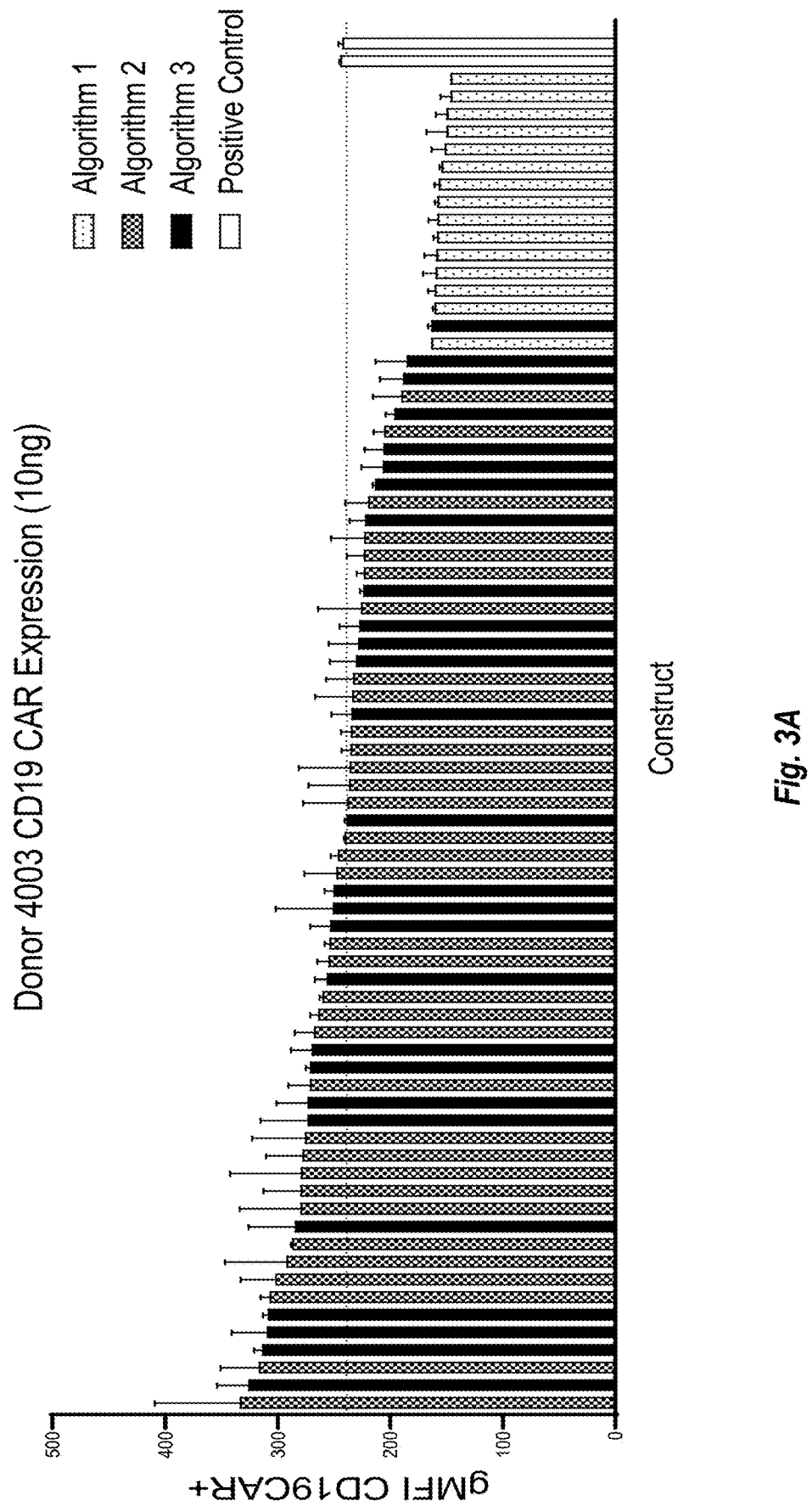
FIG. 3A and FIG. 3B depict the effects of three different codon optimization algorithms. CD19 CAR+expression (gMFI) was evaluated via flow cytometry for each construct in two different donors (donor 4003 and donor 609C) and plotted in rank-order for all sequences and coded by codon optimization algorithm. White bars on the right indicate expression for the non-codon optimized CD19 CAR sequence (positive control).
Figure 3B:
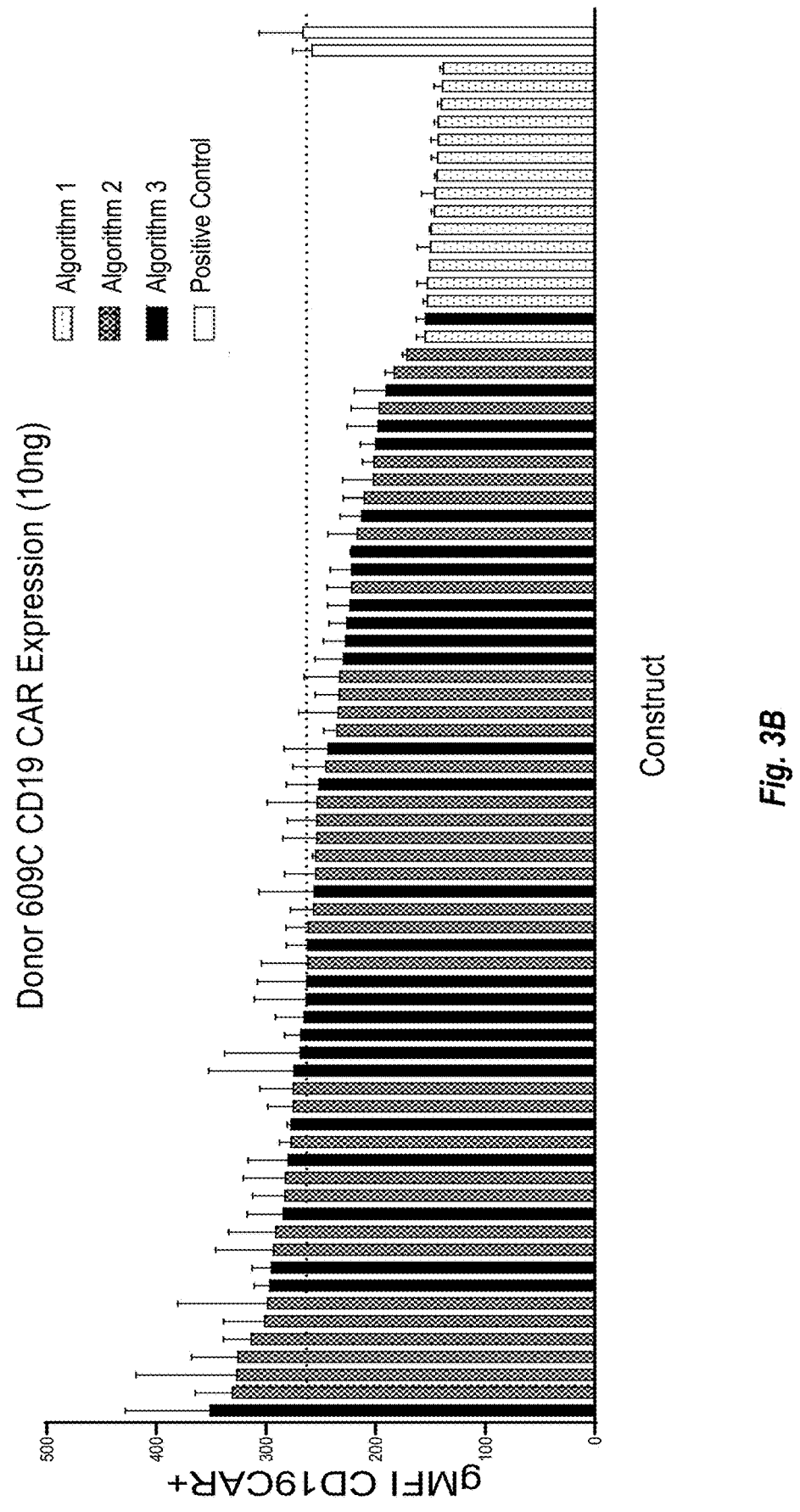
Figures 4A, 4B:
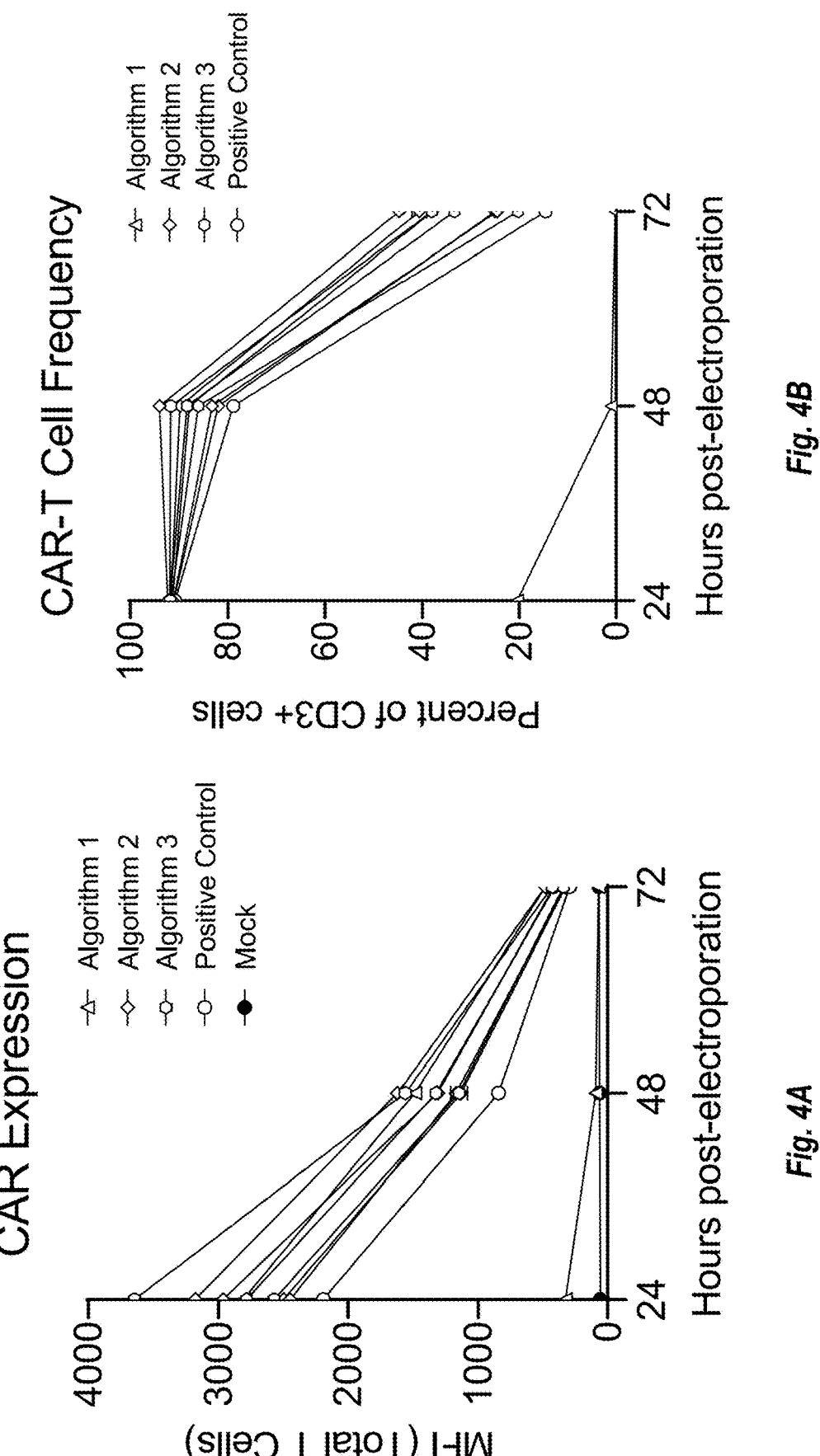
FIGS. 4A, 4B, and 4C depict the effects of three different codon optimization algorithms. MFI (Total T cells), percent of CD3+ cells (CAR-T cell frequency), and Total cell count (CAR-T cell number) were evaluated over time post electroporation using the three algorithms as compared to a positive control and mock negative control.
Figure 4C:
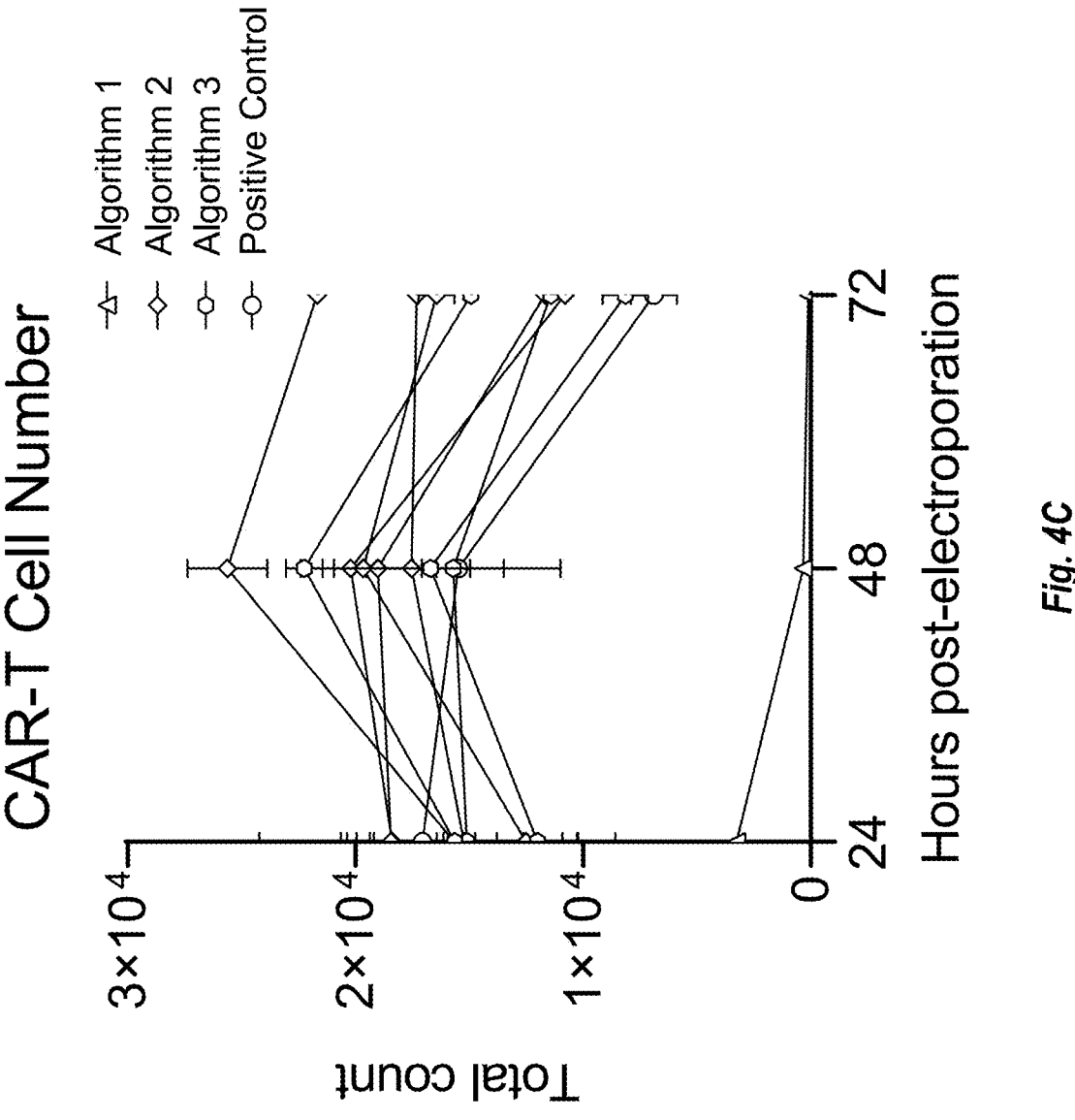
Figure 5A:
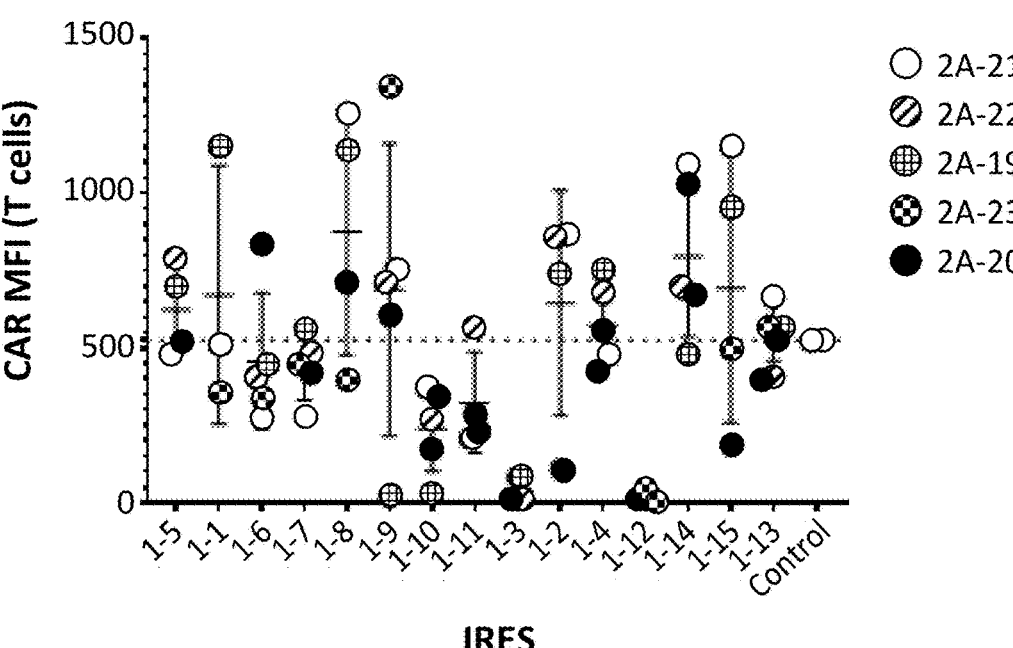
FIGS. 5A, 5B, 5C, 5D, 5E, 5F, 5G, 5H, 5I, and 5J show T cell MFI (expression) by IRES for two donors (donor 4003 and donor 609C) over time (5 days) for circular RNA constructs comprising combinations of IRESes and expression sequences. Each point on the X axis is an IRES from Table 1A and each dot is a different expression sequence from Table 2A (codon optimized; anti-CD19 28-ζ).
Figure 5B:
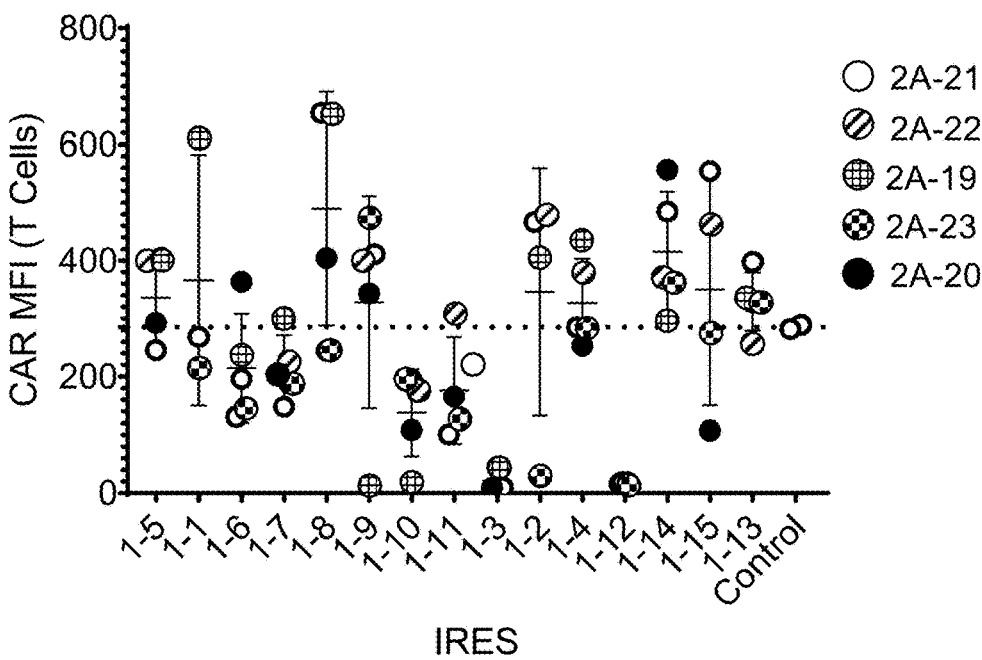
Figure 5C:
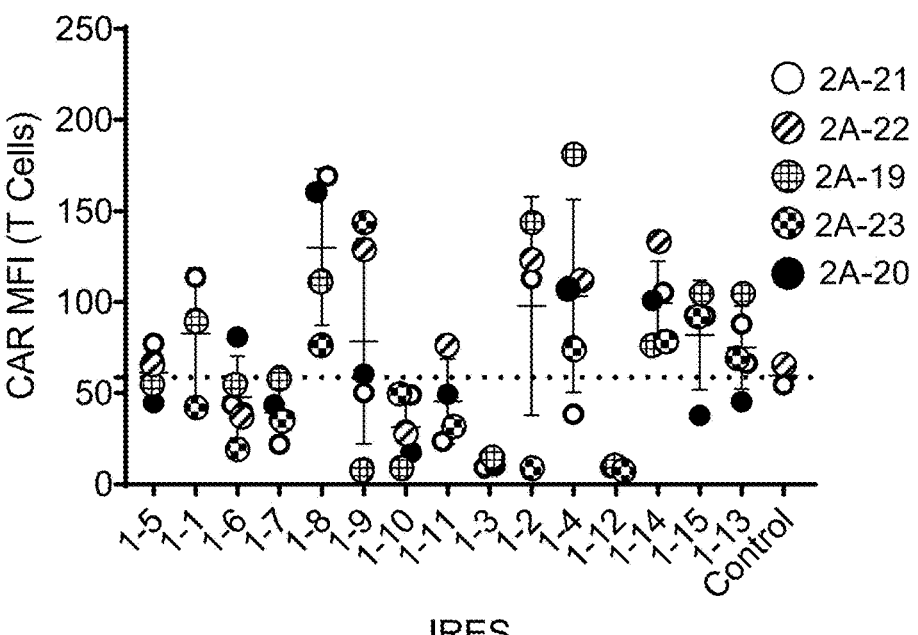
Figure 5D:
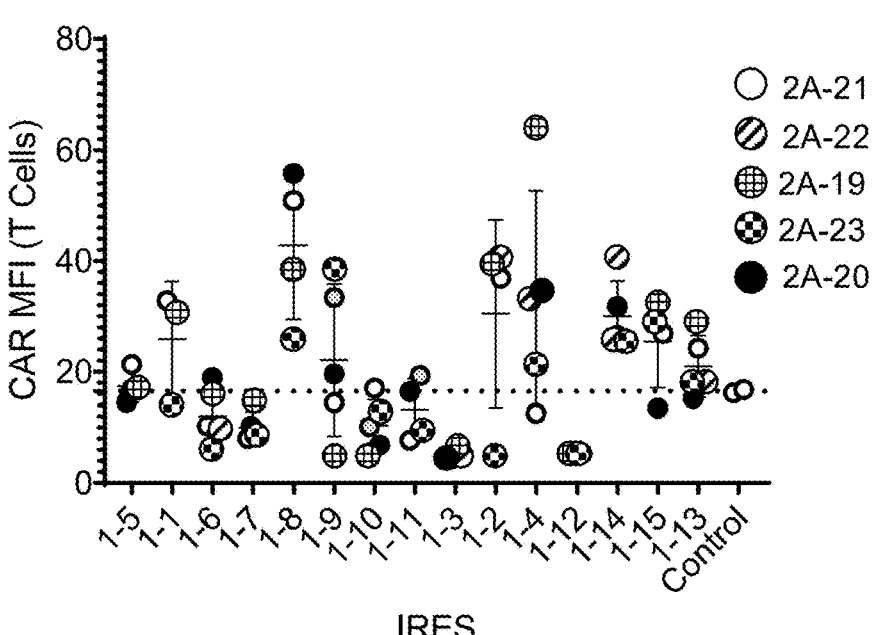
Figure 5E:
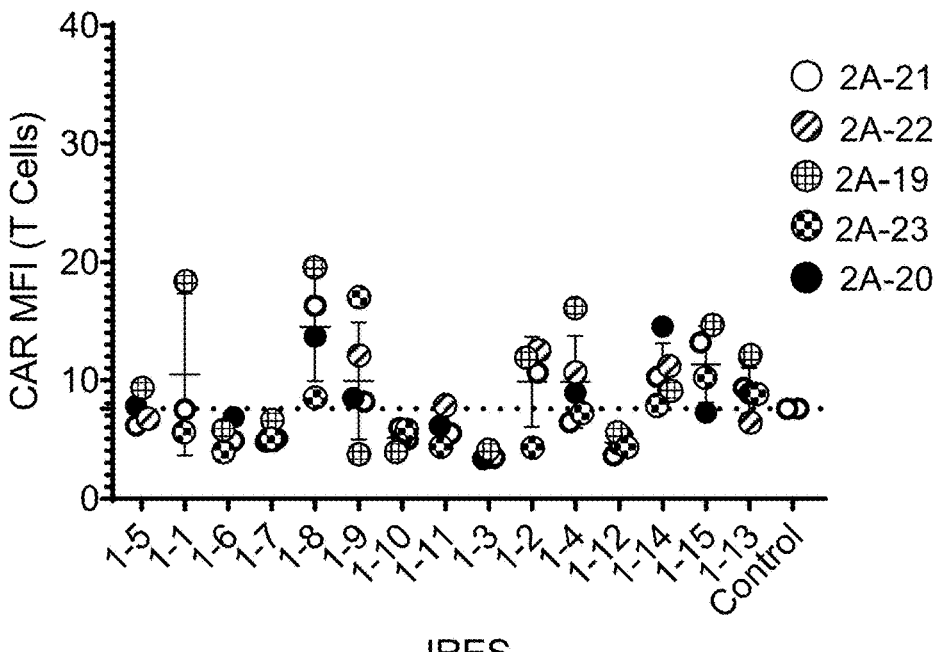
Figure 5F:
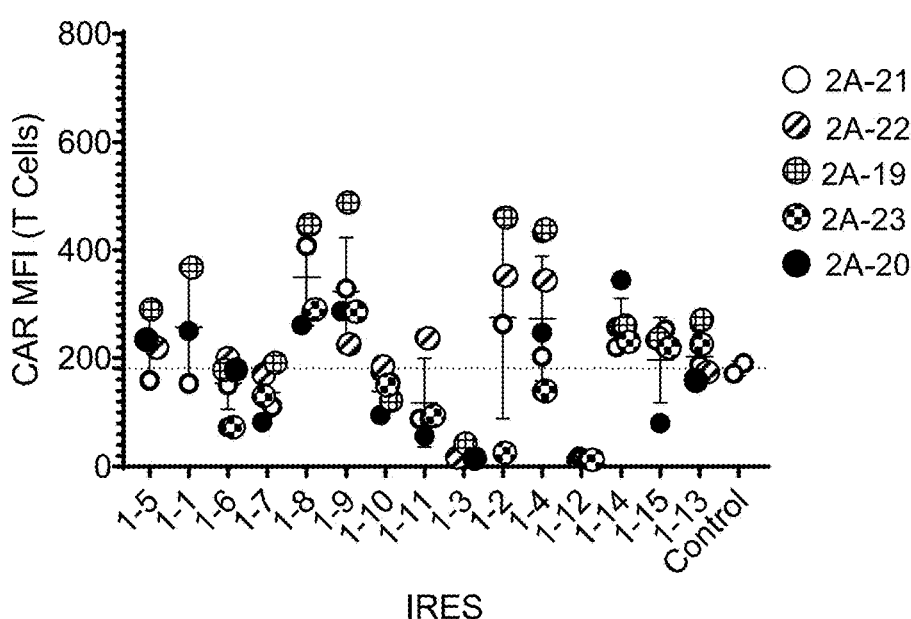
Figure 5G:
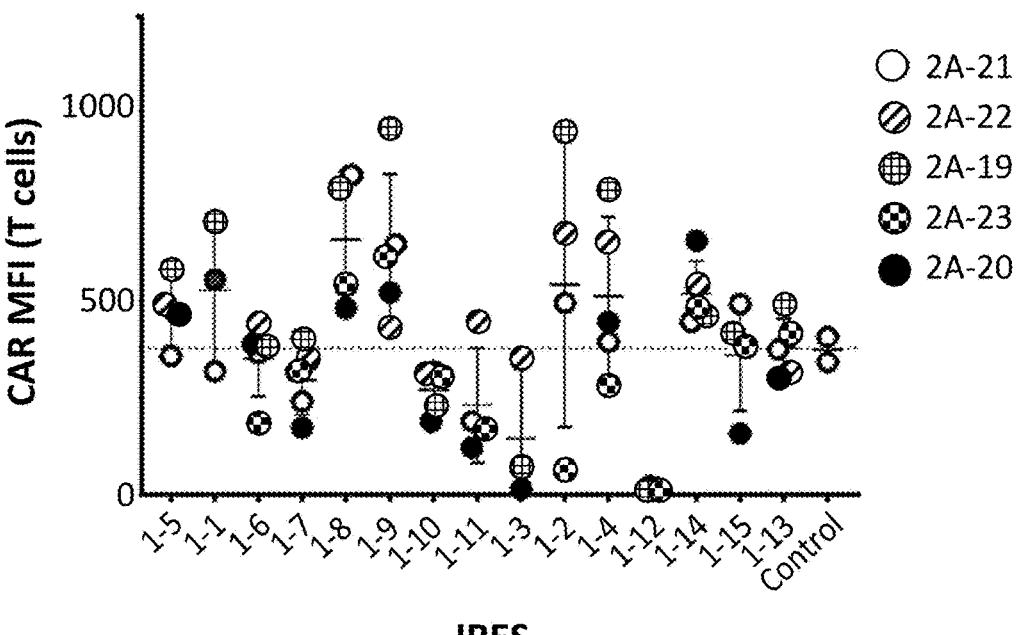
Figure 5H:
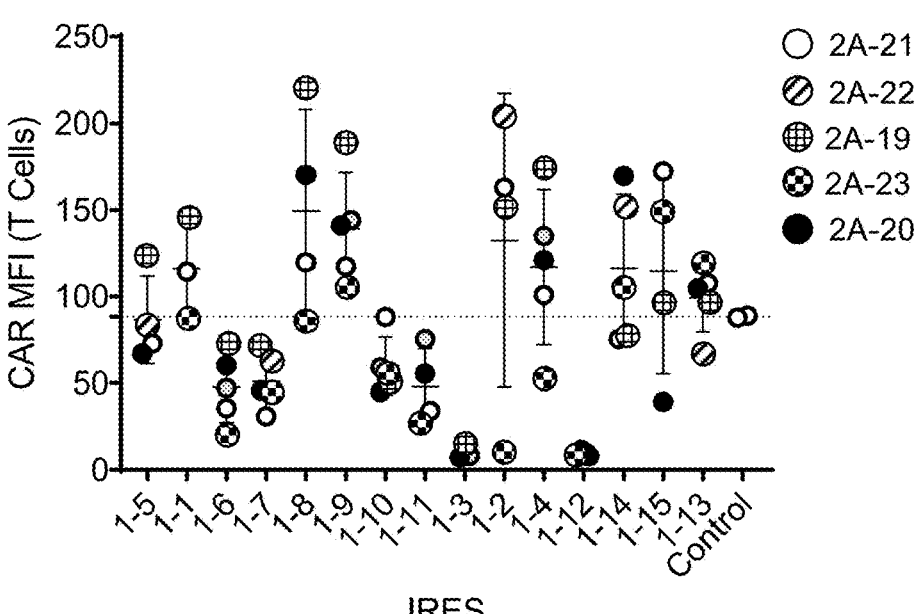
Figure 5I:
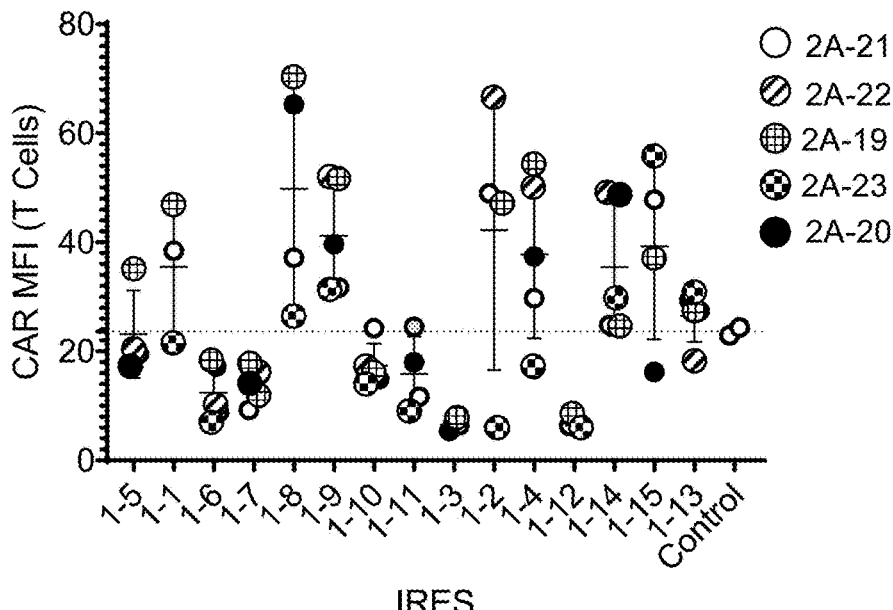
Figure 5J:
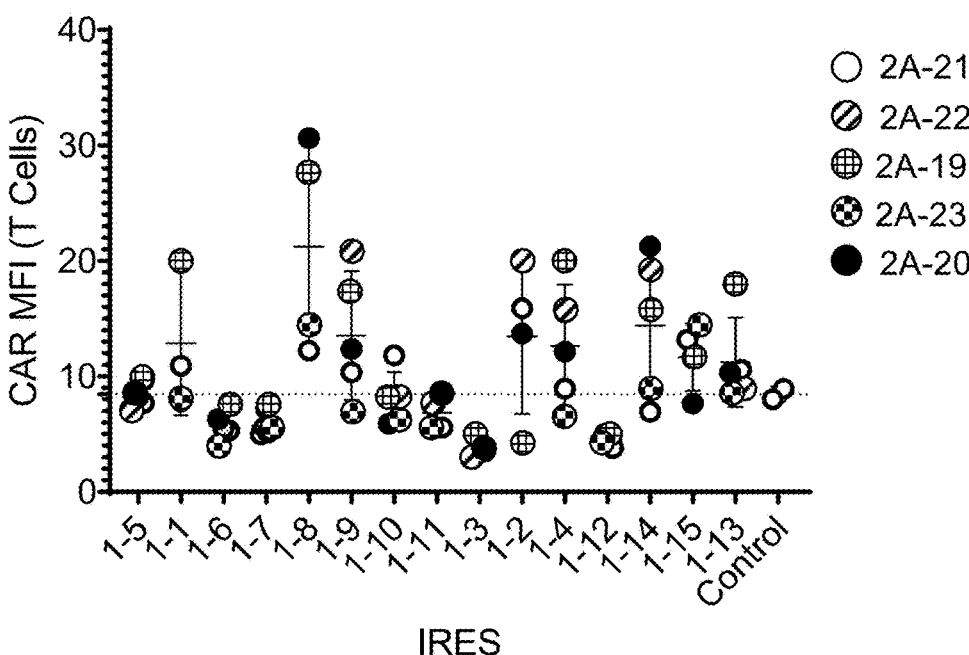
Figure 6A:
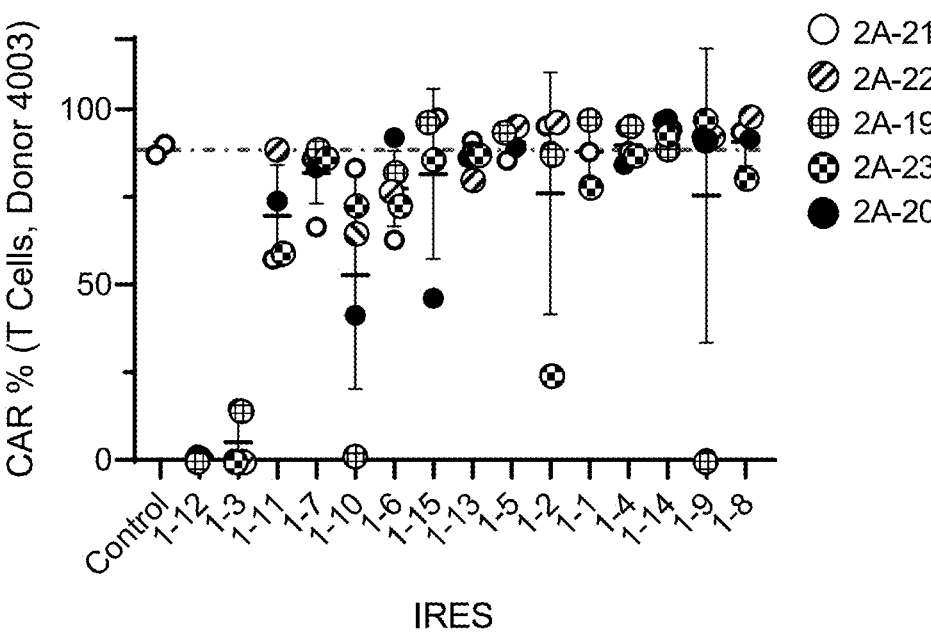
FIGS. 6A, 6B, 6C, 6D, 6E, 6F, 6G, 6H, 6I, and 6J show % CAR positive cells by IRES over time, i.e., the percent of cells or average signal of the cells expressing over time (5 days) for two donors (donor 4003 and donor 609C) for circular RNA constructs comprising combinations of IRESes and expression sequences. Each point on the X axis is an IRES from Table 1A and each dot is a different expression sequence from Table 2A (codon optimized; anti-CD19 28-ζ).
Figure 6B:
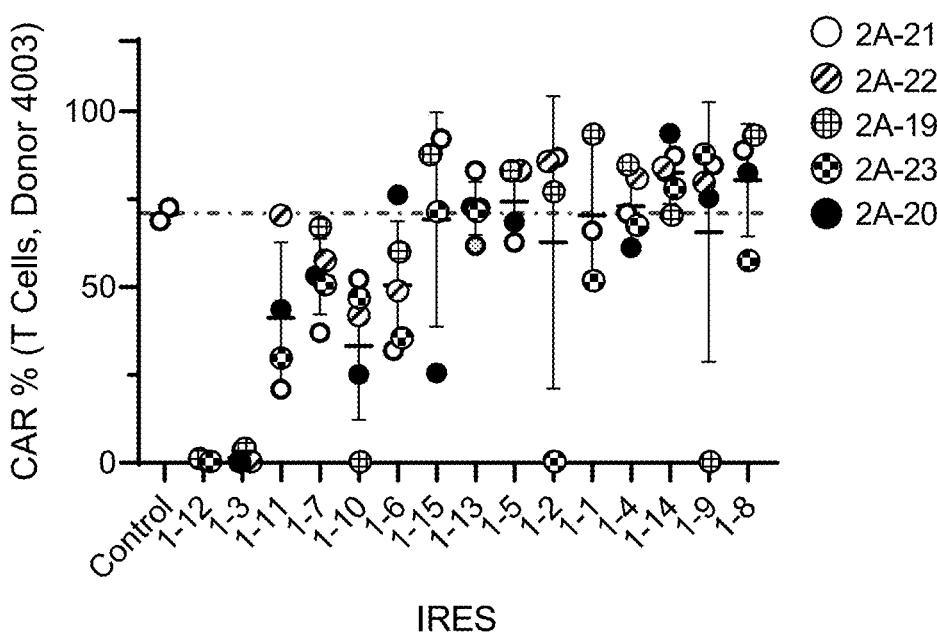
Figure 6C:
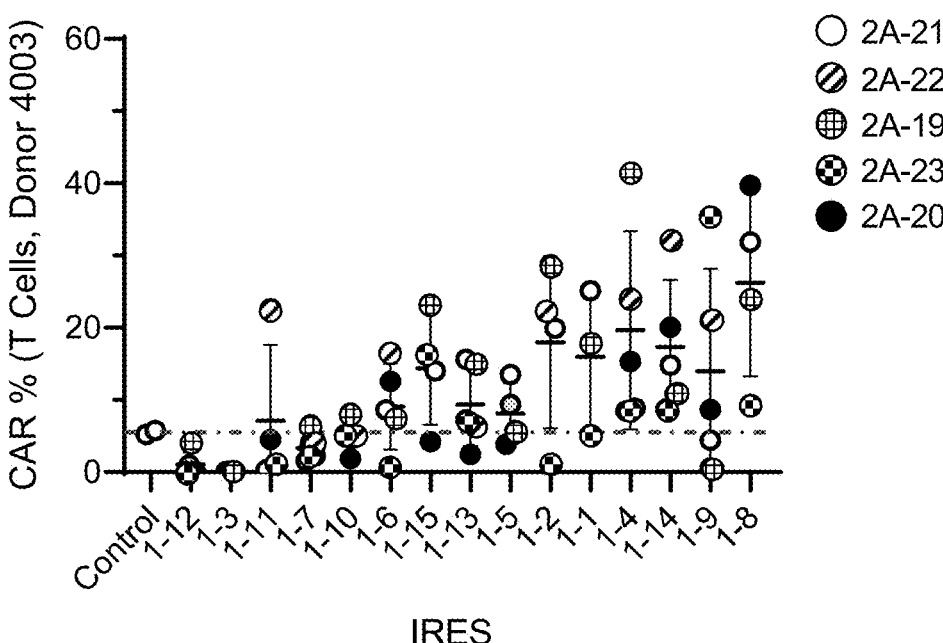
Figure 6D:
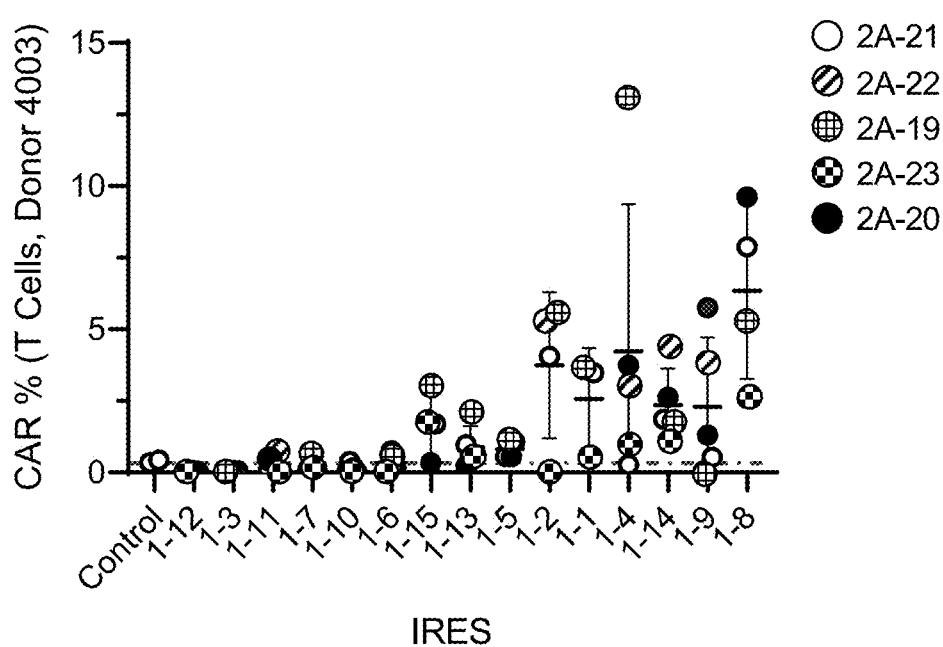
Figure 6E:
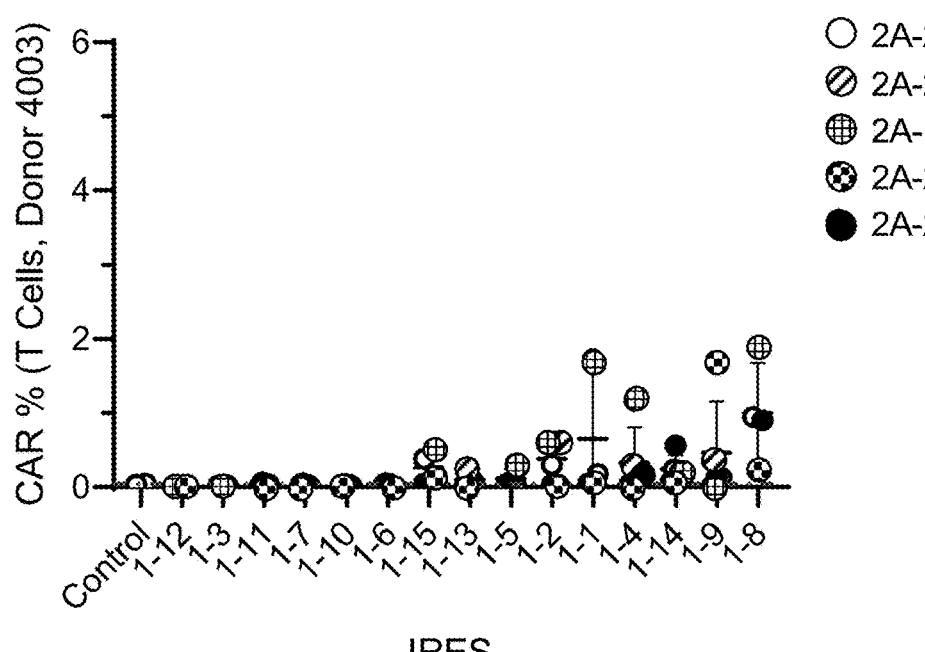
Figure 6F:
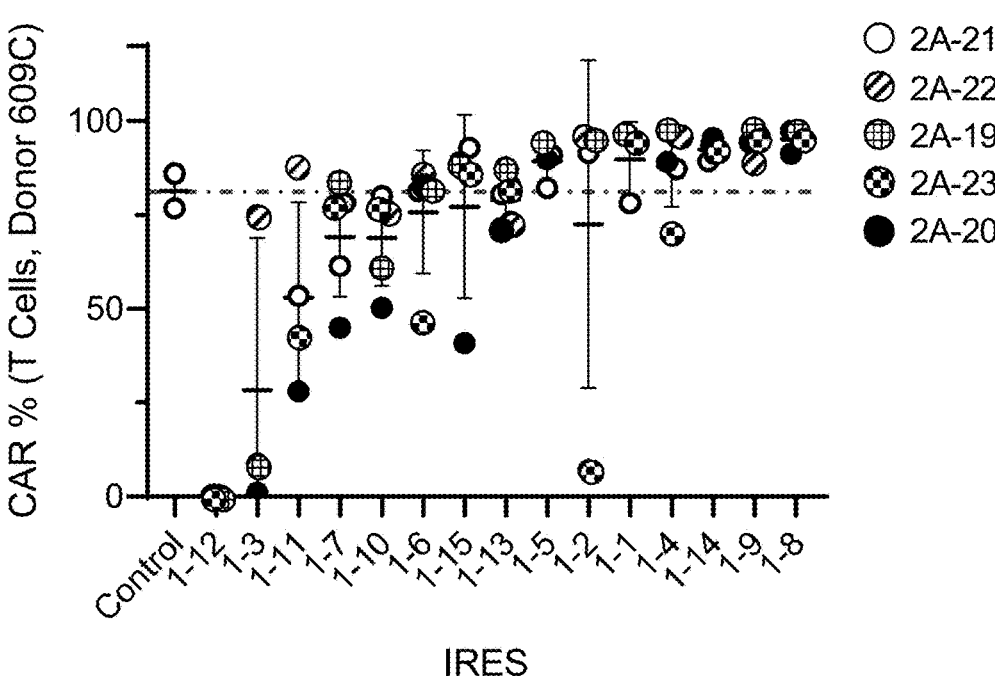
Figure 6G:
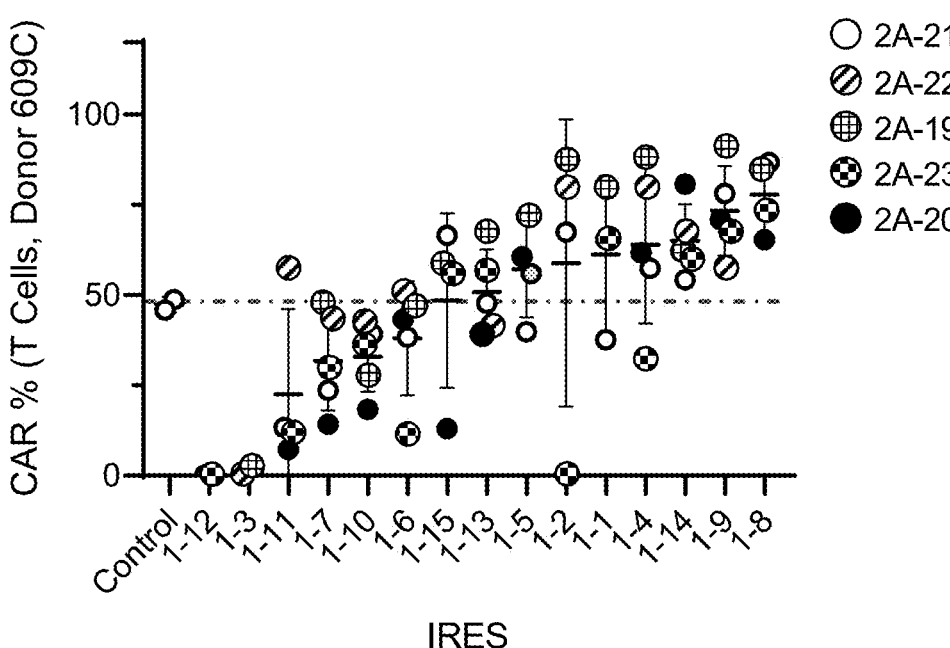
Figure 6H:
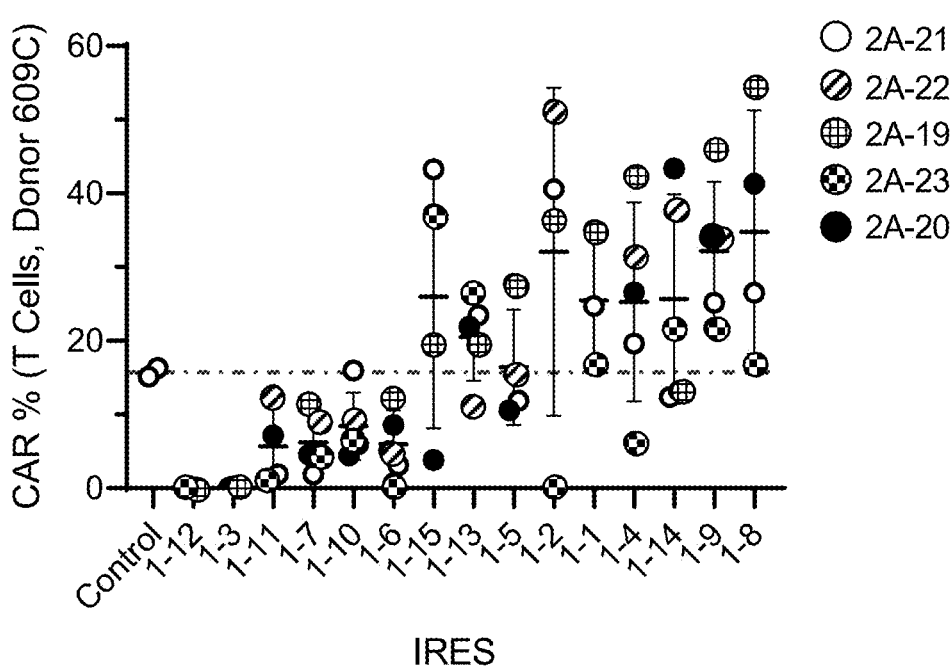
Figure 6I:
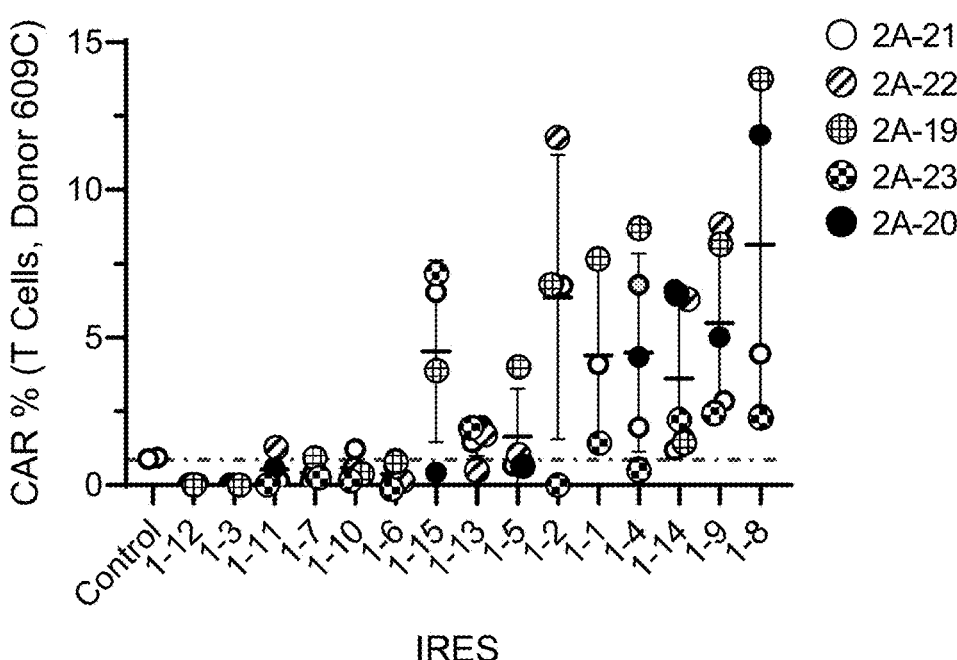
Figure 6J:
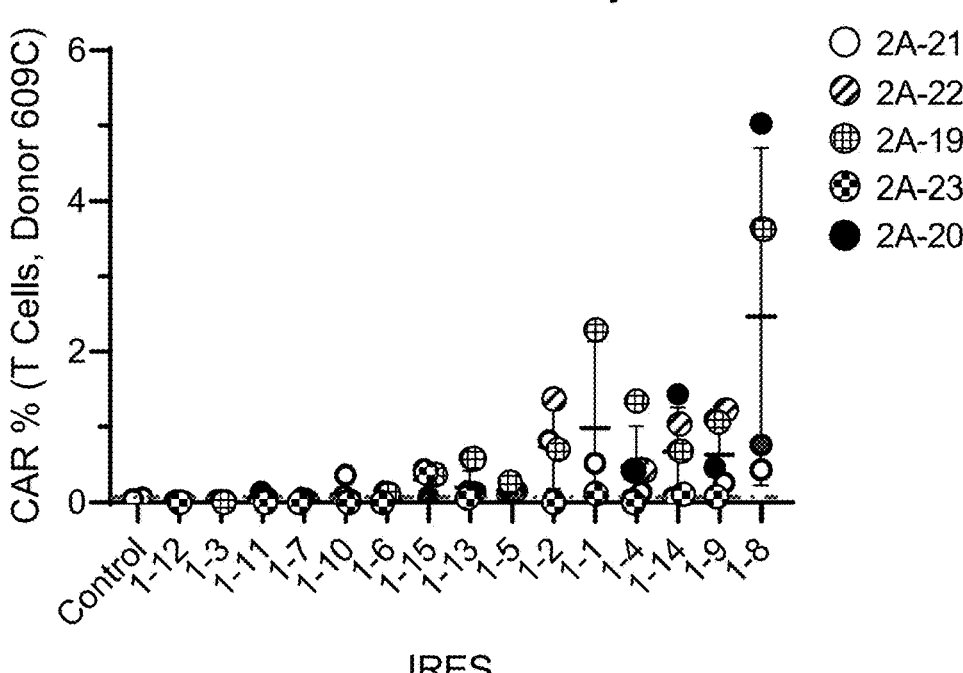

Reference will now be made in detail to certain embodiments of the invention, examples of which are illustrated in the accompanying drawings. While the invention is described in conjunction with the illustrated embodiments, it will be understood that they are not intended to limit the invention to those embodiments. On the contrary, the invention is intended to cover all alternatives, modifications, and equivalents, which may be included within the invention as defined by the appended claims and included embodiments.

Before describing the present teachings in detail, it is to be understood that the disclosure is not limited to specific compositions or process steps, as such may vary. It should be noted that, as used in this specification and the appended claims, the singular form "a", "an" and "the" include plural references unless the context clearly dictates otherwise. Thus, for example, reference to "a guide" includes a plurality of guides and reference to "a cell" includes a plurality of cells and the like.

Numeric ranges are inclusive of the numbers defining the range. Measured and measurable values are understood to be approximate, taking into account significant digits and the error associated with the measurement. Also, the use of "comprise", "comprises", "comprising", "contain", "contains", "containing", "include", "includes", and "including" are not intended to be limiting. It is to be understood that both the foregoing general description and detailed description are exemplary and explanatory only and are not restrictive of the teachings.

Unless specifically noted in the specification, embodiments in the specification that recite "comprising" various components are also contemplated as "consisting of" or "consisting essentially of" the recited components; embodiments in the specification that recite "consisting of" various components are also contemplated as "comprising" or "consisting essentially of" the recited components; and embodiments in the specification that recite "consisting essentially of" various components are also contemplated as "consisting of" or "comprising" the recited components (this interchangeability does not apply to the use of these terms in the claims). The term "or" is used in an inclusive sense, i.e., equivalent to "and/or," unless the context clearly indicates otherwise.

The section headings used herein are for organizational purposes only and are not to be construed as limiting the desired subject matter in any way. In the event that any material incorporated by reference contradicts any term defined in this specification or any other express content of this specification, this specification controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

I. Definitions

Unless stated otherwise, the following terms and phrases as used herein are intended to have the following meanings:

As used herein, the term "circRNA," "circular polyribonucleotide," "circular RNA," "circularized RNA," or "ORNA" are used interchangeably and refer to a single-stranded RNA polynucleotide wherein the 3' and 5' ends that are normally present in a linear RNA polynucleotide have been joined together.

As used herein, the term "DNA template" refers to a DNA sequence capable of transcribing a linear RNA polynucleotide. For example, but not intending to be limiting, a DNA template may include a DNA vector, PCR product or plasmid.

As used herein, the term "3' group I intron fragment" refers to a sequence with 75% or higher similarity to the 3'-proximal end of a natural group I intron including the splice site dinucleotide and optionally a stretch of natural exon sequence. In some embodiments, a circular RNA comprises a post splicing 3' group I intron fragment. In some embodiments, the post splicing 3' group I intron fragment in the circular RNA is a post splicing stretch of exon sequence. In some embodiments, the circular RNA further comprises a desired expression sequence, and the post splicing stretch of exon sequence is (e.g., designed) to be a portion of the desired expression sequence, contiguous with the desired expression sequence, and/or in frame with the desired expression sequence.

As used herein, the term "5' group I intron fragment" refers to a sequence with 75% or higher similarity to the 5'-proximal end of a natural group I intron including the splice site dinucleotide and optionally a stretch of natural exon sequence. In some embodiments, a circular RNA comprises a post splicing 5' group I intron fragment. In some embodiments, the post splicing 5' group I intron fragment in the circular RNA is a post splicing stretch of exon sequence. In some embodiments, the circular RNA further comprises a desired expression sequence, and the post splicing stretch of exon sequence is (e.g., designed) to be a portion of the desired expression sequence, contiguous with the desired expression sequence, and/or in frame with the desired expression sequence.

As used herein, the term "permutation site" refers to the site in a group I intron where a cut is made prior to permutation of the intron. This cut generates 3' and 5' group I intron fragments that are permuted to be on either side of a stretch of precursor RNA to be circularized.

As used herein, the term "splice site" refers to a dinucleotide that is partially or fully included in a group I intron and between which a phosphodiester bond is cleaved during RNA circularization. (As used herein, "splice site" refers to the dinucleotide or dinucleotides between which cleavage of the phosphodiester bond occurs during a splicing reaction. A "5' splice site" refers to the natural 5' dinucleotide of the intron e.g., group I intron, while a "3' splice site" refers to the natural 3' dinucleotide of the intron).

As used herein, the term "expression sequence" refers to a nucleic acid sequence that encodes a product, e.g., a peptide or polypeptide, regulatory nucleic acid, or non-coding nucleic acid. An exemplary expression sequence that codes for a peptide or polypeptide can comprise a plurality of nucleotide triads, each of which can code for an amino acid and is termed as a "codon."

As used herein, "coding element" or "coding region" is region located within the expression sequence and encodings for one or more proteins or polypeptides (e.g., therapeutic protein).

As used herein, a "noncoding element," "noncoding region," or "non-coding nucleic acid" is a region located within the expression sequence. This sequence by itself does not encode for a protein or polypeptide, but may have other regulatory functions, including but not limited to allowing the overall polynucleotide to act as a biomarker or adjuvant to a specific cell.

As used herein, the term "therapeutic protein" refers to any protein that, when administered to a subject directly or indirectly in the form of a translated nucleic acid, has a therapeutic, diagnostic, and/or prophylactic effect and/or elicits a desired biological and/or pharmacological effect.

As used herein, the term "immunogenic" refers to a potential to induce an immune response to a substance. An immune response may be induced when an immune system of an organism or a certain type of immune cells is exposed to an immunogenic substance. The term "non-immunogenic" refers to a lack of or absence of an immune response above a detectable threshold to a substance. No immune response is detected when an immune system of an organism or a certain type of immune cells is exposed to a non-immunogenic substance. In some embodiments, a non-immunogenic circular polyribonucleotide as provided herein, does not induce an immune response above a predetermined threshold when measured by an immunogenicity assay. In some embodiments, no innate immune response is detected when an immune system of an organism or a certain type of immune cells is exposed to a non-immunogenic circular polyribonucleotide as provided herein. In some embodiments, no adaptive immune response is detected when an immune system of an organism or a certain type of immune cell is exposed to a non-immunogenic circular polyribonucleotide as provided herein.

As used herein, the term "translation efficiency" refers to a rate or amount of protein or peptide production from a ribonucleotide transcript. In some embodiments, translation efficiency can be expressed as amount of protein or peptide produced per given amount of transcript that codes for the protein or peptide.

The term "nucleotide" refers to a ribonucleotide, a deoxyribonucleotide, a modified form thereof, or an analog thereof. Nucleotides include species that comprise purines, e.g., adenine, hypoxanthine, guanine, and their derivatives and analogs, as well as pyrimidines, e.g., cytosine, uracil, thymine, and their derivatives and analogs. Nucleotide analogs include nucleotides having modifications in the chemical structure of the base, sugar and/or phosphate, including, but not limited to, 5'-position pyrimidine modifications, 8'-position purine modifications, modifications at cytosine exocyclic amines, and substitution of 5-bromo-uracil; and 2'-position sugar modifications, including but not limited to, sugar-modified ribonucleotides in which the 2'-OH is replaced by a group such as an H, OR, R, halo, SH, SR, NH2, NHR, NR2, or CN, wherein R is an alkyl moiety as defined herein. Nucleotide analogs are also meant to include nucleotides with bases such as inosine, queuosine, xanthine; sugars such as 2'-methyl ribose; non-natural phosphodiester linkages such as methylphosphonate, phosphorothioate and peptide linkages. Nucleotide analogs include 5-methoxyuridine, 1-methylpseudouridine, and 6-methyladenosine.

"Polynucleotide," "nucleic acid," and "nucleic acid molecule," are used interchangeably herein to refer to a multimeric compound comprising nucleosides or nucleoside analogs which have nitrogenous heterocyclic bases or base analogs linked together along a backbone, including conventional RNA, DNA, mixed RNA-DNA, and polymers that are analogs thereof. The terms can be used to describe a polymer of any length, e.g., greater than about 2 bases, greater than about 10 bases, greater than about 100 bases, greater than about 500 bases, greater than 1000 bases, or up to about 10,000 or more bases, composed of nucleotides, e.g., deoxyribonucleotides or ribonucleotides, and may be produced enzymatically or synthetically (e.g., as described in U.S. Pat. No. 5,948,902 and the references cited therein), which can hybridize with naturally occurring nucleic acids in a sequence specific manner analogous to that of two naturally occurring nucleic acids, e.g., can participate in Watson-Crick base pairing interactions. A nucleic acid "backbone" can be made up of a variety of linkages, including one or more of sugar-phosphodiester linkages, peptide-nucleic acid bonds ("peptide nucleic acids" or PNA; PCT No. WO 95/32305), phosphorothioate linkages, methylphosphonate linkages, or combinations thereof. Sugar moieties of a nucleic acid can be ribose, deoxyribose, or similar compounds with substitutions, e.g., 2' methoxy or 2' halide substitutions. Nitrogenous bases can be conventional bases (A, G, C, T, U), analogs thereof (e.g., modified uridines such as 5-methoxyuridine, pseudouridine, or N1-methylpseudouridine, or others); inosine; derivatives of purines or pyrimidines (e.g., N4-methyl deoxyguanosine, deaza- or aza-purines, deaza- or aza-pyrimidines, pyrimidine bases with substituent groups at the 5 or 6 position (e.g., 5-methylcytosine), purine bases with a substituent at the 2, 6, or 8 positions, 2-amino-6-methylaminopurine, 06-methylguanine, 4-thio-pyrimidines, 4-amino-pyrimidines, 4-dimethylhydrazine-pyrimidines, and 04-alkyl-pyrimidines; U.S. Pat. No. 5,378,825 and PCT No. WO 93/13121). For general discussion see The Biochemistry of the Nucleic Acids 5-36, Adams et al., ed., 11th ed., 1992). Nucleic acids can include one or more "abasic" residues where the backbone includes no nitrogenous base for position(s) of the polymer (U.S. Pat. No. 5,585,481). A nucleic acid can comprise only conventional RNA or DNA sugars, bases and linkages, or can include both conventional components and substitutions (e.g., conventional bases with 2' methoxy linkages, or polymers containing both conventional bases and one or more base analogs). All nucleotide sequences disclosed herein can represent an RNA sequence or a corresponding DNA sequence. It is understood that deoxythymidine (dT or T) in a DNA is transcribed into a uridine (U) in an RNA. As such, "T" and "U" are used interchangeably herein in nucleotide sequences.

An "oligonucleotide" is a polynucleotide comprising fewer than 1000 nucleotides, such as a polynucleotide comprising fewer than 500 nucleotides or fewer than 100 nucleotides.

As used herein, the terms "monotron," "monotron sequence," or "monotron element" are used interchangeably to refer a segment of a precursor RNA polynucleotide that is located at either the 5' or 3' end of the polynucleotide, i.e., either 5' or 3' from the intervening region. A monotron element refers to a sequence with 70% or higher similarity to a natural group I or group II intron including the splice site dinucleotide. In some embodiments, the monotron is capable of contributing to ribozymatic activity that allows it to enzymatically self-cleave. In some embodiments, the monotron is capable of forming a phosphodiester bond with a terminal sequence, i.e., a sequence containing a splice site dinucleotide and optionally a natural exon sequence or fragment thereof. In some embodiments, the terminal sequence is upstream of the monotron in a linear precursor. In some embodiments, the monotron sequence is upstream of the terminal sequence in a linear precursor. When the terminal sequence is upstream to the monotron in a linear precursor, the monotron can perform two transesterification reactions, e.g., sequentially, self-cleavage and formation of a phosphodiester bond with the terminal sequence. In embodiments in which the terminal sequence is upstream to the monotron in the linear precursor, (a) the monotron is capable of interacting with a nucleophile that is capable of cleaving at the splice site dinucleotide at or near the 5' end of the monotron, and (b) the cleavage product of (a), i.e., the 5' splice site nucleotide, e.g., having a 3' hydroxyl group, engages in a transesterification reaction (cleaves) at the splice site nucleotide of the terminal sequence, yielding a circular RNA or ORNA. In these embodiments, the monotron interacts with the nucleophile (e.g., a guanosine, e.g., a free guanosine that is introduced to the precursor) by forming a binding pocket with the nucleophile, and the linear precursor is capable of adopting a conformation in which the nucleophile is in proximity to and is capable of cleaving at the splice site dinucleotide at or near the 5' end of the monotron. When the monotron is upstream of the terminal sequence in a linear precursor, the monotron can also perform two transesterification reactions. In embodiments in which the monotron is upstream of the terminal sequence in the linear precursor, (a) the monotron is capable of interacting with a nucleophile that is capable of cleaving at the splice site nucleotide of the terminal element, and (b) the cleavage product of (a), i.e., the 5' splice site nucleotide, e.g., having a 3' hydroxyl group, engages in a transesterification reaction (cleaves) at the splice site dinucleotide at or near the 3' end of the monotron, yielding a circular RNA or oRNA. In these embodiments, the monotron interacts with the nucleophile (e.g., a guanosine, e.g., a free guanosine that is introduced to the precursor) by forming a binding pocket with the nucleophile, and the linear precursor is capable of adopting a conformation in which the nucleophile is in proximity to and is capable of cleaving the splice site nucleotide of the terminal element.

In some embodiments, the monotron comprises a 5' proximal end of a natural group I or group II intron including the splice site dinucleotide and optionally a natural exon sequence or fragment thereof. In some embodiments, the 5' end of the monotron refers to nucleotides within the 5' half of the monotron. In some embodiments, the 3' end of the monotron refers to nucleotides within the 3' half of the monotron. In some embodiments, at or near the 5' end of the monotron refers to within the 5' half of the monotron. In some embodiments, at or near the 5' end of the monotron refers to within the first ten 5' positions in the monotron. In some embodiments, at the 5' end of the monotron refers to the first 5' position(s) in the monotron. In some embodiments, at or near the 3' end of the monotron refers to within the 3' half of the monotron. In some embodiments, at or near the 3' end of the monotron refers to within the last ten 3' positions in the monotron. In some embodiments, at the 3' end of the monotron refers to last 3' position(s) in the monotron.

As used herein, the term "terminal sequence" or "terminal element" are used interchangeably to refer to an RNA sequence capable of complexing with a monotron sequence or monotron element. The terminal sequence comprises a splice site nucleotide from the natural group I or group II intron present in the monotron. In some embodiments, the terminal sequence further comprises a natural exon or a fragment thereof and/or a synthetic sequence.

The term "nucleophile" refers to a nucleophilic nucleotide or nucleoside capable of initiating a nucleophilic attack at a splice site and/or transesterification reaction (cleavage) at a splice site.

As used herein, "polyA" means a polynucleotide or a portion of a polynucleotide consisting of nucleotides comprising adenine. As used herein, "polyT" means a polynucleotide or a portion of a polynucleotide consisting of nucleotides comprising thymine. As used herein, "polyAC" means a polynucleotide or a portion of a polynucleotide consisting of nucleotides comprising adenine or cytosine.

"Isolated" or "purified" generally refers to isolation of a substance (for example, in some embodiments, a compound, a polynucleotide, a protein, a polypeptide, a polynucleotide composition, or a polypeptide composition) such that the substance comprises a significant percent (e.g., greater than 1%, greater than 2%, greater than 5%, greater than 10%, greater than 20%, greater than 50%, or more, usually up to about 90%-100%) of the sample in which it resides. In certain embodiments, a substantially purified component comprises at least 50, 60, 70, 75, 80, 85, 90, 95, 96, 97, 98, or 99% of the sample. In additional embodiments, a substantially purified component comprises about, 80%-85%, or 90%-95%, 95-99%, 96-99%, 97-99%, or 95-100% of the sample. Techniques for purifying polynucleotides and polypeptides of interest are well-known in the art and include, for example, ion-exchange chromatography, affinity chromatography and sedimentation according to density. Generally, a substance is purified when it exists in a sample in an amount, relative to other components of the sample, that is more than as it is found naturally.

As used herein, "unstructured" with regard to RNA refers to an RNA sequence that is not predicted by RNA structure predictive tools to form a structure (e.g., a hairpin loop) with itself or other sequences in the same RNA molecule. In some embodiments, unstructured RNA can be functionally characterized using nuclease protection assays.

As used herein, "structured" with regard to RNA refers to an RNA sequence that is predicted by the RNAFold software or similar predictive tools to form a structure (e.g., a hairpin loop) with itself or other sequences in the same RNA molecule.

As used herein, two "duplex sequences," "duplex region," "duplex regions," "homology arms," or "homology regions" may be any two regions that are thermodynamically favored to cross-pair in a sequence specific interaction. In some embodiments, two duplex sequences, duplex regions, homology arms, or homology regions, share a sufficient level of sequence identity to one another's reverse complement to act as substrates for a hybridization reaction. As used herein, polynucleotide sequences have "homology" when they are either identical or share sequence identity to a reverse complement or "complementary" sequence. The percent sequence identity between a homology region and a counterpart homology region's reverse complement can be any percent of sequence identity that allows for hybridization to occur. In some embodiments, an internal duplex region of an inventive polynucleotide is capable of forming a duplex with another internal duplex region and does not form a duplex with an external duplex region.

As used herein, an "affinity sequence" or "affinity tag" is a region of polynucleotide sequences polynucleotide sequence ranging from 1 nucleotide to hundreds or thousands of nucleotides containing a repeated set of nucleotides for the purposes of aiding purification of a polynucleotide sequence. For example, an affinity sequence may comprise, but is not limited to, a polyA or polyAC sequence. In some embodiments, affinity tags are used in purification methods, referred to herein as "affinity-purification," in which selective binding of a binding agent to molecules comprising an affinity tag facilitates separation from molecules that do not comprise an affinity tag. In some embodiments, an affinity-purification method is a "negative selection" purification method, in which unwanted species, such as linear RNA, are selectively bound and removed and wanted species, such as circular RNA, are eluted and separated from unwanted species.

As used herein, a "spacer" refers to a region of a polynucleotide sequence ranging from 1 nucleotide to hundreds or thousands of nucleotides separating two other elements along a polynucleotide sequence. The sequences can be defined or can be random. A spacer is typically non-coding. In some embodiments, spacers include duplex regions.

Linear nucleic acid molecules are said to have a "5'-terminus" (5' end) and a "3'-terminus" (3' end) because nucleic acid phosphodiester linkages occur at the 5' carbon and 3' carbon of the sugar moieties of the substituent mononucleotides. The end nucleotide of a polynucleotide at which a new linkage would be to a 5' carbon is its 5' terminal nucleotide. The end nucleotide of a polynucleotide at which a new linkage would be to a 3' carbon is its 3' terminal nucleotide. A terminal nucleotide, as used herein, is the nucleotide at the end position of the 3'- or 5'-terminus.

As used herein, a "leading untranslated sequence" is a region of polynucleotide sequences ranging from 1 nucleotide to hundreds of nucleotides located at the upmost 5' end of a polynucleotide sequence. The sequences can be defined or can be random. A leading untranslated sequence is non-coding.

As used herein, a "terminal untranslated sequence" is a region of polynucleotide sequences ranging from 1 nucleotide to hundreds of nucleotides located at the downmost 3' end of a polynucleotide sequence. The sequences can be defined or can be random. A terminal untranslated sequence is non-coding.

"Transcription" means the formation or synthesis of an RNA molecule by an RNA polymerase using a DNA molecule as a template. The disclosure is not limited with respect to the RNA polymerase that is used for transcription. For example, in some embodiments, a T7-type RNA polymerase can be used.

"Translation" means the formation of a polypeptide molecule by a ribosome based upon an RNA template.

As used herein, an "internal ribosome entry site" or "IRES" refers to an RNA sequence or structural element ranging in size from 10 nt to 1000 nt or more, capable of initiating translation of a polypeptide in the absence of a typical RNA cap structure. An exemplary IRES can be about 500 nt to about 700 nt in length.

As used herein, the terms "about" or "approximately" means an acceptable error for a particular value as determined by one of ordinary skill in the art, which depends in part on how the value is measured or determined. Unless specifically stated or obvious from context, as used herein, the term "about," is understood as within a range of normal tolerance in the art, for example within 2 standard deviations of the mean. Unless otherwise clear from the context, all numerical values provided herein are modified by the term "about."

As used herein, the term "encode" refers broadly to any process whereby the information in a polymeric macromolecule is used to direct the production of a second molecule that is different from the first. The second molecule may have a chemical structure that is different from the chemical nature of the first molecule.

As used herein, "aptamer" refers in general to either an oligonucleotide of a single defined sequence or a mixture of said nucleotides, wherein the mixture retains the properties of binding specifically to the target molecule (e.g., eukaryotic initiation factor, 40S ribosome, polyC binding protein, polyA binding protein, polypyrimidine tract-binding protein, argonaute protein family, Heterogeneous nuclear ribonucleoprotein K and La and related RNA-binding protein). Thus, as used herein "aptamer" denotes both singular and plural sequences of nucleotides, as defined hereinabove. The term "aptamer" is meant to refer to a single- or double-stranded nucleic acid which is capable of binding to a protein or other molecule. In general, aptamers preferably comprise about 10 to about 100 nucleotides, preferably about 15 to about 40 nucleotides, more preferably about 20 to about 40 nucleotides, in that oligonucleotides of a length that falls within these ranges are readily prepared by conventional techniques. Optionally, aptamers can further comprise a minimum of approximately 6 nucleotides, preferably 10, and more preferably 14 or 15 nucleotides, that are necessary to effect specific binding.

As used herein, a "miRNA site" or "miRNA binding site" refers to a stretch of nucleotides within a polynucleotide that is capable of forming a duplex with at least 8 nucleotides of a natural miRNA sequence.

As used herein, "bicistronic RNA" refers to a polynucleotide that includes two expression sequences coding for two distinct proteins. These expression sequences can be separated by a nucleotide sequence encoding a cleavable peptide such as a protease cleavage site. They can also be separated by a ribosomal skipping element.

As used herein, the term "ribosomal skipping element" refers to a nucleotide sequence encoding a short peptide sequence capable of causing generation of two peptide chains from translation of one RNA molecule. While not wishing to be bound by theory, it is hypothesized that ribosomal skipping elements function by (1) terminating translation of the first peptide chain and re-initiating translation of the second peptide chain; or (2) cleavage of a peptide bond in the peptide sequence encoded by the ribosomal skipping element by an intrinsic protease activity of the encoded peptide, or by another protease in the environment (e.g., cytosol).

As used herein, the terms "transfect" or "transfection" refer to the intracellular introduction of one or more encapsulated materials (e.g., nucleic acids and/or polynucleotides) into a cell, or preferably into a target cell. The term "transfection efficiency" refers to the relative amount of such encapsulated material (e.g., polynucleotides) up-taken by, introduced into and/or expressed by the target cell which is subject to transfection. In some embodiments, transfection efficiency may be estimated by the amount of a reporter polynucleotide product produced by the target cells following transfection. In some embodiments, a transfer vehicle has high transfection efficiency. In some embodiments, a transfer vehicle has at least about 10%, 20%, 30%, 40%, 50%, 60%, 70%, 80%, or 90% transfection efficiency.

As used herein, "transfer vehicle" includes any of the standard pharmaceutical carriers, diluents, excipients, and the like, which are generally intended for use in connection with the administration of biologically active agents, including nucleic acids.

As used herein, the phrase "nanoparticle" refers to a delivery or transfer vehicle, for example, having a diameter of less than about 1000 nm. A nanoparticle can be a "lipid nanoparticle," and in certain instances herein, the terms are used interchangeably herein.

As used herein, the phrase "LNP" or "lipid nanoparticle" refers to a delivery or transfer vehicle comprising one or more cationic or ionizable lipids, stabilizing lipids, structural lipids, and helper lipids.

As used herein, the phrase "cationic lipid" or "ionizable lipid" refers to any of a number of lipid species that carry a net positive charge at a selected pH, such as physiological pH 4 and a neutral charge at other pHs such as physiological pH 7.

In some embodiments, a lipid, e.g., an ionizable lipid, disclosed herein comprises one or more cleavable groups. The terms "cleave" and "cleavable" are used herein to mean that one or more chemical bonds (e.g., one or more of covalent bonds, hydrogen-bonds, van der Waals' forces and/or ionic interactions) between atoms in or adjacent to the subject functional group are broken (e.g., hydrolyzed) or are capable of being broken upon exposure to selected conditions (e.g., upon exposure to enzymatic conditions). In certain embodiments, the cleavable group is a disulfide functional group, and in particular embodiments a disulfide group that is capable of being cleaved upon exposure to selected biological conditions (e.g., intracellular conditions). In certain embodiments, the cleavable group is an ester functional group that is capable of being cleaved upon exposure to selected biological conditions. For example, the disulfide groups may be cleaved enzymatically or by a hydrolysis, oxidation or reduction reaction. Upon cleavage of such disulfide functional group, the one or more functional moieties or groups (e.g., one or more of a head-group and/or a tail-group) that are bound thereto may be liberated. Exemplary cleavable groups may include, but are not limited to, disulfide groups, ester groups, ether groups, and any derivatives thereof (e.g., alkyl and aryl esters). In certain embodiments, the cleavable group is not an ester group or an ether group. In some embodiments, a cleavable group is bound (e.g., bound by one or more of hydrogen-bonds, van der Waals' forces, ionic interactions and covalent bonds) to one or more functional moieties or groups (e.g., at least one head-group and at least one tail-group). In certain embodiments, at least one of the functional moieties or groups is hydrophilic (e.g., a hydrophilic head-group comprising one or more of imidazole, guanidinium, amino, imine, enamine, optionally-substituted alkyl amino and pyridyl).

As used herein, the term "liposome" generally refers to a vesicle composed of lipids (e.g., amphiphilic lipids) arranged in one or more spherical bilayer or bilayers. Such liposomes may be unilamellar or multilamellar vesicles which have a membrane formed from a lipophilic material and an aqueous interior that contains the encapsulated circRNA to be delivered to one or more target cells, tissues and organs. In certain embodiments, the compositions described herein comprise one or more lipid nanoparticles. Examples of suitable lipids (e.g., ionizable lipids) that may be used to form the liposomes and lipid nanoparticles contemplated include one or more of the compounds disclosed herein (e.g., HGT4001, HGT4002, HGT4003, HGT4004 and/or HGT4005). Such liposomes and lipid nanoparticles may also comprise additional ionizable lipids such as C12-200, DLin-KC2-DMA, and/or HGT5001, helper lipids, structural lipids, PEG-modified lipids, MC3, DLinDMA, DLinkC2DMA, cKK-E12, ICE, HGT5000, DODAC, DDAB, DMRIE, DOSPA, DOGS, DODAP, DODMA, DMDMA, DODAC, DLenDMA, DMRIE, CLinDMA, CpLinDMA, DMOBA, DOcarbDAP, DLin-DAP, DLincarbDAP, DLinCDAP, KLin-K-DMA, DLin-K-XTC2-DMA, HGT4003, and combinations thereof.

As used herein, the phrase "biodegradable lipid" or "degradable lipid" refers to any of a number of lipid species that are broken down in a host environment on the order of minutes, hours, or days ideally making them less toxic and unlikely to accumulate in a host over time. Common modifications to lipids include ester bonds, and disulfide bonds among others to increase the biodegradability of a lipid.

As used herein, the term "structural lipid" refers to sterols and also to lipids containing sterol moieties.

As defined herein, "sterols" are a subgroup of steroids consisting of steroid alcohols.

As used herein, the term "PEG" means any polyethylene glycol or other polyalkylene ether polymer. As generally defined herein, a "PEG-OH lipid" (also referred to herein as "hydroxy-PEGylated lipid") is a PEGylated lipid having one or more hydroxyl (—OH) groups on the lipid. As used herein, the phrase "biodegradable PEG lipid" or "degradable PEG lipid" refers to any of a number of lipid species where the PEG molecules are cleaved from the lipid in a host environment on the order of minutes, hours, or days ideally making them less immunogenic. Common modifications to PEG lipids include ester bonds, and disulfide bonds among others to increase the biodegradability of a lipid.

As used herein, the term "hydrophilic" is used to indicate in qualitative terms that a functional group is water-preferring, and typically such groups are water-soluble. For example, disclosed herein are compounds that comprise a cleavable disulfide (S—S) functional group bound to one or more hydrophilic groups (e.g., a hydrophilic head-group), wherein such hydrophilic groups comprise or are selected from the group consisting of imidazole, guanidinium, amino, imine, enamine, an optionally-substituted alkyl amino(e.g., an alkyl amino such as dimethylamino) and pyridyl.

In certain embodiments, at least one of the functional groups of moieties that comprise the compounds disclosed herein is hydrophobic in nature (e.g., a hydrophobic tail-group comprising a naturally occurring lipid such as cholesterol). As used herein, the term "hydrophobic" is used to indicate in qualitative terms that a functional group is water-avoiding, and typically such groups are not water soluble. For example, disclosed herein are compounds that comprise a cleavable functional group (e.g., a disulfide (S—S) group) bound to one or more hydrophobic groups, wherein such hydrophobic groups comprise one or more naturally occurring lipids such as cholesterol, and/or an optionally substituted, variably saturated or unsaturated C6-C20 alkyl and/or an optionally substituted, variably saturated or unsaturated C6-C20 acyl.

Compounds described herein may also comprise one or more isotopic substitutions. For example, H may be in any isotopic form, including 1H, 2H (D or deuterium), and 3H (T or tritium); C may be in any isotopic form, including 12C, 13C, and 14C; O may be in any isotopic form, including 16O and 18O; F may be in any isotopic form, including 18F and 19F; and the like.

As used herein, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein.

When a range of values is listed, it is intended to encompass each value and sub-range within the range. For example, "C1-6 alkyl" is intended to encompass, C1, C2, C3, C4, C5, C6, C1-6, C1-5, C1-4, C1-3, C1-2, C2-6, C2-5, C2-4, C2-3, C3-6, C3-5, C3-4, C4-6, C4-5, and C5-6 alkyl.

As used herein, the term "alkyl" refers to both straight and branched chain C1-C40 hydrocarbons (e.g., C6-C20 hydrocarbons), and include both saturated and unsaturated hydrocarbons. In certain embodiments, the alkyl may comprise one or more cyclic alkyls and/or one or more heteroatoms such as oxygen, nitrogen, or sulfur and may optionally be substituted with substituents (e.g., one or more of alkyl, halo, alkoxyl, hydroxy, amino, aryl, ether, ester or amide). In certain embodiments, a contemplated alkyl includes (9Z, 12Z)-octadeca-9,12-dien. The use of designations such as, for example, "C6-C20" is intended to refer to an alkyl (e.g., straight or branched chain and inclusive of alkenes and alkyls) having the recited range carbon atoms. In some embodiments, an alkyl group has 1 to 10 carbon atoms ("C1-10 alkyl"). In some embodiments, an alkyl group has 1 to 9 carbon atoms ("C1-9 alkyl"). In some embodiments, an alkyl group has 1 to 8 carbon atoms ("C1-8 alkyl"). In some embodiments, an alkyl group has 1 to 7 carbon atoms ("C1-7 alkyl"). In some embodiments, an alkyl group has 1 to 6 carbon atoms ("C1-6 alkyl"). In some embodiments, an alkyl group has 1 to 5 carbon atoms ("C1-5 alkyl"). In some embodiments, an alkyl group has 1 to 4 carbon atoms ("C1-4 alkyl"). In some embodiments, an alkyl group has 1 to 3 carbon atoms ("C1-3 alkyl"). In some embodiments, an alkyl group has 1 to 2 carbon atoms ("C1-2 alkyl"). In some embodiments, an alkyl group has 1 carbon atom ("C1 alkyl"). Examples of C1-6 alkyl groups include methyl, ethyl, propyl, isopropyl, butyl, isobutyl, pentyl, hexyl, and the like.

As used herein, "alkenyl" refers to a radical of a straight-chain or branched hydrocarbon group having from 2 to 20 carbon atoms, one or more carbon-carbon double bonds (e.g., 1, 2, 3, or 4 carbon-carbon double bonds), and optionally one or more carbon-carbon triple bonds (e.g., 1, 2, 3, or 4 carbon-carbon triple bonds) ("C2-20 alkenyl"). In certain embodiments, alkenyl does not contain any triple bonds. In some embodiments, an alkenyl group has 2 to 10 carbon atoms ("C2-10 alkenyl"). In some embodiments, an alkenyl group has 2 to 9 carbon atoms ("C2-9 alkenyl"). In some embodiments, an alkenyl group has 2 to 8 carbon atoms ("C2-8 alkenyl"). In some embodiments, an alkenyl group has 2 to 7 carbon atoms ("C2-7 alkenyl"). In some embodiments, an alkenyl group has 2 to 6 carbon atoms ("C2-6 alkenyl"). In some embodiments, an alkenyl group has 2 to 5 carbon atoms ("C2-5 alkenyl"). In some embodiments, an alkenyl group has 2 to 4 carbon atoms ("C2-4 alkenyl"). In some embodiments, an alkenyl group has 2 to 3 carbon atoms ("C2-3 alkenyl"). In some embodiments, an alkenyl group has 2 carbon atoms ("C2 alkenyl"). The one or more carbon-carbon double bonds can be internal (such as in 2-butenyl) or terminal (such as in 1-butenyl). Examples of C2-4 alkenyl groups include ethenyl (C2), 1-propenyl (C3), 2-propenyl (C3), 1-butenyl (C4), 2-butenyl (C4), butadienyl (C4), and the like. Examples of C2-6 alkenyl groups include the aforementioned C2-4 alkenyl groups as well as pentenyl (C5), pentadienyl (C5), hexenyl (C6), and the like. Additional examples of alkenyl include heptenyl (C7), octenyl (C8), octatrienyl (C8), and the like.

As used herein, the term "aryl" refers to aromatic groups (e.g., monocyclic, bicyclic and tricyclic structures) containing six to ten carbons in the ring portion. The aryl groups may be optionally substituted through available carbon atoms and in certain embodiments may include one or more heteroatoms such as oxygen, nitrogen or sulfur. In some embodiments, an aryl group has six ring carbon atoms ("C6 aryl"; e.g., phenyl). In some embodiments, an aryl group has ten ring carbon atoms ("C10 aryl"; e.g., naphthyl such as 1-naphthyl and 2-naphthyl).

As used herein, "heteroaryl" refers to a radical of a 5-10 membered monocyclic or bicyclic 4n+2 aromatic ring system (e.g., having 6 or 10 electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

As used herein, "heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. The terms "heterocycle," "heterocyclyl," "heterocyclyl ring," "heterocyclic group," "heterocyclic moiety," and "heterocyclic radical," may be used interchangeably.

As used herein, "cyano" refers to —CN.

The terms "halo" and "halogen" as used herein refer to an atom selected from fluorine (fluoro, F), chlorine (chloro, Cl), bromine (bromo, Br), and iodine (iodo, I). In certain embodiments, the halo group is either fluoro or chloro.

The term "alkoxy," as used herein, refers to an alkyl group which is attached to another moiety via an oxygen atom (—O(alkyl)). Non-limiting examples include e.g., methoxy, ethoxy, propoxy, and butoxy.

As used herein, "oxo" refers to —C═O.

In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position.

As used herein, "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in J. Pharmaceutical Sciences (1977) 66:1-19. Pharmaceutically acceptable salts include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, ethanesulfonate, dodecylsulfate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and N+(C1-4alkyl)4 salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "composition" or "formulation" refers to a preparation which is in such form as to permit the biological activity of an active ingredient contained therein to be effective, and which contains no additional components which are unacceptably toxic to a subject to which the composition would be administered.

As used herein, "antigen" refers to any molecule that provokes an immune response or is capable of being bound by an antibody or an antigen binding molecule. The immune response may involve either antibody production, or the activation of specific immunologically-competent cells, or both. A person of skill in the art would readily understand that any macromolecule, including virtually all proteins or peptides, may serve as an antigen. An antigen may be endogenously expressed, i.e., expressed by genomic DNA, or may be recombinantly expressed. An antigen may be specific to a certain tissue, such as a cancer cell, or it may be broadly expressed. In addition, fragments of larger molecules may act as antigens. In some embodiments, antigens are tumor antigens.

As used herein, "treatment" (and variations thereof such as "treat" or "treating") refers to any administration or application of a therapeutic for disease or disorder in a subject, and includes inhibiting the disease or development of the disease (which may occur before or after the disease is formally diagnosed, e.g., in cases where a subject has a genotype that has the potential or is likely to result in development of the disease), arresting its development, relieving one or more symptoms of the disease, curing the disease, or preventing reoccurrence of one or more symptoms of the disease. As used herein, "treatment" can include administrating a therapeutic or therapeutic regimen including optional adjuvant or pre-conditioning regimen to achieve a therapeutic or prophylactic benefit. As used herein, "treatment" also encompasses "ameliorating," which refers to any beneficial effect on a phenotype or symptom, such as reducing its severity, slowing or delaying its development, arresting its development, or partially or completely reversing or eliminating it.

As used herein, "cancer" refers to a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. A "cancer" or "cancer tissue" may include a tumor. Examples of cancers that may be treated by the methods disclosed herein include, but are not limited to, cancers of the immune system including lymphoma, leukemia, myeloma, and other leukocyte malignancies. In some embodiments, the methods disclosed herein may be used to reduce the tumor size of a tumor derived from, for example, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, multiple myeloma, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, cancer of the urethra, cancer of the penis, chronic or acute leukemia, acute myeloid leukemia, chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, neoplasm of the central nervous system (CNS), primary CNS lymphoma, tumor angiogenesis, spinal axis tumor, brain stem glioma, pituitary adenoma, epidermoid cancer, squamous cell cancer, T cell lymphoma, environmentally induced cancers including those induced by asbestos, other B cell malignancies, and combinations of said cancers. In some embodiments, the methods disclosed herein may be used to reduce the tumor size of a tumor derived from, for example, sarcomas and carcinomas, fibrosarcoma, myxosarcoma, liposarcoma, chondrosarcoma, osteogenic sarcoma, Kaposi's sarcoma, sarcoma of soft tissue, and other sarcomas, synovioma, mesothelioma, Ewing's tumor, leiomyosarcoma, rhabdomyosarcoma, colon carcinoma, pancreatic cancer, breast cancer, ovarian cancer, prostate cancer, hepatocellular carcinoma, lung cancer, colorectal cancer, squamous cell carcinoma, basal cell carcinoma, adenocarcinoma (for example adenocarcinoma of the pancreas, colon, ovary, lung, breast, stomach, prostate, cervix, or esophagus), sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, carcinoma of the fallopian tubes, carcinoma of the endometrium, carcinoma of the cervix, carcinoma of the vagina, carcinoma of the vulva, carcinoma of the renal pelvis, CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma). The particular cancer may be responsive to chemo- or radiation therapy or the cancer may be refractory. A refractory cancer refers to a cancer that is not amenable to surgical intervention and the cancer is either initially unresponsive to chemo- or radiation therapy or the cancer becomes unresponsive over time.

As used herein, an "autoimmune disease" refers to a disease or disorder directed against and/or arising from a subject's own tissues and/or organs. Clinical and laboratory markers of autoimmune disease are known in the art. Exemplary markers include, but are not limited to, high levels of autoantibodies, antigen-antibody complex deposits (e.g., in the subject's tissue(s)), lymphoid cell aggregates in affected tissues, hypergammaglobulinemia. Exemplary autoimmune diseases include, but are not limited to, lupus, e.g., systemic lupus erythematosus (SLE), cutaneous lupus erythematosus (CLE), lupus nephritis (LN), antisynthetase syndrome, multifocal motor neuropathy, myasthenia gravis, neuromyelitis optica, pemphigus vulgaris, and systemic sclerosis. In some embodiments, the autoimmune disease is one that is B-cell mediated. Autoimmunity may be associated with autoantibody production, immune complex formation, dendritic cell activation, T cell activation, cytokine synthesis, and/or chemokine release. For example, SLE "is a life-threatening autoimmune disease characterized by adaptive immune system activation, formation of double-stranded DNA autoantibodies and organ inflammation." Mackensen et al., Anti-CD19 CAR T cell therapy for refractory systemic lupus erythematosus, Nature Medicine (2022). SLE may be assessed using the Systemic Lupus Erythematosus Disease Activity Index and/or DORIS criteria. Id.

An "anti-tumor effect" as used herein, refers to a biological effect that may present as a decrease in tumor volume, a decrease in the number of tumor cells, a decrease in tumor cell proliferation, a decrease in the number of metastases, an increase in overall or progression-free survival, an increase in life expectancy, or amelioration of various physiological symptoms associated with the tumor. An anti-tumor effect may also refer to the prevention of the occurrence of a tumor, e.g., a vaccine.

As used herein, the term "administering" refers to the physical introduction of an agent to a subject, using any of the various methods and delivery systems known to those skilled in the art. Exemplary routes of administration for the agents disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the agents disclosed herein may be administered via a non-parenteral route, e.g., orally. Other non-parenteral routes include a topical, epidermal, or mucosal route of administration, for example, intranasally, vaginally, rectally, sublingually or topically. The phrase "systemic injection" as used herein non-exclusively relates to intravenous, intraperitoneally, subcutaneous, via nasal submucosa, lingual, via bronchoscopy, intravenous, intra-arterial, intra-muscular, intro-ocular, intra-striatal, subcutaneous, intradermal, by dermal patch, by skin patch, by patch, into the cerebrospinal fluid, into the portal vein, into the brain, into the lymphatic system, intra-pleural, retro-orbital, intra-dermal, into the spleen, intra-lymphatic, among others.

The term "genetically engineered" or "engineered" refers to a method of modifying the genome of a cell, including, but not limited to, deleting a coding or non-coding region or a portion thereof or inserting a coding region or a portion thereof. In some embodiments, the cell that is modified is a lymphocyte, e.g., a T cell, which may either be obtained from a patient or a donor. The cell may be modified to express an exogenous construct, such as, e.g., a chimeric antigen receptor (CAR) or a T cell receptor (TCR), which is incorporated into the cell's genome.

A "cytokine," as used herein, refers to a non-antibody protein that is released by one cell in response to contact with a specific antigen, wherein the cytokine interacts with a second cell to mediate a response in the second cell. "Cytokine" as used herein is meant to refer to proteins released by one cell population that act on another cell as intercellular mediators. A cytokine may be endogenously expressed by a cell or administered to a subject. Cytokines may be released by immune cells, including macrophages, B cells, T cells, neutrophils, dendritic cells, eosinophils and mast cells to propagate an immune response. Cytokines may induce various responses in the recipient cell. Cytokines may include homeostatic cytokines, chemokines, pro-inflammatory cytokines, effectors, and acute-phase proteins. For example, homeostatic cytokines, including interleukin (IL) 7 and IL-15, promote immune cell survival and proliferation, and pro-inflammatory cytokines may promote an inflammatory response. Examples of homeostatic cytokines include, but are not limited to, IL-2, IL-4, IL-5, IL-7, IL-10, IL-12p40, IL-12p70, IL-15, and interferon (IFN) gamma. Examples of pro-inflammatory cytokines include, but are not limited to, IL-la, IL-1b, IL-6, IL-13, IL-17a, IL-23, IL-27, tumor necrosis factor (TNF)-alpha, TNF-beta, fibroblast growth factor (FGF) 2, granulocyte macrophage colony-stimulating factor (GM-CSF), soluble intercellular adhesion molecule 1 (sICAM-1), soluble vascular adhesion molecule 1 (sVCAM-1), vascular endothelial growth factor (VEGF), VEGF-C, VEGF-D, and placental growth factor (PLGF). Examples of effectors include, but are not limited to, granzyme A, granzyme B, soluble Fas ligand (sFasL), TGF-beta, IL-35, and perforin. Examples of acute phase-proteins include, but are not limited to, C-reactive protein (CRP) and serum amyloid A (SAA).

The term "lymphocyte" as used herein includes natural killer (NK) cells, T cells, or B cells. NK cells are a type of cytotoxic (cell toxic) lymphocyte that represent a major component of the innate immune system. NK cells reject tumors and cells infected by viruses. It works through the process of apoptosis or programmed cell death. They were termed "natural killers" because they do not require activation in order to kill cells. T cells play a major role in cell-mediated-immunity (no antibody involvement). T cell receptors (TCR) differentiate T cells from other lymphocyte types. The thymus, a specialized organ of the immune system, is the primary site for T cell maturation. There are numerous types of T cells, including: helper T cells (e.g., CD4+ cells), cytotoxic T cells (also known as TC, cytotoxic T lymphocytes, CTL, T-killer cells, cytolytic T cells, CD8+ T cells or killer T cells), memory T cells ((i) stem memory cells (TSCM), like naive cells, are CD45RO−, CCR7+, CD45RA+, CD62L+ (L-selectin), CD27+, CD28+ and IL-7R$_a$+, but also express large amounts of CD95, IL-2R, CXCR3, and LFA-1, and show numerous functional attributes distinctive of memory cells); (ii) central memory cells (TCM) express L-selectin and CCR7, they secrete IL-2, but not IFNγ or IL-4, and (iii) effector memory cells (TEM), however, do not express L-selectin or CCR7 but produce effector cytokines like IFNγ and IL-4), regulatory T cells (Tregs, suppressor T cells, or CD4+CD25+ or CD4+FoxP3+ regulatory T cells), natural killer T cells (NKT) and gamma delta T cells. B-cells, on the other hand, play a principal role in humoral immunity (with antibody involvement). B-cells make antibodies, are capable of acting as antigen-presenting cells (APCs), and turn into memory B-cells and plasma cells, both short-lived and long-lived, after activation by antigen interaction. In mammals, immature B-cells are formed in the bone marrow.

An "immune response" refers to the action of a cell of the immune system (for example, T lymphocytes, B lymphocytes, natural killer (NK) cells, macrophages, cosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

A "costimulatory signal," as used herein, refers to a signal, which in combination with a primary signal, such as TCR/CD3 ligation, leads to a T cell response, such as, but not limited to, proliferation and/or upregulation or down regulation of key molecules.

A "costimulatory ligand," as used herein, includes a molecule on an antigen presenting cell that specifically binds a cognate co-stimulatory molecule on a T cell. Binding of the costimulatory ligand provides a signal that mediates a T cell response, including, but not limited to, proliferation, activation, differentiation, and the like. A costimulatory ligand induces a signal that is in addition to the primary signal provided by a stimulatory molecule, for instance, by binding of a T cell receptor (TCR)/CD3 complex with a major histocompatibility complex (MHC) molecule loaded with peptide. A co-stimulatory ligand may include, but is not limited to, 3/TR6, 4-IBB ligand, agonist or antibody that binds Toll-like receptor, B7-1 (CD80), B7-2 (CD86), CD30 ligand, CD40, CD7, CD70, CD83, herpes virus entry mediator (HVEM), human leukocyte antigen G (HLA-G), ILT4, immunoglobulin-like transcript (ILT) 3, inducible costimulatory ligand (ICOS-L), intercellular adhesion molecule (ICAM), ligand that specifically binds with B7-H3, lymphotoxin beta receptor, MHC class I chain-related protein A (MICA), MHC class I chain-related protein B (MICB), OX40 ligand, PD-L2, or programmed death (PD) LI. A co-stimulatory ligand includes, without limitation, an antibody that specifically binds with a co-stimulatory molecule present on a T cell, such as, but not limited to, 4-1BB, B7-H3, CD2, CD27, CD28, CD30, CD40, CD7, ICOS, ligand that specifically binds with CD83, lymphocyte function-associated antigen-1 (LFA-1), natural killer cell receptor C (NKG2C), OX40, PD-1, or tumor necrosis factor superfamily member 14 (TNFSF14 or LIGHT).

A "costimulatory molecule" is a cognate binding partner on a T cell that specifically binds with a costimulatory ligand, thereby mediating a costimulatory response by the T cell, such as, but not limited to, proliferation. Costimulatory molecules include, but are not limited to, 4-1BB/CD137, B7-H3, BAFFR, BLAME (SLAMF8), BTLA, CD 33, CD 45, CD100 (SEMA4D), CD103, CD134, CD137, CD154, CD16, CD160 (BY55), CD 18, CD19, CD19a, CD2, CD22, CD247, CD27, CD276 (B7-H3), CD28, CD29, CD3 (alpha; beta; delta; epsilon; gamma; zeta), CD30, CD37, CD4, CD4, CD40, CD49a, CD49D, CD49f, CD5, CD64, CD69, CD7, CD80, CD83 ligand, CD84, CD86, CD8alpha, CD8beta, CD9, CD96 (Tactile), CD1-1a, CD1-1b, CD1-1c, CD1-1d, CDS, CEACAM1, CRT AM, DAP-10, DNAMI (CD226), Fc gamma receptor, GADS, GITR, HVEM (LIGHTR), IA4, ICAM-1, ICAM-1, ICOS, Ig alpha (CD79a), IL2R beta, IL2R gamma, IL7R alpha, integrin, ITGA4, ITGA4, ITGA6, IT GAD, ITGAE, ITGAL, ITGAM, ITGAX, ITGB2, ITGB7, ITGB1, KIRDS2, LAT, LFA-1, LFA-1, LIGHT, LIGHT (tumor necrosis factor superfamily member 14; TNFSF14), LTBR, Ly9 (CD229), lymphocyte function-associated antigen-1 (LFA-1 (CD11a/CD18), MHC class I molecule, NKG2C, NKG2D, NKp30, NKp44, NKp46, NKp80 (KLRF1), OX40, PAG/Cbp, PD-1, PSGL1, SELPLG (CD162), signaling lymphocytic activation molecule, SLAM (SLAMF1; CD150; IPO-3), SLAMF4 (CD244; 2B4), SLAMF6 (NTB-A; Ly108), SLAMF7, SLP-76, TNF, TNFr, TNFR2, Toll ligand receptor, TRANCE/RANKL, VLA1, or VLA-6, or fragments, truncations, or combinations thereof.

As used herein, "subject" may be a mammal, such as a primate, ungulate (e.g., cow, pig, horse), cat, dog, domestic pet or domesticated mammal. In some cases, the mammal may be a rabbit, pig, horse, sheep, cow, cat or dog, or a human. In some embodiments, the subject is a human. In some embodiments, the subject is an adult human. In some embodiments, the subject is a juvenile human.

II. Circular RNA and Compositions Thereof

Provided herein are circular RNA constructs and related pharmaceutical compositions comprising transfer vehicles, wherein the circular RNA constructs are capable of in vivo delivery to immune cells for therapy or production of proteins. According to the present disclosure, the circular RNA provided herein can be injected into an animal (e.g., a human), such that a polypeptide encoded by the circular RNA molecule is expressed inside the animal, for example by immune cells and T cells.

In certain embodiments, the circular RNA constructs comprise an IRES. In certain embodiments, the circular RNA constructs comprise at least one expression sequence encoding a binding molecule, wherein the binding molecule binds to or associates with a tumor cell antigen. In certain embodiments, the circular RNA constructs comprise an IRES and at least one expression sequence encoding a binding molecule.

In some embodiments, provided herein are circular RNA polynucleotides comprising a post splicing 3' group I intron fragment (e.g., a stretch of exon sequence), optionally a first spacer, an Internal Ribosome Entry Site (IRES), an expression sequence, optionally a second spacer, and a post splicing 5' group I intron fragment (e.g., a stretch of exon sequence). In some embodiments, these regions are in that order.

In certain embodiments, a circular RNA constructed is formulated into a pharmaceutical composition. In certain embodiments, the pharmaceutical composition comprises a transfer vehicle. In certain embodiments, a circular RNA construct comprising an IRES and at least one expression sequence encoding a binding molecule is formulated into a pharmaceutical composition comprising a transfer vehicle.

In certain embodiments, pharmaceutical compositions comprising a circular RNA construct comprising an IRES and at least one expression sequence encoding a binding molecule, and a transfer vehicle are disclosed. In certain embodiments, the transfer vehicle facilitates and/or enhances the delivery and release of circular RNA to one or more target cells.

In certain embodiments, the circular RNA constructs and related pharmaceutical compositions comprise an IRES and at least one expression sequence encoding a therapeutic protein, wherein the IRES is capable of facilitating expression of the protein when delivered in vivo.

In certain embodiments, the circular RNA constructs comprise an IRES and at least one expression sequence encoding a cytokine, immune checkpoint inhibitor, agonist, chimeric antigen receptor (CAR), inhibitory receptor agonist, one or more T-Cell Receptors, and/or B-cell Receptors.

In some embodiments, a polynucleotide encodes a protein that is made up of subunits that are encoded by more than one gene. For example, the protein may be a heterodimer, wherein each chain or subunit of the protein is encoded by a separate gene. It is possible that more than one circular RNA molecule is delivered in the transfer vehicle and each circular RNA encodes a separate subunit of the protein. Alternatively, a single circular RNA may be engineered to encode more than one subunit. In certain embodiments, separate circular RNA molecules encoding the individual subunits may be administered in separate transfer vehicles.

In certain embodiments, the circular RNA comprises an IRES and at least one expression sequence encoding a CAR construct. In some embodiments, the CAR targets a cancer antigen. In some embodiments, the CAR may be programmed to both recognize a specific antigen and, when bound to that antigen, activate the immune cell to attack and destroy the cell. In certain embodiments, the payload encoded by the circular RNA polynucleotide may be optimized through use of a specific internal ribosome entry sites (IRES) within the translation initiation element (TIE). The TIE can comprise an untranslated region (UTR), aptamer complex, or a combination thereof. The UTR can be in whole or in part from a viral or eukaryotic mRNA. In some embodiments, IRES specificity within a circular RNA can significantly enhance expression of specific proteins encoded within the coding element.

The circular RNA is produced by transcription of a DNA template that results in formation of a precursor linear RNA polynucleotide capable of circularizing. Linear precursor RNA polynucleotides are provided for producing circular RNA constructs and related pharmaceutical compositions.

The DNA template shares the same sequence as the precursor linear RNA polynucleotide prior to splicing of the precursor linear RNA polynucleotide. The DNA template shares the same sequence as the precursor linear RNA polynucleotide prior to splicing of the precursor linear RNA polynucleotide (e.g., a 3' enhanced intron element, a 3' enhanced exon element, a core functional element, and a 5' enhanced exon element, a 5' enhanced intron element). In some embodiments, said linear precursor RNA polynucleotide undergoes splicing leading to the removal of the 3' enhanced intron element and 5' enhanced intron element during the process of circularization. In some embodiments, the resulting circular RNA polynucleotide lacks a 3' enhanced intron fragment and a 5' enhanced intron fragment, but maintains a 3' enhanced exon fragment, a core functional element, and a 5' enhanced exon element. Circularization strategies are known in the art and described elsewhere herein. In certain embodiments, the resulting circular RNA can include a PIE (permuted intron-exon) region, a translation region (IRES and coding/noncoding elements), and a PIE region. The resulting permuted intron-exon (PIE) regions allow for 5' and 3' ends of the RNA to covalently link and form the circular RNA.

In some embodiments, the precursor RNA polynucleotide comprises, in the following order, (a) a terminal element; (b) an intervening region, and (c) a monotron element. In some embodiments, the terminal sequence is upstream of the monotron sequence in the precursor RNA polynucleotide. In such embodiments: (i) the terminal element comprises a splice site nucleotide, (ii) the monotron element comprises a splice site dinucleotide at or near the 5' end of the monotron, and (iii) the monotron element is capable of interacting with a nucleophile that is capable of cleaving at the splice site dinucleotide at or near the 5' end of the monotron, where the cleavage product of (iii) comprises a 5' splice site nucleotide that is capable of cleaving at the splice site nucleotide of the terminal element. In some embodiments, the nucleophile is a free nucleophile that is introduced to the precursor RNA polynucleotide, e.g., not in cis and/or covalently linked to the precursor RNA polynucleotide. In some embodiments, the nucleophile is a guanosine that is capable of cleaving at the splice site dinucleotide at or near the 5' end of the monotron. In some embodiments, the guanosine is a free guanosine that is introduced to the precursor RNA polynucleotide, e.g., not in cis and/or covalently linked to the precursor RNA polynucleotide. In some embodiments, the cleavage product of (iii) comprises a 5' splice site nucleotide having a 3' hydroxyl group that is capable of cleaving at the splice site nucleotide of the terminal element.

In some embodiments, the precursor RNA polynucleotide comprises, in the following order, (a) a monotron element; (b) an intervening region, and (c) terminal element. In some embodiments, the monotron sequence is upstream of the terminal sequence in the precursor RNA polynucleotide. In such embodiments: (i) the monotron element comprises a splice site dinucleotide at or near the 3' end of the monotron, (ii) the terminal element comprises a splice site nucleotide, and (iii) the monotron element is capable of interacting with a nucleophile that is capable of cleaving at the splice site nucleotide of the terminal element, where the cleavage product of (iii) comprises a 5' splice site nucleotide that is capable of cleaving at the splice site dinucleotide at or near the 3' end of the monotron. In some embodiments, the nucleophile is a free nucleophile that is introduced to the precursor RNA polynucleotide, e.g., not in cis and/or covalently linked to the precursor RNA polynucleotide. In some embodiments, the nucleophile is a guanosine that is capable of cleaving at the splice site nucleotide of the terminal element. In some embodiments, the guanosine is a free guanosine that is introduced to the precursor RNA polynucleotide, e.g., not in cis and/or covalently linked to the precursor RNA polynucleotide. In some embodiments, the cleavage product of (iii) comprises a 5' splice site nucleotide having a 3' hydroxyl group that is capable of cleaving at the splice site nucleotide of the terminal element.

In some embodiments, the precursor linear RNA polynucleotide circularizes when incubated in the presence of one or more guanosine nucleotides or nucleoside (e.g., GTP) and a divalent cation (e.g., $Mg^{2+}$). In some embodiments, the 3' enhanced exon element, 5' enhanced exon element, and/or core functional element in whole or in part promotes the circularization of the precursor linear RNA polynucleotide to form the circular RNA polynucleotide provided herein.

In certain embodiments circular RNA provided herein is produced inside a cell. In some embodiments, precursor RNA is transcribed using a DNA template (e.g., in some embodiments, using a vector provided herein) in the cytoplasm by a bacteriophage RNA polymerase, or in the nucleus by host RNA polymerase II and then circularized.

In certain embodiments, the circular RNA provided herein is injected into an animal (e.g., a human), such that a polypeptide encoded by the circular RNA molecule is expressed inside the animal.

In some embodiments, the DNA (e.g., vector), linear RNA (e.g., precursor RNA), and/or circular RNA polynucleotide provided herein is between 300 and 10000, 400 and 9000, 500 and 8000, 600 and 7000, 700 and 6000, 800 and 5000, 900 and 5000, 1000 and 5000, 1100 and 5000, 1200 and 5000, 1300 and 5000, 1400 and 5000, and/or 1500 and 5000 nucleotides in length. In some embodiments, the polynucleotide is at least 300 nt, 400 nt, 500 nt, 600 nt, 700 nt, 800 nt, 900 nt, 1000 nt, 1100 nt, 1200 nt, 1300 nt, 1400 nt, 1500 nt, 2000 nt, 2500 nt, 3000 nt, 3500 nt, 4000 nt, 4500 nt, or 5000 nt in length. In some embodiments, the polynucleotide is no more than 3000 nt, 3500 nt, 4000 nt, 4500 nt, 5000 nt, 6000 nt, 7000 nt, 8000 nt, 9000 nt, or 10000 nt in length. In some embodiments, the length of a DNA, linear RNA, and/or circular RNA polynucleotide provided herein is about 300 nt, 400 nt, 500 nt, 600 nt, 700 nt, 800 nt, 900 nt, 1000 nt, 1100 nt, 1200 nt, 1300 nt, 1400 nt, 1500 nt, 2000 nt, 2500 nt, 3000 nt, 3500 nt, 4000 nt, 4500 nt, 5000 nt, 6000 nt, 7000 nt, 8000 nt, 9000 nt, or 10000 nt.

In some embodiments, the circular RNA provided herein has higher functional stability than mRNA comprising the same expression sequence. In some embodiments, the circular RNA provided herein has higher functional stability than mRNA comprising the same expression sequence, modified nucleotides (e.g., 5moU modifications), an optimized UTR, a cap, and/or a polyA tail.

In some embodiments, the circular RNA polynucleotide provided herein has a functional half-life of at least 5 hours, 10 hours, 15 hours, 20 hours. 30 hours, 40 hours, 50 hours, 60 hours, 70 hours or 80 hours. In some embodiments, the circular RNA polynucleotide provided herein has a functional half-life of 5-80, 10-70, 15-60, and/or 20-50 hours. In some embodiments, the circular RNA polynucleotide provided herein has a functional half-life greater than (e.g., at least 1.5-fold greater than, at least 2-fold greater than) that of an equivalent linear RNA polynucleotide encoding the same protein. In some embodiments, functional half-life can be assessed through the detection of functional protein synthesis.

In some embodiments, the circular RNA polynucleotide provided herein has a half-life of at least 5 hours, 10 hours, 15 hours, 20 hours. 30 hours, 40 hours, 50 hours, 60 hours, 70 hours, or 80 hours. In some embodiments, the circular RNA polynucleotide provided herein has a half-life of 5-80, 10-70, 15-60, and/or 20-50 hours. In some embodiments, the circular RNA polynucleotide provided herein has a half-life greater than (e.g., at least 1.5-fold greater than, at least 2-fold greater than) that of an equivalent linear RNA polynucleotide encoding the same protein. In some embodiments, the circular RNA polynucleotide, or pharmaceutical composition thereof, has a functional half-life in a human cell greater than or equal to that of a pre-determined threshold value. In some embodiments the functional half-life is determined by a functional protein assay. For example in some embodiments, the functional half-life is determined by an in vitro luciferase assay, wherein the activity of *Gaussia* luciferase (GLuc) is measured in the media of human cells (e.g. HepG2) expressing the circular RNA polynucleotide every 1, 2, 6, 12, or 24 hours over 1, 2, 3, 4, 5, 6, 7, or 14 days. In other embodiments, the functional half-life is determined by an in vivo assay, wherein levels of a protein encoded by the expression sequence of the circular RNA polynucleotide are measured in patient serum or tissue samples every 1, 2, 6, 12, or 24 hours over 1, 2, 3, 4, 5, 6, 7, or 14 days. In some embodiments, the pre-determined threshold value is the functional half-life of a reference linear RNA polynucleotide comprising the same expression sequence as the circular RNA polynucleotide.

In some embodiments, the circular RNA provided herein may have a higher magnitude of expression than equivalent linear mRNA, e.g., a higher magnitude of expression 24 hours after administration of RNA to cells. In some embodiments, the circular RNA provided herein has a higher magnitude of expression than mRNA comprising the same expression sequence, 5moU modifications, an optimized UTR, a cap, and/or a polyA tail.

In some embodiments, the circular RNA provided herein may be less immunogenic than an equivalent mRNA when exposed to an immune system of an organism or a certain type of immune cell. In some embodiments, the circular RNA provided herein is associated with modulated production of cytokines when exposed to an immune system of an organism or a certain type of immune cell. For example, in some embodiments, the circular RNA provided herein is associated with reduced production of IFN-β1, RIG-I, IL-2, IL-6, IFNγ, and/or TNFα when exposed to an immune system of an organism or a certain type of immune cell as compared to mRNA comprising the same expression sequence. In some embodiments, the circular RNA provided herein is associated with less IFN-β1, RIG-I, IL-2, IL-6, IFNγ, and/or TNFα transcript induction when exposed to an immune system of an organism or a certain type of immune cell as compared to mRNA comprising the same expression sequence. In some embodiments, the circular RNA provided herein is less immunogenic than mRNA comprising the same expression sequence. In some embodiments, the circular RNA provided herein is less immunogenic than mRNA comprising the same expression sequence, modified nucleotides (e.g., 5moU modifications), an optimized UTR, a cap, and/or a polyA tail.

In some embodiments, the circular RNA provided herein can be encapsulated by a transfer vehicle (e.g., LNPs), which can deliver the circular RNA constructs. Encapsulating the circular RNA in the transfer vehicle, for example can efficiently introduce the CAR genes to the T cells. The transfer vehicles can comprise, e.g., ionizable lipids, PEG-modified lipids, helper lipids, and/or structural lipids, that are capable of encapsulating the circular RNAs. Pharmaceutical compositions are provided for circular RNA constructs comprising an IRES, an expression sequence, and a transfer vehicle.

In certain embodiments, the circular RNA constructs provided herein can be transfected into a cell as is or can be transfected in DNA vector form and transcribed in the cell. Transcription of circular RNA from a transfected DNA vector can be via added polymerases or polymerases encoded by nucleic acids transfected into the cell, or preferably via endogenous polymerases. Accordingly, also provided herein is a eukaryotic cell comprising a circular RNA polynucleotide provided herein. In some embodiments, the eukaryotic cell is a human cell. In some embodiments, the eukaryotic cell is an immune cell. In some embodiments, the eukaryotic cell is a T cell, dendritic cell, macrophage, B cell, neutrophil, or basophil. Also provided herein is a prokaryotic cell comprising a circular RNA polynucleotide provided herein.

In some embodiments, provided herein is a T cell, e.g., human T cell, comprising the circular RNA constructs provided herein. In some embodiments, provided herein is a helper T cell, e.g., human helper T cell, comprising the circular RNA constructs provided herein. In some embodiments, provided herein is a cytotoxic T cell, e.g., human cytotoxic T cell, comprising the circular RNA constructs provided herein. In some embodiments, provided herein is a NK cell, e.g., human NK cell, comprising the circular RNA constructs provided herein. In some embodiments, provided herein is a macrophage, e.g., human macrophage, comprising the circular RNA constructs provided herein. In some embodiments, provided herein is a monocyte, e.g., human monocyte, comprising the circular RNA constructs provided herein. In some embodiments, provided herein is a myeloid cell, human monocyte, comprising the circular RNA constructs provided herein. In some embodiments, these cells are present in the bone marrow. In some embodiments, these cells are present in the spleen. In some embodiments, these cells are present in the blood, e.g., peripheral blood.

In some embodiments, provided herein is a CD3+ cell, e.g., human CD3+ cell, comprising the circular RNA constructs provided herein. In some embodiments, provided herein is a CD4+ cell, e.g., human CD4+ cell, comprising the circular RNA constructs provided herein. In some embodiments, provided herein is a CD8+ cell, e.g., human CD8+ cell, comprising the circular RNA constructs provided herein. In some embodiments, provided herein is a CD14+ cell, e.g., human CD14+ cell, comprising the circular RNA constructs provided herein. In some embodiments, provided herein is a CD16+ cell, e.g., human CD16+ cell, comprising the circular RNA constructs provided herein. In some embodiments, provided herein is a CD56+ cell, e.g., human CD56+ cell, comprising the circular RNA constructs provided herein. In some embodiments, provided herein is a CD11B+ cell, e.g., human CD11B+ cell, comprising the circular RNA constructs provided herein. In some embodiments, provided herein is a CD33+ cell, e.g., human CD33+ cell, comprising the circular RNA constructs provided herein. In some embodiments, provided herein is a CD33+ CD14+ cell, e.g., human CD33+CD14+ cell, comprising the circular RNA constructs provided herein. In some embodiments, provided herein is a CD33+CD14+ cell, e.g., human CD33+CD64+ cell, comprising the circular RNA constructs provided herein. In some embodiments, these cells are present in the bone marrow. In some embodiments, these cells are present in the spleen. In some embodiments, these cells are present in the blood, e.g., peripheral blood.

The circular RNA can be unmodified, partially modified or completely modified. In one embodiment, the circular RNA contains at least one nucleoside modification. In one embodiment, up to 100% of the nucleosides of the circular RNA are modified. In one embodiment, at least one nucleoside modification is a uridine modification or an adenosine modification. In one embodiment, at least one nucleoside modification is selected from N6-methyladenosine (m6A), pseudouridine ($\psi$), N1-methylpseudouridine (m1$\psi$), and 5-methoxyuridine (5moU). In one embodiment, the precursor RNA is modified with methylpseudouridine (m1$\psi$).

In certain embodiments, a provided polynucleotide (e.g., a DNA template, a precursor RNA polynucleotide, or a circular RNA polynucleotide) comprises modified nucleotides and/or modified nucleosides. In some embodiments, the modified nucleoside is $m^5C$ (5-methylcytidine). In another embodiment, the modified nucleoside is $m^5U$ (5-methyluridine). In another embodiment, the modified nucleoside is $m^6A$ ($N^6$-methyladenosine). In another embodiment, the modified nucleoside is $s^2U$ (2-thiouridine). In another embodiment, the modified nucleoside is $\Psi$ (pseudouridine). In another embodiment, the modified nucleoside is Um (2'-O-methyluridine). In other embodiments, the modified nucleoside is $m^1A$ (1-methyladenosine); m2A (2-methyladenosine); Am (2'-O-methyladenosine); $ms^2 m^6A$ (2-methylthio-$N^6$-methyladenosine); $i^6A$ ($N^6$-isopentenyladenosine); $ms^2i6A$ (2-methylthio-$N^6$ isopentenyladenosine); $i^6A$ ($N^6$-(cis-hydroxyisopentenyl) adenosine); $ms^2io^6A$ (2-methylthio-$N^6$-(cis-hydroxyisopentenyl) adenosine); $g^6A$ ($N^6$-glycinylcarbamoyladenosine); $t^6A$ ($N^6$-threonylcarbamoyladenosine); $ms^2t^6A$ (2-methylthio-$N^6$-threonyl carbamoyladenosine); $m^6t^6A$ (N6-methyl-N-threonylcarbamoyladenosine); $hn^6A$ ($N^6$-hydroxynorvalylcarbamoyladenosine); $ms^2hn^6$ A (2-methylthio-$N^6$-hydroxynorvalyl carbamoyladenosine); Ar(p) (2'-O-ribosyladenosine (phosphate)); I (inosine); $m^1I$ (1-methylinosine); $m^1Im$ (1,2'-O-dimethylinosine); $m^3C$ (3-methylcytidine); Cm (2'-O-methylcytidine); $s^2C$ (2-thio-cytidine); $ac^4C$ ($N^4$-acetylcytidine); $f^5C$ (5-formylcytidine); $m^5Cm$ (5,2'-O-dimethylcytidine); $ac^4Cm$ ($N^4$-acetyl-2'-O-methylcytidine); $k^2C$ (lysidine); $m^1G$ (1-methylguanosine); $m^2G$ ($N^2$-methylguanosine); $m^7G$ (7-methylguanosine); Gm (2'-O-methylguanosine); $m^2_2G$ ($N^2,N^2$-dimethylguanosine); $m^2Gm$ (N2,2'-O-dimethylguanosine); $m^2_2Gm$ ($N^2,N^2$, 2'-O-trimethylguanosine); Gr(p) (2'-O-ribosylguanosine (phosphate)); yW (wybutosine); $o_2yW$ (peroxywybutosine); OHyW (hydroxywybutosine); OHyW* (undermodified hydroxywybutosine); imG (wyosine); mimG (methylwyosine); Q (queuosine); oQ (epoxyqueuosine); galQ (galactosyl-queuosine); manQ (mannosyl-queuosine); $preQ_0$ (7-cyano-7-deazaguanosine); $preQ_1$ (7-aminomethyl-7-deazaguanosine); G' (archaeosine); D (dihydrouridine); $m^5Um$ (5,2'-O-dimethyluridine); $s^4U$ (4-thiouridine); $m^5s^2U$ (5-methyl-2-thiouridine); $s^2Um$ (2-thio-2'-O-methyluridine); $acp^3U$ (3-(3-amino-3-carboxypropyl) uridine); $ho^5U$ (5-hydroxyuridine); $mo^5U$ (5-methoxyuridine); $cmo^5U$ (uridine 5-oxyacetic acid); $memo^5U$ (uridine 5-oxyacetic acid methyl ester); $chm^5U$ (5-(carboxyhydroxymethyl) uridine)); $mchm^5U$ (5-(carboxyhydroxymethyl) uridine methyl ester); $mcm^5U$ (5-methoxycarbonylmethyluridine); $mcm^5Um$ (5-methoxycarbonylmethyl-2'-O-methyluridine); $mcm^5s^2U$ (5-methoxycarbonylmethyl-2-thiouridine); $nm^5S^2U$ (5-aminomethyl-2-thiouridine); $mnm^5U$ (5-methylaminomethyluridine); $mnm^5s^2U$ (5-methylaminomethyl-2-thiouridine); $mnm^5sc^2U$ (5-methylaminomethyl-2-selenouridine);

$ncm^5U$ (5-carbamoylmethyluridine); $ncm^5Um$ (5-carbamoylmethyl-2'-O-methyluridine); $cmnm^3U$ (5-carboxymethylaminomethyluridine); $cmnm^5Um$ (5-carboxymethylaminomethyl-2'-O-methyluridine); $cmnm^5s^2U$ (5-carboxymethylaminomethyl-2-thiouridine); $m^6_2A$ ($N^6$, $N^6$-dimethyladenosine); Im (2'-O-methylinosine); $m^4C$ ($N^4$-methylcytidine); $m^4Cm$ ($N^4$,2'-O-dimethylcytidine); $hm^5C$ (5-hydroxymethylcytidine); $m^3U$ (3-methyluridine); $cm^5U$ (5-carboxymethyluridine); $m^6Am$ ($N^6$,2'-O-dimethyladenosine); $m^6_2Am$ ($N^6,N^6$,O-2'-trimethyladenosine); $m^{2,7}G$ ($N^2$,7-dimethylguanosine); $m^{2,2,7}G$ ($N^2,N^2$,7-trimethylguanosine); $m^3Um$ (3,2'-O-dimethyluridine); $m^5D$ (5-methyldihydrouridine); $f^5Cm$ (5-formyl-2'-O-methylcytidine); $m^1Gm$ (1,2'-O-dimethylguanosine); $m^1Am$ (1,2'-O-dimethyladenosine); $\tau m^5U$ (5-taurinomethyluridine); $\tau m^5 s^2U$ (5-taurinomethyl-2-thiouridine)); imG-14 (4-demethylwyosine); imG2 (isowyosine); or $ac^6A$ ($N^6$-acetyladenosine).

In some embodiments, the modified nucleoside may include a compound selected from the group of: pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-m ethoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2, 6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl) adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine. In another embodiment, the modifications are independently selected from the group consisting of 5-methylcytosine, pseudouridine and 1-methylpseudouridine.

In some embodiments, the modified ribonucleosides include 5-methylcytidine, 5-methoxyuridine, 1-methyl-pseudouridine, N6-methyladenosine, and/or pseudouridine. In some embodiments, such modified nucleosides provide additional stability and resistance to immune activation.

Various circular RNA, circular RNA constructs, compositions comprising circular RNA, precursor RNA, and related methods are described, for example in WO2019236673, WO2020237227, WO2021113777, WO2021226597, WO2021189059, WO2021236855, WO2022261490, WO2023056033, and WO2023081526, which are each incorporated by reference in their entireties.

A. Enhanced Intron Elements and Enhanced Exon Elements

The circular RNA provided herein can comprise an enhanced intron element or fragment and enhanced exon element or fragment. In certain embodiments, as provided herein, the enhanced intron elements and enhanced exon elements may comprise spacers, duplex regions, affinity sequences, intron fragments, exon fragments and various untranslated elements. These sequences within the enhanced intron elements or enhanced exon elements are arranged to optimize circularization or protein expression.

In certain embodiments, the DNA template, precursor linear RNA polynucleotide and circular RNA provided herein comprise a first (5') and/or a second (3') spacer. In some embodiments, the DNA template or precursor linear RNA polynucleotide comprises one or more spacers in the enhanced intron elements. In some embodiments, the DNA template, precursor linear RNA polynucleotide comprises one or more spacers in the enhanced exon elements. In certain embodiments, the DNA template or linear RNA polynucleotide comprises a spacer in the 3' enhanced intron fragment and a spacer in the 5' enhanced intron fragment. In certain embodiments, DNA template, precursor linear RNA polynucleotide, or circular RNA comprises a spacer in the 3' enhanced exon fragment and another spacer in the 5' enhanced exon fragment to aid with circularization or protein expression due to symmetry created in the overall sequence.

In some embodiments, including a spacer between the 3' group I intron fragment and the core functional element may conserve secondary structures in those regions by preventing them from interacting, thus increasing splicing efficiency. In some embodiments, the first (between 3' group I intron fragment and core functional element) and second (between the two expression sequences and core functional element) spacers comprise additional base pairing regions that are predicted to base pair with each other and not to the first and second duplex regions. In other embodiments, the first (between 3' group I intron fragment and core functional element) and second (between the one of the core functional element and 5' group I intron fragment) spacers comprise additional base pairing regions that are predicted to base pair with each other and not to the first and second duplex regions. In some embodiments, such spacer base pairing brings the group I intron fragments in close proximity to each other, further increasing splicing efficiency. Additionally, in some embodiments, the combination of base pairing between the first and second duplex regions, and separately, base pairing between the first and second spacers, promotes the formation of a splicing bubble containing the group I intron fragments flanked by adjacent regions of base pairing. Typical spacers are contiguous sequences with one or more of the following qualities: 1) predicted to avoid interfering with proximal structures, for example, the IRES, expression sequence, aptamer, or intron; 2) is at least 7 nt long and no longer than 100 nt; 3) is located after and adjacent to the 3' intron fragment and/or before and adjacent to the 5' intron fragment; and 4) contains one or more of the following: a) an unstructured region at least 5 nt long, b) a region of base pairing at least 5 nt long to a distal sequence, including another spacer, and c) a structured region at least 7 nt long limited in scope to the sequence of the spacer. Spacers may have several regions, including an unstructured region, a base pairing region, a hairpin/structured region, and combinations thereof. In an embodiment, the spacer has a structured region with high GC content. In an embodiment, a region within a spacer base pairs with another region within the same spacer. In an embodiment, a region within a spacer base pairs with a region within another spacer. In an embodiment, a spacer comprises one or more hairpin structures. In an embodiment, a spacer comprises one or more hairpin structures with a stem of 4 to 12 nucleotides and a loop of 2 to 10 nucleotides. In an embodiment, there is an additional spacer between the 3' group I intron fragment and the core functional element. In an embodiment, this additional spacer prevents the structured regions of the IRES or aptamer of a TIE from interfering with the folding of the 3' group I intron fragment or reduces the extent to which this occurs. In some embodiments, the 5' spacer sequence is at least 7, 8, 9, 10, 11, 12, 13, 14, 15, 16, 17, 18, 19, 20, 25 or 30 nucleotides in length. In some embodiments, the 5' spacer sequence is no more than 100, 90, 80, 70, 60, 50, 45, 40, 35 or 30 nucleotides in length. In some embodiments the 5' spacer sequence is between 5 and 50, 10 and 50, 20 and 50, 20 and 40, and/or 25 and 35 nucleotides in length. In certain embodiments, the 5' spacer sequence is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides in length. In one embodiment, the 5' spacer sequence is a polyA sequence. In another embodiment, the 5' spacer sequence is a polyAC sequence. In one embodiment, a spacer comprises about 10%, 20%, 30%, 40%, 50%, 60%, 70%, 80%, 90%, or 100% polyAC content. In one embodiment, a spacer comprises about 10%, 20%, 30%, 40%, 50%, 60%, 70%, 80%, 90%, or 100% polypyrimidine (C/T or C/U) content.

In some embodiments, the DNA template and precursor linear RNA polynucleotides and circular RNA polynucleotide provided herein comprise a first (5') duplex region and a second (3') duplex region. In certain embodiments, the DNA template and precursor linear RNA polynucleotide comprises a 5' external duplex region located within the 3' enhanced intron fragment and a 3' external duplex region located within the 5' enhanced intron fragment. In some embodiments, the DNA template, precursor linear RNA polynucleotide and circular RNA polynucleotide comprise a 5' internal duplex region located within the 3' enhanced exon fragment and a 3' internal duplex region located within the 5' enhanced exon fragment. In some embodiments, the DNA polynucleotide and precursor linear RNA polynucleotide comprises a 5' external duplex region, 5' internal duplex region, a 3' internal duplex region, and a 3' external duplex region.

In certain embodiments, the first and second duplex regions may form perfect or imperfect duplexes. Thus, in certain embodiments at least 75%, 80%, 85%, 90%, 91%, 92%, 93%, 94%, 95%, 96%, 97%, 98%, 99% or 100% of the first and second duplex regions may be base paired with one another. In some embodiments, the duplex regions are predicted to have less than 50% (e.g., less than 45%, less than 40%, less than 35%, less than 30%, less than 25%) base pairing with unintended sequences in the RNA (e.g., non-duplex region sequences). In some embodiments, including such duplex regions on the ends of the precursor RNA strand, and adjacent or very close to the group I intron fragment, bring the group I intron fragments in close proximity to each other, increasing splicing efficiency. In some embodiments, the duplex regions are 3 to 100 nucleotides in length (e.g., 3-75 nucleotides in length, 3-50 nucleotides in length, 20-50 nucleotides in length, 35-50 nucleotides in length, 5-25 nucleotides in length, 9-19 nucleotides in length). In some embodiments, the duplex regions are about 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides in length. In some embodiments, the duplex regions have a length of about 9 to about 50 nucleotides. In one embodiment, the duplex regions have a length of about 9 to about 19 nucleotides. In some embodiments, the duplex regions have a length of about 20 to about 40 nucleotides. In certain embodiments, the duplex regions have a length of about 30 nucleotides.

In other embodiments, the DNA template, precursor linear RNA polynucleotide, or circular RNA polynucleotide does not comprise of any duplex regions to optimize translation or circularization.

In certain embodiments, as provided herein, the DNA template or precursor linear RNA polynucleotide may comprise an affinity tag. In some embodiments, the affinity tag is located in the 3' enhanced intron element. In some embodiments, the affinity tag is located in the 5' enhanced intron element. In some embodiments, both (3' and 5') enhanced intron elements each comprise an affinity tag. In one embodiment, an affinity tag of the 3' enhanced intron element is the length as an affinity tag in the 5' enhanced intron element. In some embodiments, an affinity tag of the 3' enhanced intron element is the same sequence as an affinity tag in the 5' enhanced intron element. In some embodiments, the affinity sequence is placed to optimize oligo-dT purification.

In some embodiments, the one or more affinity tags present in a precursor linear RNA polynucleotide are removed upon circularization. In some embodiments, affinity tags are added to remaining linear RNA after circularization of RNA is performed. In some such embodiments, the affinity tags are added enzymatically to linear RNA. The presence of one or more affinity tags in linear RNA and their absence from circular RNA can facilitate purification of circular RNA. In some embodiments, such purification is performed using a negative selection or affinity-purification method. In some embodiments, such purification is performed using a binding agent that preferentially or specifically binds to the affinity tag.

In some embodiments, an affinity tag comprises a polyA region. In some embodiments the polyA region is at least 15, 30, or 60 nucleotides long. In some embodiments, the affinity tag comprising a polyA region is present in two places in a precursor linear RNA. In some embodiments, one or both polyA regions is 15-50 nucleotides long. In some embodiments, one or both polyA regions is 20-25 nucleotides long. The polyA sequence(s) is removed upon circularization. Thus, an oligonucleotide hybridizing with the polyA sequence, such as a deoxythymidine oligonucleotide (oligo (dT)) conjugated to a solid surface (e.g., a resin), can be used to separate circular RNA from its precursor RNA.

In some embodiments, an affinity tag comprises a sequence that is absent from the circular RNA product. In some such embodiments, the sequence that is absent from the circular RNA product is a dedicated binding site (DBS). In some embodiments, the DBS is an unstructured sequence, i.e., a sequence that does not form a defined structural element, such as a hairpin loop, contiguous dsRNA region, or triple helix. In some embodiments, the DBS sequence forms a random coil. In some embodiments, the DBS comprises at least 25% GC content, at least 50% GC content, at least 75% GC content, or at least 100% GC content. In some embodiments, the DBS comprises at least 25% AC content, at least 50% AC content, at least 75% AC content, or 100% AC content. In some embodiments, the DBS is at least 15, 30, or 60 nucleotides long. In some embodiments, the affinity tag comprising a DBS is present in two places in a precursor linear RNA. In some embodiments, the DBS sequences are each independently 15-50 nucleotides long. In some embodiments, the DBS sequences are each independently 20-25 nucleotides long.

In some embodiments, the DBS sequence(s) is removed upon circularization. Thus, binding agents comprising oligonucleotides comprising a sequence that is complementary to the DBS can be used to facilitate purification of circular RNA. For example, the binding agent may comprise an oligonucleotide complementary to a DBS conjugated to a solid surface (e.g., a resin).

In some embodiments, an affinity sequence or other type of affinity handle, such as biotin, is added to linear RNA by ligation. In some embodiments, an oligonucleotide comprising an affinity sequence is ligated to the linear RNA. In some embodiments, an oligonucleotide conjugated to an affinity handle is ligated to the linear RNA. In some embodiments, a solution comprising the linear RNA ligated to the affinity sequence or handle and the circular RNA that does not comprise an affinity sequence or handle are contacted with a binding agent comprising a solid support conjugated to an oligonucleotide complementary to the affinity sequence or to a binding partner of the affinity handle, such that the linear RNA binds to the binding agent, and the circular RNA is eluted or separated from the solid support.

Any purification method for circular RNA described herein may comprise one or more buffer exchange steps. In some embodiments, buffer exchange is performed after in vitro transcription (IVT) and before additional purification steps. In some such embodiments, the IVT reaction solution is buffer exchanged into a buffer comprising Tris. In some embodiments, the IVT reaction solution is buffer exchanged into a buffer comprising greater than 1 mM or greater than 10 mM one or more monovalent salts, such as NaCl or KCl, and optionally comprising EDTA. In some embodiments, buffer exchange is performed after purification of circular RNA is complete. In some embodiments, buffer exchange is performed after IVT and after purification of circular RNA. In some embodiments, the buffer exchange that is performed after purification of circular RNA comprises exchange of the circular RNA into water or storage buffer. In some embodiments, the storage buffer comprises 1 mM sodium citrate, pH 6.5.

In certain embodiments, the 3' enhanced intron element comprises a leading untranslated sequence. In some embodiments, the leading untranslated sequence is a the 5' end of the 3' enhanced intron fragment. In some embodiments, the leading untranslated sequence comprises of the last nucleotide of a transcription start site (TSS). In some embodiments, the TSS is chosen from a viral, bacterial, or eukaryotic DNA template. In one embodiment, the leading untranslated sequence comprise the last nucleotide of a TSS and 0 to 100 additional nucleotides. In some embodiments, the TSS is a terminal spacer. In one embodiment, the leading untranslated sequence contains a guanosine at the 5' end upon translation of an RNA T7 polymerase.

In certain embodiments, the 5' enhanced intron element comprises a trailing untranslated sequence. In some embodiments, the 5' trailing untranslated sequence is located at the 3' end of the 5' enhanced intron element. In some embodiments, the trailing untranslated sequence is a partial restriction digest sequence. In one embodiment, the trailing untranslated sequence is in whole or in part a restriction digest site used to linearize the DNA template. In some embodiments, the restriction digest site is in whole or in part from a natural viral, bacterial or eukaryotic DNA template. In some embodiments, the trailing untranslated sequence is a terminal restriction site fragment.

1. Enhanced Intron Fragments

In certain embodiments, as provided herein, the 3' enhanced intron element and 5' enhanced intron element each comprise an intron fragment. In certain embodiments, a 3' intron fragment is a contiguous sequence at least 75% homologous (e.g., at least 80%, 85%, 90%, 91%, 92%, 93%, 94%, 95%, 96%, 97%, 98%, 99% or 100% homologous) to a 3' proximal fragment of a natural group I intron including the 3' splice site dinucleotide. Typically, a 5' intron fragment is a contiguous sequence at least 75% homologous (e.g., at least 80%, 85%, 90%, 91%, 92%, 93%, 94%, 95%, 96%, 97%, 98%, 99% or 100% homologous) to a 5' proximal fragment of a natural group I intron including the 5' splice site dinucleotide. In some embodiments, the 3' intron fragment includes the first nucleotide of a 3' group I splice site dinucleotide. In some embodiments, the 5' intron fragment includes the first nucleotide of a 5' group I splice site dinucleotide. In other embodiments, the 3' intron fragment includes the first and second nucleotides of a 3' group I intron fragment splice site dinucleotide; and the 5' intron fragment includes the first and second nucleotides of a 3' group I intron fragment dinucleotide.

2. Enhanced Exon Fragments

In certain embodiments, as provided herein, the DNA template, linear precursor RNA polynucleotide, and circular RNA polynucleotide each comprise an enhanced exon fragment. In some embodiments, following a 5' to 3' order, the 3' enhanced exon element is located upstream to core functional element. In some embodiments, following a 5' to 3' order, the 5' enhanced intron element is located downstream to the core functional element.

According to the present disclosure, the 3' enhanced exon element and 5' enhanced exon element each comprise an exon fragment. In some embodiments, the 3' enhanced exon element comprises a 3' exon fragment. In some embodiments, the 5' enhanced exon element comprises a 5' exon fragment. In certain embodiments, as provided herein, the 3' exon fragment and 5' exon fragment each comprises a group I intron fragment and 1 to 100 nucleotides of an exon sequence. In certain embodiments, a 3' intron fragment is a contiguous sequence at least 75% homologous (e.g., at least 80%, 85%, 90%, 91%, 92%, 93%, 94%, 95%, 96%, 97%, 98%, 99% or 100% homologous) to a 3' proximal fragment of a natural group I intron including the 3' splice site dinucleotide. Typically, a 5' group I intron fragment is a contiguous sequence at least 75% homologous (e.g., at least 80%, 85%, 90%, 91%, 92%, 93%, 94%, 95%, 96%, 97%, 98%, 99% or 100% homologous) to a 5' proximal fragment of a natural group I intron including the 5' splice site dinucleotide. In some embodiments, the 3' exon fragment comprises a second nucleotide of a 3' group I intron splice site dinucleotide and 1 to 100 nucleotides of an exon sequence. In some embodiments, the 5' exon fragment comprises the first nucleotide of a 5' group I intron splice site dinucleotide and 1 to 100 nucleotides of an exon sequence.

In some embodiments, the exon sequence comprises in part or in whole from a naturally occurring exon sequence from a virus, bacterium or eukaryotic DNA vector. In other embodiments, the exon sequence further comprises a synthetic, genetically modified (e.g., containing modified nucleotide), or other engineered exon sequence.

In one embodiment, where the 3' intron fragment comprises both nucleotides of a 3' group I splice site dinucleotide and the 5' intron fragment comprises both nucleotides of a 5' group I splice site dinucleotide, the exon fragments located within the 5' enhanced exon element and 3' enhanced exon element does not comprise of a group I splice site dinucleotide.

3. Exemplary Permutation of the Enhanced Intron Elements & Enhanced Exon Elements For means of example and not intended to be limiting, in some embodiment, a 3' enhanced intron element comprises in the following 5' to 3' order: a leading untranslated sequence, a 5' affinity tag, an optional 5' external duplex region, a 5' external spacer, and a 3' intron fragment. In the same embodiments, the 3' enhanced exon element comprises in the following 5' to 3' order: a 3' exon fragment, an optional 5' internal duplex region, an optional 5' internal duplex region, and a 5' internal spacer. In the same embodiments, the 5' enhanced exon element comprises in the following 5' to 3' order: a 3' internal spacer, an optional 3' internal duplex region, and a 5' exon fragment. In still the same embodiments, the 3' enhanced intron element comprises in the following 5' to 3' order: a 5' intron fragment, a 3' external spacer, an optional 3' external duplex region, a 3' affinity tag, and a trailing untranslated sequence.

B. Core Functional Element-IRES

In some embodiments, the DNA template, linear precursor RNA polynucleotide, and circular RNA polynucleotide comprise a core functional element. In some embodiments, the core functional element comprises a coding and/or noncoding element. In some embodiments, the core functional element further comprises a translation initiation element (TIE) upstream to the coding or noncoding element, and/or a termination element.

In some embodiments, the core functional element comprises a termination element. In some embodiments, the termination sequence comprises a stop codon. In one embodiment, the termination sequence comprises a stop cassette. In some embodiments, the stop cassette comprises at least 2 stop codons. In some embodiments, the stop cassette comprises at least 2 frames of stop codons. In the same embodiment, the frames of the stop codons in a stop cassette each comprise 1, 2 or more stop codons. In some embodiments, the stop cassette comprises a LoxP or a RoxStopRox, or fit-flanked stop cassette. In the same embodiment, the stop cassette comprises a lox-stop-lox stop cassette.

In some embodiments, the polynucleotides herein comprise a coding or noncoding element or a combination of both. In some embodiments, the coding element comprises an expression sequence. In some embodiments, the coding element encodes at least one therapeutic protein. In some embodiments, the circular RNA encodes two or more polypeptides.

In some embodiments, the core functional element comprises at least one translation initiation element (TIE). TIEs are designed to allow translation efficiency of an encoded protein. In some embodiments, core functional elements comprising one or more coding elements will further comprise one or more TIEs. In some embodiments, a translation initiation element (TIE) comprises a synthetic TIE. In some embodiments, a synthetic TIE comprises aptamer complexes, synthetic IRES or other engineered TIES capable of initiating translation of a linear RNA or circular RNA polynucleotide.

In some embodiments, a TIE comprises an untranslated region (UTR) or a fragment thereof, an aptamer complex or a fragment thereof, or a combination thereof. In certain embodiments, the TIE contains modified nucleotides. In certain embodiments, the TIE provided herein comprise an internal ribosome entry site (IRES). In certain embodiments, the IRES comprises one or more modified nucleotides compared to the wile-type viral IRES or eukaryotic IRES. See, e.g., WO2022/261490, which is incorporated herein by reference in its entirety.

Since the discovery of viral IRESes, there have been difficulties in their classification due to their dissimilarity. It has been observed that there is no common mechanism for functioning of all IRESes. Additionally, no particular structure element has been found that is shared by all IRESes; their sequences lack significant homology. See Nikonov, Biochemistry (Moscow), 2017, Vol. 82, No. 13, pp. 1615-1631. According to one author, four IRES classes have been defined. Type I and II IRESes are found in picornaviruses and can be around 400-500nt long. Type III IRESes concern the Flaviviridae (including HCV) and HCV-like picornaviruses and are characterized by the presence of a pseudoknot upstream from the AUG codon and by the requirement of the first 30nt of the coding sequence. Type IV IRESes are intergenic region (IGR) IRESes, originally identified in cricket paralysis virus (CrPV), which can function in the absence of any start codon and where translation starts at a GCU triplet. See Godet, Int. J. Mol. Sci. 2019, 20, 924; doi: 10.3390/ijms20040924.

Inclusion of an IRES permits the translation of one or more open reading frames from a circular RNA (e.g., open reading frames that form the expression sequences). The IRES element attracts a eukaryotic ribosomal translation initiation complex and promotes translation initiation. See, e.g., Kaufman et al., Nuc. Acids Res. (1991) 19:4485-4490; Gurtu et al., Biochem. Biophys. Res. Comm. (1996) 229: 295-298; Rees et al., BioTechniques (1996) 20:102-110; Kobayashi et al., BioTechniques (1996) 21:399-402; and Mosser et al., BioTechniques 1997 22 150-161. In some embodiments, the IRES is capable of facilitating expression of a protein encoded by the precursor RNA in a cell. In some embodiments, the IRES is capable of facilitating expression of the protein, such that the expression level of the protein is comparable to or higher than when a control IRES is used.

A multitude of IRES sequences are available and include sequences derived from a wide variety of viruses, such as from leader sequences of picornaviruses such as the encephalomyocarditis virus (EMCV) UTR (Jang et al., J. Virol. (1989) 63:1651-1660), the polio leader sequence, the hepatitis A virus leader, the hepatitis C virus IRES, human rhinovirus type 2 IRES (Dobrikova et al., Proc. Natl. Acad. Sci. (2003) 100 (25): 15125-15130), an IRES element from the foot and mouth disease virus (Ramesh et al., Nucl. Acid Res. (1996) 24:2697-2700), a giardiavirus IRES (Garlapati et al., J. Biol. Chem. (2004) 279 (5): 3389-3397), and the like. Different IRES sequences have varying ability to drive protein expression, and the ability of any particular identified or predicted IRES sequence to drive protein expression from linear mRNA or circular RNA constructs is unknown and unpredictable. In certain embodiments, potential IRES sequences can be bioinformatically identified based on sequence positions in viral sequences. However, the activity of such sequences has been previously uncharacterized. As demonstrated herein, such IRES sequences may have differing protein expression capability depending on cell type, for example in T cells, liver cells, or muscle cells. In some embodiments, the novel IRES sequences described herein may have at least 2, 3, 4, 5, 6, 7, 8, 9, 10, 20, 50, or 100 fold increased expression in a particular cell type compared to previously described EMCV IRES sequences.

In some embodiments, the IRES is an Aalivirus, Ailurivirus, Ampivirus, Anativirus, Aphthovirus, Aquamavirus, Avihepatovirus, Avisivirus, Boosepivirus, Bopivirus, Caccilivirus, Cardiovirus, Cosavirus, Crahelivirus, Crohivirus, Danipivirus, Dicipivirus, Diresapivirus, Enterovirus, Erbovirus, Felipivirus, Fipivirus, Gallivirus, Gruhelivirus, Grusopivirus, Harkavirus, Hemipivirus, Hepatovirus, Hunnivirus, Kobuvirus, Kunsagivirus, Limnipivirus, Livupivirus, Ludopivirus, Malagasivirus, Marsupivirus, Megrivirus, Mischivirus, Mosavirus, Mupivirus, Myrropivirus, Orivirus, Oscivirus, Parabovirus, Parechovirus, Pasivirus, Passerivirus, Pemapivirus, Poecivirus, Potamipivirus, Pygoscepivirus, Rabovirus, Rafivirus, Rajidapivirus, Rohelivirus, Rosavirus, Sakobuvirus, Salivirus, Sapelovirus, Senecavirus, Shanbavirus, Sicinivirus, Symapivirus, Teschovirus, Torchivirus, Tottorivirus, Tremovirus, Tropivirus, Hepacivirus, Pegivirus, Pestivirus, Flavivirus IRES. In some embodiments herein, the IRES is selected from an Enterovirus, Kobuvirus, Parechovirus, Hunnivirus, Passerivirus, Mischivirus, and Cardiovirus.

In some embodiments, the IRES is an IRES sequence of Taura syndrome virus, *Triatoma* virus, Theiler's encephalomyelitis virus, Simian Virus 40, *Solenopsis invicta* virus 1, *Rhopalosiphum padi* virus, Reticuloendotheliosis virus, Human poliovirus 1, *Plautia stali* intestine virus, Kashmir bee virus, Human rhinovirus 2, Homalodisca coagulata virus-1, Human Immunodeficiency Virus type 1, Himetobi P virus, Hepatitis C virus, Hepatitis A virus, Hepatitis GB virus, Foot and mouth disease virus, Human enterovirus 71, Equine rhinitis virus, Ectropis obliqua picoma-like virus, Encephalomyocarditis virus, *Drosophila* C Virus, Human coxsackievirus B3, Crucifer tobamovirus, Cricket paralysis virus, Bovine viral diarrhea virus 1, Black Queen Cell Virus, Aphid lethal paralysis virus, Avian encephalomyelitis virus, Acute bee paralysis virus, Hibiscus chlorotic ringspot virus, Classical swine fever virus, Human FGF2, Human SFTPAI, Human AMLI/RUNX1, *Drosophila* antennapedia, Human AQP4, Human ATIR, Human BAG-1, Human BCL2, Human BiP, Human c-IAPI, Human c-myc, Human eIF4G, Mouse NDST4L, Human LEF1, Mouse HIFI alpha, Human n.myc, Mouse Gtx, Human p27kipl, Human PDGF2/c-sis, Human p53, Human Pim-1, Mouse Rbm3, *Drosophila* reaper, Canine Scamper, *Drosophila* Ubx, Human UNR, Mouse UtrA, Human VEGF-A, Human XIAP, *Drosophila* hairless, *S. cerevisiae* TFIID, *S. cerevisiae* YAPI, tobacco etch virus, turnip crinkle virus, EMCV-A, EMCV-B, EMCV-Bf, EMCV-Cf, EMCV pEC9, Picobirnavirus, HCV QC64, Human Cosavirus E/D, Human Cosavirus F, Human Cosavirus JMY, Rhinovirus NAT001, HRV14, HRV89, HRVC-02, HRV-A21, Salivirus A SHI, Salivirus FHB, Salivirus NG-JI, Human Parechovirus 1, Crohivirus B, Yc-3, Rosavirus M-7, Shanbavirus A, Pasivirus A, Pasivirus A 2, Echovirus E14, Human Parechovirus 5, Aichi Virus, Hepatitis A Virus HA16, Phopivirus, CVA10, Enterovirus C, Enterovirus D, Enterovirus J, Human Pegivirus 2, GBV-C GT110, GBV-C K1737, GBV-C Iowa, Pegivirus A 1220, Pasivirus A 3, Sapelovirus, Rosavirus B, Bakunsa Virus, Tremovirus A, Swine Pasivirus 1, PLV-CHN, Pasivirus A, Sicinivirus, Hepacivirus K, Hepacivirus A, BVDV1, Border Disease Virus, BVDV2, CSFV-PK15C, SF573 Dicistrovirus, Hubei Picorna-like Virus, CRPV, Salivirus A BN5, Salivirus A BN2, Salivirus A 02394, Salivirus A GUT, Salivirus A CH, Salivirus A SZ1, Salivirus FHB, CVB3, CVB1, Echovirus 7, CVB5, EVA71, CVA3, CVA12, EV24 or an aptamer to eIF4G.

In some embodiments, the IRES comprises in whole or in part a eukaryotic or cellular IRES. In certain embodiments, the IRES is from a human gene, where the human gene is ABCF1, ABCG1, ACAD10, ACOT7, ACSS3, ACTG2, ADCYAP1, ADK, AGTR1, AHCYL2, AHI1, AKAP8L, AKRIA1, ALDH3A1, ALDOA, ALG13, AMMECR1L, ANGPTL4, ANK3, AOC3, AP4B1, AP4E1, APAF1, APBB1, APC, APH1A, APOBEC3D, APOM, APP, AQP4, ARHGAP36, ARL13B, ARMC8, ARMCX6, ARPC1A, ARPC2, ARRDC3, ASAPI, ASB3, ASB5, ASCL1, ASMTL, ATF2, ATF3, ATG4A, ATP5B, ATP6V0A1, ATXN3, AURKA, AURKA, AURKA, AURKA, B3GALNT1, B3GNTL1, B4GALT3, BAAT, BAG1, BAIAP2, BAIAP2L2, BAZ2A, BBX, BCAR1, BCL2, BCSIL, BET1, BID, BIRC2, BPGM, BPIFA2, BRINP2, BSG, BTN3A2, C12orf43, C14orf93, C17orf62, C1orf226, C21orf62, C2orf15, C4BPB, C4orf22, C9orf84, CACNAIA, CAL-COCO2, CAPN11, CASP12, CASP8AP2, CAVI, CBX5, CCDC120, CCDCl7, CCDCl86, CCDC51, CCNI, CCND1, CCNTI, CD2BP2, CD9, CDC25C, CDC42, CDC7, CDCA7L, CDIPI, CDKI, CDKIIA, CDKNIB, CEACAM7, CEP295NL, CFLAR, CHCHD7, CHIA, CHICI, CHMP2A, CHRNA2, CLCN3, CLEC12A, CLEC7A, CLECL1, CLRN1, CMSS1, CNIH1, CNR1, CNTN5, COG4, COMMD1, COMMD5, CPEB1, CPS1, CRACR2B, CRBN, CREM, CRYBG1, CSDE1, CSF2RA, CSNK2A1, CSTF3, CTCFL, CTH, CTNNA3, CINNB1, CTNNB1, CTNND1, CTSL, CUTA, CXCR5, CYB5R3, CYP24A1, CYP3A5, DAGI, DAP3, DAP5, DAXX, DCAF4, DCAF7, DCLRE1A, DCP1A, DCTN1, DCTN2, DDX19B, DDX46, DEFB123, DGKA, DGKD, DHRS4, DHX15, DIO3, DLG1, DLL4, DMD UTR, DMD ex5, DMKN, DNAH6, DNAL4, DUSP13, DUSP19, DYNCII2, DYNLRB2, DYRKIA, ECI2, ECT2, EIFIAD, EIF2B4, EIF4G1, EIF4G2, EIF4G3, ELANE, ELOVL6, ELP5, EMCN, ENO1, EPB41, ERMN, ERVV-1, ESRRG, ETFB, ETFBKMT, ETV1, ETV4, EXD1, EXT1, EZH2, FAM111B, FAM157A, FAM213A, FBX025, FBX09, FBXW7, FCMR, FGF1, FGF1, FGFIA, FGF2, FGF2, FGF-9, FHL5, FMRI, FN1, FOXP1, FTHI, FUBP1, G3BP1, GABBRI, GALC, GART, GAS7, gastrin, GATA1, GATA4, GFM2, GHR, GJB2, GLI1, GLRA2, GMNN, GPAT3, GPATCH3, GPR137, GPR34, GPR55, GPR89A, GPRASP1, GRAP2, GSDMB, GSTO2, GTF2B, GTF2H4, GUCY1B2, HAX1, HCST, HIGD1A, HIGD1B, HIPK1, HISTIH1C, HISTIH3H, HK1, HLA-DRB4, HMBS, HMGA1, HNRNPC, HOPX, HOXA2, HOXA3, HPCAL1, HR, HSP90AB1, HSPA1A, HSPA4L, HSPA5, HYPK, IFFO1, IFT74, IFT81, IGF1, IGF1R, IGF1R, IGF2, IL11, IL17RE, ILIRL1, IL1RN, IL32, IL6, ILF2, ILVBL, INSR, INTS13, IP6K1, ITGA4, ITGAE, KCNE4, KERA, KIAA0355, KIAA0895L, KIAA1324, KIAA1522, KIAA1683, KIF2C, KIZ, KLHL31, KLK7, KRRI, KRT14, KRT17, KRT33A, KRT6A, KRTAP10-2, KRTAP13-3, KRTAP13-4, KRTAP5-11, KRTCAP2, LACRT, LAMBI, LAMB3, LANCLI, LBX2, LCAT, LDHA, LDHAL6A, LEF1, LINC-PINT, LMO3, LRRC4C, LRRC7, LRTOMT, LSM5, LTB4R, LYRM1, LYRM2, MAGEA1I, MAGEA8, MAGEBI, MAGEB16, MAGEB3, MAPT, MARS, MCIR, MCCCI, METTL12, METTL7A, MGC16025, MGC16025, MIA2, MIA2, MITF, MKLN1, MNT, MORF4L2, MPD6, MRFAP1, MRPL21, MRPS12, MSI2, MSLN, MSN, MT2A, MTFRIL, MTMR2, MTRR, MTUSI, MYB, MYC, MYCL, MYCN, MYL10, MYL3, MYLK, MYOIA, MYT2, MZBI, NAPILI, NAVI, NBAS, NCF2, NDRGI, NDST2, NDUFA7, NDUFB11, NDUFC1, NDUFS1, NEDD4L, NFAT5, NFE2L2, NFE2L2, NFIA, NHEJ1, NHP2, NITI, NKRF, NME1-NME2, NPAT, NR3C1, NRBF2, NRF1, NTRK2, NUDCD1, NXF2, NXT2, ODCI, ODF2, OPTN, OR10R2, OR1IL1, OR2M2, OR2M3, OR2M5, OR2T10, OR4C15, OR4F17, OR4F5, OR5H1, OR5K1, OR6C3, OR6C75, OR6N1, OR7G2, p53, P2RY4, PAN2, PAQR6, PARP4, PARP9, PC, PCBP4, PCDHGC3, PCLAF, PDGFB, PDZRN4, PELO, PEMT, PEX2, PFKM, PGBD4, PGLYRP3, PHLDA2, PHTFI, PI4 KB, PIGC, P1M1, PKD2L1, PKM, PLCB4, PLD3, PLEKHAI, PLEKHBI, PLS3, PML, PNMA5, PNN, POCIA, POCIB, POLD2, POLD4, POU5F1, PPIG, PQBPI, PRAME, PRPF4, PRRII, PRRTI, PRSS8, PSMA2, PSMA3, PSMA4, PSMD11, PSMD4, PSMD6, PSME3, PSMG3, PTBP3, PTCHI, PTHLH, PTPRD, PUS7L, PVRIG, QPRT, RAB27A, RAB7B, RABGGTB, RAETIE, RALGDS, RALYL, RARB, RCVRN, REG3G, RFC5, RGL4, RGS19, RGS3, RHD, RINL, RIPOR2, RITA1, RMDN2, RNASEI, RNASE4, RNF4, RPA2, RPL17, RPL21, RPL26L1, RPL28, RPL29, RPL41, RPL9, RPS11, RPS13, RPS14, RRBP1, RSUI, RTP2, RUNX1, RUNXITI, RUNXITI, RUNX2, RUSCI, RXRG, S100A13, S100A4, SATI, SCHIP1, SCMHI, SEC14L1, SEMA4A, SERPINA1, SERPINB4, SERTAD3, SFTPD, SH3D19, SHC1, SHMTI, SHPRH, SIMI, SIRT5, SLC11A2, SLC12A4, SLC16A1, SLC25A3, SLC26A9, SLC5A11, SLC6A12, SLC6A19, SLC7A1, SLFNII, SLIRP, SMAD5, SMARCADI, SMNI, SNCA, SNRNP200, SNRPB2, SNX12, SODI, SOX13, SOX5, SP8, SPARCLI, SPATA12, SPATA31C2, SPN, SPOP, SQSTMI, SRBDI, SRC, SREBFI, SRPK2, SSB, SSB, SSBP1, ST3GAL6, STABI, STAMBP, STAUI, STAUI, STAUI, STAUI, STAUI, STK16, STK24, STK38, STMNI, STX7, SULT2B1, SYK, SYNPR, TAFIC, TAGLN, TANK, TAS2R40, TBCID15, TBXASI, TCF4, TDGF1, TDP2, TDRD3, TDRD5, TESK2, THAP6, THBD, THTPA, TIAM2, TKFC, TKTLI, TLR10, TM9SF2, TMC6, TMC02, TMED10, TMEM116, TMEM126A, TMEM159, TMEM208, TMEM230, TMEM67, TMPRSS13, TMUB2, TNFSF4, TNIP3, TP53, TP53, TP73, TRAFI, TRAKI, TRIM31, TRIM6, TRMT1, TRMT2B, TRPM7, TRPM8, TSPEAR, TTC39B, TTLL11, TUBB6, TXLNB, TXNIP, TXNLI, TXNRDI, TYROBP, U2AFI, UBAI, UBE2D3, UBE2I, UBE2L3, UBE2V1, UBE2V2, UMPS, UNG, UPP2, USMG5, USP18, UTP14A, UTRN, UTS2, VDR, VEGFA, VEGFA, VEPHI, VIPAS39, VPS29, VSIGIOL, WDHDI, WDR12, WDR4, WDR45, WDYHVI, WRAP53, XIAP, XPNPEP3, YAPI, YWHAZ, YYIAPI, ZBTB32, ZNF146, ZNF250, ZNF385A, ZNF408, ZNF410, ZNF423, ZNF43, ZNF502, ZNF512, ZNF513, ZNF580, ZNF609, ZNF707, or ZNRD1.

In some embodiments, the cell is a myotube. In some embodiments, the IRES is derived from Bopivirus, Oscivirus, Hunnivirus, Passerivirus, Mischivirus, Kobuvirus, Enterovirus, Cardiovirus, Salivirus, Rabovirus, Parechovirus, Gallivirus, or Sicinivirus. In some embodiments, the IRES is derived from Hunnivirus, Passerivirus, Kobuvirus, Bopivirus, or Enterovirus. In some embodiments, the IRES is derived from Enterovirus I, Enterovirus F, Enterovirus E, Enterovirus J, Enterovirus C, Enterovirus A, Enterovirus B, Aichivirus B, Parechovirus A, Cardiovirus F, Cardiovirus B, or Cardiovirus E.

In some embodiments, the cell is a hepatocyte. In some embodiments, the IRES is derived from Enterovirus, Bopivirus, Mischivirus, Gallivirus, Oscivirus, Cardiovirus, Kobuvirus, Rabovirus, Salivirus, Parechovirus, Hunnivirus, Tottorivirus, Passerivirus, Cosavirus, or Sicinivirus. In some embodiments, the IRES is derived from Enterovirus, Mischivirus, Kobuvirus, Bopivirus, or Gallivirus. In some embodiments, the IRES is derived from Enterovirus B, Enterovirus A, Enterovirus D, Enterovirus J, Enterovirus C, Rhinovirus B, Enterovirus H, Enterovirus I, Enterovirus E, Enterovirus F, Aichivirus B, Aichivirus A, Parechovirus A, Cardiovirus F, Cardiovirus E, or Cardiovirus B.

In some embodiments, the cell is a T cell. In some embodiments, the IRES is derived from Passerivirus, Bopivirus, Hunnivirus, Mischivirus, Enterovirus, Kobuvirus, Rabovirus, Tottorivirus, Salivirus, Cardiovirus, Parechovirus, Megrivirus, Allexivirus, Oscivirus, or Shanbavirus. In some embodiments, the IRES is derived from Passerivirus, Hunnivirus, Mischivirus, Enterovirus, or Kobuvirus. In some embodiments, the IRES is derived from Enterovirus I, Enterovirus D, Enterovirus C, Enterovirus A, Enterovirus J, Enterovirus H, Aichivirus B, Parechovirus A, or Cardiovirus B.

For driving protein expression, the circular RNA comprises an IRES operably linked to a protein coding sequence. Exemplary IRES sequences are provided in Table 1A. In some embodiments, the circular RNA constructs and related pharmaceutical compositions disclosed herein comprise an IRES sequence that is at least 80%, 85%, 90%, 91%, 92%, 93%, 94%, 95%, 96%, 97%, 98%, or 99% identical to an IRES sequence in Table 1A or an IRES from a construct of SEQ ID NOs: 50-61 or any of Constructs A-P of Table IB. In some embodiments, the circular RNA constructs and related pharmaceutical compositions disclosed herein comprise an IRES sequence in Table 1A or an IRES from a construct of SEQ ID NOs: 50-61 or any of Constructs A-P of Table 1B. Modifications of IRES and accessory sequences are disclosed herein to increase or reduce IRES activities, for example, by truncating the 5' and/or 3' ends of the IRES, adding a spacer 5' to the IRES, modifying the 6 nucleotides 5' to the translation initiation site (Kozak sequence), modification of alternative translation initiation sites, and creating chimeric/hybrid IRES sequences. In some embodiments, the IRES sequence in the circular RNA constructs and related pharmaceutical compositions disclosed herein comprises one or more of these modifications relative to a native IRES.

In particular embodiments, the circular RNA constructs disclosed herein comprise an IRES and at least one expression sequence encoding a binding molecule. In particular embodiments, the IRES sequences are the exemplary IRES sequences provided in Table 1A, below, or an IRES from a construct of SEQ ID NOs: 50-61 or any of Constructs A-P of Table 1B. In some embodiments, the circular RNA constructs and related pharmaceutical compositions disclosed herein comprise an IRES sequence that is at least 80%, 85%, 90%, 91%, 92%, 93%, 94%, 95%, 96%, 97%, 98%, or 99% identical to an IRES sequence in Table IA or an IRES from a construct of SEQ ID NOs: 50-61 or any of Constructs A-P of Table 1B. In some embodiments, the circular RNA constructs and related pharmaceutical compositions disclosed herein comprise an IRES sequence in Table 1A or an IRES from a construct of SEQ ID NOs: 50-61 or any of Constructs A-P of Table 1B and at least one expression sequence encoding a binding molecule.

TABLE 1A

IRES Sequences

| IRES NO: | SEQ ID NO: | Sequence |
|---|---|---|
| 1-1 | 1 | TTAAAACAGCTCTGGGGTTGTTCCCACCCCAGAGGCCCACGTGGCGGCCAGTACTCC GGTATTACGGTACCCTTGTACGCCTGTTTTATACTCCCTTCCCCTGTAACTTAGAAGC ATACAAACCAAGTTCAATAGAAGGGGGTACAAACCAGTACCACCACGAACAAGCAC TCCTGTTTCCCCGGTGACATTGCATAGACTGTACCCACGGTTGAAAGCGATCGATCC GTTACCCGCTCCTGTACTTCGAGAAGCCTAGTATCATCTTGGAATCTTCGATGCGTTG CGCTCAGCACTCAACCCCAGAGTGTAGCTTAGGCTGATGAGTCTGGACGTCCCCCAC CGGCGACGGTGGTCCAGGCTGCGTTGGCGGCCTACCTGTGGCCCAAAGCCACAGGAC GCTAGTTGTGAACAAGGTGTGAAGAGCCTATTGAGCTACAAGAGAGTCCTCCGGCCC CTGAATGCGGCTAATCCTAACCACGGAGCAGGCAGTTGCAAACCAGCAACCGGCCT GTCGTAACGCGCAAGTCTGTGGCGGAACCGACTACTTTGGGTGTCCGTGTTTCCTTTT ATTTTTACAATGGCTGCTTATGGTGACAATCATAGATTGTTATCATAAAGCGACTTGG ATTGGCCATCCGGTGAAAGTAAAACACATTGTTTACTTGTTTGTTGGATTCACTCCAA TTAACACTTTTACTTACAAACTCATTACAACAACTCTATTAATTAGAGATAAGCATCA CA |
| 1-2 | 2 | TTTCCCCTGTTCGTAACTAAGTGTGTGCCCAATCTCCTCACTCCTGCTGGCTTCACCG ACCGGCAGTGTCCAAAATGCTAGGTGAATCCCCTCCCTTTCCTCTGGGCTTCTGCCCA GCTTCCTCCCCCAGCCTGACGTGACACAGGCTGTGCAAAGACCCCGCGAAAGCTGC CAAAAGTGGCAATTGTGGGTCCCCCCTTTGTAAAGGCGTCGAGTCTTTCTCCCTCAAG GCTAGACCCGTCAGTGAATTCTGTCGGGCAACTAGTGACGCCACTGCACGCCTCTGA CCTCGGCCGCGGAGTGCTGCCCCCCAAGTCGTGCCCCTGACCACAAGTTGTGCTGTC TGGCAAACATTGTCTGTGAGAATGTTCCGCTGTGGCTGCCAAGCCTGGCAACAGGCT GCCCCAGTGTGCGTAGTTCTCATCCAGACTTCGGTCTGGCAACTTGCTGTTAAGACAC GGCGTAAGGGGCGTGTGCCAACGCCCTGGAACGAGTGTCCACTCTAATACCCCGAGG AATGCTACGCAGGTACCCCTGGTTCGCCAGGGATCTGAGCGTAGGCTAATTGTCTAA GGGTATTTTCATTTCCCATTCTTTCTTTCTTGTTCATA |
| 1-3 | 3 | TCCCCGGCATGAGAGGAATAGACTCTTTCAGGGGTTGAAGCCACGAGTGTCGTTACCC GCACTGGTACTACGCAAAGCCTAGTAACATCTTGAAACTCTTTTTGGTTGGTCGTTCC ACTAGTTACCCCCTAGTAGACCTGGCAGATGAGGCAGGACGCTCCCCACTGGCGACA GTGGTCCTGCCTGCGTGGCTGCCTGCACACCCTTCGGGGTGTGAAGCCAAAAGAAAG ACAAGGTGTGAAGAGCCCCGTGTGCTACCAGTGAATCCTCCGGCCCCTGAATGCGGC TAATCTTACCCCACAGCTATTGCACACAATCCAGTGTGTATGTAGTCGTAATGAGCA ATTGTGGGACGGAACCGACTACTTTGGGTGTCCGTGTTTCCTTTTATTCCCATGTTTCT GCTTATGGTGACAATACTGACGTATAGTGTTGTTACC |

TABLE 1A-continued

IRES Sequences

| IRES NO: | SEQ ID NO: | Sequence |
|---|---|---|
| 1-4 | 4 | TTAAAACAGCGGATGGGTATCCCACCATCCGGCCCACTGGGTGTAGTACTCTGGTAC<br>ATTGTACCTTTGTACGCCTGTTTTCCCCCTCTTGTACCCGCCCTTCAAGCTCCTTGCCC<br>AAGTAACGTTAGAAGTTTGAACATTGGTACAATAGGAAGCATCACATCCAGTGGTGT<br>ACTGTACAAACACTTCTGTTGCCCCGGAGCGAGGTATAGATGGTCCCCACCGTCAAA<br>AGCCTTTAACCGTTATCCGCCAATCAACTACGTAATGGCTAGTAGCACCTTGGATTTA<br>AGTTGGCGTTCGATCAGGTGGTAACCCCCACTAGTTTGGTCGATGAGGCTAGGAATT<br>CCCCACGGGTGACCGTGTCCTAGCCTGCGTGGCGGCCAACCCAGCATCCGCTGGGAC<br>GCCAATTTAATGACATGGTGTGAAGACCTGCATGTGCTTGATTGTGAGTCCTCCGGC<br>CCCTGAATGCGGCTAACCCTAACCCCGGAGCCTTGCAGCACAATCCAGTGTTGTTAA<br>GGTCGTAATGAGCAATTCTGGGATGGGACCGACTACTTTGGGTGTCCGTGTTTCTTAT<br>TTTTCTTGAATTTTTCTTATGGTCACAGCATATATACATTATATACTGTGATC |
| 1-5 | 5 | TTAAAATAGCCTCAGGGTTGTTCCCACCCTGAGGGCCCACGTGGTGTAGTACTCTGG<br>TATTACGGTACCTTTGTACGCCTATTTTATACCCCCTTCCCCAAGTAATTTAGAAGCA<br>AGCACAAACCAGTTCAGTAGTAAGCAGTACAATCCAGTACTGTAATGAACAAGTACT<br>TCTGTTACCCCGGAAGGGTCTATCGGTAAGCTGTACCCACGGCTGAAGAATGACCTA<br>CCGTTAACCGGCTACCTACTTCGAGAAGCCTAGTAATGCCGTTGAAGTTTTATTGACG<br>TTACGCTCAGCACACTACCCCGTGTGTAGTTTTGGCTGATGAGTCACGGCACTCCCCA<br>CGGGCGACCGTGGCCGTGGCTGCGTTGGCGGCCAACCAAGGAGTGCAAGCTCCTTGG<br>ACGTCATATTACAGACATGGTGTGAAGAGCCTATTGAGCTAGGTGGTAGTCCTCCGG<br>CCCCTGAATGCGGCTAATCCTAACTCCGGAGCATATCGGTGCGAACCAGCACTTGGT<br>GTGTTGTAATACGTAAGTCTGGAGCGGAACCGACTACTTTGGGTGTCCGTGTTTCCTG<br>TTTTAACTTTTATGGCTGCTTATGGTGACAATTTAACATTGTTACCATATAGCTGTTG<br>GGTTGGCCATCCGGATTTTGTTATAAAACCATTTCCTCGTGCCTTGACCTTTAACACA<br>TTTGTGAACTTCTTTAAATCCCTTTTATTAGTCCTTAAATACTAAGA |
| 1-6 | 6 | TTCAAACAGCCTGGGGGTTGTACCCACCCCTGGGGCCCACGTGGCGCTAGTACTCTG<br>GTACGTTAGTACCTTTGTACGCCTGTTTTCCCCTCCCTTAAACAAATTAAGATTACCA<br>CTACTGAGGGGAGTAGTCCGACTCCGCTCCGGTACTGCCGCACCAGTACTCCGGTAC<br>ACTTAGTACCCTAGTACGGAGTAGATGGTATCCCCACCCCGCAACTTAGAAGCATGC<br>AAACAAACCGACCAATAGGCGCACGATATCCAGTCGTGTTTCGGTCAAGCACTTCTG<br>TCTCCCCGGTCCGAAAGGATCGTTACCCGCCCGACCCACTACGAGAAGCCCAGTAAC<br>TGGCCAAGTGATTGCGAAGTTGCGCTCAGCCACAACCCCAGTGGTAGCTCTGGAAGA<br>TGGGGCTCGCGTCTCCCCCGTGGTGACACGGTCGCTTGCCCGCGTGTGCTTCCGGGTT<br>CGGCCTACGCCGTTCACTTCAATGTCACGTAACCAGCCAAGAGCCTATTGTGCTGGG<br>ACGGTTTTCCTCCGGGGCCGTGAATGCTGCTAATCCCAACCTCCGAGCGTGTGCGCA<br>CAACCCAGTGTTGCTACGTCGTAATGCGTAAGTTGGAGGCGGAACAGACTACTTTCG<br>GTACCCCGTGTTTCCTTTAAATTTTATTCATTATTTTATGGTGACAATTGCTGAGATCT<br>GCGAATTAGCGACTCTGCCGTTGAATATTGCTCTGTACTATTTGGTTGCATTCCACAA<br>AACCTCTGACATCCCCAGTACATACATTACTTTACTTGTTTACCTCAATCTAAAGCAC<br>AAGCTAGATAATACAAA |
| 1-7 | 7 | TTTAAACAGCCTGGGGGTTGTTCCCACCCCTGGGGCCCACGTGGCGCTAGTACTCTG<br>GTACGCTAGTACCTTTGTACGCCTGTTTTTCCCCTCCCTTAAATAAATCAAGGTTGCC<br>ACTACTGAGGGGAGTAGTCCGACTCCGCTCCAGCAATGCTGCACCAGTGCACTGGTA<br>CGCTAGTACCTTTTCACGGAGTAGATGGTATCCCTTACCCCGGAACCTAGAAGATTG<br>CACACAAACCGACCAATAGGCGCACCGCATCCAGCCGTGCAGCGGTCAAGCACTTCT<br>GTCTCCCCGGTCTGTAAAGATCGTTATCCGCCCGACCCACTACGAAAAGCCTAGTAA<br>CTGGCCAAGTGAACGCGAAGTTGCGCTCCGCCACAACCCAGTGGTAGCTCTGGAAG<br>ATGGGGCTCGCACCACCCCCGTGGTAACACGGTTGCCTGCCCGCGTGTGCTTCCGGG<br>TTCGGTCTCGTGCCGTTCACTTCAACTTCACGCAACCAGCCAAGAGCCTATTGTGCTG<br>GGACGGTTTTCCTCCGGGGCCGTGAATGCTGCTAATCCCAACCTCCGAGCGTGTGCG<br>CACAATCCAGTGTTGCTACGTCGTAACGCGTAAGTTGGAGGCGGAACAGACTACTTT<br>CGGTACCCCGTGTTTCCTCTCATTTTATTTAATATTTTATGGTGACAATTGTTGAGATT<br>TGCGCTCTTGCAACGTTGCCATTGAATATTGGCTTATACTATTTGGTTGCCTTTTACA<br>AAACCTCTGATATACCCAGTTCTTACATTGATCTGCTTGTTTTTCTCAATTTGAAGTAT<br>AGACTACAAATAGCAAA |
| 1-8 | 8 | CCCCCCTCCCCCCCTTCCCTTCCCTTTGCAACGCAACAATTGTAAGTGCCCTCACCTG<br>TCAATTGGGACCACCACTTTCAGTGACCCCATGCGAAGTGCTGAGAGAAAGGAAGCT<br>TTCTTACCCTTCATTTGTGAACCCACTGGTCTAAGCCGCTTGGAATACGATGAGTGGA<br>AAAGTTCATTCTTAATGGAGTGAAACATGCTTAAATTTCCAGCTCGTGCTGGTCTTTC<br>CAGTACGGGGCGGCCCTGTCTGGCCGTAATTCTTCAGAGTGTCACGCCACACTTGTG<br>GATCTCACGTGCCACATGACAGCGCTACAGCTGGAACTGGGTGCTTGGTGCCCATGG<br>AGTAACAGCGAAAGTGTTAGATCAAGCCTTGCTTGGGCTATGAGCCTGCGGAACAA<br>CAACTGGTAACAGTTGCCTCAGGGGCCGAAAGCCACGGTGTTAACAGCACCCTCATA<br>GTTTGATCCACCTCAGGGTGGTGATGTTTAGCAGTTAGTAGTTGCCAATCTGTGTTCA<br>CTGAAATCTCGGCATACCGTGTAGTGTACAGGGGTGAAGGATGCCCAGAAGGTACCC<br>GTAGGTAACCTTAAGAGACTATGGATCTGATCTGGGGCCTTGTCCGGAGTGCTTTAC<br>ACACGGCTCAAGGTTAAAAAACGTCTAGCCCCACAGAGCCCGAGGGATTCGGGTTTT<br>CCCTTTAAAAACCCGACTAGAGCTTATGGTGACAATTATTGCTGTTCAGACGAACAG<br>TGTAATTGTTGTCTATTCACAGCAGTTCTATCAGAGCTTTTCCCACAACGGATCTTCT<br>TGGCAAGCAAATACAGCAGGAGTCAAT |

TABLE 1A-continued

| | | IRES Sequences |
|---|---|---|

| IRES NO: | SEQ ID NO: | Sequence |
|---|---|---|
| 1-9 | 9 | CACTACGTTACGGTTCCCGCCCGGGACAACTGGTACCCCATTAGGCTACAACATGGC TGAAAAGGGTATTGGGTCCCCCCGGATTGTGTCCGTTCGTAGTGTGTGTAACGTGGTT TACCATCTCCACTAACATTGGACTAAGCATTTCATCTTTCCTCCCCGATTGTGTACTC ACTTGGCTAACGCTGGGTGGTCGCGGTTGGGTCCTTGATTTACTTTTTCTCGTCTAAG CATTCCGACTGTCCTCCCCGATTATGTGCTCATTCAGTTAACTGCTGGGTGGTCATGA CTAACATCGAGGAACCTTCTGTCCACGCTTACTTTGAGCTCCGGTCGCTTGACGCTTG TAGGGCGATAGGGTTATCTTCCTGACAACATCTTTATTCTACCTCCATAGGCTCTATC TATGGAGACGGAGTGTGGCACCCGTCCCTTCTTTGGGAGCTTCGGTAGTGACGCCCT TTGTCACTCTCGCCAGCCGAGGCATGCCTGGTGCCAGGTAGCAAAGAAAGCATATGT TTAAGGACTTGACTGATTTAGCGCAAGAGTTTGTAGCGATGTCCATAGTGTCTGCGG ATTCCCCACACGGCGACGTGTGCCGCGGAGGCCAAAAGCCACGGTGTTCACAGCACC CCTATGGATGCCCACAGACCCCAGTGGGCACTCTTGTTGCCGGACTTTCAGGAAATT AGGCATAGGCTCTTCTCAAACTCCTGGCATTGGACTAGGTAAGAATGCCCCGGAGGT ACCCCAGTACTCCTTCGGGAGTCTGGGATCTGACCGGGGGCCCCACAAACATGCTTT ACGTGTTTCGTGCGGTCAAAAATTGTCTAACTAGTCCCAACCTTGAACAAGGGATTG TTCTTTCCTTTTTATTACTGAGACTGGCCTATGGTGACAACAGAGATTGACTGTGAAT ACAGTTATTTTCTGGTGTTTATCATTTGGTTTTTCTCCGTGCTCTTTTACCTTTGTGGTA TTTGTTCTTTAGATAGGCAAA |
| 1-10 | 10 | CCCGGCCACCCCCTTTCGACGCGGGTACTGCGATAGTGCCACCCCAGTCTTTCCTACT CCCGACTCCCGACTCTAACCCAGGTTCCTTGGAACAGGAACACCAATATACTCATCC CCTGGATGCTGACTAATCAGAGGAACGTCAGCATTTTCCGGCCCAGGCTAAGAGAAG TAGATAAGTTAGATTCCAAATTGATTTATCATCCCCTTGACGAATTCGCGTTGGAAAT GCACCTCTCACTTGCCGCTCTTCACACCCATTAACTTGATTCGGCCTCTGTGTTGAGC CCCTTGTTGAAGTGCTTCCCTCCATCGTGACGTGGTTGGAGATCTAAGTCAACCGACT CCGACGAAACTACCATCATGCCTCCCCGATTATGTGATGCTTTCTGCCCTGCTGGGTG GAGCATCCTCGGGTTGAGAAAACCTTCTTCCTTTTTCCTTGGACCCCGGTCCCCCGGT CTAAGCCGCTTGGAATAAGACAGGGTTATCTTCACCTCTTCCTTCTTCTACTTCATAG TGTTCTATACTATGAAAGGGTATGTGTCGCCCCTTCCTTCTTTGGAGAACACGCGCGG CGGTCTTTCCGTCTCTCGAAAAGCGCGTGTGCGACATGCAGAGAACCGTGAAGAAAG CAGTTTGCGGACTAGCTTTAGTGCCCACAAGAAAACAGCTGTAGCGACCACACAAAG GCAGCGGACCCCCCCTCCTGGCAACAGGAGCCTCTGCGGCCAAAAGCCACGTGGAT AAGATCCACCTTTGTGTGCGGCACAACCCCAGTGCCCTGGTTTCTTGGTGACACTTCA GTGAAAACGCAAATGGCGATCTGAAGCGCCTCTGTAGGAAAGCCAAGAATGTCCAG GAGGTACCCCTTCCCTCGGGAAGGGATCTGACCTGGAGACACATCACATGTGCTTTA CACCTGTGCTTGTGTTTAAAAATTGTCACAGCTTTCCCAAACCAAGTGGTCTTGGTTT TCACTCTTTAAACTGATTTCACT |
| 1-11 | 11 | CCCCCGGTTACCCCCTTTCGACGCGGGTACTGCGATAGTGCCACCCCAGTCTTTCCTA CTCCCGACTCCCGACCCTAACCCAGGTTCCTCGGAACAGGAACACAAATTTACTCAT CCCCTGGATGCTGACTAATCAGAGGAACGTCAGCATTTTCCGGCCCAGGCTTAGAGA AGTAGATAAGTTAGAATCTAAATTGATATGACTTCCCCTTGACGAATTCACGTTGGA AATGCACCCCTCACTTGCCGCTCTTCACACCCACTAATTGATTCGGCCTACTGTGTTG AGCCCCTTGTTGAAGTGCTTCCCTCCCTCGTGACGTGGTTGGAGAAATCTTGTCACCC GACTCCGACGAAACTACCATCATGCCTCCCCGATTATGTGATGCTTTCTGCCCTGCTG GGTGGAGTATCCTCGGGTTGAGAAATCCTTCTTCCTTTTACCTTGGACCTTGGTCCCC CGGTCTAAGCCGCTTGGAATAAGACAGGGTTATTTTCACCTCTTCTTCTTCTACTTCA TGGTGCTCTATACCATGAAAGGGTATGTGTCGCCCCTTCCTTCTTGGAGAACTCACGC GGCGGTCTTCCGTCTCTCAAAAAGCGCGAGTGCGACATGCAGAGTAACGCGGAAGAA AGCAGTTCCTGGCCTAGCTCTAGTGCCCACAAGAAAACGGCTGTAGCGACCACACAA AGGCAGCGGAACTCCCCTCCTGGTAACAGGAGCCTCTGCGGCCAAAAGCCACGTGGG ATTAGATCCACCTTTGTGTGCGGTGCAACCCCAGCACCCCGGTTTCTTGTTGACACTC TAGTGAATCCTTGAATGGCAATCTCAAGCGCCTCTGTAGGAAAGCCAAGAATGTCCA GGAGGTACCCCTTCCTCGCGGAAGGGATCTGACCTGGAGACACATCACACGTGCTTT ACACTTGTGCTTGTGTTTAAAAATTGTCACAGCTTTCCCAAACCAAGTGGTCTTGGTT TTCCTTTTTTATCCTACTGTCAAT |
| 1-12 | 12 | TCCTCACCCATGCTTTTCCTACCCCCACCACGCCCGCATGTTTACTGCTTTCCTTGATG CTGCCCGTGACTACTTCCATGACCTCCCCAACCCAAACCTCAAACGCCTTAAGCTATC ATGGGCTCTCTATCACCAATCCCCTTCCTTCCCACCCAGAACCCCCCCCCTCCCTCCCC TACAACGTGTATGAGCAAGACGAGTTTGACAAGCTCGCCGAAGCCATGCTCACCCAC TCTCCCTTCCCCACATCCCATTACCTCTTCCACCCCCTCCCGTCCAACGCCCGCACCA TCGTCGAGCGTGAGGCTGACTGGGATGGCTGTGATCTAGAAAAGAAATGGCTCGACC TCGTCATAGAGGACGATGCCAAGTTCCTTCTGGAGAACGGCTCTCTCCCGTTTGGCTC CACCCTTGCC |
| 1-13 | 13 | TTCTCGCCTGAGTCAACAAAGCGAGAAACCTGCCCCTCCAGCGCCAGACGAGCGGCA TAAAACTTGAACTTCTGGCATGCTCCACCACCCTTTTCCCCATTCCAACCCCCATTGC GCTCTCAAGGTCGCGCTTTTTCGAGACTAGCTCGGATTCAAAAGTTCCTGGCACCCTT TGCCCCTTCAGGCCCTTAAGGTAGGAACTGACCTTGTGCTGTGCCCTCGGTGCGGAA GTGCTACTGCGTAGCGATTGTAAGATCCCTTTGTGGTTCTGCCCTGGCAAGGTTATAG AGTACTGTGATCCGCTGCGGATGCCATCCTGGTAACAGGACCCCAGTGTGCGCAAC AGTATGTTCACGGTCTTCCGTGTCCACCACATTCGGAACACTGCTCTCGTGAAACAGT GTGTGTCCAATCCCTGCAATCAGTATCAACTACACCACTAGGAATGCTAGGAAGGT ACCCCGGTCCGCCGGGATCTGATCCTAGGCTAATTGTCTACGGTGGTGCTCCTTTTTA |

TABLE 1A-continued

IRES Sequences

| IRES NO: | SEQ ID NO: | Sequence |
|---|---|---|
| | | TTTTCCACTTCAATTCATTGGTTACAACTGCTCGATCCCTGTGTTTGCTGCCCTTCTCT<br>GCTCTCATCGCCATTCTCAAGTGTTCACACTGTCCAAGTTCCTTTGGTTGTTCGCTTCC<br>ACTTGCCACTGTCAACTCTTGTC |
| 1-14 | 14 | TCACCCTCTTTTCCGGTGGTCCGGACCCAGACCACCGTTACTCCATTCAGCTTCTTCG<br>GAACCTGTTTGGAGGAATTAAACGGGCACCCACCCACCTTCACCCCCTTTTCGTAACT<br>AAGTGTGTGCCCAATCTCATGACTCCTGCTGACTTCACCGACCAGCAGTGTCCAAAA<br>CGCTAGGTGAATTTCCTTCCTCCCCCTCTGGGCTTCTGCCCAGCTCCCTCCCTCCAGC<br>CTGACGTGCCACAGGCTGTGCAAAGACCCCGCGAAAGCTGCCAAAAGTGGCAATTG<br>TGGGTCCCCCCTTTGTAAAGGCGTCGAGTCTTTCTCCCTTAAGGCTAGACCCGTCAGT<br>GAATTCTGTCGGGCAACTAGTGACGCCACTGCATGCCTCCGACCTCGGCCGCGGAGT<br>GCTGCCCCCCAAGTCGTGCCCCTGACTACAAGTTGTGCTGTCTGGCAAACATTGTCTG<br>TGAGAATGTTCCGCTGTGGCTGCCAAGCCTGGTAACAGGCTGCCCCAGTGTGCGTAG<br>TTCTCATCCAGACTTCGGTCTGGCAACTTGCTGTTAAGACACGGCGTAAGGGGCGTG<br>TGCCAACGCCCTGGAACGAGTGTCCACTCTAATACCCCGAGGAATGCTACGCAGGTA<br>CCCCTGGCTCCCCAGGGATCTGAGCGTAGGCTAATTGTCTAAGGGTATTTTCATTTCC<br>CACTCTTTCTTTCTTGTTCATA |
| 1-15 | 15 | TCTGTCCTCACCCCATCTTCCCTTCTTTCCTGCACCGTTACGCTTACTCGCATGTGCAT<br>TGAGTGGTGCACGTGCTTGAACAAACAGCTACACTCACATGGGGGCGGGTTTTCCCG<br>CCCTGCGGCCTCTCGCGAGGCCCACCCCTCCCCTTCCTCCCATAACTACAGTGCTTTG<br>GTAGGTAAGCATCCTGATCCCCCGCGGAAGCTGCTCACGTGGCAACTGTGGGGACCC<br>AGACAGGTTATCAAAGGCACCCGGTCTTTCCGCCTTCAGGAGTATCCCTGCTAGTGA<br>ATTCTAGTAGGGCTCTGCTTGGTGCCAACCTCCCCCAAATGCGCGCTGCGGGAGTGC<br>TCTTCCCCAACTCACCCTAGTATCCTCTCATGTGTGTGCTTGGTCAGCATATCTGAGA<br>CGATGTTCCGCTGTCCCAGACCAGTCCAGTAATGGACGGGCCAGTGTGCGTAGTCGT<br>CTTCCGGCTTGTCCGGCGCATGTTTGGTGAACCGGTGGGGTAAGGTTGGTGTGCCCA<br>ACGCCCGTACTTTGGTGATACCTCAAGACCACCCAGGAATGCCAGGGAGGTACCCCG<br>CTTCACAGCGGGATCTGACCCTGGGCTAATTGTCTACGGTGGTTCTTCTTGCTTCCAC<br>TTCTTTCTACTGTTCATG |
| 1-16 | 16 | ATTCTCGGGCTACGGCCCTGGAGCCACTCCGGCTCCTAAAGATTTAGAAGTTTGAGC<br>ACACCCGCCCACTAGGGCCCCCCATCCAGGGGGGCAACGGGCAAGCACTTCTGTTTC<br>CCCGGTATGATCTGATAGGCTGTAACCACGGCTGAAACAGAGATTATCGTTATCCGC<br>TTCACTACTTCGAGAAGCCTAGTAATGATGGGTGAAATTGAATCCGTTGATCCGGTG<br>TCTCCCCCACACCAGAAACTCATGATGAGGGTTGCCATCCCGGCTACGGCGACGTAG<br>CGGGCATCCCTGCGCTGGCATGAGGCCTCTTAGGAGGACGGATGATATGGATCTTGT<br>CGTGAAGAGCCTATTGAGCTAGTGTCGACTCCTCCGCCCCCGTGAATGCGGCTAATC<br>CTAACCCCGGAGCAGGTGGGTCCAATCCAGGGCCTGGCCTGTCGTAATGCGTAAGTC<br>TGGGACGGAACCGACTACTTTCGGGAAGGCGTGTTTCCATTTGTTCATTATTTGTGTG<br>TTTATGGTGACAACTCTGGGTAAACGTTCTATTGCGTTTATTGAGAGATTCCCAACAA<br>TTGAACAAACGAGAACTACCTGTTTTATTAAATTTACACAGAGAAGAATTACA |
| 1-17 | 17 | IGTGGCCACGCCCGGGCCACCGATACTTCCCTTCACTCCTTCGGGACTGTTGGGGAGG<br>AACACAACAGGGCTCCCCTGTTTTCCCATTCCTTCCCCCTTTTCCCAACCCCAACCGC<br>CGTATCTGGTGGCGGCAAGACACACGGGTCTTTCCCTCTAAAGCACAATTGTGTGTG<br>TGTCCCAGGTCCTCCTGCGTACGGTGCGGGAGTGCTCCCACCCAACTGTTGTAAGCCT<br>GTCCAACGCGTCGTCCTGGCAAGACTATGACGTCGCATGTTCCGCTGCGGATGCCGA<br>CCGGGTAACCGGTTCCCCAGTGTGTGTAGTGCGATCTTCCAGGTCCTCCTGGTTGGCG<br>TTGTCCAGAAACTGCTTCAGGTAAGTGGGGTGTGCCCAATCCCTACAAAGGTTGATT<br>CTTTCACCACCTTAGGAATGCTCCGGAGGTACCCCAGCAACAGCTGGGATCTGACCG<br>GAGGCTAATTGTCTACGGGTGGTGTTTCCTTTTTCTTTTCACACAACTCTACTGCTGA<br>CAACTCACTGACTATCCACTTGCTCTGTCACG |
| 1-18 | 18 | TTTGCTCAGCGTAACTTCTCCGGGTTACGTGGAGACCAAAAGGCTACGGAGACTCGG<br>GCTACGGCCCTGGAGCACCTAGGTGCTCCTAAAGACGTTAGAAGTTGTACAAACTCG<br>CCCAATAGGGCCCCCCAACCAGGGGGGGTAGCGGGCAAGCACTTCTGTTTCCCCGGTA<br>TGATCTCATAGGCTGTACCCACGGCTGAAAGAGAGATTATCGTTACCCGCCTCACTA<br>CTTCGAGAAGCCCAGTAATGGTTCATGAAGTTGATCTCGTTGACCCGGTGTTTCCCCC<br>ACACCAGAAACCTGTGATGGGGGTGGTCATCCCGGTCATGGCGACATGACGGACCTC<br>CCCGCGCCGGCACAGGGCCTCTTCGGAGGACGAGTGACATGGATTCAACCGTGAAG<br>AGCCTATTGAGCTAGTGTTGATTCCTCCGCCCCCGTGAATGCGGCTAATCCCAACTCC<br>GGAGCAGGCGGGCCCAAACCAGGGTCTGGCCTGTCGTAACGCGAAAGTCTGGAGCG<br>GAACCGACTACTTTCGGGAAGGCGTGTTTCCTTTTGTTCCTTTTATCAAGTTTTATGGT<br>GACAACTCCTGGTAGACGTTTTATTGCGTTTATTGAGAGATTTCCAACAATTGAACAG<br>ACTAGAACCACTTGTTTTATCAAACCCTCACAGAATAAGATAACA |

In some embodiments, the circular RNA comprises an IRES sequence having at least 85%, 86%, 87%, 88%, 89%, 90%, 91%, 92%, 93%, 94%, 95%, 96%, 97%, 98%, 99%, or 100% sequence identity to an IRES sequence in Table IA, an IRES sequence from a construct of SEQ ID NOs: 50-61, or shown below for any of Constructs A-P of Table IB, and a CAR sequence encoding a polypeptide having at least 85%, 86%, 87%, 88%, 89%, 90%, 91%, 92%, 93%, 94%, 95%, 96%, 97%, 98%, 99%, or 100% sequence identity to a CAR shown below for any of Constructs A-P of Table 1B. In some embodiments, said circular RNA further comprises a CD28z or 4-1BB costimulatory domain as described herein.

In some embodiments, the circular RNA comprises an IRES sequence having at least 85%, 86%, 87%, 88%, 89%, 90%, 91%, 92%, 93%, 94%, 95%, 96%, 97%, 98%, 99%, or 100% sequence identity to the IRES sequence of Construct A, and a CAR sequence encoding a polypeptide having at least 85%, 86%, 87%, 88%, 89%, 90%, 91%, 92%, 93%, 94%, 95%, 96%, 97%, 98%, 99%, or 100% sequence identity to a CAR of Construct A. In some embodiments, the circular RNA comprises an IRES sequence having at least 95%, 96%, 97%, 98%, 99%, or 100% sequence identity to the IRES sequence of Construct A, and a CAR sequence encoding a polypeptide having at least 95%, 96%, 97%, 98%, 99%, or 100% sequence identity to a CAR of Construct A. In some embodiments, said circular RNA exhibits increased expression and/or activity compared to a suitable control having an alternate IRES. In some embodiments, said circular RNA further comprises a CD28z costimulatory domain as described herein and optionally exhibits increased activity compared to a suitable control having an alternate costimulatory domain. In some embodiments, said circular RNA further comprises a 4-1BB costimulatory domain as described herein and optionally exhibits increased activity compared to a suitable control having an alternate costimulatory domain.

In some embodiments, the circular RNA comprises an IRES sequence having at least 85%, 86%, 87%, 88%, 89%, 90%, 91%, 92%, 93%, 94%, 95%, 96%, 97%, 98%, 99%, or 100% sequence identity to the IRES sequence of Construct B, and a CAR sequence encoding a polypeptide having at least 85%, 86%, 87%, 88%, 89%, 90%, 91%, 92%, 93%, 94%, 95%, 96%, 97%, 98%, 99%, or 100% sequence identity to a CAR of Construct B. In some embodiments, the circular RNA comprises an IRES sequence having at least 95%, 96%, 97%, 98%, 99%, or 100% sequence identity to the IRES sequence of Construct B, and a CAR sequence encoding a polypeptide having at least 95%, 96%, 97%, 98%, 99%, or 100% sequence identity to a CAR of Construct B. In some embodiments, said circular RNA exhibits increased expression and/or activity compared to a suitable control having an alternate IRES. In some embodiments, said circular RNA further comprises a CD28z costimulatory domain as described herein and optionally exhibits increased activity compared to a suitable control having an alternate costimulatory domain. In some embodiments, said circular RNA further comprises a 4-1BB costimulatory domain as described herein and optionally exhibits increased activity compared to a suitable control having an alternate costimulatory domain.

In some embodiments, the circular RNA comprises an IRES sequence having at least 85%, 86%, 87%, 88%, 89%, 90%, 91%, 92%, 93%, 94%, 95%, 96%, 97%, 98%, 99%, or 100% sequence identity to the IRES sequence of Construct C, and a CAR sequence encoding a polypeptide having at least 85%, 86%, 87%, 88%, 89%, 90%, 91%, 92%, 93%, 94%, 95%, 96%, 97%, 98%, 99%, or 100% sequence identity to a CAR of Construct C. In some embodiments, the circular RNA comprises an IRES sequence having at least 95%, 96%, 97%, 98%, 99%, or 100% sequence identity to the IRES sequence of Construct C, and a CAR sequence encoding a polypeptide having at least 95%, 96%, 97%, 98%, 99%, or 100% sequence identity to a CAR of Construct C. In some embodiments, said circular RNA exhibits increased expression and/or activity compared to a suitable control having an alternate IRES. In some embodiments, said circular RNA further comprises a CD28z costimulatory domain as described herein and optionally exhibits increased activity compared to a suitable control having an alternate costimulatory domain. In some embodiments, said circular RNA further comprises a 4-1BB costimulatory domain as described herein and optionally exhibits increased activity compared to a suitable control having an alternate costimulatory domain.

In some embodiments, the circular RNA comprises an IRES sequence having at least 85%, 86%, 87%, 88%, 89%, 90%, 91%, 92%, 93%, 94%, 95%, 96%, 97%, 98%, 99%, or 100% sequence identity to the IRES sequence of Construct D, and a CAR sequence encoding a polypeptide having at least 85%, 86%, 87%, 88%, 89%, 90%, 91%, 92%, 93%, 94%, 95%, 96%, 97%, 98%, 99%, or 100% sequence identity to a CAR of Construct D. In some embodiments, the circular RNA comprises an IRES sequence having at least 95%, 96%, 97%, 98%, 99%, or 100% sequence identity to the IRES sequence of Construct D, and a CAR sequence encoding a polypeptide having at least 95%, 96%, 97%, 98%, 99%, or 100% sequence identity to a CAR of Construct D. In some embodiments, said circular RNA exhibits increased expression and/or activity compared to a suitable control having an alternate IRES. In some embodiments, said circular RNA further comprises a CD28z costimulatory domain as described herein and optionally exhibits increased activity compared to a suitable control having an alternate costimulatory domain. In some embodiments, said circular RNA further comprises a 4-1BB costimulatory domain as described herein and optionally exhibits increased activity compared to a suitable control having an alternate costimulatory domain.

In some embodiments, the circular RNA comprises an IRES sequence having at least 85%, 86%, 87%, 88%, 89%, 90%, 91%, 92%, 93%, 94%, 95%, 96%, 97%, 98%, 99%, or 100% sequence identity to the IRES sequence of Construct E, and a CAR sequence encoding a polypeptide having at least 85%, 86%, 87%, 88%, 89%, 90%, 91%, 92%, 93%, 94%, 95%, 96%, 97%, 98%, 99%, or 100% sequence identity to a CAR of Construct E. In some embodiments, the circular RNA comprises an IRES sequence having at least 95%, 96%, 97%, 98%, 99%, or 100% sequence identity to the IRES sequence of Construct E, and a CAR sequence encoding a polypeptide having at least 95%, 96%, 97%, 98%, 99%, or 100% sequence identity to a CAR of Construct E. In some embodiments, said circular RNA exhibits increased expression and/or activity compared to a suitable control having an alternate IRES. In some embodiments, said circular RNA further comprises a CD28z costimulatory domain as described herein and optionally exhibits increased activity compared to a suitable control having an alternate costimulatory domain. In some embodiments, said circular RNA further comprises a 4-1BB costimulatory domain as described herein and optionally exhibits increased activity compared to a suitable control having an alternate costimulatory domain.

In some embodiments, the circular RNA comprises an IRES sequence having at least 85%, 86%, 87%, 88%, 89%, 90%, 91%, 92%, 93%, 94%, 95%, 96%, 97%, 98%, 99%, or 100% sequence identity to the IRES sequence of Construct F, and a CAR sequence encoding a polypeptide having at least 85%, 86%, 87%, 88%, 89%, 90%, 91%, 92%, 93%, 94%, 95%, 96%, 97%, 98%, 99%, or 100% sequence identity to a CAR of Construct F. In some embodiments, the circular RNA comprises an IRES sequence having at least 95%, 96%, 97%, 98%, 99%, or 100% sequence identity to the IRES sequence of Construct F, and a CAR sequence encoding a polypeptide having at least 95%, 96%, 97%, 98%, 99%, or 100% sequence identity to a CAR of Construct F. In some embodiments, said circular RNA exhibits increased expression and/or activity compared to a suitable control having an alternate IRES. In some embodiments, said circular RNA further comprises a CD28z costimulatory domain as described herein and optionally exhibits increased activity compared to a suitable control having an alternate costimulatory domain. In some embodiments, said circular RNA further comprises a 4-1BB costimulatory domain as described herein and optionally exhibits increased activity compared to a suitable control having an alternate costimulatory domain.

In some embodiments, the circular RNA comprises an IRES sequence having at least 85%, 86%, 87%, 88%, 89%, 90%, 91%, 92%, 93%, 94%, 95%, 96%, 97%, 98%, 99%, or 100% sequence identity to the IRES sequence of Construct G, and a CAR sequence encoding a polypeptide having at least 85%, 86%, 87%, 88%, 89%, 90%, 91%, 92%, 93%, 94%, 95%, 96%, 97%, 98%, 99%, or 100% sequence identity to a CAR of Construct G. In some embodiments, the circular RNA comprises an IRES sequence having at least 95%, 96%, 97%, 98%, 99%, or 100% sequence identity to the IRES sequence of Construct G, and a CAR sequence encoding a polypeptide having at least 95%, 96%, 97%, 98%, 99%, or 100% sequence identity to a CAR of Construct G. In some embodiments, said circular RNA exhibits increased expression and/or activity compared to a suitable control having an alternate IRES. In some embodiments, said circular RNA further comprises a CD28z costimulatory domain as described herein and optionally exhibits increased activity compared to a suitable control having an alternate costimulatory domain. In some embodiments, said circular RNA further comprises a 4-1BB costimulatory domain as described herein and optionally exhibits increased activity compared to a suitable control having an alternate costimulatory domain.

In some embodiments, the circular RNA comprises an IRES sequence having at least 85%, 86%, 87%, 88%, 89%, 90%, 91%, 92%, 93%, 94%, 95%, 96%, 97%, 98%, 99%, or 100% sequence identity to the IRES sequence of Construct H, and a CAR sequence encoding a polypeptide having at least 85%, 86%, 87%, 88%, 89%, 90%, 91%, 92%, 93%, 94%, 95%, 96%, 97%, 98%, 99%, or 100% sequence identity to a CAR of Construct H. In some embodiments, the circular RNA comprises an IRES sequence having at least 95%, 96%, 97%, 98%, 99%, or 100% sequence identity to the IRES sequence of Construct H, and a CAR sequence encoding a polypeptide having at least 95%, 96%, 97%, 98%, 99%, or 100% sequence identity to a CAR of Construct H. In some embodiments, said circular RNA exhibits increased expression and/or activity compared to a suitable control having an alternate IRES. In some embodiments, said circular RNA further comprises a CD28z costimulatory domain as described herein and optionally exhibits increased activity compared to a suitable control having an alternate costimulatory domain. In some embodiments, said circular RNA further comprises a 4-1BB costimulatory domain as described herein and optionally exhibits increased activity compared to a suitable control having an alternate costimulatory domain.

In some embodiments, the circular RNA comprises an IRES sequence having at least 85%, 86%, 87%, 88%, 89%, 90%, 91%, 92%, 93%, 94%, 95%, 96%, 97%, 98%, 99%, or 100% sequence identity to the IRES sequence of Construct I, and a CAR sequence encoding a polypeptide having at least 85%, 86%, 87%, 88%, 89%, 90%, 91%, 92%, 93%, 94%, 95%, 96%, 97%, 98%, 99%, or 100% sequence identity to a CAR of Construct I. In some embodiments, the circular RNA comprises an IRES sequence having at least 95%, 96%, 97%, 98%, 99%, or 100% sequence identity to the IRES sequence of Construct I, and a CAR sequence encoding a polypeptide having at least 95%, 96%, 97%, 98%, 99%, or 100% sequence identity to a CAR of Construct I. In some embodiments, said circular RNA exhibits increased expression and/or activity compared to a suitable control having an alternate IRES. In some embodiments, said circular RNA further comprises a CD28z costimulatory domain as described herein and optionally exhibits increased activity compared to a suitable control having an alternate costimulatory domain. In some embodiments, said circular RNA further comprises a 4-1BB costimulatory domain as described herein and optionally exhibits increased activity compared to a suitable control having an alternate costimulatory domain.

In some embodiments, the circular RNA comprises an IRES sequence having at least 85%, 86%, 87%, 88%, 89%, 90%, 91%, 92%, 93%, 94%, 95%, 96%, 97%, 98%, 99%, or 100% sequence identity to the IRES sequence of Construct J, and a CAR sequence encoding a polypeptide having at least 85%, 86%, 87%, 88%, 89%, 90%, 91%, 92%, 93%, 94%, 95%, 96%, 97%, 98%, 99%, or 100% sequence identity to a CAR of Construct J. In some embodiments, the circular RNA comprises an IRES sequence having at least 95%, 96%, 97%, 98%, 99%, or 100% sequence identity to the IRES sequence of Construct J, and a CAR sequence encoding a polypeptide having at least 95%, 96%, 97%, 98%, 99%, or 100% sequence identity to a CAR of Construct J. In some embodiments, said circular RNA exhibits increased expression and/or activity compared to a suitable control having an alternate IRES. In some embodiments, said circular RNA further comprises a CD28z costimulatory domain as described herein and optionally exhibits increased activity compared to a suitable control having an alternate costimulatory domain. In some embodiments, said circular RNA further comprises a 4-1BB costimulatory domain as described herein and optionally exhibits increased activity compared to a suitable control having an alternate costimulatory domain.

In some embodiments, the circular RNA comprises an IRES sequence having at least 85%, 86%, 87%, 88%, 89%, 90%, 91%, 92%, 93%, 94%, 95%, 96%, 97%, 98%, 99%, or 100% sequence identity to the IRES sequence of Construct K, and a CAR sequence encoding a polypeptide having at least 85%, 86%, 87%, 88%, 89%, 90%, 91%, 92%, 93%, 94%, 95%, 96%, 97%, 98%, 99%, or 100% sequence identity to a CAR of Construct K. In some embodiments, the circular RNA comprises an IRES sequence having at least 95%, 96%, 97%, 98%, 99%, or 100% sequence identity to the IRES sequence of Construct K, and a CAR sequence encoding a polypeptide having at least 95%, 96%, 97%, 98%, 99%, or 100% sequence identity to a CAR of Construct K. In some embodiments, said circular RNA exhibits increased expression and/or activity compared to a suitable control having an alternate IRES. In some embodiments, said circular RNA further comprises a CD28z costimulatory domain as described herein and optionally exhibits increased activity compared to a suitable control having an alternate costimulatory domain. In some embodiments, said circular RNA further comprises a 4-1BB costimulatory domain as described herein and optionally exhibits increased activity compared to a suitable control having an alternate costimulatory domain.

In some embodiments, the circular RNA comprises an IRES sequence having at least 85%, 86%, 87%, 88%, 89%, 90%, 91%, 92%, 93%, 94%, 95%, 96%, 97%, 98%, 99%, or 100% sequence identity to the IRES sequence of Construct L, and a CAR sequence encoding a polypeptide having at least 85%, 86%, 87%, 88%, 89%, 90%, 91%, 92%, 93%, 94%, 95%, 96%, 97%, 98%, 99%, or 100% sequence identity to a CAR of Construct L. In some embodiments, the circular RNA comprises an IRES sequence having at least 95%, 96%, 97%, 98%, 99%, or 100% sequence identity to the IRES sequence of Construct L, and a CAR sequence encoding a polypeptide having at least 95%, 96%, 97%, 98%, 99%, or 100% sequence identity to a CAR of Construct L. In some embodiments, said circular RNA exhibits increased expression and/or activity compared to a suitable control having an alternate IRES. In some embodiments, said circular RNA further comprises a CD28z costimulatory domain as described herein and optionally exhibits increased activity compared to a suitable control having an alternate costimulatory domain. In some embodiments, said circular RNA further comprises a 4-1BB costimulatory domain as described herein and optionally exhibits increased activity compared to a suitable control having an alternate costimulatory domain.

In some embodiments, the circular RNA comprises an IRES sequence having at least 85%, 86%, 87%, 88%, 89%, 90%, 91%, 92%, 93%, 94%, 95%, 96%, 97%, 98%, 99%, or 100% sequence identity to the IRES sequence of Construct M, and a CAR sequence encoding a polypeptide having at least 85%, 86%, 87%, 88%, 89%, 90%, 91%, 92%, 93%, 94%, 95%, 96%, 97%, 98%, 99%, or 100% sequence identity to a CAR of Construct M. In some embodiments, the circular RNA comprises an IRES sequence having at least 95%, 96%, 97%, 98%, 99%, or 100% sequence identity to the IRES sequence of Construct M, and a CAR sequence encoding a polypeptide having at least 95%, 96%, 97%, 98%, 99%, or 100% sequence identity to a CAR of Construct M. In some embodiments, said circular RNA exhibits increased expression and/or activity compared to a suitable control having an alternate IRES. In some embodiments, said circular RNA further comprises a CD28z costimulatory domain as described herein and optionally exhibits increased activity compared to a suitable control having an alternate costimulatory domain. In some embodiments, said circular RNA further comprises a 4-1BB costimulatory domain as described herein and optionally exhibits increased activity compared to a suitable control having an alternate costimulatory domain.

In some embodiments, the circular RNA comprises an IRES sequence having at least 85%, 86%, 87%, 88%, 89%, 90%, 91%, 92%, 93%, 94%, 95%, 96%, 97%, 98%, 99%, or 100% sequence identity to the IRES sequence of Construct N, and a CAR sequence encoding a polypeptide having at least 85%, 86%, 87%, 88%, 89%, 90%, 91%, 92%, 93%, 94%, 95%, 96%, 97%, 98%, 99%, or 100% sequence identity to a CAR of Construct N. In some embodiments, the circular RNA comprises an IRES sequence having at least 95%, 96%, 97%, 98%, 99%, or 100% sequence identity to the IRES sequence of Construct N, and a CAR sequence encoding a polypeptide having at least 95%, 96%, 97%, 98%, 99%, or 100% sequence identity to a CAR of Construct N. In some embodiments, said circular RNA exhibits increased expression and/or activity compared to a suitable control having an alternate IRES. In some embodiments, said circular RNA further comprises a CD28z costimulatory domain as described herein and optionally exhibits increased activity compared to a suitable control having an alternate costimulatory domain. In some embodiments, said circular RNA further comprises a 4-1BB costimulatory domain as described herein and optionally exhibits increased activity compared to a suitable control having an alternate costimulatory domain.

In some embodiments, the circular RNA comprises an IRES sequence having at least 85%, 86%, 87%, 88%, 89%, 90%, 91%, 92%, 93%, 94%, 95%, 96%, 97%, 98%, 99%, or 100% sequence identity to the IRES sequence of Construct O, and a CAR sequence encoding a polypeptide having at least 85%, 86%, 87%, 88%, 89%, 90%, 91%, 92%, 93%, 94%, 95%, 96%, 97%, 98%, 99%, or 100% sequence identity to a CAR of Construct O. In some embodiments, the circular RNA comprises an IRES sequence having at least 95%, 96%, 97%, 98%, 99%, or 100% sequence identity to the IRES sequence of Construct O, and a CAR sequence encoding a polypeptide having at least 95%, 96%, 97%, 98%, 99%, or 100% sequence identity to a CAR of Construct O. In some embodiments, said circular RNA exhibits increased expression and/or activity compared to a suitable control having an alternate IRES. In some embodiments, said circular RNA further comprises a CD28z costimulatory domain as described herein and optionally exhibits increased activity compared to a suitable control having an alternate costimulatory domain. In some embodiments, said circular RNA further comprises a 4-1BB costimulatory domain as described herein and optionally exhibits increased activity compared to a suitable control having an alternate costimulatory domain.

In some embodiments, the circular RNA comprises an IRES sequence having at least 85%, 86%, 87%, 88%, 89%, 90%, 91%, 92%, 93%, 94%, 95%, 96%, 97%, 98%, 99%, or 100% sequence identity to the IRES sequence of Construct P, and a CAR sequence encoding a polypeptide having at least 85%, 86%, 87%, 88%, 89%, 90%, 91%, 92%, 93%, 94%, 95%, 96%, 97%, 98%, 99%, or 100% sequence identity to a CAR of Construct P. In some embodiments, the circular RNA comprises an IRES sequence having at least 95%, 96%, 97%, 98%, 99%, or 100% sequence identity to the IRES sequence of Construct P, and a CAR sequence encoding a polypeptide having at least 95%, 96%, 97%, 98%, 99%, or 100% sequence identity to a CAR of Construct P. In some embodiments, said circular RNA exhibits increased expression and/or activity compared to a suitable control having an alternate IRES. In some embodiments, said circular RNA further comprises a CD28z costimulatory domain as described herein and optionally exhibits increased activity compared to a suitable control having an alternate costimulatory domain. In some embodiments, said circular RNA further comprises a 4-1BB costimulatory domain as described herein and optionally exhibits increased activity compared to a suitable control having an alternate costimulatory domain.

In some embodiments, the circular RNA comprises an IRES sequence having at least 85%, 86%, 87%, 88%, 89%, 90%, 91%, 92%, 93%, 94%, 95%, 96%, 97%, 98%, 99%, or 100% sequence identity to the IRES sequence of SEQ ID NO: 8 and a sequence encoding a CAR polypeptide. In some embodiments, said circular RNA further comprises a CD28z costimulatory domain as described herein and optionally exhibits increased activity compared to a suitable control having an alternate costimulatory domain. In some embodiments, said circular RNA further comprises a 4-1BB costimulatory domain as described herein and optionally exhibits increased activity compared to a suitable control having an alternate costimulatory domain.

In some embodiments, the circular RNA comprises an IRES sequence having at least 85%, 86%, 87%, 88%, 89%, 90%, 91%, 92%, 93%, 94%, 95%, 96%, 97%, 98%, 99%, or 100% sequence identity to the IRES sequence of SEQ ID NO: 8 and a sequence encoding a HER2 CAR polypeptide. In some embodiments, the circular RNA comprises an IRES sequence having at least 85%, 86%, 87%, 88%, 89%, 90%, 91%, 92%, 93%, 94%, 95%, 96%, 97%, 98%, 99%, or 100% sequence identity to the IRES sequence of SEQ ID NO: 8 and a sequence encoding a CD19 CAR polypeptide. In some embodiments, the circular RNA comprises an IRES sequence having at least 85%, 86%, 87%, 88%, 89%, 90%, 91%, 92%, 93%, 94%, 95%, 96%, 97%, 98%, 99%, or 100% sequence identity to the IRES sequence of SEQ ID NO: 8 and a sequence encoding a BCMA polypeptide. In some embodiments, said circular RNA further comprises a CD28z costimulatory domain as described herein and optionally exhibits increased activity compared to a suitable control having an alternate costimulatory domain. In some embodiments, said circular RNA further comprises a 4-1BB costimulatory domain as described herein and optionally exhibits increased activity compared to a suitable control having an alternate costimulatory domain.

In some embodiments, the circular RNA comprises an IRES sequence having at least 85%, 86%, 87%, 88%, 89%, 90%, 91%, 92%, 93%, 94%, 95%, 96%, 97%, 98%, 99%, or 100% sequence identity to the IRES sequence of SEQ ID NO: 18 and a sequence encoding a CAR polypeptide. In some embodiments, said circular RNA further comprises a CD28z costimulatory domain as described herein and optionally exhibits increased activity compared to a suitable control having an alternate costimulatory domain. In some embodiments, said circular RNA further comprises a 4-1BB costimulatory domain as described herein and optionally exhibits increased activity compared to a suitable control having an alternate costimulatory domain.

In some embodiments, the circular RNA comprises an IRES sequence having at least 85%, 86%, 87%, 88%, 89%, 90%, 91%, 92%, 93%, 94%, 95%, 96%, 97%, 98%, 99%, or 100% sequence identity to the IRES sequence of SEQ ID NO: 18 and a sequence encoding a HER2 CAR polypeptide. In some embodiments, the circular RNA comprises an IRES sequence having at least 85%, 86%, 87%, 88%, 89%, 90%, 91%, 92%, 93%, 94%, 95%, 96%, 97%, 98%, 99%, or 100% sequence identity to the IRES sequence of SEQ ID NO: 18 and a sequence encoding a CD19 CAR polypeptide. In some embodiments, the circular RNA comprises an IRES sequence having at least 85%, 86%, 87%, 88%, 89%, 90%, 91%, 92%, 93%, 94%, 95%, 96%, 97%, 98%, 99%, or 100% sequence identity to the IRES sequence of SEQ ID NO: 18 and a sequence encoding a BCMA polypeptide. In some embodiments, said circular RNA further comprises a CD28z costimulatory domain as described herein and optionally exhibits increased activity compared to a suitable control having an alternate costimulatory domain. In some embodiments, said circular RNA further comprises a 4-1BB costimulatory domain as described herein and optionally exhibits increased.

In some embodiments, the circular RNA comprises a CAR sequence encoding a polypeptide having at least 85%, 86%, 87%, 88%, 89%, 90%, 91%, 92%, 93%, 94%, 95%, 96%, 97%, 98%, 99%, or 100% sequence identity to a CAR of any one of Constructs A-P of Table 1B or binding fragments thereof. In some embodiments, said circular RNA further comprises a CD28z costimulatory domain as described herein and optionally exhibits increased activity compared to a suitable control having an alternate costimulatory domain. In some embodiments, said circular RNA further comprises a 4-1BB costimulatory domain as described herein and optionally exhibits increased activity compared to a suitable control having an alternate costimulatory domain.

TABLE 1B

Exemplary Constructs (DNA Templates)

| ID | IRES Sequence | CAR Sequence | CAR Sequence |
|---|---|---|---|
| Construct A | CCCCCCTCCCCCCCTTCC | ATGGCTCTCCCCGTGACCGCTCTGCTGC | MALPVTALLL |
|  | CTTCCCTTTGCAACGCAA | TCCCTCTGGCCCTCCTTCTGCACGCAGC | PLALLLHAAR |
|  | CAATTGTAAGTGCCCTCA | CAGACCACAGGTCAAGCTGGAGGAGTC | PQVKLEESGG |
|  | CCTGTCAATTGGGACCAC | TGGTGGCGGTCTGGTGCAGGCAGGGAG | GLVQAGRSLR |
|  | CACTTTCAGTGACCCCAT | GAGCCTGAGGCTGAGCTGTGCAGCTTCC | LSCAASEHTFS |
|  | GCGAAGTGCTGAGAGAA | GAGCACACATTCTCAAGCCACGTCATGG | SHVMGWFRQ |
|  | AGGAAGCTTTCTTACCCT | GGTGGTTCAGACAGGCTCCCGGTAAAG | APGKERESVA |
|  | TCATTTGTGAACCCACTG | AGAGGGAGTCCGTCGCCGTGATCGGATG | VIGWRDISTSY |
|  | GTCTAAGCCGCTTGGAAT | GCGGGACATCTCCACCTCCTACGCCGAC | ADSVKGRFTIS |
|  | ACGATGAGTGGAAAAGTT | TCTGTGAAGGGCCGGTTCACAATCTCAC | RDNAKKTLYL |
|  | CATTCTTAATGGAGTGAA | GCGATAATGCCAAGAAGACACTGTATCT | QMNSLKPEDT |
|  | ACATGCTTAAATTTCCAG | GCAGATGAATTCCTTGAAGCCCGAAGAC | AVYYCAARRI |
|  | CTCGTGCTGGTCTTTCCA | ACCGCCGTCTATTACTGTGCTGCTAGAC | DAADPFDSWG |
|  | GTACGGGGCGGCCCTGTC | GGATCGACGCTGCCGACTTCGACAGCTG | QGTQVTVSSG |
|  | TGGCCGTAATTCTTCAGA | GGGACAGGGTACCCAAGTGACCGTTTCC | GGGSGGGGSG |
|  | GTGTCACGCCACACTTGT | TCCGGAGGCGGAGGTTCTGGAGGAGGT | GGGSEVQLVE |
|  | GGATCTCACGTGCCACAT | GGGTCAGGTGGAGGTGGCTCCGAGGTG | SGGGLVQAGG |
|  | GACAGCGCTACAGCTGG | CAGCTGGTCGAGTCTGGCGGTGGCTTGG | SLRLSCAASG |
|  | AACTGGGTGCTTGGTGCC | TCCAGGCTGGAGGCAGTCTCAGACTCTC | RTFTMGWFRQ |
|  | CATGGAGTAACAGCGAAA | CTGCGCTGCTTCAGGGCGGACCTTCACC | APGKEREFVA |
|  | AGTGTTAGATCAAGCCTT | ATGGGCTGGTTCAGGCAGGCCCCAGGTA | AISLSPTLAYY |
|  | GCTTGGGCTATGAGCCTG | AGGAGAGGGAGTTCGTGGCCGCCATCTC | AESVKGRFTIS |
|  | CGGAACAACAACTGGTA | CCTCTCCCCTACCCTGGCATACTACGCTG | RDNAKNTVVL |
|  | ACAGTTGCCTCAGGGGCC | AGTCCGTGAAGGGACGGTTTACCATCTC | QMNSLKPEDT |
|  | GAAAGCCACGGTGTTAAC | CCGGGATAACGCAAAGAACACTGTGGT | ALYYCAADRK |
|  | AGCACCCTCATAGTTTGA | CCTCCAAATGAACTCCCTCAAACCCGAG | SVMSIRPDYW |
|  | TCCACCTCAGGGTGGTGA | GACACCGCTCTCTACTATTGTGCCGCAG | GQGTQVTVSS |
|  | TGTTTAGCAGTTAGTAGT | ATCGGAAGAGCGTCATGTCCATCCGGCC | TSTTTPAPRPP |
|  | TGCCAATCTGTGTTCACT | CGATTACTGGGGCCAAGGCACACAGGT | TPAPTIASQPL |
|  | GAAATCTCGGCATACCGT | GACTGTGTCCAGCACCTCCACCACCACC | SLRPEACRPAA |

TABLE 1B-continued

Exemplary Constructs (DNA Templates)

| ID | IRES Sequence | CAR Sequence | CAR Sequence |
|---|---|---|---|
| | GTAGTGTACAGGGGTGAA GGATGCCCAGAAGGTACC CGTAGGTAACCTTAAGAG ACTATGGATCTGATCTGG GGCCTTGTCCGGAGTGCT TTACACACGGCTCAAGGT TAAAAAACGTCTAGCCCC ACAGAGCCCGAGGGATTC GGGTTTTCCCTTTAAAAA CCCGACTAGAGCTTATGG TGACAATTATTGCTGTTCA GACGAACAGTGTAATTGT TGTCTATTCACAGCAGTT CTATCAGAGCTTTTCCCA CAACGGATCTTCTTGGCA AGCAAATACAGCAGGAGT CAAT (SEQ ID NO: 8) | CCAGCACCAAGGCCTCCAACCCCTGCA CCAACCATCGCCTCCCAGCCACTGTCTT TGCGGCCAGAAGCATGCCGCCCAGCAG CAGGTGGAGCCGTGCATACAAGAGGCC TGGACTTCGCCTGCGATATCTACATCTGG GCTCCTCTGGCCGGAACATGCGGAGTCC TGCTCTTGTCCCTGGTGATCACCCTGTAC TGCAAGCGGGGTCGGAAGAAGCTCCTC TACATCTTCAAGCAGCCCTTCATGAGAC CCGTCCAGACCACCCAGGAGGAGGACG GGTGCTCATGCAGGTTCCCCGAAGAGGA GGAGGGTGGCTGTGAGCTGCGGGTGAA GTTCAGCAGGTCAGCAGACGCCCCTGCC TATCAGCAGGGCCAAAACCAGTTGTACA ACGAGCTGAATCTGGGGGAGACGGGAGG AGTACGATGTCCTTGACAAGAGAAGGG GCCGGGATCCAGAGATGGGCGGGAAGC CAAGACGGAAGAATCCTCAGGAGGGTC TGTATAACGAGCTGCAGAAGGACAAGAT GGCCGAGGCCTACTCCGAGATCGGCATG AAAGGGGAGCGCCGCAGAGGAAAAGGT CACGATGGTCTGTACCAGGGGTTGAGCA CCGCTACCAAGGATACTTACGACGCTCT GCACATGCAAGCTCTGCCACCCCGG (SEQ ID NO: 106) | GGAVHTRGLD FACDIYIWAPL AGTCGVLLLS LVITLYCKRGR KKLLYIFKQPF MRPVQTTQEE DGCSCRFPEEE EGGCELRVKF SRSADAPAYQ QGQNQLYNEL NLGRREEYDV LDKRRGRDPE MGGKPRRKNP QEGLYNELQK DKMAEAYSEI GMKGERRRG KGHDGLYQGL STATKDTYDA LHMQALPPR (SEQ ID NO: 122) |
| Construct B | GTGGCCACGCCCGGGCC ACCGATACTTCCCTTCAC TCCTTCGGGACTGTTGGG GAGGAACACAACAGGGC TCCCCTGTTTTCCCATTCC TTCCCCCTTTTCCCAACC CCAACCGCCGTATCTGGT GGCGGCAAGACACACGG GTCTTTCCCTCTAAAGCA CAATTGTGTGTGTGTCCC AGGTCCTCCTGCGTACGG TGCGGGAGTGCTCCCACC CAACTGTTGTAAGCCTGT CCAACGCGTCGTCCTGGC AAGACTATGACGTCGCAT GTTCCGCTGCGGATGCCG ACCGGGTAACCGGTTCCC CAGTGTGTGTAGTGCGAT CTTCCAGGTCCTCCTGGT TGGCGTTGTCCAGAAACT GCTTCAGGTAAGTGGGGT GTGCCCAATCCCTACAAA GGTTGATTCTTTCACCAC CTTAGGAATGCTCCGGAG GTACCCCAGCAACAGCTG GGATCTGACCGGAGGCTA ATTGTCTACGGGTGGTGT TTCCTTTTTCTTTTCACAC AACTCTACTGCTGACAAC TCACTGACTATCCACTTG CTCTGTCACG (SEQ ID NO: 17) | ATGGCACTCCCGGTAACCGCCTTATTGCT TCCCCTTGCCCTCTTGCTCCACGCAGCA CGCCCCGATATAGTCTTGACTCAATCCCC ACCCAGTTTGGCAATGTCATTAGGCAAA CGAGCAACAATTTCATGTAGGGCATCCG AAAGTGTAACGATTTTGGGGAGTCATTT AATTCATTGGTACCAACAAAAGCCTGGA CAACCCCCGACGCTCTTGATCCAATTAG CATCTAACGTCCAAACCGGAGTCCCCGC ACGATTCTCAGGATCCGGTTCCCGGACT GATTTTACATTAACTATTGATCCGGTAGA GGAAGATGACGTCGCTGTCTATTATTGTC TTCAAAGTAGGACGATTCCACGGACATT CGGTGGCGGAACTAAATTGGAGATTAAA GGTTCCACCTCTGGTAGTGGGAAACCCG GGTCCGGTGAAGGGTCCACTAAAGGCC AAAATCAACTCGTTCAATCCGGACCAGA ACTGAAGAAGCCAGGAGAAACTGTCAA AATAAGCTGTAAAGCTTCCGGTTATACAT TTACAGATTATTCCATAAATTGGGTGAAA AGGGCGCCAGGAAAAGGGTTAAAGTGG ATGGGTTGGATTAATACAGAGACTCGGG AACCTGCATATGCTTATGATTTTAGGGGA AGGTTTGCCTTTTCTCTGGAGACTTCCG CTTCAACTGCTTATCTCCAAATTAATAAT CTTAAATATGAGGACACAGCAACATACT TCTGTGCTTTGGACTATAGTTATGCTATG GATTACTGGGGACAAGGAACCAGTGTC ACTGTAAGTTCCGCTGCTGCGACGACCA CTCCTGCACCGCGACCACCCACTCCTGC CCCTACTATTGCTAGTCAACCACTTAGCT TGCGACCTGAGGCATGTCGGCCCGCGGC AGGTGGCGCAGTCCACACCAGGGGTTT AGACTTTGCTTGTGATATTTATATTTGGG CACCACTCGCCGGGACTTGCGGTGTTCT TCTCTTGTCCCTTGTTATAACTCTTTATTG TAAGCGCGGAAGGAAGAAATTGTTATAT ATTTTCAAACAACCTTTTATGCGACCCGT ACAAACAACTCAGGAAGAGGACGGGTG TTCTTGTCGGTTTCCAGAAGAGGAAGAG GGTGGGGTGTGAACTCCGGGTCAAATTTA GTAGGTCAGCAGATGCGCCGGCGTACCA ACAAGGCCAAAACCAACTGTATAATGAA CTCAATCTCGGTAGGCGTGAGGAATATG ATGTCCTTGATAAAAGGCGCGGGAGAGA TCCAGAAATGGGCGGAAAACCACGGCG AAAGAATCCGCAGGAAGGGTTATATAAC GAACTTCAAAAGGATAAAATGGCTGAA GCTTATTCCGAAATTGGCATGAAAGGAG | MALPVTALLL PLALLLHAAR PDIVLTQSPPS LAMSLGKRAT ISCRASESVTIL GSHLIHWYQQ KPGQPPTLLIQ LASNVQTGVP ARFSGSGSRTD FTLTIDPVEED DVAVYYCLQS RTIPRTFGGGT KLEIKGSTSGS GKPGSGEGST KGQIQLVQSGP ELKKPGETVKI SCKASGYTFT DYSINWVKRA PGKGLKWMG WINTETREPAY AYDFRGRPAFS LETSASTAYLQ INNLKYEDTAT YFCALDYSYA MDYWGQGTS VTVSSAAATT TPAPRPPTPAP TIASQPLSLRP EACRPAAGGA VHTRGLDFAC DIYIWAPLAGT CGVLLLSLVIT LYCKRGRKKL LYIFKQPFMRP VQTTQEEDGC SCRFPEEEGG CELRVKFSRSA DAPAYQQGQN QLYNELNLGR REEYDVLDKR RGRDPEMGGK PRRKNPQEGL YNELQKDKM AEAYSEIGMK GERRRGKGHD GLYQGLSTAT KDTYDALHM QALPPR (SEQ ID NO: 119) |

TABLE 1B-continued

Exemplary Constructs (DNA Templates)

| ID | IRES Sequence | CAR Sequence | CAR Sequence |
|---|---|---|---|
| | | AGCGACGTAGGGGCAAAGGGCATGATG GCCTTTACCAAGGGCTCTCAACCGCTAC AAAAGATACTTACGACGCTTTACATATGC AAGCACTTCCACCCAGG (SEQ ID NO: 103) | |
| Construct C | CCCCCCTCCCCCCCTTCC CTTCCCTTTGCAACGCAA CAATTGTAAGTGCCCTCA CCTGTCAATTGGGACCAC CACTTTCAGTGACCCCAT GCGAAGTGCTGAGAGAA AGGAAGCTTTCTTACCCT TCATTTGTGAACCCACTG GTCTAAGCCGCTTGGAAT ACGATGAGTGGAAAAGTT CATTCTTAATGGAGTGAA ACATGCTTAAATTTCCAG CTCGTGCTGGTCTTTCCA GTACGGGGCGGCCCTGTC TGGCCGTAATTCTTCAGA GTGTCACGCCACACTTGT GGATCTCACGTGCCACAT GACAGCGCTACAGCTGG AACTGGGTGCTTGGTGCC CATGGAGTAACAGCGAAA AGTGTTAGATCAAGCCTT GCTTGGGCTATGAGCCTG CGGAACAACAACTGGTA ACAGTTGCCTCAGGGGCC GAAAGCCACGGTGTTAAC AGCACCCTCATAGTTTGA TCCACCTCAGGGTGGTGA TGTTTAGCAGTTAGTAGT TGCCAATCTGTGTTCACT GAAATCTCGGCATACCGT GTAGTGTACAGGGGTGAA GGATGCCCAGAAGGTACC CGTAGGTAACCTTAAGAG ACTATGGATCTGATCTGG GGCCTTGTCCGGAGTGCT TTACACACGGCTCAAGGT TAAAAAACGTCTAGCCCC ACAGAGCCCGAGGGATTC GGGTTTTCCCTTTAAAAA CCCGACTAGAGCTTATGG TGACAATTATTGCTGTTCA GACGAACAGTGTAATTGT TGTCTATTCACAGCAGTT CTATCAGAGCTTTTCCCA CAACGGATCTTCTTGGCA AGCAAATACAGCAGGAGT CAAT (SEQ ID NO: 8) | ATGGCACTCCCGGTAACCGCCTTATTGCT TCCCCTTGCCCTCTTGCTCCACGCAGCA CGCCCCGATATAGTCTTGACTCAATCCCC ACCCAGTTTGGCAATGTCATTAGGCAAA CGAGCAACAATTTCATGTAGGGCATCCG AAAGTGTAACGATTTTGGGGAGTCATTT AATTCATTGGTACCAACAAAGCCTGGA CAACCCCCGACGCTCTTGATCCAATTAG CATCTAACGTCCAAACCGGAGTCCCCGC ACGATTCTCAGGATCCGGTTCCCGGACT GATTTTACATTAACTATTGATCCGGTAGA GGAAGATGACGTCGCTGTCTATTATTGTC TTCAAAGTAGGACGATTCCACGGACATT CGGTGGCGGAACTAAATTGGAGATTAAA GGTTCCACCTCGGTAGTGGGAAACCCG GGTCCGGTGAAGGGTCCACTAAAGGCC AAATTCAACTCGTTCAATCGGACCAGA ACTGAAGAAGCCAGGAGAAACTGTCAA AATAAGCTGTAAAGCTTCCGGTTATACAT TTACAGATTATTCCATAAATTGGGTGAAA AGGGCGCCAGGAAAAGGGTTAAAGTGG ATGGGTTGGATTAATACAGAGACTCGGG AACCTGCATATGCTTATGATTTTAGGGGA AGGTTTGCCTTTTCTCTGGAGACTTCCG CTTCAACTGCTTATCTCCAAATTAATAAT CTTAAATATGAGGACACAGCAACATACT TCTGTGCTTTGGACTATAGTTATGCTATG GATTACTGGGGACAAGGAACCAGTGTC ACTGTAAGTTCCGCTGCTGCGACGACCA CTCCTGCACCGCGACCACCCACTCCTGC CCCTACTATTGCTAGTCAACCACTTAGCT TGCGACCTGAGGCATGTCGGCCCGCGGC AGGTGGCGCAGTCCACACCAGGGGTTT AGACTTTGCTTGTGATATTTATATTTGGG CTATCACTCGCTGGGACTTGCGGTGTTCT TCTCTTGTCCCTTGTTATAACTCTTTATTG TAAGCGCGGAAGGAAGAAATTGTTATAT ATTTTCAAACAACCTTTTATGCGACCCGT ACAAACAACTCAGGAAGGACGGGGTG TTCTTGTCGGTTTCCAGAAGAGGAAGAG GGTGGGTGTGAACTCCGGGTCAAATTTA GTAGGTCAGCAGATGCGCCGGCGTACCA ACAAGGCCAAAACCAACTGTATAATGAA CTCAATCTCGGTAGGCGTGAGGAATATG ATGTCCTTGATAAAAGGCGCGGGAGAGA TCCAGAAATGGGCGGAAAACCACGGCG AAAGAATCCGCAGGAAGGGTTATATAAC GAACTTCAAAAGGATAAAATGGCTGAA GCTTATTCCGAAATTGGCATGAAAGGAG AGCGACGTAGGGGCAAAGGGCATGATG GCCTTTACCAAGGGCTCTCAACCGCTAC AAAAGATACTTACGACGCTTTACATATGC AAGCACTTCCACCCAGG (SEQ ID NO: 103) | MALPVTALLL PLALLLHAAR PDIVLTQSPPS LAMSLGKRAT ISCRASESVTIL GSHLIHWYQQ KPGQPPTLLIQ LASNVQTGVP ARFSGSGSRTD FTLTIDPVEED DVAVYYCLQS RTIPRTFGGGT KLEIKGSTSGS GKPGSGEGST KGQIQLVQSGP ELKKPGETVKI SCKASGYTFT DYSINWVKRA PGKGLKWMG WINTETREPAY AYDFRGRFAFS LETSASTAYLQ INNLKYEDTAT YFCALDYSYA MDYWGQGTS VTVSSAAATT TPAPRPPTPAP TIASQPLSLRP EACRPAAGGA VHTRGLDFAC DIYIWAPLAGT CGVLLLSLVIT LYCKRGRKKL LYIFKQPFMRP VQTTQEEDGC SCRFPEEEEGG CELRVKFSRSA DAPAYQQGQN QLYNELNLGR REEYDVLDKR RGRDPEMGGK PRRKNPQEGL YNELQKDKM AEAYSEIGMK GERRRGKGHD GLYQGLSTAT KDTYDALHM QALPPR (SEQ ID NO: 119) |
| Construct D | TTTGCTCAGCGTAACTTC TCCGGGTTACGTGGAGAC CAAAAGGCTACGGAGAC TCGGGCTACGGCCCTGGA GCACCTAGGTGCTCCTAA AGACGTTAGAAGTTGTAC AAACTCGCCCAATAGGGC CCCCCAACCAGGGGGGT AGCGGGCAAGCACTTCTG TTTCCCCGGTATGATCTCA TAGGCTGTACCCACGGCT GAAAGAGAGATTATCGTT ACCCGCCTCACTACTTCG AGAAGCCCAGTAATGGTT | ATGGCACTCCCGGTAACCGCCTTATTGCT TCCCCTTGCCCTCTTGCTCCACGCAGCA CGCCCCGATATAGTCTTGACTCAATCCCC ACCCAGTTTGGCAATGTCATTAGGCAAA CGAGCAACAATTTCATGTAGGGCATCCG AAAGTGTAACGATTTTGGGGAGTCATTT AATTCATTGGTACCAACAAAGCCTGGA CAACCCCCGACGCTCTTGATCCAATTAG CATCTAACGTCCAAACCGGAGTCCCCGC ACGATTCTCAGGATCCGGTTCCCGGACT GATTTTACATTAACTATTGATCCGGTAGA GGAAGATGACGTCGCTGTCTATTATTGTC TTCAAAGTAGGACGATTCCACGGACATT CGGTGGCGGAACTAAATTGGAGATTAAA | MALPVTALLL PLALLLHAAR PDIVLTQSPPS LAMSLGKRAT ISCRASESVTIL GSHLIHWYQQ KPGQPPTLLIQ LASNVQTGVP ARFSGSGSRTD FTLTIDPVEED DVAVYYCLQS RTIPRTFGGGT KLEIKGSTSGS GKPGSGEGST |

TABLE 1B-continued

Exemplary Constructs (DNA Templates)

| ID | IRES Sequence | CAR Sequence | CAR Sequence |
|---|---|---|---|
| | CATGAAGTTGATCTCGTT<br>GACCCGGTGTTTCCCCCA<br>CACCAGAAACCTGTGATG<br>GGGGTGGTCATCCCGGTC<br>ATGGCGACATGACGGACC<br>TCCCCGCGCCGGCACAGG<br>GCCTCTTCGGAGGACGAG<br>TGACATGGATTCAACCGT<br>GAAGAGCCTATTGAGCTA<br>GTGTTGATTCCTCCGCCC<br>CCGTGAATGCGGCTAATC<br>CCAACTCCGGAGCAGGC<br>GGGCCCAAACCAGGGTC<br>TGGCCTGTCGTAACGCGA<br>AAGTCTGGAGCGGAACC<br>GACTACTTTCGGGAAGGC<br>GTGTTTCCTTTTGTTCCTT<br>TTATCAAGTTTTATGGTGA<br>CAACTCCTGGTAGACGTT<br>TTATTGCGTTTATTGAGAG<br>ATTTCCAACAATTGAACA<br>GACTAGAACCACTTGTTT<br>TATCAAACCCTCACAGAA<br>TAAGATAACA (SEQ ID NO:<br>18) | GGTTCCACCTCTGGTAGTGGGAAACCCG<br>GGTCCGGTGAAGGGTCCACTAAAGGCC<br>AAATTCAACTCGTTCAATCCGGACCAGA<br>ACTGAAGAAGCCAGGAGAAACTGTCAA<br>AATAAGCTGTAAAGCTTCCGGTTATACAT<br>TTACAGATTATTCCATAAATTGGGTGAAA<br>AGGGCGCCAGGAAAAGGGTTAAAGTGG<br>ATGGGTTGGATTAATACAGAGACTCGGG<br>AACCTGCATATGCTTATGATTTTAGGGGA<br>AGGTTTGCCTTTTCTCTGGAGACTTCCG<br>CTTCAACTGCTTATCTCCAAATTAATAAT<br>CTTAAATATGAGGACACAGCAACATACT<br>TCTGTGCTTTGGACTATAGTTATGCTATG<br>GATTACTGGGGACAAGGAACCAGTGTC<br>ACTGTAAGTTCCGCTGCTGCGACGACCA<br>CTCCTGCACCGCGACCACCCACTCCTGC<br>CCCTACTATTGCTAGTCAACCACTTAGCT<br>TGCGACCTGAGGCATGTCGGCCCGCGGC<br>AGGTGGCGCAGTCCACACCAGGGGTTT<br>AGACTTTGCTTGTGATATTTATATTTGGG<br>CACCACTCGCCGGGACTTGCGGTGTTCT<br>TCTCTTGTCCCTTGTTATAACTCTTTATTG<br>TAAGCGCGGAAGGAAGAAATTGTTATAT<br>ATTTTCAAACAACCTTTTATGCGACCCGT<br>ACAAACAACTCAGGAAGAGGACGGGTG<br>TTCTTGTCGGTTTCCAGAAGAGGAAGAG<br>GGTGGGTGTGAACTCCGGGTCAAATTTA<br>GTAGGTCAGCAGATGCGCCGGCGTACCA<br>ACAAGGCCAAAACCAACTGTATAATGAA<br>CTCAATCTCGGTAGGCGTGAGGAATATG<br>ATGTCCTTGATAAAAGGCGCGGGAGAGA<br>TCCAGAAATGGGCGGAAAACCACGGCG<br>AAAGAATCCGCAGGAAGGGTTATATAAC<br>GAACTTCAAAAGGATAAAATGGCTGAA<br>GCTTATTCCGAAATTGGCATGAAAGGAG<br>AGCGACGTAGGGGCAAAGGGCATGATG<br>GCCTTTACCAAGGGCTCTCAACCGCTAC<br>AAAAGATACTTACGACGCTTTACATATGC<br>AAGCACTTCCACCCAGG (SEQ ID NO:<br>103) | KGQIQLVQSGP<br>ELKKPGETVKI<br>SCKASGYTFT<br>DYSINWVKRA<br>PGKGLKWMG<br>WINTETREPAY<br>AYDFRGRFAFS<br>LETSASTAYLQ<br>INNLKYEDTAT<br>YFCALDYSYA<br>MDYWGQGTS<br>VTVSSAAATT<br>TPAPRPPTPAP<br>TIASQPLSLRP<br>EACRPAAGGA<br>VHTRGLDFAC<br>DIYIWAPLAGT<br>CGVLLLSLVIT<br>LYCKRGRKKL<br>LYIFKQPFMRP<br>VQTTQEEDGC<br>SCRFPEEEEGG<br>CELRVKFSRSA<br>DAPAYQQGQN<br>QLYNELNLGR<br>REEYDVLDKR<br>RGRDPEMGGK<br>PRRKNPQEGL<br>YNELQKDKM<br>AEAYSEIGMK<br>GERRRGKGHD<br>GLYQGLSTAT<br>KDTYDALHM<br>QALPPR (SEQ<br>ID NO: 119) |
| Construct<br>E | ATTCTCGGGCTACGGCCC<br>TGGAGCCACTCCGGCTCC<br>TAAAGATTTAGAAGTTTG<br>AGCACACCCGCCCACTAG<br>GGCCCCCCATCCAGGGGG<br>GCAACGGGCAAGCACTT<br>CTGTTTCCCCGGTATGATC<br>TGATAGGCTGTAACCACG<br>GCTGAAACAGAGATTATC<br>GTTATCCGCTTCACTACTT<br>CGAGAAGCCTAGTAATGA<br>TGGGTGAAATTGAATCCG<br>TTGATCCGGTGTCTCCCC<br>CACACCAGAAACTCATGA<br>TGAGGGTTGCCATCCCGG<br>CTACGGCGACGTAGCGGG<br>CATCCCTGCGCTGGCATG<br>AGGCCTCTTAGGAGGACG<br>GATGATATGGATCTTGTCG<br>TGAAGAGCCTATTGAGCT<br>AGTGTCGACTCCTCCGCC<br>CCCGTGAATGCGGCTAAT<br>CCTAACCCCGGAGCAGGT<br>GGGTCCAATCCAGGGCCT<br>GGCCTGTCGTAATGCGTA<br>AGTCTGGGACGGAACCG<br>ACTACTTTCGGGAAGGCG<br>TGTTTCCATTTGTTCATTA<br>TTTGTGTGTTTATGGTGAC<br>AACTCTGGGTAAACGTTC<br>TATTGCGTTTATTGAGAGA<br>TTCCCAACAATTGAACAA<br>ACGAGAACTACCTGTTTT<br>ATTAAATTTACACAGAGA | ATGGCACTCCCGGTAACCGCCTTATTGCT<br>TCCCCTTGCCCTCTTGCTCCACGCAGCA<br>CGCCCCGATATAGTCTTGACTCAATCCCC<br>ACCCAGTTTGGCAATGTCATTAGGCAAA<br>CGAGCAACAATTTCATGTAGGGCATCCG<br>AAAGTGTAACGATTTTGGGGAGTCATTT<br>AATTCATTGGTACCAACAAAAGCCTGGA<br>CAACCCCCGACGCTCTTGATCCAATTAG<br>CATCTAACGTCCAAACCGGAGTCCCCGC<br>ACGATTCTCAGGATCCGGTTCCCGGACT<br>GATTTTACATTAACTATTGATCCGGTAGA<br>GGAAGATGACGTCGCTGCTGTCTATTATTGTC<br>TTCAAAGTAGGACGATTCCACGGACATT<br>CGGTGGCGGAACTAAATTGGAGATTAAA<br>GGTTCCACCTCTGGTAGTGGGAAACCCG<br>GGTCCGGTGAAGGGTCCACTAAAGGCC<br>AAATTCAACTCGTTCAATCCGGACCAGA<br>ACTGAAGAAGCCAGGAGAAACTGTCAA<br>AATAAGCTGTAAAGCTTCCGGTTATACAT<br>TTACAGATTATTCCATAAATTGGGTGAAA<br>AGGGCGCCAGGAAAAGGGTTAAAGTGG<br>ATGGGTTGGATTAATACAGAGACTCGGG<br>AACCTGCATATGCTTATGATTTTAGGGGA<br>AGGTTTGCCTTTTCTCTGGAGACTTCCG<br>CTTCAACTGCTTATCTCCAAATTAATAAT<br>CTTAAATATGAGGACACAGCAACATACT<br>TCTGTGCTTTGGACTATAGTTATGCTATG<br>GATTACTGGGGACAAGGAACCAGTGTC<br>ACTGTAAGTTCCGCTGCTGCGACGACCA<br>CTCCTGCACCGCGACCACCCACTCCTGC<br>CCCTACTATTGCTAGTCAACCACTTAGCT<br>TGCGACCTGAGGCATGTCGGCCCGCGGC<br>AGGTGGCGCAGTCCACACCAGGGGTTT<br>AGACTTTGCTTGTGATATTTATATTTGGG | MALPVTALLL<br>PLALLLHAAR<br>PDIVLTQSPPS<br>LAMSLGKRAT<br>ISCRASESVTIL<br>GSHLIHWYQQ<br>KPGQPPTLLIQ<br>LASNVQTGVP<br>ARFSGSGSRTD<br>FTLTIDPVEED<br>DVAVYYCLQS<br>RTIPRTFGGGT<br>KLEIKGSTSGS<br>GKPGSGEGST<br>KGQIQLVQSGP<br>ELKKPGETVKI<br>SCKASGYTFT<br>DYSINWVKRA<br>PGKGLKWMG<br>WINTETREPAY<br>AYDFRGRFAFS<br>LETSASTAYLQ<br>INNLKYEDTAT<br>YFCALDYSYA<br>MDYWGQGTS<br>VTVSSAAATT<br>TPAPRPPTPAP<br>TIASQPLSLRP<br>EACRPAAGGA<br>VHTRGLDFAC<br>DIYIWAPLAGT<br>CGVLLLSLVIT<br>LYCKRGRKKL<br>LYIFKQPFMRP |

TABLE 1B-continued

| ID | IRES Sequence | CAR Sequence | CAR Sequence |
|---|---|---|---|
| | AGAATTACA (SEQ ID NO: 16) | CACCACTCGCCGGGACTTGCGGTGTTCT TCTCTTGTCCCTTGTTATAACTCTTTATTG TAAGCGCGGAAGGAAGAAATTGTTATAT ATTTTCAAACAACCTTTTATGCGACCCGT ACAAACAACTCAGGAAGAGGACGGGTG TTCTTGTCGGTTTCCAGAAGAGGAAGAG GGTGGGTGTGAACTCCGGGTCAAATTTA GTAGGTCAGCAGATGCGCCGGCGTACCA ACAAGGCCAAAACCAACTGTATAATGAA CTCAATCTCGGTAGGCGTGAGGAATATG ATGTCCTTGATAAAAGGCGCGGGAGAGA TCCAGAAATGGGCGGAAAACCACGGCG AAAGAATCCGCAGGAAGGGTTATATAAC GAACTTCAAAAGGATAAAATGGCTGAA GCTTATTCCGAAATTGGCATGAAAGGAG AGCGACGTAGGGGCAAAGGGCATGATG GCCTTTACCAAGGGCTCTCAACCGCTAC AAAAGATACTTACGACGCTTTACATATGC AAGCACTTCCACCCAGG (SEQ ID NO: 103) | VQTTQEEDGC SCRFPEEEEGG CELRVKFSRSA DAPAYQQGQN QLYNELNLGR REEYDVLDKR RGRDPEMGGK PRRKNPQEGL YNELQKDKM AEAYSEIGMK GERRRGKGHD GLYQGLSTAT KDTYDALHM QALPPR (SEQ ID NO: 119) |
| Construct F | GTGGCCACGCCCGGGCC ACCGATACTTCCCTTCAC TCCTTCGGGACTGTTGGG GAGGAACACAACAGGGC TCCCCTGTTTTCCCATTCC TTCCCCCTTTTCCCAACC CCAACCGCCGTATCTGGT GGCGGCAAGACACACGG GTCTTTCCCTCTAAAGCA CAATTGTGTGTGTGTCCC AGGTCCTCCTGCGTACGG TGCGGGAGTGCTCCCACC CAACTGTTGTAAGCCTGT CCAACGCGTCGTCCTGGC AAGACTATGACGTCGCAT GTTCCGCTGCGGATGCCG ACCGGGTAACCGGTTCCC CAGTGTGTGTAGTGCGAT CTTCCAGGTCCTCCTGGT TGGCGTTGTCCAGAAACT GCTTCAGGTAAGTGGGGT GTGCCCAATCCCTACAAA GGTTGATTCTTTCACCAC CTTAGGAATGCTCCGGAG GTACCCCAGCAACAGCTG GGATCTGACCGGAGGCTA ATTGTCTACGGGTGGTGT TTCCTTTTTCTTTTCACAC AACTCTACTGCTGACAAC TCACTGACTATCCACTTG CTCTGTCACG (SEQ ID NO: 17) | ATGGCTCTGCCTGTGACAGCTCTGCTGC TGCCTCTGGCTCTGCTTCTGCATGCCGCC AGACCTGACATCCAGATGACCCAGACAA CCAGCAGCCTGTCTGCCAGCCTGGGCGA TAGAGTGACCATCAGCTGTAGAGCCAGC CAGGACATCAGCAAGTACCTGAACTGGT ATCAGCAGAAACCCGACGGCACCGTGA AGCTGCTGATCTACCACACCAGCAGACT GCACAGCGGCGTGCCAAGCAGATTTTCT GGCAGCGGCTCTGGCACCGACTACAGC CTGACAATCAGCAACCTGGAACAAGAG GATATCGCTACCTACTTCTGCCAGCAAG GCAACACCCTGCCTTACACCTTTGGCGG AGGCACCAAGCTGGAAATCACAGGCGG CGGAGGAAGCGGAGGCGGAGGATCTGG TGGTGGTGGATCTGAAGTGAAACTGCAA GAGTCTGGCCCTGGCCTGGTGGCCCCAT CTCAATCTCTGAGCGTGACCTGTACCGT CAGCGGAGTGTCCCTGCCTGATTATGGC GTGTCCTGGATCCGGCAGCCTCCTAGAA AAGGCCTGGAATGGCTGGGCGTGATCTG GGGCAGCGAGACAACCTACTACAACAG CGCCCTGAAGTCCCGGCTGACCATCATC AAGGACAACTCCAAGAGCCAGGTGTTC CTGAAGATGAACAGCCTGCAGACCGAC GACACCGCCATCTACTATTGCGCCAAGC ACTACTACTACGGCGGCAGCTACGCCAT GGATTATTGGGGCCAGGGCACCAGCGTG ACCGTGTCTAGCATCGAAGTGATGTACC CTCCACCTTACCTGGACAACGAGAAGTC CAACGGCACCATCATCCACGTGAAGGGC AAGCACCTGTGTCCTTCTCCACTGTTCC CCGGACCTAGCAAGCCTTTCTGGGTGCT CGTTGTTGTTGGCGGCGTGCTGGCCTGT TACTCTCTGCTGGTTACCGTGGCCTTCAT CATCTTTTGGGTCCGAAGCAAGCGGAGC CGGCTGCTGCACTCCGACTACATGAACA TGACCCCTAGACGGCCCGGACCAACCA GAAAGCACTACCAGCCTTACGCTCCTCC TAGAGACTTCGCCGCCTACCGGTCCAGA GTGAAGTTCAGCAGATCCGCCGATGCTC CCGCCTATCAGCAGGGCCAAAACCAGCT GTACAACGAGCTGAACCTGGGGAGAAG AGAAGAGTACGACGTGCTGGACAAGCG GAGAGGCAGAGATCCTGAAATGGGCGG CAAGCCCAGACGGAAGAATCCTCAAGA GGGCCTGTATAATGAGCTGCAGAAAGAC AAGATGGCCGAGGCCTACAGCGAGATC GGAATGAAGGGCGAGCGCAGAAGAGGC AAGGGACACGATGGACTGTACCAGGGC CTGAGCACCGCCACCAAGGATACCTATG ATGCCCTGCACATGCAGGCCCTGCCTCC AAGA (SEQ ID NO: 21) | MALPVTALLL PLALLLHAAR PDIQMTQTTSS LSASLGDRVTI SCRASQDISKY LNWYQQKPD GTVKLLIYHTS RLHSGVPSRFS GSGSGTDYSL TISNLEQEDIA TYFCQQGNTL PYTFGGGTKL EITGGGGSGG GGSGGGGSEV KLQESGPGLV APSQSLSVTCT VSGVSLPDYG VSWIRQPPRK GLEWLGVIWG SETTYYNSAL KSRLTIIKDNS KSQVFLKMNS LQTDDTAIYY CAKHYYYGGS YAMDYWGQG TSVTVSSIEVM YPPPYLDNEK SNGTIIHVKGK HLCPSPLFPGP SKPFWVLVVV GGVLACYSLL VTVAFIIFWVR SKRSRLLHSD YMNMTPRRPG PTRKHYQPYA PPRDFAAYRSR VKFSRSADAP AYQQGQNQLY NELNLGRREE YDVLDKRRGR DPEMGGKPRR KNPQEGLYNE LQKDKMAEA YSEIGMKGER RRGKGHDGLY QGLSTATKDT YDALHMQALP PR (SEQ ID NO: 29) |

TABLE 1B-continued

Exemplary Constructs (DNA Templates)

| ID | IRES Sequence | CAR Sequence | CAR Sequence |
|---|---|---|---|
| Construct G | CCCCCCTCCCCCCCTTCC CTTCCCTTTGCAACGCAA CAATTGTAAGTGCCCTCA CCTGTCAATTGGGACCAC CACTTTCAGTGACCCCAT GCGAAGTGCTGAGAGAA AGGAAGCTTTCTTACCCT TCATTTGTGAACCCACTG GTCTAAGCCGCTTGGAAT ACGATGAGTGGAAAAGTT CATTCTTAATGGAGTGAA ACATGCTTAAATTTCCAG CTCGTGCTGGTCTTTCCA GTACGGGGCGGCCCTGTC TGGCCGTAATTCTTCAGA GTGTCACGCCACACTTGT GGATCTCACGTGCCACAT GACAGCGCTACAGCTGG AACTGGGTGCTTGGTGCC CATGGAGTAACAGCGAAA AGTGTTAGATCAAGCCTT GCTTGGGCTATGAGCCTG CGGAACAACAACTGGTA ACAGTTGCCTCAGGGGCC GAAAGCCACGGTGTTAAC AGCACCCTCATAGTTTGA TCCACCTCAGGGTGGTGA TGTTTAGCAGTTAGTAGT TGCCAATCTGTGTTCACT GAAATCTCGGCATACCGT GTAGTGTACAGGGGTGAA GGATGCCCAGAAGGTACC CGTAGGTAACCTTAAGAG ACTATGGATCTGATCTGG GGCCTTGTCCGGAGTGCT TTACACACGGCTCAAGGT TAAAAAACGTCTAGCCCC ACAGAGCCCGAGGGATTC GGGTTTTCCCTTTAAAAA CCCGACTAGAGCTTATGG TGACAATTATTGCTGTTCA GACGAACAGTGTAATTGT TGTCTATTCACAGCAGTT CTATCAGAGCTTTTCCCA CAACGGATCTTCTTGGCA AGCAAATACAGCAGGAGT CAAT (SEQ ID NO: 8) | ATGGCCCTCCCCGTCACAGCTCTCCTGC TCCCACTGGCCCTTCTTTTGCACGCTGCT CGCCCCGATATCGTGCTCACCCAGTCAC CTCCAAGCCTTGCCATGAGCCTCGGGAA ACGGGCTACCATCTCCTGCCGGGCTTCA GAGTCCGTCACCATCCTCGGGTCACACC TCATCCACTGGTACCAACAGAAACCAGG GCAGCCTCCTACCCTCTTGATCCAGTTG GCCTCCAACGTGCAAACTGGGGTTCCCG CCAGGTTCAGTGGCTCCGGATCCCGGAC AGATTTCACACTTACCATCGATCCTGTGG AGGAGGACGATGTGGCCGTCTATTACTG CCTGCAGTCTCGCACCATCCCTCGGACC TTCGGTGGAGGCACCAAGCTCGAGATCA AGGGTAGCACCTCCGGCTCTGGAAAGC CAGGCTCTGGTGAGGGTTCTACCAAGGG CCAAATCCAGCTGGTCCAGTCTGGGCCC GAGCTGAAGAAACCCGGGGAGACCGTG AAGATCTCCTGCAAGGCCTCCGGTTATA CCTTCACCGACTACTCCATCAACTGGGT CAAGCGCGCTCCTGGAAAGGGCCTCAA GTGGATGGGCTGGATCAACACCGAAACC CGCGAGCCTGCCTATGCTTACGACTTCA GGGGCCGGTTCGCTTTCTCACTGGAGAC CTCCGCTTCCACAGCCTACCTCCAGATC AACAACCTCAAGTACGAAGACACCGCC ACCTATTTCTGCGCTCTCGACTATTCCTA CGCTATGGACTACTGGGGTCAGGGCACC TCTGTGACCGTCTCTAGCGCAGCCGCCA CCACAACACCAGCCCCACGGCCACCTAC TCCCGCACCCACCATCGCATCCCAACCA CTCAGTCTGAGGCCCGAGGCCTGTAGAC CTGCTGCTGGAGGCCGATGCATACCCG CGGTCTCGACTTCGCCTGCGACATCTATA TCTGGGCCCCATTGGCAGGTACCTGTGG CGTGCTGCTGCTGTCACTCGTCATCACC CTGTACTGCCGGAGTAAGCGCTCTAGGC TGTTGCACAGCGACTACATGAACATGAC CCCAAGAAGACCAGGGCCTACCCGGAA GCACTACCAGCCATACGCACCTCCCCGG CGTGGGAGGGATCCTGAGATGGGAGGCAAG GACTTTGCCGCTATCGGTCTCGGGTGA AGTTCTCACGCTCCGCTGATGCCCCAGC ATACCAGCAGGGCAGAACCAGCTGTA CAATGAGCTCAACCTCGGTCGCCGCGAA GAGTACGACGTGCTCGACAAGAGAAGG GGCAGGGACCCTGAGATGGGAGGCAAG CCCCGCAGAAAGAATCCCCAGGAAGGT CTGTACAACGAGCTGCAAAAGGATAAG ATGGCTGAGGCCTACAGCGAGATCGGCA TGAAGGGCGAAAGGAGACGGGGAAAG GGCCACGACGGGCTCTACCAGGGACTCT CCACCGCCACCAAGGACACCTACGACG CCCTCCACATGCAGGCTCTGCCACCCAG G (SEQ ID NO: 104) | MALPVTALLL PLALLLHAAR PDIVLTQSPPS LAMSLGKRAT ISCRASESVTIL GSHLIHWYQQ KPGQPPTLLIQ LASNVQTGVP ARFSGSGSRTD FTLTIDPVEED DVAVYYCLQS RTIPRTFGGGT KLEIKGSTSGS GKPGSGEGST KGQIQLVQSGP ELKKPGETVKI SCKASGYTFT DYSINWVKRA PGKGLKWMG WINTETREPAY AYDFRGRFAFS LETSASTAYLQ INNLKYEDTAT YFCALDYSYA MDYWGQGTS VTVSSAAATT TPAPRPPTPAP TIASQPLSLRP EACRPAAGGA VHTRGLDFAC DIYIWAPLAGT CGVLLLSLVIT LYCRSKRSRLL HSDYMNMTP RRPGPTRKHY QPYAPPRDFA AYRSRVKFSRS ADAPAYQQGQ NQLYNELNLG RREEYDVLDK RRGRDPEMGG KPRRKNPQEG LYNELQKDKM AEAYSEIGMK GERRRGKGHD GLYQGLSTAT KDTYDALHM QALPPR (SEQ ID NO: 120) |
| Construct H | CCCCCCTCCCCCCCTTCC CTTCCCTTTGCAACGCAA CAATTGTAAGTGCCCTCA CCTGTCAATTGGGACCAC CACTTTCAGTGACCCCAT GCGAAGTGCTGAGAGAA AGGAAGCTTTCTTACCCT TCATTTGTGAACCCACTG GTCTAAGCCGCTTGGAAT ACGATGAGTGGAAAAGTT CATTCTTAATGGAGTGAA ACATGCTTAAATTTCCAG CTCGTGCTGGTCTTTCCA GTACGGGGCGGCCCTGTC TGGCCGTAATTCTTCAGA GTGTCACGCCACACTTGT GGATCTCACGTGCCACAT GACAGCGCTACAGCTGG AACTGGGTGCTTGGTGCC CATGGAGTAACAGCGAAA | ATGGCACTTCCCGTCACCGCTCTCCTGC TGCCCCTCGCACTGCTGCTCCATGCAGC CCGCCCAGACATCGTCCTGACCCAGTCC CCTCCCTCCCTCGCAATGTCCCTCGGGA AACGGGCCACCATCAGCTGCCGGGCCTC TGAGTCAGTGACAATCCTCGGAAGCCAT CTGATCCATTGGTACCAGCAGAAACCCG GTCAGCCTCCAACCCTCCTCATCCAGCT GGCCTCCAACGTGCAGACAGGAGTCCC CGCTCGGTTCTCAGGCAGCGGTTCCAGG ACCGACTTCACCCTGACCATCGACCCCG TGGAAGAGGACGATGTGGCTGTGTACTA CTGCCTCCAGTCCCGGACCATCCCACGG ACCTTCGGAGGTGGGACAAAGCTGGAG ATCAAAGGCAGCACCTCCGGTTCTGGC AAGCCAGGGTCAGGTGAGGGGAGCACA AAGGGTCAGATCCAGCTGGTGCAGAGC GGTCCCGAGCTGAAGAAGCCCGGGGAG ACCGTTAAGATCTCCTGCAAGGCTAGCG GGTACACCTTCACCGACTATAGTATCAAC | MALPVTALLL PLALLLHAAR PDIVLTQSPPS LAMSLGKRAT ISCRASESVTIL GSHLIHWYQQ KPGQPPTLLIQ LASNVQTGVP ARFSGSGSRTD FTLTIDPVEED DVAVYYCLQS RTIPRTFGGGT KLEIKGSTSGS GKPGSGEGST KGQIQLVQSGP ELKKPGETVKI SCKASGYTFT DYSINWVKRA PGKGLKWMG WINTETREPAY |

TABLE 1B-continued

<u>Exemplary Constructs (DNA Templates)</u>

| ID | IRES Sequence | CAR Sequence | CAR Sequence |
|---|---|---|---|
| | AGTGTTAGATCAAGCCTT | TGGGTCAAGCGCGCTCCTGGCAAGGGG | AYDFRGRFAFS |
| | GCTTGGGCTATGAGCCTG | CTCAAGTGGATGGGGTGGATCAACACCG | LETSASTAYLQ |
| | CGGAACAACAACTGGTA | AAACCAGGGAGCCCGCATACGCTTATGA | INNLKYEDTAT |
| | ACAGTTGCCTCAGGGGCC | CTTTCGGGGCCGGTTCGCCTTTTCCCTG | YFCALDYSYA |
| | GAAAGCCACGGTGTTAAC | GAGACCAGCGCCTCTACCGCCTACCTCC | MDYWGQGTS |
| | AGCACCCTCATAGTTTGA | AGATCAACAACCTGAAGTACGAGGACA | VTVSSIEVMYP |
| | TCCACCTCAGGGTGGTGA | CCGCCACCTACTTCTGCGCACTCGACTA | PPYLDNEKSN |
| | TGTTTAGCAGTTAGTAGT | CTCCTACGCTATGGACTACTGGGGTCAG | GTIIHVKGKHL |
| | TGCCAATCTGTGTTCACT | GGTACCTCCGTCACCGTCTCCAGCATCG | CPSPLFPGPSK |
| | GAAATCTCGGCATACCGT | AGGTCATGTACCCTCCTCCCTACCTGGA | PFWVLVVVGG |
| | GTAGTGTACAGGGGTGAA | CAACGAGAAGTCCAACGGCACCATCATC | VLACYSLLVT |
| | GGATGCCCAGAAGGTACC | CATGTGAAGGGCAAGCATCTCTGCCCCA | VAFIIFWVRSK |
| | CGTAGGTAACCTTAAGAG | GCCCACTGTTCCCCGGACCCTCTAAGCC | RSRLLHSDYM |
| | ACTATGGATCTGATCTGG | CTTCTGGGTCCTGGTCGTCGTCGGCGGT | NMTPRRPGPT |
| | GGCCTTGTCCGGAGTGCT | GTTCTGGCTTGCTACAGCTTGCTGGTCA | RKHYQPYAPP |
| | TTACACACGGCTCAAGGT | CCGTCGCCTTCATCATCTTCTGGGTGCGC | RDFAAYRSRV |
| | TAAAAAACGTCTAGCCCC | TCCAAGAGGAGCCGGCTGCTGCATAGCG | KFSRSADAPA |
| | ACAGAGCCCGAGGGATTC | ACTACATGAACATGACCCCTAGAAGGCC | YQQGQNQLYN |
| | GGGTTTTCCCTTTAAAAA | TGGTCCAACCCGCAAGCACTACCAGCCT | ELNLGRREEY |
| | CCCGACTAGAGCTTATGG | TACGCCCCTCCACGGGACTTCGCAGCCT | DVLDKRRGRD |
| | TGACAATTATTGCTGTTCA | ACCGGTCACGGGTGAAGTTCTCTCGGAG | PEMGGKPRRK |
| | GACGAACAGTGTAATTGT | CGCAGATGCCCCAGCATACCAGCAGGGC | NPQEGLYNEL |
| | TGTCTATTCACAGCAGTT | CAGAACCAGCTGTACAACGAACTTAACC | QKDKMAEAYS |
| | CTATCAGAGCTTTTCCCA | TTGGTCGGCGGGAGGAATACGATGTGCT | EIGMKGERRR |
| | CAACGGATCTTCTTGGCA | GGACAAGCGCAGGGGTCGGGATCCTGA | GKGHDGLYQG |
| | AGCAAATACAGCAGGAGT | AATGGGGGGAAACCACGCCGGAAGAA | LSTATKDTYD |
| | CAAT (SEQ ID NO: 8) | CCCACAGGAGGGGCTCTATAACGAGCTC | ALHMQALPPR |
| | | CAAAAGGATAAGATGGCTGAGGCTTACA | (SEQ ID NO: |
| | | GCGAGATTGGAATGAAGGGAGAAAGAA | 121) |
| | | GACGGGGCAAGGGTCACGACGGGTTGT | |
| | | ACCAGGGTCTGAGCACCGCCACCAAGG | |
| | | ACACCTACGACGCCCTCCACATGCAAGC | |
| | | CCTTCCACCCCGC (SEQ ID NO: 105) | |
| Construct I | CCCCCCTCCCCCCCTTCC | ATGGCACTCCCCGTTACCGCCCTTCTGCT | MALPVTALLL |
| | CTTCCCTTTGCAACGCAA | GCCTCTCGCCTTGCTGCTGCACGCAGCC | PLALLLHAAR |
| | CAATTGTAAGTGCCCTCA | AGACCACAGGTCAAGCTGGAGGAGTCT | PQVKLEESGG |
| | CCTGTCAATTGGGACCAC | GGTGGCGGGGCTCGTTCAAGCAGGTCGG | GLVQAGRSLR |
| | CACTTTCAGTGACCCCAT | AGTCTCCGCCTGTCTTGCGCAGCATCAG | LSCAASEHTFS |
| | GCGAAGTGCTGAGAGAA | AGCATACCTTCTCCTCACACGTGATGGG | SHVMGWFRQ |
| | AGGAAGCTTTCTTACCCT | GTGGTTCAGGCAAGCTCCCGGTAAGGA | APGKERESVA |
| | TCATTTGTGAACCCACTG | GAGGGAGTCCGTGGCCGTTATCGGCTGG | VIGWRDISTSY |
| | GTCTAAGCCGCTTGGAAT | CGCGATATCAGCACCTCCTACGCAGACA | ADSVKGRFTIS |
| | ACGATGAGTGGAAAAGTT | GCGTTAAGGGCCGGTTCACTATCTCCAG | RDNAKKTLYL |
| | CATTCTTAATGGAGTGAA | GGACAACGCTAAGAAGACACTTACCTC | QMNSLKPEDT |
| | ACATGCTTAAATTTCCAG | CAGATGAACAGTCTGAAGCCCGAGGAC | AVYYCAARRI |
| | CTCGTGCTGGTCTTTCCA | ACCGCAGTGTACTATTGCGCTGCTCGGC | DAADFDSWG |
| | GTACGGGGCGGCCCTGTC | GGATCGATGCTGCCGACTTCGACAGCTG | QGTQVTVSSG |
| | TGGCCGTAATTCTTCAGA | GGGTCAAGGGACCCAGGTCACCGTTTCC | GGGSGGGGSG |
| | GTGTCACGCCACACTTGT | AGCGGAGGTGGCGGAAGTGGTGGCGGA | GGGSEVQLVE |
| | GGATCTCACGTGCCACAT | GGATCAGGTGGTGGAGGCTCCGAGGTC | SGGGLVQAGG |
| | GACAGCGCTACAGCTGG | CAGCTGGTGGAATCAGGAGGCGGCTTG | SLRLSCAASG |
| | AACTGGGTGCTTGGTGCC | GTGCAGGCTGGTGGGTCTTTGCGGTTGT | RTFTMGWFRQ |
| | CATGGAGTAACAGCGAAA | CCTGCGCAGCTTCCGGCAGGACCTTCAC | APGKEREFVA |
| | AGTGTTAGATCAAGCCTT | CATGGGATGGTTCAGACAAGCCCCAGGT | AISLSPTLAYY |
| | GCTTGGGCTATGAGCCTG | AAGGAGCGGGAGTTTGTGGCCGCAATCT | AESVKGRFTIS |
| | CGGAACAACAACTGGTA | CACTGTCTCCCACCCTCGCTTACTACGC | RDNAKNTVVL |
| | ACAGTTGCCTCAGGGGCC | CGAGAGTGTGAAGGGGCGCTTCACAAT | QMNSLKPEDT |
| | GAAAGCCACGGTGTTAAC | CAGTCGCGACAACGCAAAGAACACCGT | ALYYCAADRK |
| | AGCACCCTCATAGTTTGA | CGTCCTGCAAATGAACTCCCTGAAGCCT | SVMSIRPDYW |
| | TCCACCTCAGGGTGGTGA | GAGGATACCGCACTCTATTACTGCGCCG | GQGTQVTVSS |
| | TGTTTAGCAGTTAGTAGT | CCGATCGGAAGAGCGTCATGTCCATCCG | TSTTTPAPRPP |
| | TGCCAATCTGTGTTCACT | GCCCGACTATTGGGGCCAAGGCACCCAA | TPAPTIASQPL |
| | GAAATCTCGGCATACCGT | GTGACCGTCAGCTCCACCTCCACAACCA | SLRPEACRPAA |
| | GTAGTGTACAGGGGTGAA | CTCCCGCCCCAAGACCACCTACCCCAGC | GGAVHTRGLD |
| | GGATGCCCAGAAGGTACC | CCCAACAATCGACAGCCTCTGTCC | FACDIYIWAPL |
| | CGTAGGTAACCTTAAGAG | CTTCGGCCCGAAGCTTGTCGCCCTGCAG | AGTCGVLLLS |
| | ACTATGGATCTGATCTGG | CAGGTGGAGCAGTGCACACCCGGGGAC | LVITLYCRSKR |
| | GGCCTTGTCCGGAGTGCT | TGGACTTCGCCTGCGACATCTACATCTG | SRLLHSDYMN |
| | TTACACACGGCTCAAGGT | GGCACCCCTGGCTGCGACATCTACATCTG | MTPRRPGPTR |
| | TAAAAAACGTCTAGCCCC | GTTGCTGCTGAGCCTGGTGATCACCCTC | KHYQPYAPPR |
| | ACAGAGCCCGAGGGATTC | TACTGCCGCTCTAAGAGAAGCCGGCTGC | DFAAYRSRVK |
| | GGGTTTTCCCTTTAAAAA | TGCATAGCGACTACATGAACATGACCCC | FSRSADAPAY |
| | CCCGACTAGAGCTTATGG | TAGGAGACCAGGACCCACCCGGAAGCA | QQGQNQLYNE |
| | TGACAATTATTGCTGTTCA | CTACCAGCCTTACGCTCCTCCACGGGAT | LNLGRREEYD |

TABLE 1B-continued

Exemplary Constructs (DNA Templates)

| ID | IRES Sequence | CAR Sequence | CAR Sequence |
|---|---|---|---|
| | GACGAACAGTGTAATTGT TGTCTATTCACAGCAGTT CTATCAGAGCTTTTCCCA CAACGGATCTTCTTGGCA AGCAAATACAGCAGGAGT CAAT (SEQ ID NO: 8) | TTCGCTGCTTACCGCAGCCGGGTGAAGT TTTCCAGGTCAGCTGACGCCCCTGCCTA CCAGCAGGGCCAGAACCAATTGTACAA CGAACTGAATCTGGGACGGCGCGAGGA ATACGACGTCCTGGACAAGAGGCGGGG TAGAGATCCCGAGATGGGCGGGAAACCT CGGCGGAAGAACCCTCAGGAGGGGCTC TACAACGAGCTGCAGAAGGATAAGATG GCCGAAGCCTACTCCGAGATCGGGATGA AGGGTGAACGGAGGAGGGGCAAGGGA CACGACGGCCTGTATCAGGGCCTCAGCA CCGCTACCAAGGACACCTACGACGCCCT GCACATGCAGGCTCTCCCACCACGG (SEQ ID NO: 107) | VLDKRRGRDP EMGGKPRRKN PQEGLYNELQ KDKMAEAYSE IGMKGERRRG KGHDGLYQGL STATKDTYDA LHMQALPPR (SEQ ID NO: 123) |
| Construct J | CCCCCCTCCCCCCCTTCC CTTCCCTTTGCAACGCAA CAATTGTAAGTGCCCTCA CCTGTCAATTGGGACCAC CACTTTCAGTGACCCCAT GCGAAGTGCTGAGAGAA AGGAAGCTTTCTTACCCT TCATTTGTGAACCCACTG GTCTAAGCCGCTTGGAAT ACGATGAGTGGAAAAGTT CATTCTTAATGGAGTGAA ACATGCTTAAATTTCCAG CTCGTGCTGGTCTTTCCA GTACGGGGCGGCCCTGTC TGGCCGTAATTCTTCAGA GTGTCACGCCACACTTGT GGATCTCACGTGCCACAT GACAGCGCTACAGCTGG AACTGGGTGCTTGGTGCC CATGGAGTAACAGCGAAA AGTGTTAGATCAAGCCTT GCTTGGGCTATGAGCCTG CGGAACAACAACTGGTA ACAGTTGCCTCAGGGGCC GAAAGCCACGGTGTTAAC AGCACCCTCATAGTTTGA TCCACCTCAGGGTGGTGA TGTTTAGCAGTTAGTAGT TGCCAATCTGTGTTCACT GAAATCTCGGCATACCGT GTAGTGTACAGGGGTGAA GGATGCCCAGAAGGTACC CGTAGGTAACCTTAAGAG ACTATGGATCTGATCTGG GGCCTTGTCCGGAGTGCT TTACACACGGCTCAAGGT TAAAAAACGTCTAGCCCC ACAGAGCCCGAGGGATTC GGGTTTTCCCTTTAAAAA CCCGACTAGAGCTTATGG TGACAATTATTGCTGTTCA GACGAACAGTGTAATTGT TGTCTATTCACAGCAGTT CTATCAGAGCTTTTCCCA CAACGGATCTTCTTGGCA AGCAAATACAGCAGGAGT CAAT (SEQ ID NO: 8) | ATGGCTCTTCCCGTCACCGCTTTGCTGCT GCCCCTGGCACTCCTCCTCCATGCTGCT CGGCCTCAGGTGAAGCTGGAGGAGAGT GGTGGCGGTCTGGTGCAAGCTGGCAGAT CTCTGCGCCTGTCTTGCGCAGCCAGCGA ACACACCTTCTCCTCCCACGTGATGGGG TGGTTTCGGCAGGCACCCGGGAAAGAG CGCGAGTCCGTCGCAGTCATCGGGTGGC GGGACATCTCTACCAGCTACGCAGATTC CGTCAAGGGCCGGTTCACCATTTCCCGG GATAACGCTAAGAAGACCCTCTACCTGC AAATGAACTCTCTGAAGCCCGAAGACA GCCGCCGTCTACTATTGCGCAGCAAGGCG CATCGACGCTGCCGACTTCGACTCTTGG GGCCAAGGAACCCAGGTCACCGTGTCTT CCGGAGGAGGAGGCTCCGGTGGTGGAG GTTCTGGAGGTGGCGGCTCAGAGGTGC AGCTCGTGGAGCAGCCGGTGGTGGACTCG TTCAGGCAGGCGGCAGTTTGCGGCTGTC CTGTGCAGCCTCCGGTCGCACTTTCACT ATGGGATGGTTCCGCCAGGCTCCTGGTA AAGAAAGGGAGTTCGTGGCCATCA GTCTGAGCCCCACCCTCGCATACTACGC CGAGAGCGTGAAGGGTAGGTTCACTATC AGCCGGGACAACGCCAAGAACACCGTG GTGCTCCAGATGAATTCCCTGAAGCCTG AGGATACCGCCCTCTACTACTGCGCTGC CGACCGCAAGAGCGTGATGAGCATCCG GCCTGACTATTGGGGTCAGGGGACACAG GTGACCGTCAGCAGCATCGAGGTGATGT ATCCACCACCCTACCTCGACAACGAGAA GTCCAACGGCACCATCATCCACGTCAAG GGGAAGCACCTCTGCCCTTCCCCTCTGT TCCCTGGCCCCTCAAAGCCCTTCTGGGT CCTGGTGGTGGTTGGTGGGGTGCTGGCT TGCTACTCCCTGCTCGTGACCGTGGCTT TCATCATCTTCTGGGTTCGGAGCAAACG GTCCAGACTGCTGCACTCCGACTACATG AACATGACCCCAAGAAGACCTGGGCCC ACACGGAAGCATTACCAACCCTATGCAC CACCTCGGGATTTCGCCGCCTACAGATC CCGGGTCAAGTTCTCCAGGTCCGCCGAT GCACCAGCCTATCAGCAGGGGCAAAAC CAGCTGTATAATGAGCTGAACCTTGGAC GGCGCGAGGAGTACGACGTGCTCGACA AAAGACGCGGTCGCGACCCAGAGATGG GCGGCAAGCCTAGACGCAAGAATCCCC AGGAGGGGCTCTATAACGAGTTGCAGA AGGATAAGATGGCCGAGGCCTACAGCG AGATCGGGATGAAAGGCGAAAGACGGC GCGGAAAGGGTCACGACGGACTCTACC AGGGCCTGAGCACAGCCACCAAAGACA CCTACGACGCTCTGCATATGCAAGCACT GCCTCCCCGG (SEQ ID NO: 108) | MALPVTALLL PLALLLHAAR PQVKLEESGG GLVQAGRSLR LSCAASEHTFS SHVMGWFRQ APGKERESVA VIGWRDISTSY ADSVKGRFTIS RDNAKKTLYL QMNSLKPEDT AVYYCAARRI DAADFDSWG QGTQVTVSSG GGGSGGGGSG GGGSEVQLVE SGGGLVQAGG SLRLSCAASG RTFTMGWFRQ APGKEREFVA AISLSPTLAYY AESVKGRFTIS RDNAKNTVVL QMNSLKPEDT ALYYCAADRK SVMSIRPDYW GQGTQVTVSSI EVMYPPPYLD NEKSNGTIIHV KGKHLCPSPLF PGPSKPFWVL VVVGGVLAC YSLLVTVAFIIF WVRSKRSRLL HSDYMNMTP RRPGPTRKHY QPYAPPRDFA AYRSRVKFSRS ADAPAYQQGQ NQLYNELNLG RREEYDVLDK RRGRDPEMGG KPRRKNPQEG LYNELQKDKM AEAYSEIGMK GERRRGKGHD GLYQGLSTAT KDTYDALHM QALPPR (SEQ ID NO: 124) |
| Construct K | GTGGCCACGCCCGGGCC ACCGATACTTCCCTTCAC TCCTTCGGGACTGTTGGG GAGGAACACAACAGGGC TCCCCTGTTTTCCCATTCC | ATGGCTCTGCCTGTGACAGCTCTGCTGC TGCCTCTGGCTCTGCTTCTGCATGCCGCC AGACCTGACATCCAGATGACTCAGAGCC CCAGCAGCCTGTCTGCCTCTGTGGGAGA CAGAGTGACAATTACCTGCCGGGCCAGC | MALPVTALLL PLALLLHAAR PDIQMTQSPSS LSASVGDRVTI TCRASQDVNT |

TABLE 1B-continued

Exemplary Constructs (DNA Templates)

| ID | IRES Sequence | CAR Sequence | CAR Sequence |
|---|---|---|---|
| | TTCCCCCTTTTCCCAACC | CAGGATGTGAATACTGCTGTCGCCTGGT | AVAWYQQKPG |
| | CCAACCGCCGTATCTGGT | ATCAACAAAAGCCTGGCAAGGCCCCTA | KAPKLLIYSAS |
| | GGCGGCAAGACACACGG | AGCTCCTGATCTACAGCGCCAGCTTTCT | FLYSGVPSRFS |
| | GTCTTTCCCTCTAAAGCA | GTACAGCGGCGTGCCCAGCAGATTCTCC | GSRSGTDFTLT |
| | CAATTGTGTGTGTGTCCC | GGAAGCAGAAGCGGCACAGATTTCACA | ISSLQPEDFAT |
| | AGGTCCTCCTGCGTACGG | CTGACCATAAGCAGCCTGCAGCCAGAG | YYCQQHYTTP |
| | TGCGGGAGTGCTCCCACC | GATTTCGCCACCTACTATTGCCAGCAGC | PTFGQGTKVEI |
| | CAACTGTTGTAAGCCTGT | ACTACACCACACCTCCAACCTTTGGCCA | KRTGSTSGSG |
| | CCAACGCGTCGTCCTGGC | GGGCACCAAGGTCGAGATTAAGAGAAC | KPGSGEGSEV |
| | AAGACTATGACGTCGCAT | AGGCAGCACATCTGGCTCTGGCAAACCT | QLVESGGGLV |
| | GTTCCGCTGCGGATGCCG | GGATCTGGCGAGGGCTCTGAAGTCCAGC | QPGGSLRLSC |
| | ACCGGGTAACCGGTTCCC | TGGTGGAATCTGGCGGAGGACTGGTTCA | AASGFNIKDT |
| | CAGTGTGTGTAGTGCGAT | ACCTGGCGGCTCTCTGAGACTGTCTTGT | YIHWVRQAPG |
| | CTTCCAGGTCCTCCTGGT | GCCGCCTCCGGCTTCAACATCAAGGACA | KGLEWVARIY |
| | TGGCGTTGTCCAGAAACT | CCTACATCCACTGGGTCCGACAAGCCCC | PTNGYTRYAD |
| | GCTTCAGGTAAGTGGGGT | AGGCAAAGGACTTGAGTGGGTCGCCAG | SVKGRFTISAD |
| | GTGCCCAATCCCTACAAA | GATCTACCCCACCAACGGCTACACCAGA | TSKNTAYLQM |
| | GGTTGATTCTTTCACCAC | TACGCCGACTCTGTGAAGGGCAGATTCA | NSLRAEDTAV |
| | CTTAGGAATGCTCCGGAG | CCATCTCTGCCGACACCAGCAAGAATAC | YYCSRWGGD |
| | GTACCCCAGCAACAGCTG | CGCCTACCTGCAGATGAACTCCCTGAGA | GFYAMDVWG |
| | GGATCTGACCGGAGGCTA | GCCGAAGATACCGCTGTGTATTACTGTTC | QGTLVTVSSIE |
| | ATTGTCTACGGGTGGTGT | CAGATGGGGAGGCGACGGCTTCTACGCC | VMYPPPYLDN |
| | TTCCTTTTTCTTTTCACAC | ATGGATGTTTGGGGCCAAGGCACCCTCG | EKSNGTIIHVK |
| | AACTCTACTGCTGACAAC | TGACCGTTTCTTCTATCGAAGTGATGTAC | GKHLCPSPLFP |
| | TCACTGACTATCCACTTG | CCTCCACCTTACCTGGACAACGAGAAGT | GPSKPFWVLV |
| | CTCTGTCACG (SEQ ID NO: | CCAACGGCACCATCATCCACGTGAAGGG | VVGGVLACYS |
| | 17) | CAAGCACCTGTGTCCTTCTCCACTGTTC | LLVTVAFIIFW |
| | | CCCGGACCTAGCAAGCCTTTCTGGGTGC | VRSKRSRLLH |
| | | TCGTTGTTGTTGGCGGCGTGCTGGCCTG | SDYMNMTPRR |
| | | TTACTCTCTGCTGGTTACCGTGGCCTTCA | PGPTRKHYQP |
| | | TCATCTTTTGGGTCCGAAGCAAGCGGAG | YAPPRDFAAY |
| | | CCGGCTGCTGCACTCCGACTACATGAAC | RSRVKFSRSA |
| | | ATGACCCCTAGACGGCCCGGACCAACCA | DAPAYQQGQN |
| | | GAAAGCACTACCAGCCTTACGCTCCTCC | QLYNELNLGR |
| | | TAGAGACTTCGCCGCCTACCGGTCCAGA | REEYDVLDKR |
| | | GTGAAGTTCAGCAGATCCGCCGATGCTC | RGRDPEMGGK |
| | | CCGCCTATCAGCAGGGCCAAAACCAGCT | PRRKNPQEGL |
| | | GTACAACGAGCTGAACCTGGGGAGAAG | YNELQKDKM |
| | | AGAAGAGTACGACGTGCTGGACAAGCG | AEAYSEIGMK |
| | | GAGAGGCAGAGATCCTGAAATGGGCGG | GERRRGKGHD |
| | | CAAGCCCAGACGGAAGAATCCTCAAGA | GLYQGLSTAT |
| | | GGGCCTGTATAATGAGCTGCAGAAAGAC | KDTYDALHM |
| | | AAGATGGCCGAGGCCTACAGCGAGATC | QALPPR (SEQ |
| | | GGAATGAAGGGCGAGCGCAGAAGAGGC | ID NO: 117) |
| | | AAGGGACACGATGGACTGTACCAGGGC | |
| | | CTGAGCACCGCCACCAAGGATACCTATG | |
| | | ATGCCCTGCACATGCAGGCCCTGCCTCC | |
| | | AAGA (SEQ ID NO: 101) | |
| Construct L | GTGGCCACGCCCGGGCC | ATGGCTCTGCCTGTGACAGCTCTGCTGC | MALPVTALLL |
| | ACCGATACTTCCCTTCAC | TGCCTCTGGCTCTGCTTCTGCATGCCGCC | PLALLLHAAR |
| | TCCTTCGGGACTGTTGGG | AGACCTGACATCCAGATGACTCAGAGCC | PDIQMTQSPSS |
| | GAGGAACACAACAGGGC | CCAGCAGCCTGTCTGCCTCTGTGGGAGA | LSASVGDRVTI |
| | TCCCCTGTTTTCCCATTCC | CAGAGTGACAATTACCTGCCGGGCCAGC | TCRASQDVNT |
| | TTCCCCCTTTTCCCAACC | CAGGATGTGAATACTGCTGTCGCCTGGT | AVAWYQQKPG |
| | CCAACCGCCGTATCTGGT | ATCAACAAAAGCCTGGCAAGGCCCCTA | KAPKLLIYSAS |
| | GGCGGCAAGACACACGG | AGCTCCTGATCTACAGCGCCAGCTTTCT | FLYSGVPSRFS |
| | GTCTTTCCCTCTAAAGCA | GTACAGCGGCGTGCCCAGCAGATTCTCC | GSRSGTDFTLT |
| | CAATTGTGTGTGTGTCCC | GGAAGCAGAAGCGGCACAGATTTCACA | ISSLQPEDFAT |
| | AGGTCCTCCTGCGTACGG | CTGACCATAAGCAGCCTGCAGCCAGAG | YYCQQHYTTP |
| | TGCGGGAGTGCTCCCACC | GATTTCGCCACCTACTATTGCCAGCAGC | PTFGQGTKVEI |
| | CAACTGTTGTAAGCCTGT | ACTACACCACACCTCCAACCTTTGGCCA | KRTGSTSGSG |
| | CCAACGCGTCGTCCTGGC | GGGCACCAAGGTCGAGATTAAGAGAAC | KPGSGEGSEV |
| | AAGACTATGACGTCGCAT | AGGCAGCACATCTGGCTCTGGCAAACCT | QLVESGGGLV |
| | GTTCCGCTGCGGATGCCG | GGATCTGGCGAGGGCTCTGAAGTCCAGC | QPGGSLRLSC |
| | ACCGGGTAACCGGTTCCC | TGGTGGAATCTGGCGGAGGACTGGTTCA | AASGFNIKDT |
| | CAGTGTGTGTAGTGCGAT | ACCTGGCGGCTCTCTGAGACTGTCTTGT | YIHWVRQAPG |
| | CTTCCAGGTCCTCCTGGT | GCCGCCTCCGGCTTCAACATCAAGGACA | KGLEWVARIY |
| | TGGCGTTGTCCAGAAACT | CCTACATCCACTGGGTCCGACAAGCCCC | PTNGYTRYAD |
| | GCTTCAGGTAAGTGGGGT | AGGCAAAGGACTTGAGTGGGTCGCCAG | SVKGRFTISAD |
| | GTGCCCAATCCCTACAAA | GATCTACCCCACCAACGGCTACACCAGA | TSKNTAYLQM |
| | GGTTGATTCTTTCACCAC | TACGCCGACTCTGTGAAGGGCAGATTCA | NSLRAEDTAV |
| | CTTAGGAATGCTCCGGAG | CCATCTCTGCCGACACCAGCAAGAATAC | YYCSRWGGD |
| | GTACCCCAGCAACAGCTG | CGCCTACCTGCAGATGAACTCCCTGAGA | GFYAMDVWG |
| | GGATCTGACCGGAGGCTA | GCCGAAGATACCGCTGTGTATTACTGTTC | QGTLVTVSSTT |

TABLE 1B-continued

Exemplary Constructs (DNA Templates)

| ID | IRES Sequence | CAR Sequence | CAR Sequence |
|---|---|---|---|
| | ATTGTCTACGGGTGGTGT<br>TTCCTTTTTCTTTTCACAC<br>AACTCTACTGCTGACAAC<br>TCACTGACTATCCACTTG<br>CTCTGTCACG (SEQ ID NO:<br>17) | CAGATGGGGAGGCGACGGCTTCTACGCC<br>ATGGATGTTTGGGGCCAAGGCACCCTCG<br>TGACCGTTTCTTCTACCACCACCAGC<br>TCCTCGGCCTCCAACTCCTGCTCCTACA<br>ATTGCCAGCCAGCCTCTGTCTCTGAGGC<br>CCGAAGCTTGTAGACCTGCTGCTGGCGG<br>AGCCGTGCATACAAGAGGACTGGATTTC<br>GCCTGCGACATCTACATCTGGGCTCCTCT<br>GGCCGGAACATGTGGCGTTCTGCTGCTG<br>AGCCTGGTCATCACCCTGTACTGTAAGC<br>GGGGCAGAAAGAAGCTGCTGTACATCTT<br>CAAGCAGCCCTTCATGCGGCCCGTGCAG<br>ACCACACAAGAGGAAGATGGCTGCTCC<br>TGCAGATTCCCCGAGGAAGAAGAAGGC<br>GGCTGCGAGCTGAGAGTGAAGTTCAGC<br>AGATCCGCCGATGCTCCCGCCTATCAGC<br>AGGGCCAAAACCAGCTGTACAACGAGC<br>TGAACCTGGGGAGAAGAGAAGAGTACG<br>ACGTGCTGGACAAGCGGAGAGGCAGAG<br>ATCCTGAAATGGGCGGCAAGCCCAGAC<br>GGAAGAATCCTCAAGAGGGCCTGTATAA<br>TGAGCTGCAGAAAGACAAGATGGCCGA<br>GGCCTACAGCGAGATCGGAATGAAGGG<br>CGAGCGCAGAAGAGGCAAGGGACACGA<br>TGGACTGTACCAGGGCCTGAGCACCGCC<br>ACCAAGGATACCTATGATGCCCTGCACA<br>TGCAGGCCCTGCCTCCAAGA (SEQ ID<br>NO: 102) | TPAPRPPTPAP<br>TIASQPLSLRP<br>EACRPAAGGA<br>VHTRGLDFAC<br>DIYIWAPLAGT<br>CGVLLLSLVIT<br>LYCKRGRKKL<br>LYIFKQPFMRP<br>VQTTQEEDGC<br>SCRFPEEEEGG<br>CELRVKFSRSA<br>DAPAYQQGQN<br>QLYNELNLGR<br>REEYDVLDKR<br>RGRDPEMGGK<br>PRRKNPQEGL<br>YNELQKDKM<br>AEAYSEIGMK<br>GERRRGKGHD<br>GLYQGLSTAT<br>KDTYDALHM<br>QALPPR (SEQ<br>ID NO: 118) |
| Construct<br>M | CCCCCCTCCCCCCCTTCC<br>CTTCCCTTTGCAACGCAA<br>CAATTGTAAGTGCCCTCA<br>CCTGTCAATTGGGACCAC<br>CACTTTCAGTGACCCCAT<br>GCGAAGTGCTGAGAGAA<br>AGGAAGCTTTCTTACCCT<br>TCATTTGTGAACCCACTG<br>GTCTAAGCCGCTTGGAAT<br>ACGATGAGTGGAAAAGTT<br>CATTCTTAATGGAGTGAA<br>ACATGCTTAAATTTCCAG<br>CTCGTGCTGGTCTTTCCA<br>GTACGGGGCGGCCCTGTC<br>TGGCCGTAATTCTTCAGA<br>GTGTCACGCCACACTTGT<br>GGATCTCACGTGCCACAT<br>GACAGCGCTACAGCTGG<br>AACTGGGTGCTTGGTGCC<br>CATGGAGTAACAGCGAAA<br>AGTGTTAGATCAAGCCTT<br>GCTTGGGCTATGAGCCTG<br>CGGAACAACAACTGGTA<br>ACAGTTGCCTCAGGGGCC<br>GAAAGCCACGGTGTTAAC<br>AGCACCCTCATAGTTTGA<br>TCCACCTCAGGGTGGTGA<br>TGTTTAGCAGTTAGTAGT<br>TGCCAATCTGTGTTCACT<br>GAAATCTCGGCATACCGT<br>GTAGTGTACAGGGGTGAA<br>GGATGCCCAGAAGGTACC<br>CGTAGGTAACCTTAAGAG<br>ACTATGGATCTGATCTGG<br>GGCCTTGTCCGGAGTGCT<br>TTACACACGGCTCAAGGT<br>TAAAAAACGTCTAGCCCC<br>ACAGAGCCCGAGGGATTC<br>GGGTTTTCCCTTTAAAAA<br>CCCGACTAGAGCTTATGG<br>TGACAATTATTGCTGTTCA<br>GACGAACAGTGTAATTGT<br>TGTCTATTCACAGCAGTT<br>CTATCAGAGCTTTTCCCA<br>CAACGGATCTTCTTGGCA<br>AGCAAATACAGCAGGAGT | ATGGCACTGCCCGTCACCGCACTCCTGC<br>TCCCACTGGCACTGCTGCTCCATGCAGC<br>TCGCCCCGATATCCAGATGACCCAGACC<br>ACCTCTAGCCTCAGCGCCTCTCTGGGTG<br>ACCGCGTCACCATCTCTTGCCGGGCCAG<br>CCAAGACATCTCTAAGTACCTGAACTGG<br>TACCAGCAGAAACCTGACGGAACCGTG<br>AAGCTGCTGATCTACCACACCAGTCGGC<br>TGCATTCCGGGGTGCCTTCCAGGTTCAG<br>CGGTTCCGGCTCTGGGACCGATTATAGT<br>CTCACCATCTCCAACCTCGAGCAGGAGG<br>ACATCGCAACCTACTTCTGCCAGCAGGG<br>GAACACCCTGCCCTACACCTTCGGTGGC<br>GGGACCAAGCTGGAGATCACTGGAGGT<br>GGTGGCAGCGGAGGTGGAGGATCAGGT<br>GGAGGCGGTAGCGAGGTGAAGCTGCAG<br>GAGTCCGGACCTGGTCTGGTGGCCCCAA<br>GCCAGTCCCTCAGCGTCACCTGCACAGT<br>GTCCGGGGTGTCCCTGCCTGACTACGGT<br>GTCTCCTGGATCAGGCAACCACCCCGGA<br>AGGGTCTCGAGTGGCTGGGCGTCATCTG<br>GGGCTCCGAGACCACCTACTACAACAGC<br>GCTCTGAAGTCCCGGCTGACCATCATCA<br>AAGACAACTCCAAGAGCCAGGTGTTCTT<br>GAAGATGAACTCCCTGCAAACCGATGAC<br>ACCGCCATCTACTACTGCGCCAAGCACT<br>ACTACTATGGCGGTAGCTACGCCATGGAT<br>TATTGGGGTCAGGGCACCAGTGTCACCG<br>TCTCCTCCATCGAGGTGATGTACCCTCCA<br>CCCTATCTGGACAACGAGAAGTCCAACG<br>GCACCATCATCCACGTGAAGGGCAAGCA<br>CCTGTGCCCTAGCCCTCTGTTCCCAGGA<br>CCCTCCAAGCCCTTCTGGGTGCTGGTCG<br>TGGTGGGAGGAGTCCTGGCCTGCTATTC<br>CCTCCTCGTCACCGTGGCATTTATCATCT<br>TCTGGGTCCGGAGCAAGCGGTCACGCCT<br>GCTCCACTCCGACTACATGAACATGACT<br>CCTCGCAGACCTGGACCCACCCGGAAG<br>CACTACCAGCCTTATGCCCCACCCCGCG<br>ACTTTGCCGCTTACCGCTCTCGGGTCAA<br>GTTCTCTCGGTCAGCAGACGCCCCTGCA<br>TACCAGCAGGGCCAGAACCAGCTGTATA<br>ACGAGCTGAACCTCGGCAGACGGGAGG<br>AGTACGATGTGCTGGACAAGAGGAGAG<br>GCAGAGACCCCGAGATGGGTGGTAAGC<br>CACGGCGCAAGAACCCACAGGAGGGCT | MALPVTALLL<br>PLALLLHAAR<br>PDIQMTQTTSS<br>LSASLGDRVTI<br>SCRASQDISKY<br>LNWYQQKPD<br>GTVKLLIYHTS<br>RLHSGVPSRFS<br>GSGSGTDYSL<br>TISNLEQEDIA<br>TYFCQQGNTL<br>PYTFGGGTKL<br>EITGGGGSGG<br>GGSGGGGSEV<br>KLQESGPGLV<br>APSQSLSVTCT<br>VSGVSLPDYG<br>VSWIRQPPRK<br>GLEWLGVIWG<br>SETTYYNSAL<br>KSRLTIIKDNS<br>KSQVFLKMNS<br>LQTDDTAIYY<br>CAKHYYYGGS<br>YAMDYWGQG<br>TSVTVSSIEVM<br>YPPPYLDNEK<br>SNGTIIHVKGK<br>HLCPSPLFPGP<br>SKPFWVLVVV<br>GGVLACYSLL<br>VTVAFIIFWVR<br>SKRSRLLHSD<br>YMNMTPRRPG<br>PTRKHYQPYA<br>PPRDFAAYRSR<br>VKFSRSADAP<br>AYQQGQNQLY<br>NELNLGRREE<br>YDVLDKRRGR<br>DPEMGGKPRR<br>KNPQEGLYNE<br>LQKDKMAEA<br>YSEIGMKGER<br>RRGKGHDGLY<br>QGLSTATKDT |

TABLE 1B-continued

Exemplary Constructs (DNA Templates)

| ID | IRES Sequence | CAR Sequence | CAR Sequence |
|---|---|---|---|
| | CAAT (SEQ ID NO: 8) | TGTACAACGAACTGCAGAAGGACAAGA TGGCCGAGGCCTACAGCGAGATCGGCAT GAAGGGAGAGAGGCGCAGGGGCAAGG GTCACGACGGCCTGTACCAAGGGCTGTC CACCGCAACCAAGGACACCTACGATGCC CTGCACATGCAGGCCCTCCCACCAAGG (SEQ ID NO: 19) | YDALHMQALP PR (SEQ ID NO: 29) |
| Construct N | ATTCTCGGGCTACGGCCC TGGAGCCACTCCGGCTCC TAAAGATTTAGAAGTTTG AGCACACCCGCCCACTAG GGCCCCCCATCCAGGGGG GCAACGGGCAAGCACTT CTGTTTCCCCGGTATGATC TGATAGGCTGTAACCACG GCTGAAACAGAGATTATC GTTATCCGCTTCACTACTT CGAGAAGCCTAGTAATGA TGGGTGAAATTGAATCCG TTGATCCGGTGTCTCCCC CACACCAGAAACTCATGA TGAGGGTTGCCATCCCGG CTACGGCGACGTAGCGGG CATCCCTGCGCTGGCATG AGGCCTCTTAGGAGGACG GATGATATGGATCTTGTCG TGAAGAGCCTATTGAGCT AGTGTCGACTCCTCCGCC CCCGTGAATGCGGCTAAT CCTAACCCCGGAGCAGGT GGGTCCAATCCAGGGCCT GGCCTGTCGTAATGCGTA AGTCTGGGACGGAACCG ACTACTTTCGGGAAGGCG TGTTTCCATTTGTTCATTA TTTGTGTGTTTATGGTGAC AACTCTGGGTAAACGTTC TATTGCGTTTATTGAGAGA TTCCCAACAATTGAACAA ACGAGAACTACCTGTTTT ATTAAATTTACACAGAGA AGAATTACA (SEQ ID NO: 16) | ATGGCTCTGCCTGTGACAGCTCTGCTGC TGCCTCTGGCTCTGCTTCTGCATGCCGCC AGACCTGACATCCAGATGACTCAGAGCC CCAGCAGCCTGTCTGCCTCTGTGGGAGA CAGAGTGACAATTACCTGCCGGGCCAGC CAGGATGTGAATACTGCTGTCGCCTGGT ATCAACAAAAGCCTGGCAAGGCCCCTA AGCTCCTGATCTACAGCGCCAGCTTTCT GTACAGCGGCGTGCCCAGCAGATTCTCC GGAAGCAGAAGCGGCACAGATTTCACA CTGACCATAAGCAGCCTGCAGCCAGAG GATTTCGCCACCTACTATTGCCAGCAGC ACTACACCACACCTCCAACCTTTGGCCA GGGCACCAAGGTCGAGATTAAGAGAAC AGGCAGCACATCTGGCTCTGGCAAACCT GGATCTGGCGAGGGCTCTGAAGTCCAGC TGGTGGAATCTGGCGGAGGACTGGTTCA ACCTGGCGGCTCTCTGAGACTGTCTTGT GCCGCCTCCGGCTTCAACATCAAGGACA CCTACATCCACTGGGTCCGACAAGCCCC AGGCAAAGGACTTGAGTGGGTCGCCAG GATCTACCCCACCAACGGCTACACCAGA TACGCCGACTCTGTGAAGGGCAGATTCA CCATCTCTGCCGACACCAGCAAGAATAC CGCCTACCTGCAGATGAACTCCCTGAGA CGCCTACCTGCAGATGAACTCCCTGAGA GCCGAAGATACCGCTGTGTATTACTGTTC CAGATGGGGAGGCGACGGCTTCTACGCC ATGGATGTTTGGGGCCAAGGCACCCTCG TGACCGTTTCTTCTATCGAAGTGATGTAC CCTCCACCTTACCTGGACAACGAGAAGT CCAACGGCACCATCATCCACGTGAAGGG CAAGCACCTGTGTCCTTCTCCACTGTTC CCCGGACCTAGCAAGCCTTTCTGGGTGC TCGTTGTTGTTGGCGGCGTGCTGGCCTG TTACTCTCTGCTGGTTACCGTGGCCTTCA TCATCTTTTGGGTCCGAAGCAAGCGGAG CCGGCTGCTGCACTCCGACTACATGAAC ATGACCCCTAGACGGCCCGGACCAACCA GAAAGCACTACCAGCCTTACGCTCCTCC TAGAGACTTCGCCGCCTACCGGTCCAGA GTGAAGTTCAGCAGATCCGCCGATGCTC CCGCCTATCAGCAGGGCCAAAACCAGCT GTACAACGAGCTGAACCTGGGGAGAAG AGAAGAGTACGACGTGCTGGACAAGCG GAGAGGCAGAGATCCTGAAATGGGCGG CAAGCCCAGACGGAAGAATCCTCAAGA GGGCCTGTATAATGAGCTGCAGAAAGAC AAGATGGCCGAGGCCTACAGCGAGATC GGAATGAAGGGCGAGCGCAGAAGAGGC AAGGGACACGGACTGTACCAGGGC CTGAGCACCGCCACCAAGGATACCTATG ATGCCCTGCACATGCAGGCCCTGCCTCC AAGA (SEQ ID NO: 101) | MALPVTALLL PLALLLHAAR PDIQMTQSPSS LSASVGDRVTI TCRASQDVNT AVAWYQQKPG KAPKLLIYSAS FLYSGVPSRFS GSRSGTDFTLT ISSLQPEDFAT YYCQQHYTTP PTFGQGTKVEI KRTGSTSGSG KPGSGEGSEV QLVESGGGLV QPGGSLRLSC AASGFNIKDT YIHWVRQAPG KGLEWVARIY PTNGYTRYAD SVKGRFTISAD TSKNTAYLQM NSLRAEDTAV YYCSRWGGD GFYAMDVWG QGTLVTVSSIE VMYPPPYLDN EKSNGTIIHVK GKHLCPSPLFP GPSKPFWVLV VVGGVLACYS LLVTVAFIIFW VRSKRSRLLH SDYMNMTPRR PGPTRKHYQP YAPPRDFAAY RSRVKFSRSA DAPAYQQGQN QLYNELNLGR REEYDVLDKR RGRDPEMGGK PRRKNPQEGL YNELQKDKM AEAYSEIGMK GERRRGKGHD GLYQGLSTAT KDTYDALHM QALPPR (SEQ ID NO: 117) |
| Construct O | CCCCCCTCCCCCCCTTCC CTTCCCTTTGCAACGCAA CAATTGTAAGTGCCCTCA CCTGTCAATTGGGACCAC CACTTTCAGTGACCCCAT GCGAAGTGCTGAGAGAA AGGAAGCTTTCTTACCCT TCATTTGTGAACCCACTG GTCTAAGCCGCTTGGAAT ACGATGAGTGGAAAAGTT CATTCTTAATGGAGTGAA ACATGCTTAAATTTCCAG CTCGTGCTGGTCTTTCCA | ATGGCTCTGCCTGTGACAGCTCTGCTGC TGCCTCTGGCTCTGCTTCTGCATGCCGCC AGACCTGACATCCAGATGACTCAGAGCC CCAGCAGCCTGTCTGCCTCTGTGGGAGA CAGAGTGACAATTACCTGCCGGGCCAGC CAGGATGTGAATACTGCTGTCGCCTGGT ATCAACAAAAGCCTGGCAAGGCCCCTA AGCTCCTGATCTACAGCGCCAGCTTTCT GTACAGCGGCGTGCCCAGCAGATTCTCC GGAAGCAGAAGCGGCACAGATTTCACA CTGACCATAAGCAGCCTGCAGCCAGAG GATTTCGCCACCTACTATTGCCAGCAGC ACTACACCACACCTCCAACCTTTGGCCA | MALPVTALLL PLALLLHAAR PDIQMTQSPSS LSASVGDRVTI TCRASQDVNT AVAWYQQKPG KAPKLLIYSAS FLYSGVPSRFS GSRSGTDFTLT ISSLQPEDFAT YYCQQHYTTP PTFGQGTKVEI KRTGSTSGSG |

TABLE 1B-continued

Exemplary Constructs (DNA Templates)

| ID | IRES Sequence | CAR Sequence | CAR Sequence |
|---|---|---|---|
| | GTACGGGGCGGCCCTGTC | GGGCACCAAGGTCGAGATTAAGAGAAC | KPGSGEGSEV |
| | TGGCCGTAATTCTTCAGA | AGGCAGCACATCTGGCTCTGGCAAACCT | QLVESGGGLV |
| | GTGTCACGCCACACTTGT | GGATCTGGCGAGGGCTCTGAAGTCCAGC | QPGGSLRLSC |
| | GGATCTCACGTGCCACAT | TGGTGGAATCTGGCGGAGGACTGGTTCA | AASGFNIKDT |
| | GACAGCGCTACAGCTGG | ACCTGGCGGCTCTCTGAGACTGTCTTGT | YIHWVRQAPG |
| | AACTGGGTGCTTGGTGCC | GCCGCCTCCGGCTTCAACATCAAGGACA | KGLEWVARIY |
| | CATGGAGTAACAGCGAAA | CCTACATCCACTGGGTCCGACAAGCCCC | PTNGYTRYAD |
| | AGTGTTAGATCAAGCCTT | AGGCAAAGGACTTGAGTGGGTCGCCAG | SVKGRFTISAD |
| | GCTTGGGCTATGAGCCTG | GATCTACCCCACCAACGGCTACACCAGA | TSKNTAYLQM |
| | CGGAACAACAACTGGTA | TACGCCGACTCTGTGAAGGGCAGATTCA | NSLRAEDTAV |
| | ACAGTTGCCTCAGGGGCC | CCATCTCTGCCGACACCAGCAAGAATAC | YYCSRWGGD |
| | GAAAGCCACGGTGTTAAC | CGCCTACCTGCAGATGAACTCCCTGAGA | GFYAMDVWG |
| | AGCACCCTCATAGTTTGA | GCCGAAGATACCGCTGTGTATTACTGTTC | QGTLVTVSSIE |
| | TCCACCTCAGGGTGGTGA | CAGATGGGGAGGCGACGGCTTCTACGCC | VMYPPPYLDN |
| | TGTTTAGCAGTTAGTAGT | ATGGATGTTTGGGGCCAAGGCACCCTCG | EKSNGTIIHVK |
| | TGCCAATCTGTGTTCACT | TGACCGTTTCTTCTATCGAAGTGATGTAC | GKHLCPSPLFP |
| | GAAATCTCGGCATACCGT | CCTCCACCTTACCTGGACAACGAGAAGT | GPSKPFWVLV |
| | GTAGTGTACAGGGGTGAA | CCAACGGCACCATCATCCACGTGAAGGG | VVGGVLACYS |
| | GGATGCCCAGAAGGTACC | CAAGCACCTGTGTCCTTCTCCACTGTTC | LLVTVAFIIFW |
| | CGTAGGTAACCTTAAGAG | CCCGGACCTAGCAAGCCTTTCTGGGTGC | VRSKRSRLLH |
| | ACTATGGATCTGATCTGG | TCGTTGTTGTTGGCGGCGTGCTGGCCTG | SDYMNMTPRR |
| | GGCCTTGTCCGGAGTGCT | TTACTCTCTGCTGGTTACCGTGGCCTTCA | PGPTRKHYQP |
| | TTACACACGGCTCAAGGT | TCATCTTTTGGGTCCGAAGCAAGCGGAG | YAPPRDFAAY |
| | TAAAAAACGTCTAGCCCC | CCGGCTGCTGCACTCCGACTACATGAAC | RSRVKFSRSA |
| | ACAGAGCCCGAGGGATTC | ATGACCCCTAGACGGCCCGGACCAACCA | DAPAYQQGQN |
| | GGGTTTTCCCTTTAAAAA | GAAAGCACTACCAGCCTTACGCTCCTCC | QLYNELNLGR |
| | CCCGACTAGAGCTTATGG | TAGAGACTTCGCCGCCTACCGGTCCAGA | REEYDVLDKR |
| | TGACAATTATTGCTGTTCA | GTGAAGTTCAGCAGATCCGCCGATGCTC | RGRDPEMGGK |
| | GACGAACAGTGTAATTGT | CCGCCTATCAGCAGGGCCAAAACCAGCT | PRRKNPQEGL |
| | TGTCTATTCACAGCAGTT | GTACAACGAGCTGAACCTGGGGGAGAAG | YNELQKDKM |
| | CTATCAGAGCTTTTCCCA | AGAAGAGTACGACGTGCTGGACAAGCG | AEAYSEIGMK |
| | CAACGGATCTTCTTGGCA | GAGAGGCAGAGATCCTGAAATGGGCGG | GERRRGKGHD |
| | AGCAAATACAGCAGGAGT | CAAGCCCAGACGGAAGAATCCTCAAGA | GLYQGLSTAT |
| | CAAT (SEQ ID NO: 8) | GGGCCTGTATAATGAGCTGCAGAAAGAC | KDTYDALHM |
| | | AAGATGGCCGAGGCCTACAGCGAGATC | QALPPR (SEQ |
| | | GGAATGAAGGGCGAGCGCAGAAGAGGC | ID NO: 117) |
| | | AAGGGACACGATGGACTGTACCAGGGC | |
| | | CTGAGCACCGCCACCAAGGATACCTATG | |
| | | ATGCCCTGCACATGCAGGCCCTGCCTCC | |
| | | AAGA (SEQ ID NO: 101) | |
| Construct P | TTTGCTCAGCGTAACTTC | ATGGCTCTGCCTGTGACAGCTCTGCTGC | MALPVTALLL |
| | TCCGGGTTACGTGGAGAC | TGCCTCTGGCTCTGCTTCTGCATGCCGCC | PLALLLHAAR |
| | CAAAAGGCTACGGAGAC | AGACCTGACATCCAGATGACTCAGAGCC | PDIQMTQSPSS |
| | TCGGGCTACGGCCCTGGA | CCAGCAGCCTGTCTGCCTCTGTGGGAGA | LSASVGDRVTI |
| | GCACCTAGGTGCTCCTAA | CAGAGTGACAATTACCTGCCGGGCCAGC | TCRASQDVNT |
| | AGACGTTAGAAGTTGTAC | CAGGATGTGAATACTGCTGTCGCCTGGT | AVAWYQQKPG |
| | AAACTCGCCCAATAGGGC | ATCAACAAAAGCCTGGCAAGGCCCCTA | KAPKLLIYSAS |
| | CCCCCAACCAGGGGGGT | AGCTCCTGATCTACAGCGCCAGCTTTCT | FLYSGVPSRFS |
| | AGCGGGCAAGCACTTCTG | GTACAGCGGCGTGCCCAGCAGATTCTCC | GSRSGTDFTLT |
| | TTTCCCCGGTATGATCTCA | GGAAGCAGAAGCGGCACAGATTTCACA | ISSLQPEDFAT |
| | TAGGCTGTACCCACGGCT | CTGACCATAAGCAGCCTGCAGCCAGAG | YYCQQHYTTP |
| | GAAAGAGAGATTATCGTT | GATTTCGCCACCTACTATTGCCAGCAGC | PTFGQGTKVEI |
| | ACCCGCCTCACTACTTCG | ACTACACCACACCTCCAACCTTTGGCCA | KRTGSTSGSG |
| | AGAAGCCCAGTAATGGTT | GGGCACCAAGGTCGAGATTAAGAGAAC | KPGSGEGSEV |
| | CATGAAGTTGATCTCGTT | AGGCAGCACATCTGGCTCTGGCAAACCT | QLVESGGGLV |
| | GACCCGGTGTTTCCCCCA | GGATCTGGCGAGGGCTCTGAAGTCCAGC | QPGGSLRLSC |
| | CACCAGAAACCTGTGATG | TGGTGGAATCTGGCGGAGGACTGGTTCA | AASGFNIKDT |
| | GGGGTGGTCATCCCGGTC | ACCTGGCGGCTCTCTGAGACTGTCTTGT | YIHWVRQAPG |
| | ATGGCGACATGACGGACC | GCCGCCTCCGGCTTCAACATCAAGGACA | KGLEWVARIY |
| | TCCCCGCGCCGGCACAGG | CCTACATCCACTGGGTCCGACAAGCCCC | PTNGYTRYAD |
| | GCCTCTTCGGAGGACGAG | AGGCAAAGGACTTGAGTGGGTCGCCAG | SVKGRFTISAD |
| | TGACATGGATTCAACCGT | GATCTACCCCACCAACGGCTACACCAGA | TSKNTAYLQM |
| | GAAGAGCCTATTGAGCTA | TACGCCGACTCTGTGAAGGGCAGATTCA | NSLRAEDTAV |
| | GTGTTGATTCCTCCGCCC | CCATCTCTGCCGACACCAGCAAGAATAC | YYCSRWGGD |
| | CCGTGAATGCGGCTAATC | CGCCTACCTGCAGATGAACTCCCTGAGA | GFYAMDVWG |
| | CCAACTCCGGAGCAGGC | GCCGAAGATACCGCTGTGTATTACTGTTC | QGTLVTVSSIE |
| | GGGCCCAAACCAGGGTC | CAGATGGGGAGGCGACGGCTTCTACGCC | VMYPPPYLDN |
| | TGGCCTGTCGTAACGCGA | ATGGATGTTTGGGGCCAAGGCACCCTCG | EKSNGTIIHVK |
| | AAGTCTGGAGCGGAACC | TGACCGTTTCTTCTATCGAAGTGATGTAC | GKHLCPSPLFP |
| | GACTACTTTCGGGAAGGC | CCTCCACCTTACCTGGACAACGAGAAGT | GPSKPFWVLV |
| | GTGTTTCCTTTTGTTCCTT | CCAACGGCACCATCATCCACGTGAAGGG | VVGGVLACYS |
| | TTATCAAGTTTTATGGTGA | CAAGCACCTGTGTCCTTCTCCACTGTTC | LLVTVAFIIFW |
| | CAACTCCTGGTAGACGTT | CCCGGACCTAGCAAGCCTTTCTGGGTGC | VRSKRSRLLH |
| | TTATTGCGTTTATTGAGAG | TCGTTGTTGTTGGCGGCGTGCTGGCCTG | SDYMNMTPRR |

TABLE 1B-continued

Exemplary Constructs (DNA Templates)

| ID | IRES Sequence | CAR Sequence | CAR Sequence |
|---|---|---|---|
| | ATTTCCAACAATTGAACA GACTAGAACCACTTGTTT TATCAAACCCTCACAGAA TAAGATAACA (SEQ ID NO: 18) | TTACTCTCTGCTGGTTACCGTGGCCTTCA TCATCTTTTGGGTCCGAAGCAAGCGGAG CCGGCTGCTGCACTCCGACTACATGAAC ATGACCCCTAGACGGCCCGGACCAACCA GAAAGCACTACCAGCCTTACGCTCCTCC TAGAGACTTCGCCGCCTACCGGTCCAGA GTGAAGTTCAGCAGATCCGCCGATGCTC CCGCCTATCAGCAGGGCCAAAACCAGCT GTACAACGAGCTGAACCTGGGGAGAAG AGAAGAGTACGACGTGCTGGACAAGCG GAGAGGCAGAGATCCTGAAATGGGCGG CAAGCCCAGACGGAAGAATCCTCAAGA GGGCCTGTATAATGAGCTGCAGAAAGAC AAGATGGCCGAGGCCTACAGCGAGATC GGAATGAAGGGCGAGCGCAGAAGAGGC AAGGGACACGATGGACTGTACCAGGGC CTGAGCACCGCCACCAAGGATACCTATG ATGCCCTGCACATGCAGGCCCTGCCTCC AAGA (SEQ ID NO: 101) | PGPTRKHYQP YAPPRDFAAY RSRVKFSRSA DAPAYQQGQN QLYNELNLGR REEYDVLDKR RGRDPEMGGK PRRKNPQEGL YNELQKDKM AEAYSEIGMK GERRRGKGHD GLYQGLSTAT KDTYDALHM QALPPR (SEQ ID NO: 117) |

C. Accessory Elements

As described in this disclosure, the circular RNA constructs and related pharmaceutical compositions, linear RNA polynucleotide, and/or DNA templates disclosed herein may further comprise certain accessory elements (also collective referred to herein as "combined accessory element"). In certain embodiments, these accessory elements may be included within the sequences of the circular RNA, linear RNA polynucleotide and/or DNA template for enhancing circularization, translation or both. Accessory elements are sequences, in certain embodiments, that are located with specificity between or within the enhanced intron elements, enhanced exon elements, or core functional element of the respective polynucleotide. As a nonlimiting example, a combined accessory element (e.g., 5' and 3') can include an IRES transacting factor region, a miRNA binding site, a restriction site, an RNA editing region, a structural or sequence element, a granule site, a zip code element, an RNA trafficking element, and/or another specialized sequence that enhances promotes circularization and/or translation of the protein encoded within the circular RNA polynucleotide.

In some embodiments, the combined accessory element comprises an IRES transacting factor (ITAF) region. In some embodiments, the IRES transacting factor region modulates the initiation of translation through binding to PCBP1-PCBP4 (polyC binding protein), PABP1 (polyA binding protein), PTB (polyprimidine tract binding), Argonaute protein family, HNRNPK (Heterogeneous nuclear ribonucleoprotein K protein), or La protein. In some embodiments, the IRES transacting factor region comprises a polyA, polyC, polyAC, or polyprimidine track. In some embodiments, the ITAF region is located within the core functional element. In some embodiments, the ITAF region is located within the TIE.

In certain embodiments, the combined accessory element comprises at least one miRNA binding site. In some embodiments the miRNA binding site is located within the 5' enhanced intron element, 5' enhanced exon element, core functional element, 3' enhanced exon element, and/or 3' enhanced intron element. In some embodiments, the miRNA binding site is located within the spacer within the enhanced intron element or enhanced exon element. In certain embodiments, the miRNA binding site comprises the entire spacer regions. In some embodiments, the 5' enhanced intron element and 3' enhanced intron elements each comprise identical miRNA binding sites. In another embodiment, the miRNA binding site of the 5' enhanced intron element comprises a different, in length or nucleotides, miRNA binding site than the 3' enhanced intron element. In one embodiment, the 5' enhanced exon element and 3' enhanced exon element comprise identical miRNA binding sites. In other embodiments, the 5' enhanced exon element and 3' enhanced exon element comprises different, in length or nucleotides, miRNA binding sites. In some embodiments, the miRNA binding sites are located adjacent to each other within the circular RNA construct, linear RNA polynucleotide precursor, and/or DNA template. In certain embodiments, the first nucleotide of one of the miRNA binding sites follows the first nucleotide last nucleotide of the second miRNA binding site.

In some embodiments, the miRNA binding site is located within a translation initiation element (TIE) of a core functional element. In one embodiment, the miRNA binding site is located before, trailing or within an internal ribosome entry site (IRES). In another embodiment, the miRNA binding site is located before, trailing, or within an aptamer complex.

Incorporation of miRNA sequences within a circular RNA molecule can permit tissue-specific expression of a coding sequence within a core functional element. For example, in a circular RNA intended to express a protein in immune cells, miRNA binding sequences resulting in expression suppression in tissues such as the liver or kidney may be desired. Such miRNA binding sequences may be selected based on the cell or tissue expression of miRNAs. The unique sequences defined by the miRNA nomenclature are widely known and accessible to those working in the microRNA field. For example, they can be found in the miRDB public database. As a non-limiting example, one or more miR-122 target sites can be inserted in the circular RNA.

In some embodiments, the miR-122 site can comprise the following sequence:

(SEQ ID NO: 200)
CAAACACCATTGTCACACTCCAA.

D. Expression Sequences and Payloads

In some embodiments, the circular RNA constructs comprise at least one expression sequence encoding a binding molecule. In certain embodiments, the circular RNA constructs comprise an IRES and at least one expression sequence encoding a therapeutic protein, wherein the IRES is capable of facilitating expression of the protein when delivered in vivo.

In some embodiments, the circular RNA may encode for various therapeutic proteins, cytokines, immune checkpoint inhibitors, agonists, chimeric antigen receptors, inhibitory receptor agonists, one or more T-Cell Receptors, and/or B-cell Receptors that are available in the art. The chimeric proteins may also include, for example, recombinant fusion proteins, chimeric mutant protein, or other fusion proteins. In some embodiments, the circular RNA comprises more than 1 expression sequence, e.g., 2, 3, 4, or 5 expression sequences. In some embodiments, the circular RNA is a bicistronic RNA. In some embodiments, the bicistronic RNA is codon optimized. Exemplary bicistronic circular RNA are described in WO2021/189059A2, which is incorporated by reference herein in its entirety.

In some embodiments, the expression sequence encodes a therapeutic protein. In some embodiments, the therapeutic protein is selected from the proteins listed in the following table.

| Payload | Exemplary Sequences | Exemplary target cell/organ | Exemplary delivery vehicle |
|---|---|---|---|
| CD19 CAR | See, e.g., Tables 2A-2C | T cells | <br>(50 mol %)<br>DSPC (10 mol %)<br>Beta-sitosterol (28.5% mol %)<br>Cholesterol (10 mol %)<br>PEG DMG (1.5 mol %) |
| BCMA CAR* | See, e.g., Table 2C<br>MALPVTALLLPLALLLHAARPDIVLTQ SPASLAVSLGERATINCRASESVSVIGA HLIHWYQQKPGQPPKLLIYLASNLETG VPARFSGSGSGTDFTLTISSLQAEDAAI YYCLQSRIFPRTFGQGTKLEIKGSTSGS GKPGSGEGSTKGQVQLVQSGSELKKP GASVKVSCKASGYTFTDYSINWVRQA PGQGLEWMGWINTETREPAYAYDFRG RFVFSLDTSVSTAYLQISSLKAEDTAV YYCARDYSYAMDYWGQGTLVTVSSA AATTTPAPRPPTPAPTIASQPLSLRPEA CRPAAGGAVHTRGLDFACDIYIWAPL AGTCGVLLLSLVITLYCKRGRKKLLYI FKQPFMRPVQTTQEEDGCSCRFPEEE GGCELRVKFSRSADAPAYQQGQNQLY NELNLGRREEYDVLDKRRGRDPEMGG KPRRKNPQEGLYNELQKDKMAEAYSE IGMKGERRRGKGHDGLYQGLSTATKD TYDALHMQALPPR<br>(SEQ ID NO: 201)<br>*The BCMA CAR may be chosen from any of the anti-BCMA CARs disclosed in US Patent Application US 2021/0128618A1 | T cells | <br>(50 mol %)<br>DSPC (10 mol %)<br>Beta-sitosterol (28.5% mol %)<br>Cholesterol (10 mol %)<br>PEG DMG (1.5 mol %) |

-continued

| Pay-load | Exemplary Sequences | Exemplary target cell/organ | Exemplary delivery vehicle |
|---|---|---|---|
| MAGE-A4 TCR | TCR alpha chain:<br>KNQVEQSPQSLIILEGKNCTLQCNYTV<br>SPFSNLRWYKQDTGRGPVSLTIMTFSE<br>NTKSNGRYTATLDADTKQSSLHITASQ<br>LSDSASYICVVNHSGGSYIPTFGRGTSL<br>IVHPYIQKPDDPAVYQLRDSKSSDKSVC<br>LFTDFDSQTNVSQSKDSDVYITDKTVL<br>DMRSMDFKSNSAVAWSNKSDFACAN<br>AFNNSIIPEDTFFPSPESS<br>(SEQ ID NO: 202)<br>TCR beta chain:<br>DVKVTQSSRYLVKRTGEKVFLECVQD<br>MDHENMFWYRQDPGLGRLIYFSYDV<br>KMKEKGDIPEGYSVSREKKERFSLILES<br>ASTNQTSMYLCASSFLMTSGDPYEQYF<br>GPGTRLTVTEDLKNVFPPEVAVFEPSE<br>AEISHTOKATLVCLATGFYPDHVELSW<br>WVNGKEVHSGVSTDPQPLKEQPALND<br>SRYCLSSRLRVSATFWQNPRNHFRCQ<br>VQFYGLSENDEWTQDRAKPVTQIVSA<br>EAWGRAD (SEQ ID NO: 203) | T cells | (50 mol %)<br>DSPC (10 mol %)<br>Beta-sitosterol (28.5% mol %)<br>Cholesterol (10 mol %)<br>PEG DMG (1.5 mol %) |
| NY-ESO TCR | TCRalpha extracellular<br>sequence<br>MQEVTQIPAALSVPEGENLVLNCSFTD<br>SAIYNLQWFRQDPGKGLTSLLLIQSSQ<br>REQTSGRLNASLDKSSGRSTLYIAASQ<br>PGDSATYLCAVRPTSGGSYIPTFGRGTS<br>LIVHPY (SEQ ID NO: 204)<br>TCRbeta extracellular<br>sequence<br>MGVTQTPKFQVLKTGQSMTLQCAQD<br>MNHEYMSWYRQDPGMGLRLIHYSVG<br>AGITDQGEVPNGYNVSRSTTEDFPLRL<br>LSAAPSQTSVYFCASSYVGNTGELFFG<br>EGSRLTVL (SEQ ID NO: 205) | T cells | (50 mol %)<br>DSPC (10 mol %)<br>Beta-sitosterol (28.5% mol %)<br>Cholesterol (10 mol %)<br>PEG DMG (1.5 mol %) |
| EPO | APPRLICDSRVLERYLLEAKEAENITTG<br>CAEHCSLNENITVPDTKVNFYAWKRM<br>EVGQQAVEVWOGLALLSEAVLRGQA<br>LLVNSSQPWEPLQLHVDKAVSGLRSLT<br>TLLRALGAQKEAISPPDAASAAPLRTIT<br>ADTFRKLFRVYSNFLRGKLKLYTGEA<br>CRTGDR (SEQ ID NO: 206) | Kidney or bone marrow | |
| PAH | MSTAVLENPGLGRKLSDFGQETSYIED<br>NCNONGAISLIFSLKEEVGALAKVLRL<br>FEENDVNLTHIESRPSRLKKDEYEFFTH<br>LDKRSLPALTNIIKILRHDIGATVHELS<br>RDKKKDTVPWFPRTIQELDRFANQILS<br>YGAELDADHPGFKDPVYRARRKQFAD<br>IAYNYRHGQPIPRVEYMEEEKKTWGT<br>VFKTLKSLYKTHACYEYNHIFPLLEKY<br>CGFHEDNIPQLEDVSQFLQTCTGFRLR<br>PVAGLLSSRDFLGGLAFRVFHCTQYIR<br>HGSKPMYTPEPDICHELLGHVPLFSDR<br>SFAQFSQEIGLASLGAPDEYIEKLATIY<br>WFTVEFGLCKQGDSIKAYGAGLLSSFG<br>ELQYCLSEKPKLLPLELEKTAIQNYTV<br>TEFQPLYYVAESFNDAKEKVRNFAATI<br>PRPFSVRYDPYTQRIEVLDNTQQLKILA<br>DSINSEIGILCSALQKIK (SEQ ID NO: 207) | Hepatic cells | (50 mol %)<br>DSPC (10 mol %)<br>Cholesterol (38.5% mol %)<br>PEG-DMG (1.5%)<br>OR<br>MC3 (50 mol %)<br>DSPC (10 mol %)<br>Cholesterol (38.5% mol %)<br>PEG-DMG (1.5%) |

-continued

| Pay-load | Exemplary Sequences | Exem-plary target cell/organ | Exemplary delivery vehicle |
|---|---|---|---|
| CPS1 | LSVKAQTAHIVLEDGTKMKGYSFGHP SSVAGEVVFNTGLGGYPEAITDPAYKG QILTMANPIIGNGGAPDTTALDELGLS KYLESNGIKVSGLLVLDYSKDYNHWL ATKSLGQWLQEEKVPAIYGVDTRMLT KIIRDKGTMLGKIEFEGQPVDFVDPNK QNLIAEVSTKDVKVYGKGNPTKVVAV DCGIKNNVIRLLVKRGAEVHLVPWNH DFTKMEYDGILIAGGPGNPALAEPLIQ NVRKILESDRKEPLFGISTGNLITGLAA GAKTYKMSMANRGQNQPVLNITNKQ AFITAQNHGYALDNTLPAGWKPLFVN VNDQTNEGIMHESKPFFAVQFHPEVTP GPIDTEYLFDSFFSLIKKGKATTITSVLP KPALVASRVEVSKVLILGSGGLSIGQA GEFDYSGSQAVKAMKEENVKTVLMN PNIASVQTNEVGLKQADTVYFLPITPQF VTEVIKAEQPDGLILGMGGQTALNCG VELFKRGVLKEYGVKVLGTSVESIMA TEDROLFSDKLNEINEKIAPSFAVESIE DALKAADTIGYPVMIRSAYALGGLGS GICPNRETLMDLSTKAFAMTNQILVEK SVTGWKEIEYEVVRDADDNCVTVCN MENVDAMGVHTGDSVVVAPAQTLSN AEFQMLRRTSINVVRHLGIVGECNIQF ALHPTSMEYCIIEVNARLSRSSALASKA TGYPLAFIAAKIALGIPLPEIKNVVSGK TSACFEPSLDYMVTKIPRWDLDRFHGT SSRIGSSMKSVGEVMAIGRTFEESFQK ALRMCHPSIEGFTPRLPMNKEWPSNLD LRKELSEPSSTRIYAIAKAIDDNMSLDE IEKLTYIDKWFLYKMRDILNMEKTLKG LNSESMTEETLKRAKEIGFSDKQISKCL GLTEAQTRELRLKKNIHPWVKQIDTLA AEYPSVTNYLYVTYNGQEHDVNFDDH GMMVLGCGPYHIGSSVEFDWCAVSSI RTLRQLGKKTVVVNCNPETVSTDFDE CDKLYFEELSLERILDIYHQEACGGCIIS VGGQIPNNLAVPLYKNGVKIMGTSPLQ IDRAEDRSIFSAVLDELKVAQAPWKAV NTLNEALEFAKSVDYPCLLRPSYVLSG SAMNVVFSEDEMKKFLEEATRVSQEH PVVLTKFVEGAREVEMDAVGKDGRVI SHAISEHVEDAGVHSGDATLMLPTQTI SQGAIEKVKDATRKIAKAFAISGPFNV QFLVKGNDVLVIECNLRASRSFPFVSK TLGVDFIDVATKVMIGENVDEKHLPTL DHPIIPADYVAIKAPMFSWPRLRDADPI LRCEMASTGEVACFGEGIHTAFLKAM LSTGFKIPQKGILIGIQQSFRPRFLGVAE QLHNEGFKLFATEATSDWLNANNVPA TPVAWPSQEGQNPSLSSIRKLIRDGSID LVINLPNNNTKFVHDNYVIRRTAVDSG IPLLTNFQVTKLFAEAVQKSRKVDSKS LFHYRQYSAGKAA (SEQ ID NO: 208) | Hepatic cells | HO-N... (50 mol %) DSPC (10 mol %) Cholesterol (38.5% mol %) PEG-DMG (1.5%) OR MC3 (50 mol %) DSPC (10 mol %) Cholesterol (38.5% mol %) PEG-DMG (1.5%) |

-continued

| Pay-load | Exemplary Sequences | Exem-plary target cell/organ | Exemplary delivery vehicle |
|---|---|---|---|
| Cas9 | MKRNYILGLDIGITSVGYGIIDYETRDV IDAGVRLFKEANVENNEGRRSKRGAR RLKRRRRHRIQRVKKLLFDYNLLTDHS ELSGINPYEARVKGLSQKLSEEEFSAAL LHLAKRRGVHNVNEVEEDTGNELSTK EQISRNSKALEEKYVAELQLERLKKDG EVRGSINRFKTSDYVKEAKQLLKVQK AYHQLDQSFIDTYIDLLETRRTYYEGP GEGSPFGWKDIKEWYEMLMGHCTYFP EELRSVKYAYNADLYNALNDLNNL VI TRDENEKLEYYEKFQIIENVFKQKKKP TLKQIAKEILVNEEDIKGYRVTSTGKPE FTNLKVYHDIKDITARKEIIENAELLDQ IAKILTIYQSSEDIQEELTNLNSELTQEEI EQISNLKGYTGTHNLSLKAINLILDEL WHTNDNQIAIFNRLKLVPKKVDLSQQ KEIPTTLVDDFILSPVVKRSFIQSIKVIN AIIKKYGLPNDIIIELAREKNSKDAQKM INEMQKRNRQTNERIEEIIRTTGKENAK YLIEKIKLHDMQEGKCLYSLEAIPLEDL LNNPFNYEVDHIIPRSVSFDNSFNNKVL VKQEENSKKGNRTPFQYLSSSDSKISY ETFKKHILNLAKGKGRISKTKKEYLLE ERDINRFSVQKDFINRNLVDTRYATRG LMNLLRSYFRVNNLDVKVKSINGGFTS FLRRKWKFKKERNKGYKHHAEDALII ANADFIFKEWKKLDKAKKVMENQMF EEKQAESMPEIETEQEYKEIFITPHQIKH IKDFKDYKYSHRVDKKPNRELINDTLY STRKDDKGNTLIVNNLNGLYDKDNDK LKKLINKSPEKLLMYHHDPQTYQKLK LIMEQYGDEKNPLYKYYEETGNYLTK YSKKDNGPVIKKIKYYGNKLNAHLDIT DDYPNSRNKVVKLSLKPYRFDVYLDN GVYKFVTVKNLDVIKKENYYEVNSKC YEEAKKLKKISNQAEFIASFYNNDLIKI NGELYRVIGVNNDLLNRIEVNMIDITY REYLENMNDKRPPRIIKTIASKTQSIKK YSTDILGNLYEVKSKKHPQIIKKG (SEQ ID NO: 209) | Immune cells | <br>(50 mol %)<br>DSPC (10 mol %)<br>Beta-sitosterol (28.5% mol %)<br>Cholesterol (10 mol %)<br>PEG DMG (1.5 mol %) |

-continued

| Pay-load | Exemplary Sequences | Exem-plary target cell/organ | Exemplary delivery vehicle |
|---|---|---|---|
| ADAMTS13 | AAGGILHLELLVAVGPDVFQAHQEDT ERYVLTNLNIGAELLRDPSLGAQFRVH LVKMVILTEPEGAPNITANLTSSLLSVC GWSQTINPEDDTDPGHADLVLYITRFD LELPDGNRQVRGVTQLGGACSPTWSC LITEDTGFDLGVTIAHEIGHSFGLEHDG APGSGCGPSGHVMASDGAAPRAGLA WSPCSRROLLSLLSAGRARCVWDPPRP QPGSAGHPPDAQPGLYYSANEQCRVA FGPKAVACTFAREHLDMCQALSCHTD PLDQSSCSRLLVPLLDGTECGVEKWCS KGRCRSLVELTPIAAVHGRWSSWGPR SPCSRSCGGGVVTRRRQCNNPRPAFGG RACVGADLQAEMCNTQACEKTQLEF MSQQCARTDGQPLRSSPGGASFYHWG AAVPHSQGDALCRHMCRAIGESFIMK RGDSFLDGTRCMPSGPREDGTLSLCVS GSCRTFGCDGRMDSQQVWDRCQVCG GDNSTCSPRKGSFTAGRAREYVTFLTV TPNLTSVYIANHRPLFTHLAVRIGGRY VVAGKMSISPNTTYPSLLEDGRVEYRV ALTEDRLPRLEEIRIWGPLQEDADIQVY RRYGEEYGNLTRPDITFTYFQPKPRQA WVWAAVRGPCSVSCGAGLRWVNYSC LDQARKELVETVQCQGSQQPPAWPEA CVLEPCPPYWAVGDFGPCSASCGGGL RERPVRCVEAQGSLLKTLPPARCRAGA QQPAVALETCNPQPCPARWEVSEPSSC TSAGGAGLALENETCVPGADGLEAPV TEGPGSVDEKLPAPEPCVGMSCPPGW GHLDATSAGEKAPSPWGSIRTGAQAA HVWTPAAGSCSVSCGRGLMELRFLCM DSALRVPVQEELCGLASKPGSRREVCQ AVPCPARWQYKLAACSVSCGRGVVR RILYCARAHGEDDGEEILLDTQCQGLP RPEPQEACSLEPCPPRWKVMSLGPCSA SCGLGTARRSVACVOLDQGQDVEVDE AACAALVRPEASVPCLIADCTYRWHV GTWMECSVSCGDGIQRRRDTCLGPQA QAPVPADFCQHLPKPVTVRGCWAGPC VGQGTPSLVPHEEAAAPGRTTATPAG ASLEWSQARGLLFSPAPQPRRLLPGPQ ENSVOSSACGRQHLEPTGTIDMRGPGQ ADCAVAIGRPLGEVVTLRVLESSLNCS AGDMLLLWGRLTWRKMCRKLLDMTF SSKTNTLVVRQRCGRPGGGVLLRYGS QLAPETFYRECDMQLFGPWGEIVSPSL SPATSNAGGCRLFINVAPHARIAIHALA TNMGAGTEGANASYILIRDTHSLRTTA FHGQQVLYWESESSQAEMEFSEGFLK AQASLRGQYWTLQSWVPEMQDPQSW KGKEGT (SEQ ID NO: 210) | Hepatic cells | (50 mol %) DSPC (10 mol %) Cholesterol (38.5% mol %) PEG-DMG (1.5%) OR MC3 (50 mol %) DSPC (10 mol %) Cholesterol (38.5% mol %) PEG-DMG (1.5%) |
| FOXP3 | MPNPRPGKPSAPSLALGPSPGASPSWR AAPKASDLLGARGPGGTFQGRDLRGG AHASSSSLNPMPPSQLQLPTLPLVMVA PSGARLGPLPHLQALLQDRPHFMHQLS TVDAHARTPVLQVHPLESPAMISLTPP TTATGVFSLKARPGLPPGINVASLEWV SREPALLCTFPNPSAPRKDSTLSAVPQS SYPLLANGVCKWPGCEKVFEEPEDFL KHCQADHLLDEKGRAQCLLQREMVQ SLEQQLVLEKEKLSAMQAHLAGKMAL TKASSVASSDKGSCCIVAAGSQGPVVP AWSGPREAPDSLFAVRRHLWGSHGNS TFPEFLHNMDYFKFHNMRPPFTYATLI RWAILEAPEKQRTLNEIYHWFTRMFAF FRNHPATWKNAIRHNLSLHKCFVRVE SEKGAVWTVDELEFRKKRSQRPSRCS NPTPGP (SEQ ID NO: 211) | Immune cells | (50 mol %) DSPC (10 mol %) Beta-sitosterol (28.5% mol %) Cholesterol (10 mol %) PEG DMG (1.5 mol %) |

-continued

| Pay-load | Exemplary Sequences | Exemplary target cell/organ | Exemplary delivery vehicle |
|---|---|---|---|
| IL-10 | SPGQGTQSENSCTHFPGNLPNMLRDLR DAFSRVKTFFQMKDQLDNLLLKESLLE DFKGYLGCQALSEMIQFYLEEVMPQA ENQDPDIKAHVNSLGENLKTLRLRLRR CHRFLPCENKSKAVEQVKNAFNKLQE KGIYKAMSEFDIFINYIEAYMTMKIRN (SEQ ID NO: 212) | Immune cells | (50 mol %) DSPC (10 mol %) Beta-sitosterol (28.5% mol %) Cholesterol (10 mol %) PEG DMG (1.5 mol %) |
| IL-2 | APTSSSTKKTQLQLEHLLLDLQMILNGI NNYKNPKLTRMLTFKFYMPKKATELK HLQCLEEELKPLEEVLNLAQSKNFHLR PRDLISNINVIVLELKGSETTFMCEYAD ETATIVEFLNRWITFCQSIISTLT (SEQ ID NO: 213) | Immune cells | (50 mol %) DSPC (10 mol %) Beta-sitosterol (28.5% mol %) Cholesterol (10 mol %) PEG DMG (1.5 mol %) |

In some embodiments, the expression sequence encodes a therapeutic protein. In some embodiments, the expression sequence encodes a cytokine, e.g., IL-12p70, IL-15, IL-2, IL-18, IL-21, IFN-α, IFN-β, IL-10, TGF-beta, IL-4, or IL-35, or a functional fragment thereof. In some embodiments, the expression sequence encodes an immune checkpoint inhibitor. In some embodiments, the expression sequence encodes an agonist (e.g., a TNFR family member such as CD137L, OX40L, ICOSL, LIGHT, or CD70). In some embodiments, the expression sequence encodes a chimeric antigen receptor. In some embodiments, the expression sequence encodes an inhibitory receptor agonist (e.g., PDL1, PDL2, Galectin-9, VISTA, B7H4, or MHCII) or inhibitory receptor (e.g., PD1, CTLA4, TIGIT, LAG3, or TIM3). In some embodiments, the expression sequence encodes an inhibitory receptor antagonist. In some embodiments, the expression sequence encodes one or more TCR chains (alpha and beta chains or gamma and delta chains). In some embodiments, the expression sequence encodes a secreted T cell or immune cell engager (e.g., a bispecific antibody such as BiTE, targeting, e.g., CD3, CD137, or CD28 and a tumor-expressed protein e.g., CD19, CD20, or BCMA etc.). In some embodiments, the expression sequence encodes a transcription factor (e.g., FOXP3, HELIOS, TOX1, or TOX2). In some embodiments, the expression sequence encodes an immunosuppressive enzyme (e.g., IDO or CD39/CD73). In some embodiments, the expression sequence encodes a GvHD (e.g., anti-HLA-A2 CAR-Tregs).

In some embodiments, circular RNA construct comprises an IRES and an expression sequence encoding a CAR. In certain embodiments, the circular RNA constructs and related pharmaceutical compositions herein comprise a CAR coding region that encodes a chimeric antigen receptor (CAR) complex protein. In certain embodiments, the expression sequence encodes a CAR targeting a cancer antigen. In certain embodiments, the CAR construct comprises, for example, an anti-CD19, anti-HER2, or anti-BCMA binder.

Chimeric antigen receptors (CARs or CAR-Ts) are genetically-engineered receptors. These engineered receptors may be inserted into and expressed by immune cells, including T cells via circular RNA as described herein. With a CAR a single receptor may be programmed to both recognize a specific antigen and, when bound to that antigen, activate the immune cell to attack and destroy the cell bearing that antigen. When these antigens exist on tumor cells, an immune cell that expresses the CAR may target and kill the tumor cell.

Accordingly, in some embodiments, the CAR encoded by the polynucleotide comprises (i) an antigen-binding molecule that specifically binds to a target antigen, (ii) a hinge domain, a transmembrane domain, and an intracellular domain, and (iii) an activating domain. In some embodiments, an orientation of the CARs in accordance with the disclosure comprises an antigen binding domain (such as an scFv) in tandem with a costimulatory domain and an activating domain. The costimulatory domain may comprise one or more of an extracellular portion, a transmembrane portion, and an intracellular portion. In other embodiments, multiple costimulatory domains may be utilized in tandem. In some embodiments, the CAR comprises a CAR protein spacer. The CAR protein spacer may be between any aforementioned domains. In some embodiments, the CAR is directed to a tumor-expressed protein, including but not limited to CD19, BCMA, and HER2.

1. Codon Optimization

In some embodiments where the circular RNA construct comprises at least one expression sequence encoding a binding molecule, the expression sequence may be codon optimized. In some embodiments, the circular RNA construct is optimized to lack at least one microRNA binding site present in an equivalent pre-optimized polynucleotide.

In some embodiments, the circular RNA construct is optimized to lack at least one microRNA binding site capable of binding to a microRNA present in a cell within which the circular RNA construct is expressed. In some embodiments, the circular RNA construct is optimized to lack at least one endonuclease susceptible site present in an equivalent pre-optimized polynucleotide. In some embodiments, the circular RNA construct is optimized to lack at least one endonuclease susceptible site capable of being cleaved by an endonuclease present in a cell within which the endonuclease is expressed. In some embodiments, the circular RNA construct is optimized to lack at least one RNA editing susceptible site present in an equivalent pre-optimized polynucleotide.

A codon optimized sequence may be one in which codons in a polynucleotide encoding a polypeptide have been substituted in order to increase the expression, stability and/or activity of the polypeptide. Factors that influence codon optimization include, but are not limited to one or more of: (i) variation of codon biases between two or more organisms or genes or synthetically constructed bias tables, (ii) variation in the degree of codon bias within an organism, gene, or set of genes, (iii) systematic variation of codons including context, (iv) variation of codons according to their decoding tRNAs, (v) variation of codons according to GC %, either overall or in one position of the triplet, (vi) variation in degree of similarity to a reference sequence for example a naturally occurring sequence, (vii) variation in the codon frequency cutoff, (viii) structural properties of mRNAs transcribed from the DNA sequence, (ix) prior knowledge about the function of the DNA sequences upon which design of the codon substitution set is to be based, and/or (x) systematic variation of codon sets for each amino acid. In some embodiments, a codon optimized polynucleotide may minimize ribozyme collisions and/or limit structural interference between the expression sequence and the IRES.

Codon optimization can be performed by methods known in the art using known algorithms. A factor that can influence codon optimization includes differences in ribosomal dwell times among sequences. Optimization based on ribosomal dwell time prioritizes low dwell-time codons, namely codons that the ribosome does not linger on for very long (associated with translation speed). These codons tend to have a lower GC with a target GC % of around, for example, 48-54%. RNA stability also influences codon optimization. Optimization based on modified stability prioritizes codons associated with RNA stability, which also tend to have a higher GC, with a target GC % of around, for example, 57-62%. Higher-GC codons tend to improve stability by forming small structures in the RNA that constrain the reactive 2' hydroxyl and for small segments of double-stranded RNA that may be resistant to endonuclease activity. These structures may also slow the ribosome and prevent it from bumping into other ribosomes. Another method of codon optimization utilizes an algorithm with specific codon usage reverse engineered from a known sequence, which has a target GC % of around 57-62%.

In embodiments using these algorithms, each algorithm will generate a random sequence that adheres to the codon usage frequencies that are associated with the algorithm. For most amino acids, multiple codons can be used (however, certain algorithms can select a single pre-defined codon for each amino acid). For the algorithms employing multiple codons, a single amino acid sequence input can have many different nucleotide sequence outputs, since the choice of codon at each position is random, and weighted. The algorithms generally exclude rare codons, which are defined slightly differently for each algorithm, but usually by codon usage in the corresponding genome. Optimization based on ribosomal dwell time and modified stability, for example use a biased codon matrix to generate a first pass sequence. The first pass bias can be, for example, set to 10. This means that, for example, for an amino acid with two potential codons at 0.6 and 0.4 usage (60%/40%), a bias of 10 makes 0.6 become: $(0.6^\wedge10)/((0.6^\wedge10)-(0.4^\wedge10))=~0.98$, and $(0.4^\wedge10)/((0.6^\wedge10)-(0.4^\wedge10))=~0.02$, resulting in a 98% chance of selecting the originally 0.6 codon, and 2% chance of selecting the originally 0.4 codon.

The primary sequence will then go through a "polishing process" to identify "problem sequences" such as: (a) self-complement regions that comprise greater than 11 contiguous nucleotides; (b) repeat regions of greater than 11 contiguous nucleotides; and (c) unwanted sequences, which include but are not limited to XbaI sites (TCTAGA), which are used to linearize plasmid and must not be present in the circular RNA region; 5+homopolymers (e.g., AAAAA), which can result in frameshift mutations in the RNA; and >75% or <33% GC % content over an 18nt window.

Once these problem sequences are identified, the algorithm will attempt to remove them by re-selecting the codon at a random position within the problematic sequence in question. The algorithm will loop, e.g., up to 25 times to remove each problem sequence, and then repeat this process, e.g., 25 times to remove each problem sequence. If the algorithm is unable to remove problem sequences, it will report the presence of problem sequences alongside the final sequence- and then repeat this process any number of times to generate unique sequences based on the same amino acid sequence.

2. Exemplary Antigen Binding Domains

In some embodiments, the circular RNA constructs comprise an IRES and at least one expression sequence encoding a binding molecule. In certain embodiments, the expression sequence encodes a therapeutic protein, for example a chimeric antigen receptor (CAR).

CARs may be engineered to bind to an antigen (such as a cell-surface antigen) by incorporating an antigen binding molecule that interacts with that targeted antigen, for example a cancer antigen. In some embodiments, the antigen binding molecule is an antibody fragment thereof, e.g., one or more single chain antibody fragment (scFv). An scFv is a single chain antibody fragment having the variable regions of the heavy and light chains of an antibody linked together. See U.S. Pat. Nos. 7,741,465, and 6,319,494 as well as Eshhar et al., Cancer Immunol Immunotherapy (1997) 45:131-136. An scFv retains the parent antibody's ability to specifically interact with target antigen. scFvs are useful in chimeric antigen receptors because they may be engineered to be expressed as part of a single chain along with the other CAR components. Id. See also Krause et al., J. Exp. Med., Volume 188, No. 4, 1998 (619-626); Finney et al., Journal of Immunology, 1998, 161:2791-2797. It will be appreciated that the antigen binding molecule is typically contained within the extracellular portion of the CAR such that it is capable of recognizing and binding to the antigen of interest. Bispecific and multispecific CARs are contemplated, with specificity to more than one target of interest.

In some embodiments, the antigen binding molecule comprises a single chain, wherein the heavy chain variable region and the light chain variable region are connected by a linker. In some embodiments, the VH is located at the N terminus of the linker and the VL is located at the C terminus of the linker. In other embodiments, the VL is located at the N terminus of the linker and the VH is located at the C terminus of the linker. In some embodiments, the linker comprises at least about 5, at least about 8, at least about 10, at least about 13, at least about 15, at least about 18, at least about 20, at least about 25, at least about 30, at least about 35, at least about 40, at least about 45, at least about 50, at least about 60, at least about 70, at least about 80, at least about 90, or at least about 100 amino acids.

In some embodiments, the antigen binding molecule comprises a nanobody. In some embodiments, the antigen binding molecule comprises a DARPin. In some embodiments, the antigen binding molecule comprises an anticalin or other synthetic protein capable of specific binding to target protein.

In some embodiments, the CAR comprises an antigen binding domain specific for an antigen selected from CD19, CD123, CD22, CD30, CD171, CS-1, C-type lectin-like molecule-1, CD33, epidermal growth factor receptor variant III (EGFRvIII), ganglioside G2 (GD2), ganglioside GD3, TNF receptor family member B cell maturation (BCMA), Tn antigen ((Tn Ag) or (GaINAca-Ser/Thr)), prostate-specific membrane antigen (PSMA), Receptor tyrosine kinase-like orphan receptor 1 (ROR1), Fms-Like Tyrosine Kinase 3 (FLT3), Tumor-associated glycoprotein 72 (TAG72), CD38, CD44v6, Carcinoembryonic antigen (CEA), Epithelial cell adhesion molecule (EPCAM), B7H3 (CD276), KIT (CD117), Interleukin-13 receptor subunit alpha-2, mesothelin, Interleukin 11 receptor alpha (IL-11Ra), prostate stem cell antigen (PSCA), Protease Serine 21, vascular endothelial growth factor receptor 2 (VEGFR2), Lewis (Y) antigen, CD24, Platelet-derived growth factor receptor beta (PDGFR-beta), Stage-specific embryonic antigen-4 (SSEA-4), CD20, Folate receptor alpha, Human Epidermal Growth Factor Receptor 2 (HER2), HER3, Mucin 1, cell surface associated (MUC1), epidermal growth factor receptor (EGFR), neural cell adhesion molecule (NCAM), Prostase, prostatic acid phosphatase (PAP), elongation factor 2 mutated (ELF2M), Ephrin B2, fibroblast activation protein alpha (FAP), insulin-like growth factor 1 receptor (IGF-1 receptor), carbonic anhydrase IX (CAIX), Proteasome (Prosome, Macropain) Subunit, Beta Type, 9 (LMP2), glycoprotein 100 (gp100), oncogene fusion protein consisting of breakpoint cluster region (BCR) and Abelson murine leukemia viral oncogene homolog 1 (Abl) (bcr-abl), tyrosinase, ephrin type-A receptor 2 (EphA2), Fucosyl GM1, sialyl Lewis adhesion molecule (sLe), ganglioside GM3, transglutaminase 5 (TGS5), high molecular weight-melanoma-associated antigen (HMWMAA), o-acetyl-GD2 ganglioside (OAcGD2), Folate receptor beta, tumor endothelial marker 1 (TEM1/CD248), tumor endothelial marker 7-related (TEM7R), claudin 6 (CLDN6), thyroid stimulating hormone receptor (TSHR), G protein-coupled receptor class C group 5, member D (GPRC5D), chromosome X open reading frame 61 (CXORF61), CD97, CD179a, anaplastic lymphoma kinase (ALK), Polysialic acid, placenta-specific 1 (PLAC1), hexasaccharide portion of globoH glycocer-amide (GloboH), mammary gland differentiation antigen (NY-BR-1), uroplakin 2 (UPK2), Hepatitis A virus cellular receptor 1 (HAVCR1), adrenoceptor beta 3 (ADRB3), pannexin 3 (PANX3), G protein-coupled receptor 20 (GPR20), lymphocyte antigen 6 complex, locus K 9 (LY6K), Olfactory receptor 51E2 (OR51E2), TCR Gamma Alternate Reading Frame Protein (TARP), Wilms tumor protein (WT1), Cancer/testis antigen 1 (NY-ESO-1), Cancer/testis antigen 2 (LAGE-1a), MAGE family members (including MAGE-A1, MAGE-A3 and MAGE-A4), ETS translocation-variant gene 6, located on chromosome 12p (ETV6-AML), sperm protein 17 (SPA17), X Antigen Family, Member 1A (XAGE1), angiopoietin-binding cell surface receptor 2 (Tie 2), melanoma cancer testis antigen-1 (MAD-CT-1), melanoma cancer testis antigen-2 (MAD-CT-2), Fos-related antigen 1, tumor protein p53 (p53), p53 mutant, prostein, surviving, telomerase, prostate carcinoma tumor antigen-1, melanoma antigen recognized by T cells 1, Rat sarcoma (Ras) mutant, human Telomerase reverse transcriptase (hTERT), sarcoma translocation breakpoints, melanoma inhibitor of apoptosis (ML-IAP), ERG (transmembrane protease, serine 2 (TM-PRSS2) ETS fusion gene), N-Acetyl glucosaminyl-transferase V (NA17), paired box protein Pax-3 (PAX3), Androgen receptor, Cyclin B1, v-myc avian myelocytomatosis viral oncogene neuroblastoma derived homolog (MYCN), Ras Homolog Family Member C (RhoC), Tyrosinase-related protein 2 (TRP-2), Cytochrome P450 1B1 (CYP1B1), CCCTC-Binding Factor (Zinc Finger Protein)-Like, Squamous Cell Carcinoma Antigen Recognized By T Cells 3 (SART3), Paired box protein Pax-5 (PAX5), proacrosin binding protein sp32 (OY-TES1), lymphocyte-specific protein tyrosine kinase (LCK), A kinase anchor protein 4 (AKAP-4), synovial sarcoma, X breakpoint 2 (SSX2), Receptor for Advanced Glycation Endproducts (RAGE-1), renal ubiquitous 1 (RU1), renal ubiquitous 2 (RU2), legumain, human papilloma virus E6 (HPV E6), human papilloma virus E7 (HPV E7), intestinal carboxyl esterase, heat shock protein 70-2 mutated (mut hsp70-2), CD79a, CD79b, CD72, Leukocyte-associated immunoglobulin-like receptor 1 (LA1R1), Fc fragment of IgA receptor (FCAR or CD89), Leukocyte immunoglobulin-like receptor subfamily A member 2 (LILRA2), CD300 molecule-like family member f (CD300LF), C-type lectin domain family 12 member A (CLEC12A), bone marrow stromal cell antigen 2 (BST2), EGF-like module-containing mucin-like hormone receptor-like 2 (EMR2), lymphocyte antigen 75 (LY75), Glypican-3 (GPC3), Fc receptor-like 5 (FCRL5), MUC16, 5T4, 8H9, αvβ0 integrin, αvβ6 integrin, alphafetoprotein (AFP), B7-H6, ca-125, CA9, CD44, CD44v7/8, CD52, E-cadherin, EMA (epithelial membrane antigen), epithelial glycoprotein-2 (EGP-2), epithelial glycoprotein-40 (EGP-40), ErbB4, epithelial tumor antigen (ETA), folate binding protein (FBP), kinase insert domain receptor (KDR), k-light chain, L1 cell adhesion molecule, MUC18, NKG2D, oncofetal antigen (h5T4), tumor/testis-antigen 1B, GAGE, GAGE-1, BAGE, SCP-1, CTZ9, SAGE, CAGE, CT10, MART-1, immunoglobulin lambda-like polypeptide 1 (IGLL1), Hepatitis B Surface Antigen Binding Protein (HBsAg), viral capsid antigen (VCA), early antigen (EA), EBV nuclear antigen (EBNA), HHV-6 p41 early antigen, HHV-6B U94 latent antigen, HHV-6B p98 late antigen, cytomegalovirus (CMV) antigen, large T antigen, small T antigen, adenovirus antigen, respiratory syncytial virus (RSV) antigen, hacmagglutinin (HA), neuraminidase (NA), parainfluenza type 1 antigen, parainfluenza type 2 antigen, parainfluenza type 3 antigen, parainfluenza type 4 antigen, Human Metapneumovirus (HMPV) antigen, hepatitis C virus (HCV) core antigen, HIV p24 antigen, human T-cell lympotrophic virus (HTLV-1) antigen, Merkel cell polyoma virus small T antigen, Merkel cell polyoma virus large T antigen, Kaposi sarcoma-associated herpesvirus (KSHV) lytic nuclear antigen and KSHV latent nuclear antigen.

As a non-limiting example, in some embodiments, the circular RNA construct comprises an IRES and at least one expression sequence encoding a CAR targeting a cancer antigen. As a non-limiting example, in some embodiments, the circular RNA construct comprises an IRES and a CAR comprising an antigen binding domain specific for CD19. In some embodiments, the circular RNA construct comprises an IRES and a CAR comprising an antigen binding domain specific for BCMA. In some embodiments, the circular RNA construct comprises an IRES and a CAR comprising an antigen binding domain specific for HER2. In some embodiments, the expression sequence is codon optimized.

As a non-limiting example, in some embodiments, the circular RNA construct comprises a CAR comprising an antigen binding domain specific for CD19 (B-lymphocyte antigen CD19). CD19 is a biomarker for normal and neoplastic B cells, as well as follicular dendritic cells. Diffuse large B cell lymphoma (DLBCL) is the most common lymphoma, accounting for about 25% to 30% of all the non-Hodgkin lymphomas, followed by FL. As CD19 is expressed in over 95% of B-cell malignancies, it is an attractive target for immunotherapeutic approaches. One known example of a CAR T cell therapy targeting CD19 is Yescarta® (Kite Pharma Inc., axicabtagene ciloleucel), an anti-CD19 28-ζ (28-zeta) CAR. Another known example of a CAR T cell therapy targeting CD19 is Kymriah® (Novartis Pharmaceutical Corp., tisagenlecleucel), an anti-CD19 BB-((BB-zeta) CAR. Accordingly, in some embodiments, the expression sequence of the circular RNA construct encodes a CAR, where the codon is directed to an anti-CD19 domain known in the art. In some embodiments, the CAR construct comprises an anti-CD19 binder. In some embodiments, the expression sequence is codon optimized.

As a further non-limiting example, in some embodiments, the circular RNA construct comprises a CAR comprising an antigen binding domain specific for B-cell maturation antigen (BCMA). BCMA (also referred to as TNFRSF17 or CD269), is a member of the tumor necrosis factor receptor (TNFR) superfamily and is expressed by normal and malignant plasma cells and a small subset of B cells. BCMA a known biomarker for certain cancers, including multiple myeloma, and several BCMA-targeted CAR T therapies have been studied, where the constructs varied in their costimulatory domains, hinge regions, transmembrane domains, species used to generate the anti-BCMA scFVs, and the use of different modifications to address safety of the CAR-T therapy. See generally Shah et al., "B-cell maturation antigen (BCMA) in multiple myeloma: rationale for targeting and current therapeutic approaches," Leukemia 34, 985-1005 (2020). Accordingly, in some embodiments, the expression sequence of the circular RNA construct encodes a CAR, where the codon is directed to an anti-BCMA domain known in the art. In some embodiments, the CAR construct comprises an anti-BCMA binder. In some embodiments, the expression sequence is codon optimized.

As a further non-limiting example, in some embodiments, the circular RNA construct comprises a CAR comprising an antigen binding domain specific for Human Epidermal Growth Factor Receptor 2 (HER2). For example, the CAR can be directed to HER2-BB-((BB-zeta) and/or HER2-286 (28-zeta). Accordingly, in some embodiments, the CAR construct comprises an anti-HER2 binder. In some embodiments, the expression sequence is codon optimized.

In some embodiments, the circular RNA constructs and related pharmaceutical compositions comprise the expression sequences described in Tables 2A-2C below. In some embodiments, the circular RNA constructs and related pharmaceutical compositions disclosed herein comprise an expression sequence that is at least 80%, 85%, 90%, 91%, 92%, 93%, 94%, 95%, 96%, 97%, 98%, or 99% identical to a sequence in Tables 2A-2C, wherein the codon sequence produces a protein having the desired sequence.

The exemplary anti-CD19 binder sequences in Table 2A are codon-optimized and correspond to an anti-CD19 28-ζ (28 zeta) CAR. The amino acid sequence corresponding to the nucleotide sequences in Table 2A is set forth in SEQ ID NO: 29:

```
                                    (SEQ ID NO: 29)
MALPVTALLLPLALLLHAARPDIQMTQTTSSLSASLGDRVTISCRASQD

ISKYLNWYQQKPDGTVKLLIYHTSRLHSGVPSRFSGSGSGTDYSLTISN

LEQEDIATYFCQQGNTLPYTFGGGTKLEITGGGGSGGGGSGGGGSEVKL

QESGPGLVAPSQSLSVTCTVSGVSLPDYGVSWIRQPPRKGLEWLGVIWG

SETTYYNSALKSRLTIIKDNSKSQVFLKMNSLQTDDTAIYYCAKHYYYG

GSYAMDYWGQGTSVTVSSIEVMYPPPYLDNEKSNGTIIHVKGKHLCPSP

LFPGPSKPFWVLVVVGGVLACYSLLVTVAFIIFWVRSKRSRLLHSDYMN

MTPRRPGPTRKHYQPYAPPRDFAAYRSRVKFSRSADAPAYQQGQNQLYN

ELNLGRREEYDVLDKRRGRDPEMGGKPRRKNPQEGLYNELQKDKMAEAY

SEIGMKGERRRGKGHDGLYQGLSTATKDTYDALHMQALPPR
```

In some embodiments, the circular RNA constructs and related pharmaceutical compositions disclosed herein comprise a CAR sequence encoding a polypeptide that comprises at least 80%, 85%, 90%, 91%, 92%, 93%, 94%, 95%, 96%, 97%, 98%, or 99% identity to SEQ ID NO: 29 or binding fragment thereof.

In some embodiments, the circular RNA constructs and related pharmaceutical compositions disclosed herein comprise an IRES sequence having at least 85%, 86%, 87%, 88%, 89%, 90%, 91%, 92%, 93%, 94%, 95%, 96%, 97%, 98%, 99%, or 100% sequence identity to an IRES from Table IA, an IRES from a construct of any one of SEQ ID NOs: 50-61 or any of Constructs A-P of Table 1B, and a CAR sequence encoding a polypeptide comprising at least 85%, 86%, 87%, 88%, 89%, 90%, 91%, 92%, 93%, 94%, 95%, 96%, 97%, 98%, 99%, or 100% sequence identity to SEQ ID NO: 29 or binding fragment thereof. In some embodiments, said circular RNA further comprises a CD28z costimulatory domain as described herein and optionally exhibits increased activity compared to a suitable control having an alternate costimulatory domain. In some embodiments, said circular RNA further comprises a 4-1BB costimulatory domain as described herein and optionally exhibits increased activity compared to a suitable control having an alternate costimulatory domain.

TABLE 2A

| Codon Optimized Sequences (anti-CD19 28-ζ) | | |
|---|---|---|
| Codon NO: | SEQ ID NO: | NT SEQUENCE |
| 2A-19 | 19 | ATGGCACTGCCCGTCACCGCACTCCTGCTCCCACTGGCACTGCTGCTCCATGCAG CTCGCCCCGATATCCAGATGACCCAGACCACCTCTAGCCTCAGCGCCTCTCTGGG TGACCGCGTCACCATCTCTTGCCGGGGCCAGCCAAGACATCTCTAAGTACCTGAA |

TABLE 2A-continued

Codon Optimized Sequences (anti-CD19 28-ζ)

| Codon NO: | SEQ ID NO: | NT SEQUENCE |
|---|---|---|
| | | CTGGTACCAGCAGAAACCTGACGGAACCGTGAAGCTGCTGATCTACCACACCAG |
| | | TCGGCTGCATTCCGGGGTGCCTTCCAGGTTCAGCGGTTCCGGCTCTGGGACCGAT |
| | | TATAGTCTCACCATCTCCAACCTCGAGCAGGAGGACATCGCAACCTACTTCTGCC |
| | | AGCAGGGGAACACCCTGCCCTACACCTTCGGTGGCGGGACCAAGCTGGAGATCA |
| | | CTGGAGGTGGTGGCAGCGGAGGTGGAGGATCAGGTGGAGGCGGTAGCGAGGTG |
| | | AAGCTGCAGGAGTCCGGACCTGGTCTGGTGGCCCCAAGCCAGTCCCTCAGCGTC |
| | | ACCTGCACAGTGTCCGGGGTGTCCCTGCCTGACTACGGTGTCTCCTGGATCAGGC |
| | | AACCACCCCGGAAGGGTCTCGAGTGGCTGGGCGTCATCTGGGGCTCCGAGACCA |
| | | CCTACTACAACAGCGCTCTGAAGTCCCGGCTGACCATCATCAAAGACAACTCCA |
| | | AGAGCCAGGTGTTCTTGAAGATGAACTCCCTGCAAACCGATGACACCGCCATCT |
| | | ACTACTGCGCCAAGCACTACTACTATGGCGGTAGCTACGCCATGGATTATTGGG |
| | | GTCAGGGCACCAGTGTCACCGTCTCCTCCATCGAGGTGATGTACCCTCCACCCTA |
| | | TCTGGACAACGAGAAGTCCAACGGCACCATCATCCACGTGAAGGGCAAGCACCT |
| | | GTGCCCTAGCCCTCTGTTCCCAGGACCCTCCAAGCCCTTCTGGGTGCTGGTCGTG |
| | | GTGGGAGGAGTCCTGGCCTGCTATTCCCTCCTCGTCACCGTGGCATTTATCATCT |
| | | TCTGGGTCGGAGCAAGCGGTCACGCCTGCTCCACTCCGACTACATGAACATGA |
| | | CTCCTCGCAGACCTGGACCCACCCGGAAGCACTACCAGCCTTATGCCCCACCCC |
| | | GCGACTTTGCCGCTTACCGCTCTCGGGTCAAGTTCTCTCGGTCAGCAGACGCCCC |
| | | TGCATACCAGCAGGGCCAGAACCAGCTGTATAACGAGCTGAACCTCGGCAGAC |
| | | GGGAGGAGTACGATGTGCTGGACAAGAGGAGAGGCAGAGACCCCGAGATGGGT |
| | | GGTAAGCCACGGCGCAAGAACCCACAGGAGGGCTTGTACAACGAACTGCAGAA |
| | | GGACAAGATGGCCGAGGCCTACAGCGAGATCGGCATGAAGGGAGAGAGGCGCA |
| | | GGGGCAAGGGTCACGACGGCCTGTACCAAGGGCTGTCCACCGCAACCAAGGAC |
| | | ACCTACGATGCCCTGCACATGCAGGCCCTCCCACCAAGG |
| 2A-20 | 20 | ATGGCACTCCCAGTCACCGCACTTCTGCTGCCTCTCGCCCTGCTGCTCCATGCAG |
| | | CCAGACCCGACATCCAGATGACCCAAACCACCAGCTCCCTGTCCGCTTCCCTGG |
| | | GTGACCGGGTGACTATCTCTTGCCGGGCCTCCCAAGACATCTCCAAGTACCTGA |
| | | ACTGGTATCAGCAAAAGCCTGACGGCACCGTCAAGCTCCTCATCTACCATACCT |
| | | CCAGACTGCACTCCGGGGTGCCTAGCAGGTTCAGCGGAAGTGGGAGCGGCACC |
| | | GACTACAGCCTCACCATCTCCAACCTGGAGCAGGAGGACATCGCCACCTACTTC |
| | | TGCCAGCAGGGGAACACACTGCCCTACACCTTCGGCGGTGGCACCAAGCTGGAG |
| | | ATCACAGGTGGCGGAGGTTCCGGAGGAGGAGGTAGTGGAGGTGGAGGCAGCGA |
| | | GGTGAAGCTCCAGGAATCCGGACCAGGTCTGGTGGCTCCCAGCCAGTCCCTCAG |
| | | CGTGACCTGCACCGTGAGCGGCGTGTCTCTTCCCGATTACGGAGTGTCCTGGATC |
| | | AGACAGCCACCCCGGAAGGGTCTGGAGTGGCTGGGAGTGATCTGGGGTTCCGA |
| | | GACCACATACTACAACTCAGCCCTCAAGAGCCGGCTCACCATCATCAAGGATAA |
| | | CTCCAAGTCCCAGGTCTTCCTGAAGATGAACTCTCTCCAGACCGACGACACCGC |
| | | CATCTACTACTGCGCCAAGCACTACTACTACGGCGGGTCCTACGCCATGGACTA |
| | | CTGGGGTCAGGGAACCTCCGTCACCGTCAGCTCTATCGAGGTGATGTACCCTCCT |
| | | CCCTACCTCGACAACGAGAAGAGCAACGGCACCATCATCCATGTGAAGGGGAA |
| | | GCATCTCTGCCCCTCACCCCTGTTCCCCGGACCATCCAAGCCATTCTGGGTGCTG |
| | | GTGGTTGTTGGTGGGGTCCTGGCTTGCTACTCACTCCTGGTCACCGTCGCCTTCA |
| | | TCATCTTCTGGGTGCGGTCAAAGAGGTCCCGGCTCTTGCACTCCGATTACATGAA |
| | | CATGACTCCAAGGAGGCCTGGTCCCACACGGAAGCACTACCAACCATATGCCCC |
| | | ACCACGCGACTTCGCTGCTTACCGGAGCCGGGTCAAGTTCAGTCGGAGTGCAGA |
| | | CGCCCCAGCCTACCAGCAGGGCCAGAACCAACTCTACAACGAGCTTAATCTGGG |
| | | TCGCCGGGAGGAGTATGACGTGCTCGATAAGAGAAGGGGCCGGGATCCTGAGA |
| | | TGGGCGGTAAGCCCAGACGGAAGAACCCTCAGGAGGGGTTGTATAATGAGCTC |
| | | CAGAAGGACAAGATGGCCGAGGCATACTCCGAGATCGGCATGAAAGGTGAGCG |
| | | GAGGAGAGGCAAGGGGCATGACGGCCTGTACCAGGGGCTCAGCACAGCCACCA |
| | | AGGATACCTATGACGCACTCCACATGCAGGCACTGCCTCCACGG |
| 2A-21 | 21 | ATGGCTCTGCCTGTGACAGCTCTGCTGCTGCCTCTGGCTCTGCTTCTGCATGCCG |
| | | CCAGACCTGACATCCAGATGACCCAGACAACCAGCAGCCTGTCTGCCAGCCTGG |
| | | GCGATAGAGTGACCATCAGCTGTAGAGCCAGCCAGGACATCAGCAAGTACCTG |
| | | AACTGGTATCAGCAGAAACCCGACGGCACCGTGAAGCTGCTGATCTACCACACC |
| | | AGCAGACTGCACAGCGGCGTGCCAAGCAGATTTTCTGGCAGCGGCTCTGGCACC |
| | | GACTACAGCCTGACAATCAGCAACCTGGAACAAGAGGATATCGCTACCTACTTC |
| | | TGCCAGCAAGGCAACACCCTGCCTTACACCTTTGGCGGAGGCACCAAGCTGGAA |
| | | ATCACAGGCGGCGGAGGAAGCGGAGGCGGAGGATCTGGTGGTGGTGGATCTGA |
| | | AGTGAAACTGCAAGAGTCTGGCCCTGGCTGGTGGCCCCATCTCAATCTCTGAG |
| | | CGTGACCTGTACCGTCAGCGGAGTGTCCCTGCCTGATTATGGCGTGTCCTGGATC |
| | | CGGCAGCCTCCTAGAAAAGGCCTGGAATGGCTGGGCGTGATCTGGGGCAGCGA |
| | | GACAACCTACTACAACAGCGCCCTGAAGTCCCGGCTGACCATCATCAAGGACAA |
| | | CTCCAAGAGCCAGGTGTTCCTGAAGATGAACAGCCTGCAGACCGACGACACCGC |
| | | CATCTACTATTGCGCCAAGCACTACTACTACGGCGGCAGCTACGCCATGGATTA |
| | | TTGGGGCCAGGGCACCAGCGTGACCGTGTCTAGCATCGAAGTGATGTACCCTCC |
| | | ACCTTACCTGGACAACGAGAAGTCCAACGGCACCATCATCCACGTGAAGGGCAA |
| | | GCACCTGTGTCCTTCCCACTGTTCCCCGGACCTAGCAAGCCTTTCTGGGTGCTC |
| | | GTTGTTGTTGGCGGCGTGCTGGCCTGTTACTCTCTGCTGGTTACCGTGGCCTTCA |
| | | TCATCTTTTGGGTCCGAAGCAAGCGGAGCCGGCTGCTGCACTCCGACTACATGA |
| | | ACATGACCCCTAGACGGCCCGGACCAACCAGAAAGCACTACCAGCCTTACGCTC |
| | | CTCCTAGAGACTTCGCCGCCTACCGGTCCAGAGTGAAGTTCAGCAGATCCGCCG |
| | | ATGCTCCCGCCTATCAGCAGGGCCAAAACCAGCTGTACAACGAGCTGAACCTGG |

TABLE 2A-continued

| Codon Optimized Sequences (anti-CD19 28-ζ) | | |
| --- | --- | --- |
| Codon NO: | SEQ ID NO: | NT SEQUENCE |
| | | GGAGAAGAGAAGAGTACGACGTGCTGGACAAGCGGAGAGGCAGAGATCCTGAA<br>ATGGGCGGCAAGCCCAGACGGAAGAATCCTCAAGAGGGCCTGTATAATGAGCT<br>GCAGAAAGACAAGATGGCCGAGGCCTACAGCGAGATCGGAATGAAGGGCGAGC<br>GCAGAAGAGGCAAGGGACACGATGGACTGTACCAGGGCCTGAGCACCGCCACC<br>AAGGATACCTATGATGCCCTGCACATGCAGGCCCTGCCTCCAAGA |
| 2A-22 | 22 | ATGGCCCTTCCCGTCACCGCTCTCCTCCTGCCACTGGCCTTGCTGCTGCACGCTG<br>CACGGCCAGACATCCAGATGACCCAGACAACCAGCTCTCTGTCAGCCTCTCTCG<br>GCGATCGCGTCACAATCAGCTGCCGCGCTTCCCAAGACATCTCCAAGTACCTGA<br>ACTGGTACCAGCAAAAGCCCGACGGCACCGTGAAGCTGCTCATCTACCACACCT<br>CCAGACTGCATAGCGGGGTGCCCAGCAGATTCAGTGGCTCAGGCTCAGGCACCG<br>ACTACAGCCTGACCATCTCCAACCTGGAGCAGGAGGACATTGCCACATACTTCT<br>GCCAGCAGGGCAACACCCTGCCCTACACCTTCGGAGGCGGCACAAAGCTGGAG<br>ATCACCGGTGGAGGAGGGAGTGGAGGAGGAGGCAGTGGTGGCGGAGGTTCCGA<br>GGTGAAGCTCCAGGAATCAGGTCCAGGACTGGTCGCCCCTTCCCAGTCCCTGTC<br>CGTCACCTGCACCGTGAGTGGCGTCAGCCTCCCAGACTACGGTGTGTCTTGGATC<br>CGCCAACCTCCTCGCAAAGGCCTGGAATGGCTCGGCGTCATCTGGGGAAGCGAG<br>ACAACCTACTATAACTCCGCACTGAAGTCCCGCCTCACCATCATCAAGGATAAT<br>AGCAAGAGCCAGGTCTTCCTCAAGATGAACTCCCTGCAGACCGACGATACCGCC<br>ATCTACTACTGTGCCAAGCACTACTACTACGGAGGTTCTTACGCCATGGATTACT<br>GGGGACAGGGAACCTCTGTCACCGTCAGCTCCATCGAGGTCATGTATCCACCAC<br>CCTACCTGGACAACGAAAAGAGCAATGGCACCATCATCCACGTGAAGGGGAAG<br>CACCTCTGCCCCTCACCCCTGTTCCCTGGTCCCTCCAAGCCTTTCTGGGTCCTGGT<br>CGTCGTGGGAGGCGTGTTGGCCTGTTACTCCCTGCTCGTCACCGTCGCCTTCATC<br>ATCTTCTGGGTTAGGAGTAAGCGGTCCCGGCTTCTGCACTCTGACTACATGAACA<br>TGACACCCAGAAGACCTGGGCCAACCCGGAAGCACTACCAGCCCTACGCTCCAC<br>CCAGGGACTTTGCAGCCTACAGGTCCCGCGTCAAGTTCTCCCGGTCTGCTGACGC<br>ACCTGCCTACCAGCAGGGCCAAAACCAGCTCTACAACGAGTTGAACCTCGGCAG<br>ACGGGAGGAGTACGACGTCCTCGACAAAAGGGGGGTCGGGATCCTGAGATGG<br>GCGGTAAGCCAAGGCGGAAGAACCCACAGGAAGGCCTCTATAATGAGCTCCAG<br>AAGGATAAGATGGCTGAGGCCTACTCCGAGATCGGGATGAAGGGCGAAAGGAG<br>ACGGGGTAAGGGGCACGACGGCCTCTATCAGGGTCTGAGCACCGCCACCAAGG<br>ACACCTACGACGCCCTGCACATGCAGGCACTGCCACCTCGG |
| 2A-23 | 23 | ATGGCTCTGCCAGTGACCGCACTGCTGCTGCCCTTAGCCTTACTCCTTCACGCAG<br>CCAGGCCCGACATCCAGATGACCCAGACCACCAGCTCCCTTTCCGCAAGCCTCG<br>GCGACAGGGTCACCATCTCCTGTCGGGCCAGCCAGGACATCAGCAAGTACCTGA<br>ACTGGTACCAGCAGAAGCCCGACGGCACCGTGAAGCTGCTGATCTACCACACCT<br>CACGGCTGCACTCAGGCGTGCCCTCACGGTTTAGCGGATCAGGCAGCGGCACCG<br>ACTACAGCCTGACTATCAGCAACCTGGAGCAGGAGGACATCGCCACCTACTTCT<br>GCCAGCAGGGCAACACCCTGCCCTACACCTTCGGAGGCGGCACCAAGCTGGAG<br>ATCACCGGTGGCGGTGGTTCAGGTGGCGGAGGCTCAGGAGGAGGCGGCAGCGA<br>GGTGAAGCTGCAGGAGTCAGGTCCAGGACTGGTGGCACCCAGCCAGAGCCTGA<br>GCGTGACTTGCACCGTGTCAGGCGTGAGCCTGCCAGACTACGGCGTGAGCTGGA<br>TCCGGCAGCCTCCTCGGAAGGGCTTAGAGTGGCTGGGCGTGATCTGGGGCAGCG<br>AGACCACCTACTACAACTCAGCCCTGAAGAGCCGGCTGACCATCATCAAGGACA<br>ACAGCAAGAGCCAGGTGTTCCTGAAGATGAACAGCCTGCAGACCGACGACACC<br>GCCATCTACTACTGCGCCAAGCACTACTACTACGGCGGCAGCTACGCCATGGAC<br>TACTGGGGACAGGGTACCAGCGTGACCGTGAGCAGCATCGAGGTGATGTACCCT<br>CCTCCCTACCTGGACAACGAGAAGAGCAACGGCACCATCATCCACGTGAAGGGC<br>AAGCACCTGTGCCCTAGCCCTTTATTCCCCGGCCCCTCAAAACCCTTCTGGGTGC<br>TGGTCGTCGTCGGTGGCGTGCTGGCATGCTACAGCCTGCTGGTGACCGTGGCCTT<br>CATCATATTCTGGGTCCGGTCAAAGCGGAGCCGGTTACTGCACAGCGACTACAT<br>GAACATGACTCCACGGCGTCCAGGTCCCACTCGGAAGCACTACCAACCCTACGC<br>TCCTCCCCGTGACTTTGCTGCCTACCGTAGCCGGGTGAAGTTCTCCAGGAGCGCC<br>GATGCCCCAGCCTACCAGCAGGGCCAGAACCAGCTCTACAATGAGCTTAACCTT<br>GGCAGGCGGGAGGAGTACGACGTGCTGGACAAGAGGAGGGGCCGTGATCCCGA<br>GATGGGAGGCAAGCCCCGTAGGAAGAATCCCCAGGAGGGCCTTTACAACGAGC<br>TCCAGAAGGACAAGATGGCCGAGGCCTACAGCGAGATCGGCATGAAGGGAGAG<br>CGTAGGCGTGGAAAGGGCCACGACGGCCTGTACCAGGGCCTGAGCACTGCTACC<br>AAGGACACCTACGACGCCCTGCACATGCAGGCTCTTCCACCCCGG |

Table 2B sets forth nucleotide and amino acid sequences for additional exemplary anti-CD19 binder sequences that are not codon-optimized. The sequences are directed to an anti-CD19 28-ζ (28 zeta) CAR. In some embodiments, the circular RNA constructs and related pharmaceutical compositions disclosed herein comprise a CAR sequence encoding a polypeptide that comprises at least 80%, 85%, 90%, 91%, 92%, 93%, 94%, 95%, 96%, 97%, 98%, or 99% identity to any one of SEQ ID NO: 30-34 or binding fragments thereof.

In some embodiments, the circular RNA constructs and related pharmaceutical compositions disclosed herein comprise an IRES sequence having at least 85%, 86%, 87%, 88%, 89%, 90%, 91%, 92%, 93%, 94%, 95%, 96%, 97%, 98%, 99%, or 100% sequence identity to an IRES from Table 1A, an IRES from a construct of any one of SEQ ID NOs: 50-61 or any of Constructs A-P of Table 1B, and a CAR sequence encoding a polypeptide comprising at least 85%, 86%, 87%, 88%, 89%, 90%, 91%, 92%, 93%, 94%, 95%, 96%, 97%, 98%, 99%, or 100% sequence identity to any one of SEQ ID NO: 30-34 or binding fragments thereof. In some embodiments, said circular RNA further comprises a CD28z costimulatory domain as described herein and optionally exhibits increased activity compared to a suitable control having an alternate costimulatory domain. In some embodiments, said circular RNA further comprises a 4-1BB costimulatory domain as described herein and optionally exhibits increased activity compared to a suitable control having an alternate costimulatory domain.

TABLE 2B

Additional Codon Amino Acid and Nucleotide Sequences (anti-CD19 28-ζ)

| SEQ ID NO | Codon nucleotide sequence | SEQ ID NO | Codon amino acid sequence |
|---|---|---|---|
| 24 | ATGCTCCTCCTGGTGACCAGCTTGCTCC TGTGCGAACTGCCACACCCCGCCTTCCT CCTCATCCCCGATATCCAGATGACCCAG ACCACCTCCTCCCTGAGCGCAAGCCTCG GCGATCGGGTGACCATCTCATGCAGGG CCTCCCAGGACATCTCCAAGTATCTGAA CTGGTATCAGCAGAAGCCTGACGGCAC CGTCAAGCTGCTCATCTACCACACCTCA CGGCTGCACTCAGGCGTCCCCTCAAGAT TCAGCGGTAGCGGATCCGGGACCGACT ACTCCCTTACCATCAGCAACCTGGAGCA GGAGGATATCGCCACATACTTCTGCCAG CAGGGTAACACCCTGCCCTATACCTTCG GCGGTGGGACCAAGCTGGAGATCACCG GTTCTACATCCGGATCCGGCAAGCCTGG TAGTGGCGAGGGCTCCACCAAAGGGGA GGTGAAGCTGCAGGAGTCCGGTCCAGG TCTGGTGGCTCCAAGTCAGTCCCTGTCT GTGACTTGCACCGTGTCAGGCGTGAGCC TGCCTGACTACGGGGTGAGCTGGATCCG GCAGCCACCTCGGAAGGGGTTGGAGTG GCTGGGAGTCATCTGGGGATCCGAGAC CACCTACTACAATTCCGCCCTCAAAAGC CGCCTCACCATCATCAAGGACAACTCCA AGTCCCAGGTCTTCCTGAAGATGAATTC CCTGCAGACCGACGACACCGCTATCTAT TACTGCGCCAAGCATTACTACTACGGCG GGTCCTACGCCATGGACTACTGGGGTCA AGGCACCTCCGTCACTGTTTCCTCCGCA GCAGCCATCGAGGTCATGTATCCTCCTC CCTACCTCGACAACGAGAAGTCCAACG GGACCATCATCCACGTGAAGGGCAAGC ACCTCTGCCCAAGCCCACTGTTCCCAGG GCCCTCCAAACCATTCTGGGTGCTCGTG GTGGTGGGTGGCGTGCTCGCTTGCTACT CCCTCCTGGTCACCGTCGCCTTCATCAT CTTTTGGGTCCGGAGTAAGCGCAGCCGC CTGCTCCATAGCGACTACATGAACATGA CCCCACGGAGACCTGGTCCCACCCGGA AACACTACCAGCCCTACGCACCACCCA GGGACTTCGCTGCCTATCGGTCCCGGGT TAAATTCTCTAGGTCCGCTGATGCCCCA GCCTACCAGCAGGGCCAGAACCAGCTG TACAATGAGCTGAACCTGGGTAGACGG GAGGAGTATGACGTCCTGGATAAGCGC AGAGGGAGAGACCCCGAGATGGGTGGA AAGCCCAGGCGGAAGAATCCCCAGGAG GGTCTCTATAACGAGCTCCAGAAGGAC AAGATGGCCGAGGCCTACAGCGAGATC GGGATGAAAGGGGAAAGAAGGCGGGG AAAGGGCCATGACGGACTGTACCAGGG TCTGTCCACCGCTACCAAGGACACCTAC GATGCACTGCACATGCAGGCACTGCCTC CTCGG | 30 | MLLLVTSLLLCELPHPAFLLIPDIQMTQT TSSLSASLGDRVTISCRASQDISKYLNWY QQKPDGTVKLLIYHTSRLHSGVPSRFSG SGSGTDYSLTISNLEQEDIATYFCQQGNT LPYTFGGGTKLEITGSTSGSGKPGSGEGS TKGEVKLQESGPGLVAPSQSLSVTCTVS GVSLPDYGVSWIRQPPRKGLEWLGVIW GSETTYYNSALKSRLTIIKDNSKSQVFLK MNSLQTDDTAIYYCAKHYYYGGSYAM DYWGQGTSVTVSSAAAIEVMYPPPYLD NEKSNGTIIHVKGKHLCPSPLFPGPSKPF WVLVVVGGVLACYSLLVTVAFIIFWVR SKRSRLLHSDYMNMTPRRPGPTRKHYQ PYAPPRDFAAYRSRVKFSRSADAPAYQQ GQNQLYNELNLGRREEYDVLDKRRGRD PEMGGKPRRKNPQEGLYNELQKDKMA EAYSEIGMKGERRRGKGHDGLYQGLST ATKDTYDALHMQALPPR |
| 25 | ATGCTGCTTCTCGTTACATCTCTGTTGCT CTGCGAGCTGCCTCATCCAGCCTTCCTC CTGATTCCCGATATCCAGATGACCCAGA CCACCTCTAGCCTCAGCGCCTCTCTGGG TGACCGCGTCACCATCTCTTGCCGGGCC AGCCAAGACATCTCTAAGTACCTGAACT GGTACCAGCAGAAACCTGACGGAACCG TGAAGCTGCTGATCTACCACACCAGTCG GCTGCATTCCGGGGTGCCTTCCAGGTTC AGCGGTTCCGGCTCTGGGACCGATTATA GTCTCACCATCTCCAACCTCGAGCAGGA GGACATCGCAACCTACTTCTGCCAGCAG | 31 | MLLLVTSLLLCELPHPAFLLIPDIQMTQT TSSLSASLGDRVTISCRASQDISKYLNWY QQKPDGTVKLLIYHTSRLHSGVPSRFSG SGSGTDYSLTISNLEQEDIATYFCQQGNT LPYTFGGGTKLEITGSTSGSGKPGSGEGS TKGEVKLQESGPGLVAPSQSLSVTCTVS GVSLPDYGVSWIRQPPRKGLEWLGVIW GSETTYYNSALKSRLTIIKDNSKSQVFLK MNSLQTDDTAIYYCAKHYYYGGSYAM DYWGQGTSVTVSSAAAIEVMYPPPYLD NEKSNGTIIHVKGKHLCPSPLFPGPSKPF WVLVVVGGVLACYSLLVTVAFIIFWVR |

TABLE 2B-continued

Additional Codon Amino Acid and Nucleotide Sequences (anti-CD19 28-ζ)

| SEQ ID NO | Codon nucleotide sequence | SEQ ID NO | Codon amino acid sequence |
|---|---|---|---|
| | GGGAACACCCTGCCCTACACCTTCGGTG GCGGGACCAAGCTGGAGATCACTGGCA GCACCTCAGGCTCTGGGAAGCCTGGCA GCGGTGAAGGCAGCACCAAGGGTGAGG TGAAGCTGCAGGAGTCCGGACCTGGTCT GGTGGCCCCAAGCCAGTCCCTCAGCGTC ACCTGCACAGTGTCCGGGGTGTCCCTGC CTGACTACGGTGTCTCCTGGATCAGGCA ACCACCCCGGAAGGGTCTCGAGTGGCT GGGCGTCATCTGGGGCTCCGAGACCAC CTACTACAACAGCGCTCTGAAGTCCCGG CTGACCATCATCAAAGACAACTCCAAG AGCCAGGTGTTCTTGAAGATGAACTCCC TGCAAACCGATGACACCGCCATCTACTA CTGCGCCAAGCACTACTACTATGGCGGT AGCTACGCCATGGATTATTGGGGTCAGG GCACCAGTGTCACCGTCTCCTCCGCTGC CGCTATCGAGGTGATGTACCCTCCACCC TATCTGGACAACGAGAAGTCCAACGGC ACCATCATCCACGTGAAGGGCAAGCAC CTGTGCCCTAGCCCTCTGTTCCCAGGAC CCTCCAAGCCCTTCTGGGTGCTGGTCGT GGTGGGAGGAGTCCTGGCCTGCTATTCC CTCCTCGTCACCGTGGCATTTATCATCTT CTGGGTCCGGAGCAAGCGGTCACGCCT GCTCCACTCCGACTACATGAACATGACT CCTCGCAGACCTGGACCCACCCGGAAG CACTACCAGCCTTATGCCCCCACCCCGCG ACTTTGCCGCTTACCGCTCTCGGGTCAA GTTCTCTCGGTCAGCAGACGCCCCTGCA TACCAGCAGGGCCAGAACCAGCTGTAT AACGAGCTGAACCTCGGCAGACGGGAG GAGTACGATGTGCTGGACAAGAGGAGA GGCAGAGACCCCGAGATGGGTGGTAAG CCACGGCGCAAGAACCCACAGGAGGGC TTGTACAACGAACTGCAGAAGGACAAG ATGGCCGAGGCCTACAGCGAGATCGGC ATGAAGGGAGAGAGGCGCAGGGGCAA GGGTCACGACGGCCTGTACCAAGGGCT GTCCACCGCAACCAAGGACACCTACGA TGCCCTGCACATGCAGGCCCTCCCACCA AGG | | SKRSRLLHSDYMNMTPRRPGPTRKHYQ PYAPPRDFAAYRSRVKFSRSADAPAYQQ GQNQLYNELNLGRREEYDVLDKRRGRD PEMGGKPRRKNPQEGLYNELQKDKMA EAYSEIGMKGERRRGKGHDGLYQGLST ATKDTYDALHMQALPPR |
| 26 | ATGGCACTTCCAGTTACAGCACTTCTGC TTCCATTGGCACTGCTGCTCCATGCAGC TCGCCCCGATATCCAGATGACCCAGACC ACCTCTAGCCTCAGCGCCTCTCTGGGTG ACCGCGTCACCATCTCTTGCCGGGCCAG CCAAGACATCTCTAAGTACCTGAACTGG TACCAGCAGAAACCTGACGGAACCGTG AAGCTGCTGATCTACCACACCAGTCGGC TGCATTCCGGGGTGCCTTCCAGGTTCAG CGGTTCCGGCTCTGGGACCGATTATAGT CTCACCATCTCCAACCTCGAGCAGGAGG ACATCGCAACCTACTTCTGCCAGCAGGG GAACACCCTGCCCTACACCTTCGGTGGC GGGACCAAGCTGGAGATCACTGGCAGC ACCTCAGGCTCTGGGAAGCCTGGCAGC GGTGAAGGCAGCACCAAGGGTGAGGTG AAGCTGCAGGAGTCCGGACCTGGTCTG GTGGCCCCAAGCCAGTCCCTCAGCGTCA CCTGCACAGTGTCCGGGGTGTCCCTGCC TGACTACGGTGTCTCCTGGATCAGGCAA CCACCCCGGAAGGGTCTCGAGTGGCTG GGCGTCATCTGGGGCTCCGAGACCACCT ACTACAACAGCGCTCTGAAGTCCCGGCT GACCATCATCAAAGACAACTCCAAGAG CCAGGTGTTCTTGAAGATGAACTCCCTG CAAACCGATGACACCGCCATCTACTACT GCGCCAAGCACTACTACTATGGCGGTA GCTACGCCATGGATTATTGGGGTCAGGG CACCAGTGTCACCGTCTCCTCCGCTGCC GCTATCGAGGTGATGTACCCTCCACCCT ATCTGGACAACGAGAAGTCCAACGGCA | 32 | MALPVTALLLPLALLLHAARPDIQMTQT TSSLSASLGDRVTISCRASQDISKYLNWY QQKPDGTVKLLIYHTSRLHSGVPSRFSG SGSGTDYSLTISNLEQEDIATYFCQQGNT LPYTFGGGTKLEITGSTSGSGKPGSGEGS TKGEVKLQESGPGLVAPSQSLSVTCTVS GVSLPDYGVSWIRQPPRKGLEWLGVIW GSETTYYNSALKSRLTIIKDNSKSQVFLK MNSLQTDDTAIYYCAKHYYYGGSYAM DYWGQGTSVTVSSAAAIEVMYPPPYLD NEKSNGTIIHVKGKHLCPSPLFPGPSKPF WVLVVVGGVLACYSLLVTVAFIIFWVR SKRSRLLHSDYMNMTPRRPGPTRKHYQ PYAPPRDFAAYRSRVKFSRSADAPAYQQ GQNQLYNELNLGRREEYDVLDKRRGRD PEMGGKPRRKNPQEGLYNELQKDKMA EAYSEIGMKGERRRGKGHDGLYQGLST ATKDTYDALHMQALPPR |

TABLE 2B-continued

Additional Codon Amino Acid and Nucleotide Sequences (anti-CD19 28-ζ)

| SEQ ID NO | Codon nucleotide sequence | SEQ ID NO | Codon amino acid sequence |
|---|---|---|---|
| | CCATCATCCACGTGAAGGGCAAGCACC TGTGCCCTAGCCCTCTGTTCCCAGGACC CTCCAAGCCCTTCTGGGTGCTGGTCGTG GTGGGAGGAGTCCTGGCCTGCTATTCCC TCCTCGTCACCGTGGCATTTATCATCTTC TGGGTCCGGAGCAAGCGGTCACGCCTG CTCCACTCCGACTACATGAACATGACTC CTCGCAGACCTGGACCCACCCGGAAGC ACTACCAGCCTTATGCCCCACCCCGCGA CTTTGCCGCTTACCGCTCTCGGGTCAAG TTCTCTCGGTCAGCAGACGCCCCTGCAT ACCAGCAGGGCCAGAACCAGCTGTATA ACGAGCTGAACCTCGGCAGACGGGAGG AGTACGATGTGCTGGACAAGAGGAGAG GCAGAGACCCCGAGATGGGTGGTAAGC CACGGCGCAAGAACCCACAGGAGGGCT TGTACAACGAACTGCAGAAGGACAAGA TGGCCGAGGCCTACAGCGAGATCGGCA TGAAGGGAGAGAGGCGCAGGGGCAAG GGTCACGACGGCCTGTACCAAGGGCTG TCCACCGCAACCAAGGACACCTACGAT GCCCTGCACATGCAGGCCCTCCCACCAA GG | | |
| 27 | ATGGCACTGCCCGTCACCGCACTCCTGC TCCCACTGGCACTGCTGCTCCATGCAGC TCGCCCCGATATCCAGATGACCCAGACC ACCTCTAGCCTCAGCGCCTCTCTGGGTG ACCGCGTCACCATCTCTTGCCGGGCCAG CCAAGACATCTCTAAGTACCTGAACTGG TACCAGCAGAAACCTGACGGAACCGTG AAGCTGCTGATCTACCACACCAGTCGGC TGCATTCCGGGGTGCCTTCCAGGTTCAG CGGTTCCGGCTCTGGGACCGATTATAGT CTCACCATCTCCAACCTCGAGCAGGAGG ACATCGCAACCTACTTCTGCCAGCAGGG GAACACCCTGCCCTACACCTTCGGTGGC GGGACCAAGCTGGAGATCACTGGCAGC ACCTCAGGCTCTGGGAAGCCTGGCAGC GGTGAAGGCAGCACCAAGGGTGAGGTG AAGCTGCAGGAGTCCGGACCTGGTCTG GTGGCCCCAAGCCAGTCCCTCAGCGTCA CCTGCACAGTGTCCGGGGTGTCCCTGCC TGACTACGGTGTCTCCTGGATCAGGCAA CCACCCCGGAAGGGTCTCGAGTGGCTG GGCGTCATCTGGGGCTCCGAGACCACCT ACTACAACAGCGCTCTGAAGTCCCGGCT GACCATCATCAAAGACAACTCCAAGAG CCAGGTGTTCTTGAAGATGAACTCCCTG CAAACCGATGACACCGCCATCTACTACT GCGCCAAGCACTACTACTATGGCGGTA GCTACGCCATGGATTATTGGGGTCAGGG CACCAGTGTCACCGTCTCCTCCGCTGCC GCTATCGAGGTGATGTACCCTCCACCCT ATCTGGACAACGAGAAGTCCAACGGCA CCATCATCCACGTGAAGGGCAAGCACC TGTGCCCTAGCCCTCTGTTCCCAGGACC CTCCAAGCCCTTCTGGGTGCTGGTCGTG GTGGGAGGAGTCCTGGCCTGCTATTCCC TCCTCGTCACCGTGGCATTTATCATCTTC TGGGTCCGGAGCAAGCGGTCACGCCTG CTCCACTCCGACTACATGAACATGACTC CTCGCAGACCTGGACCCACCCGGAAGC ACTACCAGCCTTATGCCCCACCCCGCGA CTTTGCCGCTTACCGCTCTCGGGTCAAG TTCTCTCGGTCAGCAGACGCCCCTGCAT ACCAGCAGGGCCAGAACCAGCTGTATA ACGAGCTGAACCTCGGCAGACGGGAGG AGTACGATGTGCTGGACAAGAGGAGAG GCAGAGACCCCGAGATGGGTGGTAAGC CACGGCGCAAGAACCCACAGGAGGGCT TGTACAACGAACTGCAGAAGGACAAGA TGGCCGAGGCCTACAGCGAGATCGGCA TGAAGGGAGAGAGGCGCAGGGGCAAG | 33 | MALPVTALLLPLALLLHAARPDIQMTQT TSSLSASLGDRVTISCRASQDISKYLNWY QQKPDGTVKLLIYHTSRLHSGVPSRFSG SGSGTDYSLTISNLEQEDIATYFCQQGNT LPYTFGGGTKLEITGSTSGSGKPGSGEGS TKGEVKLQESGPGLVAPSQSLSVTCTVS GVSLPDYGVSWIRQPPRKGLEWLGVIW GSETTYYNSALKSRLTIIKDNSKSQVFLK MNSLQTDDTAIYYCAKHYYYGGSYAM DYWGQGTSVTVSSAAAIEVMYPPPYLD NEKSNGTIIHVKGKHLCPSPLFPGPSKPF WVLVVVGGVLACYSLLVTVAFIIFWVR SKRSRLLHSDYMNMTPRRPGPTRKHYQ PYAPPRDFAAYRSRVKFSRSADAPAYQQ GQNQLYNELNLGRREEYDVLDKRRGRD PEMGGKPRRKNPQEGLYNELQKDKMA EAYSEIGMKGERRRGKGHDGLYQGLST ATKDTYDALHMQALPPR |

TABLE 2B-continued

Additional Codon Amino Acid and Nucleotide Sequences (anti-CD19 28-ζ)

| SEQ ID NO | Codon nucleotide sequence | SEQ ID NO | Codon amino acid sequence |
|---|---|---|---|
| | GGTCACGACGGCCTGTACCAAGGGCTG TCCACCGCAACCAAGGACACCTACGAT GCCCTGCACATGCAGGCCCTCCCACCAA GG | | |
| 28 | ATGGCACTTCCAGTTACAGCACTTCTGC TTCCATTGGCACTGCTGCTCCATGCAGC TCGCCCCGATATCCAGATGACCCAGACC ACCTCTAGCCTCAGCGCCTCTCTGGGTG ACCGCGTCACCATCTCTTGCCGGGCCAG CCAAGACATCTCTAAGTACCTGAACTGG TACCAGCAGAAACCTGACGGAACCGTG AAGCTGCTGATCTACCACACCAGTCGGC TGCATTCCGGGGTGCCTTCCAGGTTCAG CGGTTCCGGCTCTGGGACCGATTATAGT CTCACCATCTCCAACCTCGAGCAGGAGG ACATCGCAACCTACTTCTGCCAGCAGGG GAACACCCTGCCCTACACCTTCGGTGGC GGGACCAAGCTGGAGATCACTGGAGGT GGTGGCAGCGGAGGTGGAGGATCAGGT GGAGGCGGTAGCGAGGTGAAGCTGCAG GAGTCCGGACCTGGTCTGGTGGCCCCAA GCCAGTCCCTCAGCGTCACCTGCACAGT GTCCGGGGTGTCCCTGCCTGACTACGGT GTCTCCTGGATCAGGCAACCACCCCGGA AGGGTCTCGAGTGGCTGGGCGTCATCTG GGGCTCCGAGACCACCTACTACAACAG CGCTCTGAAGTCCCGGCTGACCATCATC AAAGACAACTCCAAGAGCCAGGTGTTC TTGAAGATGAACTCCCTGCAAACCGATG ACACCGCCATCTACTACTGCGCCAAGCA CTACTACTATGGCGGTAGCTACGCCATG GATTATTGGGGTCAGGGCACCAGTGTCA CCGTCTCCTCCATCGAGGTGATGTACCC TCCACCCTATCTGGACAACGAGAAGTCC AACGGCACCATCATCCACGTGAAGGGC AAGCACCTGTGCCCTAGCCCTCTGTTCC CAGGACCCTCCAAGCCCTTCTGGGTGCT GGTCGTGGTGGGAGGAGTCCTGGCCTG CTATTCCCTCCTCGTCACCGTGGCATTT ATCATCTTCTGGGTCCGGAGCAAGCGGT CACGCCTGCTCCACTCCGACTACATGAA CATGACTCCTCGCAGACCTGGACCCACC CGGAAGCACTACCAGCCTTATGCCCCAC CCCGCGACTTTGCCGCTTACCGCTCTCG GGTCAAGTTCTCTCGGTCAGCAGACGCC CCTGCATACCAGCAGGGCCAGAACCAG CTGTATAACGAGCTGAACCTCGGCAGA CGGGAGGAGTACGATGTGCTGGACAAG AGGAGAGGCAGAGACCCCGAGATGGGT GGTAAGCCACGGCGCAAGAACCCACAG GAGGGCTTGTACAACGAACTGCAGAAG GACAAGATGGCCGAGGCCTACAGCGAG ATCGGCATGAAGGGAGAGAGGCGCAGG GGCAAGGGTCACGACGGCCTGTACCAA GGGCTGTCCACCGCAACCAAGGACACC TACGATGCCCTGCACATGCAGGCCCTCC CACCAAGG | 34 | MALPVTALLLPLALLLHAARPDIQMTQT TSSLSASLGDRVTISCRASQDISKYLNWY QQKPDGTVKLLIYHTSRLHSGVPSRFSG SGSGTDYSLTISNLEQEDIATYFCQQGNT LPYTFGGGTKLEITGGGGSGGGGSGGGG SEVKLQESGPGLVAPSQSLSVTCTVSGV SLPDYGVSWIRQPPRKGLEWLGVIWGSE TTYYNSALKSRLTIIKDNSKSQVFLKMN SLQTDDTAIYYCAKHYYYGGSYAMDY WGQGTSVTVSSIEVMYPPPYLDNEKSNG TIIHVKGKHLCPSPLFPGPSKPFWVLVVV GGVLACYSLLVTVAFIIFWVRSKRSRLL HSDYMNMTPRRPGPTRKHYQPYAPPRD FAAYRSRVKFSRSADAPAYQQGQNQLY NELNLGRREEYDVLDKRRGRDPEMGGK PRRKNPQEGLYNELQKDKMAEAYSEIG MKGERRRGKGHDGLYQGLSTATKDTY DALHMQALPPR |

Table 2C sets forth nucleotide and amino acid sequences for additional exemplary binder sequences that are not codon-optimized, including a mouse anti-CD19 binder, anti-BCMA binders, and anti-HER2 binders. In some embodiments, the circular RNA constructs and related pharmaceutical compositions disclosed herein comprise a CAR sequence encoding a polypeptide that comprises at least 80%, 85%, 90%, 91%, 92%, 93%, 94%, 95%, 96%, 97%, 98%, or 99% identity to any one of SEQ ID NO: 116-135 or binding fragments thereof.

In some embodiments, the circular RNA constructs and related pharmaceutical compositions disclosed herein com-prise an IRES sequence having at least 85%, 86%, 87%, 88%, 89%, 90%, 91%, 92%, 93%, 94%, 95%, 96%, 97%, 98%, 99%, or 100% sequence identity to an IRES from Table 1A, an IRES from a construct of any one of SEQ ID NOs: 50-61 or any of Constructs A-P of Table 1B, and a CAR sequence encoding a polypeptide comprising at least 85%, 86%, 87%, 88%, 89%, 90%, 91%, 92%, 93%, 94%, 95%, 96%, 97%, 98%, 99%, or 100% sequence identity to any one of SEQ ID NO: 116-135 or binding fragments thereof. In some embodiments, said circular RNA further comprises a CD28z costimulatory domain as described herein and optionally exhibits increased activity compared to a suitable control having an alternate costimulatory domain. In some embodiments, said circular RNA further comprises a 4-1BB costimulatory domain as described herein and optionally exhibits increased activity compared to a suitable control having an alternate costimulatory domain.

TABLE 2C

| | SEQ ID NO | Codon nucleotide sequence | SEQ ID NO | Codon amino acid sequence |
|---|---|---|---|---|
| | | Additional Codon Amino Acid and Nucleotide Sequences | | |
| Mouse CD19 | 100 | ATGGGCGTGCCTACCCAGCTGCTCGGTCT CCTGCTGCTCTGGATCACCGACGCTATCT GCGACATCCAAATGACCCAGAGTCCCGC TTCCCTCAGCACCTCCCTGGGTGAGACCG TCACCATCCAGTGCCAGGCATCCGAGGA CATCTACAGTGGTCTCGCCTGGTACCAGC AGAAGCCTGGTAAGTCCCCTCAGCTGCT GATCTACGGTGCTTCCGATCTGCAGGAC GGAGTCCCTAGCCGCTTCTCAGGCTCTGG CTCCGGTACCCAGTACTCCCTGAAGATC ACATCCATGCAGACCGAAGACGAGGGAG TGTACTTCTGCCAGCAGGGGCTGACCTA CCCTCGGACATTCGGCGGTGGAACCAAG CTCGAGCTGAAGGGAGGTGGAGGCAGTG GTGGCGGAGGATCTGGTGGTGGTGGCTC CGAGGTCCAACTGCAGCAGTCCGGCGCT GAGCTGGTGAGGCCCGGAACCAGCGTCA AACTCAGCTGCAAGGTGAGCGGGGACAC CATCACCTTCTACTACATGCACTTCGTCA AGCAGAGGCCTGGGCAGGGTCTTGAATG GATCGGCCGGATCGATCCAGAGGACGAG TCTACAAAGTACTCCGAGAAGTTCAAGA ACAAAGCAACCCTGACCGCCGACACAAG CTCCAACACCGCCTACCTGAAGCTGTCC AGCCTCACCTCTGAGGACACCGCCACCT ACTTCTGCATCTACGGCGGGTACTACTTC GACTATTGGGGCCAAGGGGTGATGGTCA CCGTGTCCTCTATCGAGTTCATGTATCCT CCTCCCTACCTGGACAACGAGCGGAGCA ACGGCACCATCATCCACATCAAAGAGAA GCACCTCTGCCACACCCAATCCTCTCCCA AACTCTTCTGGGCCCTCGTTGTGGTCGCA GGCGTGCTCTTCTGCTACGGGCTGCTGGT GACTGTGGCCTTGTGCGTGATCTGGACC AACAGTAGACGGAATCGGGGAGGTCAG AGCGACTACATGAACATGACACCTCGCA GACCAGGCCTGACACGGAAGCCCTACCA ACCATACGCTCCTGCCCGGGATTTTGCAG CATATCGGCCACGGGCCAAGTTTAGCAG GTCCGCAGAGACCGCAGCCAACCTGCAA GACCCTAACCAGCTGTACAACGAGCTGA ACCTTGGTCGCCGGGAGGAGTACGACGT CCTGGAGAAGAAGAGAGCACGGGATCCC GAGATGGGCGGAAAGCAACAACGCCGG CGGAATCCTCAGGAGGGTGTCTACAACG CCCTCCAGAAGGACAAGATGGCTGAGGC CTACTCCGAGATCGGCACTAAGGGCGAG CGCAGACGGGGAAAGGGTCACGACGGG CTGTACCAGGGTCTCAGCACCGCAACCA AGGATACCTACGACGCCCTGCACATGCA AACCCTCGCACCCCGG | 116 | MGVPTQLLGLLLLWITDAICDIQ MTQSPASLSTSLGETVTIQCQAS EDIYSGLAWYQQKPGKSPQLLIY GASDLQDGVPSRFSGSGSGTQYS LKITSMQTEDEGVYFCQQGLTYP RTFGGGTKLELKGGGGSGGGGS GGGGSEVQLQQSGAELVRPGTS VKLSCKVSGDTITFYYMHFVKQ RPGQGLEWIGRIDPEDESTKYSE KFKNKATLTADTSSNTAYLKLSS LTSEDTATYFCIYGGYYFDYWG QGVMVTVSSIEFMYPPPYLDNER SNGTIIHIKEKHLCHTQSSPKLFW ALVVVAGVLFCYGLLVTVALCV IWTNSRRNRGGQSDYMNMTPRR PGLTRKPYQPYAPARDFAAYRP RAKFSRSAETAANLQDPNQLYN ELNLGRREEYDVLEKKRARDPE MGGKQQRRRNPQEGVYNALQK DKMAEAYSEIGTKGERRGKGH DGLYQGLSTATKDTYDALHMQT LAPR |
| HER2 | 101 | ATGGCTCTGCCTGTGACAGCTCTGCTGCT GCCTCTGGCTCTGCTTCTGCATGCCGCCA GACCTGACATCCAGATGACTCAGAGCCC CAGCAGCCTGTCTGCCTCTGTGGGAGAC AGAGTGACAATTACCTGCCGGGCCAGCC AGGATGTGAATACTGCTGTCGCCTGGTA TCAACAAAAGCCTGGCAAGGCCCCTAAG CTCCTGATCTACAGCGCCAGCTTTCTGTA CAGCGGCGTGCCCAGCAGATTCTCCGGA AGCAGAAGCGGCACAGATTTCACACTGA CCATAAGCAGCCTGCAGCCAGAGGATTT CGCCACCTACTATTGCCAGCAGCACTAC ACCACACCTCCAACCTTTGGCCAGGGCA CCAAGGTCGAGATTAAGAGAACAGGCAG CACATCTGGCTCTGGCAAACCTGGATCT GGCGAGGGCTCTGAAGTCCAGCTGGTGG AATCTGGCGGAGGACTGGTTCAACCTGG | 117 | MALPVTALLLPLALLLHAARPDI QMTQSPSSLSASVGDRVTITCRA SQDVNTAVAWYQQKPGKAPKL LIYSASFLYSGVPSRFSGSRSGTD FTLTISSLQPEDFATYYCQQHYT TPPTFGQGTKVEIKRTGSTSGSG KPGSGEGSEVQLVESGGGLVQP GGSLRLSCAASGFNIKDTYIHWV RQAPGKGLEWVARIYPTNGYTR YADSVKGRFTISADTSKNTAYLQ MNSLRAEDTAVYYCSRWGGDG FYAMDVWGQGTLVTVSSIEVMY PPPYLDNEKSNGTIIHVKGKHLC PSPLFPGPSKPFWVLVVVGGVLA CYSLLVTVAFIIFWVRSKRSRLL HSDYMNMTPRRPGPTRKHYQPY APPRDFAAYRSRVKFSRSADAPA |

TABLE 2C-continued

Additional Codon Amino Acid and Nucleotide Sequences

| SEQ ID NO | Codon nucleotide sequence | SEQ ID NO | Codon amino acid sequence |
|---|---|---|---|
| | CGGCTCTCTGAGACTGTCTTGTGCCGCCT<br>CCGGCTTCAACATCAAGGACACCTACAT<br>CCACTGGGTCCGACAAGCCCCAGGCAAA<br>GGACTTGAGTGGGTCGCCAGGATCTACC<br>CCACCAACGGCTACACCAGATACGCCGA<br>CTCTGTGAAGGGCAGATTCACCATCTCTG<br>CCGACACCAGCAAGAATACCGCCTACCT<br>GCAGATGAACTCCCTGAGAGCCGAAGAT<br>ACCGCTGTGTATTACTGTTCCAGATGGGG<br>AGGCGACGGCTTCTACGCCATGGATGTT<br>TGGGGCCAAGGCACCCTCGTGACCGTTT<br>CTTCTATCGAAGTGATGTACCCTCCACCT<br>TACCTGGACAACGAGAAGTCCAACGGCA<br>CCATCATCCACGTGAAGGGCAAGCACCT<br>GTGTCCTTCTCCACTGTTCCCCGGACCTA<br>GCAAGCCTTTCTGGGTGCTCGTTGTTGTT<br>GGCGGCGTGCTGGCCTGTTACTCTCTGCT<br>GGTTACCGTGGCCTTCATCATCTTTTGGG<br>TCCGAAGCAAGCGGAGCCGGCTGCTGCA<br>CTCCGACTACATGAACATGACCCCTAGA<br>CGGCCCGGACCAACCAGAAAGCACTACC<br>AGCCTTACGCTCCTCCTAGAGACTTCGCC<br>GCCTACCGGTCCAGAGTGAAGTTCAGCA<br>GATCCGCCGATGCTCCCGCCTATCAGCA<br>GGGCCAAAACCAGCTGTACAACGAGCTG<br>AACCTGGGGAGAAGAGAAGAGTACGAC<br>GTGCTGGACAAGCGGAGAGGCAGAGATC<br>CTGAAATGGGCGGCAAGCCCAGACGGAA<br>GAATCCTCAAGAGGGCCTGTATAATGAG<br>CTGCAGAAAGACAAGATGGCCGAGGCCT<br>ACAGCGAGATCGGAATGAAGGGCGAGC<br>GCAGAAGAGGCAAGGGACACGATGGAC<br>TGTACCAGGGCCTGAGCACCGCCACCAA<br>GGATACCTATGATGCCCTGCACATGCAG<br>GCCCTGCCTCCAAGA | | YQQGQNQLYNELNLGRREEYDV<br>LDKRRGRDPEMGGKPRRKNPQE<br>GLYNELQKDKMAEAYSEIGMKG<br>ERRRGKGHDGLYQGLSTATKDT<br>YDALHMQALPPR |
| HER2   102 | ATGGCTCTGCCTGTGACAGCTCTGCTGCT<br>GCCTCTGGCTCTGCTTCTGCATGCCGCCA<br>GACCTGACATCCAGATGACTCAGAGCCC<br>CAGCAGCCTGTCTGCCTCTGTGGGAGAC<br>AGAGTGACAATTACCTGCCGGGCCAGCC<br>AGGATGTGAATACTGCTGTCGCCTGGTA<br>TCAACAAAAGCCTGGCAAGGCCCCTAAG<br>CTCCTGATCTACAGCGCCAGCTTTCTGTA<br>CAGCGGCGTGCCCAGCAGATTCTCCGGA<br>AGCAGAAGCGGCACAGATTTCACACTGA<br>CCATAAGCAGCCTGCAGCCAGAGGATTT<br>CGCCACCTACTATTGCCAGCAGCACTAC<br>ACCACACCTCCAACCTTTGGCCAGGGCA<br>CCAAGGTCGAGATTAAGAGAACAGGCAG<br>CACATCTGGCTCTGGCAAACCTGGATCT<br>GGCGAGGGCTCTGAAGTCCAGCTGGTGG<br>AATCTGGCGGAGGACTGGTTCAACCTGG<br>CGGCTCTCTGAGACTGTCTTGTGCCGCCT<br>CCGGCTTCAACATCAAGGACACCTACAT<br>CCACTGGGTCCGACAAGCCCCAGGCAAA<br>GGACTTGAGTGGGTCGCCAGGATCTACC<br>CCACCAACGGCTACACCAGATACGCCGA<br>CTCTGTGAAGGGCAGATTCACCATCTCTG<br>CCGACACCAGCAAGAATACCGCCTACCT<br>GCAGATGAACTCCCTGAGAGCCGAAGAT<br>ACCGCTGTGTATTACTGTTCCAGATGGGG<br>AGGCGACGGCTTCTACGCCATGGATGTT<br>TGGGGCCAAGGCACCCTCGTGACCGTTT<br>CTTCTACCACCACACCAGCTCCTCGGCCT<br>CCAACTCCTGCTCCTACAATTGCCAGCCA<br>GCCTCTGTCTCTGAGGCCCGAAGCTTGTA<br>GACCTGCTGCTGGCGGAGCCGTGCATAC<br>AAGAGGACTGGATTTCGCCTGCGACATC<br>TACATCTGGGCTCCTCTGGCCGGAACAT<br>GTGGCCGTTCTGCTGCTGAGCCTGGTCATC<br>ACCCTGTACTGTAAGCGGGGCAGAAAGA<br>AGCTGCTGTACATCTTCAAGCAGCCCTTC<br>ATGCGGCCCGTGCAGACCACACAAGAGG | 118 | MALPVTALLLPLALLLHAARPDI<br>QMTQSPSSLSASVGDRVTITCRA<br>SQDVNTAVAWYQQKPGKAPKL<br>LIYSASFLYSGVPSRFSGSRSGTD<br>FTLTISSLQPEDFATYYCQQHYT<br>TPPTFGQGTKVEIKRTGSTSGSG<br>KPGSGEGSEVQLVESGGGLVQP<br>GGSLRLSCAASGFNIKDTYIHWV<br>RQAPGKGLEWVARIYPTNGYTR<br>YADSVKGRFTISADTSKNTAYLQ<br>MNSLRAEDTAVYYCSRWGGDG<br>FYAMDVWGQGTLVTVSSTTTPA<br>PRPPTPAPTIASQPLSLRPEACRP<br>AAGGAVHTRGLDFACDIYIWAP<br>LAGTCGVLLLSLVITLYCKRGRK<br>KLLYIFKQPFMRPVQTTQEEDGC<br>SCRFPEEEEGGCELRVKFSRSAD<br>APAYQQGQNQLYNELNLGRREE<br>YDVLDKRRGRDPEMGGKPRRK<br>NPQEGLYNELQKDKMAEAYSEI<br>GMKGERRRGKGHDGLYQGLST<br>ATKDTYDALHMQALPPR |

TABLE 2C-continued

Additional Codon Amino Acid and Nucleotide Sequences

| | SEQ ID NO | Codon nucleotide sequence | SEQ ID NO | Codon amino acid sequence |
|---|---|---|---|---|
| | | AAGATGGCTGCTCCTGCAGATTCCCCGA GGAAGAAGAAGGCGGCTGCGAGCTGAG AGTGAAGTTCAGCAGATCCGCCGATGCT CCCGCCTATCAGCAGGGCCAAAACCAGC TGTACAACGAGCTGAACCTGGGGAGAAG AGAAGAGTACGACGTGCTGGACAAGCGG AGAGGCAGAGATCCTGAAATGGGCGGCA AGCCCAGACGGAAGAATCCTCAAGAGGG CCTGTATAATGAGCTGCAGAAAGACAAG ATGGCCGAGGCCTACAGCGAGATCGGAA TGAAGGGCGAGCGCAGAAGAGGCAAGG GACACGATGGACTGTACCAGGGCCTGAG CACCGCCACCAAGGATACCTATGATGCC CTGCACATGCAGGCCCTGCCTCCAAGA | | |
| BCMA | 103 | ATGGCACTCCCGGTAACCGCCTTATTGCT TCCCCTTGCCCTCTTGCTCCACGCAGCAC GCCCCGATATAGTCTTGACTCAATCCCCA CCCAGTTTGGCAATGTCATTAGGCAAAC GAGCAACAATTTCATGTAGGGCATCCGA AAGTGTAACGATTTTGGGGAGTCATTTA ATTCATTGGTACCAACAAAAGCCTGGAC AACCCCGACGCTCTTGATCCAATTAGC ATCTAACGTCCAAACCGGAGTCCCCGCA CGATTCTCAGGATCCGGTTCCCGGACTG ATTTTACATTAACTATTGATCCGGTAGAG GAAGATGACGTCGCTGTCTATTATTGTCT TCAAAGTAGGACGATTCCACGGACATTC GGTGGCGGAACTAAATTGGAGATTAAAG GTTCCACCTCTGGTAGTGGGAAACCCGG GTCCGGTGAAGGGTCCACTAAAGGCCAA ATTCAACTCGTTCAATCCGGACCAGAAC TGAAGAAGCCAGGAGAAACTGTCAAAT AAGCTGTAAAGCTTCCGGTTATACATTTA CAGATTATTCCATAAAATTGGGTGAAAG GGCGCCAGGAAAAGGGTTAAAGTGGATG GGTTGGATTAATACAGAGACTCGGGAAC CTGCATATGCTTATGATTTTAGGGGAG GTTTGCCTTTTCTCTGGAGACTTCCGCTT CAACTGCTTATCTCCAAATTAATAATCTT AAATATGAGGACACAGCAACATACTTCT GTGCTTTGGACTATAGTTATGCTATGGAT TACTGGGGACAAGGAACCAGTGTCACTG TAAGTTCCGCTGCTGCGACGACCACTCCT GCACCGCGACCACCCACTCCTGCCCCTA CTATTGCTAGTCAACCACTTAGCTTGCGA CCTGAGGCATGTCGGCCCGCGGCAGGTG GCGCAGTCCACACCAGGGGTTTAGACTT TGCTTGTGATATTTATATTTGGGCACCAC TCGCCGGGACTTGCGGTGTTCTTCTCTTG TCCCTTGTTATAACTCTTTATTGTAAGCG CGGAAGGAAGAAATTGTTATATATTTTC AAACAACCTTTTATGCGACCCGTACAAA CAACTCAGGAAGAGGACGGGTGTTCTTG TCGGTTTCCAGAAGAGGAAGAGGGTGGG TGTGAACTCCGGGTCAAATTTAGTAGGT CAGCAGATGCGCCGGCGTACCAACAAGG CCAAAACCAACTGTATAATGAACTCAAT CTCGGTAGGCGTGAGGAATATGATGTCC TTGATAAAAGGCGCGGGAGAGATCCAGA AATGGGCGGAAAACCACGGCGAAAGAA TCCGCAGGAAGGGTTATATAACGAACTT CAAAAGGATAAAATGGCTGAAGCTTATT CCGAAATTGGCATGAAAGGAGAGCGACG TAGGGGCAAAGGGCATGATGGCCTTTAC CAAGGGCTCTCAACCGCTACAAAAGATA CTTACGACGCTTTACATATGCAAGCACTT CCACCCAGG | 119 | MALPVTALLLPLALLLHAARPDI VLTQSPPSLAMSLGKRATISCRA SESVTILGSHLIHWYQQKPGQPP TLLIQLASNVQTGVPARFSGSGS RTDFTLTIDPVEEDDVAVYYCLQ SRTIPRTFGGGTKLEIKGSTSGSG KPGSGEGSTKGQIQLVQSGPELK KPGETVKISCKASGYTFTDYSIN WVKRAPGKGLKWMGWINTETR EPAYAYDFRGRFAFSLETSASTA YLQINNLKYEDTATYFCALDYS YAMDYWGQGTSVTVSSAAATT TPAPRPPTPAPTIASQPLSLRPEA CRPAAGGAVHTRGLDFACDIYI WAPLAGTCGVLLLSLVITLYCKR GRKKLLYIFKQPFMRPVQTTQEE DGCCRFPEEEEGGCELRVKFSR SADAPAYQQGQNQLYNELNLGR REEYDVLDKRRGRDPEMGGKPR RKNPQEGLYNELQKDKMAEAYS EIGMKGERRRGKGHDGLYQGLS TATKDTYDALHMQALPPR |
| BCMA | 104 | ATGGCCCTCCCCGTCACAGCTCTCCTGCT CCCACTGGCCCTTCTTTTGCACGCTGCTC GCCCCGATATCGTGCTCACCCAGTCACCT CCAAGCCTTGCCATGAGCCTCGGGAAAC GGGCTACCATCTCCTGCCGGGCTTCAGA | 120 | MALPVTALLLPLALLLHAARPDI VLTQSPPSLAMSLGKRATISCRA SESVTILGSHLIHWYQQKPGQPP TLLIQLASNVQTGVPARFSGSGS RTDFTLTIDPVEEDDVAVYYCLQ |

TABLE 2C-continued

| | | | | |
|---|---|---|---|---|
| | | Additional Codon Amino Acid and Nucleotide Sequences | | |
| SEQ ID NO | Codon nucleotide sequence | | SEQ ID NO | Codon amino acid sequence |
| | GTCCGTCACCATCCTCGGGTCACACCTCA TCCACTGGTACCAACAGAAACCAGGGCA GCCTCCTACCCTCTTGATCCAGTTGGCCT CCAACGTGCAAACTGGGGGTTCCCGCCAG GTTCAGTGGCTCCGGATCCCGGACAGAT TTCACACTTACCATCGATCCTGTGGAGGA GGACGATGTGGCCGTCTATTACTGCCTGC AGTCTCGCACCATCCCTCGGACCTTCGGT GGAGGCACCAAGCTCGAGATCAAGGGTA GCACCTCCGGCTCTGGAAAGCCAGGCTC TGGTGAGGGTTCTACCAAGGGCCAAATC CAGCTGGTCCAGTCTGGGCCCGAGCTGA AGAAACCCGGGGAGACCGTGAAGATCTC CTGCAAGGCCTCCGGTTATACCTTCACCG ACTACTCCATCAACTGGGTCAAGCGCGC TCCTGGAAAGGGCCTCAAGTGGATGGGC TGGATCAACACCGAAACCCGCGAGCCTG CCTATGCTTACGACTTCAGGGGCCGGTTC GCTTTCTCACTGGAGACCTCCGCTTCCAC AGCCTACCTCCAGATCAACAACCTCAAG TACGAAGACACCGCCACCTATTTCTGCG CTCTCGACTATTCCTACGCTATGGACTAC TGGGGTCAGGGCACCTCTGTGACCGTCT CTAGCGCAGCCGCCACCACAACACCAGC CCCACGGCCACCTACTCCCGCACCCACC ATCGCATCCCAACCACTCAGTCTGAGGC CCGAGGCCTGTAGACCTGCTGCTGGAGG CGCAGTGCATACCCGCGGTCTCGACTTC GCCTGCGACATCTATATCTGGGCCCCATT GGCAGGTACCTGTGGCGTGCTGCTGCTG TCACTCGTCATCACCCTGTACTGCCGGAG TAAGCGCTCTAGGCTGTTGCACAGCGAC TACATGAACATGACCCCAAGAAGACCAG GGCCTACCCGGAAGCACTACCAGCCATA CGCACCTCCCCGGGACTTTGCCGCCTATC GGTCTCGGGTGAAGTTCTCACGCTCCGCT GATGCCCCAGCATACCAGCAGGGGCAGA ACCAGCTGTACAATGAGCTCAACCTCGG TCGCCGCGAAGAGTACGACGTGCTCGAC AAGAGAAGGGGCAGGGACCCTGAGATG GGAGGCAAGCCCCGCAGAAAGAATCCCC AGGAAGGTCTGTACAACGAGCTGCAAAA GGATAAGATGGCTGAGGCCTACAGCGAG ATCGGCATGAAGGGCGAAAGGAGACGG GGAAAGGGCCACGACGGGCTCTACCAGG GACTCTCCACCGCCACCAAGGACACCTA CGACGCCCTCCACATGCAGGCTCTGCCA CCCAGG | | | SRTIPRTFGGGTKLEIKGSTSGSG KPGSGEGSTKGQIQLVQSGPELK KPGETVKISCKASGYTFTDYSIN WVKRAPGKGLKWMGWINTETR EPAYAYDERGRFAFSLETSASTA YLQINNLKYEDTATYFCALDYS YAMDYWGQGTSVTVSSAAATT TPAPRPPTPAPTIASQPLSLRPEA CRPAAGGAVHTRGLDFACDIYI WAPLAGTCGVLLLSLVITLYCRS KRSRLLHSDYMNMTPRRPGPTR KHYQPYAPPRDFAAYRSRVKFS RSADAPAYQQGQNQLYNELNLG RREEYDVLDKRRGRDPEMGGKP RRKNPQEGLYNELQKDKMAEA YSEIGMKGERRRGKGHDGLYQG LSTATKDTYDALHMQALPPR |
| BCMA | 105 | ATGGCACTTCCCGTCACCGCTCTCCTGCT GCCCCTCGCACTGCTGCTCCATGCAGCCC GCCCAGACATCGTCCTGACCCAGTCCCCT CCCCCCTCGCAATGTCCCTCGGGAAAC GGGCCACCATCAGCTGCCGGGCCTCTGA GTCAGTGACAATCCTCGGAAGCCATCTG ATCCATTGGTACCAGCAGAAACCCGGTC AGCCTCCAACCCTCCTCATCCAGCTGCC TCCAACGTGCAGACAGGAGTCCCCGCTC GGTTCTCAGGCAGCGGTTCCAGGACCGA CTTCACCCTGACCATCGACCCCGTGGAA GAGGACGATGTGGCTGTACTACTGCC TCCAGTCCCGGACCATCCCACGGACCTTC GGAGGTGGGACAAAGCTGGAGATCAAA GGCAGCACCAGCGGTTCTGGCAAGCCAG GGTCAGGTGAGGGGAGCACAAAGGGTC AGATCCAGCTGGTCAGAGCGGTCCCGA GCTGAAGAAGCCCGGGGAGACCGTTAAG ATCTCCTGCAAGGCTAGCGGGTACACCT TCACGGACTATAGTATCAACTGGGTCAA GCGCGCTCCTGGCAAGGGGCTCAAGTGG ATGGGGTGGATCAACACCGAAACCAGGG AGCCCGCATACGCTTATGACTTTCGGGG CCGGTTCGCCTTTTCCCTGGAGACCAGCG CCTCTACCGCCTACCTCCAGATCAACAAC | | 121 | MALPVTALLLPLALLLHAARPDI VLTQSPPSLAMSLGKRATISCRA SESVTILGSHLIHWYQQKPGQPP TLLIQLASNVQTGVPARFSGSGS RTDFLTIDPVEEDDVAVYYCLQ SRTIPRTFGGGTKLEIKGSTSGSG KPGSGEGSTKGQIQLVQSGPELK KPGETVKISCKASGYTFTDYSIN WVKRAPGKGLKWMGWINTETR EPAYAYDFRGRFAFSLETSASTA YLQINNLKYEDTATYFCALDYS YAMDYWGQGTSVTVSSIEVMYP PPYLDNEKSNGTIIHVKGKHLCP SPLFPGPSKPFWVLVVVGGVLAC YSLLVTVAFIIFWVRSKRSRLLHS DYMNMTPRRPGPTRKHYQPYAP PRDFAAYRSRVKFSRSADAPAY QQGQNQLYNELNLGRREEYDVL DKRRGRDPEMGGKPRRKNPQEG LYNELQKDKMAEAYSEIGMKGE RRRGKGHDGLYQGLSTATKDTY DALHMQALPPR |

TABLE 2C-continued

| | | | | |
|---|---|---|---|---|
| | | Additional Codon Amino Acid and Nucleotide Sequences | | |
| | SEQ ID NO | Codon nucleotide sequence | SEQ ID NO | Codon amino acid sequence |
| | | CTGAAGTACGAGGACACCGCCACCTACT TCTGCGCACTCGACTACTCCTACGCTATG GACTACTGGGGTCAGGGTACCTCCGTCA CCGTCTCCAGCATCGAGGTCATGTACCCT CCTCCCTACCTGGACAACGAGAAGTCCA ACGGCACCATCATCCATGTGAAGGGCAA GCATCTCTGCCCCAGCCCACTGTTCCCCG GACCCTCTAAGCCCTTCTGGGTCCTGGTC GTCGTCGGCGGTGTTCTGGCTTGCTACAG CTTGCTGGTCACCGTCGCCTTCATCATCT TCTGGGTGCGCTCCAAGAGGAGCCGGCT GCTGCATAGCGACTACATGAACATGACC CCTAGAAGGCCTGGTCCAACCCGCAAGC ACTACCAGCCTTACGCCCCTCCACGGGA CTTCGCAGCCTACCGGTCACGGGTGAAG TTCTCTCGGAGCGCAGATGCCCCAGCAT ACCAGCAGGGCCAGAACCAGCTGTACAA CGAACTTAACCTTGGTCGGCGGGAGGAA TACGATGTGCTGGACAAGCGCAGGGGTC GGGATCCTGAAATGGGCGGGAAACCACG CCGGAAGAACCCACAGGAGGGGCTCTAT AACGAGCTCCAAAAGGATAAGATGGCTG AGGCTTACAGCGAGATTGGAATGAAGGG AGAAAGAAGACGGGGCAAGGGTCACGA CGGGTTGTACCAGGGTCTGAGCACCGCC ACCAAGGACACCTACGACGCCCTCCACA TGCAAGCCCTTCCACCCCGC | | |
| BCMA | 106 | ATGGCTCTCCCCGTGACCGCTCTGCTGCT CCCTCTGGCCCTCCTTCTGCACGCAGCCA GACCACAGGTCAAGCTGGAGGAGTCTGG TGGCGGTCTGGTGCAGGCAGGGAGGAGC CTGAGGCTGAGCTGTGCAGCTTCCGAGC ACACATTCTCAAGCCACGTCATGGGGTG GTTCAGACAGGCTCCCGGTAAAGAGAGG GAGTCCGTCGCCGTGATCGGATGGCGGG ACATCTCCACCTCCTACGCCGACTCTGTG AAGGGCCGGTTCACAATCTCACGCGATA ATGCCAAGAAGACACTGTATCTGCAGAT GAATTCCTTGAAGCCCGAAGACACCGCC GTCTATTACTGTGCTGCTAGACGGATCGA CGCTGCCGACTTCGACAGCTGGGGACAG GGTACCCAAGTGACCGTTTCCTCCGGAG GCGGAGGTTCTGGAGGAGGTGGGTCAGG TGGAGGTGGCTCCGAGGTGCAGCTGGTC GAGTCTGGCGGTGGCTTGGTCCAGGCTG GAGGCAGTCTCAGACTCTCCTGCGCTGCT TCAGGGCGGACCTTCACCATGGGCTGGT TCAGGCAGGCCCCAGGTAAGGAGAGGG AGTTCGTGGCCGCCATCTCCCTCTCCCCT ACCCTGGCATACTACGCTGAGTCCGTGA AGGGACGGTTTACCATCTCCCGGGATAA CGCAAAGAACACTGTGGTCCTCCAAATG AACTCCCTCAAACCCGAGGACACCGCTC TCTACTATTGTGCCGCAGATCGGAAGAG CGTCATGTCCATCCGGCCCGATTACTGGG GCCAAGGCACACAGGTGACTGTGTCCAG CACCTCCACCACCACCCCAGCACCAAGG CCTCCAACCCCTGCACCAACCATCGCCTC CCAGCCACTGTCTTTGCGGCCAGAAGCA TGCCGCCCAGCAGCAGGTGGAGCCGTGC ATACAAGAGGCCTGGACTTCGCCTGCGA TATCTACATCTGGGCTCCTCTGGCCGGAA CATGCGGAGTCCTGCTCTTGTCCCTGGTG ATCACCCTGTACTGCAAGCGGGGTCGGA AGAAGCTCCTCTACATCTTCAAGCAGCC CTTCATGAGACCCGTCCAGACCACCCAG GAGGAGGACGGGTGCTCATGCAGGTTCC CCGAAGAGGAGGAGGGTGGCTGTGAGCT GCGGGTGAAGTTCAGCAGGTCAGCAGAC GCCCCTGCCTATCAGCAGGGCCAAAACC AGTTGTACAACGAGCTGAATCTGGGGAG ACGGGAGGAGTACGATGTCCTTGACAAG AGAAGGGGCCGGGATCCAGAGATGGGC | 122 | MALPVTALLLPLALLLHAARPQ VKLEESGGGLVQAGRSLRLSCA ASEHTFSSHVMGWFRQAPGKER ESVAVIGWRDISTSYADSVKGRF TISRDNAKKTLYLQMNSLKPEDT AVYYCAARRIDAADFDSWGQGT QVTVSSGGGGSGGGGSGGGGSE VQLVESGGGLVQAGGSLRLSCA ASGRTFTMGWFRQAPGKEREFV AAISLSPTLAYYAESVKGRFTISR DNAKNTVVLQMNSLKPEDTALY YCAADRKSVMSIRPDYWGQGTQ VTVSSTSTTTPAPRPPTPAPTIAS QPLSLRPEACRPAAGGAVHTRG LDFACDIYIWAPLAGTCGVLLLS LVITLYCKRGRKKLLYIFKQPFM RPVQTTQEEDGCSCRFPEEEEGG CELRVKFSRSADAPAYQQGQNQ LYNELNLGRREEYDVLDKRRGR DPEMGGKPRRKNPQEGLYNELQ KDKMAEAYSEIGMKGERRRGK GHDGLYQGLSTATKDTYDALH MQALPPR |

TABLE 2C-continued

Additional Codon Amino Acid and Nucleotide Sequences

| | SEQ ID NO | Codon nucleotide sequence | SEQ ID NO | Codon amino acid sequence |
|---|---|---|---|---|
| | | GGGAAGCCAAGACGGAAGAATCCTCAG GAGGGTCTGTATAACGAGCTGCAGAAGG ACAAGATGGCCGAGGCCTACTCCGAGAT CGGCATGAAAGGGGAGCGCCGCAGAGG AAAAGGTCACGATGGTCTGTACCAGGGG TTGAGCACCGCTACCAAGGATACTTACG ACGCTCTGCACATGCAAGCTCTGCCACC CCGG | | |
| BCMA | 107 | ATGGCACTCCCCGTTACCGCCCTTCTGCT GCCTCTCGCCTTGCTGCTGCACGCAGCCA GACCACAGGTCAAGCTGGAGGAGTCTGG TGGCGGGCTCGTTCAAGCAGGTCGGAGT CTCCGCCTGTCTTGCGCAGCATCAGAGC ATACCTTCTCCTCACACGTGATGGGGTGG TTCAGGCAAGCTCCCGGTAAGGAGAGGG AGTCCGTGGCCGTTATCGGCTGGCGCGA TATCAGCACCTCCTACGCAGACAGCGTT AAGGGCCGGTTCACTATCTCCAGGGACA ACGCTAAGAAGACACTCTACCTCCAGAT GAACAGTCTGAAGCCCGAGGACACCGCA GTGTACTATTGCGCTGCTCGGCGGATCG ATGCTGCCGACTTCGACAGCTGGGGTCA AGGGACCCAGGTCACCGTTTCCAGCGGA GGTGGCGGAAGTGGTGGCGGAGGATCAG GTGGTGGAGGCTCCGAGGTCCAGCTGGT GGAATCAGGAGGCGGCTTGGTGCAGGCT GGTGGGTCTTTGCGGTTGTCCTGCGCAGC TTCCGGCAGGACCTTCACCATGGGATGG TTCAGACAAGCCCCAGGTAAGGAGCGGG AGTTTGTGGCCGCAATCTCACTGTCTCCC ACCCTCGCTTACTACGCCGAGAGTGTGA AGGGGCGCTTCACAATCAGTCGCGACAA CGCAAAGAACACCGTCGTCCTGCAAATG AACTCCCTGAAGCCTGAGGATACCGCAC TCTATTACTGCGCCGCCGATCGGAAGAG CGTCATGTCCATCCGGCCCGACTATTGGG GCCAAGGCACCCAAGTGACCGTCAGCTC CACCTCCACAACCACTCCCGCCCCAAGA CCACCTACCCCAGCCCCAACAATCGCAT CCCAGCCTCTGTCCCTTCGGCCCGAAGCT TGTCGCCCTGCAGCAGGTGGAGCAGTGC ACACCCGGGGACTGGACTTCGCCTGCGA CATCTACATCTGGGCACCCCTGGCTGGA ACCTGCGGCGTGTTGCTGCTGAGCCTGGT GATCACCCTCTACTGCCGCTCTAAGAGA AGCCGGCTGCTGCATAGCGACTACATGA ACATGACCCCTAGGAGACCAGGACCCAC CCGGAAGCACTACCAGCCTTACGCTCCT CCACGGGATTTCGCTGCTTACCGCAGCC GGGTGAAGTTTTCCAGGTCAGCTGACGC CCCTGCCTACCAGCAGGGCCAGAACCAA TTGTACAACGAACTGAATCTGGGACGGC GCGAGGAATACGACGTCCTGGACAAGAG GCGGGGTAGAGATCCCGAGATGGGCGGG AAACCTCGGCGGAAGAACCCTCAGGAGG GGCTCTACAACGAGCTGCAGAAGGATAA GATGGCCGAAGCCTACTCCGAGATCGGG ATGAAGGGTGAACGGAGGAGGGGCAAG GGACACGACGGCCTGTATCAGGGCCTCA GCACCGCTACCAAGGACACCTACGACGC CCTGCACATGCAGGCTCTCCCACCACGG | 123 | MALPVTALLLPLALLLHAARPQ VKLEESGGGLVQAGRSLRLSCA ASEHTFSSHVMGWFRQAPGKER ESVAVIGWRDISTSYADSVKGRF TISRDNAKKTLYLQMNSLKPEDT AVYYCAARRIDAADFDSWGQGT QVTVSSGGGGSGGGGSGGGGSE VQLVESGGGLVQAGGSLRLSCA ASGRTFTMGWFRQAPGKEREFV AAISLSPTLAYYAESVKGRFTISR DNAKNTVVLQMNSLKPEDTALY YCAADRKSVMSIRPDYWGQGTQ VTVSSTSTTTPAPRPPTPAPTIAS QPLSLRPEACRPAAGGAVHTRG LDFACDIYIWAPLAGTCGVLLLS LVITLYCRSKRSRLLHSDYMNM TPRRPGPTRKHYQPYAPPRDFAA YRSRVKFSRSADAPAYQQGQNQ LYNELNLGRREEYDVLDKRRGR DPEMGGKPRRKNPQEGLYNELQ KDKMAEAYSEIGMKGERRRGK GHDGLYQGLSTATKDTYDALH MQALPPR |
| BCMA | 108 | ATGGCTCTTCCCGTCACCGCTTTGCTGCT GCCCCTGGCACTCCTCCTCCATGCTGCTC GGCCTCAGGTGAAGCTGGAGGAGAGTGG TGGCGGTCTGGTGCAAGCTGGCAGATCT CTGCGCCTGTCTTGCGCAGCCAGCGAAC ACACCTTCTCCTCCCACGTGATGGGGTGG TTTCGGCAGGCACCCGGGAAAGAGCGCG AGTCCGTCGCAGTCATCGGGTGGCGGGA CATCTCTACCAGCTACGCAGATTCCGTCA AGGGCCGGTTCACCATTTCCGGGATAA CGCTAAGAAGACCCTCTACCTGCAAATG | 124 | MALPVTALLLPLALLLHAARPQ VKLEESGGGLVQAGRSLRLSCA ASEHTFSSHVMGWFRQAPGKER ESVAVIGWRDISTSYADSVKGRF TISRDNAKKTLYLQMNSLKPEDT AVYYCAARRIDAADFDSWGQGT QVTVSSGGGGSGGGGSGGGGSE VQLVESGGGLVQAGGSLRLSCA ASGRTFTMGWFRQAPGKEREFV AAISLSPTLAYYAESVKGRFTISR DNAKNTVVLQMNSLKPEDTALY |

TABLE 2C-continued

Additional Codon Amino Acid and Nucleotide Sequences

| SEQ ID NO | Codon nucleotide sequence | SEQ ID NO | Codon amino acid sequence |
|---|---|---|---|
| | AACTCTCTGAAGCCCGAAGACACCGCCG TCTACTATTGCGCAGCAAGGCGCATCGA CGCTGCCGACTTCGACTCTTGGGGCCAA GGAACCCAGGTCACCGTGTCTTCCGGAG GAGGAGGCTCCGGTGGTGGAGGTTCTGG AGGTGGCGGCTCAGAGGTGCAGCTCGTG GAGAGCGGTGGTGGACTCGTTCAGGCAG GCGGCAGTTTGCGGCTGTCCTGTGCAGC CTCCGGTCGCACTTTCACTATGGGATGGT TCCGCCAGGCTCCTGGTAAAGAAAGGGA GTTCGTGGCCGCCATCAGTCTGAGCCCC ACCCTCGCATACTACGCCGAGAGCGTGA AGGGTAGGTTCACTATCAGCCGGGACAA CGCCAAGAACACCGTGGTGCTCCAGATG AATTCCCTGAAGCCTGAGGATACCGCCC TCTACTACTGCGCTGCCGACCGCAAGAG CGTGATGAGCATCCGGCCTGACTATTGG GGTCAGGGGACACAGGTGACCGTCAGCA GCATCGAGGTGATGTATCCACCACCCTA CCTCGACAACGAGAAGTCCAACGGCACC ATCATCCACGTCAAGGGGAAGCACCTCT GCCCTTCCCCTCTGTTCCCTGGCCCCTCA AAGCCCTTCTGGGTCCTGGTGGTGGTTGG TGGGGTGCTGGCTTGCTACTCCCTGCTCG TGACCGTGGCTTTCATCATCTTCTGGGTT CGGAGCAAACGGTCCAGACTGCTGCACT CCGACTACATGAACATGACCCCAAGAAG ACCTGGGCCCACACGGAAGCATTACCAA CCCTATGCACCACCTCGGGATTTCGCCGC CTACAGATCCCGGGTCAAGTTCTCCAGG TCCGCCGATGCACCAGCCTATCAGCAGG GGCAAAACCAGCTGTATAATGAGCTGAA CCTTGGACGGCGCGAGGAGTACGACGTG CTCGACAAAAGACGCGGTCGCGACCCAG AGATGGGCGGCAAGCCTAGACGCAAGA ATCCCCAGGAGGGGCTCTATAACGAGTT GCAGAAGGATAAGATGGCCGAGGCCTAC AGCGAGATCGGGATGAAAGGCGAAAGA CGGCGCGCGAAAGGGTCACGACGGACTCT ACCAGGGCCTGAGCACAGCCACCAAAGA CACCTACGACGCTCTGCATATGCAAGCA CTGCCTCCCCGG | | YCAADRKSVMSIRPDYWGQGTQ VTVSSIEVMYPPPYLDNEKSNGT IIHVKGKHLCPSPLFPGPSKPFWV LVVVGGVLACYSLLVTVAFIIFW VRSKRSRLLHSDYMNMTPRRPG PTRKHYQPYAPPRDFAAYRSRV KFSRSADAPAYQQGQNQLYNEL NLGRREEYDVLDKRRGRDPEMG GKPRRKNPQEGLYNELQKDKM AEAYSEIGMKGERRRGKGHDGL YQGLSTATKDTYDALHMQALPP R |
| BCMA | 109 | ATGGCTCTCCCCGTGACCGCTCTCCTCCT TCCCTTGGCCTTGTTGCTGCACGCCGCAA GGCCTCAGGTGAAGCTGGAGGAATCCGG AGGCGGACTCGTCCAAGCAGGTCGGTCC CTCAGGCTGTCTTGCGCTGCCAGCGAGC ACACCTTCTCTAGCCACGTGATGGGTTGG TTCAGACAGGCCCCAGGAAAGGAGCGGG AATCCGTGGCAGTGATCGGCTGGCGGGA CATCAGCACCTCCTACGCCGACTCGTCA AGGGCCGGTTCACCATCAGCCGCGACAA CGCCAAGAAGACCCTGTACCTGCAGATG AACAGCCTCAAGCCTGAGGACACCGCCG TGTACTACTGCGCCGCCAGAAGGATCGA CGCCGCAGACTTCGACTCCTGGGGTCAG GGAACCCAGGTGACCGTGTCCTCCACCT CTACCACCACACCAGCACCCAGACCTCC TACTCCCGCTCCCACCATCGCTTCCCAGC CCCTGTCCCTCAGACCCGAAGCCTGCAG ACCAGCAGCTGGCGGTGCAGTGCACACC AGGGGTCTTGACTTCGCCTGTGACATCTA CATCTGGGCTCCACTGGCTGGGACTTGC GGCGTTCTGCTGCTGAGCCTGGTGATCAC CCTGTACTGCAAGCGGGGCCGGAAGAAG CTGCTCTACATCTTCAAGCAGCCTTTCAT GCGGCCCGTTCAGACCACCCAGGAGGAA GACGGGTGCAGTGCCGCTTCCCTGAGG AGGAGGAGGGAGGATGCGAGCTGCGGG TCAAGTTCTCTCGGTCCGCTGATGCCCCA GCCTACCAGCAGGGCCAGAACCAGCTCT ATAACGAGCTGAACCTCGGTAGGCGGGA GGAGTACGACGTCCTGGACAAAAGGAGG | 125 | MALPVTALLLPLALLLHAARPQ VKLEESGGGLVQAGRSLRLSCA ASEHTFSSHVMGWFRQAPGKER ESVAVIGWRDISTSYADSVKGRF TISRDNAKKTLYLQMNSLKPEDT AVYYCAARRIDAADFDSWGQGT QVTVSSTSTTTPAPRPPTPAPTIA SQPLSLRPEACRPAAGGAVHTRG LDFACDIYIWAPLAGTCGVLLLS LVITLYCKRGRKKLLYIFKQPFM RPVQTTQEEDGCSCRFPEEEEGG CELRVKFSRSADAPAYQQGQNQ LYNELNLGRREEYDVLDKRRGR DPEMGGKPRRKNPQEGLYNELQ KDKMAEAYSEIGMKGERRRGK GHDGLYQGLSTATKDTYDALH MQALPPR |

TABLE 2C-continued

| | | Additional Codon Amino Acid and Nucleotide Sequences | | |
|---|---|---|---|---|
| | SEQ ID NO | Codon nucleotide sequence | SEQ ID NO | Codon amino acid sequence |
| | | GGACGGGATCCTGAGATGGGAGGAAAG CCACGGCGGAAGAACCCTCAAGAGGGGC TGTACAACGAACTCCAGAAGGACAAGAT GGCTGAGGCTTATTCTGAGATCGGCATG AAGGGAGAGCGCAGACGCGGCAAGGGA CACGATGGCCTGTATCAGGGACTGAGCA CCGCCACCAAGGATACCTACGACGCCCT CCATATGCAGGCTCTCCCACCACGG | | |
| BCMA | 110 | ATGGCACTGCCCGTCACAGCTCTGCTGCT GCCCTTGGCCCTCTTGTTGCACGCAGCAC GGCCAGAGGTGCAACTTGTCGAGAGCGG TGGTGGCCTTGTGCAGGCCGGAGGCAGT TTGCGCCTCAGTTGTGCAGCTTCTGGCCG GACCTTCACCATGGGCTGGTTCAGACAG GCCCCTGGTAAGGAACGCGAGTTCGTGG CCGCCATCAGCCTGTCCCCAACCCTGGCC TACTACGCAGAGAGCGTGAAGGGTCGGT TCACCATCTCCCGCGACAACGCAAAGAA CACCGTGGTGCTCCAGATGAACTCCCTG AAGCCAGAAGACACCGCCCTGTACTACT GCGCAGCCGACCGGAAGAGCGTGATGTC CATCCGCCCTGACTACTGGGGCCAAGGC ACACAGGTCACAGTGTCCAGCACCTCCA CTACCACTCCAGCTCCACGCCCTCCAACA CCCGCACCAACCATCGCCAGCCAGCCTC TGAGTCTGAGACCCGAAGCATGCCGGCC AGCTGCTGGAGGTGCCGTGCACACCAGA GGGCTGGACTTCGCCTGCGACATCTACA TCTGGGCTCCTCTGGCCGGAACTTGCGG GGTGCTGCTCCTCTCACTGGTCATCACCC TGTACTGCAAGAGGGGCAGGAAGAAGCT CCTGTACATCTTCAAGCAGCCCTTCATGC GGCCAGTCCAGACAACCCAGGAGGAAG ACGGATGCAGCTGTCGCTTCCCCGAGGA GGAGGAAGGCGGCTGCGAATTGCGGGTC AAGTTCAGCAGATCCGCTGACGCTCCTG CCTACCAACAGGGACAGAACCAGCTCTA CAACGAGCTGAACCTGGGAAGGCGGGA GGAGTACGACGTCCTGGACAAGAGAAGA GGACGCGACCCCGAGATGGGGAGGTAAGC CCAGACGCAAGAACCCTCAAGAGGGGACT GTATAACGAGCTGCAGAAGGACAAGATG GCCGAGGCCTACAGCGAGATCGGCATGA AGGGTGAAAGAAGACGGGGAAAGGGGC ACGACGGTCTGTATCAGGGGCTCTCCAC CGCAACCAAGGATACCTATGACGCTCTG CACATGCAGGCACTCCCTCCACGC | 126 | MALPVTALLLPLALLLHAARPEV QLVESGGGLVQAGGSLRLSCAA SGRTFTMGWFRQAPGKEREFVA AISLSPTLAYYAESVKGRFTISRD NAKNTVVLQMNSLKPEDTALYY CAADRKSVMSIRPDYWGQGTQV TVSSTSTTTPAPRPPTPAPTIASQP LSLRPEACRPAAGGAVHTRGLD FACDIYIWAPLAGTCGVLLLSLVI TLYCKRGRKKLLYIFKQPFMRPV QTTQEEDGCSCRFPEEEEGGCEL RVKFSRSADAPAYQQGQNQLYN ELNLGRREEYDVLDKRRGRDPE MGGKPRRKNPQEGLYNELQKD KMAEAYSEIGMKGERRRGKGH DGLYQGLSTATKDTYDALHMQ ALPPR |
| BCMA | 111 | ATGGCACTGCCCGTGACCGCTCTGCTGCT GCCTCTCGCCCTGCTGCTGCATGCTGCCA GGCCCCAAGTCAAGCTCGAGGAGTCTGG TGGTGGGCTCGTCCAAGCTGGCAGGTCC CTGAGACTGAGTTGTGCCGCCTCCGAGC ACACTTTCAGCTCTCACGTGATGGGCTGG TTCAGGCAGGCACCCGGTAAGGAGCGGG AGTCTGTGGCTGTTATCGGGTGGCGGGA TATCTCTACCTCCTACGCCGACTCCGTCA AGGGCCGGTTCACCATCTCCAGGGACAA CGCAAAGAAGACCCTCTACCTCCAGATG AACTCACTCAAGCCCGAGGACACCGCTG TGTACTACTGCGCAGCCAGACGCATCGA TGCCGCAGACTTCGACTCCTGGGGCCAA GGTACCCAAGTGACAGTGTCCAGCATCG AGGTGATGTACCCACCTCCCTACCTCGAC AACGAGAAGAGCAACGGCACCATCATCC ACGTGAAGGGGAAGCACCTGTGTCCCTC TCCCCTTTTCCCAGGACCCTCCAAGCCAT TCTGGGTCCTGGTCGTTGTCGGAGGCGTG CTCGCTTGCTATTCCCTGCTCGTCACCGT GGCCTTCATCATCTTCTGGGTGCGGTCCA AGAGATCCCGGCTGCTGCACTCTGATTA CATGAACATGACACCCAGGAGGCCAGGG CCTACCAGGAAGCACTACCAGCCCTACG | 127 | MALPVTALLLPLALLLHAARPQ VKLEESGGGLVQAGRSLRLSCA ASEHTFSSHVMGWFRQAPGKER ESVAVIGWRDISTSYADSVKGRF TISRDNAKKTLYLQMNSLKPEDT AVYYCAARRIDAADFDSWGQGT QVTVSSIEVMYPPPYLDNEKSNG TIIHVKGKHLCPSPLFPGPSKPFW VLVVVGGVLACYSLLVTVAFIIF WVRSKRSRLLHSDYMNMTPRRP GPTRKHYQPYAPPRDFAAYRSR VKFSRSADAPAYQQGQNQLYNE LNLGRREEYDVLDKRRGRDPEM GGKPRRKNPQEGLYNELQKDK MAEAYSEIGMKGERRRGKGHD GLYQGLSTATKDTYDALHMQAL PPR |

TABLE 2C-continued

| | | Additional Codon Amino Acid and Nucleotide Sequences | | |
|---|---|---|---|---|
| | SEQ ID NO | Codon nucleotide sequence | SEQ ID NO | Codon amino acid sequence |
| | | CTCCTCCACGCGACTTCGCAGCATACCG GTCCCGCGTCAAGTTCTCCCGGTCCGCAG ATGCTCCAGCCTATCAGCAGGGCCAGAA CCAGCTGTACAACGAACTCAATTTGGGG AGGCGCGAGGAGTATGATGTGCTCGATA AGAGAAGGGGCCGGGATCCTGAGATGG GAGGCAAGCCCAGACGGAAGAACCCTCA GGAGGGCCTGTACAATGAGCTGCAGAAG GACAAGATGGCCGAGGCCTACTCCGAGA TCGGGATGAAGGGTGAAAGAAGGAGGG GTAAGGGCACGACGGGCTCTACCAAGG CCTGAGCACCGCTACCAAGGACACCTAC GATGCACTGCATATGCAAGCCCTGCCAC CACGG | | |
| BCMA | 112 | ATGGCCCTCCCTGTCACAGCCCTCTTGCT GCCCCTCGCACTCCTTCTGCACGCAGCTC GGCCTGAGGTCCAGCTGGTCGAGAGTGG AGGCGGACTGGTCCAGGCAGGTGGGAGT CTTCGGCTTTCCTGCGCAGCTTCCGGACG GACCTTCACCATGGGTTGGTTCCGGCAG GCACCTGGGAAGGAGAGGGAGTTCGTTG CCGCTATCAGCCTCTCACCAACCCTGGCC TACTATGCAGAGAGCGTCAAGGGCCGCT TCACCATCAGCCGCGACAACGCCAAGAA CACCGTCGTGCTGCAGATGAACTCCCTC AAGCCCGAGGATACCGCCCTGTACTACT GCGCTGCCGATCGGAAGTCCGTCATGTC CATTCGGCCCGACTACTGGGGACAGGGC ACACAGGTGACCGTCAGCAGCATCGAGG TCATGTACCCTCCACCCTACCTGGACAAC GAGAAGAGCAACGGGACCATCATCCACG TGAAGGGGAAGCACCTCTGTCCAAGTCC CCTCTTCCCAGGACCCTCCAAGCCATTCT GGGTCCTCGTGGTGGTTGGAGGAGTGCT CGCCTGCTACTCTCTGCTGGTGACCGTCG CCTTCATCATCTTCTGGGTGCGGTCCAAG CGGTCTCGCCTCCTCCACTCCGACTACAT GAACATGACACCACGCAGACCTGGGCCC ACTAGGAAGCACTATCAGCCCTATGCAC CACCCCGGGATTTCGCAGCCTACCGGTC ACGGGTGAAGTTCAGCAGATCCGCAGAC GCACCAGCCTACCAGCAGGGGCAGAACC AGCTGTATAACGAGCTGAACCTCGGTCG CAGGGAGGAGTACGATGTCCTGGATAAG AGAAGGGGCAGGGATCCCGAGATGGGT GGCAAGCCCAGACGGAAGAATCCTCAGG AGGGGCTCTACAACGAGCTGCAGAAGGA CAAGATGGCCGAGGCTTACTCAGAGATC GGCATGAAAGGGGAGAGGAGGCGCGGA AAAGGCCACGACGGCCTCTACCAGGGAC TGTCCACCGCAACCAAGGATACCTACGA CGCCCTGCACATGCAAGCCCTCCCACCTC GG | 128 | MALPVTALLLPLALLLHAARPEV QLVESGGGLVQAGGSLRLSCAA SGRTFTMGWFRQAPGKEREFVA AISLSPTLAYYAESVKGRFTISRD NAKNTVVLQMNSLKPEDTALYY CAADRKSVMSIRPDYWGQGTQV TVSSIEVMYPPPYLDNEKSNGTII HVKGKHLCPSPLFPGPSKPFWVL VVVGGVLACYSLLVTVAFIIFWV RSKRSRLLHSDYMNMTPRRPGP TRKHYQPYAPPRDFAAYRSRVK FSRSADAPAYQQGQNQLYNELN LGRREEYDVLDKRRGRDPEMGG KPRRKNPQEGLYNELQKDKMAE AYSEIGMKGERRRGKGHDGLYQ GLSTATKDTYDALHMQALPPR |
| BCMA | 113 | ATGGCTCTCCCCGTGACCGCTCTCCTCCT TCCCTTGGCCTTGTTGCTGCACGCCGCAA GGCCTCAGGTGAAGCTGGAGGAATCCGG AGGCGGACTCGTCCAAGCAGGTCGGTCC CTCAGGCTGTCTTGCGCTGCCAGCGAGC ACACCTTCTCTAGCCACGTGATGGGTTGG TTCAGACAGGCCCCAGGAAAGGAGCGGG AATCCGTGGCAGTGATCGGCTGGCGGGA CATCAGCACCTCCTACGCCGACTCCGTCA AGGGCCGGTTCACCATCAGCCGCGACAA CGCCAAGAAGACCCTGTACCTGCAGATG AACAGCCTCAAGCCTGAGGACACCGCCG TGTACTACTGCGCCGCCAGAAGGATCGA CGCCGCAGACTTCGACTCCTGGGGTCAG GGAACCCAGGTGACCGTGTCCTCCACCT CTACCACCACACCAGCACCCAGACCTCC TACTCCCGCTCCCACCATCGCTTCCCAGC CCCTGTCCCTCAGACCCGAAGCCTGCAG ACCAGCAGCTGGCGGTGCAGTGCACACC | 129 | MALPVTALLLPLALLLHAARPQ VKLEESGGGLVQAGRSLRLSCA ASEHTFSSHVMGWFRQAPGKER ESVAVIGWRDISTSYADSVKGRF TISRDNAKKTLYLQMNSLKPEDT AVYYCAARRIDAADFDSWGQGT QVTVSSTSTTTPAPRPPTPAPTIA SQPLSLRPEACRPAAGGAVHTRG LDFACDIYIWAPLAGTCGVLLLS LVITLYCKRGRKKLLYIFKQPFM RPVQTTQEEDGCSCRFPEEEGG CELRVKFSRSADAPAYQQGQNQ LYNELNLGRREEYDVLDKRRGR DPEMGGKPRRKNPQEGLYNELQ KDKMAEAYSEIGMKGERRRGK GHDGLYQGLSTATKDTYDALH MQALPPRGSGEGRGSLLTCGDV EENPGPMALPVTALLLPLALLLH AARPEVQLVESGGGLVQAGGSL |

TABLE 2C-continued

| | | Additional Codon Amino Acid and Nucleotide Sequences | | | |
|---|---|---|---|---|---|
| SEQ ID NO | | Codon nucleotide sequence | SEQ ID NO | | Codon amino acid sequence |
| | | AGGGGTCTTGACTTCGCCTGTGACATCTA | | | RLSCAASGRTFTMGWFRQAPGK |
| | | CATCTGGGCTCCACTGGCTGGGACTTGC | | | EREFVAAISLSPTLAYYAESVKG |
| | | GGCGTTCTGCTGCTGAGCCTGGTGATCAC | | | RFTISRDNAKNTVVLQMNSLKPE |
| | | CCTGTACTGCAAGCGGGGCCGGAAGAAG | | | DTALYYCAADRKSVMSIRPDYW |
| | | CTGCTCTACATCTTCAAGCAGCCTTTCAT | | | GQGTQVTVSSIEVMYPPPYLDNE |
| | | GCGGCCCGTTCAGACCACCCAGGAGGAA | | | KSNGTIIHVKGKHLCPSPLFPGPS |
| | | GACGGGTGCAGTTGCCGCTTCCCTGAGG | | | KPFWVLVVVGGVLACYSLLVTV |
| | | AGGAGGAGGGAGGATGCGAGCTGCGGG | | | AFIIFWVRSKRSRLLHSDYMNMT |
| | | TCAAGTTCTCTCGGTCCGCTGATGCCCCA | | | PRRPGPTRKHYQPYAPPRDFAAY |
| | | GCCTACCAGCAGGGCCAGAACCAGCTCT | | | RSRVKFSRSADAPAYQQGQNQL |
| | | ATAACGAGCTGAACCTCGGTAGGCGGGA | | | YNELNLGRREEYDVLDKRRGRD |
| | | GGAGTACGACGTCCTGGACAAAAGGAGG | | | PEMGGKPRRKNPQEGLYNELQK |
| | | GGACGGGATCCTGAGATGGGAGGAAAG | | | DKMAEAYSEIGMKGERRRGKG |
| | | CCACGGCGGAAGAACCCTCAAGAGGGGC | | | HDGLYQGLSTATKDTYDALHM |
| | | TGTACAACGAACTCCAGAAGGACAAGAT | | | QALPPR |
| | | GGCTGAGGCTTATTCTGAGATCGGCATG | | | |
| | | AAGGGAGAGCGCAGACGCGGCAAGGGA | | | |
| | | CACGATGGCCTGTATCAGGGACTGAGCA | | | |
| | | CCGCCACCAAGGATACCTACGACGCCCT | | | |
| | | CCATATGCAGGCTCTCCCACCACGGGGA | | | |
| | | TCTGGCGAAGGCAGAGGATCTCTGCTGA | | | |
| | | CATGCGGCGACGTGGAAGAGAACCCTGG | | | |
| | | ACCTATGGCCCTCCCTGTCACAGCCCTCT | | | |
| | | TGCTGCCCCTCGCACTCCTTCTGCACGCA | | | |
| | | GCTCGGCCTGAGGTCCAGCTGGTCGAGA | | | |
| | | GTGGAGGCGGACTGGTCCAGGCAGGTGG | | | |
| | | GAGTCTTCGGCTTTCCTGCGCAGCTTCCG | | | |
| | | GACGGACCTTCACCATGGGTTGGTTCCG | | | |
| | | GCAGGCACCTGGGAAGGAGAGGGAGTTC | | | |
| | | GTTGCCGCTATCAGCCTCTCACCAACCCT | | | |
| | | GGCCTACTATGCAGAGAGCGTCAAGGGC | | | |
| | | CGCTTCACCATCAGCCGCGACAACGCCA | | | |
| | | AGAACACCGTCGTGCTGCAGATGAACTC | | | |
| | | CCTCAAGCCCGAGGATACCGCCCTGTAC | | | |
| | | TACTGCGCTGCCGATCGGAAGTCCGTCA | | | |
| | | TGTCCATTCGGCCCGACTACTGGGGACA | | | |
| | | GGGCACACAGGTGACCGTCAGCAGCATC | | | |
| | | GAGGTCATGTACCCTCCACCCTACCTGG | | | |
| | | ACAACGAGAAGAGCAACGGGACCATCAT | | | |
| | | CCACGTGAAGGGGAAGCACCTCTGTCCA | | | |
| | | AGTCCCCTCTTCCCAGGACCCTCCAAGCC | | | |
| | | ATTCTGGGTCCTCGTGGTGGTTGGAGGA | | | |
| | | GTGCTCGCCTGCTACTCTCTGCTGGTGAC | | | |
| | | CGTCGCCTTCATCATCTTCTGGGTGCGGT | | | |
| | | CCAAGCGGTCTCGCCTCCTCCACTCCGAC | | | |
| | | TACATGAACATGACACCACGCAGACCTG | | | |
| | | GGCCCACTAGGAAGCACTATCAGCCCTA | | | |
| | | TGCACCACCCCGGGATTTCGCAGCCTAC | | | |
| | | CGGTCACGGGTGAAGTTCAGCAGATCCG | | | |
| | | CAGACGCACCAGCCTACCAGCAGGGGCA | | | |
| | | GAACCAGCTGTATAACGAGCTGAACCTC | | | |
| | | GGTCGCAGGGAGGAGTACGATGTCCTGG | | | |
| | | ATAAGAGAAGGGGCAGGGATCCCGAGA | | | |
| | | TGGGTGGCAAGCCCAGACGGAAGAATCC | | | |
| | | TCAGGAGGGGCTCTACAACGAGCTGCAG | | | |
| | | AAGGACAAGATGGCCGAGGCTTACTCAG | | | |
| | | AGATCGGCATGAAAGGGGAGAGGAGGC | | | |
| | | GCGGAAAAGGCCACGACGGCCTCTACCA | | | |
| | | GGGACTGTCCACCGCAACCAAGGATACC | | | |
| | | TACGACGCCCTGCACATGCAAGCCCTCC | | | |
| | | CACCTCGG | | | |
| BCMA | 114 | ATGGCACTGCCCGTCACAGCTCTGCTGCT | 130 | | MALPVTALLLPLALLLHAARPEV |
| | | GCCCTTGGCCCTCTTGTTGCACGCAGCAC | | | QLVESGGGLVQAGGSLRLSCAA |
| | | GGCCAGAGGTGCAACTTGTCGAGAGCGG | | | SGRTFTMGWFRQAPGKEREFVA |
| | | TGGTGGCCTTGTGCAGGCCGGAGGCAGT | | | AISLSPTLAYYAESVKGRFTISRD |
| | | TTGCGCCTCAGTTGTGCAGCTTCTGGCCG | | | NAKNTVVLQMNSLKPEDTALYY |
| | | GACCTTCACCATGGGCTGGTTCAGACAG | | | CAADRKSVMSIRPDYWGQGTQV |
| | | GCCCCTGGTAAGGAACGCGAGTTCGTGG | | | TVSSTSTTTPAPRPPTPAPTIASQP |
| | | CCGCCATCAGCCTGTCCCCAACCCTGGCC | | | LSLRPEACRPAAGGAVHTRGLD |
| | | TACTACGCAGAGAGCGTGAAGGGTCGGT | | | FACDIYIWAPLAGTCGVLLLSLVI |
| | | TCACCATCTCCCGCGACAACGCAAAGAA | | | TLYCKRGRKKLLYIFKQPFMRPV |
| | | CACCGTGGTGCTCCAGATGAACTCCCTG | | | QTTQEEDGCSCRFPEEEEGGCEL |
| | | AAGCCAGAAGACACCGCCCTGTACTACT | | | RVKFSRSADAPAYQQGQNQLYN |

TABLE 2C-continued

| | | Additional Codon Amino Acid and Nucleotide Sequences | | | |
|---|---|---|---|---|---|
| | SEQ ID NO | Codon nucleotide sequence | | SEQ ID NO | Codon amino acid sequence |
| | | GCGCAGCCGACCGGAAGAGCGTGATGTC | | | ELNLGRREEYDVLDKRRGRDPE |
| | | CATCCGCCCTGACTACTGGGGCCAAGGC | | | MGGKPRRKNPQEGLYNELQKD |
| | | ACACAGGTCACAGTGTCCAGCACCTCCA | | | KMAEAYSEIGMKGERRRGKGH |
| | | CTACCACTCCAGCTCCACGCCCTCCAACA | | | DGLYQGLSTATKDTYDALHMQ |
| | | CCCGCACCAACCATCGCCAGCCAGCCTC | | | ALPPRGSGEGRGSLLTCGDVEEN |
| | | TGAGTCTGAGACCCGAAGCATGCCGGCC | | | PGPMALPVTALLLPLALLLHAAR |
| | | AGCTGCTGGAGGTGCCGTGCACACCAGA | | | PQVKLEESGGGLVQAGRSLRLSC |
| | | GGGCTGGACTTCGCCTGCGACATCTACA | | | AASEHTFSSHVMGWFRQAPGKE |
| | | TCTGGGCTCCTCTGGCCGGAACTTGCGG | | | RESVAVIGWRDISTSYADSVKGR |
| | | GGTGCTGCTCCTCTCACTGGTCATCACCC | | | FTISRDNAKKTLYLQMNSLKPED |
| | | TGTACTGCAAGAGGGGCAGGAAGAAGCT | | | TAVYYCAARRIDAADFDSWGQG |
| | | CCTGTACATCTTCAAGCAGCCCTTCATGC | | | TQVTVSSIEVMYPPPYLDNEKSN |
| | | GGCCAGTCCAGACAACCCAGGAGGAAG | | | GTIIHVKGKHLCPSPLFPGPSKPF |
| | | ACGGATGCAGCTGTCGCTTCCCCGAGGA | | | WVLVVVGGVLACYSLLVTVAFII |
| | | GGAGGAAGGCGGCTGCGAATTGCGGGTC | | | FWVRSKRSRLLHSDYMNMTPRR |
| | | AAGTTCAGCAGATCCGCTGACGCTCCTG | | | PGPTRKHYQPYAPPRDFAAYRSR |
| | | CCTACCAACAGGGACAGAACCAGCTCTA | | | VKFSRSADAPAYQQGQNQLYNE |
| | | CAACGAGCTGAACCTGGGAAGGCGGGA | | | LNLGRREEYDVLDKRRGRDPEM |
| | | GGAGTACGACGTCCTGGACAAGAGAAGA | | | GGKPRRKNPQEGLYNELQKDK |
| | | GGACGCGACCCCGAGATGGGGAGGTAAGC | | | MAEAYSEIGMKGERRRGKGHD |
| | | CCAGACGCAAGAACCCTCAAGAGGGACT | | | GLYQGLSTATKDTYDALHMQAL |
| | | GTATAACGAGCTGCAGAAGGACAAGATG | | | PPR |
| | | GCCGAGGCCTACAGCGAGATCGGCATGA | | | |
| | | AGGGTGAAAGAAGACGGGGAAAGGGGC | | | |
| | | ACGACGGTCTGTATCAGGGGCTCTCCAC | | | |
| | | CGCAACCAAGGATACCTATGACGCTCTG | | | |
| | | CACATGCAGGCACTCCCTCCACGCGGAT | | | |
| | | CTGGCGAAGGCAGAGGATCTCTGCTGAC | | | |
| | | ATGCGGCGACGTGGAAGAGAACCCTGGA | | | |
| | | CCTATGGCACTGCCCGTGACCGCTCTGCT | | | |
| | | GCTGCCTCTCGCCCTGCTGCTGCATGCTG | | | |
| | | CCAGGCCCCAAGTCAAGCTCGAGGAGTC | | | |
| | | TGGTGGTGGGCTCGTCCAAGCTGGCAGG | | | |
| | | TCCCTGAGACTGAGTTGTGCCGCCTCCGA | | | |
| | | GCACACTTTCAGCTCTCACGTGATGGGCT | | | |
| | | GGTTCAGGCAGGCACCCGGTAAGGAGCG | | | |
| | | GGAGTCTGTGGCTGTTATCGGGTGGCGG | | | |
| | | GATATCTCTACCTCCTACGCCGACTCCGT | | | |
| | | CAAGGGCCGGTTCACCATCTCCAGGGAC | | | |
| | | AACGCAAAGAAGACCCTCTACCTCCAGA | | | |
| | | TGAACTCACTCAAGCCCGAGGACACCGC | | | |
| | | TGTGTACTACTGCGCAGCCAGACGCATC | | | |
| | | GATGCCGCAGACTTCGACTCCTGGGGCC | | | |
| | | AAGGTACCCAAGTGACAGTGTCCAGCAT | | | |
| | | CGAGGTGATGTACCCACCTCCCTACCTCG | | | |
| | | ACAACGAGAAGAGCAACGGCACCATCAT | | | |
| | | CCACGTGAAGGGGAAGCACCTGTGTCCC | | | |
| | | TCTCCCCTTTTCCCAGGACCCTCCAAGCC | | | |
| | | ATTCTGGGTCCTGGTCGTTGTCGGAGGCG | | | |
| | | TGCTCGCTTGCTATTCCCTGCTCGTCACC | | | |
| | | GTGGCCTTCATCATCTTCTGGGTGCGGTC | | | |
| | | CAAGAGATCCCGGCTGCTGCACTCTGAT | | | |
| | | TACATGAACATGACACCCAGGAGGCCAG | | | |
| | | GGCCTACCAGGAAGCACTACCAGCCCTA | | | |
| | | CGCTCCTCCACGCGACTTCGCAGCATACC | | | |
| | | GGTCCCGCGTCAAGTTCTCCCGGTCCGCA | | | |
| | | GATGCTCCAGCCTATCAGCAGGGCCAGA | | | |
| | | ACCAGCTGTACAACGAACTCAATTTGGG | | | |
| | | GAGGCGCGAGGAGTATGATGTGCTCGAT | | | |
| | | AAGAGAAGGGGCCGGGATCCTGAGATG | | | |
| | | GGAGGCAAGCCCAGACGGAAGAACCCTC | | | |
| | | AGGAGGGCCTGTACAATGAGCTGCAGAA | | | |
| | | GGACAAGATGGCCGAGGCCTACTCCGAG | | | |
| | | ATCGGGATGAAGGGTGAAAGAAGGAGG | | | |
| | | GGTAAGGGGCACGACGGGCTCTACCAAG | | | |
| | | GCCTGAGCACCGCTACCAAGGACACCTA | | | |
| | | CGATGCACTGCATATGCAAGCCCTGCCA | | | |
| | | CCACGG | | | |
| BCMA | 115 | ATGGCACTCCCGGTAACCGCCTTATTGCT | 131 | MALPVTALLLPLALLLHAARPDI |
| | | TCCCCTTGCCCTCTTGCTCCACGCAGCAC | | | VLTQSPPSLAMSLGKRATISCRA |
| | | GCCCCGATATAGTCTTGACTCAATCCCCA | | | SESVTILGSHLIHWYQQKPGQPP |
| | | CCCAGTTTGGCAATGTCATTAGGCAAAC | | | TLLIQLASNVQTGVPARFSGSGS |
| | | GAGCAACAATTTCATGTAGGGCATCCGA | | | RTDFTLTIDPVEEDDVAVYYCLQ |

TABLE 2C-continued

Additional Codon Amino Acid and Nucleotide Sequences

| SEQ ID NO | Codon nucleotide sequence | SEQ ID NO | Codon amino acid sequence |
|---|---|---|---|
| | AAGTGTAACGATTTTGGGGAGTCATTTA<br>ATTCATTGGTACCAACAAAAGCCTGGAC<br>AACCCCCGACGCTCTTGATCCAATTAGC<br>ATCTAACGTCCAAACCGGAGTCCCCGCA<br>CGATTCTCAGGATCCGGTTCCCGGACTG<br>ATTTTACATTAACTATTGATCCGGTAGAG<br>GAAGATGACGTCGCTGTCTATTATTGTCT<br>TCAAAGTAGGACGATTCCACGGACATTC<br>GGTGGCGGAACTAAATTGGAGATTAAAG<br>GTTCCACCTCTGGTAGTGGGAAACCCGG<br>GTCCGGTGAAGGGTCCACTAAAGGCCAA<br>ATTCAACTCGTTCAATCCGGACCAGAAC<br>TGAAGAAGCCAGGAGAAACTGTCAAAAT<br>AAGCTGTAAAGCTTCCGGTTATACATTTA<br>CAGATTATTCCATAAATTGGGTGAAAAG<br>GGCGCCAGGAAAAGGGTTAAAGTGGATG<br>GGTTGGATTAATACAGAGACTCGGGAAC<br>CTGCATATGCTTATGATTTTAGGGGAAG<br>GTTTGCCTTTTCTCTGGAGACTTCCGCTT<br>CAACTGCTTATCTCCAAATTAATAATCTT<br>AAATATGAGGACACAGCAACATACTTCT<br>GTGCTTTGGACTATAGTTATGCTATGGAT<br>TACTGGGGACAAGGAACCAGTGTCACTG<br>TAAGTTCCGCTGCTGCGACGACCACTCCT<br>GCACCGCGACCACCCACTCCTGCCCCTA<br>CTATTGCTAGTCAACCACTTAGCTTGCGA<br>CCTGAGGCATGTCGGCCCGCGGCAGGTG<br>GCGCAGTCCACACCAGGGGTTTAGACTT<br>TGCTTGTGATATTTATATTTGGGCACCAC<br>TCGCCGGGACTTGCGGTGTTCTTCTCTTG<br>TCCCTTGTTATAACTCTTTATTGTAAGCG<br>CGGAAGGAAGAAATTGTTATATATTTTC<br>AAACAACCTTTTATGCGACCCGTACAAA<br>CAACTCAGGAAGAGGACGGGTGTTCTTG<br>TCGGTTTCCAGAAGAGGAAGAGGGTGGG<br>TGTGAACTCCGGGTCAAATTTAGTAGGT<br>CAGCAGATGCGCCGGCGTACCAACAAGG<br>CCAAAACCAACTGTATAATGAACTCAAT<br>CTCGGTAGGCGTGAGGAATATGATGTCC<br>TTGATAAAAGGCGCGGGAGAGATCCAGA<br>AATGGGCGGAAAACCACGGCGAAAGAA<br>TCCGCAGGAAGGGTTATATAACGAACTT<br>CAAAAGGATAAAATGGCTGAAGCTTATT<br>CCGAAATTGGCATGAAAGGAGAGCGACG<br>TAGGGGCAAAGGGCATGATGGCCTTTAC<br>CAAGGGCTCTCAACCGCTACAAAGATA<br>CTTACGACGCTTTACATATGCAAGCACTT<br>CCACCCAGG | | SRTIPRTFGGGTKLEIKGSTSGSG<br>KPGSGEGSTKGQIQLVQSGPELK<br>KPGETVKISCKASGYTFTDYSIN<br>WVKRAPGKGLKWMGWINTETR<br>EPAYAYDFRGRFAFSLETSASTA<br>YLQINNLKYEDTATYFCALDYS<br>YAMDYWGQGTSVTVSSAAATT<br>TPAPRPPTPAPTIASQPLSLRPEA<br>CRPAAGGAVHTRGLDFACDIYI<br>WAPLAGTCGVLLLSLVITLYCKR<br>GRKKLLYIFKQPFMRPVQTTQEE<br>DGCSCRFPEEEEGGCELRVKFSR<br>SADAPAYQQGQNQLYNELNLGR<br>REEYDVLDKRRGRDPEMGGKPR<br>RKNPQEGLYNELQKDKMAEAYS<br>EIGMKGERRRGKGHDGLYQGLS<br>TATKDTYDALHMQALPPR |
| HER2 | 132 | ATGGCTCTGCCTGTGACAGCTCTGCTGCT<br>GCCTCTGGCTCTGCTTCTGCATGCCGCCA<br>GACCTGACATCCAGATGACTCAGAGCCC<br>CAGCAGCCTGTCTGCCTCTGTGGGAGAC<br>AGAGTGACAATTACCTGCCGGGCCAGCC<br>AGGATGTGAATACTGCTGTCGCCTGGTA<br>TCAACAAAAGCCTGGCAAGGCCCCTAAG<br>CTCCTGATCTACAGCGCCAGCTTTCTGTA<br>CAGCGGCGTGCCCAGCAGATTCTCCGGA<br>AGCAGAAGCGGCACAGATTTCACACTGA<br>CCATAAGCAGCCTGCAGCCAGAGGATTT<br>CGCCACCTACTATTGCCAGCAGCACTAC<br>ACCACACCTCCAACCTTTGGCCAGGGCA<br>CCAAGGTCGAGATTAAGAGAACAGGCAG<br>CACATCTGGCTCTGGCAAACCTGGATCT<br>GGCGAGGGCTCTGAAGTCCAGCTGGTAG<br>AATCTGGCGGAGGACTGGTTCAACCTGG<br>CGGCTCTCTGAGACTGTCTTGTGCCGCCT<br>CCGGCTTCAACATCAAGGACACCTACAT<br>CCACTGGGTCCGACAAGCCCCAGGCAAA<br>GGACTTGAGTGGGTCGCCAGGATCTACC<br>CCACCAACGGCTACACCAGATACGCCGA<br>CTCTGTGAAGGGCAGATTCACCATCTCTG<br>CCGACACCAGCAAGAATACCGCCTACCT<br>GCAGATGAACTCCCTGAGAGCCGAAGAT | 134 | MALPVTALLLPLALLLHAARPDI<br>QMTQSPSSLSASVGDRVTITCRA<br>SQDVNTAVAWYQQKPGKAPKL<br>LIYSASFLYSGVPSRFSGSRSGTD<br>FTLTISSLQPEDFATYYCQQHYT<br>TPPTFGQGTKVEIKRTGSTSGSG<br>KPGSGEGSEVQLVESGGGLVQP<br>GGSLRLSCAASGFNIKDTYIHWV<br>RQAPGKGLEWVARIYPTNGYTR<br>YADSVKGRFTISADTSKNTAYLQ<br>MNSLRAEDTAVYYCSRWGGDG<br>FYAMDVWGQGTLVTVSSIEVMY<br>PPPYLDNEKSNGTIIHVKGKHLC<br>PSPLFPGPSKPFWVLVVVGGVLA<br>CYSLLVTVAFIIFWVRSKRSRLL<br>HSDYMNMTPRRPGPTRKHYQPY<br>APPRDFAAYRSRVKFSRSADAPA<br>YQQGQNQLYNELNLGRRREEYDV<br>LDKRRGRDPEMGGKPRRKNPQE<br>GLYNELQKDKMAEAYSEIGMKG<br>ERRRGKGHDGLYQGLSTATKDT<br>YDALHMQALPPR |

TABLE 2C-continued

| | | Additional Codon Amino Acid and Nucleotide Sequences | | |
|---|---|---|---|---|
| SEQ ID NO | Codon nucleotide sequence | | SEQ ID NO | Codon amino acid sequence |
| | ACCGCTGTGTATTACTGTTCCAGATGGGG AGGCGACGGCTTCTACGCCATGGATGTT TGGGGCCAAGGCACCCTCGTGACCGTTT CTTCTATCGAAGTGATGTACCCTCCACCT TACCTGGACAACGAGAAGTCCAACGGCA CCATCATCCACGTGAAGGGCAAGCACCT GTGTCCTTCTCCACTGTTCCCCGGACCTA GCAAGCCTTTCTGGGTGCTCGTTGTTGTT GGCGGCGTGCTGGCCTGTTACTCTCTGCT GGTTACCGTGGCCTTCATCATCTTTTGGG TCCGAAGCAAGCGGAGCCGGCTGCTGCA CTCCGACTACATGAACATGACCCCCTAGA CGGCCCGGACCAACCAGAAAGCACTACC AGCCTTACGCTCCTCCTAGAGACTTCGCC GCCTACCGGTCCAGAGTGAAGTTCAGCA GATCCGCCGATGCTCCCGCCTATCAGCA GGGCCAAAACCAGCTGTACAACGAGCTG AACCTGGGGAGAAGAGAAGAGTACGAC GTGCTGGACAAGCGGAGAGGCAGAGATC CTGAAATGGGCGGCAAGCCCAGACGGAA GAATCCTCAAGAGGGCCTGTATAATGAG CTGCAGAAAGACAAGATGGCCGAGGCCT ACAGCGAGATCGGAATGAAGGGCGAGC GCAGAAGAGGCAAGGGACACGATGGAC TGTACCAGGGCCTGAGCACCGCCACCAA GGATACCTATGATGCCCTGCACATGCAG GCCCTGCCTCCAAGA | | | |
| HER2 | 133 | ATGGCTCTGCCTGTGACAGCTCTGCTGCT GCCTCTGGCTCTGCTTCTGCATGCCGCCA GACCTGACATCCAGATGACTCAGAGCCC CAGCAGCCTGTCTGCCTCTGTGGGAGAC AGAGTGACAATTACCTGCCGGGCCAGCC AGGATGTGAATACTGCTGTCGCCTGGTA TCAACAAAGCCTGGCAAGGCCCCTAAG CTCCTGATCTACAGCGCCAGCTTTCTGTA CAGCGGCGTGCCCAGCAGATTCTCCGGA AGCAGAAGCGGCACAGATTTCACACTGA CCATAAGCAGCCTGCAGCCAGAGGATTT CGCCACCTACTATTGCCAGCAGCACTAC ACCACACCTCCAACCTTTGGCCAGGGCA CCAAGGTCGAGATTAAGAGAACAGGCAG CACATCTGGCTCTGGCAAACCTGGATCT GGCGAGGGCTCTGAAGTCCAGCTGGTG AATCTGGCGGAGGACTGGTTCAACCTGG CGGCTCTCTGAGACTGTCTTGTGCCGCCT CCGGCTTCAACATCAAGGACACCTACAT CCACTGGGTCCGACAAGCCCCAGGCAAA GGACTTGAGTGGGTCGCCAGGATCTACC CCACCAACGGCTACACCAGATACGCCGA CTCTGTGAAGGGCAGATTCACCATCTCTG CCGACACCAGCAAGAATACCGCCTACCT GCAGATGAACTCCCTGAGAGCCGAAGAT ACCGCTGTGTATTACTGTTCCAGATGGGG AGGCGACGGCTTCTACGCCATGGATGTT TGGGGCCAAGGCACCCTCGTGACCGTTT CTTCTACCACCACACCAGCTCCTCGGCCT CCAACTCCTGCTCCTACAATTGCCAGCCA GCCTCTGTCTCTGAGGCCCGAAGCTTGTA GACCTGCTGCTGGCGGAGCCGTGCATAC AAGAGGACTGGATTTCGCCTGCGACATC TACATCTGGGCTCCTCTGGCCGGAACAT GTGGCGTTCTGCTGCTGAGCCTGGTCATC ACCCTGTACTGTAAGCGGGGCAGAAAGA AGCTGCTGTACATCTTCAAGCAGCCCTTC ATGCGGCCCGTGCAGACCACACAAGAGG AAGATGGCTGCTCCTGCAGATTCCCCGA GGAAGAAGAAGGCGGCTGCGAGCTGAG AGTGAAGTTCAGCAGATCCGCCGATGCT CCCGCCTATCAGCAGGGCCAAAACCAGC TGTACAACGAGCTGAACCTGGGGAGAAG AGAAGAGTACGACGTGCTGGACAAGCGG AGAGGCAGAGATCCTGAAATGGGCGGCA AGCCCAGACGGAAGAATCCTCAAGAGGG | | 135 | MALPVTALLLPLALLLHAARPDI QMTQSPSSLSASVGDRVTITCRA SQDVNTAVAWYQQKPGKAPKL LIYSASFLYSGVPSRFSGSRSGTD FTLTISSLQPEDFATYYCQQHYT TPPTFGQGTKVEIKRTGSTSGSG KPGSGEGSEVQLVESGGGLVQP GGSLRLSCAASGFNIKDTYIHWV RQAPGKGLEWVARIYPINGYTR YADSVKGRFTISADTSKNTAYLQ MNSLRAEDTAVYYCSRWGGDG FYAMDVWGQGTLVTVSSTTTPA PRPPTPAPTIASQPLSLRPEACRP AAGGAVHTRGLDFACDIYIWAP LAGTCGVLLLSLVITLYCKRGRK KLLYIFKQPFMRPVQTTQEEDGC SCRFPEEEEGGCELRVKFSRSAD APAYQQGQNQLYNELNLGRREE YDVLDKRRGRDPEMGGKPRRK NPQEGLYNELQKDKMAEAYSEI GMKGERRRGKGHDGLYQGLST ATKDTYDALHMQALPPR |

TABLE 2C-continued

Additional Codon Amino Acid and Nucleotide Sequences

| SEQ ID NO | Codon nucleotide sequence | SEQ ID NO | Codon amino acid sequence |
|---|---|---|---|
| | CCTGTATAATGAGCTGCAGAAAGACAAG ATGGCCGAGGCCTACAGCGAGATCGGAA TGAAGGGCGAGCGCAGAAGAGGCAAGG GACACGATGGACTGTACCAGGGCCTGAG CACCGCCACCAAGGATACCTATGATGCC CTGCACATGCAGGCCCTGCCTCCAAGA | | |

3. Hinge/Spacer Domain

In some embodiments, a CAR of the instant disclosure comprises a hinge or spacer domain. In some embodiments, the hinge/spacer domain may comprise a truncated hinge/ spacer domain (THD), wherein the THD domain is a truncated version of a complete hinge/spacer domain ("CHD"). In some embodiments, an hinge or spacer domain is from or derived from (e.g., comprises all or a fragment of) ErbB2, glycophorin A (GpA), CD2, CD3 delta, CD3 epsilon, CD3 gamma, CD4, CD7, CD8a, CD8b, Cd11a (IT GAL), CD11b (IT GAM), CD11c (ITGAX), CD11d (IT GAD), CD18 (ITGB2), CD19 (B4), CD27 (TNFRSF7), CD28, CD28T, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (0X40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAMI), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRT AM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, a Toll ligand receptor, and fragments or combinations thereof. A hinge or spacer domain may be derived either from a natural or from a synthetic source.

In some embodiments, a hinge or spacer domain is positioned between an antigen binding molecule (e.g., an scFv) and a transmembrane domain. In this orientation, the hinge/spacer domain provides distance between the antigen binding molecule and the surface of a cell membrane on which the CAR is expressed. In some embodiments, a hinge or spacer domain is from or derived from an immunoglobulin. In some embodiments, a hinge or spacer domain is selected from the hinge/spacer regions of IgG1, IgG2, IgG3, IgG4, IgA, IgD, IgE, IgM, or a fragment thereof. In some embodiments, a hinge or spacer domain comprises, is from, or is derived from the hinge/spacer region of CD8 alpha. In some embodiments, a hinge or spacer domain comprises, is from, or is derived from the hinge/spacer region of CD28. In some embodiments, a hinge or spacer domain comprises a fragment of the hinge/spacer region of CD8 alpha or a fragment of the hinge/spacer region of CD28, wherein the fragment is anything less than the whole hinge/spacer region. In some embodiments, the fragment of the CD8 alpha hinge/spacer region or the fragment of the CD28 hinge/spacer region comprises an amino acid sequence that excludes at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 amino acids at the N-terminus or C-Terminus, or both, of the CD8 alpha hinge/spacer region, or of the CD28 hinge/spacer region.

4. Transmembrane Domain

The CAR of the present disclosure may further comprise a transmembrane domain and/or an intracellular signaling domain. The transmembrane domain may be designed to be fused to the extracellular domain of the CAR. It may similarly be fused to the intracellular domain of the CAR. In some embodiments, the transmembrane domain that naturally is associated with one of the domains in a CAR is used. In some instances, the transmembrane domain may be selected or modified (e.g., by an amino acid substitution) to avoid binding of such domains to the transmembrane domains of the same or different surface membrane proteins to minimize interactions with other members of the receptor complex. The transmembrane domain may be derived either from a natural or from a synthetic source. Where the source is natural, the domain may be derived from any membrane-bound or transmembrane protein.

Transmembrane regions may be derived from (i.e., comprise) a receptor tyrosine kinase (e.g., ErbB2), glycophorin A (GpA), 4-1BB/CD137, activating NK cell receptors, an immunoglobulin protein, B7-H3, BAFFR, BFAME (SEAMF8), BTEA, CD100 (SEMA4D), CD103, CD160 (BY55), CD18, CD19, CD19a, CD2, CD247, CD27, CD276 (B7-H3), CD28, CD29, CD3 delta, CD3 epsilon, CD3 gamma, CD30, CD4, CD40, CD49a, CD49D, CD49f, CD69, CD7, CD84, CD8alpha, CD8beta, CD96 (Tactile), CD11a, CD11b, CD11c, CD11d, CDS, CEACAM1, CRT AM, cytokine receptor, DAP-10, DNAM1 (CD226), Fc gamma receptor, GADS, GITR, HVEM (EIGHTR), IA4, ICAM-1, ICAM-1, Ig alpha (CD79a), IE-2R beta, IE-2R gamma, IE-7R alpha, inducible T cell costimulator (ICOS), integrins, ITGA4, ITGA4, ITGA6, IT GAD, ITGAE, ITGAE, IT GAM, ITGAX, ITGB2, ITGB7, ITGB1, KIRDS2, EAT, LFA-1, LFA-1, a ligand that specifically binds with CD83, LIGHT, LIGHT, LTBR, Ly9 (CD229), lymphocyte function-associated antigen-1 (LFA-1; CD11a/ CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A; Ly108), SLAMF7, SLP-76, TNF receptor proteins, TNFR2, TNFSF14, a Toll ligand receptor, TRANCE/RANKL, VLA1, or VLA-6, or a fragment, truncation, or a combination thereof.

In some embodiments, suitable intracellular signaling domain include, but are not limited to, activating Macrophage/Myeloid cell receptors CSFR1, MYD88, CD14, TIE2, TLR4, CR3, CD64, TREM2, DAP10, DAP12, CD169, DECTIN1, CD206, CD47, CD163, CD36, MARCO, TIM4, MERTK, F4/80, CD91, C1QR, LOX-1, CD68, SRA, BAI-1, ABCA7, CD36, CD31, Lactoferrin, or a fragment, truncation, or combination thereof.

In some embodiments, a receptor tyrosine kinase may be derived from (e.g., comprise) Insulin receptor (InsR), Insulin-like growth factor I receptor (IGFIR), Insulin receptor-related receptor (IRR), platelet derived growth factor receptor alpha (PDGFRa), platelet derived growth factor receptor beta (PDGFRfi). KIT proto-oncogene receptor tyrosine kinase (Kit), colony stimulating factor 1 receptor (CSFR), fis related tyrosine kinase 3 (FLT3), fms related tyrosine kinase 1 (VEGFR-1), kinase insert domain receptor (VEGFR-2), fms related tyrosine kinase 4 (VEGFR-3), fibroblast growth factor receptor 1 (FGFR1), fibroblast growth factor receptor 2 (FGFR2), fibroblast growth factor receptor 3 (FGFR3), fibroblast growth factor receptor 4 (FGFR4), protein tyrosine kinase 7 (CCK4), neurotrophic receptor tyrosine kinase 1 (trkA), neurotrophic receptor tyrosine kinase 2 (trkB), neurotrophic receptor tyrosine kinase 3 (trkC), receptor tyrosine kinase like orphan receptor 1 (ROR1), receptor tyrosine kinase like orphan receptor 2 (ROR2), muscle associated receptor tyrosine kinase (MuSK), MET proto-oncogene, receptor tyrosine kinase (MET), macrophage stimulating 1 receptor (Ron), AXL receptor tyrosine kinase (Axl), TYR03 protein tyrosine kinase (Tyro3), MER proto-oncogene, tyrosine kinase (Mer), tyrosine kinase with immunoglobulin like and EGF like domains 1 (TIE1), TEK receptor tyrosine kinase (TIE2), EPH receptor A1 (EphAl), EPH receptor A2 (EphA2), (EPH receptor A3) EphA3, EPH receptor A4 (EphA4), EPH receptor A5 (EphA5), EPH receptor A6 (EphA6), EPH receptor A7 (EphA7), EPH receptor A8 (EphA8), EPH receptor A10 (EphAIO), EPH receptor B1 (EphB1), EPH receptor B2 (EphB2), EPH receptor B3 (EphB3), EPH receptor B4 (EphB4), EPH receptor B6 (EphB6), ret proto oncogene (Ret), receptor-like tyrosine kinase (RYK), discoidin domain receptor tyrosine kinase 1 (DDR1), discoidin domain receptor tyrosine kinase 2 (DDR2), c-ros oncogene 1, receptor tyrosine kinase (ROS), apoptosis associated tyrosine kinase (Lmrl), lemur tyrosine kinase 2 (Lmr2), lemur tyrosine kinase 3 (Lmr3), leukocyte receptor tyrosine kinase (LTK), ALK receptor tyrosine kinase (ALK), or serine/threonine/tyrosine kinase 1 (STYK1).

5. Costimulatory Domain

In certain embodiments, the CAR comprises a costimulatory domain. In some embodiments, the costimulatory domain comprises 4-1BB (CD137), CD28, or both, and/or an intracellular T cell signaling domain. In a preferred embodiment, the costimulatory domain is human CD28, human 4-1BB, or both, and the intracellular T cell signaling domain is human CD3 zeta (ζ). 4-1BB, CD28, CD3 zeta may comprise less than the whole 4-1BB, CD28 or CD3 zeta, respectively. Chimeric antigen receptors may incorporate costimulatory (signaling) domains to increase their potency. See U.S. Pat. Nos. 7,741,465, and 6,319,494, as well as Krause et al. and Finney et al. (supra), Song et al., Blood 119:696-706 (2012); Kalos et al., Sci Transl. Med. 3:95 (2011); Porter et al., N. Engl. J. Med. 365:725-33 (2011), and Gross et al., Amur. Rev. Pharmacol. Toxicol. 56:59-83 (2016).

6. Intracellular Signaling Domain

In certain embodiments, the CAR comprises an intracellular (signaling) domain.

In some embodiments, suitable intracellular signaling domains comprise, but are not limited, to 4-1BB/CD137, activating NK cell receptors, an Immunoglobulin protein, B7-H3, BAFFR, BLAME (SLAMF8), BTLA, CD100 (SEMA4D), CD103, CD160 (BY55), CD18, CD19, CD 19a, CD2, CD247, CD27, CD276 (B7-H3), CD28, CD29, CD3 delta, CD3 epsilon, CD3 gamma, CD30, CD4, CD40, CD49a, CD49D, CD49f, CD69, CD7, CD84, CD8alpha, CD8beta, CD96 (Tactile), CD11a, CD11b, CD11c, Cd11d, CDS, CEACAMI, CRT AM, cytokine receptor, DAP-10, DNAMI (CD226), Fc gamma receptor, GADS, GITR, HVEM (LIGHTR), IA4, ICAM-1, Ig alpha (CD79a), IL-2R beta, IL-2R gamma, IL-7R alpha, inducible T cell costimulator (ICOS), integrins, ITGA4, ITGA6, ITGAD, ITGAE, ITGAL, ITGAM, ITGAX, ITGB2, ITGB7, ITGB1, KIRDS2, LAT, LFA-1, ligand that specifically binds with CD83, LIGHT, LTBR, Ly9 (CD229), Ly108, lymphocyte function-associated antigen-1 (LFA-1; CD11a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A), SLAMF7, SLP-76, TNF receptor proteins, TNFR2, TNFSF14, a Toll ligand receptor, TRANCE/RANKL, VLA1, or VLA-6, or a fragment, truncation, or a combination thereof.

CD3 is an element of the T cell receptor on native T cells, and has been shown to be an important intracellular activating element in CARs. In some embodiments, the CD3 is CD3 zeta.

E. Transfer Vehicles

In one aspect, provided herein is a pharmaceutical composition comprising one or more circular RNA constructs comprising an Internal Ribosome Entry Site (IRES) and an expression sequence encoding a binding molecule and a transfer vehicle. In certain embodiments, the pharmaceutical composition comprises at least one circular RNA construct comprising an IRES and an expression sequence encoding a chimeric antigen receptor (CAR); and a transfer vehicle.

In certain embodiments, the transfer vehicle comprises a lipid. In certain embodiments, the transfer vehicle comprises an ionizable lipid. In certain embodiments, the transfer vehicle comprises an ionizable lipid in combination with other lipids, e.g., a structural lipid, and/or a PEG-modified lipid. In certain embodiments, the transfer vehicle is a lipid nanoparticle (LNP). In certain embodiments the transfer vehicle is capable of delivering the circular RNA construct to a human immune cell present in a human subject, such that the expression sequence encoding a binding molecule (e.g., CAR) is translated in the human immune cell and expressed on the surface of the human immune cell.

In certain embodiments, the transfer vehicles are prepared to encapsulate one or more materials or therapeutic agents (e.g., circular RNA). The process of incorporating a desired therapeutic agent (e.g., circular RNA) into a transfer vehicle is referred to herein as or "loading" or "encapsulating" (Lasic, et al., FEBS Lett., 312:255-258, 1992). The transfer vehicle-loaded or -encapsulated materials (e.g., circular RNA) may be completely or partially located in the interior space of the transfer vehicle, within a bilayer membrane of the transfer vehicle, or associated with the exterior surface of the transfer vehicle.

In some embodiments, a transfer vehicle encapsulates circular RNA. In some embodiments, the transfer vehicle encapsulates at least one circular RNA construct and comprises an ionizable lipid. In some embodiments, the transfer vehicle encapsulates at least one circular RNA construct and comprises an ionizable lipid and an additional lipid selected from a structural lipid, a helper lipid, and a PEG-modified lipid. In some embodiments, the transfer vehicle encapsulates at least one circular RNA construct and comprises an ionizable lipid, a structural lipid, a helper lipid, and/or a PEG-modified lipid. In some embodiments, a transfer vehicle encapsulates at least one circular RNA construct and comprises an ionizable lipid, a structural lipid, a PEG-modified lipid, and a helper lipid. In some embodiments, the transfer vehicle is a lipid nanoparticle.

Without wishing to be bound by theory, it is thought that transfer vehicles described herein shield encapsulated circular RNA from degradation and provide for effective delivery of circular RNA to target cells in vivo and in vitro.

In certain embodiments, the transfer vehicles are formulated based in part upon their ability to facilitate the transfection (e.g., of a circular RNA) of a target cell. In another embodiment, the transfer vehicles may be selected and/or prepared to optimize delivery of circular RNA to a target cell, tissue or organ. For example, if the target cell is a hepatocyte, the properties of the compositions (e.g., size, charge and/or pH) may be optimized to effectively deliver such composition (e.g., lipid nanoparticles) to the target cell or organ, reduce immune clearance and/or promote retention in the target cell or organ. Alternatively, if the target tissue is the central nervous system, the selection and preparation of the transfer vehicle must consider penetration of, and retention within. the blood brain barrier and/or the use of alternate means of directly delivering such compositions to such target tissue (e.g., via intracerebrovascular administration). In certain embodiments, the transfer vehicles may be combined with agents that facilitate the transfer of encapsulated materials across the blood brain barrier (e.g., agents which disrupt or improve the permeability of the blood brain barrier and thereby enhance the transfer of circular RNA to the target cells). While the transfer vehicles described herein can facilitate introduction of circular RNA into target cells, the addition of polycations (e.g., poly L-lysine and protamine) as a copolymer to one or more of the lipid nanoparticles that comprise the pharmaceutical compositions can in some instances markedly enhance the transfection efficiency of several types of transfer vehicles by 2-28 fold in a number of cell lines both in vitro and in vivo (See, N. J. Caplen, et al., Gene Ther. 1995; 2:603; S. Li, et al., Gene Ther. 1997; 4, 891.).

Transfer vehicles described herein can allow the encapsulated polynucleotide to reach the target cell or may preferentially allow the encapsulated polynucleotide to reach the target cells or organs on a discriminatory basis. Alternatively, the transfer vehicles may limit the delivery of encapsulated polynucleotides to other non-targeted cells or organs where the presence of the encapsulated polynucleotides may be undesirable or of limited utility.

Loading or encapsulating a polynucleotide, e.g., circular RNA, into a transfer vehicle may serve to protect the polynucleotide from an environment (e.g., serum) which may contain enzymes or chemicals that degrade such polynucleotides and/or systems or receptors that cause the rapid excretion of such polynucleotides. Accordingly, in some embodiments, the compositions described herein are capable of enhancing the stability of the encapsulated polynucleotide(s), particularly with respect to the environments into which such polynucleotides will be exposed.

In certain embodiments, the transfer vehicles described herein are prepared by combining multiple lipid components (e.g., one or more of the compounds disclosed herein) with one or more polymer components.

A lipid nanoparticle may be comprised of additional lipid combinations in various ratios. Example 1 at Tables 4a and 4b describes exemplary lipid vehicle formulations comprising different molar ratios. The selection of ionizable lipids, helper lipids, structural lipids, and/or PEG-modified lipids that make up the lipid nanoparticles, as well as the relative molar ratio of such lipids to each other, is based upon the characteristics of the selected lipid(s), the nature of the intended target cells or tissues and the characteristics of the materials or polynucleotides to be delivered by the lipid nanoparticle. Additional considerations include, for example, the saturation of the alkyl chain, as well as the size, charge, pH, pKa, fusogenicity and toxicity of the selected lipid(s).

1. Lipid Nanoparticles ("LNP")

In one embodiment, the circular RNA may be formulated in or encapsulated into a transfer or delivery vehicle where the vehicle is a lipid nanoparticle, which may be capable of delivering the one or more circular RNA constructs to one or more target cells.

The formation of a lipid nanoparticle (LNP) described herein may be accomplished by any methods known in the art. See, e.g., U.S. Pat. Pub. No. US2012/0178702 A1, which is incorporated herein by reference in its entirety. Non-limiting examples of lipid nanoparticle compositions and methods of making them are described, for example, in Semple et al. (2010) Nat. Biotechnol. 28:172-176; Jayarama et al. (2012), Angew. Chem. Int. Ed., 51:8529-8533; and Maier et al. (2013) Molecular Therapy 21, 1570-1578 (the contents of each of which are incorporated herein by reference in their entirety). Lipid nanoparticles, formulations, and methods of preparation are described in, e.g., International Pat. Pub. No. WO 2011/127255 or WO 2008/103276, U.S. Pat. Pub. No. US2005/0222064 A1, U.S. Pat. Pub. No. US2013/0156845 A1, International Pat. Pub. No. WO2013/093648 A2, WO2012/024526 A2, U.S. Pat. Pub. No. US2013/0164400 A1, and U.S. Pat. No. 8,492,359, all of which are incorporated herein by reference in their entirety.

A lipid nanoparticle may be comprised of lipid combinations in various ratios. The selection of ionizable lipids, helper lipids, structural lipids, and/or PEG-modified lipids which comprise the lipid nanoparticles, as well as the relative molar ratio of such lipids to each other, is based upon the characteristics of the selected lipid(s), the nature of the intended target cells or tissues and the characteristics of the materials or polynucleotides to be delivered by the lipid nanoparticle. Additional considerations include, for example, the saturation of the alkyl chain, as well as the size, charge, pH, pKa, fusogenicity and toxicity of the selected lipid(s). Example 1 at Tables 4a and 4b describes exemplary lipid vehicle formulations comprising different molar ratios. Additional lipids are described in WO2022261490, WO2023056033, and WO2023081526, which are each incorporated herein by reference in their entireties.

In some embodiments, the lipid nanoparticle comprises one or more cationic lipids, ionizable lipids, or poly β-amino esters. In some embodiments, the nanoparticle comprises one or more non-cationic lipids. In some embodiments, the lipid nanoparticle comprises one or more PEG-modified lipids, polyglutamic acid lipids, or hyaluronic acid lipids. In some embodiments, the lipid nanoparticle comprises cholesterol. In some embodiments, the lipid nanoparticle comprises arachidonic acid, leukotriene, or oleic acid. In some embodiments, the lipid nanoparticle comprises a targeting moiety, wherein the targeting moiety mediates receptor-mediated endocytosis selectively into cells of a selected cell population in the absence of cell selection or purification. In some embodiments, the lipid nanoparticle comprises more than one circular RNA construct.

Examples of further suitable lipids include the phosphatidyl compounds (e.g., phosphatidylglycerol, phosphatidylcholine, phosphatidylserine, phosphatidylethanolamine, sphingolipids, cerebrosides, and gangliosides). Also contemplated is the use of polymers as transfer vehicles, whether alone or in combination with other transfer vehicles. Suitable polymers may include, for example, poly-acrylates, polyalkycyanoacrylates, polylactide, polylactide-polyglycolide copolymers, polycaprolactones, dextran, albumin, gelatin, alginate, collagen, chitosan, cyclodextrins, dendrimers and polyethylenimine.

A lipid nanoparticle composition may optionally comprise one or more coatings. For example, a nanoparticle composition may be formulated in a capsule, film, or tablet having a coating. A capsule, film, or tablet including a composition described herein may have any useful size, tensile strength, hardness, or density.

In one embodiment, the lipid nanoparticles may have a diameter from about 10 to about 100 nm such as, but not limited to, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm. In one embodiment, the lipid nanoparticles may have a diameter from about 10 to 500 nm. In one embodiment, the lipid nanoparticle may have a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm. Each possibility represents a separate embodiment.

In some embodiments, a nanoparticle (e.g., a lipid nanoparticle) has a mean diameter of 10-500 nm, 20-400 nm, 30-300 nm, or 40-200 nm. In some embodiments, a nanoparticle (e.g., a lipid nanoparticle) has a mean diameter of 50-150 nm, 50-200 nm, 80-100 nm, or 80-200 nm.

In some embodiments, the lipid nanoparticles described herein can have a diameter from below 0.1 μm to up to 1 mm such as, but not limited to, less than 0.1 μm, less than 1.0 μm, less than 5 μm, less than 10 μm, less than 15 μm, less than 20 μm, less than 25 μm, less than 30 μm, less than 35 μm, less than 40 μm, less than 50 μm, less than 55 μm, less than 60 μm, less than 65 μm, less than 70 μm, less than 75 μm, less than 80 μm, less than 85 μm, less than 90 μm, less than 95 μm, less than 100 μm, less than 125 μm, less than 150 μm, less than 175 μm, less than 200 μm, less than 225 μm, less than 250 μm, less than 275 μm, less than 300 μm, less than 325 μm, less than 350 μm, less than 375 μm, less than 400 μm, less than 425 μm, less than 450 μm, less than 475 μm, less than 500 μm, less than 525 μm, less than 550 μm, less than 575 μm, less than 600 μm, less than 625 μm, less than 650 μm, less than 675 μm, less than 700 μm, less than 725 μm, less than 750 μm, less than 775 μm, less than 800 μm, less than 825 μm, less than 850 μm, less than 875 μm, less than 900 μm, less than 925 μm, less than 950 μm, less than 975 μm.

In another embodiment, LNPs may have a diameter from about 1 nm to about 100 nm, from about 1 nm to about 10 nm, about 1 nm to about 20 nm, from about 1 nm to about 30 nm, from about 1 nm to about 40 nm, from about 1 nm to about 50 nm, from about 1 nm to about 60 nm, from about 1 nm to about 70 nm, from about 1 nm to about 80 nm, from about 1 nm to about 90 nm, from about 5 nm to about from 100 nm, from about 5 nm to about 10 nm, about 5 nm to about 20 nm, from about 5 nm to about 30 nm, from about 5 nm to about 40 nm, from about 5 nm to about 50 nm, from about 5 nm to about 60 nm, from about 5 nm to about 70 nm, from about 5 nm to about 80 nm, from about 5 nm to about 90 nm, about 10 to about 50 nM, from about 20 to about 50 nm, from about 30 to about 50 nm, from about 40 to about 50 nm, from about 20 to about 60 nm, from about 30 to about 60 nm, from about 40 to about 60 nm, from about 20 to about 70 nm, from about 30 to about 70 nm, from about 40 to about 70 nm, from about 50 to about 70 nm, from about 60 to about 70 nm, from about 20 to about 80 nm, from about 30 to about 80 nm, from about 40 to about 80 nm, from about 50 to about 80 nm, from about 60 to about 80 nm, from about 20 to about 90 nm, from about 30 to about 90 nm, from about 40 to about 90 nm, from about 50 to about 90 nm, from about 60 to about 90 nm and/or from about 70 to about 90 nm. Each possibility represents a separate embodiment.

A nanoparticle composition may be relatively homogenous. A polydispersity index may be used to indicate the homogeneity of a nanoparticle composition, e.g., the particle size distribution of the lipid nanoparticle compositions. A small (e.g., less than 0.3) polydispersity index generally indicates a narrow particle size distribution. A nanoparticle composition may have a polydispersity index from about 0 to about 0.25, such as 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, or 0.25. In some embodiments, the polydispersity index of a nanoparticle composition may be from about 0.10 to about 0.20. Each possibility represents a separate embodiment.

The zeta potential of a nanoparticle composition may be used to indicate the electrokinetic potential of the composition. For example, the zeta potential may describe the surface charge of a nanoparticle composition. Nanoparticle compositions with relatively low charges, positive or negative, are generally desirable, as more highly charged species may interact undesirably with cells, tissues, and other elements in the body. In some embodiments, the zeta potential of a nanoparticle composition may be from about −20 mV to about +20 mV, from about −20 mV to about +15 mV, from about −20 mV to about +10 mV, from about −20 mV to about +5 mV, from about −20 m V to about 0 mV, from about −20 mV to about −5 mV, from about −20 mV to about −10 mV, from about −20 mV to about −15 mV from about −20 mV to about +20 m V, from about −20 m V to about +15 mV, from about −20 m V to about +10 mV, from about −20 mV to about +5 mV, from about −20 m V to about 0 mV, from about 0 m V to about +20 mV, from about 0 m V to about +15 mV, from about 0 m V to about +10 mV, from about 0 mV to about +5 mV, from about +5 mV to about +20 m V, from about +5 m V to about +15 m V, or from about +5 mV to about +10 mV. Each possibility represents a separate embodiment.

The efficiency of encapsulation of a therapeutic agent describes the amount of therapeutic agent that is encapsulated or otherwise associated with a nanoparticle composition after preparation, relative to the initial amount provided. The encapsulation efficiency is desirably high (e.g., close to 100%). The encapsulation efficiency may be measured, for example, by comparing the amount of therapeutic agent in a solution containing the lipid nanoparticle composition before and after breaking up the lipid nanoparticle composition with one or more organic solvents or detergents. Fluorescence may be used to measure the amount of free therapeutic agent (e.g., nucleic acids) in a solution. For the lipid nanoparticle compositions described herein, the encapsulation efficiency of a therapeutic agent may be at least 50%, for example 50%, 55%, 60%, 65%, 70%, 75%, 80%, 85%, 90%, 91%, 92%, 93%, 94%, 95%, 96%, 97%, 98%, 99%, or 100%. In some embodiments, the encapsulation efficiency may be at least 80%. In certain embodiments, the encapsulation efficiency may be at least 90%.

In some embodiments, the lipid nanoparticle has a polydiversity value of less than 0.4. In some embodiments, the lipid nanoparticle has a net neutral charge at a neutral pH. In some embodiments, the lipid nanoparticle has a mean diameter of 50-200 nm.

The properties of a lipid nanoparticle formulation may be influenced by factors including, but not limited to, the selection of the cationic lipid component, the degree of cationic lipid saturation, the selection of the non-cationic lipid component, the degree of noncationic lipid saturation, the selection of the structural lipid component, the nature of the PEGylation, ratio of all components and biophysical parameters such as size. As described herein, the purity of a PEG lipid component is also important to an LNP's properties and performance.

a) Ionizable Lipids

In certain embodiments, the transfer vehicle comprises an ionizable lipid. Ionizable lipids may be used as a component of the transfer vehicle to facilitate or enhance the delivery and release of circular RNA to one or more target cells (e.g., by permeating or fusing with the lipid membranes of such target cells). In certain embodiments, an ionizable lipid comprises one or more cleavable functional groups (e.g., a disulfide) that allow, for example, a hydrophilic functional head-group to dissociate from a lipophilic functional tail-group of the compound (e.g., upon exposure to oxidative, reducing or acidic conditions), thereby facilitating a phase transition in the lipid bilayer of the one or more target cells.

In some embodiments, an ionizable lipid is as described in international patent application PCT/US2020/038678. In some embodiments, an ionizable lipid is a lipid as represented by formula 1 of or as listed in Tables 1 or 2 of U.S. Pat. No. 9,708,628, the content of which is herein incorporated by reference in its entirety. In some embodiments, an ionizable lipid is as described in pages 7-13 of U.S. Pat. No. 9,765,022 or as represented by formula 1 of U.S. Pat. No. 9,765,022, the content of which is herein incorporated by reference in its entirety. In some embodiments, an ionizable lipid is described in pages 12-24 of International Patent Application No. PCT/US2019/016362 or as represented by formula 1 of International Patent Application PCT/US2019/016362, the contents of which are herein incorporated by reference in their entirety. In some embodiments, a lipid or transfer vehicle is a lipid as described in International Patent Application Nos. PCT/US2010/061058, PCT/US2018/058555, PCT/US2018/053569, PCT/US2017/028981, PCT/US2019/025246, PCT/US2019/015913, PCT/US2019/016362, PCT/US2019/016362, US Application Publication Nos. US2019/0314524, US2019/0321489, US2019/0314284, and US2019/0091164, the contents of which are herein incorporated by reference in their entireties. Suitable cationic lipids for use in the compositions and methods herein include those described in international patent publication WO 2010/053572 and/or U.S. patent application Ser. No. 15/809,680, e.g., C12-200. In certain embodiments, the compositions and methods herein employ a lipid nanoparticles comprising an ionizable cationic lipid described in U.S. provisional patent application 61/617,468, filed Mar. 29, 2012 (incorporated herein by reference), such as, e.g, (15Z,18Z)—N,N-dimethyl-6-(9Z,12Z)-octadeca-9,12-dien-1-yl)tetracosa-15,18-dien-1-amine (HGT5000), (15Z,18Z)—N,N-dimethyl-6-((9Z,12Z)-octadeca-9,12-dien-1-yl) tetracosa-4,15,18-trien-1-amine (HGT5001), and (15Z, 18Z)—N,N-dimethyl-6-((9Z,12Z)-octadeca-9,12-dien-1-yl) tetracosa-5,15,18-trien-1-amine (HGT5002).

In some embodiments, the cationic lipid N-[1-(2,3-dioleyloxy) propyl]-N,N,N-trimethylammonium chloride or "DOTMA" is used. (Felgner et al. (Proc. Nat'l Acad. Sci. 84, 7413 (1987); U.S. Pat. No. 4,897,355). DOTMA can be formulated alone or can be combined with the neutral lipid, dioleoylphosphatidyl-ethanolamine or "DOPE" or other cationic or non-cationic lipids into a transfer vehicle or a lipid nanoparticle, and such liposomes can be used to enhance the delivery of nucleic acids into target cells. Other suitable cationic lipids include, for example, 5-carboxyspermylglycinedioctadecylamide or "DOGS," 2,3-dioleyloxy-N-[2 (spermine-carboxamido)ethyl]-N,N-dimethyl-1-propanaminium or "DOSPA" (Behr et al. Proc. Nat.'l Acad. Sci. 86, 6982 (1989); U.S. Pat. Nos. 5,171,678; 5,334,761), 1,2-Dioleoyl-3-Dimethylammonium-Propane or "DODAP," 1,2-Dioleoyl-3-Trimethylammonium-Propane or "DOTAP." Contemplated cationic lipids also include 1,2-distearyloxy-N,N-dimethyl-3-aminopropane or "DSDMA", 1,2-dioleyloxy-N,N-dimethyl-3-aminopropane or "DODMA," 1,2-dilinoleyloxy-N,N-dimethyl-3-aminopropane or "DLinDMA," 1,2-dilinolenyloxy-N,N-dimethyl-3-aminopropane or "DLenDMA," N-dioleyl-N,N-dimethylammonium chloride or "DODAC," N,N-distearyl-N,N-dimethyl-ammonium bromide or "DDAB," N-(1,2-dimyristyloxyprop-3-yl)-N,N-dimethyl-N-hydroxyethyl ammonium bromide or 3-dimethylamino-2-(cholest-5-en-3-beta-oxybutan-4-oxy)-1-(cis,cis-9,12-"DMRIE," octadecadienoxy) propane or "CLinDMA," 2-[5'-(cholest-5-en-3-beta-oxy)-3'-oxapentoxy)-3-dimethy 1-1-(cis, cis-9', 1-2'-octadecadienoxy) propane or "CpLinDMA," N,N-dimethyl-3,4-dioleyloxybenzylamine or "DMOBA," 1,2-N,N'-dioleylcarbamyl-3-dimethylaminopropane or "DOcarbDAP," 2,3-Dilinoleoyloxy-N,N-dimethylpropylamine or "DLinDAP," 1,2-N,N'-Dilinoleylcarbamyl-3-dimethylaminopropane or "DLincarbDAP," 1,2-Dilinoleylcarbamyl-3-dimethylaminopropane or "DLinCDAP,"

2,2-dilinoleyl-4-dimethylaminomethyl-[1,3]-dioxolane or "DLin-K-DMA," 2,2-dilinoleyl-4-dimethylaminoethyl-[1, 3]-dioxolane or "DLin-K-XTC2-DMA," and 2-(2,2-di((9Z, 12Z)-octadeca-9,12-dien-1-yl)-1,3-dioxolan-4-yl)-N,N-dimethylethanamine (DLin-KC2-DMA)) (See, WO 2010/042877; Semple et al., Nature Biotech. 28:172-176 (2010)), or mixtures thereof. (Heyes, J., et al., J Controlled Release 107:276-287 (2005); Morrissey, D V., et al., Nat. Biotechnol. 23 (8): 1003-1007 (2005); PCT Publication WO2005/121348A1).

The use of cholesterol-based cationic lipids is also contemplated herein. Such cholesterol-based cationic lipids can be used, either alone or in combination with other cationic or non-cationic lipids. Suitable cholesterol-based cationic lipids include, for example, GL67, DC-Chol (N,N-dimethyl-N-ethylcarboxamidocholesterol), 1,4-bis(3-N-oleylamino-propyl) piperazine (Gao, et al. Biochem. Biophys. Res. Comm. 179, 280 (1991); Wolf et al. BioTechniques 23, 139 (1997); U.S. Pat. No. 5,744,335), or ICE.

In some embodiments, the one or more of the cationic or ionizable lipids provide increased activity of the nucleic acid and improved tolerability of the compositions in vivo.

In some embodiments, the one or more of the cationic or ionizable lipids are represented by Formula (I):

Formula (I)

wherein:

n is an integer between 1 and 4;

$R_a$ is hydrogen or hydroxyl; and $R_1$ and $R_2$ are each independently a linear or branched $C_6$-$C_{30}$ alkyl, $C_6$-$C_{30}$ alkenyl, or $C_6$-$C_{30}$ heteroalkyl, optionally substituted by one or more substituents selected from a group consisting of oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl) (alkyl)aminoalkyl, heterocyclyl, heteroaryl, alkylheteroaryl, alkynyl, alkoxy, amino, dialkylamino, aminoalkylcarbonylamino, aminocarbonylalkylamino, (aminocarbonylalkyl) (alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl) (alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl, and alkylsulfonealkyl.

In some embodiments, Ra is hydrogen. In some embodiments, Ra is hydroxyl.

In some embodiments, the ionizable lipid is represented by Formula (Ia-1), Formula (Ia-2), or Formula (Ia-3):

Formula (Ia-1)

Formula (Ia-2)

Formula (Ia-3)

In some embodiments, the ionizable lipid is represented by Formula (Ib-1), Formula (Ib-2), or Formula (Ib-3):

Formula (Ib-1)

Formula (Ib-2)

Formula (Ib-3)

In some embodiments, the ionizable lipid is represented by Formula (Ib-4), Formula (Ib-5), Formula (Ib-6), Formula (Ib-7), Formula (Ib-8), or Formula (Ib-9):

Formula (Ib-4)

Formula (Ib-5)

201

-continued

Formula (Ib-6)

Formula (Ib-7)

Formula (Ib-8)

202

-continued

Formula (Ib-9)

In some embodiments, the one or more of the cationic or ionizable lipids are represented by Formula (I), wherein $R_1$ and $R_2$ are each independently selected from:

-continued

-continued

, and

.

In some embodiments, $R_1$ and $R_2$ are the same. In some embodiments, R, and R2 are different.

In various embodiments, the one or more of the cationic or ionizable lipids are represented by Formula (I*):

Formula (I*)

wherein:
n* is an integer between 1 to 7,
$R^a$ is hydrogen or hydroxyl,
$R^b$ is hydrogen or $C_1$-$C_6$ alkyl,
$R_1$ and $R_2$ are each independently a linear or branched $C_1$-$C_{30}$ alkyl, $C_2$-$C_{30}$ alkenyl, or $C_1$-$C_{30}$ heteroalkyl, optionally substituted by one or more substituents selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl) (alkyl)aminoalkyl, heterocyclyl, heteroaryl, alkylheteroaryl, alkynyl, alkoxy, amino, dialkylamino, aminoalkylcarbonylamino, aminocarbonylalkylamino, (aminocarbonylalkyl) (alkyl)amino, alkenylcarbonylamino, hydroxycarbonyl, alkyloxycarbonyl, alkylcarbonyloxy, alkylcarbonate, alkenyloxycarbonyl, alkenylcarbonyloxy, alkenylcarbonate, alkynyloxycarbonyl, alkynylcarbonyloxy, alkynylcarbonate, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl) (alkyl)

aminocarbonyl, alkylaminoalkylcarbonyl, dialkylaminoalkylcarbonyl, alkynylcarbonyl, alkylsulfoxide, alkylsulfoxidealkyl, heterocyclylcarbonyl, alkenylcarbonyl, alkylsulfonyl, and alkylsulfonealkyl.

In some embodiments, the one or more of the cationic or ionizable lipids are represented by Formula (II):

Formula (II)

wherein:
each n is independently an integer from 2-15;
$L_1$ and $L_3$ are each independently —OC(O)—* or —C(O)O—*, wherein "*" indicates the attachment point to $R_1$ or R3;
$R_1$ and $R_3$ are each independently a linear or branched $C_9$-$C_{20}$ alkyl or $C_9$-$C_{20}$ alkenyl, optionally substituted by one or more substituents selected from a group consisting of oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl) (alkyl)aminoalkyl, heterocyclyl, heteroaryl, alkylheteroaryl, alkynyl, alkoxy, amino, dialkylamino, aminoalkylcarbonylamino, aminocarbonylalkylamino, (aminocarbonylalkyl) (alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl) (alkyl) aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl, and alkylsulfonealkyl; and

207

R₂ is selected from a group consisting of:

208

-continued

In some embodiments, the ionizable lipid is selected from an ionizable lipid of Formula II, wherein $R_1$ and $R_3$ are each independently selected from a group consisting of:

In some embodiments, $R_1$ and $R_5$ are the same. In some embodiments, $R_1$ and $R_3$ are different.

In some embodiments, the one or more of the cationic or ionizable lipids are represented by Formula (II-1) or Formula (II-2):

Formula (II-1)

Formula (II-2)

In some embodiments, the ionizable lipid is selected from an ionizable lipid of WO2015/095340 (lipid number 123 of Table 3). In some embodiments, the ionizable lipid is selected from an ionizable lipid of WO2021/021634, WO2020/237227, or WO2019/236673 (lipid numbers 124-127 of Table 3). In some embodiments, the ionizable lipid is selected from an ionizable lipid of WO2021226597 and WO2021113777 (lipid numbers 128-131 of Table 3).

In some embodiments, the transfer vehicle comprises an ionizable lipid selected from an ionizable lipid represented in Table 3. In particular embodiments, where the ionizable lipid is of Formula I, the ionizable lipid is selected from lipid numbers 16, 45, 86, 89, and 90 of Table 3, below. In particular embodiments where the ionizable lipid is an ionizable lipid of Formula II, the ionizable lipid is selected from lipid numbers 128-131 of Table 3, below.

Example 2 describes exemplary methods of synthesizing certain ionizable lipids that are represented by Formula I and II and described in Table 3.

In some embodiments, the one or more of the cationic or ionizable lipids are represented by Formula (III):

Formula (III)

or a pharmaceutically acceptable salt thereof, wherein
$L^1$ is $C_2$-$C_{11}$ alkylene, $C_4$-$C_{10}$-alkenylene, or $C_4$-$C_{10}$-alkynylene;

$X^1$ is $OR^1$, $SR^1$, or $N(R^1)_2$, where $R^1$ is independently H or unsubstituted $C_1$-$C_6$ alkyl; and
$R^2$ and $R^3$ are each independently $C_6$-$C_{30}$-alkyl, $C_6$-$C_{30}$-alkenyl, or $C_6$-$C_{30}$-alkynyl.

In some embodiments, the one or more of the cationic or ionizable lipids are represented by Formula (III*):

Formula (III*)

or a pharmaceutically acceptable salt thereof, wherein
$L^1$ is $C_2$-$C_{11}$ alkylene, $C_4$-$C_{10}$-alkenylene, or $C_4$-$C_{10}$-alkynylene;
$X^1$ is $OR^1$, $SR^1$, or $N(R^1)_2$, where $R^1$ is independently H or unsubstituted $C_1$-$C_6$ alkyl; and
$R^2$ and $R^3$ are each independently a linear or branched $C_1$-$C_{30}$ alkyl, $C_2$-$C_{30}$ alkenyl, or $C_1$-$C_{30}$ heteroalkyl, optionally substituted by one or more substituents selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl) (alkyl)aminoalkyl, heterocyclyl, heteroaryl, alkylheteroaryl, alkynyl, alkoxy, amino, dialkylamino, aminoalkylcarbonylamino, aminocarbonylalkylamino, (aminocarbonylalkyl) (alkyl)amino, alkenylcarbonylamino, hydroxycarbonyl, alkyloxycarbonyl, alkylcarbonyloxy, alkylcarbonate, alkenyloxycarbonyl, alkenylcarbonyloxy, alkenylcarbonate, alkynyloxycarbonyl, alkynylcarbonyloxy, alkynylcarbonate, aminocarbonyl, aminoalkylaminocarbonyl, alkylaminoalkylaminocarbonyl, heterocyclylalkylaminocarbonyl, dialkylaminoalkylaminocarbonyl, (alkylaminoalkyl) (alkyl) aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl, and alkylsulfonealkyl.

TABLE 3

| Ionizable lipid number | Structure |
| --- | --- |
| 1 | |
| 2 | |
| 3 | |
| 4 | |
| 5 | |
| 6 | |

Exemplary Ionizable Lipid Structures

TABLE 3-continued

Exemplary Ionizable Lipid Structures

| Ionizable lipid number | Structure |
| --- | --- |
| 7 | |
| 8 | |
| 9 | |
| 10 | |
| 11 | |
| 12 | |

TABLE 3-continued

Exemplary Ionizable Lipid Structures

| Ioniz-able lipid num-ber | Structure |
| --- | --- |
| 13 | |
| 14 | |
| 15 | |
| 16 | |
| 17 | |
| 18 | |

TABLE 3-continued

Exemplary Ionizable Lipid Structures

| Ionizable lipid number | Structure |
|---|---|
| 19 | |
| 20 | |
| 21 | |
| 22 | |
| 23 | |

TABLE 3-continued

Exemplary Ionizable Lipid Structures

| Ionizable lipid number | Structure |
| --- | --- |
| 24 | |
| 25 | |
| 26 | |
| 27 | |

TABLE 3-continued

| Exemplary Ionizable Lipid Structures | |
| --- | --- |
| Ionizable lipid number | Structure |
| 28 | |
| 29 | |
| 30 | |
| 31 | |
| 32 | |
| 33 | |

TABLE 3-continued

Exemplary Ionizable Lipid Structures

| Ionizable lipid number | Structure |
| --- | --- |
| 34 | |
| 35 | |
| 36 | |
| 37 | |
| 38 | |
| 39 | |

TABLE 3-continued

| Exemplary Ionizable Lipid Structures | |
|---|---|
| Ionizable lipid number | Structure |
| 40 | |
| 41 | |
| 42 | |
| 43 | |
| 44 | |
| 45 | |

TABLE 3-continued

Exemplary Ionizable Lipid Structures

| Ionizable lipid number | Structure |
|---|---|
| 46 | |
| 47 | |
| 48 | |
| 49 | |
| 50 | |

TABLE 3-continued

Exemplary Ionizable Lipid Structures

| Ioniz-able lipid num-ber | Structure |
| --- | --- |
| 51 | |
| 52 | |
| 53 | |
| 54 | |
| 55 | |

TABLE 3-continued

| Exemplary Ionizable Lipid Structures | |
| --- | --- |
| Ioniz-able lipid num-ber | Structure |
| 56 | |
| 57 | |
| 58 | |
| 59 | |

TABLE 3-continued

| Exemplary Ionizable Lipid Structures | |
|---|---|
| Ioniz-able lipid num-ber | Structure |
| 60 | |
| 61 | |
| 62 | |

TABLE 3-continued

| Exemplary Ionizable Lipid Structures | |
|---|---|
| Ionizable lipid number | Structure |
| 63 | |
| 64 | |
| 65 | |

TABLE 3-continued

| Exemplary Ionizable Lipid Structures | |
| --- | --- |
| Ioniz-able lipid num-ber | Structure |
| 66 | |
| 67 | |
| 68 | |
| 69 | |

TABLE 3-continued

| Exemplary Ionizable Lipid Structures | |
| --- | --- |
| Ioniz-able lipid num-ber | Structure |
| 70 | |
| 71 | |
| 72 | |
| 73 | |

TABLE 3-continued

Exemplary Ionizable Lipid Structures

| Ioniz-<br>able<br>lipid<br>num-<br>ber | Structure |
| --- | --- |
| 74 | |
| 75 | |
| 76 | |

TABLE 3-continued

| Exemplary Ionizable Lipid Structures | |
|---|---|
| Ioniz-able lipid num-ber | Structure |
| 77 | |
| 78 | |
| 79 | |

TABLE 3-continued

Exemplary Ionizable Lipid Structures

| Ionizable lipid number | Structure |
| --- | --- |
| 80 | |
| 81 | |
| 82 | |

TABLE 3-continued

Exemplary Ionizable Lipid Structures

| Ionizable lipid number | Structure |
|---|---|
| 83 | |
| 84 | |
| 85 | |

TABLE 3-continued

| Exemplary Ionizable Lipid Structures | |
|---|---|
| Ioniz- able lipid num- ber | Structure |
| 86 | |
| 87 | |
| 88 | |

TABLE 3-continued

Exemplary Ionizable Lipid Structures

| Ionizable lipid number | Structure |
|---|---|
| 89 | |
| 90 | |
| 91 | |

TABLE 3-continued

| Exemplary Ionizable Lipid Structures | |
|---|---|
| Ioniz-able lipid num-ber | Structure |
| 92 | |
| 93 | |
| 94 | |

TABLE 3-continued

Exemplary Ionizable Lipid Structures

| Ioniz-able lipid num-ber | Structure |
|---|---|
| 95 | |
| 96 | |
| 97 | |

TABLE 3-continued

| Exemplary Ionizable Lipid Structures | |
| --- | --- |
| Ioniz-able lipid num-ber | Structure |
| 98 | |
| 99 | |
| 100 | |

TABLE 3-continued

| Exemplary Ionizable Lipid Structures | |
|---|---|
| Ionizable lipid number | Structure |
| 101 | |
| 102 | |
| 103 | |

TABLE 3-continued

| Exemplary Ionizable Lipid Structures | |
|---|---|
| Ioniz-able lipid num-ber | Structure |
| 104 | |
| 105 | |
| 106 | |

TABLE 3-continued

| Exemplary Ionizable Lipid Structures | |
|---|---|
| Ioniz-able lipid num-ber | Structure |
| 107 | |
| 108 | |
| 109 | |

TABLE 3-continued

| | |
|---|---|
| | Exemplary Ionizable Lipid Structures |

| Ioniz-<br>able<br>lipid<br>num-<br>ber | Structure |
|---|---|
| 110 | |
| 111 | |
| 112 | |

TABLE 3-continued

| Exemplary Ionizable Lipid Structures | |
|---|---|
| Ioniz-able lipid num-ber | Structure |
| 113 | |
| 114 | |
| 115 | |

TABLE 3-continued

Exemplary Ionizable Lipid Structures

| Ioniz-able lipid num-ber | Structure |
| --- | --- |
| 116 | |
| 117 | |
| 118 | |

TABLE 3-continued

| Exemplary Ionizable Lipid Structures |
| --- |

| Ioniz-<br>able<br>lipid<br>num-<br>ber | Structure |
| --- | --- |
| 119 | |
| 120 | |
| 121 | |

TABLE 3-continued

| Exemplary Ionizable Lipid Structures | |
| --- | --- |
| Ioniz-able lipid num-ber | Structure |
| 122 | |
| 123 | |
| 124 | |
| 125 | |

TABLE 3-continued

| | |
|---|---|
| | Exemplary Ionizable Lipid Structures |

| Ionizable lipid number | Structure |
|---|---|
| 126 | |
| 127 | |
| 128 | |

TABLE 3-continued

Exemplary Ionizable Lipid Structures

| Ioniz-able lipid num-ber | Structure |
|---|---|
| 129 | |
| 130 | |
| 131 | |

TABLE 3-continued

Exemplary Ionizable Lipid Structures

| Ionizable lipid number | Structure |
| --- | --- |
| | |
| 132 | |
| 133 | |
| 134 | |
| 135 | |

TABLE 3-continued

Exemplary Ionizable Lipid Structures

| Ioniz-able lipid num-ber | Structure |
| --- | --- |
| 136 | |
| 137 | |
| 138 | |
| 139 | |
| 140 | |

TABLE 3-continued

| Exemplary Ionizable Lipid Structures | |
|---|---|
| Ionizable lipid number | Structure |
| 141 | |
| 142 | |
| 143 | |
| 144 | |
| 145 | |

TABLE 3-continued

Exemplary Ionizable Lipid Structures

| Ionizable lipid number | Structure |
|---|---|
| 146 | |
| 147 | |
| 148 | |
| 149 | |
| 150 | |

TABLE 3-continued

| Exemplary Ionizable Lipid Structures | |
|---|---|
| Ioniz-able lipid num-ber | Structure |
| 151 | |
| 152 | |
| 153 | |
| 154 | |
| 155 | |

TABLE 3-continued

Exemplary Ionizable Lipid Structures

| Ionizable lipid number | Structure |
| --- | --- |
| 156 | |
| 157 | |
| 158 | |
| 159 | |
| 160 | |
| 161 | |

TABLE 3-continued

| | |
|---|---|
| | Exemplary Ionizable Lipid Structures |

| Ionizable lipid number | Structure |
|---|---|
| 162 | |
| 163 | |
| 164 | |
| 165 | |
| 166 | |
| 167 | |

TABLE 3-continued

Exemplary Ionizable Lipid Structures

| Ioniz-able lipid num-ber | Structure |
|---|---|
| 168 | |
| 169 | |
| 170 | |
| 171 | |
| 172 | |
| 173 | |

TABLE 3-continued

Exemplary Ionizable Lipid Structures

| Ioniz-able lipid num-ber | Structure |
|---|---|
| 174 | |
| 175 | |
| 176 | |
| 177 | |
| 178 | |
| 179 | |

TABLE 3-continued

Exemplary Ionizable Lipid Structures

| Ioniz-able lipid num-ber | Structure |
| --- | --- |
| 180 | |
| 181 | |
| 182 | |
| 183 | |
| 184 | |
| 185 | |

In some embodiments, an ionizable lipid is a compound of Formula (15):

Formula (15)

or is a pharmaceutically acceptable salt thereof, wherein:
  $n*$ is an integer from 1 to 7;
  $R^a$ is hydrogen or hydroxyl;
  $R^h$ is hydrogen or $C_1$-$C_6$ alkyl;
  $R^1$ is $C_1$-$C_{30}$ alkyl or $R^{1*}$
  $R^2$ is $C_1$-$C_{30}$ alkyl or $R^{2*}$,
  $R^{1*}$ and $R^{2*}$ are independently selected from:
    —$(CH_2)_qC(O)O(CH_2)_rC(R^8)(R^9)(R^{10})$,
    —$(CH_2)_qOC(O)(CH_2)_rC(R^8)(R^9)(R^{10})$, and
    —$(CH_2)_qOC(O)O(CH_2)_rC(R^8)(R^9)(R^{10})$;
  wherein:
    q is an integer from 0 to 12,
    r is an integer from 0 to 6, wherein at least one occurrence of r is not 0;
    $R^8$ is H or $R^{11}$;
    $R^9$, $R^{10}$, and $R^{11}$ are each independently $C_1$-$C_{20}$ alkyl or $C_2$-$C_{20}$-alkenyl; and
  wherein (i) $R^1$ is $R^{1*}$, (ii) $R^2$ is $R^{2*}$, or (iii) $R^1$ is $R^{1*}$ and $R^2$ is $R^{2*}$.
In some embodiments of Formula (15), $R_a$ is hydrogen and the ionizable lipid is of Formula (16):

Formula (16)

or is a pharmaceutically acceptable salt thereof, wherein:
n* is an integer from 1 to 7.
In some embodiments of Formula (16), the ionizable lipid is of Formula (17):

Formula (17)

or a pharmaceutically acceptable salt thereof, wherein:
  n is an integer from 1 to 7;
  q and q' are each independently integers from 0 to 12;
  r and r' are each independently integers from 0 to 6, wherein at least one of r or r' is not 0;

$Z^A$ and $Z^B$ are each independently selected from $\wedge$—C(O)O—, $\wedge$—OC(O), and —OC(O)O—; where $\wedge$ denotes the attachment point to —$(CH_2)_q$— or —$(CH_2)_q$'-; and
$R^{9A}$, $R^{9B}$, $R^{10A}$, and $R^{10B}$ are each independently $C_1$-$C_{20}$ alkyl or $C_2$-$C_{20}$ alkenyl.
In some embodiments of Formula (17), $Z^A$ and $Z^B$ are $\wedge$—C(O)O—, and the ionizable lipid is of Formula (17a-1)

Formula (17a-1)

In some embodiments of Formula (17), $Z^A$ and $Z^B$ are $\wedge$—OC(O)—, and the ionizable lipid is of Formula (17a-2)

Formula (17a-2)

In some embodiments of Formula (17), $Z^A$ and $Z^B$ are —O(C)(O)O—, and the ionizable lipid is represented by Formula (17a-3):

Formula (17a-3)

In some embodiments of Formula (15), $R^a$ is hydroxyl and the ionizable lipid is of Formula (18):

Formula (18)

or is a pharmaceutically acceptable salt thereof, wherein:
  n* is an integer from 1 to 7;
  $R^h$ is hydrogen or $C_1$-$C_6$ alkyl;
  $R^1$ is $C_1$-$C_{30}$ alkyl or $R^{1*}$
  $R^2$ is $C_1$-$C_{30}$ alkyl or $R^{2*}$, $R^{1*}$ and $R^{2*}$ are independently selected from:

—$(CH_2)_qC(O)O(CH_2)_rC(R^8)(R^9)(R^{10})$,

—$(CH_2)_qOC(O)(CH_2)_rC(R^8)(R^9)(R^{10})$, and

—$(CH_2)_qOC(O)O(CH_2)_rC(R^8)(R^9)(R^{10})$;

wherein:

q is an integer from 0 to 12, r is an integer from 0 to 6, wherein at least one occurrence of r is not 0;

$R^8$ is hydrogen or $R^{11}$;

$R^9$, $R^{10}$, and $R^{11}$ are each independently $C_1$-$C_{20}$ alkyl or $C_2$-$C_{20}$-alkenyl;

wherein (i) $R^1$ is $R^{1*}$, (ii) $R^2$ is $R^{2*}$, or (iii) $R^1$ is $R^{1*}$ and $R^2$ is $R^{2*}$, and wherein, for (iii), (a) $R^{1*}$ and $R^{2*}$ are different or (b) $R^9$ and $R^{10}$ have different numbers of carbon atoms for at least one of $R^{1*}$ and $R^{2*}$.

In some embodiments of Formula (18), the ionizable lipid of is of Formula (19):

Formula (19)

or is a pharmaceutically acceptable salt thereof, wherein:

n is an integer from 1 to 7;

q and q' are each independently integers from 0 to 12;

r and r' are each independently integers from 0 to 6, wherein at least one of r or r' is not 0;

$Z^A$ and $Z^B$ are each independently selected from ∧—C(O)O—, ∧—OC(O), and —OC(O)O—;

where ∧ denotes the attachment point to —$(CH_2)_q$— or —$(CH_2)_{q'}$; and $R^{9A}$, $R^{9B}$, $R^{10A}$ and $R^{10B}$ are each independently $C_1$-$C_{20}$ alkyl or $C_2$-$C_{20}$ alkenyl.

In some embodiments of Formula (19), $Z^A$ and $Z^B$ are ∧—C(O)O—, and the ionizable lipid is of Formula (19a-1):

Formula (19a-1)

In some embodiments of Formula (19), $Z^A$ and $Z^B$ are ∧—OC(O)—, and the ionizable lipid is of Formula (19a-2):

Formula (19a-2)

In some embodiments of Formula (19), $Z^A$ and $Z^B$ are —O(C) (0)O—, and the ionizable lipid is represented by Formula (19a-3):

Formula (19a-3)

In some embodiments of Formula (15), R' is C1-C30 alkyl, and the ionizable lipid is of Formula (20):

Formula (20)

or is a pharmaceutically acceptable salt thereof, wherein:

$Z^A$ is selected from ∧—C(O)O—, ∧—OC(O)—, and —OC(O)O—; where ∧ denotes the attachment point to —$(CH_2)_q$—;

$R^{9A}$ and $R^{10A}$ are each independently $C_1$-$C_{20}$ alkyl or $C_2$-$C_{20}$ alkenyl;

n is an integer from 1 to 7;

q is an integer from 0 to 12; and r is an integer from 1 to 6.

In some embodiments of Formula (20), $Z^A$ is ∧—C(O) O—, and the ionizable lipid is of Formula (20a-1):

Formula (20a-1)

In some embodiments of Formula (20), $Z^A$ is ∧—OC (O)—, and the ionizable lipid is of Formula (20a-2):

US 12,599,679 B2

303 304

Formula (20a-2)

In some embodiments of Formula (20), $Z^A$ is —OC(O)O—, and the ionizable lipid is of Formula (20a-3):

Formula (20a-3)

In some embodiments of Formula (15), R2 is $C_1$-C30 alkyl, and the ionizable lipid is of Formula (21):

Formula (21)

or is a pharmaceutically acceptable salt thereof, wherein:
Z^B is selected from ∧—C(O)O—, ∧—OC(O)—, and —OC(O)O—; where ∧ denotes the attachment point to —(CH₂) q' ~;
$R^{9B}$ and $R^{10B}$ are each independently $C_1$-$C_{20}$ alkyl or $C_2$-$C_{20}$ alkenyl;
n is an integer from 1 to 7;

q' is an integer from 0 to 12; and
r' is an integer from 1 to 6.
In some embodiments of Formula (21), $Z^B$ is ∧—C(O)O—, and the ionizable lipid is of Formula (21a-1):

Formula (21a-1)

In some embodiments of Formula (21), $Z^B$ is ∧—OC(O)—, and the ionizable lipid is of Formula (21a-2):

Formula (21a-2)

In some embodiments of Formula (21), $Z^B$ is —OC(O)O—, and the ionizable lipid is of Formula (21a-3):

Formula (21a-3)

In some embodiments, an ionizable lipid is selected from the table below:

| Ionizable lipid number | Structure |
| --- | --- |
| 1-a | |

-continued

| Ionizable lipid number | Structure |
|---|---|
| 1-b | |
| 1-c | |
| 1-d | |
| 1-e | |
| 1-f | |

-continued

| Ionizable lipid number | Structure |
|---|---|
| 1-g | |
| 1-h | |
| 1-i | |
| 1-j | |
| 1-k | |

-continued

| Ionizable lipid number | Structure |
|---|---|
| 1-l | |
| 1-m | |
| 1-m | |
| 1-n | |
| 1-o | |

-continued

| Ionizable lipid number | Structure |
|---|---|
| 1-p | |
| 1-q | |
| 1-r | |
| 1-s | |
| 1-t | |
| 1-u | |

-continued

| Ionizable lipid number | Structure |
|---|---|
| 1-v | |
| 1-w | |
| 1-x | |
| 1-y | |
| 1-z | |

-continued

| Ionizable lipid number | Structure |
|---|---|
| 1-aa | |
| 1-ab | |
| 1-ac | |
| 1-ad | |
| 1-ae | |

-continued

| Ionizable lipid number | Structure |
|---|---|
| 1-af | |
| 1-ag | |
| 1-ah | |
| 1-ai | |
| 1-aj | |

-continued

| Ionizable lipid number | Structure |
|---|---|
| 1-ak | |

In some embodiments, an ionizable lipid of the present disclosure is represented by Formula (22):

Formula (22)

or is a pharmaceutically acceptable salt thereof, wherein:

$R^a$ is hydrogen or hydroxyl;

$R^1$ is $C_1$-$C_{30}$ alkyl or $R^{1*}$ $R^2$ is $C_1$-$C_{30}$ alkyl or $R^{2*}$;

$R^{1*}$ and $R^{2*}$ are independently selected from:

$(CH_2)_qC(O)O(CH_2)_rC(R^4)(R^5)(R^6)$, $(CH_2)_qOC(O)(CH_2)_rC(R^4)(R^5)(R^6)$, and $(CH_2)_qOC(O)O(CH_2)_rC(R^4)(R^5)(R^6)$;

wherein:

q is an integer from 0 to 12, r is an integer from 0 to 6, wherein at least one occurrence of r is not 0;

$R^4$ is hydrogen or $R^7$;

$R^5$, $R^6$, and $R^7$ are each independently $C_1$-$C_{20}$ alkyl or $C_2$-$C_{20}$-alkenyl;

wherein (i) $R^1$ is $R^{1*}$, (ii) $R^2$ is $R^{2*}$, or (iii) $R^1$ is $R^{1*}$ and $R^2$ is $R^{2*}$; and $R^3$ is L-R', wherein L is linear or branched $C_1$-$C_{10}$ alkylene, and R' is (i) mono- or bicyclic heterocyclyl or heteroaryl, such as imidazolyl, pyrazolyl, 1,2,4-triazolyl, or benzimidazolyl, each optionally substituted at one or more available carbon and nitrogen by $C_1$-$C_6$ alkyl, or (ii) $R^A$, $R^B$, or $R^C$, wherein $R^A$ is selected from:

-continued

321

-continued

322

-continued

RB is selected from:

323

324 and $R^C$ is selected from:

325

-continued

326

-continued with the proviso that the ionizable lipid is not:

329

330

-continued
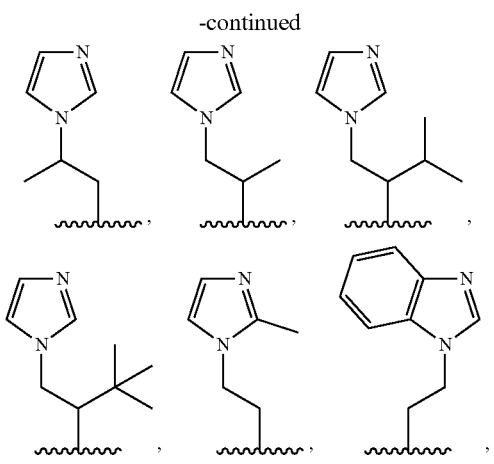
In some embodiments of Formula (22), R³ is selected from:
-continued -continued In some embodiments of Formula (22), $R^1$ is $R^{1*}$, $R^2$ is $R^{2*}$, and the ionizable lipid is of Formula (23):

Formula (23)

wherein:

q and q' are each independently integers from 0 to 12;

r and r' are each independently integers from 0 to 6, wherein at least one of r or r' is not 0; $Z^A$ and $Z^B$ are each independently selected from $\wedge$—C(O)O—, $\wedge$—OC(O), and —OC(O)O—; where $\wedge$ denotes the attachment point to —(CH$_2$)$_q$— or —(CH$_2$)$_q$'-; and $R^{5A}$, $R^{5B}$, $R^{6A}$ and $R^{6B}$ are each independently C$_1$-C$_{20}$ alkyl or C$_2$-C$_{20}$ alkenyl.

In some embodiments of Formula (23), $Z^A$ and $Z^B$ are $\wedge$—C(O)O—, and the ionizable lipid is of Formula (23a-1):

Formula (23a-1)

In some embodiments of Formula (23), $Z^A$ and $Z^B$ are $\wedge$—OC(O)—, and the ionizable lipid is of Formula (23a-2)

Formula (23a-2)

In some embodiments of Formula (23), $Z^A$ and $Z^B$ are —O(C)(O)O—, and the ionizable lipid is represented by Formula (23a-3):

Formula (23a-3)

In some embodiments of Formula (22), $R^2$ is C$_1$-C$_{30}$ alkyl, and the ionizable lipid is of Formula (25):

Formula (25)

or is a pharmaceutically acceptable salt thereof, wherein:

$Z^B$ is selected from $\wedge$—C(O)O—, $\wedge$—OC(O)—, and —OC(O)O—; where $\wedge$ denotes the attachment point to —(CH$_2$)$_q$'-;

$R^{5B}$ and $R^{6B}$ are each independently C$_1$-C$_{20}$ alkyl or C$_2$-C$_{20}$ alkenyl;

q' is an integer from 0 to 12; and r' is an integer from 1 to 6.

In some embodiments of Formula (25), $Z^B$ is $\wedge$—C(O)O—, and the ionizable lipid is of Formula (25a-1):

In some embodiments of Formula (25), $Z^B$ is —OC(O)O—, and the ionizable lipid is of Formula (25a-3):

Formula (24a-1)

In some embodiments of Formula (25), $Z^B$ is $\wedge$—OC(O)—, and the ionizable lipid is of Formula (25a-2):

Formula (25a-3)

Formula (24a-2)

In some embodiments, an ionizable lipid is selected from the table below:

| Lipid | Structure |
|---|---|
| 100-a | |
| 100-b | |
| 100-c | |

-continued

| Lipid | Structure |
|-------|-----------|
| 100-d | |
| 100-e | |
| | and |
| 100-f | |

In some embodiments, an ionizable lipid is selected from the table below.

| Lipid | Structure |
|-------|-----------|
| 1-al | |
| 1-am | |

-continued

| Lipid | Structure |
|-------|-----------|
| 1-an | |
| 1-ao | |
| 1-ap | |
| 1-aq | |
| 1-ar | |

-continued

| Lipid | Structure |
|-------|-----------|
| 1-as | |
| 1-at | |
| 1-au | |

In some embodiments, an ionizable lipid is described in US patent publication number 20190321489. In some embodiments, an ionizable lipid is described in international patent publication WO 2010/053572, incorporated herein by reference. In some embodiments, an ionizable lipid is C12-200, described at paragraph of WO 2010/053572.

Several ionizable lipids have been described in the literature, many of which are commercially available. In certain embodiments, such ionizable lipids are included in the transfer vehicles described herein. In some embodiments, the ionizable lipid N-[1-(2,3-dioleyloxy) propyl]-N,N,N-trimethylammonium chloride or "DOTMA" is used. (Felgner et al. Proc. Nat'l Acad. Sci. 84, 7413 (1987); U.S. Pat. No. 4,897,355). DOTMA can be formulated alone or can be combined with a neutral lipid, dioleoylphosphatidyletha-nolamine or "DOPE" or other cationic or non-cationic lipids into a lipid nanoparticle. Other suitable cationic lipids include, for example, ionizable cationic lipids as described in U.S. provisional patent application 61/617,468, filed Mar. 29, 2012 (incorporated herein by reference), such as, e.g., (15Z,18Z)—N,N-dimethyl-6-(9Z, 12Z)-octadeca-9,12-dien-1-yl)tetracosa-15,18-dien-1-amine (HGT5000), (15Z, 18Z)—N,N-dimethyl-6-((9Z,12Z)-octadeca-9,12-dien-1-yl) tetracosa-4,15,18-trien-1-amine (HGT5001), and (15Z, 18Z)—N,N-dimethyl-6-((9Z,12Z)-octadeca-9,12-dien-1-yl) tetracosa-5,15,18-trien-1-amine (HGT5002), C12-200 (described in WO 2010/053572, 2-(2,2-di((9Z,12Z)-octadeca-9,12-dien-1-yl)-1,3-dioxolan-4-yl)-N,N-dimethyl-ethanamine (DLinKC2-DMA)) (See, WO 2010/042877; Semple et al., Nature Biotech. 28:172-176 (2010)), 2-(2,2-di((9Z,2Z)-octadeca-9,12-dien-1-yl)-1,3-dioxolan-4-yl)-N,N-dimethylethanamine (DLin-KC2-DMA), (3S,10R, 13R, 17R)-10, 13-dimethyl-17-((R)-6-methylheptan-2-yl)-2, 3, 4, 7, 8, 9, 10, 11, 12, 13, 14, 15, 16, 17-tetradecahydro-1H-cyclopenta[a]phenanthren-3-yl 3-(1H-imidazol-4-yl) pro-panoate (ICE), (15Z,18Z)—N,N-dimethyl-6-(9Z,12Z)-octadeca-9,12-dien-1-yl)tetracosa-15,18-dien-1-amine (HGT5000), (15Z,18Z)—N,N-dimethyl-6-((9Z,12Z)-octa-deca-9,12-dien-1-yl)tetracosa-4,15,18-trien-1-amine (HGT5001), (15Z,18 Z)—N,N-dimethyl-6-((9Z,12Z)-octa-deca-9,12-dien-1-yl)tetracosa-5,15,18-trien-1-amine (HGT5002), 5-carboxyspermylglycine-dioctadecylamide (DOGS), 2,3-dioleyloxy-N-[2 (spermine-carboxamido) ethyl]-N,N-dimethyl-1-propanaminium (DOSPA) (Behr et al. Proc. Nat.'l Acad. Sci. 86, 6982 (1989); U.S. Pat. Nos. 5,171,678; 5,334,761), 1,2-Dioleoyl-3-Dimethylammo-nium-Propane (DODAP), 1,2-Dioleoyl-3-Trimethylammo-nium-Propane or (DOTAP). Contemplated ionizable lipids also include 1,2-distcaryloxy-N,N-dimethyl-3-aminopro-pane (DSDMA), 1,2-dioleyloxy-N,N-dimethyl-3-aminopro-pane (DODMA), 1,2-dilinoleyloxy-N,N-dimethyl-3-amino-propane (DLinDMA), 1,2-dilinolenyloxy-N,N-dimethyl-3-aminopropane (DLenDMA), N-dioleyl-N,N-dimethylammonium chloride (DODAC), N,N-distearyl-N, N-dimethylammonium bromide (DDAB), N-(1,2-dimyristyloxyprop-3-yl)-N,N-dimethyl-N-hydroxyethyl ammonium bromide (DMRIE), 3-dimethylamino-2-(cholest-5-en-3-beta-oxybutan-4-oxy)-1-(cis,cis-9,12-octa-decadienoxy) propane (CLinDMA), 2-[5'-(cholest-5-en-3-beta-oxy)-3'-oxapentoxy)-3-dimethyl-1-(cis,cis-9', 1-2'-octadecadienoxy) propane (CpLinDMA), N,N-dimethyl-3, 4-dioleyloxybenzylamine (DMOBA), 1,2-N,N'-dioleylcarbamyl-3-dimethylaminopropane (DOcarbDAP), 2,3-Dilinoleoyloxy-N,N-dimethylpropylamine (DLinDAP), 1,2-N,N'-Dilinoleylcarbamyl-3-dimethylamninopropane (DLincarbDAP), 1,2-Dilinoleoylcarbamyl-3-dimethylami-nopropane (DLinCDAP), 2,2-dilinoleyl-4-dimethylami-nomethyl-[1,3]-dioxolane (DLin-K-DMA), 2,2-dilinoleyl-4-dimethylaminocthyl-[1,3]-dioxolane (DLin-K-XTC2-DMA) or GL67, or mixtures thereof. (Heyes, J., et al., J Controlled Release 107:276-287 (2005); Morrissey, D V., et al., Nat. Biotechnol. 23 (8): 1003-1007 (2005); PCT Publi-cation WO2005/121348A1). The use of cholesterol-based ionizable lipids to formulate the transfer vehicles (e.g., lipid nanoparticles) is also contemplated herein. Such cholesterol-based ionizable lipids can be used, either alone or in combination with other lipids. Suitable cholesterol-based ionizable lipids include, for example, DC-Cholesterol (N,N-dimethyl-N-ethylcarboxamidocholesterol), and 1,4-bis(3-N-oleylamino-propyl) piperazine (Gao, et al., Biochem. Biophys. Res. Comm. 179, 280 (1991); Wolf et al. BioTechniques 23, 139 (1997); U.S. Pat. No. 5,744,335).

Also contemplated are cationic lipids such as dialkylamino-based, imidazole-based, and guanidinium-based lipids. For example, also contemplated is the use of the ionizable lipid (3S,10R, 13R, 17R)-10,13-dimethyl-17-((R)-6-methylheptan-2-yl)-2, 3, 4, 7, 8, 9, 10, 11, 12, 13, 14, 15, 16, 17-tetradecahydro-1H-cyclopenta[a]phenanthren-3-yl 3-(1H-imidazol-4-yl) propanoate (ICE), as disclosed in International Application No. PCT/US2010/058457, incorporated herein by reference.

Also contemplated are ionizable lipids such as the dialkylamino-based, imidazole-based, and guanidinium-based lipids.

In some embodiments, an ionizable lipid is described by US patent publication number 20190314284.

The ionizable lipids include those disclosed in international patent application PCT/US2019/025246, and US patent publications 2017/0190661 and 2017/0114010, incorporated herein by reference in their entirety.

In some embodiments, an ionizable lipid is as described in international patent application PCT/US2019/015913.

Preparation methods for the above compounds and compositions are described herein below and/or known in the art.

It will be appreciated by those skilled in the art that in the process described herein the functional groups of intermediate compounds may need to be protected by suitable protecting groups. Such functional groups include, e.g., hydroxyl, amino, mercapto, and carboxylic acid. Suitable protecting groups for hydroxyl include, e.g., trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino, and guanidino include, e.g., t-butoxycarbonyl, benzyloxycarbonyl, and the like. Suitable protecting groups for mercapto include, e.g., —C(O)—R" (where R" is alkyl, aryl, or arylalkyl), p-methoxybenzyl, trityl, and the like. Suitable protecting groups for carboxylic acid include, e.g., alkyl, aryl, or arylalkyl esters. Protecting groups may be added or removed in accordance with standard techniques, which are known to one skilled in the art and as described herein. The use of protecting groups is described in detail in, e.g., Green, T. W. and P. G. M. Wutz, Protective Groups in Organic Synthesis (1999), 3rd Ed., Wiley. As one of skill in the art would appreciate, the protecting group may also be a polymer resin such as a Wang resin, Rink resin, or a 2-chloro-trityl-chloride resin.

It will also be appreciated by those skilled in the art, although such protected derivatives of compounds described herein may not possess pharmacological activity as such, they may be administered to a mammal and thereafter metabolized in the body to form compounds described herein which are pharmacologically active. Such derivatives may therefore be described as prodrugs. All prodrugs of compounds described herein are included within the scope of the present disclosure.

Furthermore, all compounds described herein which exist in free base or acid form can be converted to their pharmaceutically acceptable salts by treatment with the appropriate inorganic or organic base or acid by methods known to one skilled in the art. Salts of the compounds described herein can also be converted to their free base or acid form by standard techniques.

Amine Lipids

In certain embodiments, transfer vehicle compositions for the delivery of circular RNA comprise an amine lipid. In certain embodiments, an ionizable lipid is an amine lipid. In some embodiments, an amine lipid is described in international patent application PCT/US2018/053569.

Amine lipids and other biodegradable lipids suitable for use in the transfer vehicles, e.g., lipid nanoparticles, described herein are biodegradable in vivo. The amine lipids described herein have low toxicity (e.g., are tolerated in animal models without adverse effect in amounts of greater than or equal to 10 mg/kg). In certain embodiments, transfer vehicles composing an amine lipid include those where at least 75% of the amine lipid is cleared from the plasma within 8, 10, 12, 24, or 48 hours, or 3, 4, 5, 6, 7, or 10 days.

Biodegradable lipids include, for example, the biodegradable lipids of WO2017/173054, WO2015/095340, and WO2014/136086.

Lipid clearance may be measured by methods known by persons of skill in the art. See, for example, Maier, M. A., et al. Biodegradable Lipids Enabling Rapidly Eliminated Lipid Nanoparticles for Systemic Delivery of RNAi Therapeutics. Mol. Ther. 2013, 21 (8), 1570-78.

Transfer vehicle compositions comprising an amine lipid can lead to an increased clearance rate. In some embodiments, the clearance rate is a lipid clearance rate, for example the rate at which a lipid is cleared from the blood, serum, or plasma. In some embodiments, the clearance rate is an RNA clearance rate, for example the rate at which a circular RNA is cleared from the blood, serum, or plasma. In some embodiments, the clearance rate is the rate at which transfer vehicles are cleared from the blood, serum, or plasma. In some embodiments, the clearance rate is the rate at which transfer vehicles are cleared from a tissue, such as liver tissue or spleen tissue. In certain embodiments, a high rate of clearance leads to a safety profile with no substantial adverse effects. The amine lipids and biodegradable lipids may reduce transfer vehicle accumulation in circulation and in tissues. In some embodiments, a reduction in transfer vehicle accumulation in circulation and in tissues leads to a safety profile with no substantial adverse effects.

Lipids may be ionizable depending upon the pH of the medium they are in. For example, in a slightly acidic medium, the lipid, such as an amine lipid, may be protonated and thus bear a positive charge. Conversely, in a slightly basic medium, such as, for example, blood, where pH is approximately 7.35, the lipid, such as an amine lipid, may not be protonated and thus bear no charge. The ability of a lipid to bear a charge is related to its intrinsic pKa. In some embodiments, the amine lipids of the present disclosure may each, independently, have a pKa in the range of from about 5.1 to about 7.4. In some embodiments, the bioavailable lipids of the present disclosure may each, independently, have a pKa in the range of from about 5.1 to about 7.4. For example, the amine lipids of the present disclosure may each, independently, have a pKa in the range of from about 5.8 to about 6.5. Lipids with a pKa ranging from about 5.1 to about 7.4 are effective for delivery of cargo in vivo, e.g., to the liver. Further, it has been found that lipids with a pKa ranging from about 5.3 to about 6.4 are effective for delivery in vivo, e.g., into tumors. See, e.g., WO2014/136086.

Lipids Containing a Disulfide Bond

In some embodiments, the ionizable lipid is described in U.S. Pat. No. 9,708,628.

In some embodiments, the lipid may have an —S—S— (disulfide) bond. The production method for such a compound includes, for example, a method including producing R$^{3a}$—(Y$^a$—R$^{2a}$)n$^a$-X$^a$—R$^{1a}$—SH, and R$^{3b}$—(Y$^b$—R$^{2b}$)n$^b$-X$^b$—R$^{1b}$—SH, and subjecting them to oxidation (coupling) to give a compound containing —S—S—, a method including sequentially bonding necessary parts to a compound containing an —S—S— bond to finally obtain the compound and the like. Preferred is the latter method.

Further Exemplary Ionizable Lipids

In some embodiments, an ionizable lipid is described in U.S. Pat. No. 9,765,022.

In some embodiments, other lipid-like compounds can be prepared using suitable routes known in the art. The methods can include an additional step(s) to add or remove suitable protecting groups in order to ultimately allow synthesis of the lipid-like compounds. In addition, various synthetic steps can be performed in an alternate sequence or order to give the desired material. Synthetic chemistry transformations and protecting group methodologies (protection and deprotection) useful in synthesizing applicable lipid-like compounds are known in the art, including, for example, R. Larock, Comprehensive Organic Transformations (2nd Ed., VCH Publishers 1999); P. G. M. Wuts and T. W. Greene, Greene's Protective Groups in Organic Synthesis (4th Ed., John Wiley and Sons 2007); L. Fieser and M. Fieser, Fieser and Fieser's Reagents for Organic Synthesis (John Wiley and Sons 1994); and L. Paquette, ed., Encyclopedia of Reagents for Organic Synthesis (2nd ed., John Wiley and Sons 2009) and subsequent editions thereof. Certain lipid-like compounds may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

As mentioned above, these lipid-like compounds are useful for delivery of pharmaceutical agents. They can be preliminarily screened for their efficacy in delivering pharmaceutical agents by an in vitro assay and then confirmed by animal experiments and clinic trials. Other methods will also be apparent to those of ordinary skill in the art.

The above described complexes can be prepared using procedures described in publications such as Wang et al., ACS Synthetic Biology, 1, 403-07 (2012). Generally, they are obtained by incubating a lipid-like compound and a pharmaceutical agent in a buffer such as a sodium acetate buffer or a phosphate buffered saline ("PBS").

Hydrophilic Groups

In certain embodiments, the selected hydrophilic functional group or moiety may alter or otherwise impart properties to the compound or to the transfer vehicle of which such compound is a component (e.g., by improving the transfection efficiencies of a lipid nanoparticle of which the compound is a component). For example, the incorporation of guanidinium as a hydrophilic head-group in the compounds disclosed herein may promote the fusogenicity of such compounds (or of the transfer vehicle of which such compounds are a component) with the cell membrane of one or more target cells, thereby enhancing, for example, the transfection efficiencies of such compounds. It has been hypothesized that the nitrogen from the hydrophilic guanidinium moiety forms a six-membered ring transition state which grants stability to the interaction and thus allows for cellular uptake of encapsulated materials. (Wender, et al., Adv. Drug Del. Rev. (2008) 60:452-472.) Similarly, the incorporation of one or more amino groups or moieties into the disclosed compounds (e.g., as a head-group) may further promote disruption of the endosomal/lysosomal membrane of the target cell by exploiting the fusogenicity of such amino groups. This is based not only on the pKa of the amino group of the composition, but also on the ability of the amino group to undergo a hexagonal phase transition and fuse with the target cell surface, i.e., the vesicle membrane. (Koltover, et al. Science (1998) 281:78-81.) The result is believed to promote the disruption of the vesicle membrane and release of the lipid nanoparticle contents into the target cell.

Similarly, in certain embodiments the incorporation of, for example, imidazole as a hydrophilic head-group in the compounds disclosed herein may serve to promote endosomal or lysosomal release of, for example, contents that are encapsulated in a transfer vehicle (e.g., lipid nanoparticle). Such enhanced release may be achieved by one or both of a proton-sponge mediated disruption mechanism and/or an enhanced fusogenicity mechanism. The proton-sponge mechanism is based on the ability of a compound, and in particular a functional moiety or group of the compound, to buffer the acidification of the endosome. This may be manipulated or otherwise controlled by the pKa of the compound or of one or more of the functional groups comprising such compound (e.g., imidazole). Accordingly, in certain embodiments the fusogenicity of, for example, the imidazole-based compounds disclosed herein (e.g., HGT4001 and HGT4004) are related to the endosomal disruption properties, which are facilitated by such imidazole groups, which have a lower pKa relative to other traditional ionizable lipids. Such endosomal disruption properties in turn promote osmotic swelling and the disruption of the liposomal membrane, followed by the transfection or intracellular release of the polynucleotide materials loaded or encapsulated therein into the target cell. This phenomenon can be applicable to a variety of compounds with desirable pKa profiles in addition to an imidazole moiety. Such embodiments also include multi-nitrogen based functionalities such as polyamines, poly-peptide (histidine), and nitrogen-based dendritic structures.

Exemplary ionizable and/or cationic lipids are described in International PCT patent publications WO2015/095340, WO2015/199952, WO2018/011633, WO2017/049245, WO2016/081029, WO2015/061467, WO2012/040184, WO2012/000104, WO2015/074085, WO2017/004 143, WO2017/075531, WO2017/117528, WO2011/022460, WO2013/148541, WO2013/116126, WO2011/153120, WO2012/044638, WO2012/054365 WO2011/090965, WO2013/016058, WO2012/162210, WO2008/042973, WO2010/129709, WO2010/144740, WO20 12/099755, WO2013/049328, WO2013/086322, WO2013/086373, WO2011/071860, WO2009/132131, WO2010/048536, WO2010/088537, WO2010/054401, WO2010/054406 WO2010/054405, WO2010/054384, WO2012/016184, WO2009/086558, WO2010/042877, WO2011/000106, WO2011/000107, WO2005/120152 WO2011/141705, WO2013/126803, WO2006/007712, WO2011/038160, WO2005/121348, WO2011/066651, WO2009/127060, WO2011/141704, WO2006/069782, WO2012/031043, WO2013/006825, WO2013/033563, WO2013/089151, WO2017/099823, WO2015/095346, and WO2013/086354, and US patent publications US2016/0311759, US2015/0376115, US2016/0151284, US2017/0210697, US2015/0140070, US2013/0178541, US2013/0303587, US2015/0141678, US2015/0239926, US2016/0376224, US2017/0119904, US2012/0149894, US2015/0057373, US2013/

0090372, US2013/0274523, US2013/0274504, US2013/
0274504, US2009/0023673, US2012/0128760, US2010/
0324120, US2014/0200257, US2015/0203446, US2018/
0005363, US2014/0308304, US2013/0338210, US2012/
0101148, US2012/0027796, US2012/0058144, US2013/
0323269, US2011/0117125, US2011/0256175, US2012/
0202871, US2011/0076335, US2006/0083780, US2013/
0123338, US2015/0064242, US2006/0051405, US2013/
0065939, US2006/0008910, US2003/0022649, US2010/
0130588, US2013/0116307, US2010/0062967, US2013/
0202684, US2014/0141070, US2014/0255472, US2014/
0039032, US2018/0028664, US2016/0317458, and
US2013/0195920, the contents of all of which are incorpo-
rated herein by reference in their entirety. International
patent application WO 2019/131770 is also incorporated
herein by reference in its entirety.

b) Stabilizing Lipids (e.g., PEG Lipids)

A stabilizing lipid or surface stabilizing lipid may be used
to enhance the structure of the LNP. A stabilizing lipid as
contemplated herein may be a polyethylene glycol (PEG)-
modified phospholipid.

The use and inclusion of polyethylene glycol (PEG)-
modified phospholipids and derivatized lipids such as
derivatized ceramides (PEG-CER), including N-Octanoyl-
Sphingosine-1-[Succinyl (Methoxy Polyethylene Glycol)-
2000](C8 PEG-2000 ceramide) in the liposomal and phar-
maceutical compositions described herein is contemplated,
preferably in combination with one or more of the com-
pounds and lipids disclosed herein. Contemplated PEG-
modified lipids include, but are not limited to, a polyethyl-
ene glycol chain of up to 5 kDa in length covalently attached
to a lipid with alkyl chain(s) of C6-C20 length. In some
embodiments, the PEG-modified lipid employed in the compositions and methods described herein is 1,2-dimyris-
toyl-sn-glycerol, methoxypolyethylene Glycol (2000 MW
PEG) "DMG-PEG2000." The addition of PEG-modified
lipids to the lipid delivery vehicle may prevent complex
aggregation and may also provide a means for increasing
circulation lifetime and increasing the delivery of the lipid-
polynucleotide composition to the target tissues, (Klibanov
et al. (1990) FEBS Letters, 268 (1): 235-237), or they may
be selected to rapidly exchange out of the formulation in
vivo (see U.S. Pat. No. 5,885,613). Particularly useful
exchangeable lipids are PEG-ceramides having shorter acyl
chains (e.g., C14 or C18). The PEG-modified phospholipid
and derivatized lipids may comprise a molar ratio from
about 0% to about 20%, about 0.5% to about 20%, about 1%
to about 15%, about 4% to about 10%, or about 2% of the
total lipid present in a liposomal lipid nanoparticle.

In some embodiments, the lipid moiety of the PEG-lipids
includes those having lengths of from about C14 to about
C22, such as from about C14 to about C16. In some
embodiments, a PEG moiety, for example a mPEG-NH2,
has a size of about 1000, about 2000, about 5000, about
10,000, about 15,000 or about 20,000 daltons In an embodiment, a PEG-modified lipid is described in
International Pat. Appl. No. PCT/US2019/015913, which is
incorporated herein by reference in their entirety. In an
embodiment, a transfer vehicle comprises one or more
PEG-modified lipids.

Non-limiting examples of PEG-modified lipids include
PEG-modified phosphatidylethanolamines and phosphatidic
acids, PEG-ceramide conjugates (e.g., PEG-CerC14 or
PEG-CerC20), PEG-modified dialkylamines and PEG-
modified 1,2-diacyloxypropan-3-amines, PEG-modified
diacylglycerols, PEG-modified dialkylglycerols, and mix-
tures thereof. In some further embodiments, a PEG-modified
lipid may be, e.g., PEG-c-DOMG, PEG-DMG, PEG-DLPE,
PEG-DMPE, PEG-DPPC, PEG-DSPE, PEG-DAG, PEG-S-
DAG, PEG-PE, PEG-S-DMG, PEG-CER, PEG-dialkoxy-
propylcarbamate, PEG-OR, PEG-OH, PEG-c-DOMG, or
PEG-1.

In some still further embodiments, the PEG-modified
lipid includes, but is not limited to 1,2-dimyristoyl-sn-
glycerol methoxypolyethylene glycol (PEG-DMG), 1,2-dis-
tearoyl-sn-glycero-3-phosphoethanolamine-N-[amino(poly-
ethylene glycol)](PEG-DSPE), PEG-disteryl glycerol (PEG-
DSG), PEG-dipalmetoleyl, PEG-dioleyl, PEG-distearyl,
PEG-diacylglycamide (PEG-DAG), PEG-dipalmitoyl phos-
phatidylethanolamine (PEG-DPPE), or PEG-1,2-dimyristy-
loxlpropyl-3-amine (PEG-c-DMA).

In one embodiment, the lipid nanoparticles described
herein can comprise a lipid modified with a non-diffusible
PEG. Non-limiting examples of non-diffusible PEGs include
PEG-DSG and PEG-DSPE. In one embodiment, the lipid
nanoparticles herein comprise PEG-DSPC.

In some embodiments the PEG-modified lipids are a
modified form of PEG-DMG. PEG-DMG has the following
structure:

In some embodiments, the PEG lipid is a compound of
Formula (PI):

or a salt or isomer thereof, wherein:

r is an integer between 1 and 100;

R is C10-40 alkyl, C10-40 alkenyl, or C10-40 alkynyl;
and optionally one or more methylene groups of R are
independently replaced with C3-10 carbocyclylene, 4
to 10 membered heterocyclylene, C6-10 arylene, 4 to
10 membered heteroarylene, —N(RN)—, —O—,
—S—, —C(O)—, —C(O)N(RN)—, —NRNC(O)—,
—NRNC(O)N(RN)—, —C(O)O—, —OC(O)—,
—OC(O)O—, —OC(O)N(RN)—, —NRNC(O)O—,
—C(O)S—, —SC (O)—, —C(═NRN)—,
—C(═NRN)N(RN)—, —NRNC(═NRN)—,
—NRNC(═NRN)N(RN)—, —C(S)—, —C(S)N —(RN)—, —NRNC(S)—, —NRNC(S)N(RN)—, —S(O)—, —OS (O)—, —S(O)O—, —OS (O)O—, —OS(O)2-, —S(O)2O—, —OS(O)2O—, —N(RN)S (O)—, —S(O)N(RN)—, —N(RN)S(O)N(RN)—, —OS (O)N(RN)—, —N (RN)S(O)O—, —S(O)2-, —N(RN)S(O)2-, —S(O)2N(RN)—, —N(RN)S(O)2N (RN)—, —OS(O)2N(RN)—, or —N(RN)S(O)2O—; and each instance of RN is independently hydrogen, C1-6 alkyl, or a nitrogen protecting group.

For example, R is C17 alkyl. For example, the PEG lipid is a compound of Formula (P1-a):

or a salt or isomer thereof, wherein r is an integer between 1 and 100.

In some embodiments the PEG-modified lipids are a modified form of PEG-C18, or PEG-1. PEG-1 has the following structure:

PEG-lipids are known in the art, such as those described in U.S. Pat. No. 8,158,601 and International Pat. Publ. No. WO2015/130584 A2, which are incorporated herein by reference in their entirety. In one embodiment, PEG lipids can be PEGylated lipids described in International Publication No. WO2012099755, the contents of which is herein incorporated by reference in its entirety. Any of these exemplary PEG lipids described herein may be modified to comprise a hydroxyl group on the PEG chain. In certain embodiments, the PEG lipid is a PEG-OH lipid. In certain embodiments, the PEG-OH lipid includes one or more hydroxyl groups on the PEG chain. In certain embodiments, a PEG-OH or hydroxy-PEGylated lipid comprises an —OH group at the terminus of the PEG chain. Each possibility represents a separate embodiment.

c) Helper Lipids

In some embodiments, the transfer vehicle (e.g., LNP) described herein comprises one or more non-cationic helper lipids. In some embodiments, the helper lipid is a phospholipid. In some embodiments, the helper lipid is a phospholipid substitute or replacement. In some embodiments, the phospholipid or phospholipid substitute can be, for example, one or more saturated or (poly) unsaturated phospholipids, or phospholipid substitutes, or a combination thereof. In general, phospholipids comprise a phospholipid moiety and one or more fatty acid moieties.

A phospholipid moiety can be selected, for example, from the non-limiting group consisting of phosphatidyl choline, phosphatidyl ethanolamine, phosphatidyl glycerol, phosphatidyl serine, phosphatidic acid, 2-lysophosphatidyl choline, and a sphingomyelin.

A fatty acid moiety can be selected, for example, from the non-limiting group consisting of lauric acid, myristic acid, myristoleic acid, palmitic acid, palmitoleic acid, stearic acid, oleic acid, linoleic acid, alpha-linolenic acid, erucic acid, phytanoic acid, arachidic acid, arachidonic acid, eicosapentaenoic acid, behenic acid, docosapentaenoic acid, and docosahexaenoic acid.

Phospholipids include, but are not limited to, glycerophospholipids such as phosphatidylcholines, phosphatidylethanolamines, phosphatidylserines, phosphatidylinositols, phosphatidy glycerols, and phosphatidic acids. Phospholipids also include phosphosphingolipid, such as sphingomyelin.

In some embodiments, the helper lipid is a 1,2-distearoyl-177-glycero-3-phosphocholine (DSPC) analog, a DSPC substitute, oleic acid, or an oleic acid analog.

In some embodiments, a helper lipid is a non-phosphatidyl choline (PC) zwitterionic lipid, a DSPC analog, oleic acid, an oleic acid analog, or a DSPC substitute.

In some embodiments, a helper lipid is described in PCT/US2018/053569. Helper lipids suitable for use in a lipid composition of the disclosure include, for example, a variety of neutral, uncharged or zwitterionic lipids. Such helper lipids are preferably used in combination with one or more of the compounds and lipids disclosed herein. Examples of helper lipids include, but are not limited to, 5-heptadecylbenzene-1,3-diol (resorcinol), dipalmitoylphosphatidylcholine (DPPC), distearoylphosphatidylcholine (DSPC), pohsphocholine (DOPC), dimyristoylphosphatidylcholine (DMPC), phosphatidylcholine (PLPC), 1,2-distearoylsn-glycero-3-phosphocholine (DAPC), phosphatidylethanolamine (PE), egg phosphatidylcholine (EPC), dilauryloylphosphatidylcholine (DLPC), dimyristoylphosphatidylcholine (DMPC), 1-myristoyl-2-palmitoyl phosphatidylcholine (MPPC), 1-paimitoyl-2-myristoyl phosphatidylcholine (PMPC), 1-palmitoyl-2-stearoyl phosphatidylcholine (PSPC), 1,2-diarachidoyl-sn-glycero-3-phosphocholine (DBPC), 1-stearoyl-2-palmitoyl phosphatidylcholine (SPPC), 1,2-dieicosenoyl-sn-glycero-3-phosphocholine (DEPC), paimitoyioieoyl phosphatidylcholine (POPC), lysophosphatidyl choline, dioleoyl phosphatidylethanol amine (DOPE)dilinoleoylphosphatidylcholine distearoylphosphatidylethanolamine (DSPE), dimyristoyl phosphatidylethanolamine (DMPE), dipalmitoyl phosphatidylethanolamine (DPPE), palmitoyloleoyl phosphatidylethanolamine (POPE), lysophosphatidylethanolamine and combinations thereof. In one embodiment, the helper lipid may be distearoylphosphatidylcholine (DSPC) or dimyristoyl phosphatidyl ethanolamine (DMPE). In another embodiment, the helper lipid may be distearoylphosphatidylcholine (DSPC). Helper lipids function to stabilize and improve processing of the transfer vehicles. Such helper lipids are preferably used in combination with other excipients, for example, one or more of the ionizable lipids disclosed herein. In some embodiments, when used in combination with an ionizable lipid, the helper lipid may comprise a molar ratio of 5% to about 90%, or about 10% to about 70% of the total lipid present in the lipid nanoparticle.

d) Structural Lipids

The transfer vehicles described herein comprise one or more structural lipids. Incorporation of structural lipids in the lipid nanoparticle may help mitigate aggregation of other lipids in the particle. Structural lipids can include, but are not limited to, cholesterol, fecosterol, ergosterol, bassicasterol, tomatidine, tomatine, ursolic, alpha-tocopherol, and mixtures thereof. In certain embodiments, the structural lipid is cholesterol. In certain embodiments, the structural lipid is an analog of cholesterol. In certain embodiments, the structural lipid includes cholesterol and a corticosteroid (such as, for example, prednisolone, dexamethasone, prednisone, and hydrocortisone), or a combination thereof.

In an embodiment, a structural lipid is described in international patent application PCT/US2019/015913.

In some embodiments, the structural lipid is a sterol (e.g., phytosterols or zoosterols). In certain embodiments, the structural lipid is a steroid. For example, sterols can include, but are not limited to, cholesterol, β-sitosterol, fecosterol, ergosterol, sitosterol, campesterol, stigmasterol, brassicasterol, ergosterol, tomatidine, tomatine, ursolic acid, or alpha-tocopherol. In certain embodiments, the structural lipid is cholesterol. In certain embodiments, the structural lipid is an analog of cholesterol. In certain embodiments, the structural lipid is alpha-tocopherol.

The transfer vehicles described herein comprise one or more structural lipids. Incorporation of structural lipids in a transfer vehicle, e.g., a lipid nanoparticle, may help mitigate aggregation of other lipids in the particle. In certain embodiments, the structural lipid includes cholesterol and a corticosteroid (such as, for example, prednisolone, dexamethasone, prednisone, and hydrocortisone), or a combination thereof.

In some embodiments, a transfer vehicle includes an effective amount of an immune cell delivery potentiating lipid, e.g., a cholesterol analog or an amino lipid or combination thereof, that, when present in a transfer vehicle, e.g., an lipid nanoparticle, may function by enhancing cellular association and/or uptake, internalization, intracellular trafficking and/or processing, and/or endosomal escape and/or may enhance recognition by and/or binding to immune cells, relative to a transfer vehicle lacking the immune cell delivery potentiating lipid. Accordingly, while not intending to be bound by any particular mechanism or theory, in one embodiment, a structural lipid or other immune cell delivery potentiating lipid of the disclosure binds to C1q or promotes the binding of a transfer vehicle comprising such lipid to C1q. Thus, for in vitro use of the transfer vehicles of the disclosure for delivery of a nucleic acid molecule to an immune cell, culture conditions that include C1q are used (e.g., use of culture media that includes serum or addition of exogenous C1q to serum-free media). For in vivo use of the transfer vehicles of the disclosure, the requirement for C1q is supplied by endogenous C1q.

In certain embodiments, the structural lipid is cholesterol. In certain embodiments, the structural lipid is an analog of cholesterol.

2. Other Delivery Vehicles Known in the Art

In certain embodiments, other delivery vehicles that are known in the art may be used to transport the circular RNA (i.e., are transfer vehicles encompassed herein).

In some embodiments, liposomes or other lipid bilayer vesicles may be used as a component or as the whole transfer vehicle to facilitate or enhance the delivery and release of circular RAN to one or more target cells. Liposomes are usually characterized by having an interior space sequestered from an outer medium by a membrane of one or more bilayers forming a microscopic sack or vesicle. Bilayer membranes of liposomes are typically formed by lipids, i.e., amphiphilic molecules of synthetic or natural origin that comprise spatially separated hydrophobic or hydrophilic domains (Lasic, D, and Papahadjopoulos, D., eds. Medical Applications of Liposomes. Elsevier, Amsterdam, 1998).

In certain embodiments, the transfer vehicle for transporting the circular RNA comprises a dendrimer. Use of "dendrimer" describes the architectural motif of the transfer vehicle. In some embodiments, the dendrimer includes but is not limited to containing an interior core and one or more layers (i.e., generations) that extend or attach out from the interior core. In some of the embodiments, the generations may contain one or more branching points and an exterior surface of terminal groups that attach to the outermost generation. The branching points, in certain embodiments, may be mostly monodispersed and contain symmetric branching units built around the interior core. In some embodiments, the interior core. Synthesis of the dendrimer may comprise the divergent method, convergent growth, hypercore and branched monomer growth, double exponential growth, lego chemistry, click chemistry and other methods as available in the art (Mendes L. et al., Molecules. 2017. 22 (9): 1401 further describes these methods).

In certain embodiments, as described herein, the transfer vehicle for the circular RNA construct comprises a polymer nanoparticle. In some embodiments, the polymer nanoparticle includes nanocapsules and nanospheres. Nanocapsules, in some embodiments, are composed of an oily core surrounded by a polymeric shell. In some embodiments, the circular RNA is contained within the core and the polymeric shell controls the release of the circular RNA. On the other hand, nanospheres comprise a continuous polymeric network in which the circular RNA is retained or absorbed onto the surface. In some embodiments, cationic polymers are used to encapsulate the circular RNA due to the favorable electrostatic interaction of the cations to the negatively charged nucleic acids and cell membrane. The polymer nanoparticle may be prepared by various methods. In some embodiments, the polymer nanoparticle may be prepared by nanoprecipitation, emulsion techniques, solvent evaporation, solvent diffusion, reverse salting-out or other methods available in the art.

In certain embodiments, as described herein, the transfer vehicle for the circular RNA construct comprises a polymer-lipid hybrid nanoparticle (LPHNP). In some embodiments, the LPHNP comprises a polymer core enveloped within a lipid bilayer. In some embodiments, the polymer core encapsulates the circular RNA construct. In some embodiments, the LPHNP further comprises an outer lipid bilayer. In certain embodiments this outer lipid bilayer comprises a PEG-lipid, helper lipid, cholesterol or other molecule as known in the art to help with stability in a lipid-based nanoparticle. The lipid bilayer closest to the polymer core mitigates the loss of the entrapped circular RNA during LPHNP formation and protects from degradation of the polymer core by preventing diffusion of water from outside of the transfer vehicle into the polymer core (Mukherjee et al., In J. Nanomedicine. 2019; 14: 1937-1952).

In certain embodiments, the circular RNA can be transported using a peptide-based delivery mechanism. In some embodiments, the peptide-based delivery mechanism comprises a lipoprotein. Based on the size of the drug to be delivered, the lipoprotein may be either a low-density (LDL) or high-density lipoprotein (HDL). As seen in U.S. Pat. No. 8,734,853B2, high-density lipoproteins are capable of transporting a nucleic acid in vivo and in vitro. In particular embodiments, the lipid component includes cholesterol. In more particular embodiments, the lipid component includes a combination of cholesterol and cholesterol oleate.

In certain embodiments, the circular RNA construct can be transported using a carbohydrate carrier or a sugar-nanocapsule. In certain embodiments, the carbohydrate carrier comprises a sugar-decorated nanoparticle, peptide- and saccharide-conjugated dendrimer, nanoparticles based on polysaccharides, and other carbohydrate-based carriers available in the art. As described herein, the incorporation of carbohydrate molecules may be through synthetic means. In some embodiments, the carbohydrate carrier comprises polysaccharides. These polysaccharides may be made from the microbial cell wall of the target cell. For example, carbohydrate carriers comprised of mannan carbohydrates have been shown to successfully deliver mRNA (Son et al., Nano Lett. 2020. 20 (3): 1499-1509).

In certain embodiments, as provided herein, the transfer vehicle for the circular RNA is a glyconanoparticle (Gly-coNP). As known in the art, glyconanoparticles comprise a core comprising gold, iron oxide, semiconductor nanoparticles or a combination thereof. In some embodiments, the glyconanoparticle is functionalized using carbohydrates. In certain embodiments, the glyconanoparticle comprises a carbon nanotube or graphene. In one embodiment the glyconanoparticle comprises a polysaccharide-based GlycoNP (e.g., chitosan-based GlycoNP). In certain embodiments, the glyconanoparticle is a glycodendrimer.

In certain embodiments, as provided herein, the circular RNA is transferred through use of an exosome, a type of extracellular vesicle. Exosomes naturally are secreted by various types of cells and are used as a transport vesicle for various forms of cargo. During delivery exosomes can contain and protect specific mRNAs, regulatory microR-NAs, lipids, and proteins (Luan et al., Acta Pharmacologica Sinica. 2017. 38:754-763). Naturally, exosomes may be 30 nm to 125 nm.

In some embodiments, the exosome may be made in part from an immune cell. As shown in Haney et al, use of immune cell derived exosomes are able to avoid mononuclear phagocytes (J Control Release. 2015. 207:18-30). In some embodiments, the exosome may be a dendritic cell, macrophage, T-cell, B-cell or derived from another immune cell. As seen in WO/2021/041473A1, various forms of RNAs of varying lengths may be transported through exosome delivery including messenger RNA (mRNA), microRNA (miRNA), long intergenic non-coding RNA (lincRNA), long non-coding RNA (lncRNA), non-coding RNA (ncRNA), non-messenger RNA (nmRNA), small RNA (sRNA), small non-messenger RNA (smnRNA), DNA damage response RNA (DD RNA), extracellular RNA (exRNA), small nuclear RNA (snRNA), small nucleolar RNA (snoRNA), and precursor messenger RNA (pre-mRNA).

In other embodiments, the transfer vehicle may comprise in whole or in part from a fusome. In some embodiments, the fusome is derived from an endoplasmic reticulum of a germline cyst. In certain embodiments, the germline cyst is from a *Drosophila* ovary.

In certain embodiments, the circular RNA construct may be transported using noncellular and instead be through mechanical delivery mechanisms. In some embodiments, this delivery method includes microneedles, electroporation, continuous pumps and/or gene guns.

In some embodiments, the transfer vehicle of the circular RNA construct is a solution or diluent comprising of a salt or a buffer.

3. Targeting

In some embodiments, the compositions use targeting moieties that may be bound (either covalently or non-covalently) to the transfer vehicle to encourage localization of such transfer vehicle at certain target cells or target tissues. For example, targeting may be mediated by the inclusion of one or more endogenous targeting moieties in or on the transfer vehicle to encourage distribution to the target cells or tissues. Recognition of the targeting moiety by the target tissues actively facilitates tissue distribution and cellular uptake of the transfer vehicle and/or its contents in the target cells and tissues (e.g., the inclusion of an apolipoprotein-E targeting ligand in or on the transfer vehicle encourages recognition and binding of the transfer vehicle to endogenous low density lipoprotein receptors expressed by hepatocytes).

As provided herein, the composition can comprise a moiety capable of enhancing affinity of the composition to the target cell. Targeting moieties may be linked to the outer bilayer of the lipid particle during formulation or post-formulation. These methods are well known in the art. In addition, some lipid particle formulations may employ fusogenic polymers such as PEAA, hemagluttinin, other lipopeptides (see U.S. patent application Ser. No. 08/835,281, and 60/083,294, which are incorporated herein by reference) and other features useful for in vivo and/or intracellular delivery. In other some embodiments, the compositions demonstrate improved transfection efficacies, and/or demonstrate enhanced selectivity towards target cells or tissues of interest. Contemplated therefore are compositions which comprise one or more moieties (e.g., peptides, aptamers, oligonucleotides, a vitamin or other molecules) that are capable of enhancing the affinity of the compositions and their nucleic acid contents for the target cells or tissues. Suitable moieties may optionally be bound or linked to the surface of the transfer vehicle. In some embodiments, the targeting moiety may span the surface of a transfer vehicle or be encapsulated within the transfer vehicle. Suitable moieties and are selected based upon their physical, chemical or biological properties (e.g., selective affinity and/or recognition of target cell surface markers or features). Cell-specific target sites and their corresponding targeting ligand can vary widely. Suitable targeting moieties are selected such that the unique characteristics of a target cell are exploited, thus allowing the composition to discriminate between target and non-target cells. For example, in some embodiments, compositions may include surface markers (e.g., apolipoprotein-B or apolipoprotein-E) that selectively enhance recognition of, or affinity to hepatocytes (e.g., by receptor-mediated recognition of and binding to such surface markers). As an example, the use of galactose as a targeting moiety would be expected to direct the compositions to parenchymal hepatocytes, or alternatively the use of mannose containing sugar residues as a targeting ligand would be expected to direct the compositions to liver endothelial cells (e.g., mannose containing sugar residues that may bind preferentially to the asialoglycoprotein receptor present in hepatocytes). (See Hillery A M, et al. "Drug Delivery and Targeting: For Pharmacists and Pharmaceutical Scientists" (2002) Taylor & Francis, Inc.) The presentation of such targeting moieties that have been conjugated to moieties present in the transfer vehicle (e.g., a lipid nanoparticle) therefore facilitate recognition and uptake of the compositions in target cells and tissues. Examples of suitable targeting moieties include one or more peptides, proteins, aptamers, vitamins and oligonucleotides.

In particular embodiments, a transfer vehicle comprises a targeting moiety. In some embodiments, the targeting moiety mediates receptor-mediated endocytosis selectively into a specific population of cells. In some embodiments, the targeting moiety is capable of binding to a T cell antigen. In some embodiments, the targeting moiety is capable of binding to a NK, NKT, or macrophage antigen. In some embodiments, the targeting moiety is capable of binding to a protein selected from the group CD3, CD4, CD8, PD-1, 4-1BB, and CD2. In some embodiments, the targeting moiety is a single chain Fv(scFv) fragment, nanobody, peptide, peptide-based macrocycle, minibody, heavy chain variable region, light chain variable region or fragment thereof. In some embodiments, the targeting moiety is selected from T-cell receptor motif antibodies, T-cell a chain antibodies, T-cell β chain antibodies, T-cell γ chain antibodies, T-cell δ chain antibodies, CCR7 antibodies, CD3 antibodies, CD4 antibodies, CD5 antibodies, CD7 antibodies, CD8 antibodies, CD11b antibodies, CD11c antibodies, CD16 antibodies, CD19 antibodies, CD20 antibodies, CD21 antibodies, CD22 antibodies, CD25 antibodies, CD28 antibodies, CD34 antibodies, CD35 antibodies, CD40 antibodies, CD45RA antibodies, CD45RO antibodies, CD52 antibodies, CD56 antibodies, CD62L antibodies, CD68 antibodies, CD80 antibodies, CD95 antibodies, CD117 antibodies, CD127 antibodies, CD133 antibodies, CD137 (4-1BB) antibodies, CD163 antibodies, F4/80 antibodies, IL-4Rα antibodies, Sca-1 antibodies, CTLA-4 antibodies, GITR antibodies GARP antibodies, LAP antibodies, granzyme B antibodies, LFA-1 antibodies, transferrin receptor antibodies, and fragments thereof. In some embodiments, the targeting moiety is a small molecule binder of an ectoenzyme on lymphocytes. Small molecule binders of ectoenzymes include A2A inhibitors CD73 inhibitors, CD39 or adesines receptors A2aR and A2bR. Potential small molecules include AB928.

In some embodiments, transfer vehicles are formulated and/or targeted as described in Shobaki N, Sato Y, Harashima H. Mixing lipids to manipulate the ionization status of lipid nanoparticles for specific tissue targeting. Int J Nanomedicine. 2018; 13:8395-8410. Published 2018 Dec. 10. In some embodiments, a transfer vehicle is made up of 3 lipid types. In some embodiments, a transfer vehicle is made up of 4 lipid types. In some embodiments, a transfer vehicle is made up of 5 lipid types. In some embodiments, a transfer vehicle is made up of 6 lipid types.

F. Pharmaceutical Compositions

Provided herein is a pharmaceutical composition comprising at least one circular RNA construct and a transfer vehicle. Also provided herein is a pharmaceutical composition comprising at least one circular RNA construct described herein and a pharmaceutically acceptable excipient. In some embodiments, and as described elsewhere herein, the pharmaceutical composition comprises at least one circular RNA construct and a transfer vehicle comprising an ionizable lipid. In some embodiments, the pharmaceutical composition comprises at least one circular RNA construct and a transfer vehicle, where the transfer vehicle is a nanoparticle or lipid nanoparticle.

In some embodiments, the pharmaceutical composition comprises at least one circular RNA construct, a nanoparticle, and optionally, a targeting moiety operably connected to the nanoparticle. In some embodiments, the nanoparticle is a lipid nanoparticle (LNP), a core-shell nanoparticle, a biodegradable nanoparticle, a biodegradable lipid nanoparticle, a polymer nanoparticle, a polyplex or a biodegradable polymer nanoparticle. In some embodiments, the pharmaceutical composition comprises a targeting moiety, wherein the targeting moiety mediates receptor-mediated endocytosis, endosome fusion, or direct fusion into selected cells of a selected cell population or tissue in the absence of cell isolation or purification. In some embodiments, the pharmaceutical composition comprises a targeting moiety operably connected to the nanoparticle. In some embodiments, the targeting moiety is a small molecule, scFv, nanobody, peptide, cyclic peptide, di or tri cyclic peptide, minibody, polynucleotide aptamer, engineered scaffold protein, heavy chain variable region, light chain variable region, or a fragment thereof. In some embodiments, less than 1%, by weight, of the polynucleotides in the composition are double stranded RNA, DNA splints, DNA template, or triphosphorylated RNA. In some embodiments, less than 1%, by weight, of the polynucleotides and proteins in the pharmaceutical composition are double stranded RNA, DNA splints, DNA template, triphosphorylated RNA, phosphatase proteins, protein ligases, RNA polymerases, and capping enzymes.

Also provided herein is a pharmaceutical composition comprising a circular RNA construct and a pharmaceutical salt, buffer, diluent or combination thereof.

In certain embodiments, provided herein are compositions (e.g., pharmaceutical compositions) comprising a therapeutic agent provided herein. In some embodiments, the therapeutic agent is a circular RNA polynucleotide provided herein. In some embodiments the therapeutic agent is a vector provided herein. In some embodiments, the therapeutic agent is a cell comprising a circular RNA or vector provided herein (e.g., a human cell, such as a human T cell). In certain embodiments, the composition further comprises a pharmaceutically acceptable carrier. In some embodiments, the compositions provided herein comprise a therapeutic agent provided herein in combination with other pharmaceutically active agents or drugs, such as anti-inflammatory drugs or antibodies capable of targeting B cell antigens, e.g., anti-CD20 antibodies, e.g., rituximab.

With respect to pharmaceutical compositions, the pharmaceutically acceptable carrier can be any of those conventionally used and is limited only by chemico-physical considerations, such as solubility and lack of reactivity with the active agent(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the therapeutic agent(s) and one which has no detrimental side effects or toxicity under the conditions of use.

The choice of carrier will be determined in part by the particular therapeutic agent, as well as by the particular method used to administer the therapeutic agent. Accordingly, there are a variety of suitable formulations of the pharmaceutical compositions known in the art. In certain embodiments, the pharmaceutical composition comprises a preservative. In some embodiments, the pharmaceutical composition comprises a buffering agent.

In some embodiments, the concentration of therapeutic agent in the pharmaceutical composition can vary, e.g., less than about 1%, or at least about 1%, 2%, 3%, 4%, 5%, 6%, 7%, 8%, 9% 10%, 15%, 20%, 25%, 30%, 35%, 40%, 45%, or about 50% or more by weight, and can be selected primarily by fluid volumes, and viscosities, in accordance with the particular mode of administration selected.

Formulations for oral, aerosol, parenteral (e.g., subcutaneous, intravenous, intraarterial, intramuscular, intradermal, intraperitoneal, and intrathecal), and topical administration are known in the art. More than one route can be used to administer the therapeutic agents provided herein, and in certain instances, a particular route can provide a more immediate and more effective response than another route.

In certain embodiments, the therapeutic agents provided herein can be formulated as inclusion complexes, such as cyclodextrin inclusion complexes, or LNPs or liposomes.

In some embodiments, the therapeutic agents provided herein are formulated in time-released, delayed release, or sustained release delivery systems such that the delivery of the composition occurs prior to, and with sufficient time to, cause sensitization of the site to be treated. Such systems can avoid repeated administrations of the therapeutic agent, thereby increasing convenience to the subject and the physician, and may be particularly suitable for certain composition embodiments provided herein. In one embodiment, the compositions are formulated such that they are suitable for extended-release of the circular RNA contained therein. Such extended-release compositions may be conveniently administered to a subject at extended dosing intervals. For example, in one embodiment, the compositions are administered to a subject twice a day, daily or every other day. In an embodiment, the compositions are administered to a subject twice a week, once a week, every ten days, every two weeks, every three weeks, every four weeks, once a month, every six weeks, every eight weeks, every three months, every four months, every six months, every eight months, every nine months or annually.

In some embodiments, a protein encoded by an inventive polynucleotide is produced by a target cell for sustained amounts of time. For example, the protein may be produced for more than one hour, more than four, more than six, more than 12, more than 24, more than 48 hours, or more than 72 hours after administration. In some embodiments the polypeptide is expressed at a peak level about six hours after administration. In some embodiments the expression of the polypeptide is sustained at least at a therapeutic level. In some embodiments, the polypeptide is expressed at least at a therapeutic level for more than one, more than four, more than six, more than 12, more than 24, more than 48, or more than 72 hours after administration. In some embodiments, the polypeptide is detectable at a therapeutic level in patient tissue (e.g., liver or lung). In some embodiments, the level of detectable polypeptide is from continuous expression from the circular RNA composition over periods of time of more than one, more than four, more than six, more than 12, more than 24, more than 48, or more than 72 hours after administration.

In some embodiments, the circular RNA constructs disclosed herein (optionally with the transfer vehicles disclosed herein) are administered to a subject twice a day, daily or every other day. In an embodiment, the compositions are administered to a subject twice a week, once a week, every ten days, every two weeks, every three weeks, every four weeks, once a month, every six weeks, every eight weeks, every three months, every four months, every six months, every eight months, every nine months or annually.

In some embodiments, the circular RNA constructs disclosed herein (optionally with the transfer vehicles disclosed herein) are administered every other day. In some embodiments, the circular RNA constructs disclosed herein (optionally with the transfer vehicles disclosed herein) are administered once a week (i.e., weekly). In some embodiments, the circular RNA constructs disclosed herein (optionally with the transfer vehicles disclosed herein) are administered every two weeks (i.e., every other week or biweekly, q2w). In some embodiments, administration of the circular RNA constructs disclosed herein (optionally with the transfer vehicles disclosed herein) occurs less frequently and/or at a lower dose than as required for a suitable comparator, for example, a corresponding linear RNA.

In certain embodiments, a protein encoded by an inventive polynucleotide is produced at levels above normal physiological levels. The level of protein may be increased as compared to a control. In some embodiments, the control is the baseline physiological level of the polypeptide in a normal individual or in a population of normal individuals. In other embodiments, the control is the baseline physiological level of the polypeptide in an individual having a deficiency in the relevant protein or polypeptide or in a population of individuals having a deficiency in the relevant protein or polypeptide. In some embodiments, the control can be the normal level of the relevant protein or polypeptide in the individual to whom the composition is administered. In other embodiments, the control is the expression level of the polypeptide upon other therapeutic intervention, e.g., upon direct injection of the corresponding polypeptide, at one or more comparable time points.

In certain embodiments, the levels of a protein encoded by an inventive polynucleotide are detectable at 3 days, 4 days, 5 days, or 1 week or more after administration. Increased levels of protein may be observed in a tissue (e.g., liver or lung).

In some embodiments, the method yields a sustained circulation half-life of a protein encoded by an inventive polynucleotide. For example, the protein may be detected for hours or days longer than the half-life observed via subcutaneous injection of the protein or mRNA encoding the protein. In some embodiments, the half-life of the protein is 1 day, 2 days, 3 days, 4 days, 5 days, or 1 week or more.

Different types of release delivery systems are available for the compositions and known to those of ordinary skill in the art.

In certain embodiments, the compositions may be loaded with diagnostic radionuclide, fluorescent materials or other materials that are detectable in both in vitro and in vivo applications. For example, suitable diagnostic materials may include Rhodamine-dioleoylphosphatidylethanolamine (Rh-PE), Green Fluorescent Protein circRNA (GFP circRNA), *Renilla* Luciferase circRNA and Firefly Luciferase circRNA.

I. Methods

A. Method of Preparing

1. Precursor RNA Preparation

Transcription of a DNA template (e.g., comprising a 3' enhanced intron element, 3' enhanced exon element, a core functional element including an IRES and expression sequence, a 5' enhanced exon element, and a 5' enhanced intron element) results in formation of a precursor linear RNA polynucleotide capable of circularizing. In some embodiments, this DNA template comprises a vector, PCR product, plasmid, minicircle DNA, cosmid, artificial chromosome, complementary DNA (cDNA), extrachromosomal DNA (ecDNA), or a fragment therein. In certain embodiments, the minicircle DNA may be linearized or non-linearized. In certain embodiments, the plasmid may be linearized or non-linearized. In some embodiments, the DNA template may be single-stranded. In other embodiments, the DNA template may be double-stranded. In some embodiments, the DNA template comprises in whole or in part from a viral, bacterial or eukaryotic vector.

In some embodiments, the DNA template shares the same sequence as the precursor linear RNA polynucleotide prior to splicing of the precursor linear RNA polynucleotide (e.g., a 3' enhanced intron element, a 3' enhanced exon element, a core functional element, and a 5' enhanced exon element, a 5' enhanced intron element). In some embodiments, said linear precursor RNA polynucleotide undergoes splicing leading to the removal of the 3' enhanced intron element and 5' enhanced intron element during the process of circular- ization. In some embodiments, the resulting circular RNA polynucleotide lacks a 3' enhanced intron fragment and a 5' enhanced intron fragment, but maintains a 3' enhanced exon fragment, a core functional element, and a 5' enhanced exon element.

In some embodiments, the precursor linear RNA poly- nucleotide circularizes when incubated in the presence of one or more guanosine nucleotides or nucleoside (e.g., GTP) and a divalent cation (e.g., Mg2+). In some embodiments, the 3' enhanced exon element, 5' enhanced exon element, and/or core functional element in whole or in part promotes the circularization of the precursor linear RNA polynucle- otide to form the circular RNA construct provided herein.

In certain embodiments, circular RNA provided herein is produced inside a cell. In some embodiments, precursor RNA is transcribed using a DNA template (e.g., in some embodiments, using a vector provided herein) in the cyto- plasm by a bacteriophage RNA polymerase, or in the nucleus by host RNA polymerase II and then circularized.

The precursor RNA provided herein can be generated by incubating a DNA template provided herein under condi- tions permissive of transcription of the precursor RNA encoded by the DNA template. For example, in some embodiments a precursor RNA is synthesized by incubating a DNA template provided herein that comprises an RNA polymerase promoter upstream of its 5' duplex sequence and/or expression sequences with a compatible RNA poly- merase enzyme under conditions permissive of in vitro transcription. In some embodiments, the DNA template is incubated inside of a cell by a bacteriophage RNA poly- merase or in the nucleus of a cell by host RNA polymerase II.

In certain embodiments, provided herein is a method of generating precursor RNA by performing in vitro transcrip- tion using a DNA template provided herein as a template (e.g., a vector provided herein with an RNA polymerase promoter positioned upstream of the 5' duplex region).

In certain embodiments, the resulting precursor RNA can be used to generate circular RNA (e.g., a circular RNA construct provided herein) by incubating it in the presence of magnesium ions and guanosine nucleotide or nucleoside at a temperature at which RNA circularization occurs (e.g., between 20° C. and 60° C.). Precursor RNA are generally described in WO2022/261490, which is incorporated herein by reference in its entirety.

2. Circular RNA Preparation

Also provided herein is a method for preparing or gen- erating circular RNA. In certain embodiments, the method comprises synthesizing precursor RNA by transcription (e.g., run-off transcription) using a vector as a template, and incubating the resulting precursor RNA in the presence of divalent cations (e.g., magnesium ions) and GTP such that it circularizes to form circular RNA. In some embodiments, an inventive precursor RNA is capable of circularizing in the absence of magnesium ions and GTP and/or without the step of incubation with magnesium ions and GTP. In some embodiments, transcription is carried out in the presence of an excess of GMP.

Thus, in certain embodiments provided herein is a method of making circular RNA. In certain embodiments, the method comprises synthesizing precursor RNA by transcrip- tion (e.g., run-off transcription) using a vector provided herein (e.g., a 5' enhanced intron element, a 5' enhanced exon element, a core functional element, a 3' enhanced exon element, and a 3' enhanced intron element) as a template, and incubating the resulting precursor RNA in the presence of divalent cations (e.g., magnesium ions) and GTP such that it circularizes to form circular RNA. In some embodiments, the precursor RNA disclosed herein is capable of circular- izing in the absence of magnesium ions and GTP and/or without the step of incubation with magnesium ions and GTP. It has been discovered that circular RNA has reduced immunogenicity relative to a corresponding mRNA, at least partially because the mRNA contains an immunogenic 5' cap. When transcribing a DNA vector from certain promot- ers (e.g., a T7 promoter) to produce a precursor RNA, it is understood that the 5' end of the precursor RNA is G. To reduce the immunogenicity of a circular RNA composition that contains a low level of contaminant linear mRNA, an excess of GMP relative to GTP can be provided during transcription such that most transcripts contain a 5' GMP, which cannot be capped. Therefore, in some embodiments, transcription is carried out in the presence of an excess of GMP. In some embodiments, transcription is carried out where the ratio of GMP concentration to GTP concentration is within the range of about 3:1 to about 15:1, for example, about 3:1 to about 10:1, about 3:1 to about 5:1, about 3:1, about 4:1, or about 5:1.

In some embodiments, a composition comprising circular RNA has been purified. Circular RNA may be purified by any known method commonly used in the art, such as column chromatography, gel filtration chromatography, and size exclusion chromatography. In some embodiments, puri- fication comprises one or more of the following steps: phosphatase treatment, HPLC size exclusion purification, and RNase R digestion. In some embodiments, purification comprises the following steps in order: RNase R digestion, phosphatase treatment, and HPLC size exclusion purifica- tion. In some embodiments, purification comprises reverse phase HPLC. In some embodiments, a purified composition contains less double stranded RNA, DNA splints, triphos- phorylated RNA, phosphatase proteins, protein ligases, cap- ping enzymes and/or nicked RNA than unpurified RNA. In some embodiments, purification of circular RNA comprises an affinity-purification or negative selection method described herein. In some embodiments, purification of circular RNA comprises separation of linear RNA from circular RNA using oligonucleotides that are complemen- tary to a sequence in the linear RNA but are not comple- mentary to a sequence in the circular RNA. In some embodi- ments, a purified composition is less immunogenic than an unpurified composition. In some embodiments, immune cells exposed to a purified composition produce less TNFα, RIG-I, IL-2, IL-6, IFNγ, and/or a type 1 interferon, e.g., IFN-β1, than immune cells exposed to an unpurified com- position.

Exemplary methods of circularization of precursor RNA can be found in, for example, WO2020/237227, which is incorporated by reference herein in its entirety. WO2020/ 237227, inter alia, describes using the permuted intron exon (PIE) circularization strategy to circularize long precursor RNA. In it, a 1.1 kb sequence containing a full-length encephalomyocarditis virus (EMCV) IRES, a *Gaussia* luciferase (GLuc) expression sequence, and two short exon fragments of the permuted intron-exon (PIE) construct were inserted between the 3' and 5' introns of the permuted group I catalytic intron in the thymidylate synthase (Td) gene of the T4 phage. Precursor RNA was synthesized by run-off transcription. Circularization was attempted by heating the precursor RNA in the presence of magnesium ions and GTP, but splicing products were not obtained. Perfectly complementary 9 nucleotide and 19 nucleotide long homology regions were designed and added at the 5' and 3' ends of the precursor RNA. The splicing product was treated with RNase R. Sequencing across the putative splice junction of RNase R-treated splicing reactions revealed ligated exons, and digestion of the RNase R-treated splicing reaction with oligonucleotide-targeted RNase H produced a single band in contrast to two bands yielded by RNase H-digested linear precursor. WO2020/237227 further indicates that a series of spacers was designed and inserted between the 3' PIE splice site and the IRES. These spacers were designed to either conserve or disrupt secondary structures within intron sequences in the IRES, 3' PIE splice site, and/or 5' splice site.

Further methods for preparing circular RNA are described in WO2022/261490, which is incorporated herein by reference in its entirety.

3. Lipid Nanoparticle Preparation

In one embodiment, a lipid nanoparticle formulation may be prepared by the methods described in International Publication Nos. WO2011127255 or WO2008103276, each of which is herein incorporated by reference in their entirety. In some embodiments, lipid nanoparticle formulations may be as described in International Publication No. WO2019131770, which is herein incorporated by reference in its entirety.

In some embodiments, circular RNA is formulated according to a process described in U.S. patent application Ser. No. 15/809,680. In some embodiments, the present disclosure provides a process of encapsulating circular RNA in transfer vehicles comprising the steps of forming lipids into pre-formed transfer vehicles (i.e., formed in the absence of RNA) and then combining the pre-formed transfer vehicles with RNA. In some embodiments, the novel formulation process results in an RNA formulation with higher potency (peptide or protein expression) and higher efficacy (improvement of a biologically relevant endpoint) both in vitro and in vivo with potentially better tolerability as compared to the same RNA formulation prepared without the step of preforming the lipid nanoparticles (e.g., combining the lipids directly with the RNA).

For certain cationic lipid nanoparticle formulations of RNA, in order to achieve high encapsulation of RNA, the RNA in buffer (e.g., citrate buffer) has to be heated. In those processes or methods, the heating is required to occur before the formulation process (i.e., heating the separate components) as heating post-formulation (post-formation of nanoparticles) does not increase the encapsulation efficiency of the RNA in the lipid nanoparticles. In contrast, in some embodiments, the order of heating of RNA does not appear to affect the RNA encapsulation percentage. In some embodiments, no heating (i.e., maintaining at ambient temperature) of one or more of the solutions comprising the pre-formed lipid nanoparticles, the solution comprising the RNA and the mixed solution comprising the lipid nanoparticle encapsulated RNA is required to occur before or after the formulation process.

RNA may be provided in a solution to be mixed with a lipid solution such that the RNA may be encapsulated in lipid nanoparticles. A suitable RNA solution may be any aqueous solution containing RNA to be encapsulated at various concentrations. For example, a suitable RNA solution may contain an RNA at a concentration of or greater than about 0.01 mg/ml, 0.05 mg/ml, 0.06 mg/ml, 0.07 mg/ml, 0.08 mg/ml, 0.09 mg/ml, 0.1 mg/ml, 0.15 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, or 1.0 mg/ml. In some embodiments, a suitable RNA solution may contain an RNA at a concentration in a range from about 0.01-1.0 mg/ml, 0.01-0.9 mg/ml, 0.01-0.8 mg/ml, 0.01-0.7 mg/ml, 0.01-0.6 mg/ml, 0.01-0.5 mg/ml, 0.01-0.4 mg/ml, 0.01-0.3 mg/ml, 0.01-0.2 mg/ml, 0.01-0.1 mg/ml, 0.05-1.0 mg/ml, 0.05-0.9 mg/ml, 0.05-0.8 mg/ml, 0.05-0.7 mg/ml, 0.05-0.6 mg/ml, 0.05-0.5 mg/ml, 0.05-0.4 mg/ml, 0.05-0.3 mg/ml, 0.05-0.2 mg/ml, 0.05-0.1 mg/ml, 0.1-1.0 mg/ml, 0.2-0.9 mg/ml, 0.3-0.8 mg/ml, 0.4-0.7 mg/ml, or 0.5-0.6 mg/ml.

Typically, a suitable RNA solution may also contain a buffering agent and/or salt. Generally, buffering agents can include HEPES, Tris, ammonium sulfate, sodium bicarbonate, sodium citrate, sodium acetate, potassium phosphate or sodium phosphate. In some embodiments, suitable concentration of the buffering agent may be in a range from about 0.1 mM to 100 mM, 0.5 mM to 90 mM, 1.0 mM to 80 mM, 2 mM to 70 mM, 3 mM to 60 mM, 4 mM to 50 mM, 5 mM to 40 mM, 6 mM to 30 mM, 7 mM to 20 mM, 8 mM to 15 mM, or 9 to 12 mM.

Exemplary salts can include sodium chloride, magnesium chloride, and potassium chloride. In some embodiments, suitable concentration of salts in an RNA solution may be in a range from about 1 mM to 500 mM, 5 mM to 400 mM, 10 mM to 350 mM, 15 mM to 300 mM, 20 mM to 250 mM, 30 mM to 200 mM, 40 mM to 190 mM, 50 mM to 180 mM, 50 mM to 170 mM, 50 mM to 160 mM, 50 mM to 150 mM, or 50 mM to 100 mM.

In some embodiments, a suitable RNA solution may have a pH in a range from about 3.5-6.5, 3.5-6.0, 3.5-5.5, 3.5-5.0, 3.5-4.5, 4.0-5.5, 4.0-5.0, 4.0-4.9, 4.0-4.8, 4.0-4.7, 4.0-4.6, or 4.0-4.5.

Various methods may be used to prepare a suitable RNA solution. In some embodiments, RNA may be directly dissolved in a buffer solution described herein. In some embodiments, an RNA solution may be generated by mixing an RNA stock solution with a buffer solution prior to mixing with a lipid solution for encapsulation. In some embodiments, an RNA solution may be generated by mixing an RNA stock solution with a buffer solution immediately before mixing with a lipid solution for encapsulation.

According to the present disclosure, a lipid solution contains a mixture of lipids suitable to form transfer vehicles for encapsulation of RNA. In some embodiments, a suitable lipid solution is ethanol based. For example, a suitable lipid solution may contain a mixture of desired lipids dissolved in pure ethanol (i.e., 100% ethanol). In another embodiment, a suitable lipid solution is isopropyl alcohol based. In another embodiment, a suitable lipid solution is dimethylsulfoxide-based. In another embodiment, a suitable lipid solution is a mixture of suitable solvents including, but not limited to, ethanol, isopropyl alcohol and dimethylsulfoxide.

A suitable lipid solution may contain a mixture of desired lipids at various concentrations. In some embodiments, a suitable lipid solution may contain a mixture of desired lipids at a total concentration in a range from about 0.1-100 mg/ml, 0.5-90 mg/ml, 1.0-80 mg/ml, 1.0-70 mg/ml, 1.0-60 mg/ml, 1.0-50 mg/ml, 1.0-40 mg/ml, 1.0-30 mg/ml, 1.0-20 mg/ml, 1.0-15 mg/ml, 1.0-10 mg/ml, 1.0-9 mg/ml, 1.0-8 mg/ml, 1.0-7 mg/ml, 1.0-6 mg/ml, or 1.0-5 mg/ml.

Nanoparticles can be made in a 1 fluid stream or with mixing processes such as microfluidics and T-junction mixing of two fluid streams, one of which contains the circular RNA and the other has the lipid components. Exemplary lipid compositions can be prepared according to the methods and at the ratios described in Example 1 and Tables 4a-b.

In some embodiments, the lipid nanoparticles described herein may be synthesized using methods comprising, for example, microfluidic mixers, microstructure-induced chaotic advection (MICA), a Slit Interdigital Microstructured Mixer (SIMM-V2) or a Standard Slit Interdigital Micro Mixer (SSIMM) or Caterpillar (CPMM) or Impinging-jet (IJMM) from the Institut fur Mikrotechnik Mainz GmbH, Mainz Germany), using a micromixer chip, and/or using technology. Exemplary mixers and methods are known in the art.

Additional lipid nanoparticle formulations and methods of producing are described in detail in WO2021226597 and WO2021113777, which are incorporated herein by reference in their entireties.

For example, disclosed in WO2021226597 and WO2021113777 is a method of preparing lipid nanoparticle formulations of ionizable lipids 128 and 129 of Table 3. Ethanol phase contained ionizable Lipid 128 or Lipid 129 from Table 3, DOPE, Cholesterol, and DSPE-PEG 2000 (Avanti Polar Lipids Inc.) at a weight ratio of 16:1:4:1 or 62:4:33:1 molar ratio combined with an aqueous phase containing circular RNA and 25 mM sodium acetate buffer at pH 5.2. A 3:1 aqueous to ethanol mixing ratio was used. The formulated LNPs were then dialyzed in 1 L of water and exchanged 2 times over 18 hours. Dialyzed LNPs were filtered using 0.2 µm filter. Prior to in vivo dosing, LNPs were diluted in PBS. LNP sizes were determined by dynamic light scattering. A cuvette with 1 mL of 20 µg/mL LNPs in PBS (pH 7.4) was measured for Z-average using the Malvern Panalytical Zetasizer Pro. The Z-average and polydispersity index were recorded.

Additional exemplary methods for preparing nanoparticle compositions and synthesis of certain ionizable lipids, e.g., for use in the lipid nanoparticles, can be found in Examples 1 and 2.

B. Method of Treating

Also provided herein is a method of treating a subject in need thereof comprising administering a therapeutically effective amount of the circular RNA construct provided herein. In some embodiments, provided herein is a method of treating a subject in need thereof comprising administering a therapeutically effective amount of a composition comprising the circular RNA construct provided herein. In some embodiments, in addition to the circular RNA construct, a delivery vehicle, and optionally, a targeting moiety operably connected to the delivery vehicle is administered.

Thus, in certain embodiments, provided herein are methods of treating and/or preventing a disease in a subject (e.g., mammalian subject, such as a human subject). Without being bound to a particular theory or mechanism, where the circular RNA encodes a CAR, the CARs have biological activity, e.g., ability to recognize an antigen, e.g., CD19, HER2, or BCMA, such that the CAR, when expressed by a cell, is able to mediate an immune response against the cell expressing the antigen, e.g., CD19, HER2, or BCMA, for which the CAR is specific. In this regard, an embodiment provided herein provides a method of treating or preventing cancer in a subject, comprising administering to the subject the circular RNA therapeutic agents, and/or the pharmaceutical compositions provided herein in an amount effective to treat or prevent cancer in the subject.

In some embodiments, the subject has a cancer selected from the group consisting of: acute myeloid leukemia (AML); alveolar rhabdomyosarcoma; B cell malignancies; bladder cancer (e.g., bladder carcinoma); bone cancer; brain cancer (e.g., medulloblastoma and glioblastoma multiforme); breast cancer; cancer of the anus, anal canal, or anorectum; cancer of the eye; cancer of the intrahepatic bile duct; cancer of the joints; cancer of the neck; gallbladder cancer; cancer of the pleura; cancer of the nose, nasal cavity, or middle ear; cancer of the oral cavity; cancer of the vulva; chronic lymphocytic leukemia; chronic myeloid cancer; colon cancer; esophageal cancer, cervical cancer; fibrosarcoma; gastrointestinal carcinoid tumor; head and neck cancer (e.g., head and neck squamous cell carcinoma); Hodgkin lymphoma; hypopharynx cancer; kidney cancer; larynx cancer; leukemia; liquid tumors; lipoma; liver cancer; lung cancer (e.g., non-small cell lung carcinoma, lung adenocarcinoma, and small cell lung carcinoma); lymphoma; mesothelioma; mastocytoma; melanoma; multiple myeloma; nasopharynx cancer; non-Hodgkin lymphoma; B-chronic lymphocytic leukemia; hairy cell leukemia; Burkitt's lymphoma; ovarian cancer; pancreatic cancer; cancer of the peritoneum; cancer of the omentum; mesentery cancer; pharynx cancer; prostate cancer; rectal cancer; renal cancer; skin cancer; small intestine cancer; soft tissue cancer; solid tumors; synovial sarcoma; gastric cancer; teratoma; testicular cancer; thyroid cancer; and ureter cancer.

In some embodiments, the subject has an autoimmune disease or disorder.

In some embodiments, the subject has an autoimmune disease or disorder selected from scleroderma, Grave's disease, Crohn's disease, Sjogren's disease, multiple sclerosis, Hashimoto's disease, psoriasis, myasthenia gravis, autoimmune polyendocrinopathy syndromes, Type I diabetes mellitus (TIDM), autoimmune gastritis, autoimmune uveoretinitis, polymyositis, colitis, thyroiditis, and the generalized autoimmune diseases typified by human Lupus.

In some embodiments, the subject has an autoimmune disease or disorder that is B-cell mediated.

In some embodiments, the subject has lupus, e.g., systemic lupus erythematosus (SLE), cutaneous lupus erythematosus (CLE), lupus nephritis (LN), neonatal lupus, drug-induced lupus.

In the subject has antisynthetase syndrome, multifocal motor neuropathy, myasthenia gravis, neuromyelitis optica, pemphigus vulgaris, and/or systemic sclerosis.

In some embodiments, provided herein is a method of treating and/or preventing cancer in a subject, comprising introducing the circular RNA and/or pharmaceutical composition thereof disclosed herein. In some embodiments, provided herein is a method of treating cancer in a subject, comprising introducing the circular RNA encoding CD19 CAR and/or pharmaceutical composition thereof disclosed herein. In some embodiments, provided herein is a method of treating cancer in a subject, comprising introducing the circular RNA encoding HER2 CAR and/or pharmaceutical composition thereof disclosed herein. In some embodiments, provided herein is a method of treating cancer in a subject, comprising introducing the circular RNA encoding BCMA CAR and/or pharmaceutical composition thereof disclosed herein.

In some embodiments, provided herein is a method of treating and/or preventing B-cell lymphoma, e.g., large B-cell lymphoma, in a subject, comprising introducing the circular RNA and/or pharmaceutical composition thereof disclosed herein. In some embodiments, provided herein is a method of treating B-cell lymphoma, e.g., large B-cell lymphoma, in a subject, comprising introducing the circular RNA encoding CD19 CAR and/or pharmaceutical composition thereof disclosed herein. In some embodiments, provided herein is a method of treating B-cell lymphoma, e.g., large B-cell lymphoma, in a subject, comprising introducing the circular RNA encoding CD19 CAR and comprising an IRES and/or pharmaceutical composition thereof disclosed herein.

In some embodiments, provided herein is a method of treating and/or preventing mantle cell lymphoma in a subject, comprising introducing the circular RNA and/or pharmaceutical composition thereof disclosed herein. In some embodiments, provided herein is a method of treating mantle cell lymphoma in a subject, comprising introducing the circular RNA encoding CD19 CAR and/or pharmaceutical composition thereof disclosed herein. In some embodiments, provided herein is a method of treating mantle cell lymphoma in a subject, comprising introducing the circular RNA encoding CD19 CAR and comprising an IRES and/or pharmaceutical composition thereof disclosed herein.

In some embodiments, provided herein is a method of treating and/or preventing multiple myeloma in a subject, comprising introducing the circular RNA and/or pharmaceutical composition thereof disclosed herein. In some embodiments, provided herein is a method of treating multiple myeloma in a subject, comprising introducing the circular RNA encoding BCMA CAR and/or pharmaceutical composition thereof disclosed herein. In some embodiments, provided herein is a method of treating multiple myeloma in a subject, comprising introducing the circular RNA encoding BCMA CAR and comprising an IRES and/or pharmaceutical composition thereof disclosed herein.

In some embodiments, provided herein is a method of treating and/or preventing a solid tumor in a subject, comprising introducing the circular RNA and/or pharmaceutical composition thereof disclosed herein. In some embodiments, provided herein is a method of treating a solid tumor in a subject, comprising introducing the circular RNA encoding HER2 CAR and/or pharmaceutical composition thereof disclosed herein. In some embodiments, provided herein is a method of treating a solid tumor in a subject, comprising introducing the circular RNA encoding HER2 CAR and comprising an IRES and/or pharmaceutical composition thereof disclosed herein.

In 2022, Mackensen et al. reported a compassionate-use anti-CD19 CAR T cell therapy for refractory systemic lupus erythematosus in which autologous T cells from SLE patients "were transduced with a lentiviral anti-CD19 CAR vector, expanded and reinfused . . . into the patients after lymphodepletion. CAR T cells expanded in vivo, led to deep depletion of B cells, improvement of clinical symptoms and normalization of laboratory parameters including seroconversion of anti-double-stranded DNA antibodies. Remission of SLE according to DORIS criteria was achieved in all five patients after 3 months and the median (range) Systemic Lupus Erythematosus Disease Activity Index score after 3 months was 0 (2)." Mackensen et al., Anti-CD19 CAR T cell therapy for refractory systemic lupus erythematosus, Nature Medicine (2022); see also Nunez et al., Cytokine and reactivity profiles in SLE patients following anti-CD19 CART therapy, Molecular Therapy (2023); the contents of both of which are hereby incorporated by reference in their entireties.

In some embodiments, provided herein is a method of treating and/or preventing an autoimmune disease, e.g., a B cell mediated autoimmune disease, e.g., lupus, in a subject, comprising introducing the circular RNA encoding CD19 CAR and/or pharmaceutical composition thereof disclosed herein. In some embodiments, provided herein is a method of treating lupus in a subject, comprising introducing the circular RNA encoding CD19 CAR and/or pharmaceutical composition thereof disclosed herein. In some embodiments, provided herein is a method of treating SLE in a subject, comprising introducing the circular RNA encoding CD19 CAR and/or pharmaceutical composition thereof disclosed herein.

In some embodiments, provided herein is a method of treating and/or preventing an autoimmune disease, e.g., a B cell mediated autoimmune disease, e.g., lupus, in a subject, comprising introducing the circular RNA encoding CD19 CAR and comprising an IRES and/or pharmaceutical composition thereof disclosed herein. In some embodiments, provided herein is a method of treating lupus in a subject, comprising introducing the circular RNA encoding CD19 CAR and comprising an IRES and/or pharmaceutical composition thereof disclosed herein. In some embodiments, provided herein is a method of treating SLE in a subject, comprising introducing the circular RNA encoding CD19 CAR and comprising an IRES and/or pharmaceutical composition thereof disclosed herein.

In some embodiments, provided herein is a method of treating and/or preventing an autoimmune disease, e.g., a B cell mediated autoimmune disease, e.g., lupus, in a subject, comprising introducing the circular RNA and/or pharmaceutical composition thereof disclosed herein. In some embodiments, provided herein is a method of treating lupus in a subject, comprising introducing the circular RNA and/or pharmaceutical composition thereof disclosed herein. In some embodiments, provided herein is a method of treating SLE in a subject, comprising introducing the circular RNA and/or pharmaceutical composition thereof disclosed herein.

In some embodiments, provided herein is a method of treating and/or preventing an autoimmune disease, e.g., a B cell mediated autoimmune disease, e.g., lupus, in a subject, comprising introducing the circular RNA encoding CD19 CAR and/or pharmaceutical composition thereof disclosed herein. In some embodiments, provided herein is a method of treating lupus in a subject, comprising introducing the circular RNA encoding CD19 CAR and/or pharmaceutical composition thereof disclosed herein. In some embodiments, provided herein is a method of treating SLE in a subject, comprising introducing the circular RNA encoding CD19 CAR and/or pharmaceutical composition thereof disclosed herein.

In some embodiments, provided herein is a method of treating and/or preventing an autoimmune disease, e.g., a B cell mediated autoimmune disease, e.g., lupus, in a subject, comprising introducing the circular RNA encoding CD19 CAR and comprising an IRES and/or pharmaceutical composition thereof disclosed herein. In some embodiments, provided herein is a method of treating lupus in a subject, comprising introducing the circular RNA encoding CD19 CAR and comprising an IRES and/or pharmaceutical composition thereof disclosed herein. In some embodiments, provided herein is a method of treating SLE in a subject, comprising introducing the circular RNA encoding CD19 CAR and comprising an IRES and/or pharmaceutical composition thereof disclosed herein.

The transfer vehicles may preferentially distribute to specific target cells such as immune cells (e.g., T cells, NK cells, macrophages, etc.), or in the heart, lungs, kidneys, liver, and spleen. In some embodiments, the compositions distribute into the cells of the liver or spleen to facilitate the delivery and the subsequent expression of the circular RNA comprised therein by the cells of the liver (e.g., hepatocytes) or the cells of spleen (e.g., immune cells). The targeted cells may function as a biological "reservoir" or "depot" capable of producing, and systemically excreting a functional protein or enzyme. Accordingly, in one embodiment of the disclosure, the transfer vehicle may target hepatocytes or immune cells and/or preferentially distribute to the cells of the liver or spleen upon delivery. In an embodiment, following transfection of the target hepatocytes or immune cells, the circular RNA loaded in the vehicle is translated and a functional protein product is produced, excreted and systemically distributed. In other embodiments, cells other than hepatocytes (e.g., lung, spleen, heart, ocular, or cells of the central nervous system) can serve as a depot location for protein production. The compositions may also be prepared to preferentially target a variety of target cells, which include, but are not limited to, hepatocytes, epithelial cells, hematopoietic cells, epithelial cells, endothelial cells, lung cells, bone cells, stem cells, mesenchymal cells, neural cells (e.g., meninges, astrocytes, motor neurons, cells of the dorsal root ganglia and anterior horn motor neurons), photoreceptor cells (e.g., rods and cones), retinal pigmented epithelial cells, secretory cells, cardiac cells, adipocytes, vascular smooth muscle cells, cardiomyocytes, skeletal muscle cells, beta cells, pituitary cells, synovial lining cells, ovarian cells, testicular cells, fibroblasts, B cells, T cells, reticulocytes, leukocytes, granulocytes and tumor cells.

In some embodiments, provided herein is a method of treating and/or preventing a disease or disorder in a subject, comprising introducing the circular RNA and/or pharmaceutical composition thereof to a T cell in the subject. In some embodiments, provided herein is a method of treating a disease or disorder in a subject, comprising introducing the circular RNA and/or pharmaceutical composition thereof to a helper T cell in the subject. In some embodiments, provided herein is a method of treating a disease or disorder in a subject, comprising introducing the circular RNA and/or pharmaceutical composition thereof to a cytotoxic T cell in the subject.

In some embodiments, provided herein is a method of treating and/or preventing a disease or disorder in a subject, comprising introducing the circular RNA and/or pharmaceutical composition thereof to a NK cell in the subject.

In some embodiments, provided herein is a method of treating and/or preventing a disease or disorder in a subject, comprising introducing the circular RNA and/or pharmaceutical composition thereof to a macrophage in the subject.

In some embodiments, provided herein is a method of treating and/or preventing a disease or disorder in a subject, comprising introducing the circular RNA and/or pharmaceutical composition thereof to a myeloid cell in the subject.

In some embodiments, provided herein is a method of treating and/or preventing a disease or disorder in a subject, comprising introducing the circular RNA and/or pharmaceutical composition thereof to a monocyte in the subject.

In some embodiments, provided herein is a method of treating and/or preventing a disease or disorder in a subject, comprising introducing the circular RNA and/or pharmaceutical composition thereof to a CD3+ cell in the subject.

In some embodiments, provided herein is a method of treating and/or preventing a disease or disorder in a subject, comprising introducing the circular RNA and/or pharmaceutical composition thereof to a CD4+ cell in the subject.

In some embodiments, provided herein is a method of treating and/or preventing a disease or disorder in a subject, comprising introducing the circular RNA and/or pharmaceutical composition thereof to a CD8+ cell in the subject.

In some embodiments, provided herein is a method of treating and/or preventing a disease or disorder in a subject, comprising introducing the circular RNA and/or pharmaceutical composition thereof to a CD14+ cell in the subject.

In some embodiments, provided herein is a method of treating and/or preventing a disease or disorder in a subject, comprising introducing the circular RNA and/or pharmaceutical composition thereof to a CD16+ cell in the subject.

In some embodiments, provided herein is a method of treating and/or preventing a disease or disorder in a subject, comprising introducing the circular RNA and/or pharmaceutical composition thereof to a CD33+ cell in the subject.

In some embodiments, provided herein is a method of treating and/or preventing a disease or disorder in a subject, comprising introducing the circular RNA and/or pharmaceutical composition thereof to a CD33+CD14+ cell in the subject.

In some embodiments, provided herein is a method of treating and/or preventing a disease or disorder in a subject, comprising introducing the circular RNA and/or pharmaceutical composition thereof to a CD33+CD64+ cell in the subject.

In some embodiments, provided herein is a method of treating and/or preventing a disease or disorder in a subject, comprising introducing the circular RNA and/or pharmaceutical composition thereof to a CD56+ cell in the subject.

In some embodiments, provided herein is a method of treating and/or preventing a disease or disorder in a subject, comprising introducing the circular RNA and/or pharmaceutical composition thereof to a CD11B+ cell in the subject.

In certain embodiments the therapeutic agents provided herein (i.e., circular RNA constructs and compositions thereof) and the transfer vehicles (e.g., lipid nanoparticles) exhibit an enhanced (e.g., increased) ability to transfect one or more target cells. Accordingly, also provided herein are methods of transfecting one or more target cells. Such methods generally comprise the step of contacting the one or more target cells with the compounds and/or pharmaceutical compositions disclosed herein such that the one or more target cells are transfected with the circular RNA encapsulated therein. As used herein, the terms "transfect" or "transfection" refer to the intracellular introduction of one or more encapsulated materials (e.g., nucleic acids and/or polynucleotides) into a cell, or preferably into a target cell. The term "transfection efficiency" refers to the relative amount of such encapsulated material (e.g., polynucleotides) uptaken by, introduced into and/or expressed by the target cell which is subject to transfection. In some embodiments, transfection efficiency may be estimated by the amount of a reporter polynucleotide product produced by the target cells following transfection. In some embodiments, a transfer vehicle has high transfection efficiency. In some embodiments, a transfer vehicle has at least about 10%, 20%, 30%, 40%, 50%, 60%, 70%, 80%, or 90% transfection efficiency.

In certain embodiments, the circular RNA constructs or compositions comprising circular RNA constructs disclosed herein are administered to a subject. In some embodiments, administration occurs twice a day, daily or every other day. In certain embodiments, administration occurs twice a week, once a week, every ten days, every two weeks, every three weeks, every four weeks, once a month, every six weeks, every eight weeks, every three months, every four months, every six months, every eight months, every nine months or annually. In some embodiments, administration occurs every other day. In some embodiments, administration occurs once a week (i.e., weekly). In some embodiments, administration occurs every two weeks (i.e., every other week or biweekly, q2w). In some embodiments, administration occurs less frequently and/or at a lower dose than as required for a suitable comparator, for example, a corresponding linear RNA.

In certain embodiments, the therapeutic agents provided herein (i.e., circular RNA constructs and compositions thereof) are co-administered with one or more additional therapeutic agents e.g., in the same pharmaceutical composition or in separate pharmaceutical compositions. In some embodiments, the therapeutic agent provided herein can be administered first and the one or more additional therapeutic agents can be administered second, or vice versa. Alternatively, the therapeutic agent provided herein and the one or more additional therapeutic agents can be administered simultaneously. In some embodiments, the therapeutic agents are co-administered sufficiently close in time such that the therapeutic agent provided herein can enhance the effect of the one or more additional therapeutic agents, or vice versa.

In certain embodiments, the methods further comprise lymphodepleting the subject prior to administering the therapeutic agent. Examples of lymphodepletion include, but may not be limited to, nonmyeloablative lymphodepleting chemotherapy, myeloablative lymphodepleting chemotherapy, total body irradiation, etc.

In some embodiments, the subject is a mammal. In some embodiments, the mammal referred to herein can be any mammal, including, but not limited to, mammals of the order Rodentia, such as mice and hamsters, or mammals of the order Logomorpha, such as rabbits. The mammals may be from the order Carnivora, including Felines (cats) and Canines (dogs). The mammals may be from the order Artiodactyla, including Bovines (cows) and Swines (pigs), or of the order Perssodactyla, including Equines (horses). The mammals may be of the order Primates, Ceboids, or Simoids (monkeys) or of the order Anthropoids (humans and apes). Preferably, the mammal is a human.

Examples

The following examples are provided to illustrate certain disclosed embodiments and are not to be construed as limiting the scope of this disclosure in any way.

Example 1: Production of Lipid Nanoparticle Compositions

In order to investigate safe and efficacious lipid nanoparticle compositions for use in the delivery of circular RNA to cells, a range of formulations were prepared and tested. Specifically, the particular elements and ratios thereof in the lipid component of nanoparticle compositions were optimized.

Nanoparticles can be made in a one fluid stream or with mixing processes such as microfluidics and T-junction mixing of two fluid streams, one of which contains the circular RNA and the other has the lipid components.

Lipid compositions can be prepared, including by combining an ionizable lipid, optionally a helper lipid (such as DOPE, DSPC, or oleic acid obtainable from Avanti Polar Lipids, Alabaster, AL), a PEG lipid (such as 1,2-dimyristoyl-sn-glycerol methoxypolyethylene glycol, also known as PEG-DMG, obtainable from Avanti Polar Lipids, Alabaster, AL), and a structural lipid such as cholesterol at concentrations of about, e.g., 40 or 50 mM in a solvent, e.g., ethanol. Solutions should be refrigerated for storage at, for example, −20° C. Lipids are combined to yield desired molar ratios (see, for example, Tables 4a and 4b below) and diluted with water and ethanol to a final lipid concentration of e.g., between about 5.5 mM and about 25 mM.

TABLE 4a

| Formulation number | Description |
|---|---|
| | Lipid Nanoparticle Formulations |
| 1 | Aliquots of 50 mg/mL ethanolic solutions of C12-200, DOPE, Chol and DMG-PEG2K (40:30:25:5) are mixed and diluted with ethanol to 3 mL final volume. Separately, an aqueous buffered solution (10 mM citrate/150 mM NaCl, pH 4.5) of circRNA is prepared from a 1 mg/mL stock. The lipid solution is injected rapidly into the aqueous circRNA solution and shaken to yield a final suspension in 20% ethanol. The resulting nanoparticle suspension is filtered, diafiltrated with 1 × PBS (pH 7.4), concentrated and stored at 2-8° C |
| 2 | Aliquots of 50 mg/mL ethanolic solutions of DODAP, DOPE, cholesterol and DMG-PEG2K (18:56:20:6) are mixed and diluted with ethanol to 3 mL final volume. Separately, an aqueous buffered solution (10 mM citrate/150 mM NaCl, pH 4.5) of EPO circRNA is prepared from a 1 mg/mL stock. The lipid solution is injected rapidly into the aqueous circRNA solution and shaken to yield a final suspension in 20% ethanol. The resulting nanoparticle suspension is filtered, diafiltrated with 1 × PBS (pH 7.4), concentrated and stored at 2-8° C. Final concentration = 1.35 mg/mL EPO circRNA (encapsulated). Zave = 75.9 nm (Dv(50) = 57.3 nm; Dv(90) = 92.1 nm). |
| 3 | Aliquots of 50 mg/mL ethanolic solutions of HGT4003, DOPE, cholesterol and DMG-PEG2K (50:25:20:5) are mixed and diluted with ethanol to 3 mL final volume. Separately, an aqueous buffered solution (10 mM citrate/150 mM NaCl, pH 4.5) of circRNA is prepared from a 1 mg/mL stock. The lipid solution is injected rapidly into the aqueous circRNA solution and shaken to yield a final suspension in 20% ethanol. The resulting nanoparticle suspension is filtered, diafiltrated with 1 × PBS (pH 7.4), concentrated and stored at 2-8° C. |
| 4 | Aliquots of 50 mg/mL ethanolic solutions of ICE, DOPE and DMG-PEG2K (70:25:5) are mixed and diluted with ethanol to 3 mL final volume. Separately, an aqueous buffered solution (10 mM citrate/150 mM NaCl, pH 4.5) of circRNA is prepared from a 1 mg/mL stock. The lipid solution is injected rapidly into the aqueous circRNA solution and shaken to yield a final suspension in 20% ethanol. The resulting nanoparticle suspension is filtered, diafiltrated with 1 × PBS (pH 7.4), concentrated and stored at 2-8° C. |
| 5 | Aliquots of 50 mg/mL ethanolic solutions of HGT5000, DOPE, cholesterol and DMG-PEG2K (40:20:35:5) are mixed and diluted with ethanol to 3 mL final volume. Separately, an aqueous buffered solution (10 mM citrate/150 mM NaCl, |

TABLE 4a-continued

| | Lipid Nanoparticle Formulations |
|---|---|

| Formulation number | Description |
|---|---|
| | pH 4.5) of EPO circRNA is prepared from a 1 mg/mL stock. The lipid solution is injected rapidly into the aqueous circRNA solution and shaken to yield a final suspension in 20% ethanol. The resulting nanoparticle suspension is filtered, diafiltrated with 1 × PBS (pH 7.4), concentrated and stored at 2-8° C. Final concentration = 1.82 mg/mL EPO mRNA (encapsulated). Zave = 105.6 nm (Dv(50) = 53.7 nm; Dv(90) = 157 nm). |
| 6 | Aliquots of 50 mg/mL ethanolic solutions of HGT5001, DOPE, cholesterol and DMG-PEG2K (40:20:35:5) are mixed and diluted with ethanol to 3 mL final volume. Separately, an aqueous buffered solution (10 mM citrate/150 mM NaCl, pH 4.5) of EPO circRNA is prepared from a 1 mg/mL stock. The lipid solution is injected rapidly into the aqueous circRNA solution and shaken to yield a final suspension in 20% ethanol. The resulting nanoparticle suspension is filtered, diafiltrated with 1 × PBS (pH 7.4), concentrated and stored at 2-8° C. |
| 7 | Aliquots of 50 mg/mL ethanolic solutions of HGT5001, DOPE, cholesterol and DMG-PEG2K (35:16:46.5:2.5) are mixed and diluted with ethanol to 3 mL final volume. Separately, an aqueous buffered solution (10 mM citrate/150 mM NaCl, pH 4.5) of EPO circRNA is prepared from a 1 mg/mL stock. The lipid solution is injected rapidly into the aqueous circRNA solution and shaken to yield a final suspension in 20% ethanol. The resulting nanoparticle suspension is filtered, diafiltrated with 1 × PBS (pH 7.4), concentrated and stored at 2-8° C. |
| 8 | Aliquots of 50 mg/mL ethanolic solutions of HGT5001, DOPE, cholesterol and DMG-PEG2K (40:10:40:10) are mixed and diluted with ethanol to 3 mL final volume. Separately, an aqueous buffered solution (10 mM citrate/150 mM NaCl, pH 4.5) of EPO circRNA is prepared from a 1 mg/mL stock. The lipid solution is injected rapidly into the aqueous circRNA solution and shaken to yield a final suspension in 20% ethanol. The resulting nanoparticle suspension is filtered, diafiltrated with 1 × PBS (pH 7.4), concentrated and stored at 2-8° C. |
| 9 | Aliquots of 50 mg/mL ethanolic solutions of LP1, DSPC, cholesterol and DMG-PEG2K (45:9:44:2) are mixed and diluted with ethanol to 3 mL final volume. Separately, an aqueous buffered solution (50 mM Na Acetate, pH 4.5) of FLuc, hEPO, micro-dystrophin, mini-dystrophin, or dystrophin circRNA is prepared from a 1 mg/mL stock. The lipid solution is injected rapidly into the aqueous circRNA solution and shaken to yield a final suspension in 25% ethanol. The resulting nanoparticle suspension is filtered, diafiltrated with 1 × PBS (pH 7.4), concentrated and stored at 2-8° C. |
| 10 | Aliquots of 50 mg/mL ethanolic solutions of LP1, DSPC, cholesterol and DMG-PEG2K, and DMSO solution of Ethyl Lauroyl Arginate (38.25:7.65:37.4:1.7:15) are mixed and diluted with ethanol to 3 mL final volume. Separately, an aqueous buffered solution (50 mM Bis-Tris, pH 7.0) of FLuc, hEPO, micro-dystrophin, mini-dystrophin, or dystrophin circRNA is prepared from a 1 mg/mL stock. The lipid solution is injected rapidly into the aqueous circRNA solution and shaken to yield a final suspension in 25% ethanol. The resulting nanoparticle suspension is filtered, diafiltrated with 1 × PBS (pH 7.4), concentrated and stored at 2-8° C. |
| 11 | Aliquots of 50 mg/mL ethanolic solutions of SM-102, DSPC, cholesterol and DMG-PEG2K (50:10:38.5:1.5) are mixed and diluted with ethanol to 3 mL final volume. Separately, an aqueous buffered solution (6.25 mM Na Acetate, pH 4.5) of FLuc, hEPO, micro-dystrophin, mini-dystrophin, or dystrophin circRNA is prepared from a 1 mg/mL stock. The lipid solution is injected rapidly into the aqueous circRNA solution and shaken to yield a final suspension in 25% ethanol. The resulting nanoparticle suspension is filtered, diafiltrated with 1 × PBS (pH 7.4), concentrated and stored at 2-8° C. |
| 12 | Aliquots of 50 mg/mL ethanolic solutions of SM-102, DSPC, cholesterol and DMG-PEG2K, and DMSO solution of Ethyl Lauroyl Arginate (42.5:8.5:32,73:1.275:15) are mixed and diluted with ethanol to 3 mL final volume. Separately, an aqueous buffered solution (20 mM Na Acetate, pH 4.5) of FLuc, hEPO, micro-dystrophin, mini-dystrophin, or dystrophin circRNA is prepared from a 1 mg/mL stock. The lipid solution is injected rapidly into the aqueous circRNA solution and shaken to yield a final suspension in 25% ethanol. The resulting nanoparticle suspension is filtered, diafiltrated with 1 × PBS (pH 7.4), concentrated and stored at 2-8° C. |

373

In some embodiments, the transfer vehicle has a formulation as described in Table 4b.

TABLE 4b

Exemplary Lipid Vehicle Formulations

| Composition (mol %) | Components |
|---|---|
| 40:20:38.5:1.5 | Compound:Phospholipid:Phytosterol*:PEG-DMG |
| 45:15:38.5:1.5 | Compound:Phospholipid:Phytosterol*:PEG-DMG |
| 50:10:38.5:1.5 | Compound:Phospholipid:Phytosterol*:PEG-DMG |
| 55:5:38.5:1.5 | Compound:Phospholipid:Phytosterol*:PEG-DMG |
| 60:5:33.5:1.5 | Compound:Phospholipid:Phytosterol*:PEG-DMG |
| 45:20:33.5:1.5 | Compound:Phospholipid:Phytosterol*:PEG-DMG |
| 50:20:28.5:1.5 | Compound:Phospholipid:Phytosterol*:PEG-DMG |
| 55:20:23.5:1.5 | Compound:Phospholipid:Phytosterol*:PEG-DMG |
| 60:20:18.5:1.5 | Compound:Phospholipid:Phytosterol*:PEG-DMG |
| 40:15:43.5:1.5 | Compound:Phospholipid:Phytosterol*:PEG-DMG |
| 50:15:33.5:1.5 | Compound:Phospholipid:Phytosterol*:PEG-DMG |
| 55:15:28.5:1.5 | Compound:Phospholipid:Phytosterol*:PEG-DMG |
| 60:15:23.5:1.5 | Compound:Phospholipid:Phytosterol*:PEG-DMG |
| 40:10:48.5:1.5 | Compound:Phospholipid:Phytosterol*:PEG-DMG |
| 45:10:43.5:1.5 | Compound:Phospholipid:Phytosterol*:PEG-DMG |
| 55:10:33.5:1.5 | Compound:Phospholipid:Phytosterol*:PEG-DMG |
| 60:10:28.5:1.5 | Compound:Phospholipid:Phytosterol*:PEG-DMG |
| 40:5:53.5:1.5 | Compound:Phospholipid:Phytosterol*:PEG-DMG |
| 45:5:48.5:1.5 | Compound:Phospholipid:Phytosterol*:PEG-DMG |
| 50:5:43.5:1.5 | Compound:Phospholipid:Phytosterol*:PEG-DMG |
| 40:20:40:0 | Compound:Phospholipid:Phytosterol*:PEG-DMG |
| 45:20:35:0 | Compound:Phospholipid:Phytosterol*:PEG-DMG |
| 50:20:30:0 | Compound:Phospholipid:Phytosterol*:PEG-DMG |
| 55:20:25:0 | Compound:Phospholipid:Phytosterol*:PEG-DMG |
| 60:20:20:0 | Compound:Phospholipid:Phytosterol*:PEG-DMG |
| 40:15:45:0 | Compound:Phospholipid:Phytosterol*:PEG-DMG |

For nanoparticle compositions including circRNA, solutions of the circRNA at concentrations of 0.1 mg/ml in deionized water are diluted in a buffer, e.g., 50 mM sodium citrate buffer at a pH between 3 and 4 to form a stock solution. Alternatively, solutions of the circRNA at concentrations of 0.15 mg/ml in deionized water are diluted in a buffer, e.g., 6.25 mM sodium acetate buffer at a pH between 3 and 4.5 to form a stock solution.

Nanoparticle compositions including a circular RNA and a lipid component are prepared by combining the lipid solution with a solution including the circular RNA at lipid component to circRNA wt:wt ratios between about 5:1 and about 50:1. The lipid solution is rapidly injected using, e.g., a NanoAssemblr microfluidic based system at flow rates between about 10 ml/min and about 18 ml/min or between about 5 ml/min and about 18 ml/min into the circRNA solution, to produce a suspension with a water to ethanol ratio between about 1:1 and about 4:1.

Nanoparticle compositions can be processed by dialysis to remove ethanol and achieve buffer exchange. Formulations are dialyzed twice against phosphate buffered saline (PBS), pH 7.4, at volumes 200 times that of the primary product using Slide-A-Lyzer cassettes (Thermo Fisher Scientific Inc., Rockford, IL) with a molecular weight cutoff of 10 kDa or 20 kDa. The formulations are then dialyzed overnight at 4° C. The resulting nanoparticle suspension is filtered through 0.2 µm sterile filters (Sarstedt, Nümbrecht, Germany) into glass vials and sealed with crimp closures. Nanoparticle composition solutions of 0.01 mg/ml to 0.15 mg/ml are generally obtained.

The method described above induces nano-precipitation and particle formation.

Alternative processes including, but not limited to, T-junction and direct injection, may be used to achieve the same nano-precipitation.

A Zetasizer Nano ZS (Malvern Instruments Ltd, Malvern, Worcestershire, UK) can be used to determine the particle size, the polydispersity index (PDI) and the zeta potential of the nanoparticle compositions in 1×PBS in determining particle size and 15 mM PBS in determining zeta potential.

Ultraviolet-visible spectroscopy can be used to determine the concentration of circRNA in nanoparticle compositions. 100 µL of the diluted formulation in 1×PBS is added to 900 µL of a 4:1 (v/v) mixture of methanol and chloroform. After mixing, the absorbance spectrum of the solution is recorded, for example, between 230 nm and 330 nm on a DU 800 spectrophotometer (Beckman Coulter, Beckman Coulter, Inc., Brea, CA). The concentration of circRNA in the nanoparticle composition can be calculated based on the extinction coefficient of the circRNA used in the composition and on the difference between the absorbance at a wavelength of, for example, 260 nm and the baseline value at a wavelength of, for example, 330 nm.

A QUANT-IT™ RIBOGREEN® RNA assay (Invitrogen Corporation Carlsbad, CA) can be used to evaluate the encapsulation of circRNA by the nanoparticle composition. The samples are diluted to a concentration of approximately 5 µg/mL or 1 µg/mL in a TE buffer solution (10 mM Tris-HCl, 1 mM EDTA, pH 7.5). 50 µL of the diluted samples are transferred to a polystyrene 96 well plate and either 50 µL of TE buffer or 50 µL of a 2-4% Triton X-100 solution is added to the wells. The plate is incubated at a temperature of 37° C. for 15 minutes. The RIBOGREEN® reagent is diluted 1:100 or 1:200 in TE buffer, and 100 µL of this solution is added to each well. The fluorescence intensity can be measured using a fluorescence plate reader (Wallac Victor 1420 Multilabel Counter; Perkin Elmer, Waltham, MA) at an excitation wavelength of, for example, about 480 nm and an emission wavelength of, for example, about 520 nm. The fluorescence values of the reagent blank are subtracted from that of each of the samples and the percentage of free circRNA is determined by dividing the fluorescence intensity of the intact sample (without addition of Triton X-100) by the fluorescence value of the disrupted sample (caused by the addition of Triton X-100).

Example 2: Synthesis of Ionizable Lipids

Example 2.1 Synthesis of heptadecan-9-yl 8-((3-hydroxypropyl) (2-hydroxytetradecyl)amino)octanoate (Table 3, Lipid 1)

375      376

-continued

Example 2.1.1 Synthesis of heptadecan-9-yl 8-bromooctanoate (3)

To a mixture of 8-bromooctanoic acid 2 (10 g, 44.82 mmol) and heptadecan-9-ol 1 (9.6 g, 37.35 mmol) in $CH_2Cl2$ (300 mL) was added DMAP (900 mg, 7.48 mmol), DIPEA (26 mL, 149.7 mmol) and EDC (10.7 g, 56.03 mmol). The reaction was stirred at room temperature overnight. After concentration of the reaction mixture, the crude residue was dissolved in ethyl acetate (300 mL), washed with 1N HCl, sat. $NaHCO_3$, water and Brine. The organic layer was dried over anhydrous Na2SO4. The solvent was evaporated, and the crude residue was purified by flash chromatography ($SiO_2$: Hexane=100% to 30% of EtOAc in Hexane) and colorless oil product 3 was obtained (5 g, 29%).

1H NMR (300 MHz, $CDCl_3$): δ ppm 4.86 (m, 1H), 3.39 (t, J=7.0 Hz, 2H), 2.27 (t, J=7.6 Hz, 2H), 1.84 (m, 2H), 1.62 (m, 2H), 1.5-1.4 (m, 8H), 1.35-1.2 (m, 26H), 0.87 (t, J=6.7 Hz, 6H).

Example 2.1.2 Synthesis of heptadecan-9-yl 8-((3-hydroxypropyl)amino)octanoate (5)

A solution of 1-octylnonyl 8-bromooctanoate 3 (7.4 g, 16.03 mmol) in EtOH (200 mL) was added 3-amino-1-propanol 4 (24.4 mL, 320 mmol) and the reaction solution was heated at 70° C. overnight. MS showed the expected product: [APCI]: [MH]+456.4. After concentration of the reaction mixture, the crude residue was dissolved in methyl tert-butyl ether (500 mL), washed with sat. NaHCO3, water and Brine. The organic layer was dried over anhydrous Na2SO4. The solvent was evaporated, and the crude residue was purified by flash chromatography (SiO$_2$: CH$_2$Cl2=100% to 10% of MeOH in CH$_2$Cl2 with 1% NH4OH) and colorless oil product 5 was obtained (6.6 g, 88%).

1H NMR (300 MHZ, CDCl3): δ ppm 4.84 (m, 1H), 3.80 (t, J=5.5 Hz, 2H), 2.87 (t, J=5.76 Hz, 2H), 2.59 (t, J=7.2 Hz, 2H), 2.27 (t, J=7.6 Hz, 2H), 1.68 (m, 2H), 1.62 (m, 2H), 1.5-1.4 (m, 5H), 1.35-1.2 (m, 32H), 0.87 (t, J=6.7 Hz, 6H). MS (APCI+): 456.4 (M+1).

Example 2.1.3 Synthesis of heptadecan-9-yl 8-((3-hydroxypropyl) (2-hydroxytetradecyl)amino)octano-ate (7)

A mixture of compound 5 (6.6 g, 14.5 mmol) and 1,2-epoxytetradecane (3.68 g, 17.4 mmol) in isopropanol (150 mL) was heated to reflux for overnight. MS showed the expected product: [APCI]: [MH]+668.6. The reaction mixture was concentrated, and crude product was purified flash chromatography (SiO$_2$: CH$_2$Cl2=100% to 10% of MeOH in CH2Cl2 with 1% NH4OH) to obtained Lipid 10e-1 as colorless oil (6.34 g, 65%).

1H NMR (300 MHz, CDCl$_3$): δ ppm 4.85 (m, 1H), 3.76 (t, J=5.49 Hz, 2H), 3.68 (m, 1H), 2.75 (m, 1H), 2.59 (m, 2H), 2.38 (m, 3H), 2.27 (m, 2H), 1.58-1.68 (m, 2H), 1.48 (m, 6H), 1.24 (m, 56H), 0.87 (m, 9H). MS (APCI+): 668.6 (M+1).

Example 2.2 Synthesis of Di (undecan-3-yl) 8,8'-((3-hydroxypropyl)azanediyl)bis(7-hydroxyoctano-ate) (Table 3, Lipid 7)

-continued

4

Example 2.2.1 Synthesis of undecan-3-yl oct-7-enoate (3)

To a mixture of oct-7-enoic acid 2 (10 g, 70.3 mmol) and undecan-3-ol 1 (10 g, 58.6 mmol) in CH2Cl2 (300 mL) was added DMAP (1.4 g, 11.6 mmol), DIPEA (40 mL, 232 mmol) and EDC (16.9 g, 87.9 mmol). The reaction was stirred at room temperature overnight. After concentration of the reaction mixture, the crude residue was dissolved in tert-butylmethyl ether (500 mL), washed with IN HCl, sat. NaHCO$_3$, water and Brine. The organic layer was dried over anhydrous Na$_2$SO4. The solvent was evaporated and the crude residue was purified by flash chromatography (SiO$_2$: Hexane=100% to 20% of EtOAc in Hexane) and colorless oil product 3 was obtained (17.2 g, 98%).

1H NMR (300 MHz, CDCl$_3$): δ ppm 5.88-5.72 (m, 1H), 5.02-4.91 (m, 1H), 4.80 (m, 1H), 2.28 (t, J=7.4 Hz, 2H), 2.05-2.03 (m, 2H), 1.62-1.49 (m, 6H), 1.37-1.25 (m, 16H), 0.87 (t, J=7.4 Hz, 6H).

Example 2.2.2 Synthesis of undecan-3-yl 6-(oxiran-2-yl) hexanoate (4)

To a mixture of undecan-3-yl oct-7-enoate 3 (17.2 g, 58.1 mmol) in CH$_2$Cl2 (300 mL) was added meta-chloroperoxy-benzoic acid (mCPBA, <77%) (19.5 g, 87 mmol) in one portion at 0° C. ice-water bath. The reaction was stirred at room temperature overnight. The white precipitate (meta-benzoic acid) was filtered and the filtrate was diluted with CH$_2$Cl2 (200 mL), washed with 10% Na2S203, sat. NaHCO3, water and Brine. The organic layer was dried over anhydrous Na2SO4. The solvent was evaporated and the crude residue was purified by flash chromatography (SiO$_2$: Hexane=100% to 30% of EtOAc in Hexane) and colorless oil product 3 was obtained (17.1 g, 97%).

1H NMR (300 MHz, CDCl$_3$): δ ppm 4.80 (m, 1H), 2.89-2.86 (m, 1H), 3.39 (t, J=7.0 Hz, 2H), 2.74 (t, J=4.7 Hz, 1H), 2.47 (dd, J=4.9, 2.2 Hz, 1H), 2.28 (t, J=7.4 Hz, 1H), 1.74-1.46 (m, 10H), 1.35-1.2 (m, 13H) 0.87 (m, 6H).

Example 2.2.3 Synthesis of Di(undecan-3-yl) 8,8'-((3-hydroxypropyl)azanediyl)bis(7-hydroxyoctanoate) (Table 3, lipid 7)

A solution of undecan-3-yl 6-(oxiran-2-yl) hexanoate 4 (8 g, 25.6 mmol) in isopropanol (50 mL) was added 3-amino-1-propanol (769.1 mg, 10.2 mmol) and the reaction solution was heated at 90° C. overnight. MS showed the expected product: [APCI]: [MH]+700.6. After concentration of the reaction mixture, the crude residue was purified by flash chromatography (SiO$_2$: CH$_2$Cl2=100% to 10% of MeOH in CH$_2$Cl2) and colorless oil product was obtained (5.1 g, 71%).

1H NMR (300 MHz, CDCl$_3$): δ ppm 4.81 (m, 2H), 3.80 (m, 2H), 3.73 (m, 2H), 2.78 (m, 2H), 2.52-2.43 (m, 4H), 2.28 (t, J=7.3 Hz, 2H), 1.68-1.48 (m, 15H), 1.35-1.17 (m, 37H), 0.88-0.83 (m, 12H). MS (APCI+): 700.6 (M+1).

Example 2.3 Synthesis of ((3-(2-methyl-1H-imida-zol-1-yl) propyl)azanediyl)bis(hexane-6,1-diyl)bis (2-hexyldecanoate) (Table 3, lipid 129) and ((3-(1H-imidazol-1-yl) propyl)azanediyl)bis(hexane-6, 1-diyl)bis(2-hexyldecanoate) (Table 3, lipid 128)

In a 100 mL round bottom flask connected with condenser, 3-(1H-imidazol-1-yl) propan-1-amine (100 mg, 0.799 mmol) or 3-(2-methyl-1H-imidazol-1-yl) propan-1-amine (0.799 mmol), 6-bromohexyl 2-hexyldecanoate (737.2 mg, 1.757 mmol), potassium carbonate (485 mg, 3.515 mmol) and potassium iodide (13 mg, 0.08 mmol) were mixed in acetonitrile (30 mL), and the reaction mixture was heated to 80° C. for 48 h. The mixture was cooled to room temperature and was filtered through a pad of Celite. The filtrate was diluted with ethyl acetate. After washing with water, brine and dried over anhydrous sodium sulfate. The solvent was evaporated and the crude residue was purified by flash chromatography (SiO$_2$: CH$_2$Cl2=100% to 10% of methanol in CH$_2$Cl2) and colorless oil product was obtained (92 mg, 15%). Molecular formula of ((3-(1H-imidazol-1-yl) propyl)azanediyl)bis(hexane-6,1-diyl)bis(2-hexyldecano-ate)) is C$_{50}$H$_{95}$N$_3$O$_4$ and molecular weight (Mw) is 801.7.

Reaction scheme for synthesis of ((3-(1H-imidazol-1-yl) propyl)azanediyl)bis(hexane-6,1-diyl)bis(2-hexyldecano-ate)) (Table 3, lipid 128).

Example 3: IRES and CodOP Screening

A. Initial Screening

An initial screen assessing roughly 3,000 potential IRES sequence candidates was conducted. IRES sequence candidates were computationally identified from viral untranslated regions in partial and complete viral sequences available in the art (e.g., Genbank). Each DNA template was cloned to include an IRES sequence or a fragment. Engineered circular RNA (oRNA) was generated from the DNA template by in vitro transcription (IVT); and ORNA was subsequently purified from non-circular RNA components of the IVT reaction. Purified oRNA was nanoprecipitated with lipids to form LNP-ORNA constructs. Primary human skeletal myotubes (MYOs), primary human hepatocytes (PHHs), and activated primary human T cells (TCLs) were treated with formulated LNP-ORNA. Exemplary constructs included a 5' enhanced intron element, a 5' enhanced exon element, a punitive IRES, a coding element encoding *Gaussia* Luciferase, a 3' enhanced exon element, and a 3' enhanced intron element. See WO2022/261490. Protein expression in supernatant was assessed by luminescence measurements 48 hours following transfection. Total luminescent signal was normalized across replicate plates to control for plate-wide differences between replicates.

The top IRES sequences were selected based on protein expression and stability measurements.

Codons directed to CD19 were assessed via % Nalm6 Lysis and mean fluorescence intensity (MFI).

The results of the initial screen led to the selection of about 180 combinations of 18 IRESes (including the IRESes represented by SEQ ID NOs: 1-15 in Table IA) and 10 codons. After synthesis, 69 constructs based on combinations of 15 IRESes (SEQ ID NOs: 1-15 in Table 1A) and 5 codon-optimized sequences (SEQ ID NOs: 19-23 in Table 2A) were further tested. See FIGS. 2A-C and Table 5, below.

B. Codon Optimization Assay

Codon optimization was performed using a ribosomal dwell time algorithm (target GC % of 48-54%), modified stability algorithm (target GC % of 57-62%) and a third algorithm based on reversed engineering of a known sequence (target GC % of 57-62%). As set forth in detail elsewhere herein, the algorithms optimized the particular codons based on GC %, unwanted sequence removal and low GC leader. CD3+ T cells from two healthy donors (4003; 609C) were activated with aCD3/CD28 tetrameric complexes for 3 days and then electroporated with CD19 CAR ORNA sequences. oRNA sequences were codon optimized using 3 algorithms (#1:15 sequences, #2:34 sequences, #3:27 sequences). CD19 CAR expression was analyzed via flow cytometry. CD19 CAR expression (gMFI) is plotted in rank-order for all sequences and color-coded by codon optimization algorithm. White bars indicate non-codon optimized CD19 CAR sequence. See FIGS. 3A and 3B and FIGS. 4A-4C.

The codon sequences were assessed and the top codon variants were elected for further evaluation. See Table 2A. The top codon variants were selected based on consistently robust expression stability and cytotoxicity against Nalm6 from previous optimization assays. From the 10 codons, 4 codons and the base were selected for further assessment: numbers 69, 24, 39, 45, and base (3276), which correspond to SEQ ID NOs: 19-23, as set forth in Table 2 based on assessing, for example, CAR expression, CAR-T cell frequency, and CAR-T cell count.

C. IRES-CO Constructs

These top four codon-optimized variants combined with the top IRES sequences were designed to be assessed in vitro for expression and anti-tumor functionality.

69 circular RNA constructs were designed comprising combinations of the 15 IRES sequences corresponding to SEQ ID NOs: 1-15 in Table 1A and the 5 anti-CD19 28-& codon-optimized expression sequences corresponding to the nucleotide sequences of SEQ ID NOs: 19-23 in Table 2A. The 69 constructs are described in Table 5 and in the examples, below. The constructs are referred to herein by the IRES/CO clone #of Table 5, for example, in FIGS. 8A and 8B.

TABLE 5

| 69 Experimental constructs | | |
|---|---|---|
| IRES/CO Clone # | IRES SEQ ID NO | Codon SEQ ID NO |
| 1 | 1 | 21 |
| 7 | 1 | 19 |
| 10 | 1 | 23 |
| 11 | 2 | 21 |
| 14 | 2 | 22 |
| 16 | 2 | 20 |
| 17 | 2 | 19 |
| 20 | 2 | 23 |
| 24 | 3 | 22 |
| 26 | 3 | 20 |
| 27 | 3 | 19 |
| 31 | 4 | 21 |
| 34 | 4 | 22 |
| 36 | 4 | 20 |
| 37 | 4 | 19 |
| 40 | 4 | 23 |
| 51 | 5 | 21 |
| 54 | 5 | 22 |
| 56 | 5 | 20 |
| 57 | 5 | 19 |
| 60 | 5 | 23 |
| 61 | 6 | 21 |
| 64 | 6 | 22 |
| 66 | 6 | 20 |
| 67 | 6 | 19 |
| 70 | 6 | 23 |
| 71 | 7 | 21 |
| 74 | 7 | 22 |
| 76 | 7 | 20 |
| 77 | 7 | 19 |
| 80 | 7 | 23 |
| 81 | 8 | 21 |
| 86 | 8 | 20 |
| 87 | 8 | 19 |
| 90 | 8 | 23 |
| 91 | 9 | 21 |
| 94 | 9 | 22 |
| 96 | 9 | 20 |

TABLE 5-continued

| 69 Experimental constructs | | |
|---|---|---|
| IRES/CO Clone # | IRES SEQ ID NO | Codon SEQ ID NO |
| 97 | 9 | 19 |
| 100 | 9 | 23 |
| 101 | 10 | 21 |
| 104 | 10 | 22 |
| 106 | 10 | 20 |
| 107 | 10 | 19 |
| 110 | 10 | 23 |
| 111 | 11 | 21 |
| 114 | 11 | 22 |
| 116 | 11 | 20 |
| 117 | 11 | 19 |
| 120 | 11 | 23 |
| 121 | 12 | 21 |
| 124 | 12 | 22 |
| 126 | 12 | 20 |
| 127 | 12 | 19 |
| 130 | 12 | 23 |
| 131 | 13 | 21 |
| 134 | 13 | 22 |
| 136 | 13 | 20 |
| 137 | 13 | 19 |
| 140 | 13 | 23 |
| 161 | 14 | 21 |
| 164 | 14 | 22 |
| 166 | 14 | 20 |
| 167 | 14 | 19 |
| 170 | 14 | 23 |
| 171 | 15 | 21 |
| 176 | 15 | 20 |
| 177 | 15 | 19 |
| 180 | 15 | 23 |

The full IRES-codon sequences for 12 of the 69 exemplary constructs of Table 5 are set forth in Table 6, below. As described in Examples 4-6, these 12 exemplary constructs generally exhibit high and durable expression and led to higher function of the CAR expressing T-cells.

TABLE 6

| 12 Exemplary construct sequences | | |
|---|---|---|
| SEQ ID NO | IRES/CO Clone # | IRES + CO Sequence |
| 50 | 7 | TTAAAACAGCTCTGGGGTTGTTCCCACCCCAGAGGCCCACGTGGCGGCCA GTACTCCGGTATTACGGTACCCTTGTACGCCTGTTTTATACTCCCTTCCCCT GTAACTTAGAAGCATACAAACCAAGTTCAATAGAAGGGGGTACAAACCA GTACCACCACGAACAAGCACTCCTGTTTCCCCGGTGACATTGCATAGACT GTACCCACGGTTGAAAGCGATCGATCCGTTACCCGCTCCTGTACTTCGAG AAGCCTAGTATCATCTTGGAATCTTCGATGCGTTGCGCTCAGCACTCAACC CCAGAGTGTAGCTTAGGCTGATGAGTCTGGACGTCCCCCACCGGCGACGG TGGTCCAGGCTGCGTTGGCGGCCTACCTGTGGCCCAAAGCCACAGGACGC TAGTTGTGAACAAGGTGTGAAGAGCCTATTGAGCTACAAGAGAGTCCTCC GGCCCCTGAATGCGGCTAATCCTAACCACGGAGCAGGCAGTTGCAAACCA GCAACCGGCCTGTCGTAACGCGCAAGTCTGTGGCGGAACCGACTACTTTG GGTGTCCGTGTTTCCTTTTATTTTTACAATGGCTGCTTATGGTGACAATCA TAGATTGTTATCATAAAGCGACTTGGATTGGCCATCCGGTGAAAGTAAAA CACATTGTTTACTTGTTTGTTGGATTCACTCCAATTAACACTTTTACTTACA AACTCATTACAACAACTCTATTAATTAGAGATAAGCATCACAATGGCACT GCCCGTCACCGCACTCCTGCTCCCACTGGCACTGCTGCTCCATGCAGCTCG CCCCGATATCCAGATGACCCAGACCACCTCTAGCCTCAGCGCCTCTCTGG GTGACCGCGTCACCATCTCTTGCCGGGCCAGCCAAGACATCTCTAAGTAC CTGAACTGGTACCAGCAGAAACCTGACGGAACCGTGAAGCTGCTGATCTA CCACACCAGTCGGCTGCATTCCGGGGTGCCTTCCAGGTTCAGCGGTTCCG GCTCTGGGACCGATTATAGTCTCACCATCTCCAACCTCGAGCAGGAGGAC ATCGCAACCTACTTCTGCCAGCAGGGGAACACCCTGCCCTACACCTTCGG TGGCGGGACCAAGCTGGAGATCACTGGAGGTGGTGGCAGCGGAGGTGGA GGATCAGGTGGAGGCGGTAGCGAGGTGAAGCTGCAGGAGTCCGGACCTG GTCTGGTGGCCCCAAGCCAGTCCCTCAGCGTCACCTGCACAGTGTCCGGG GTGTCCCTGCCTGACTACGGTGTGTCTCCTGGATCAGGCAACCACCCCGGAA |

TABLE 6-continued

<u>12 Exemplary construct sequences</u>

SEQ
ID  IRES/CO
NO  Clone #  IRES + CO Sequence

```
              GGGTCTCGAGTGGCTGGGCGTCATCTGGGGCTCCGAGACCACCTACTACA
              ACAGCGCTCTGAAGTCCCGGCTGACCATCATCAAAGACAACTCCAAGAGC
              CAGGTGTTCTTGAAGATGAACTCCCTGCAAACCGATGACACCGCCATCTA
              CTACTGCGCCAAGCACTACTACTATGGCGGTAGCTACGCCATGGATTATT
              GGGGTCAGGGCACCAGTGTCACCGTCTCCTCCATCGAGGTGATGTACCCT
              CCACCCTATCTGGACAACGAGAAGTCCAACGGCACCATCATCCACGTGAA
              GGGCAAGCACCTGTGCCCTAGCCCTCTGTTCCCAGGACCCTCCAAGCCCT
              TCTGGGTGCTGGTCGTGGTGGGAGGAGTCCTGGCCTGCTATTCCCTCCTCG
              TCACCGTGGCATTTATCATCTTCTGGGTCCGGAGCAAGCGGTCACGCCTG
              CTCCACTCCGACTACATGAACATGACTCCTCGCAGACCTGGACCCACCCG
              GAAGCACTACCAGCCTTATGCCCCACCCCGCGACTTTGCCGCTTACCGCTC
              TCGGGTCAAGTTCTCTCGGTCAGCAGACGCCCCTGCATACCAGCAGGGCC
              AGAACCAGCTGTATAACGAGCTGAACCTCGGCAGACGGGAGGAGTACGA
              TGTGCTGGACAAGAGGAGAGGCAGAGACCCCGAGATGGGTGGTAAGCCA
              CGGCGCAAGAACCCACAGGAGGGCTTGTACAACGAACTGCAGAAGGACA
              AGATGGCCGAGGCCTACAGCGAGATCGGCATGAAGGGAGAGAGGCGCAG
              GGGCAAGGGTCACGACGGCCTGTACCAAGGGCTGTCCACCGCAACCAAG
              GACACCTACGATGCCCTGCACATGCAGGCCCTCCCACCAAGG 51    17      TTTCCCCTGTTCGTAACTAAGTGTGTGCCCAATCTCCTCACTCCTGCTGGC
              TTCACCGACCGGCAGTGTCCAAAATGCTAGGTGAATCCCCTCCCTTTCCTC
              TGGGCTTCTGCCCAGCTTCCTCCCCCCAGCCTGACGTGACACAGGCTGTGC
              AAAGACCCCGCGAAAGCTGCCAAAAGTGGCAATTGTGGGTCCCCCCTTTG
              TAAAGGCGTCGAGTCTTTCTCCCTCAAGGCTAGACCCGTCAGTGAATTCT
              GTCGGGCAACTAGTGACGCCACTGCACGCCTCTGACCTCGGCCGCGGAGT
              GCTGCCCCCCAAGTCGTGCCCCTGACCACAAGTTGTGCTGTCTGGCAAAC
              ATTGTCTGTGAGAATGTTCCGCTGTGGCTGCCAAGCCTGGCAACAGGCTG
              CCCCAGTGTGCGTAGTTCTCATCCAGACTTCGGTCTGGCAACTTGCTGTTA
              AGACACGGCGTAAGGGGCGTGTGCCAACGCCCTGGAACGAGTGTCCACT
              CTAATACCCCGAGGAATGCTACGCAGGTACCCCTGGTTCGCCAGGGATCT
              GAGCGTAGGCTAATTGTCTAAGGGTATTTTCATTTCCCATTCTTTCTTTCTT
              GTTCATAATGGCACTGCCCGTCACCGCACTCCTGCTCCCACTGGCACTGCT
              GCTCCATGCAGCTCGCCCCGATATCCAGATGACCCAGACCACCTCTAGCC
              TCAGCGCCTCTCTGGGTGACCGCGTCACCATCTCTTGCCGGGCCAGCCAA
              GACATCTCTAAGTACCTGAACTGGTACCAGCAGAAACCTGACGGAACCGT
              GAAGCTGCTGATCTACCACACCAGTCGGCTGCATTCCGGGGTGCCTTCCA
              GGTTCAGCGGTTCCGGCTCTGGGACCGATTATAGTCTCACCATCTCCAACC
              TCGAGCAGGAGGACATCGCAACCTACTTCTGCCAGCAGGGGAACACCCTG
              CCCTACACCTTCGGTGGCGGGACCAAGCTGGAGATCACTGGAGGTGGTGG
              CAGCGGAGGTGGAGGATCAGGTGGAGGCGGTAGCGAGGTGAAGCTGCAG
              GAGTCCGGACCTGGTCTGGTGGCCCCAAGCCAGTCCCTCAGCGTCACCTG
              CACAGTGTCCGGGGTGTCCCTGCCTGACTACGGTGTCTCCTGGATCAGGC
              AACCACCCCGGAAGGGTCTCGAGTGGCTGGGCGTCATCTGGGGCTCCGAG
              ACCACCTACTACAACAGCGCTCTGAAGTCCCGGCTGACCATCATCAAAGA
              CAACTCCAAGAGCCAGGTGTTCTTGAAGATGAACTCCCTGCAAACCGATG
              ACACCGCCATCTACTACTGCGCCAAGCACTACTACTATGGCGGTAGCTAC
              GCCATGGATTATTGGGGTCAGGGCACCAGTGTCACCGTCTCCTCCATCGA
              GGTGATGTACCCTCCACCCTATCTGGACAACGAGAAGTCCAACGGCACCA
              TCATCCACGTGAAGGGCAAGCACCTGTGCCCTAGCCCTCTGTTCCCAGGA
              CCCTCCAAGCCCTTCTGGGTGCTGGTCGTGGTGGGAGGAGTCCTGGCCTG
              CTATTCCCTCCTCGTCACCGTGGCATTTATCATCTTCTGGGTCCGGAGCAA
              GCGGTCACGCCTGCTCCACTCCGACTACATGAACATGACTCCTCGCAGAC
              CTGGACCCACCCGGAAGCACTACCAGCCTTATGCCCCACCCCGCGACTTT
              GCCGCTTACCGCTCTCGGGTCAAGTTCTCTCGGTCAGCAGACGCCCCTGC
              ATACCAGCAGGGCCAGAACCAGCTGTATAACGAGCTGAACCTCGGCAGA
              CGGGAGGAGTACGATGTGCTGGACAAGAGGAGAGGCAGAGACCCCGAGA
              TGGGTGGTAAGCCACGGCGCAAGAACCCACAGGAGGGCTTGTACAACGA
              ACTGCAGAAGGACAAGATGGCCGAGGCCTACAGCGAGATCGGCATGAAG
              GGAGAGAGGCGCAGGGGCAAGGGTCACGACGGCCTGTACCAAGGGCTGT
              CCACCGCAACCAAGGACACCTACGATGCCCTGCACATGCAGGCCCTCCCA
              CCAAGG 52    37      TTAAAACAGCGGATGGGTATCCCACCATCCGGCCCACTGGGTGTAGTACT
              CTGGTACATTGTACCTTTGTACGCCTGTTTTCCCCCTCTTGTACCCGCCCTT
              CAAGCTCCTTGCCCAAGTAACGTTAGAAGTTTGAACATTGGTACAATAGG
              AAGCATCACATCCAGTGGTGTACTGTACAAACACTTCTGTTGCCCCGGAG
              CGAGGTATAGATGGTCCCCACCGTCAAAAGCCTTTAACCGTTATCCGCCA
              ATCAACTACGTAATGGCTAGTAGCACCTTGGATTTAAGTTGGCGTTCGAT
              CAGGTGGTAACCCCCACTAGTTTGGTCGATGAGGCTAGGAATTCCCCACG
              GGTGACCGTGTCCTAGCCTGCGTGGCGGCCAACCCAGCATCCGCTGGGAC
              GCCAATTTAATGACATGGTGTGAAGACCTGCATGTGCTTGATTGTGAGTC
              CTCCGGCCCCTGAATGCGGCTAACCCTAACCCCGGAGCCTTGCAGCACAA
              TCCAGTGTTGTTAAGGTCGTAATGAGCAATTCTGGGATGGGACCGACTAC
              TTTGGGTGTCCGTGTTTCTTATTTTTCTTGAATTTTTCTTATGGTCACAGCA
```

TABLE 6-continued

| 12 Exemplary construct sequences |
| --- |

SEQ
ID IRES/CO
NO Clone #  IRES + CO Sequence

```
        TATATACATTATATACTGTGATCATGGCACTGCCCGTCACCGCACTCCTGC
        TCCCACTGGCACTGCTGCTCCATGCAGCTCGCCCCGATATCCAGATGACC
        CAGACCACCTCTAGCCTCAGCGCCTCTCTGGGTGACCGCGTCACCATCTCT
        TGCCGGGCCAGCCAAGACATCTCTAAGTACCTGAACTGGTACCAGCAGAA
        ACCTGACGGAACCGTGAAGCTGCTGATCTACCACACCAGTCGGCTGCATT
        CCGGGGTGCCTTCCAGGTTCAGCGGTTCCGGCTCTGGGACCGATTATAGT
        CTCACCATCTCCAACCTCGAGCAGGAGGACATCGCAACCTACTTCTGCCA
        GCAGGGGAACACCCTGCCCTACACCTTCGGTGGCGGGACCAAGCTGGAG
        ATCACTGGAGGTGGTGGCAGCGGAGGTGGAGGATCAGGTGGAGGCGGTA
        GCGAGGTGAAGCTGCAGGAGTCCGGACCTGGTCTGGTGGCCCCAAGCCA
        GTCCCTCAGCGTCACCTGCACAGTGTCCGGGGTGTCCCTGCCTGACTACG
        GTGTCTCCTGGATCAGGCAACCACCCCGGAAGGGTCTCGAGTGGCTGGGC
        GTCATCTGGGGCTCCGAGACCACCTACTACAACAGCGCTCTGAAGTCCCG
        GCTGACCATCATCAAAGACAACTCCAAGAGCCAGGTGTTCTTGAAGATGA
        ACTCCCTGCAAACCGATGACACCGCCATCTACTACTGCGCCAAGCACTAC
        TACTATGGCGGTAGCTACGCCATGGATTATTGGGGTCAGGGCACCAGTGT
        CACCGTCTCCTCCATCGAGGTGATGTACCCTCCACCCTATCTGGACAACG
        AGAAGTCCAACGGCACCATCATCCACGTGAAGGGCAAGCACCTGTGCCCT
        AGCCCTCTGTTCCCAGGACCCTCCAAGCCCTTCTGGGTGCTGGTCGTGGTG
        GGAGGAGTCCTGGCCTGCTATTCCCTCCTCGTCACCGTGGCATTTATCATC
        TTCTGGGTCCGGAGCAAGCGGTCACGCCTGCTCCACTCCGACTACATGAA
        CATGACTCCTCGCAGACCTGGACCCACCCGGAAGCACTACCAGCCTTATG
        CCCCACCCCGCGACTTTGCCGCTTACCGCTCTCGGGTCAAGTTCTCTCGGT
        CAGCAGACGCCCCTGCATACCAGCAGGGCCAGAACCAGCTGTATAACGA
        GCTGAACCTCGGCAGACGGGAGGAGTACGATGTGCTGGACAAGAGGAGA
        GGCAGAGACCCCGAGATGGGTGGTAAGCCACGCGCAAGAACCCACAGG
        AGGGCTTGTACAACGAACTGCAGAAGGACAAGATGGCCGAGGCCTACAG
        CGAGATCGGCATGAAGGGAGAGAGGCGCAGGGGCAAGGGTCACGACGG
        CCTGTACCAAGGGCTGTCCACCGCCAACCAAGGACACCTACGATGCCCTGC
        ACATGCAGGCCCTCCCACCAAGG 53  67    TTCAAACAGCCTGGGGGTTGTACCCACCCCTGGGGCCCACGTGGCGCTAG
        TACTCTGGTACGTTAGTACCTTTGTACGCCTGTTTTCCCCTCCCTTAAACA
        AATTAAGATTACCACTACTGAGGGGAGTAGTCCGACTCCGCTCCGGTACT
        GCCGCACCAGTACTCCGGTACACTTAGTACCCTAGTACGGAGTAGATGGT
        ATCCCCACCCCGCAACTTAGAAGCATGCAAACAAACCGACCAATAGGCG
        CACGATATCCAGTCGTGTTTCGGTCAAGCACTTCTGTCTCCCCGGTCCGAA
        AGGATCGTTACCCGCCCGACCCACTACGAGAAGCCCAGTAACTGGCCAAG
        TGATTGCGAAGTTGCGCTCAGCCACAACCCCAGTGGTAGCTCTGGAAGAT
        GGGGCTCGCGTCTCCCCCGTGGTGACACGGTCGCTTGCCCGCGTGTGCTTC
        CGGGTTCGGCCTACGCCGTTCACTTCAATGTCACGTAACCAGCCAAGAGC
        CTATTGTGCTGGGACGGTTTTCCTCCGGGGCCGTGAATGCTGCTAATCCCA
        ACCTCCGAGCGTGTGCGCACAACCCAGTGTTGCTACGTCGTAATGCGTAA
        GTTGGAGGCGGAACAGACTACTTTCGGTACCCCGTGTTTCCTTTAAATTTT
        ATTCATTATTTTATGGTGACAATTGCTGAGATCTGCGAATTAGCGACTCTG
        CCGTTGAATATTGCTCTGTACTATTTGGTTGCATTCCACAAAACCTCTGAC
        ATCCCCAGTACATACATTACTTTACTTGTTTACCTCAATCTAAAGCACAAG
        CTAGATAATACAAAATGGCACTGCCCGTCACCGCACTCCTGCTCCCACTG
        GCACTGCTGCTCCATGCAGCTCGCCCCGATATCCAGATGACCCAGACCAC
        CTCTAGCCTCAGCGCCTCTCTGGGTGACCGCGTCACCATCTCTTGCCGGGC
        CAGCCAAGACATCTCTAAGTACCTGAACTGGTACCAGCAGAAACCTGACG
        GAACCGTGAAGCTGCTGATCTACCACACCAGTCGGCTGCATTCCGGGGTG
        CCTTCCAGGTTCAGCGGTTCCGGCTCTGGGACCGATTATAGTCTCACCATC
        TCCAACCTCGAGCAGGAGGACATCGCAACCTACTTCTGCCAGCAGGGGAA
        CACCCTGCCCTACACCTTCGGTGGGGGACCAAGCTGGAGATCACTGGAG
        GTGGTGGCAGCGGAGGTGGAGGATCAGGTGGAGGCGGTAGCGAGGTGAA
        GCTGCAGGAGTCCGGACCTGGTCTGGTGGCCCCAAGCCAGTCCCTCAGCG
        TCACCTGCACAGTGTCCGGGGTGTCCCTGCCTGACTACGGTGTCTCCTGGA
        TCAGGCAACCACCCCGGAAGGGTCTCGAGTGGCTGGGCGTCATCTGGGGC
        TCCGAGACCACCTACTACAACAGCGCTCTGAAGTCCCGGCTGACCATCAT
        CAAAGACAACTCCAAGAGCCAGGTGTTCTTGAAGATGAACTCCCTGCAAA
        CCGATGACACCGCCATCTACTACTGCGCCAAGCACTACTACTATGGCGGT
        AGCTACGCCATGGATTATTGGGGTCAGGGCACCAGTGTCACCGTCTCCTC
        CATCGAGGTGATGTACCCTCCACCCTATCTGGACAACGAGAAGTCCAACG
        GCACCATCATCCACGTGAAGGGCAAGCACCTGTGCCCTAGCCCTCTGTTC
        CCAGGACCCTCCAAGCCCTTCTGGGTGCTGGTCGTGGTGGGAGGAGTCCT
        GGCCTGCTATTCCCTCCTCGTCACCGTGGCATTTATCATCTTCTGGGTCCG
        GAGCAAGCGGTCACGCCTGCTCCACTCCGACTACATGAACATGACTCCTC
        GCAGACCTGGACCCACCCGGAAGCACTACCAGCCTTATGCCCCACCCCGC
        GACTTTGCCGCTTACCGCTCTCGGGTCAAGTTCTCTCGGTCAGCAGACGCC
        CCTGCATACCAGCAGGGCCAGAACCAGCTGTATAACGAGCTGAACCTCGG
        CAGACGGGAGGAGTACGATGTGCTGGACAAGAGGAGAGGCAGAGACCCC
        GAGATGGGTGGTAAGCCACGCGCAAGAACCCACAGGAGGGCTTGTACA
        ACGAACTGCAGAAGGACAAGATGGCCGAGGCCTACAGCGAGATCGGCAT
```

TABLE 6-continued

| 12 Exemplary construct sequences | | |
|---|---|---|

| SEQ ID NO | IRES/CO Clone # | IRES + CO Sequence |
|---|---|---|
| | | GAAGGGAGAGAGGCGCAGGGGCAAGGGTCACGACGGCCTGTACCAAGG GCTGTCCACCGCAACCAAGGACACCTACGATGCCCTGCACATGCAGGCCC TCCCACCAAGG |
| 54 | 86 | CCCCCCTCCCCCCCTTCCCTTCCCTTTGCAACGCAACAATTGTAAGTGCCC TCACCTGTCAATTGGGACCACCACTTTCAGTGACCCCATGCGAAGTGCTG AGAGAAAGGAAGCTTTCTTACCCTTCATTTGTGAACCCACTGGTCTAAGC CGCTTGGAATACGATGAGTGGAAAAGTTCATTCTTAATGGAGTGAAACAT GCTTAAATTTCCAGCTCGTGCTGGTCTTTCCAGTACGGGGCGGCCCTGTCT GGCCGTAATTCTTCAGAGTGTCACGCCACACTTGTGGATCTCACGTGCCA CATGACAGCGCTACAGCTGGAACTGGGTGCTTGGTGCCCATGGAGTAACA GCGAAAAGTGTTAGATCAAGCCTTGCTTGGGCTATGAGCCTGCGGAACAA CAACTGGTAACAGTTGCCTCAGGGGCCGAAAGCCACGGTGTTAACAGCAC CCTCATAGTTTGATCCACCTCAGGGTGGTGATGTTTAGCAGTTAGTAGTTG CCAATCTGTGTTCACTGAAATCTCGGCATACCGTGTAGTGTACAGGGGTG AAGGATGCCCAGAAGGTACCCGTAGGTAACCTTAAGAGACTATGGATCTG ATCTGGGGCCTTGTCCGGAGTGCTTTACACACGGCTCAAGGTTAAAAAAC GTCTAGCCCCACAGAGCCCGAGGGATTCGGGTTTTCCCTTTAAAAACCCG ACTAGAGCTTATGGTGACAATTATTGCTGTTCAGACGAACAGTGTAATTG TTGTCTATTCACAGCAGTTCTATCAGAGCTTTTCCCACAACGGATCTTCTT GGCAAGCAAATACAGCAGGAGTCAATATGGCACTCCCAGTCACCGCACTT CTGCTGCCTCTCGCCCTGCTGCTCCATGCAGCCAGACCCGACATCCAGAT GACCCAAACCACCAGCTCCCTGTCCGCTTCCCTGGGTGACCGGGTGACTA TCTCTTGCCGGGCCTCCCAAGACATCTCCAAGTACCTGAACTGGTATCAG CAAAAGCCTGACGGCACCGTCAAGCTCCTCATCTACCATACCTCCAGACT GCACTCCGGGGTGCCTAGCAGGTTCAGCGGAAGTGGGAGCGGCACCGAC TACAGCCTCACCATCTCCAACCTGGAGCAGGAGGACATCGCCACCTACTT CTGCCAGCAGGGGAACACACTGCCCTACACCTTCGGCGGTGGCACCAAGC TGGAGATCACAGGTGGCGGAGGTTCCGGAGGAGGAGGTAGTGGAGGTGG AGGCAGCGAGGTGAAGCTCCAGGAATCCGGACCAGGTCTGGTGGCTCCC AGCCAGTCCCTCAGCGTGACCTGCACCGTGAGCGGCGTGTCTCTTCCCGA TTACGGAGTGTCCTGGATCAGACAGCCACCCCGGAAGGGTCTGGAGTGGC TGGGAGTGATCTGGGGTTCCGAGACCACATACTACAACTCAGCCCTCAAG AGCCGGCTCACCATCATCAAGGATAACTCCAAGTCCCAGGTCTTCCTGAA GATGAACTCTCTCCAGACCGACGACACCGCCATCTACTACTGCGCCAAGC ACTACTACTACGGGGGTCCTACGCCATGGACTACTGGGGTCAGGGAACC TCCGTCACCGTCAGCTCTATCGAGGTGATGTACCCTCCTCCCTACCTCGAC AACGAGAAGAGCAACGGCACCATCATCCATGTGAAGGGGAAGCATCTCT GCCCCTCACCCCTGTTCCCCGGACCATCCAAGCCATTCTGGGTGCTGGTGG TTGTTGGTGGGGTCCTGGCTTGCTACTCACTCCTGGTCACCGTCGCCTTCA TCATCTTCTGGGTGCGGTCAAAGAGGTCCCGGCTCTTGCACTCCGATTACA TGAACATGACTCCAAGGAGGCCTGGTCCCACACGGAAGCACTACCAACC ATATGCCCCACCACGCGACTTCGCTGCTTACCGGAGCCGGGTCAAGTTCA GTCGGAGTGCAGACGCCCCAGCCTACCAGCAGGGCCAGAACCAACTCTA CAACGAGCTTAATCTGGGTCGCCGGGAGGAGTATGACGTGCTCGATAAGA GAAGGGGCCGGGATCCTGAGATGGGGGGTAAGCCCAGACGGAAGAACCC TCAGGAGGGGTTGTATAATGAGCTCCAGAAGGACAAGATGGCCGAGGCA TACTCCGAGATCGGCATGAAAGGTGAGCGGAGGAGAGGCAAGGGGCATG ACGGCCTGTACCAGGGGCTCAGCACAGCCACCAAGGATACCTATGACGC ACTCCACATGCAGGCACTGCCTCCACGG |
| 55 | 87 | CCCCCCTCCCCCCCTTCCCTTCCCTTTGCAACGCAACAATTGTAAGTGCCC TCACCTGTCAATTGGGACCACCACTTTCAGTGACCCCATGCGAAGTGCTG AGAGAAAGGAAGCTTTCTTACCCTTCATTTGTGAACCCACTGGTCTAAGC CGCTTGGAATACGATGAGTGGAAAAGTTCATTCTTAATGGAGTGAAACAT GCTTAAATTTCCAGCTCGTGCTGGTCTTTCCAGTACGGGGCGGCCCTGTCT GGCCGTAATTCTTCAGAGTGTCACGCCACACTTGTGGATCTCACGTGCCA CATGACAGCGCTACAGCTGGAACTGGGTGCTTGGTGCCCATGGAGTAACA GCGAAAAGTGTTAGATCAAGCCTTGCTTGGGCTATGAGCCTGCGGAACAA CAACTGGTAACAGTTGCCTCAGGGGCCGAAAGCCACGGTGTTAACAGCAC CCTCATAGTTTGATCCACCTCAGGGTGGTGATGTTTAGCAGTTAGTAGTTG CCAATCTGTGTTCACTGAAATCTCGGCATACCGTGTAGTGTACAGGGGTG AAGGATGCCCAGAAGGTACCGTAGGTAACCTTAAGAGACTATGGATCTG ATCTGGGGCCTTGTCCGGAGTGCTTTACACACGGCTCAAGGTTAAAAAAC GTCTAGCCCCACAGAGCCCGAGGGATTCGGGTTTTCCCTTTAAAAACCCG ACTAGAGCTTATGGTGACAATTATTGCTGTTCAGACGAACAGTGTAATTG TTGTCTATTCACAGCAGTTCTATCAGAGCTTTTCCCACAACGGATCTTCTT GGCAAGCAAATACAGCAGGAGTCAATATGGCACTGCCCGTCACCGCACTC CTGCTCCCACTGGCACTGCTGCTCCATGCAGCTCGCCCCGATATCCAGATG ACCCAGACCACCTCTAGCCTCAGCGCCTCTCTGGGTGACCGCGTCACCAT CTCTTGCCGGGCCAGCCAAGACATCTCTAAGTACCTGAACTGGTACCAGC AGAAACCTGACGGAACCGTGAAGCTGCTGATCTACCACACCAGTCGGCTG CATTCCGGGGTGCCTTCCAGGTTCAGCGGTTCCGGCTCTGGGACCGATTAT AGTCTCACCATCTCCAACCTCGAGCAGGAGGACATCGCAACCTACTTCTG |

TABLE 6-continued

<u>12 Exemplary construct sequences</u>

| SEQ ID NO | IRES/CO Clone # | IRES + CO Sequence |
|---|---|---|

CCAGCAGGGGAACACCCTGCCCTACACCTTCGGTGGCGGGACCAAGCTGG
AGATCACTGGAGGTGGTGGCAGCGGAGGTGGAGGATCAGGTGGAGGCGG
TAGCGAGGTGAAGCTGCAGGAGTCCGGACCTGGTCTGGTGGCCCCAAGCC
AGTCCCTCAGCGTCACCTGCACAGTGTCCGGGGTGTCCCTGCCTGACTAC
GGTGTCTCCTGGATCAGGCAACCACCCCGGAAGGGTCTCGAGTGGCTGGG
CGTCATCTGGGGCTCCGAGACCACCTACTACAACAGCGCTCTGAAGTCCC
GGCTGACCATCATCAAAGACAACTCCAAGAGCCAGGTGTTCTTGAAGATG
AACTCCCTGCAAACCGATGACACCGCCATCTACTACTGCGCCAAGCACTA
CTACTATGGCGGTAGCTACGCCATGGATTATTGGGGTCAGGGCACCAGTG
TCACCGTCTCCTCCATCGAGGTGATGTACCCTCCACCCTATCTGGACAACG
AGAAGTCCAACGGCACCATCATCCACGTGAAGGGCAAGCACCTGTGCCCT
AGCCCTCTGTTCCCAGGACCCTCCAAGCCCTTCTGGGTGCTGGTCGTGGTG
GGAGGAGTCCTGGCCTGCTATTCCCTCCTCGTCACCGTGGCATTTATCATC
TTCTGGGTCCGGAGCAAGCGGTCACGCCTGCTCCACTCCGACTACATGAA
CATGACTCCTCGCAGACCTGGACCCACCCGGAAGCACTACCAGCCTTATG
CCCCACCCCGCGACTTTGCCGCTTACCGCTCTCGGGTCAAGTTCTCTCGGT
CAGCAGACGCCCCTGCATACCAGCAGGGCCAGAACCAGCTGTATAACGA
GCTGAACCTCGGCAGACGGGAGGAGTACGATGTGCTGGACAAGAGGAGA
GGCAGAGACCCCGAGATGGGTGGTAAGCCACGGCGCAAGAACCCACAGG
AGGGCTTGTACAACGAACTGCAGAAGGACAAGATGGCCGAGGCCTACAG
CGAGATCGGCATGAAGGGAGAGAGGCGCAGGGGCAAGGGTCACGACGG
CCTGTACCAAGGGCTGTCCACCGCAACCAAGGACACCTACGATGCCCTGC
ACATGCAGGCCCTCCCACCAAGG

| 56 | 97 | CACTACGTTACGGTTCCCGCCCGGGACAACTGGTACCCCATTAGGCTACA |

CACTACGTTACGGTTCCCGCCCGGGACAACTGGTACCCCATTAGGCTACA
ACATGGCTGAAAAGGGTATTGGGTCCCCCCGGATTGTGTCCGTTCGTAGT
GTGTGTAACGTGGTTTACCATCTCCACTAACATTGGACTAAGCATTTCATC
TTTCCTCCCCGATTGTGTACTCACTTGGCTAACGCTGGGTGGTCGCGGTTG
GGTCCTTGATTTACTTTTTCTCGTCTAAGCATTCCGACTGTCCTCCCCGATT
ATGTGCTCATTCAGTTAACTGCTGGGTGGTCATGACTAACATCGAGGAAC
CTTCTGTCCACGCTTACTTTGAGCTCCGGTCGCTTGACGCTTGTAGGGCGA
TAGGGTTATCTTCCTGACAACATCTTTATTCTACCTCCATAGGCTCTATCT
ATGGAGACGGAGTGTGGCACCCGTCCCTTCTTTGGGAGCTTCGGTAGTGA
CGCCCTTTGTCACTCTCGCCAGCCGAGGCATGCCTGGTGCCAGGTAGCAA
AGAAAGCATATGTTTAAGGACTTGACTGATTTAGCGCAAGAGTTTGTAGC
GATGTCCATAGTGTCTGCGGATTCCCCACACGGCGACGTGTGCCGCGGAG
GCCAAAAGCCACGGTGTTCACAGCACCCCTATGGATGCCCACAGACCCCA
GTGGGCACTCTTGTTGCCGGACTTTCAGGAAATTAGGCATAGGCTCTTCTC
AAACTCCTGGCATTGGACTAGGTAAGAATGCCCCGGAGGTACCCCAGTAC
TCCTTCGGGAGTCTGGGATCTGACCGGGGGCCCCACAAACATGCTTTACG
TGTTTCGTGCGGTCAAAAATTGTCTAACTAGTCCCAACCTTGAACAAGGG
ATTGTTCTTTCCTTTTTATTACTGAGACTGGCCTATGGTGACAACAGAGAT
TGACTGTGAATACAGTTATTTTCTGGTGTTTATCATTTGGTTTTTTCTCCGTG
CTCTTTTACCTTTGTGGTATTTGTTCTTTAGATAGGCAAAATGGCACTGCC
CGTCACCGCACTCCTGCTCCCACTGGCACTGCTGCTCCATGCAGCTCGCCC
CGATATCCAGATGACCCAGACCACCTCTAGCCTCAGCGCCTCTCTGGGTG
ACCGCGTCACCATCTCTTGCCGGGCCAGCCAAGACATCTCTAAGTACCTG
AACTGGTACCAGCAGAAACCTGACGGAACCGTGAAGCTGCTGATCTACCA
CACCAGTCGGCTGCATTCCGGGGTGCCTTCCAGGTTCAGCGGTTCCGGCT
CTGGGACCGATTATAGTCTCACCATCTCCAACCTCGAGCAGGAGGACATC
GCAACCTACTTCTGCCAGCAGGGGAACACCCTGCCCTACACCTTCGGTGG
CGGGACCAAGCTGGAGATCACTGGAGGTGGTGGCAGCGGAGGTGGAGGA
TCAGGTGGAGGCGGTAGCGAGGTGAAGCTGCAGGAGTCCGGACCTGGTC
TGGTGGCCCCAAGCCAGTCCCTCAGCGTCACCTGCACAGTGTCCGGGGTG
TCCCTGCCTGACTACGGTGTCTCCTGGATCAGGCAACCACCCCGGAAGGG
TCTCGAGTGGCTGGGCGTCATCTGGGGCTCCGAGACCACCTACTACAACA
GCGCTCTGAAGTCCCGGCTGACCATCATCAAAGACAACTCCAAGAGCCAG
GTGTTCTTGAAGATGAACTCCCTGCAAACCGATGACACCGCCATCTACTA
CTGCGCCAAGCACTACTACTATGGCGGTAGCTACGCCATGGATTATTGGG
GTCAGGGCACCAGTGTCACCGTCTCCTCCATCGAGGTGATGTACCCTCCA
CCCTATCTGGACAACGAGAAGTCCAACGGCACCATCATCCACGTGAAGGG
CAAGCACCTGTGCCCTAGCCCTCTGTTCCCAGGACCCTCCAAGCCCTTCTG
GGTGCTGGTCGTGGTGGGAGGAGTCCTGGCCTGCTATTCCCTCCTCGTCAC
CGTGGCATTTATCATCTTCTGGGTCCGGAGCAAGCGGTCACGCCTGCTCC
ACTCCGACTACATGAACATGACTCCTCGCAGACCTGGACCCACCCGGAAG
CACTACCAGCCTTATGCCCCACCCCGCGACTTTGCCGCTTACCGCTCTCGG
GTCAAGTTCTCTCGGTCAGCAGACGCCCCTGCATACCAGCAGGGCCAGAA
CCAGCTGTATAACGAGCTGAACCTCGGCAGACGGGAGGAGTACGATGTG
CTGGACAAGAGGAGAGGCAGAGACCCCGAGATGGGTGGTAAGCCACGGC
GCAAGAACCCACAGGAGGGCTTGTACAACGAACTGCAGAAGGACAAGAT
GGCCGAGGCCTACAGCGAGATCGGCATGAAGGGAGAGAGGCGCAGGGGC
AAGGGTCACGACGGCCTGTACCAAGGGCTGTCCACCGCAACCAAGGACA
CCTACGATGCCCTGCACATGCAGGCCCTCCCACCAAGG

TABLE 6-continued

| 12 Exemplary construct sequences |
| --- |

SEQ
ID IRES/CO
NO Clone # IRES + CO Sequence 57 161     TCACCCTCTTTTCCGGTGGTCCGGACCCAGACCACCGTTACTCCATTCAGC
TTCTTCGGAACCTGTTTGGAGGAATTAAACGGGCACCCACCCACCTTCAC
CCCCTTTTCGTAACTAAGTGTGTGCCCAATCTCATGACTCCTGCTGACTTC
ACCGACCAGCAGTGTCCAAAACGCTAGGTGAATTTCCTTCCTCCCCCTCTG
GGCTTCTGCCCAGCTCCCTCCCTCCAGCCTGACGTGCCACAGGCTGTGCA
AAGACCCCGCGAAAGCTGCCAAAAGTGGCAATTGTGGGTCCCCCCTTTGT
AAAGGCGTCGAGTCTTTCTCCCTTAAGGCTAGACCCGTCAGTGAATTCTGT
CGGGCAACTAGTGACGCCACTGCATGCCTCCGACCTCGGCCGCGGAGTGC
TGCCCCCCAAGTCGTGCCCCTGACTACAAGTIGTGCTGTCTGGCAAACATT
GTCTGTGAGAATGTTCCGCTGTGGCTGCCAAGCCTGGTAACAGGCTGCCC
CAGTGTGCGTAGTTCTCATCCAGACTTCGGTCTGGCAACTTGCTGTTAAGA
CACGGCGTAAGGGGCGTGTGCCAACGCCCTGGAACGAGTGTCCACTCTAA
TACCCCGAGGAATGCTACGCAGGTACCCCTGGCTCCCCAGGGATCTGAGC
GTAGGCTAATTGTCTAAGGGTATTTTCATTTCCCACTCTTTCTTTCTTGTTC
ATAATGGCTCTGCCTGTGACAGCTCTGCTGCTGCCTCTGGCTCTGCTTCTG
CATGCCGCCAGACCTGACATCCAGATGACCCAGACAACCAGCAGCCTGTC
TGCCAGCCTGGGCGATAGAGTGACCATCAGCTGTAGAGCCAGCCAGGAC
ATCAGCAAGTACCTGAACTGGTATCAGCAGAAACCCGACGGCACCGTGA
AGCTGCTGATCTACCACACCAGCAGACTGCACAGCGGCGTGCCAAGCAG
ATTTTCTGGCAGCGGCTCTGGCACCGACTACAGCCTGACAATCAGCAACC
TGGAACAAGAGGATATCGCTACCTACTTCTGCCAGCAAGGCAACACCCTG
CCTTACACCTTTGGCGGAGGCACCAAGCTGGAAATCACAGGCGGCGGAG
GAAGCGGAGGCGGAGGATCTGGTGGTGGTGGATCTGAAGTGAAACTGCA
AGAGTCTGGCCCTGGCCTGGTGGCCCCATCTCAATCTCTGAGCGTGACCT
GTACCGTCAGCGGAGTGTCCCTGCCTGATTATGGCGTGTCCTGGATCCGG
CAGCCTCCTAGAAAAGGCCTGGAATGGCTGGGCGTGATCTGGGGCAGCG
AGACAACCTACTACAACAGCGCCCTGAAGTCCCGGCTGACCATCATCAAG
GACAACTCCAAGAGCCAGGTGTTCCTGAAGATGAACAGCCTGCAGACCG
ACGACACCGCCATCTACTATTGCGCCAAGCACTACTACTACGGCGGCAGC
TACGCCATGGATTATTGGGGCCAGGGCACCAGCGTGACCGTGTCTAGCAT
CGAAGTGATGTACCCTCCACCTTACCTGGACAACGAGAAGTCCAACGGCA
CCATCATCCACGTGAAGGGCAAGCACCTGTGTCCTTCTCCACTGTTCCCCG
GACCTAGCAAGCCTTTCTGGGTGCTCGTTGTTGTTGGCGGCGTGCTGGCCT
GTTACTCTCTGCTGGTTACCGTGGCCTTCATCATCTTTTGGGTCCGAAGCA
AGCGGAGCCGGCTGCTGCACTCCGACTACATGAACATGACCCCTAGACGG
CCCGGACCAACCAGAAAGCACTACCAGCCTTACGCTCCTCCTAGAGACTT
CGCCGCCTACCGGTCCAGAGTGAAGTTCAGCAGATCCGCCGATGCTCCCG
CCTATCAGCAGGGCCAAAACCAGCTGTACAACGAGCTGAACCTGGGGAG
AAGAGAAGAGTACGACGTGCTGGACAAGCGGAGAGGCAGAGATCCTGAA
ATGGGCGGCAAGCCCAGACGGAAGAATCCTCAAGAGGGCCTGTATAATG
AGCTGCAGAAAGACAAGATGGCCGAGGCCTACAGCGAGATCGGAATGAA
GGGCGAGCGCAGAAGAGGCAAGGGACACGATGGACTGTACCAGGGCCTG
AGCACCGCCACCAAGGATACCTATGATGCCCTGCACATGCAGGCCCTGCC
TCCAAGA 58 164     TCACCCTCTTTTCCGGTGGTCCGGACCCAGACCACCGTTACTCCATTCAGC
TTCTTCGGAACCTGTTTGGAGGAATTAAACGGGCACCCACCCACCTTCAC
CCCCTTTTCGTAACTAAGTGTGTGCCCAATCTCATGACTCCTGCTGACTTC
ACCGACCAGCAGTGTCCAAAACGCTAGGTGAATTTCCTTCCTCCCCCTCTG
GGCTTCTGCCCAGCTCCCTCCCTCCAGCCTGACGTGCCACAGGCTGTGCA
AAGACCCCGCGAAAGCTGCCAAAAGTGGCAATTGTGGGTCCCCCCTTTGT
AAAGGCGTCGAGTCTTTCTCCCTTAAGGCTAGACCCGTCAGTGAATTCTGT
CGGGCAACTAGTGACGCCACTGCATGCCTCCGACCTCGGCCGCGGAGTGC
TGCCCCCCAAGTCGTGCCCCTGACTACAAGTTGTGCTGTCTGGCAAACATT
GTCTGTGAGAATGTTCCGCTGTGGCTGCCAAGCCTGGTAACAGGCTGCCC
CAGTGTGCGTAGTTCTCATCCAGACTTCGGTCTGGCAACTTGCTGTTAAGA
CACGGCGTAAGGGGCGTGTGCCAACGCCCTGGAACGAGTGTCCACTCTAA
TACCCCGAGGAATGCTACGCAGGTACCCCTGGCTCCCCAGGGATCTGAGC
GTAGGCTAATTGTCTAAGGGTATTTTCATTTCCCACTCTTTCTTTCTTGTTC
ATAATGGCCCTTCCCGTCACCGCTCTCCTCCTGCCACTGGCCTTGCTGCTG
CACGCTGCACGGCCAGACATCCAGATGACCCAGACAACCAGCTCTCTGTC
AGCCTCTCTCGGCGATCGCGTCACAATCAGCTGCCGCGCTTCCCAAGACA
TCTCCAAGTACCTGAACTGGTACCAGCAAAAGCCCGACGGCACCGTGAAG
CTGCTCATCTACCACACCTCCAGACTGCATAGCGGGGTGCCCAGCAGATT
CAGTGGCTCAGGCTCAGGCACCGACTACAGCCTGACCATCTCCAACCTGG
AGCAGGAGGACATTGCCACATACTTCTGCCAGCAGGGCAACACCCTGCCC
TACACCTTCGGAGGCGGCACAAAGCTGGAGATCACCGGTGGAGGAGGGA
GTGGAGGAGGAGGCAGTGGTGGCGGAGGTTCCGAGGTGAAGCTCCAGGA
ATCAGGTCCAGGACTGGTCGCCCCTTCCCAGTCCCTGTCCGTCACCTGCAC
CGTGAGTGGCGTCAGCCTCCCAGACTACGGTGTGTCTTGGATCCGCCAAC
CTCCTCGCAAAGGCCTGGAATGGCTCGGCGTCATCTGGGGAAGCGAGACA
ACCTACTATAACTCCGCACTGAAGTCCCGCCTCACCATCATCAAGGATAA
TAGCAAGAGCCAGGTCTTCCTCAAGATGAACTCCCTGCAGACCGACGATA
CCGCCATCTACTACTGTGCCAAGCACTACTACTACGGAGGTTCTTACGCC TABLE 6-continued <u>12 Exemplary construct sequences</u>

| SEQ ID NO | IRES/CO Clone # | IRES + CO Sequence |
|---|---|---|

ATGGATTACTGGGGACAGGGAACCTCTGTCACCGTCAGCTCCATCGAGGT
CATGTATCCACCACCCTACCTGGACAACGAAAAGAGCAATGGCACCATCA
TCCACGTGAAGGGGAAGCACCTCTGCCCCTCACCCCTGTTCCCTGGTCCCT
CCAAGCCTTTCTGGGTCCTGGTCGTCGTGGGAGGCGTGTTGGCCTGTTACT
CCCTGCTCGTCACCGTCGCCTTCATCATCTTCTGGGTTAGGAGTAAGCGGT
CCCGGCTTCTGCACTCTGACTACATGAACATGACACCCAGAAGACCTGGG
CCAACCCGGAAGCACTACCAGCCCTACGCTCCACCCAGGGACTTTGCAGC
CTACAGGTCCCGCGTCAAGTTCTCCCGGTCTGCTGACGCACCTGCCTACCA
GCAGGGCCAAAACCAGCTCTACAACGAGTTGAACCTCGGCAGACGGGAG
GAGTACGACGTCCTCGACAAAAGGCGGGGTCGGGATCCTGAGATGGGCG
GTAAGCCAAGGCGGAAGAACCCACAGGAAGGCCTCTATAATGAGCTCCA
GAAGGATAAGATGGCTGAGGCCTACTCCGAGATCGGGATGAAGGGCGAA
AGGAGACGGGGTAAGGGGCACGACGGCCTCTATCAGGGTCTGAGCACCG
CCACCAAGGACACCTACGACGCCCTGCACATGCAGGCACTGCCACCTCGG

| 59 | 171 | TCTGTCCTCACCCCATCTTCCCTTCTTTCCTGCACCGTTACGCTTACTCGCA |
|---|---|---|

TGTGCATTGAGTGGTGCACGTGCTTGAACAAACAGCTACACTCACATGGG
GGCGGGTTTTCCCGCCCTGCGGCCTCTCGCGAGGCCCACCCCTCCCCTTCC
TCCCATAACTACAGTGCTTTGGTAGGTAAGCATCCTGATCCCCCGCGGAA
GCTGCTCACGTGGCAACTGTGGGGACCCAGACAGGTTATCAAAGGCACCC
GGTCTTTCCGCCTTCAGGAGTATCCCTGCTAGTGAATTCTAGTAGGGCTCT
GCTTGGTGCCAACCTCCCCCAAATGCGCGCTGCGGGAGTGCTCTTCCCCA
ACTCACCCTAGTATCCTCTCATGTGTGTGCTTGGTCAGCATATCTGAGACG
ATGTTCCGCTGTCCCAGACCAGTCCAGTAATGGACGGGCCAGTGTGCGTA
GTCGTCTTCCGGCTTGTCCGGCGCATGTTTGGTGAACCGGTGGGGTAAGG
TTGGTGTGCCCAACGCCCGTACTTTGGTGATACCTCAAGACCACCCAGGA
ATGCCAGGGAGGTACCCCGCTTCACAGCGGGATCTGACCCTGGGCTAATT
GTCTACGGTGGTTCTTCTTGCTTCCACTTCTTTCTACTGTTCATGATGGCTC
TGCCTGTGACAGCTCTGCTGCTGCCTCTGGCTCTGCTTCTGCATGCCGCCA
GACCTGACATCCAGATGACCCAGACAACCAGCAGCCTGTCTGCCAGCCTG
GGCGATAGAGTGACCATCAGCTGTAGAGCCAGCCAGGACATCAGCAAGT
ACCTGAACTGGTATCAGCAGAAACCCGACGGCACCGTGAAGCTGCTGATC
TACCACACCAGCAGACTGCACAGCGGCGTGCCAAGCAGATTTTCTGGCAG
CGGCTCTGGCACCGACTACAGCCTGACAATCAGCAACCTGGAACAAGAG
GATATCGCTACCTACTTCTGCCAGCAAGGCAACACCCTGCCTTACACCTTT
GGCGGAGGCACCAAGCTGGAAATCACAGGGGGGGGGAGGAAGCGGAGGC
GGAGGATCTGGTGGTGGTGGATCTGAAGTGAAACTGCAAGAGTCTGGCCC
TGGCCTGGTGGCCCCATCTCAATCTCTGAGCGTGACCTGTACCGTCAGCG
GAGTGTCCCTGCCTGATTATGGCGTGTCCTGGATCCGGCAGCCTCCTAGA
AAAGGCCTGGAATGGCTGGGCGTGATCTGGGGCAGCGAGACAACCTACT
ACAACAGCGCCCTGAAGTCCCGGCTGACCATCATCAAGGACAACTCCAAG
AGCCAGGTGTTCCTGAAGATGAACAGCCTGCAGACCGACGACACCGCCAT
CTACTATTGCGCCAAGCACTACTACTACGGCGGCAGCTACGCCATGGATT
ATTGGGGCCAGGGCACCAGCGTGACCGTGTCTAGCATCGAAGTGATGTAC
CCTCCACCTTACCTGGACAACGAGAAGTCCAACGGCACCATCATCCACGT
GAAGGGCAAGCACCTGTGTCCTTCTCCACTGTTCCCCGGACCTAGCAAGC
CTTTCTGGGTGCTCGTTGTTGTTGGCGGCGTGCTGGCCTGTTACTCTCTGC
TGGTTACCGTGGCCTTCATCATCTTTTGGGTCCGAAGCAAGCGGAGCCGG
CTGCTGCACTCCGACTACATGAACATGACCCCTAGACGGCCCGGACCAAC
CAGAAAGCACTACCAGCCTTACGCTCCTCCTAGAGACTTCGCCGCCTACC
GGTCCAGAGTGAAGTTCAGCAGATCCGCCGATGCTCCCGCCTATCAGCAG
GGCCAAAACCAGCTGTACAACGAGCTGAACCTGGGGGAGAAGCAAGAGT
ACGACGTGCTGGACAAGCGGAGAGGCAGAGATCCTGAAATGGGCGGCAA
GCCCAGACGGAAGAATCCTCAAGAGGGCCTGTATAATGAGCTGCAGAAA
GACAAGATGGCCGAGGCCTACAGCGAGATCGGAATGAAGGGCGAGCGCA
GAAGAGGCAAGGGACACGATGGACTGTACCAGGGCCTGAGCACCGCCAC
CAAGGATACCTATGATGCCCTGCACATGCAGGCCCTGCCTCCAAGA

| 60 | 177 | TCTGTCCTCACCCCATCTTCCCTTCTTTCCTGCACCGTTACGCTTACTCGCA |
|---|---|---|

TGTGCATTGAGTGGTGCACGTGCTTGAACAAACAGCTACACTCACATGGG
GGCGGGTTTTCCCGCCCTGCGGCCTCTCGCGAGGCCCACCCCTCCCCTTCC
TCCCATAACTACAGTGCTTTGGTAGGTAAGCATCCTGATCCCCCGCGGAA
GCTGCTCACGTGGCAACTGTGGGGACCCAGACAGGTTATCAAAGGCACCC
GGTCTTTCCGCCTTCAGGAGTATCCCTGCTAGTGAATTCTAGTAGGGCTCT
GCTTGGTGCCAACCTCCCCCAAATGCGCGCTGCGGGAGTGCTCTTCCCCA
ACTCACCCTAGTATCCTCTCATGTGTGTGCTTGGTCAGCATATCTGAGACG
ATGTTCCGCTGTCCCAGACCAGTCCAGTAATGGACGGGCCAGTGTGCGTA
GTCGTCTTCCGGCTTGTCCGGCGCATGTTTGGTGAACCGGTGGGGTAAGG
TTGGTGTGCCCAACGCCCGTACTTTGGTGATACCTCAAGACCACCCAGGA
ATGCCAGGGAGGTACCCCGCTTCACAGCGGGATCTGACCCTGGGCTAATT
GTCTACGGTGGTTCTTCTTGCTTCCACTTCTTTCTACTGTTCATGATGGCAC
TGCCCGTCACCGCACTCCTGCTCCCACTGGCACTGCTGCTCCATGCAGCTC
GCCCCGATATCCAGATGACCCAGACCACCTCTAGCCTCAGCGCCTCTCTG
GGTGACCGCGTCACCATCTCTTGCCGGGCCAGCCAAGACATCTCTAAGTA

TABLE 6-continued

12 Exemplary construct sequences

```
SEQ
ID  IRES/CO
NO  Clone #  IRES + CO Sequence
```

CCTGAACTGGTACCAGCAGAAACCTGACGGAACCGTGAAGCTGCTGATCT
ACCACACCAGTCGGCTGCATTCCGGGGTGCCTTCCAGGTTCAGCGGTTCC
GGCTCTGGGACCGATTATAGTCTCACCATCTCCAACCTCGAGCAGGAGGA
CATCGCAACCTACTTCTGCCAGCAGGGGAACACCCTGCCCTACACCTTCG
GTGGCGGGACCAAGCTGGAGATCACTGGAGGTGGTGGCAGCGGAGGTGG
AGGATCAGGTGGAGGCGGTAGCGAGGTGAAGCTGCAGGAGTCCGGACCT
GGTCTGGTGGCCCCAAGCCAGTCCCTCAGCGTCACCTGCACAGTGTCCGG
GGTGTCCCTGCCTGACTACGGTGTCTCCTGGATCAGGCAACCACCCCGGA
AGGGTCTCGAGTGGCTGGGCGTCATCTGGGGCTCCGAGACCACCTACTAC
AACAGCGCTCTGAAGTCCCGGCTGACCATCATCAAAGACAACTCCAAGAG
CCAGGTGTTCTTGAAGATGAACTCCCTGCAAACCGATGACACCGCCATCT
ACTACTGCGCCAAGCACTACTACTATGGCGGTAGCTACGCCATGGATTAT
TGGGGTCAGGGCACCAGTGTCACCGTCTCCTCCATCGAGGTGATGTACCC
TCCACCCTATCTGGACAACGAGAAGTCCAACGGCACCATCATCCACGTGA
AGGGCAAGCACCTGTGCCCTAGCCCTCTGTTCCCAGGACCCTCCAAGCCC
TTCTGGGTGCTGGTCGTGGTGGGGAGGAGTCCTGGCCTGCTATTCCCTCCTC
GTCACCGTGGCATTTATCATCTTCTGGGTCCGGAGCAAGCGGTCACGCCT
GCTCCACTCCGACTACATGAACATGACTCCTCGCAGACCTGGACCCACCC
GGAAGCACTACCAGCCTTATGCCCCACCCCGCGACTTTGCCGCTTACCGC
TCTCGGGTCAAGTTCTCTCGGTCAGCAGACGCCCCTGCATACCAGCAGGG
CCAGAACCAGCTGTATAACGAGCTGAACCTCGGCAGACGGGAGGAGTAC
GATGTGCTGGACAAGAGGAGAGGCAGAGACCCCGAGATGGGTGGTAAGC
CACGGCGCAAGAACCCACAGGAGGGCTTGTACAACGAACTGCAGAAGGA
CAAGATGGCCGAGGCCTACAGCGAGATCGGCATGAAGGGAGAGAGGCGC
AGGGGCAAGGGTCACGACGGCCTGTACCAAGGGCTGTCCACCGCCAACCA
AGGACACCTACGATGCCCTGCACATGCAGGCCCTCCCACCAAGG 61  180  TCTGTCCTCACCCCATCTTCCCTTCTTTCCTGCACCGTTACGCTTACTCGCA
TGTGCATTGAGTGGTGCACGTGCTTGAACAAACAGCTACACTCACATGGG
GGCGGGTTTTCCCGCCCTGCGGCCTCTCGCGAGGCCCACCCCTCCCCTTCC
TCCCATAACTACAGTGCTTTGGTAGGTAAGCATCCTGATCCCCCGCGGAA
GCTGCTCACGTGGCAACTGTGGGGACCCAGACAGGTTATCAAAGGCACCC
GGTCTTTCCGCCTTCAGGAGTATCCCTGCTAGTGAATTCTAGTAGGGCTCT
GCTTGGTGCCAACCTCCCCCAAATGCGCGCTGCGGGAGTGCTCTTCCCCA
ACTCACCCTAGTATCCTCTCATGTGTGTGCTTGGTCAGCATATCTGAGACG
ATGTTCCGCTGTCCCAGACCAGTCCAGTAATGGACGGGCCAGTGTGCGTA
GTCGTCTTCCGGCTTGTCCGGCGCATGTTTGGTGAACCGGTGGGGTAAGG
TTGGTGTGCCCAACGCCCGTACTTTGGTGATACCTCAAGACCACCCAGGA
ATGCCAGGGAGGTACCCCGCTTCACAGCGGGATCTGACCCTGGGCTAATT
GTCTACGGTGGTTCTTCTTGCTTCCACTTCTTTCTACTGTTCATGATGGCTC
TGCCAGTGACCGCACTGCTGCTGCCCTTAGCCTTACTCCTTCACGCAGCCA
GGCCCGACATCCAGATGACCCAGACCACCAGCTCCCTTTCCGCAAGCCTC
GGCGACAGGGTCACCATCTCCTGTCGGGCCAGCCAGGACATCAGCAAGTA
CCTGAACTGGTACCAGCAGAAGCCCGACGGCACCGTGAAGCTGCTGATCT
ACCACACCTCACGGCTGCACTCAGGCGTGCCCTCACGGTTTAGCGGATCA
GGCAGCGGCACCGACTACAGCCTGACTATCAGCAACCTGGAGCAGGAGG
ACATCGCCACCTACTTCTGCCAGCAGGGCAACACCCTGCCCTACACCTTC
GGAGGCGGCACCAAGCTGGAGATCACCGGTGGCGGTGGTTCAGGTGGCG
GAGGCTCAGGAGGAGGCGGCAGCGAGGTGAAGCTGCAGGAGTCAGGTCC
AGGACTGGTGGCACCCAGCCAGAGCCTGAGCGTGACTTGCACCGTGTCAG
GCGTGAGCCTGCCAGACTACGGCGTGAGCTGGATCCGGCAGCCTCCTCGG
AAGGGCTTAGAGTGGCTGGGCGTGATCTGGGGCAGCGAGACCACCTACT
ACAACTCAGCCCTGAAGAGCCGGCTGACCATCATCAAGGACAACAGCAA
GAGCCAGGTGTTCCTGAAGATGAACAGCCTGCAGACCGACGACACCGCC
ATCTACTACTGCGCCAAGCACTACTACTACGGCGGCAGCTACGCCATGGA
CTACTGGGGACAGGGTACCAGCGTGACCGTGAGCGCAGCATCGAGGTGATG
TACCCTCCTCCCTACCTGGACAACGAGAAGAGCAACGGCACCATCATCCA
CGTGAAGGGCAAGCACCTGTGCCCTAGCCCTTTATTCCCCGGCCCCTCAA
AACCCTTCTGGGTGCTGGTCGTCGTCGGTGGCGTGCTGGCATGCTACAGC
CTGCTGGTGACCGTGGCCTTCATCATATTCTGGGTCCGGTCAAAGCGGAG
CCGGTTACTGCACAGCGACTACATGAACATGACTCCACGGCGTCCAGGTC
CCACTCGGAAGCACTACCAACCCTACGCTCCTCCCCGTGACTTTGCTGCCT
ACCGTAGCCGGGTGAAGTTCTCCAGGAGCGCCGATGCCCCCAGCCTACCAG
CAGGGCCAGAACCAGCTCTACAATGAGCTTAACCTTGGCAGGCGGGAGG
AGTACGACGTGCTGGACAAGAGGAGGGGCCGTGATCCCGAGATGGGGAGG
CAAGCCCCGTAGGAAGAATCCCCAGGAGGGCCTTTACAACGAGCTCCAG
AAGGACAAGATGGCCGAGGCCTACAGCGAGATCGGCATGAAGGGAGAGC
GTAGGCGTGGAAAAGGGCCACGACGGCCTGTACCAGGGCCTGAGCACTGC
TACCAAGGACACCTACGACGCCCTGCACATGCAGGCTCTTCCACCCCGG

Additional exemplary circular RNA constructs were designed that comprise an IRES of Table 1A and an anti-CD19 binder of Table 2B are set forth in Table 7A below or sequences from the constructs of Table 1B. Certain of the circular RNA constructs in Table 7A include a miR-122 site.

TABLE 7A

Other CD19 constructs (anti-CD19 28-ζ)

| IRES SEQ ID NO: | Codon NT SEQ ID NO: | |
|---|---|---|
| 8 | 24 | |
| 8 | 24 | Includes miR-122 site: SEQ ID NO: 200 |
| 8 | 25 | |
| 8 | 25 | Includes miR-122 site: SEQ ID NO: 200 |
| 8 | 26 | |
| 8 | 27 | |
| 8 | 26 | Includes miR-122 site: SEQ ID NO: 200 |
| 8 | 27 | |
| 8 | 28 | Includes miR-122 site: SEQ ID NO: 200 |
| 8 | 19 | Includes miR-122 site: SEQ ID NO: 200 |
| 4 | 24 | |
| 4 | 24 | Includes miR-122 site: SEQ ID NO: 200 |
| 4 | 25 | |
| 4 | 25 | |

Table 7B describes circular RNA constructs that were designed comprising an expression sequence directed to mouse CD19 and an IRES of Table 1A. Certain of the circular RNA constructs in Table 7B include a miR-122 site.

TABLE 7B

Mouse CD19 constructs

| IRES/CO Clone # | IRES SEQ ID NO: | Codon NT SEQ ID NO: | |
|---|---|---|---|
| mCD19-1 | 16 | 100 | |
| mCD19-2 | 8 | 100 | |

TABLE 7B-continued

Mouse CD19 constructs

| IRES/CO Clone # | IRES SEQ ID NO: | Codon NT SEQ ID NO: | |
|---|---|---|---|
| mCD19-3 | 8 | 100 | Includes miR-122 site: SEQ ID NO: 200 |
| mCD19-4 | 18 | 100 | |

Example 4: Assessment of IRES-CO Constructs

A. Effect of IRES Sequence on Expression

CD3+ T cells from two healthy donors (609C, first row; 4003, second row) were activated with aCD3/CD28 tetrameric complexes for 3 days and then electroporated with CD19 CAR ORNA sequences at a 10 ng/100K cells oRNA dose and evaluated. 74 total sequences were evaluated, comprising a combination of 5 CD19 CAR sequences comprising SEQ ID NOs: 19-23 (the 5 codon optimized sequences of Table 2A) and 16 IRES sequences (including IRESes comprising SEQ ID NOs: 1-15 of Table 1A, and an IRES corresponding to a base CD19 control). Starting at 24 hours post-electroporation up to 120 hours, CD19 CAR expression (T cell MFI), i.e., the level of expression per cell over time, was evaluated via flow cytometry using the anti-idiotypic antibody FMC63. See FIGS. 5A-5J. Starting at 24 hours post-electroporation and up to 120 hours, frequency of CD19 CAR expressing cells (% CAR positive cells by IRES over time, i.e., the percent of cells or average signal of the cells expressing over time) was evaluated via flow cytometry using the anti-idiotypic antibody FMC63. See FIGS. 6A-6J.

B. Effect of IRES Sequence on oCAR™ Stability

CD3+ T cells from two healthy donors (4003, first row; 609C, second row) were activated with aCD3/CD28 tetrameric complexes for 3 days and then electroporated with CD19 CAR ORNA sequences. 74 total sequences were evaluated, comprising a combination of 5 CD19 CAR sequences comprising SEQ ID NOs: 19-23 (the 5 codon optimized sequences of Table 2A) and 18 IRES sequences (including IRESes comprising SEQ ID NOs: 1-15 of Table 1A) (see, e.g., Table 1B). Frequency of CD19 CAR expressing cells was analyzed via flow cytometry at 24-120 hr timepoints post-electroporation. Frequency of CD19 CAR expression was rank ordered for each timepoint pursuant to the tables below for each of Donor 609C and Donor 4003 as compared to a base control CD19 CAR and a combination HER2 standard control sequence.

TABLE

Donor 609C oCAR + cells (% T cells post- electroporation)

| Day 1 | | | Day 2 | | | Day 3 | | | Day 4 | | | Day 5 | | |
|---|---|---|---|---|---|---|---|---|---|---|---|---|---|---|
| 97 | | | 97 | | | 87 | | | 87 | | | 86 | | |
| 97.9 | 97.5 | 97.8 | 91.1 | 90.8 | 92.3 | 53.3 | 53.7 | 56.2 | 13.1 | 13.6 | 14.8 | 3.28 | 4.74 | 7.06* |
| 81 | | | 37 | | | 14 | | | 86 | | | 87 | | |
| 97.1 | 97.5 | 97.4 | 86.9 | 89.8 | 88.5 | 48.6 | 52.7 | 52.8 | 9.96 | 13.2 | 12.4 | 3.11 | 4.07 | 3.77 |
| 87 | | | 17 | | | 97 | | | 14 | | | 7 | | |
| 97 | 97.4 | 97.5 | 85.8 | 88.7 | 88.1 | 43.9 | 45.6 | 48.3 | 9.55 | 12.5 | 13.3 | 2.03 | 1.74 | 3.12 |
| 37 | | | 81 | | | 166 | | | 94 | | | 166 | | |
| 97.3 | 97.2 | 97.1 | 83.9 | 89.1 | 87.4 | 44.4 | 41.7 | 44 | 4.27 | 17.1* | 5.14 | 1.01 | 1.52 | 1.77 |
| 7 | | | 87 | | | 171 | | | 37 | | | 14 | | |
| 97 | 96.5 | 71.4* | 84.7 | 86.7 | 85 | 41 | 44.1 | 44.7 | 8.35 | 8.54 | 9.41 | 1.54 | 1.17 | 1.46 |
| 14 | | | 166 | | | 37 | | | 97 | | | 37 | | |
| 96.7 | 96.1 | 95.9 | 79.1 | 80.7 | 82.4 | 41.7 | 44.6 | 40.9 | 7.41 | 7.86 | 9.42 | 1.1 | 1.83 | 1.16 |
| 91 | | | 7 | | | 86 | | | 7 | | | 94 | | |
| 96.8 | 95.8 | 95.7 | 79.8 | 78.4 | 83.5 | 41.6 | 41.6 | 40.8 | 7.4 | 7.8 | 7.92 | 0.71 | 0.96 | 2.03 |
| 34 | | | 14 | | | 11 | | | 180 | | | 97 | | |

TABLE-continued

| Donor 609C oCAR + cells (% T cells post- electroporation) | | | | | | | | | | | | | | | | | | | |
|---|---|---|---|---|---|---|---|---|---|---|---|---|---|---|---|---|---|---|---|
| Day 1 | | | | Day 2 | | | | Day 3 | | | | Day 4 | | | | Day 5 | | | |
| 96.1 | 95.6 | 95.2 | 166 | 75.5 | 82 | 82.4 | 34 | 43.5 | 39.5 | 38.7 | 164 | 6.65 | 7.44 | 7.58 | 17 | 0.93 | 0.83 | 1.53 | 164 |
| 95.4 | 95.4 | 95.4 | 17 | 78.7 | 79.9 | 80.1 | 91 | 37.9 | 36.1 | 39 | 180 | 5.91 | 6.38 | 8.26 | 34 | 0.96 | 1.17 | 1 | 11 |
| 95.6 | 95.1 | 95.3 | 90 | 76.6 | 78.1 | 79.8 | 90 | 37.3 | 36.6 | 37.6 | 17 | 4.26 | 11.3* | 4.83 | 11 | 0.89 | 0.65 | 0.91 | 90 |
| 94.6 | 94.6 | 94.4 | 100 | 72.5 | 75.3 | 73 | 57 | 37.8 | 35.8 | 35.2 | 7 | 6.45 | 7.04 | 6.83 | 166 | 0.71 | 0.76 | 0.8 | 17 |
| 94.6 | 94.4 | 94.5 | 96 | 69.5 | 73.3 | 73 | 96 | 35.6 | 35 | 34.5 | 94 | 6.77 | 6.11 | 6.96 | 171 | 0.75 | 0.62 | 0.71 | 167 |
| 94.9 | 93.6 | 94.5 | 57 | 70.1 | 70.8 | 72 | 164 | 31.6 | 34.7 | 35.9 | 96 | 4.79 | 6.72 | 8.12 | 164 | 0.55 | 0.9 | 0.6 | 137 |
| 95 | 93.9 | 93.9 | 10 | 67.2 | 69 | 68.6 | 137 | 31.7 | 35.8 | 34.4 | 34 | 6.15 | 6.77 | 6.2 | 96 | 0.084 | 0.35 | 1.33 | 1 |
| 95 | 94.2 | 93.4 | 164 | 68.5 | 68.6 | 67.1 | 100 | 32.5 | 31.2 | 30.8 | 57 | 4.92 | 4.8 | 5.33 | 81 | 0.33 | 0.4 | 0.82 | 96 |
| 94.3 | 93.3 | 93.6 | 171 | 68.5 | 69.7 | 65.7 | 11 | 27.8 | 28 | 27.4 | 36 | 4.17 | 4.62 | 4.57 | 36 | 0.42 | 0.41 | 0.56 | 34 |
| 93.3 | 92.2 | 93 | 170 | 64 | 71.2 | 67.1 | 171 | 26.4 | 26.5 | 26.8 | 140 | 5.6 | 3.47 | 3.97 | 1 | 0.51 | 0.45 | 0.39 | 180 |
| 93.1 | 91.5 | 77.8* | 11 | 67.9 | 67 | 64.8 | 10 | 25.7 | 24.7 | 29.2 | 81 | 4.02 | 3.65 | 4.61 | 57 | 0.3 | 0.55 | 0.45 | 81 |
| 92.1 | 91.9 | 90.4 | 167 | 63.9 | 65.3 | 67.2 | 86 | 24.3 | 28.6 | 26.6 | 91 | 4.36 | 3.92 | 3.92 | 177 | 0.34 | 0.46 | 0.49 | 36 |
| 91.9 | 90.8 | 91.1 | 86 | 57.3* | 66 | 64.7 | 167 | 25 | 24.6 | 25.9 | 1 | 3.88 | 2.51 | 5.45 | 91 | 0.47 | 0.42 | 0.38 | 177 |
| 92 | 90.4 | 91.2 | 54 | 61.3 | 62.5 | 62.5 | 36 | 24.3 | 26.9 | 23 | 131 | 2.66 | 2.95 | 2.94 | 100 | 0.32 | 0.47 | 0.31 | 171 |
| 91.5 | 90.2 | 100* | 56 | 59.7 | 63.2 | 62.5 | 56 | 23 | 22.5 | 24.9 | 136 | 2.4 | 2.93 | 2.27 | 90 | 0.28 | 0.36 | 0.45 | 101 |
| 89.7 | 89.9 | 89.8 | 94 | 60.4 | 60 | 61.4 | 170 | 21.8 | 21.1 | 22.9 | 170 | 2.45 | 2.39 | 2.36 | 170 | 0.18 | 0.38 | 0.52 | 57 |
| 91 | 89.2 | 88.5 | 161 | 61.3 | 58.9 | 60.1 | 177 | 21.7 | 20.5 | 23 | 100 | 2.17 | 2.38 | 2.32 | HER2 std_2 | 0.19 | 0.2 | 0.46 | 91 |
| 90.1 | 88.3 | 89.2 | 36 | 57 | 60.1 | 58.9 | 94 | 21.9 | 21.8 | 21.5 | 137 | 0.03 | 6.42 | 0.054 | 136 | 0.11 | 0.25 | 0.42 | 51 |
| 90.8 | 88.4 | 87.9 | 177 | 56.3 | 59 | 59.1 | 114 | 21.2 | 17.9 | 19.9 | 31 | 2.33 | 2.11 | 1.57 | 140 | 0.12 | 0.13 | 0.21 | 131 |
| 88.9 | 90.2 | 87.9 | 114 | 56.5 | 58.6 | 58.2 | 31 | 21.5 | 20.2 | 17.2 | 177 | 1.13 | 2.15 | 2.72 | 31 | 0.085 | 0.15 | 0.22 | 67 |
| 88.4 | 87.5 | 87.5 | 137 | 56.3 | 55.4 | 60.6 | 140 | 19.7 | 19.9 | 19.2 | 90 | 1.89 | 1.8 | 2.19 | 137 | 0.11 | 0.15 | 0.18 | 116 |
| 88.1 | 86.9 | 87.9 | 31 | 55.3 | 58.2 | 57.9 | 54 | 16.2 | 16.5 | 17.8 | 10 | 1.59 | 1.66 | 1.98 | 167 | 0.065 | 0.13 | 0.24 | 10 |
| 88.4 | 87 | 86.2 | 180 | 55.2 | 62.5 | 50.2 | 180 | 16.4 | 18.1 | 15.3 | CD19 base_1 | 1.55 | 1.58 | 1.73 | 131 | 0.15 | 0.11 | 0.16 | 31 |
| 87.6 | 84.6 | 86.9 | CD19 base_1 | 72.2 | 47.4 | 47.7 | 161 | 16 | 15.8 | 17.2 | 101 | 1.54 | 1.09 | 1.75 | 10 | 0.071 | 0.11 | 0.23 | 136 |
| 87 | 85 | 84.6* | 64 | 53.1 | 55.5 | 54 | 64 | 15.4 | 15.6 | 16.9 | 54 | 1.38 | 1.36 | 1.36 | 114 | 0.12 | 0.1 | 0.19 | 54 |
| 86.3 | 86.5 | 84.5 | 77 | 49.5 | 51.3 | 51.4 | CD19 base_1 | 16 | 15.2 | 15.2 | CD19 base_2 | 1.11 | 1.51 | 1.28 | 101 | 0.11 | 0.038 | 0.19 | 170 |
| 85.5 | 82.3 | 83 | 66 | 50.7 | 46.7 | 49 | 131 | 14.8 | 16.1 | 14.5 | 167 | 1.16 | 1.22 | 1.29 | 161 | 0.076 | 0.075 | 0.17 | 56 |
| 84.4 | 82.7 | 83.3 | 140 | 48.7 | 46.2 | 48.3 | 77 | 13.4 | 12 | 14.1 | 114 | 1.15 | 1.38 | 1.06 | 54 | 0.098 | 0.13 | 0.079 | 104 |
| 83.6 | 82.2 | 82.2 | 51 | 46.8 | 48.8 | 47 | 67 | 11.2 | 13.4 | 13.3 | 67 | 1.1 | 1.09 | 1.01 | 77 | 0.064 | 0.083 | 0.13 | 100 |
| 83.6 | 80.8 | 0* | 67 | 31.3* | 45.9 | 47.4 | CD19 base_2 | 12.6 | 11.7 | 12.9 | 161 | 1.08 | 1.04 | 0.81 | CD19 base_1 | 0.062 | 0.065 | 0.12 | 176 |
| 83.9 | 81.1 | 79.9 | 61 | 46.8 | 46.1 | 44.6 | 66 | 12.7 | 11.6 | 12.8 | 51 | 0.9 | 0.89 | 1 | 67 | 0.071 | 0.065 | 0.088 | CD19 base_1 |
| 83.2 | 30.8* | 79.6 | 131 | 41.4* | 47.9 | 38.5 | 74 | 11.9 | 11.4 | 12.3 | 77 | 0.74 | 0.79 | 1.14 | CD19 base_2 | 0.093 | 0.024 | 0.08 | 161 |
| 82.2 | 79.8 | 80 | 101 | 39.9 | 46.7 | 41.9 | 134 | 10.5 | 10.5 | 12.6 | 134 | 0.64 | 0.93 | 1.06 | 56 | 0.048 | 0.075 | 0.074 | 134 |
| 82.6 | 79.2 | 78.7 | 1 | 48.6 | 38.5 | 38.6 | 104 | 10.4 | 10.9 | 11.4 | 56 | 0.65 | 0.87 | 0.89 | 51 | 0.072 | 0.082 | 0.037 | 77 |
| 80.4 | 77.9 | 76.3 | 74 | 40.1 | 41.9 | 43.6 | 51 | 10.6 | 10.1 | 11.1 | 104 | 0.69 | 0.48 | 0.81 | 66 | 0.096 | 0.067 | 0.023 | 114 |
| 79.7 | 77.2 | 77.7 | 80 | 29.2* | 40.6 | 39.2 | 136 | 8.91 | 8.79 | 10.3 | 74 | 0.59 | 0.63 | 0.66 | 104 | 0.062 | 0.051 | 0.054 | 40 |
| 79.1 | 77.5 | 76.5 | CD19 base_2 | 38.3 | 41.4 | 39.1 | 101 | 8.17 | 8.22 | 11 | 66 | 0.6 | 0.49 | 0.76 | 134 | 0.049 | 0.048 | 0.048 | 76 |
| 77.9 | 75.7 | 76.9 | 110 | 27.6* | 40.4 | 38.2 | 61 | 7.68 | 9.72 | 8.4 | 116 | 0.54 | 0.59 | 0.7 | 40 | 0.032 | 0.043 | 0.069 | HER2 std_2 |

TABLE-continued

Donor 609C oCAR + cells (% T cells post- electroporation)

| Day 1 | | | Day 2 | | | Day 3 | | | Day 4 | | | Day 5 | | |
|---|---|---|---|---|---|---|---|---|---|---|---|---|---|---|
| 77.3 | 76.8 | 75.8 | 37.7 | 39.3 | 38 | 7.06 | 6.8 | 7.64 | 0.63 | 0.64 | 0.54 | 0.00737 | 0.055 | 0.078 |
| 104 | | | 1 | | | 110 | | | 116 | | | CD19 base_2 | | |
| 77.3 | 75.4 | 48.4* | 24.4* | 36.2 | 39.1 | 7 | 6.32 | 5.8 | 0.48 | 0.65 | 0.6 | 0.029 | 0.037 | 0.063 |
| 24 | | | 110 | | | 40 | | | 107 | | | 20 | | |
| 0.2* | 75 | 100* | 36.6 | 34.7 | 38.8 | 6.14 | 6.1 | 6.58 | 0.46 | 0.39 | 0.5 | 0.051 | 0.021 | 0.051 |
| 134 | | | 40 | | | 107 | | | 176 | | | 74 | | |
| 75 | 76.6 | 68.2 | 30.9* | 35 | 29.6 | 5.82 | 5.96 | 6.21 | 0.49 | 0.35 | 0.43 | 0.042 | 0.042 | 0.037 |
| 136 | | | 80 | | | 64 | | | 74 | | | 140 | | |
| 72.5 | 71 | 71 | 28.3 | 30.8 | 32.2 | 5.21 | 4.55 | 5.36 | 0.41 | 0.34 | 0.45 | 0.037 | 0.046 | 0.035 |
| 40 | | | 107 | | | 76 | | | 106 | | | 64 | | |
| 69.4 | 70.1 | 71.8 | 26 | 28.9 | 30.2 | 3.97 | 4.97 | 4.8 | 0.3 | 0.37 | 0.33 | 0.047 | 0.035 | 0.036 |
| 71 | | | 71 | | | 80 | | | 76 | | | 66 | | |
| 63.8 | 60 | 60.5 | 23 | 25.3 | 22.8 | 4.17 | 4.91 | 4.25 | 0.31 | 0.46 | 0.2 | 0.041 | 0.046 | 0.031 |
| 107 | | | 106 | | | 106 | | | 110 | | | 106 | | |
| 63.8 | 59.7 | 60.2 | 16.3 | 18.9 | 19.7 | 4.24 | 4.04 | 5.03 | 0.42 | 0.16 | 0.26 | 0.033 | 0.024 | 0.052 |
| 111 | | | 76 | | | 176 | | | 80 | | | 80 | | |
| 55.5 | 52.7 | 52 | 13.9 | 14 | 14.8 | 3.79 | 3.9 | 3.81 | 0.26 | 0.25 | 0.2 | 0.031 | 0.04 | 0.025 |
| 106 | | | 111 | | | 61 | | | 64 | | | Mock | | |
| 52.3 | 48.7 | 49.6 | 12.3 | 13.7 | 14.1 | 2.8 | 3.41 | 3.09 | 0.21 | 0.21 | 0.14 | 0.026 | 0.027 | 0.041 |
| 70 | | | 176 | | | 71 | | | 111 | | | 70 | | |
| 48.2 | 45.2 | 100* | 13.2 | 13.2 | 12.6 | 1.64 | 1.9 | 2.1 | 0.17 | 0.11 | 0.18 | 0.028 | 0.032 | 0.032 |
| 76 | | | 120 | | | 111 | | | 71 | | | 27 | | |
| 47.8 | 43.2 | 43.8 | 10.1 | 13.7 | 12.2 | 1.68 | 2.27 | 1.61 | 0.13 | 0.12 | 0.11 | 0.023 | 0.042 | 0.026 |
| 120 | | | 70 | | | 120 | | | 61 | | | 124 | | |
| 44 | 41.4 | 0.3* | 10.2 | 10.4 | 12.7 | 0.9 | 1.08 | 1.18 | 0.14 | 0.1 | 0.11 | 0.049 | 0.019 | 0.015 |
| 176 | | | 116 | | | 70 | | | 120 | | | 26 | | |
| 42.9 | 38.3 | 41.3 | 7.32 | 7.19 | 7.23 | 0.56 | 0.72 | 0.73 | 0.097 | 0.086 | 0.094 | 0.03 | 0.022 | 0.031 |
| 116 | | | 27 | | | 24 | | | 127 | | | 120 | | |
| 30.4 | 26.3 | 27.2 | 1.67 | 2.32 | 2.02 | 0.17 | 0.17 | 0.29 | 0.077 | 0.098 | 0.047 | 0.023 | 0.016 | 0.044 |
| 27 | | | 20 | | | 27 | | | 20 | | | 110 | | |
| 10 | 8.34 | 7.66 | 0 | 0.76 | 1.06 | 0.19 | 0.16 | 0.16 | 0.11 | 0.067 | 0.04 | 0.00876 | 0.035 | 0.039 |
| 20 | | | 26 | | | 126 | | | 121 | | | 24 | | |
| 6.93 | 7.06 | 7.31 | 0.47 | 0.37 | 0.9 | 0.16 | 0.2 | 0.055 | 0.065 | 0.089 | 0.039 | 0.021 | 0.026 | 0.034 |
| 26 | | | 127 | | | 121 | | | 27 | | | 127 | | |
| 1.89 | 0.16 | 0* | 0.35 | 0.1 | 0.42 | 0.076 | 0.14 | 0.081 | 0.031 | 0.062 | 0.08 | 0.016 | 0.031 | 0.031 |
| 126 | | | 124 | | | HER2 std_1 | | | 126 | | | 61 | | |
| 0.46 | 0.46 | 0.6 | 0.32 | 0.096 | 0.21 | 0.059 | 0.14 | 0.094 | 0.09 | 0.049 | 0.033 | 0.028 | 0.012 | 0.034 |
| HER2 std_2 | | | 126 | | | 124 | | | 24 | | | HER2 std_1 | | |
| 0.46 | 0.67 | 0.31 | 0.25 | 0.26 | 0.067 | 0.11 | 0.12 | 0.045 | 0 | 0.052 | 0.11 | 0.015 | 0.025 | 0.028 |
| 124 | | | 130 | | | 130 | | | Mock | | | 71 | | |
| 0.4 | 0.39 | 0.44 | 0.028 | 0.28 | 0.086 | 0.042 | 0.099 | 0.12 | 0.05 | 0.047 | 0.065 | 0.02 | 0.022 | 0.025 |
| HER2 std_1 | | | 24 | | | HER2 std_2 | | | 26 | | | 130 | | |
| 0.32 | 0.12 | 0.61 | 0* | 0.13 | 0.13 | 0.03 | 0.13 | 0.082 | 0.043 | 0.055 | 0.063 | 0.02 | 0.024 | 0.02 |
| 127 | | | HER2 std_1 | | | Mock | | | HER2 std_1 | | | 121 | | |
| 0.24 | 0.35 | 0.27 | 0.024 | 0.076 | 0.2 | 0.078 | 0.094 | 0.06 | 0.056 | 0.034 | 0.071 | 0.026 | 0.00905 | 0.023 |
| Mock | | | 121 | | | 20 | | | 124 | | | 126 | | |
| 0.24 | 0.23 | 0.25 | 0.13 | 0 | 0.056 | 0.13 | 0.04 | 0.051 | 0.051 | 0.041 | 0.049 | 0.00939 | 0.01 | 0.018 |
| 130 | | | HER2 std_2 | | | 26 | | | 70 | | | 107 | | |
| 0.33 | 0.2 | 0.17 | 0.087 | 0.038 | 0 | 0.072 | 0.05 | 0.096 | 0.021 | 0.064 | 0.048 | 0.037 | 0 | 0 |
| 121 | | | Mock | | | 127 | | | 130 | | | 111 | | |
| 0.22 | 0.32 | 0.11 | 0 | 0 | 0 | 0 | 0.1 | 0.021 | 0.055 | 0.037 | 0.036 | 0.00878 | 0.027 | 0 |

TABLE

Donor 4003 oCAR + cells (% T cells post- electroporation)

| Day 1 | | | Day 2 | | | Day 3 | | |
|---|---|---|---|---|---|---|---|---|
| 171 | | | 166 | | | 37 | | |
| 97.8 | 97.5 | 97.6 | 93.7 | 93.9 | 93.5 | 50.9 | 43 | 30.5* |
| 7 | | | 7 | | | 81 | | |
| 97.6 | 97.8 | 96.8 | 92.9 | 93.5 | 93.5 | 43.1 | 41.5 | 11* |
| 161 | | | 87 | | | 86 | | |
| 97.1 | 97.1 | 97.4 | 93.6 | 92.3 | 93.2 | 43.6 | 38.6 | 36.9 |
| 87 | | | 171 | | | 17 | | |
| 97.4 | 97.6 | 96.4 | 91.9 | 93 | 91.8 | 38 | 34.2 | 13.9* |
| 166 | | | 81 | | | 100 | | |
| 96.8 | 97.2 | 96.2 | 91.2 | 88.1 | 87.4 | 36 | 30.5 | 39.5 |
| 100 | | | 100 | | | 164 | | |
| 96.8 | 96.1 | 97.1 | 87.2 | 88 | 88.9 | 33.8 | 29.2 | 33.2 |
| 177 | | | 177 | | | 94 | | |
| 96.6 | 96.8 | 96.6 | 88.7 | 100* | 87.2 | 34.8 | 25.6 | 2.61* |
| 14 | | | 161 | | | 14 | | |

TABLE-continued

| Donor 4003 oCAR + cells (% T cells post- electroporation) | | | | | | | | |
|---|---|---|---|---|---|---|---|---|
| 0* | 96.3 | 96 | 89.3 | 84.2 | 88.6 | 29.4 | 27.6 | 9.76* |
| 91 | | | 11 | | | 1 | | |
| 95.5 | 95.3 | 95.5 | 86.9 | 87.1 | 86.7 | 24 | 26.2 | 25.2 |
| 11 | | | 14 | | | 11 | | |
| 95.7 | 94.9 | 95.3 | 86.7 | 85.7 | 85.3 | 24.6 | 24.3 | 10.9* |
| 34 | | | 91 | | | 34 | | |
| 94.8 | 95.4 | 94.4 | 84.9 | 84.6 | 84.7 | 22.6 | 24.6 | 25.1 |
| 37 | | | 37 | | | 87 | | |
| 95.3 | 94.6 | 94.5 | 85.5 | 84.1 | 83.9 | 26 | 22.1 | 23.6 |
| 54 | | | 54 | | | 36 | | |
| 94.3 | 94.5 | 94.6 | 83.7 | 83.8 | 82.6 | 23.9 | 22.1 | 2.5e−002* |
| 164 | | | 131 | | | 177 | | |
| 94 | 95.5 | 93.3 | 83.5 | 83.1 | 82.9 | 25.7 | 22.6 | 20.6 |
| 57 | | | 57 | | | 137 | | |
| 94.4 | 93.7 | 92.8 | 83.5 | 82.8 | 82.2 | 23.4 | 21.4 | 0.11* |
| 81 | | | 164 | | | 161 | | |
| 93.9 | 93.2 | 93.4 | 83.2 | 82.6 | 82.6 | 23.5 | 20.9 | 0.12* |
| 170 | | | 86 | | | 166 | | |
| 93 | 93.4 | 92.1 | 82.6 | 81.9 | 83 | 23 | 19 | 18.2 |
| 94 | | | 34 | | | 7 | | |
| 92.8 | 91.9 | 92.4 | 81.4 | 80.7 | 81.1 | 19.9 | 18 | 14.9 |
| 96 | | | 94 | | | 171 | | |
| 91.6 | 91.8 | 93 | 81.7 | 78.8 | 80 | 17.9 | 15.6 | 8.54* |
| 66 | | | 170 | | | 180 | | |
| 92.4 | 90.9 | 92.4 | 77.8 | 78 | 78.5 | 16.2 | 13.2 | 19.3 |
| 86 | | | 17 | | | 131 | | |
| 91.3 | 91.7 | 91.8 | 78.5 | 77.4 | 76.4 | 16.9 | 16.1 | 13.9 |
| 131 | | | 66 | | | 90 | | |
| 91 | 91.3 | 90.6 | 74.2 | 77.5 | 76.9 | 15.5 | 12.1 | 0.5* |
| CD19 base__1 | | | 96 | | | 51 | | |
| 91.6 | 91.2 | 87.5 | 74.9 | 77 | 74.2 | 14.6 | 13.8 | 12.1 |
| 56 | | | 136 | | | 167 | | |
| 88.7 | 89 | 89.8 | 72.7 | 72.4 | 73.3 | 13.7 | 12.3 | 6.67* |
| 167 | | | CD19 base__1 | | | 114 | | |
| 89.6 | 87.7 | 89 | 74 | 71.6 | 72.4 | 13.5 | 12.1 | 42.2* |
| 114 | | | 137 | | | 66 | | |
| 88.3 | 88.7 | 88 | 73.3 | 72.6 | 71.9 | 15.3 | 13.2 | 9.24 |
| 17 | | | 140 | | | 40 | | |
| 88 | 87.6 | 88.9 | 71.8 | 72 | 70.9 | 14.1 | 11 | 0.31* |
| 137 | | | 180 | | | 170 | | |
| 87.7 | 89 | 87.5 | 72.3 | 71.1 | 70.7 | 13.2 | 10.2 | 2.72* |
| 31 | | | 31 | | | 140 | | |
| 88.3 | 88.3 | 87.4 | 72.8 | 70.7 | 69.7 | 11.4 | 10.2 | 0.072* |
| 1 | | | 167 | | | 134 | | |
| 86.1 | 87.9 | 89.5 | 72 | 72 | 67.6 | 10.3 | 8.59 | 0.62* |
| 140 | | | 114 | | | 77 | | |
| 87.2 | 87.5 | 88.2 | 70.1 | 69.3 | 71.3 | 9.34 | 8.03 | 2.29* |
| 77 | | | CD19 base__2 | | | 96 | | |
| 87.8 | 85.6 | 88 | 69.3 | 69.2 | 58 | 11.2 | 8.15 | 6.62 |
| CD19 base__2 | | | 56 | | | CD19 base__2 | | |
| 86.4 | 87.3 | 87.4 | 70 | 0* | 67.2 | 9.65 | 7.56 | 0.08* |
| 40 | | | 40 | | | 54 | | |
| 87.6 | 85.1 | 87.6 | 69.5 | 67.8 | 64.9 | 12* | 8.48 | 7.66 |
| 80 | | | 77 | | | 57 | | |
| 86.7 | 86.5 | 86.2 | 67.3 | 66.1 | 67.2 | 8.17 | 6.99 | 2.09* |
| 136 | | | 1 | | | 67 | | |
| 86.4 | 87.3 | 84.9 | 66.1 | 66.2 | 65.7 | 8.85 | 7.18 | 6.31 |
| 180 | | | 51 | | | 91 | | |
| 84.1 | 87.1 | 86.6 | 64 | 61.8 | 62.5 | 5.79 | 5.81 | 1.73* |
| 74 | | | 134 | | | 56 | | |
| 86.5 | 84.4 | 86.6 | 61.6 | 63.1 | 60.8 | 5.73 | 5.73 | 0.19* |
| 51 | | | 36 | | | 10 | | |
| 84.8 | 84.6 | 86.8 | 62.9 | 60.5 | 60.5 | 5.14 | 5.34 | 0* |
| 36 | | | 67 | | | CD19 base__1 | | |
| 83.8 | 83.8 | 85.2 | 60.6 | 58.5 | 61.4 | 5.83 | 4.6 | 5.17 |
| 76 | | | 90 | | | 101 | | |
| 82.6 | 83.5 | 84 | 58 | 57.1 | 57.1 | 5.03 | 4.06 | 4.72 |
| 101 | | | 74 | | | 116 | | |
| 82.5 | 83.9 | 83.5 | 59.1 | 57.6 | 54 | 4.81 | 4.43 | 4.28 |
| 67 | | | 76 | | | 110 | | |
| 81.8 | 81.2 | 83.4 | 56.1 | 51.4 | 52.2 | 4.09 | 3.55 | 8.14* |
| 90 | | | 101 | | | 61 | | |
| 81.1 | 79.5 | 82.2 | 53.4 | 51.3 | 51.9 | 4.21 | 3.25 | 18.4* |
| 134 | | | 10 | | | 136 | | |
| 81 | 79.4 | 81.4 | 54 | 50 | 20* | 4.56 | 2.81 | 0.08* |
| 10 | | | 80 | | | 64 | | |
| 75.6 | 80.4 | 79.5 | 52.8 | 50.8 | 49.1 | 4.21 | 2.73 | 42* |
| 64 | | | 64 | | | 76 | | |

TABLE-continued

| Donor 4003 oCAR + cells (% T cells post- electroporation) | | | | | | | | |
|---|---|---|---|---|---|---|---|---|
| 76.9 | 76.4 | 77.5 | 51.3 | 49 | 47 | 3.34 | 3.22 | 0.22* |
| 116 | | | 110 | | | 176 | | |
| 72.4 | 74.3 | 74.9 | 47.3 | 46.6 | 46.3 | 3.67 | 2.78 | 6.18* |
| 70 | | | 116 | | | 31 | | |
| 74.2 | 73.5 | 72.1 | 44.1 | 43.2 | 43.7 | 3.29 | 2.96 | 20.4* |
| 110 | | | 104 | | | 74 | | |
| 72.3 | 73 | 73.3 | 43.5 | 42 | 40.3 | 2.95 | 2.42 | 6.53* |
| 71 | | | 71 | | | 80 | | |
| 65.1 | 66.3 | 68 | 41.3 | 35.8 | 34.1 | 2.79 | 2.03 | 2.19 |
| 104 | | | 70 | | | 104 | | |
| 64.8 | 62.2 | 66.3 | 37.6 | 35.9 | 32.9 | 1.94 | 1.25 | 11.8* |
| 61 | | | 61 | | | 120 | | |
| 63.6 | 59.7 | 65.1 | 33.9 | 30.5 | 31.4 | 1.31 | 0.98 | 1.25 |
| 120 | | | 120 | | | 70 | | |
| 59.7 | 57.4 | 60.9 | 30.5 | 29.8 | 30.1 | 0.58 | 0.58 | 0.28 |
| 111 | | | 176 | | | 111 | | |
| 56.4 | 56.7 | 58.5 | 24.9 | 26.5 | 25.1 | 0.58 | 0.33 | 0.018* |
| 176 | | | 106 | | | 71 | | |
| 45.9 | 46.1 | 46.4 | 26.2 | 24.6 | 24.6 | 0.27 | 0.53 | 3.85* |
| 106 | | | 111 | | | 106 | | |
| 41.8 | 40.7 | 41.2 | 21.9 | 19.1 | 21.9 | 0.35 | 0.27 | 5.01* |
| 20 | | | 27 | | | HER2 std_2 | | |
| 22.41 | 26.2 | 25 | 3.77 | 50* | 3.45 | 0.17 | 0.13 | 18* |
| 27 | | | 127 | | | 107 | | |
| 12.1 | 15.5 | 16.3 | 1.75 | 0.66 | 1.21 | 0.17 | 0.084 | 24.3* |
| 107 | | | 20 | | | 24 | | |
| 1.25 | 1.73 | 2.1 | 1.03 | 0.63 | 0.45 | 0.15 | 0.067* | 0.1 |
| 126 | | | 24 | | | 26 | | |
| 1.48 | 0.84 | 1.93 | 1.16 | 0.21 | 0.066 | 0.14 | 0.022* | 0.1 |
| 124 | | | 107 | | | 130 | | |
| 1.06 | 1.14 | 0.58 | 0.47 | 0.37 | 0.34 | 0.11 | 0.13 | 0.048* |
| 130 | | | 124 | | | 127 | | |
| 0.8 | 0.59 | 0.047 | 0.28 | 0.33 | 0.32 | 0.15 | 0.088 | 11.8* |
| 127 | | | 126 | | | 27 | | |
| 0.26 | 0.4 | 0.63 | 0.24 | 0.37 | 0.22 | 0.059 | 0.14 | 4.33* |
| 97 | | | HER2 std_2 | | | 124 | | |
| 0.21 | 0.4 | 0.62 | 0.18 | 0.29 | 0.094 | 0.12 | 0.053 | 2.9* |
| HER2 std_2 | | | 121 | | | 97 | | |
| 0.31 | 0.42 | 0.23 | 0.075 | 0.17 | 0.2 | 0.077 | 0.069 | 1.54* |
| 24 | | | 26 | | | 20 | | |
| 0.34 | 0.23 | 0.31 | 0.21 | 0.19 | 0.03 | 0.067 | 0.056 | 2.96* |
| 26 | | | Mock | | | 126 | | |
| 0.23 | 0.39 | 0.19 | 0.17 | 0.21 | 0.042 | 0.058 | 0.058 | 0.33* |
| Mock | | | HER2 std_1 | | | Mock | | |
| 0.19 | 0.082 | 0.066 | 0.081 | 0.19 | 0.14 | 0 | 0.17 | 0 |
| HER2 std_1 | | | 97 | | | 121 | | |
| 0.15 | 0.12 | 0.045 | 0.16 | 0.19 | 0.042 | 0.05 | 0.058 | 0.17* |
| 121 | | | 130 | | | HER2 std_1 | | |
| 0.14 | 0.08 | 0.074 | 0.13 | 0.12 | 0.098 | 0 | 0.081 | 0.037 |

| Day 4 | | | Day 5 | | |
|---|---|---|---|---|---|
| | | 37 | | | 100 |
| 11.6 | 14.5 | 30.7* | 2.1 | 2.56 | 0.4* |
| 86 | | | 87 | | |
| 10.2 | 9.99 | 8.67 | 2.02 | 1.73 | 1.94 |
| 81 | | | 7 | | |
| 8.76 | 7.62 | 7.26 | 2.02 | 1.64 | 1.52 |
| 17 | | | 37 | | |
| 6.18 | 5.09 | 5.45 | 1.32 | 0.89* | 1.29 |
| 14 | | | 86 | | |
| 6.13 | 4.9 | 4.84 | 1.01 | 0.84 | 0.86 |
| 87 | | | 81 | | |
| 6.31 | 4.82 | 4.71 | 1.09* | 0.86 | 0.89 |
| 164 | | | 17 | | |
| 5.22 | 4.52 | 3.54 | 0.69 | 0.61 | 0.51 |
| 11 | | | 14 | | |
| 4.74 | 3.6 | 3.84 | 0.83 | 0.5 | 0.47 |
| 94 | | | 166 | | |
| 4.18 | 3.88 | 3.42 | 0.74 | 0.49 | 0.46 |
| 36 | | | 177 | | |
| 3.89 | 4.36 | 2.98 | 0.57 | 0.53 | 0.4 |
| 7 | | | 171 | | |
| 4.21 | 3.81 | 3.07 | 0.38 | 0.41 | 0.36 |
| 1 | | | 94 | | |
| 3.96 | 3.29 | 3.2 | 0.41 | 0.33 | 0.33 |
| 100 | | | 57 | | |

TABLE-continued

| Donor 4003 oCAR + cells (% T cells post- electroporation) | | | | | |
|---|---|---|---|---|---|
| 10.4* | 4.19 | 2.68 | 0.35 | 0.31 | 0.28 |
| 177 | | | 11 | | |
| 3.18 | 3.04 | 3.1 | 0.34 | 0.29 | 0.27 |
| 34 | | | 164 | | |
| 3.76 | 3.01 | 2.5 | 0.3 | 0.26 | 0.15* |
| 166 | | | 34 | | |
| 2.81 | 3 | 2.07 | 0.31 | 0.28 | 0.23 |
| 90 | | | 137 | | |
| 2.5 | 2.04 | 3.25 | 0.26 | 0.18 | 0.21 |
| 137 | | | 167 | | |
| 2.73 | 1.77 | 1.86 | 0.21 | 0.23 | 0.19 |
| 161 | | | 1 | | |
| 1.91 | 1.99 | 1.68 | 0.22 | 0.17 | 0.14 |
| 167 | | | 90 | | |
| 1.73 | 1.66 | 1.84 | 0.38* | 0.16 | 0.19 |
| 180 | | | 91 | | |
| 1.98 | 1.73 | 1.5 | 0.16 | 0.14 | 0.086* |
| 171 | | | 96 | | |
| 1.94 | 1.81 | 1.32 | 0.18 | 0.096* | 0.12 |
| 96 | | | 180 | | |
| 1.58 | 1.25 | 1.1 | 0.19 | 0.12 | 0.12 |
| 40 | | | 161 | | |
| 1.1 | 0.94 | 1.03 | 0.14 | 0.12 | 0.11 |
| 131 | | | 56 | | |
| 1 | 1.09 | 0.83 | 0.029* | 0.1 | 0.098 |
| 51 | | | 131 | | |
| 1.3* | 0.95 | 0.96 | 0.12* | 0.092 | 0.082 |
| 57 | | | 170 | | |
| 1.52* | 0.96 | 0.78 | 0.085 | 0.059 | 0.092 |
| 170 | | | 36 | | |
| 1.6* | 0.88 | 0.82 | 0.28* | 0.072 | 0.084 |
| 66 | | | 136 | | |
| 0.89 | 0.78 | 0.59 | 0.13* | 0.065 | 0.078 |
| 114 | | | 114 | | |
| 0.92 | 0.73 | 0.56 | 0.072 | 0.053 | 0.069 |
| 67 | | | 66 | | |
| 0.84 | 0.52 | 0.49 | 0.057 | 0.038 | 0.061 |
| 77 | | | 77 | | |
| 0.79 | 0.56 | 0.49 | 0.042 | 0.064 | 0.045 |
| 54 | | | 176 | | |
| 0.64 | 0.59 | 0.44 | 0.06 | 0.051 | 0.035 |
| 56 | | | 54 | | |
| 0.38 | 0.61 | 0.68 | 0.058 | 0.015* | 0.037 |
| 140 | | | CD19 base_1 | | |
| 0.72 | 0.62 | 0.32 | 0.045 | 0.07 | 0.027 |
| 91 | | | 10 | | |
| 0.6 | 0.6 | 0.41 | 0.02 | 0.064 | 0.055 |
| 10 | | | 40 | | |
| 0.33 | 0.7 | 0.52 | 0.065 | 0.034 | 0.04 |
| 134 | | | 140 | | |
| 0.65 | 0.42 | 0.46 | 0.051 | 0.024 | 0.061 |
| CD19 base_2 | | | 134 | | |
| 0.54 | 0.4 | 0.34 | 0.044 | 0.058 | 0.028 |
| 116 | | | 31 | | |
| 0.43 | 0.43 | 0.31 | 0.034 | 0.047 | 0.042 |
| 101 | | | 67 | | |
| 0.57 | 0.33 | 0.26 | 0.07 | 0.023 | 0.029 |
| CD19 base_1 | | | 110 | | |
| 0.42 | 0.19 | 0.43 | 0.035 | 0.039 | 0.047 |
| 176 | | | 51 | | |
| 0.38 | 0.36 | 0.3 | 0.033 | 0.031 | 0.047 |
| 31 | | | 76 | | |
| 0.3 | 0.25 | 0.27 | 0.049 | 0.027 | 0.027 |
| 136 | | | 101 | | |
| 0.29 | 0.2 | 0.22 | 0.025 | 0.038 | 0.037 |
| 104 | | | 20 | | |
| 0.16 | 0.16 | 0.17 | 0.035 | 0.039 | 0.025 |
| 71 | | | Mock | | |
| 0.07 | 0.15 | 0.16 | 0.028 | 0.05 | 0.018 |
| 110 | | | 74 | | |
| 0.12 | 0.13 | 0.13 | 0.022 | 0.023 | 0.045 |
| 61 | | | CD19 base_2 | | |
| 0.1 | 0.16 | 0.086 | 0.031 | 0.031 | 0.028 |
| 64 | | | 124 | | |
| 0.13 | 0.11 | 0.1 | 0.042 | 0.028 | 0.017 |
| 74 | | | 107 | | |
| 0.12 | 0.14 | 0.066 | 0.037 | 0.02 | 0.023 |
| 80 | | | 126 | | |

TABLE-continued

| Donor 4003 oCAR + cells (% T cells post- electroporation) | | | | | |
|---|---|---|---|---|---|
| 0.12 | 0.1 | 0.095 | 0.014 | 0.029 | 0.044 |
| 76 | | | 80 | | |
| 0.11 | 0.071 | 0.12 | 0.027 | 0.025 | 0.033 |
| 120 | | | 27 | | |
| 0.072 | 0.1 | 0.075 | 0.042 | 0.026 | 0.013 |
| HER2 std_1 | | | HER2 std_1 | | |
| 0.079 | 0.088 | 0.063 | 0.026 | 0.024 | 0.023 |
| 111 | | | 116 | | |
| 0.1 | 0.025 | 0.092 | 0.06* | 0.029 | 0.019 |
| 121 | | | 104 | | |
| 0.12 | 0.068 | 0.026 | 0.028 | 0.015 | 0.027 |
| 106 | | | 97 | | |
| 0.083 | 0.062 | 0.068 | 0.014 | 0.033 | 0.022 |
| HER2 std_2 | | | 61 | | |
| 0.054 | 0.071 | 0.07 | 0.02 | 0.02 | 0.027 |
| 26 | | | 26 | | |
| 0.059 | 0.1 | 0.032 | 0.02 | 0.017 | 0.028 |
| 126 | | | 127 | | |
| 0.08 | 0.029 | 0.075 | 0 | 0.037 | 0.028 |
| 70 | | | 64 | | |
| 0.052 | 0.042 | 0.089 | 0.00729 | 0.031 | 0.025 |
| Mock | | | 121 | | |
| 0.032 | 0.059 | 0.089 | 0.035 | 0.01 | 0.017 |
| 24 | | | 24 | | |
| 0.1 | 0.046 | 0.027 | 0.028 | 0.013 | 0.019 |
| 27 | | | 130 | | |
| 0.066 | 0 | 0.098 | 0.02 | 0.018 | 0.021 |
| 20 | | | 106 | | |
| 0.061 | 0.048 | 0.039 | 0.016 | 0.017 | 0.023 |
| 127 | | | HER2 std_2 | | |
| 0.053 | 0.062 | 0.029 | 0.024 | 0.017 | 0.013 |
| 97 | | | 71 | | |
| 0.041 | 0.057 | 0.042 | 0 | 0.022 | 0.031 |
| 107 | | | 120 | | |
| 0.032 | 0.066 | 0.028 | 0.014 | 0.022 | 0.015 |
| 124 | | | 70 | | |
| 0.05 | 0.027 | 0.029 | 0.00858 | 0.029 | 0.00597 |
| 130 | | | 111 | | |
| 0.052 | 0.016 | 0.015 | 0 | 0.014 | 0.0081 |

Figure 7A:
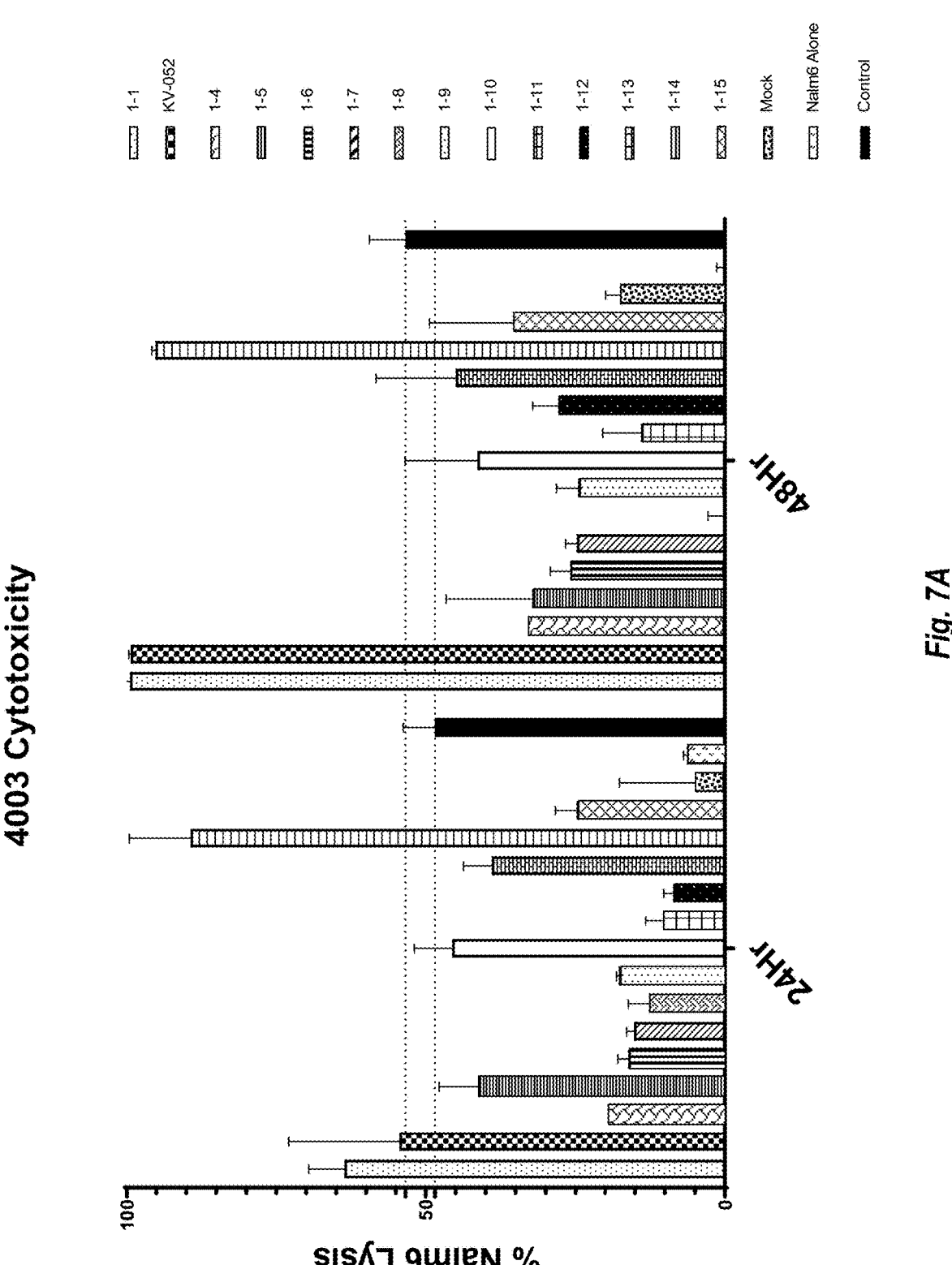
FIG. 7A and FIG. 7B show the effect of varying the IRES on % Nalm6 Lysis data at 24 hours and 48 hours. Different constructs were created comprising the base CD19 codon (3276) were created in combination with different IRESes, including the IRES nos. 1-1, 1-4, 1-5, 1-6, 1-7, 1-8, 1-9, 1-10, 1-11, 1-12, 1-13, 1-14, and 1-15 in Table 1A (comprising SEQ ID NOs: 1, 4-15), as compared to a mock negative control, the IRES for a base CD19 CAR control, and Nalm6 alone in two different donors (609C and 4003).
Figure 7B:
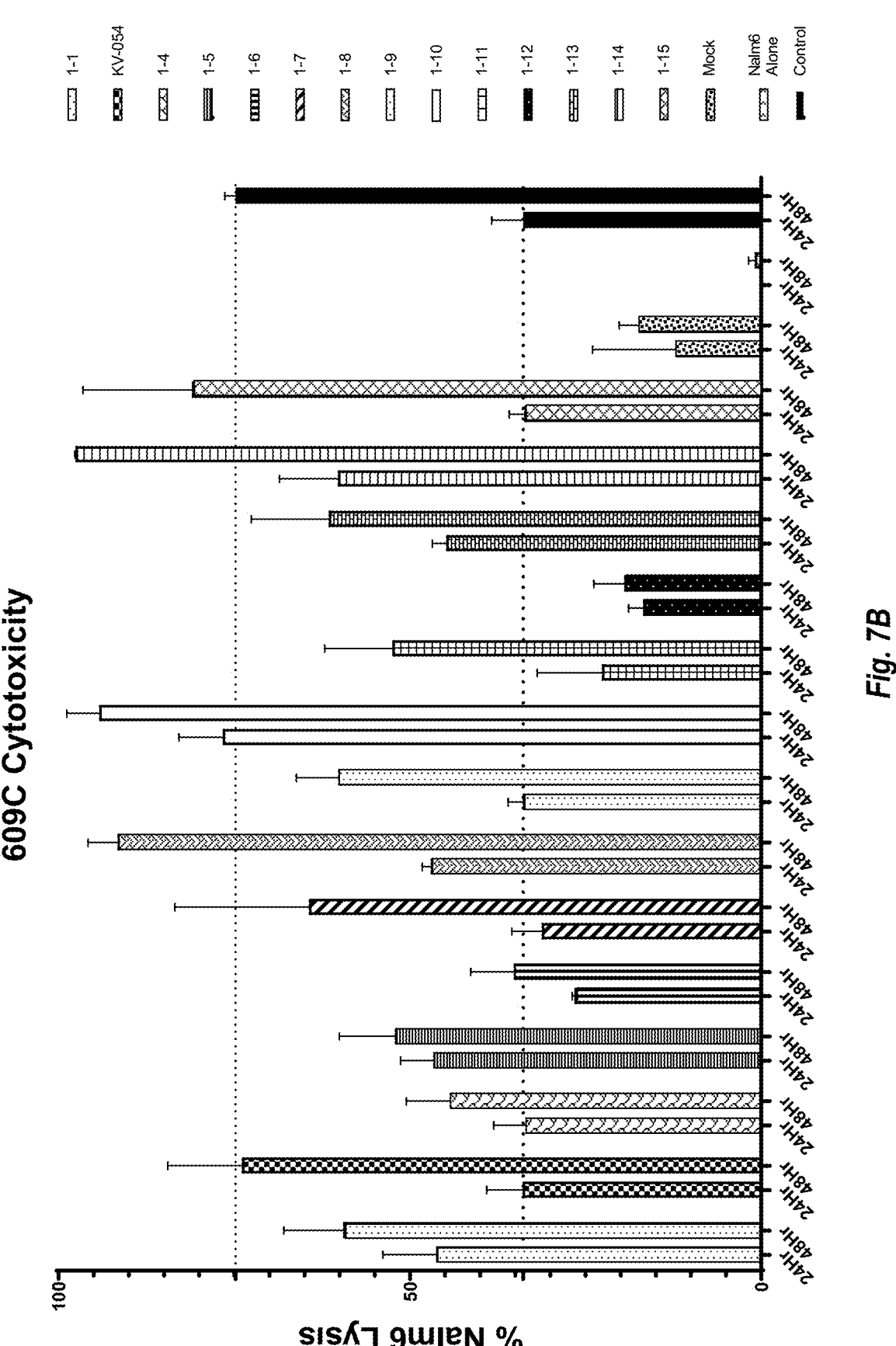

Example 5: Effects of IRES on Cytotoxicity oRNA constructs comprising a base CD19 CAR construct in combination with different IRESes described in Table 1A (see, e.g., Table 1B), including the IRES sequences corresponding to SEQ ID NOs: 1, 4-15 were assessed for % Nalm6 lysis in two donors (Donor 4003 and Donor 609C). CD3+ T cells from two healthy donors (609C; 4003) were activated with aCD3/CD28 tetrameric complexes for 3 days and then electroporated with the CD19 CAR ORNA sequences. Nalm6 killing was assessed at 24 and 48 hours for each CD19 CAR base oRNA construct along with a mock negative control, Nalm6 alone, and the base alone. See FIGS. 7A-7B. Dotted horizontal lines reflect Nalm6 killing at 24- and 48-hour timepoints using the control CD19 CAR oRNA base construct (3276).

Example 6: Cytotoxicity

A. Cytotoxicity (69 Constructs)

CD3+ T cells from two healthy donors (609C; 4003) were activated with aCD3/CD28 tetrameric complexes for 3 days and then electroporated with CD19 CAR ORNA sequences. 74 total sequences including the 69 constructs of Table 5 were evaluated, comprising a combination of 5 CD19 CAR sequences comprising SEQ ID NOs: 19-23 (the 5 codon optimized sequences of Table 2A) and 18 IRES sequences (including controls). 24 hours post-electroporation, transfected T cells were co-cultured with Nalm6 cells for up to 48 hours. Nalm6 killing was assessed at 24 and 48 hours for each CD19 CAR oRNA construct and all constructs were rank ordered based on Nalm6 killing at 24 hours. Dotted horizontal lines reflect Nalm6 killing at 24 and 48 hour timepoints using the control CD19 CAR oRNA base construct (3276).

Figure 8A:
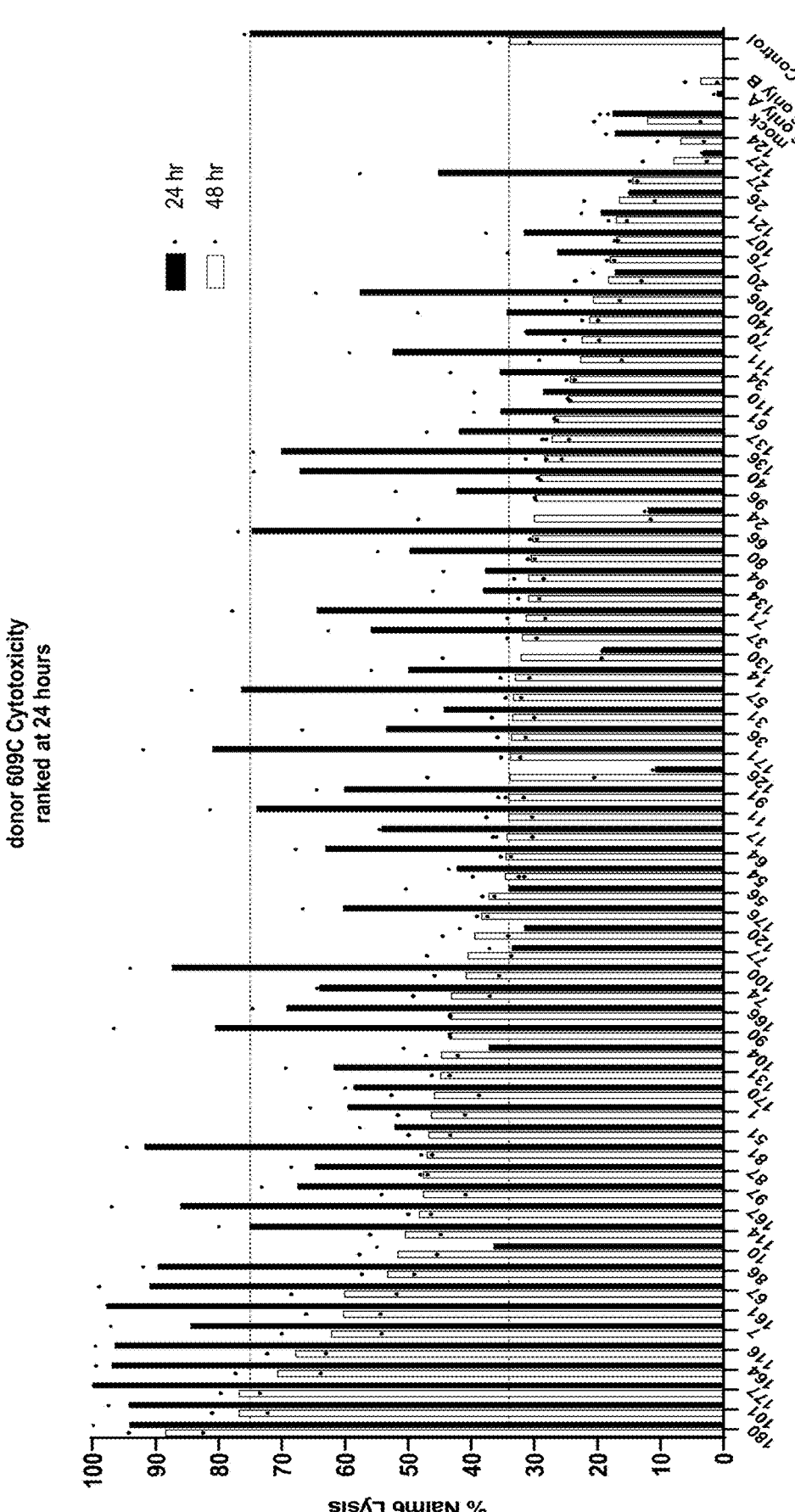
FIG. 8A and FIG. 8B show cytotoxicity data in two different donors (609C and 4003) for the 69 CD19 CAR ORNA constructs identified by IRES/CO construct numbers in Table 5 as compared to a mock negative control, a base CD19 CAR control, and Nalm6 alone, ranked at 24 and 48 hours.
Figure 8B:
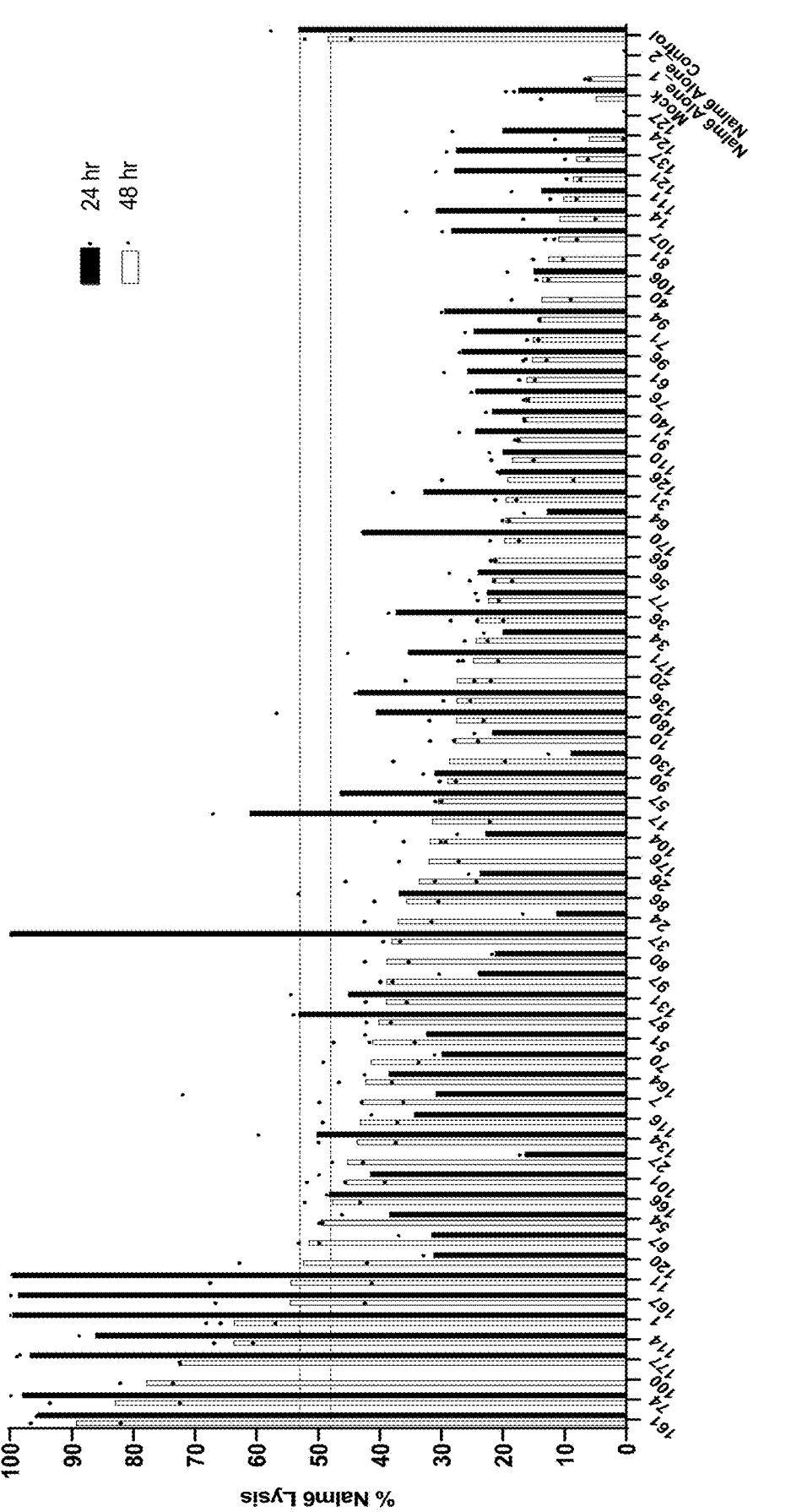
Figure 9A:
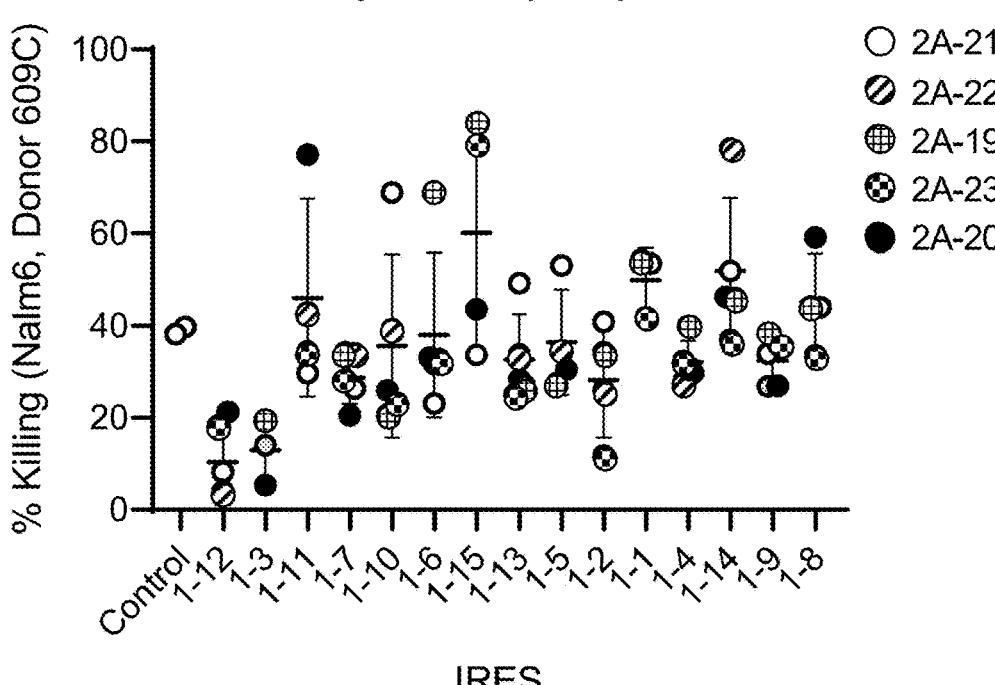
FIGS. 9A, 9B, 9C, and 9D reflect similar % Nalm6 killing cytotoxicity data for the CD19 CAR ORNA constructs as in FIGS. 8A and 8B for days 1 and 2 for the two donors, but is presented in a different visual format. Each point on the X axis is an IRES comprising the sequences of SEQ ID NOs: 1-15 (IRES nos. 1-1 to 1-15, described in Table 1A). Each dot is a different codon comprising the sequences of SEQ ID NOs 19-23 (codon nos. 2A-19 to 2A-23, described in Table 2A, codon optimized; anti-CD19 28-¿). The control is the IRES for a base CD19 CAR control (3276).
Figure 9B:
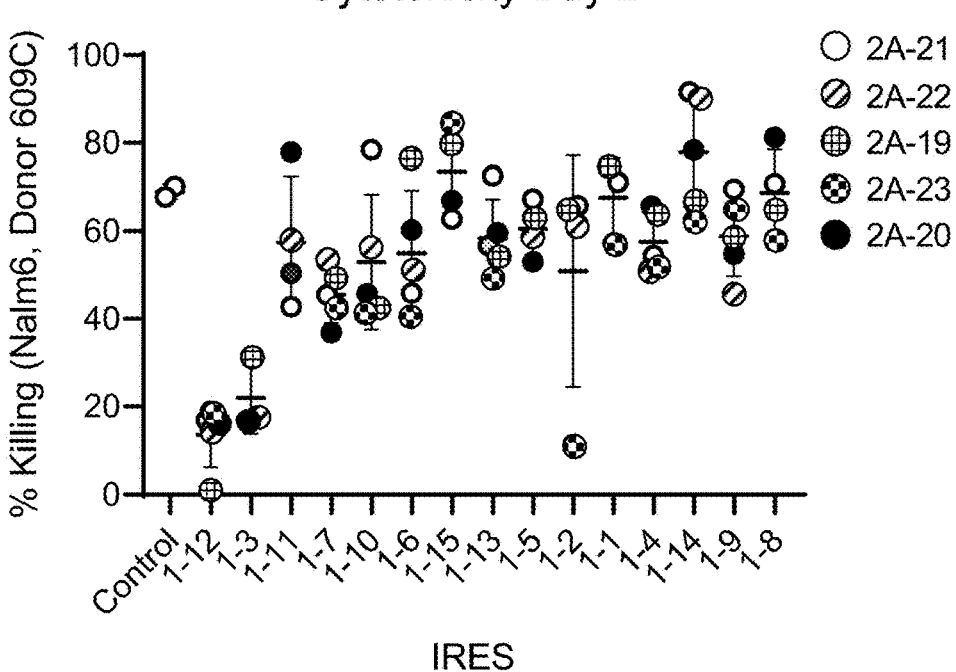
Figure 9C:
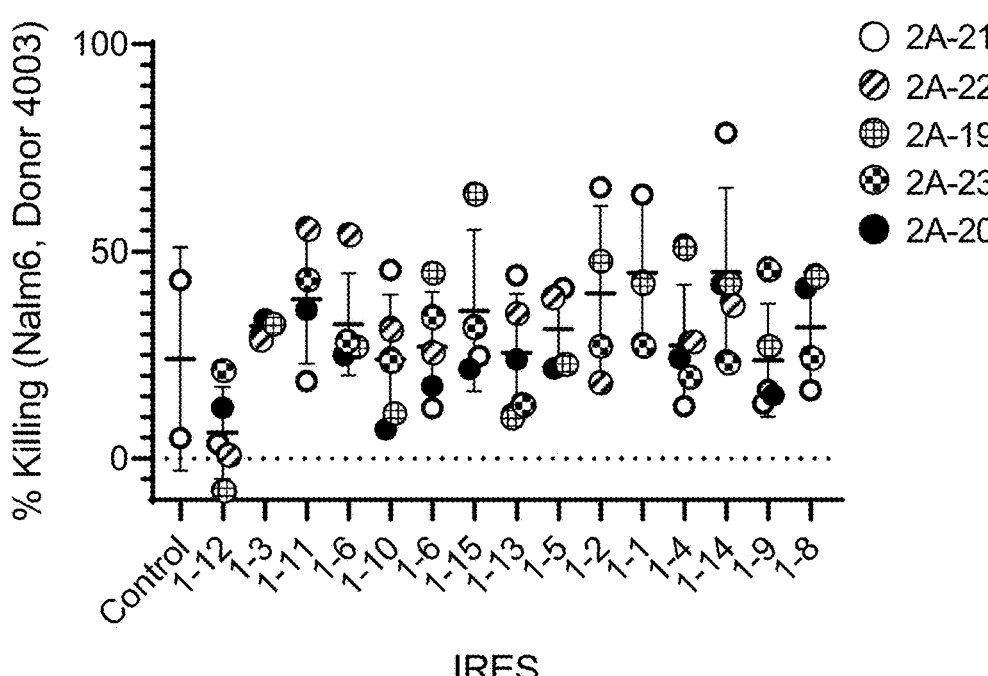
Figure 9D:
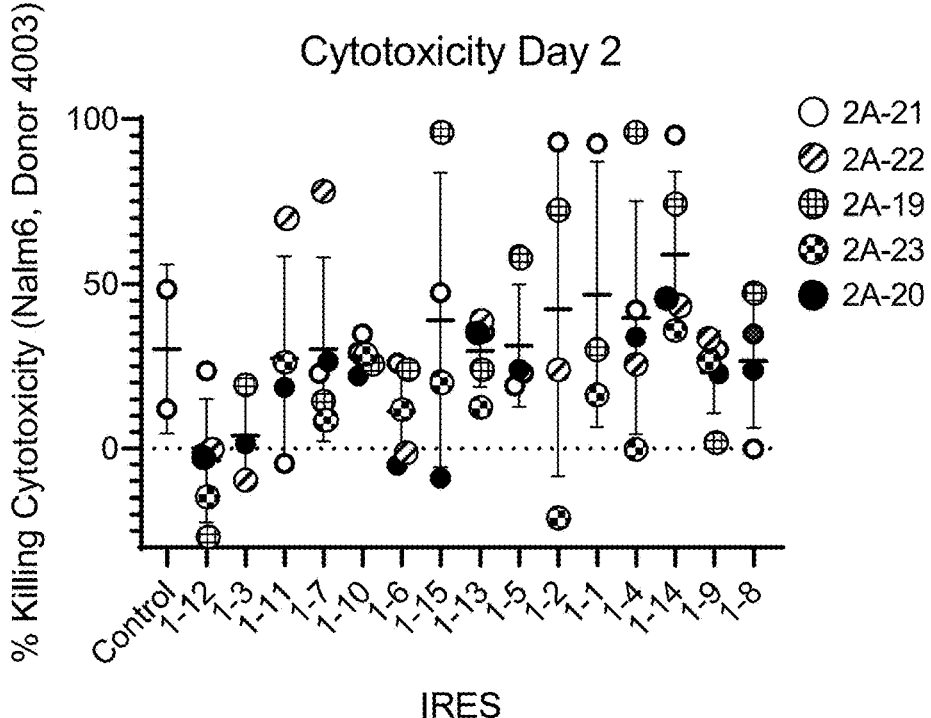
Figure 10A:
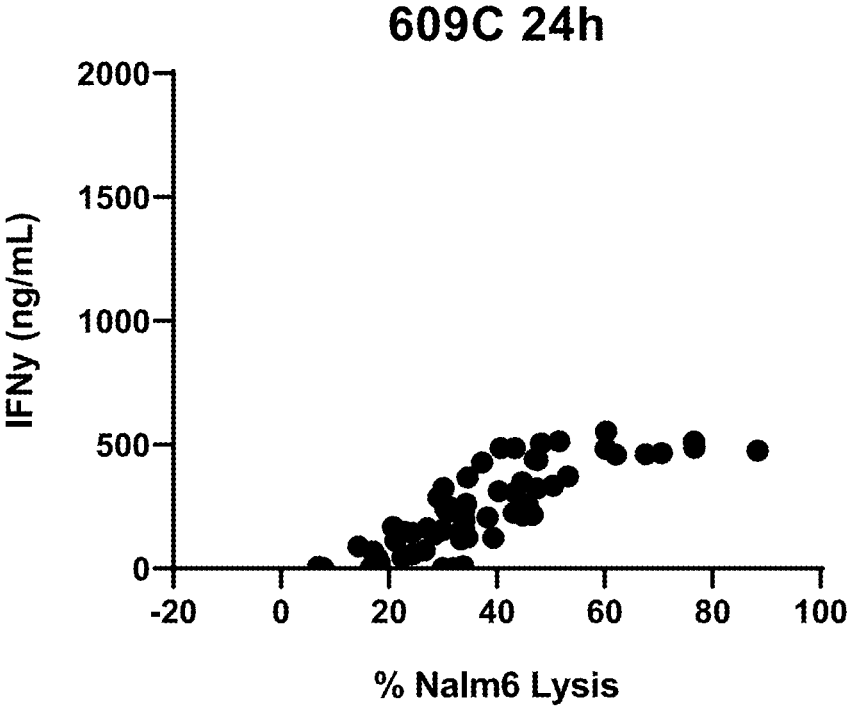
FIGS. 10A, 10B, 10C, and 10D reflect IFNγ expression and FIGS. 10E, 10F, 10G, and 10H reflect IL-2 expression at 24- and 48-hours post-electroporation for 69 CD19 CAR circular RNA constructs in two different donors (609C and 4003).
Figure 10B:
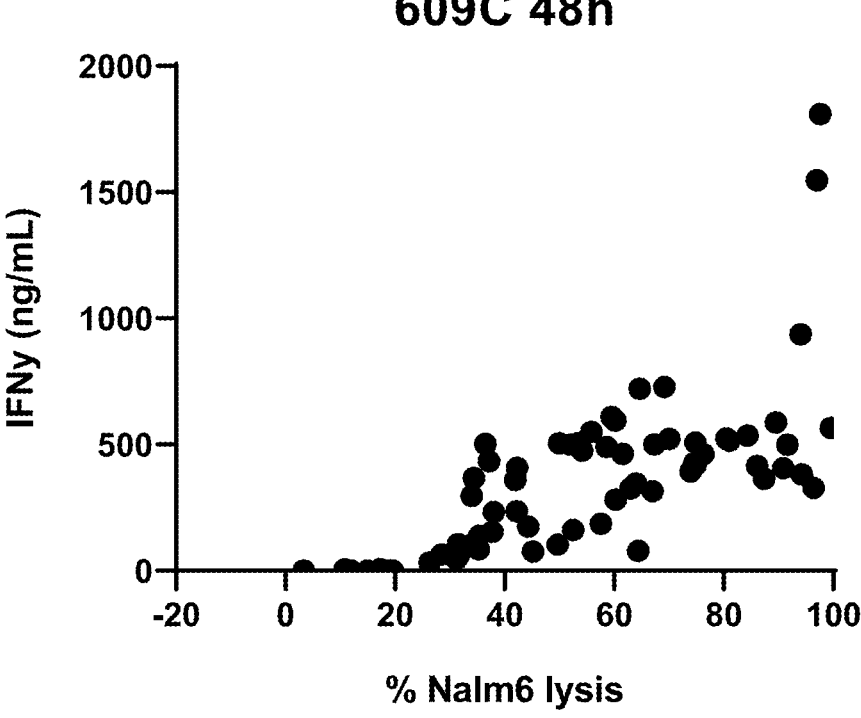
Figure 10C:
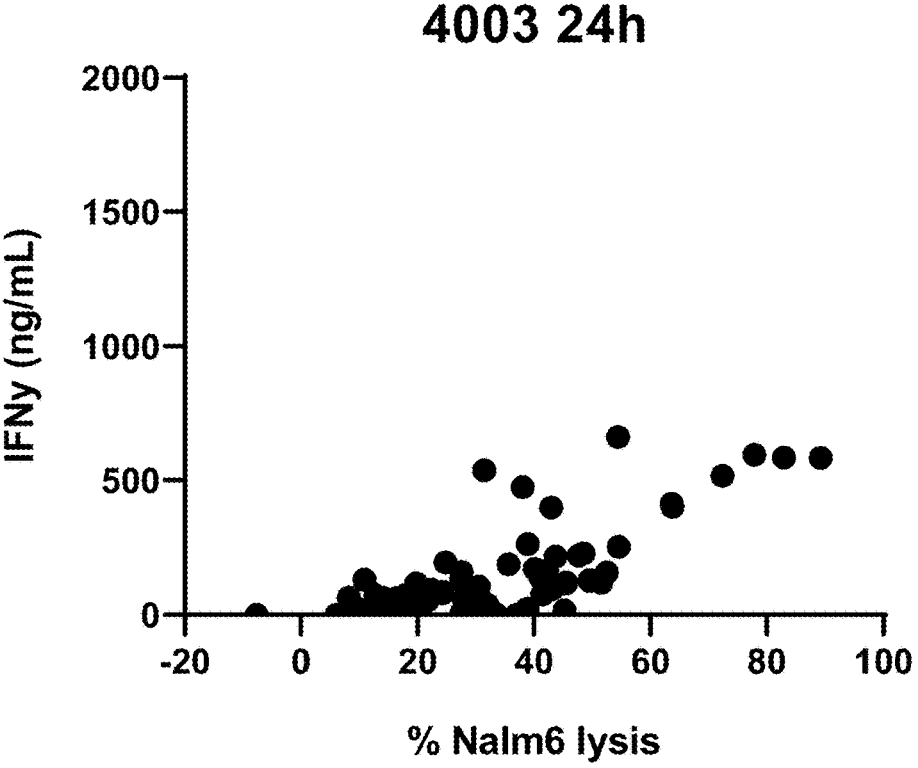
Figure 10D:
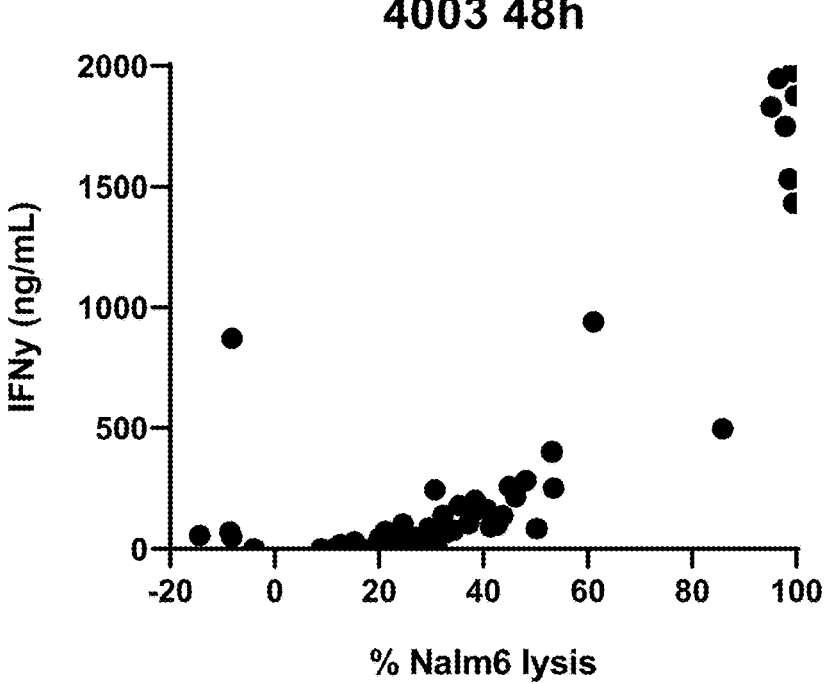
Figure 10E:
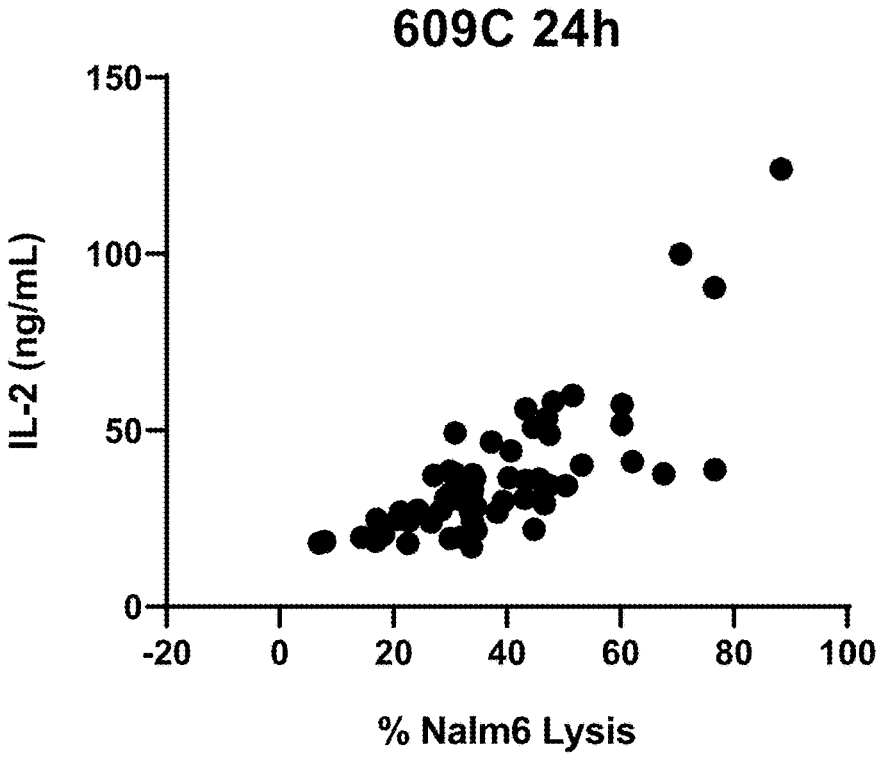
Figure 10F:
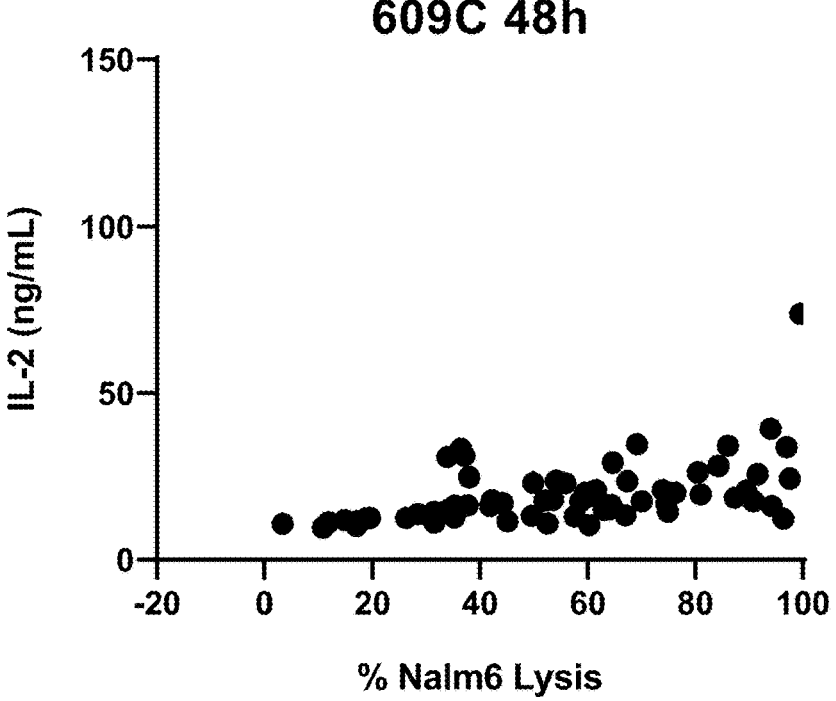
Figure 10G:
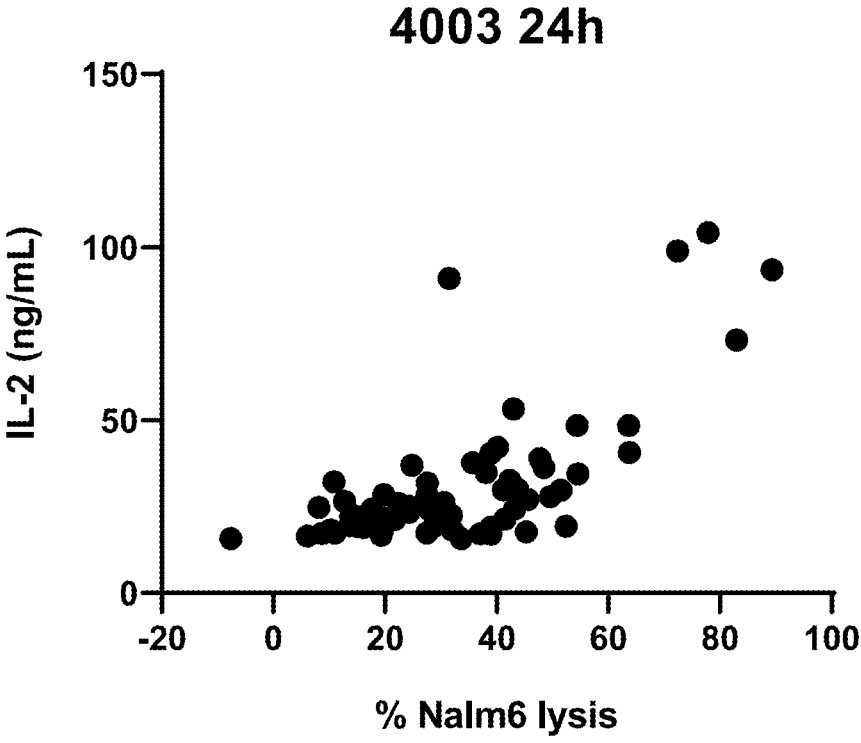
Figure 10H:
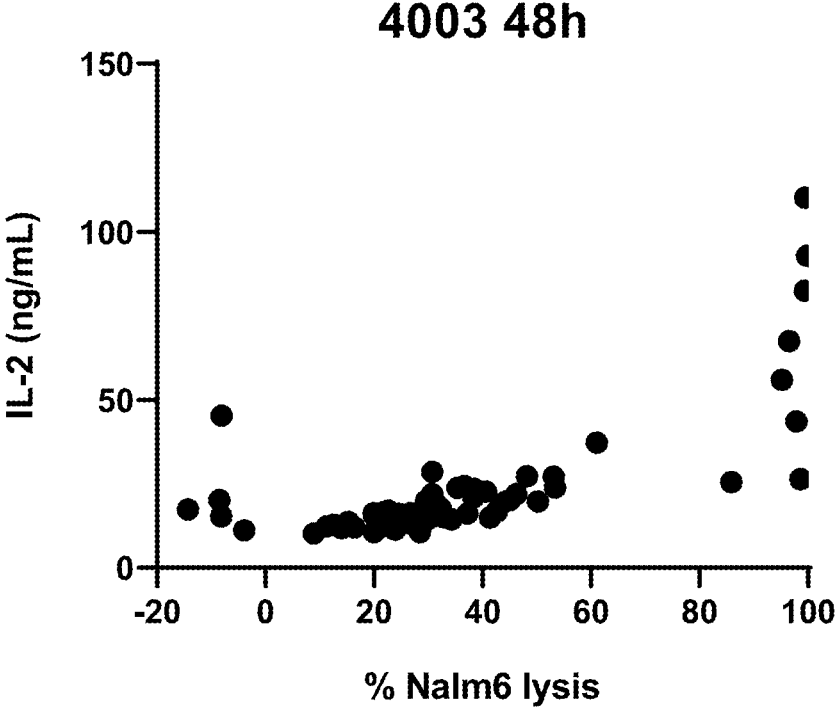

FIGS. 8A-8B and the tables below show a gradient across the constructs with certain constructs performing better than the base. FIG. 9A-9D present the same cytotoxicity data as FIGS. 8A-8B, but is organized by the IRESes in Table 1A (including IRESes comprising SEQ ID NOs: 1-15 of Table IA, and an IRES corresponding to a base CD19 control) and the expression sequences in Table 2A, for days 1 and 2 for the two donors.

TABLE

| Donor 609C (cytotoxicity) | | | | | |
|---|---|---|---|---|---|
| Construct number | 24 hours | | | 48 hours | |
| 180 | 82.47 | | 94.26 | 99.83 | 88.28 |
| 101 | 72.26 | | 81.07 | 97.48 | 90.96 |
| 177 | 73.46 | 79.66 | | 99.3 | 99.86 |
| 164 | 77.31 | 63.82 | | 99.42 | 94.53 |
| 116 | 72.3 | 62.95 | | 99.48 | 93.29 |
| 7 | 54.22 | | 69.98 | 97.14 | 71.58 |
| 161 | 54.38 | 66.14 | | 97.65 | 97.55 |
| 67 | 68.49 | 51.85 | | 98.96 | 82.72 |
| 86 | 57.35 | 49.01 | | 91.98 | 87.07 |
| 10 | 57.74 | | 45.42 | | 17.95 | 54.97 |
| 114 | | 44.83 | 56.02 | 79.97 | 69.84 |

TABLE-continued

Donor 609C (cytotoxicity)

| Construct number | 24 hours | | | 48 hours | | |
|---|---|---|---|---|---|---|
| 167 | 50.01 | | 46.4 | 96.99 | | 75.15 |
| 97 | | 40.88 | 54.2 | 73.19 | 61.54 | |
| 87 | 48.07 | | 46.87 | | 68.47 | 60.87 |
| 81 | 46.21 | 47.9 | | 94.59 | 88.67 | |
| 51 | 49.97 | 43.35 | | | 57.7 | 46.32 |
| 1 | 40.97 | 51.64 | | 65.48 | 53.55 | |
| 170 | | 38.78 | 52.68 | | 59.99 | 57.11 |
| 131 | 46.25 | 43.41 | | 69.35 | 53.78 | |
| 104 | 47.21 | | 42.14 | 23.61 | 50.69 | |
| 90 | 43.32 | | 43.42 | 96.65 | | 64.33 |
| 166 | | 43.33 | 43.35 | 74.59 | 63.71 | |
| 74 | | 37.07 | 49.22 | 64.39 | 63.58 | |
| 100 | 35.55 | 45.84 | | 94.07 | 80.59 | |
| 77 | | 33.67 | 47.04 | 37.12 | 29.73 | |
| 120 | 44.55 | | 34.14 | 21.06 | 41.83 | |
| 176 | 37.43 | | 39.09 | 66.66 | 53.82 | |
| 56 | 36.33 | | 38.22 | 17.58 | 50.35 | |
| 54 | 32.47 | 31.56 | 39.74 | 43.57 | 40.91 | |
| 64 | | 35.31 | 33.68 | 67.78 | 58.17 | |
| 17 | 30.28 | 36.02 | 36.52 | 54.59 | 53.72 | |
| 11 | 30.34 | 37.59 | | 81.38 | 66.48 | |
| 91 | 35.71 | 34.52 | 31.65 | 64.43 | 55.96 | |
| 126 | | 20.54 | 46.96 | 11.28 | | 10.29 |
| 171 | | 32.24 | 35.25 | 91.99 | | 70.07 |
| 36 | | 35.83 | 31.36 | 66.75 | 40.24 | |
| 31 | | 36.7 | 30.02 | 48.7 | 39.85 | |
| 57 | | 34.55 | 32.07 | 84.31 | 68.29 | |
| 14 | 30.75 | | 35.34 | 55.87 | 44.05 | |
| 130 | | 19.37 | 44.52 | 18.27 | 19.24 | 19.19 |
| 37 | 29.61 | 34.24 | | 62.62 | 48.96 | |
| 71 | 28.23 | | | 34.26 | 77.87 | 50.88 |
| 134 | | 29.23 | 32.53 | 29.88 | 46.09 | |
| 94 | | 28.51 | 33.15 | 44.42 | 31.05 | |
| 80 | | 30.98 | 29.93 | 54.84 | 44.52 | |
| 66 | 29.56 | | | 30.69 | 76.9 | 72.33 |
| 24 | | 11.57 | 48.39 | | 12.55 | 11.18 |
| 96 | | 29.77 | 29.91 | 52.02 | 32.35 | |
| 40 | 29.42 | | 28.99 | 74.42 | 59.57 | |
| 136 | 31.34 | 28.04 | 25.67 | 74.52 | 65.51 | |
| 137 | 24.52 | 28.72 | 28.08 | | 47.09 | 36.73 |
| 61 | | 26.37 | 26.82 | 39.57 | 30.87 | |
| 110 | | 24.19 | 24.62 | 39.51 | 17.47 | |
| 34 | 23.6 | 24.86 | | 43.28 | 27.4 | |
| 111 | 16.2 | | 29.21 | 45.69 | 59.32 | |
| 70 | 25.21 | 19.8 | | 31.08 | 31.29 | |
| 140 | 19.92 | 22.47 | | 20.23 | 48.47 | |
| 106 | 16.52 | | 24.97 | 64.57 | 50.56 | |
| 20 | | 13.03 | 23.51 | 20.73 | 13.61 | |
| 76 | 17.4 | 18.49 | | 34.25 | 18.25 | |
| 107 | 17.3 | 16.75 | | 37.66 | 25.44 | |
| 121 | | 15.41 | 18.29 | 16.45 | 22.58 | |
| 26 | | 10.96 | 22.16 | 14.97 | 14.86 | |
| 27 | 13.72 | 14.92 | | 57.7 | | 32.66 |
| 127 | | 2.7 | 12.85 | 3.5 | 3.11 | |
| 124 | | 3.15 | 10.52 | 18.67 | 15.48 | |
| mock | | 3.68 | 20.55 | 14.35 | 19.67 | 18.38 |
| Nalm6 only A | −6.09 | −1.05 | | 0.36 | | 1.56 |
| Nalm6 only B | 6.09 | 1.05 | | −0.36 | | −1.56 |
| PL3276.1* | | | | | | |
| PL3276.2 | 30.74 | | | 37.05 | 75.91 | 73.75 |

TABLE

Donor 4003 (cytotox)

| Construct Number | Donor 4003 | | | | | |
|---|---|---|---|---|---|---|
| | 24 hours | | | 48 hours | | |
| 161 | 82.07 | | 96.59 | 95.34 | 94.55 | 95.66 |
| 74 | 72.42 | 93.48 | | | 95.92 | 99.87 |
| 100 | 82.18 | 73.54 | | | −0.82 | −15.45 |

TABLE-continued

Donor 4003 (cytotox)

| Construct Number | Donor 4003 | | | | | |
|---|---|---|---|---|---|---|
| | 24 hours | | | 48 hours | | |
| 177 | 72.49 | | 72.33 | 92.42 | 98.85 | 98.39 |
| 114 | 66.9 | 60.59 | | 88.82 | 82.94 | |
| 1 | 65.83 | 56.91 | 68.18 | | 99.96 | 99.03 |
| 167 | 42.45 | | 66.65 | | 99.9 | 97.3 |
| 11 | 41.33 | | 67.52 | | 99.61 | 99.19 |
| 120 | | 42.12 | 62.76 | 29.21 | | 32.94 |
| 67 | | 53.2 | 49.86 | 36.92 | 26.15 | |
| 54 | | 49.35 | 49.85 | 46.19 | | 30.5 |
| 166 | | 43.19 | 52.24 | 47.79 | 48.65 | |
| 101 | 51.86 | 39.2 | 45.65 | 49.91 | 32.88 | |
| 27 | | 47.8 | 42.77 | | 15.45 | 17.24 |
| 134 | 50.02 | 37.41 | | 59.67 | 40.79 | |
| 116 | 49.3 | 37.15 | | 41.38 | | 27.21 |
| 7 | 36.2 | 42.97 | 49.86 | 71.98 | 0.2 | 19.92 |
| 164 | | 38.03 | 46.68 | | 42.48 | 34.38 |
| 70 | | 33.71 | 49.2 | 31.1 | | 28.42 |
| 51 | 47.51 | 41.68 | 34.37 | 42.39 | | 22.13 |
| 87 | 38.23 | 42.17 | | 52.26 | 53.98 | |
| 131 | 35.64 | 42.33 | | 54.41 | | 35.62 |
| 97 | | 39.91 | 37.95 | | 17.42 | 30.36 |
| 80 | 35.32 | 42.43 | | | 20.7 | 21.77 |
| 37 | | 39.48 | 36.72 | | 99.82 | 99.81 |
| 24 | | 31.64 | 42.49 | 16.79 | | 5.88 |
| 86 | 30.49 | 40.88 | | 53.23 | | 20.11 |
| 26 | 31.09 | 24.27 | 45.6 | 21.73 | | 25.58 |
| 176 | | 36.89 | 27.19 | −39.29 | | −1.09 |
| 104 | 36.13 | 29.29 | 30.11 | | 27.42 | 18.1 |
| 17 | | 40.86 | 22.09 | | 67.06 | 55.07 |
| 57 | 29.99 | 31 | | 46.16 | | 46.3 |
| 90 | | 30.29 | 27.67 | | 32.92 | 28.97 |
| 130 | 37.81 | 19.66 | | 12.68 | | 5.09 |
| 10 | 27.93 | 31.85 | 24.06 | 24.62 | 18.81 | |
| 180 | 23.14 | 31.97 | | 56.71 | | 24.62 |
| 136 | 25.31 | | 29.72 | 43.45 | 44.03 | |
| 20 | 21.97 | 24.62 | 35.85 | −56.38 | | −9.6 |
| 171 | 26.48 | 27.24 | 20.75 | | 45.25 | 25.48 |
| 34 | 26.22 | 22.48 | | | 23.08 | 16.9 |
| 36 | 28.52 | 19.96 | 24.21 | 38.59 | 35.78 | |
| 77 | 24.08 | 20.69 | | | 24.45 | 20.86 |
| 56 | 18.5 | 25.39 | 21.38 | 28.7 | 22.11 | 21.25 |
| 66 | 21.96 | 21.16 | | −24.9 | | −3.67 |
| 170 | 17.4 | 22.07 | | 42.8 | 42.58 | |
| 64 | 20.12 | 19.01 | | | 16.55 | 8.62 |
| 31 | 21.26 | 17.77 | | 37.89 | | 27.69 |
| 126 | | 8.62 | 29.94 | | 20.47 | 20.84 |
| 110 | 21.86 | 15.09 | | | 17.68 | 22.17 |
| 91 | 17.42 | 18.01 | | | 27.14 | 22.06 |
| 140 | 16.51 | 16.48 | | | 22.75 | 20.98 |
| 76 | 16.59 | 15.86 | | | 25.11 | 23.59 |
| 61 | | 17.37 | 14.91 | 29.58 | 25.06 | 23.1 |
| 96 | 16.69 | 16.26 | 13.01 | | 27.07 | 26.36 |
| 71 | 14.31 | | 16.06 | 26.14 | 23.43 | |
| 94 | 14.17 | | 14.13 | | 29.96 | 29.18 |
| 40 | | 18.59 | 9.03 | −15.65 | | −0.65 |
| 106 | 14.66 | 12.69 | | | 19.27 | 11.37 |
| 81 | | 15.11 | 10.29 | −16.59 | | −0.47 |
| 107 | 8.08 | 11.77 | 13.21 | 29.86 | | 27.01 |
| 14 | | 16.68 | 5.03 | 35.76 | 25.75 | |
| 111 | 8.1 | 12.36 | | | 18.59 | 9.42 |
| 121 | 9.76 | 7.55 | | 30.91 | | 24.92 |
| 137 | 6.3 | | 9.98 | 29.17 | 26.4 | |
| 124 | 11.62 | 0.53 | | | 11.61 | 28.24 |
| 127 | −4.27 | −3.68 | −14.9 | | 0.37 | −8.26 |
| Mock | −4 | 13.88 | | 14.87 | 18.18 | 19.52 |
| Nalm6 Alone_1 | 5.93 | 6.74 | | −0.39 | −0.04 | −6.8 |
| Nalm6 Alone_2 | −5.93 | −6.74 | | 0.39 | 0.04 | |
| 3276_1 | | 44.73 | 52.2 | 57.63 | 49.11 | |

B. Comparison of Cytokine Production and Cytotoxicity

Coculture supernatants were collect and analyzed using Meso Scale Discovery (MSD) (Agilent Technologies, Santa Clara, CA) for IFNγ (FIGS. 10A-D) and IL-2 expression (FIGS. 10E-H). CD3+ T cells from two healthy donors (609C, first row; 4003, second row) were activated with αCD3/CD28 tetrameric complexes for 3 days and then electroporated with CD19 CAR ORNA sequences. 74 total sequences were evaluated, comprising a combination of 5 CD19 CAR sequences comprising SEQ ID NOs: 19-23 (the 5 codon optimized sequences of Table 2A) and 18 IRES sequences (which include IRES sequences corresponding to SEQ ID NOs: 1-15 in Table 1A) (see, e.g., Table 1B). 24 hours post-electroporation, transfected T cells were co-cultured with Nalm6 cells for up to 48 hours. At 24-hour and 48-hour timepoints, supernatants were collected and IL-2 and IFN-γ amounts were quantified via MSD.

Example 7: Cytotoxicity (12 Constructs of Table 6)

Figure 11:
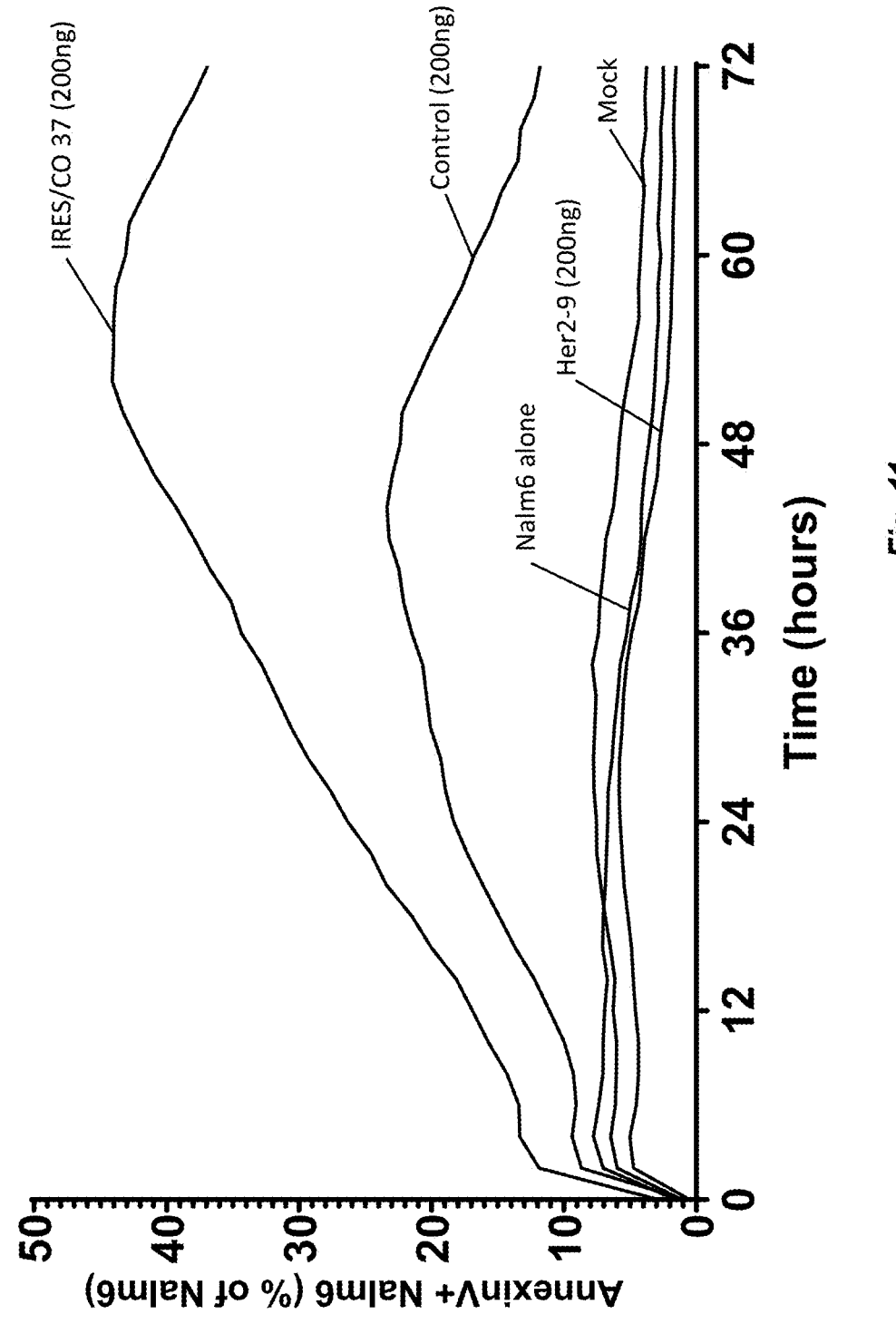
FIG. 11 shows Annexin V+Nalm6 (% of Nalm6) for a CD19 CAR construct of IRES/CO Clone #37 (SEQ ID NO: 52) as compared to a base CD19 CAR construct (3276) containing a non- optimized CAR sequence, a HER2 circular RNA construct (comprising HER2_9), a mock negative control, and Nalm6 alone.

Cytotoxicity was assessed for the 12 circular RNA constructs of Table 6 by administering the circular RNA constructs over 3 days (24, 48, 72 hours) and assessing cytotoxicity at 2 E: T up to 72 hours, luminescence and Incucyte based cytotoxicity readouts, and cytokine readouts from luminescence plates. CD3+ T cells were activated with aCD3/CD28 tetrameric complexes for 3 days and then transfected with PEG-modified lipid 86 of Table 3 (lipid of Formula I) delivering a HER2 construct (HER2_9, Table 9), a base CD19 CAR construct (3276 comprising SEQ ID NO: 21) containing a non-optimized CAR sequence, or the CD19 CAR construct of IRES/CO Clone #37 (Table 5) of SEQ ID NO: 52. 24 hours post-transfection, T cells were co-cultured with GFP+Nalm6 B-ALL cells at 1:20 T cell to Nalm6 ratio. Annexin V was added to mark dead cells. Co-cultures were imaged via Incucyte every 2 hours to identify Nalm6, dead/dying cells, and dead/dying Nalm6 cells. Results are plotted as percentage of dead/dying Nalm6 cells divided by total Nalm6 cells. See FIG. 11. These data show the oRNA construct comprising the sequence of SEQ ID NO: 43 as compared to a base CD19 CAR construct (3276) and as compared to a HER2 oRNA with a mock negative control and as compared to Nalm6 alone.

Example 8: In Vitro Experimentation (12 Constructs)

Figure 12A:
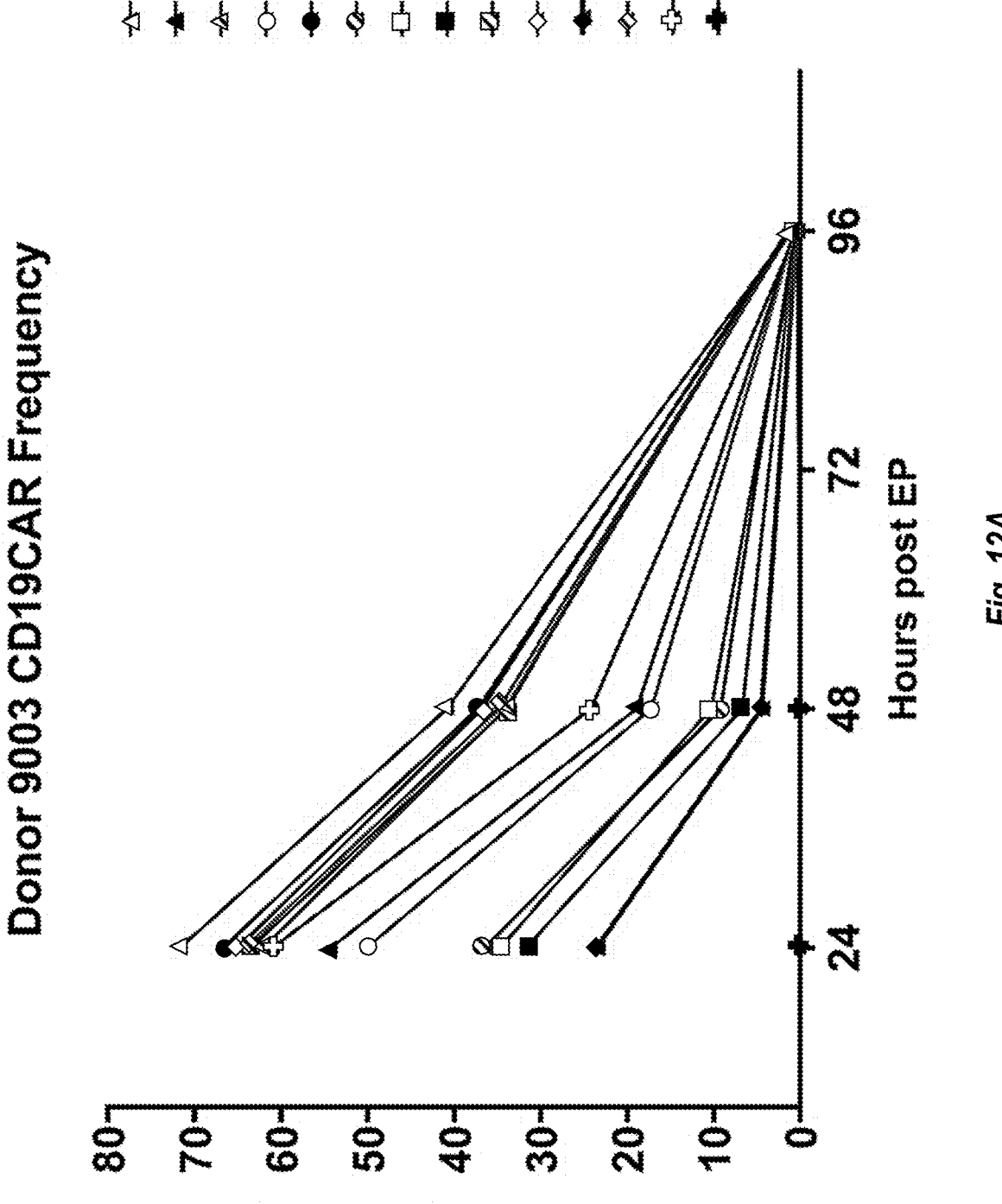
FIG. 12A shows % of T cells over 96 hours for the 12 CD19 CAR constructs of Table 6 (identified by IRES/CO clone number) for Donor 9003.
Figure 12C:
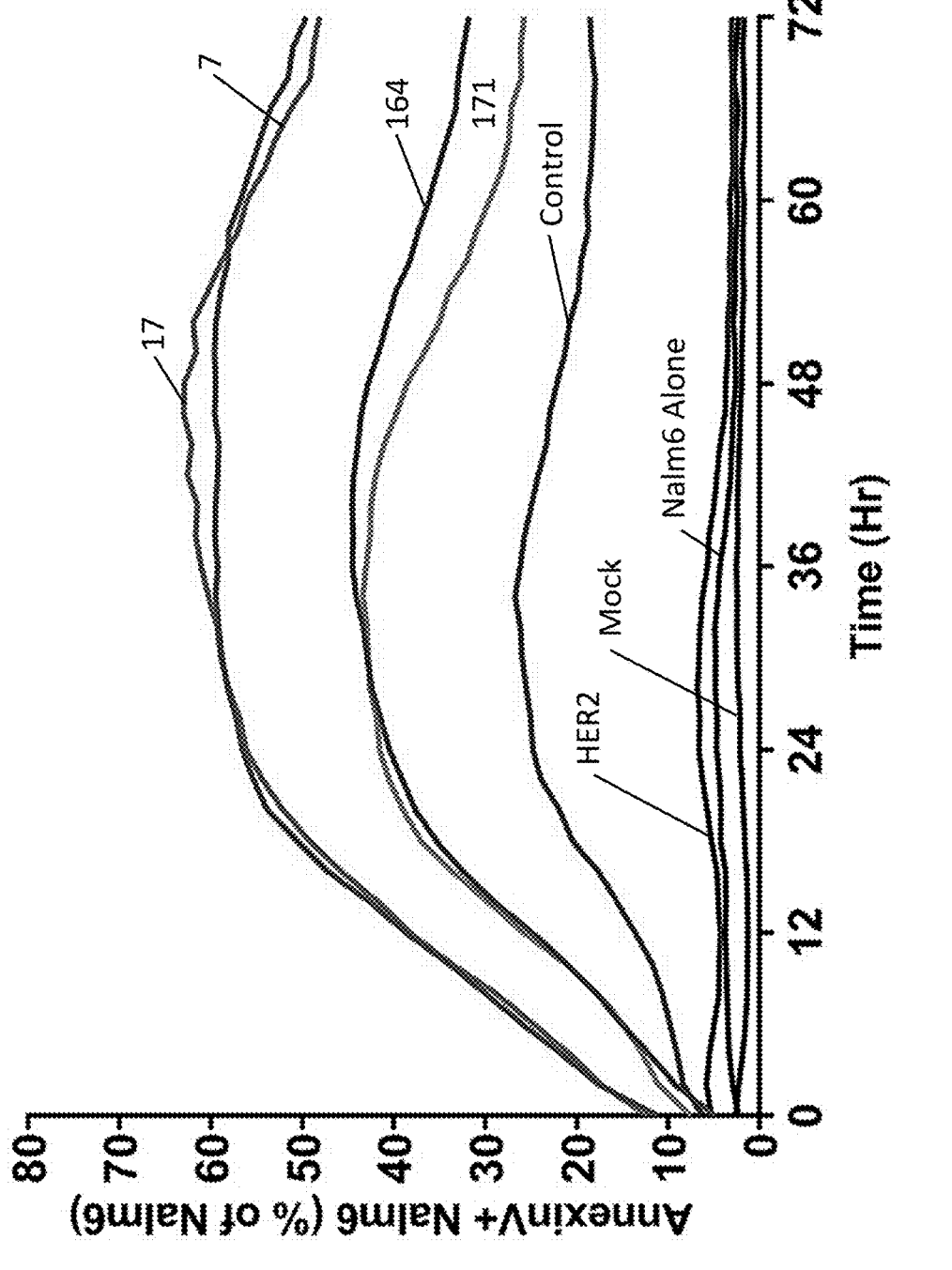
FIG. 12C shows Annexin V+Nalm6 over 72 hours as compared to a base CD19 CAR control (3276), a mock negative control, Nalm6 alone, and HER2.
Figure 13A:
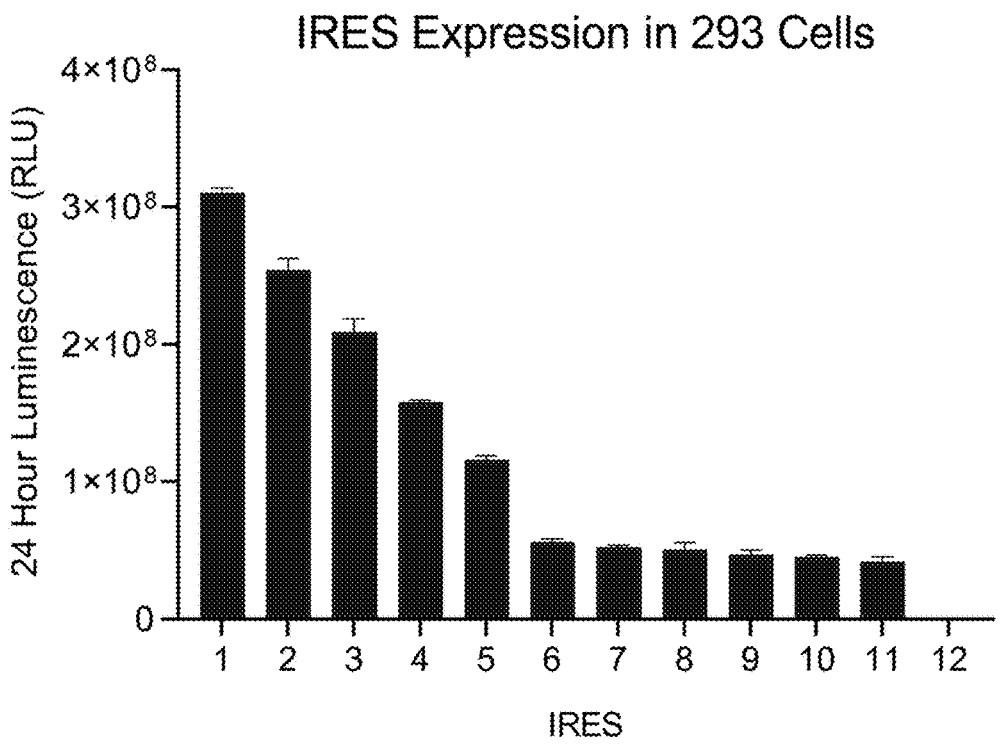
FIG. 13A and FIG. 13B show IRES expression by luminescence for 12 different IRESes in 293 cells and Jurkat cell types.
Figure 13B:
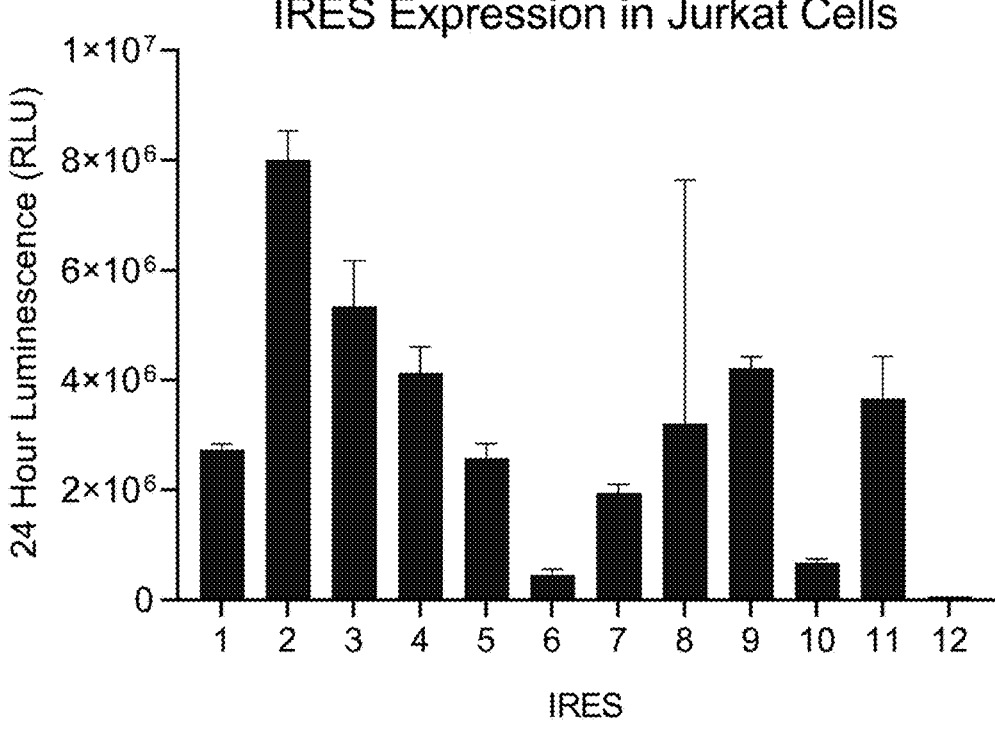

Twelve oRNA constructs were designed to comprise a combination of IRESes and codon optimized sequences (Table 6) and tested against (1) a base oRNA construct comprising a non-optimized CD19 CAR expression sequence and a kobuvirus IRES for expression, and (2) an oRNA construct comprising a HER2 CAR expression sequence. A mock construct (vehicle control) was used as a negative control. oRNA constructs were electroporated into activated T cells from a single donor (Donor 9003) using standard practices in the art. The cells were then incubated overnight. See FIG. 12A, showing % of T cells over 96 hours.

Expression of the CD19 CAR was collected 24, 48, 72, and 96 hours post electroporation of the T cells. 24 hours following electroporation, the T cells were stained with either Live/Dead Near IR stain, Fc block, and either biotinylated anti-FMC63, and either biotinylated anti-HER2 antibody, CD3, Streptavidin antibody and then incubated. The cells were then washed with a stain buffer.

The same oRNA constructs from above, including the base oRNA and ORNA construct encoding for HER2, along with the mock construct were analyzed for cytotoxicity. Said ORNA constructs were electroporated in either T cell or Nalm6 plates (Nalm 6 only control plates). T cells were from two donors (Donor 4003 and Donor 9003). The T cells were then cocultured with Nalm6 cells at a E: T ratio of 1:20. Cytotoxicity was analyzed using FACS at 24 hours and 48 hours post electroporation. Both the cocultured cells along with the Nalm6 only cells were dyed with Annexin V Red and then scanned in a standard tissue culture incubator (Incucyte). See FIG. 12B (CAR+MFI over 48 hours post electroporation) and 12C (Annexin V+Nalm6 over 72 hours for construct nos. 7, 164, 17, and 171 as compared to a base CD19 and HER2 control, mock negative control and Nalm6 alone).

Example 9: IRESCO Constructs Enhance In Vivo Tumor Efficacy

NSG mice were engrafted with Nalm6-Luciferase (Luc) tumor cells and 4 days later were engrafted with human PBMCs. Starting on Day 5, the mice were treated 4 times every other day with vehicle (PBS), control, or anti-CD19 LNP-oCAR compounds at doses of 1.0 mg/kg, 0.3 mg/kg, and 0.1 mg/kg. PBS control is representative of mice with engrafted Nalm6-luc tumor cells only and treated with vehicle. LNP used herein comprised PEG-ionizable lipid 86 of Table 3. Animals were then whole-body imaged via IVIS to monitor luciferase expression from Nalm6 cells. Nalm6 tumor burden is plotted as Total Flux (photons/second over a region of interest) of the liver, spleen, kidney, lung, and heart of luciferase expression at each imaging timepoint.

Figure 14:
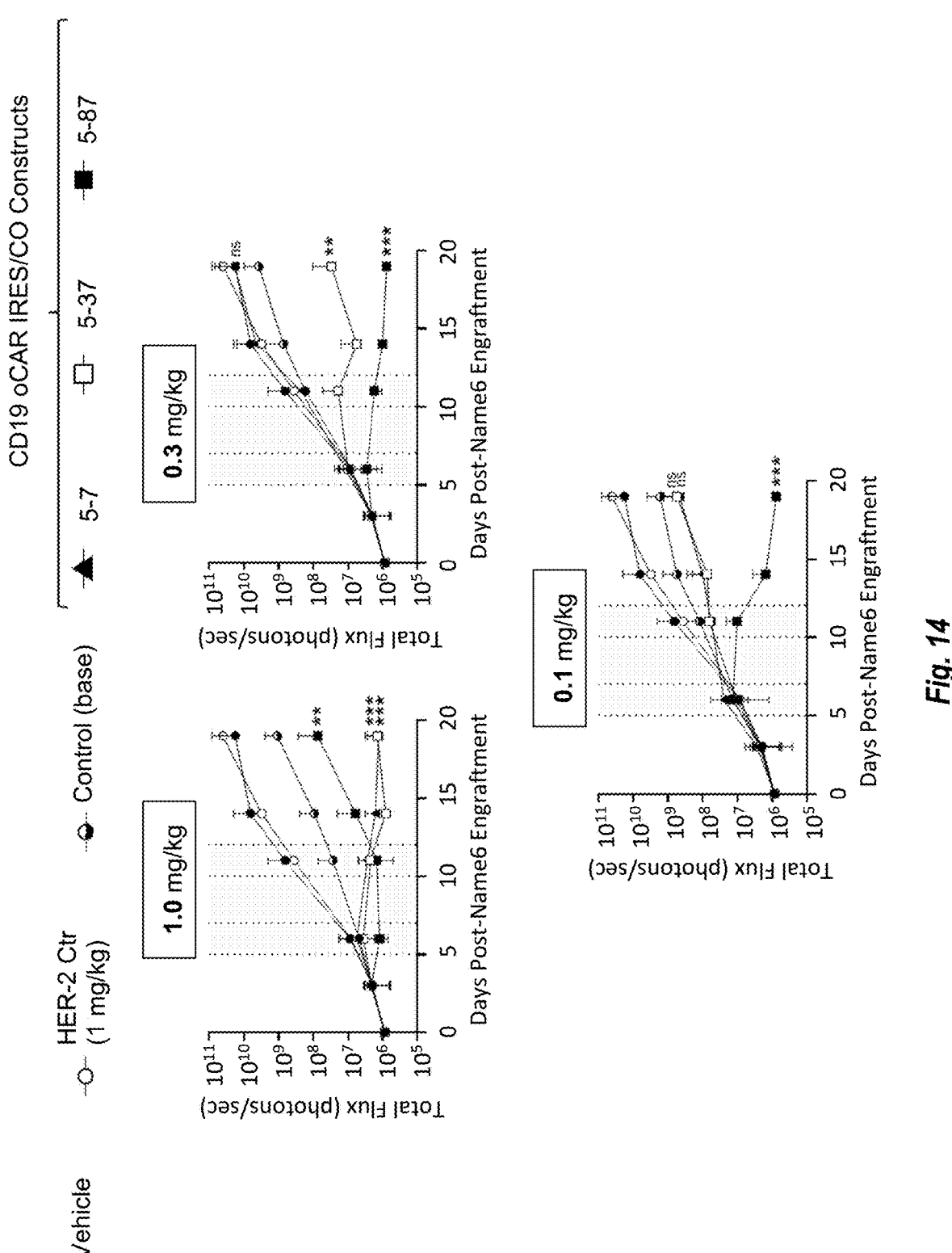
FIG. 14 shows in vivo anti-tumor efficacy of CD19 oCAR constructs comprising IRES/CO clone numbers 7, 37, and 87 (SEQ ID NOs: 50, 52, 55, respectively) as compared to a base CD19 CAR control (3276), PBS, and a HER2 control, at dosages of 1.0 mg/kg, 0.3 mg/kg, and 0.1 mg/kg. Multiple Mann-Whitney test with Holm-Sidak correction, *p≤0.05,  p≤0.01, * p≤0.001.
Figure 15:
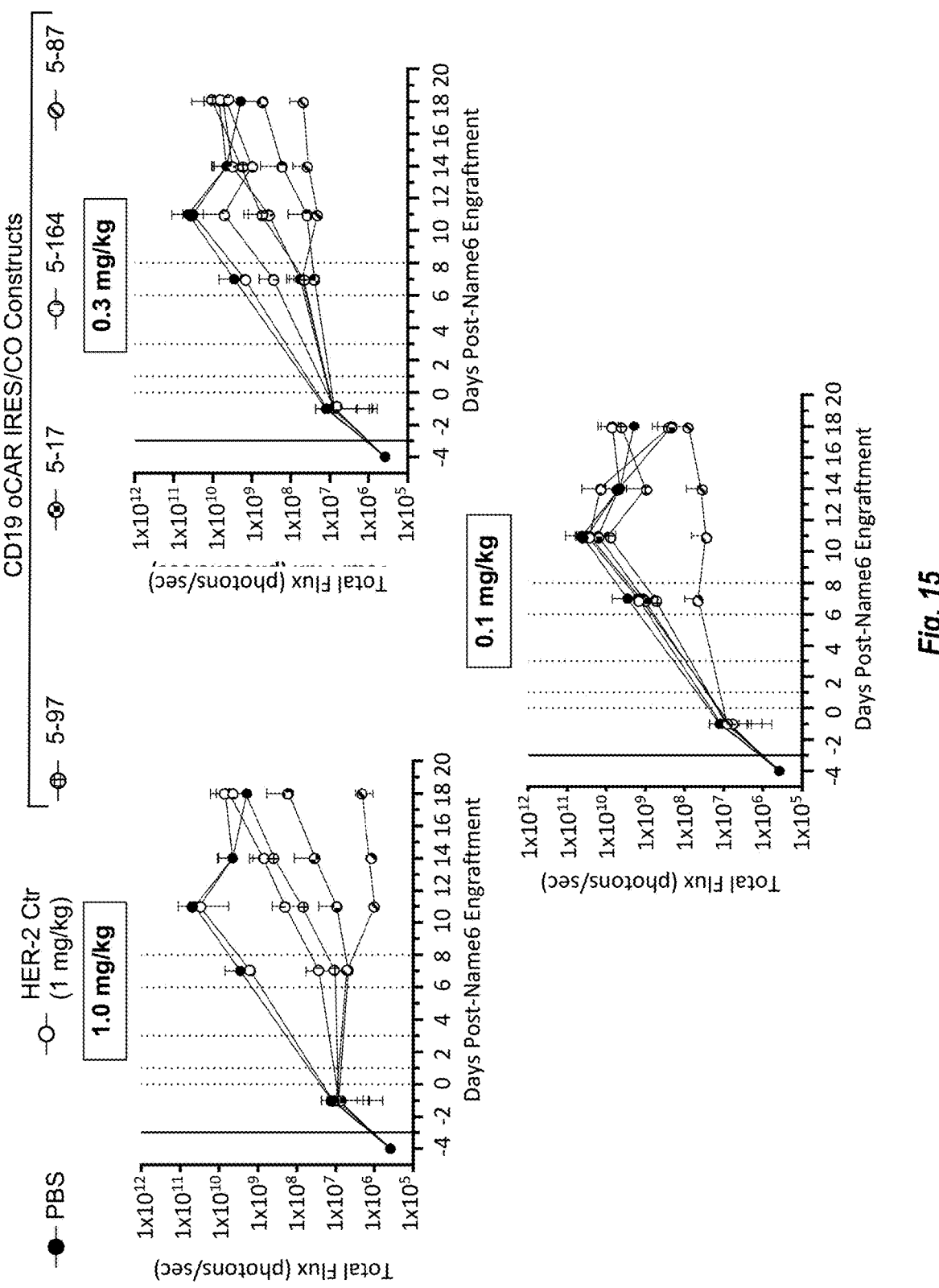
FIG. 15 shows in vivo anti-tumor efficacy of CD19 oCAR constructs comprising IRES/CO clone numbers 97, 17, 164, and 87 (SEQ ID NOs: 56, 51, 58, 55, respectively) as compared to a base CD19 CAR control (3276), PBS, and a HER2 control, at dosages of 1.0 mg/kg, 0.3 mg/kg, and 0.1 mg/kg.

FIG. 14 shows that CD19 oCAR constructs comprising SEQ ID NOs: 50, 52, and 55 (IRES/CO clone #s 7, 37, and 87) have higher anti-tumor efficacy compared to a base CD19 CAR control, PBS, and a HER2 control construct. FIG. 15 shows that CD19 oCAR constructs comprising SEQ ID NOs: 56, 51, 58, and 55 (IRES/CO clone #s 97, 17, 164, and 87) have higher anti-tumor efficacy compared to PBS and a HER2 control construct.

Example 10: Anti-Tumor Efficacy is Observed with all Lipids after 4 Doses of LNP/oCAR Total Flux (photons/second) was observed over time for oRNA constructs with expression sequences directed to HER2 and CD19 (see, e.g., Table 1B) and to assess the effect of anti-tumor efficacy after 4 doses using different lipids of LNP-circRNAs, where the effects of PEG lipids in the transfer vehicle was also assessed. NSG mice were engrafted with Nalm6-Luciferase (Luc) tumor cells and 3 days later were engrafted with human PBMCs. Starting on Day 1, the mice were treated 4 times every other day with vehicle (PBS) or anti-CD19 LNP-oCAR compounds. LNPs delivering the oCAR constructs comprised of PEG-modified lipids of control lipids (11 and 62) and lipids of Formula I, including lipids 16, 45, and 86 of Table 3) at an ionizable lipid to phosphate ratio (IL:P) of 5.7. The ionizable lipid:helper lipid:cholesterol:PEG-lipid molar ratio of these LNPs was 50:10:38.5:1.5. The formulation of the LNPs are further detailed below. PBS control is representative of mice with engrafted Nalm6-luc tumor cells only and treated with vehicle. Animals were then whole-body imaged via IVIS to monitor luciferase expression from Nalm6 cells. Nalm6 tumor burden is plotted as Total Flux of luciferase expression at each imaging timepoint. See FIG. 16.

| Formulation | Ionizable Lipid | Helper Lipid | PEG-Lipid | Ionizable Lipid:Helper Lipid:Cholesterol:PEG-lipid (Mol %) | HER2/CD19 | Z-Average (nm) | RNA Encapsulation Efficiency (%) | PDI |
|---|---|---|---|---|---|---|---|---|
| 3-126 [5.7A] | Lipid 126 of Table 3 | DSPC | DMG-PEG 2000 | 50:10:38.5:1.5 | HER2 CD19 | 93 81 | 93 96 | 0.03 0.07 |
| (3-128)/3L [5.7A] | Lipid 128 of Table 3 | DSPC | DMG-PEG 2000 | 50:10:38.5:1.5 | HER2 CD19 | 97 82 | 97 95 | 0.04 0.02 |
| (3-128)/3 [5.5A] | Lipid 128 of Table 3 | DSPC | DMG-PEG 2000 | 50:10:38.5:1.5 | HER2 CD19 | 97 106 | 97 96 | 0.14 0.15 |
| (3-16)/3 [5.5A] | Lipid 16 of Table 3 | DSPC | DMG-PEG 2000 | 50:10:38.5:1.5 | HER2 CD19 | 91 65 | 91 96 | 0.06 0.05 |
| (3-45)/3 [5.5A] | Lipid 45 of Table 3 | DSPC | DMG-PEG 2000 | 50:10:38.5:1.5 | HER2 CD19 | 97 67 | 97 96 | 0.03 0.05 |
| (3-86)/3 [5.5A] | Lipid 86 of Table 3 | DSPC | DMG-PEG 2000 | 50:10:38.5:1.5 | HER2 CD19 | 94 81 | 94 94 | 0.05 0.03 |

Example 11: Circular RNA Constructs Comprising an Anti-HER2 Binder

Additional circular RNA constructs comprising an anti-HER2 binder were designed and assessed. Certain of the circular RNA constructs in Table 9 include a miR-122 site.

TABLE 9

Additional Codon-IRES Constructs (HER2)

| IRES/CO Clone # | IRES SEQ ID NO: | Codon NT SEQ ID NO: | |
|---|---|---|---|
| HER2_1 | 16 | 101 | |
| HER2_2 | 17 | 101 | Includes miR-122 site: SEQ ID NO: 200 |
| HER2_3 | 8 | 101 | |
| HER2_4 | 18 | 101 | |
| HER2_5 | 16 | 102 | |

TABLE 9-continued

Additional Codon-IRES Constructs (HER2)

| IRES/CO Clone # | IRES SEQ ID NO: | Codon NT SEQ ID NO: | |
|---|---|---|---|
| HER2_6 | 17 | 102 | Includes miR-122 site: SEQ ID NO: 200 |
| HER2_7 | 8 | 102 | |
| HER2_8 | 18 | 102 | |
| HER2_9 | 17 | 132 | |
| HER2_10 | 17 | 133 | |

A. Cytotoxicity Assay

Two oRNA constructs (HER2_9 and HER2_10 in Table 9) were designed that comprise a combination of IRESes and expression sequences directed to HER2. The IRES-CO sequences for the constructs are set forth in SEQ ID NOs: 136 and 137:

HER2 9:

(SEQ ID NO: 136)

GTGGCCACGCCCGGGCCACCGATACTTCCCTTCACTCCTTCGGGACTGTTGGGGA

GGAACACAACAGGGCTCCCCTGTTTTCCCATTCCTTCCCCCTTTTCCCAACCCCAA

CCGCCGTATCTGGTGGCGGCAAGACACACGGGTCTTTCCCTCTAAAGCACAATTG

TGTGTGTGTCCCAGGTCCTCCTGCGTACGGTGCGGGAGTGCTCCCACCCAACTGT

TGTAAGCCTGTCCAACGCGTCGTCCTGGCAAGACTATGACGTCGCATGTTCCGCT

GCGGATGCCGACCGGGTAACCGGTTCCCCAGTGTGTGTAGTGCGATCTTCCAGGT

CCTCCTGGTTGGCGTTGTCCAGAAACTGCTTCAGGTAAGTGGGGTGTGCCCAATC

CCTACAAAGGTTGATTCTTTCACCACCTTAGGAATGCTCCGGAGGTACCCCAGCA

ACAGCTGGGATCTGACCGGAGGCTAATTGTCTACGGGTGGTGTTTCCTTTTTCTTT

TCACACAACTCTACTGCTGACAACTCACTGACTATCCACTTGCTCTGTCACGATGG

CTCTGCCTGTGACAGCTCTGCTGCTGCCTCTGGCTCTGCTTCTGCATGCCGCCAGA

CCTGACATCCAGATGACTCAGAGCCCCAGCAGCCTGTCTGCCTCTGTGGGAGACA

GAGTGACAATTACCTGCCGGGCCAGCCAGGATGTGAATACTGCTGTCGCCTGGTA

TCAACAAAAGCCTGGCAAGGCCCCTAAGCTCCTGATCTACAGCGCCAGCTTTCTG

TACAGCGGCGTGCCCAGCAGATTCTCCGGAAGCAGAAGCGGCACAGATTTCACA

CTGACCATAAGCAGCCTGCAGCCAGAGGATTTCGCCACCTACTATTGCCAGCAGC

ACTACACCACACCTCCAACCTTTGGCCAGGGCACCAAGGTCGAGATTAAGAGAA

-continued

```
CAGGCAGCACATCTGGCTCTGGCAAACCTGGATCTGGCGAGGGCTCTGAAGTCCA

GCTGGTGGAATCTGGCGGAGGACTGGTTCAACCTGGCGGCTCTCTGAGACTGTCT

TGTGCCGCCTCCGGCTTCAACATCAAGGACACCTACATCCACTGGGTCCGACAAG

CCCCAGGCAAAGGACTTGAGTGGGTCGCCAGGATCTACCCCACCAACGGCTACA

CCAGATACGCCGACTCTGTGAAGGGCAGATTCACCATCTCTGCCGACACCAGCAA

GAATACCGCCTACCTGCAGATGAACTCCCTGAGAGCCGAAGATACCGCTGTGTAT

TACTGTTCCAGATGGGGAGGCGACGGCTTCTACGCCATGGATGTTTGGGGCCAAG

GCACCCTCGTGACCGTTTCTTCTATCGAAGTGATGTACCCTCCACCTTACCTGGAC

AACGAGAAGTCCAACGGCACCATCATCCACGTGAAGGGCAAGCACCTGTGTCCT

TCTCCACTGTTCCCCGGACCTAGCAAGCCTTTCTGGGTGCTCGTTGTTGTTGGCGG

CGTGCTGGCCTGTTACTCTCTGCTGGTTACCGTGGCCTTCATCATCTTTTGGGTCC

GAAGCAAGCGGAGCCGGCTGCTGCACTCCGACTACATGAACATGACCCCTAGAC

GGCCCGGACCAACCAGAAAGCACTACCAGCCTTACGCTCCTCCTAGAGACTTCGC

CGCCTACCGGTCCAGAGTGAAGTTCAGCAGATCCGCCGATGCTCCCGCCTATCAG

CAGGGCCAAAACCAGCTGTACAACGAGCTGAACCTGGGGAGAAGAGAAGAGTA

CGACGTGCTGGACAAGCGGAGAGGCAGAGATCCTGAAATGGGCGGCAAGCCCAG

ACGGAAGAATCCTCAAGAGGGCCTGTATAATGAGCTGCAGAAAGACAAGATGGC

CGAGGCCTACAGCGAGATCGGAATGAAGGGCGAGCGCAGAAGAGGCAAGGGAC

ACGATGGACTGTACCAGGGCCTGAGCACCGCCACCAAGGATACCTATGATGCCCT

GCACATGCAGGCCCTGCCTCCAAGA
```

HER_10:

(SEQ ID NO: 137)

```
GTGGCCACGCCCGGGCCACCGATACTTCCCTTCACTCCTTCGGGACTGTTGGGGA

GGAACACAACAGGGCTCCCCTGTTTTCCCATTCCTTCCCCCTTTTCCCAACCCCAA

CCGCCGTATCTGGTGGCGGCAAGACACACGGGTCTTTCCCTCTAAAGCACAATTG

TGTGTGTGTCCCAGGTCCTCCTGCGTACGGTGCGGGAGTGCTCCCACCCAACTGT

TGTAAGCCTGTCCAACGCGTCGTCCTGGCAAGACTATGACGTCGCATGTTCCGCT

GCGGATGCCGACCGGGTAACCGGTTCCCCAGTGTGTGTAGTGCGATCTTCCAGGT

CCTCCTGGTTGGCGTTGTCCAGAAACTGCTTCAGGTAAGTGGGGTGTGCCCAATC

CCTACAAAGGTTGATTCTTTCACCACCTTAGGAATGCTCCGGAGGTACCCCAGCA

ACAGCTGGGATCTGACCGGAGGCTAATTGTCTACGGGTGGTGTTTCCTTTTTCTTT

TCACACAACTCTACTGCTGACAACTCACTGACTATCCACTTGCTCTGTCACGATGG

CTCTGCCTGTGACAGCTCTGCTGCTGCCTCTGGCTCTGCTTCTGCATGCCGCCAGA

CCTGACATCCAGATGACTCAGAGCCCCAGCAGCCTGTCTGCCTCTGTGGGAGACA

GAGTGACAATTACCTGCCGGGCCAGCCAGGATGTGAATACTGCTGTCGCCTGGTA

TCAACAAAAGCCTGGCAAGGCCCCTAAGCTCCTGATCTACAGCGCCAGCTTTCTG

TACAGCGGCGTGCCCAGCAGATTCTCCGGAAGCAGAAGCGGCACAGATTTCACA

CTGACCATAAGCAGCCTGCAGCCAGAGGATTTCGCCACCTACTATTGCCAGCAGC

ACTACACCACACCTCCAACCTTTGGCCAGGGCACCAAGGTCGAGATTAAGAGAA

CAGGCAGCACATCTGGCTCTGGCAAACCTGGATCTGGCGAGGGCTCTGAAGTCCA

GCTGGTGGAATCTGGCGGAGGACTGGTTCAACCTGGCGGCTCTCTGAGACTGTCT
```

-continued
TGTGCCGCCTCCGGCTTCAACATCAAGGACACCTACATCCACTGGGTCCGACAAG

CCCCAGGCAAAGGACTTGAGTGGGTCGCCAGGATCTACCCCACCAACGGCTACA

CCAGATACGCCGACTCTGTGAAGGGCAGATTCACCATCTCTGCCGACACCAGCAA

GAATACCGCCTACCTGCAGATGAACTCCCTGAGAGCCGAAGATACCGCTGTGTAT

TACTGTTCCAGATGGGGAGGCGACGGCTTCTACGCCATGGATGTTTGGGGCCAAG

GCACCCTCGTGACCGTTTCTTCTACCACCACACCAGCTCCTCGGCCTCCAACTCCT

GCTCCTACAATTGCCAGCCAGCCTCTGTCTCTGAGGCCCGAAGCTTGTAGACCTG

CTGCTGGCGGAGCCGTGCATACAAGAGGACTGGATTTCGCCTGCGACATCTACAT

CTGGGCTCCTCTGGCCGGAACATGTGGCGTTCTGCTGCTGAGCCTGGTCATCACC

CTGTACTGTAAGCGGGGCAGAAAGAAGCTGCTGTACATCTTCAAGCAGCCCTTCA

TGCGGCCCGTGCAGACCACACAAGAGGAAGATGGCTGCTCCTGCAGATTCCCCG

AGGAAGAAGAAGGCGGCTGCGAGCTGAGAGTGAAGTTCAGCAGATCCGCCGATG

CTCCCGCCTATCAGCAGGGCCAAAACCAGCTGTACAACGAGCTGAACCTGGGGA

GAAGAGAAGAGTACGACGTGCTGGACAAGCGGAGAGGCAGAGATCCTGAAATG

GGCGGCAAGCCCAGACGGAAGAATCCTCAAGAGGGCCTGTATAATGAGCTGCAG

AAAGACAAGATGGCCGAGGCCTACAGCGAGATCGGAATGAAGGGCGAGCGCAG

AAGAGGCAAGGGACACGATGGACTGTACCAGGGCCTGAGCACCGCCACCAAGGA

TACCTATGATGCCCTGCACATGCAGGCCCTGCCTCCAAGA

Figure 17:
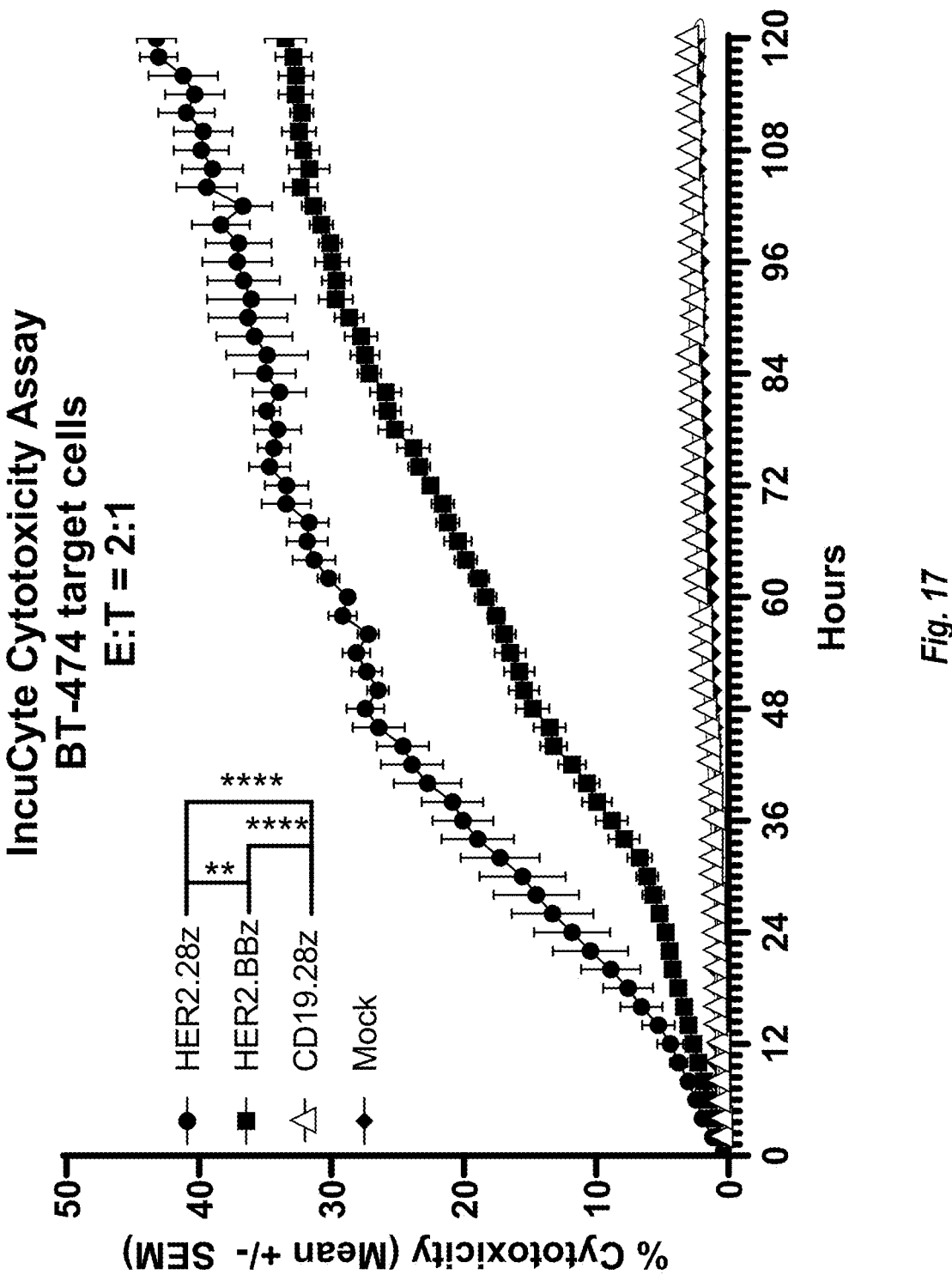
FIG. 17 shows % cytotoxicity (IncuCyte Cytotoxicity Assay) over time for the circular RNA constructs comprising HER2_9 and HER2_10 as compared to a base CD19 CAR control (3276) and a mock negative control.
Figure 18A:
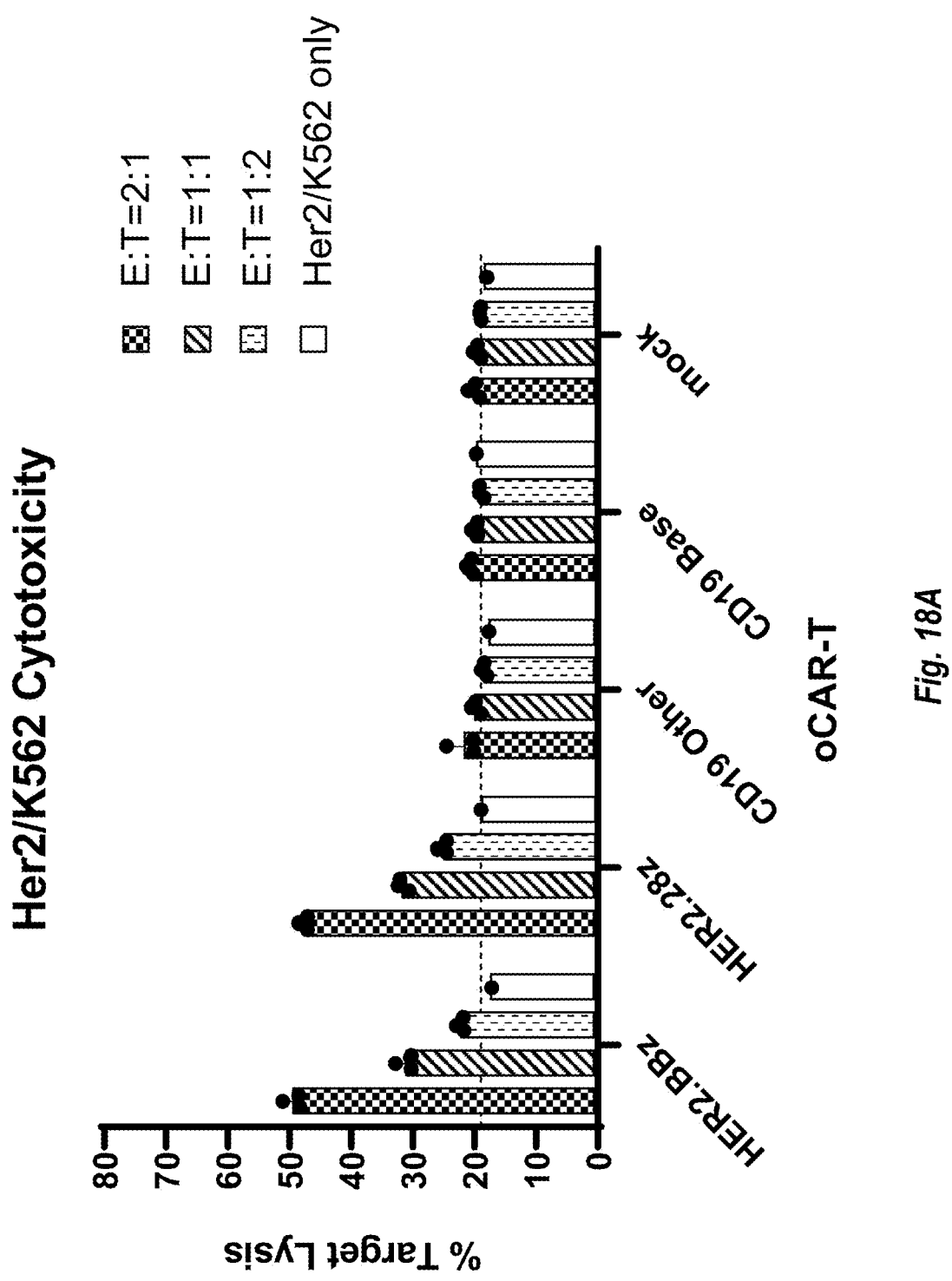
FIGS. 18A, 18B, and 18C show % target lysis for a HER2.BBC oCAR construct and a HER2 285 oCAR construct as compared to a CD19 oCAR construct, a base CD19 CAR control, and mock negative control, evaluated using FACS based cytotoxicity assay after 24 hours co-culture using engineered HER2/K562 cell line (FIG. 18A), CD19/K562 (FIG. 18B), and Nalm6 (CD19+/HER2−) (FIG. 18C) cells.
Figure 18B:
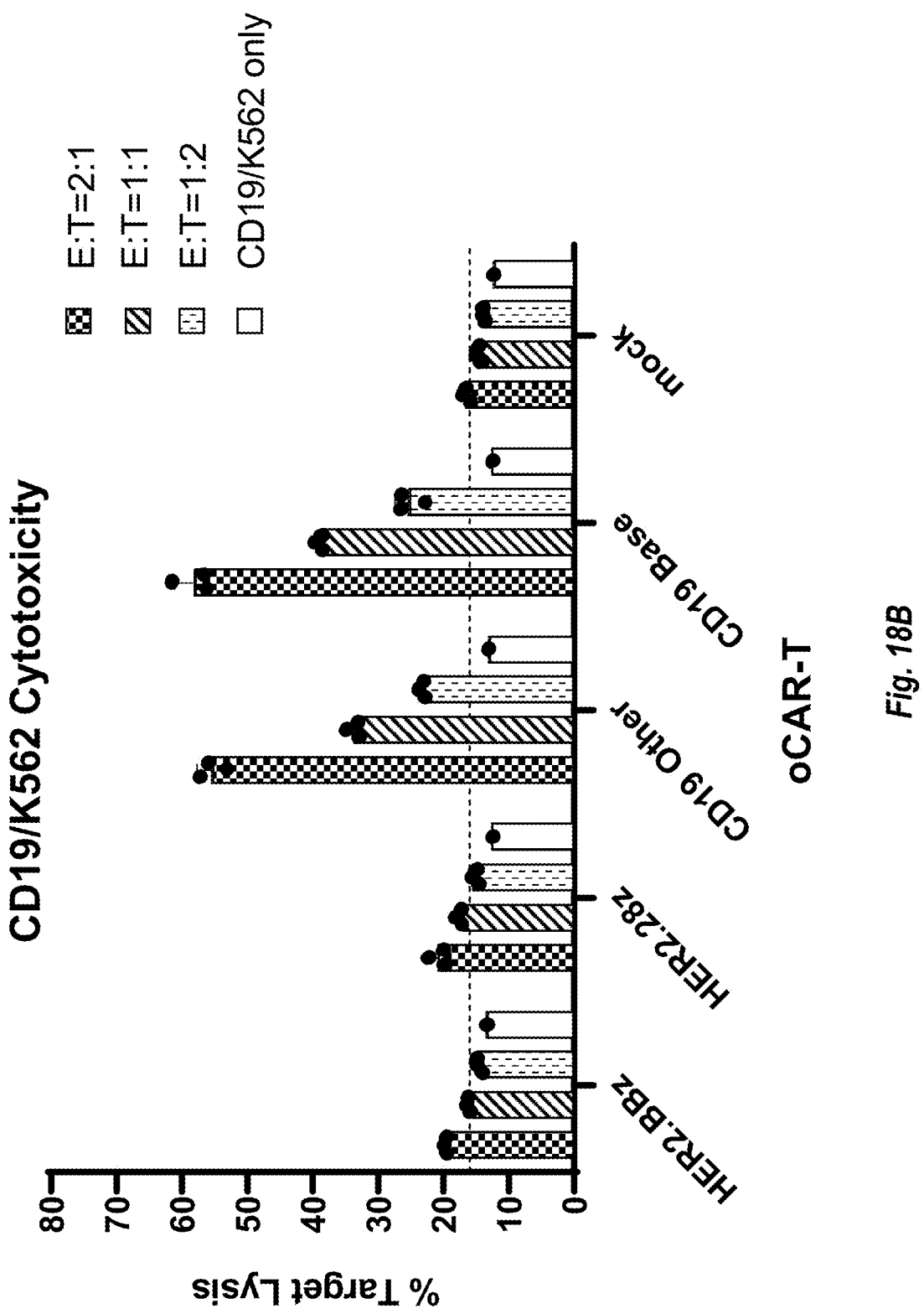
Figure 18C:
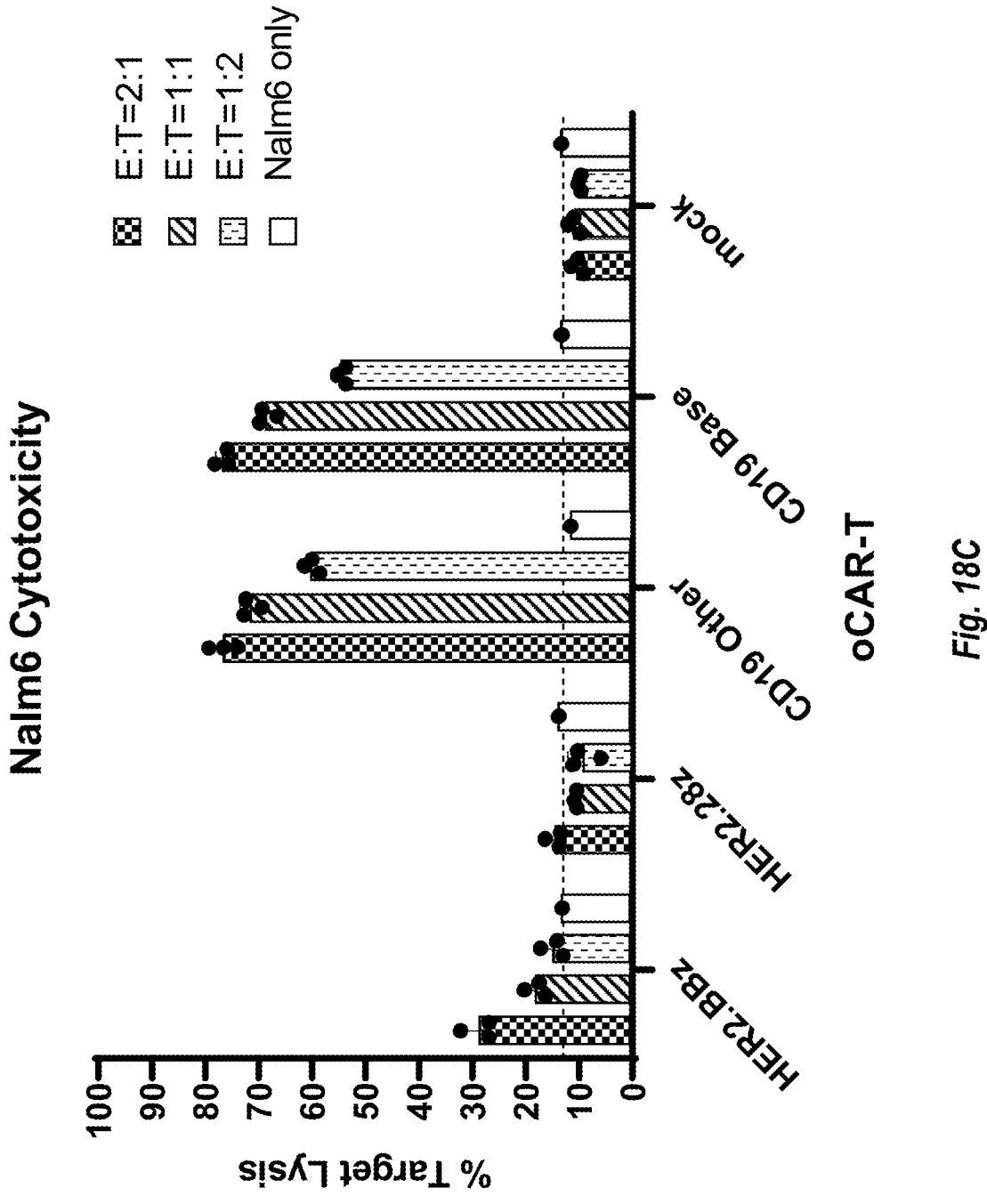

The two oRNA constructs HER2_9 and HER2_10 were tested against the control CD19 CAR oRNA base construct 3276 (codon optimized) and a mock negative control in an IncuCyte Cytotoxicity assay. Activated T cells (from BT-474 cell line) from a single donor (9003) were transfected in vitro with LNP-oCAR (200 ng/0.1e6 T cells). 24 hours after transfection, the CAR-T cells were evaluated for expression & co-cultured with target cells (2:1 E: T) over time for five days. See FIG. 17. Both HER2_9 and HER2_10 demonstrate cytotoxic function in a target-dependent manner.
B. HER2 and CD19 oCAR Cytotoxicity A HER2. BBC oCAR construct, HER2 280 oCAR construct, and a CD19 oCAR construct, were assessed against a base CD19 CAR control, and mock negative control for % target lysis using a FACS based cytotoxicity assay using an engineered HER2/K562 cell line (HER2-28ζ or HER2-BBζ), CD19/K562 cell line (CD19-28ζ or CD19-BBζ), and Nalm6 cell line (CD19+/HER2−). All oCAR constructs were electroporated into activated T cells to form CAR-T cells. The CAR-T cells were then co-cultured (2:1 E: T, 1:1 E: T, and 1:2 E: T) with target cells for 24 hours at 37° C. Target cells were engineered using the K562 cell line as a backbone (K562 cells overexpressing HER2 or CD19, GFP, and luciferase). 24 hours after co-culture, the CAR-T cells were evaluated using a single timepoint FACS assay to determine number of dead GFP positive target cells. See FIGS. 18A-18C. Both HER2 and CD19 CAR oCAR constructs were able to elicit target specific killing.

Example 12: Circular RNA Constructs Comprising an Anti-BCMA Binder

Additional circular RNA constructs comprising an anti-BCMA binder were designed and assessed. See Table 8, below.

Figure 19A:
FIGS. 19A, 19B, and 19C show target specific cytotoxicity for the oCAR construct comprising the sequence of BCMA_16 as compared to base CD19 CAR (3276) and a mock negative control in MM.1S cells, U266B1 cells, and Nalm 6 cells.
Figure 19B:
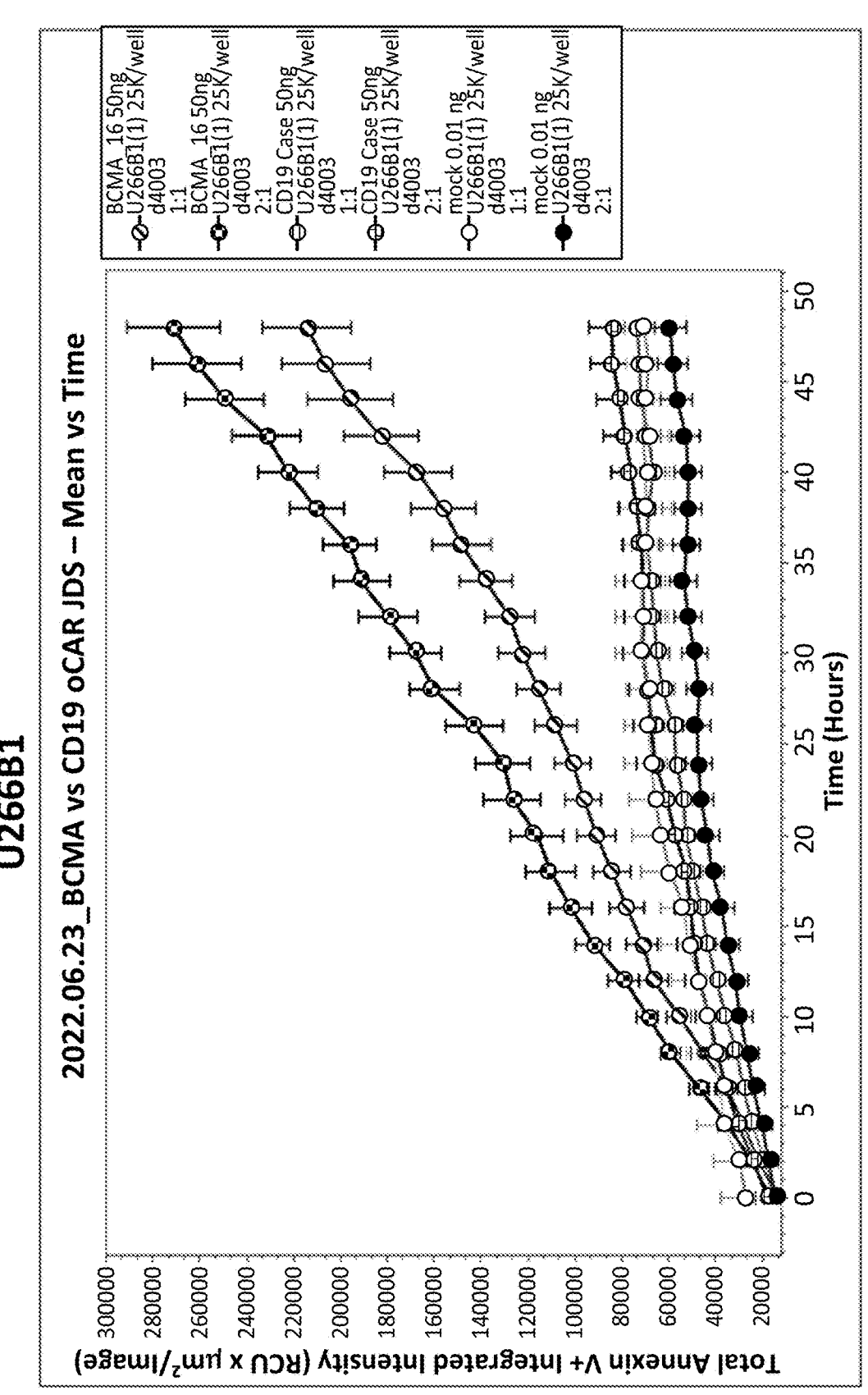
Figure 19C:
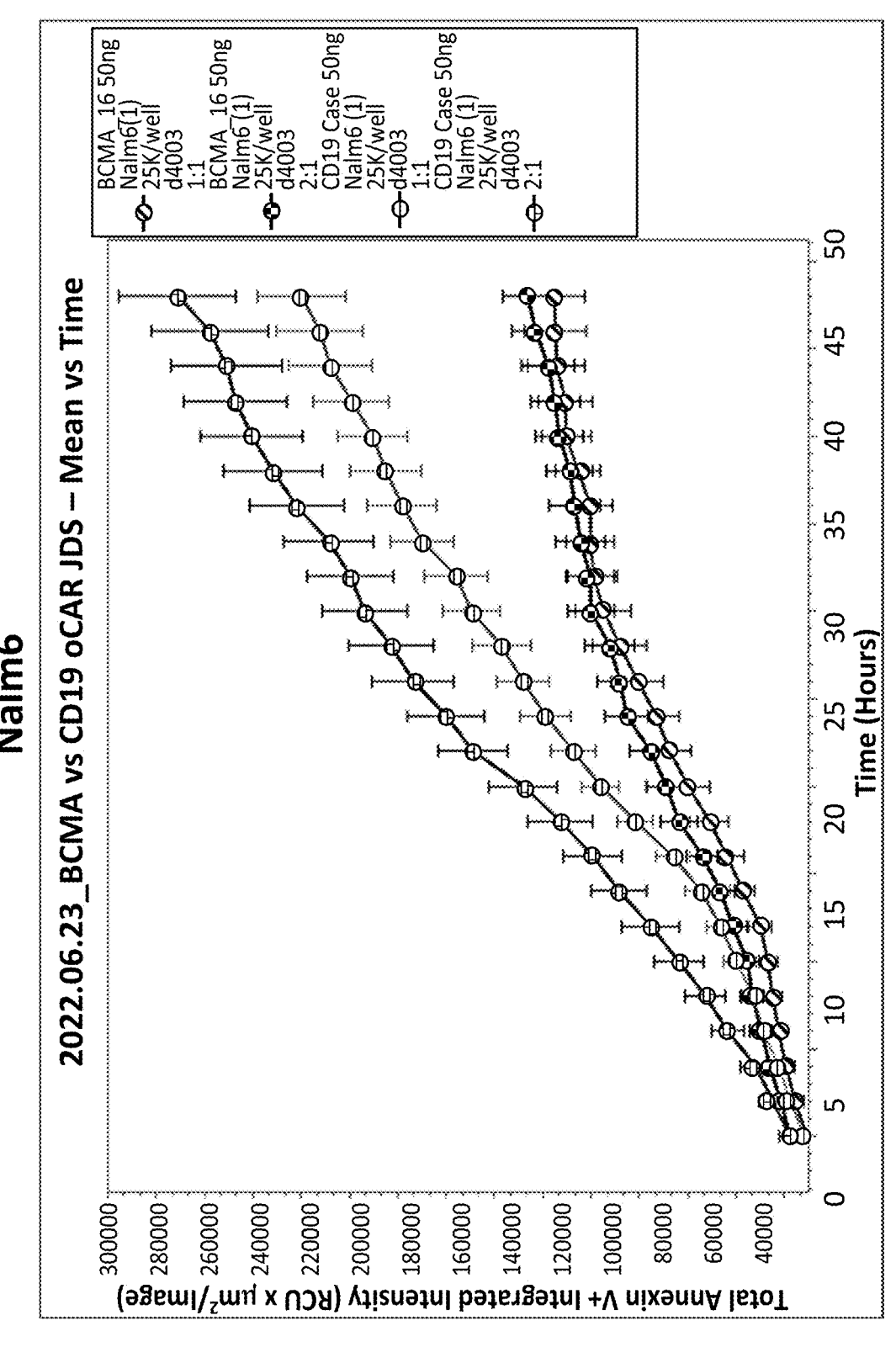

An oCAR construct comprising BCMA_16 was designed to comprise a combination of an IRES and expression sequences directed to surface expression of BCMA. Human T cells from Donor 4003 were activated with aCD3/aCD28. Two days post activation, the BCMA_16 oCAR construct, CD19 base construct, and mock negative control were electroporated via Nucleofect (50 ng oCAR/0.1e6 T cells). 24 hour later, the T cells were cocultured with MM. 1 s, U266B1 or Nalm 6 (CD19+/HER2−) cell lines analyzed at E:T=1:1 and 2:1 for target specific cytotoxicity for a span of three days via total accumulation of cell death. See FIGS. 19A-19C. BCMA_16 and CD19 (Base) oCARs showed target specific killing.

The IRES-CO sequences for the BCMA_16 construct is set forth in SEQ ID NO: 138:

(SEQ ID NO: 138)
GTGGCCACGCCCGGGCCACCGATACTTCCCTTCACTCCTTCGGGACTGTTGGGGA

GGAACACAACAGGGCTCCCCTGTTTTCCCATTCCTTCCCCCTTTTCCCAACCCCAA

CCGCCGTATCTGGTGGCGGCAAGACACACGGGTCTTTCCCTCTAAAGCACAATTG

TGTGTGTGTCCCAGGTCCTCCTGCGTACGGTGCGGGAGTGCTCCCACCCAACTGT

TGTAAGCCTGTCCAACGCGTCGTCCTGGCAAGACTATGACGTCGCATGTTCCGCT

-continued

```
GCGGATGCCGACCGGGTAACCGGTTCCCCAGTGTGTGTAGTGCGATCTTCCAGGT

CCTCCTGGTTGGCGTTGTCCAGAAACTGCTTCAGGTAAGTGGGGTGTGCCCAATC

CCTACAAAGGTTGATTCTTTCACCACCTTAGGAATGCTCCGGAGGTACCCCAGCA

ACAGCTGGGATCTGACCGGAGGCTAATTGTCTACGGGTGGTGTTTCCTTTTTCTTT

TCACACAACTCTACTGCTGACAACTCACTGACTATCCACTTGCTCTGTCACGATGG

CACTCCCGGTAACCGCCTTATTGCTTCCCCTTGCCCTCTTGCTCCACGCAGCACGC

CCCGATATAGTCTTGACTCAATCCCCACCCAGTTTGGCAATGTCATTAGGCAAAC

GAGCAACAATTTCATGTAGGGCATCCGAAAGTGTAACGATTTTGGGGAGTCATTT

AATTCATTGGTACCAACAAAAGCCTGGACAACCCCCGACGCTCTTGATCCAATTA

GCATCTAACGTCCAAACCGGAGTCCCCGCACGATTCTCAGGATCCGGTTCCCGGA

CTGATTTTACATTAACTATTGATCCGGTAGAGGAAGATGACGTCGCTGTCTATTAT

TGTCTTCAAAGTAGGACGATTCCACGGACATTCGGTGGCGGAACTAAATTGGAGA

TTAAAGGTTCCACCTCTGGTAGTGGGAAACCCGGGTCCGGTGAAGGGTCCACTAA

AGGCCAAATTCAACTCGTTCAATCCGGACCAGAACTGAAGAAGCCAGGAGAAAC

TGTCAAAATAAGCTGTAAAGCTTCCGGTTATACATTTACAGATTATTCCATAAATT

GGGTGAAAAGGGCGCCAGGAAAAGGGTTAAAGTGGATGGGTTGGATTAATACAG

AGACTCGGGAACCTGCATATGCTTATGATTTTAGGGGAAGGTTTGCCTTTTCTCTG

GAGACTTCCGCTTCAACTGCTTATCTCCAAATTAATAATCTTAAATATGAGGACA

CAGCAACATACTTCTGTGCTTTGGACTATAGTTATGCTATGGATTACTGGGGACA

AGGAACCAGTGTCACTGTAAGTTCCGCTGCTGCGACGACCACTCCTGCACCGCGA

CCACCCACTCCTGCCCCTACTATTGCTAGTCAACCACTTAGCTTGCGACCTGAGGC

ATGTCGGCCCGCGGCAGGTGGCGCAGTCCACACCAGGGGTTTAGACTTTGCTTGT

GATATTTATATTTGGGCACCACTCGCCGGGACTTGCGGTGTTCTTCTCTTGTCCCT

TGTTATAACTCTTTATTGTAAGCGCGGAAGGAAGAAATTGTTATATATTTTCAAA

CAACCTTTTATGCGACCCGTACAAACAACTCAGGAAGAGGACGGGTGTTCTTGTC

GGTTTCCAGAAGAGGAAGAGGGTGGGTGTGAACTCCGGGTCAAATTTAGTAGGT

CAGCAGATGCGCCGGCGTACCAACAAGGCCAAAACCAACTGTATAATGAACTCA

ATCTCGGTAGGCGTGAGGAATATGATGTCCTTGATAAAAGGCGCGGGAGAGATC

CAGAAATGGGCGGAAAACCACGGCGAAAGAATCCGCAGGAAGGGTTATATAAC

GAACTTCAAAAGGATAAAATGGCTGAAGCTTATTCCGAAATTGGCATGAAAGGA

GAGCGACGTAGGGGCAAAGGGCATGATGGCCTTTACCAAGGGCTCTCAACCGCT

ACAAAAGATACTTACGACGCTTTACATATGCAAGCACTTCCACCCAGG
```

TABLE 8

| Additional Codon-IRES Constructs (BCMA) | | |
| --- | --- | --- |
| IRES/CO Clone # | IRES SEQ ID NO: | Codon NT SEQ ID NO: |
| BCMA_1 | 16 | 103 |
| BCMA_2 | 17 | 103 |
| BCMA_3 | 8 | 103 |
| BCMA_4 | 18 | 103 |
| BCMA_5 | 8 | 104 |
| BCMA_6 | 8 | 105 |
| BCMA_7 | 8 | 106 |
| BCMA_8 | 8 | 107 |
| BCMA_9 | 8 | 108 |
| BCMA_10 | 8 | 109 |
| BCMA_11 | 8 | 110 |
| BCMA_12 | 8 | 111 |
| BCMA_13 | 8 | 112 |
| BCMA_14 | 8 | 113 |
| BCMA_15 | 8 | 114 |
| BCMA_16 | 17 | 115 |

Example 13: In Vivo Dosing Post-Nalm6 Engraftment

The anti-CD19 oRNA-LNP construct described in Example 10 was assessed in vivo in mice engrafted with Nalm6 tumor cells and dosing schedules (every-other-day dosing post-engraftment, weekly dosing post-engraftment, and every-other-week dosing post-engraftment) were compared. Dose timing groups were evaluated at doses of 1.0 mg/kg, 0.3 mg/kg, and 0.1 mg/kg across four PBMC donors (two studies, two donors per study, A and B). The experimental protocol is shown in the table below.

NSG MHC I/II double knockout mice were engrafted with Nalm6-Luciferase (Luc) tumor cells and 4 days later were engrafted with human PBMCs. Starting on Day 5 post-Nalm6 engraftment, the mice were treated 4 times (as shown in the table below in the dosing days column) with the anti-CD19 oRNA-LNP, PBS control, or HER2 control as shown herein. Total flux (photons/second) was observed over time for the CD19 oRNA construct. Animals were then whole-body imaged twice weekly via IVIS to monitor luciferase expression from Nalm6 cells.

| # | oRNA | Dose (mg/kg) | # of Doses | Dose Timing | Dosing Days (Post-Nalm6) | LNP Formulation | Mice/ Group | PBMC Donor |
| --- | --- | --- | --- | --- | --- | --- | --- | --- |
| 1 | 1X PBS | N/A | 4 | 1X/week | 5, 12, 19, 26 | N/A | 5 | A |
| 2 | HER2 CAR | 1.0 | 4 | 1X/week | 5, 12, 19, 26 | 1X TSS, −80 C. | 5 | A |
| 3 | CD19 CAR | 1.0 | 4 | 1X/week | 5, 12, 19, 26 | IX TSS, −80 C. | 8 | A |
| 4 | CD19 CAR | 0.3 | 4 | 1X/week | 5, 12, 19, 26 | 1X TSS, −80 C. | 8 | A |
| 5 | CD19 CAR | 0.1 | 4 | 1X/week | 5, 12, 19, 26 | 1X TSS, −80 C. | 8 | A |
| 6 | 1X PBS | N/A | 4 | Every other week | 5, 19, 33, 47 | N/A | 5 | A |
| 7 | HER2 CAR | 1.0 | 4 | Every other week | 5, 19, 33, 47 | 1X TSS, −80 C. | 5 | A |
| 8 | CD19 CAR | 1.0 | 4 | Every other week | 5, 19, 33, 47 | 1X TSS, −80 C. | 8 | A |
| 9 | CD19 CAR | 0.3 | 4 | Every other week | 5, 19, 33, 47 | 1X TSS, −80 C. | 8 | A |
| 10 | CD19 CAR | 0.1 | 4 | Every other week | 5, 19, 33, 47 | 1X TSS, −80 C. | 8 | A |
| 11 | 1X PBS | N/A | 4 | 1X/week | 5, 12, 19, 26 | N/A | 5 | B |
| 12 | HER2 CAR | 1.0 | 4 | 1X/week | 5, 12, 19, 26 | 1X TSS, −80 C. | 5 | B |
| 13 | CD19 CAR | 1.0 | 4 | 1X/week | 5, 12, 19, 26 | 1X TSS, −80 C. | 8 | B |
| 14 | CD19 CAR | 0.3 | 4 | 1X/week | 5, 12, 19, 26 | 1X TSS, −80 C. | 8 | B |
| 15 | CD19 CAR | 0.1 | 4 | 1X/week | 5, 12, 19, 26 | 1X TSS, −80 C. | 8 | B |
| 16 | 1X PBS | N/A | 4 | Every other week | 5, 19, 33, 47 | N/A | 5 | B |
| 17 | HER2 CAR | 1.0 | 4 | Every other week | 5, 19, 33, 47 | 1X TSS, −80 C. | 5 | B |
| 18 | CD19 CAR | 1.0 | 4 | Every other week | 5, 19, 33, 47 | 1X TSS, −80 C. | 8 | B |
| 19 | CD19 CAR | 0.3 | 4 | Every other week | 5, 19, 33, 47 | 1X TSS, −80 C. | 8 | B |

-continued

| # | oRNA | Dose (mg/kg) | # of Doses | Dose Timing | Dosing Days (Post-Nalm6) | LNP Formulation | Mice/ Group | PBMC Donor |
|---|------|------|------|------|------|------|------|------|
| 20 | CD19 CAR | 0.1 | 4 | Every other week | 5, 19, 33, 47 | 1X TSS, –80 C. | 8 | B |

Figure 20:
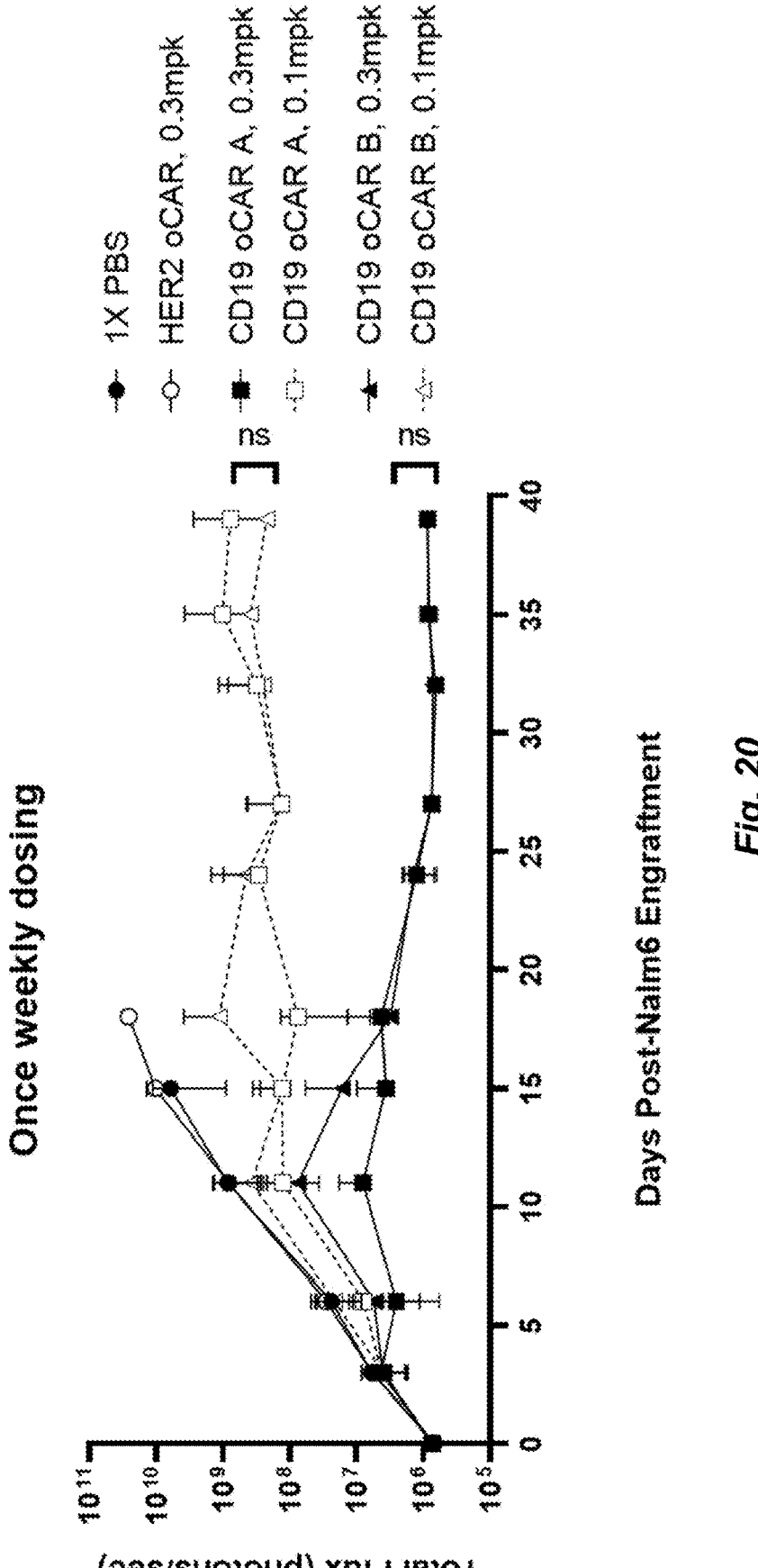
FIG. 20 shows tumor control as measured by total flux (photons/sec) post-Nalm6 engraftment using weekly dosing at 0.1 mg/kg (mpk) and 0.3 mg/kg (mpk).
Figure 21A:
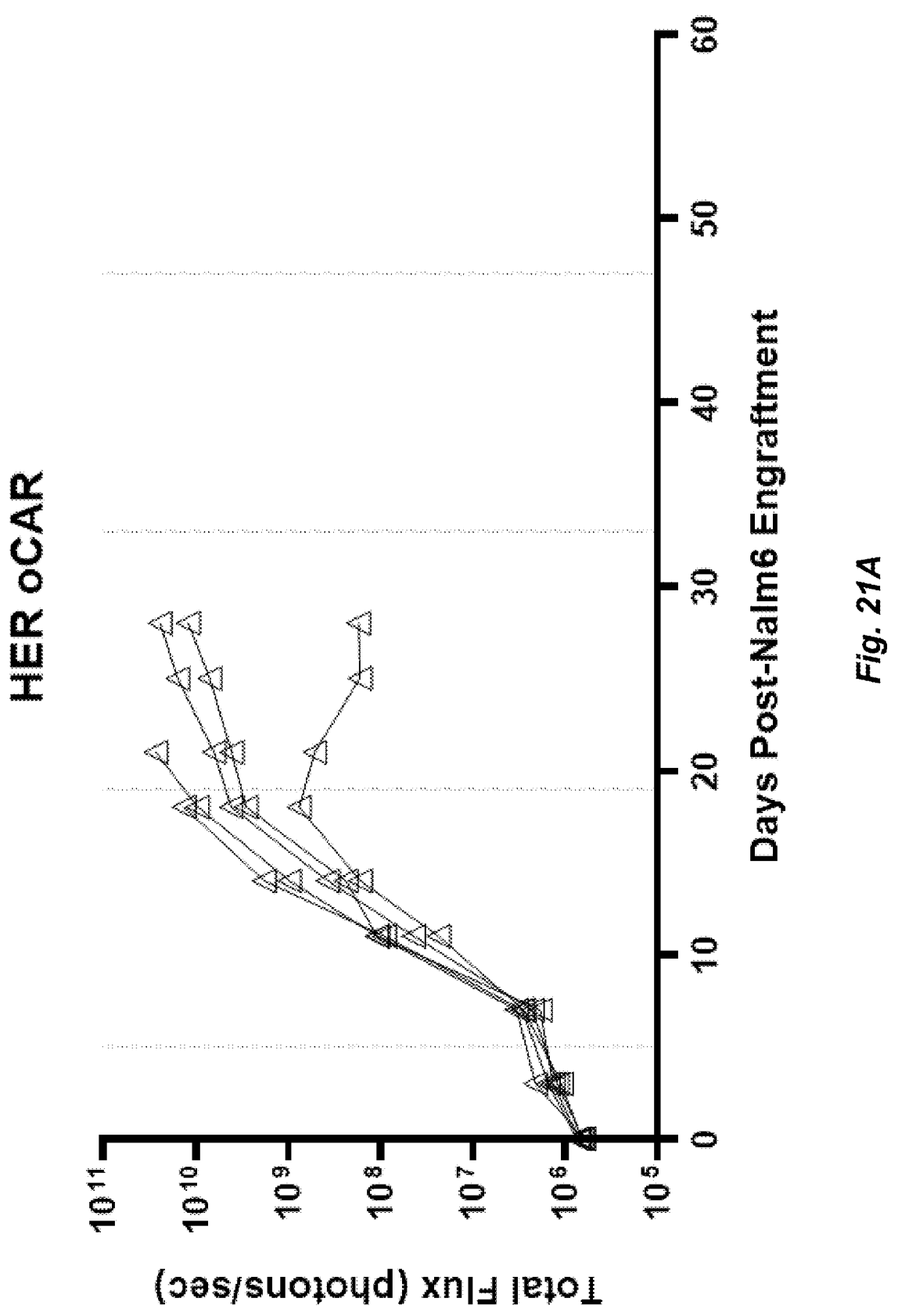
FIGS. 21A, 21B, and 21C show tumor control as measured by total flux (photons/sec) post-Nalm6 engraftment using every-other-week (biweekly or q2w) dosing at 0.1 mg/kg and 0.3 mg/kg. Lipid 86 of Table 3 ("3-86") was used for these oRNA CAR constructs.
Figure 21B:
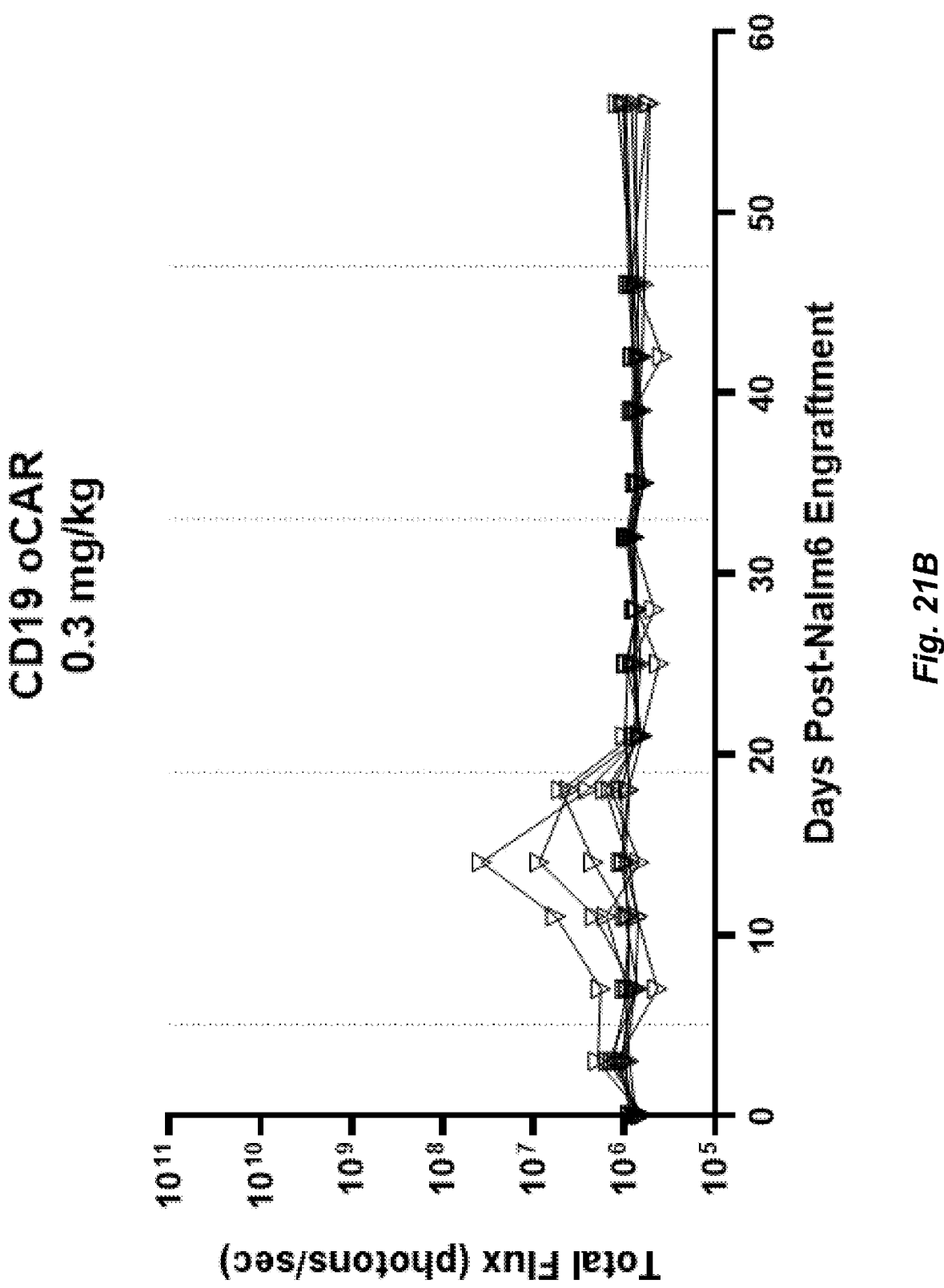
Figure 21C:
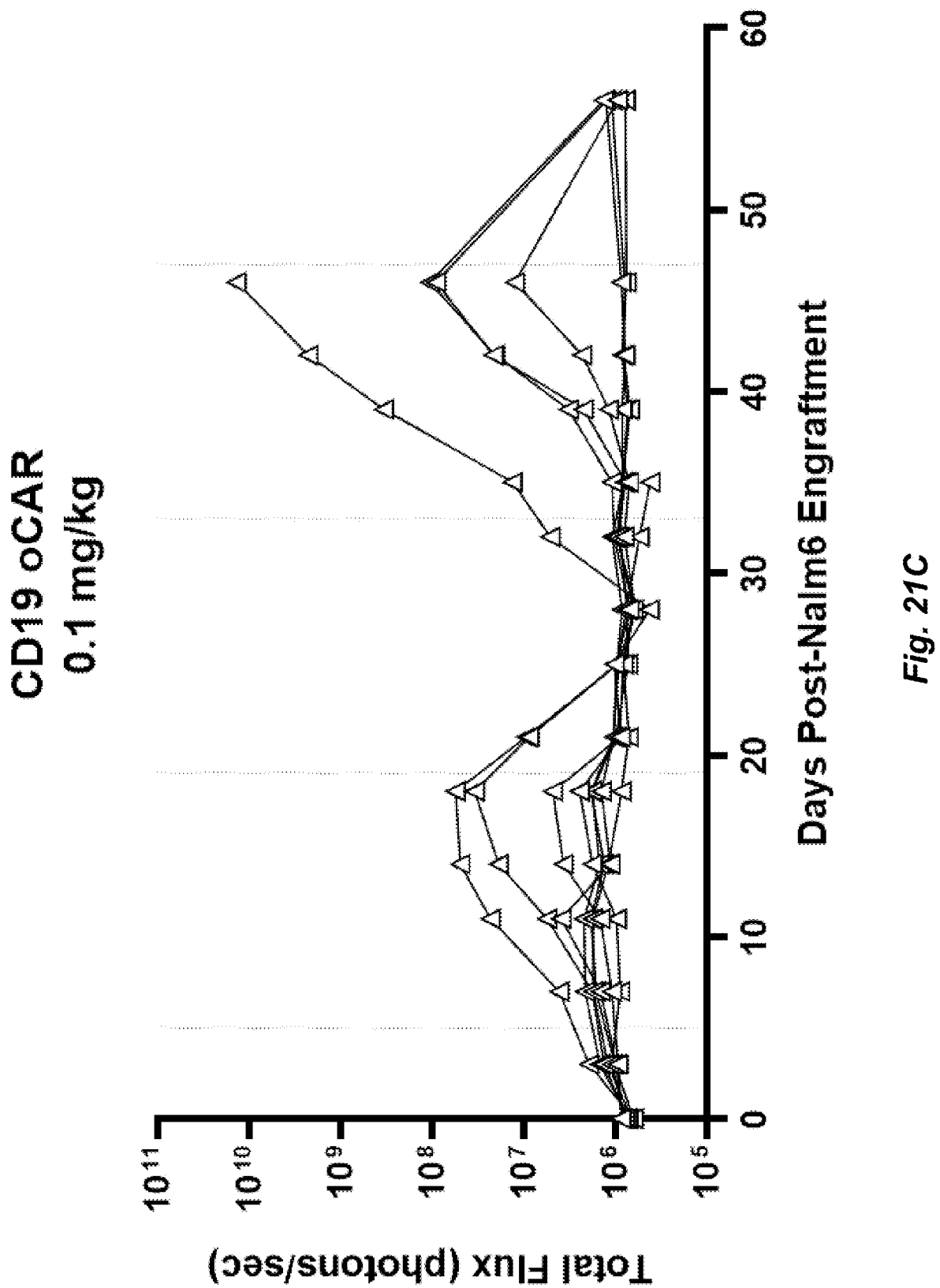
Figure 22:
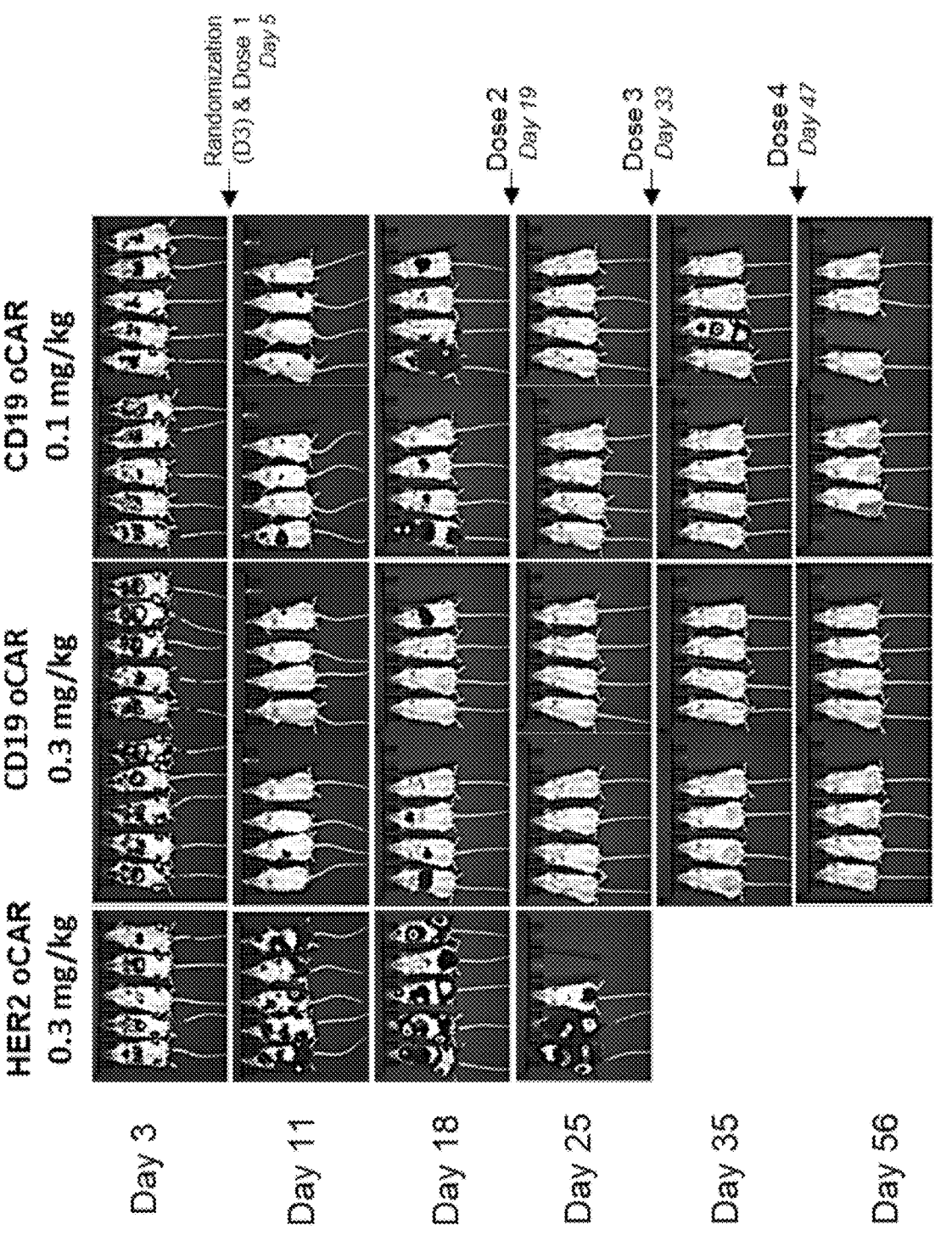
FIG. 22 shows tumor control in vivo using every-other-week dosing at 0.1 mg/kg and 0.3 mg/kg.
Figure 23A:
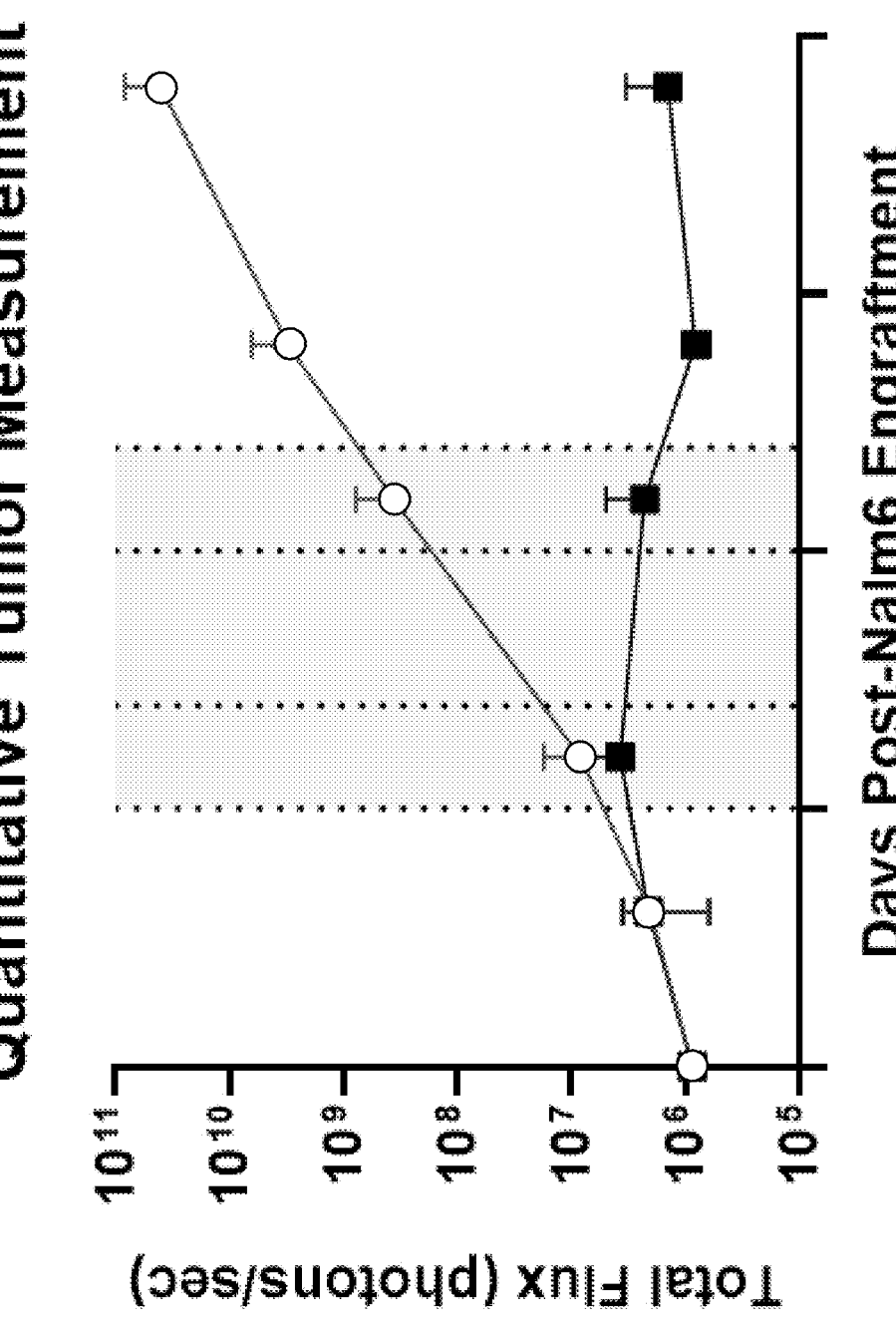
FIG. 23A and FIG. 23B show quantitative tumor measurement over time post-Nalm6 engraftment.
Figure 23B:
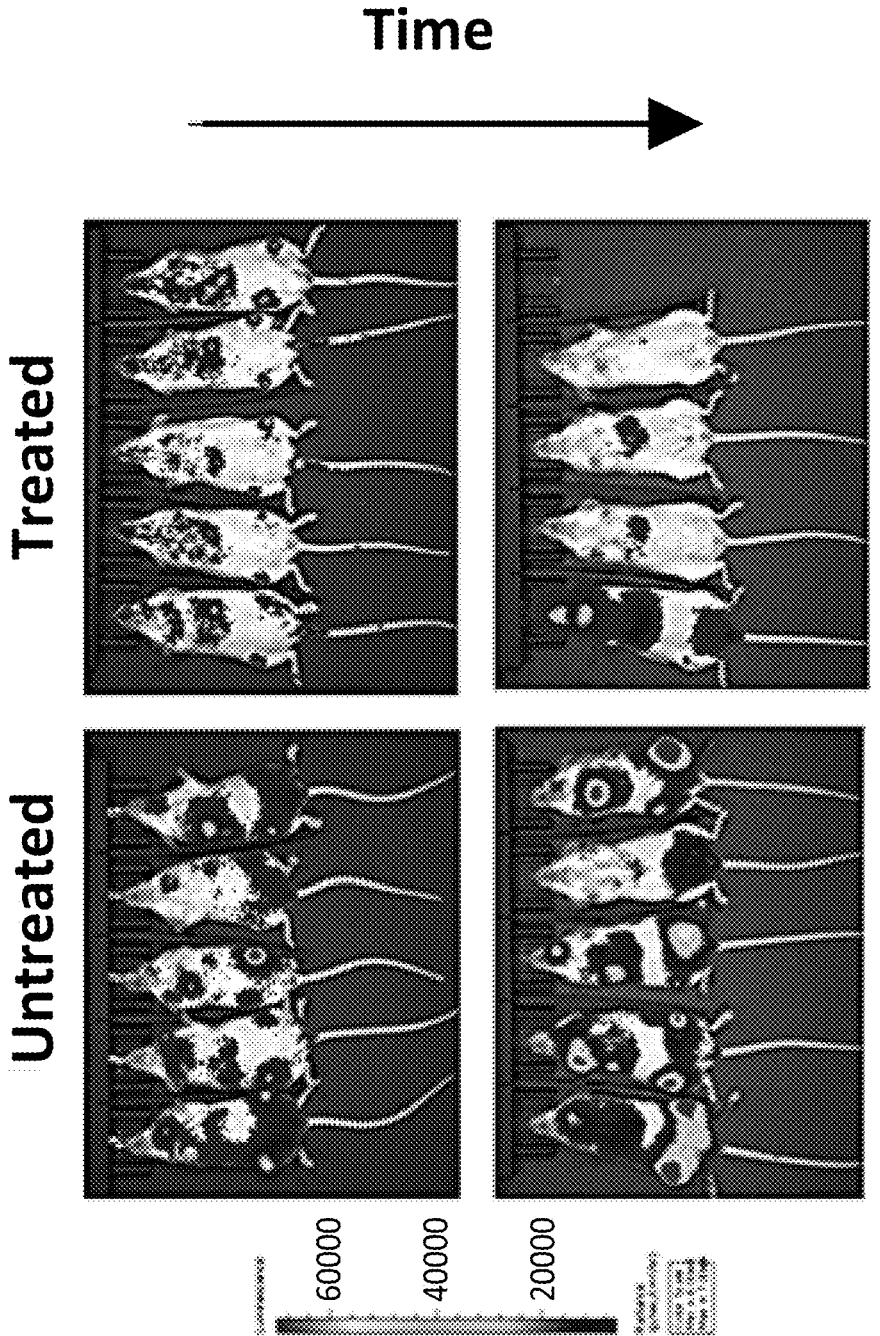

The CD19 oRNA-LNP treated animals showed tumor control and improved survival compared to controls treated with the HER2 oRNA construct described herein. Tumor control for weekly dosing is shown in FIG. 20. Tumor control for every-other-week dosing is shown in FIGS. 21A-C and FIG. 22. Tumor control was observed for up to 56 days in animals treated with every-other-week dosing. FIG. 23A and FIG. 23B show tumor control for CD19 oRNA-LNP as compared to a control.

Example 14: Expression of Circular RNAs Encoding Anti-BCMA CARS

Expression of Circular RNAs Encoding Anti-BCMA CAR In Vitro

T cells from a single donor were activated for 3 days with anti-CD3 and CD28 beads and allowed to rest for 24 hours. Concurrently, engineered circular RNA constructs were designed to encode a BCMA-41BBζ chimeric antigen receptor (CAR). For comparison purposes, "mock" or control circular RNAs encoded a HER2 or CD19 CAR. The circular RNAs were developed from an in vitro translation (IVT) reaction of DNA comprising a T7 polymerase promoter, permuted *Anabaena* intron exon segments, internal ribosome entry site (IRES) from Caprine Kobuvirus, Hunnivirus, Apodemus Picornavirus, or Picornavirales internal spacers, optionally internal homology arms, and a Xlab restriction site. DNA templates comprised of sequences from the table below. The donor T cells were electroporated with the circular RNAs at either 10 ng, 30 ng, or 100 ng per $0.1\times10^6$ T cell to form CAR-T cells. As a control, "Mock"

Figure 26:
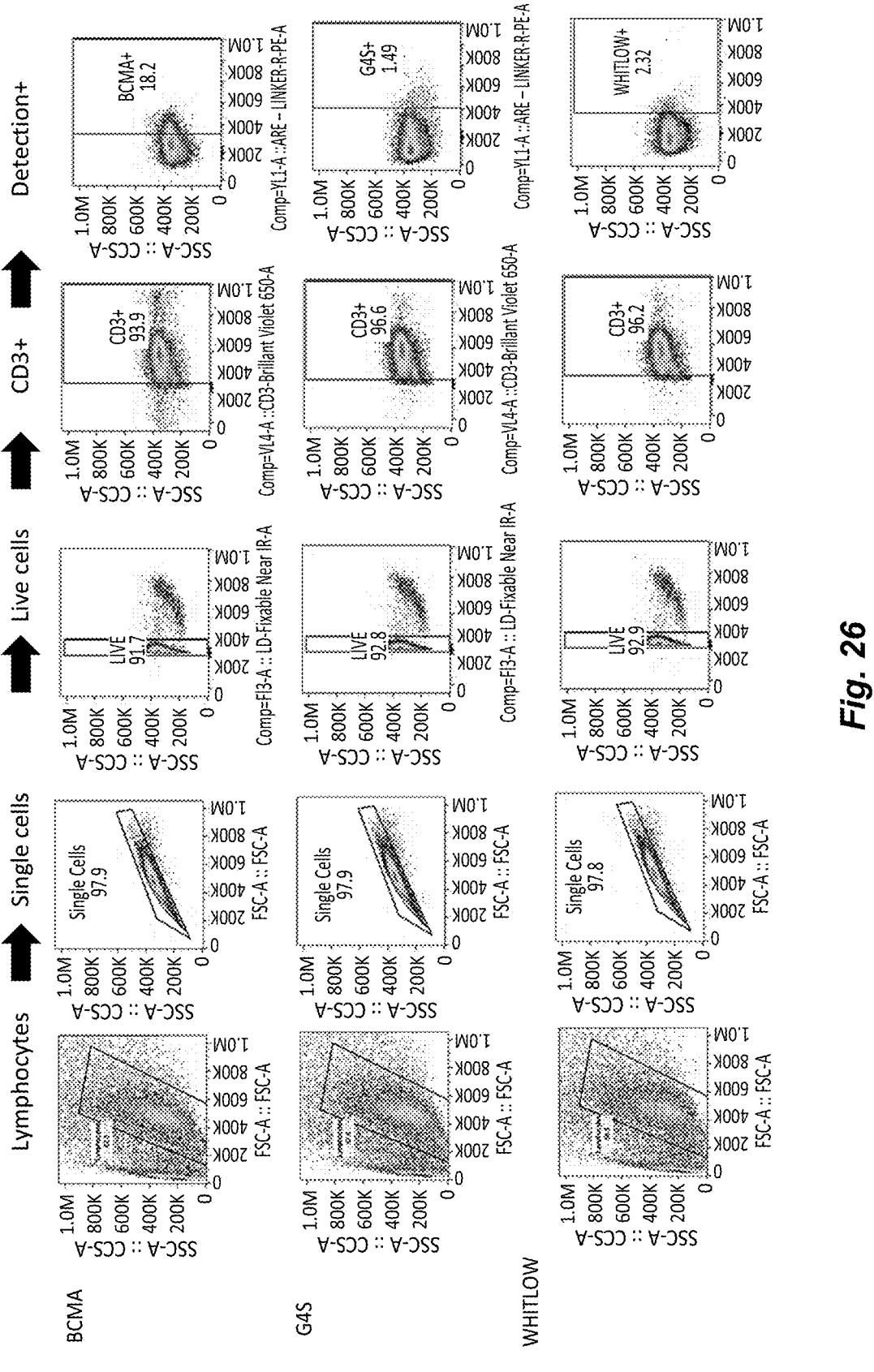
FIG. 26 depicts an exemplary gating method used to analyze flow cytometry results for T cells electroporated with circular RNAs encoding BCMA CARs at a dose of 10 ng×10. BCMA CAR expression was detected with either soluble BCMA PE, anti-Whitlow PE or anti-G4S linker.

T cells not electroporated with circular RNAs were analyzed. T cells were then allowed to rest for 24 hours after electroporation. 24 hours after electroporation, the CAR-T cells were counted and assessed for BCMA CAR expression. Resulting circular RNA with anti-BCMA CAR encoding regions were given a commercially available soluble BCMA detection reagent containing R-phycoerythrin (PE) fluorophore (e.g., from AcroBiosystems, Delaware), anti-Whitlow PE linker antibody detection reagent, or an anti-G4S linker PE detection reagent (e.g., G4S-AF647). Anti-BCMA, CD19, or HER2 expression was assessed using fluorescence activated cell sorting (FACS) and gating flow cytometry methods known in the art (e.g., illustrated in FIG. 26 for T cells electroporated with circular RNAs derived from DNA Template B and dosed at 10 ng per $0.1\times10^6$ T cells) at one or more timepoints from 24 to 72 hours post electroporation.

Figure 24A:
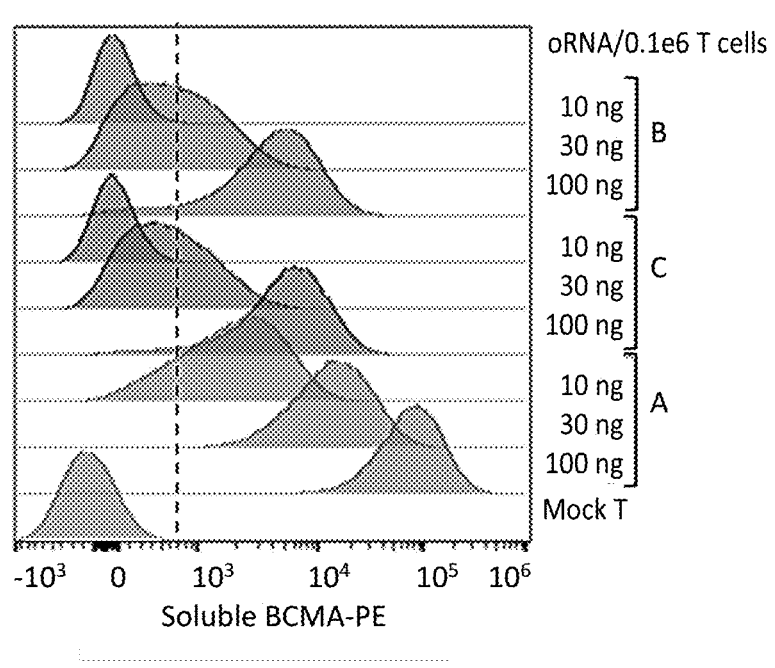
FIG. 24A depicts expression of BCMA CARs detected with soluble BCMA.PE post introduction of exemplary circular RNAs (circRNAs) via electroporation encoding BCMA-41BBζ CARs at 10 ng, 30 ng, or 100 ng dosages per 0.1×10⁶ T cell in comparison a "mock" control T cell not electroporated with any circRNAs. Expression was analyzed for the T cell at 24 hours, 48 hours, and 72 hours post introduction of the circular RNAs.
Figure 24B:
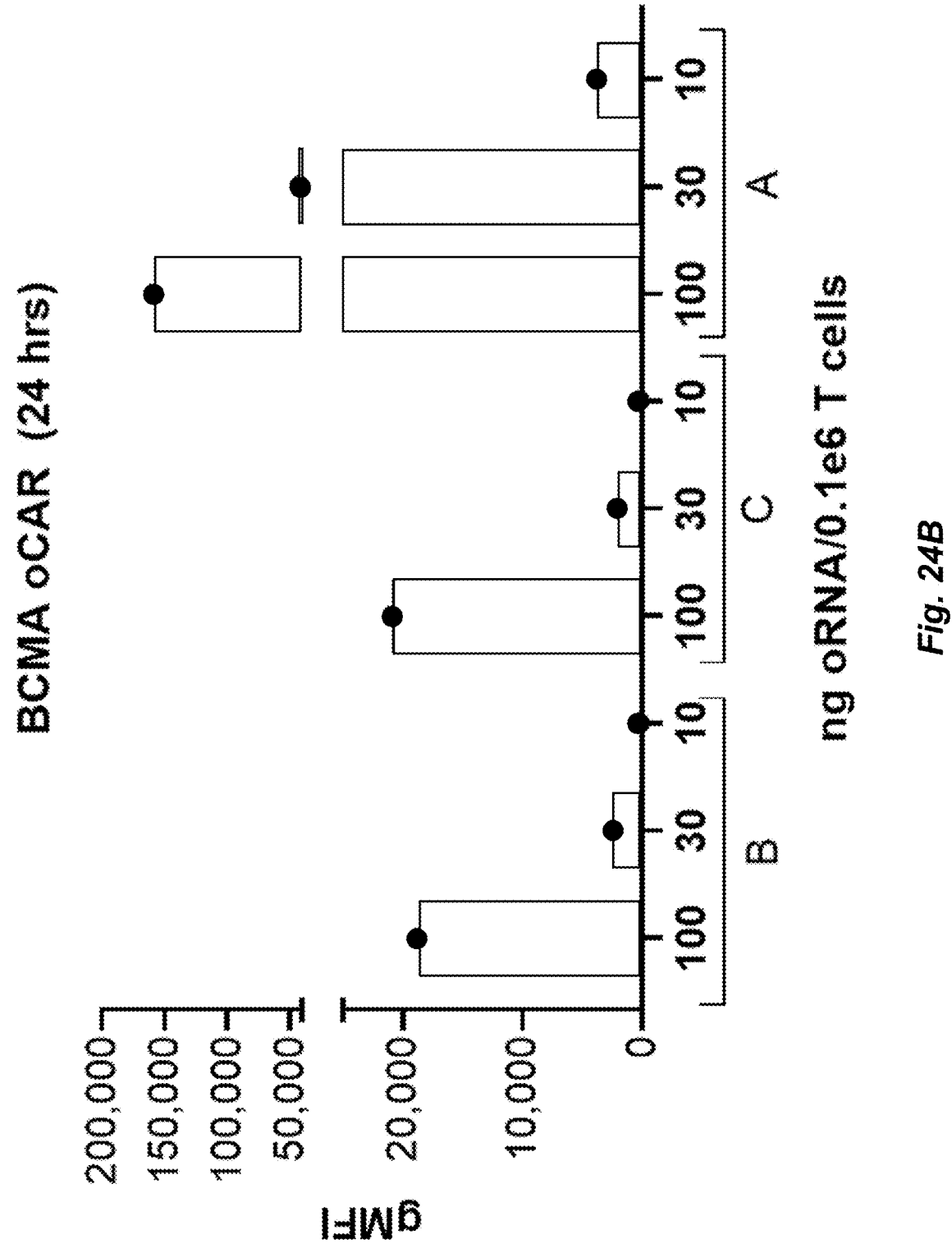
FIG. 24B depicts expression of BCMA CARS quantified using geometric mean fluorescent intensity (gMFI) activity over the span of 24 hours post introduction of circular RNAs encoding BCMA-41BB (CARs at 10 ng, 30 ng, or 100 ng dosages per 0.1×10⁶ T cell. "A", "B" and "C" correspond to "DNA Template A", "DNA Template B", and "DNA Template C" in Table al respectively, i.e., circular RNA construct "A" comprises the IRES sequence of DNA Template A and the BCMA sequence of DNA Template A; circular RNA construct B" comprises the IRES sequence of DNA Template B and the BCMA sequence of DNA Template B; circular RNA construct "C" comprises the IRES sequence of DNA Template C and the BCMA sequence of DNA Template C; etc.
Figure 25A:
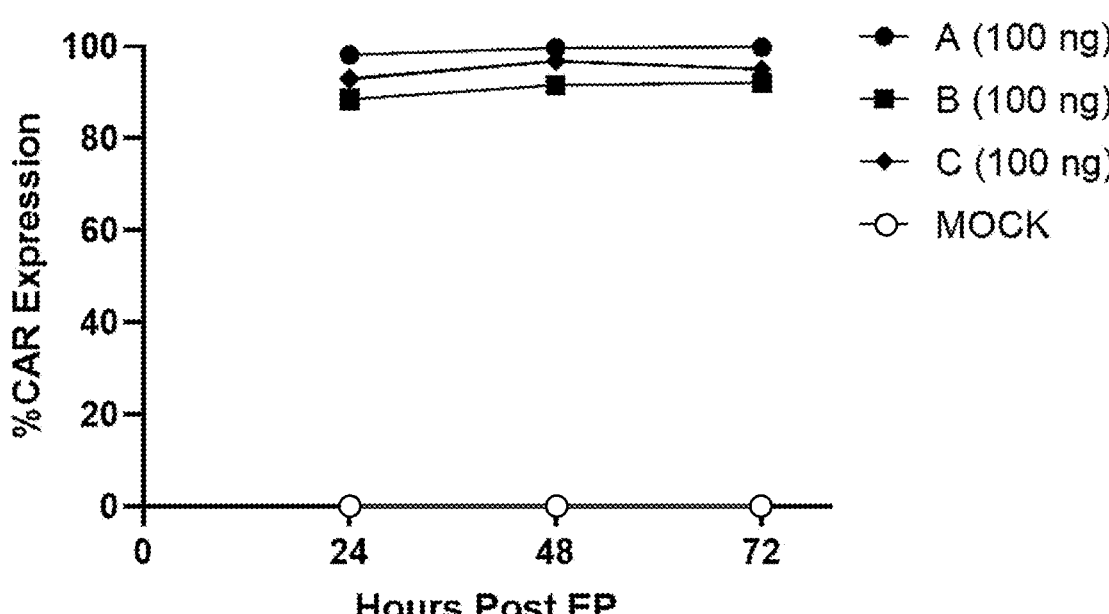
Figure 25B:
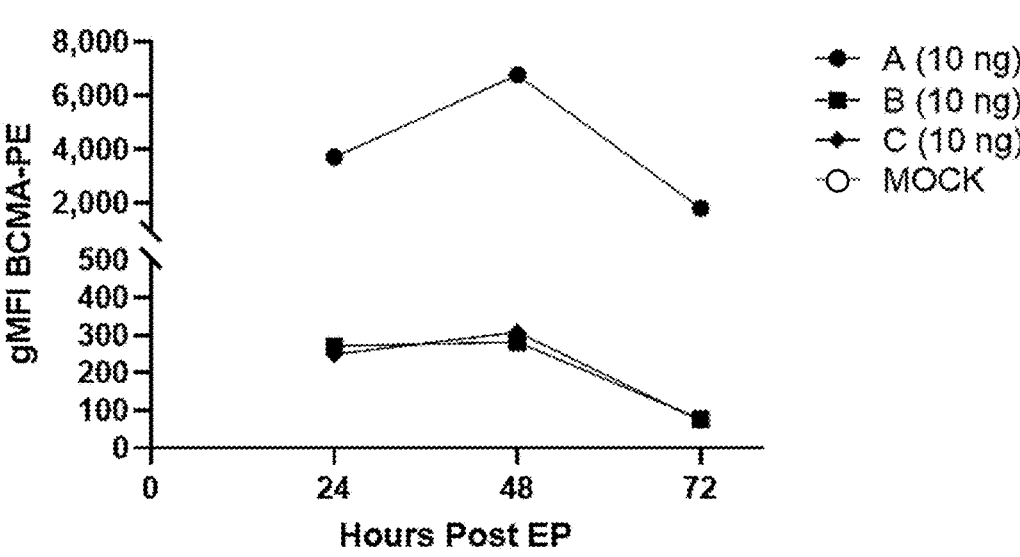
Figure 25D:
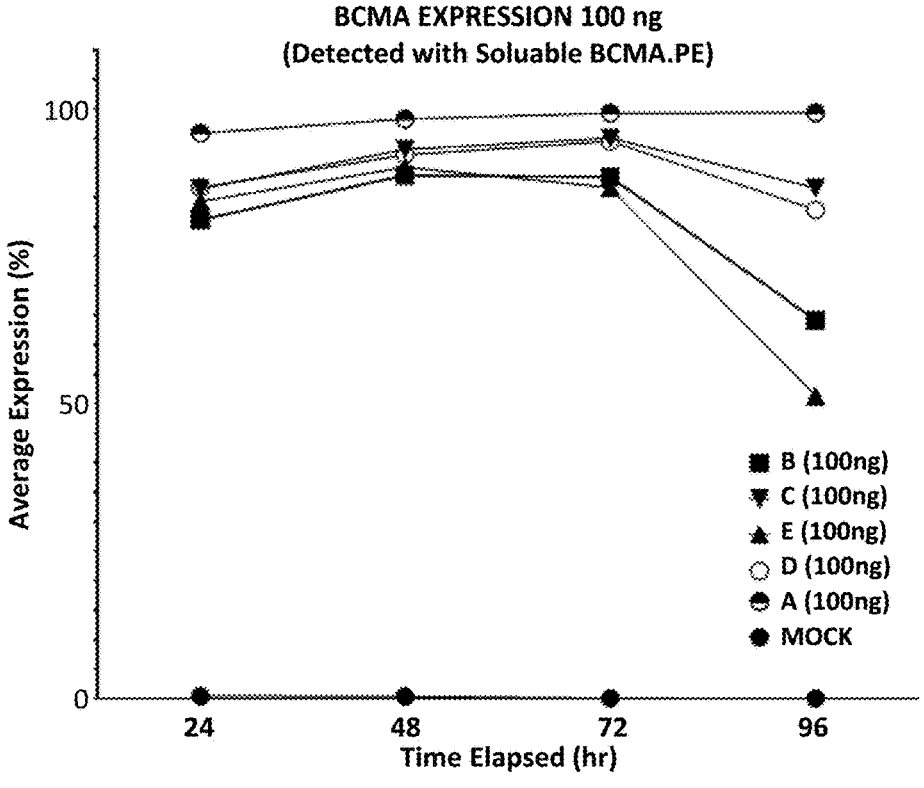
Figure 25E:
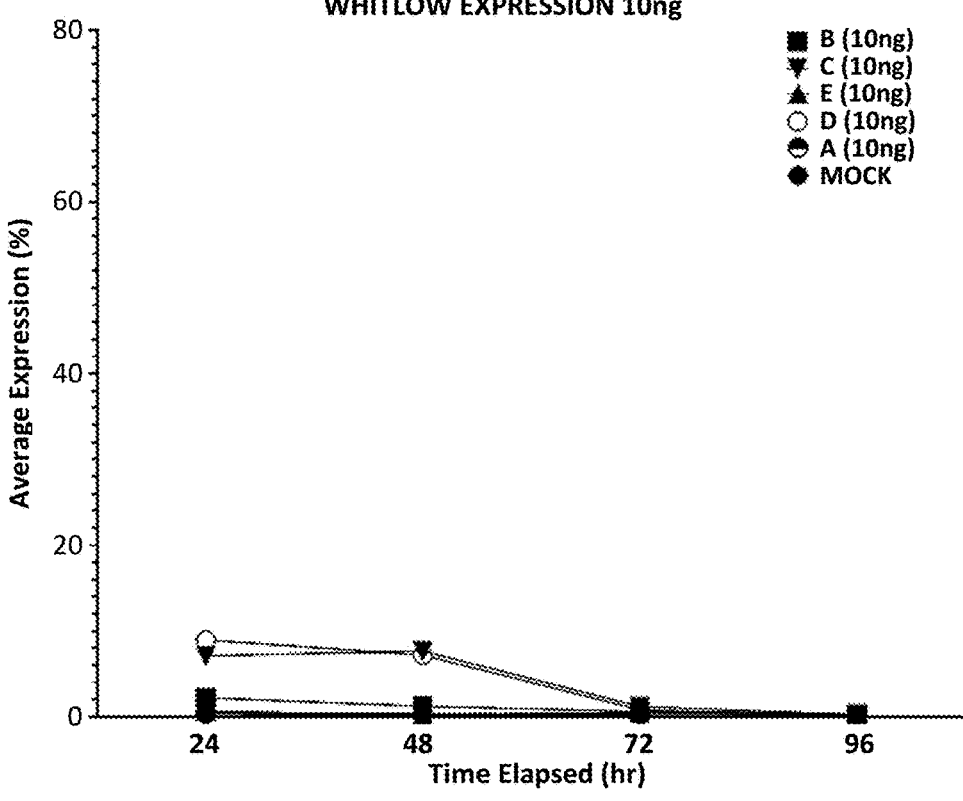
Figure 25F:
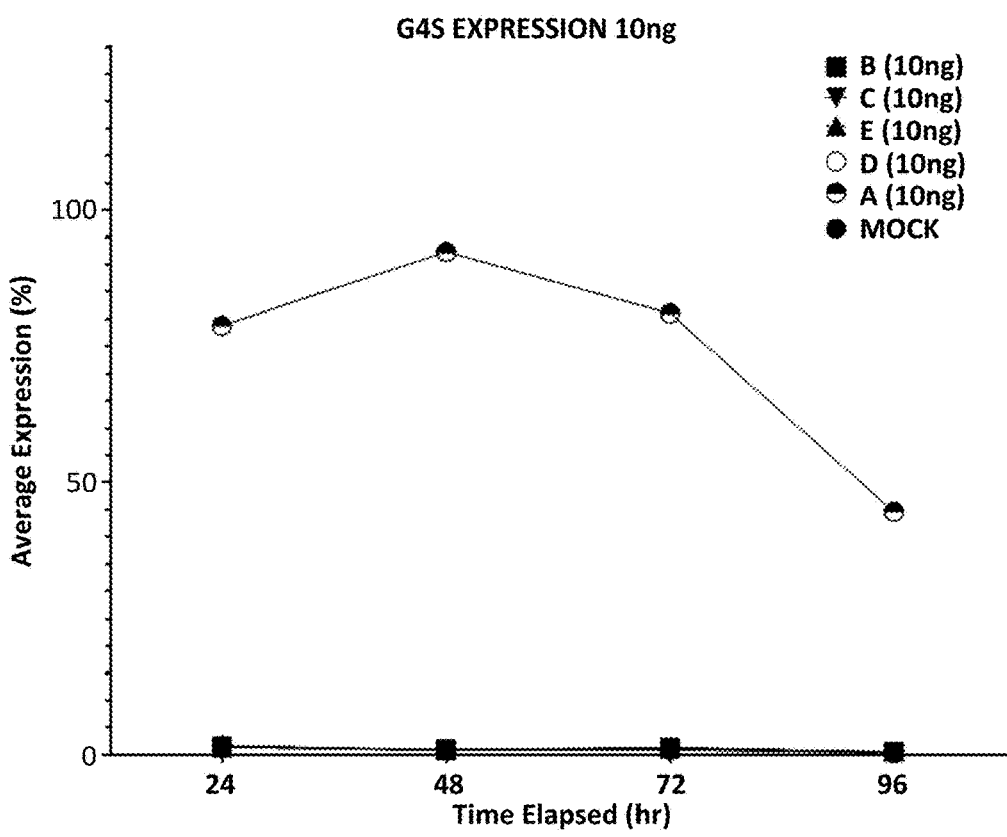
Figure 25G:
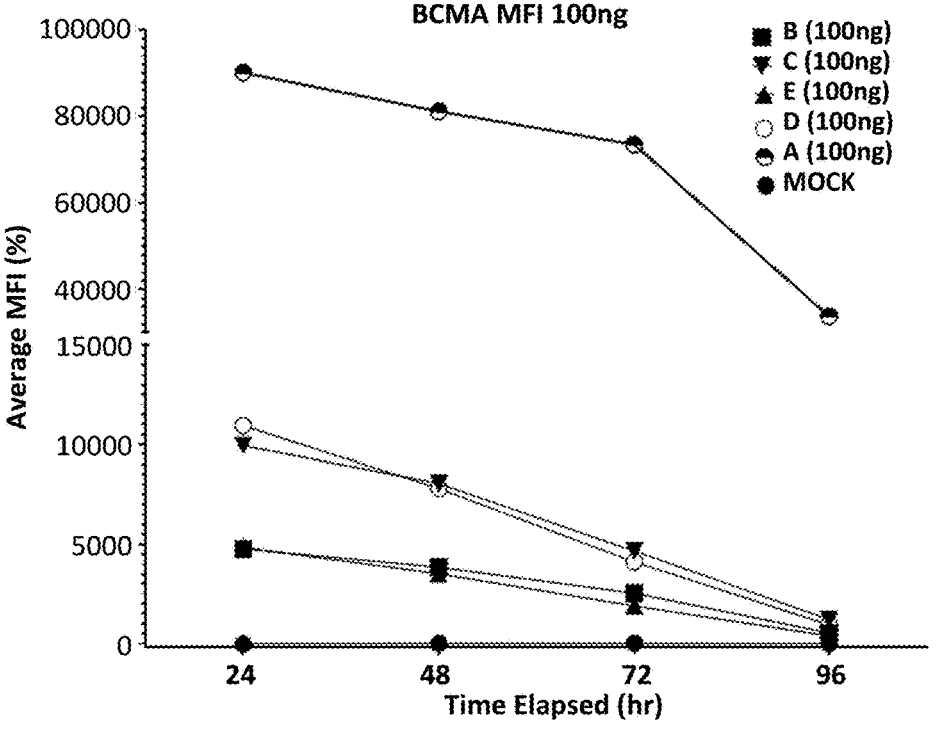

FIG. 24A provides the flow cytometry histogram, for each of the circular RNA constructs at the three different dosages collected at 24 hours, 48 hours and 72 hours. FIG. 24B shows the gMFI expression of each of the circular RNA constructs at the three different dosages collected at 24 hours. FIGS. 25A, 25D-25F depict percent CAR expression detected by either soluble BCMA PE, anti-Whitlow PE or anti-G4S linker PE detection reagent. FIGS. 25B and 25G gMFI and average MFI % respectively over the span of 24 hours to 96 hours post electroporation for each of the three dosages. FIG. 25C illustrates FACS imaging of the BCMA CARs as detected by the soluble BCMA detection reagent at 24 hours post electroporation.

TABLE α1

| ID | Internal Ribosome Entry Site (IRES) Sequence | CAR Sequence | CAR Sequence |
|---|---|---|---|
| DNA Template A (Construct A) | CCCCCCTCCCCCCCTTCCCT | ATGGCTCTCCCCGTGACCGCTCTGCT | MALPVTALLL |
| | TCCCTTTGCAACGCAACAAT | GCTCCCTCTGGCCCTCCTTCTGCACG | PLALLLHAAR |
| | TGTAAGTGCCCTCACCTGTC | CAGCCAGACCACAGGTCAAGCTGGAG | PQVKLEESGG |
| | AATTGGGACCACCACTTTCA | GAGTCTGGTGGCGGTCTGGTGCAGGC | GLVQAGRSLR |
| | GTGACCCCATGCGAAGTGCT | AGGGAGGAGCCTGAGGCTGAGCTGTG | LSCAASEHTE |
| | GAGAGAAAGGAAGCTTTCTT | CAGCTTCCGAGCACACATTCTCAAGC | SSHVMGWFRQ |
| | ACCCTTCATTTGTGAACCCA | CACGTCATGGGGTGGTTCAGACAGGC | APGKERESVA |
| | CTGGTCTAAGCCGCTTGGAA | TCCCGGTAAAGAGAGGGAGTCCGTCG | VIGWRDISTS |
| | TACGATGAGTGGAAAAGTTC | CCGTGATCGGATGGCGGGACATCTCC | YADSVKGRFT |
| | ATTCTTAATGGAGTGAAACA | ACCTCCTACGCCGACTCTGTGAAGGG | ISRDNAKKTL |
| | TGCTTAAATTTCCAGCTCGT | CCGGTTCACAATCTCACGCGATAATG | YLQMNSLKPE |
| | GCTGGTCTTTCCAGTACGGG | CCAAGAAGACACTGTATCTGCAGATG | DTAVYYCAAR |
| | GCGGCCCTGTCTGGCCGTAA | AATTCCTTGAAGCCCGAAGACACCGC | RIDAADEDSW |
| | TTCTTCAGAGTGTCACGCCA | CGTCTATTACTGTGCTGCTAGACGGA | GQGTQVTVSS |
| | CACTTGTGGATCTCACGTGC | TCGACGCTGCCGACTTCGACAGCTGG | GGGGSGGGGS |
| | CACATGACAGCGCTACAGCT | GGACAGGGTACCCAAGTGACCGTTTC | GGGGSEVQLV |
| | GGAACTGGGTGCTTGGTGCC | CTCCGGAGGCGGAGGTTCTGGAGGAG | ESGGGLVQAG |
| | CATGGAGTAACAGCGAAAAG | GTGGGTCAGGTGGAGGTGGCTCCGAG | GSLRLSCAAS |
| | TGTTAGATCAAGCCTTGCTT | GTGCAGCTGGTCGAGTCTGGCGGTGG | GRTFTMGWER |
| | GGGCTATGAGCCTGCGGAAC | CTTGGTCCAGGCTGGAGGCAGTCTCA | QAPGKEREFV |
| | AACAACTGGTAACAGTTGCC | GACTCTCCTGCGCTGCTTCAGGGCGG | AAISLSPTLA |
| | TCAGGGGCCGAAAGCCACGG | ACCTTCACCATGGGCTGGTTCAGGCA | YYAESVKGRE |
| | TGTTAACAGCACCCTCATAG | GGCCCCAGGTAAGGAGAGGGAGTTCG | TISRDNAKNT |
| | TTTGATCCACCTCAGGGTGG | TGGCCGCCATCTCCCTCTCCCCTACC | VVLQMNSLKP |

TABLE α1-continued

| ID | Internal Ribosome Entry Site (IRES) Sequence | CAR Sequence | CAR Sequence |
|---|---|---|---|
| | TGATGTTTAGCAGTTAGTAG TTGCCAATCTGTGTTCACTG AAATCTCGGCATACCGTGTA GTGTACAGGGGTGAAGGATG CCCAGAAGGTACCCGTAGGT AACCTTAAGAGACTATGGAT CTGATCTGGGGCCTTGTCCG GAGTGCTTTACACACGGCTC AAGGTTAAAAAACGTCTAGC CCCACAGAGCCCGAGGGATT CGGGTTTTCCCTTTAAAAAC CCGACTAGAGCTTATGGTGA CAATTATTGCTGTTCAGACG AACAGTGTAATTGTTGTCTA TTCACAGCAGTTCTATCAGA GCTTTTCCCACAACGGATCT TCTTGGCAAGCAAATACAGC AGGAGTCAAT (SEQ ID NO: 8) | CTGGCATACTACGCTGAGTCCGTGAA GGGACGGTTTACCATCTCCCGGGATA ACGCAAAGAACACTGTGGTCCTCCAA ATGAACTCCCTCAAACCCGAGGACAC CGCTCTCTACTATTGTGCCGCAGATC GGAAGAGCGTCATGTCCATCCGGCCC GATTACTGGGGCCAAGGCACACAGGT GACTGTGTCCAGCACCTCCACCACCA CCCCAGCACCAAGGCCTCCAACCCCT GCACCAACCATCGCCTCCCAGCCACT GTCTTTGCGGCCAGAAGCATGCCGCC CAGCAGCAGGTGGAGCCGTGCATACA AGAGGCCTGGACTTCGCCTGCGATAT CTACATCTGGGCTCCTCTGGCCGGAA CATGCGGAGTCCTGCTCTTGTCCCTG GTGATCACCCTGTACTGCAAGCGGGG TCGGAAGAAGCTCCTCTACATCTTCA AGCAGCCCTTCATGAGACCCGTCCAG ACCACCCAGGAGGAGGACGGGTGCTC ATGCAGGTTCCCCGAAGAGGAGGAGG GTGGCTGTGAGCTGCGGGTGAAGTTC AGCAGGTCAGCAGACGCCCCTGCCTA TCAGCAGGGCCAAAACCAGTIGTACA ACGAGCTGAATCTGGGGAGACGGGAG GAGTACGATGTCCTTGACAAGAGAAG GGGCCGGGATCCAGAGATGGGCGGGA AGCCAAGACGGAAGAATCCTCAGGAG GGTCTGTATAACGAGCTGCAGAAGGA CAAGATGGCCGAGGCCTACTCCGAGA TCGGCATGAAAGGGGAGCGCCGCAGA GGAAAAGGTCACGATGGTCTGTACCA GGGGTTGAGCACCGCTACCAAGGATA CTTACGACGCTCTGCACATGCAAGCT CTGCCACCCCGG (SEQ ID NO: 106) | EDTALYYCAA DRKSVMSIRP DYWGQGTQVT VSSTSTTTPA PRPPTPAPTI ASQPLSLRPE ACRPAAGGAV HTRGLDFACD IYIWAPLAGT CGVLLLSLVI TLYCKRGRKK LLYIFKQPFM RPVQTTQEED GCSCRFPEEE EGGCELRVKF SRSADAPAYQ QGQNQLYNEL NLGRREEYDV LDKRRGRDPE MGGKPRRKNP QEGLYNELQK DKMAEAYSEI GMKGERRGK GHDGLYQGLS TATKDTYDAL HMQALPPR (SEQ ID NO: 122) |
| DNA Template B (Construct B) | GTGGCCACGCCCGGGCCACC GATACTTCCCTTCACTCCTT CGGGACTGTTGGGGAGGAAC ACAACAGGGCTCCCCTGTTT TCCCATTCCTTCCCCCTTTT CCCAACCCCAACCGCCGTAT CTGGTGGCGGCAAGACACAC GGGTCTTTCCCTCTAAAGCA CAATTGTGTGTGTGTCCCAG GTCCTCCTGCGTACGGTGCG GGAGTGCTCCCACCCAACTG TTGTAAGCCTGTCCAACGCG TCGTCCTGGCAAGACTATGA CGTCGCATGTTCCGCTGCGG ATGCCGACGGGTAACCGGT TCCCCAGTGTGTGTAGTGCG ATCTTCCAGGTCCTCCTGGT TGGCGTTGTCCAGAAACTGC TTCAGGTAAGTGGGGTGTGC CCAATCCCTACAAAGGTTGA TTCTTTCACCACCTTAGGAA TGCTCCGGAGGTACCCCAGC AACAGCTGGGATCTGACCGG AGGCTAATTGTCTACGGGTG GTGTTTCCTTTTTCTTTTCA CACAACTCTACTGCTGACAA CTCACTGACTATCCACTTGC TCTGTCACG (SEQ ID NO: 17; | ATGGCACTCCCGGTAACCGCCTTATT GCTTCCCCTTGCCCTCTTGCTCCACG CAGCACGCCCCGATATAGTCTTGACT CAATCCCCACCCAGTTTGGCAATGTC ATTAGGCAAACGAGCAACAATTTCAT GTAGGGCATCCGAAAGTGTAACGATT TTGGGGAGTCATTTAATTCATTGGTA CCAACAAAAGCCTGGACAACCCCCGA CGCTCTTGATCCAATTAGCATCTAAC GTCCAAACCGGAGTCCCCGCACGATT CTCAGGATCCGGTTCCCGGACTGATT TTACATTAACTATTGATCCGGTAGAG GAAGATGACGTCGCTGTCTATTATTG TCTTCAAAGTAGGACGATTCCACGGA CATTCGGTGGCGGAACTAAATTGGAG ATTAAAGGTTCCACCTCTGGTAGTGG GAAACCCGGGTCCGGTGAAGGGTCCA CTAAAGGCCAAATTCAACTCGTTCAA TCCGGACCAGAACTGAAGAAGCCAGG AGAAACTGTCAAAATAAGCTGTAAAG CTTCCGGTTATACATTTACAGATTAT TCCATAAATTGGGTGAAAAGGGCGCC AGGAAAAGGGTTAAAGTGGATGGGTT GGATTAATACAGAGACTCGGGAACCT GCATATGCTTATGATTTTAGGGGAAG GTTTGCCTTTTCTCTGGAGACTTCCG CTTCAACTGCTTATCTCCAAATTAAT AATCTTAAATATGGGCACAGCAAC ATACTTCTGTGCTTTGGACTATAGTT ATGCTATGGATTACTGGGGACAAGGA ACCAGTGTCACTGTAAGTTCCGCTGC TGCGACGACCACTCCTGCACCGCGAC CACCCACTCCTGCCCCTACTATTGCT AGTCAACCACTTAGCTTGCGACCTGA GGCATGTCGGCCCGCGGCAGGTGGCG CAGTCCACACCAGGGGTTTAGACTTT GCTTGTGATATTTATATTTGGGCACC ACTCGCCGGGACTTGCGGTGTTCTTC TCTTGTCCCTTGTTATAACTCTTTAT TGTAAGCGCGGAAGGAAGAAATTGTT ATATATTTTCAAACAACCTTTTATGC | MALPVTALLL PLALLLHAAR PDIVLTQSPP SLAMSLGKRA TISCRASESV TILGSHLIHW YQQKPGQPPT LLIQLASNVQ TGVPARFSGS GSRTDFTLTI DPVEEDDVAV YYCLQSRTIP RTFGGGTKLE IKGSTSGSGK PGSGEGSTKG QIQLVQSGPE LKKPGETVKI SCKASGYTFT DYSINWVKRA PGKGLKWMGW INTETREPAY AYDERGRFAF SLETSASTAY LQINNLKYED TATYFCALDY SYAMDYWGQG TSVTVSSAAA TTTPAPRPPT PAPTIASQPL SLRPEACRPA AGGAVHTRGL DFACDIYIWA PLAGTCGVLL LSLVITLYCK RGRKKLLYIF KQPFMRPVQT TQEEDGCSCR FPEEEEGGCE LRVKFSRSAD APAYQQGQNQ LYNELNLGRR |

TABLE α1-continued

| ID | Internal Ribosome Entry Site (IRES) Sequence | CAR Sequence | CAR Sequence |
|---|---|---|---|
| | | GACCCGTACAAACAACTCAGGAAGAG GACGGGTGTTCTTGTCGGTTTCCAGA AGAGGAAGAGGGTGGGTGTGAACTCC GGGTCAAATTTAGTAGGTCAGCAGAT GCGCCGGCGTACCAACAAGGCCAAAA CCAACTGTATAATGAACTCAATCTCG GTAGGCGTGAGGAATATGATGTCCTT GATAAAAGGCGCGGGAGAGATCCAGA AATGGGCGGAAAACCACGGCGAAAGA ATCCGCAGGAAGGGTTATATAACGAA CTTCAAAAGGATAAAATGGCTGAAGC TTATTCCGAAATTGGCATGAAAGGAG AGCGACGTAGGGGCAAAGGGCATGAT GGCCTTTACCAAGGGCTCTCAACCGC TACAAAAGATACTTACGACGCTTTAC ATATGCAAGCACTTCCACCCAGG (SEQ ID NO: 103) | EEYDVLDKRR GRDPEMGGKP RRKNPQEGLY NELQKDKMAE AYSEIGMKGE RRRGKGHDGL YQGLSTATKD TYDALHMQAL PPR (SEQ ID NO: 119) |
| DNA Template C (Construct C) | CCCCCCTCCCCCCCTTCCCT TCCCTTTGCAACGCAACAAT TGTAAGTGCCCTCACCTGTC AATTGGGACCACCACTTTCA GTGACCCCATGCGAAGTGCT GAGAGAAAGGAAGCTTTCTT ACCCTTCATTTGTGAACCCA CTGGTCTAAGCCGCTTGGAA TACGATGAGTGGAAAAGTTC ATTCTTAATGGAGTGAAACA TGCTTAAATTTCCAGCTCGT GCTGGTCTTTCCAGTACGGG GCGGCCCTGTCTGGCCGTAA TTCTTCAGAGTGTCACGCCA CACTTGTGGATCTCACGTGC CACATGACAGCGCTACAGCT GGAACTGGGTGCTTGGTGCC CATGGAGTAACAGCGAAAAG TGTTAGATCAAGCCTTGCTT GGGCTATGAGCCTGCGGAAC AACAACTGGTAACAGTTGCC TCAGGGGCCGAAAGCCACGG TGTTAACAGCACCCTCATAG TTTGATCCACCTCAGGGTGG TGATGTTTAGCAGTTAGTAG TTGCCAATCTGTGTTCACTG AAATCTCGGCATACCGTGTA GTGTACAGGGGTGAAGGATG CCCAGAAGGTACCCGTAGGT AACCTTAAGAGACTATGGAT CTGATCTGGGGCCTTGTCCG GAGTGCTTTACACACGGCTC AAGGTTAAAAAACGTCTAGC CCCACAGAGCCCGAGGGATT CGGGTTTTCCCTTTAAAAAC CCGACTAGAGCTTATGGTGA CAATTATTGCTGTTCAGACG AACAGTGTAATTGTTGTCTA TTCACAGCAGTTCTATCAGA GCTTTTCCCACAACGGATCT TCTTGGCAAGCAAATACAGC AGGAGTCAAT (SEQ ID NO: 8) | ATGGCACTCCCGGTAACCGCCTTATT GCTTCCCCTTGCCCTCTTGCTCCACG CAGCACGCCCCGATATAGTCTTGACT CAATCCCCACCCAGTTTGGCAATGTC ATTAGGCAAACGAGCAACAATTTCAT GTAGGGCATCCGAAAGTGTAACGATT TTGGGGAGTCATTTAATTCATTGGTA CCAACAAAAGCCTGGACAACCCCCGA CGCTCTTGATCCAATTAGCATCTAAC GTCCAAACCGGAGTCCCCGCACGATT CTCAGGATCCGGTTCCCGGACTGATT TTACATTAACTATTGATCCGGTAGAG GAAGATGACGTCGCTGTCTATTATTG TCTTCAAAGTAGGACGATTCCACGGA CATTCGGTGGCGGAACTAAATTGGAG ATTAAAGGTTCCACCTCTGGTAGTGG GAAACCCGGGTCCGGTGAAGGGTCCA CTAAAGGCCAAATTCAACTCGTTCAA TCCGGACCAGAACTGAAGAAGCCAGG AGAAACTGTCAAAATAAGCTGTAAAG CTTCCGGTTATACATTTACAGATTAT TCCATAAATTGGGTGAAAAGGGCGCC AGGAAAAGGGTTAAAGTGGATGGGTT GGATTAATACAGAGACTCGGGAACCT GCATATGCTTATGATTTTAGGGGAAG GTTTGCCTTTTCTCTGGAGACTTCCG CTTCAACTGCTTATCTCCAAATTAAT AATCTTAAATATGAGGACACAGCAAC ATACTTCTGTGCTTTGGACTATAGTT ATGCTATGGATTACTGGGGACAAGGA ACCAGTGTCACTGTAAGTTCCGCTGC TGCGACGACCACTCCTGCACCGCGAC CACCCACTCCTGCCCCTACTATTGCT AGTCAACCACTTAGCTTGCGACCTGA GGCATGTCGGCCCGCGGCAGGTGGCG CAGTCCACACCAGGGGTTTAGACTTT GCTTGTGATATTTATATTTGGGCACC ACTCGCCGGGACTTGCGGTGTTCTTC TCTTGTCCCTTGTTATAACTCTTTAT TGTAAGCGCGGAAGGAAGAAATTGTT ATATATTTTCAAACAACCTTTTATGC GACCCGTACAAACAACTCAGGAAGAG GACGGGTGTTCTTGTCGGTTTCCAGA AGAGGAAGAGGGTGGGTGTGAACTCC GGGTCAAATTTAGTAGGTCAGCAGAT GCGCCGGCGTACCAACAAGGCCAAAA CCAACTGTATAATGAACTCAATCTCG GTAGGCGTGAGGAATATGATGTCCTT GATAAAAGGCGCGGGAGAGATCCAGA AATGGGCGGAAAACCACGGCGAAAGA ATCCGCAGGAAGGGTTATATAACGAA CTTCAAAAGGATAAAATGGCTGAAGC TTATTCCGAAATTGGCATGAAAGGAG AGCGACGTAGGGGCAAAGGGCATGAT GGCCTTTACCAAGGGCTCTCAACCGC TACAAAAGATACTTACGACGCTTTAC ATATGCAAGCACTTCCACCCAGG (SEQ ID NO: 103) | MALPVTALLL PLALLLHAAR PDIVLTQSPP SLAMSLGKRA TISCRASESV TILGSHLIHW YQQKPGQPPT LLIQLASNVQ TGVPARFSGS GSRTDFTLTI DPVEEDDVAV YYCLQSRTIP RTFGGGTKLE IKGSTSGSGK PGSGEGSTKG QIQLVQSGPE LKKPGETVKI SCKASGYTFT DYSINWVKRA PGKGLKWMGW INTETREPAY AYDERGRFAF SLETSASTAY LQINNLKYED TATYFCALDY SYAMDYWGQG TSVTVSSAAA TTTPAPRPPT PAPTIASQPL SLRPEACRPA AGGAVHTRGL DFACDIYIWA PLAGTCGVLL LSLVITLYCK RGRKKLLYIF KQPFMRPVQT TQEEDGCSCR FPEEEEGGCE LRVKFSRSAD APAYQQGQNQ LYNELNLGRR EEYDVLDKRR GRDPEMGGKP RRKNPQEGLY NELQKDKMAE AYSEIGMKGE RRRGKGHDGL YQGLSTATKD TYDALHMQAL PPR (SEQ ID NO: 119) |

TABLE α1-continued

| ID | Internal Ribosome Entry Site (IRES) Sequence | CAR Sequence | CAR Sequence |
|---|---|---|---|
| DNA Template D (Construct D) | TTTGCTCAGCGTAACTTCTC CGGGTTACGTGGAGACCAAA AGGCTACGGAGACTCGGGCT ACGGCCCTGGAGCACCTAGG TGCTCCTAAAGACGTTAGAA GTTGTACAAACTCGCCCAAT AGGGCCCCCCAACCAGGGGG GTAGCGGGCAAGCACTTCTG TTTCCCCGGTATGATCTCAT AGGCTGTACCCACGGCTGAA AGAGAGATTATCGTTACCCG CCTCACTACTTCGAGAAGCC CAGTAATGGTTCATGAAGTT GATCTCGTTGACCCGGTGTT TCCCCCACACCAGAAACCTG TGATGGGGGTGGTCATCCCG GTCATGGCGACATGACGGAC CTCCCCGCGCGGCACAGGG CCTCTTCGGAGGACGAGTGA CATGGATTCAACCGTGAAGA GCCTATTGAGCTAGTGTTGA TTCCTCCGCCCCCGTGAATG CGGCTAATCCCAACTCCGGA GCAGGCGGGCCCAAACCAGG GTCTGGCCTGTCGTAACGCG AAAGTCTGGAGCGGAACCGA CTACTTTCGGGAAGGCGTGT TTCCTTTTGTTCCTTTTATC AAGTTTTATGGTGACAACTC CTGGTAGACGTTTTATTGCG TTTATTGAGAGATTTCCAAC AATTGAACAGACTAGAACCA CTTGTTTTATCAAACCCTCA CAGAATAAGATAACA (SEQ ID NO: 18) | ATGGCACTCCCGGTAACCGCCTTATT GCTTCCCCTTGCCCTCTTGCTCCACG CAGCACGCCCCGATATAGTCTTGACT CAATCCCCACCCAGTTTGGCAATGTC ATTAGGCAAACGAGCAACAATTTCAT GTAGGGCATCCGAAAGTGTAACGATT TTGGGGAGTCATTTAATTCATTGGTA CCAACAAAAGCCTGGACAACCCCCGA CGCTCTTGATCCAATTAGCATCTAAC GTCCAAACCGGAGTCCCCGCACGATT CTCAGGATCCGGTTCCCGGACTGATT TTACATTAACTATTGATCCGGTAGAG GAAGATGACGTCGCTGTCTATTATTG TCTTCAAAGTAGGACGATTCCACGGA CATTCGGTGGCGGAACTAAATTGGAG ATTAAAGGTTCCACCTCTGGTAGTGG GAAACCCGGGTCCGGTGAAGGGTCCA CTAAAGGCCAAATTCAACTCGTTCAA TCCGGACCAGAACTGAAGAAGCCAGG AGAAACTGTCAAAATAAGCTGTAAAG CTTCCGGTTATACATTTACAGATTAT TCCATAAATTGGGTGAAAAGGGCGCC AGGAAAAGGGTTAAAGTGGATGGGTT GGATTAATACAGAGACTCGGGAACCT GCATATGCTTATGATTTTAGGGGAAG GTTTGCCTTTTCTCTGGAGACTTCCG CTTCAACTGCTTATCTCCAAATTAAT AATCTTAAATATGAGGACACAGCCAAC ATACTTCTGTGCTTTGGACTATAGTT ATGCTATGGATTACTGGGGACAAGGA ACCAGTGTCACTGTAAGTTCCGCTGC TGCGACGACCACTCCTGCACCGCGAC CACCCACTCCTGCCCCTACTATTGCT AGTCAACCACTTAGCTTGCGACCTGA GGCATGTCGGCCCCGCGGCAGGTGGCG CAGTCCACACCAGGGGTTTAGACTTT GCTTGTGATATTTATATTTGGGCACC ACTCGCCGGGACTTGCGGTGTTCTTC TCTTGTCCCTTGTTATAACTCTTTAT TGTAAGCGCGGAAGGAAGAAATTGTT ATATATTTTCAAACAACCTTTTATGC GACCCGTACAAACAACTCAGGAAGAG GACGGGTGTTCTTGTCGGTTTCCAGA AGAGGAAGAGGGTGGGTGTGAACTCC GGGTCAAATTTAGTAGGTCAGCAGAT GCGCCGGCGTACCAACAAGGCCAAAA CCAACTGTATAATGAACTCAATCTCG GTAGGCGTGAGGAATATGATGTCCTT GATAAAAGGCGCGGGAGAGATCCAGA AATGGGCGGAAAACCACGGCGAAAGA ATCCGCAGGAAGGGTTATATAACGAA CTTCAAAAGGATAAAATGGCTGAAGC TTATTCCGAAATTGGCATGAAAGGAG AGCGACGTAGGGGCAAAGGGCATGAT GGCCTTTACCAAGGGCTCTCAACCGC TACAAAAGATACTTACGACGCTTTAC ATATGCAAGCACTTCCACCCAGG (SEQ ID NO: 103) | MALPVTALLL PLALLLHAAR PDIVLTQSPP SLAMSLGKRA TISCRASESV TILGSHLIHW YQQKPGQPPT LLIQLASNVQ TGVPARFSGS GSRTDETLTI DPVEEDDVAV YYCLQSRTIP RTFGGGTKLE IKGSTSGSGK PGSGEGSTKG QIQLVQSGPE LKKPGETVKI SCKASGYTFT DYSINWVKRA PGKGLKWMGW INTETREPAY AYDERGRFAF SLETSASTAY LQINNLKYED TATYFCALDY SYAMDYWGQG TSVTVSSAAA TTTPAPRPPT PAPTIASQPL SLRPEACRPA AGGAVHTRGL DFACDIYIWA PLAGTCGVLL LSLVITLYCK RGRKKLLYIF KQPFMRPVQT TQEEDGCSCR FPEEEEGGCE LRVKFSRSAD APAYQQGQNQ LYNELNLGRR EEYDVLDKRR GRDPEMGGKP RRKNPQEGLY NELQKDKMAE AYSEIGMKGE RRRGKGHDGL YQGLSTATKD TYDALHMQAL PPR (SEQ ID NO: 119) |
| DNA Template E (Construct E) | ATTCTCGGGCTACGGCCCTG GAGCCACTCCGGCTCCTAAA GATTTAGAAGTTTGAGCACA CCCGCCCACTAGGGCCCCCC ATCCAGGGGGGCAACGGGCA AGCACTTCTGTTTCCCCGGT ATGATCTGATAGGCTGTAAC CACGGCTGAAACAGAGATTA TCGTTATCCGCTTCACTACT TCGAGAAGCCTAGTAATGAT GGGTGAAATTGAATCCGTTG ATCCGGTGTCTCCCCCACAC CAGAAACTCATGATGAGGGT TGCCATCCCGGCTACGGCGA CGTAGCGGGCATCCCTGCGC TGGCATGAGGCCTCTTAGGA GGACGGATGATATGGATCTT GTCGTGAAGAGCCTATTGAG | ATGGCACTCCCGGTAACCGCCTTATT GCTTCCCCTTGCCCTCTTGCTCCACG CAGCACGCCCCGATATAGTCTTGACT CAATCCCCACCCAGTTTGGCAATGTC ATTAGGCAAACGAGCAACAATTTCAT GTAGGGCATCCGAAAGTGTAACGATT TTGGGGAGTCATTTAATTCATTGGTA CCAACAAAAGCCTGGACAACCCCCGA CGCTCTTGATCCAATTAGCATCTAAC GTCCAAACCGGAGTCCCCGCACGATT CTCAGGATCCGGTTCCCGGACTGATT TTACATTAACTATTGATCCGGTAGAG GAAGATGACGTCGCTGTCTATTATTG TCTTCAAAGTAGGACGATTCCACGGA CATTCGGTGGCGGAACTAAATTGGAG ATTAAAGGTTCCACCTCTGGTAGTGG GAAACCCGGGTCCGGTGAAGGGTCCA CTAAAGGCCAAATTCAACTCGTTCAA | MALPVTALLL PLALLLHAAR PDIVLTQSPP SLAMSLGKRA TISCRASESV TILGSHLIHW YQQKPGQPPT LLIQLASNVQ TGVPARFSGS GSRTDFTLTI DPVEEDDVAV YYCLQSRTIP RTFGGGTKLE IKGSTSGSGK PGSGEGSTKG QIQLVQSGPE LKKPGETVKI SCKASGYTFT |

TABLE α1-continued

| ID | Internal Ribosome Entry Site (IRES) Sequence | CAR Sequence | CAR Sequence |
|---|---|---|---|
| | CTAGTGTCGACTCCTCCGCC | TCCGGACCAGAACTGAAGAAGCCAGG | DYSINWVKRA |
| | CCCGTGAATGCGGCTAATCC | AGAAACTGTCAAAATAAGCTGTAAAG | PGKGLKWMGW |
| | TAACCCCGGAGCAGGTGGGT | CTTCCGGTTATACATTTACAGATTAT | INTETREPAY |
| | CCAATCCAGGGCCTGGCCTG | TCCATAAATTGGGTGAAAAGGGCGCC | AYDERGRFAF |
| | TCGTAATGCGTAAGTCTGGG | AGGAAAAGGGTTAAAGTGGATGGGTT | SLETSASTAY |
| | ACGGAACCGACTACTTTCGG | GGATTAATACAGAGACTCGGGAACCT | LQINNLKYED |
| | GAAGGCGTGTTTCCATTTGT | GCATATGCTTATGATTTTAGGGGAAG | TATYFCALDY |
| | TCATTATTTGTGTGTTTATG | GTTTGCCTTTTCTCTGGAGACTTCCG | SYAMDYWGQG |
| | GTGACAACTCTGGGTAAACG | CTTCAACTGCTTATCTCCAAATTAAT | TSVTVSSAAA |
| | TTCTATTGCGTTTATTGAGA | AATCTTAAATATGAGGACACAGCAAC | TTTPAPRPPT |
| | GATTCCCAACAATTGAACAA | ATACTTCTGTGCTTTGGACTATAGTT | PAPTIASQPL |
| | ACGAGAACTACCTGTTTTAT | ATGCTATGGATTACTGGGGACAAGGA | SLRPEACRPA |
| | TAAATTTACACAGAGAAGAA | ACCAGTGTCACTGTAAGTTCCGCTGC | AGGAVHTRGL |
| | TTACA (SEQ ID NO: | TGCGACGACCACTCCTGCACCGCGAC | DFACDIYIWA |
| | 16) | CACCCACTCCTGCCCCTACTATTGCT | PLAGTCGVLL |
| | | AGTCAACCACTTAGCTTGCGACCTGA | LSLVITLYCK |
| | | GGCATGTCGGCCCGCGGCAGGTGGCG | RGRKKLLYIF |
| | | CAGTCCACACCAGGGGTTTAGACTTT | KQPFMRPVQT |
| | | GCTTGTGATATTTATATTTGGGCACC | TQEEDGCSCR |
| | | ACTCGCCGGGACTTGCGGTGTTCTTC | FPEEEEGGCE |
| | | TCTTGTCCCTTGTTATAACTCTTTAT | LRVKFSRSAD |
| | | TGTAAGCGCGGAAGGAAGAAATTGTT | APAYQQGQNQ |
| | | ATATATTTTCAAACAACCTTTTATGC | LYNELNLGRR |
| | | GACCCGTACAAACAACTCAGGAAGAG | EEYDVLDKRR |
| | | GACGGGTGTTCTTGTCGGTTTCCAGA | GRDPEMGGKP |
| | | AGAGGAAGAGGGTGGGTGTGAACTCC | RRKNPQEGLY |
| | | GGGTCAAATTTAGTAGGTCAGCAGAT | NELQKDKMAE |
| | | GCGCCGGCGTACCAACAAGGCCAAAA | AYSEIGMKGE |
| | | CCAACTGTATAATGAACTCAATCTCG | RRRGKGHDGL |
| | | GTAGGCGTGAGGAATATGATGTCCTT | YQGLSTATKD |
| | | GATAAAAGGCGCGGGAGAGATCCAGA | TYDALHMQAL |
| | | AATGGGCGGAAAACCACGGCGAAAGA | PPR (SEQ ID |
| | | ATCCGCAGGAAGGGTTATATAACGAA | NO: 119) |
| | | CTTCAAAAGGATAAAATGGCTGAAGC | |
| | | TTATTCCGAAATTGGCATGAAAGGAG | |
| | | AGCGACGTAGGGGCAAAGGGCATGAT | |
| | | GGCCTTTACCAAGGGCTCTCAACCGC | |
| | | TACAAAAGATACTTACGACGCTTTAC | |
| | | ATATGCAAGCACTTCCACCCAGG | |
| | | (SEQ ID NO: 103) | |

Expression of circular RNAs encoding anti-BCMA CAR C0-Cultured with MMIS

Figure 27:
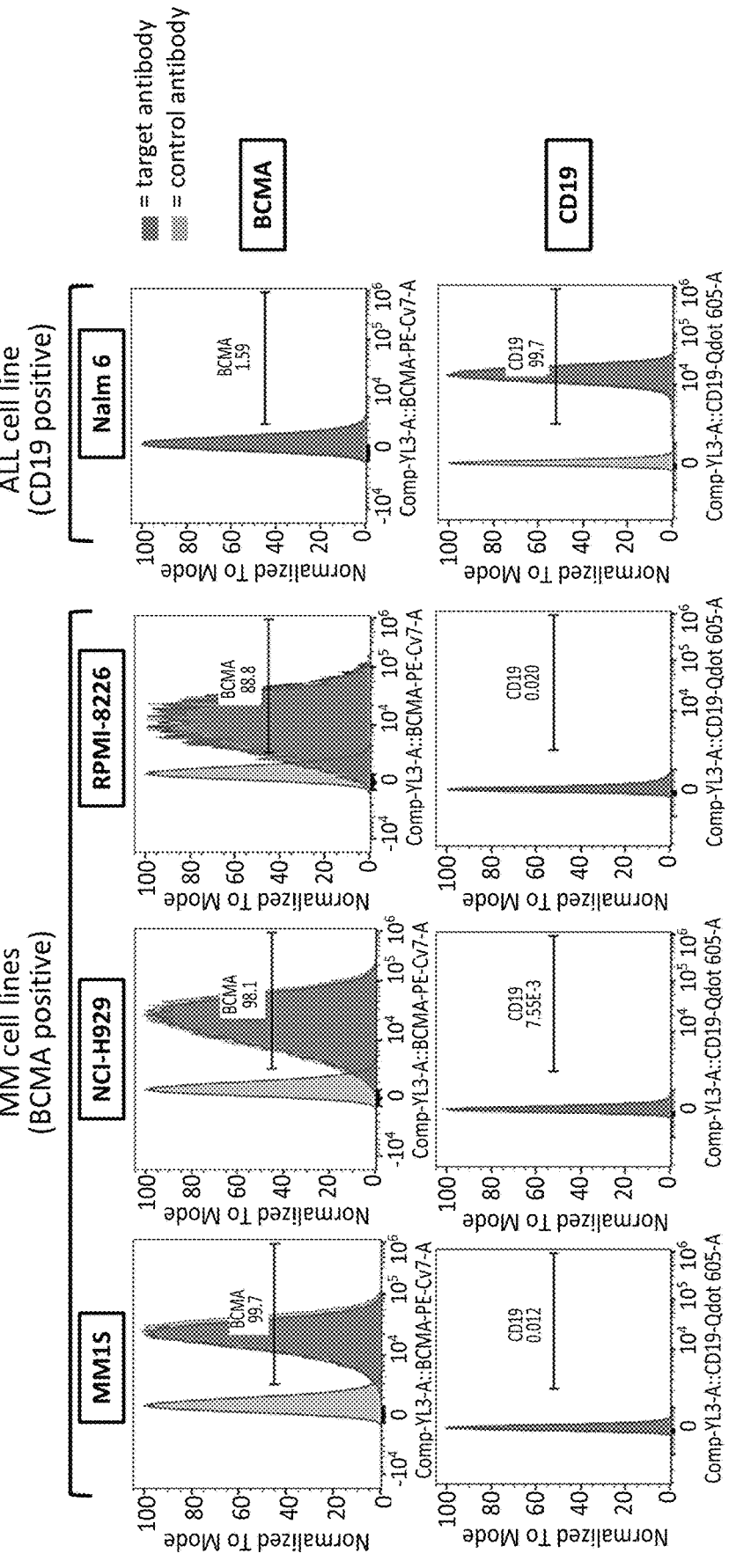
FIG. 27 shows target protein expression on multiple myeloma positive cells (e.g., MMIS, NCI-H929, and RPMI-8226) and negative target cell line (e.g., Nalm6 target cell line).

As a preliminary testing of various cell lines used, target protein expression on multiple myeloma positive cells (e.g., MMIS, NCI-H929, and RPMI-8226) and negative target cell line (e.g., Nalm6 target cell line) was analyzed using methods known in the art. Results of the preliminary testing were shown in FIG. 27.

Figure 28:
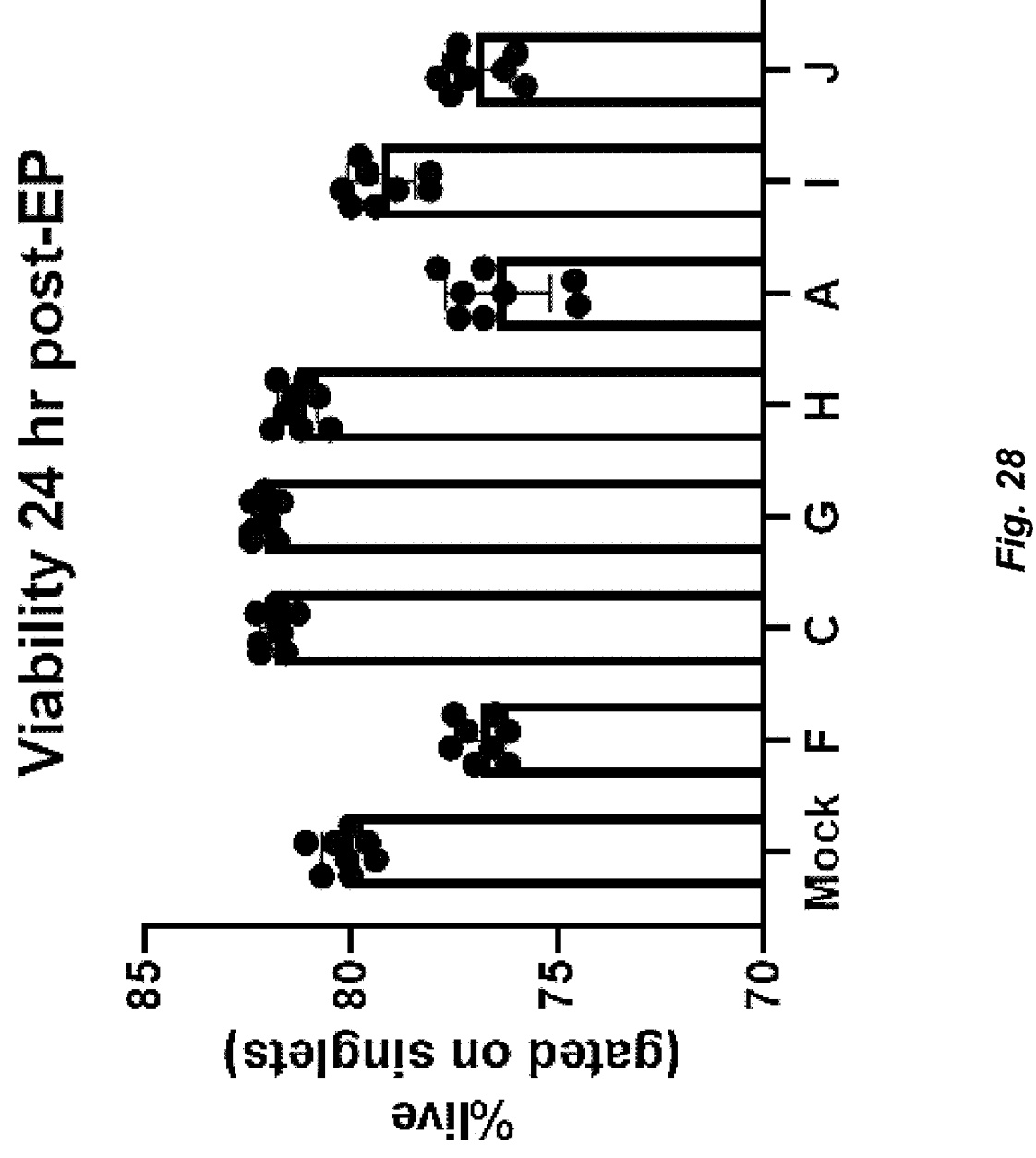
FIG. 28 depicts percent of live T cells collected at 24 hours post electroporation of circular RNAs comprising BCMA-41BB (CAR or CD19-CD285 CAR compared to "Mock" solutions comprising no circular RNA and only electroporation buffer solution. "F", "C", "G", "H", "A", "I" and "J" correspond to "DNA Template F", "DNA Template C", "DNA Template G", "DNA Template H", "DNA Template A", "DNA Template I", and "DNA Template J" that were used to form the circular RNAs.
Figure 29B:
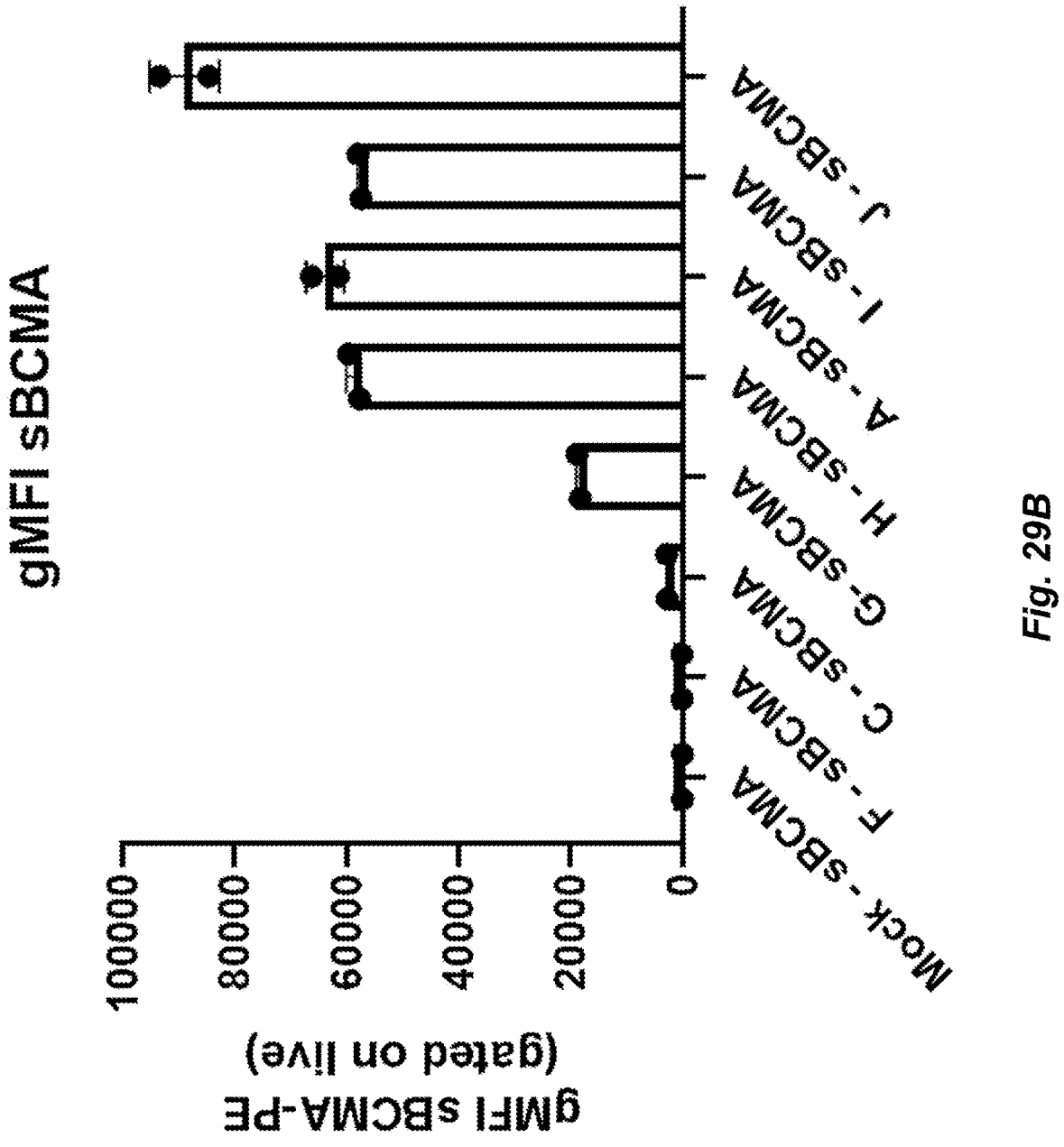
Figures 29C, 29D:
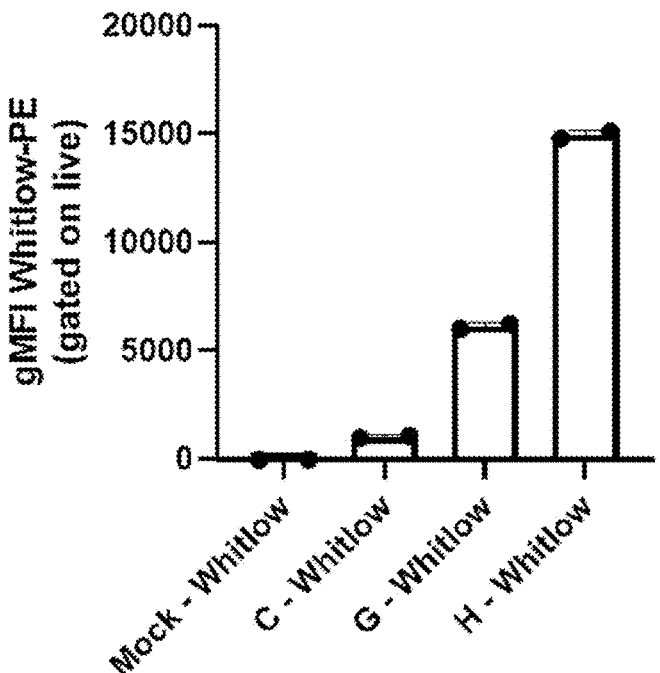
Figure 30:
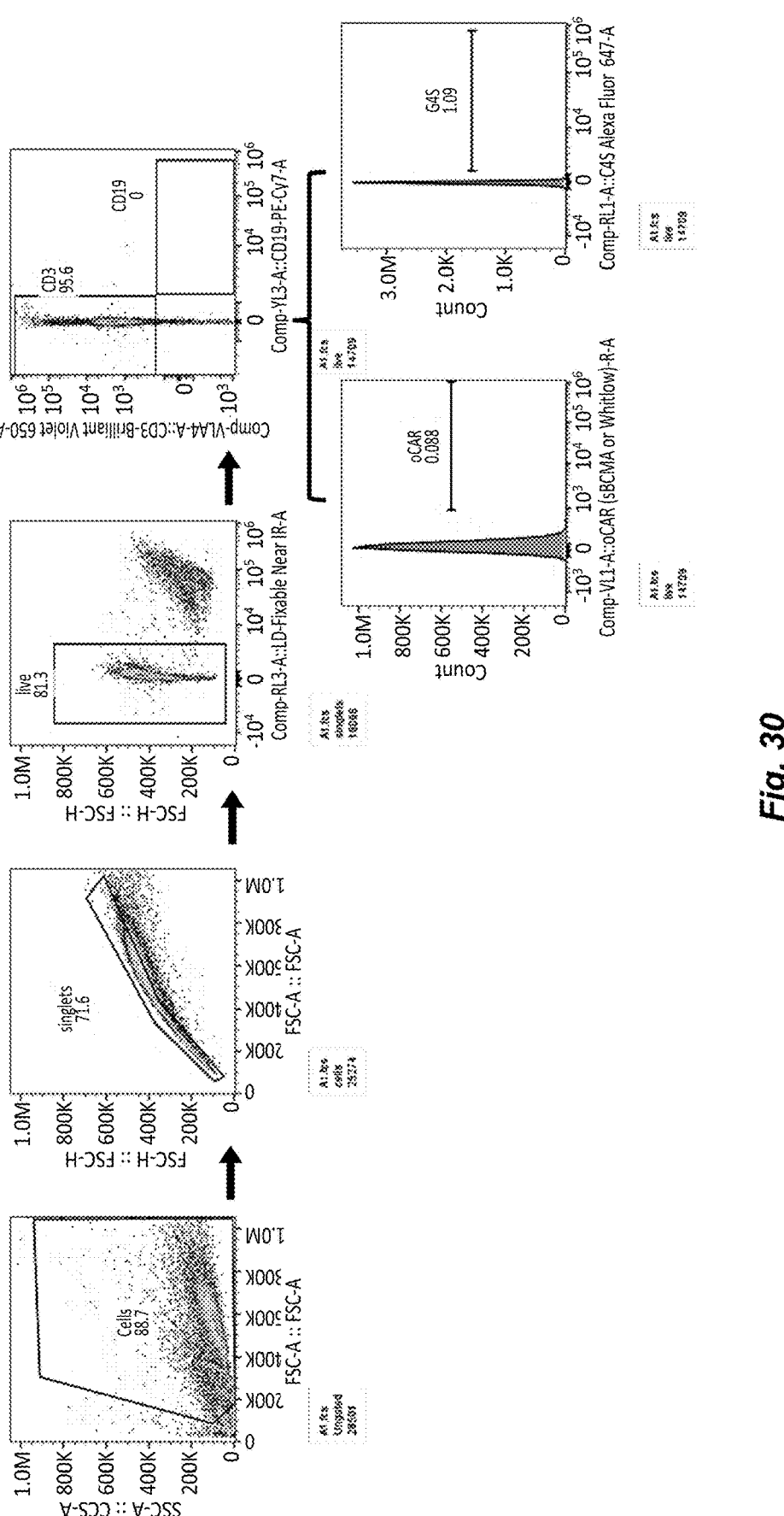
FIG. 30 depicts an exemplary gating process of the oCAR-T cells 24 hours post electroporation. On the top row of boxes (from left to right) provides the FACS imaging of lymphocytes, CD3 negative cells, live T cells, and BCMA positive cells. The bottom two boxes are histograms of BCMA CAR detected by either soluble BCMA or anti-Whitlow detection reagent (left bottom) or anti-GS4-PE Fluorescence (right bottom).
Figure 31A:
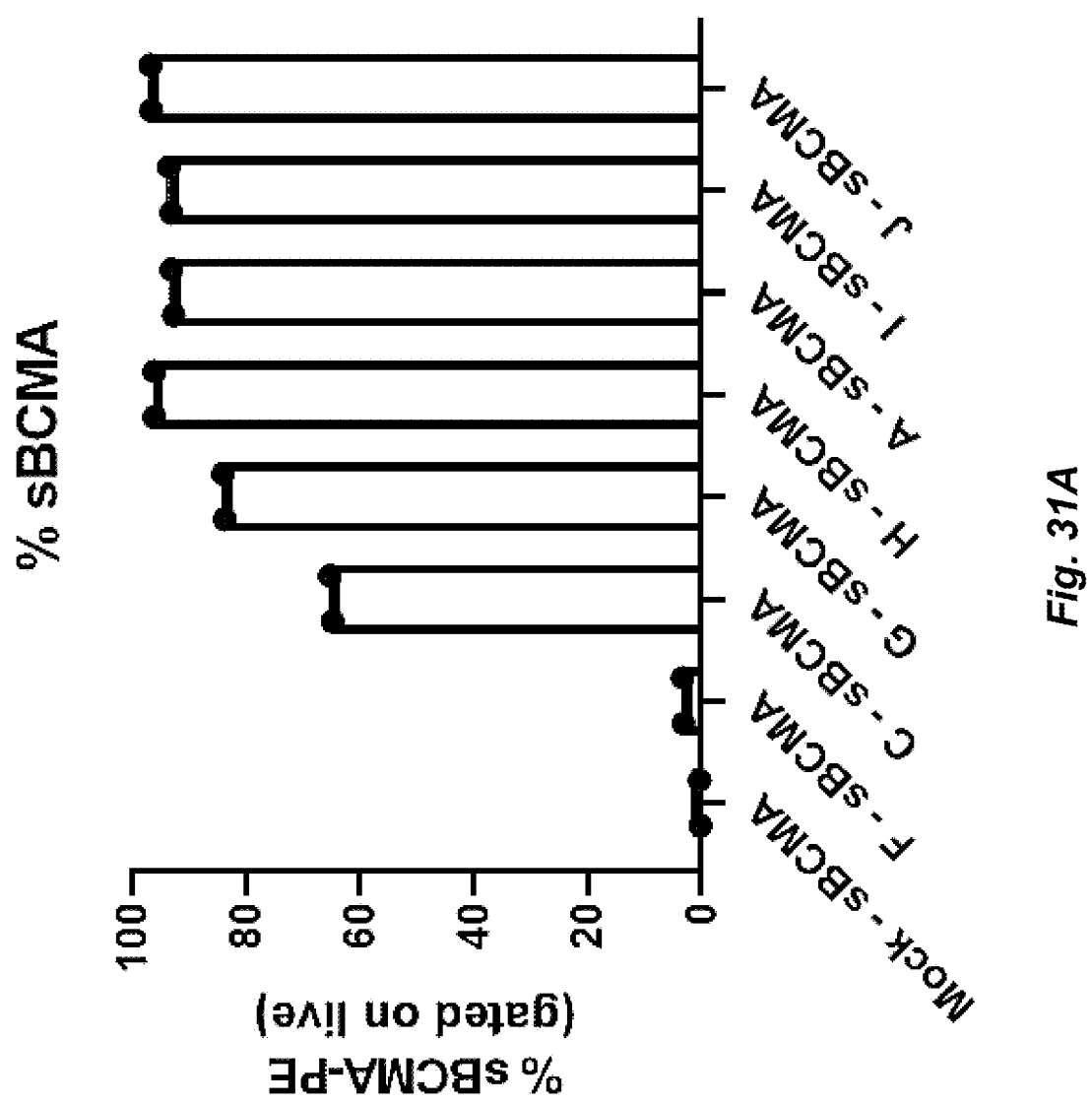
FIGS. 31A-31C depict percent expression of the detection reagent used (i.e., soluble BCMA PE (indicated by "sBCMA" in FIG. 31A), anti-Whitlow-PE (indicated by "Whitlow" in FIG. 31B) and anti-G4S linker PE (indicated by "G4S" in 31C)). Percent expression was calculated from the presence of the relevant detection reagent at 24 hours post electroporation of circular RNAs encoding BCMA-41BB (, BCMA-CD28ζ, or HER2 CAR gated on live T cells. "F", "C", "G", "H", "A", "T" and "J" correspond to "DNA Template F", "DNA Template C", "DNA Template G", "DNA Template H", "DNA Template A", "DNA Template I", and "DNA Template J" that were used to form the circular RNAs. "Mock" in the figure represents data for a control T cell that was not electroporated with circular RNA.
Figure 31B:
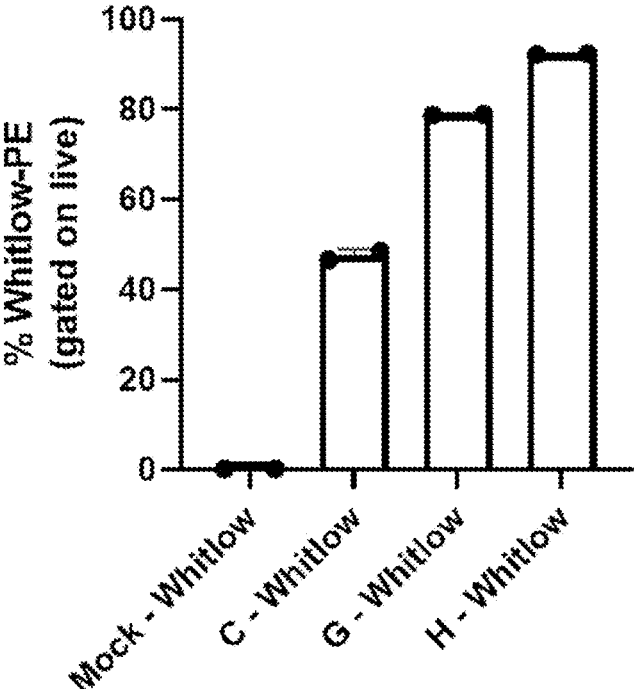
Figure 31C:
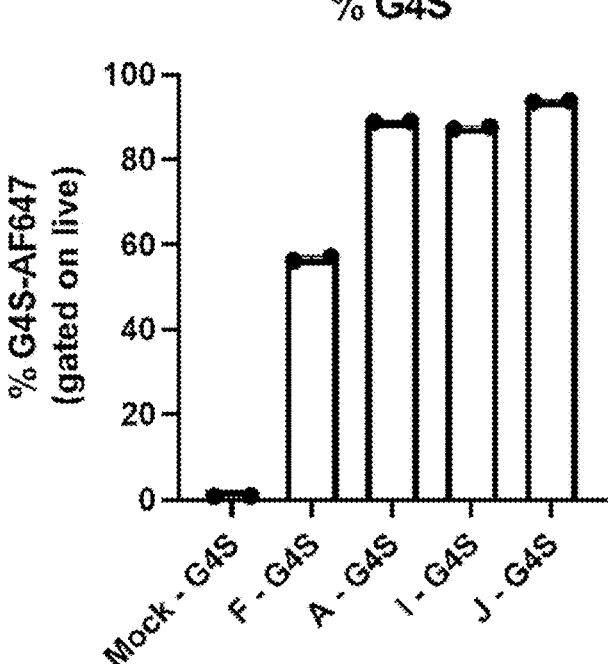
Figure 32A:
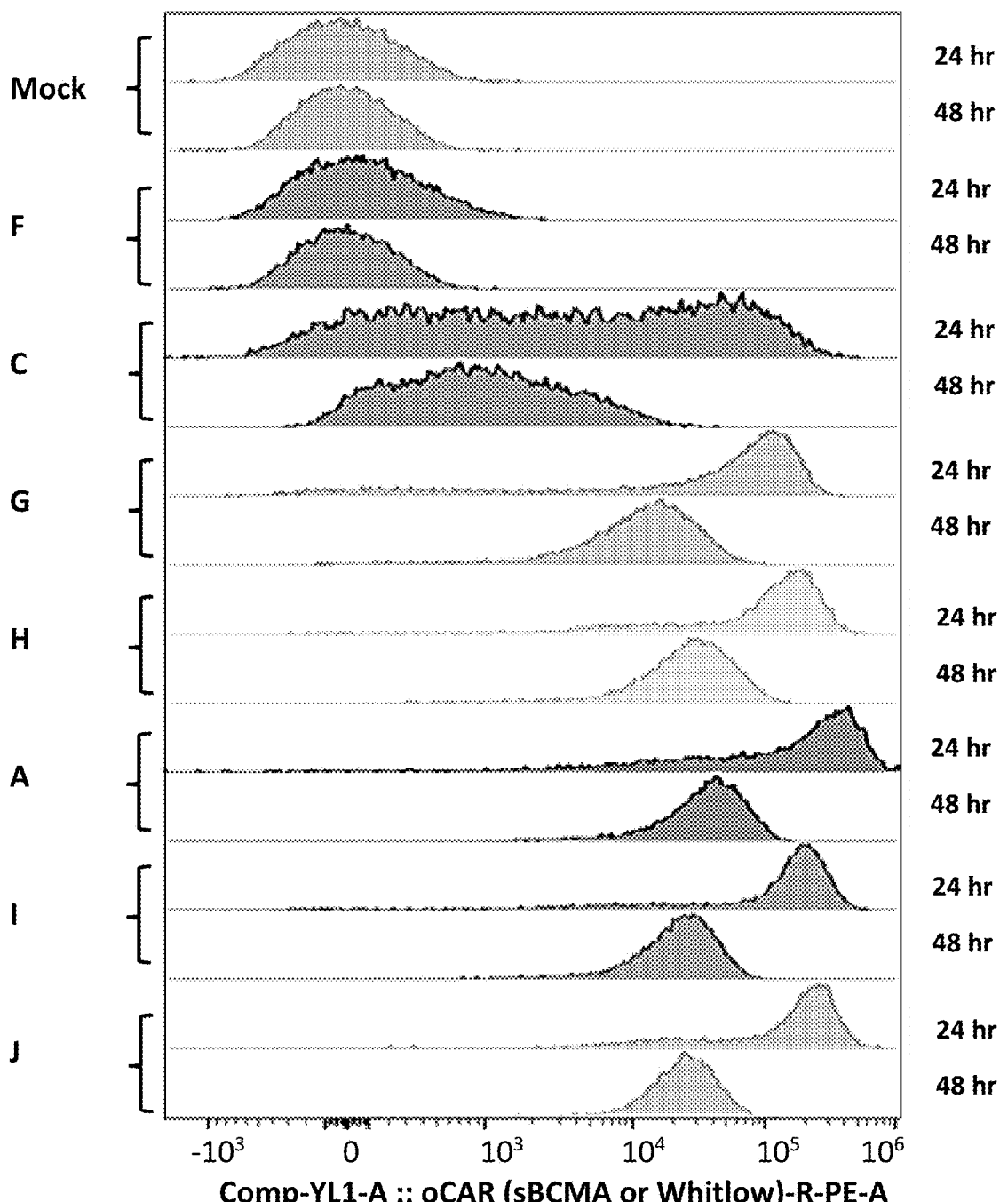
Figure 32D:
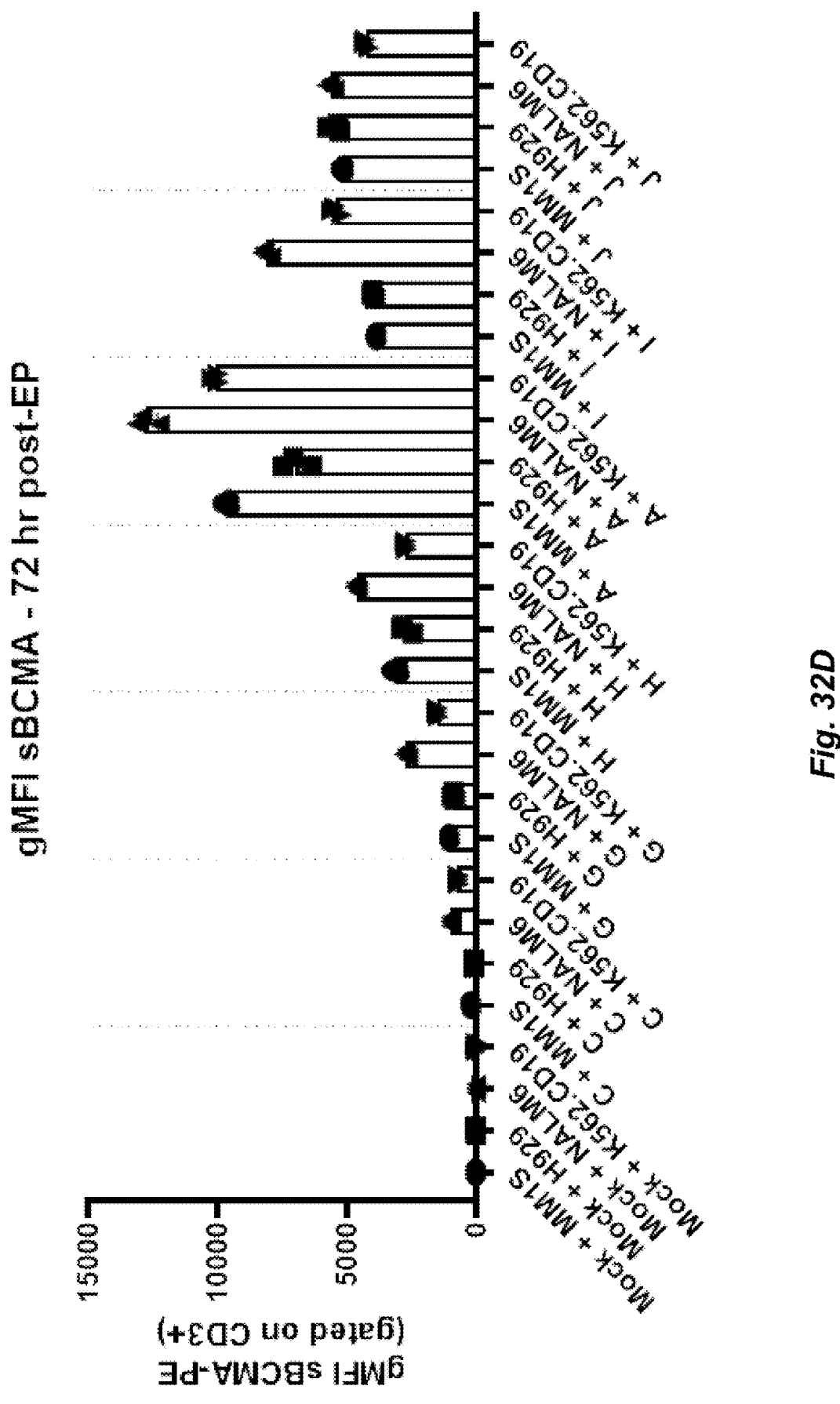
Figure 32E:
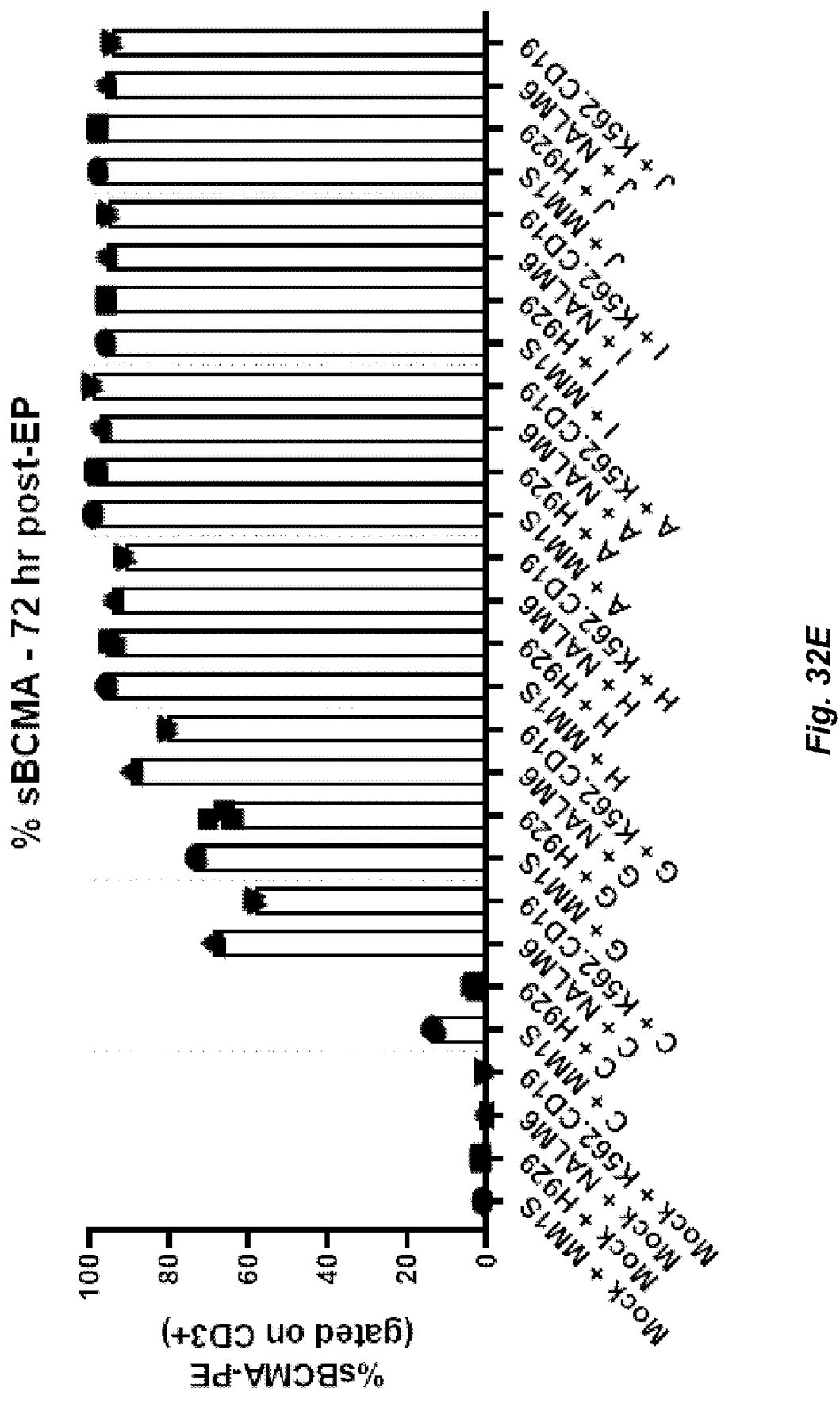

Donor T cells were thawed and activated with anti-CD3/CD28 solutions. Three days after activation, the cells were washed. On the following day, the cells were electroporated with a range of 50 ng dosages of circular RNA encoding a BCMA-41BBζ or BCMA-CD28ζ CAR or CD19-CD28ζ CAR per 0.1×10⁶ T cells to form engineered CAR-T cells (oCAR-T cells). Selected oCAR-T cells were analyzed for percent live cells for 6 circular RNA constructs encoding BCMA CARs and compared to the circular RNA construct comprising a CD19 280 CAR and a control comprising an EP Buffer only (results provided in FIG. 28). Circular RNAs were formed from DNA templates present in Table α1 and/or β. The cells were given a commercially available soluble BCMA detection reagent containing R-phycoerythrin (PE) fluorophore (e.g., from AcroBiosystems, Delaware), anti-Whitlow PE detection reagent, or anti-G4S linker detection reagent (e.g., G4S-AF647). 24 hours post electroporation of the circular RNA into the T cells, oCAR-T cells were sub-gated on live T cells based on FACS results (e.g., illustrated in FIG. 30) and amount of detectable reagent was collected. Results are provided in FIG. 29A-29D and the table below. From the collected detectable reagent, percent expression was calculated (e.g., percent soluble BCMA-PE, percent anti-Whitlow.PE, and percent G4S-AF647) and provided in FIG. 31A-31C.

The selected oCAR-T cells were co-cultured with targeted multiple myeloma cells (e.g., MMIS), NCI-H929, Nalm6 or K562.CD19 cells at an ET ratio of 1:1 on the day following electroporation of the circular RNAs to the donor T cells. The oCAR-T cells were given soluble BCMA-PE or anti-Whitlow.PE detection reagent. BMCA expression via gMFI was collected (32A-32B and 32D) and percent soluble BCMA-PE was calculated (32C and 32E) at 24-72 hours.

TABLE α2

| ID | Soluble BCMA-PE | | Whitlow-PE | | G4S-AF647 | |
|---|---|---|---|---|---|---|
| Mock | −11.1 | −12.4 | −54.3 | −66.5 | −74.2 | −88.4 |
| DNA Template F | 71.7 | 81.5 | −54.6 | −54.2 | 6973 | 7037 |
| DNA Template G | 18239 | 18887 | 6221 | 6000 | −80.1 | −94.6 |

TABLE α2-continued

| ID | Soluble BCMA-PE | | Whitlow-PE | | G4S-AF647 | |
|---|---|---|---|---|---|---|
| DNA Template H | 57811 | 59733 | 14787 | 15078 | −95 | −87.8 |
| DNA Template A | 61524 | 66292 | −73.3 | −85.4 | 27263 | 27709 |
| DNA Template I | 57409 | 58003 | −71.3 | −73.7 | 21881 | 22384 |
| DNA Template J | 84711 | 93417 | −66 | −73.1 | 30438 | 28273 |

TABLE β

| ID | Internal Ribosome Entry Site (IRES) Sequence | CAR Sequence | CAR Sequence |
|---|---|---|---|
| DNA Template F (Construct F) | GTGGCCACGCCCGGGCCA CCGATACTTCCCTTCACT CCTTCGGGACTGTTGGGG AGGAACACAACAGGGCTC CCCTGTTTTCCCATTCCT TCCCCCTTTTCCCAACCC CAACCGCCGTATCTGGTG GCGGCAAGACACACGGGT CTTTCCCTCTAAAGCACA ATTGTGTGTGTGTCCCAG GTCCTCCTGCGTACGGTG CGGGAGTGCTCCCACCCA ACTGTTGTAAGCCTGTCC AACGCGTCGTCCTGGCAA GACTATGACGTCGCATGT TCCGCTGCGGATGCCGAC CGGGTAACCGGTTCCCCA GTGTGTGTAGTGCGATCT TCCAGGTCCTCCTGGTTG GCGTTGTCCAGAAACTGC TTCAGGTAAGTGGGGTGT GCCCAATCCCTACAAAGG TTGATTCTTTCACCACCT TAGGAATGCTCCGGAGGT ACCCCAGCAACAGCTGGG ATCTGACCGGAGGCTAAT TGTCTACGGGTGGTGTTT CCTTTTTCTTTTCACACA ACTCTTACTGCTGACAACT CACTGACTATCCACTTGC TCTGTCACG (SEQ ID NO: 17) | ATGGCTCTGCCTGTGACAGCTCTGCTGCTGCCTCT GGCTCTGCTTCTGCATGCCGCCAGACCTGACATCC AGATGACCCAGACAACCAGCAGCCTGTCTGCCAGC CTGGGCGATAGAGTGACCATCAGCTGTAGAGCCAG CCAGGACATCAGCAAGTACCTGAACTGGTATCAGC AGAAACCCGACGGCACCGTGAAGCTGCTGATCTAC CACACCAGCAGACTGCACAGCGGCGTGCCAAGCAG ATTTTCTGGCAGCGGCTCTGGCACCGACTACAGCC TGACAATCAGCAACCTGGAACAAGAGGATATCGCT ACCTACTTCTGCCAGCAAGGCAACACCCTGCCTTA CACCTTTGGCGGAGGCACCAAGCTGGAAATCACAG GCGGCGGAGGAAGCGGAGGCGGAGGATCTGGTGGT GGTGGATCTGAAGTGAAACTGCAAGAGTCTGGCCC TGGCCTGGTGGCCCCATCTCAATCTCTGAGCGTGA CCTGTACCGTCAGCGGAGTGTCCCTGCCTGATTAT GGCGTGTCCTGGATCCGGCAGCCTCCTAGAAAAGG CCTGGAATGGCTGGGCGTGATCTGGGGCAGCGAGA CAACCTACTACAACAGCGCCCTGAAGTCCCGGCTG ACCATCATCAAGGACAACTCCAAGAGCCAGGTGTT CCTGAAGATGAACAGCCTGCAGACCGACGACACCG CCATCTACTATTGCGCCAAGCACTACTACTACGGC GGCAGCTACGCCATGGATTATTGGGGCCAGGGCAC CAGCGTGACCGTGTCTAGCATCGAAGTGATGTACC CTCCACCTTACCTGGACAACGAGAAGTCCAACGGC ACCATCATCCACGTGAAGGGCAAGCACCTGTGTCC TTCTCCACTGTTCCCCGGACCTAGCAAGCCTTTCT GGGTGCTCGTTGTTGTTGGCGGCGTGCTGGCCTGT TACTCTCTGCTGGTTACCGTGGCCTTCATCATCTT TTGGGTCCGAAGCAAGCGGAGCCGGCTGCTGCACT CCGACTACATGAACATGACCCCTAGACGGCCCGGA CCAACCAGAAAGCACTACCAGCCTTACGCTCCTCC TAGAGACTTCGCCGCCTACCGGTCCAGAGTGAAGT TCAGCAGATCCGCCGATGCTCCCGCCTATCAGCAG GGCCAAAACCAGCTGTACAACGAGCTGAACCTGGG GAGAGAGGAAGAGTACGACGTGCTGGACAAGCGGA GAGGCAGAGATCCTGAAATGGGCGGCAAGCCCAGA CGGAAGAATCCTCAAGAGGGCCTGTATAATGAGCT GCAGAAAGACAAGATGGCCGAGGCCTACAGCGAGA TCGGAATGAAGGGCGAGCGCAGAAGAGGCAAGGGA CCTAAGAAACCCCAGGAAGGACTGTACAACGAGCTGAACCTGGG... | MALPVTALLLP LALLLHAARPD IQMTQTTSSLS ASLGDRVTISC RASQDISKYLN WYQQKPDGTVK LLIYHTSRLHS GVPSRFSGSGS GTDYSLTISNL EQEDIATYFCQ QGNTLPYTFGG GTKLEITGGGG SGGGGSGGGGS EVKLQESGPGL VAPSQSLSVTC TVSGVSLPDYG VSWIRQPPRKG LEWLGVIWGSE TTYYNSALKSR LTIIKDNSKSQ VFLKMNSLQTD DTAIYYCAKHY YYGGSYAMDYW GQGTSVTVSSI EVMYPPPYLDN EKSNGTIIHVK GKHLCPSPLFP GPSKPFWVLVV VGGVLACYSLL VTVAFIIFWVR SKRSRLLHSDY MNMTPRRPGPT RKHYQPYAPPR DFAAYRSRVKF SRSADAPAYQQ GQNQLYNELNL GRREEYDVLDK RRGRDPEMGGK PRRKNPQEGLY NELQKDKMAEA YSEIGMKGERR RGKGHDGLYQG LSTATKDTYDA LHMQALPPR (SEQ ID NO: 29) |
| DNA Template G (Construct G) | CCCCCCTCCCCCCCTTCC CTTCCCTTTGCAACGCAA CAATTGTAAGTGCCCTCA CCTGTCAATTGGGACCAC CACTTTCAGTGACCCCAT GCGAAGTGCTGAGAGAAA GGAAGCTTTCTTACCCTT CATTTGTGAACCCACTGG TCTAAGCCGCTTGGAATA CGATGAGTGGAAAAGTTC ATTCTTAATGGAGTGAAA CATGCTTAAATTTCCAGC TCGTGCTGGTCTTTCCAG TACGGGGCGGCCCTGTCT GGCCGTAATTCTTCAGAG TGTCACGCCACACTTGTG GATCTCACGTGCCACATG ACAGCGCTACAGCTGGAA | ATGGCCCTCCCCGTCACAGCTCTCCTGCTCCCACT GGCCCTTCTTTTGCACGCTGCTCGCCCCGATATCG TGCTCACCCAGTCACCTCCAAGCCTTGCCATGAGC CTCGGGAAACGGGCTACCATCTCCTGCCGGGCTTC AGAGTCCGTCACCATCCTCGGGCTCACACCTCATCC ACTGGTACCAACAGAAACCAGGGCAGCCTCCTACC CTCTTGATCCAGTTGGCCTCCAACGTGCAAACTGG GGTTCCCGCCAGGTTCAGTGGCTCCGGATCCCGGA CAGATTTCACACTTACCATCAGCCTCGTGGAGGAG GACGATGTGGCCGTCTATTACTGCCTGCAGTCTCG CACCATCCCTCGGACCTTCGGTGGAGGCACCAAGC TCGAGATCAAGGGTAGCACCTCCGGCTCTGGAAAG CCAGGCTCTGGTGAGGGTTCTACCAAGGGCCAAAT CCAGCTGGTCCAGTCTGGGCCGAGCTGAAGAAAC CCGGGGAGACCGTGAAGATCTCCTGCAAGGCCTCC GGTTATACCTTCACCGACTACTCCATCAACTGGGT CAAGCGCGCTCCTGGAAAGGGCCTCAAGTGGATGG GCTGGATCAACACCGAAACCCGCGAGCCTGCCTAT | MALPVTALLLP LALLLHAARPD IVLTQSPPSLA MSLGKRATISC RASESVTILGS HLIHWYQQKPG QPPTLLIQLAS NVQTGVPARFS GSGSRTDFTLT IDPVEEDDVAV YYCLQSRTIPR TFGGGTKLEIK GSTSGSGKPGS GEGSTKGQIQL VQSGPELKKPG ETVKISCKASG YTFTDYSINWV KRAPGKGLKWM |

TABLE β-continued

| ID | Internal Ribosome Entry Site (IRES) Sequence | CAR Sequence | CAR Sequence |
|---|---|---|---|
| | CTGGGTGCTTGGTGCCCA<br>TGGAGTAACAGCGAAAAG<br>TGTTAGATCAAGCCTTGC<br>TTGGGCTATGAGCCTGCG<br>GAACAACAACTGGTAACA<br>GTTGCCTCAGGGGCCGAA<br>AGCCACGGTGTTAACAGC<br>ACCCTCATAGTTTGATCC<br>ACCTCAGGGTGGTGATGT<br>TTAGCAGTTAGTAGTTGC<br>CAATCTGTGTTCACTGAA<br>ATCTCGGCATACCGTGTA<br>GTGTACAGGGGTGAAGGA<br>TGCCCAGAAGGTACCCGT<br>AGGTAACCTTAAGAGACT<br>ATGGATCTGATCTGGGGC<br>CTTGTCCGGAGTGCTTTA<br>CACACGGCTCAAGGTTAA<br>AAAACGTCTAGCCCCACA<br>GAGCCCGAGGGATTCGGG<br>TTTTCCCTTTAAAAACCC<br>GACTAGAGCTTATGGTGA<br>CAATTATTGCTGTTCAGA<br>CGAACAGTGTAATTGTTG<br>TCTATTCACAGCAGTTCT<br>ATCAGAGCTTTTCCCACA<br>ACGGATCTTCTTGGCAAG<br>CAAATACAGCAGGAGTCA<br>AT (SEQ ID NO: 8) | GCTTACGACTTCAGGGGCCGGTTCGCTTTCTCACT<br>GGAGACCTCCGCTTCCACAGCCTACCTCCAGATCA<br>ACAACCTCAAGTACGAAGACACCGCCACCTATTTC<br>TGCGCTCTCGACTATTCCTACGCTATGGACTACTG<br>GGGTCAGGGCACCTCTGTGACCGTCTCTAGCGCAG<br>CCGCCACCACAACACCAGCCCCACGGCCACCTACT<br>CCCGCACCCACCATCGCATCCCAACCACTCAGTCT<br>GAGGCCCGAGGCCTGTAGACCTGCTGCTGGAGGCG<br>CAGTGCATACCCGCGGTCTCGACTTCGCCTGCGAC<br>ATCTATATCTGGGCCCCATTGGCAGGTACCTGTGG<br>CGTGCTGCTGCTGTCACTCGTCATCACCCTGTACT<br>GCCGGAGTAAGCGCTCTAGGCTGTTGCACAGCGAC<br>TACATGAACATGACCCCAAGAAGACCAGGGCCTAC<br>CCGGAAGCACTACCAGCCATCACGCACCTCCCCGGG<br>ACTTTGCCGCCTATCGGTCTCGGGTGAAGTTCTCA<br>CGCTCCGCTGATGCCCAGCATACCAGCAGGGGCA<br>GAACCAGCTGTACAATGAGCTCAACCTCGGTCGCC<br>GCGAAGAGTACGACGTGCTCGACAAGAGAAGGGGC<br>AGGGACCCTGAGATGGGAGGCAAGCCCCGCAGAAA<br>GAATCCCCAGGAAGGTCTGTACAACGAGCTGCAAA<br>AGGATAAGATGGCTGAGGCCTACAGCGAGATCGGC<br>ATGAAGGGCGAAAGGAACGGGGAAAGGGCCACGA<br>CGGGCTCTACCAGGGACTCTCCACCGCCACCAAGG<br>ACACCTACGACGCCCTCCACATGCAGGCTCTGCCA<br>CCCAGG (SEQ ID NO: 104) | GWINTETREPA<br>YAYDFRGRFAF<br>SLETSASTAYL<br>QINNLKYEDTA<br>TYFCALDYSYA<br>MDYWGQGTSVT<br>VSSAAATTTPA<br>PRPPTPAPTIA<br>SQPLSLRPEAC<br>RPAAGGAVHTR<br>GLDFACDIYIW<br>APLAGTCGVLL<br>LSLVITLYCRS<br>KRSRLLHSDYM<br>NMTPRRPGPTR<br>KHYQPYAPPRD<br>FAAYRSRVKFS<br>RSADAPAYQQG<br>QNQLYNELNLG<br>RREEYDVLDKR<br>RGRDPEMGGKP<br>RRKNPQEGLYN<br>ELQKDKMAEAY<br>SEIGMKGERRR<br>GKGHDGLYQGL<br>STATKDTYDAL<br>HMQALPPR<br>(SEQ ID NO:<br>120) |
| DNA Template H (Construct H) | CCCCCCTCCCCCCCTTCC<br>CTTCCCTTTGCAACGCAA<br>CAATTGTAAGTGCCCTCA<br>CCTGTCAATTGGGACCAC<br>CACTTTCAGTGACCCCAT<br>GCGAAGTGCTGAGAGAAA<br>GGAAGCTTTCTTACCCTT<br>CATTTGTGAACCCACTGG<br>TCTAAGCCGCTTGGAATA<br>CGATGAGTGGAAAAGTTC<br>ATTCTTAATGGAGTGAAA<br>CATGCTTAAATTTCCAGC<br>TCGTGCTGGTCTTTCCAG<br>TACGGGGCGGCCCTGTCT<br>GGCCGTAATTCTTCAGAG<br>TGTCACGCCACACTTGTG<br>GATCTCACGTGCCACATG<br>ACAGCGCTACAGCTGGAA<br>CTGGGTGCTTGGTGCCCA<br>TGGAGTAACAGCGAAAAG<br>TGTTAGATCAAGCCTTGC<br>TTGGGCTATGAGCCTGCG<br>GAACAACAACTGGTAACA<br>GTTGCCTCAGGGGCCGAA<br>AGCCACGGTGTTAACAGC<br>ACCCTCATAGTTTGATCC<br>ACCTCAGGGTGGTGATGT<br>TTAGCAGTTAGTAGTTGC<br>CAATCTGTGTTCACTGAA<br>ATCTCGGCATACCGTGTA<br>GTGTACAGGGGTGAAGGA<br>TGCCCAGAAGGTACCCGT<br>AGGTAACCTTAAGAGACT<br>ATGGATCTGATCTGGGGC<br>CTTGTCCGGAGTGCTTTA<br>CACACGGCTCAAGGTTAA<br>AAAACGTCTAGCCCCACA<br>GAGCCCGAGGGATTCGGG<br>TTTTCCCTTTAAAAACCC<br>GACTAGAGCTTATGGTGA<br>CAATTATTGCTGTTCAGA<br>CGAACAGTGTAATTGTTG<br>TCTATTCACAGCAGTTCT<br>ATCAGAGCTTTTCCCACA<br>ACGGATCTTCTTGGCAAG<br>CAAATACAGCAGGAGTCA<br>AT (SEQ ID NO: 8) | ATGGCACTTCCCGTCACCGCTCTCCTGCTGCCCCT<br>CGCACTGCTGCTCATGCAGCCCGCCCAGACATCG<br>TCCTGACCCAGTCCCCTCCCTCCCTCGCAATGTCC<br>CTCGGGAAACGGGCCACCATCAGCTGCCGGGCCTC<br>TGAGTCAGTGACAATCCTCGGAAGCCATCTGATCC<br>ATTGGTACCAGCAGAAACCCGGTCAGCCTCCAACC<br>CTCCTCATCCAGCTGGCCTCCAACGTGCAGACAGG<br>AGTCCCCGCTCGGTTCTCAGGCAGCGGTTCCAGGA<br>CCGACTTCACCCTGACCATCGACCCCGTGGAAGAG<br>GACGATGTGGCTGTGTACTACTGCCTCCAGTCCCG<br>GACCATCCCACGGACCTTCGGAGGTGGGACAAAGC<br>TGGAGATCAAAGGCAGCACCAGCGGTTCTGGCAAG<br>CCAGGGTCAGGTGAGGGGAGCACAAAGGGTCAGAT<br>CCAGCTGGTGCAGAGCGGTCCCGAGCTGAAGAAGC<br>CCGGGGAGACCGTTAAGATCTCCTGCAAGGCTAGC<br>GGGTACACCTTCACCGACTATAGTATCAACTGGGT<br>CAAGCGGCCTCCTGGCAAGGGGCTCAAGTGGATGG<br>GGTGGATCAACACCGAAACCAGGGAGCCCGCATAC<br>GCTTATGACTTTCGGGGCCGGTTCGCCTTTTCCCT<br>GGAGACCAGCGCCTCTACCGCCTACCTCCAGATCA<br>ACAACCTGAAGTACGAAGACACCGCCACCTACTTC<br>TGCGCACTCGACTACTCCTACGCTATGGACTACTG<br>GGGTCAGGGTACCTCCGTCACCGTCTCCAGCATCG<br>AGGTCATGTACCCTCCTCCCTACCTGGACAACGAG<br>AAGTCCAACGGCACCATCATCCATGTGAAGGGCAA<br>GCATCTCTGCCCCAGCCCACTGTTCCCCGGACCCT<br>CTAAGCCCTTCTGGGTCCTGGTCGTCGTCGGCGGT<br>GTTCTGGCTTGCTACAGCTTGCTGGTCACCGTCGC<br>CTTCATCATCTTCTGGGTGCGCTCCAAGAGGAGCC<br>GGCTGCTGCATAGCGACTACATGAACATGACCCCT<br>AGAAGGCCTGGTCCAACCCGCAAGCACTACCAGCC<br>TTACGCCCCTCCACGGGACTTCGCAGCCTACCGGT<br>CACGGGTGAAGTTCTCTCGGAGCGCAGATGCCCCA<br>GCATACGACAGGGCCAGAACCAGCTGTACAACGA<br>ACTTAACCTTGGTCGGGGGGAGGAATACGATGTGC<br>TGGACAAGCGCAGGGGTCGGGATCCTGAAATGGGC<br>GGGAAACCACGCCGGAAGAACCCACAGGAGGGGCT<br>CTATAACGAGCTCCAAAAGGATAAGATGGCTGAGG<br>CTTACAGCGAGATTGGAATGAAGGGAGAAAGAAGA<br>CGGGGCAAGGGTCACGACGGGTTGTACCAGGGTCT<br>GAGCACCGCCACCAAGGACACCTACGACGCCCTCC<br>ACATGCAAGCCCTTCCACCCCGC (SEQ ID NO:<br>105) | MALPVTALLLP<br>LALLLHAARPD<br>IVLTQSPPSLA<br>MSLGKRATISC<br>RASESVTILGS<br>HLIHWYQQKPG<br>QPPTLLIQLAS<br>NVQTGVPARES<br>GSGSRTDFTLT<br>IDPVEEDDVAV<br>YYCLQSRTIPR<br>TFGGGTKLEIK<br>GSTSGSGSKPGS<br>GEGSTKGQIQL<br>VQSGPELKKPG<br>ETVKISCKASG<br>YTFTDYSINWV<br>KRAPGKGLKWM<br>GWINTETREPA<br>YAYDERGRFAF<br>SLETSASTAYL<br>QINNLKYEDTA<br>TYFCALDYSYA<br>MDYWGQGTSVT<br>VSSIEVMYPPP<br>YLDNEKSNGTI<br>IHVKGKHLCPS<br>PLFPGPSKPFW<br>VLVVVGGVLAC<br>YSLLVTVAFII<br>FWVRSKRSRLL<br>HSDYMNMTPRR<br>PGPTRKHYQPY<br>APPRDFAAYRS<br>RVKFSRSADAP<br>AYQQGQNQLYN<br>ELNLGRREEYD<br>VLDKRRGRDPE<br>MGGKPRRKNPQ<br>EGLYNELQKDK<br>MAEAYSEIGMK<br>GERRRGKGHDG<br>LYQGLSTATKD<br>TYDALHMQALP<br>PR (SEQ ID<br>NO: 121) |

TABLE β-continued

| ID | Internal Ribosome Entry Site (IRES) Sequence | CAR Sequence | CAR Sequence |
|---|---|---|---|
| DNA Template I (Construct | CCCCCCTCCCCCCCTTCC CTTCCCTTTGCAACGCAA CAATTGTAAGTGCCCTCA CCTGTCAATTGGGACCAC CACTTTCAGTGACCCCAT GCGAAGTGCTGAGAGAAA GGAAGCTTTCTTACCCTT CATTTGTGAACCCACTGG TCTAAGCCGCTTGGAATA CGATGAGTGGAAAAGTTC ATTCTTAATGGAGTGAAA CATGCTTAAATTTCCAGC TCGTGCTGGTCTTTCCAG TACGGGGCGGCCCTGTCT GGCCGTAATTCTTCAGAG TGTCACGCCACACTTGTG GATCTCACGTGCCACATG ACAGCGCTACAGCTGGAA CTGGGTGCTTGGTGCCCA TGGAGTAACAGCGAAAAG TGTTAGATCAAGCCTTGC TTGGGCTATGAGCCTGCG GAACAACAACTGGTAACA GTTGCCTCAGGGGCCGAA AGCCACGGTGTTAACAGC ACCCTCATAGTTTGATCC ACCTCAGGGTGGTGATGT TTAGCAGTTAGTAGTTGC CAATCTGTGTTCACTGAA ATCTCGGCATACCGTGTA GTGTACAGGGGTGAAGGA TGCCCAGAAGGTACCCGT AGGTAACCTTAAGAGACT ATGGATCTGATCTGGGGC CTTGTCCGGAGTGCTTTA CACACGGCTCAAGGTTAA AAAACGTCTAGCCCCACA GAGCCCGAGGGATTCGGG TTTTCCCTTTAAAAACCC GACTAGAGCTTATGGTGA CAATTATTGCTGTTCAGA CGACAGTGTAATTGTTG TCTATTCACAGCAGTTCT ATCAGAGCTTTTCCCACA ACGGATCTTCTTGGCAAG CAAATACAGCAGGAGTCA AT (SEQ ID NO: 8) | ATGGCACTCCCCGTTACCGCCCTTCTGCTGCCTCT CGCCTTGCTGCTGCACGCAGCCAGACCACAGGTCA AGCTGGAGGAGTCTGGTGGCGGGCTCGTTCAAGCA GGTCGGAGTCTCCGCCTGTCTTGCGCAGCATCAGA GCATACCTTCTCCTCACACGTGATGGGGTGGTTCA GGCAAGCTCCCGGTAAGGAGAGGGAGTCCGTGGCC GTTATCGGCTGGCGCGATATCAGCACCTCCTACGC AGACAGCGTTAAGGGCCGGTTCACTATCTCCAGGG ACAACGCTAAGAAGACACTCTACCTCCAGATGAAC AGTCTGAAGCCCGAGGACACCGCAGTGTACTATTG CGCTGCTCGGCGGATCGATGCTGCCGACTTCGACA GCTGGGGTCAAGGGACCCAGGTCACCGTTTCCAGC GGAGGTGGCGGAAGTGGTGGCGGAGGATCAGGTGG TGGAGGCTCCGAGGTCCAGCTGGTGGAATCAGGAG GCGGCTTGGTGCAGGCTGGTGGGTCTTTGCGGTTG TCCTGCGCAGCTTCCGGCAGGACCTTCACCATGGG ATGGTTCAGACAAGCCCCAGGTAAGGAGCGGGAGT TTGTGGCCGCAATCTCACTGTCTCCCACCCTCGCT TACTACGCCGAGAGTGTGAAGGGGCGCTTCACAAT CAGTCGCGACAACGCAAAGAACACCGTCGTCCTGC AAATGAACTCCCTGAAGCCTGAGGATACCGCACTC TATTACTGCGCCGCCGATCGGAAGAGCGTCATGTC CATCCGGCCCGACTATTGGGGCCAAGGCACCCAAG TGACCGTCAGCTCCACCTCCACAACCACTCCCGCC CCAAGACCACCTACCCCAGCCCCAACAATCGCATC CCAGCCTCTGTCCCTTCGGCCCGAAGCTTGTCGCC CTGCAGCAGGTGGAGCAGTGCACACCCGGGGACTG GACTTCGCCTGCGACATCTACATCTGGGCACCCCT GGCTGGAACCTGCGGCGTGTTGCTGCTGAGCCTGG TGATCACCCTCTACTGCCGCTCTAAGAGAAGCCGG CTGCTGCATAGCGACTACATGAACATGACCCCTAG GAGACCAGGACCCACCCGGAAGCACTACCAGCCTT ACGCTCCTCCACGGGATTTCGCTGCTTACCGCAGC CGGGTGAAGTTTTCCAGGTCAGCTGACGCCCCTGC CTACCAGCAGGGCCAGAACCAATTGTACAACGAAC TGAATCTGGGACGGCGCGAGGAATACGACGTCCTG GACAAGAGGCGGGGTAGAGATCCCGAGATGGGCGG AGCTGCTGCTCGGAAGAGCCCGATGGATCTTGATCC AAGGTGGCCTGGAATGGATGGCCGAAGCC ACAACGAGCTGCAGAAGGATAAGATGGCCGAAGCC TACTCCGAGATCGGGATGAAGGGTGAACGGAGGAG GGGCAAGGGACACGACGGCCTGTATCAGGGCCTCA GCACCGCTACCAAGGACACCTACGACGCCCTGCAC ATGCAGGCTCTCCCCACCACGG (SEQ ID NO: 107) | MALPVTALLLP LALLLHAARPQ VKLEESGGGLV QAGRSLRLSCA ASEHTFSSHVM GWFRQAPGKER ESVAVIGWRDI STSYADSVKGR FTISRDNAKKT LYLQMNSLKPE DTAVYYCAARR IDAADFDSWGQ GTQVTVSSGGG GSGGGGSGGGG SEVQLVESGGG LVQAGGSLRLS CAASGRTFTMG WFRQAPGKERE FVAAISLSPTL AYYAESVKGRE TISRDNAKNTV VLQMNSLKPED TALYYCAADRK SVMSIRPDYWG QGTQVTVSSTS TTTPAPRPPTP APTIASQPLSL RPEACRPAAGG AVHTRGLDFAC DIYIWAPLAGT CGVLLLSLVIT LYCRSKRSRLL HSDYMNMTPRR PGPTRKHYQPY APPRDFAAYRS RVKFSRSADAP AYQQGQNQLYN ELNLGRREEYD VLDKRRGRDPE MGGKPRRKNPQ EGLYNELQKDK MAEAYSEIGMK GERRRGKGHDG LYQGLSTATKD TYDALHMQALP PR (SEQ ID NO: 123) |
| DNA Template J (Construct J | CCCCCCTCCCCCCCTTCC CTTCCCTTTGCAACGCAA CAATTGTAAGTGCCCTCA CCTGTCAATTGGGACCAC CACTTTCAGTGACCCCAT GCGAAGTGCTGAGAGAAA GGAAGCTTTCTTACCCTT CATTTGTGAACCCACTGG TCTAAGCCGCTTGGAATA CGATGAGTGGAAAAGTTC ATTCTTAATGGAGTGAAA CATGCTTAAATTTCCAGC TCGTGCTGGTCTTTCCAG TACGGGGCGGCCCTGTCT GGCCGTAATTCTTCAGAG TGTCACGCCACACTTGTG GATCTCACGTGCCACATG ACAGCGCTACAGCTGGAA CTGGGTGCTTGGTGCCCA TGGAGTAACAGCGAAAAG TGTTAGATCAAGCCTTGC TTGGGCTATGAGCCTGCG GAACAACAACTGGTAACA GTTGCCTCAGGGGCCGAA AGCCACGGTGTTAACAGC ACCCTCATAGTTTGATCC ACCTCAGGGTGGTGATGT TTAGCAGTTAGTAGTTGC | ATGGCTCTTCCCGTCACCGCTTTGCTGCTGCCCCT GGCACTCCTCCTCATGCTGCTCGGCCTCAGGTGA AGCTGGAGGAGAGTGGTGGCGGTCTGGTCAAGCT GGCAGATCTCTGCGCCTGTCTTGCGCAGCCAGCGA ACACACCTTCTCCTCCCACGTGATGGGGTGGTTTC GGCAGGCACCCGGGAAAGAGCGCGAGTCCGTCGCA GTCATCGGGTGGCGGGACATCTCTACCAGCTACGC AGATTCCGTCAAGGGCCGGTTCACCATTTCCCGGG ATAACGCTAAGAAGACCCTCTACCTGCAAATGAAC TCTCTGAAGCCCGAAGACACCGCCGTCTACTATTG CGCAGCAAGGCGCATCGACGCTGCCGACTTCGACT CTTGGGGCCAAGGAACCCAGGTCACCGTGTCTTCC GGAGGAGGAGGCTCCGGTGGTGGAGGTTCTGGAGG TGGCGGCTCAGAGGTGCAGCTCGTGGAGAGCGGTG GTGGACTCGTTCAGGCAGGCGGCAGTTTGCGGCTG TCCTGTGCAGCCTCCGGTCGCACTTTCACTATGGG ATGGTTCCGCCAGGCTCCTGGTAAAGAAAGGGAGT TCGTGGCCGCCATCAGTCTGAGCCCCACCCTCGCA TACTACGCCGAGAGCGTGAAAGGGTAGGTTCACTAT CAGCCGGGACAACGCCAAGAACACCGTGGTGCTCC AGATGAATTCCCTGAAGCCTGAGGATACCGCCCTC TACTACTGCGCTGCCGACCGCAAGAGCGTGATGAG CATCCGGCCTGACTATTGGGGTCAGGGCACCCAGG TGACCGTCAGCAGCATCGAGGTGATGTATCCACCA CCCTACCTCGACAACGAGAAGTCCAACGGCACCAT CATCCACGTCAAGGGGAAGCACCTCTGCCCTTCCC CTCTGTTCCCTGGCCCCTCAAAGCCCTTCTGGGTC CTGGTGGTGGTTGGTGGGGTGCTGGCTTGCTACTC | MALPVTALLLP LALLLHAARPQ VKLEESGGGLV QAGRSLRISCA ASEHTESSHVM GWFRQAPGKER ESVAVIGWRDI STSYADSVKGR FTISRDNAKKT LYLQMNSLKPE DTAVYYCAARR IDAADFDSWGQ GTQVTVSSGGG GSGGGGSGGGG SEVQLVESGGG LVQAGGSLRLS CAASGRTFTMG WFRQAPGKERE FVAAISLSPTL AYYAESVKGRE TISRDNAKNTV VLQMNSLKPED TALYYCAADRK SVMSIRPDYWG QGTQVTVSSIE VMYPPPYLDNE KSNGTIIHVKG KHLCPSPLFPG |

TABLE β-continued

| ID | Internal Ribosome Entry Site (IRES) Sequence | CAR Sequence | CAR Sequence |
|---|---|---|---|
| | CAATCTGTGTTCACTGAA | CCTGCTCGTGACCGTGGCTTTCATCATCTTCTGGG | PSKPFWVLVVV |
| | ATCTCGGCATACCGTGTA | TTCGGAGCAAACGGTCCAGACTGCTGCACTCCGAC | GGVLACYSLLV |
| | GTGTACAGGGGTGAAGGA | TACATGAACATGACCCCAAGAAGACCTGGGCCCAC | TVAFIIFWVRS |
| | TGCCCAGAAGGTACCCGT | ACGGAAGCATTACCAACCCTATGCACCACCTCGGG | KRSRLLHSDYM |
| | AGGTAACCTTAAGAGACT | ATTTCGCCGCCTACAGATCCCGGGTCAAGTTCTCC | NMTPRRPGPTR |
| | ATGGATCTGATCTGGGGC | AGGTCCGCCGATGCACCAGCCTATCAGCAGGGGCA | KHYQPYAPPRD |
| | CTTGTCCGGAGTGCTTTA | AAACCAGCTGTATAATGAGCTGAACCTTGGACGGC | FAAYRSRVKES |
| | CACACGGCTCAAGGTTAA | GCGAGGAGTACGACGTGCTCGACAAAAGACGCGGT | RSADAPAYQQG |
| | AAAACGTCTAGCCCCACA | CGCGACCCAGAGATGGGCGGCAAGCCTAGACGCAA | QNQLYNELNLG |
| | GAGCCCGAGGGATTCGGG | GAATCCCCAGGAGGGGCTCTATAACGAGTTGCAGA | RREEYDVLDKR |
| | TTTTCCCTTTAAAAACCC | AGGATAAGATGGCCGAGGCCTACAGCGAGATCGGG | RGRDPEMGGKP |
| | GACTAGAGCTTATGGTGA | ATGAAAGGCGAAAGACGGCGCGGAAAGGGTCACGA | RRKNPQEGLYN |
| | CAATTATTGCTGTTCAGA | CGGACTCTACCAGGGCCTGAGCACAGCCACCAAAG | ELQKDKMAEAY |
| | CGAACAGTGTAATTGTTG | ACACCTACGACGCTCTGCATATGCAAGCACTGCCT | SEIGMKGERRR |
| | TCTATTCACAGCAGTTCT | CCCCGG (SEQ ID NO: 108) | GKGHDGLYQGL |
| | ATCAGAGCTTTTCCCACA | | STATKDTYDAL |
| | ACGGATCTTCTTGGCAAG | | HMQALPPR |
| | CAAATACAGCAGGAGTCA | | (SEQ ID NO: |
| | AT (SEQ ID NO: 8) | | 124) |

Example 15: Cytotoxicity Analysis of CAR Expression

Figure 33A:
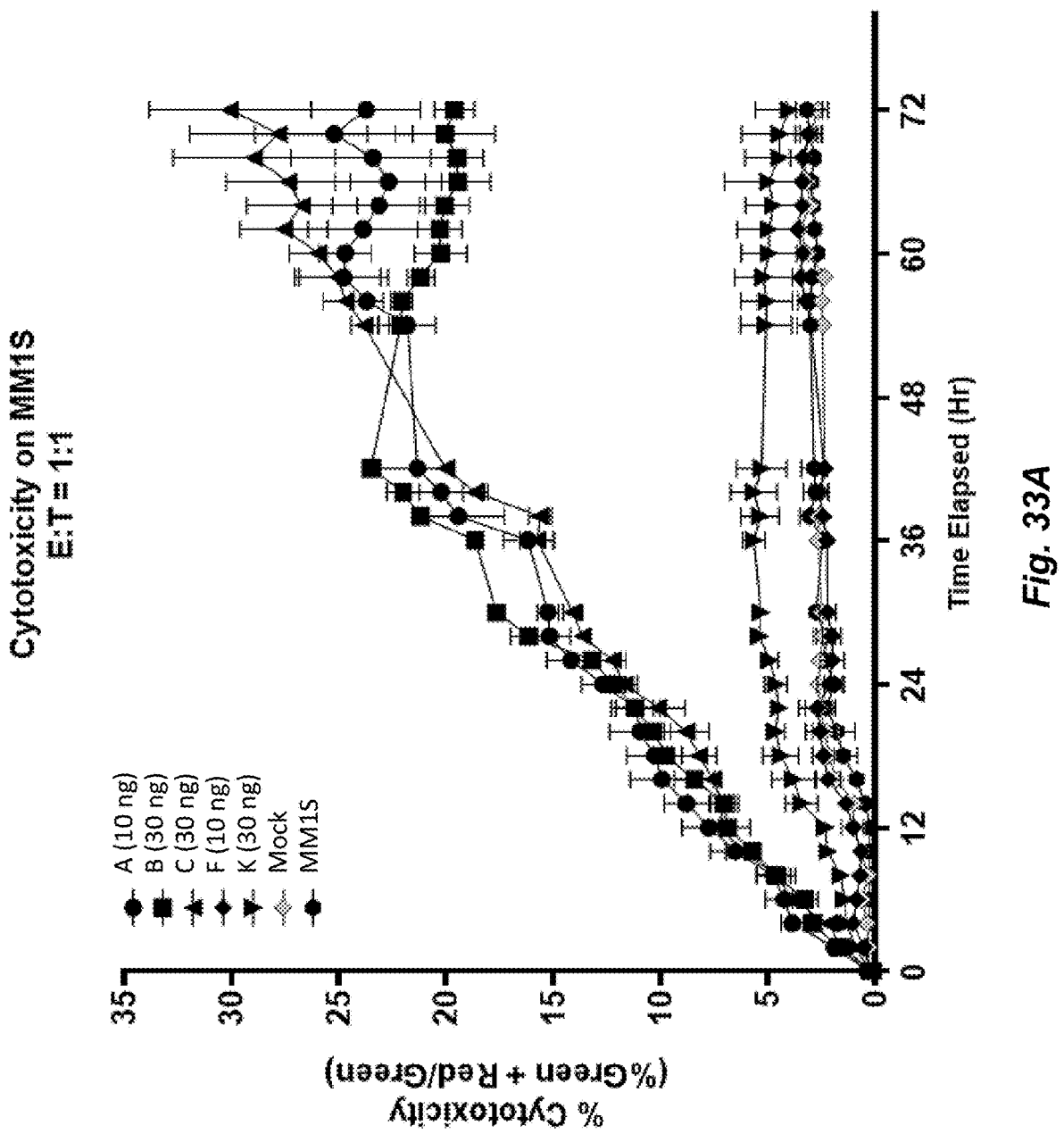
FIGS. 33A-33C depict cytotoxicity of circular RNA constructs encoding a BCMA-41BBC chimeric antigen receptor (CAR), wherein the circular RNA comprises a BCMA sequence and IRES sequence from Table al, B or y CD19-CD28ζ CAR or HER2-CD28° C. CARs on various cell types over the span of 0 to 72 or 96 hours post co-culture.
Figure 33B:
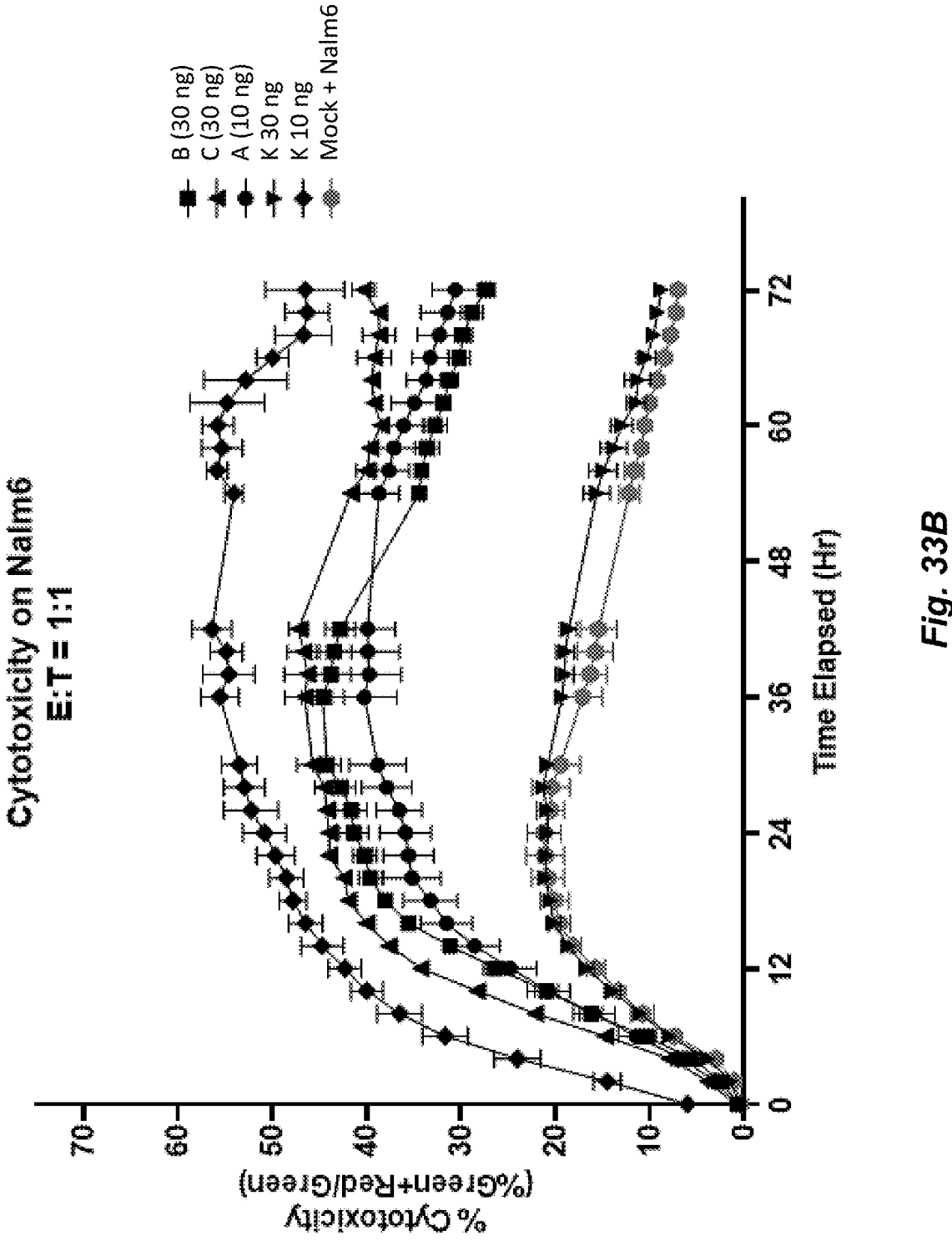
Figure 33C:
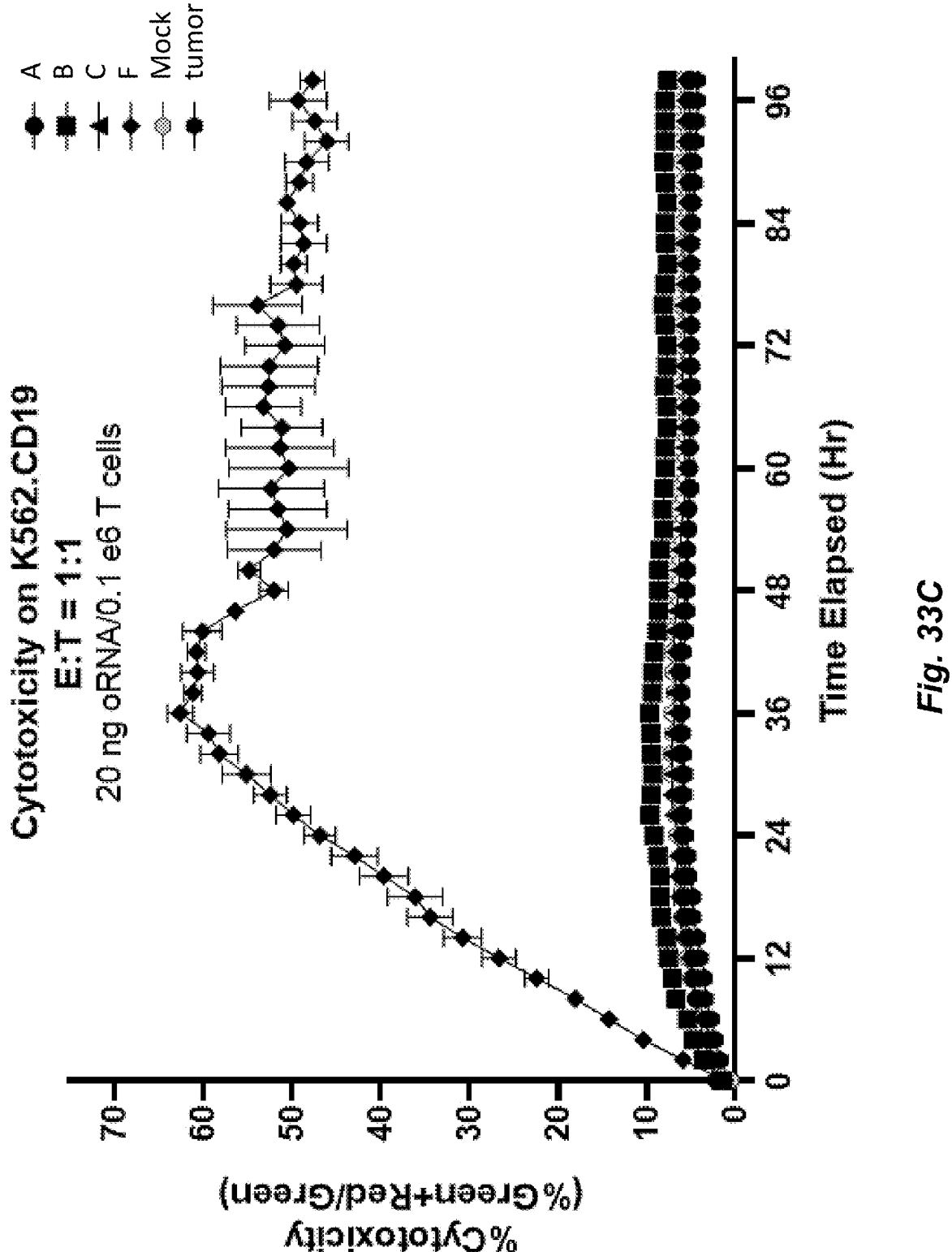

BCMA CAR Expression and CD19 CAR Expression on Multiple Myeloma Positive and Negative Target Cell Lines Donor T cells were thawed and activated with anti-CD3/CD28 solutions. Three days after activation, the cells were washed. On the following day, the cells were electroporated with a range of 10-30 ng dosages of circular RNA encoding a BCMA-41BBζ CAR or CD19CD28ζ CAR per $0.1 \times 10^6$ T cells to form engineered CAR-T cells (oCAR-T cells). Circular RNAs comprised in the following order: a '3 *Anabaena* exon, an internal ribosome entry site (IRES), a coding region encoding a BCMA CAR or CD19 CAR, and a 5' *Anabaena* exon. Circular RNAs were formed from an IVT reaction of DNA templates from Table al, Table B and Table Y1. As a control, Mock T cells were used, wherein the Mock T cells were not electroporated with any circular RNAs. A day following electroporation of the circular RNAs to the T cells, the oCAR-T cells were co-cultured with target multiple myeloma (MM) positive or negative T cells at a 1:1 E:T ratio. MM positive T cells comprised of MMIS, NCI-H929 or RPM1-8226. MM negative T cells comprised of a CD19 positive T cell line (i.e., Nalm6 cell line). As a control, the target tumor cell without co-culturing with the T cells was analyzed for comparison purposes. The circular RNAs were given a commercially available soluble BCMA detection reagent containing R-phycoerythrin (PE) fluorophore or soluble CD19 detection reagent containing quantum dot (qdot) fluorophore (e.g., from AcroBiosystems, Delaware). The oCAR-T cells were also placed into a commercially available live-cell analysis portfolio system (e.g., an IncuCyte) and analyzed 0-72 or 0-96 hours post co-culture for cytotoxicity. The cytotoxicity results can be seen in FIGS. 33A-33C for each of the circular RNAs encoding BCMA, CD19, or HER2 CARs, respectively. Cross-reactivity for the various circular RNAs encoding the various CARs was observed on MMIS, Nalm6 and CD19 positive T cell line in FIGS. 33A, 33B, and 33C respectively.

Cytotoxicity of BCMA Targeted Killing on MMIS Via FACS

BMCA positive cells were acquired and prepped. The cells were electroporated with 30 ng per $0.1 \times 10^6$ cells of circular RNA comprising a 3' *Anabaena* exon, an internal ribosome entry site (IRES), a BCMA-41BB (CAR, and a 5'

Figure 34A:
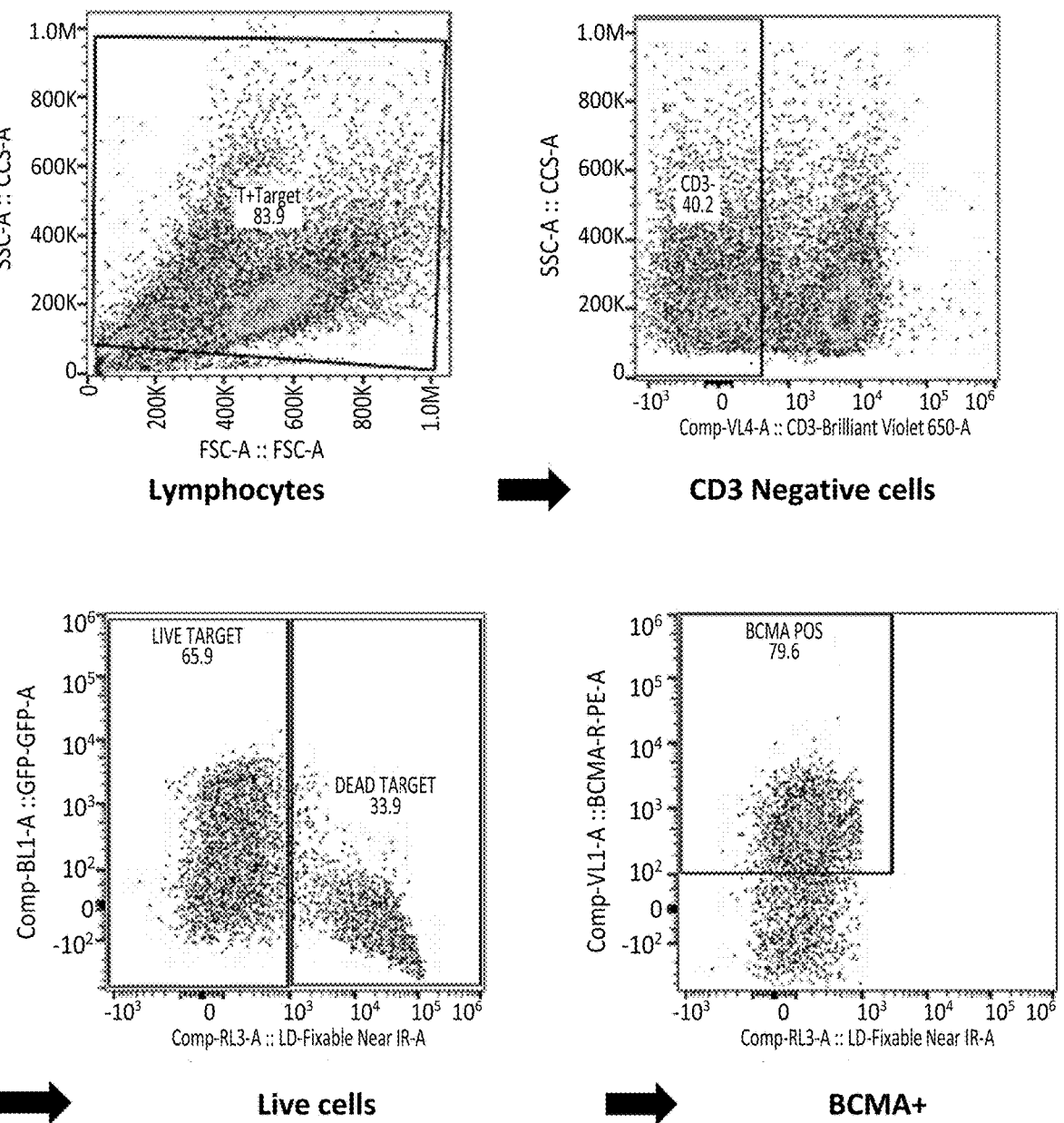
FIGS. 34A-34C depict cytotoxicity analysis of various engineered circular RNAs across multiple cell types.

*Anabaena* exon. Circular RNAs were formed from an IVT reaction of DNA templates from Table α1, Table β and Table γ1. On the following day, the cells were then co-cultured with MMIS cells and dyed with FSC-A, CD3-Brilliant Violet 650-A, LD-fixable Near IR-A for fluorescence activated cell sorting analysis (FACS). Resulting FACS imaging for cell post 24 hours after co-culturing with MMIS can be seen in FIG. 34A. From the FACS imaging, percent cell lysis was calculated (e.g., % cell lysis=(1−((% of live Target Cells in Test Sample)/(% of live Target Cells in Control Sample)))×100).

Figure 34B:
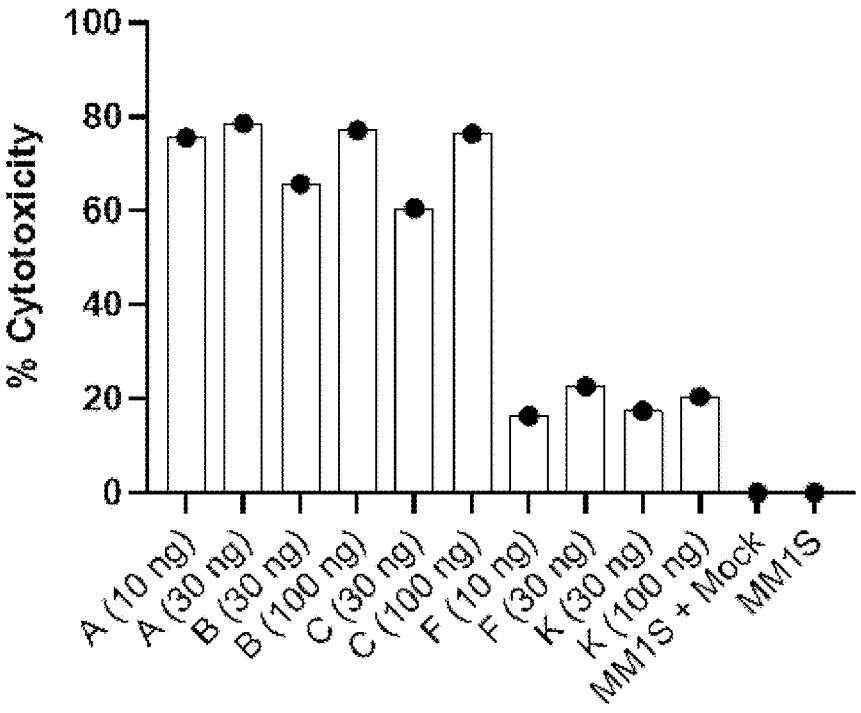
Figure 34C:
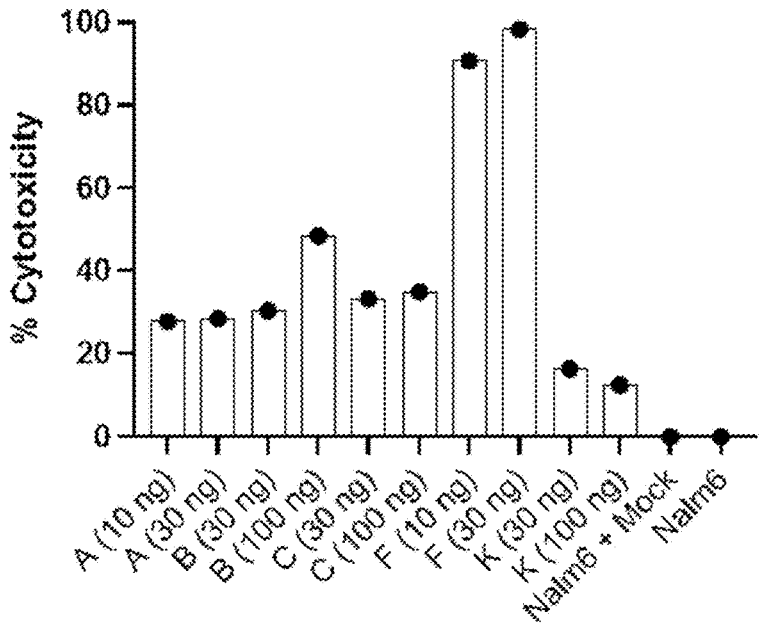
Figure 35B:
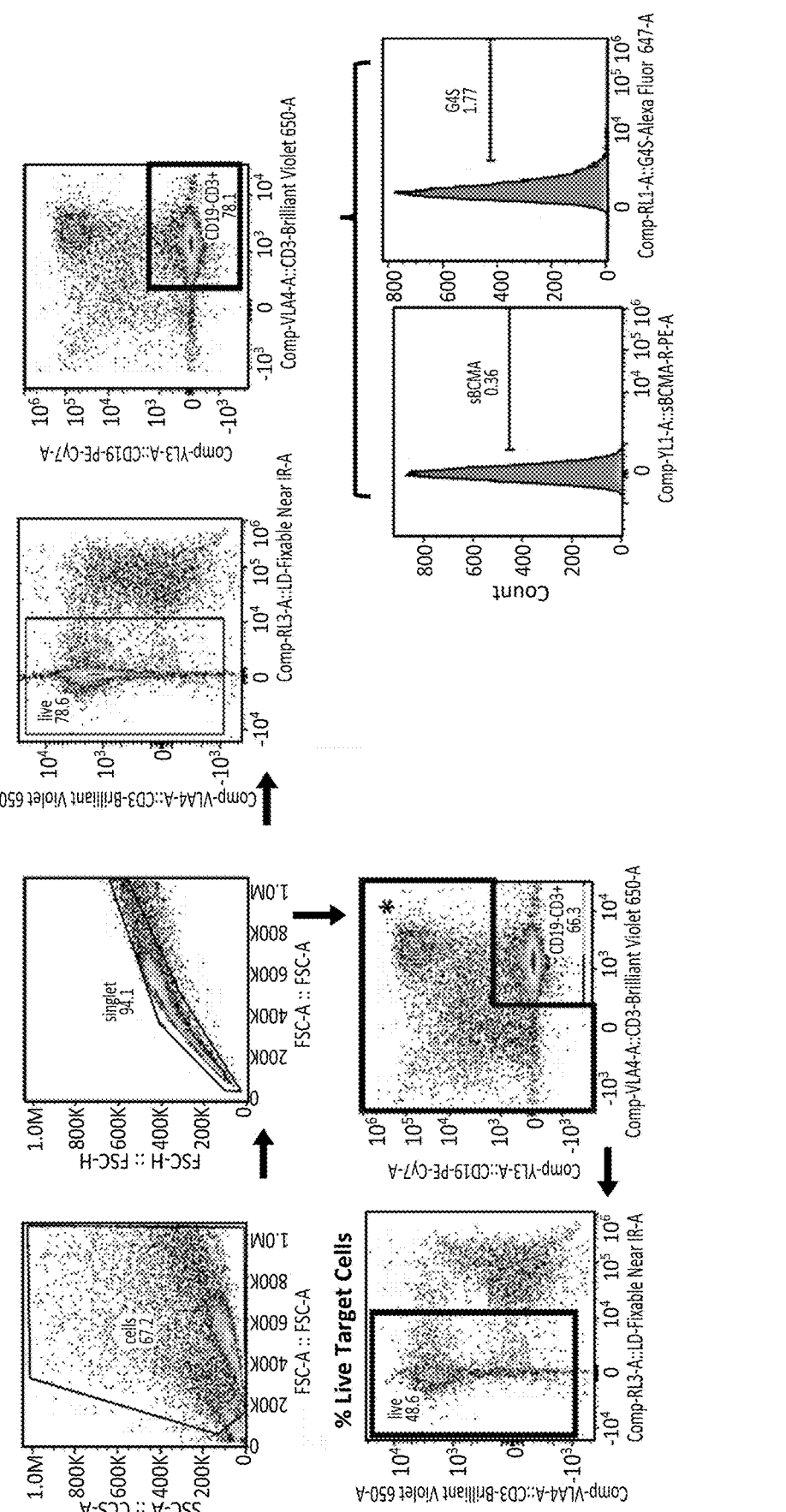
FIG. 35B depicts FACS imaging for CD19+CD3+ cells.
Figure 36A:
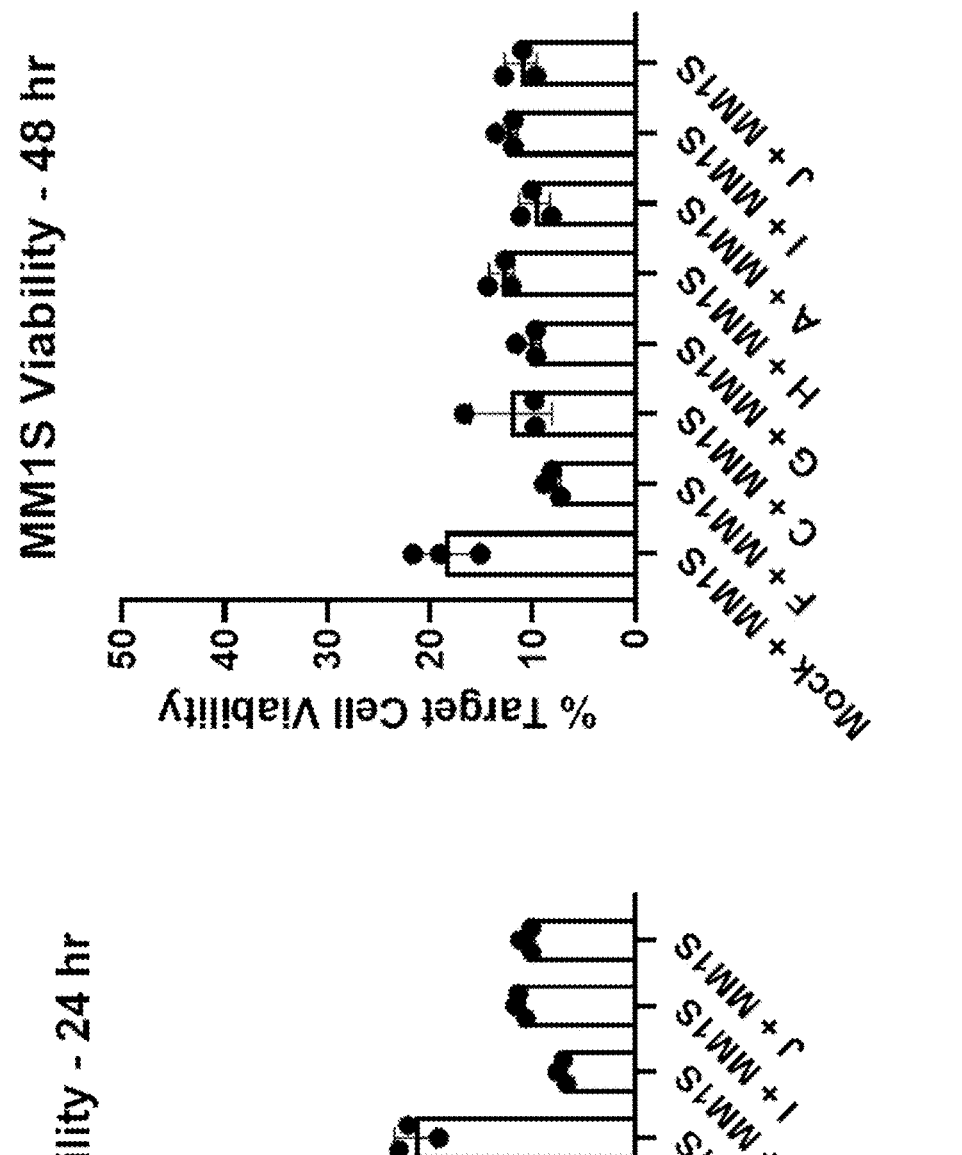
FIG. 36A-36D depicts % target cell viability (top) and % target cell killing of T cells (bottom) that have been electroporated with circular RNAs derived from DNA Templates in Tables al, β and/or γ1 and later co-cultured with a target cell (e.g., MMIS (FIG. 36A), NCI-H929 (depicted as "H929" in FIG. 36B), Nalm6 (FIG. 36C), or K562.CD19 (FIG. 36D)) for 24 (left) or 48 (right) hours post co-culture. "Mock+MMIS" (i.e., MMIS tumor cells cocultured with T cells not electroporated with circular RNAs, "Mock+Nalm6" (i.e., Nalm6 tumor cells cocultured with T cells not electroporated with circular RNAs), "Mock+H929" (i.e., NCI-H929 tumor cells cocultured with T cells not electroporated with circular RNAs), and "Mock+K562.CD19" (i.e., K562.CD19 tumor cells cocultured with T cells not electroporated with circular RNAs). "A", "G", "C", "F", "H", "I", and "J" correspond to "DNA Template A", "DNA Template G", "DNA Template C", "DNA Template F", "DNA Template H", "DNA Template I", and "DNA Template J" that were used to form the circular RNAs.
Figure 36A:
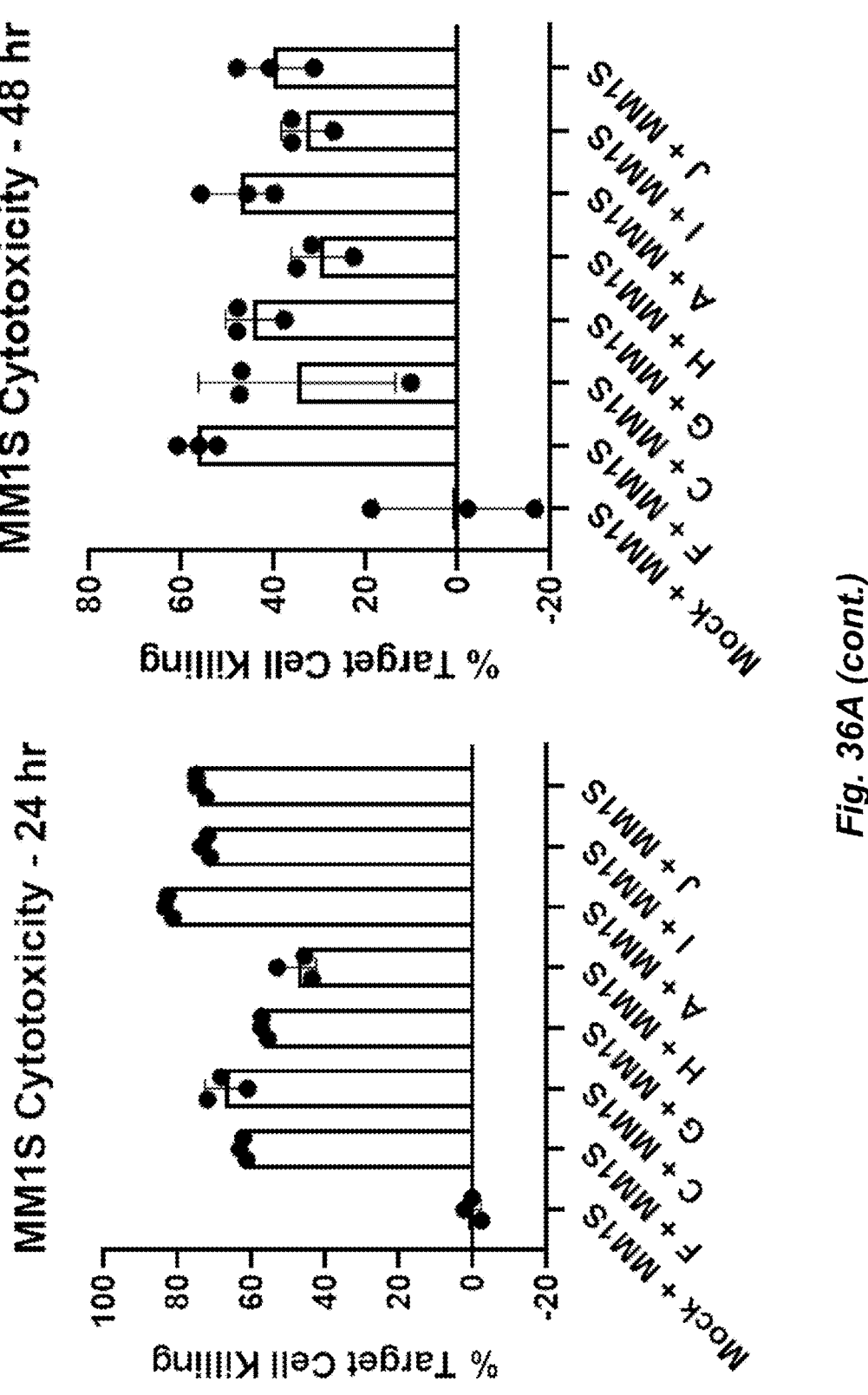
Figure 36B:
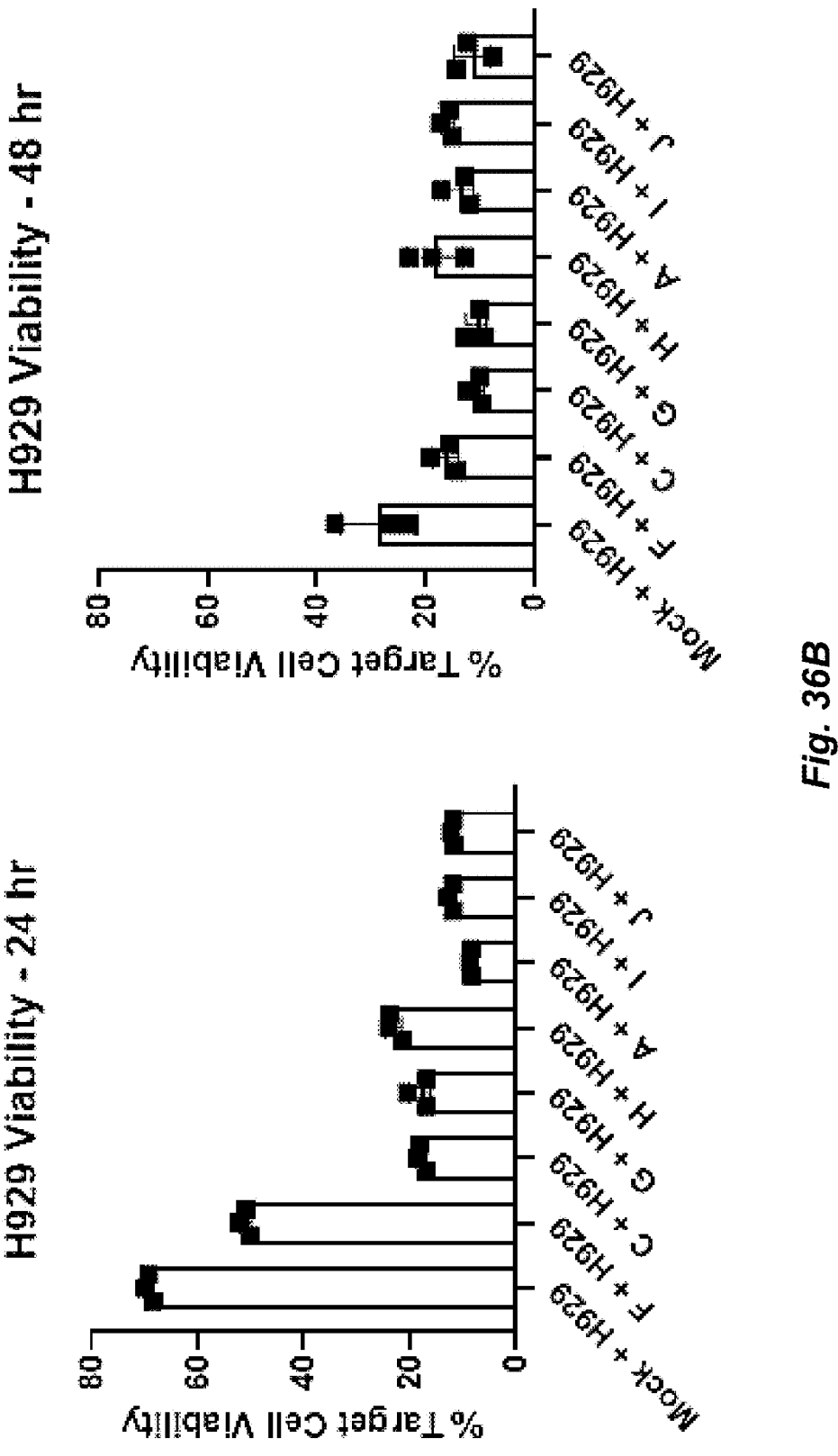
Figure 36B:
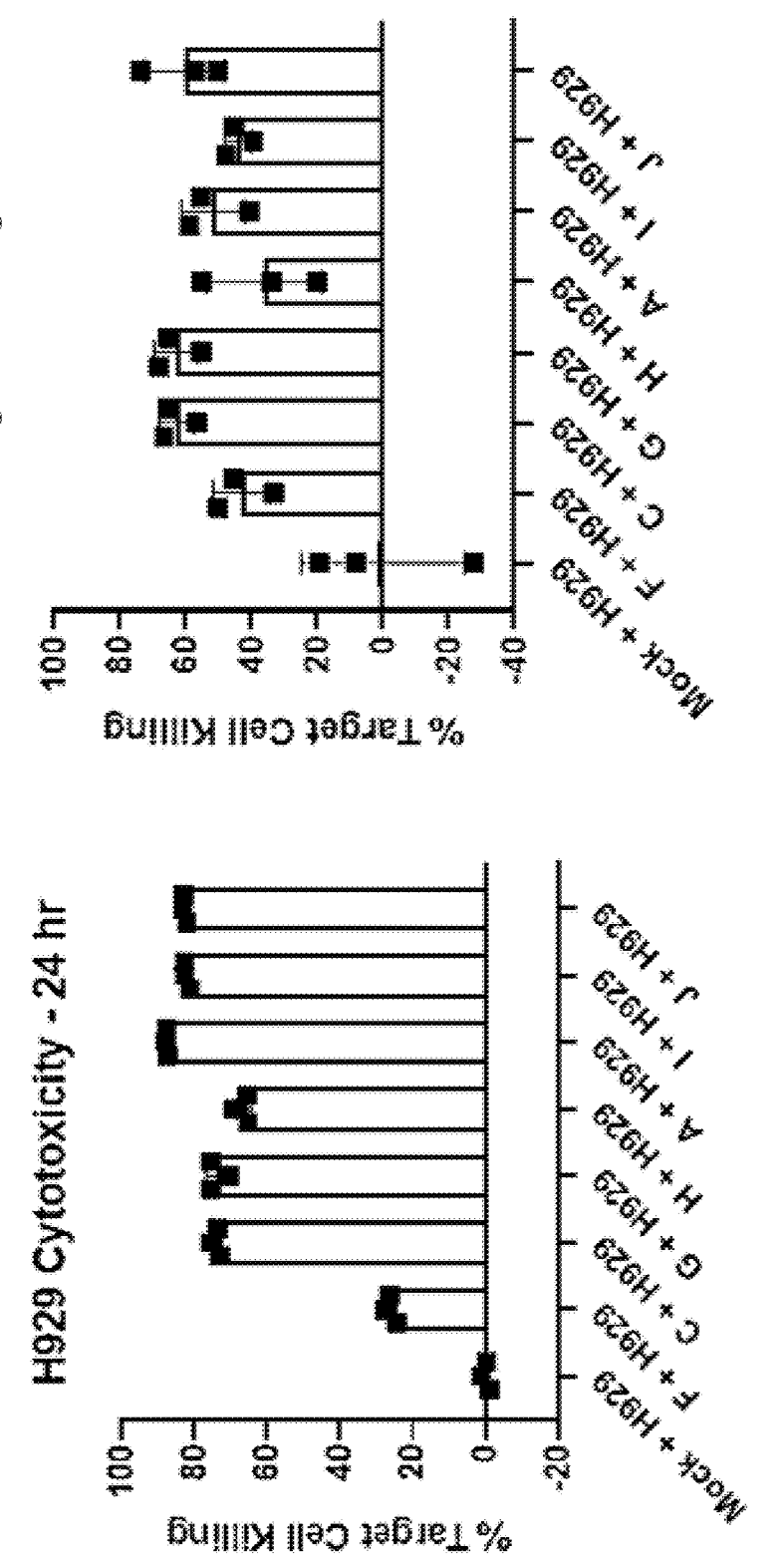
Figure 36C:
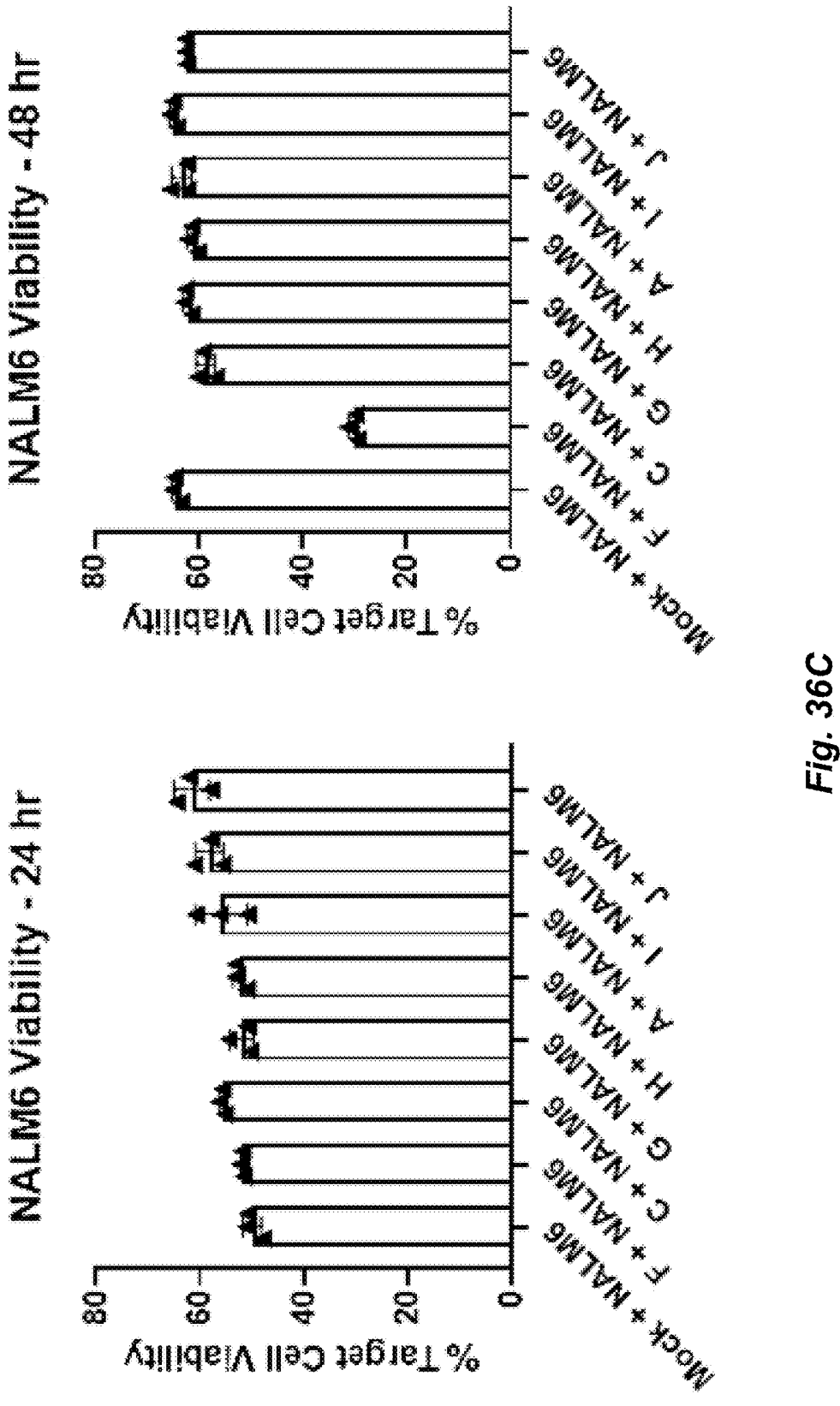
Figure 36C:
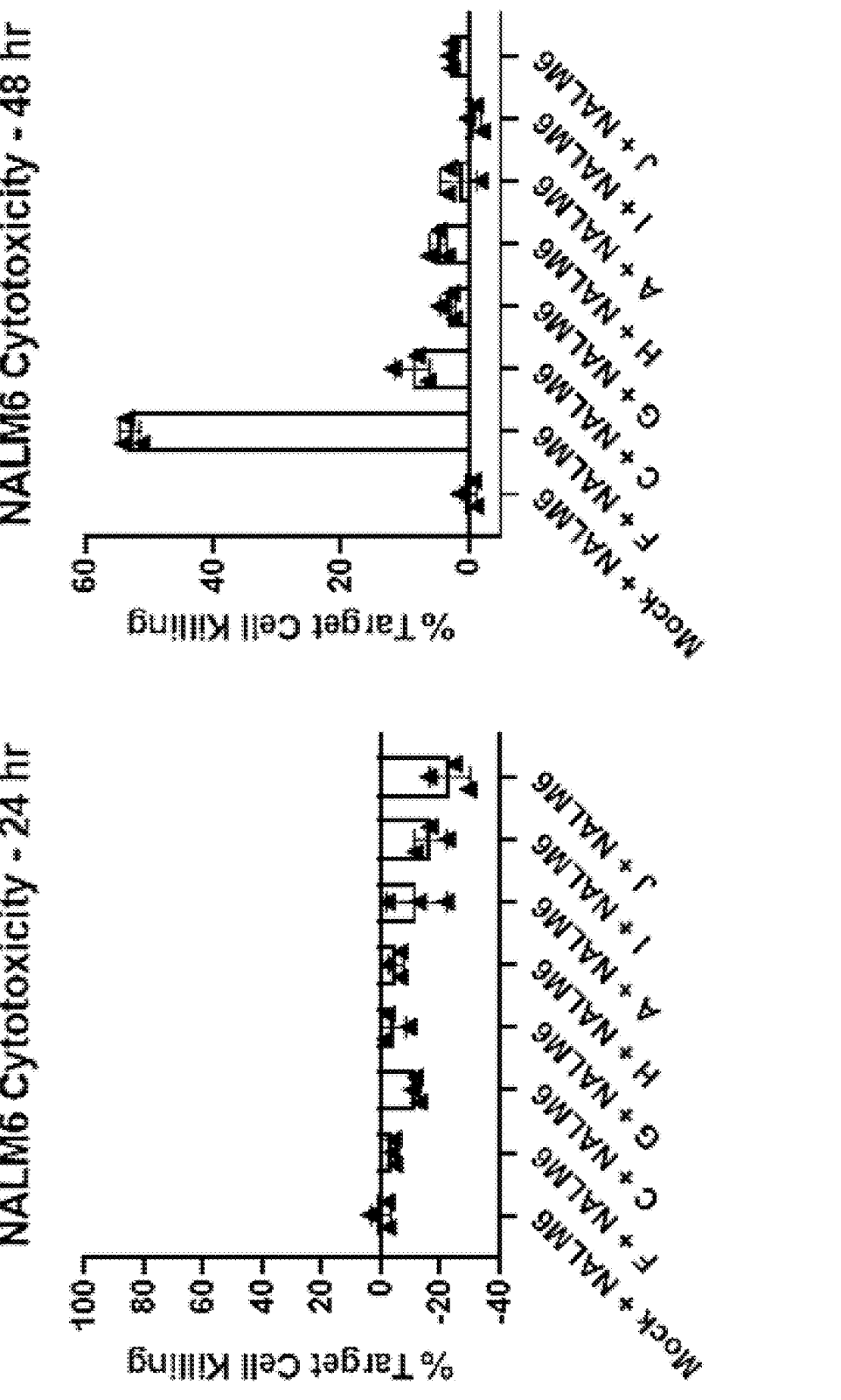
Figure 36D:
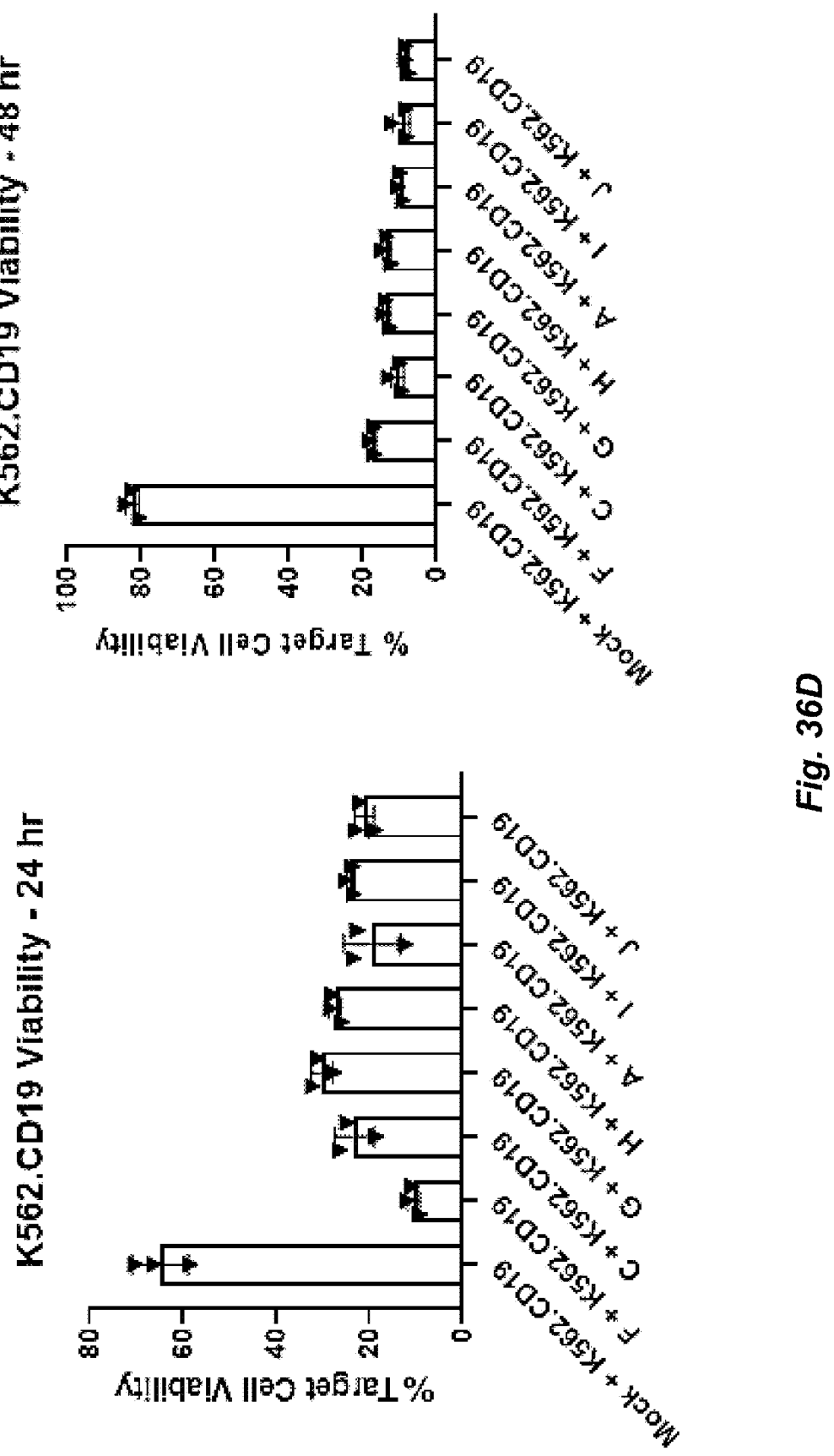
Figure 36D:
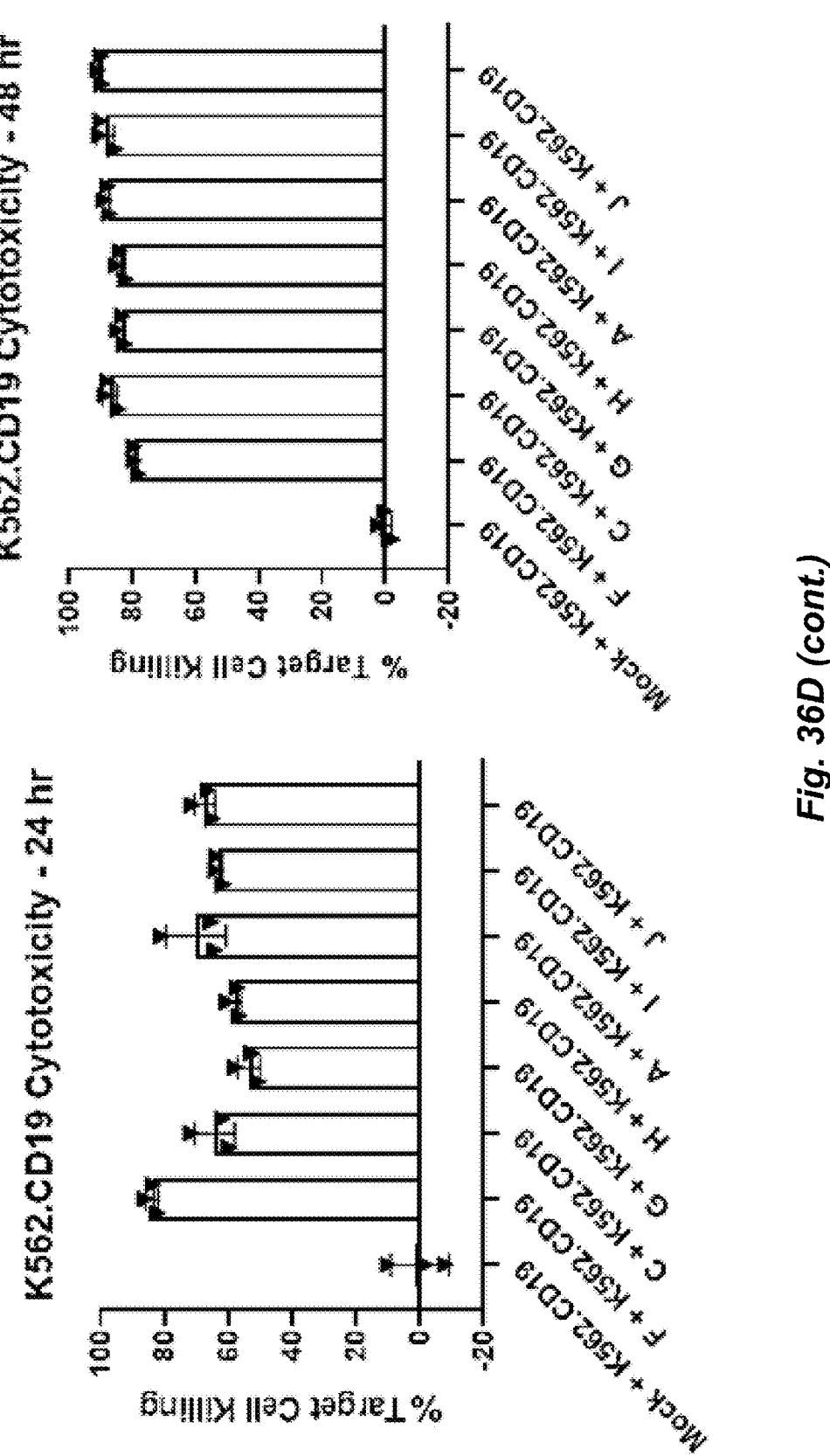
Figure 37A:
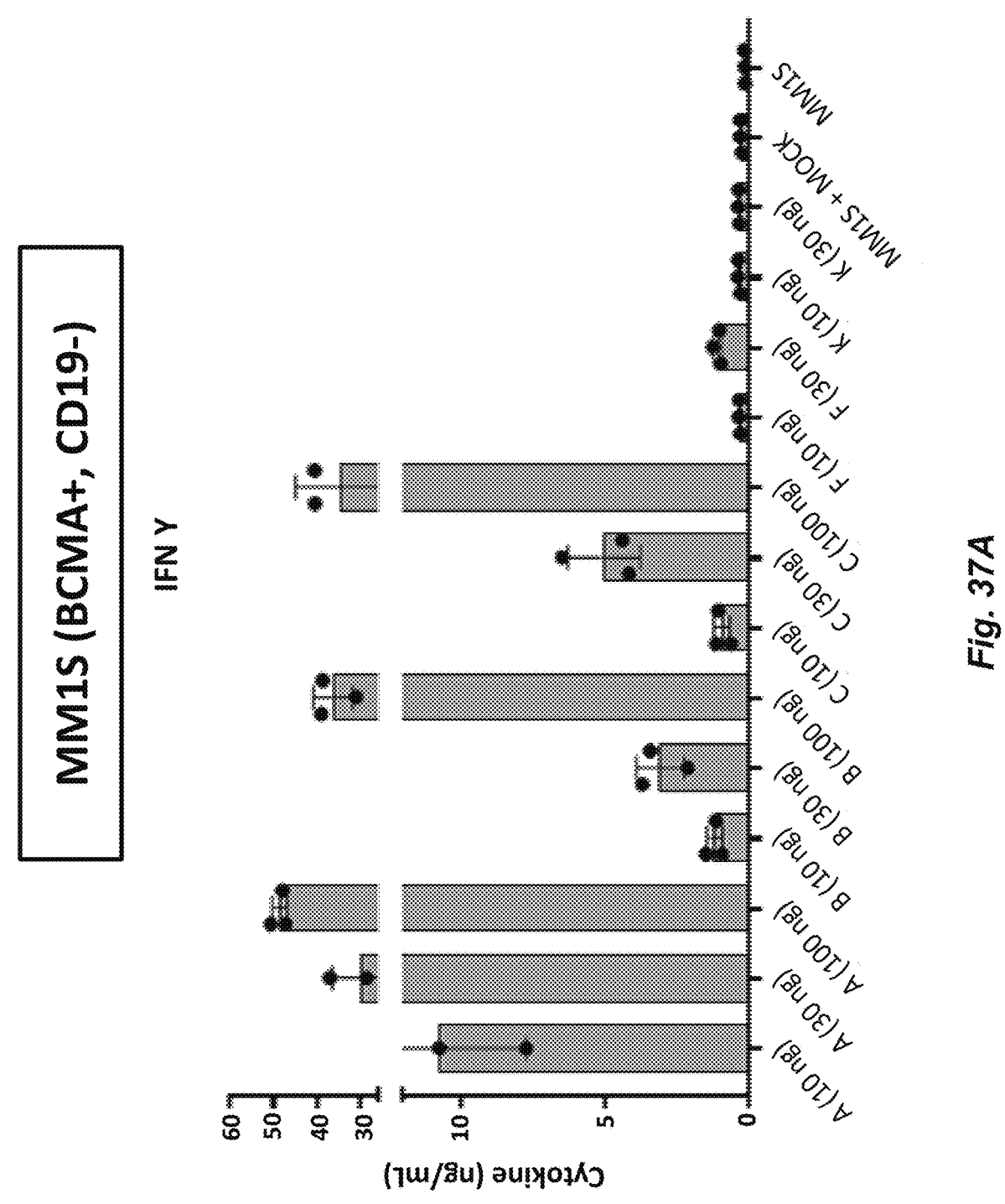
FIGS. 37A and 37B depict INγ cytokine secretion produced from circular RNAs encoding BCMA-41BBζ, CD19-CD28ζ and HER2-CD286 CARs at 10, 30, or 100 ng dose per $0.1\times10^6$ T cells on MMIS (FIG. 37A) or Nalm6 (FIG. 37B) cells post co-culture of the MMIS or Nalm6 with T cells containing the circular RNAs. Cytotoxicity levels were calculated from a cytokine and chemokine kit (e.g., MSD). "MMIS+Mock" refers to MMIS tumor cells that were co-cultured with T cells that had not be electroporated with circular RNAs. "MMIS" refers to tumor cells that were not co-cultured with T cells. "Nalm6+Mock" refers to Nalm6 tumor cells that were co-cultured with T cells that had not been electroporated with circular RNAs. "Nalm6" refers to tumor cells that were not co-cultured with T cells. "A", "B", "C", "F", and "K" correspond to "DNA Template A", "DNA Template B", "DNA Template C", "DNA Template F", and "DNA Template K" that were used to form the circular RNAs.
Figure 37B:
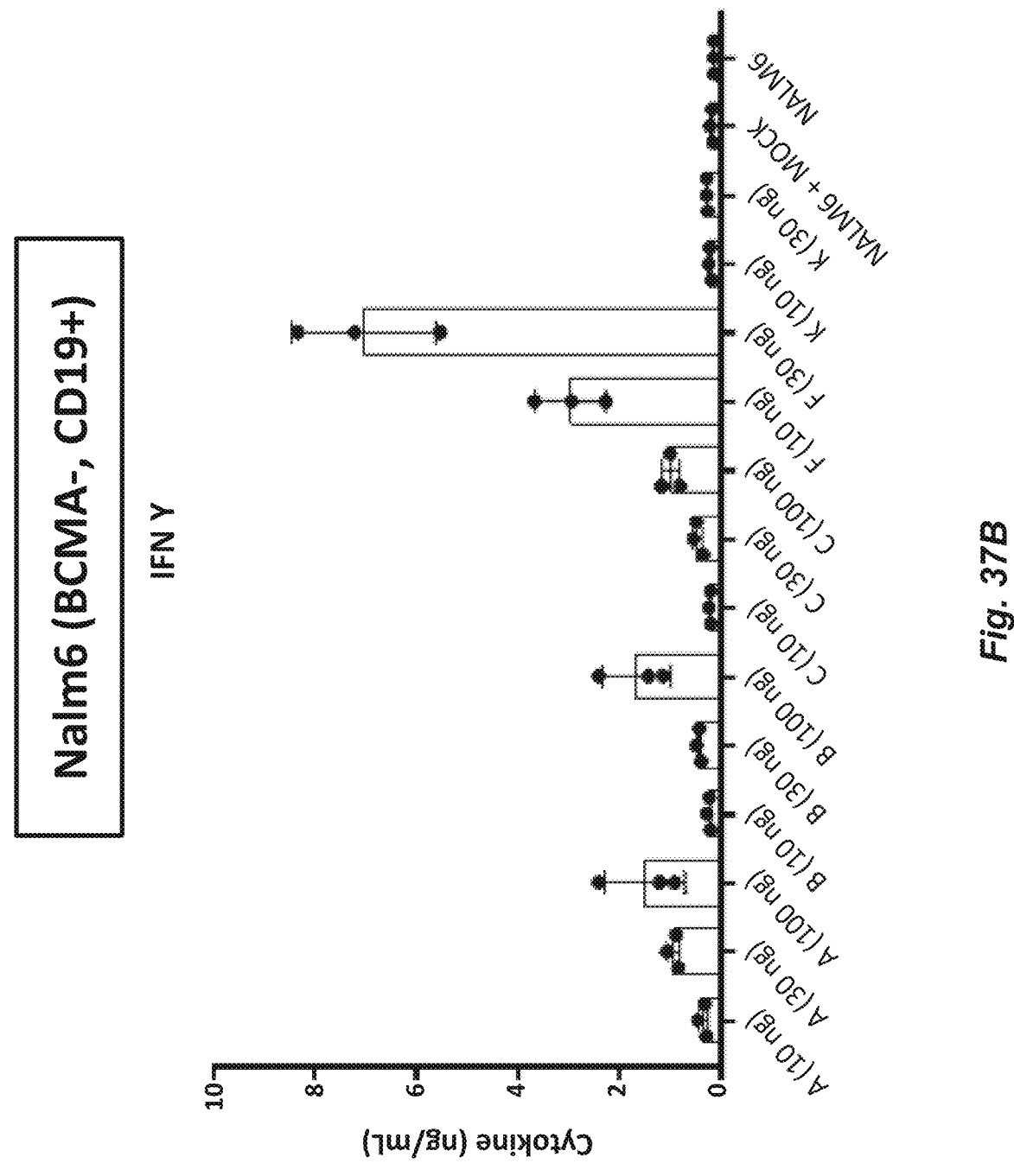
Figure 38A:
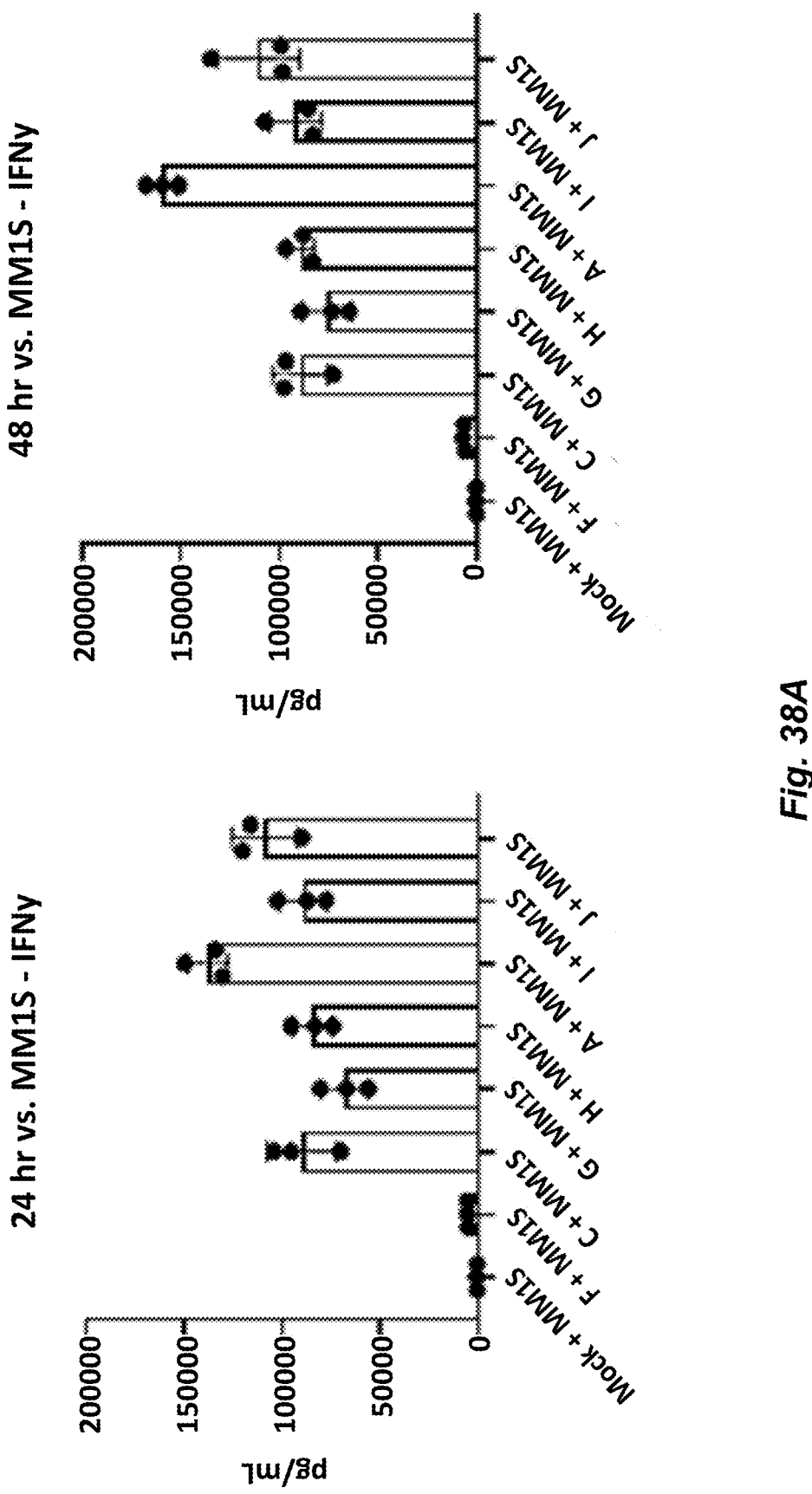
FIGS. 38A-38P depict cytokine levels (pg/mL) at 24 and 48 hours (left and right respectively in each figure) in cocultured T cells comprising circular RNA encoding BMCA-41BBζ, BCMA-CD28ζ, or CD19-CD28ζ CAR and target cells. The target cells include MMIS (FIGS. 38A, 38E, 38I and 38M), NCI-H929 (indicated as "H929") (FIGS. 38B, 38F, 38J, 38N), Nalm6 (FIGS. 38C, 38G, 38K, 38O), and K562.CD19 (FIGS. 38D, 38H, 38L, 38P).
Figure 38B:
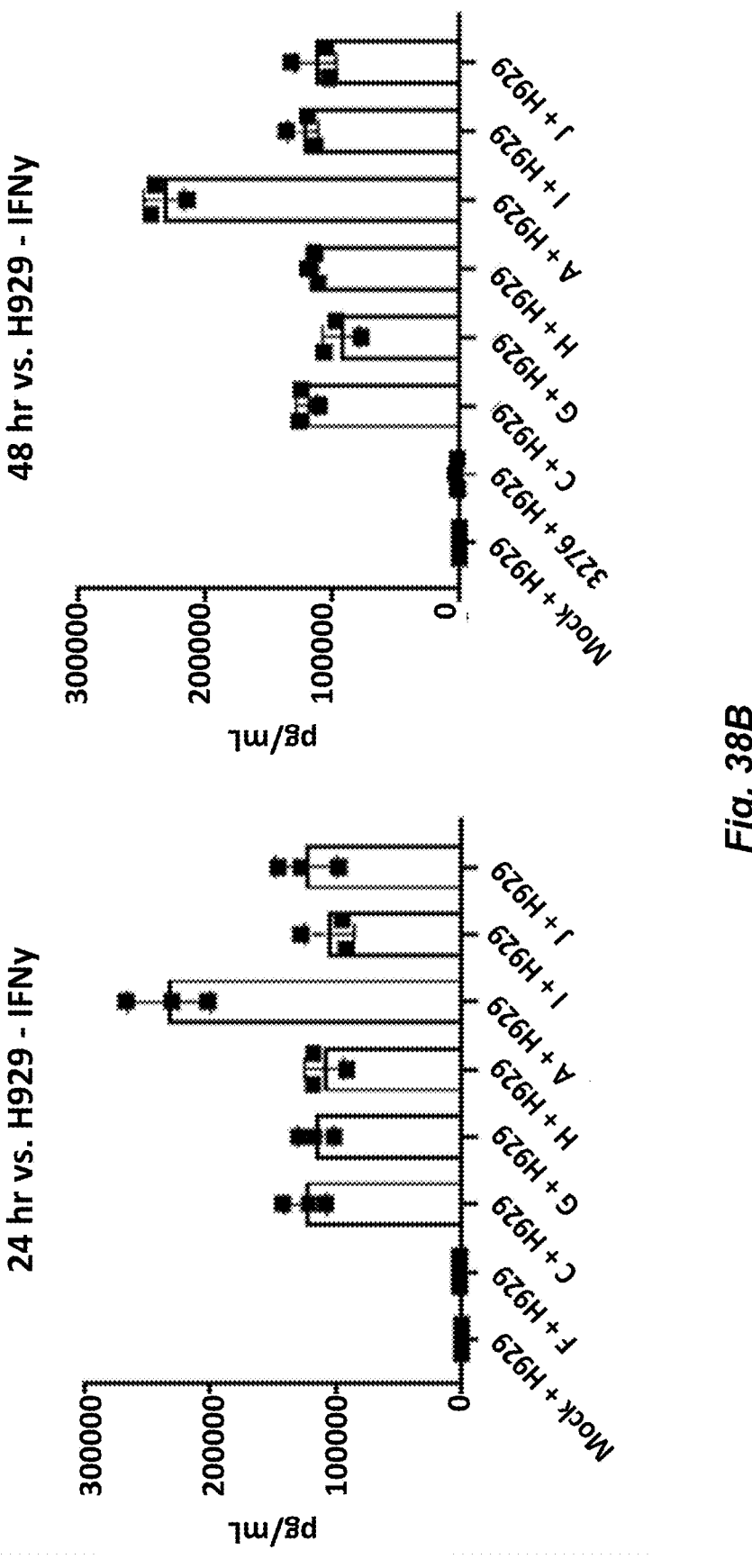
Figure 38C:
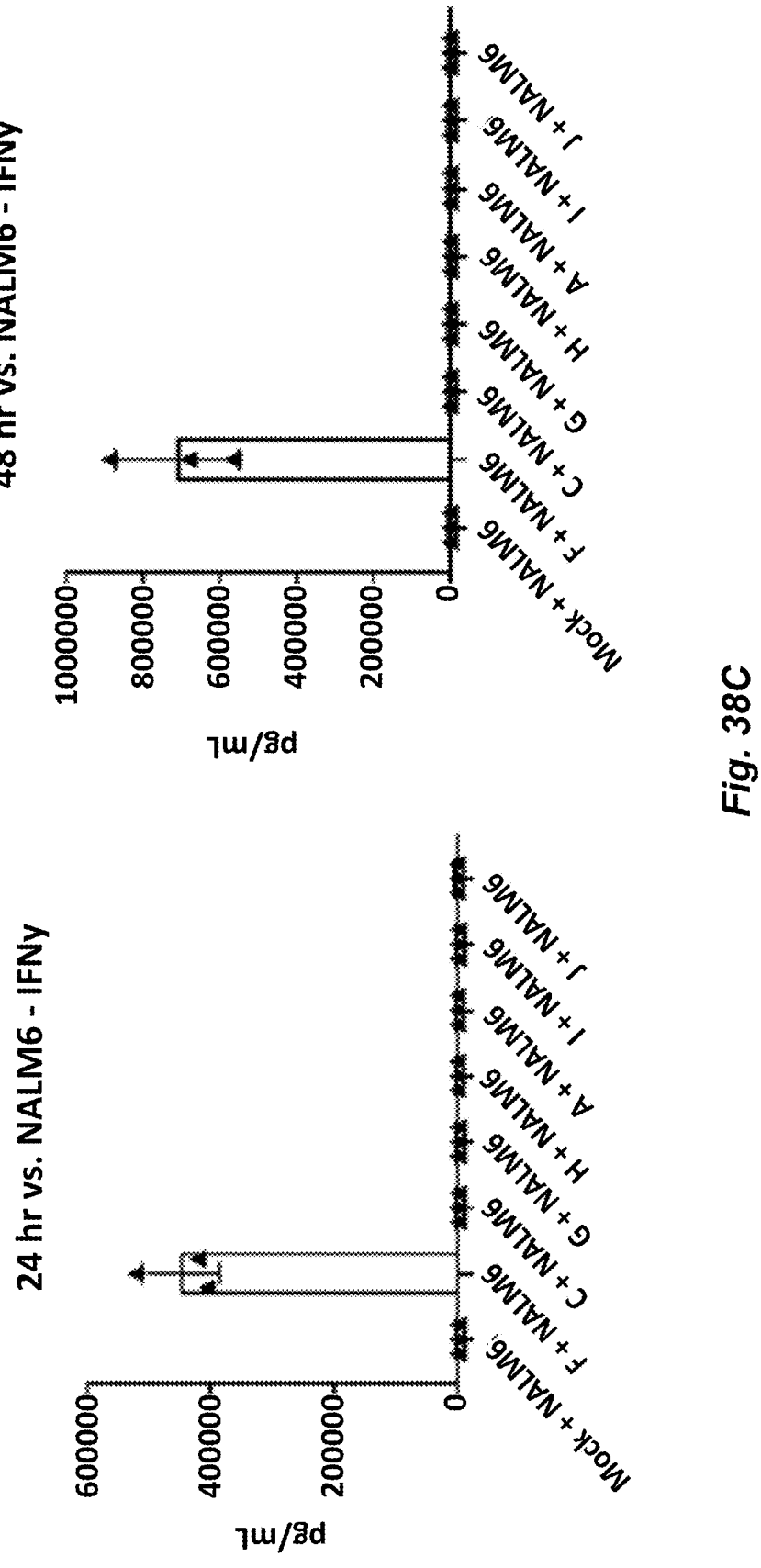
Figure 38D:
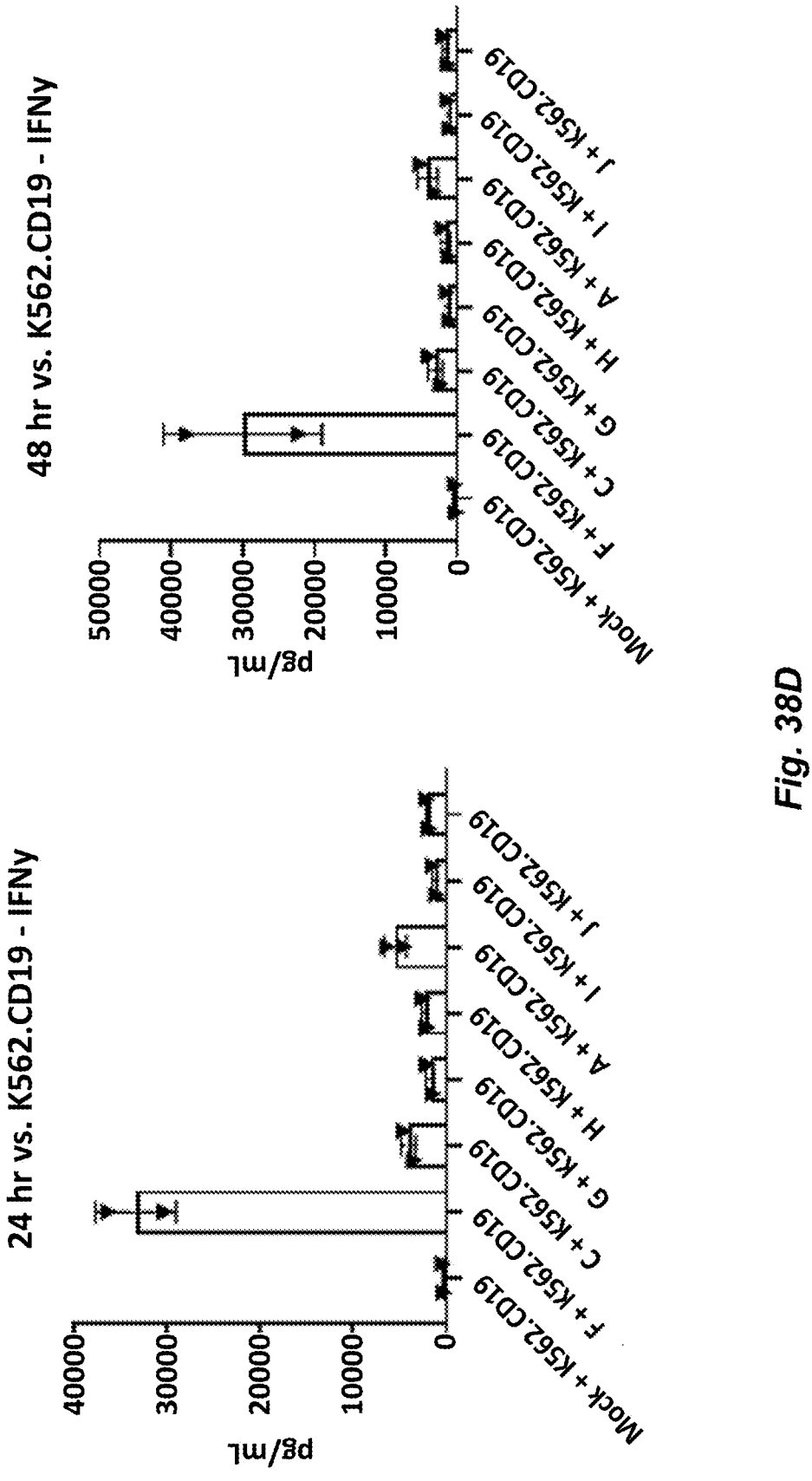
Figure 38E:
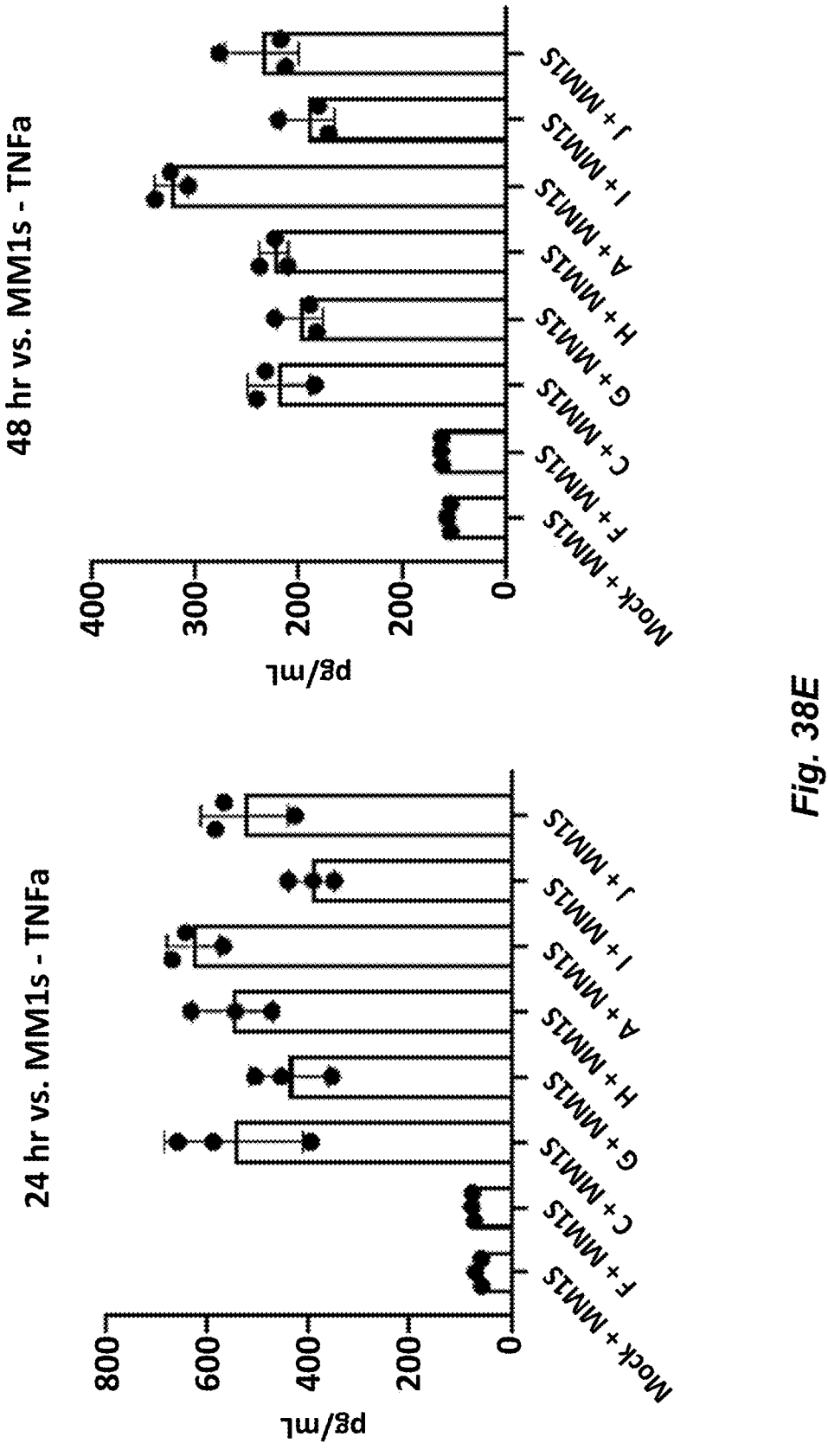
Figure 38F:
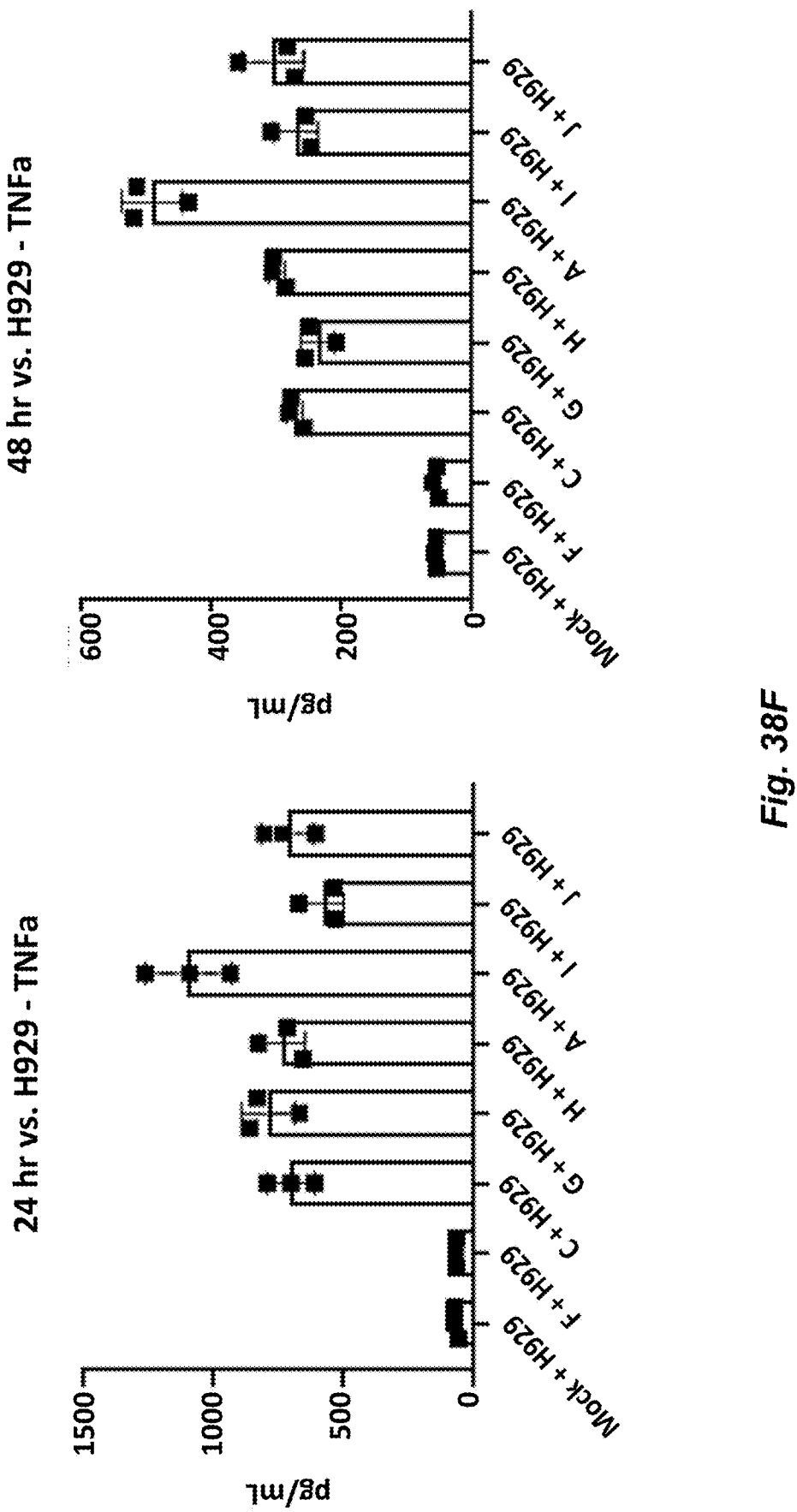
Figure 38G:
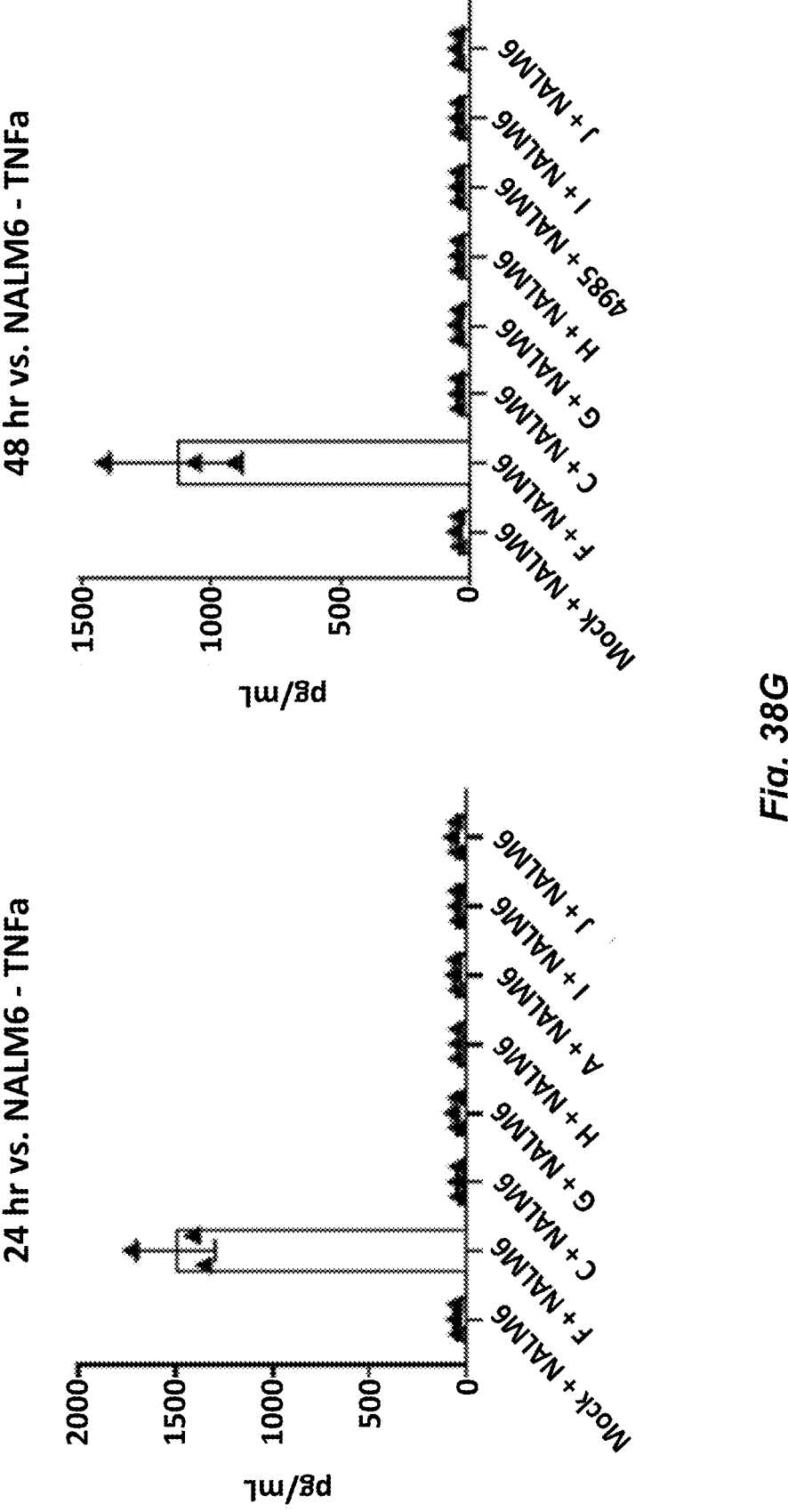
Figure 38H:
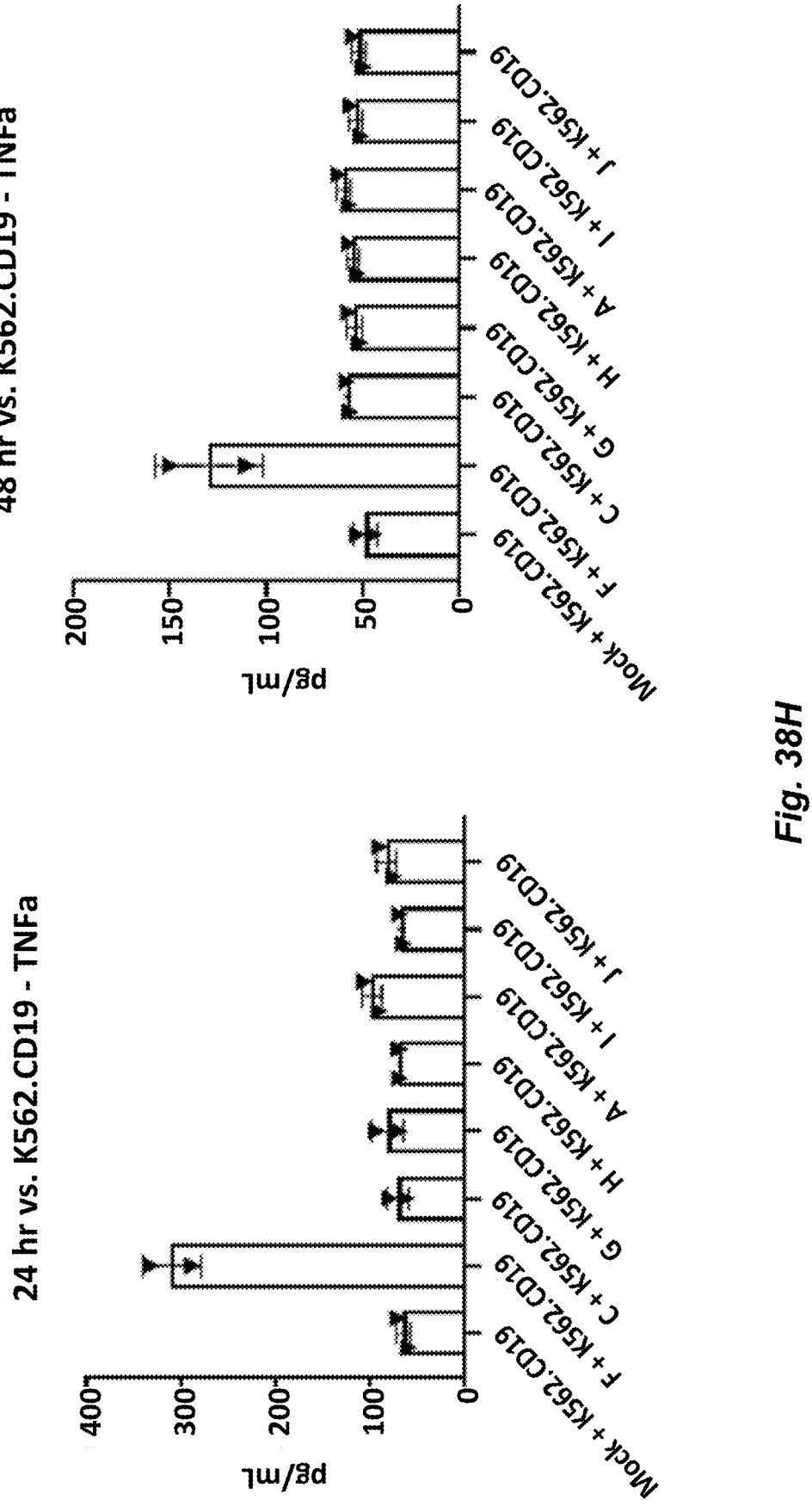
Figure 38I:
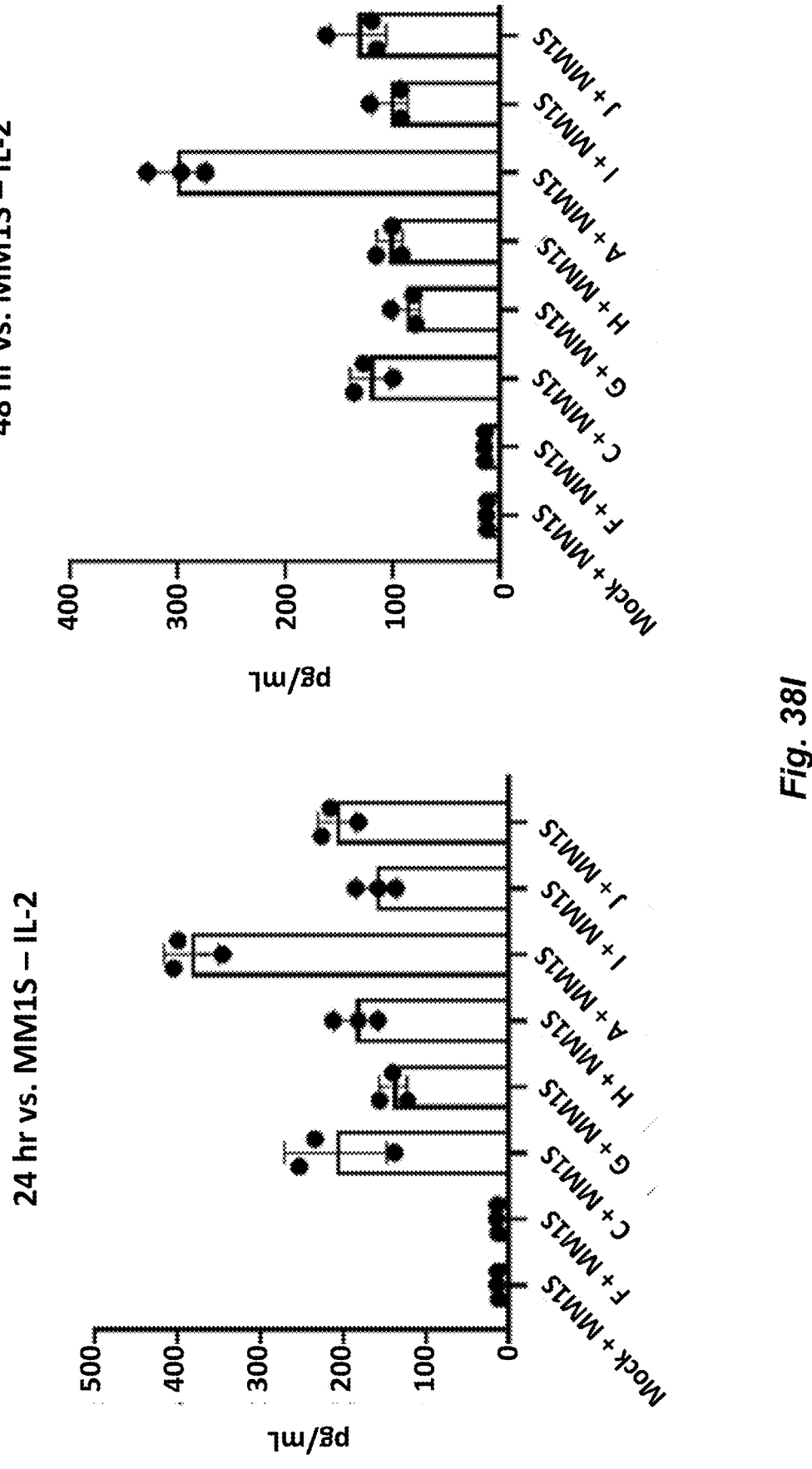
Figure 38J:
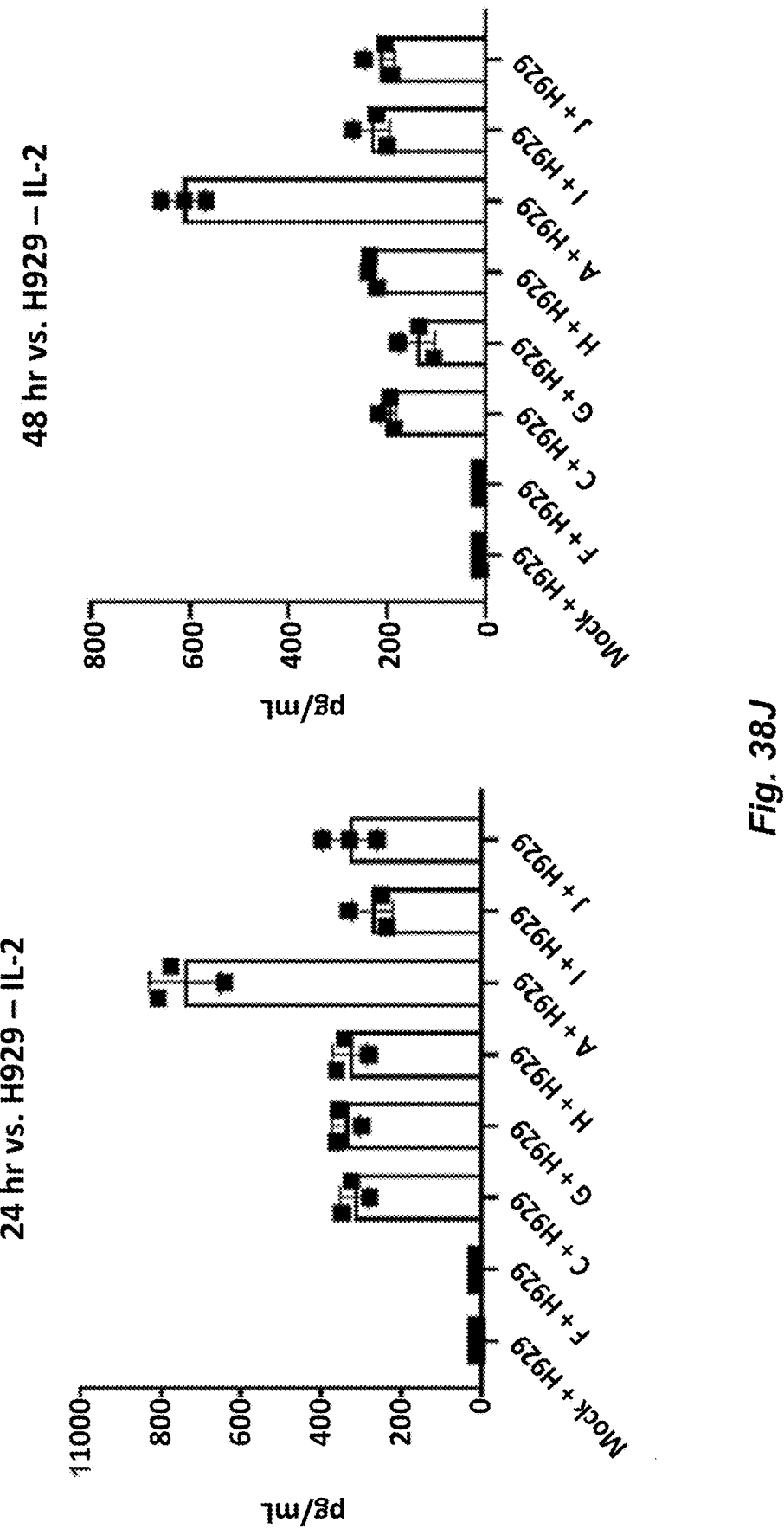
Figure 38K:
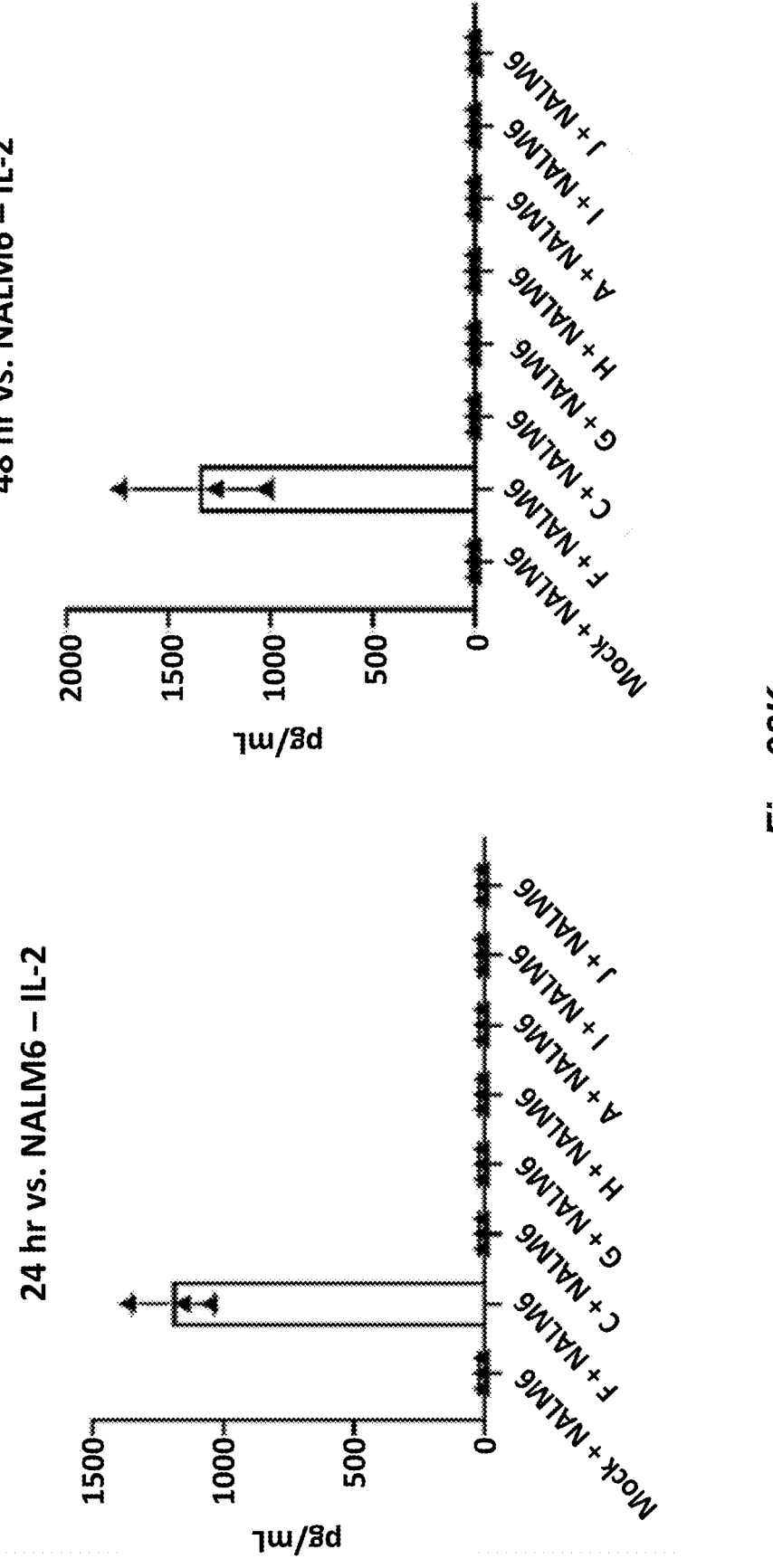
Figure 38L:
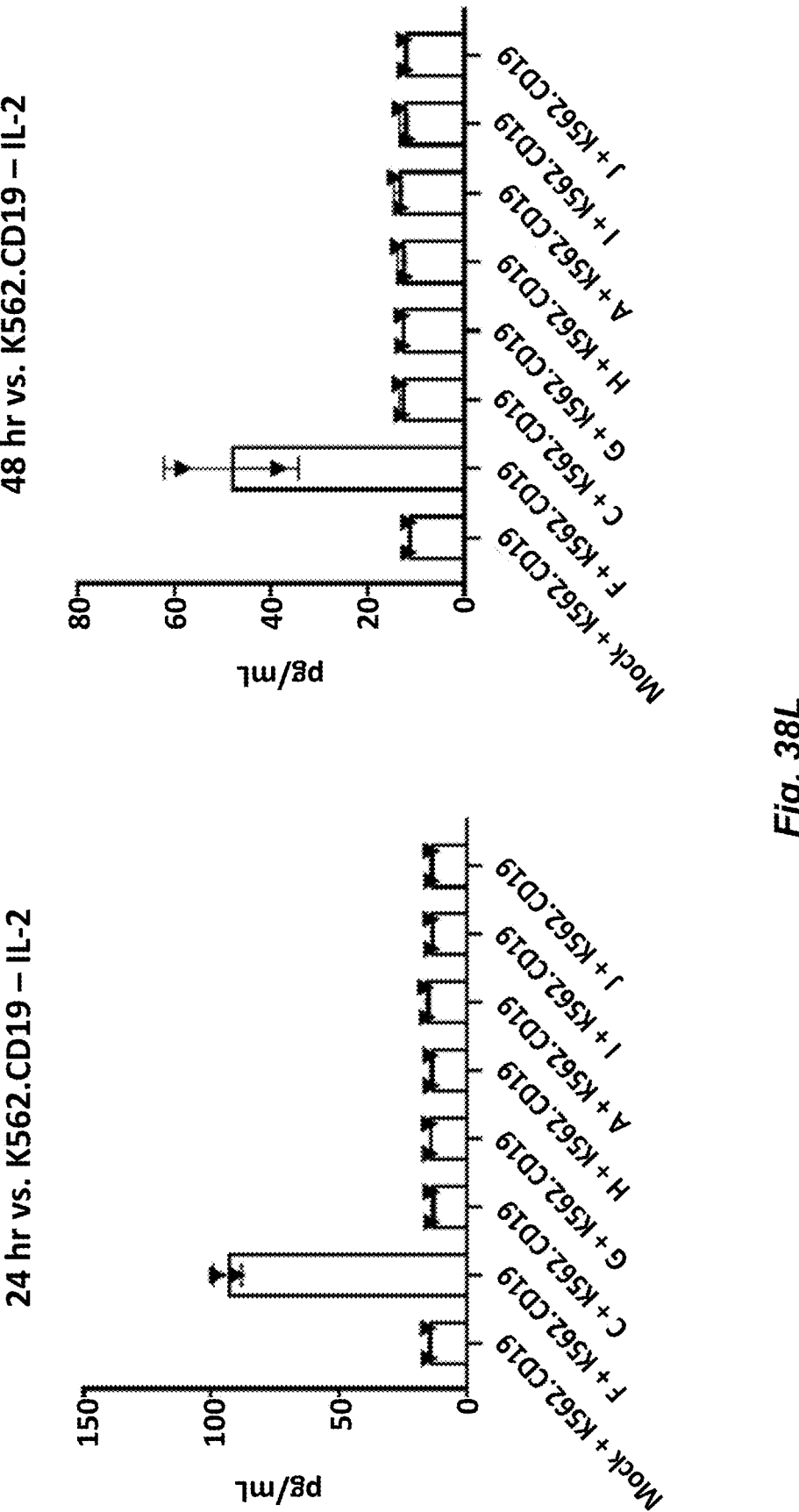
Figure 38M:
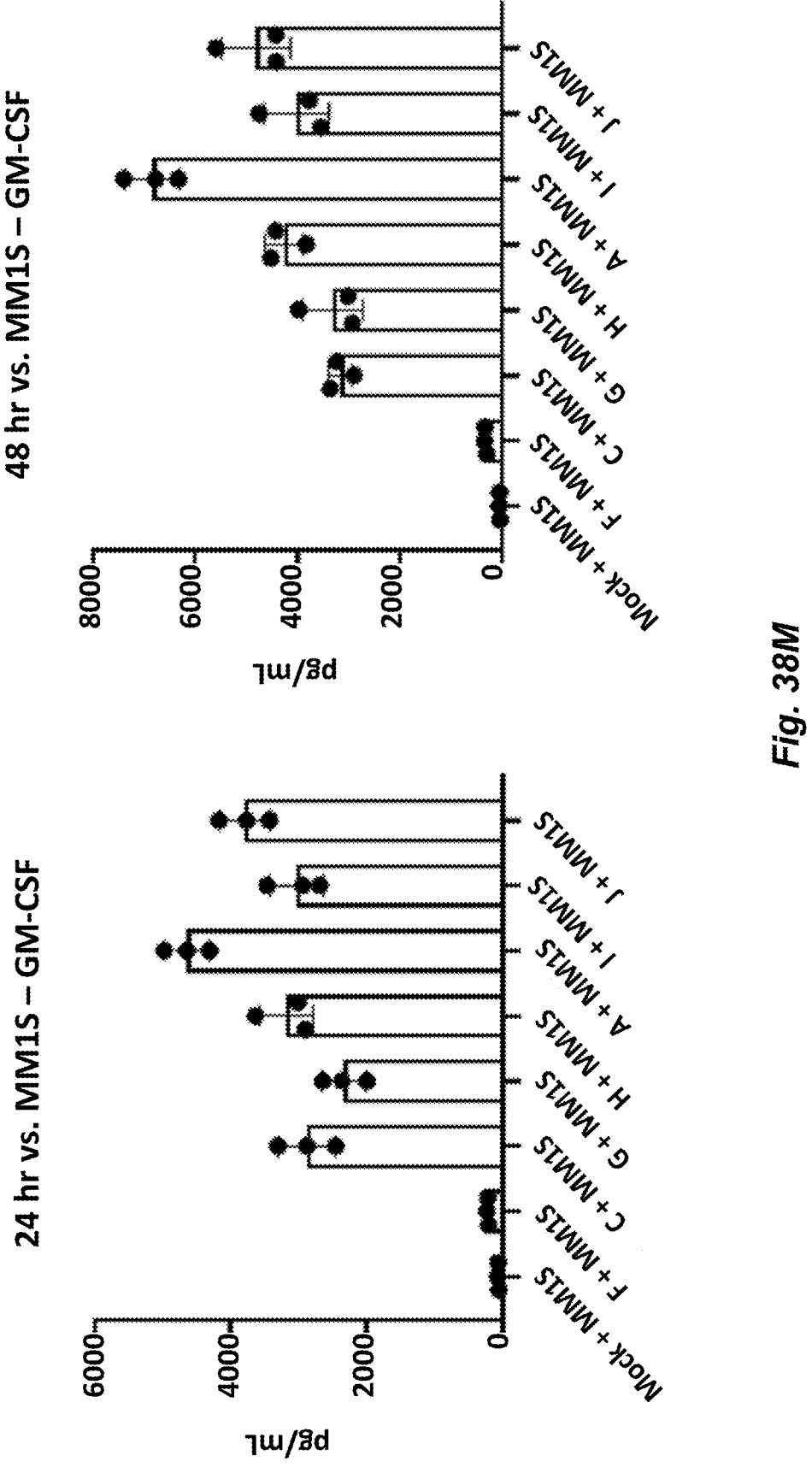
Figure 38N:
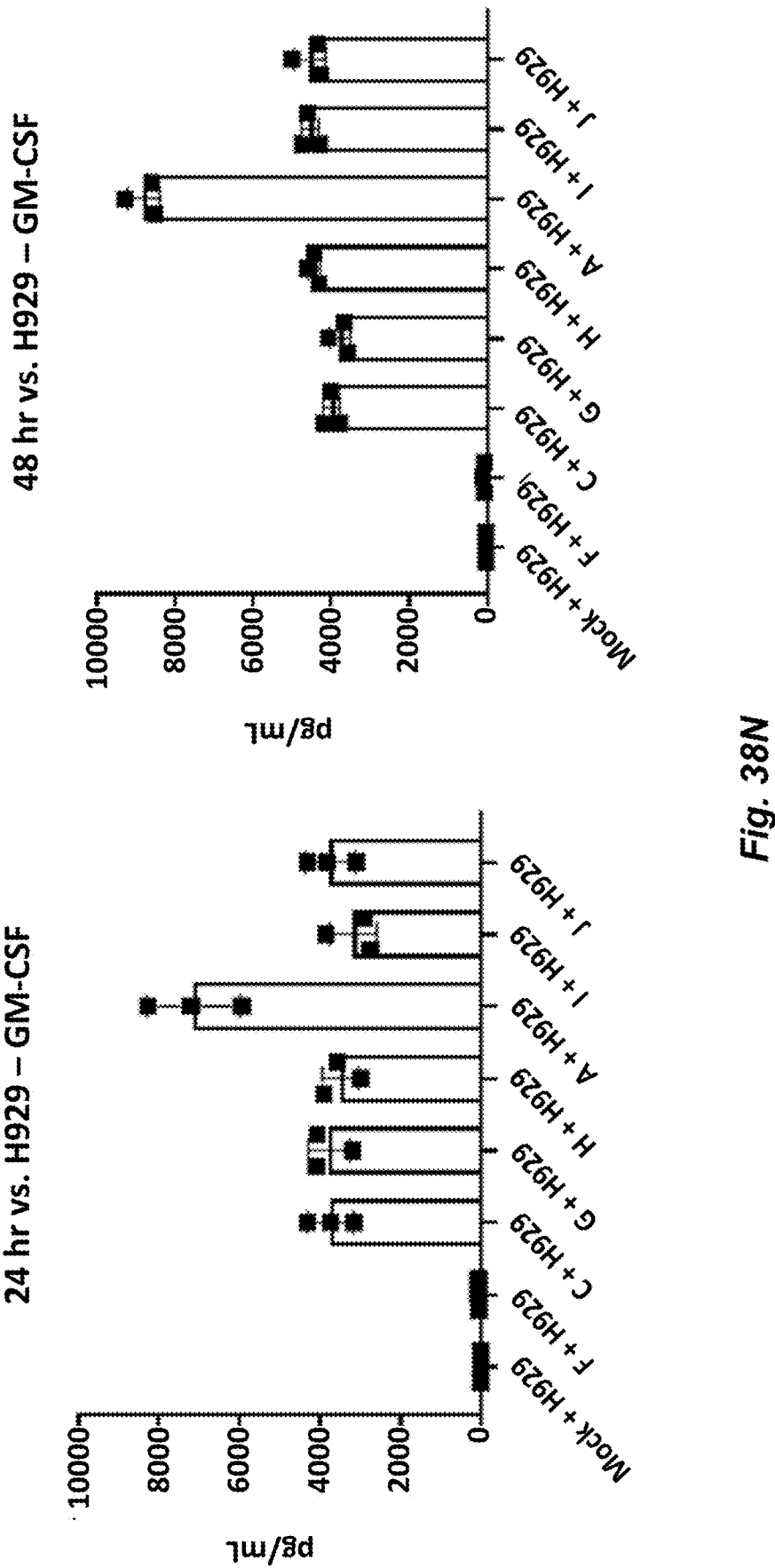
Figure 38O:
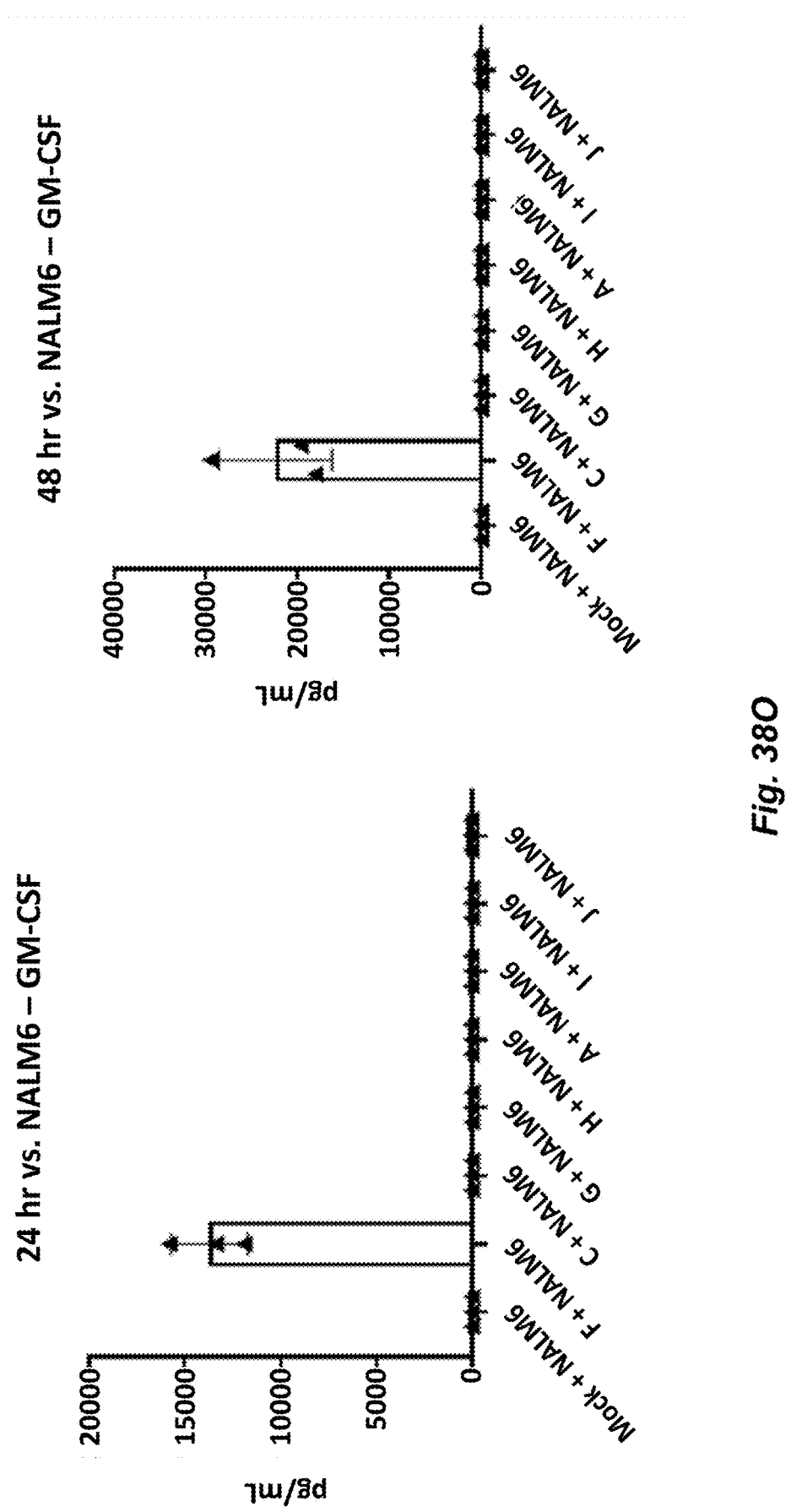
Figure 38P:
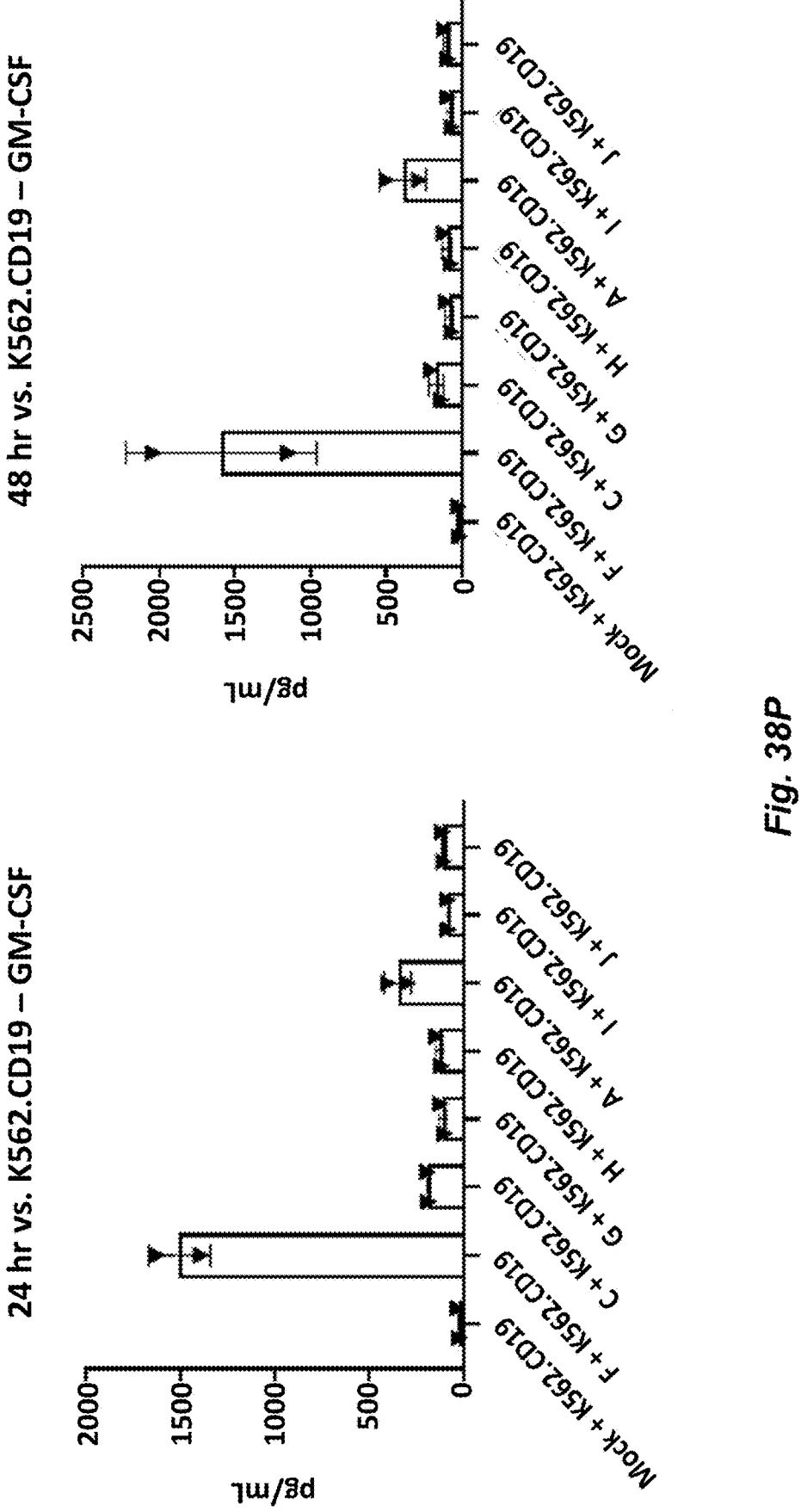

As a follow up, FACS cytotoxicity assays were performed for circular RNAs encoding BCMA-41BBζ, CD19-CD285 or HER2-CD28° C. CAR and an IRES at either 10, 30, 50 or 100 ng per $0.1 \times 10^6$ T cells (FACS imaging for the T cell electroporated with circular RNAs along with their mock counterpart (T cells lacking circular RNAs) was shown in FIGS. 35A and 35B). Circular RNAs were formed from an IVT reaction of DNA templates from Table α1, Table β and Table γ1. The T cells containing circular RNAs (oCAR-T) were co-cultured with one of four target cell-either MMIS (a BCMA positive cell line), NCI-H929 (a BCMA positive cell line) Nalm6 cells (a CD19 positive cell line), a CD19 T stable cell line (e.g., K562.CD19)—at an E:T ratio of 1:1. 24 hours post co-culture of the oCAR-T cells with the MMIS, Nalm6, NCI-H929, or CD19 T stable cells. MMIS+Mock (i.e., MMIS tumor cells cocultured with T cells not electroporated with circular RNAs), MMIS (i.e., MMIS tumor cells not cocultured with T cells), Nalm6+Mock (i.e., Nalm6 tumor cells cocultured with T cells not electroporated with circular RNAs), Nalm6 (i.e., Nalm6 tumor cells not co-cultured with T cells), Mock+NCI-H929 (i.e., NCI-H929 tumor cells cocultured with T cells not electroporated with circular RNAs), and Mock+K562.CD19 (i.e., K562.CD19 tumor cells cocultured with T cells not electroporated with circular RNAs) were used as controls. Resulting FACS imaging for each of the cell types post 24 hours after co-culturing the T cells with the target cells was calculated. From the FACS imaging, percent cell lysis was calculated (e.g., % cell lysis=(1−((% of live Target Cells in Test Sample)/(% of live Target Cells in Control Sample)))×100) and provided in FIG. 34B (FACS cytotoxicity in MMIS) and 34C (FACS cytotoxicity in Nalm6). Percent target killing for MMIS, NCI-H929, Nalm6 and K562.CD19 cocultured with the T cells along with their viabilities were provided in FIG. 36A-36D. INγ (shown in FIGS. 37A and 37B, 38A-38P), IL2, Granzyme and B, GM-CSF, IL2 and TNFα production was evaluated by a commercially available cytokine secretion kit (e.g., MSD) for cytokine secretion levels at either 24 or 48 hours post co-culture of target cell to the T cell.

TABLE γ1

| ID | Internal Ribosome Entry Site (IRES) Sequence | CAR Sequence | CAR Sequence |
|---|---|---|---|
| DNA Template K (Construct K | GTGGCCACGCCCGGGCCACCGAT ACTTCCTTCACTCCTTCGGGAC TGTTGGGGAGGAACACAACAGGG CTCCCCTGTTTTCCCATTCCTTC CCCCTTTTCCCAACCCCAACCGC CGTATCTGGTGGCGGCAAGACAC ACGGGTCTTTCCCTCTAAAGCAC AATTGTGTGTGTGTCCCAGGTCC TCCTGCGTACGGTGCGGGAGTGC TCCCACCCAACTGTTGTAAGCCT GTCCAACGCGTCGTCCTGGCAAG ACTATGACGTCGCATGTTCCGCT GCGGATGCCGACCGGGTAACCGG TTCCCCAGTGTGTGTAGTGCGAT CTTCCAGGTCCTCCTGGTTGGCG TTGTCCAGAAACTGCTTCAGGTA AGTGGGGTGTGCCCAATCCCTAC AAAGGTTGATTCTTTCACCACCT TAGGAATGCTCCGGAGGTACCCC AGCAACAGCTGGGATCTGACCGG AGGCTAATTGTCTACGGGTGGTG TTTCCTTTTTCTTTTCACACAAC TCTACTGCTGACAACTCACTGAC TATCCACTTGCTCTGTCACG (SEQ ID NO: 17) | ATGGCTCTGCCTGTGACAGCTCTGC TGCTGCCTCTGGCTCTGCTTCTGCA TGCCGCCAGACCTGACATCCAGATG ACTCAGAGCCCCAGCAGCCTGTCTG CCTCTGTGGGAGACAGAGTGACAAT TACCTGCCGGGCCAGCCAGGATGTG AATACTGCTGTCGCCTGGTATCAAC AAAAGCCTGGCAAGGCCCCTAAGCT CCTGATCTACAGCGCCAGCTTTCTG TACAGCGGCGTGCCCAGCAGATTCT CCGGAAGCAGAAGCGGCACAGATTT CACACTGACCATAAGCAGCCTGCAG CCAGAGGATTTCGCCACCTACTATT GCCAGCAGCACTACACCACACCTCC AACCTTTGGCCAGGGCACCAAGGTC GAGATTAAGAGAACAGGCAGCACAT CTGGCTCTGGCAAACCTGGATCTGG CGAGGGCTCTGAAGTCCAGCTGGTG GAATCTGGCGGAGGACTGGTTCAAC CTGGCGGCTCTCTGAGACTGTCTTG TGCCGCCTCCGGCTTCAACATCAAG GACACCTACATCCACTGGGTCCGAC AAGCCCCAGGCAAAGGACTTGAGTG GGTCGCCAGGATCTACCCCACCAAC GGCTACACCAGATACGCCGACTCTG TGAAGGGCAGATTCACCATCTCTGC CGACACCAGCAAGAATACCGCCTAC CTGCAGATGAACTCCCTGAGAGCCG AAGATACCGCTGTGTATTACTGTTC CAGATGGGGAGGCGACGGCTTCTAC GCCATGGATGTTTGGGGCCAAGGCA CCCTCGTGACCGTTTCTTCTATCGA AGTGATGTACCCTCCACCTTACCTG GACAACGAGAAGTCCAACGGCACCA TCATCCACGTGAAGGGCAAGCACCT GTGTCCTTCTCCACTGTTCCCCGGA CCTAGCAAGCCTTTCTGGGTGCTCG TTGTTGTTGGCGGCGTGCTGGCCTG TTACTCTCTGCTGGTTACCGTGGCC TTCATCATCTTTTGGGTCCGAAGCA AGCGGAGCCGGCTGCTGCACTCCGA CTACATGAACATGACCCCTAGACGG CCCGGACCAACCAGAAAGCACTACC AGCCTTACGCTCCTCCTAGAGACTT CGCCGCCTACCGGTCCAGAGTGAAG TTCAGCAGATCCGCCGATGCTCCCG CCTATCAGCAGGGCCAAAACCAGCT GTACAACGAGCTGAACCTGGGGAGA AGAGAAGAGTACGACGTGCTGGACA AGCGGAGAGGCAGAGATCCTGAAAT GGGCGGCAAGCCCAGACGGAAGAAT CCTCAAGAGGGCCTGTATAATGAGC TGCAGAAAGACAAGATGGCCGAGGC CTACAGCGAGATCGGAATGAAGGGC GAGCGCAGAAGAGGCAAGGGACACG ATGGACTGTACCAGGGCCTGAGCAC CGCCACCAAGGATACCTATGATGCC CTGCACATGCAGGCCCTGCCTCCAA GA (SEQ ID NO: 101) | MALPVTALLL PLALLLHAAR PDIQMTQSPS SLSASVGDRV TITCRASQDV NTAVAWYQQK PGKAPKLLIY SASFLYSGVP SRFSGSRSGT DFTLTISSLQ PEDFATYYCQ QHYTTPPTFG QGTKVEIKRT GSTSGSGKPG SGEGSEVQLV ESGGGLVQPG GSLRLSCAAS GFNIKDTYIH WVRQAPGKGL EWVARIYPTN GYTRYADSVK GRFTISADTS KNTAYLQMNS LRAEDTAVYY CSRWGGDGFY AMDVWGQGTL VTVSSIEVMY PPPYLDNEKS NGTIIHVKGK HLCPSPLFPG PSKPFWVLVV VGGVLACYSL LVTVAFIIFW VRSKRSRLLH SDYMNMTPRR PGPTRKHYQP YAPPRDFAAY RSRVKFSRSA DAPAYQQGQN QLYNELNLGR REEYDVLDKR RGRDPEMGGK PRRKNPQEGL YNELQKDKMA EAYSEIGMKG ERRRGKGHDG LYQGLSTATK DTYDALHMQA LPPR (SEQ ID NO: 117) |

Figure 61A:
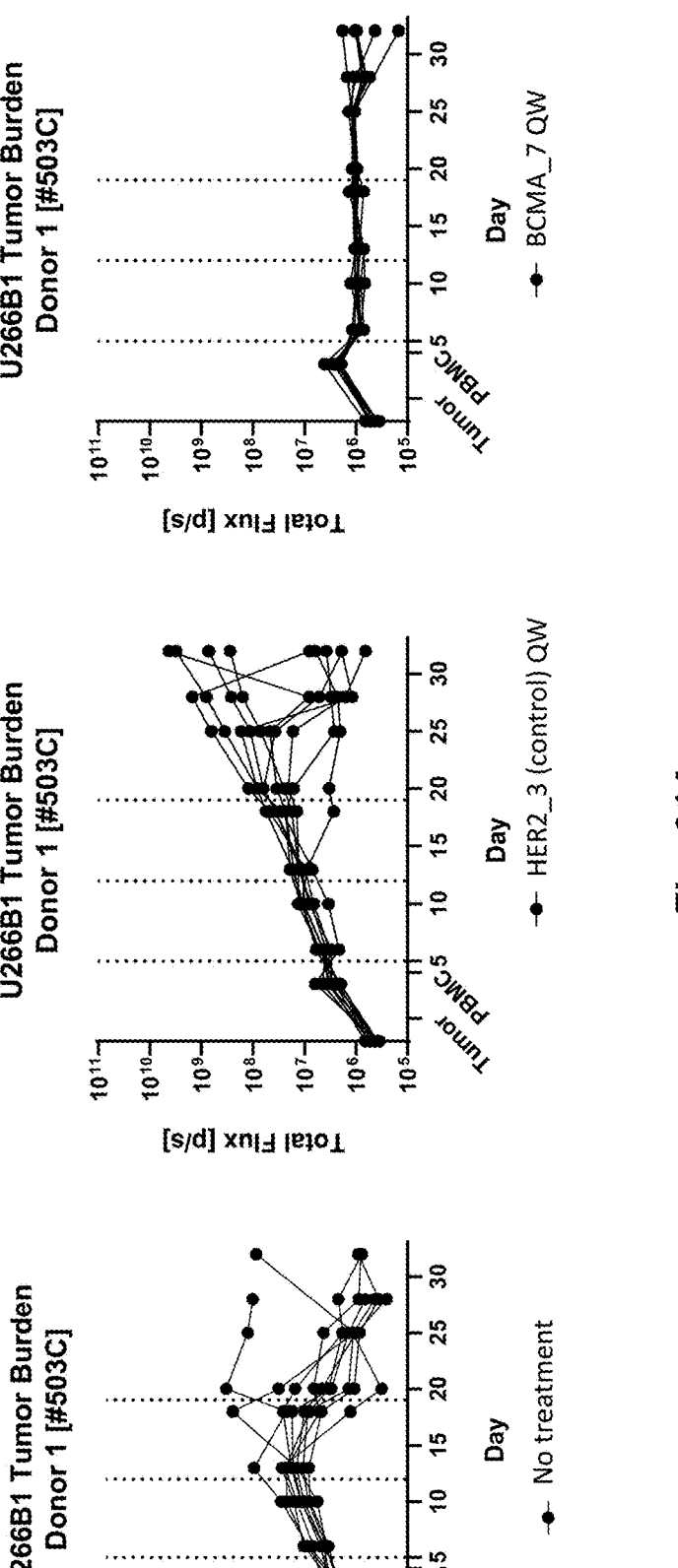
FIGS. 61A and B show tumor control in vivo by circular RNA encoding BCMA CAR (BCMA oCAR, BCMA_7) when dosed once weekly (QW) in multiple donors as compared to HER2 and no-treatment controls.
Figure 61B:
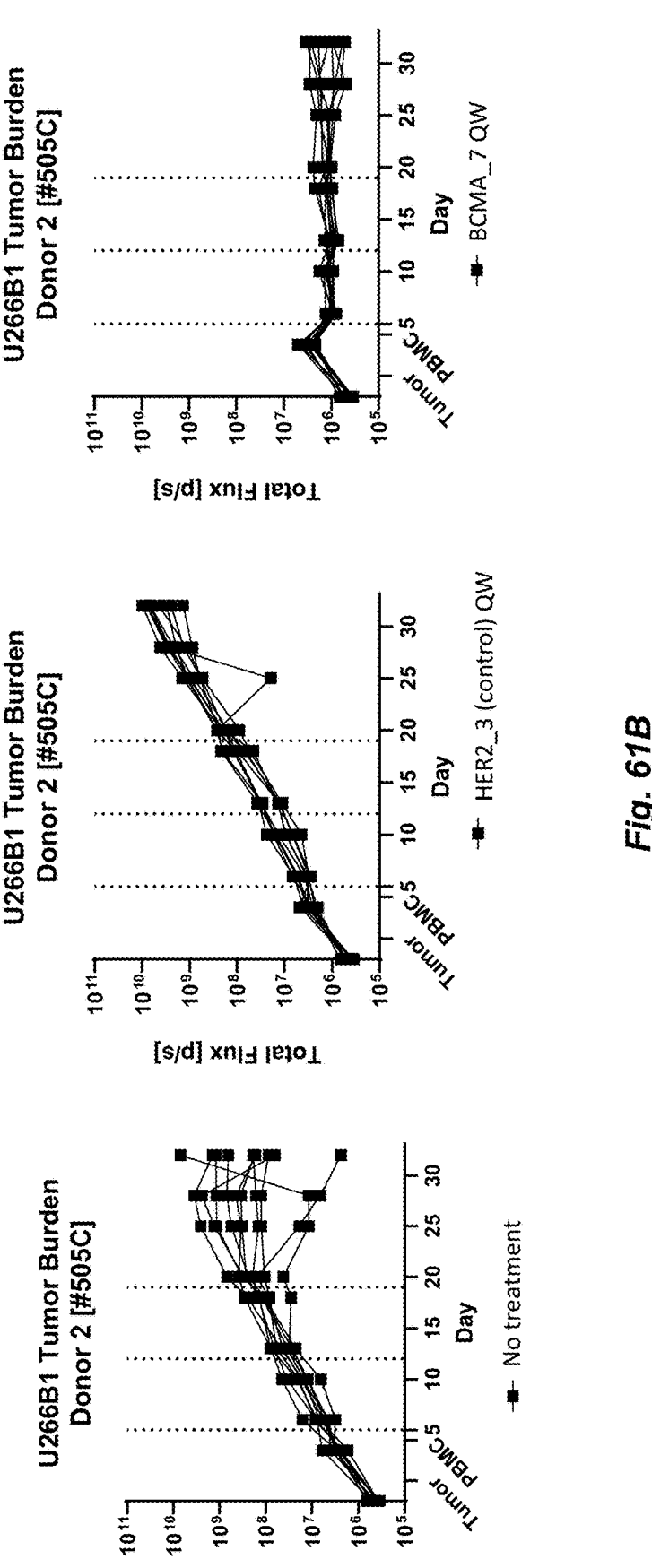
Figure 62:
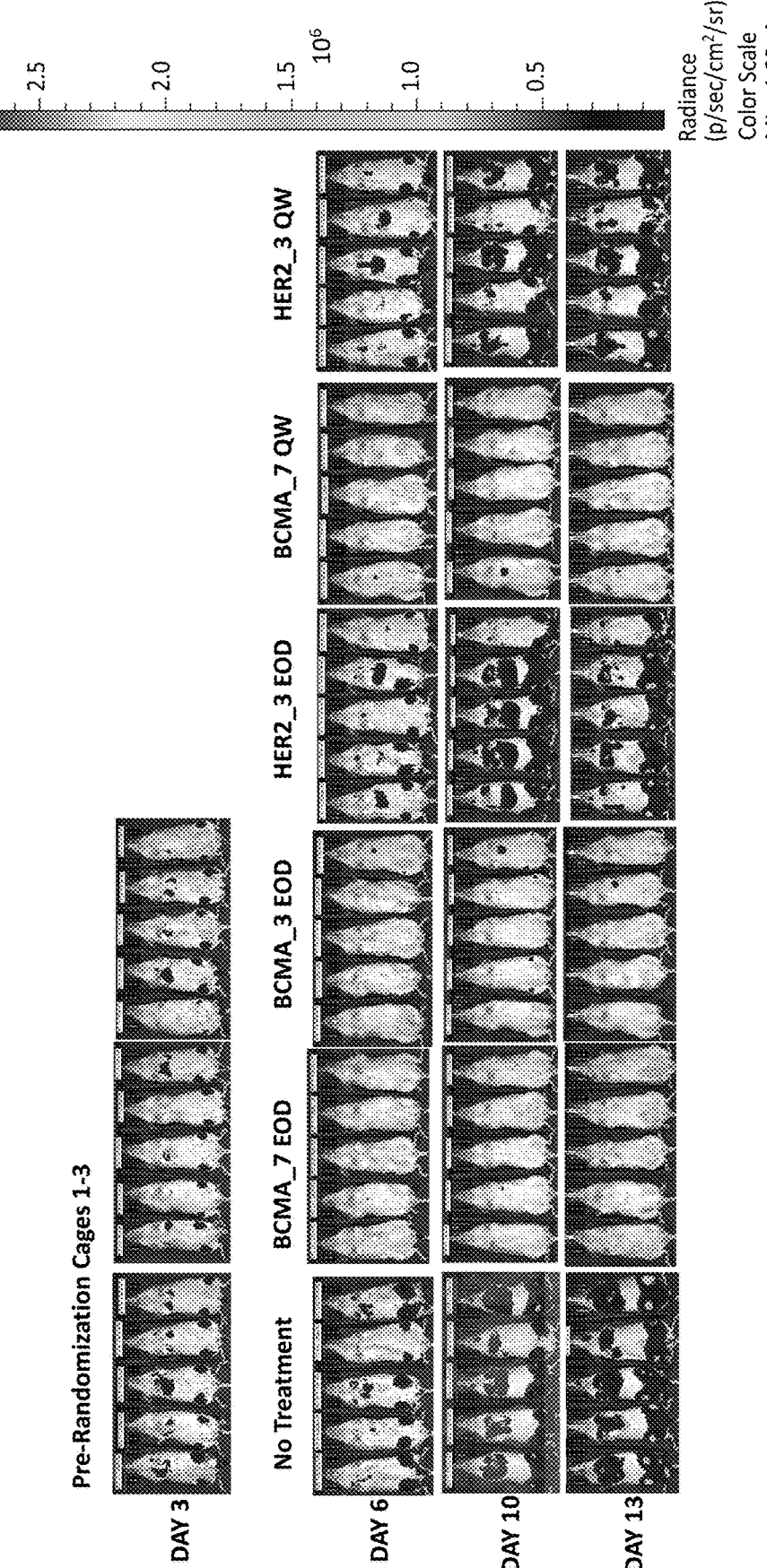
FIG. 62 shows tumor control in vivo by circular RNA encoding BCMA CAR (BCMA oCAR, BCMA_7 and BCMA_3) in exemplary IVIS images when dosed every other day (EOD) and once weekly (QW) as compared to HER2 and no-treatment controls.

The circular RNA constructs encoding BCMA CAR were tested in vivo. NSG mice were prepared at Day −1. 5M U266 cells were injected at Day 0. 10M PBMC cells (n=2 donors) were injected at Day 4. The circular RNA constructs were injected either at EOD (2 mpk), i.e., Day 8, Day 10, Day 13, and Day 15, or QW (2 mpk), i.e., Day 8, Day 15, and Day 22. Controls were HER2 oCAR-treated mice and untreated mice. Twice weekly, tumor burden was quantified via IVIS as described herein. EOD dosing demonstrated BCMA oCAR-dependent tumor control (FIG. 60). QW dosing demonstrated BCMA oCAR-dependent tumor control (FIG. 61). Exemplary IVIS images show tumor control by BCMA oCAR as compared to control (FIG. 62).

Figure 39:
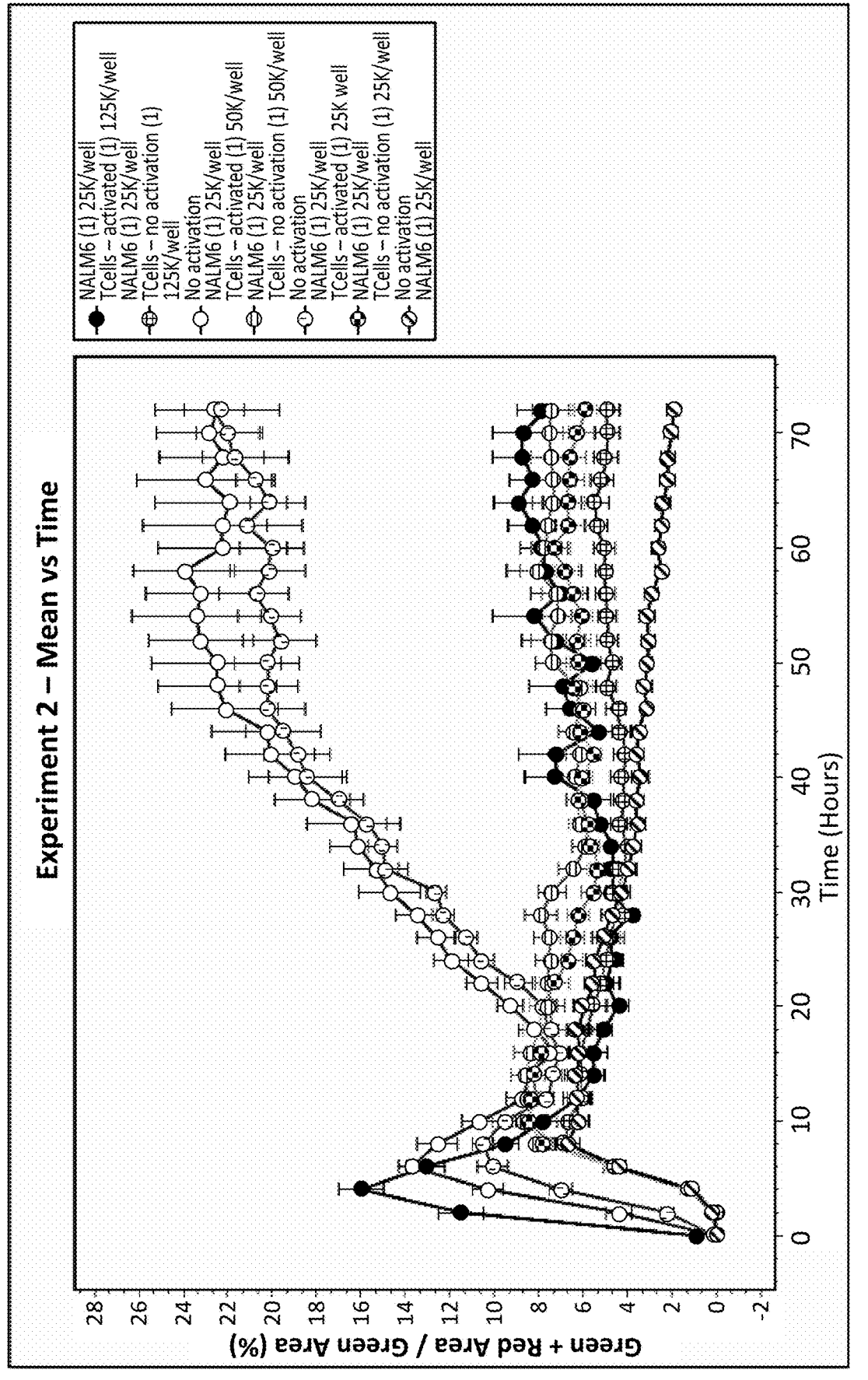
FIG. 39 depicts percent apoptosis of target cell (e.g., Nalm6) collected from live-cell analysis portfolio system (e.g., an IncuCyte) (e.g., % apoptotic target cells=(green area+red area)/green area) over the span of 72 hours post introduction of circular RNAs encoding HER2 CAR. Green areas indicate target cells. Red areas indicate Annexin V reagent present in the apoptotic cells. For control, Nalm6 comprising no circular RNAs was used.

Example 16: Circular RNAs Encoding HER2 CARs Induction of Cytotoxicity In Vitro Plates were coated with 0.01% poly-L-omithine solution or 5 µL/mL fibronectin diluted in 0.1% BSA. The dilute apoptosis reagent (e.g., Annexin V) was prepared in a medium and cell treatments are prepared. Cell treatments comprised of circular RNAs comprising a 3' exon segment, a Caprine Kobuvirus or a Hunnivirus internal ribosome entry site (IRES), a coding region encoding HER2, and a 5' exon segment with an E:T ratio of 1:1 or 1:2. Circular RNAs were derived from DNA Templates from Table Y1 or Table & that underwent IVT reactions 100 µL/well of 25,000-50,000 of HER2 positive BT474 or SKBR2 target cells were placed into the coated 96-well plates and allowed to adhere overnight. After about 24 hours, the BT474/SKBR3 cells were adhered and the cell treatment at 0 and 100 ng dosages containing the circular RNAs and Annexin V were added to the BT474 or SKBR2 cells. As a control, some BT474/ SKBR3 cells were not given any circular RNAs but were given Annexin V. All the plates containing the target cells were analyzed in a live-cell analysis portfolio system (e.g., an IncuCyte) which captured images every 2-3 hours. In the imaging alive Nalm6 cells retained a green fluorescence, and Annexin V apoptotic cells had a red luminescence. % apoptotic cells were then calculated by measuring the amount of ((green area+red area)/green area). Resulting % apoptotic cells was shown in FIG. 39.

Figure 40A:
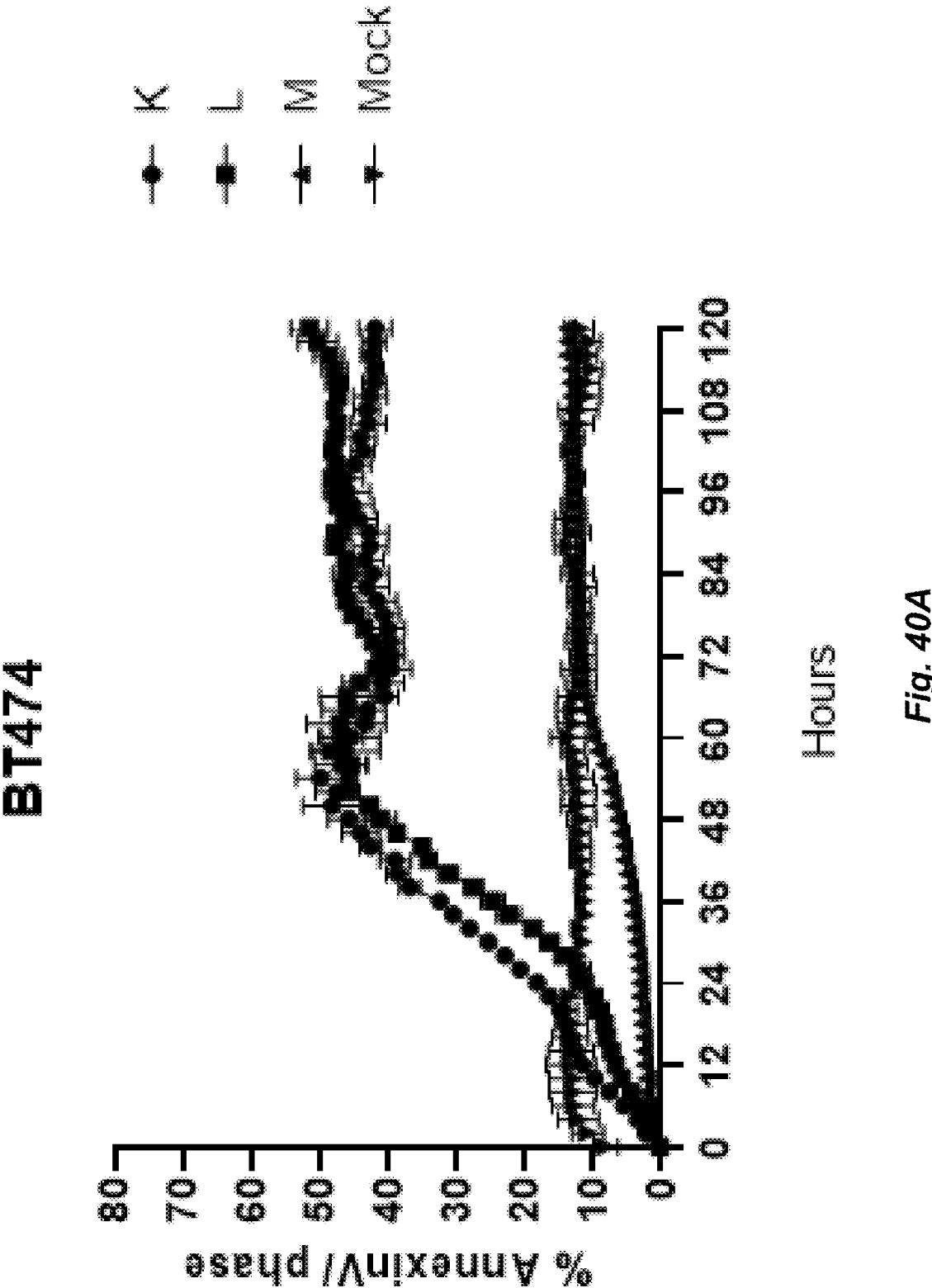
FIGS. 40A-40C depicts % Annexin V/phase post introduction of circular RNAs encoding HER2.28ζ, HER2. BBC or CD19.28ζ CAR to activated PBMC T cells and cocultured in BT474 (FIG. 40A), SKBR3 (FIG. 40B), and JIMT1 (FIG. 40C) HER2 positive cell. For comparison purposes, activated PBMC T cells lacking any circular RNAs were used (indicated as "Mock"). "% Annexin V/phase" as referenced in FIGS. 40A-40C pertains to percent of apoptotic cells per phase. "K", "L", and "M" correspond to "DNA Template K", "DNA Template L", and "DNA Template M" that were used to form the circular RNAs.
Figure 40B:
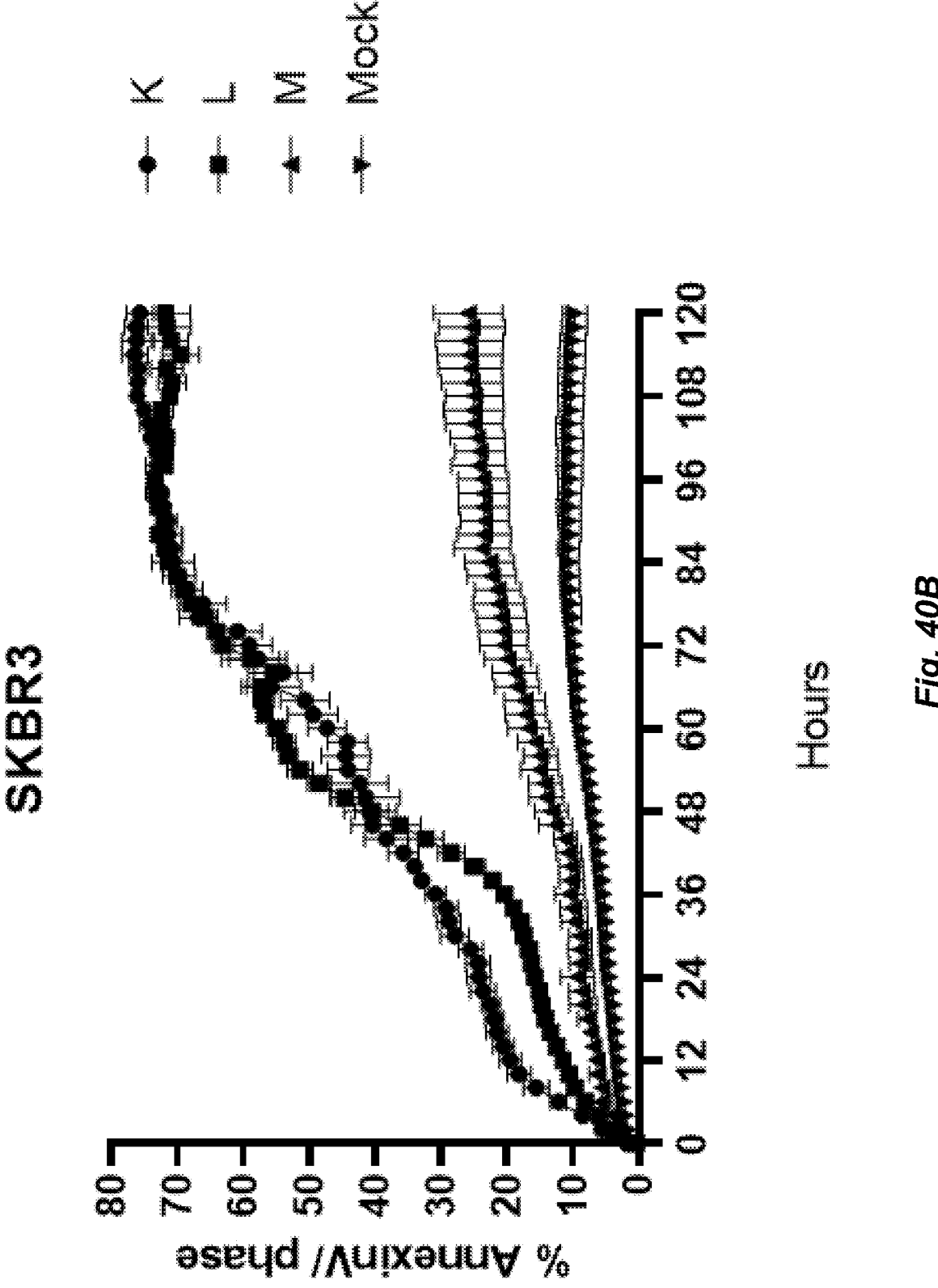
Figure 40C:
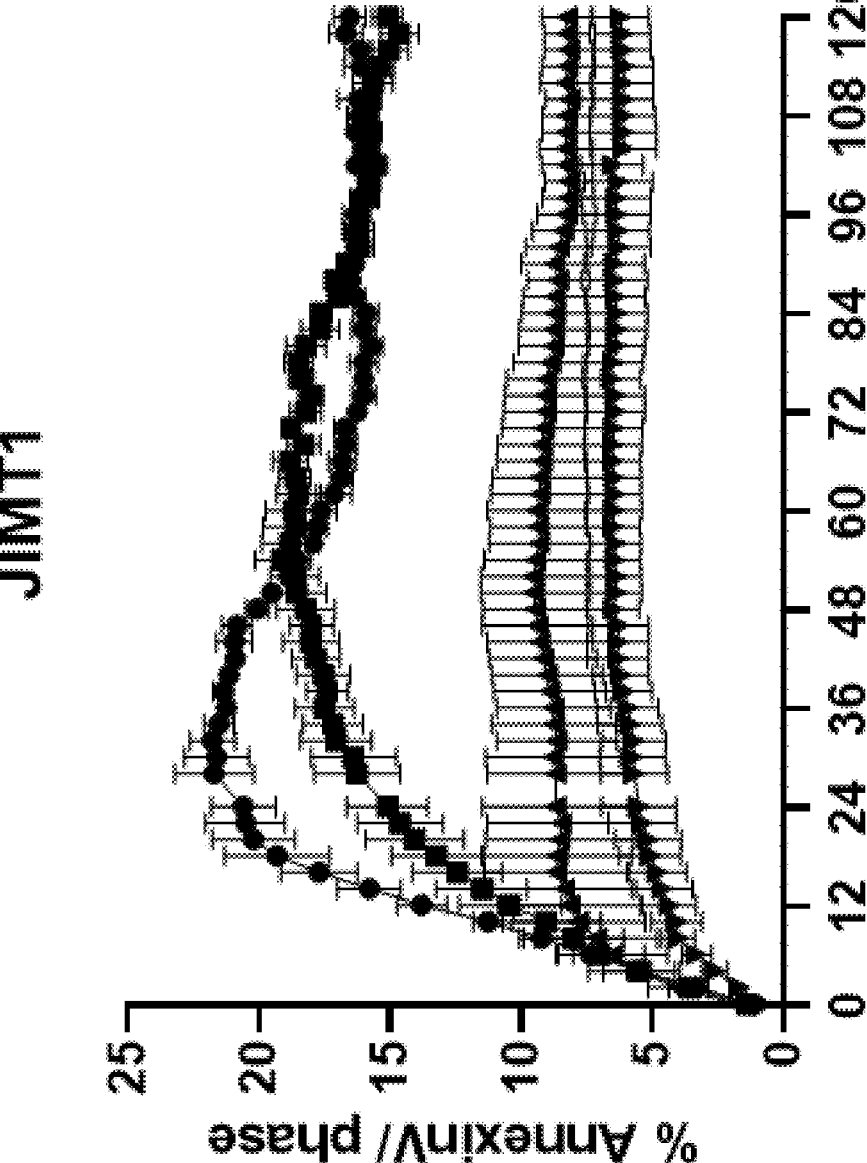
Figure 41A:
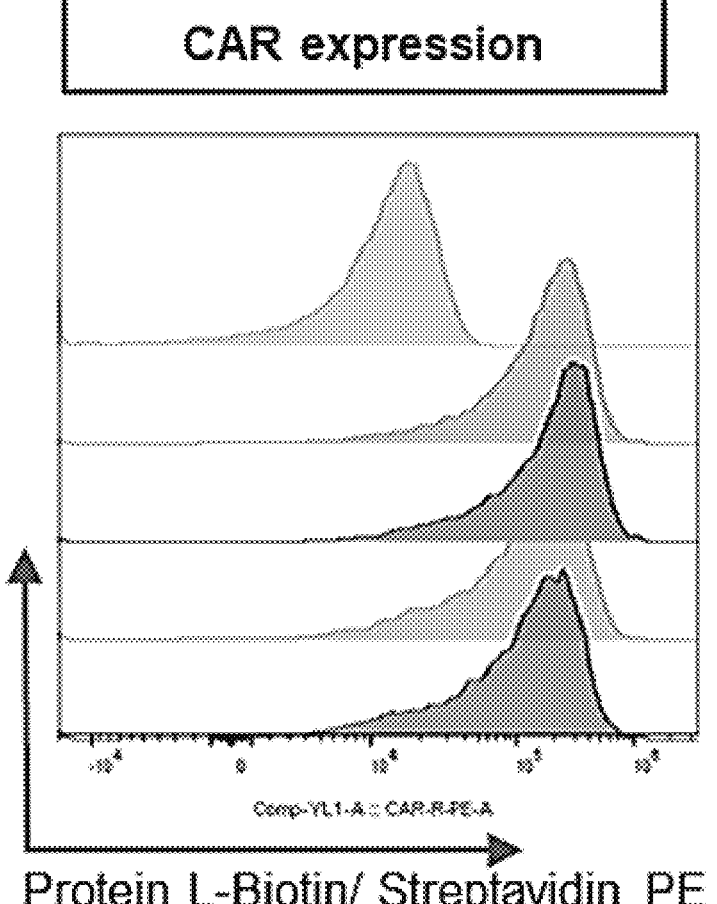
FIG. 41A depicts frozen and fresh LNP delivered CAR expression of three different circular RNA constructs encoding HER2 CAR. "Mock" cells were T cells given empty LNPs (without circular RNAs).
Figure 41B:
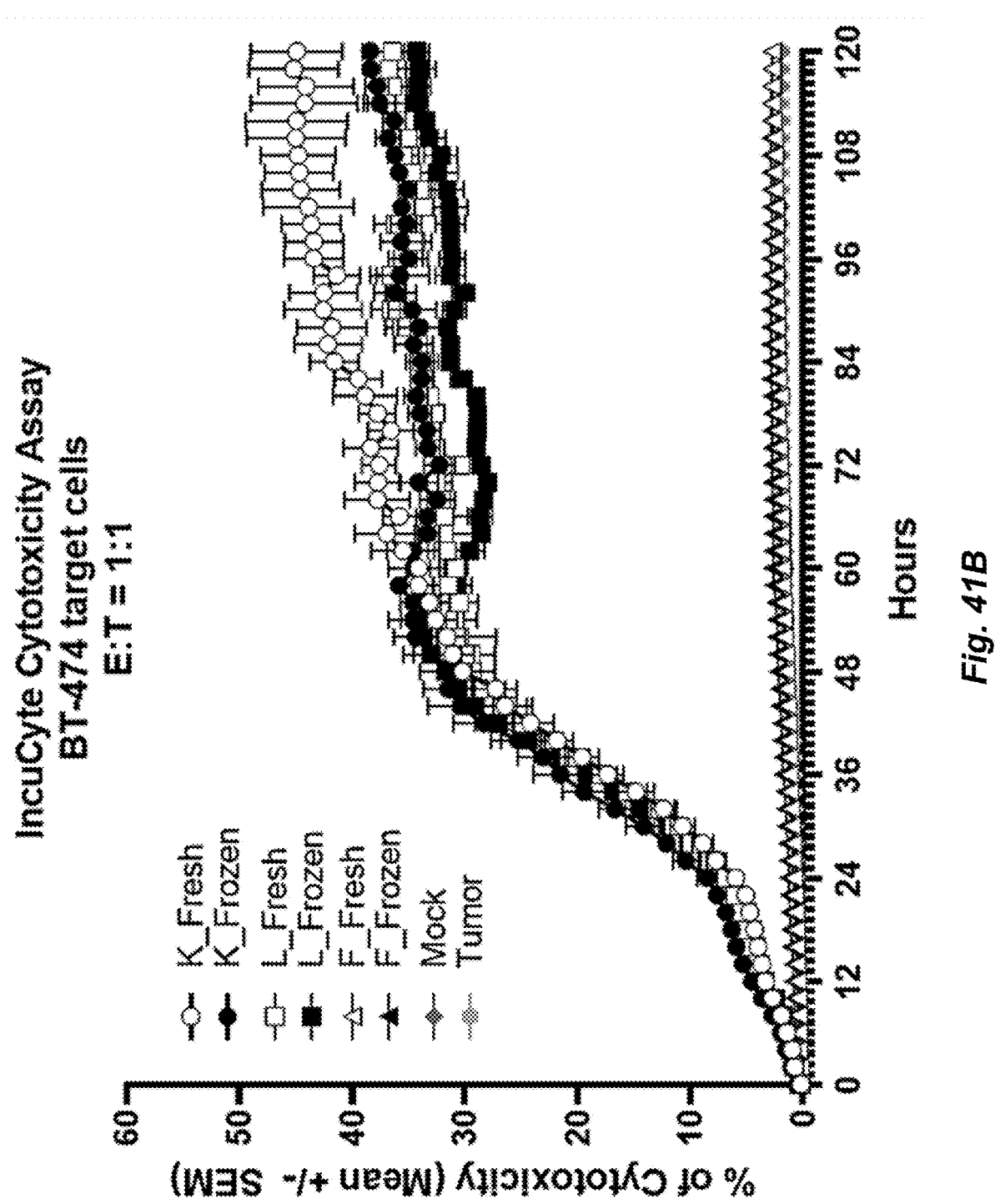
FIG. 41B provides % cytotoxicity collected from live-cell analysis portfolio system (e.g., an IncuCyte) analysis of T cells comprising circular RNA constructs encoding HER2-28ζ, HER2-BBζ or CD19-28ζ CAR cocultured with BT-474 target cells at a 1:1 ET ratio, wherein the circular RNAs were delivered with either a fresh or frozen LNP. The fresh and frozen LNPs comprised an ionizable lipid from Table 3.
Figure 41C:
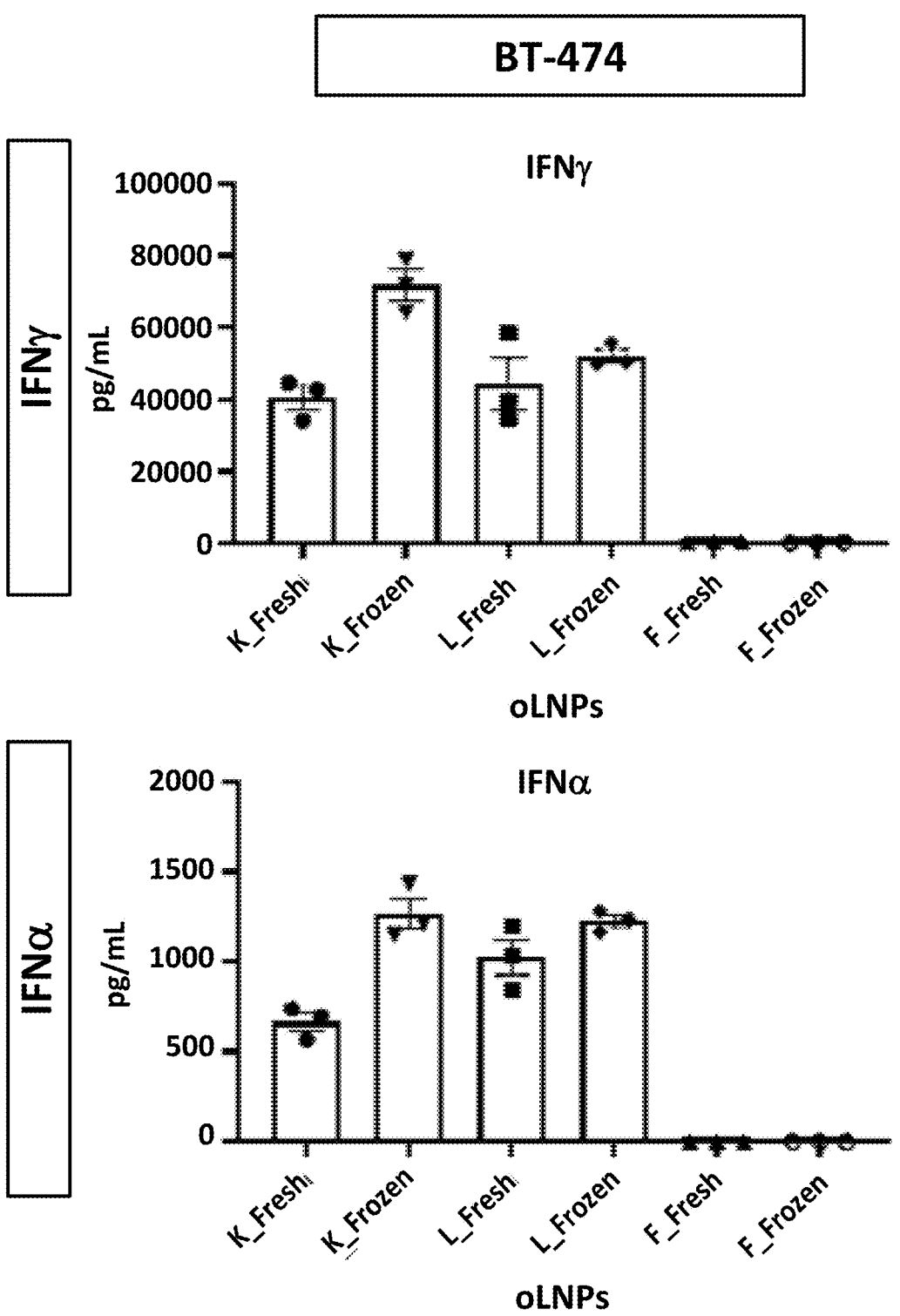
FIG. 41C provides the cytokine release (top graph of FIG. 41C: INFγ and bottom graph of FIG. 41C: TNFα) produced by the T cells cocultured in the BT-474 for each of the circular RNA constructs. "K", "L", and "F" correspond to "DNA Template K", "DNA Template L", and "DNA Template F" that were used to form the circular RNAs. "Fresh" indicates that the LNP was not previously frozen. "Frozen" indicates that the LNP was previously frozen.
Figure 42A:
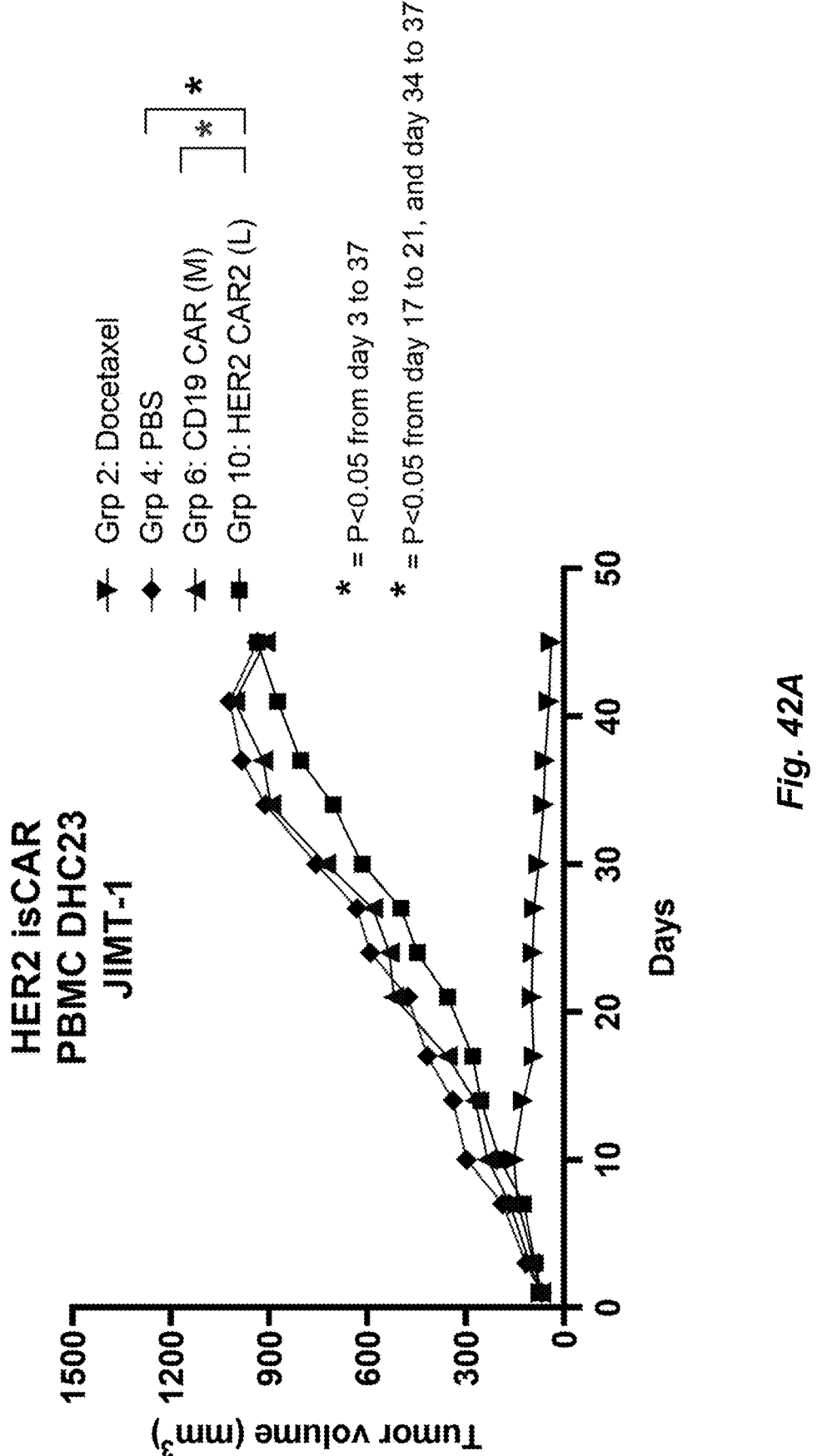
FIGS. 42A-42L depict anti-HER2 expression of circular RNAs encoding HER2.286, HER2.BBC or CD19.28ζ CAR injected intravenously and delivered using lipid nanoparticles into JIMT-1 (FIGS. 42A-42L) and BT-474 (FIGS. 42G-42L) mouse models.
Figure 42B:
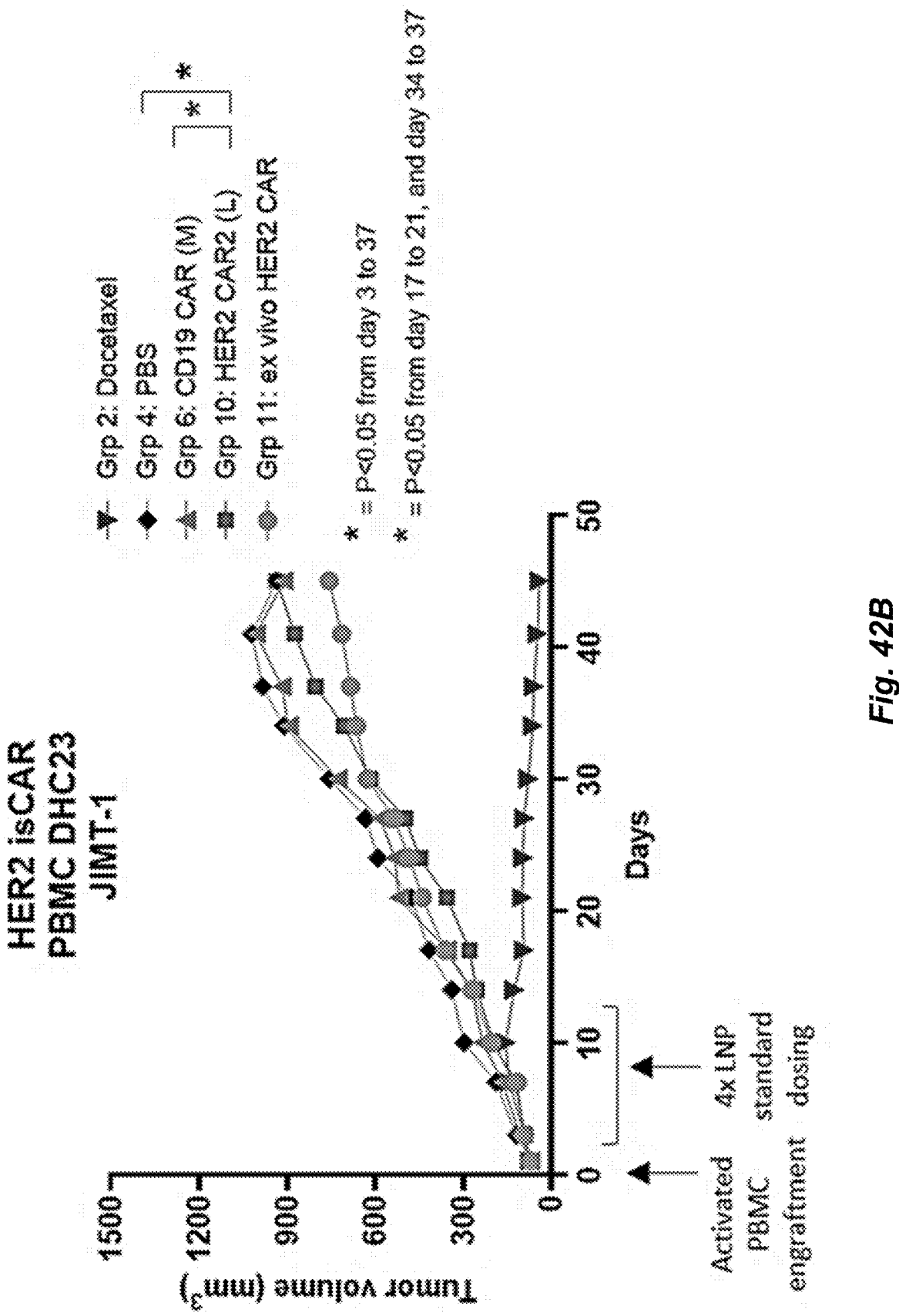
Figure 42C:
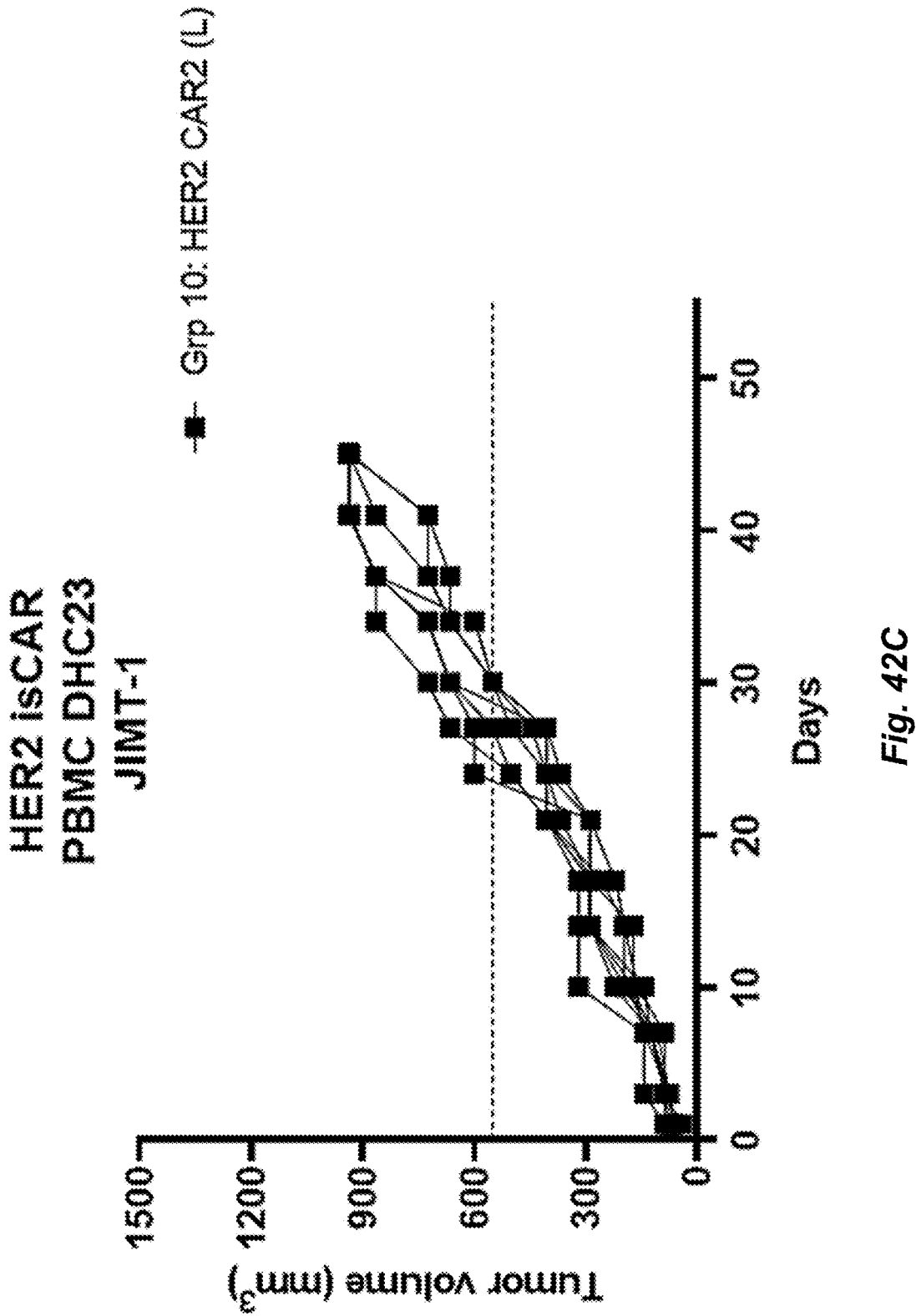
Figure 42D:
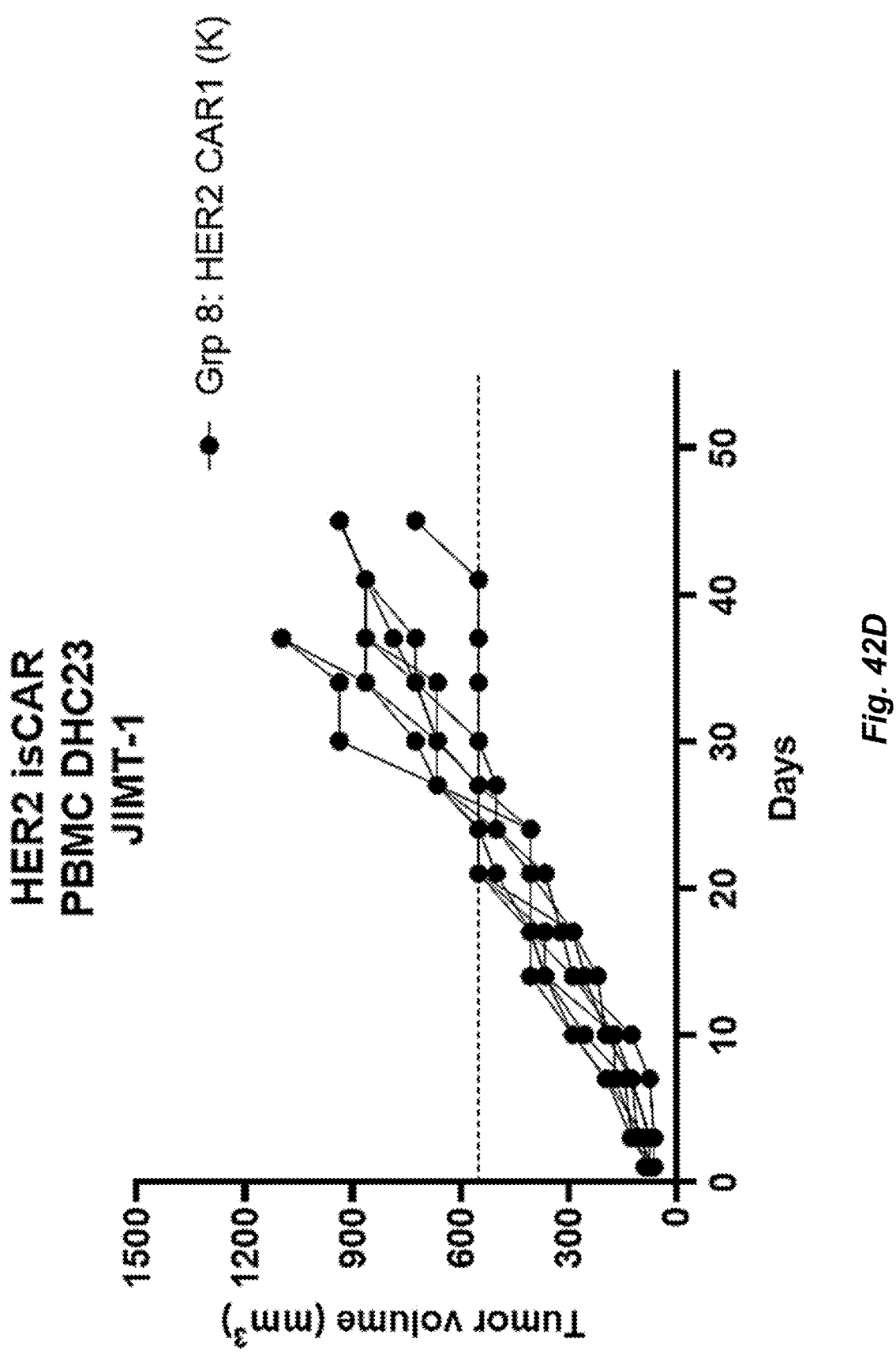
Figure 42E:
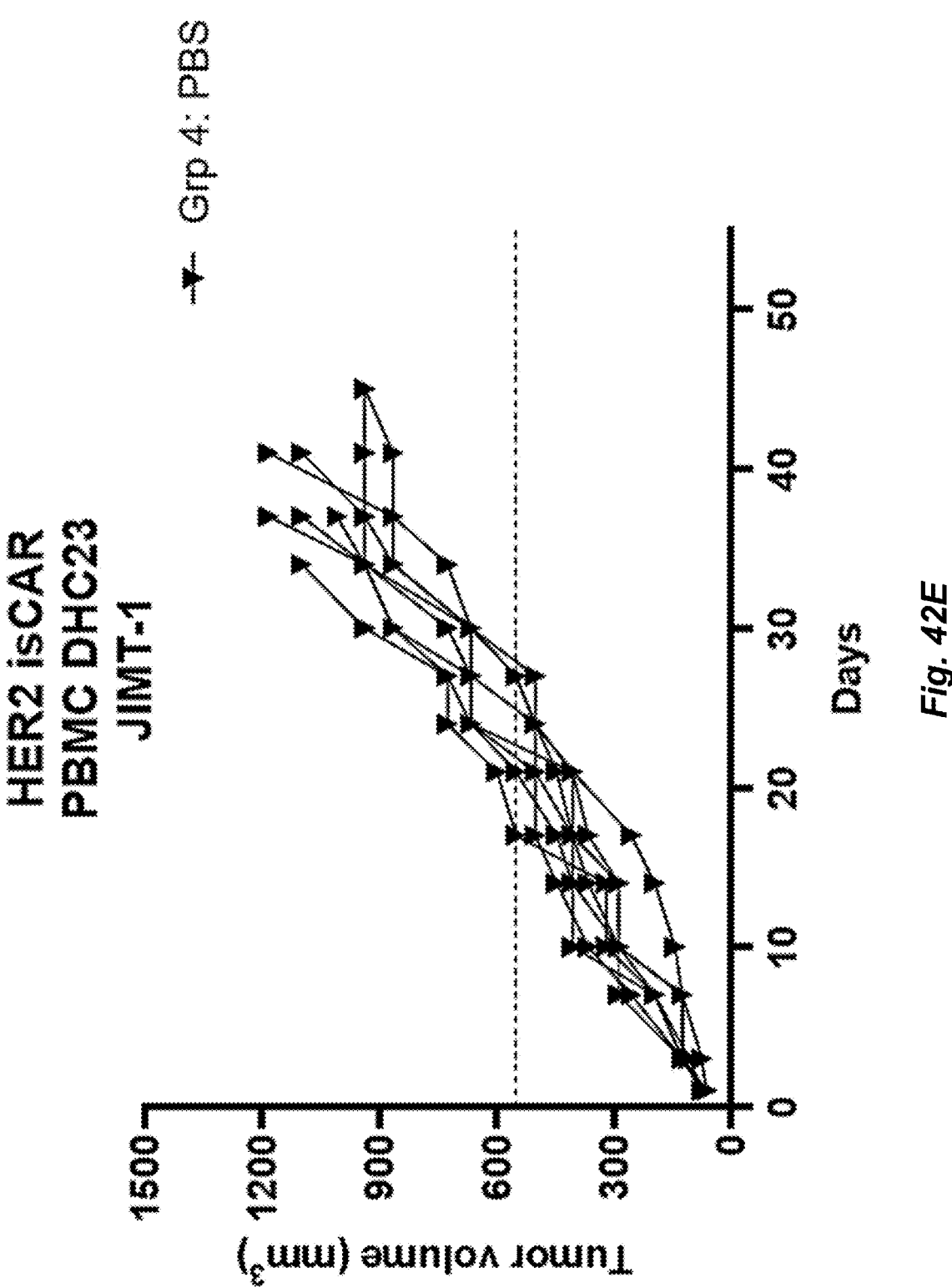
Figure 42F:
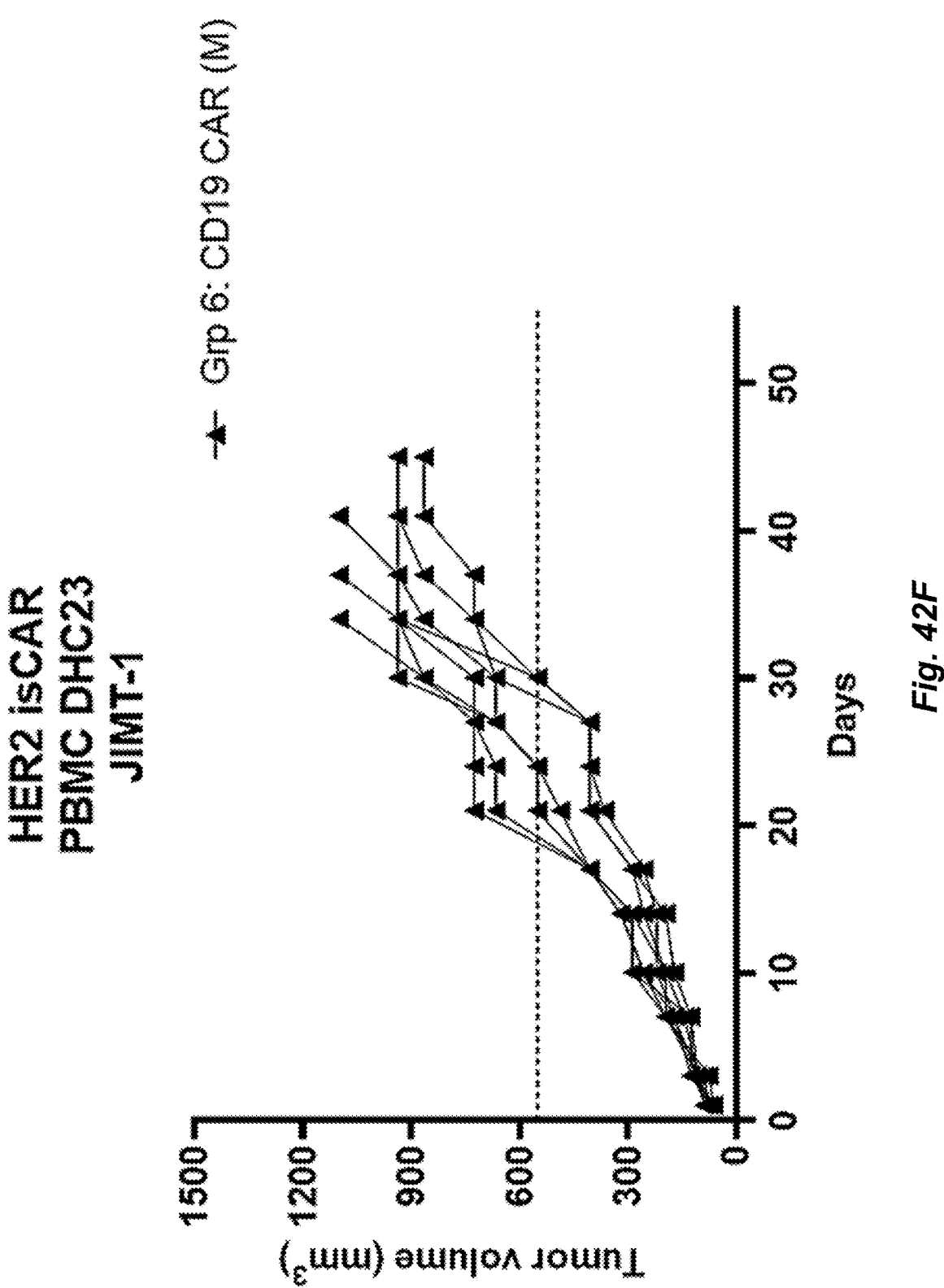
Figure 42G:
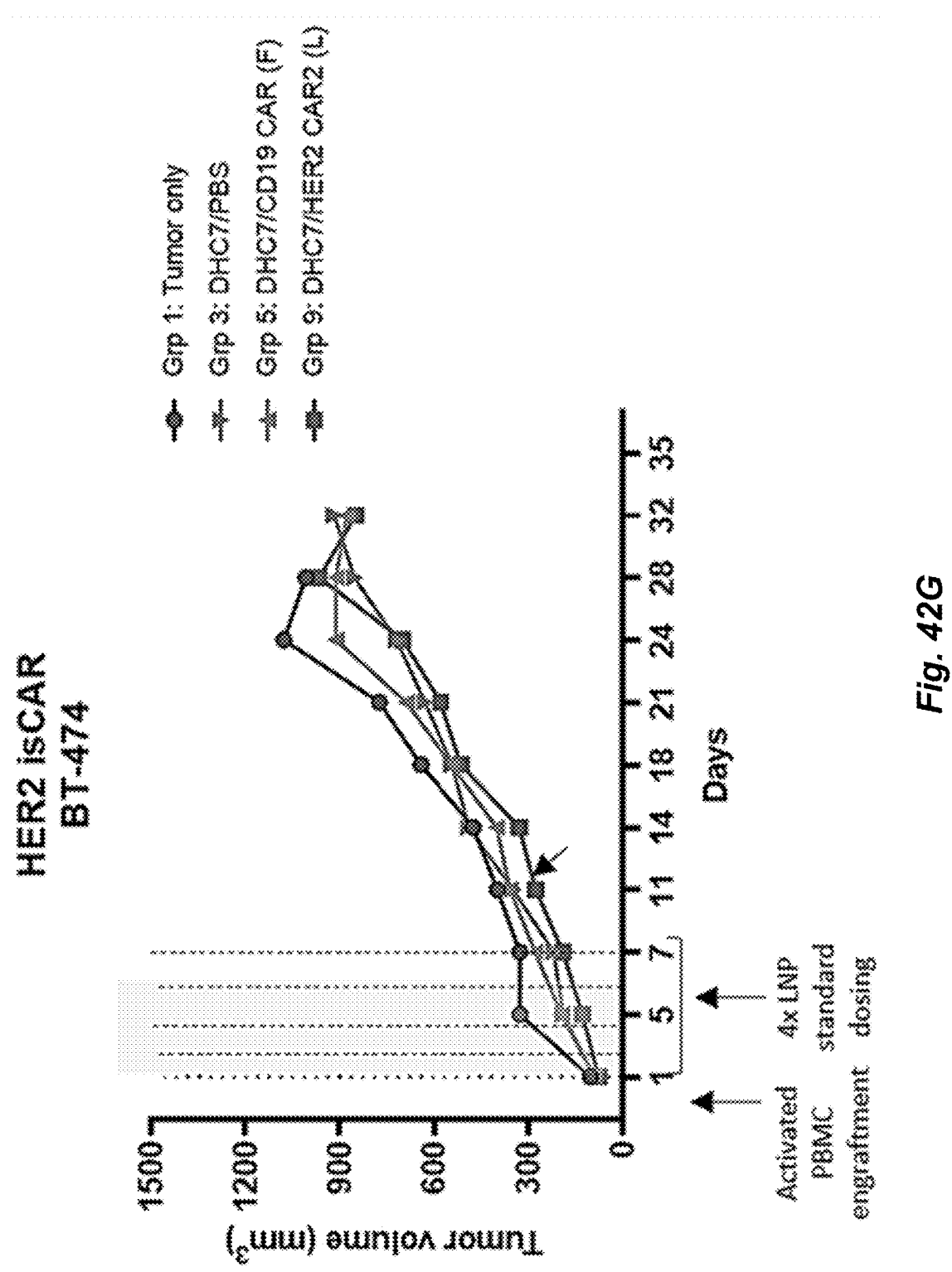
Figure 42H:
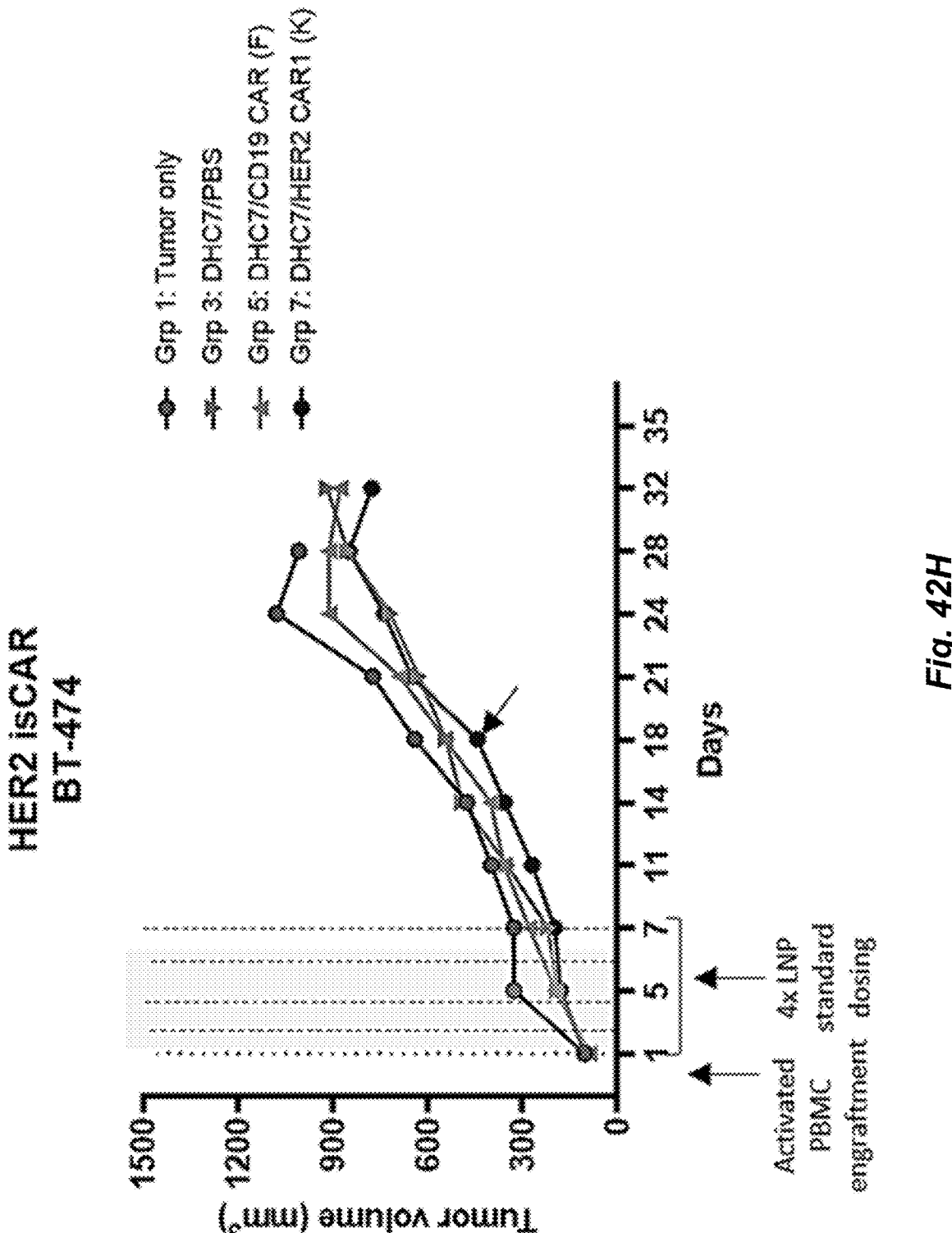
Figure 42I:
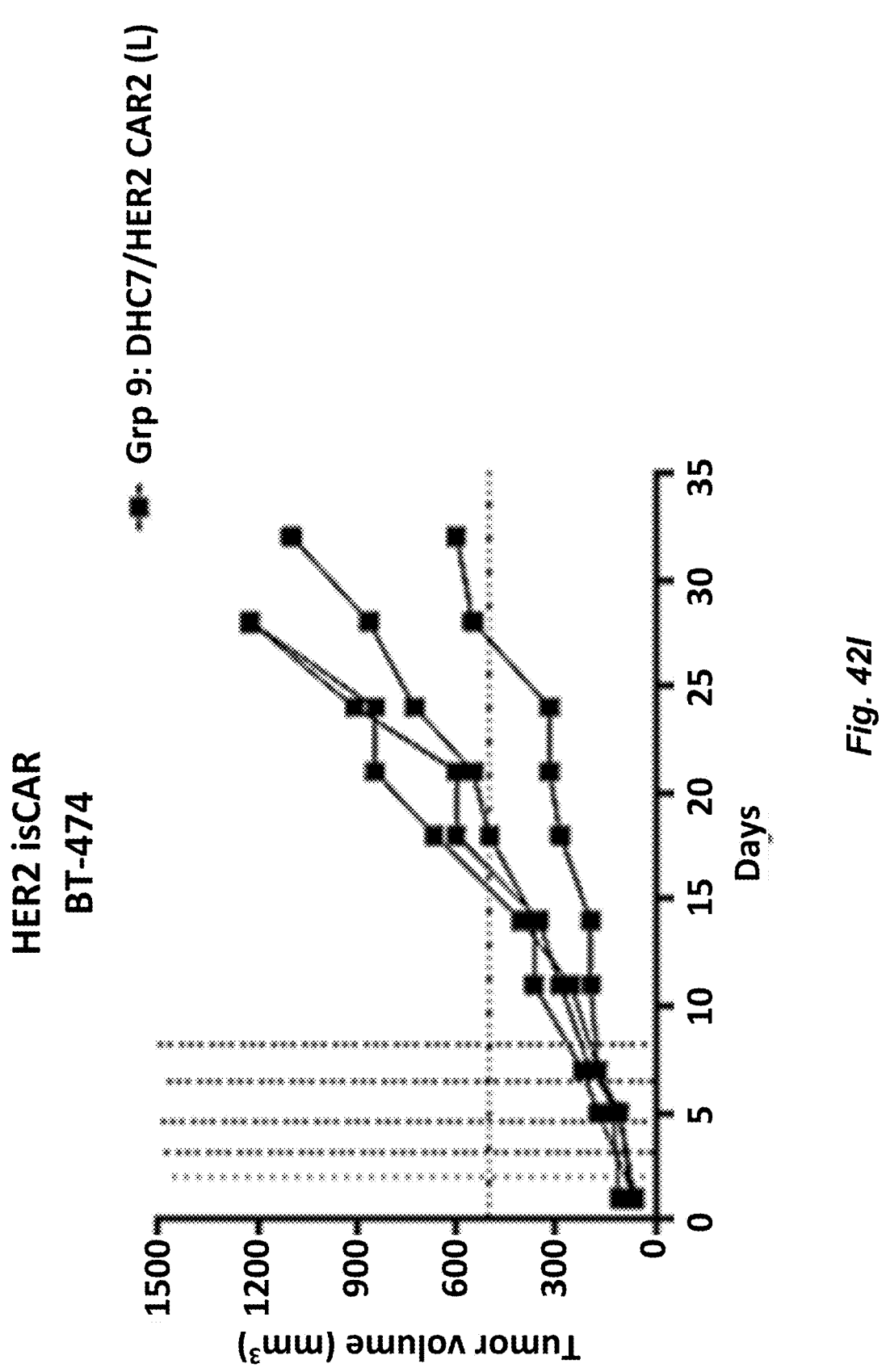
Figure 42J:
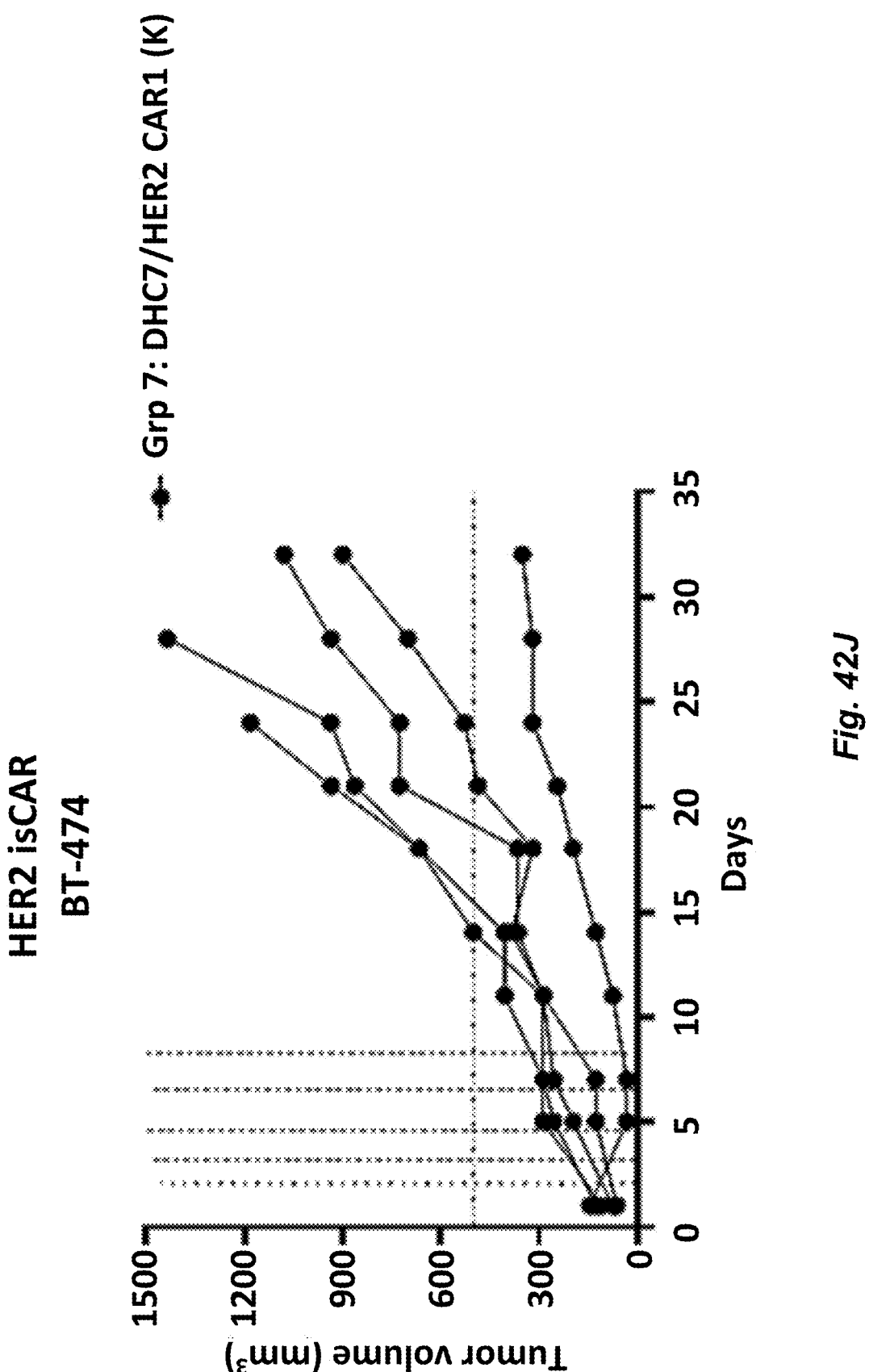
Figure 42K:
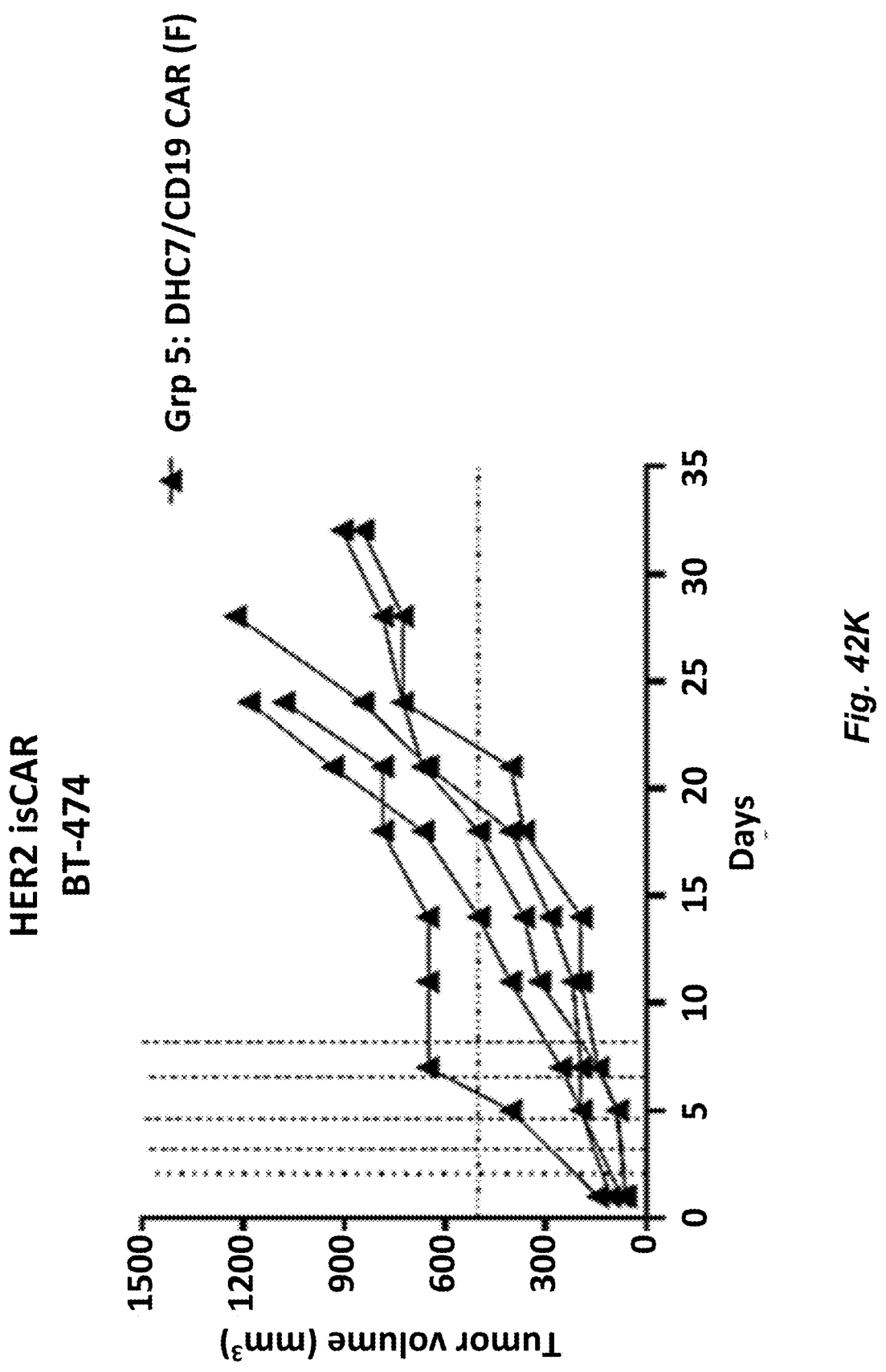
Figure 42L:
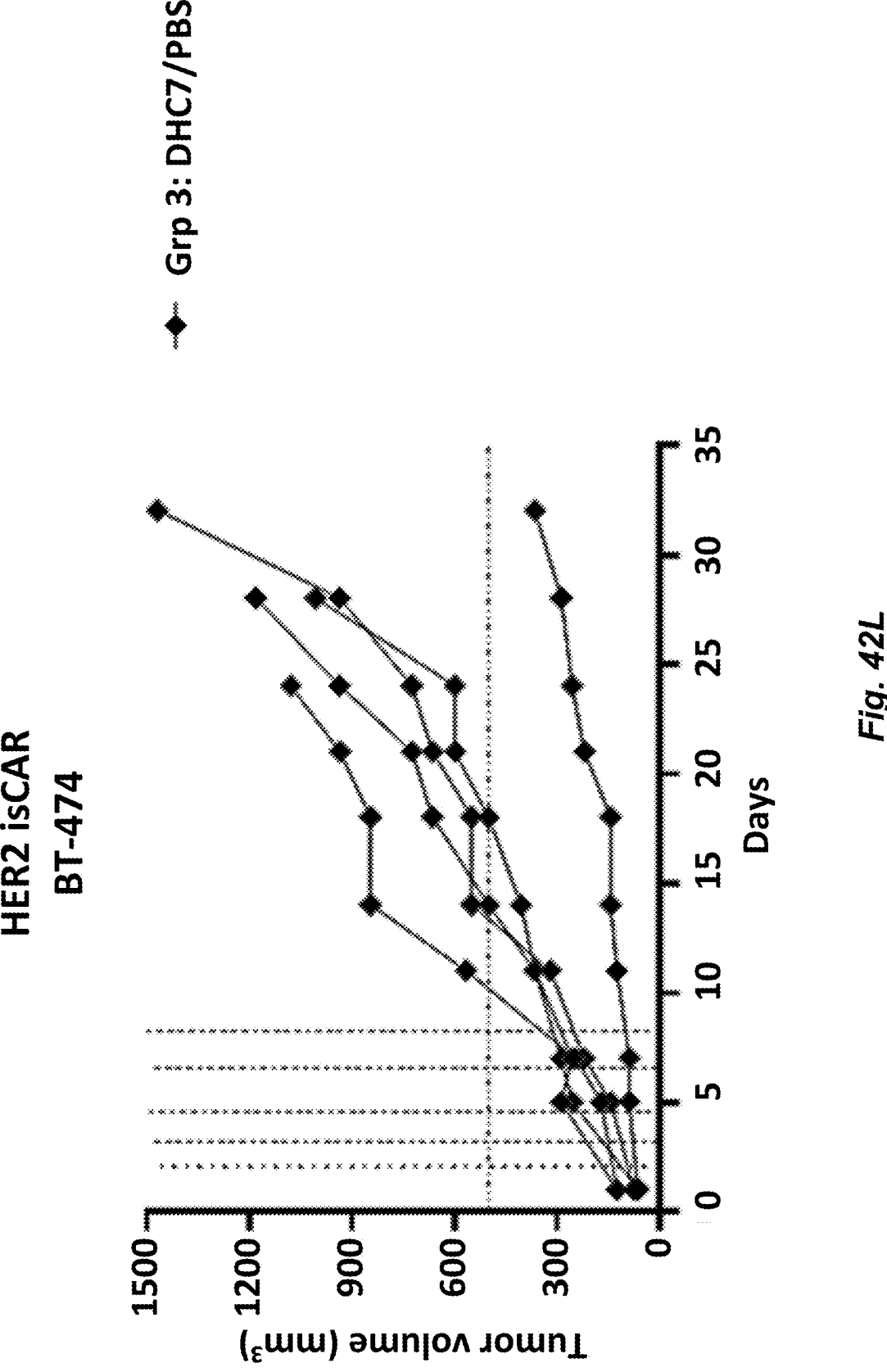
Figure 43A:
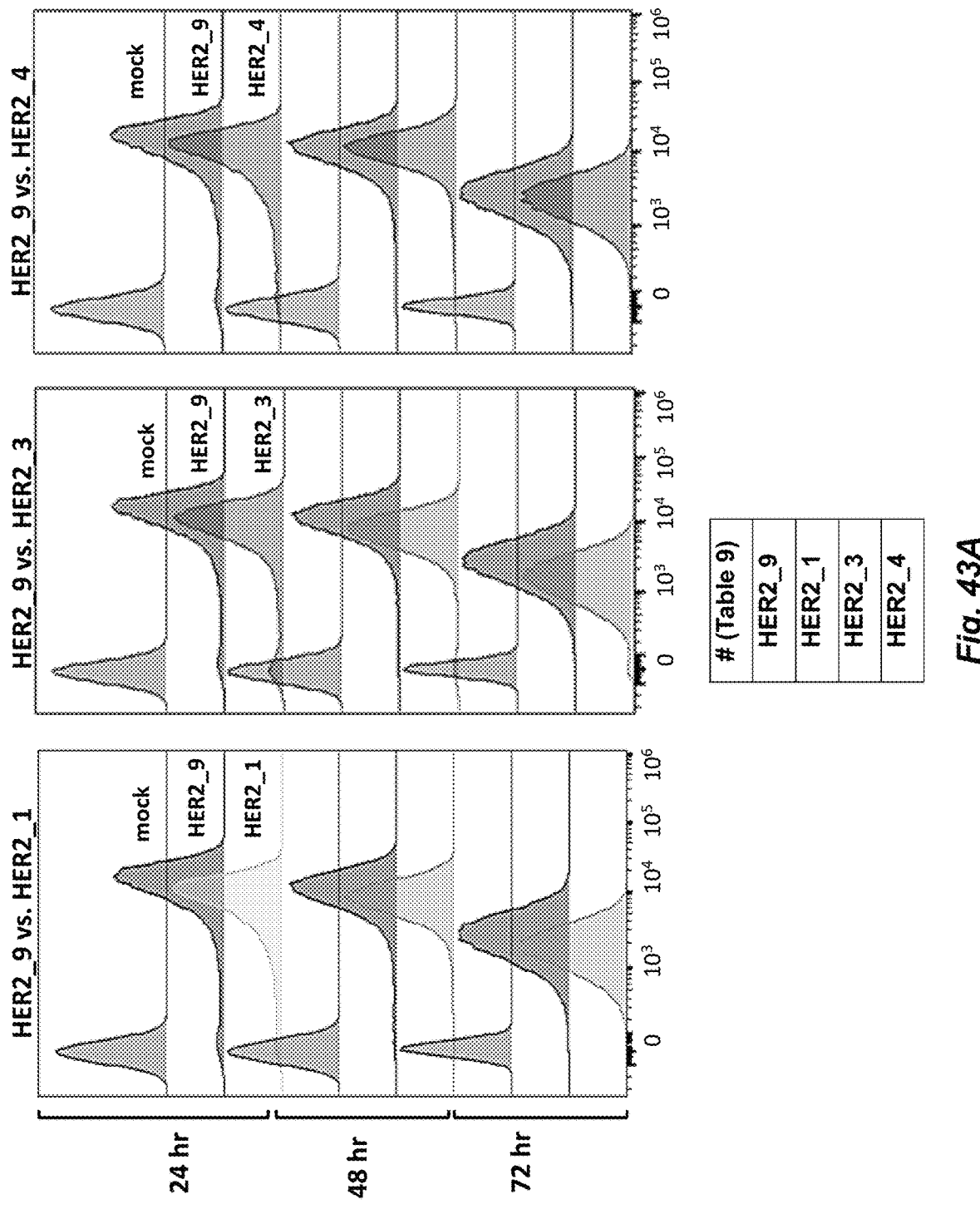
Figure 44A:
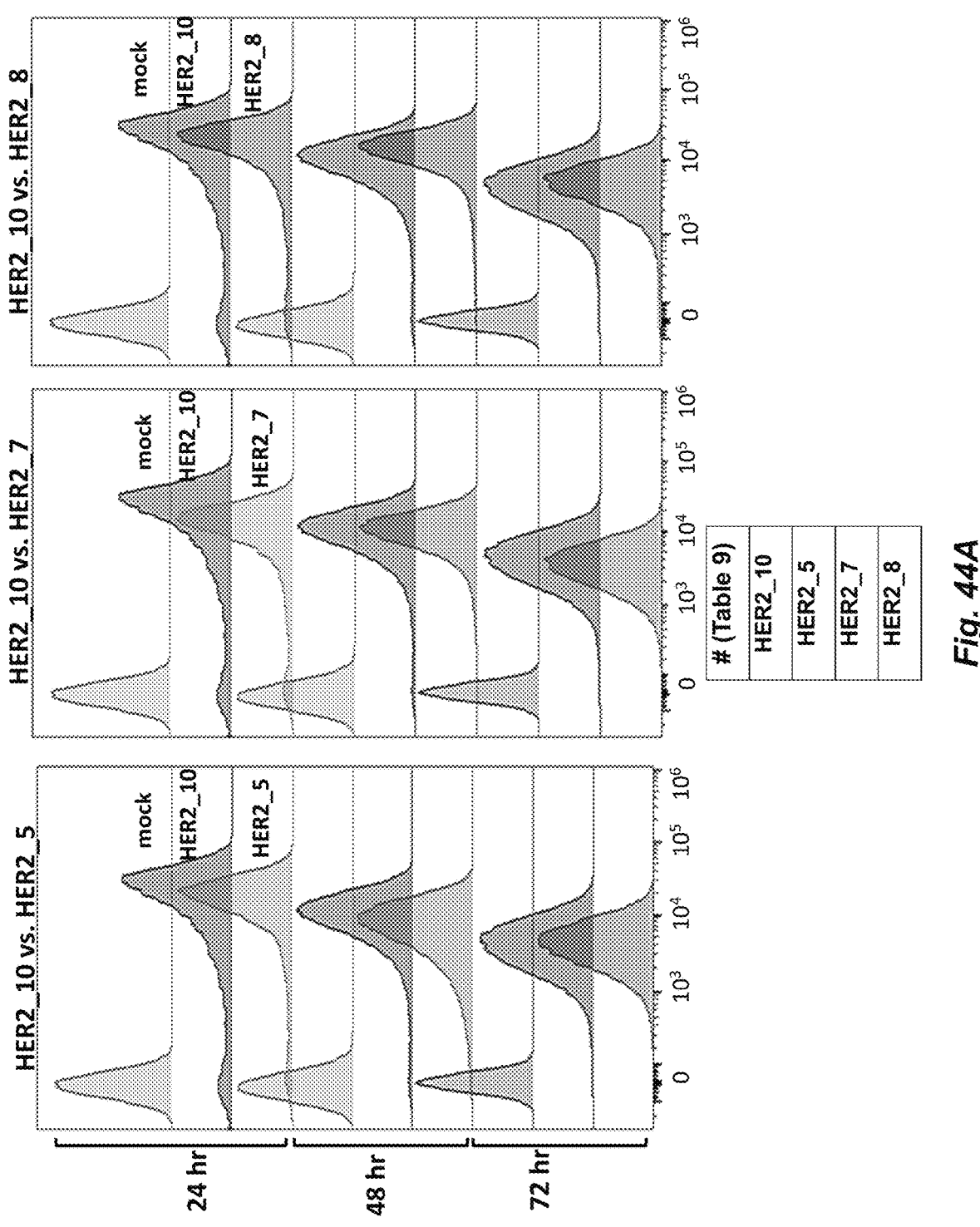
FIGS. 44A-D show CAR expression after electroporation in circular RNA constructs comprising an IRES sequence, an anti-HER2 CAR, and a BBz domain (HER2_10, HER2_5, HER2_7, HER2_8, described herein in Table 9).
Figures 44B, 44C, 44D:
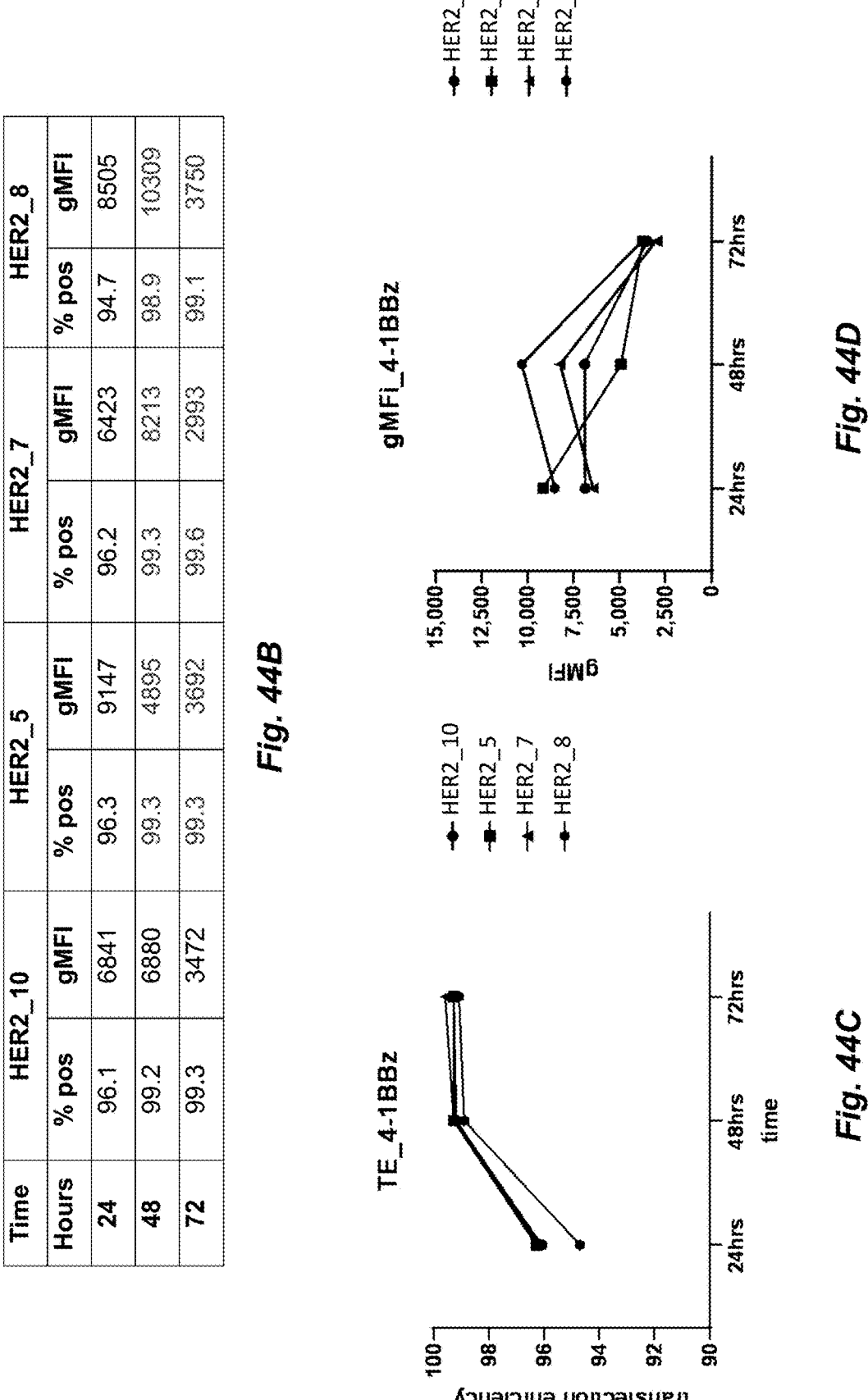
Figure 45A:
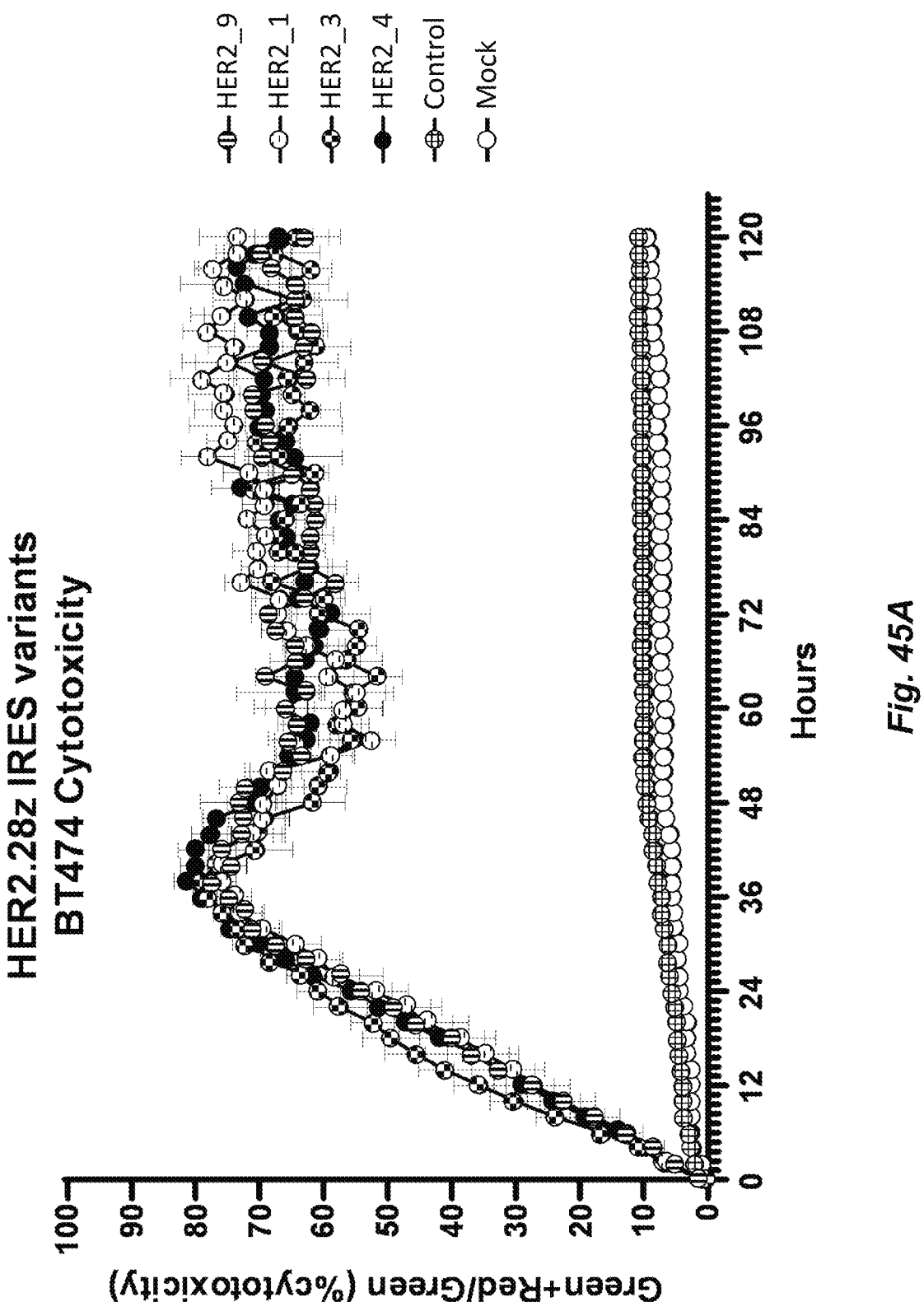
FIGS. 45A and 45B show performance of circular RNA constructs comprising an IRES sequence, an anti-HER2 CAR, and a 28z or BBz domain (HER2_10, HER2_5, HER2_7, HER2_8), as compared to control (3273 (base) and mock), in BT474 target cells.
Figure 45B:
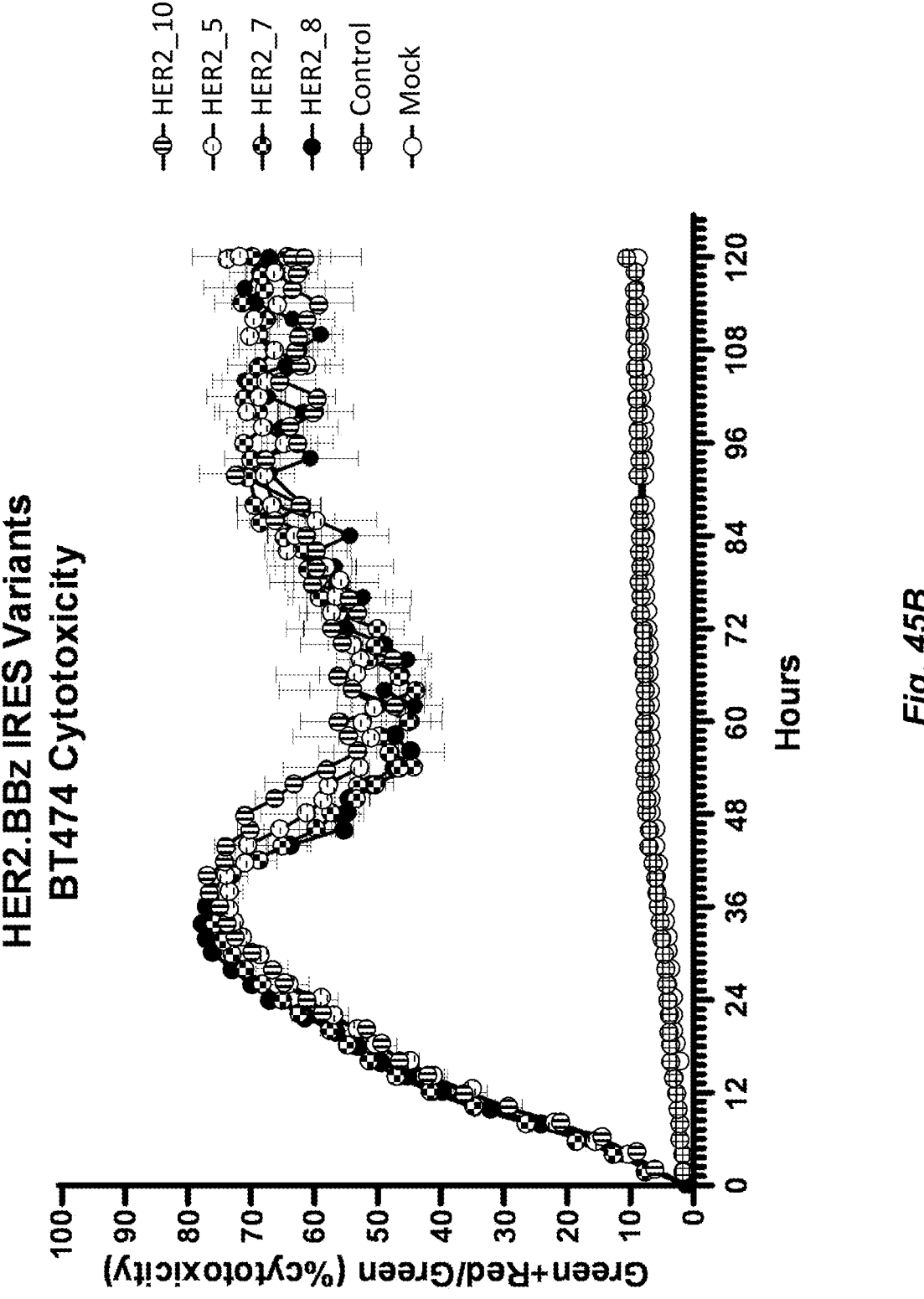
Figure 48A:
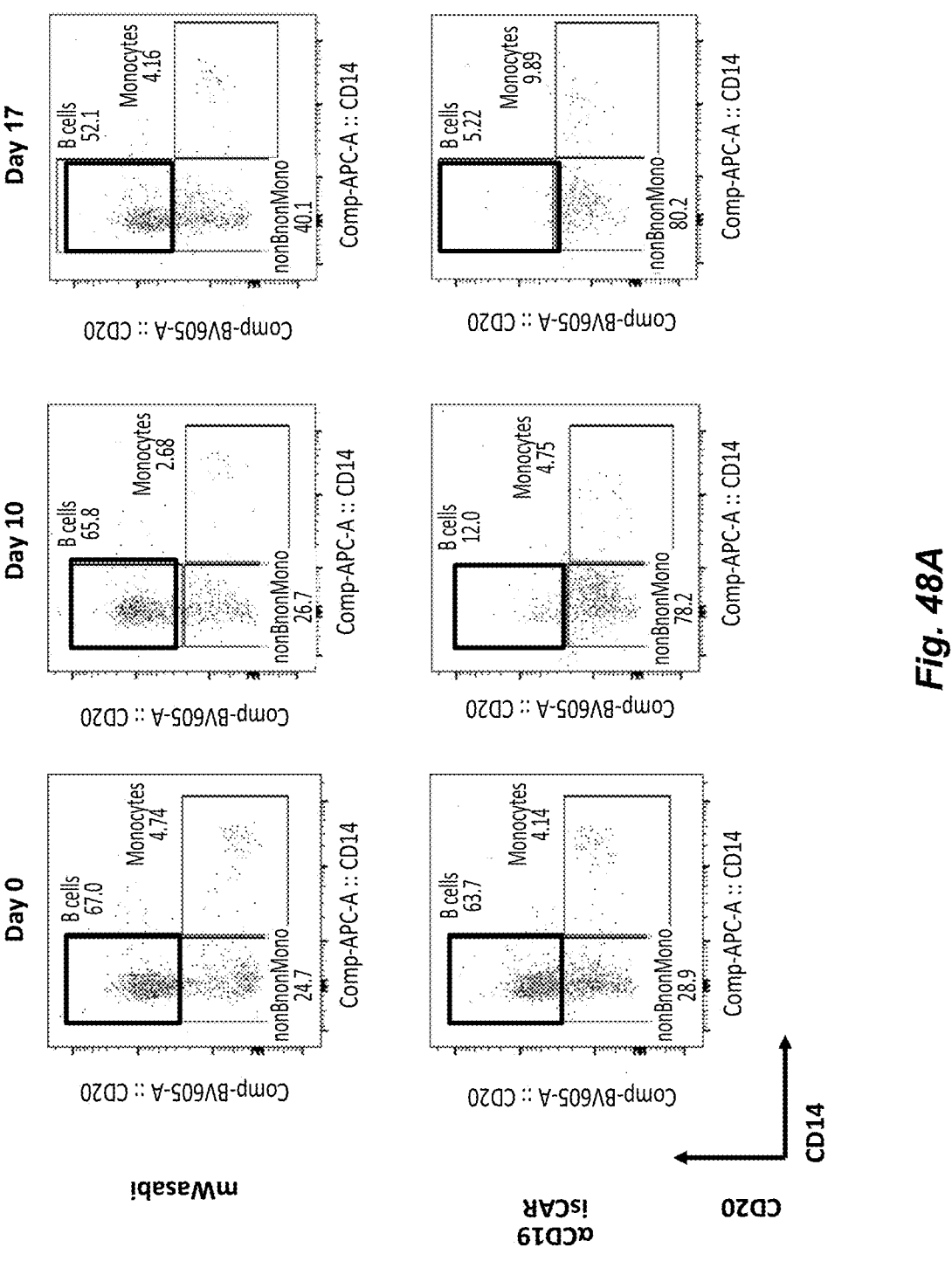
FIGS. 48A-C show B cell depletion mediated by a circular RNA comprising anti-CD19 CAR.
Figure 48A:
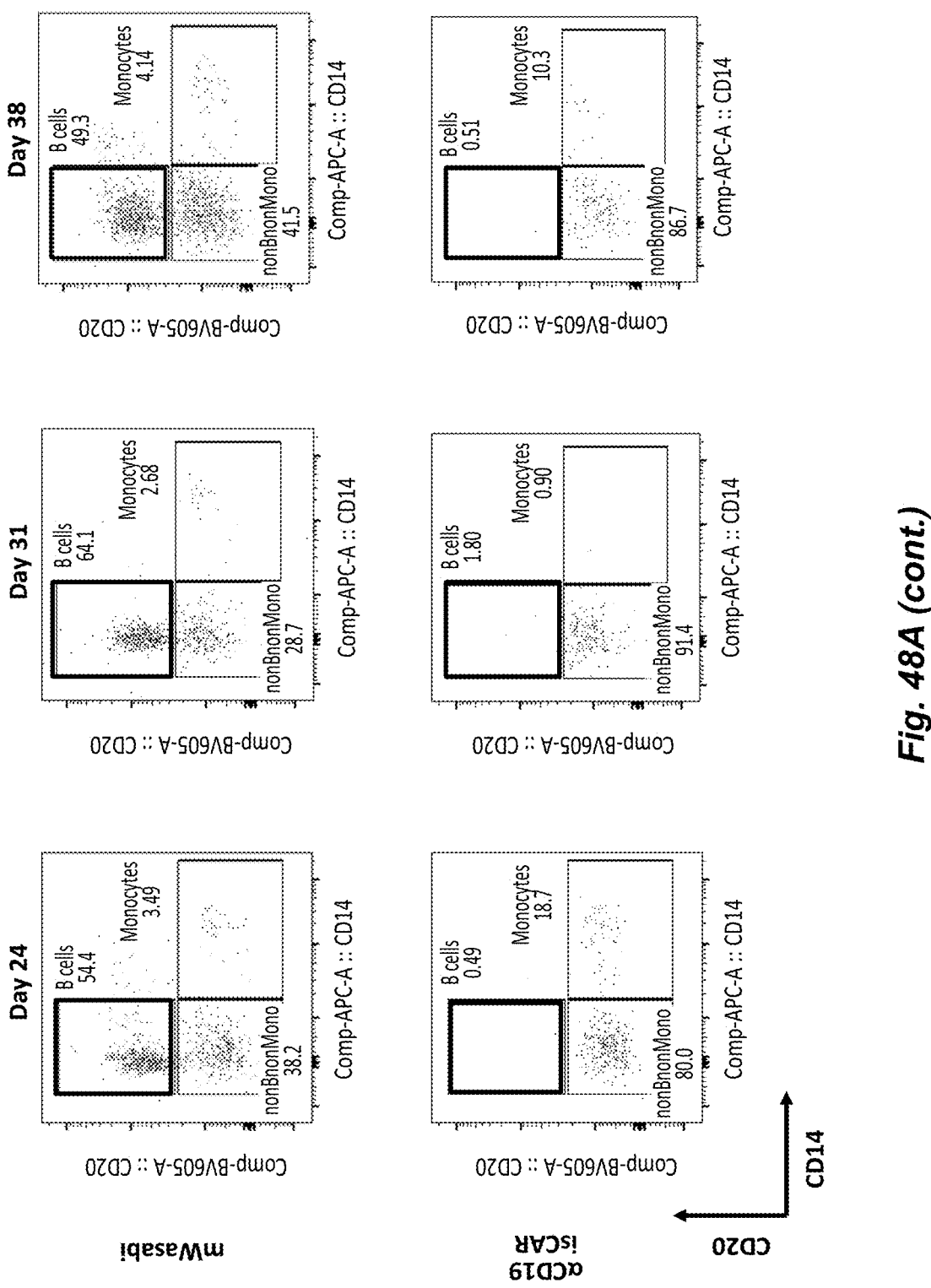
Figure 48B:
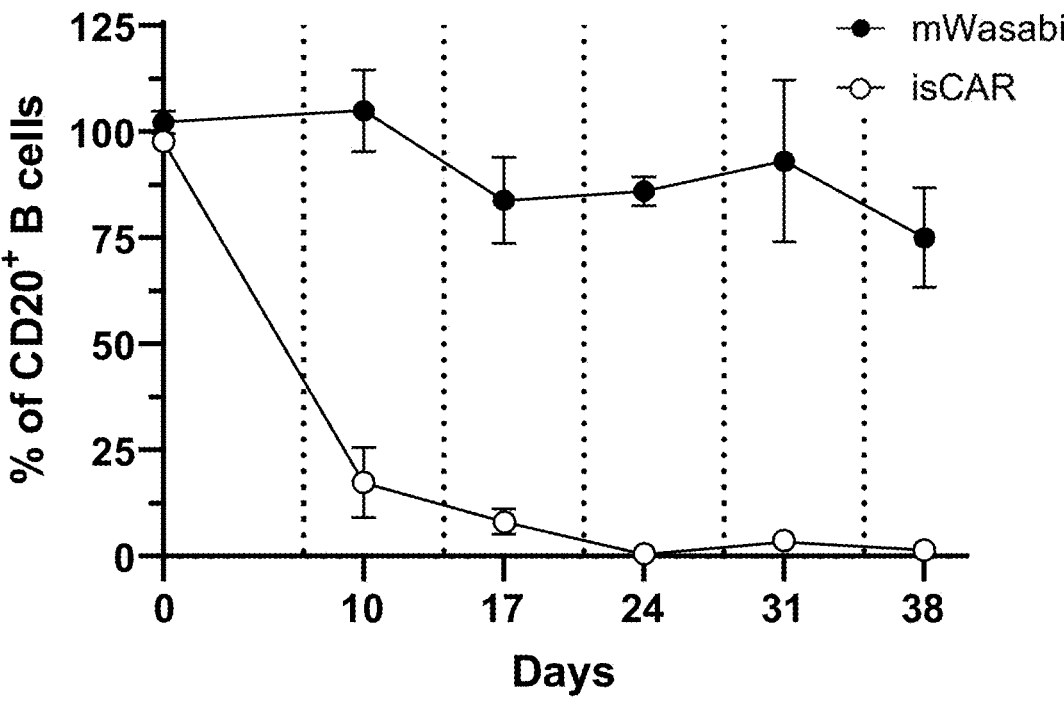
Figure 48C:
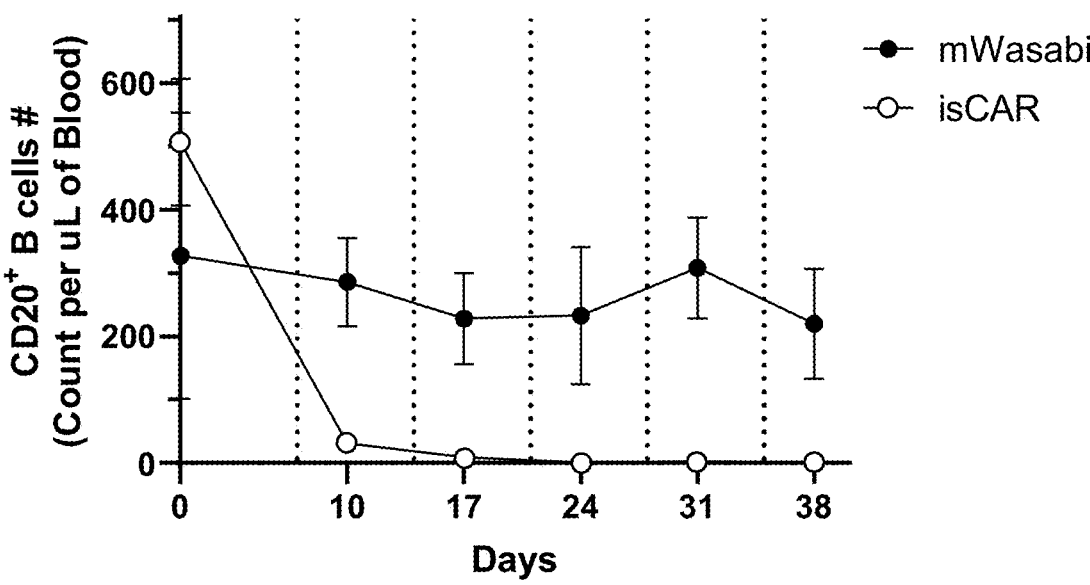

Further, activated PBMC T cells from a single donor were prepared. Separately, circular RNAs encoding HER2-CD28ζ, HER2-41BBζ or CD19-CD28ζ CAR prepared from an IVT reaction of DNA templates comprising a 3' intron segment, a 3' exon segment, an internal ribosome entry site (IRES), a coding region encoding either a HER2.28ζ, HER2.BBζ or CD19-28ζ CAR, a 5' exon segment, and a 5' intron segment. The circular RNAs were transfected onto the activated PBMC T cells using frozen or fresh lipid nanoparticles comprising an ionizable lipid from Table 3 at a concentration listed in the table below (Table γ2). For comparison purposes, activated PBMC T cells were given no circular RNAs as a control. On the day of post-delivery of the circular RNAs to activated PBMC T cells, the circular RNA-activated PBMC T cells were co-cultured with one of three HER2 positive cell lines (i.e., BT474, SKBR3, JIMT1). The resulting co-cultured cells given Annexin V and were analyzed in live-cell analysis portfolio system (e.g., an IncuCyte). FIGS. 40A-40C depict the results of the live-cell analysis portfolio system as calculated by % Annexin V/phase. FIG. 41A-41B illustrates fresh and frozen LNP delivery of the circular RNAs and FIG. 41C depicts cytokine release (e.g., INFγ and/or TNFα) of the cocultured cells.

TABLE γ2

| Coding Region of Circular RNA | DNA Template | RNA Concentration (µg/mL) | EE (%) | Diameter (nm) | PDI |
|---|---|---|---|---|---|
| HER2-CD28ζ CAR | K | 494 | 93 | 82 | 0.06 |
| HER2-41BBζ CAR | L | 463 | 93 | 80 | 0.06 |
| CD19-CD28ζ CAR | M | 498 | 93 | 85 | 0.00 |

TABLE 8

| ID | Internal Ribosome Entry Site (IRES) Sequence | CAR Sequence | CAR Sequence |
|---|---|---|---|
| DNA Template L (Construct L) | GTGGCCACGCCCGGGCCACCGAT | ATGGCTCTGCCTGTGACAGCTCTGCT | MALPVTAL |
| | ACTTCCCTTCACTCCTTCGGGAC | GCTGCCTCTGGCTCTGCTTCTGCATG | LLPLALLL |
| | TGTTGGGGAGGAACACAACAGGG | CCGCCAGACCTGACATCCAGATGACT | HAARPDIQ |
| | CTCCCCTGTTTTCCCATTCCTTC | CAGAGCCCCAGCAGCCTGTCTGCCTC | MTQSPSSL |
| | CCCCTTTTCCCAACCCCAACCGC | TGTGGGAGACAGAGTGACAATTACCT | SASVGDRV |
| | CGTATCTGGTGGCGGCAAGACAC | GCCGGGCCAGCCAGGATGTGAATACT | TITCRASQ |
| | ACGGGTCTTTCCCTCTAAAGCAC | GCTGTCGCCTGGTATCAACAAAAGCC | DVNTAVAW |
| | AATTGTGTGTGTGTCCCAGGTCC | TGGCAAGGCCCCTAAGCTCCTGATCT | YQQKPGKA |
| | TCCTGCGTACGGTGCGGGAGTGC | ACAGCGCCAGCTTTCTGTACAGCGGC | PKLLIYSA |
| | TCCCACCCAACTGTTGTAAGCCT | GTGCCCAGCAGATTCTCCGGAAGCAG | SFLYSGVP |
| | GTCCAACGCGTCGTCCTGGCAAG | AAGCGGCACAGATTTCACACTGACCA | SRFSGSRS |
| | ACTATGACGTCGCATGTTCCGCT | TAAGCAGCCTGCAGCCAGAGGATTTC | GTDFTLTI |
| | GCGGATGCCGACCGGGTAACCGG | GCCACCTACTATTGCCAGCAGCACTA | SSLQPEDF |
| | TTCCCCAGTGTGTGTAGTGCGAT | CACCACACCTCCAACCTTTGGCCAGG | ATYYCQQH |
| | CTTCCAGGTCCTCCTGGTTGGCG | GCACCAAGGTCGAGATTAAGAGAACA | YTTPPTFG |
| | TTGTCCAGAAACTGCTTCAGGTA | GGCAGCACATCTGGCTCTGGCAAACC | QGTKVEIK |
| | AGTGGGGTGTGCCCAATCCCTAC | TGGATCTGGCGAGGGCTCTGAAGTCC | RTGSTSGS |
| | AAAGGTTGATTCTTTCACCACCT | AGCTGGTGGAATCTGGCGGAGGACTG | GKPGSGEG |
| | TAGGAATGCTCCGGAGGTACCCC | GTTCAACCTGGCGGCTCTCTGAGACT | SEVQLVES |
| | AGCAACAGCTGGGATCTGACCGG | GTCTTGTGCCGCCTCCGGCTTCAACA | GGGLVQPG |
| | AGGCTAATTGTCTACGGGTGGTG | TCAAGGACACCTACATCCACTGGGTC | GSLRISCA |
| | TTTCCTTTTTCTTTTCACACAAC | CGACAAGCCCCAGGCAAAGGACTTGA | ASGENIKD |
| | TCTACTGCTGACAACTCACTGAC | GTGGGTCGCCAGGATCTACCCCACCA | TYIHWVRQ |
| | TATCCACTTGCTCTGTCACG | ACGGCTACACCAGATACGCCGACTCT | APGKGLEW |
| | (SEQ ID NO: 17) | GTGAAGGGCAGATTCACCATCTCTGC | VARIYPTN |
| | | CGACACCAGCAAGAATACCGCCTACC | GYTRYADS |
| | | TGCAGATGAACTCCCTGAGAGCCGAA | VKGRFTIS |

TABLE 8-continued

| ID | Internal Ribosome Entry Site (IRES) Sequence | CAR Sequence | CAR Sequence |
|---|---|---|---|
| | | GATACCGCTGTGTATTACTGTTCCAG | ADTSKNTA |
| | | ATGGGGAGGCGACGGCTTCTACGCCA | YLQMNSLR |
| | | TGGATGTTTGGGGCCAAGGCACCCTC | AEDTAVYY |
| | | GTGACCGTTTCTTCTACCACCACACC | CSRWGGDG |
| | | AGCTCCTCGGCCTCCAACTCCTGCTC | FYAMDVWG |
| | | CTACAATTGCCAGCCAGCCTCTGTCT | QGTLVTVS |
| | | CTGAGGCCCGAAGCTTGTAGACCTGC | STTTPAPR |
| | | TGCTGGCGGAGCCGTGCATACAAGAG | PPTPAPTI |
| | | GACTGGATTTCGCCTGCGACATCTAC | ASQPLSLR |
| | | ATCTGGGCTCCTCTGGCCGGAACATG | PEACRPAA |
| | | TGGCGTTCTGCTGCTGAGCCTGGTCA | GGAVHTRG |
| | | TCACCCTGTACTGTAAGCGGGGCAGA | LDFACDIY |
| | | AAGAAGCTGCTGTACATCTTCAAGCA | IWAPLAGT |
| | | GCCCTTCATGCGGCCCGTGCAGACCA | CGVLLLSL |
| | | CACAAGAGGAAGATGGCTGCTCCTGC | VITLYCKR |
| | | AGATTCCCCGAGGAAGAAGAAGGCGG | GRKKLLYI |
| | | CTGCGAGCTGAGAGTGAAGTTCAGCA | FKQPFMRP |
| | | GATCCGCCGATGCTCCCGCCTATCAG | VQTTQEED |
| | | CAGGGCCAAAACCAGCTGTACAACGA | GCSCREPE |
| | | GCTGAACCTGGGGAGAAGAGAAGAGT | EEEGGCEL |
| | | ACGACGTGCTGGACAAGCGGAGAGGC | RVKFSRSA |
| | | AGAGATCCTGAAATGGGGGGCAAGCC | DAPAYQQG |
| | | CAGACGGAAGAATCCTCAAGAGGGCC | QNQLYNEL |
| | | TGTATAATGAGCTGCAGAAAGACAAG | NLGRREEY |
| | | ATGGCCGAGGCCTACAGCGAGATCGG | DVLDKRRG |
| | | AATGAAGGGCGAGCGCAGAAGAGGCA | RDPEMGGK |
| | | AGGGACACGATGGACTGTACCAGGGC | PRRKNPQE |
| | | CTGAGCACCGCCACCAAGGATACCTA | GLYNELQK |
| | | TGATGCCCTGCACATGCAGGCCCTGC | DKMAEAYS |
| | | CTCCAAGA (SEQ ID NO: 102) | EIGMKGER |
| | | | RRGKGHDG |
| | | | LYQGLSTA |
| | | | TKDTYDAL |
| | | | HMQALPPR |
| | | | (SEQ ID |
| | | | NO: 118) |
| DNA Template M (Construct M) | CCCCCCTCCCCCCCTTCCCTTCC CTTTGCAACGCAACAATTGTAAG TGCCCTCACCTGTCAATTGGGAC CACCACTTTCAGTGACCCCATGC GAAGTGCTGAGAGAAAGGAAGCT TTCTTACCCTTCATTTGTGAACC CACTGGTCTAAGCCGCTTGGAAT ACGATGAGTGGAAAAGTTCATTC TTAATGGAGTGAAACATGCTTAA ATTTCCAGCTCGTGCTGGTCTTT CCAGTACGGGGCGGCCCTGTCTG GCCGTAATTCTTCAGAGTGTCAC GCCACACTTGTGGATCTCACGTG CCACATGACAGCGCTACAGCTGG AACTGGGTGCTTGGTGCCCATGG AGTAACAGCGAAAAGTGTTAGAT CAAGCCTTGCTTGGGCTATGAGC CTGCGGAACAACAACTGGTAACA GTTGCCTCAGGGGCCGAAAGCCA CGGTGTTAACAGCACCCTCATAG TTTGATCCACCTCAGGGTGGTGA TGTTTAGCAGTTAGTAGTTGCCA ATCTGTGTTCACTGAAATCTCGG CATACCGTGTAGTGTACAGGGGT GAAGGATGCCCAGAAGGTACCCG TAGGTAACCTTAAGAGACTATGG ATCTGATCTGGGGCCTTGTCCGG AGTGCTTTACACACGGCTCAAGG TTAAAAAACGTCTAGCCCCACAG AGCCCGAGGGATTCGGGTTTTCC CTTTAAAAACCCGACTAGAGCTT ATGGTGACAATTATTGCTGTTCA GACGAACAGTGTAATTGTTGTCT ATTCACAGCAGTTCTATCAGAGC TTTTCCCACAACGGATCTTCTTG GCAAGCAAATACAGCAGGAGTCA AT (SEQ ID NO: 8) | ATGGCACTGCCCGTCACCGCACTCCT GCTCCCACTGGCACTGCTGCTCCATG CAGCTCGCCCCGATATCCAGATGACC CAGACCACCTCTAGCCTCAGCGCCTC TCTGGGTGACCGCGTCACCATCTCTT GCCGGGCCAGCCAAGACATCTCTAAG TACCTGAACTGGTACCAGCAGAAACC TGACGGAACCGTGAAGCTGCTGATCT ACCACACCAGTCGGCTGCATTCCGGG GTGCCTTCCAGGTTCAGCGGTTCCGG CTCTGGGACCGATTATAGTCTCACCA TCTCCAACCTCGAGCAGGAGGACATC GCAACCTACTTCTGCCAGCAGGGGAA CACCCTGCCCTACACCTTCGGTGGCG GGACCAAGCTGGAGATCACTGGAGGT GGTGGCAGCGGAGGTGGAGGATCAGG TGGAGGCGGTAGCGAGGTGAAGCTGC AGGAGTCCGGACCTGGTCTGGTGGCC CCAAGCCAGTCCCTCAGCGTCACCTG CACAGTGTCCGGGGTGTCCCTGCCTG ACTACGGTGTCTCCTGGATCAGGCAA CCACCCCGGAAGGGTCTCGAGTGGCT GGGCGTCATCTGGGGCTCCGAGACCA CCTACTACAACAGCGCTCTGAAGTCC CGGCTGACCATCATCAAAGACAACTC CAAGAGCCAGGTGTTCTTGAAGATGA ACTCCCTGCAAACCGATGACACCGCC ATCTACTACTGCGCCAAGCACTACTA CTATGGCGGTAGCTACGCCATGGATT ATTGGGGTCAGGGCACCAGTGTCACC GTCTCCTCATCGAAGGTGATGTACCC TCCACCCTATCTGGACAACGAGAAGT CCAACGGCACCATCATCCACGTGAAG GGCAAGCACCTGTGCCCCTAGCCCTCT GTTCCCAGGACCTCCCGGCTGACGCCCTTCT GGGTGCTGGTCGTGGTGGGGAGGAGTC CTGGCCTGCTATTCCCTCCTCGTCAC CGTGGCATTATCATCTTCTGGGTCC GGAGCAAGCGGTCACGCCTGCTCCAC TCCGACTACATGAACATGACTCCTCG | MALPVTAL LLPLALLL HAARPDIQ MTQTTSSL SASLGDRV TISCRASQ DISKYLNW YQQKPDGT VKLLIYHT SRLHSGVP SRFSGSGS GTDYSLTI SNLEQEDI ATYFCQQG NTLPYTFG GGTKLEIT GGGGSGGG GSGGGGSE VKLQESGP GLVAPSQS LSVTCTVS GVSLPDYG VSWIRQPP RKGLEWLG VIWGSETT YYNSALKS RLTIIKDN SKSQVELK MNSLQTDD TAIYYCAK HYYGGSY AMDYWGQG TSVTVSSI EVMYPPPY LDNEKSNG TIIHVKGK HLCPSPLF PGPSKPFW VLVVVGGV LACYSLLV |

TABLE 8-continued

| ID | Internal Ribosome Entry Site (IRES) Sequence | CAR Sequence | CAR Sequence |
|---|---|---|---|
| | | CAGACCTGGACCCACCCGGAAGCACT | TVAFIIFW |
| | | ACCAGCCTTATGCCCCACCCCGCGAC | VRSKRSRL |
| | | TTTGCCGCTTACCGCTCTCGGGTCAA | LHSDYMNM |
| | | GTTCTCTCGGTCAGCAGACGCCCCTG | TPRRPGPT |
| | | CATACCAGCAGGGCCAGAACCAGCTG | RKHYQPYA |
| | | TATAACGAGCTGAACCTCGGCAGACG | PPRDFAAY |
| | | GGAGGAGTACGATGTGCTGGACAAGA | RSRVKFSR |
| | | GGAGAGGCAGAGACCCCGAGATGGGT | SADAPAYQ |
| | | GGTAAGCCACGGCGCAAGAACCCACA | QGQNQLYN |
| | | GGAGGGCTTGTACAACGAACTGCAGA | ELNLGRRE |
| | | AGGACAAGATGGCCGAGGCCTACAGC | EYDVLDKR |
| | | GAGATCGGCATGAAGGGAGAGAGGCG | RGRDPEMG |
| | | CAGGGGCAAGGGTCACGACGGCCTGT | GKPRRKNP |
| | | ACCAAGGGCTGTCCACCGCAACCAAG | QEGLYNEL |
| | | GACACCTACGATGCCCTGCACATGCA | QKDKMAEA |
| | | GGCCCTCCCACCAAGG (SEQ ID | YSEIGMKG |
| | | NO: 19) | ERRRGKGH |
| | | | DGLYQGLS |
| | | | TATKDTYD |
| | | | ALHMQALP |
| | | | PR (SEQ |
| | | | ID NO: |
| | | | 29) |
| DNA Template N (Construct N) | ATTCTCGGGCTACGGCCCTGGAG CCACTCCGGCTCCTAAAGATTTA GAAGTTTGAGCACACCCGCCCAC TAGGGCCCCCCATCCAGGGGGGC AACGGGCAAGCACTTCTGTTTCC CCGGTATGATCTGATAGGCTGTA ACCACGGCTGAAACAGAGATTAT CGTTATCCGCTTCACTACTTCGA GAAGCCTAGTAATGATGGGTGAA ATTGAATCCGTTGATCCGGTGTC TCCCCCACACCAGAAACTCATGA TGAGGGTTGCCATCCCGGCTACG GCGACGTAGCGGGCATCCCTGCG CTGGCATGAGGCCTCTTAGGAGG ACGGATGATATGGATCTTGTCGT GAAGAGCCTATTGAGCTAGTGTC GACTCCTCCGCCCCCGTGAATGC GGCTAATCCTAACCCCGGAGCAG GTGGGTCCAATCCAGGGCCTGGC CTGTCGTAATGCGTAAGTCTGGG ACGGAACCGACTACTTTCGGGAA GGCGTGTTTCCATTTGTTCATTA TTTGTGTGTTATGGTGACAACT CTGGGTAAACGTTCTATTGCGTT TATTGAGAGATTCCCAACAATTG AACAAACGAGAACTACCTGTTTT ATTAAATTTACACAGAGAAGAAT TACA (SEQ ID NO: 16) | ATGGCTCTGCCTGTGACAGCTCTGCT GCTGCCTCTGGCTCTGCTTCTGCATG CCGCCAGACCTGACATCCAGATGACT CAGAGCCCCAGCAGCCTGTCTGCCTC TGTGGGAGACAGAGTGACAATTACCT GCCGGGCCAGCCAGGATGTGAATACT GCTGTCGCCTGGTATCAACAAAAGCC TGGCAAGGCCCCTAAGCTCCTGATCT ACAGCGCCAGCTTTCTGTACAGCGGC GTGCCCAGCAGATTCTCCGGAAGCAG AAGCGGCACAGATTTCACACTGACCA TAAGCAGCCTGCAGCCAGAGGATTTC GCCACCTACTATTGCCAGCAGCACTA CACCACACCTCCAACCTTTGGCCAGG GCACCAAGGTCGAGATTAAGAGAACA GGCAGCACATCTGGCTCTGGCAAACC TGGATCTGGCGAGGGCTCTGAAGTCC AGCTGGTGGAATCTGGCGGAGGACTG GTTCAACCTGGCGGCTCTCTGAGACT GTCTTGTGCCGCCTCCGGCTTCAACA TCAAGGACACCTACATCCACTGGGTC CGACAAGCCCCAGGCAAAGGACTTGA GTGGGTCGCCAGGATCTACCCCACCA ACGGCTACACCAGATACGCCGACTCT GTGAAGGGCAGATTCACCATCTCTGC CGACACCAGCAAGAATACCGCCTACC TGCAGATGAACTCCCTGAGAGCCGAA GATACCGCTGTGTATTACTGTTCCAG ATGGGGAGGCGACGGCTTCTACGCCA TGGATGTTTGGGGCCAAGGCACCCTC GTGACCGTTTCTTCTATCGAAGTGAT GTACCCTCCACCTTACCTGGACAACG AGAAGTCCAACGGCACCATCATCCAC GTGAAGGGCAAGCACCTGTGTCCTTC TCCACTGTTCCCCGGACCTAGCAAGC CTTTCTGGGTGCTCGTTGTTGTTGGC GGCGTGCTGGCCTGTTACTCTCTGCT GGTTACCGTGGCCTTCATCATCTTTT GGGTCCGAAGCAAGCGGAGCCGGCTG CTGCACTCCGACTACATGAACATGAC CCCTAGACGGCCCGGACCAACCAGAA AGCACTACCAGCCTTACGCTCCTCCT AGAGACTTCGCCGCCTACCGGTCCAG AGTGAAGTTCAGCAGATCCGCCGATG CTCCCGCCTATCAGCAGGGCCAAAAC CAGCTGTACAACGAGCTGAACCTGGG AGAAGAGAAGAGTACGACGTGCTGG ACAAGCGGAGGAGGCAGAGATCCTGAA ATGGGGGGCAAGCCCAGACGGAAGAA TCCTCAAGAGGGCCTGTATAATGAGC TGCAGAAAGACAAGATGGCCGAGGCC TACAGCGAGATCGGAATGAAGGGCGA GCGCAGAAGAGGCAAGGGACACGATG | MALPVTAL LLPLALLL HAARPDIQ MTQSPSSL SASVGDRV TITCRASQ DVNTAVAW YQQKPGKA PKLLIYSA SFLYSGVP SRFSGSRS GTDFTLTI SSLQPEDE ATYYCQQH YTTPPTFG QGTKVEIK RTGSTSGS GKPGSGEG SEVQLVES GGGLVQPG GSLRLSCA ASGENIKD TYIHWVRQ APGKGLEW VARIYPTN GYTRYADS VKGRFTIS ADTSKNTA YLQMNSLR AEDTAVYY CSRWGGDG FYAMDVWG QGTLVTVS SIEVMYPP PYLDNEKS NGTIIHVK GKHLCPSP LFPGPSKP FWVLVVVG GVLACYSL LVTVAFII FWVRSKRS RLLHSDYM NMTPRRPG PTRKHYQP YAPPRDFA AYRSRVKF SRSADAPA YQQGQNQL YNELNLGR REEYDVLD KRRGRDPE MGGKPRRK |

TABLE 8-continued

| ID | Internal Ribosome Entry Site (IRES) Sequence | CAR Sequence | CAR Sequence |
|---|---|---|---|
| | | GACTGTACCAGGGCCTGAGCACCGCC ACCAAGGATACCTATGATGCCCTGCA CATGCAGGCCCTGCCTCCAAGA (SEQ ID NO: 101) | NPQEGLYN ELQKDKMA EAYSEIGM KGERRRGK GHDGLYQG LSTATKDT YDALHMQA LPPR (SEQ ID NO: 117) |
| DNA Template O (Construct O) | CCCCCCTCCCCCCCTTCCCTTCC CTTTGCAACGCAACAATTGTAAG TGCCCTCACCTGTCAATTGGGAC CACCACTTTCAGTGACCCCATGC GAAGTGCTGAGAGAAAGGAAGCT TTCTTACCCTTCATTTGTGAACC CACTGGTCTAAGCCGCTTGGAAT ACGATGAGTGGAAAAGTTCATTC TTAATGGAGTGAAACATGCTTAA ATTTCCAGCTCGTGCTGGTCTTT CCAGTACGGGGCGGCCCTGTCTG GCCGTAATTCTTCAGAGTGTCAC GCCACACTTGTGGATCTCACGTG CCACATGACAGCGCTACAGCTGG AACTGGGTGCTTGGTGCCCATGG AGTAACAGCGAAAAGTGTTAGAT CAAGCCTTGCTTGGGCTATGAGC CTGCGGAACAACAACTGGTAACA GTTGCCTCAGGGGCCGAAAGCCA CGGTGTTAACAGCACCCTCATAG TTTGATCCACCTCAGGGTGGTGA TGTTTAGCAGTTAGTAGTTGCCA ATCTGTGTTCACTGAAATCTCGG CATACCGTGTAGTGTACAGGGGT GAAGGATGCCCAGAAGGTACCCG TAGGTAACCTTAAGAGACTATGG ATCTGATCTGGGGCCTTGTCCGG AGTGCTTTACACACGGCTCAAGG TTAAAAAACGTCTAGCCCCACAG AGCCCGAGGGATTCGGGTTTTCC CTTTAAAAACCCGACTAGAGCTT ATGGTGACAATTATTGCTGTTCA GACGAACAGTGTAATTGTTGTCT ATTCACAGCAGTTCTATCAGAGC TTTTCCCACAACGGATCTTCTTG GCAAGCAAATACAGCAGGAGTCA AT (SEQ ID NO: 8) | ATGGCTCTGCCTGTGACAGCTCTGCT GCTGCCTCTGGCTCTGCTTCTGCATG CCGCCAGACCTGACATCCAGATGACT CAGAGCCCCAGCAGCCTGTCTGCCTC TGTGGGAGACAGAGTGACAATTACCT GCCGGGCCAGCCAGGATGTGAATACT GCTGTCGCCTGGTATCAACAAAAGCC TGGCAAGGCCCCTAAGCTCCTGATCT ACAGCGCCAGCTTTCTGTACAGCGGC GTGCCCAGCAGATTCTCCGGAAGCAG AAGCGGCACAGATTTCACACTGACCA TAAGCAGCCTGCAGCCAGAGGATTTC GCCACCTACTATTGCCAGCAGCACTA CACCACACCTCCAACCTTTGGCCAGG GCACCAAGGTCGAGATTAAGAGAACA GGCAGCACATCTGGCTCTGGCAAACC TGGATCTGGCGAGGGCTCTGAAGTCC AGCTGGTGGAATCTGGCGGAGGACTG GTTCAACCTGGCGGCTCTCTGAGACT GTCTTGTGCCGCCTCCGGCTTCAACA TCAAGGACACCIACATCCACTGGGTC CGACAAGCCCCAGGCAAAGGACTTGA GTGGGTCGCCAGGATCTACCCCACCA ACGGCTACACCAGATACGCCGACTCT GTGAAGGGCAGATTCACCATCTCTGC CGACACCAGCAAGAATACCGCCTACC TGCAGATGAACTCCCTGAGAGCCGAA GATACCGCTGTGTATTACTGTTCCAG ATGGGGAGGCGACGGCTTCTACGCCA TGGATGTTTGGGGCCAAGGCACCCTC GTGACCGTTTCTTCTATCGAAGTGAT GTACCCTCCACCTTACCTGGACAACG AGAAGTCCAACGGCACCATCATCCAC GTGAAGGGCAAGCACCTGTGTCCTTC TCCACTGTTCCCCGGACCTAGCAAGC CTTTCTGGGTGCTCGTTGTTGTTGGC GGCGTGCTGGCCTGTTACTCTCTGCT GGTTACCGTGGCCTTCATCATCTTTT GGGTCCGAAGCAAGCGGAGCCGGCTG CTGCACTCCGACTACATGAACATGAC CCCTAGACGGCCCGGACCAACCAGAA AGCACTACCAGCCTTACGCTCCTCCT AGAGACTTCGCCGCCTACCGGTCCAG AGTGAAGTTCAGCAGATCCGCCGATG CTCCCGCCTATCAGCAGGGCCAAAAC CAGCTGTACAACGAGCTGAACCTGGG GAGAAGAGAAGAGTACGACGTGCTGG ACAAGCGGAGAGGCAGAGATCCTGAA ATGGGGGGCAAGCCCAGACGGAAGAA TCCTCAAGAGGGCCTGTATAATGAGC TGCAGAAAGACAAGATGGCCGAGGCC TACAGCGAGATCGGAATGAAGGGCGA GCGCAGAAGAGGCAAGGGACACGATG GACTGTACCAGGGCCTGAGCACCGCC ACCAAGGATACCTATGATGCCCTGCA CATGCAGGCCCTGCCTCCAAGA (SEQ ID NO: 101) | MALPVTAL LLPLALLL HAARPDIQ MTQSPSSL SASVGDRV TITCRASQ DVNTAVAW YQQKPGKA PKLLIYSA SFLYSGVP SRFSGSRS GTDFTLTI SSLQPEDF ATYYCQQH YTTPPTFG QGTKVEIK RTGSTSGS GKPGSGEG SEVQLVES GGGLVQPG GSLRISCA ASGFNIKD TYIHWVRQ APGKGLEW VARIYPTN GYTRYADS VKGRFTIS ADTSKNTA YLQMNSLR AEDTAVYY CSRWGGDG FYAMDVWG QGTLVTVS SIEVMYPP PYLDNEKS NGTIIHVK GKHLCPSP LFPGPSKP FWVLVVVG GVLACYSL LVTVAFII FWVRSKRS RLLHSDYM NMTPRRPG PTRKHYQP YAPPRDFA AYRSRVKF SRSADAPA YQQGQNQL YNELNLGR REEYDVLD KRRGRDPE MGGKPRRK NPQEGLYN ELQKDKMA EAYSEIGM KGERRRGK GHDGLYQG LSTATKDT YDALHMQA LPPR (SEQ ID NO: 117) |
| DNA Template P | TTTGCTCAGCGTAACTTCTCCGG GTTACGTGGAGACCAAAAGGCTA | ATGGCTCTGCCTGTGACAGCTCTGCT GCTGCCTCTGGCTCTGCTTCTGCATG | MALPVTAL LLPLALLL |

TABLE 8-continued

| ID | Internal Ribosome Entry Site (IRES) Sequence | CAR Sequence | CAR Sequence |
|---|---|---|---|
| (Construct P) | CGGAGACTCGGGCTACGGCCCTG<br>GAGCACCTAGGTGCTCCTAAAGA<br>CGTTAGAAGTTGTACAAACTCGC<br>CCAATAGGGCCCCCCAACCAGGG<br>GGGTAGCGGGCAAGCACTTCTGT<br>TTCCCCGGTATGATCTCATAGGC<br>TGTACCCACGGCTGAAAGAGAGA<br>TTATCGTTACCCGCCTCACTACT<br>TCGAGAAGCCCAGTAATGGTTCA<br>TGAAGTTGATCTCGTTGACCCGG<br>TGTTTCCCCCACACCAGAAACCT<br>GTGATGGGGGTGGTCATCCCGGT<br>CATGGCGACATGACGGACCTCCC<br>CGCGCCGGCACAGGGCCTCTTCG<br>GAGGACGAGTGACATGGATTCAA<br>CCGTGAAGAGCCTATTGAGCTAG<br>TGTTGATTCCTCCGCCCCCGTGA<br>ATGCGGCTAATCCCAACTCCGGA<br>GCAGGCGGGCCCAAACCAGGGTC<br>TGGCCTGTCGTAACGCGAAAGTC<br>TGGAGCGGAACCGACTACTTTCG<br>GGAAGGCGTGTTTCCTTTTGTTC<br>CTTTTATCAAGTTTTATGGTGAC<br>AACTCCTGGTAGACGTTTTATTG<br>CGTTTATTGAGAGATTTCCAACA<br>ATTGAACAGACTAGAACCACTTG<br>TTTTATCAAACCCTCACAGAATA<br>AGATAACA (SEQ ID NO: 18) | CCGCCAGACCTGACATCCAGATGACT<br>CAGAGCCCCAGCAGCCTGTCTGCCTC<br>TGTGGGAGACAGAGTGACAATTACCT<br>GCCGGGCCAGCCAGGATGTGAATACT<br>GCTGTCGCCTGGTATCAACAAAAGCC<br>TGGCAAGGCCCCTAAGCTCCTGATCT<br>ACAGCGCCAGCTTTCTGTACAGCGGC<br>GTGCCCAGCAGATTCTCCGGAAGCAG<br>AAGCGGCACAGATTTCACACTGACCA<br>TAAGCAGCCTGCAGCCAGAGGATTTC<br>GCCACCTACTATTGCCAGCAGCACTA<br>CACCACACCTCCAACCTTTGGCCAGG<br>GCACCAAGGTCGAGATTAAGAGAACA<br>GGCAGCACATCTGGCTCTGGCAAACC<br>TGGATCTGGCGAGGGCTCTGAAGTCC<br>AGCTGGTGGAATCTGGCGGAGGACTG<br>GTTCAACCTGGCGGCTCTCTGAGACT<br>GTCTTGTGCCGCCTCCGGCTTCAACA<br>TCAAGGACACCTACATCCACTGGGTC<br>CGACAAGCCCCAGGCAAAGGACTTGA<br>GTGGGTCGCCAGGATCTACCCCACCA<br>ACGGCTACACCAGATACGCCGACTCT<br>GTGAAGGGCAGATTCACCATCTCTGC<br>CGACACCAGCAAGAATACCGCCTACC<br>TGCAGATGAACTCCCTGAGAGCCGAA<br>GATACCGCTGTGTATTACTGTTCCAG<br>ATGGGGAGGCGACGGCTTCTACGCCA<br>TGGATGTTTGGGGCCAAGGCACCCTC<br>GTGACCGTTTCTTCTATCGAAGTGAT<br>GTACCCTCCACCTTACCTGGACAACG<br>AGAAGTCCAACGGCACCATCATCCAC<br>GTGAAGGGCAAGCACCTGTGTCCTTC<br>TCCACTGTTCCCCGGACCTAGCAAGC<br>CTTTCTGGGTGCTCGTTGTTGTTGGC<br>GGCGTGCTGGCCTGTTACTCTCTGCT<br>GGTTACCGTGGCCTTCATCATCTTTT<br>GGGTCCGAAGCAAGCGGAGCCGGCTG<br>CTGCACTCCGACTACATGAACATGAC<br>CCCTAGACGGCCCGGACCAACCAGAA<br>AGCACTACCAGCCTTACGCTCCTCCT<br>AGAGACTTCGCCGCCTACCGGTCCAG<br>AGTGAAGTTCAGCAGATCCGCCGATG<br>CTCCCGCCTATCAGCAGGGCCAAAAC<br>CAGCTGTACAACGAGCTGAACCTGGG<br>GAGAAGAGAAGAGTACGACGTGCTGG<br>ACAAGCGGAGAGGCAGAGATCCTGAA<br>ATGGGCGGCAAGCCCAGACGGAAGAA<br>TCCTCAAGAGGGCCTGTATAATGAGC<br>TGCAGAAAGACAAGATGGCCGAGGCC<br>TACAGCGAGATCGGAATGAAGGGCGA<br>GCGCAGAAGAGGCAAGGGACACGATG<br>GACTGTACCAGGGCCTGAGCACCGCC<br>ACCAAGGATACCTATGATGCCCTGCA<br>CATGCAGGCCCTGCCTCCAAGA (SEQ ID NO: 101) | HAARPDIQ<br>MTQSPSSL<br>SASVGDRV<br>TITCRASQ<br>DVNTAVAW<br>YQQKPGKA<br>PKLLIYSA<br>SFLYSGVP<br>SRFSGSRS<br>GTDFTLTI<br>SSLQPEDE<br>ATYYCQQH<br>YTTPPTFG<br>QGTKVEIK<br>RTGSTSGS<br>GKPGSGEG<br>SEVQLVES<br>GGGLVQPG<br>GSLRLSCA<br>ASGFNIKD<br>TYIHWVRQ<br>APGKGLEW<br>VARIYPTN<br>GYTRYADS<br>VKGRFTIS<br>ADTSKNTA<br>YLQMNSLR<br>AEDTAVYY<br>CSRWGGDG<br>FYAMDVWG<br>QGTLVTVS<br>SIEVMYPP<br>PYLDNEKS<br>NGTIIHVK<br>GKHLCPSP<br>LFPGPSKP<br>FWVLVVVG<br>GVLACYSL<br>LVTVAFII<br>FWVRSKRS<br>RLLHSDYM<br>NMTPRRPG<br>PTRKHYQP<br>YAPPRDFA<br>AYRSRVKF<br>SRSADAPA<br>YQQGQNQL<br>YNELNLGR<br>REEYDVLD<br>KRRGRDPE<br>MGGKPRRK<br>NPQEGLYN<br>ELQKDKMA<br>EAYSEIGM<br>KGERRRGK<br>GHDGLYQG<br>LSTATKDT<br>YDALHMQA<br>LPPR<br>(SEQ ID NO: 117) |

Example 17: Circular RNAs Encoding HER2 CARs Tumor Killing Activity In Vivo

Female NSG immune deficient mice (aged 8 to 12 weeks) with $1\times10^7$ JIMT-1 or BT-474 tumor cells (in subcutaneous flank engraftment) were prepared to have an average tumor size of 50-100 mm³. $1\times10^7$ human PBMC T cells from two different donors were activated with anti-CD3 and anti-CD8 for 72 hours, then activation was removed and cells were prepared in PBS for injection. On the fifth day after human PBMC thawed, 200 µL of $50\times10^6$/mL of the stimulated human PBMC T cells were injected into the tail vein of mice intravenously. A day after the activated human PBMC T cells were injected, the mice were dosed with either doc-etaxel (control, no PBMC) at 10 mL/kg, PBS (control), or LNP comprising circular RNAs encoding HER2.28° C., HER2.BBC or CD19.28 CAR at 3 mg/kg intravenously. Circular RNAs further comprised internal ribosome entry sites (IRESes) derived from Caprine Kobuvirus or Hunnivi-rus. LNPs comprised the ionizable referenced in the preced-ing example. The mice were dosed every other day (within a four-hour timeframe) for a total of 4 dosages. FIGS. 42A-42G provides total tumor volume accumulated over the span of 50 days for mice comprising the JIMT-1 (FIGS. 42A-42F) and BT-474 (FIGS. 42F-42L) tumor cells.

Example 18: Circular RNA Encoding HER2 CAR

Frozen human T cells were thawed and activated with Stemcell CD3/CD28 antibody cocktail for 72 hours. Post activation T cells were electroporated with circular RNA as described herein comprising different IRES sequences and the HER2 CAR sequences as shown in Construct N and Construct O above, with either 28z or BBz domains. T cells that were electroporated (EP) but had no circular RNA (mock) or had a circular RNA encoding CD19 CAR served as controls. After EP, cells were allowed to recover for 24 hours, following which they were assessed for expression by FACS at 24, 48 and 72 hours post transfection. HER2 CAR was detected using soluble HER2 fluorokines (soluble proteins conjugated to fluorophores).

Incucyte assays were performed. 24 hours after EP, cells expressing the circular RNA encoding HER2 CAR were plated on Incucyte plates at an E: T of 1:1 with HER2 positive, GFP positive BT474 target cells in T cell growth media without IL2. Annexin V, which stains dead cells, was added to the co-culture to track the accumulation of dead cells. The plate was read on the Incucyte instrument for 5 days. Target cell death was assessed by analyzing the percent of green target cells that were stained with Annexin V and comparing to the total GFP positive population in the well as well as to the mock control.

Expression kinetics were assessed for circular RNAs encoding HER2 CAR and comprising different IRES sequences over 72 hours. Cytotoxicity function of BT474 target cells by Incucyte was assessed for circular RNAs encoding HER2 CAR and comprising different IRES sequences. See, e.g., FIGS. 43A-D, FIGS. 44A-D, FIGS. 45A-B, and FIG. 46.

Example 19: Use of Circular RNA Encoding CD19 CAR in Autoimmune Disease

The ability of circular RNA encoding CD19 CAR to deplete human B cells in a CD34+ engrafted humanize mouse model was assessed using a CD34+ NOD.Cg-PrkdcscidIL-2rgem 1/Smoc strain at 19 weeks. The CD34+ Humanized Mice (HiMice) were generated by Invivocue. Five- to six-week-old, female NOD-PrkdescidIL2rgem l/Smoc mice, at approximately 16-22 g, were sub-lethally irradiated and engrafted with human CD34+ hematopoietic stem cells via i.v. During the humanization process, mice were monitored over the course of 12 to 14 weeks post engraftment to ensure immune lineage differentiation & maturation. HiMice with minimal 10% of human CD45+ reconstitution at week 12- or 14 were used in this experiment. HiMice were also supplemented with cytokines GM-CSF, IL-3, and IL-4 to enhance myeloid lineage, B cell differentiation, and preserve T cell development. Once engraftment was confirmed, a total of 5 doses of either mWasabi oRNA encapsulated in an LNP disclosed herein or CD19 CAR oRNA encapsulated in the same LNP were administered i.v. weekly. Peripheral blood was collected post 3 days of each LNP-ORNA injection and analyzed for immune subsets. Spleens were harvested and processed 3 days after the 5th LNP-ORNA injection for immune profiling.

Cells from blood or spleen were first stained with 50 µl of live/dead solution (1:400 dilution in PBS) for 10 minutes at room temperature. The cells were then pelleted by centrifugation and resuspended with mouse and human Fc receptor blocking reagent (in 25 µl of FACS buffer) for 10 minutes at room temperature to prevent non-specific binding. Subsequently, fluorescent-labeled surface markers (in 25 µl of FACS buffer) were added to the cells. After approximately 30 minutes of incubation in the dark, the cells were washed before acquiring the FACS data using a Fortessa™ X-20 flow cytometer (BD Biosciences) with FACSDiva software. The FACS data were then analyzed with FlowJo software (Tree Star Inc).

The circular RNA encoding CD19 CAR mediated B-cell specific depletion in CD34+ humanized mice. B cell-mediated killing in groups treated with CD19 CAR ORNA encapsulated in LNP was maintained upon 5 doses within the peripheral blood and spleen. Minimal LNP effect was observed on total CD20+B cell frequency and count in the peripheral blood. See, e.g., FIG. 47, FIGS. 48A-C, FIGS. 49A-C.

Example 20: Circular RNA Encoding CD19 CAR in NK Cells

RAJI control in natural killer (NK) cells using circular RNA encoding CD19 CAR in NOG-IL15 mice was assess. See, e.g., Katano et al., Long-term maintenance of peripheral blood derived human NK cells in a novel human IL-15-transgenic NOG mouse, Sci Rep (2017), the contents of which are hereby incorporated by reference herein ("mouse strain expressing transgenic human interleukin-15 (IL-15) using the severe immunodeficient NOD/Shi-scid-IL-2Rγnull (NOG) mouse genetic background (NOG-IL-15 Tg). Human natural killer (NK) cells, purified from the peripheral blood (hu-PB—NK) of normal healthy donors, proliferated when transferred into NOG-IL-15 Tg mice").

NOG-IL15 mice were engrafted with a CD19+Raji-luciferase cell line at Day 0. On Day 3, primary human NK cells purified from peripheral blood were engrafted into recipient animals. On Day 8, mice were left untreated, or treated i.v. with vehicle, circular RNA encoding mOX40L CAR encapsulated in LNP (1 mg/kg), or circular RNA encoding CD19 CAR encapsulated in LNP (1 mg/kg). Mice were treated every two days for 10 doses. Tumor burden was assessed using IVIS imaging as described herein.

Figure 50:
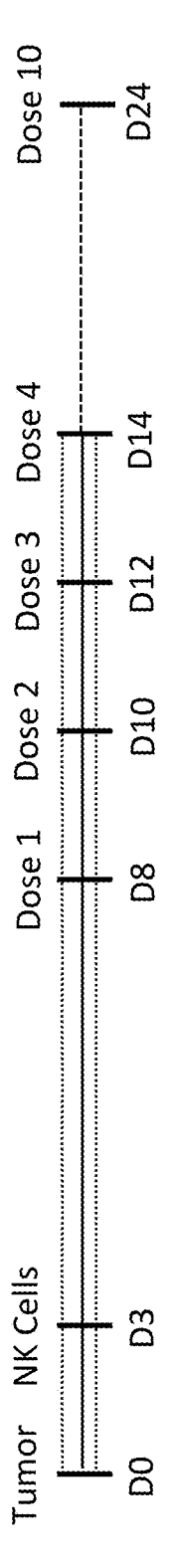
FIG. 50 shows an exemplary method for assessing RAJI control in NK cells using circular RNA comprising anti-CD19 CAR in NOG-IL15 mice.
Figure 51:
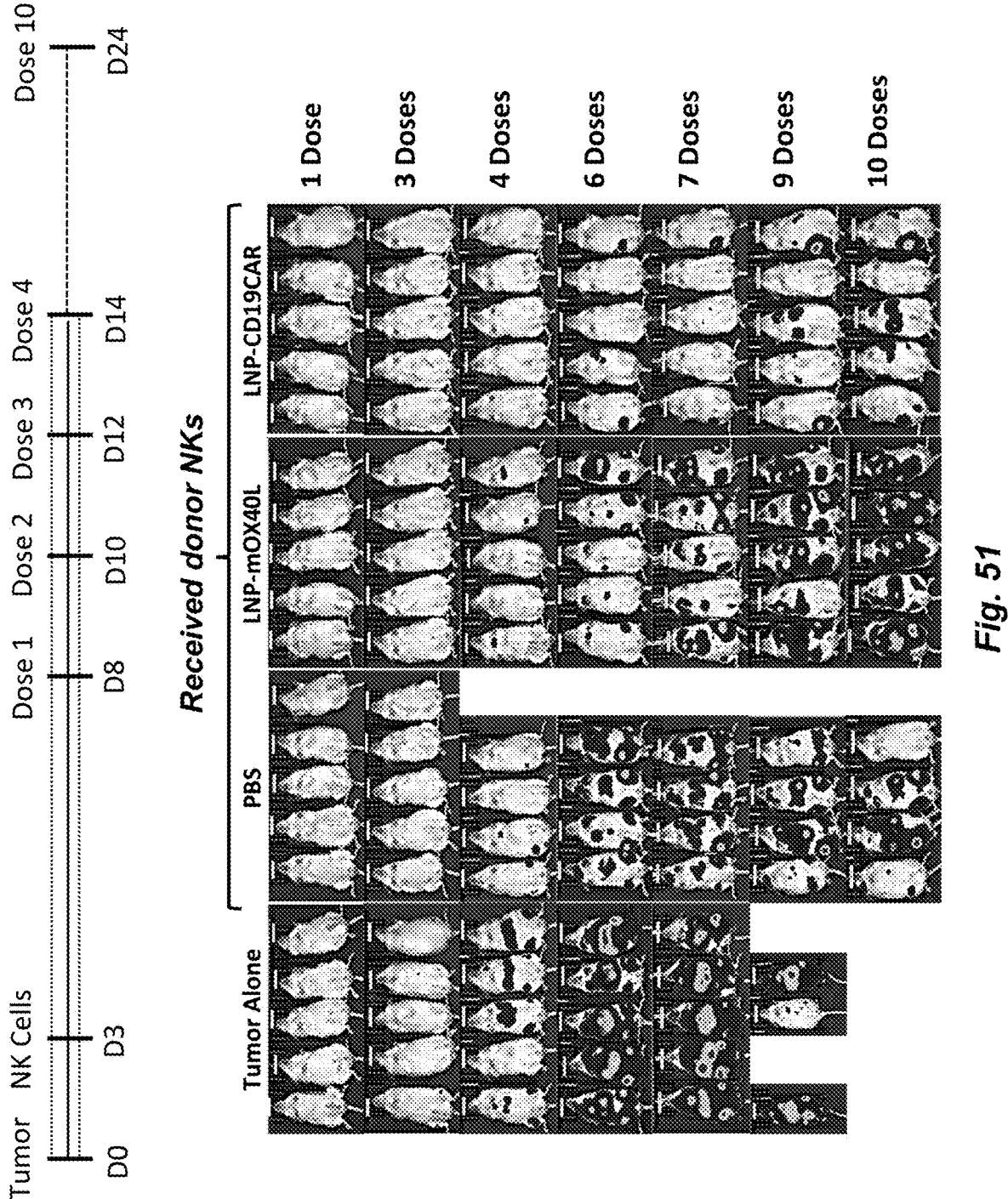
FIG. 51 shows NOG-IL15 mice engrafted with CD19+ Raji-luc cell line at Day 0. On Day 3, primary human NK cells were purified from peripheral blood and were engrafted into recipient animals. On day 8, mice were left untreated, or treated with i.v. with vehicle, LNP-1 mg/kg mOX40L CAR or 1 mg/kg LNP-CD19 CAR. Mice were treated every two days for 10 doses. Tumor burden was imaged using IVIS imaging. Data show that mice treated with LNP-CD19 CAR show tumor control until day 24, study endpoint.

Tumor clearance was observed in this mouse model mouse model. Mice treated with circular RNA encoding CD19 CAR encapsulated in LNP exhibited tumor control until the study endpoint at Day 24. See, e.g., FIG. 50 and FIG. 51.

Example 21: Circular RNA Encoding CD19 CAR in Macrophages

Figure 52:
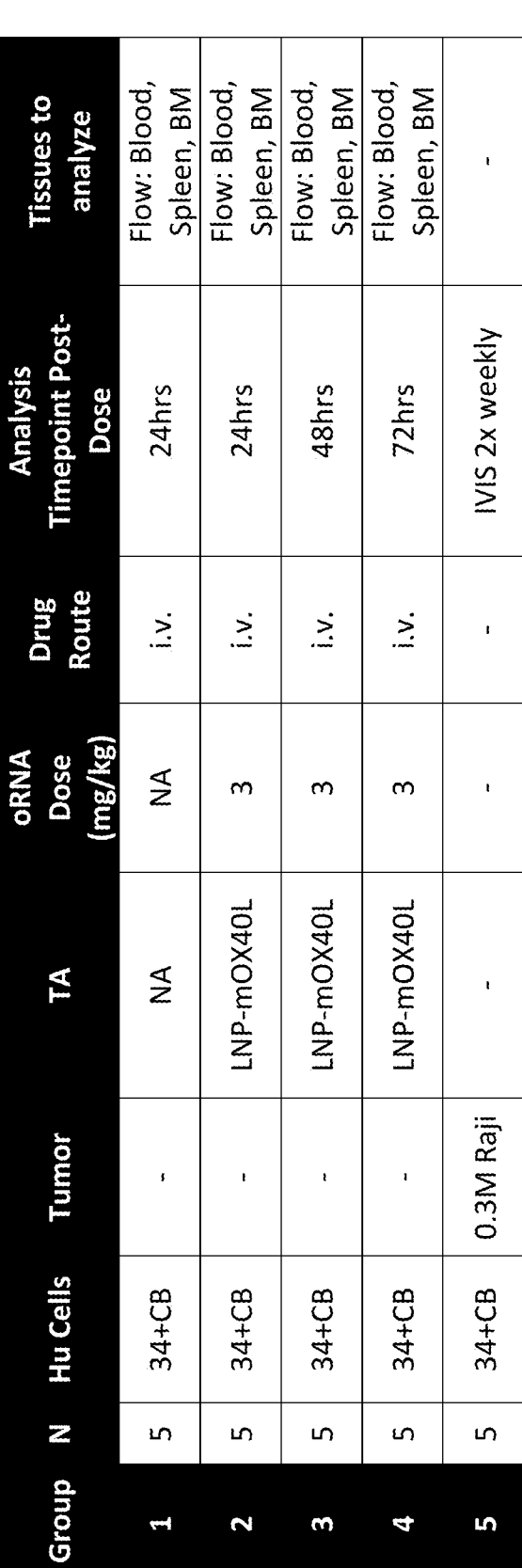
FIG. 52 shows an exemplary method for assessing circular RNA in macrophages.
Figure 53:
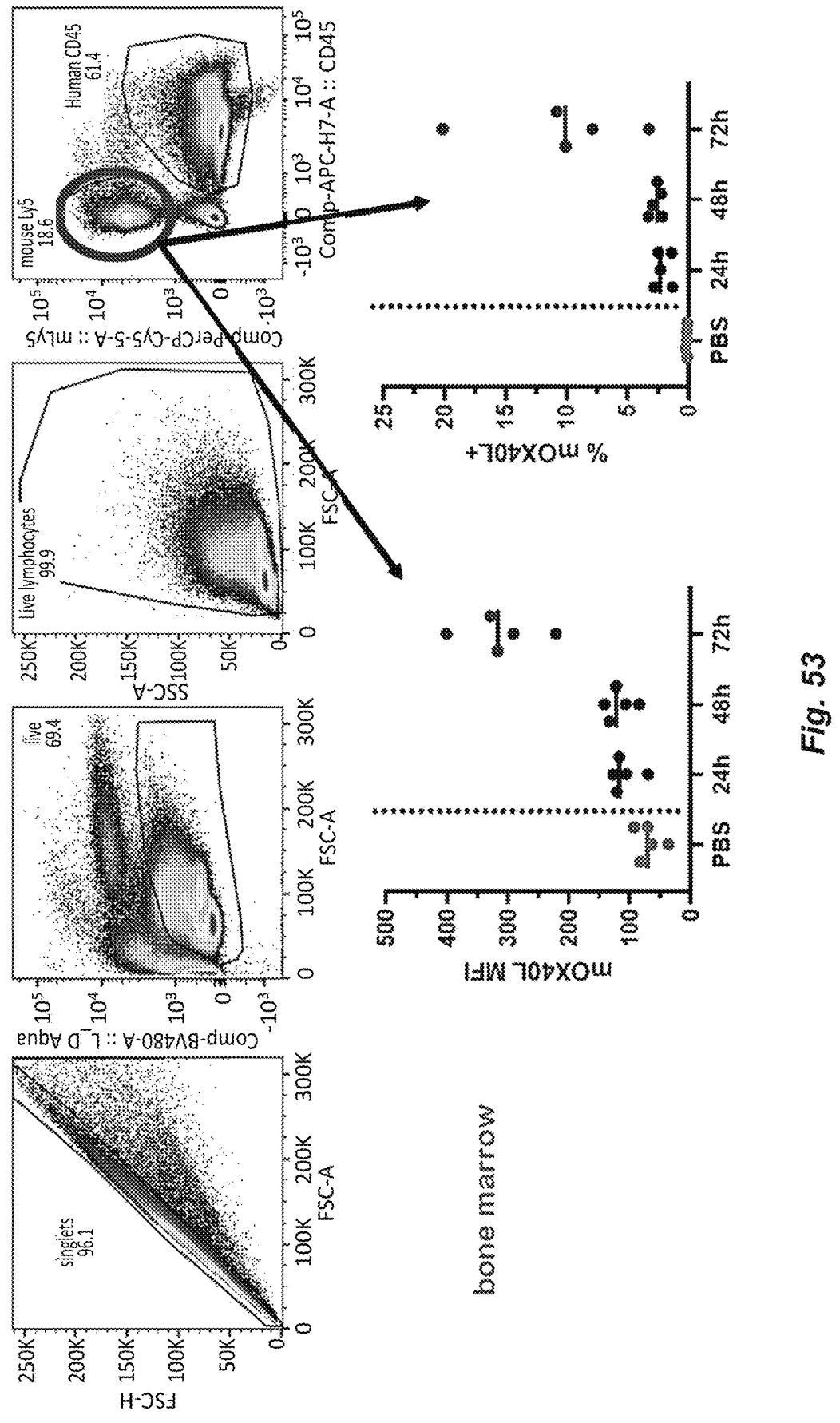
FIG. 53 shows an exemplary FACS gating strategy for establishing circular RNA delivery to monocytes as applied elsewhere herein.
Figure 54A:
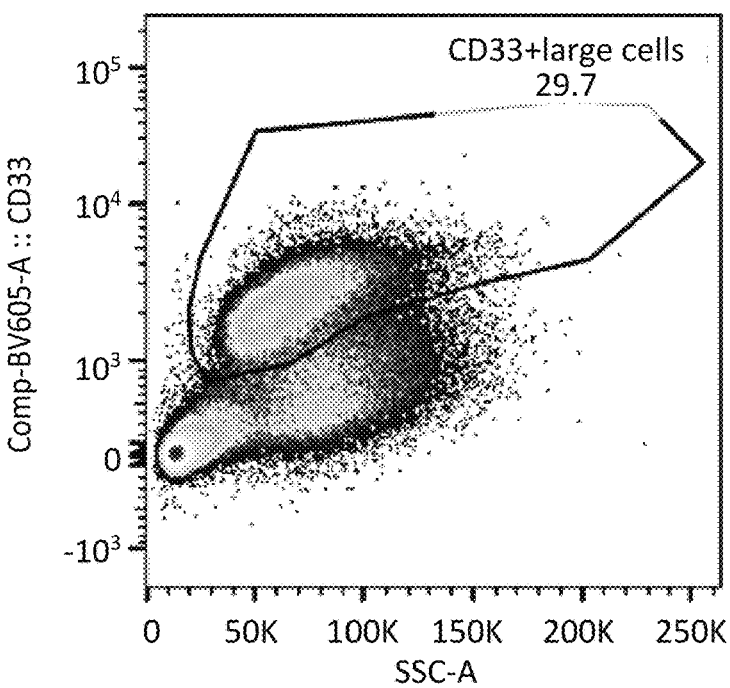
FIGS. 54A-D show mOX40L expression in myeloid cells in bone marrow.
Figure 54B:
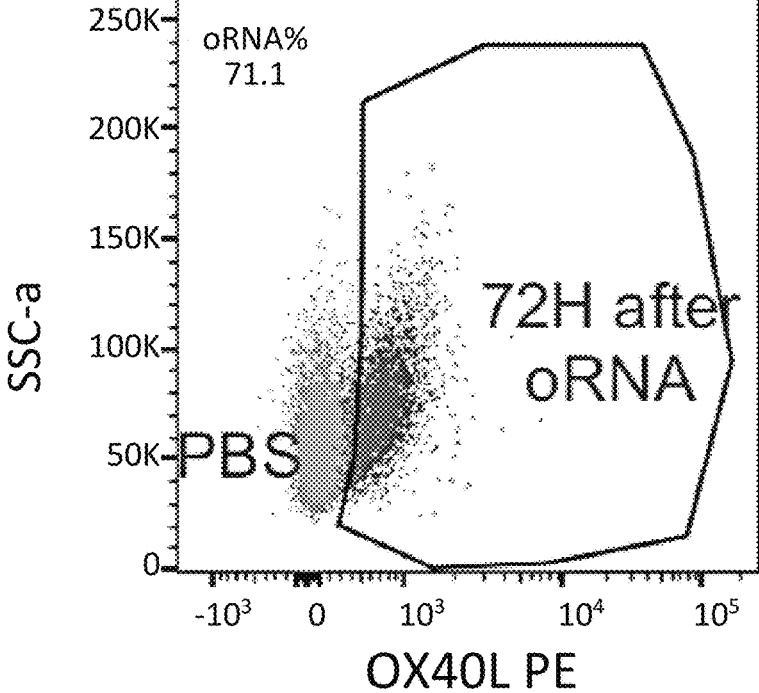
Figure 54C:
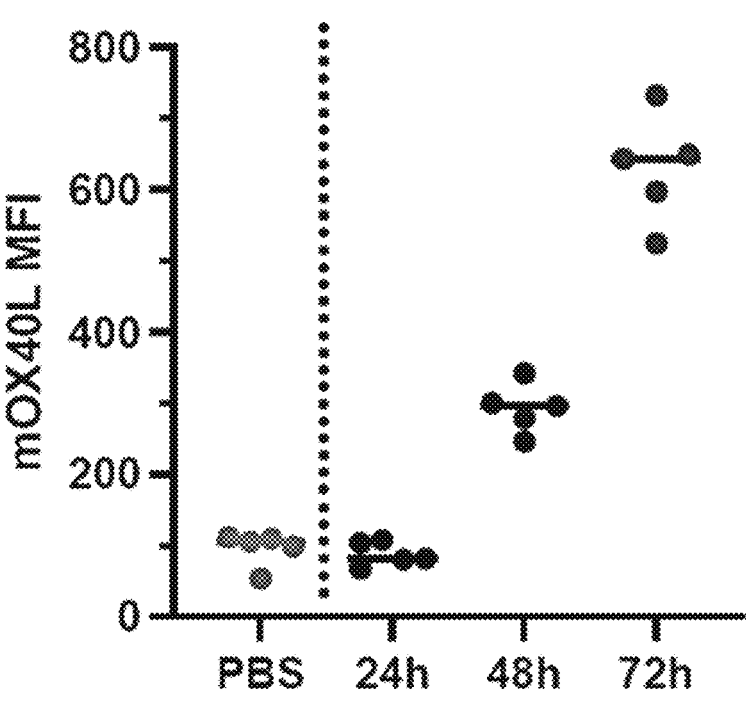
Figure 54D:
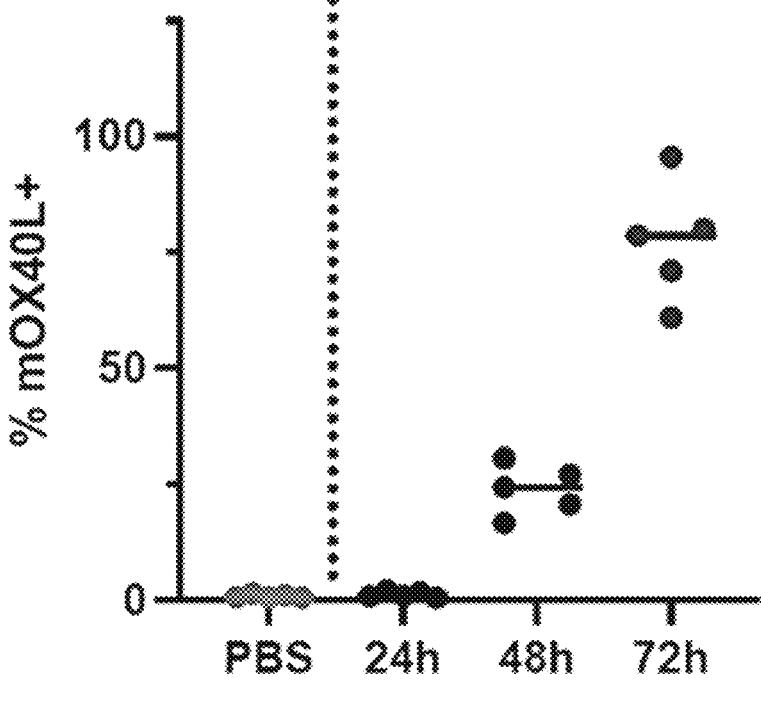
Figures 55D, 55E, 55F, 55G:
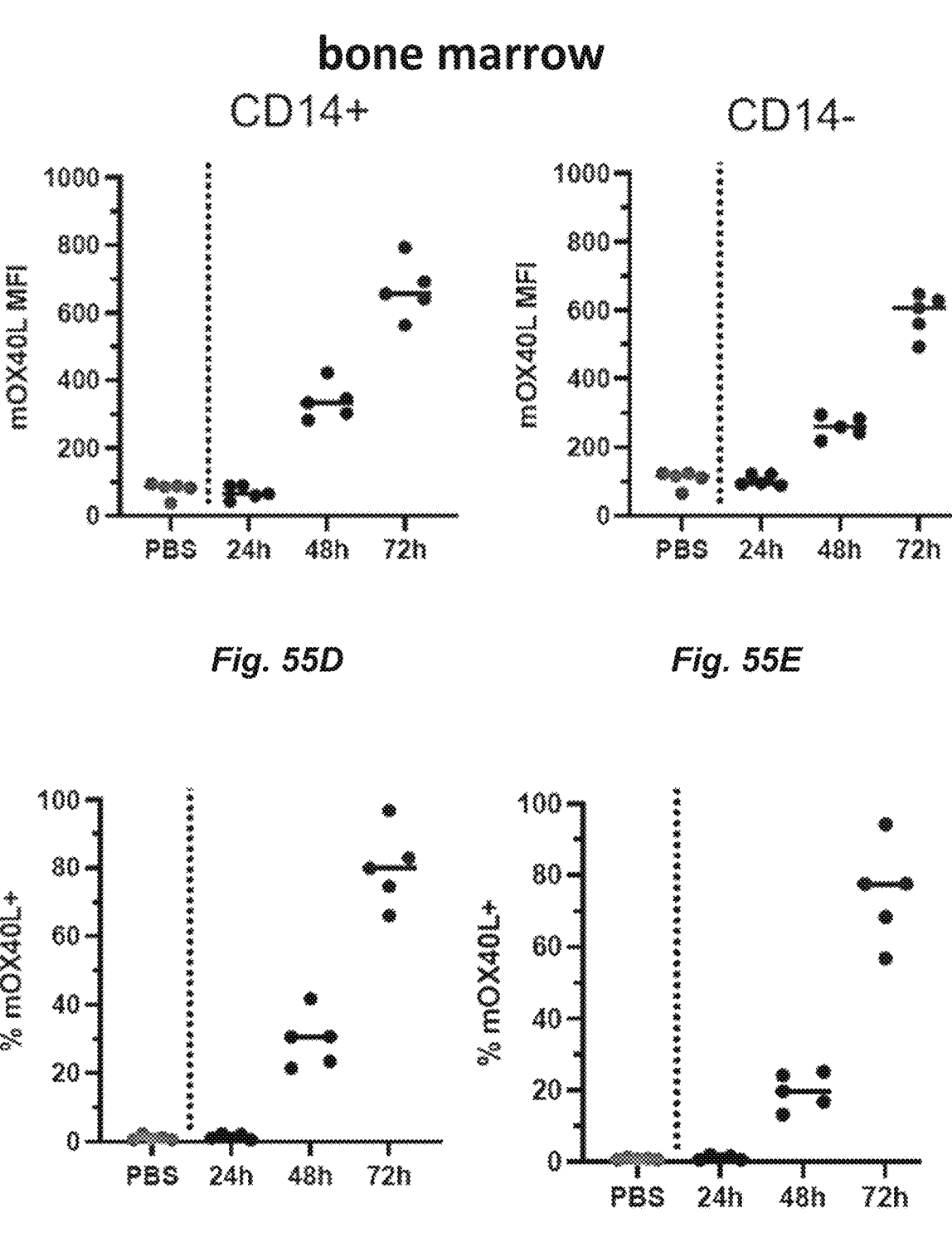
Figure 57A:
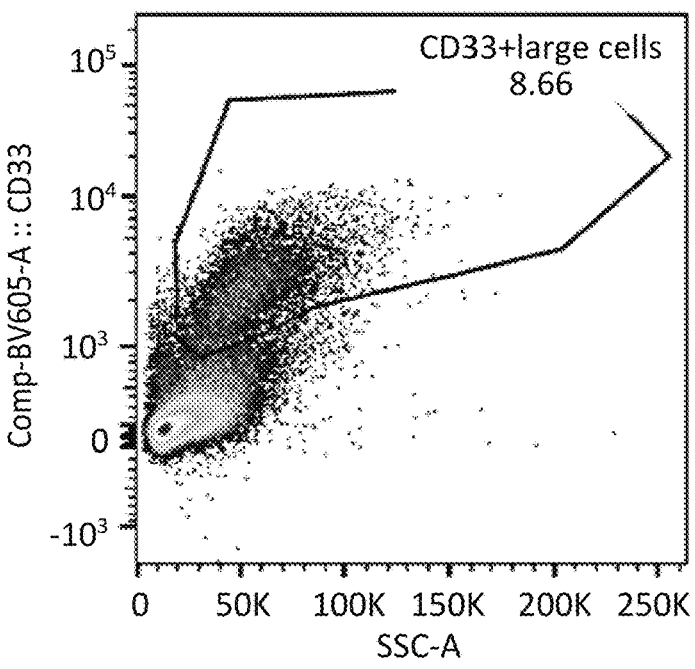
FIGS. 57A-D show mOX40L expression in myeloid cells in spleen.
Figure 57B:
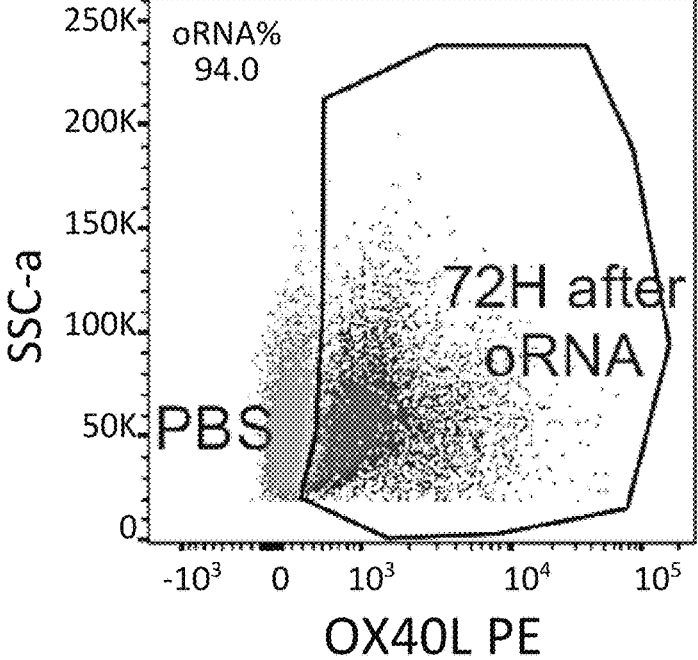
Figure 57C:
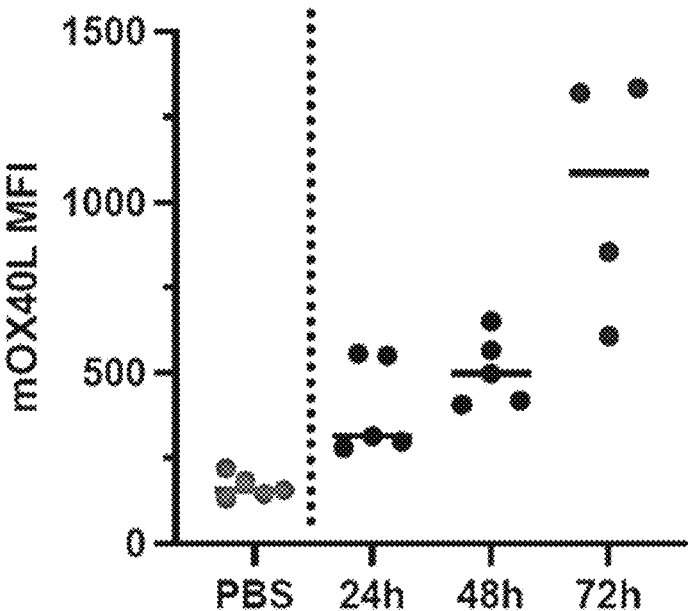
Figure 57D:
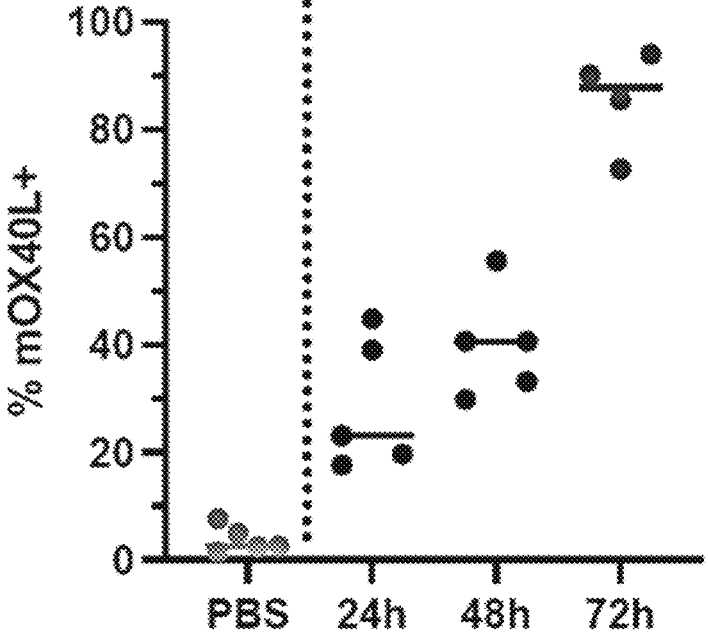
Figure 58A:
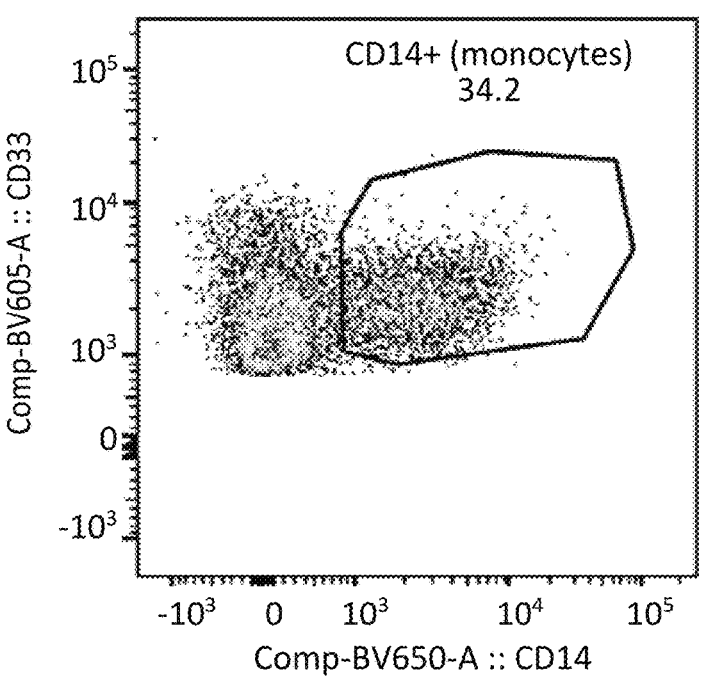
Figure 58B:
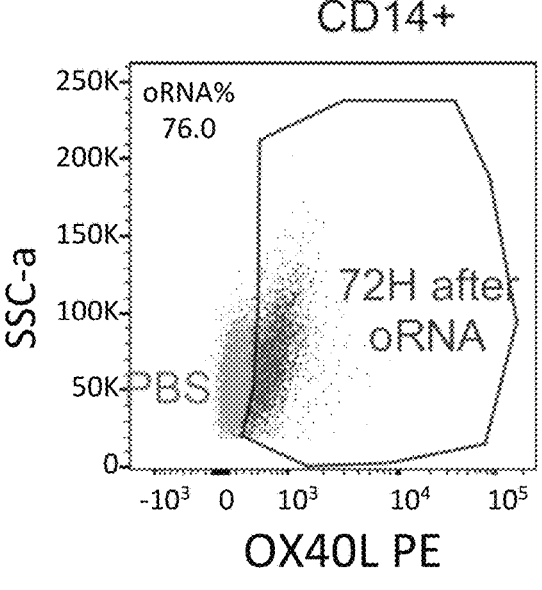
Figure 58C:
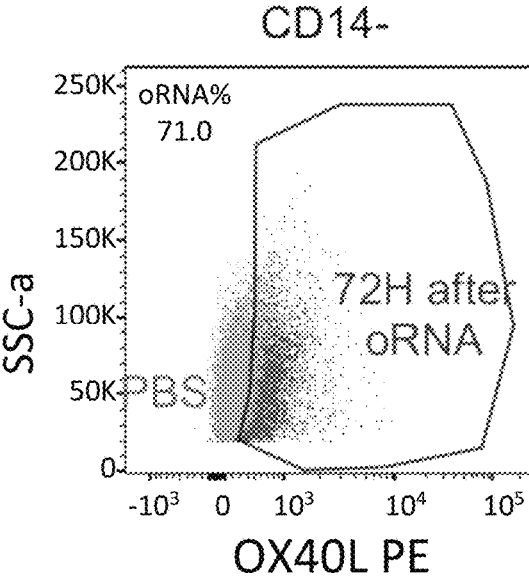
Figure 59A:
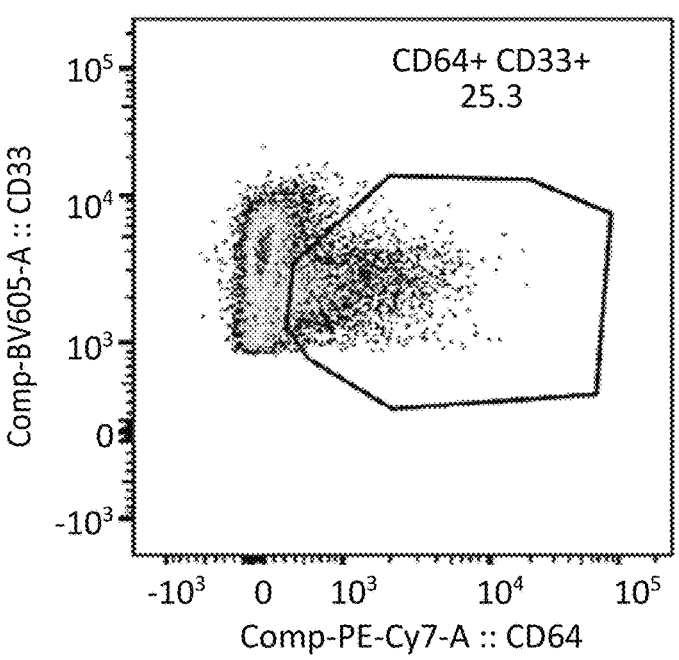
Figure 59B:
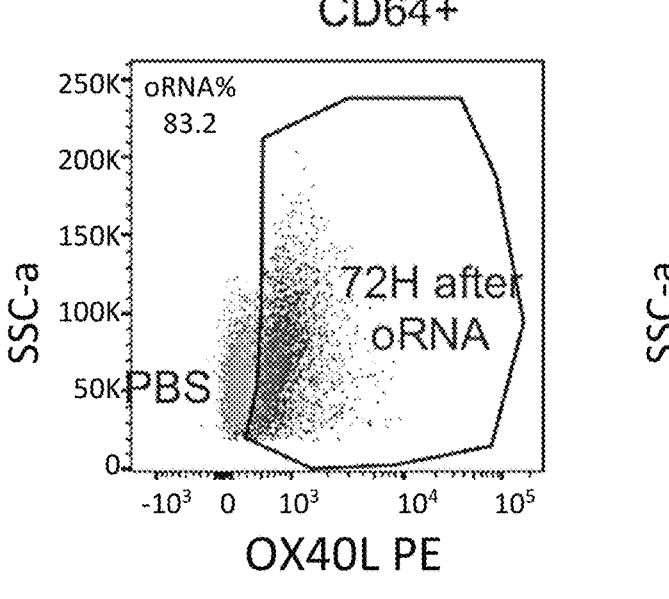
Figure 59C:
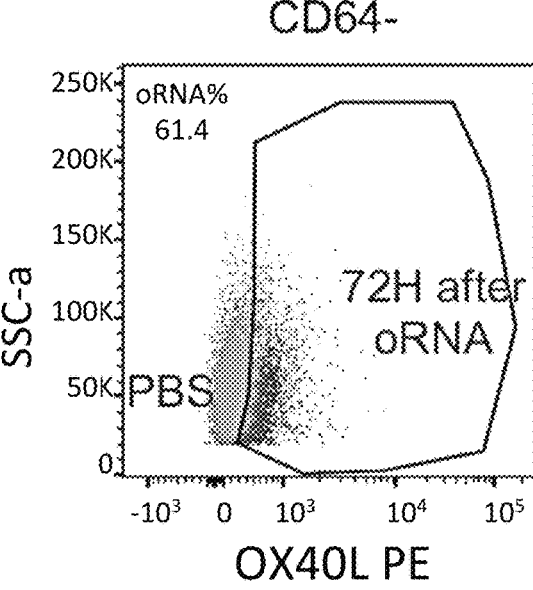

NSG-QUAD mice were engrafted with human CD34+ cord blood. At 10 weeks post-engraftment, animals were left untreated (control) or treated with circular RNA comprising a sequence for mOX40L encapsulated in LNP (see FIG. 52). Animals were sacrificed after 24, 48, or 72 hours. mOX40L expression was analyzed by flow cytometry on CD33+, CD33+CD14+ or CD33+CD64+ myeloid cells in the blood, bone marrow and spleen. mOX40L was detected on the surface of CD33+ myeloid cells in the bone marrow and spleen at each timepoint, with peak expression observed at 72 hours LNP-circRNA treatment. See, e.g., FIG. 53, FIGS. 54A-D, FIGS. 55A-G, FIGS. 56A-G, FIGS. 57A-D, FIGS. 58A-G, and FIGS. 59A-G.

This description and exemplary embodiments should not be taken as limiting. For the purposes of this specification and appended claims, unless otherwise indicated, all num-
bers expressing quantities, percentages, or proportions, and
other numerical values used in the specification and claims,
are to be understood as being modified in all instances by the
term "about," to the extent they are not already so modified.
Accordingly, unless indicated to the contrary, the numerical
parameters set forth in the following specification and
attached claims are approximations that may vary depending
upon the desired properties sought to be obtained. At the
very least, and not as an attempt to limit the application of
the doctrine of equivalents to the scope of the claims, each numerical parameter should at least be construed in light of
the number of reported significant digits and by applying
ordinary rounding techniques.

It is noted that, as used in this specification and the
appended claims, the singular forms "a," "an," and "the,"
and any singular use of any word, include plural referents
unless expressly and unequivocally limited to one referent.
As used herein, the term "include" and its grammatical
variants are intended to be non-limiting, such that recitation
of items in a list is not to the exclusion of other like items
that can be substituted or added to the listed items.

---

What is claimed is:

1. A circular RNA construct comprising:
(A) a translation initiation element comprising a sequence that is at least 80% identical to the corresponding RNA sequence of any one of SEQ ID NO: 8, SEQ ID NOs: 1-7, and SEQ ID NOs: 9-18, and
(B) at least one expression sequence that encodes a chimeric antigen receptor (CAR), wherein the CAR comprises an antigen binding domain, a hinge domain, a transmembrane domain, a costimulatory domain, and a signaling domain, wherein:
   a. the antigen binding domain specifically binds to CD19 and comprises a light chain variable region (VL) comprising VL CDR1, VL CDR2, and VL CDR3 of SEQ ID NO: 29, and a heavy chain variable region (VH) comprising VH CDR1, VH CDR2, and VH CDR3 of SEQ ID NO: 29, wherein the VL and VH are linked by a linker;
   b. the antigen binding domain specifically binds to BCMA and comprises a first variable heavy domain of heavy chain (VHH) comprising VHH CDR1, VHH CDR2, and VHH CDR3 of SEQ ID NO: 122, and a second VHH comprising a VHH CDR4, VHH CDR5, and VHH CDR6 of SEQ ID NO: 122;
   c. the antigen binding domain specifically binds to BCMA and comprises a VL comprising a VL CDR1, VL CDR2, and VL CDR3 of SEQ ID NO: 121, and a VH comprising a VH CDR1, VH CDR2, and VH CDR3 of SEQ ID NO: 121, wherein the VL and VH are linked by a linker; or
   d. the antigen binding domain specifically binds to HER2 and comprises a VL comprising VL CDR1, VL CDR2, and VL CDR3 of SEQ ID NO: 117, and VH comprising VH CDR1, VH CDR2, and VH CDR3 of SEQ ID NO: 117, wherein the VL and VH are linked by a linker.

2. The circular RNA construct of claim 1, wherein the translation initiation element comprises a sequence that is at least 90% identical to SEQ ID NO: 8.

3. The circular RNA construct of claim 1, wherein the antigen binding domain specifically binds to CD19 and comprises a light chain variable region (VL) comprising VL CDR1, VL CDR2, and VL CDR3 of SEQ ID NO: 29, and a heavy chain variable region (VH) comprising the VH CDR1, VH CDR2, and VH CDR3 of SEQ ID NO: 29, wherein the VL and VH are linked by a linker.

4. The circular RNA construct of claim 1, wherein the expression sequence encodes a single chain antibody fragment (scFv).

5. The circular RNA construct of claim 1, wherein the circular RNA further comprises a polyA region, at least one miRNA binding site, and/or at least one miR-122 binding site.

6. The circular RNA construct of claim 1, wherein the expression sequence is codon optimized.

7. The circular RNA construct of claim 1, wherein the expression sequence further encodes a signal peptide.

8. The circular RNA construct of claim 1, wherein:
(a) the hinge domain is derived from a ErbB2, glycophorin A (GpA), CD2, CD3 delta, CD3 epsilon, CD3 gamma, CD4, CD7, CD8a, CD8b, CD11a (IT GAL), CD11b (IT GAM), CD11c (ITGAX), CD11d (IT GAD), CD18 (ITGB2), CD19 (B4), CD27 (TN-FRSF7), CD28, CD28T, CD29 (ITGB1), CD30 (TN-FRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (0X40), CD137

(4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRT AM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), or PAG1/CBP;

(b) the transmembrane domain is derived from ErbB2, glycophorin A (GpA), 4-1BB/CD137, activating NK cell receptors, an immunoglobulin protein, B7-H3, BAFFR, BFAME (SEAMF8), BTEA, CD100 (SEMA4D), CD103, CD160 (BY55), CD18, CD19, CD19a, CD2, CD247, CD27, CD276 (B7-H3), CD28, CD29, CD3 delta, CD3 epsilon, CD3 gamma, CD30, CD4, CD40, CD49a, CD49D, CD49f, CD69, CD7, CD84, CD8alpha, CD8beta, CD96 (Tactile), CD11a, CD11b, CD11c, CD11d, CDS, CEACAM1, CRT AM, cytokine receptor, DAP-10, DNAMI (CD226), Fc gamma receptor, GADS, GITR, HVEM (EIGHTR), IA4, ICAM-1, ICAM-1, Ig alpha (CD79a), IE-2R beta, IE-2R gamma, IE-7R alpha, inducible T cell costimulator (ICOS), integrins, ITGA4, ITGA4, ITGA6, IT GAD, ITGAE, ITGAE, IT GAM, ITGAX, ITGB2, ITGB7, ITGB1, KIRDS2, EAT, LFA-1, LFA-1, a ligand that specifically binds with CD83, LIGHT, LIGHT, LTBR, Ly9 (CD229), lymphocyte function-associated antigen-1 (LFA-1; CD11a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A; Ly108), SLAMF7, SLP-76, TNF receptor proteins, TNFR2, TNFSF14, a Toll ligand receptor, TRANCE/RANKL, VLA1, or VLA-6;

(c) the costimulatory domain is selected from a CD137 costimulatory domain or CD28 costimulatory domain; and (d) the signaling domain is derived from B7-H3, BAFFR, BLAME (SLAMF8), BTLA, CD100 (SEMA4D), CD103, CD160 (BY55), CD18, CD19, CD 19a, CD2, CD247, CD27, CD276 (B7-H3), CD28, CD29, CD3 delta, CD3 epsilon, CD3 gamma, CD3 zeta, CD30, CD4, CD40, CD49a, CD49D, CD49f, CD69, CD7, CD84, CD8alpha, CD8beta, CD96 (Tactile), CD11a, CD11b, CD11c, CD11d, CDS, CEACAM1, CRT AM, cytokine receptor, DAP-10, DNAMI (CD226), Fc gamma receptor, GADS, GITR, HVEM (LIGHTR), IA4, ICAM-1, Ig alpha (CD79a), IL-2R beta, IL-2R gamma, IL-7R alpha, inducible T cell costimulator (ICOS), integrins, ITGA4, ITGA6, ITGAD, ITGAE, ITGAL, ITGAM, ITGAX, ITGB2, ITGB7, ITGB1, KIRDS2, LAT, LFA-1, ligand that specifically binds with CD83, LIGHT, LTBR, Ly9 (CD229), Ly108, lymphocyte function-associated antigen-1 (LFA-1; CD11a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A), SLAMF7, SLP-76, TNF receptor proteins, TNFR2, TNFSF14, a Toll ligand receptor, TRANCE/RANKL, VLA1, or VLA-6.

9. A pharmaceutical composition comprising the circular RNA construct of claim 1; and a transfer vehicle.

10. The pharmaceutical composition of claim 9, wherein the transfer vehicle comprises: (i) an ionizable lipid of Formula (I)

Formula (I)

wherein n is an integer between 1 and 4;

$R_a$ is hydrogen or hydroxyl; and $R_1$ and $R_2$ are each independently a linear or branched $C_6$-$C_{30}$ alkyl, $C_6$-$C_{30}$ alkenyl, or $C_6$-$C_{30}$ heteroalkyl, optionally substituted by one or more substituents selected from a group consisting of oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl) aminoalkyl, heterocyclyl, heteroaryl, alkylheteroaryl, alkynyl, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl) aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl, and alkylsulfonealkyl;

or (ii) an ionizable lipid of Formula (II)

Formula (II)

wherein each n is independently an integer from 2-15;

$L_1$ and $L_3$ are each independently —OC(O)—* or —C(O)O—*, wherein "*" indicates the attachment point to $R_1$ or $R_3$;

$R_1$ and $R_3$ are each independently a linear or branched $C_9$-$C_{20}$ alkyl or $C_9$-$C_{20}$ alkenyl, optionally substituted by one or more substituents selected from a group consisting of oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl) (alkyl) aminoalkyl, heterocyclyl, heteroaryl, alkylheteroaryl, alkynyl, alkoxy, amino, dialkylamino, aminoalkylcarbonylamino, aminocarbonylalkylamino, (aminocarbonylalkyl) (alkyl) amino, alkenylcarbonylamino, hydroxycarbonyl, alkyloxycarbonyl, aminocarbonyl, aminoalkylaminocarbonyl, alkylaminoalkylaminocarbonyl, dialkylamino-alkylaminocarbonyl,
heterocyclylalkylaminocarbonyl, (alkylaminoalkyl) (alkyl) aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl, and alkylsulfone-alkyl; and R₂ is selected from a group consisting of:

538

-continued

11. The pharmaceutical composition of claim 9, wherein the transfer vehicle has a lipid molar ratio formation selected from a Compound:Phospholipid:Phytosterol:PEG-DMG ratio of:40:20:38.5:1.5, 45:15:38.5:1.5, 50:10:38.5:1.5, 55:5:38.5:1.5, 60:5:33.5:1.5, 45:20:33.5:1.5, 50:20:28.5:1.5, 55:20:23.5:1.5, 60:20: 18.5:1.5, 40:15:43.5:1.5, 50:15:33.5: 1.5, 55:15:28.5:1.5, 60:15:23.5:1.5, 40:10:48.5:1.5, 45:10: 43.5:1.5, 55:10:33.5:1.5, 60:10:28.5:1.5, 40:5:53.5:1.5, 45:5:48.5:1.5, 50:5:43.5:1.5, 40:20:40:0, 45:20:35:0, 50:20: 30:0, 55:20:25:0, 60:20:20:0, and 40:15:45:0.

12. The pharmaceutical composition of claim 9, wherein the transfer vehicle comprises an ionizable lipid selected from:

-continued

13. The pharmaceutical composition of claim 9, wherein the transfer vehicle further comprises (a) a helper lipid, a structural lipid, and/or a PEG-lipid; and (b) a pharmaceutical salt, buffer, or diluent, or combination thereof.

14. The pharmaceutical composition of claim 13, wherein the transfer vehicle comprises PEG-DSPC.

15. The pharmaceutical composition of claim 9, wherein the transfer vehicle is a lipid nanoparticle.

16. The pharmaceutical composition of claim 9, wherein the transfer vehicle further comprises a targeting moiety selected from a small molecule, scFv, nanobody, peptide, cyclic peptide, di or tri cyclic peptide, minibody, polynucleotide aptamer, engineered scaffold protein, heavy chain variable region, light chain variable region, or a fragment thereof.

17. A method of treating cancer or an autoimmune disorder in a subject by administering an effective amount of a composition comprising the circular RNA construct of claim 1 or a pharmaceutical composition thereof, thereby treating the cancer or autoimmune disorder.

18. The circular RNA of claim 1, wherein:
a. the antigen binding domain specifically binds to CD19 and comprises a VL comprising amino acids 22-128 of SEQ ID NO: 29; and a VH comprising amino acids 143-262 of SEQ ID NO: 29;

b. the antigen binding domain specifically binds to BCMA and comprises a first VHH comprising amino acids 22-140 of SEQ ID NO: 122; and a second VHH comprising amino acids 156-273 of SEQ ID NO: 122;
c. the antigen binding domain specifically binds to BCMA and comprises a VL comprising amino acids 22-132 of SEQ ID NO: 121, and a VH comprising amino acids 151-267 of SEQ ID NO: 121;
d. the antigen binding domain specifically binds to HER2 and comprises a VL comprising amino acids 22-128 of SEQ ID NO: 117; and a VH comprising amino acids 146-265 of SEQ ID NO: 117.

19. The circular RNA of claim 1, wherein the antigen binding domain specifically binds to CD19 and comprises a VL comprising amino acids 22-128 of SEQ ID NO: 29; and a VH comprising amino acids 143-262 of SEQ ID NO: 29.

20. The circular RNA construct of claim 1, wherein the translation initiation element comprises a sequence that is at least 95% identical to the corresponding RNA sequence of SEQ ID NO: 8.

21. The circular RNA construct of claim 1, wherein the translation initiation element comprises a sequence that is identical to the corresponding sequence of SEQ ID NO: 8.

22. The circular RNA construct of claim 1, wherein the antigen binding domain specifically binds to BCMA and comprises a first variable heavy domain of heavy chain (VHH) comprising a VHH CDR1, VHH CDR2, and VHH CDR3 of SEQ ID NO: 122, and a second VHH comprising a VHH CDR4, VHH CDR5, and VHH CDR6 of SEQ ID NO: 122.

23. The circular RNA of claim 1, wherein the antigen binding domain specifically binds to BCMA and comprises a VL comprising a VL CDR1, VL CDR2, and VL CDR3 of SEQ ID NO: 121, and a VH comprising a VH CDR1, VH CDR2, and VH CDR3 of SEQ ID NO: 121, wherein the VL and VH are linked by a linker.

24. The circular RNA of claim 1, wherein the antigen binding domain specifically binds to HER2 and comprises a VL comprising a VL CDR1, VL CDR2, and VL CDR3 of SEQ ID NO: 117, and VH comprising a VH CDR1, VH CDR2, and VH CDR3 of SEQ ID NO: 117, wherein the VL and VH are linked by a linker.

25. The circular RNA of claim 1, wherein the antigen binding domain specifically binds to BCMA and comprises a first VHH comprising amino acids 22-140 of SEQ ID NO: 122; and a second VHH comprising amino acids 156-273 of SEQ ID NO: 122.

26. The circular RNA of claim 1, wherein the antigen binding domain specifically binds to BCMA and comprises a VL comprising amino acids 22-132 of SEQ ID NO: 121, and a VH comprising amino acids 151-267 of SEQ ID NO: 121.

27. The circular RNA of claim 1, wherein the antigen binding domain specifically binds to HER2 and comprises a VL comprising amino acids 22-128 of SEQ ID NO: 117; and a VH comprising amino acids 146-265 of SEQ ID NO: 117.

28. A linear precursor RNA polynucleotide comprising:

(A) a translation initiation element comprising a sequence that is at least 80% identical to any one of SEQ ID NO: 8, SEQ ID NOs: 1-7, SEQ ID NOs: 9-18, or fragment thereof, and (B) at least one expression sequence that encodes a chimeric antigen receptor (CAR), wherein the CAR comprises an antigen binding domain, a hinge domain, a transmembrane domain, a costimulatory domain, and a signaling domain, wherein:

a. the antigen binding domain specifically binds to CD19 and comprises a light chain variable region (VL) comprising a VL CDR1, VL CDR2, VL CDR3 of SEQ ID NO: 29, and a heavy chain variable region (VH) comprising a VH CDR1, VH CDR2, and VH CDR3 of SEQ ID NO: 29, wherein the VL and VH are linked by a linker;

b. the antigen binding domain specifically binds to BCMA and comprises a first variable heavy domain of heavy chain (VHH) comprising a VHH CDR1, VHH CDR2, VHH CDR3 of SEQ ID NO: 122, and a second VHH comprising a VHH CDR4, VHH CDR5, and VHH CDR6 of SEQ ID NO: 122;

c. the antigen binding domain specifically binds to BCMA and comprises a VL comprising a VL CDR1, VL CDR2, VL CDR3 of SEQ ID NO: 121, and a VH comprising a VH CDR1, VH CDR2, and VH CDR3 of SEQ ID NO: 121, wherein the VL and VH are linked by a linker; and/or d. the antigen binding domain specifically binds to HER2 and comprises a VL comprising a VL CDR1, VL CDR2, VL CDR3 of SEQ ID NO: 117, and VH comprising a VH CDR1, VH CDR2, and VH CDR3 of SEQ ID NO: 117, wherein the VL and VH are linked by a linker.

29. A method of preparing a circular RNA construct, the method comprising incubating the linear RNA polynucleotide of claim 22 under suitable conditions for circularization.

30. The linear precursor RNA of claim 28, wherein the translation initiation element comprises a sequence that is at least 90% identical to SEQ ID NO: 8.

31. The linear precursor RNA of claim 28, wherein the antigen binding domain specifically binds to CD19 and comprises a light chain variable region (VL) comprising the VL CDR1, VL CDR2, and VL CDR3 of SEQ ID NO: 29, and a heavy chain variable region (VH) comprising the VH CDR1, VH CDR2, and VH CDR3 of SEQ ID NO: 29, wherein the VL and VH are linked by a linker.

32. The linear precursor RNA of claim 28, wherein the antigen binding domain specifically binds to BCMA and comprises a first variable heavy domain of heavy chain (VHH) comprising a VHH CDR1, VHH CDR2, and VHH CDR3 of SEQ ID NO: 122, and a second VHH comprising a VHH CDR4, VHH CDR5, and VHH CDR6 of SEQ ID NO: 122.

33. The linear precursor RNA of claim 28, wherein the antigen binding domain specifically binds to BCMA and comprises a VL comprising a VL CDR1, VL CDR2, and VL CDR3 of SEQ ID NO: 121, and a VH comprising a VH CDR1, VH CDR2, and VH CDR3 of SEQ ID NO: 121, wherein the VL and VH are linked by a linker.

34. The linear precursor RNA of claim 28, wherein the antigen binding domain specifically binds to HER2 and comprises a VL comprising a VL CDR1, VL CDR2, and VL CDR3 of SEQ ID NO: 117, and VH comprising a VH CDR1, VH CDR2, and VH CDR3 of SEQ ID NO: 117, wherein the VL and VH are linked by a linker.

35. The linear precursor RNA of claim 28, wherein the antigen binding domain specifically binds to CD19 and comprises a VL comprising amino acids 22-128 of SEQ ID NO: 29; and a VH comprising amino acids 143-262 of SEQ ID NO: 29.

36. The linear precursor RNA of claim 28, wherein the antigen binding domain specifically binds to BCMA and comprises a first VHH comprising amino acids 22-140 of SEQ ID NO: 122; and a second VHH comprising amino acids 156-273 of SEQ ID NO: 122.

37. The linear precursor RNA of claim 28, wherein the antigen binding domain specifically binds to BCMA and comprises a VL comprising amino acids 22-132 of SEQ ID NO: 121, and a VH comprising amino acids 151-267 of SEQ ID NO: 121.

38. The linear precursor RNA of claim 28, wherein the antigen binding domain specifically binds to HER2 and comprises a VL comprising amino acids 22-128 of SEQ ID NO: 117; and a VH comprising amino acids 146-265 of SEQ ID NO: 117.

39. A DNA vector encoding a linear RNA polynucleotide comprising:

(A) a translation initiation element comprising a sequence that is at least 80% identical to the corresponding RNA sequence of any one of SEQ ID NO: 8, SEQ ID NOs: 1-7, or SEQ ID NOs: 9-18, and (B) at least one expression sequence that encodes a chimeric antigen receptor (CAR), wherein the CAR comprises an antigen binding domain, a hinge domain, a transmembrane domain, a costimulatory domain, and a signaling domain, wherein:

a. the antigen binding domain specifically binds to CD19 and comprises a light chain variable region (VL) comprising VL CDR1, VL CDR2, and VL CDR3 of SEQ ID NO: 29, and a heavy chain variable region (VH) comprising VH CDR1, VH CDR2, and VH CDR3 of SEQ ID NO: 29, wherein the VL and VH are linked by a linker;

b. the antigen binding domain specifically binds to BCMA and comprises a first variable heavy domain of heavy chain (VHH) comprising VHH CDR1, VHH CDR2, and VHH CDR3 of SEQ ID NO: 122, and a second VHH comprising a VHH CDR4, VHH CDR5 and VHH CDR6 of SEQ ID NO: 122;

c. the antigen binding domain specifically binds to BCMA and comprises a VL comprising a VL CDR1, VL CDR2, and VL CDR3 of SEQ ID NO: 121, and a VH comprising a VH CDR1, VH CDR2, and VH CDR3 of SEQ ID NO: 121, wherein the VL and VH are linked by a linker; or d. the antigen binding domain specifically binds to HER2 and comprises a VL comprising VL CDR1, VL CDR2, and VL CDR3 of SEQ ID NO: 117, and VH comprising VH CDR1, VH CDR2, and VH CDR3 of SEQ ID NO: 117, wherein the VL and VH are linked by a linker.

40. The DNA vector of claim 39, wherein the translation initiation element comprises a sequence that is at least 90% identical to SEQ ID NO: 8.

41. The DNA vector of claim 39, wherein the antigen binding domain specifically binds to CD19 and comprises a light chain variable region (VL) comprising the VL CDR1, VL CDR2, and VL CDR3 of SEQ ID NO: 29, and a heavy chain variable region (VH) comprising the VH CDR1, VH CDR2, and VH CDR3 of SEQ ID NO: 29, wherein the VL and VH are linked by a linker.

42. The DNA vector of claim 39, wherein the antigen binding domain specifically binds to BCMA and comprises a first variable heavy domain of heavy chain (VHH) comprising a VHH CDR1, VHH CDR2, and VHH CDR3 of SEQ ID NO: 122, and a second VHH comprising a VHH CDR4, VHH CDR5, and VHH CDR6 of SEQ ID NO: 122.

43. The DNA vector of claim 39, wherein the antigen binding domain specifically binds to BCMA and comprises a VL comprising a VL CDR1, VL CDR2, and VL CDR3 of SEQ ID NO: 121, and a VH comprising a VH CDR1, VH CDR2, and VH CDR3 of SEQ ID NO: 121, wherein the VL and VH are linked by a linker.

44. The DNA vector of claim 39, wherein the antigen binding domain specifically binds to HER2 and comprises a VL comprising a VL CDR1, VL CDR2, and VL CDR3 of SEQ ID NO: 117, and VH comprising a VH CDR1, VH CDR2, and VH CDR3 of SEQ ID NO: 117, wherein the VL and VH are linked by a linker.

45. The DNA vector of claim 39, wherein the antigen binding domain specifically binds to CD19 and comprises a VL comprising amino acids 22-128 of SEQ ID NO: 29; and a VH comprising amino acids 143-262 of SEQ ID NO: 29.

46. The DNA vector of claim 39, wherein the antigen binding domain specifically binds to BCMA and comprises a first VHH comprising amino acids 22-140 of SEQ ID NO: 122; and a second VHH comprising amino acids 156-273 of SEQ ID NO: 122.

47. The DNA vector of claim 39, wherein the antigen binding domain specifically binds to BCMA and comprises a VL comprising amino acids 22-132 of SEQ ID NO: 121, and a VH comprising amino acids 151-267 of SEQ ID NO: 121.

48. The DNA vector of claim 39, wherein the antigen binding domain specifically binds to HER2 and comprises a VL comprising amino acids 22-128 of SEQ ID NO: 117; and a VH comprising amino acids 146-265 of SEQ ID NO: 117.

* * * * *